(12) United States Patent
Sasahara et al.

(10) Patent No.: US 7,973,030 B2
(45) Date of Patent: Jul. 5, 2011

(54) BENZOTHIAZEPINE AND BENZOTHIEPINE COMPOUNDS

(75) Inventors: Takehiko Sasahara, Numazu (JP);
Mitsunobu Mohri, Mishima (JP);
Ken-Ichi Kasahara, Shizuoka (JP)

(73) Assignee: Asahi Kasei Pharma Corporation, Tokyo (JP)

( * ) Notice: Subject to any disclaimer, the term of this patent is extended or adjusted under 35 U.S.C. 154(b) by 959 days.

(21) Appl. No.: 10/590,458

(22) PCT Filed: Feb. 25, 2005

(86) PCT No.: PCT/JP2005/003686
§ 371 (c)(1),
(2), (4) Date: Aug. 24, 2006

(87) PCT Pub. No.: WO2005/082874
PCT Pub. Date: Sep. 9, 2005

(65) Prior Publication Data
US 2007/0190041 A1  Aug. 16, 2007

(30) Foreign Application Priority Data
Feb. 27, 2004 (JP) ................................ 2004-128992

(51) Int. Cl.
*A61P 1/16* (2006.01)
*A61P 3/04* (2006.01)
*A61P 3/06* (2006.01)
*A61P 9/10* (2006.01)
*A61K 31/22* (2006.01)
*A61K 31/366* (2006.01)
*A61K 31/38* (2006.01)
*A61K 31/381* (2006.01)
*A61K 31/395* (2006.01)
*A61K 31/4025* (2006.01)
*A61K 31/428* (2006.01)
*A61K 31/439* (2006.01)
*A61K 31/4995* (2006.01)
*A61K 31/5375* (2006.01)
*A61K 31/541* (2006.01)
*A61K 31/554* (2006.01)
*C07D 281/10* (2006.01)
*C07D 337/08* (2006.01)
*C07D 409/12* (2006.01)
*C07D 453/02* (2006.01)
*C07D 471/08* (2006.01)
*C07D 487/08* (2006.01)

(52) U.S. Cl. .......... 514/210.19; 514/217.03; 514/228.2; 514/232.5; 514/233.5; 514/249; 514/252.13; 514/297; 514/305; 514/307; 514/314; 514/316; 514/324; 514/333; 514/337; 514/414; 514/422; 514/431; 540/467; 540/596; 544/58.2; 544/62; 544/79; 544/145; 544/351; 544/376; 546/102; 546/134; 546/137; 546/139; 546/170; 546/175; 546/187; 546/202; 546/256; 546/279.7; 548/504; 548/525; 548/950; 549/9

(58) Field of Classification Search ............ 514/210.19, 514/217.03, 228.2, 232.5, 233.5, 249, 252.13, 514/297, 305, 307, 314, 316, 324, 333, 337, 514/414, 422, 431; 540/467, 596; 544/58.2, 544/62, 79, 145, 351, 376; 546/102, 134, 546/137, 139, 170, 175, 187, 202, 256, 279.7; 548/504, 525, 950; 549/9
See application file for complete search history.

(56) References Cited

U.S. PATENT DOCUMENTS

| 5,723,458 | A | 3/1998 | Brieaddy et al. |
| 5,817,652 | A | 10/1998 | Brieaddy et al. |
| 5,910,494 | A | 6/1999 | Brieaddy et al. |
| 6,277,831 | B1 | 8/2001 | Frick et al. |
| 7,312,208 | B2 | 12/2007 | Sasahara et al. |
| 2005/0032776 | A1 | 2/2005 | Starke et al. |

FOREIGN PATENT DOCUMENTS

| CA | 2 497 345 | 8/2003 |
| EP | 0 864 582 | 9/1998 |
| JP | 2002-519418 A | 7/2002 |
| JP | 2002-536440 A | 7/2002 |
| JP | 2002-533413 A | 10/2002 |
| JP | 2002-541248 A | 12/2002 |
| WO | WO 93/16055 | 8/1993 |

(Continued)

OTHER PUBLICATIONS

Canadian Official Action—Application No. 2,557,576, Nov. 27, 2008.

(Continued)

*Primary Examiner* — Brenda L Coleman
(74) *Attorney, Agent, or Firm* — Young & Thompson

(57) ABSTRACT

A pharmaceutical useful as a therapeutic agent and a preventive agent for hyperlipemia, and a pharmaceutical useful as a therapeutic agent and a preventive agent for hepatic disorders associated with cholestasis, particularly, primary biliary cirrhosis and primary sclerosing cholangitis, and a pharmaceutical useful as a therapeutic agent and a preventive agent for obesity, fatty liver and steatohepatitis are provided. A benzothiazepine or benzothiepine compound represented by the following formula (1A) having a thioamide bond and a quaternary ammonium substitutent:

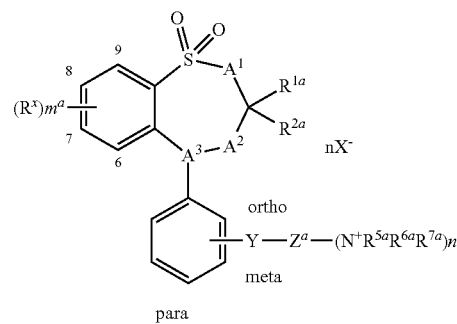

28 Claims, No Drawings

FOREIGN PATENT DOCUMENTS

| | | |
|---|---|---|
| WO | WO 97/33882 | 9/1997 |
| WO | WO 98/40375 | 9/1998 |
| WO | WO 99/32478 | 7/1999 |
| WO | WO 00/01687 | 1/2000 |
| WO | WO 00/47568 | 8/2000 |
| WO | 02/08211 A2 | 1/2002 |
| WO | 02/50051 A1 | 6/2002 |
| WO | WO 02/053548 | 7/2002 |
| WO | 2004/020421 A1 | 3/2004 |

OTHER PUBLICATIONS

U.S. Appl. No. 11/790,975, filed Apr. 30, 2007, Sasahara et al.

Telford D. E. et al., Inhibition of both the apical sodium-dependent bile acid transporter and HMG-CoA reductase markedly enhances the clearance of LDL apoB., J. Lipid. Rsd., 2003, vol. 44, No. 5, pp. 943 to 952.

Australian Patent Office issued an Australian Office Action dated Jun. 12, 2009, Application No. 2005217318.

BENZOTHIAZEPINE AND BENZOTHIEPINE COMPOUNDS

This application is a national stage entry under 35 U.S.C. §371 of PCT/JP05/03686, filed Feb. 25, 2005.

TECHNICAL FIELD

The present invention relates to a novel benzothiazepine or benzothiepine compound having a thioamide bond and a quaternary ammonium substitutent, and a pharmaceutical composition containing the same. The present invention also relates to a combined use and/or a medical mixture combination for simultaneously or separately administering the novel benzothiazepine or benzothiepine compound having a thioamide bond and a quaternary ammonium substitutent with another compound used for prevention and/or treatment of coronary artery diseases.

BACKGROUND ART

Hyperlipemia has been known to be a state in which levels of neutral fat and cholesterol in blood are higher than normal levels. Hyperlipemia is subjected to the treatment because it is a major risk factor of ischemic diseases. Hyperlipemia has been also known to cause arteriosclerosis. In particular, it is effective for the prevention and the treatment of arteriosclerosis to lower the level of cholesterol in the blood. The arteriosclerosis has been known to cause myocardial infarction, cerebral thrombosis, peripheral arterial obstruction and arteriosclerotic obliteration. Syndrome X has been proposed by Reaven et al. (e.g., see Non-patent Document 1 [Reaven et al., "Diabetes", 37:1595-1607, 1988]), and is a multiple risk factor syndrome in which the arteriosclerosis occurs by accumulating the multiple risk factors of hyperinsulinism, hyperlipemia, hypertension and impaired glucose tolerance in an individual body although each factor is not pathogenic when each factor is present independently. It has been believed that a cholesterol lowering agent is effective for the prevention or the treatment of these diseases (e.g., see Non-patent Document 2 ["Nippon Rinsho, Koshikessho Jo (Japanese Journal of Clinical Medicine, Hyperlipemia Volume 1)" ISSN 0047-1852]).

Examples of therapeutic agents for hyperlipemia which are currently commercially available may include 3-hydroxy-3-methylglutaryl coenzyme A (abbreviated hereinbelow as HMG-CoA) reductase inhibitors and bile acid absorbers (anion exchange resin drug). These are used particularly for the prevention or the treatment of hypercholesterolemia and arteriosclerosis in hyperlipemia. These are further used for the prevention or the treatment of myocardial infarction, cerebral thrombosis, peripheral arterial obstruction and arteriosclerotic obliteration caused by hypercholesterolemia and arteriosclerosis.

Other therapeutic agents for hyperlipemia may include anti-oxidants, nicotinic acid derivatives and cholesterol absorption inhibitors. Fibrate drugs which act upon α-receptor of peroxisome proliferator-activated receptors (abbreviated hereinbelow as PPAR) are also included in this category because they have neutral fat lowering and cholesterol lowering effects.

The HMG-CoA reductase inhibitors, which are generally referred to as statins, inhibit a cholesterol synthesis pathway and exhibit the strong cholesterol lowering effect, but rarely cause a severe side effect such as rhabdomyolysis and also cause myopathy and hepatic disorders in some cases. Thus, statins are generally used below the excessive amount.

Therefore, when the use of statin alone can not lower the level of cholesterol sufficiently, co-administration with another therapeutic agent for hyperlipemia having a different action mechanism is considered for lowering cholesterol to a target level. However, when considering the combination with the fibrate drug for an example, the fibrate drug itself also causes rhabdomyolysis in some cases. Thus, the therapy by this combination is not usually used because of the higher risk of rhabdomyolysis.

The combination of the statin drugs and the anion exchange resin drug augments the cholesterol lowering effect compared with the use of statin alone. Thus, when the use of statin alone does not lower to the target level, this combination can be used. However, it is necessary to take the bile acid absorber in a large amount in order to obtain a commeasurable drug effect. Thus, the bile acid absorber has difficulty upon taking and largely affects gastrointestinal tract to cause constipation. In addition, the anion exchange resin drug also absorbs vitamins A, D, E and K or simultaneously administered anionic drugs. Considering these effects, the combination of the HMG-CoA reductase inhibitor with the bile acid absorber such as anion exchange resin drug is not the best mode of the treatment which patients should receive.

The combination of the cholesterol absorption inhibitor with the HMG-CoA reductase inhibitor is effective. However, the cholesterol absorption inhibitor is also incorporated in the body and metabolized in liver. Thus the cholesterol absorption inhibitor can not be administered to a patient having a disease in liver. The combination of the cholesterol absorption inhibitor with the fibrate drugs is not usually used because a drug interaction is concerned.

Additional examples of drugs capable of treating hyperlipemia may include a cholesterol ester transfer protein (abbreviated hereinbelow as CETP) inhibitor, nicotinic acid and derivatives thereof, an acylcoenzyme A: cholesterol acetyltransferase (abbreviated hereinbelow as ACAT) inhibitor and a microsomal transfer protein (abbreviated hereinbelow as MTP) inhibitor. They are commonly absorbed in the body to exert medicinal effects, and thus the drug interaction is likely to occur when combined with the other cholesterol lowering drug such as HMG-CoA reductase inhibitor.

It is generally effective in the treatment to combine the drugs each having different action mechanisms for exerting the effect over a certain level. However, when each drug is absorbed to plasma proteins or when a drug metabolism process is shared by the combined drugs, the risk of side effect occurrence becomes high because of more rapid increase of drug concentrations in blood and larger effect on tissues than those which occur with the use of a single drug. In addition, in the case of the patient having a plurality of risk factors for the coronary artery disease, a plurality of drugs are often prescribed for coping with respective risk factors. For example, in the cases of the combination of hyperlipemia and hypertension and the combination of hyperlipemia and diabetes, the therapeutic drug for hyperlipemia is combined with the therapeutic drug for another disease. At that time, the interaction between the drugs must be sufficiently considered.

DISCLOSURE OF INVENTION

An object of the present invention is to provide a useful compound as a therapeutic and/or preventive agent for hyperlipemia. A further object of the present invention is to provide a combination of the compound of the present invention with another drug. In particular, the present invention provides a combination of pharmaceuticals which safely exhibits an augmented effect of the combination without interaction with other drugs.

In order to solve the aforementioned problems, the present inventors synthesized various compounds and analyzed their activities. As a result, it has been found out that a novel benzothiazepine compound or benzothiepine compound represented by the following formula (1A), (1B) or (1C) having a thioamide bond and a quaternary ammonium substituent has a high therapeutic and preventive effect on the treatment of hyperlipemia. Furthermore, it has also been found out that the compound has an extremely potent inhibitory activity for ileal bile acid transporter and a blood cholesterol lowering effect, and that the compound can be used as a cholesterol lowering agent, particularly, as a therapeutic and preventive agent for hyperlipemia, arteriosclerosis and syndrome X. In addition, it has been found out that the compound has a therapeutic and preventive effect on hepatic disorder associated with cholestasis, and can be used as the therapeutic agent and the preventive agent for hepatic disorder associated with cholestasis, particularly primary biliary cirrhosis and primary sclerosing cholangitis. Further it has been found out that the compound has a body weight decreasing effect and the therapeutic effect on fatty liver and can be used as a therapeutic and preventive agent for obesity and the fatty liver. Further, it has been found out that the compound has the therapeutic and preventive effect on steatohepatitis and can be used as a therapeutic and preventive agent for the steatohepatitis. Additionally, it has been found out that compared with the use of a single drug, the therapeutic effect on hyperlipemia is further augmented by combining the compound represented by the following formula (1A), (1B) or (1C) with another compound which is an active component of the therapeutic and/or preventive agent for the coronary artery diseases.

That is, the present invention relates to:
(1) A compound represented by the following formula:

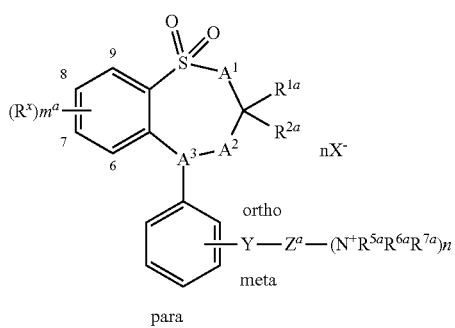

(1A)

wherein $R^{1a}$ and $R^{2a}$ may be the same as or different from each other, and each represents alkyl group having 1 to 10 carbon atoms, alkenyl group having 2 to 10 carbon atoms or alkynyl group having 2 to 10 carbon atoms;

$m^a$ is an integer of 0 to 4;

—$R^x$ represents halogen atom, nitro group, amino group, cyano group, hydroxy group, carboxy group, —$CONH_2$, —$SO_3H$, —$NR^3R^4$ ($R^3$ and $R^4$ may be the same as or different from each other, and each represents alkyl group having 1 to 5 carbon atoms), alkyl group having 1 to 10 carbon atoms, alkenyl group having 2 to 10 carbon atoms or alkynyl group having 2 to 10 carbon atoms; wherein the alkyl group, the alkenyl group and the alkynyl group may be substituted with one or more groups of phenyl, naphthyl, pyridyl, quinolyl, thienyl, furyl, piperidyl, pyrrolidyl, morpholyl, cycloalkyl having 3 to 7 carbon atoms, cyano, nitro, hydroxy, oxo, thioxo, carboxy, —$CONH_2$ and —$SO_3H$; one or more methylenes which constitute the alkyl group, the alkenyl group and the alkynyl group may be replaced with any of phenylene, thienylene, furylene, cyclohexylene, cyclopentylene, —O—, —S—, —$CO_2$—, —NHCO—, —$NR^{8a}$—, and —$N^+W^{a-}R^{9a}R^{10a}$— ($R^{8a}$ represents alkyl group having 1 to 5 carbon atoms or alkenyl group having 2 to 5 carbon atoms; the alkyl group and the alkenyl group in $R^{8a}$ may be substituted with one or more groups of phenyl, cycloalkyl having 3 to 7 carbon atoms and hydroxy. $R^{9a}$ and $R^{10a}$ may be the same as or different from each other, and each represents alkyl group having 1 to 5 carbon atoms or alkenyl group having 2 to 5 carbon atoms, and may be substituted with one or more groups of phenyl, cycloalkyl having 3 to 7 carbon atoms and hydroxy. $W^{a-}$ represents counteranion.);

the combination of ($A^1$, $A^2$, $A^3$) represents ($CH_2$, NH, CH), ($CH_2$, CH(OH), CH), (NH, CH(OH), CH) or ($CH_2$, $CH_2$, N);

Y represents any of —NHCS—, —NHCSNH— or —NHCSO—, wherein —NH of —NHCS— represents a bond which binds to the adjacent benzene ring and CS— represents a bond which binds to the adjacent $Z^a$, and —NH of —NHCSO— represents a bond which binds to the adjacent benzene ring and CSO— represents a bond which binds to the adjacent $Z^a$;

$Z^a$—$(N^+R^{5a}R^{6a}R^{7a})_n$ represents alkyl group or alkenyl group having 2 to 10 carbon atoms which is substituted with —$N^+R^{5a}R^{6a}R^{7a}$, the number of the substituent being n; wherein one or more methylenes which constitute $Z^a$ may be replaced with any of phenylene which may have a substitutent or —O—; wherein the substitutent(s) in the phenylene which may have the substituent are 1 to 4 substitutents selected from the group consisting of alkyl groups having 1 to 5 carbon atoms, alkoxy groups having 1 to 5 carbon atoms, nitro group, halogen atom, trifluoromethyl group and —$CH_2N^+R^{5a}R^{6a}R^{7a}$; wherein the substitutents may be the same as or different from each other; and wherein n is an integer of 1 or 2; and each of $N^+R^{5a}R^{6a}R^{7a}$ is independently any of the following I), II) or III):

I) $R^{5a}$, $R^{6a}$ and $R^{7a}$ may be the same as or different from one another, and each represents alkyl group having 1 to 10 carbon atoms, alkenyl group having 2 to 10 carbon atoms or alkynyl group having 2 to 10 carbon atoms; wherein the alkyl group, the alkenyl group and the alkynyl group may be substituted with one or more groups of phenyl, naphthyl, pyridyl, quinolyl, thienyl, furyl, piperidyl, pyrrolidyl, morpholyl, cycloalkyl having 3 to 7 carbon atoms, cyano, nitro, hydroxy, oxo, thioxo, carboxy, —$CONH_2$ and —$SO_3H$; and wherein one or more methylenes which constitute the alkyl group, the alkenyl group and the alkynyl group may be replaced with any of phenylene, thienylene, furylene, cyclohexylene, cyclopentylene, —O—, —S—, —$CO_2$—, —NHCO—, —$NR^8$—, and —$N^+W^-R^9R^{10}$— ($R^8$ represents alkyl group having 1 to 5 carbon atoms or alkenyl group having 2 to 5 carbon atoms. The alkyl group and the alkenyl group in $R^8$ may be substituted with one or more groups of phenyl, cycloalkyl having 3 to 7 carbon atoms and hydroxy. $R^9$ and $R^{10}$ may be the same as or different from each other, and each represents alkyl group having 1 to 5 carbon atoms or alkenyl group having 2 to 5 carbon atoms, and may be substituted with one or more groups of phenyl, cycloalkyl having 3 to 7 carbon atoms and hydroxy. $W^-$ represents counteranion.);

II) $N^+R^{5a}R^{6a}R^{7a}$ represents a monocyclo or bicyclo ring formed of 4 to 9 carbon atoms in addition to the ammonium nitrogen atom, with a proviso that a position of binding to $Z^a$ is the ammonium nitrogen atom; wherein, in the monocyclo and bicyclo rings, one of the carbon atoms which constitutes the ring may be replaced with any of oxygen, nitrogen or sulfur atom; and the monocyclo and bicyclo rings may be substituted with one or more groups of hydroxy, oxo, thioxo, cyano, phenyl, naphthyl, thienyl, pyridyl, cycloalkyl having 3 to 7 carbon atoms, carboxy, —$CONH_2$, —$SO_3H$ and —$R^{11}$ ($R^{11}$ represents alkyl group having 1 to 8 carbon atoms or alkenyl group having 2 to 8 carbon atoms. The alkyl group and the alkenyl group in $R^{11}$ may be substituted with one or more groups of phenyl, naphthyl, pyridyl, quinolyl, thienyl, furyl, piperidyl, pyrrolidyl, morpholyl, cycloalkyl having 3 to 7 carbon atoms, cyano, nitro, hydroxy, oxo, thioxo, carboxy, —$CONH_2$ and —$SO_3H$; and one or more methylenes which constitute the alkyl group and the alkenyl group may be replaced with any of phenylene, thienylene, furylene, cyclohexylene, cyclopentylene, —O—, —S—, —$CO_2$—, —NHCO—, —$NR^8$—, and —$N^+W^-R^9R^{10}$—; $R^8$, $R^9$, $R^{10}$ and $W^-$ are the same as the above); and the group which is not involved in the formation of the monocyclo ring and the bicyclo ring in $R^{5a}$, $R^{6a}$ and $R^{7a}$ is the same as the above I); and III) $N^+R^{5a}R^{6a}R^{7a}$ represents a pyridinium ring, a quinolinium ring or an isoquinolinium ring, with a proviso that a position of binding to $Z^a$ is the ammonium nitrogen atom; wherein the pyridinium ring, the quinolinium ring and the isoquinolinium ring may be substituted with one or more groups of cyano, nitro, phenyl, naphthyl, thienyl, pyridyl, cycloalkyl having 3 to 7 carbon atoms, alkoxy having 1 to 5 carbon atoms, carboxy, —$CONH_2$, —$SO_3H$, halogen, hydroxy, tetrahydropyranyl and —$R^{12a}$ ($R^{12a}$ represents alkyl group having 1 to 9 carbon atoms or alkenyl group having 2 to 9 carbon atoms. The alkyl group and the alkenyl group in $R^{12a}$ may be substituted with one or more groups of phenyl, naphthyl, pyridyl, quinolyl, thienyl, furyl, cycloalkyl having 3 to 7 carbon atoms, cyano, nitro, hydroxy, oxo, thioxo, carboxy, —$CONH_2$ and —$SO_3H$; and one or more methylenes which constitute the alkyl group and the alkenyl group may be replaced with any of phenylene, thienylene, furylene, cyclohexylene, cyclopentylene, —S—, —O—, —$CO_2$—, —NHCO—, —$NR^8$— and —$N^+W^-R^9R^{10}$—; $R^8$, $R^9$, $R^{10}$ and $W^-$ are the same as the above); and $X^-$ represent counteranion.

(2) a compound represented by the following formula (1B):

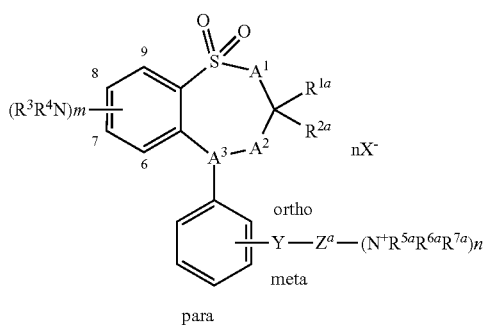

(1B)

wherein $R^1$ and $R^2$ may be the same as or different from each other, and each represents alkyl group having 1 to 10 carbon atoms; m is an integer of 1 or 2; and $R^3$, $R^4$, $A^1$, $A^2$, $A^3$, y, $Z^a$—$(N^+R^{5a}R^{6a}R^{7a})$, n and $X^-$ are the same as the above.

(3) the compound according to (2) above, represented by the above formula (1B), wherein:

when the combination of ($A^1$, $A^2$, $A^3$) is ($CH_2$, NH, CH), one or more methylenes which constitute $Z^a$ must be replaced with a phenylene group having a substitutent; the substitutent(s) in the phenylene group having the substitutent are 1 to 4 substitutents selected from the group consisting of alkyl having 1 to 5 carbon atoms, alkoxy having 1 to 5 carbon atoms, nitro group, halogen atom, trifluoromethyl group and —$CH_2N^+R^{5a}R^{6a}R^{7a}$, and the substitutents may be the same as or different from one another.

(4) the compound according to (3) above wherein $Z^a$—($N^+R^{5a}R^{6a}R^{7a}$)$_n$ represents alkyl group having 2 to 10 carbon atoms substituted with one —$N^+R^{5a}R^{6a}R^{7a}$; $Z^a$ represents a straight methylene chain having 2 to 10 carbon atoms, or a straight methylene chain having 2 to 10 carbon atoms in which one methylene is replaced with phenylene which may have a substitutent, or a straight methylene chain having 2 to 10 carbon atoms in which one methylene is replaced with —O—, or a straight methylene chain having 2 to 10 carbon atoms in which one methylene is replaced with phenylene which may have a substitutent and another methylene is replaced with —O—; and Y represents —NHCS— or —NHCSNH— at para-position or meta-position.

(5) the compound according to (4) above wherein the combination of ($A^1$, $A^2$, $A^3$) represents ($CH_2$, CH(OH), CH), Y represents —NHCSNH— at meta position, and $Z^a$ represents the following formula (sp-14):

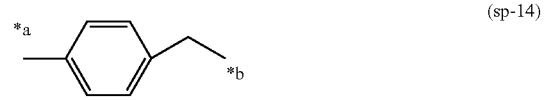

(sp-14)

wherein *a binds to Y and *b binds to $N^+R^{5a}R^{6a}R^{7a}$ in the formula (1B).

(6) the compound according to (4) above wherein the combination of ($A^1$, $A^2$, $A^3$) represents ($CH_2$, NH, CH), Y represents —NHCSNH— at meta position, and $Z^a$ represents any of the following formulae:

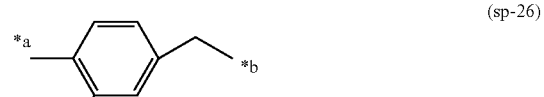

(sp-26)

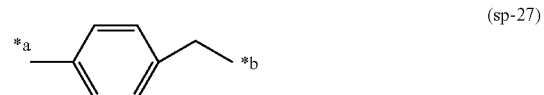

(sp-27)

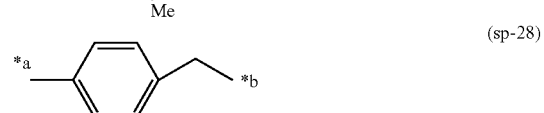

(sp-28)

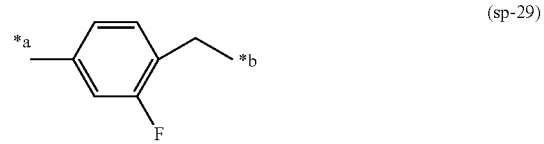

(sp-29)

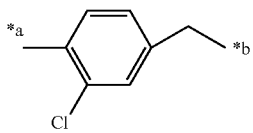
(sp-30)

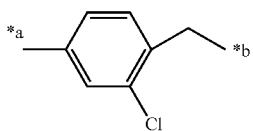
(sp-31)

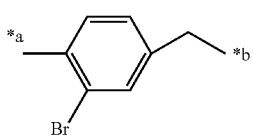
(sp-32)

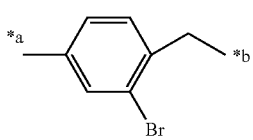
(sp-33)

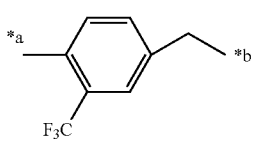
(sp-34)

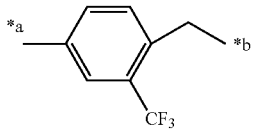
(sp-35)

wherein *a binds to Y and *b binds to $N^+R^{5a}R^{6a}R^{7a}$ in the formula (1B).

(7) the compound according to (5) or (6) above wherein $R^1$ and $R^2$ may be the same as or different from each other, and each represents straight alkyl groups having 2 to 6 carbon atoms, and $(R^3R^4N)_m$ represents any of dimethylamino group substituted at position 7, diethylamino group substituted at position 7, ethylmethylamino group substituted at position 7, dimethylamino group substituted at position 9 and dimethylamino groups substituted at two positions 7 and 9.

(8) the compound according to (7) above wherein $(R^3R^4N)_m$ represents any of dimethylamino group substituted at position 7, diethylamino group substituted at position 7 or ethylmethylamino group substituted at position 7, and $N^+R^{5a}R^{6a}R^{7a}$ represents any of 4-t-butylpyridinium group, 3-(3-hydroxypropyl)-pyridinium group, 3-[2-(methoxycarbonyl)ethyl]-pyridinium group, 2-(n-propyl)-pyridinium group, 4-phenylquinuclidinium group or 1,4-diazabicyclo[2.2.2]octanium group.

(9) a pharmaceutical composition containing as an active component a compound represented by the following formula (1):

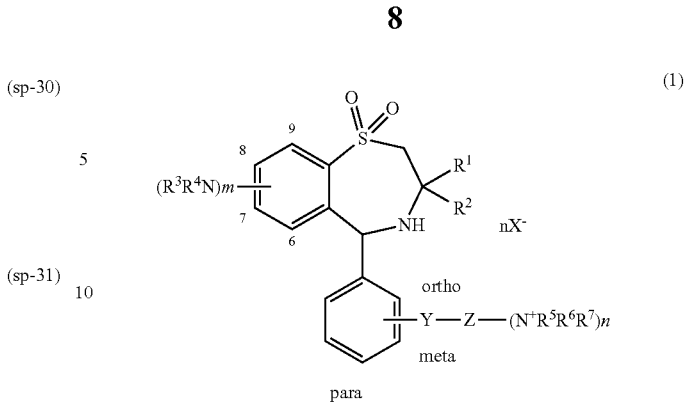

wherein $R^1$, $R^2$, $R^3$, $R^4$, m, n and $X^-$ are the same as the above;

Y represents any of —NHCS—, —NHCSNH— or —NHCSO—, wherein —NH of —NHCS— represents a bond of binding to the adjacent benzene ring and CS— represents a bond of binding to the adjacent Z, and —NH of —NHCSO— represents a bond of binding to the adjacent benzene ring and CSO— represents a bond of binding to the adjacent Z;

Z—$(N^+R^{5a}R^{6a}R^{7a})_n$ represents alkyl or alkenyl having 2 to carbon atoms which is substituted with —$N^+R^{5a}R^{6a}R^{7a}$, the number of the substitutent being n, and one or more methylenes which constitute Z may be replaced with any of phenylene or —O—; and each of $N^+R^{5a}R^{6a}R^{7a}$ is independently any of the following I), II) or III):

I) $R^5$, $R^6$ and $R^7$ may be the same as or different from one another, and each represents alkyl group having 1 to 10 carbon atoms, alkenyl group having 2 to 10 carbon atoms or alkynyl group having 2 to 10 carbon atoms; wherein the alkyl group, the alkenyl group and the alkynyl group may be substituted with one or more groups of phenyl, naphthyl, pyridyl, quinolyl, thienyl, furyl, piperidyl, pyrrolidyl, morpholyl, cycloalkyl having 3 to 7 carbon atoms, cyano, nitro, hydroxy, oxo, thioxo, carboxy, —$CONH_2$ and —$SO_3H$; and wherein one or more methylenes which constitute the alkyl group, the alkenyl group and the alkynyl group may be replaced with any of phenylene, thienylene, furylene, cyclohexylene, cyclopentylene, —O—, —S—, —$CO_2$—, —NHCO—, —$NR^8$—, and —$N^+W^-R^9R^{10}$—; and $R^8$, $R^9$, $R^{10}$ and $W^-$ are the same as the above;

II) $N^+R^5R^6R^7$ represents a monocyclo or bicyclo ring formed of 4 to 9 carbon atoms in addition to the ammonium nitrogen atom, with a proviso that a position of binding to Z is the ammonium nitrogen atom; wherein, in the monocyclo and bicyclo rings, one of the carbon atoms which constitutes the ring may be replaced with any of oxygen, nitrogen or sulfur atom; and the monocyclo and bicyclo rings may be substituted with one or more groups of hydroxy, oxo, thioxo, cyano, phenyl, naphthyl, thienyl, pyridyl, cycloalkyl having 3 to 7 carbon atoms, carboxy, —$CONH_2$, —$SO_3H$ and —$R^{11}$ ($R^{11}$ is the same as the above); and the group which is not involved in the formation of the monocyclo ring and the bicyclo ring in $R^5$, $R^6$ and $R^7$ is the same as the above I); and III) $N^+R^5R^6R^7$ represents a pyridinium ring, a quinolinium ring or an isoquinolinium ring, with a proviso that a position of binding to Z is the ammonium nitrogen atom; wherein the pyridinium ring, the quinolinium ring and the isoquinolinium ring may be substituted with one or more groups of cyano, nitro, phenyl, naphthyl, thienyl, pyridyl, cycloalkyl having 3 to 7 carbon atoms, alkoxy having 1 to 5 carbon atoms, carboxy, —$CONH_2$, —$SO_3H$, and —$R^{12}$ ($R^{12}$ represents alkyl group having 1 to 9 carbon atoms or alkenyl group having 2 to 9 carbon atoms. The alkyl group and the alkenyl group in $R^{12}$ may be substituted with one or more groups of phenyl, naphthyl, pyridyl, quinolyl, thienyl, furyl, cycloalkyl having 3 to 7 carbon atoms, cyano, nitro, hydroxy, oxo, thioxo, carboxy, —$CONH_2$ and —$SO_3H$; and one or more methylenes which constitute the alkyl group and the alkenyl group may be replaced with any of phenylene, thienylene, furylene, cyclohexylene, cyclopentylene, —S—, —$CO_2$—, —NHCO—, —$NR^8$—, and —$N^+W^-R^9R^{10}$—; and $R^8$, $R^9$, $R^{10}$ and $W^-$ are the same as the above).

(10) a pharmaceutical composition containing the compound according to any of (1) to (8) above as an active component.

(11) the pharmaceutical composition according to (9) or (10) above wherein the pharmaceutical composition is a cholesterol lowering agent.

(12) the pharmaceutical composition according to (11) above wherein the pharmaceutical composition is a therapeutic agent or a preventive agent for any of hyperlipemia, arteriosclerosis or syndrome X.

(13) a pharmaceutical comprising a combination of the pharmaceutical composition according to any of (9) to (12) above with another therapeutic agent or preventive agent for coronary artery diseases.

(14) a pharmaceutical comprising a combination of the pharmaceutical composition according to any of (9) to (12) above with another cholesterol lowering agent.

(15) the pharmaceutical according to (14) above wherein another cholesterol lowering agent is one or more selected from an HMG-CoA reductase inhibitor, a fibrate drug, a cholesterol absorption inhibitor, a bile acid absorber, probucol, AGI-1067, nicotinic acid and derivatives thereof, an MTP inhibitor, an ACAT inhibitor, a CETP inhibitor, a squalene synthase inhibitor, a peroxisome proliferator-activated receptor (abbreviated hereinbelow as PPAR) agent and phytosterol.

(16) the pharmaceutical according to (15) above wherein the selected cholesterol lowering agent is the HMG-CoA reductase inhibitor.

(17) the pharmaceutical according to (16) above wherein the HMG-CoA reductase inhibitor is selected from the group consisting of pravastatin, simvastatin, fluvastatin, lovastatin, atorvastatin, rosuvastatin and pitavastatin.

(18) the pharmaceutical according to (15) above wherein both the HMG-CoA reductase inhibitor and the cholesterol absorption inhibitor are selected as the cholesterol lowering agents.

(19) the pharmaceutical according to (18) above wherein the HMG-CoA reductase inhibitor is selected from the group consisting of pravastatin, simvastatin, fluvastatin, lovastatin, atorvastatin, rosuvastatin and pitavastatin, and the cholesterol absorption inhibitor is ezetimibe.

The compound of the present invention in which the thioamide bond and the quaternary ammonium substituent have been introduced is a novel compound which exhibits potent inhibitory activity for ileal bile acid transporter, has a stability against in vivo metabolism, and has a low toxicity against the gastrointestinal tract, when compared with publicly known compounds having a benzothiazepine or benzothiepine skeleton. According to the above Test Example, it has been confirmed that the present compound is useful as the cholesterol lowering agent, and is useful as the pharmaceutical composition for the treatment and the prevention of, e.g., hyperlipemia, arteriosclerosis and syndrome X. It is also confirmed that the present compound is useful for ameliorating the hepatic disorder associated with cholestasis, and is useful as the pharmaceutical composition for the treatment and the prevention of the hepatic disorder associated with cholestasis, e.g., primary biliary cirrhosis or primary sclerosing cholangitis. Furthermore, it has been confirmed that the compound is useful as the pharmaceutical composition for the treatment and the prevention of obesity and fatty liver. In addition, it has been confirmed that the compound is useful as the pharmaceutical composition for the treatment and the prevention of steatohepatitis.

The compound of the present invention also has an activity to improve hyperlipemia and a high safety upon administration, as well as a low in vivo absorbability. Thus, it has been confirmed that not only the present compound can be used alone, but also can be used in combination with another preventive agent or therapeutic agent where the safety has been particularly concerned when combined with the conventional drugs. It is also confirmed that the amount of the combined drug can be reduced. In addition, even when the patient having a risk factor of the coronary artery disease, particularly hyperlipemia as the factor, has another complication, it is possible to treat hyperlipemia simultaneously with using the therapeutic agent for the complication because of the extremely low risk for drug interaction of the compound of the present invention.

BEST MODES FOR CARRYING OUT THE INVENTION

Each substituent in the compound represented by the formula (1A) will be described hereinbelow.

$R^{1a}$ and $R^{2a}$ may be the same as or different from each other, and each represents alkyl group having 1 to 10 carbon atoms, alkenyl group having 2 to 10 carbon atoms or alkenyl group having 2 to 10 carbon atoms. Among them, the alkyl groups having 1 to 10 carbon atoms (straight or branched alkyl groups having 1 to 10 carbon atoms) are preferable, the straight alkyl groups having 1 to 10 carbon atoms are more preferable, and the straight alkyl groups having 2 to 6 carbon atoms are particularly preferable.

Although it may be preferable even if $R^{1a}$ and $R^{2a}$ are different from each other, it is more preferable that $R^{1a}$ and $R^{2a}$ are the same alkyl group. Specific preferable embodiments of $R^{1a}$ and $R^{2a}$ may include that both $R^{1a}$ and $R^{2a}$ are n-propyl, n-butyl, n-pentyl or n-hexyl, or that $R^{1a}$ is ethyl and $R^{2a}$ is n-butyl.

$(R^x)m^a$ means that any of positions 6 to 9 is substituted with $R^x$, wherein the number of substituent $R^x$ is $m^a$. $m^a$ is an integer of 0 to 4, preferably 1 or 2 and more preferably 1. The substituted position is preferably the position 7 or 9 and more preferably the position 7 when ma is 1. When ma is 2, it is preferable that 2 positions of positions 7 and 9 are substituted with the same $R^x$.

$R^x$ represents halogen atom, nitro group, amino group, cyano group, hydroxy group, carboxy group, —$CONH_2$, —$SO_3H$, —$NR^3R^4$, alkyl group having 1 to 10 carbon atoms, alkenyl group having 2 to 10 carbon atoms or alkynyl group having 2 to 10 carbon atoms. The alkyl group, the alkenyl group and the alkynyl group may be substituted with one or more groups of phenyl, naphthyl, pyridyl, quinolyl, thienyl, furyl, piperidyl, pyrrolidyl, morpholyl, cycloalkyl having 3 to 7 carbon atoms, cyano, nitro, hydroxy, oxo, thioxo, carboxy, —$CONH_2$ and —$SO_3H$; and one or more methylenes which constitute the alkyl group, the alkenyl group and the alkynyl group may be replaced with any of phenylene, thienylene, furylene, cyclohexylene, cyclopentylene, —O—, —S—, —$CO_2$—, —NHCO—, —$NR^{8a}$—, and —$N^+W^{a-}R^{9a}R^{10a}$—. $R^{8a}$ represents alkyl group having 1 to 5 carbon atoms or alkenyl group having 2 to 5 carbon atoms. The alkyl group and the alkenyl group in $R^{8a}$ may be substituted with one or more groups of phenyl, cycloalkyl having 3 to 7 carbon atoms and hydroxy. $R^{9a}$ and $R^{10a}$ may be the same as or different from each other, and each represents alkyl group having 1 to 5 carbon atoms or alkenyl group having 2 to 5 carbon atoms, and may be substituted with one or more groups of phenyl, cycloalkyl having 3 to 7 carbon atoms and hydroxy.

$R^x$ is preferably —$NR^3R^4$. $R^3$ and $R^4$ may be the same as or different from each other, and each represents straight or branched alkyl group having 1 to 5 carbon atoms. Among them, the straight alkyl groups having 1 to 3 carbon atoms are preferable, methyl or ethyl is more preferable, and methyl is the most preferable.

Specific preferable embodiments of $(R^x)m^a$ may include 7-dimethylamino, 7-diethylamino, 7-ethylmethylamino, 9-dimethylamino or 7,9-bis(dimethylamino).

The compound in which $R^{1a}$ and $R^{2a}$ are alkyl groups having 1 to 10 carbon atoms and $(R^x)m^a$ is $(R^3R^4N)_m$ in the formula (1A) corresponds to the formula (1B). $A^1, A^2, A^3, Y, Z^a, n, R^{5a}, R^{6a}, R^{7a}$ and $X^-$ are common in the formulae (1A) and (1B). These will be described below as substitutents in the compound represented by the formula (1B).

$R^1$ and $R^2$ may be the same as or different from each other, and each represents straight or branched alkyl group having 1 to 10 carbon atoms. Among them, the straight alkyl group having 1 to 10 carbon atoms is preferable, and the straight alkyl group having 2 to 6 carbon atoms is more preferable. Although it may be preferable even if $R^1$ and $R^2$ are different from each other, it is more preferable that $R^1$ and $R^2$ are the same alkyl group. Specific preferable embodiments of $R^1$ and $R^2$ may include that both $R^1$ and $R^2$ are n-propyl, n-butyl, n-pentyl or n-hexyl, or that $R^1$ is ethyl and $R^2$ is n-butyl.

$(R^3R^4N)_m$ means that any of positions 6 to 9 is substituted with —$R^3R^4N$, wherein the number of the substitutent —$R^3R^4N$ is m. m is an integer of 1 or 2. Any of 1 or 2 is preferable, and 1 is more preferable. The substituted position is preferably the position 7 or 9 and more preferably the position 7 when m is 1. When m is 2, it is preferable that 2 positions 7 and 9 are substituted with the same —$R^3R^4N$. $R^3$ and $R^4$ may be the same as or different from each other, and each represents straight or branched alkyl group having 1 to 5 carbon atoms. Among them, the straight alkyl groups having 1 to 3 carbon atoms are preferable, methyl or ethyl is more preferable, and methyl is the most preferable. Specific preferable embodiments of $(R^3R^4N)_m$ may include 7-dimethylamino, 7-diethylamino, 7-ethylmethylamino, 9-dimethylamino or 7,9-bis(dimethylamino).

The combination of $(A^1, A^2, A^3)$ represents $(CH_2, NH, CH)$, $(CH_2, CH(OH), CH)$, $(NH, CH(OH), CH)$ or $(CH_2, CH_2, N)$. The preferable combination of $(A^1, A^2, A^3)$ is $(CH_2, NH, CH)$, $(CH_2, CH(OH), CH)$ or $(NH, CH(OH), CH)$. The more preferable combination of $(A^1, A^2, A^3)$ is $(CH_2, NH, CH)$ or $(CH_2, CH(OH), CH)$. The most preferable combination of $(A^1, A^2, A^3)$ is $(CH_2, CH(OH), CH)$.

Y represents any of —NHCS—, —NHCSNH— or —NHCSO—, wherein —NH of —NHCS— represents a bond which binds to the adjacent benzene ring and CS— represents a bond which binds to the adjacent $Z^a$, and —NH of —NHCSO— represents a bond which binds to the adjacent benzene ring and CSO— represents a bond which binds to the adjacent $Z^a$. Among them, Y is preferably —NHCS— or —NHCSNH—, and particularly preferably —NHCSNH—. The substituted position on the benzene ring is any one of ortho, meta and para positions, preferably meta or para position, and most preferably meta position.

$Z^a$—$(N^+R^{5a}R^{6a}R^{7a})_n$ represents alkyl group or alkenyl group having 2 to 10 carbon atoms, which has been substituted with —$N^+R^{5a}R^{6a}R^{7a}$, wherein the number of the substitutent —$N^+R^{5a}R^{6a}R^{7a}$ is n. Further, one or more methylenes which constitute $Z^a$ may be replaced with any of phenylene which may have a substitutent or —O—. n is an integer of 1 or 2. Any of 1 or 2 is preferable, 1 is more preferable.

Among alkyl group or alkenyl group having 2 to 10 carbon atoms which is substituted with —$N^+R^{5a}R^{6a}R^{7a}$ (the number of the substitutent being n), the straight or branched alkyl group having 2 to 10 carbon atoms is preferable, and the straight alkyl group having 2 to 10 carbon atoms or the branched alkyl group having 3 to 7 carbon atoms is more preferable. When substituted with one —$N^+R^{5a}R^{6a}R^{7a}$, any of the straight alkyl group having 2 to 10 carbon atoms or the branched alkyl group having 3 to 7 carbon atoms is preferable, and the straight alkyl group having 2 to 10 carbon atoms is more preferable. When substituted with two —$N^+R^{5a}R^{6a}R^{7a}$, the branched alkyl group having 3 to 7 carbon atoms is preferable. In the case of the straight alkyl group having 2 to 10 carbon atoms substituted with one —$N^+R^{5a}R^{6a}R^{7a}$, it is particularly preferable that $Z^a$ represents a straight methylene chain having 2 to 10 carbon atoms.

Although it may be preferable even if one or more methylenes which constitute the $Z^a$ are replaced with any of phenylene which may have a substitutent or —O—, no replacement is more preferable when Y is —NHCS—. When Y is —NHCSNH—, it is more preferable that methylene is replaced with phenylene which may have a substitutent, and in that case, the preferable embodiment of $Z^a$ is as described above.

When one or more methylenes which constitute $Z^a$ are replaced with any of phenylene which may have a substitutent or —O—, the straight alkyl group having 2 to 10 carbon atoms substituted with one —$N^+R^{5a}R^{6a}R^{7a}$ is preferable, and it is particularly preferable that $Z^a$ represents the straight methylene chain having 2 to 10 carbon atoms. As a manner of replacement, it is preferable that one methylene is replaced with phenylene which may have a substitutent, or one methylene is replaced with —O—, or one methylene is replaced with phenylene which may have a substitutent and another methylene is replaced with —O—. It is more preferable that one methylene is replaced with phenylene which may have a substitutent. Note that the replaced —O— for methylene discussed herein is different from an oxygen atom in —NHCSO— which represents Y. When methylene which constitutes $Z^a$ is replaced with phenylene which may have a substitutent, it is preferable that the phenylene is not substituted, and it is also preferable that the phenylene is substituted with one to four of alkyl having 1 to 5 carbon atoms, alkoxy having 1 to 5 carbon atoms, nitro, halogen, trifluoromethyl, and $CH_2N^+R^{5a}R^{6a}R^{7a}$. It is more preferable that the phenylene is substituted with any one of methyl, trifluoromethyl, —F, —Cl and —Br. Unsubstituted phenylene is any of the following formula (phe-1), (phe-2) or (phe-3), preferably (phe-1) or (phe-2), and more preferably (phe-1). When the phenylene is substituted, it is preferable that the phenylene is substituted with any of one methyl, two methyls, one —F, one —Cl, one —Br, one trifluoromethyl, one nitro, one methoxy, or a combination of one methyl and one nitro. It is more preferable that the phenylene is substituted with any of one methyl, one —F, one —Cl, one —Br or one trifluoromethyl.

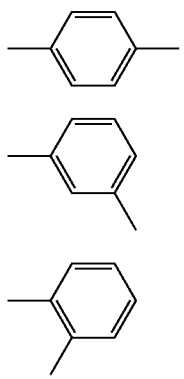
(phe-1)
(phe-2)
(phe-3)

"Replacement of one or more methylenes with phenylene or —O—" means replacement exemplified as follows.

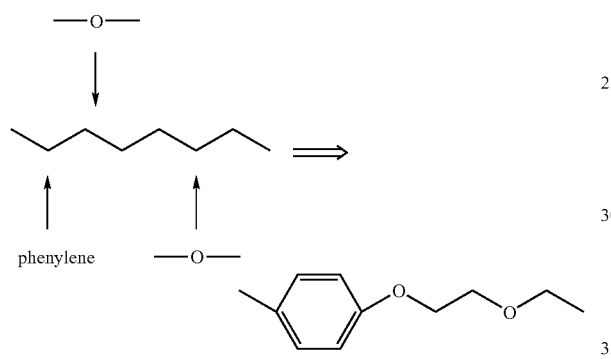

Specific preferable embodiments of $Z^a$ may include the following formulae, (sp-1) to (sp-25) or (sp-26) to (sp-44). In the formulae, *a binds to Y and *b binds to $N^+R^{5a}R^{6a}R^{7a}$ in the formula (1B). The formulae (sp-19) and (sp-20) are specific examples when n is 2, and the others are specific examples when n is 1.

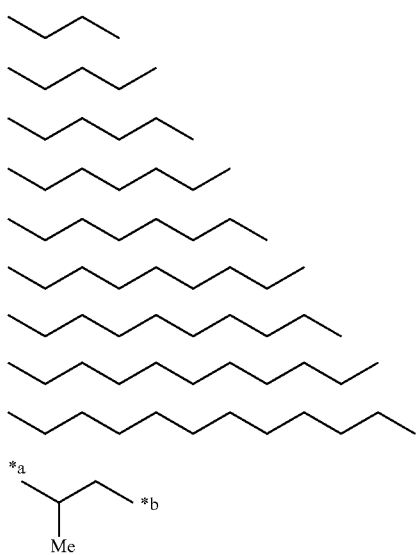
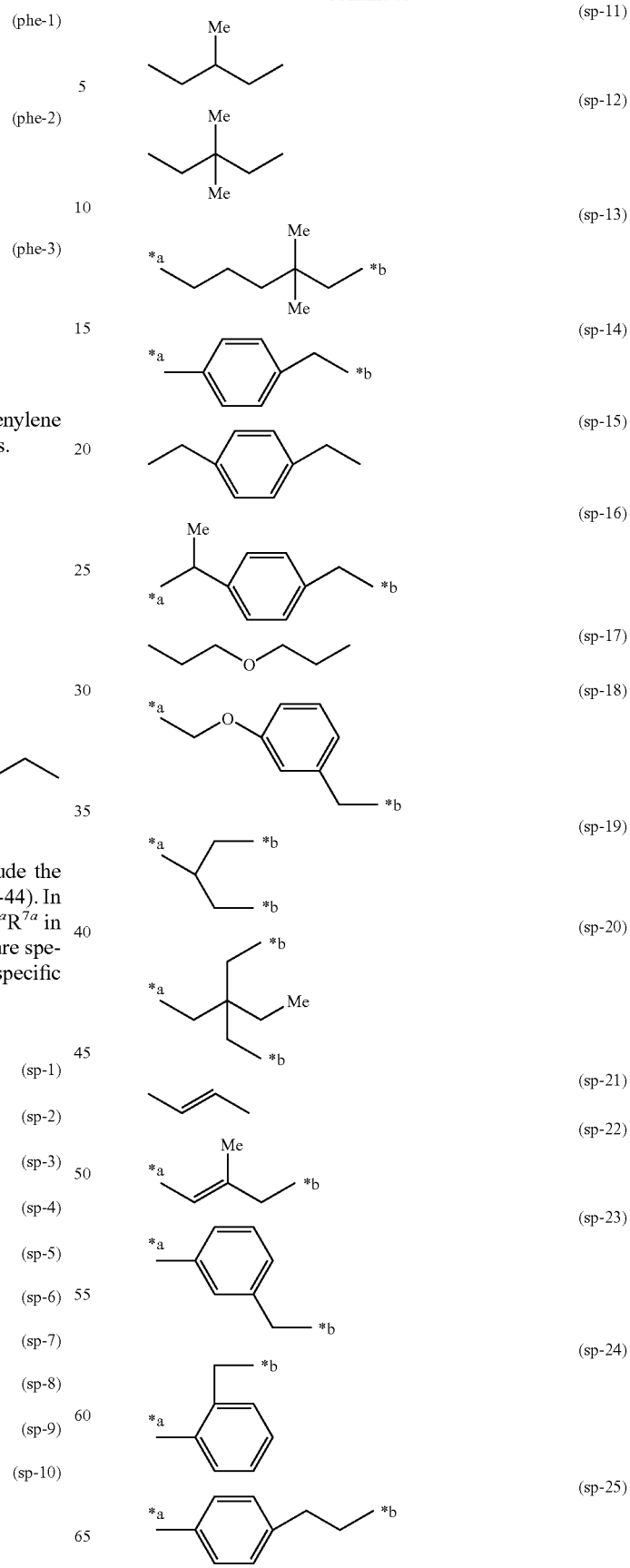

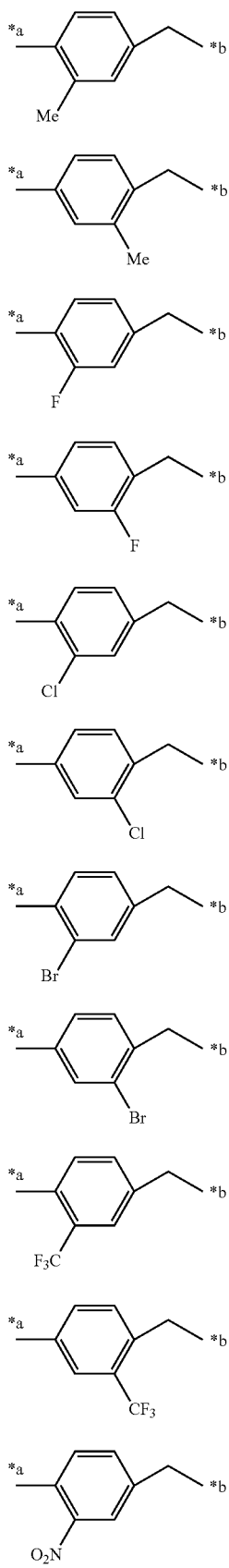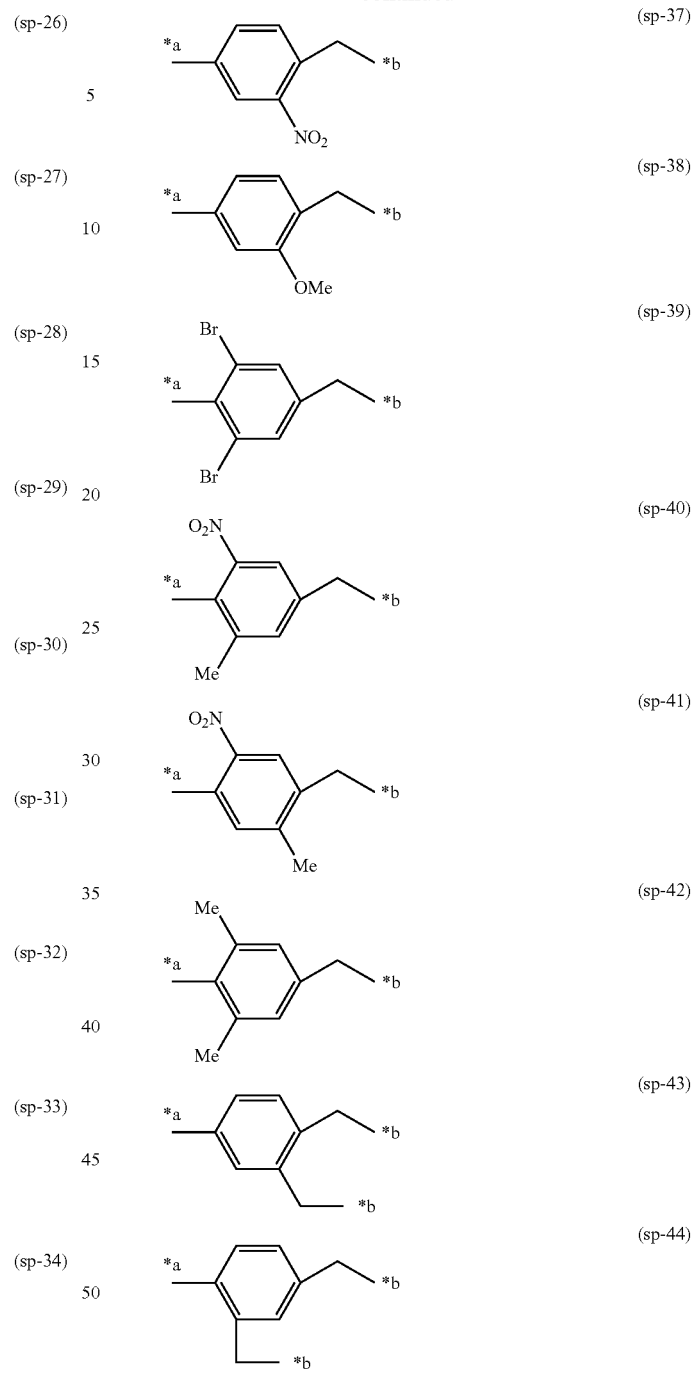

When Y is —NHCS—, $Z^a$ is particularly preferably any of the above formulae (sp-1) to (sp-10), (sp-14) to (sp-16), (sp-18), (sp-19), (sp-21) or (sp-22), among them, more preferably (sp-1) to (sp-9), and most preferably (sp-4). When Y is —NHCSNH—, $Z^a$ is particularly preferably any of the above formulae (sp-1) to (sp-9), (sp-12) to (sp-14), (sp-17), (sp-20), (sp-23) to (sp-25) or (sp-26) to (sp-44), among them, more preferably (sp-14), (sp-23) to (sp-25) or (sp-26) to (sp-44), and most preferably (sp-14) or (sp-26) to (sp-35). When Y is —NHCSO—, $Z^a$ is particularly preferably any of the above formulae (sp-1) to (sp-9) and (sp-11), among them, more preferably (sp-1) to (sp-9).

Each of $N^+R^{5a}R^{6a}R^{7a}$ is independently any of the following I), II) or III).

I) $R^{5a}$, $R^{6a}$ and $R^{7a}$ may be the same as or different from one another, and each represents alkyl group having 1 to 10 carbon atoms, alkenyl group having 2 to 10 carbon atoms or alkynyl group having 2 to 10 carbon atoms. The alkyl group, the alkenyl group and the alkynyl group may be substituted with one or more groups of phenyl, naphthyl, pyridyl, quinolyl, thienyl, furyl, piperidyl, pyrrolidyl, morpholyl, cycloalkyl having 3 to 7 carbon atoms, cyano, nitro, hydroxy, oxo, thioxo, carboxy, —$CONH_2$ and —$SO_3H$. Further, one or more methylenes which constitute the alkyl group, the alkenyl group and the alkynyl group may be replaced with any of phenylene, thienylene, furylene, cyclohexylene, cyclopentylene, —O—, —S—, —$CO_2$—, —NHCO—, —$NR^8$—, and —$N^+W^-R^9R^{10}$—. $R^8$ represents alkyl group having 1 to 5 carbon atoms or alkenyl group having 2 to 5 carbon atoms. The alkyl group and the alkenyl group may be substituted with one or more groups of phenyl, cycloalkyl having 3 to 7 carbon atoms and hydroxy. $R^9$ and $R^{10}$ may be the same as or different from each other, and each represents alkyl group having 1 to 5 carbon atoms or alkenyl group having 2 to 5 carbon atoms, and may be substituted with one or more groups of phenyl, cycloalkyl having 3 to 7 carbon atoms and hydroxy. $W^-$ represents counteranion.

When $R^{5a}$, $R^{6a}$ and $R^{7a}$ represent alkyl groups, any carbon number of 1 to 10 is preferable, and the straight alkyl groups having 1 to 10 carbon atoms are more preferable. Specific preferable examples of the alkyl groups may include methyl, ethyl, n-propyl, n-butyl, i-butyl, n-pentyl, i-pentyl, n-hexyl, 3,3-dimethylbutyl, n-heptyl, 2,2-dimethylpentyl, n-octyl, n-nonyl, n-decanyl and 2,3-diethylhexyl. When $R^{5a}$, $R^{6a}$ and $R^{7a}$ represent alkenyl groups, the carbon number is preferably 3 to 8. The straight alkenyl groups having 3, 4, 5, 6 or 8 carbon atoms or the branched alkenyl groups having 4, 6 or 7 carbon atoms are more preferable. Specific preferable examples of the alkenyl groups may include 2-propenyl, 2-methyl-2-propenyl, 3-butenyl, 4-pentenyl, 4-methyl-4-pentenyl, 5-hexenyl, 2-hexenyl, 5-methyl-5-hexenyl and 2,7-octadienyl. When $R^{5a}$, $R^{6a}$ and $R^{7a}$ represent alkynyl groups, the carbon number is preferably 3 to 9. The straight alkynyl groups having 3, 5, 6, 7 or 9 carbon atoms or the branched alkynyl groups having 6 carbon atoms are more preferable. Specific preferable examples of the alkynyl groups may include 2-propynyl, 2-pentynyl, 4-methyl-2-pentynyl, 2-hexynyl, 2-heptynyl and 2-nonynyl.

These preferable alkyl, alkenyl and alkynyl groups, particularly the alkyl groups may be substituted with one or more groups of phenyl, thienyl, cyclohexyl, cyano, hydroxy, oxo, carboxy, —$CONH_2$ and —$SO_3H$. Furthermore, one or more methylenes which constitute the alkyl group, the alkenyl group and the alkynyl group, particularly one or more methylenes which constitute the alkyl group may be replaced with any of phenylene, thienylene, furylene, —O—, —$CO_2$—, —NHCO—, —$NR^8$— ($R^8$ represents alkyl group having 1 to 3 carbon atoms or alkenyl group having 3 carbon atoms, preferably straight alkyl group having 1 to 3 carbon atoms or straight alkenyl group having 3 carbon atoms, and the alkyl group may be substituted with one or more groups of phenyl or hydroxy) and —$N^+W^-R^9R^{10}$— ($R^9$ and $R^{10}$ may be the same as or different from each other, and each represents alkyl group having 1 to 3 carbon atoms or alkenyl group having 3 carbon atoms, preferably straight alkyl group having 1 to 3 carbon atoms or straight alkenyl group having 3 carbon atoms, and the alkyl groups may be substituted with one or more groups of phenyl or hydroxy). It is more preferable that the alkenyl group and the alkynyl group are not substituted or replaced.

More preferable embodiments are any of the followings in which 1) preferable alkyl, alkenyl and alkynyl groups, particularly alkyl groups represented by $R^{5a}$, $R^{6a}$ and $R^{7a}$ are substituted with any one group of phenyl, thienyl, cyclohexyl, cyano, hydroxy, oxo, carboxy, —$CONH_2$ and —$SO_3H$;
2) the alkyl, alkenyl and alkynyl groups, particularly the alkyl groups are substituted with two hydroxy groups;
3) the alkyl, alkenyl and alkynyl groups, particularly the alkyl groups are substituted with one hydroxy group and one —$SO_3H$;
4) the alkyl, alkenyl and alkynyl groups, particularly the alkyl groups are substituted with one oxo group and one phenyl group;
5) the alkyl, alkenyl and alkynyl groups, particularly the alkyl groups are substituted with one hydroxy group and two phenyl groups;
6) one methylene which constitutes the alkyl, alkenyl and alkynyl groups, particularly one methylene which constitutes the alkyl groups is replaced with any of phenylene, furylene, —$CO_2$—, —NHCO—, —$NR^8$— ($R^8$ represents straight alkyl group having 1 to 3 carbon atoms, straight alkenyl group having 3 carbon atoms, straight alkyl group having 1 to 3 carbon atoms substituted with one hydroxy group or straight alkyl group having 1 to 3 carbon atoms substituted with one phenyl group, and specifically includes methyl, ethyl, n-propyl, 2-propenyl, 2-hydroxyethyl, 2-hydroxypropyl and benzyl), —$N^+W^-R^9R^{10}$— ($R^9$ and $R^{10}$ may be the same as or different from each other and each represents straight alkyl group having 1 to 3 carbon atoms, straight alkenyl group having 3 carbon atoms, straight alkyl group having 1 to 3 carbon atoms substituted with one hydroxy group or straight alkyl group having 1 to 3 carbon atoms substituted with one phenyl group, and specifically includes methyl, ethyl, n-propyl, 2-propenyl, 2-hydroxyethyl, and benzyl);
7) two methylenes which constitute the alkyl, alkenyl and alkynyl groups, particularly two methylenes which constitute the alkyl groups are replaced with any of two —O—, one phenylene and one —O—, one —O— and one —$NR^8$—, or one —NHCO— and one —O—;
8) three methylenes which constitute the alkyl, alkenyl and alkynyl groups, particularly three methylenes which constitute the alkyl groups are substituted with any of two —O— and one —$NR^8$—, or one phenylene and two-NHCO—;
9) the alkyl, alkenyl and alkynyl groups, particularly the alkyl groups are substituted with one hydroxy group, and further one methylene which constitutes the alkyl, alkenyl and alkynyl groups, particularly one methylene which constitutes the alkyl groups is replaced with —O—;
10) the alkyl, alkenyl and alkynyl groups, particularly the alkyl groups are substituted with one hydroxy group, and further one methylene which constitutes the alkyl, alkenyl and alkynyl groups, particularly one methylene which constitutes the alkyl groups is replaced with —$NR^8$—;
11) the alkyl, alkenyl and alkynyl groups, particularly the alkyl groups are substituted with one hydroxy group, and further one methylene which constitutes the alkyl, alkenyl and alkynyl groups, particularly one methylene which constitutes the alkyl groups is replaced with furylene;
12) the alkyl, alkenyl and alkynyl groups, particularly the alkyl groups are substituted with one oxo group, and further one methylene which constitutes the alkyl, alkenyl and alkynyl groups, particularly one methylene which constitutes the alkyl groups is replaced with thienylene; and 13) the alkyl, alkenyl and alkynyl groups, particularly the alkyl groups are substituted with one oxo group, and further two methylenes which constitute the alkyl, alkenyl and alkynyl groups, particularly two methylenes which constitute the alkyl groups are replaced with one —O— and one phenylene. Alternatively, the alkyl, alkenyl and alkynyl groups represented by $R^{5a}$, $R^{6a}$ and $R^{7a}$ are not substituted.

The most preferable embodiment is any of straight alkyl groups having 1 to 10 carbon atoms, straight alkyl groups having 1 to 10 carbon atoms substituted with one phenyl group, straight alkyl groups having 1 to 10 carbon atoms substituted with one hydroxy group, straight alkenyl groups having 3 to 6 or 8 carbon atoms, branched alkenyl group having 4, 6 or 7 carbon atoms, straight alkynyl groups having 3, 5, 6, 7 or 9 carbon atoms and branched alkynyl groups having 6 carbon atoms.

Specifically, N,N-dimethyl-N(n-hexyl) ammonium, N-benzyl-N,N-dimethyl ammonium, N-benzyl-N-methyl-N-(propargyl) ammonium, or N,N-dimethyl-N-(n-butyl) ammonium is preferable, and N-benzyl-N,N-dimethyl ammonium or N-benzyl-N-methyl-N-(propargyl) ammonium is particularly preferable.

II) $N^+R^{5a}R^{6a}R^{7a}$ represents a monocyclo or bicyclo ring formed by 4 to 9 carbon atoms in addition to the ammonium nitrogen atom, with a proviso that a position of binding to $Z^a$ is the ammonium nitrogen atom. In the monocyclo and bicyclo rings, one of the carbon atoms which constitute the ring may be substituted with any of oxygen, nitrogen or sulfur atom, and further the monocyclo and bicyclo rings may be substituted with one or more groups of hydroxy, oxo, thioxo, cyano, phenyl, naphthyl, thienyl, pyridyl, cycloalkyl having 3 to 7 carbon atoms, carboxy, —$CONH_2$, —$SO_3H$ and —$R^{11}$. $R^{11}$ represents alkyl group having 1 to 8 carbon atoms or alkenyl group having 2 to 8 carbon atoms. The alkyl group and the alkenyl group may be substituted with one or more groups of phenyl, naphthyl, pyridyl, quinolyl, thienyl, furyl, piperidyl, pyrrolidyl, morpholyl, cycloalkyl having 3 to 7 carbon atoms, cyano, nitro, hydroxy, oxo, thioxo, carboxy, —$CONH_2$ and —$SO_3H$, and further one or more methylenes which constitute the alkyl group and the alkenyl group may be replaced with any of phenylene, thienylene, furylene, cyclohexylene, cyclopentylene, —O—, —S—, —$CO_2$—, —NHCO—, —$NR^8$—, and —$N^+W^-R^9R^{10}$—. $R^8$ represents alkyl group having 1 to 5 carbon atoms or alkenyl group having 2 to 5 carbon atoms. The alkyl group and the alkenyl group may be substituted with one or more groups of phenyl, cycloalkyl having 3 to 7 carbon atoms and hydroxy. $R^9$ and $R^{10}$ may be the same as or different from each other, and each represents alkyl group having 1 to 5 carbon atoms or alkenyl group having 2 to 5 carbon atoms, and may be substituted with one or more groups of phenyl, cycloalkyl having 3 to 7 carbon atoms and hydroxy. $W^-$ represents counteranion. The group which is not involved in the formation of the monocyclo ring and the bicyclo ring in $R^{5a}$, $R^{6a}$ and $R^{7a}$ represents alkyl group having 1 to 10 carbon atoms, alkenyl group having 2 to 10 carbon atoms or alkynyl group having 2 to 10 carbon atoms. The alkyl group, the alkenyl group and the alkynyl group may be substituted with one or more groups of phenyl, naphthyl, pyridyl, quinolyl, thienyl, furyl, piperidyl, pyrrolidyl, morpholyl, cycloalkyl having 3 to 7 carbon atoms, cyano, nitro, hydroxy, oxo, thioxo, carboxy, —$CONH_2$ and —$SO_3H$, and further one or more methylenes which constitute the alkyl group, the alkenyl group and the alkynyl group may be replaced with any of phenylene, naphthylene, thienylene, furylene, pyridylene, cyclohexylene, cyclopentylene, —O—, —S—, —$CO_2$—, —NHCO—, —$NR^8$—, and —$N^+W^-R^9R^{10}$—. $R^8$ represents alkyl group having 1 to 5 carbon atoms or alkenyl group having 2 to 5 carbon atoms. The alkyl group and the alkenyl group may be substituted with one or more groups of phenyl, cycloalkyl having 3 to 7 carbon atoms and hydroxy. $R^9$ and $R^{10}$ may be the same as or different from each other, and each represents alkyl group having 1 to 5 carbon atoms or alkenyl group having 2 to 5 carbon atoms, and may be substituted with one or more groups of phenyl, cycloalkyl having 3 to 7 carbon atoms and hydroxy. $W^-$ represents counteranion.

The monocyclo ring or the bicyclo ring represented by $N^+R^{5a}R^{6a}R^{7a}$ is preferably any of pyrrolidinium ring, piperidinium ring, morpholinium ring, thiomorpholinium ring, piperazinium ring, azepanium ring, quinuclidinium ring or 1,4-diazabicyclo[2.2.2]octanium ring. The monocyclo ring and the bicyclo ring may be substituted with one or more groups of hydroxy, oxo, cyano, phenyl, —$CONH_2$ and —$R^{11}$. As $R^{11}$, alkyl group having 1 to 6 carbon atoms or alkenyl group having 3 carbon atoms is preferable, and straight alkyl group having 1 to 5 carbon atoms (e.g., methyl, ethyl, n-propyl, n-butyl, n-pentyl), branched alkyl group having 6 carbon atoms (e.g., 3,3-dimethylbutyl) or straight alkenyl group having 3 carbon atoms (e.g., 2-propenyl) is more preferable. The alkyl group may be substituted with one or more groups of hydroxy, cyano, phenyl and —$CONH_2$. Furthermore, one or more methylenes which constitute the alkyl group may be replaced with any of —O—, —$CO_2$— and —NHCO—. The group which is not involved in the formation of the ring in $R^{5a}$, $R^{6a}$ and $R^{7a}$ represents alkyl group having 1 to 6 carbon atoms (preferably straight alkyl group having 1 to 6 carbon atoms), alkenyl group having 3 to 4 carbon atoms (preferably straight alkenyl group having 3 to 4 carbon atoms) or alkynyl group having 3 to 6 carbon atoms (preferably straight alkynyl group having 3, 4 or 6 carbon atoms). The alkyl group, the alkenyl group and the alkynyl group, particularly the alkyl group may be substituted with one or more groups of phenyl, thienyl, furyl, piperidyl, pyrrolidyl, morpholyl, cyclopropyl, cyclopentyl, cyano, hydroxy, oxo, nitro, carboxy and —$SO_3H$, and further one or more methylenes which constitute the alkyl group may be replaced with any of phenylene, —O—, and —$CO_2$—. It is more preferable that the alkenyl group and the alkynyl group are not substituted or replaced.

In the more preferable embodiment, the pyrrolidinium ring, the piperidinium ring, the morpholinium ring, the thiomorpholinium ring, the piperazinium ring, the azepanium ring, the quinuclidinium ring and the 1,4-diazabicyclo[2.2.2] octanium ring are substituted with 1) one of any of hydroxy, oxo, cyano, phenyl, $CONH_2$ or —$R^{11}$; 2) one cyano and one hydroxy; 3) one hydroxy group and one —$R^{11}$; 4) one oxo group and one —$R^{11}$; 5) two oxo groups or 6) two —$R^{11}$. Alternatively, the pyrrolidinium ring, the piperidinium ring, the morpholinium ring, the thiomorpholinium ring, the piperazinium ring, the azepanium ring, the quinuclidinium ring and the 1,4-diazabicyclo[2.2.2]octanium ring are not substituted. In this embodiment, $R^{11}$ represents straight alkyl group having 1 to 5 carbon atoms (e.g., methyl, ethyl, n-propyl, n-butyl, n-pentyl), branched alkyl group having 6 carbon atoms (e.g., 3,3-dimethylbutyl) or straight alkenyl group having 3 carbon atoms (e.g., 2-propenyl), wherein 1) the alkyl group is substituted with either one of hydroxy and phenyl; or 2) one methylene which constitutes the alkyl group is replaced with any of —$CO_2$— and —NHCO—; or 3) two methylenes which constitute the alkyl group are replaced with one —O— and one —NHCO—; or 4) the alkyl group is substituted with one cyano and further one methylene which constitutes the alkyl group is substituted with —O—; or 5) the alkyl group is substituted with one —$CONH_2$ and further one methylene which constitutes the alkyl group is replaced with —O—; or 6) the alkyl group is substituted with one phenyl and further one methylene which constitutes the alkyl group is replaced with —$CO_2$—; or 7) the alkyl group is substituted with one phenyl and further one methylene which constitutes the alkyl group is replaced with —NHCO—; or 8) the alkyl group is not substituted or replaced. Specific examples of $R^{11}$ may include methyl, ethyl, n-propyl, n-butyl, n-pentyl, 2-propenyl, benzyl, acetylamino, t-butoxycarbonylamino, hydroxymethyl, 2-hydroxyethyl, 3-hydroxypropyl, 2-cyanoethoxy, (2-cyanoethoxy)methyl, 2-carbamoylethoxy, ethoxycarbonyl, t-butoxycarbonyl, benzoyloxy, phenylacetylamino, butanoylamino and pentanoylamino. The group which is not involved in the formation of the ring in $R^{5a}$, $R^{6a}$ and $R^{7a}$ represents straight alkyl group having 1 to 6 carbon atoms, straight alkenyl group having 3 to 4 carbon atoms or straight alkynyl group having 3, 4 or 6 carbon atoms, wherein 1) the alkyl group, the alkenyl group and the alkynyl group, particularly the alkyl group are substituted with one of any of phenyl, thienyl, furyl, piperidyl, pyrrolidyl, morpholyl, cyclopropyl, cyclopentyl, cyano, hydroxy, carboxy or —$SO_3H$; or 2) the alkyl group, the alkenyl group and the alkynyl group, particularly the alkyl group are substituted with two hydroxy groups; or 3) the alkyl group, the alkenyl group and the alkynyl group, particularly the alkyl group are substituted with one hydroxy group and one —$SO_3H$; or 4) the alkyl group, the alkenyl group and the alkynyl group, particularly the alkyl group are substituted with four hydroxy groups and one oxo group; or 5) the alkyl group, the alkenyl group and the alkynyl group, particularly the alkyl group are substituted with one nitro group and one morpholyl group; or 6) one methylene which constitutes the alkyl group, the alkenyl group and the alkynyl group, particularly one methylene which constitutes the alkyl group is replaced with —$CO_2$—; or 7) the alkyl group, the alkenyl group and the alkynyl group, particularly the alkyl group are substituted with one morpholyl, and further one methylene which constitutes the alkyl group, the alkenyl group and the alkynyl group, particularly one methylene which constitutes the alkyl group is replaced with —O—. Alternatively, the alkyl group, the alkenyl group and the alkynyl group are not substituted or replaced.

The particularly preferable embodiment is the pyrrolidinium ring, the piperidinium ring, the azepanium ring, the quinuclidinium ring or the 1,4-diazabicyclo[2.2.2]octanium ring which is substituted with one of any of methyl, ethyl, n-propyl, n-butyl, n-pentyl, 2-propenyl, phenyl, benzyl, hydroxy, hydroxymethyl, 2-hydroxyethyl or 3-hydroxypropyl, or is not substituted, wherein the group which is not involved in the formation of the ring in $R^{5a}$, $R^{6a}$ and $R^{7a}$ represents any of straight alkyl group having 1 to 6 carbon atoms, straight alkyl group having 1 to 6 carbon atoms substituted with one phenyl, straight alkyl group having 1 to 6 carbon atoms substituted with one hydroxy, straight alkenyl group having 3 to 4 carbon atoms or straight alkynyl group having 3, 4 or 6 carbon atoms.

Concerning the group which is not involved in the ring formation, specific preferable examples of the straight alkyl group having 1 to 6 carbon atoms may include methyl, ethyl, n-propyl, n-butyl, n-pentyl and n-hexyl. Specific preferable examples of the straight alkenyl group having 3 to 4 carbon atoms may include 2-propenyl, 3-butenyl and 2,7-octadienyl. Specific preferable examples of the straight alkynyl group having 3, 4 or 6 carbon atoms may include 2-propynyl, 2-butynyl and 2,4-hexadiinyl.

The most preferable embodiment is the quinuclidinium ring or the 1,4-diazabicyclo[2.2.2]octanium ring which is substituted with one of any of n-butyl, phenyl, benzyl or hydroxy, or is not substituted.

Specifically, preferable examples may include quinuclidinium-1-yl, 4-phenylquinuclidinium-1-yl, 3-hydroxyquinuclidinium-1-yl, 1,4-diazabicyclo[2.2.2]octanium-1-yl, 4-n-butyl-1,4-diazabicyclo[2.2.2]octanium-1-yl and 4-benzyl-1,4-diazabicyclo[2.2.2]octanium-1-yl, and particularly preferable examples may include quinuclidinium-1-yl, 4-phenylquinuclidinium-1-yl and 1,4-diazabicyclo[2.2.2]octanium-1-yl. Among them, 4-phenylquinuclidinium-1-yl is the most preferable. Alternatively, 1,4-diazabicyclo[2.2.2]octanium-1-yl is also the most preferable in another case. In addition, quinuclidinium-1-yl is the most preferable in another case.

The other most preferable embodiment is the pyrrolidinium ring, the piperidinium ring or the azepanium ring which is substituted with one of any of methyl, phenyl, benzyl, hydroxy, hydroxymethyl, 2-hydroxyethyl or 3-hydroxypropyl, or is not substituted, wherein the group which is not involved in the formation of the ring in $R^{5a}$, $R^{6a}$ and $R^{7a}$ represents any of straight alkyl group having 1 to 6 carbon atoms, straight alkyl group having 1 to 6 carbon atoms substituted with one phenyl, straight alkyl groups having 1 to 6 carbon atoms substituted with one hydroxy, straight alkenyl group having 3 to 4 carbon atoms or straight alkynyl group having 3, 4 or 6 carbon atoms. Specifically, preferable examples may include 1-methyl-pyrrolidinium-1-yl, 1-ethyl-pyrrolidinium-1-yl, 1-n-butyl-pyrrolidinium-1-yl, 1-n-pentyl-pyrrolidinium-1-yl, 3-hydroxy-1-methyl-pyrrolidinium1-1-yl, 1-ethyl-3-hydroxy-pyrrolidinium-1-yl, 1-benzyl-3-hydroxy-pyrrolidinium-1-yl, 1-methyl-piperidinium-1-yl, 1-ethyl-piperidinium-1-yl, 1-n-butyl-piperidinium-1-yl, 1-n-pentyl-piperidinium-1-yl, 4-benzyl-1-n-butyl-piperidinium-1-yl, 4-benzyl-1-n-pentyl-piperidinium-1-yl, 3-hydroxy-1-methyl-piperidinium-1-yl, 4-hydroxy-1-methyl-piperidinium-1-yl, 3-hydroxymethyl-1-methyl-piperidinium-1-yl, 1-benzyl-4-hydroxymethyl-piperidinium-1-yl, 1-benzyl-4-hydroxyethyl-piperidinium-1-yl, 1-benzyl-4-hydroxy-piperidinium-1-yl, 1-ethyl-azepanium-1-yl, 1-n-butyl-azepanium-1-yl, 1-n-pentyl-azepanium-1-yl, 1-benzyl-azepanium-1-yl and 1-hydroxyethyl-azepanium-1-yl. More preferable examples may include 1-n-butyl-pyrrolidinium-1-yl, 1-ethyl-piperidinium-1-yl, 4-benzyl-1-n-butyl-piperidinium-1-yl, 4-benzyl-1-n-pentyl-piperidinium-1-yl and 1-benzyl-4-hydroxy-piperidinium-1-yl. The most preferable example may include 1-benzyl-4-hydroxy-piperidinium-1-yl.

III) $N^+R^{5a}R^{6a}R^{7a}$ represents a pyridinium ring, a quinolinium ring or an isoquinolinium ring, with a proviso that a position of binding to $Z^a$ is the ammonium nitrogen atom. The pyridinium ring, the quinolinium ring and the isoquinolinium ring may be substituted with one or more groups of cyano, nitro, phenyl, naphthyl, thienyl, pyridyl, cycloalkyl having 3 to 7 carbon atoms, alkoxy having 1 to 5 carbon atoms, carboxy, —$CONH_2$, —$SO_3H$, halogen, hydroxy, tetrahydropyranyl and —$R^{12a}$. $R^{12a}$ represents alkyl group having 1 to 9 carbon atoms or alkenyl group having 2 to 9 carbon atoms. The alkyl group and the alkenyl group may be substituted with one or more groups of phenyl, naphthyl, pyridyl, quinolyl, thienyl, furyl, cycloalkyl having 3 to 7 carbon atoms, cyano, nitro, hydroxy, oxo, thioxo, carboxy, —$CONH_2$ and —$SO_3H$; and further one or more methylenes which constitute the alkyl group and the alkenyl group may be replaced with any of phenylene, thienylene, furylene, cyclohexylene, cyclopentylene, —S—, —O—, —$CO_2$—, —NHCO—, —$NR^8$—, and —$N^+W^-R^9R^{10}$—. $R^8$ represents alkyl group having 1 to 5 carbon atoms or alkenyl group having 2 to 5 carbon atoms. The alkyl group and the alkenyl group may be substituted with one or more groups of phenyl, cycloalkyl having 3 to 7 carbon atoms and hydroxy. $R^9$ and $R^{10}$ may be the same as or different from each other, and each represents alkyl group having 1 to 5 carbon atoms or alkenyl group having 2 to 5 carbon atoms, and may be substituted with one or more groups of phenyl, cycloalkyl having 3 to 7 carbon atoms and hydroxy. $W^-$ represents counteranion.

Preferably, in the pyridinium ring, the quinolinium ring and the isoquinolinium ring, the pyridinium ring and the quinolinium ring, particularly the pyridinium ring, may be substituted with one or more groups of cyano, nitro, phenyl, thienyl, pyridyl, alkoxy having 1 to 3 carbon atoms, carboxy, —$CONH_2$ and —$R^{12a}$, wherein $R^{12a}$ represents alkyl group having 1 to 9 carbon atoms (preferably straight alkyl group having 1 to 7 carbon atom or branched alkyl group having 3 to 5 or 9 carbon atoms) or alkenyl group having 2 to 4 carbon atoms (preferably straight alkenyl group having 2 to 4 carbon atoms). The alkyl group and the alkenyl group, particularly the alkyl group, may be substituted with one or more groups of phenyl, naphthyl, pyridyl, cyano, nitro, hydroxy, oxo, carboxy, and —$SO_3H$; and further one or more methylenes which constitute the alkyl group and the alkenyl group, particularly one methylene which constitutes the alkyl group may be replaced with any of —S—, —$CO_2$—, —NHCO— and —$NR^8$—. $R^8$ represents alkyl group having 1 to 3 carbon atoms (preferably straight alkyl group having 1 to 3 carbon atoms), and the alkyl group may be substituted with one or more (preferably one) hydroxy.

The more preferable embodiment is any of 1) the pyridinium ring substituted with one of any of cyano, phenyl, thienyl, pyridyl, methoxy, ethoxy, propoxy, carboxy, —$CONH_2$ or —$R^{12a}$; 2) the pyridinium ring substituted with two cyano groups; 3) the pyridinium ring substituted with two —$R^{12a}$; 4) the pyridinium ring substituted with one cyano group and one —$R^{12a}$; 5) the pyridinium ring substituted with one phenyl group and one —$R^{12a}$; 6) the quinolinium ring substituted with one of any of cyano, nitro, carboxy, methoxy, ethoxy, propoxy or —$R^{12a}$; 7) the quinolinium ring substituted with one methoxy group and one —$R^{12a}$; 8) the quinolinium ring substituted with one nitro group and one —$R^{12a}$; 9) the unsubstituted pyridinium ring; 10) the unsubstituted quinolinium ring or 11) the unsubstituted isoquinolinium, wherein $R^{12a}$ represents straight alkyl group having 1 to 7 carbon atoms (e.g., methyl, ethyl, n-propyl, n-butyl, n-pentyl, n-heptyl), branched alkyl group having 3 to 5 or 9 carbon atoms (e.g., i-propyl, t-butyl, 3-pentyl, 5-nonyl), or straight alkenyl group having 2 to 4 carbon atoms (e.g., vinyl, 3-butenyl), wherein 1) the alkyl group and the alkenyl group, particularly the alkyl group are substituted with one of any of phenyl, naphthyl, pyridyl, cyano, nitro, hydroxy, oxo, carboxy or —$SO_3H$; or 2) the alkyl group and the alkenyl group, particularly the alkyl group are substituted with one oxo group and one phenyl group; or 3) the alkyl group and the alkenyl group, particularly the alkyl group are substituted with two hydroxy group and one pyridyl group; or 4) one methylene which constitutes the alkyl group and the alkenyl group, particularly one methylene which constitutes the alkyl group is replaced with —$CO_2$—; or 5) the alkyl group and the alkenyl group, particularly the alkyl group are substituted with one hydroxy, and further one methylene which constitutes the alkyl group and the alkenyl group, particularly one methylene which constitutes the alkyl group is replaced with —NHCO—; or 6) the alkyl group and the alkenyl group, particularly the alkyl group are substituted with one oxo group, and further one methylene which constitutes the alkyl group and the alkenyl group, particularly one methylene which constitutes the alkyl group is replaced with —$CO_2$—; or 7) the alkyl group and the alkenyl group, particularly the alkyl group are substituted with one phenyl group, and further one methylene which constitutes the alkyl group and the alkenyl group, particularly one methylene which constitutes the alkyl group is replaced with —$CO_2$—; or 8) the alkyl group and the alkenyl group, particularly the alkyl group are substituted with one carboxy group, and further one methylene which constitutes the alkyl group and the alkenyl group, particularly one methylene which constitutes the alkyl group is replaced with —S—; or 9) the alkyl group and the alkenyl group, particularly the alkyl group are substituted with one hydroxy group and one oxo group, and further one methylene which constitutes the alkyl group and the alkenyl group, particularly one methylene which constitutes the alkyl group is replaced with —$NR^8$— ($R^8$ represents methyl, ethyl, n-propyl, 2-hydroxyethyl or 3-hydroxypropyl); or 10) the alkyl group and the alkenyl group are not substituted or replaced. Specific examples of $R^{12a}$ may include methyl, ethyl, n-propyl, i-propyl, n-butyl, t-butyl, n-pentyl, 3-pentyl, 5-nonyl, vinyl, benzyl, 3-phenylpropyl, 2-(1-naphthyl)vinyl, hydroxymethyl, 2-hydroxyethyl, 3-hydroxypropyl, formyl, acetyl, propionyl, benzoyl, methoxycarbonyl, ethoxycarbonyl, butoxycarbonyl, hexoxycarbonyl, benzyloxycarbonyl, 2-propenyloxycarbonyl, ethoxycarbonylmethyl, 2-(methoxycarbonyl)ethyl, ethoxycarbonylmethylcarbonyl, 2-hydroxyethylaminocarbonyl, bis(2-hydroxyethyl)aminocarbonyl, 2-carboxyvinyl, carboxymethylthio, cyanomethyl, 2-nitrovinyl, 2-(4-pyridyl)ethyl, 2-(4-pyridyl)vinyl, 3-(4-pyridyl)propyl, 2-(4-pyridyl)-1,2-dihydroxyethyl and 2-sulfoethyl.

The particularly preferable embodiment is any of the unsubstituted pyridinium ring, the unsubstituted quinolinium, the unsubstituted isoquinolinium, the pyridinium ring substituted with one of any of methyl, ethyl, n-propyl, i-propyl, n-butyl, t-butyl, n-pentyl, vinyl, phenyl, benzyl, 3-phenylpropyl, hydroxymethyl, 2-hydroxyethyl or 3-hydroxypropyl, the pyridinium ring substituted with two of methyl or ethyl group, the pyridinium ring substituted with one phenyl group and one methyl group, or the quinolinium ring substituted with any one of methyl or i-propyl.

The most preferable embodiment is the pyridinium ring substituted with one of any of t-butyl, n-butyl, n-propyl, ethyl, methyl, hydroxypropyl or methoxycarbonylethyl, or the unsubstituted pyridinium ring.

Specifically, isoquinolinium-1-yl, 4-methylpyridinium-1-yl, 3-(n-butyl)pyridinium-1-yl, 4-ethylpyridinium-1-yl, 4-(t-butyl)pyridinium-1-yl, 3-(3-hydroxypropyl)pyridinium-1-yl, 3-[2-(methoxycarbonyl)ethyl]-pyridinium-1-yl and 2-(n-propyl)-pyridinium-1-yl are preferable, and 4-(t-butyl)pyridinium-1-yl, 3-(3-hydroxypropyl)pyridinium-1-yl, 3-[2-(methoxycarbonyl)ethyl]-pyridinium-1-yl and 2-(n-propyl)-pyridinium-1-yl are particularly preferable.

Eventually, as $N^+R^{5a}R^{6a}R^{7a}$, one group selected from the group consisting of N-benzyl-N,N-dimethylammonium, N-benzyl-N-methyl-N-propargylammonium, 4-phenylquinuclidinium-1-yl, 1,4-diazabicyclo[2.2.2]octanium-1-yl, 1-benzyl-4-hydroxy-piperidinium-1-yl, 4-(t-butyl)pyridinium-1-yl, 3-(3-hydroxypropyl)-pyridinium-1-yl, 3-[2-(methoxycarbonyl)ethyl]-pyridinium-1-yl and 2-(n-propyl)-pyridinium-1-yl is preferable.

Naphthyl in the description of I) to III) may include 1-naphthyl and 2-naphthyl, and preferably 1-naphthyl. Pyridyl may include 1-pyridyl, 2-pyridyl, 3-pyridyl and 4-pyridyl, preferably 1-pyridyl and 4-pyridyl, and more preferably 4-pyridyl. Quinolyl may include 1-quinolyl, 2-quinolyl, 3-quinolyl, 4-quinolyl, 5-quinolyl, 6-quinolyl, 7-quinolyl and 8-quinolyl, and preferably 1-quinolyl or 4-quinolyl. Thienyl may include 2-thienyl and 3-thienyl, and preferably 2-thienyl. Furyl may include 2-furyl and 3-furyl, and preferably 2-furyl. Piperidyl may include 1-piperidyl, 2-piperidyl, 3-piperidyl and 4-piperidyl, preferably 1-piperidyl or 4-piperidyl, and more preferably 1-piperidyl. Pyrrolidyl may include 1-pyrrolidyl, 2-pyrrolidyl and 3-pyrrolidyl, and preferably 1-pyrrolidyl. Morpholyl may include 2-morpholyl, 3-morpholyl and 4-morpholyl, and particularly preferably 4-morpholyl. Cycloalkyl having 3 to 7 carbon atoms may include cyclopropyl, cyclobutyl, cyclopentyl, cyclohexyl and cycloheptyl as preferable examples. Phenylene is any of the above formulae (phe-1) to (phe-3), preferably the formula (phe-1) or (phe-2), and more preferably the formula (phe-1). Thienylene is any of the following formulae (thi-1) to (thi-4), and the formula (thi-1) is particularly preferable.

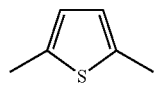
(thi-1)

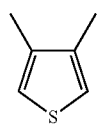
(thi-2)

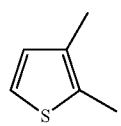
(thi-3)

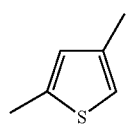
(thi-4)

Furylene is any of the following formulae (fur-1) to (fur-4), and the formula (fur-1) is particularly preferable.

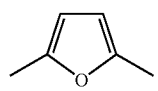
(fur-1)

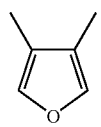
(fur-2)

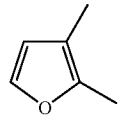
(fur-3)

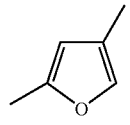
(fur-4)

Cyclohexylene is any of the following formulae (hex-1) to (hex-3), preferably the formula (hex-1) or (hex-2), and more preferably the formula (hex-1).

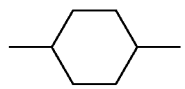
(hex-1)

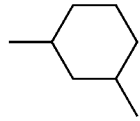
(hex-2)

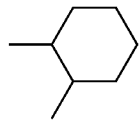
(hex-3)

Cyclopentylene is any of the following formula (pen-1) or (pen-2), and preferably the formula (pen-1).

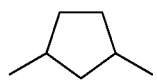
(pen-1)

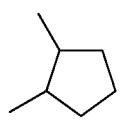
(pen-2)

Specific examples of $-N^+R^{5a}R^{6a}R^{7a}$ corresponding to I) may include the following formulae (an-1) to (an-158), (an-380) and (an-381).

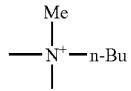
(an-1)

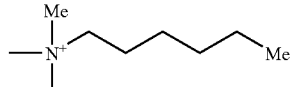
(an-2)

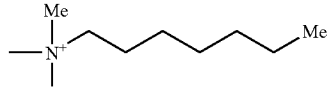
(an-3)

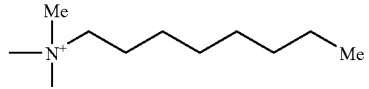
(an-4)

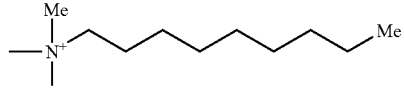
(an-5)

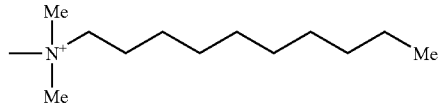
(an-6)

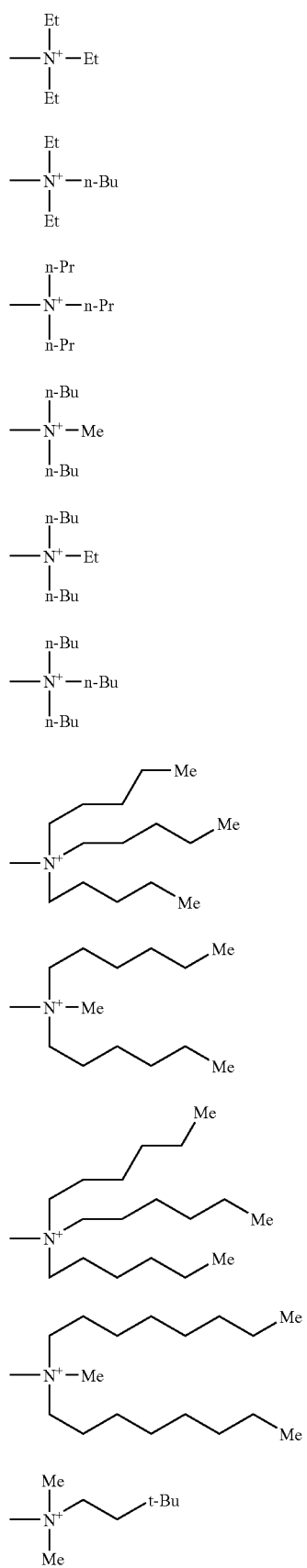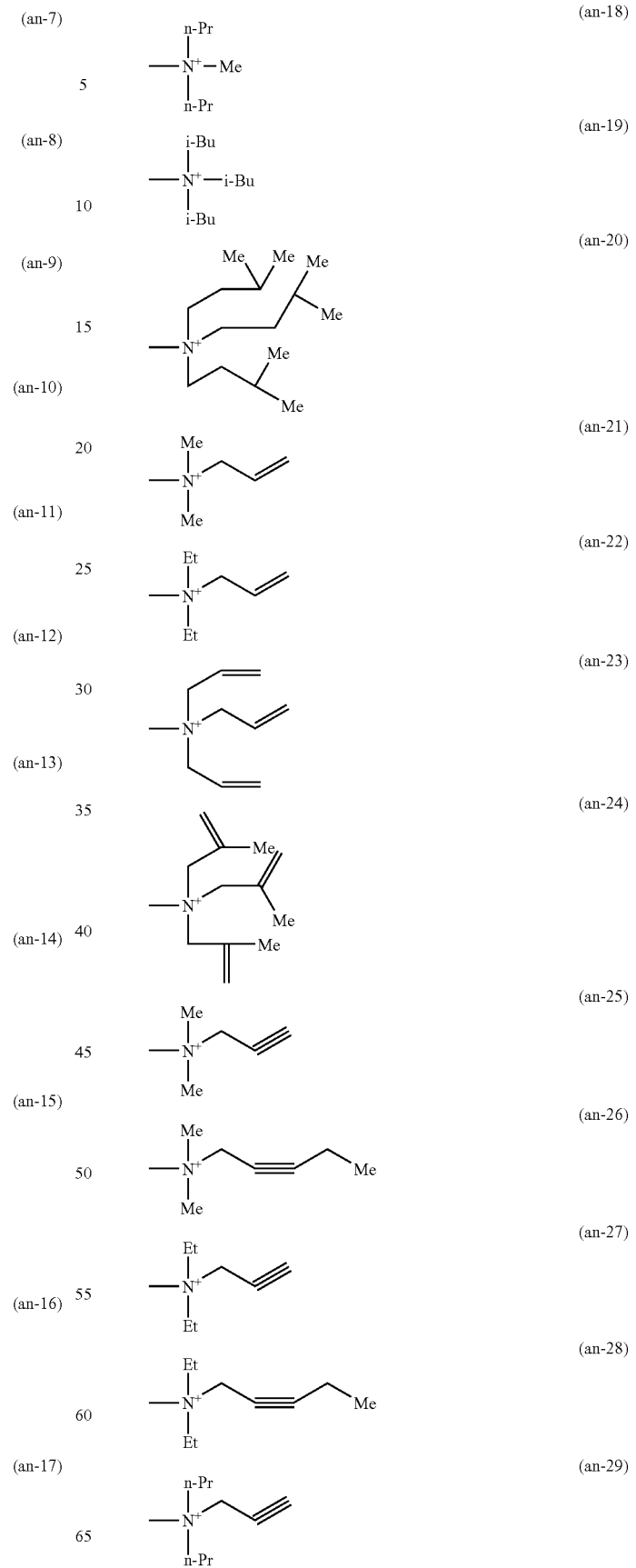

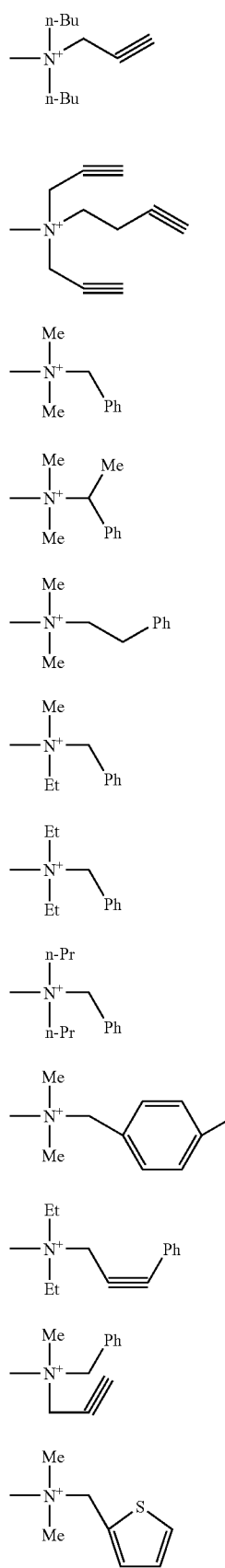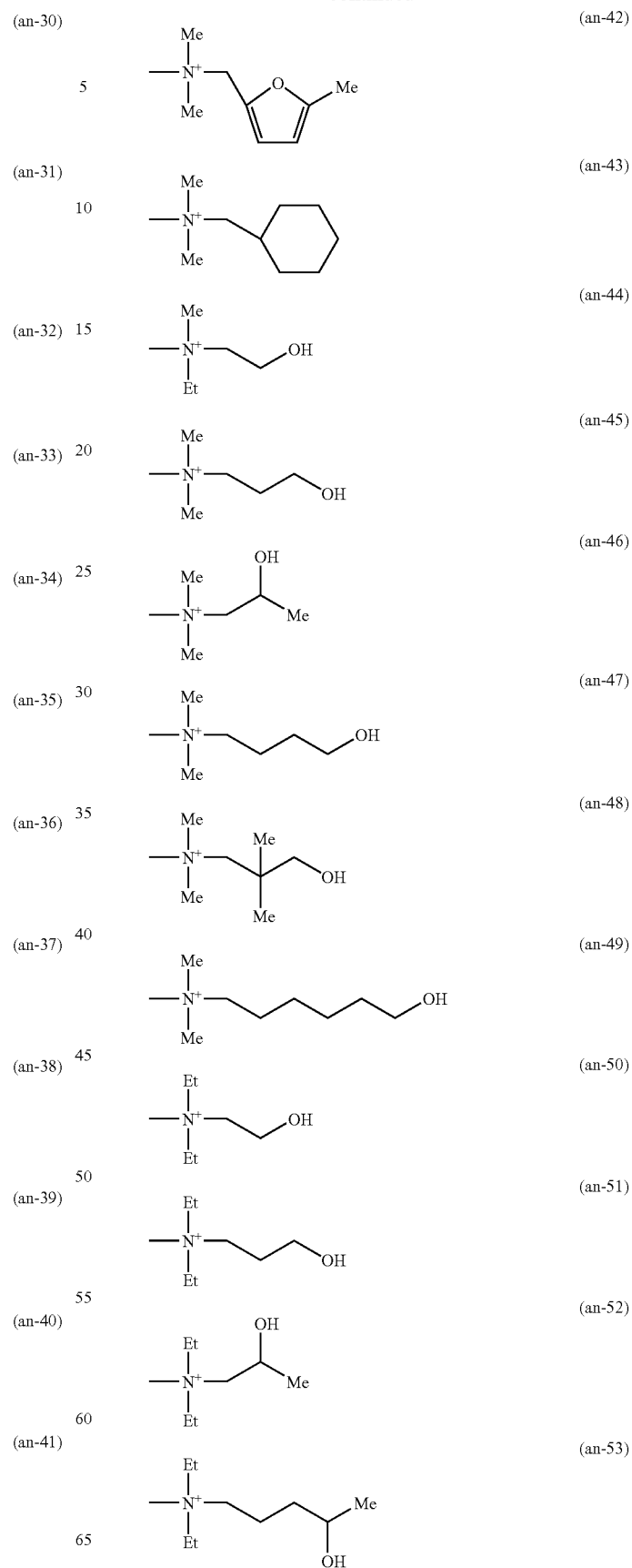

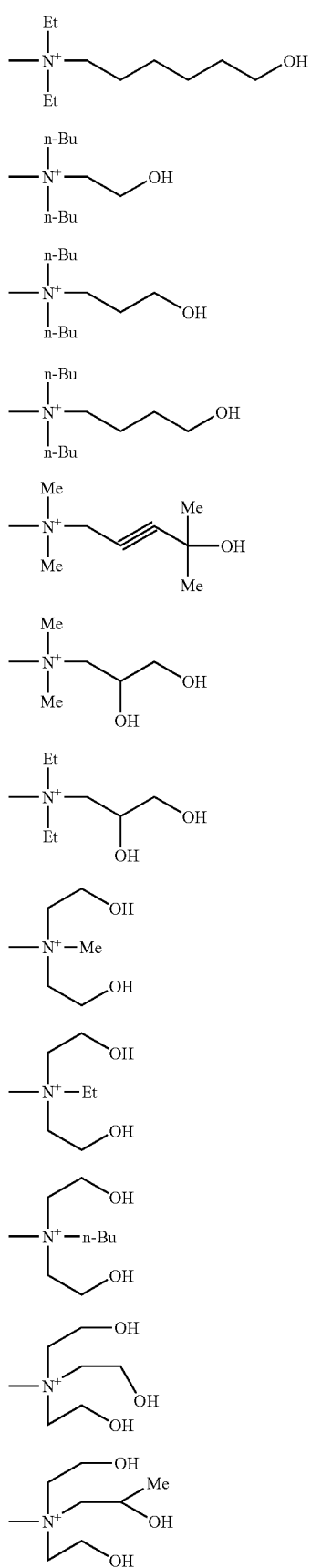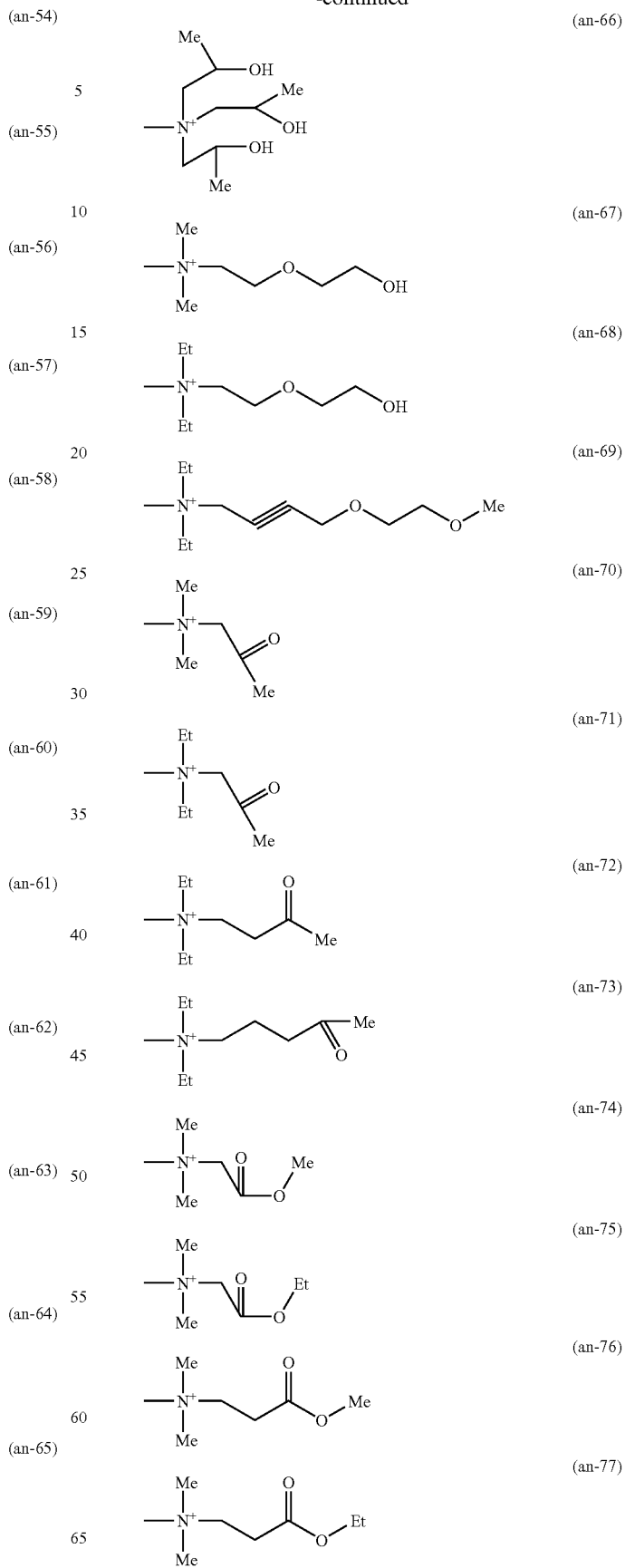

-continued (an-78) [structure]
(an-79) [structure]
(an-80) [structure]
(an-81) [structure]
(an-82) [structure]
(an-83) [structure]
(an-84) [structure]
(an-85) [structure]
(an-86) [structure]
(an-87) [structure]
(an-88) [structure]
(an-89) [structure]

-continued (an-90) [structure]
(an-91) [structure]
(an-92) [structure]
(an-93) [structure]
(an-94) [structure]
(an-95) [structure]
(an-96) [structure]
(an-97) [structure]
(an-98) [structure]
(an-99) [structure]
(an-100) [structure]
(an-101) [structure]
(an-102) [structure]

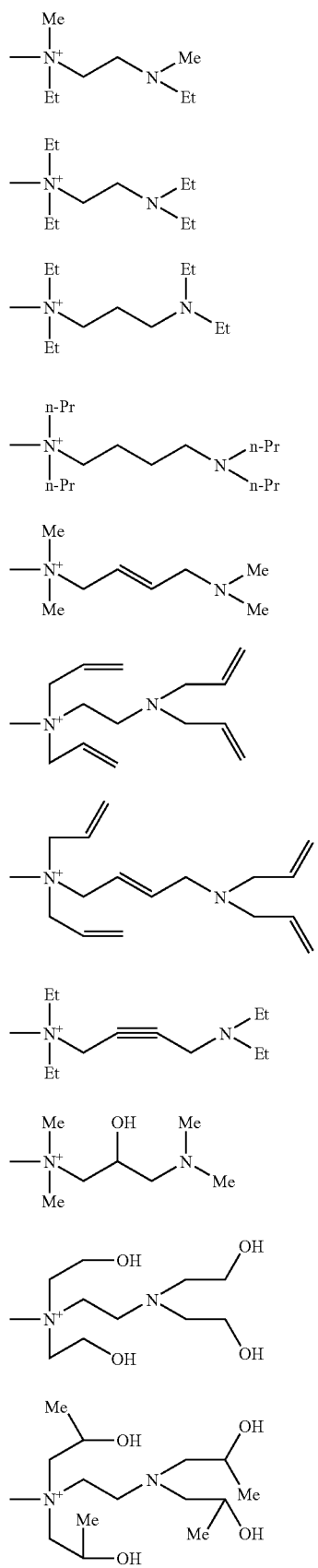
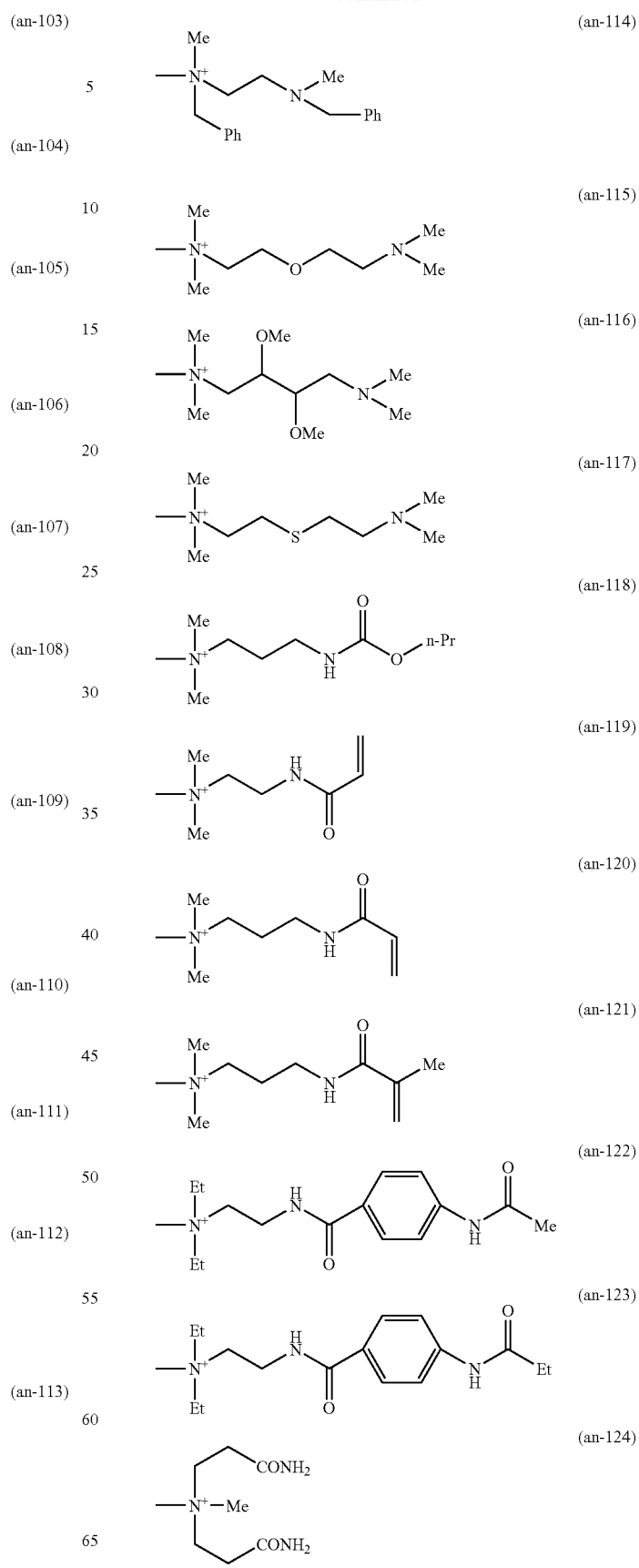

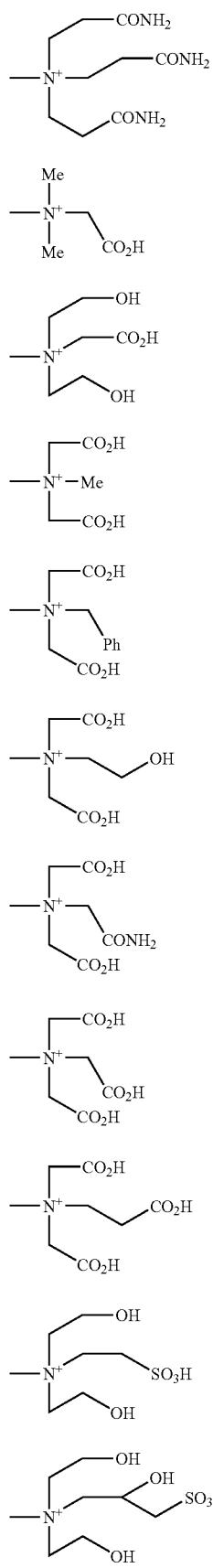
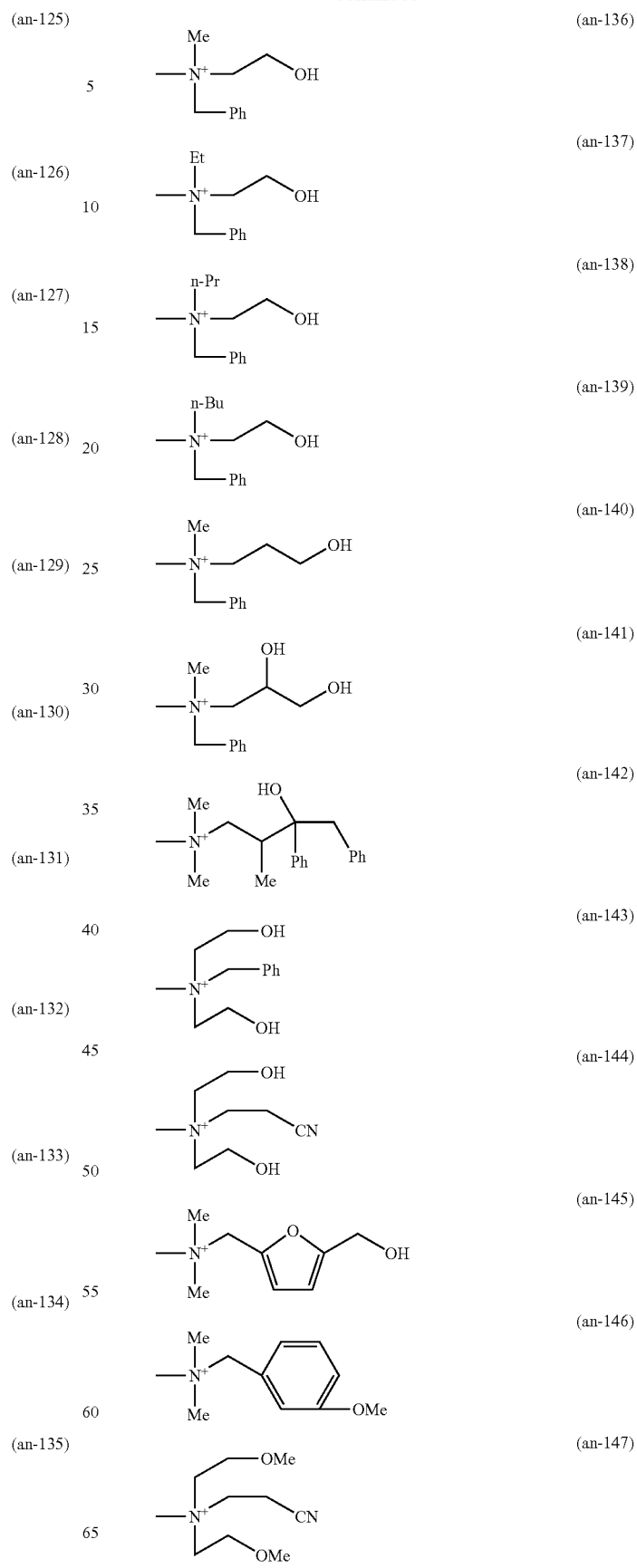

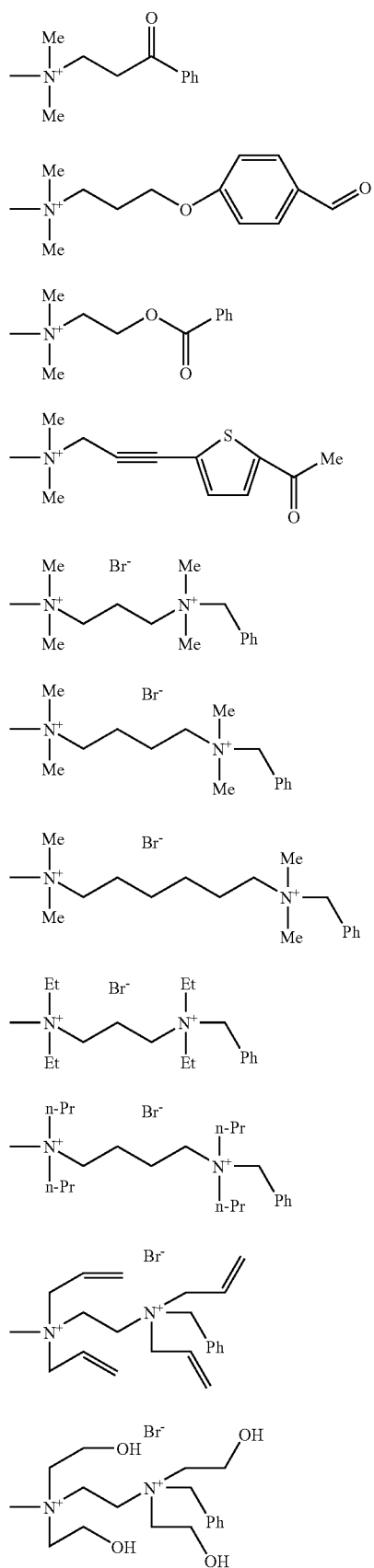
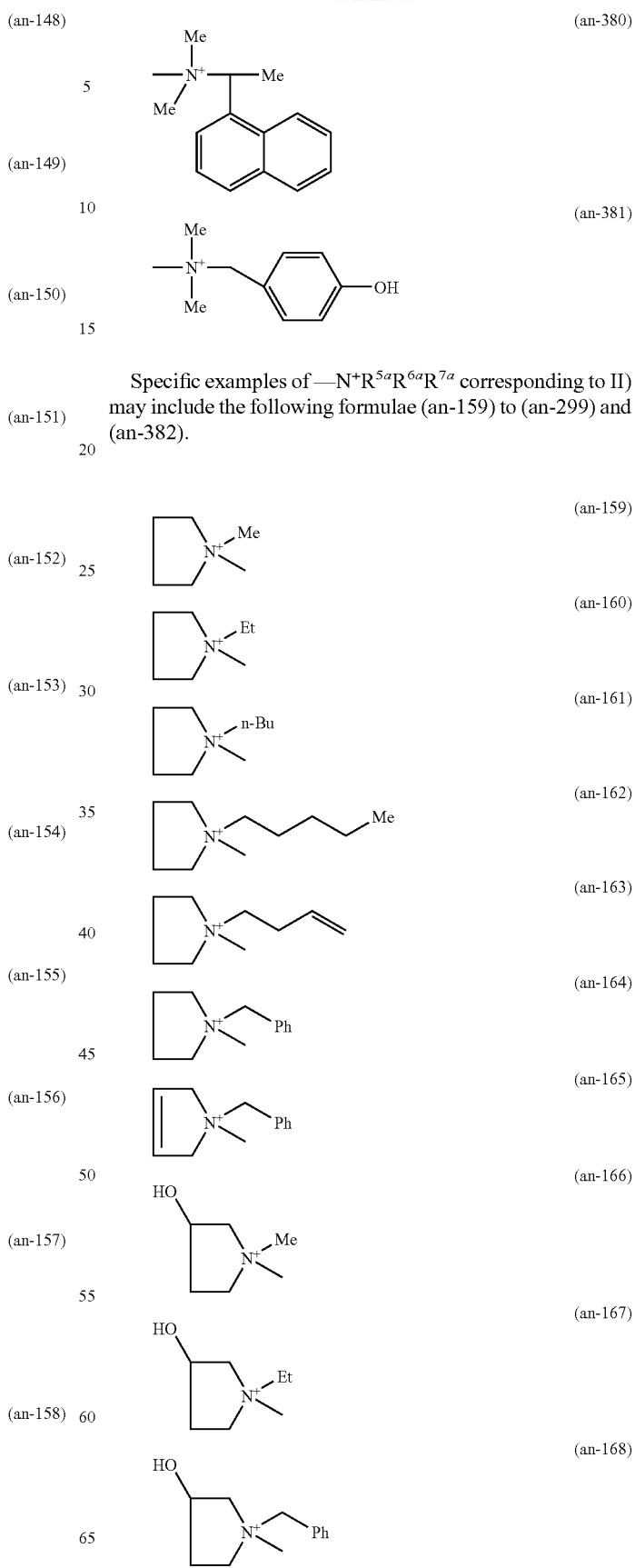
Specific examples of —N⁺R$^{5a}$R$^{6a}$R$^{7a}$ corresponding to II) may include the following formulae (an-159) to (an-299) and (an-382).

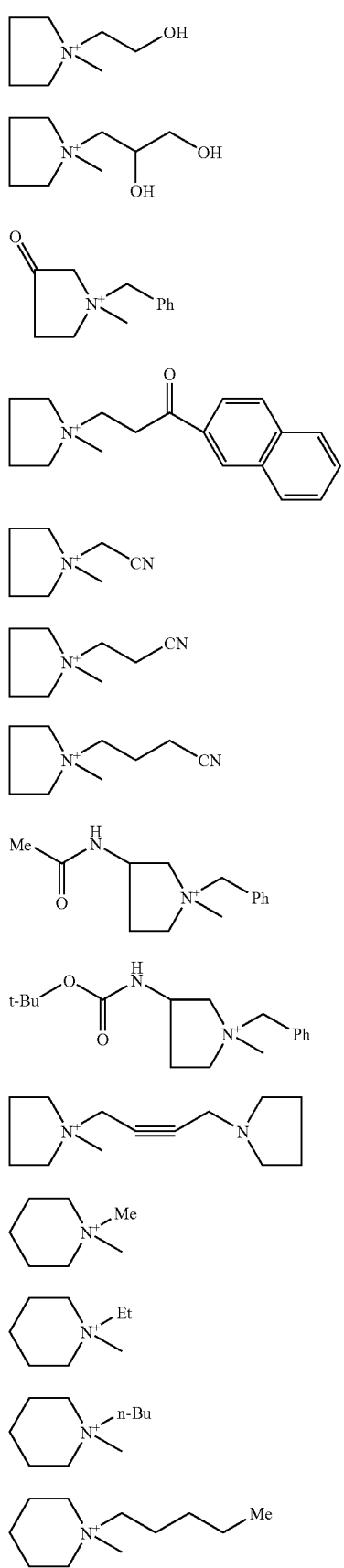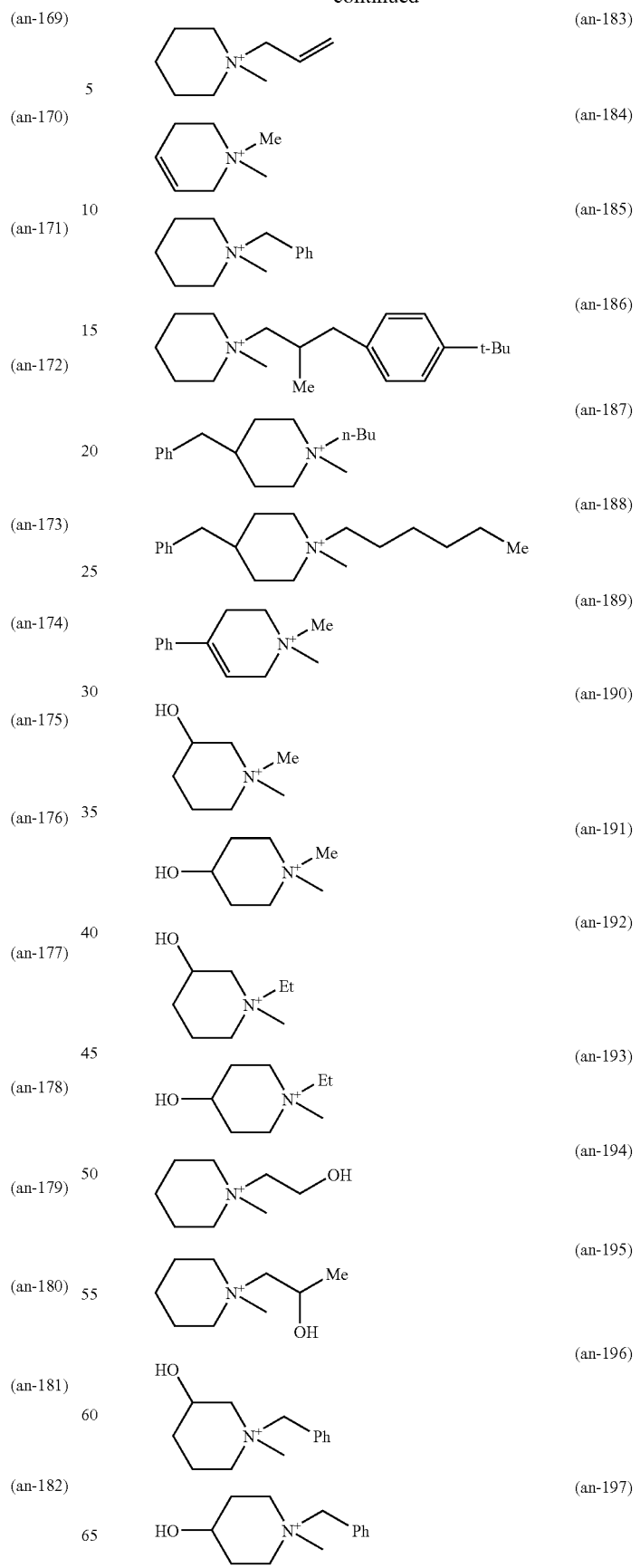

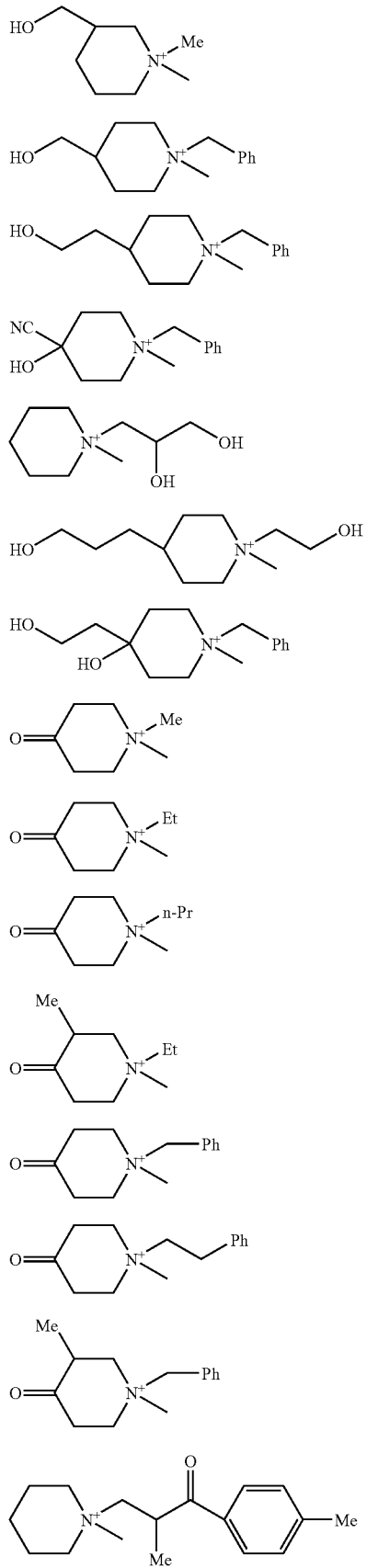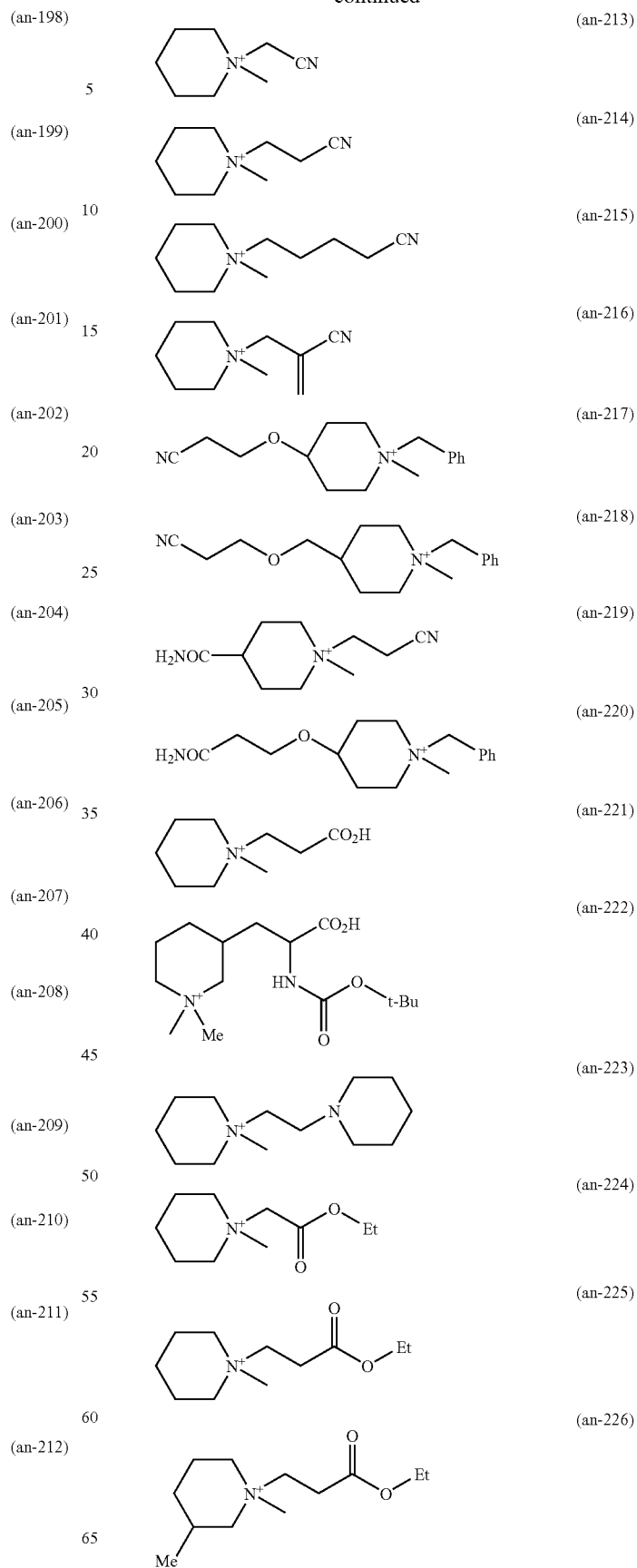

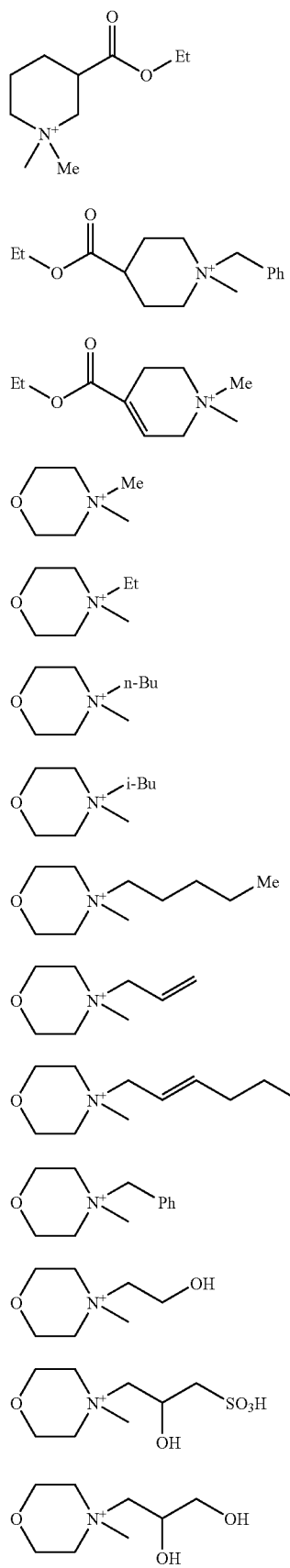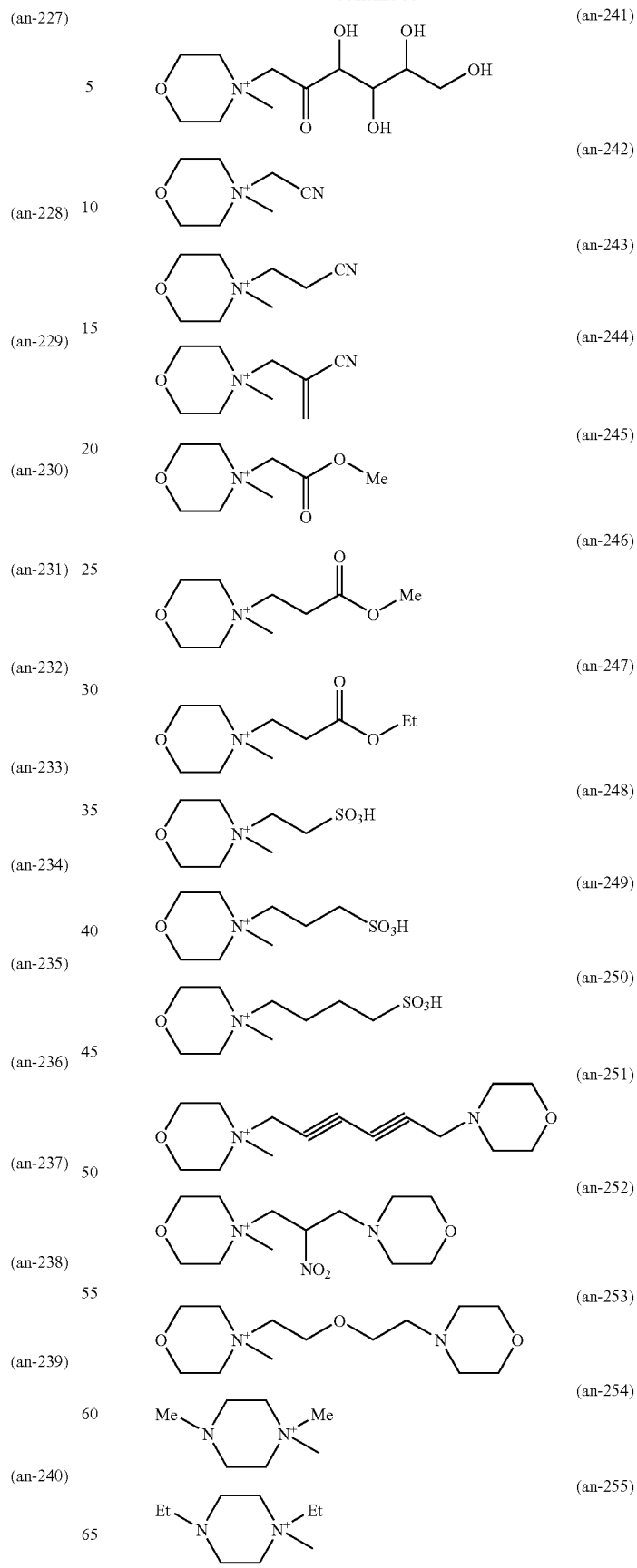

-continued
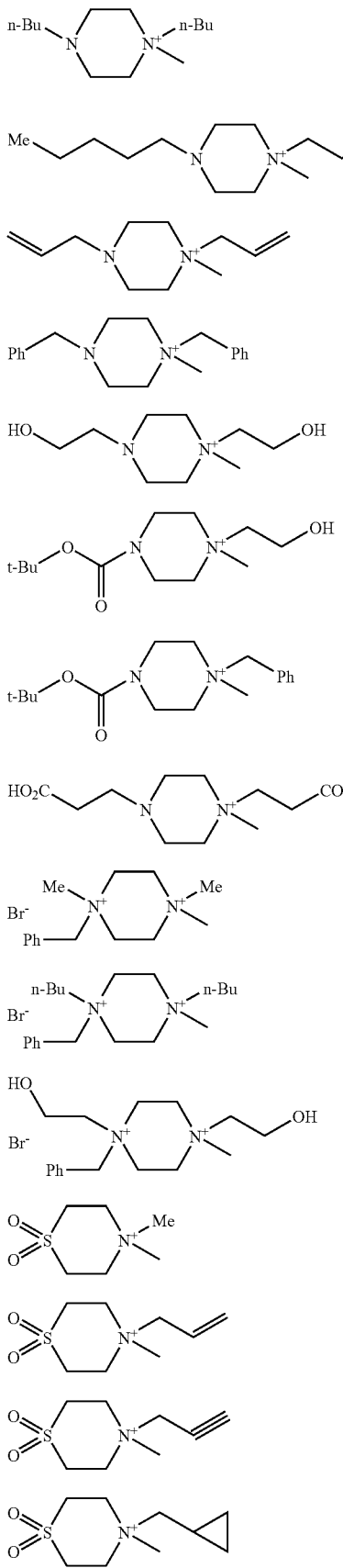
(an-256)
(an-257)
(an-258)
(an-259)
(an-260)
(an-261)
(an-262)
(an-263)
(an-264)
(an-265)
(an-266)
(an-267)
(an-268)
(an-269)
(an-270)
-continued
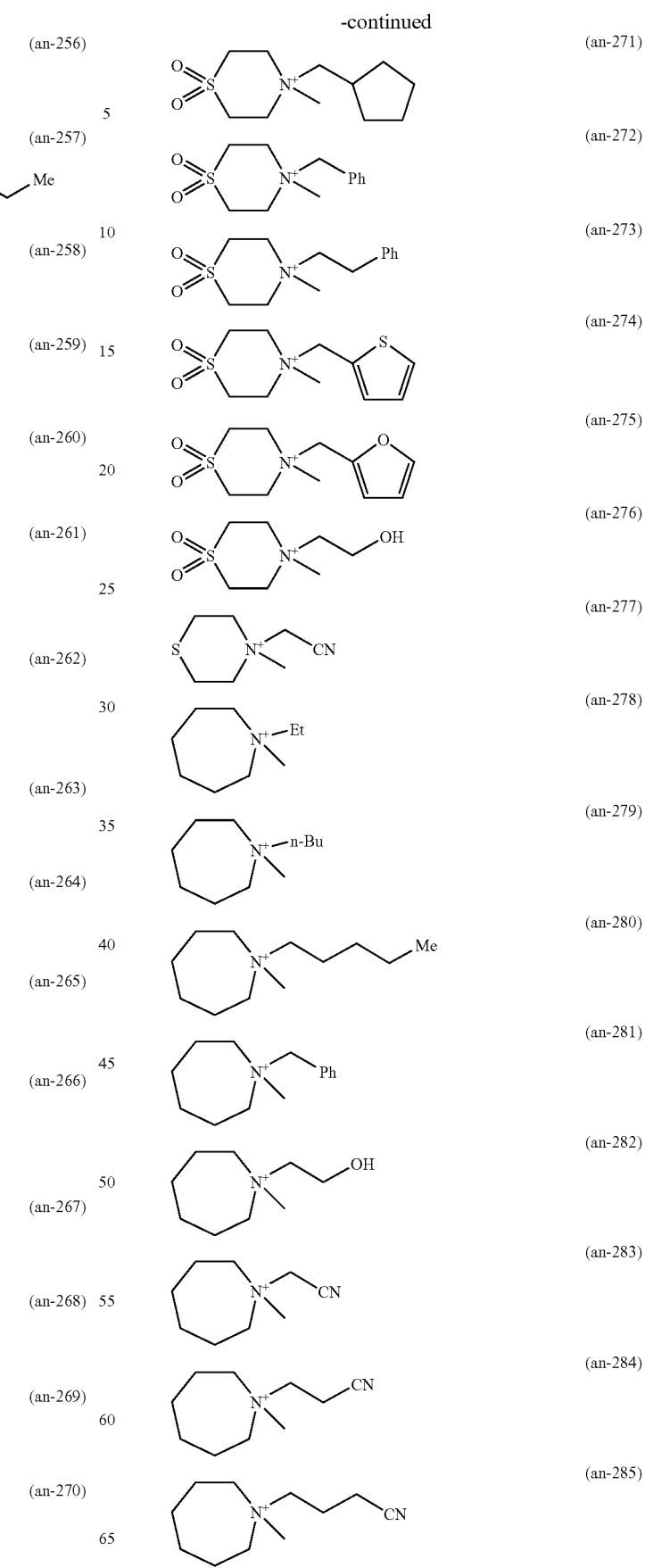
(an-271)
(an-272)
(an-273)
(an-274)
(an-275)
(an-276)
(an-277)
(an-278)
(an-279)
(an-280)
(an-281)
(an-282)
(an-283)
(an-284)
(an-285)

-continued
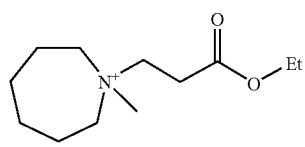
(an-286)
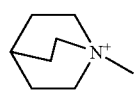
(an-287)
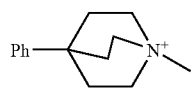
(an-288)
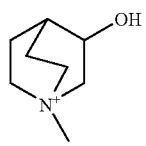
(an-289)
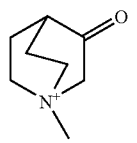
(an-290)
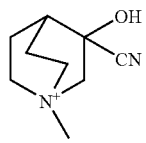
(an-291)
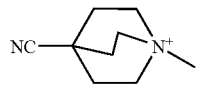
(an-292)
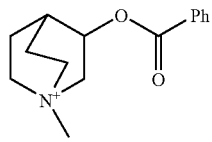
(an-293)
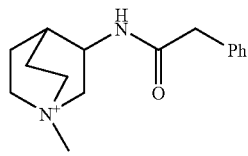
(an-294)
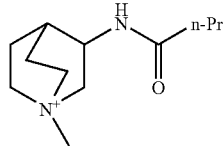
(an-295)
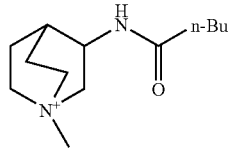
(an-296)
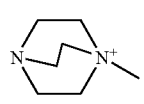
(an-297)
-continued
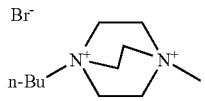
(an-298)
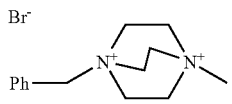
(an-299)
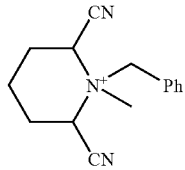
(an-382)
Specific examples of —N$^+$R$^{5a}$R$^{6a}$R$^{7a}$ corresponding to III) may include the following formulae (an-300) to (an-379) and (an-394) to (an-407).
(an-300)
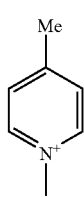
(an-301)
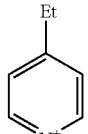
(an-302)
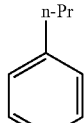
(an-303)
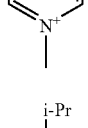
(an-304)
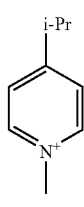

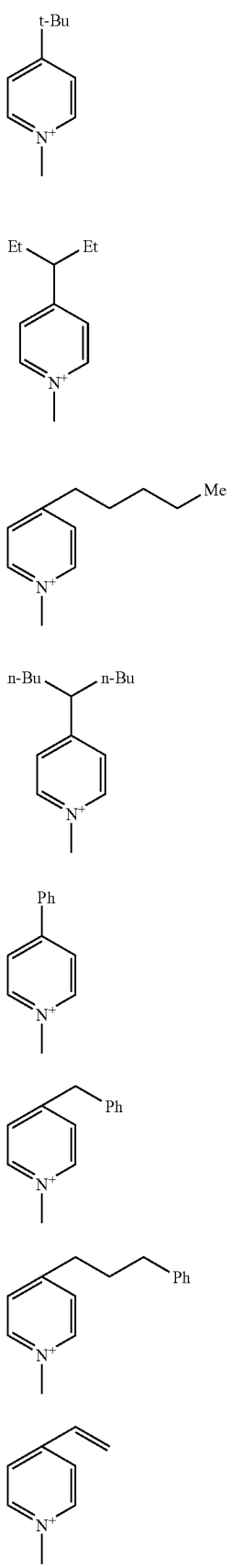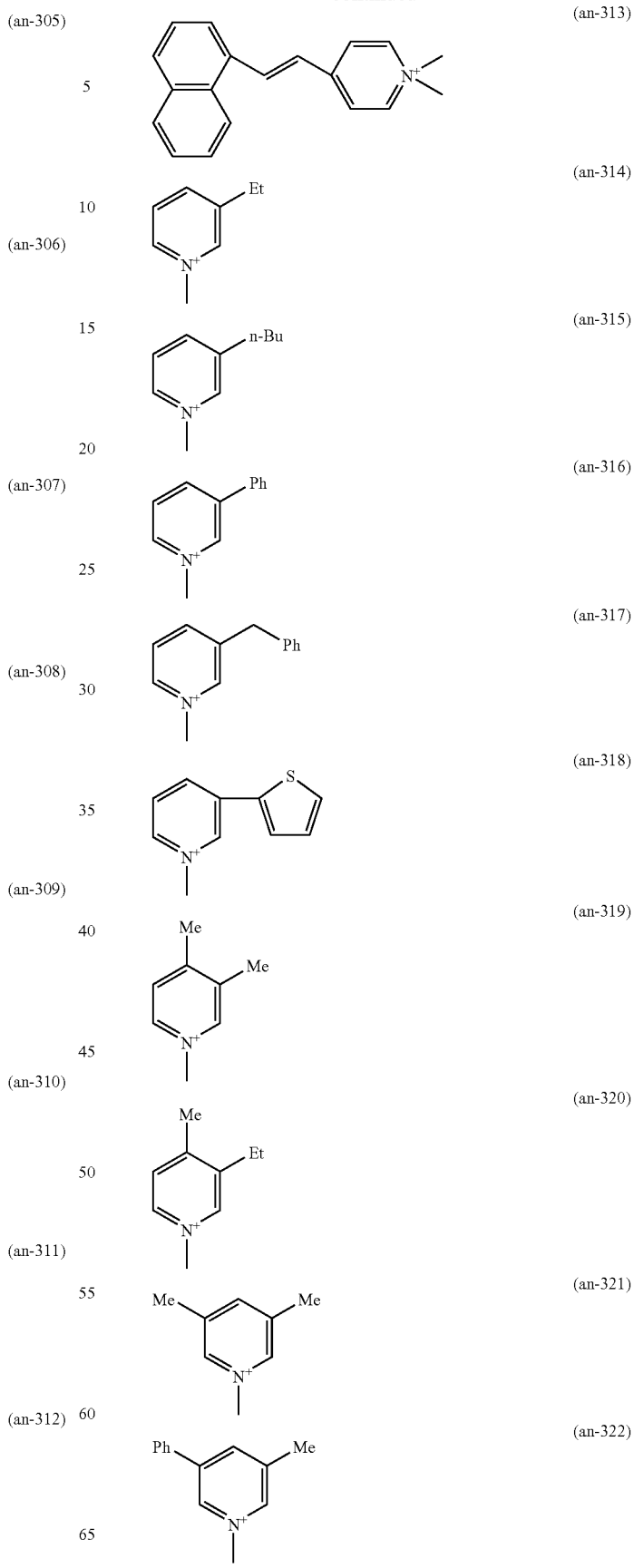

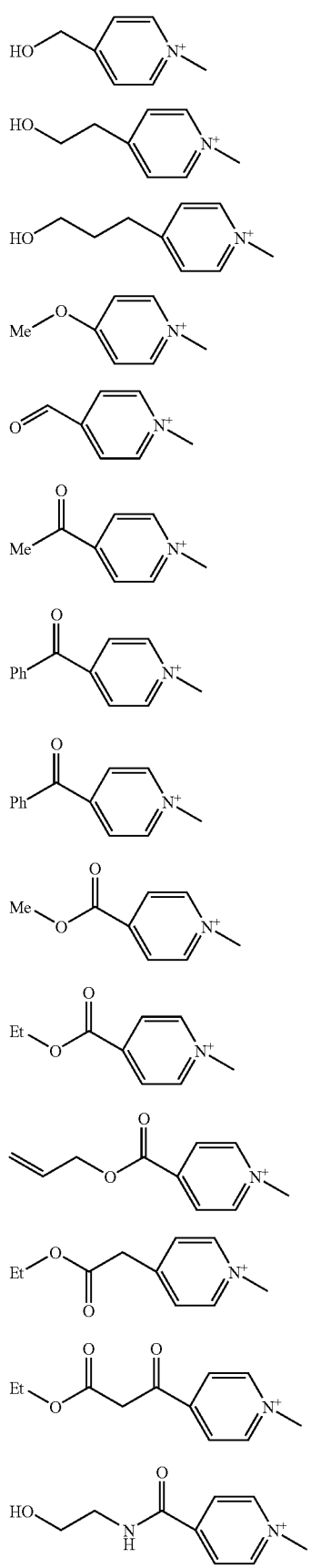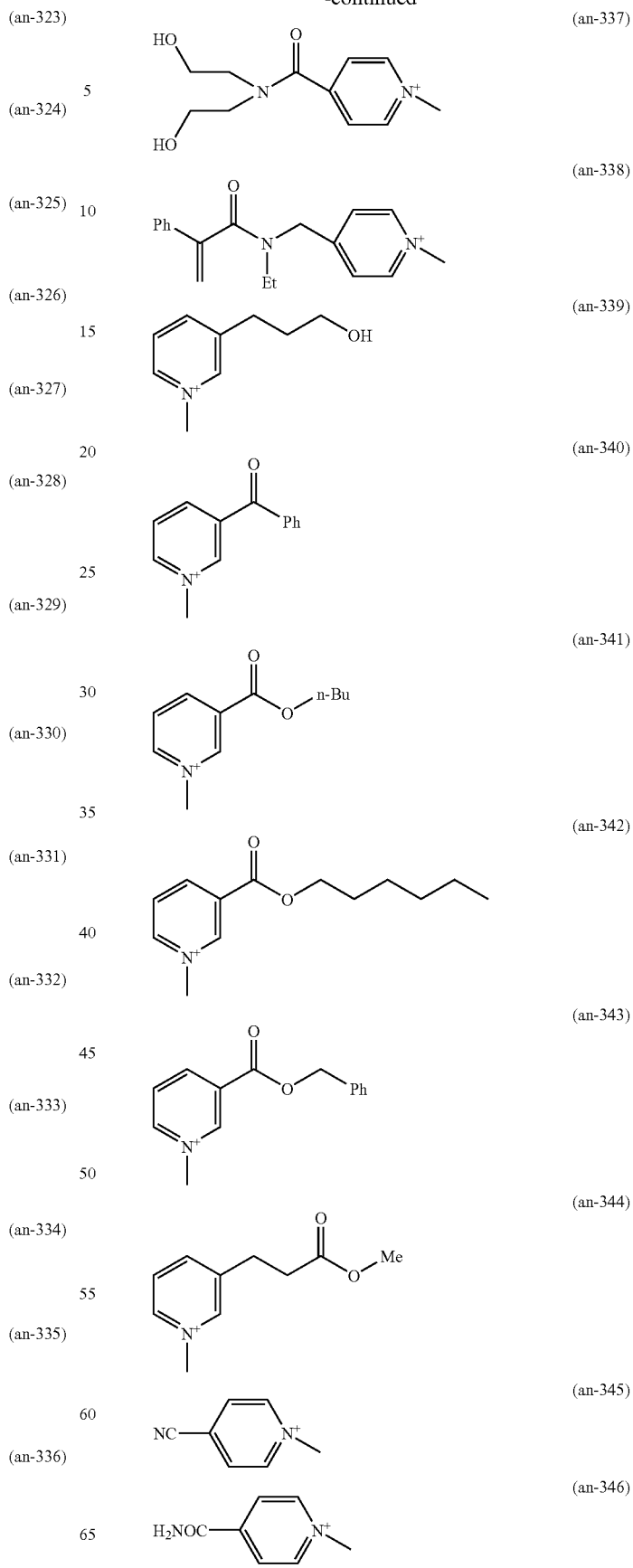

| | |
|---|---|
| 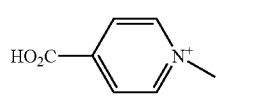 (an-347) | 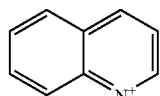 (an-360) |
| 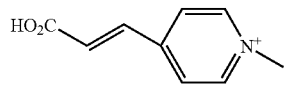 (an-348) | 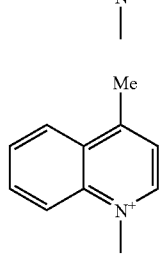 (an-361) |
| 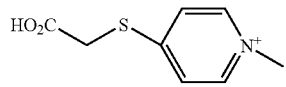 (an-349) | 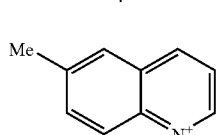 (an-362) |
| 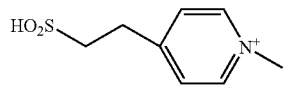 (an-350) | 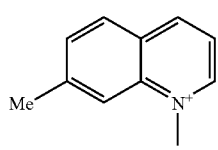 (an-363) |
| 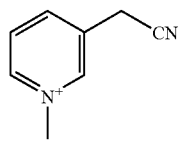 (an-351) | 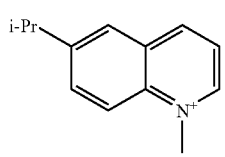 (an-364) |
| 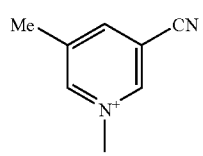 (an-352) | 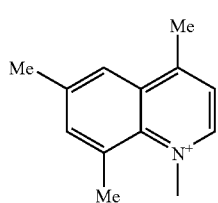 (an-365) |
| 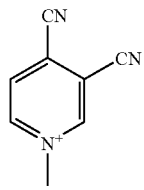 (an-353) | 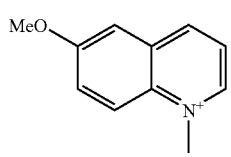 (an-366) |
| 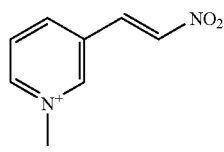 (an-354) | 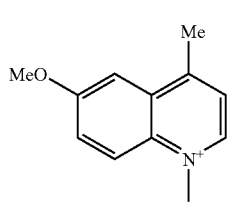 (an-367) |
| 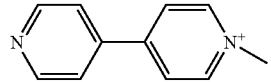 (an-355) | 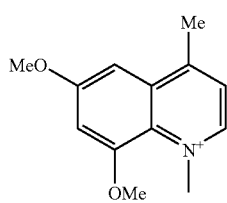 (an-368) |
| 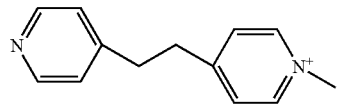 (an-356) | |
| 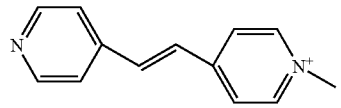 (an-357) | |
| 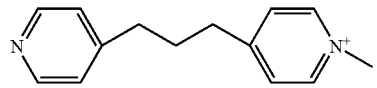 (an-358) | |
| 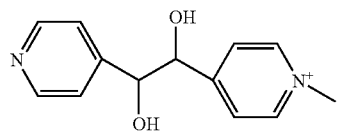 (an-359) | |

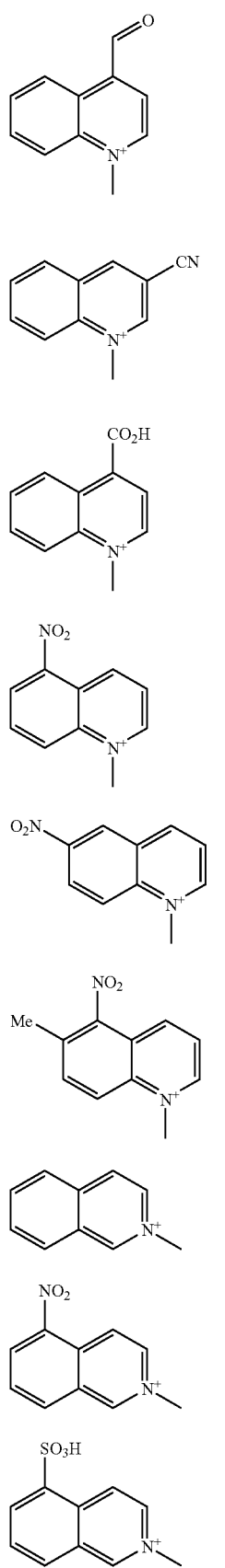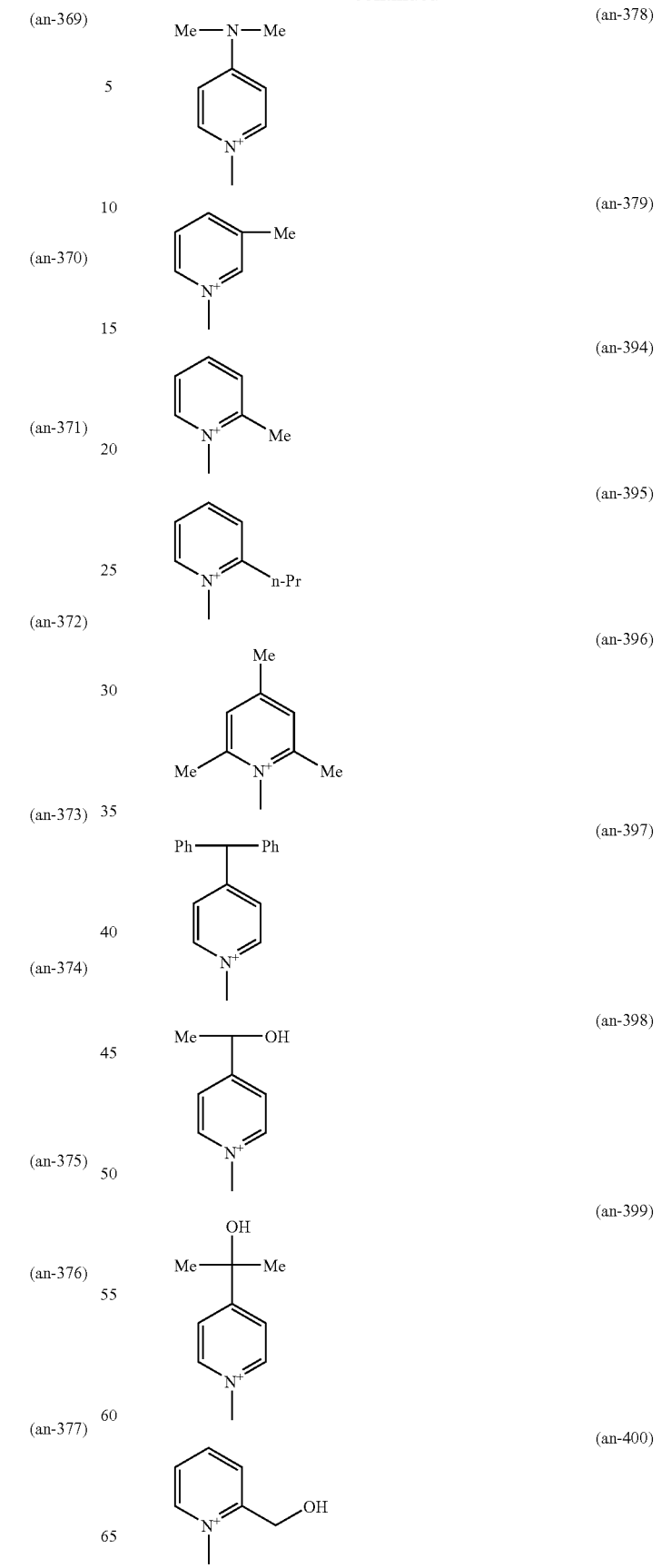

-continued (an-401) 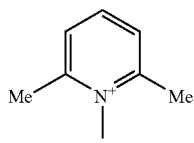

(an-402) 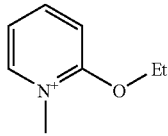

(an-403) 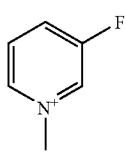

(an-404) 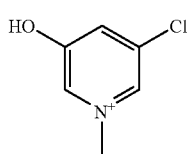

(an-405) 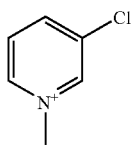

(an-406) 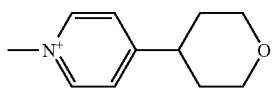

(an-407) 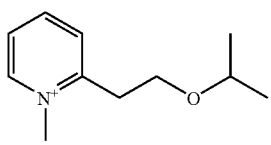

Specific examples of —$N^+R^{5a}R^{6a}R^{7a}$ other than those corresponding to I) to III) may include the following formulae (an-383) to (an-393).

(an-383) 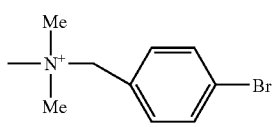

(an-384) 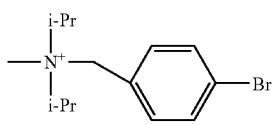

(an-385) 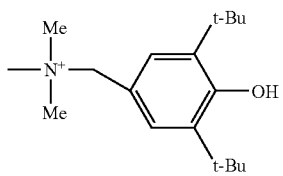

-continued (an-386) 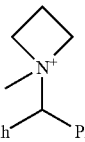

(an-387) 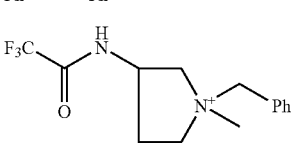

(an-388) 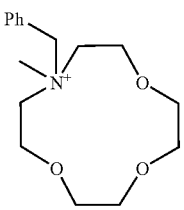

(an-389) 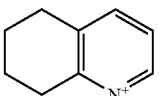

(an-390) 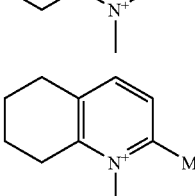

(an-391) 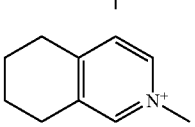

(an-392) 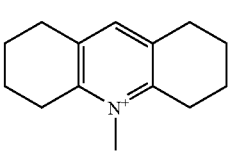

(an-393) 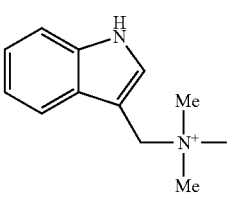

Each of $W^-$ and $X^-$ represents a counteranion. The counteranion may be, regardless of its valence, any of negatively charged ions which can electrically neutralize positively charged ammonium ion in the compound of the present invention. A pharmaceutically acceptable anion is preferable. Preferable examples thereof may include $F^-$, $Cl^-$, $Br^-$, $I^-$, $OH^-$, $CH_3SO_3^-$, $CF_3SO_3^-$, $HCO_2^-$, $CH_3CO_2^-$, $CF_3CO_2^-$, $ClO_4^-$, $IO_4^-$, $HCO_3^-$, $CO_3^{2-}$, $NO_3^-$, $HSO_4^-$, $SO_4^{2-}$, $H_2PO_4^-$, $HPO_4^{2-}$, or $PO_4^{3-}$. Among them, $Cl^-$ and $Br^-$ are particularly preferable. $W^-$ and $X^-$ may be the same as or different from each other, but it is more preferable that they are the same.

The combination of the substitutents in the formula (1B) is not particularly limited, but the following compounds (1) to (46) are particularly preferable.

(1) The compound represented by the above general formula (1B) wherein the combination of ($A^1$, $A^2$, $A^3$) represents ($CH_2$, CH(OH), CH), $Z^a$—$(N^+R^{5a}R^{6a}R^{7a})_n$ represents alkyl group having 2 to 10 carbon atoms substituted with the substitutent —$N^+R^{5a}R^{6a}R^{7a}$, the number of the substituent —$N^+R^{5a}R^{6a}R^{7a}$ being n, and one or more methylenes which constitute $Z^a$ may be replaced with any of phenylene which may have a substitutent or —O—.

(2) The compound according to (1) above wherein $Z^a$—$(N^+R^{5a}R^{6a}R^{7a})_n$ represents straight alkyl group having 2 to 10 carbon atoms substituted with the one —$N^+R^{5a}R^{6a}R^{7a}$, and one or more methylenes which constitute $Z^a$ may be replaced with any of phenylene which may have a substitutent or —O—.

(3) The compound according to (2) above wherein $Z^a$—$(N^+R^{5a}R^{6a}R^{7a})_n$ represents straight alkyl group having 2 to 10 carbon atoms substituted with one —$N^+R^{5a}R^{6a}R^{7a}$, or straight alkyl group having 2 to 10 carbon atoms substituted with one —$N^+R^{5a}R^{6a}R^{7a}$ wherein one methylene which constitutes $Z^a$ is replaced with phenylene which may have a substitutent, or straight alkyl group having 2 to 10 carbon atoms substituted with one —$N^+R^{5a}R^{6a}R^{7a}$ wherein one methylene which constitutes $Z^a$ is replaced with —O—, or straight alkyl group having 2 to 10 carbon atoms substituted with one —$N^+R^{5a}R^{6a}R^{7a}$ wherein one methylene which constitutes $Z^a$ is replaced with phenylene which may have a substitutent and further another methylene is replaced with —O—.

(4) The compound according to (3) above wherein $Z^a$ is a straight methylene chain having 2 to 10 carbon atoms, or a straight methylene chain having 2 to 10 carbon atoms wherein one methylene is replaced with phenylene which may have a substitutent, or a straight methylene chain having 2 to 10 carbon atoms wherein one methylene is replaced with —O—, or a straight methylene chain having 2 to 10 carbon atoms wherein one methylene is replaced with phenylene which may have a substitutent and further another methylene is replaced with —O—.

(5) The compound according to any of (1) to (4) above wherein Y is —NHCS— or —NHCSNH— at para or meta position.

(6) The compound according to (5) above wherein Y is —NHCS— at meta position and $Z^a$ is a straight methylene chain having 2 to 10 carbon atoms.

(7) The compound according to (6) above wherein Y is —NHCS— at meta position and $Z^a$ is a straight methylene chain having 5 carbon atoms.

(8) The compound according to (5) above wherein Y is —NHCSNH— at meta position and $Z^a$ is a straight methylene chain having 2 to 10 carbon atoms wherein one methylene is replaced with phenylene which may have a substitutent.

(9) The compound according to (8) above wherein Y is —NHCSNH— at meta position and $Z^a$ is the following formula (sp-14):

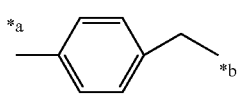

(sp-14)

wherein *a is bound to Y and *b is bound to $N^+R^{5a}R^{6a}R^{7a}$ in the formula (1B).

(10) The same compound as the compound according to any of (1) to (9) above except that the combination of ($A^1, A^2, A^3$) is (NH, CH(OH), CH).

(11) The same compound as the compound according to any of (1) to (9) above except that the combination of ($A^1, A^2, A^3$) is ($CH_2, CH_2$, N).

(12) The compound represented by the aforementioned general formula (1B) wherein Y is —NHCSNH— at meta position, $Z^a$—$(N^+R^{5a}R^{6a}R^{7a})_n$ represents straight alkyl group having 2 to 10 carbon atoms substituted with one —$N^+R^{5a}R^{6a}R^{7a}$, wherein one methylene which constitutes $Z^a$ must be replaced with phenylene which has a substitutent, the substitutent(s) on phenylene having the substitutent(s) are 1 to 4 substitutents selected from the group consisting of alkyl group having 1 to 5 carbon atoms, alkoxy group having 1 to 5 carbon atoms, nitro group, halogen atom, trifluoromethyl group and —$CH_2N^+R^{5a}R^{6a}R^{7a}$, and the substitutents may be the same or different from one another.

(13) The compound according to (12) above wherein the combination of ($A^1, A^2, A^3$) is ($CH_2$, NH, CH).

(14) The compound according to (12) above wherein the combination of ($A^1, A^2, A^3$) is ($CH_2$, CH(OH), CH).

(15) The compound according to (12) above wherein the combination of ($A^1, A^2, A^3$) is (NH, CH(OH), CH).

(16) The compound according to (12) above wherein the combination of ($A^1, A^2, A^3$) is ($CH_2, CH_2$, N).

(17) The compound according to (12) above wherein Y is —NHCSNH— at meta position and $Z^a$ represents the straight methylene chain having 2 to 10 carbon atoms, and one methylene which constitutes $Z^a$ is replaced with phenylene substituted with one of any of methyl, —F, —Cl, —Br or trifluoromethyl.

(18) The compound according to (17) above wherein the combination of ($A^1, A^2, A^3$) is ($CH_2$, NH, CH).

(19) The compound according to (17) above wherein the combination of ($A^1, A^2, A^3$) is ($CH_2$, CH(OH), CH).

(20) The compound according to (17) above wherein the combination of ($A^1, A^2, A^3$) is (NH, CH(OH), CH).

(21) The compound according to (17) above wherein the combination of ($A^1, A^2, A^3$) is ($CH_2, CH_2$, N).

(22) The compound according to (17) above wherein Y is —NHCSNH— at meta position, $Z^a$ is any of the following formulae:

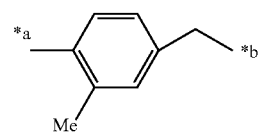

(sp-26)

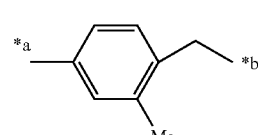

(sp-27)

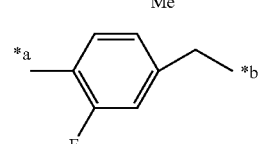

(sp-28)

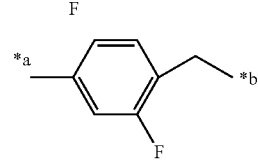

(sp-29)

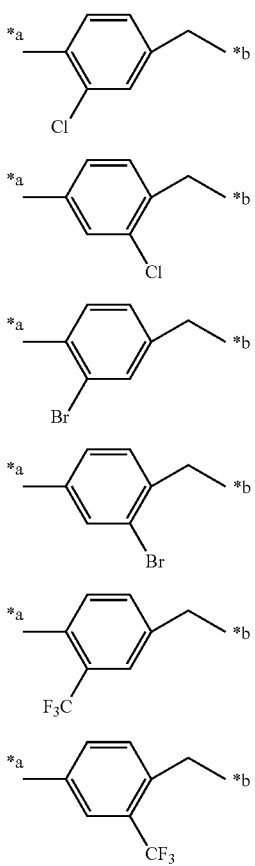

(sp-30)
(sp-31)
(sp-32)
(sp-33)
(sp-34)
(sp-35)

wherein *a is bound to Y and *b is bound to $N^+R^{5a}R^{6a}R^{7a}$ in the formula (1B).

(23) The compound according to (22) above wherein the combination of $(A^1, A^2, A^3)$ is $(CH_2, NH, CH)$.

(24) The compound according to (22) above wherein the combination of $(A^1, A^2, A^3)$ is $(CH_2, CH(OH), CH)$.

(25) The compound according to (22) above wherein the combination of $(A^1, A^2, A^3)$ is $(NH, CH(OH), CH)$.

(26) The compound according to (17) above wherein the combination of $(A^1, A^2, A^3)$ is $(CH_2, CH_2, N)$

(27) The compound according to any of (1) to (26) above wherein each of $N^+R^{5a}R^{6a}R^{7a}$ is independently any of the following I), II) or III):

I) $R^{5a}, R^{6a}$ and $R^{7a}$ may be the same as or different from one another, and each represents alkyl group having 1 to 10 carbon atoms, alkenyl group having 3 to 8 carbon atoms or alkynyl group having 3 to 9 carbon atoms. The alkyl group, the alkenyl group and the alkynyl group may be substituted with one or more groups of phenyl, thienyl, cyclohexyl, cyano, hydroxy, oxo, carboxy, —$CONH_2$ and —$SO_3H$, and further one or more methylenes which constitute the alkyl group, the alkenyl group and the alkynyl group may be replaced with any of phenylene, thienylene, furylene, —O—, —$CO_2$—, —NHCO—, —$NR^8$—, and —$N^+W^-R^9R^{10}$—. $R^8$ represents alkyl group having 1 to 3 carbon atoms or alkenyl group having 3 carbon atoms. The alkyl group may be substituted with one or more groups of phenyl or hydroxy. $R^9$ and $R^{10}$ may be the same as or different from each other, and each represents alkyl group having 1 to 3 carbon atoms or alkenyl group having 3 carbon atoms, and the alkyl group may be substituted with one or more groups of phenyl or hydroxy;

II) $N^+R^{5a}R^{6a}R^{7a}$ represents a monocyclo or bicyclo ring which is any of pyrrolidinium ring, piperidinium ring, morpholinium ring, thiomorpholinium ring, piperazinium ring, azepanium ring, quinuclidinium ring and 1,4-diazabicyclo[2.2.2]octanium ring, with a proviso that the position of binding to $Z^a$ is the ammonium nitrogen atom. The monocyclo and bicyclo rings may be substituted with one or more groups of hydroxy, oxo, cyano, phenyl, —$CONH_2$, and —$R^{11}$. $R^{11}$ represents alkyl group having 1 to 6 carbon atoms or alkenyl group having 3 carbon atoms. The alkyl group in $R^{11}$ may be substituted with one or more groups of hydroxy, cyano, phenyl and —$CONH_2$, and further one or more methylenes which constitute the alkyl group may be replaced with any of —O—, —$CO_2$—, and —NHCO—. The group which is not involved in the formation of the ring in $R^{5a}$, $R^{6a}$ and $R^{7a}$ represents alkyl group having 1 to 6 carbon atoms, alkenyl group having 3 to 4 carbon atoms or alkynyl group having 3 to 6 carbon atoms. The alkyl group, the alkenyl group and the alkynyl group in $R^{5a}$, $R^{6a}$ and $R^{7a}$ may be substituted with one or more groups of phenyl, thienyl, furyl, piperidyl, pyrrolidyl, morpholyl, cyclopropyl, cyclopentyl, cyano, hydroxy, oxo, nitro, carboxy, —$CONH_2$ and —$SO_3H$, and further one or more methylenes which constitute the alkyl group may be replaced with any of phenylene, —O—, and —$CO_2$—; and III) $N^+R^{5a}R^{6a}R^{7a}$ represents pyridinium ring, quinolinium ring or isoquinolinium ring, with a proviso that the position of binding to $Z^a$ is the ammonium nitrogen atom. The pyridinium ring and the quinolinium ring may be substituted with one or more groups of cyano, nitro, phenyl, thienyl, pyridyl, alkoxy having 1 to 3 carbon atoms, carboxy, —$CONH_2$, and —$R^{12a}$. $R^{12a}$ represents alkyl group having 1 to 9 carbon atoms or alkenyl group having 2 to 4 carbon atoms. The alkyl group and the alkenyl group in $R^{12a}$ may be substituted with one or more groups of phenyl, naphthyl, pyridyl, cyano, nitro, hydroxy, oxo, carboxy, and —$SO_3H$; and further one or more methylenes which constitute the alkyl group and the alkenyl group may be replaced with any of —S—, —$CO_2$—, —NHCO— and —$NR^8$—. $R^8$ represents alkyl group having 1 to 3 carbon atom, and the alkyl group may be substituted with one or more hydroxy groups.

(28) The compound according to (1) to (26) above wherein each of $N^+R^{5a}R^{6a}R^{7a}$ is independently any of the following I), II) or III):

I) $R^{5a}, R^{6a}$ and $R^{7a}$ may be the same as or different from one another, and each represents straight alkyl group having 1 to 10 carbon atoms, straight alkenyl group having 3 to 6 or 8 carbon atoms, branched alkenyl group having 4, 6 or 7 carbon atoms, straight alkynyl group having 3, 5, 6, 7 or 9 carbon atoms or branched alkynyl group having 6 carbon atoms, wherein: 1) the alkyl group, the alkenyl group and the alkynyl group in $R^{5a}$, $R^{6a}$ and $R^{7a}$ are substituted with any one of phenyl, thienyl, cyclohexyl, cyano, hydroxy, oxo, carboxy, —$CONH_2$ or —$SO_3H$; or 2) the alkyl group, the alkenyl group and the alkynyl group are substituted with two hydroxy groups; or 3) the alkyl group, the alkenyl group and the alkynyl group are substituted with one hydroxy group and one —$SO_3H$; or 4) the alkyl group, the alkenyl group and the alkynyl group are substituted with one oxo group and one phenyl group; or 5) the alkyl group, the alkenyl group and the alkynyl group are substituted with one hydroxy group and two phenyl groups; or 6) one methylene which constitutes the alkyl group, the alkenyl group and the alkynyl group is replaced with any of phenylene, furylene, —$CO_2$—, —NHCO—, —$NR^8$— ($R^8$ represents any of methyl, ethyl, n-propyl, 2-propenyl, 2-hydroxyethyl, 2-hydroxypropyl or benzyl) or —$N^+W^-R^9R^{10}$— ($R^9$ and $R^{10}$ represent any of methyl, ethyl, n-propyl, 2-propenyl, 2-hydroxyethyl, or benzyl); or 7) two methylenes which constitute the alkyl group, the alkenyl group and the alkynyl group are replaced with any of two —O—, one phenylene and one —O—, one —O— and one —NR$^8$— or one —NHCO— and one —O—; or 8) three methylenes which constitute the alkyl group, the alkenyl group and the alkynyl group are replaced with any of two —O— and one —NR$^8$— or one phenylene and two —NHCO—; or 9) the alkyl group, the alkenyl group and the alkynyl group are substituted with one hydroxy group, and further one methylene which constitutes the alkyl group, the alkenyl group and the alkynyl group is replaced with —O—; or 10) the alkyl group, the alkenyl group and the alkynyl group are substituted with one hydroxy group, and further one methylene which constitutes the alkyl group, the alkenyl group and the alkynyl group is replaced with —NR$^8$—; or 11) the alkyl group, the alkenyl group and the alkynyl group are substituted with one hydroxy group, and further one methylene which constitutes the alkyl group, the alkenyl group and the alkynyl group is replaced with furylene; or 12) the alkyl group, the alkenyl group and the alkynyl group are substituted with one oxo group, and further one methylene which constitutes the alkyl group, the alkenyl group and the alkynyl group is replaced with thienylene; or 13) the alkyl group, the alkenyl group and the alkynyl group are substituted with one oxo group, and further two methylenes which constitute the alkyl group, the alkenyl group and the alkynyl group are replaced with one —O— and one phenylene. Alternatively, the alkyl group, the alkenyl group and the alkynyl group are not substituted or replaced;

II) N$^+$R$^{5a}$R$^{6a}$R$^{7a}$ represents a monocyclo or bicyclo ring which is any of pyrrolidinium ring, piperidinium ring, morpholinium ring, thiomorpholinium ring, piperazinium ring, azepanium ring, quinuclidinium ring and 1,4-diazabicyclo[2.2.2]octanium ring, with a proviso that the position of binding to Z$^a$ is the ammonium nitrogen atom. The monocyclo and bicyclo rings are 1) substituted with any one of hydroxy, oxo, cyano, phenyl, —CONH or —R$^{11}$; or 2) substituted with one cyano group and one hydroxy group; or 3) substituted with one hydroxy group and one —R$^{11}$; or 4) substituted with one oxo group and one —R$^{11}$; or 5) substituted with two oxo groups; or 6) substituted with two —R$^{11}$. Alternatively, the monocyclo and bicyclo rings are not substituted. In this embodiment, R$^{11}$ represents any group of methyl, ethyl, n-propyl, n-butyl, n-pentyl, 2-propenyl, benzyl, acetylamino, t-butoxycarbonylamino, hydroxymethyl, 2-hydroxyethyl, 3-hydroxypropyl, 2-cyanoethoxy, (2-cyanoethoxy)methyl, 2-carbamoylethoxy, ethoxycarbonyl, t-butoxycarbonyl, benzoyloxy, phenylacetylamino, butanoylamino and pentanoylamino.

The group which is not involved in the formation of the ring in R$^{5a}$, R$^{6a}$ and R$^{7a}$ represents straight alkyl group having 1 to 6 carbon atoms, straight alkenyl group having 3 to 4 carbon atoms or straight alkynyl group having 3, 4 or 6 carbon atoms, wherein 1) the alkyl group, the alkenyl group and the alkynyl group in R$^{5a}$, R$^{6a}$ and R$^{7a}$ are substituted with any one of phenyl, thienyl, furyl, piperidyl, pyrrolidyl, morpholyl, cyclopropyl, cyclopentyl, cyano, hydroxy, carboxy or —SO$_3$H; or 2) the alkyl group, the alkenyl group and the alkynyl group are substituted with two hydroxy groups; or 3) the alkyl group, the alkenyl group and the alkynyl group are substituted with one hydroxy group and one —SO$_3$H; or 4) the alkyl group, the alkenyl group and the alkynyl group are substituted with four hydroxy groups and one oxo group; or 5) the alkyl group, the alkenyl group and the alkynyl group are substituted with one nitro group and one morpholyl group; or 6) one methylene which constitutes the alkyl group, the alkenyl group and the alkynyl group is replaced with —CO$_2$—; or 7) the alkyl group, the alkenyl group and the alkynyl group are substituted with one morpholyl group and further one methylene which constitutes the alkyl group, the alkenyl group and the alkynyl group is replaced with —O—. Alternatively the alkyl group, the alkenyl group and the alkynyl group are not substituted or replaced; and III) N$^+$R$^{5a}$R$^{6a}$R$^{7a}$ represents any of 1) the pyridinium ring substituted with one of any of cyano, phenyl, thienyl, pyridyl, methoxy, ethoxy, propoxy, carboxy, —COHN$_2$— or —R$^{12a}$; 2) the pyridinium ring substituted with two cyano groups; 3) the pyridinium ring substituted with two —R$^{12a}$; 4) the pyridinium ring substituted with one cyano group and one —R$^{12a}$; 5) the pyridinium ring substituted with one phenyl group and one —R$^{12a}$; 6) the quinolinium ring substituted with one of any of cyano, nitro, carboxy, methoxy, ethoxy, propoxy or —R$^{12a}$; 7) the quinolinium ring substituted with one methoxy group and one —R$^{12a}$; 8) the quinolinium ring substituted with one nitro group and one —R$^{12a}$; 9) the unsubstituted pyridinium ring; 10) the unsubstituted quinolinium ring; or 11) the unsubstituted isoquinolinium ring. In this embodiment, R$^{12a}$ represents any of methyl, ethyl, n-propyl, i-propyl, n-butyl, t-butyl, n-pentyl, 3-pentyl, 5-nonyl, vinyl, benzyl, 3-phenylpropyl, 2-(1-naphthyl)vinyl, hydroxymethyl, 2-hydroxyethyl, 3-hydroxypropyl, formyl, acetyl, propionyl, benzoyl, methoxycarbonyl, ethoxycarbonyl, butoxycarbonyl, hexoxycarbonyl, benzyloxycarbonyl, 2-propenyloxycarbonyl, ethoxycarbonylmethyl, 2-(methoxycarbonyl)ethyl, ethoxycarbonylmethylcarbonyl, 2-hydroxyethylaminocarbonyl, bis(2-hydroxyethyl)aminocarbonyl, 2-carboxyvinyl, carboxymethylthio, cyanomethyl, 2-nitrovinyl, 2-(4-pyridyl)ethyl, 2-(4-pyridyl)vinyl, 3-(4-pyridyl)propyl, 2-(4-pyridyl)-1,2-dihydroxyethyl and 2-sulfoethyl. The binding position to Z$^a$ is the ammonium nitrogen atom.

(29) The compound according to any of (1) to (26) above wherein each of N$^+$R$^{5a}$R$^{6a}$R$^{7a}$ is independently any of the following I), II) or III):

I) R$^{5a}$, R$^{6a}$ and R$^{7a}$ may be the same as or different from one another, and each represents any of straight alkyl group having 1 to 10 carbon atoms, straight alkyl group having 1 to 10 carbon atoms substituted with one phenyl group, straight alkyl group having 1 to 10 carbon atoms substituted with one hydroxy group, straight alkenyl group having 3 to 6 or 8 carbon atoms, branched alkenyl group having 4, 6 or 7 carbon atoms, straight alkynyl group having 3, 5, 6, 7 or 9 carbon atoms or branched alkynyl group having 6 carbon atoms;

II) N$^+$R$^{5a}$R$^{6a}$R$^{7a}$ represents the pyrrolidinium ring, the piperidinium ring, the azepanium ring, the quinuclidinium ring or the 1,4-diazabicyclo[2.2.2]octanium ring substituted with one of any of methyl, ethyl, n-propyl, n-butyl, n-pentyl, 2-propenyl, benzyl, hydroxy, hydroxymethyl, 2-hydroxyethyl or 3-hydroxypropyl, or unsubstituted.

The binding position thereof to Z$^a$ is the ammonium nitrogen atom. The group which is not involved in the formation of the ring in R$^{5a}$, R$^{6a}$ and R$^{7a}$ represents straight alkyl group having 1 to 6 carbon atoms, straight alkyl group having 1 to 6 carbon atoms substituted with one phenyl group, straight alkyl group having 1 to 6 carbon atoms substituted with one hydroxy group, straight alkenyl group having 3 to 4 carbon atoms or straight alkynyl group having 3, 4 or 6 carbon atoms; and (III) N$^+$R$^{5a}$R$^{6a}$R$^{7a}$ represents any of the unsubstituted pyridinium ring, the unsubstituted quinolinium ring, the unsubstituted isoquinolinium ring, the pyridinium ring substituted with one of any of methyl, ethyl, n-propyl, i-propyl, n-butyl, t-butyl, n-pentyl, vinyl, phenyl, benzyl, 3-phenylpropyl, hydroxymethyl, 2-hydroxyethyl or 3-hydroxypropyl, the pyridinium ring substituted with two of any of methyl or ethyl, the pyridinium ring substituted with one phenyl group and one methyl group, or the quinolinium ring substituted with any one of methyl or i-propyl. The position of binding to $Z^a$ is the ammonium nitrogen atom.

(30) The compound according to any of (1) to (26) above wherein $N^+R^{5a}R^{6a}R^{7a}$ is any of N,N-dimethyl-N-(n-hexyl) ammonium, N-benzyl-N,N-dimethyl ammonium, N-benzyl-N-methyl-N-(propargyl) ammonium, N,N-dimethyl-N-(n-butyl) ammonium, 1-methyl-pyrrolidinium-1-yl, 1-ethyl-pyrrolidinium-1-yl, 1-n-butyl-pyrrolidinium-1-yl, 1-n-pentyl-pyrrolidinium-1-yl, 3-hydroxy-1-methyl-pyrrolidinium-1-yl, 1-ethyl-3-hydroxy-pyrrolidinium-1-yl, 1-benzyl-3-hydroxy-pyrrolidinium-1-yl, 1-methyl-piperidinium-1-yl, 1-ethyl-piperidinium-1-yl, 1-n-butyl-piperidinium-1-yl, 1-n-pentyl-piperidinium-1-yl, 4-benzyl-1-n-butyl-piperidinium-1-yl, 4-benzyl-1-n-pentyl-piperidinium-1-yl, 3-hydroxy-1-methyl-piperidinium-1-yl, 4-hydroxy-1-methyl-piperidinium-1-yl, 3-hydroxymethyl-1-methyl-piperidinium-1-yl, 1-benzyl-4-hydroxymethyl-piperidinium-1-yl, 1-benzyl-4-hydroxyethyl-piperidinium-1-yl, 1-benzyl-4-hydroxy-piperidinium-1-yl, 1-ethyl-azepanium-1-yl, 1-n-butyl-azepanium-1-yl, 1-n-pentyl-azepanium-1-yl, 1-benzyl-azepanium-1-yl, 1-hydroxyethyl-azepanium-1-yl, quinuclidinium-1-yl, 4-phenylquinuclidinium-1-yl, 3-hydroxyquinuclidinium-1-yl, 1,4-diazabicyclo[2.2.2]octanium-1-yl, 4-n-butyl-1,4-diazabicyclo[2.2.2]octanium-1-yl, 4-benzyl-1,4-diazabicyclo[2.2.2]octanium-1-yl, isoquinolinium-1-yl, 4-methylpyridinium-1-yl, 3-(n-butyl)pyridinium-1-yl, 4-ethylpyridinium-1-yl, 4-(t-butyl)pyridinium-1-yl, 3-(3-hydroxypropyl)pyridinium-1-yl, 3-[2-(methoxycarbonyl)ethyl]-pyridinium-1-yl and 2-(n-propyl)-pyridinium-1-yl.

(31) The compound according to any of (1) to (26) above wherein $N^+R^{5a}R^{6a}R^{7a}$ is any of N-benzyl-N,N-dimethyl ammonium, N-benzyl-N-methyl-N-(propargyl) ammonium, 4-phenylquinuclidinium-1-yl, 1,4-diazabicyclo[2.2.2]octanium-1-yl, 1-benzyl-4-hydroxy-piperidinium-1-yl, 4-(t-butyl)pyridinium-1-yl, 3-(3-hydroxypropyl)-pyridinium-1-yl, 3-[2-(methoxycarbonyl)ethyl]-pyridinium-1-yl and 2-(n-propyl)-pyridinium-1-yl.

(32) The compound according to any of (1) to (26) above wherein $N^+R^{5a}R^{6a}R^{7a}$ is any of 4-t-butylpyridinium, 3-(3-hydroxypropyl)-pyridinium, 3-[2-(methoxycarbonyl)ethyl]-pyridinium, 2-(n-propyl)-pyridinium, 4-phenylquinuclidinium and 1,4-diazabicyclo[2.2.2]octanium groups.

(33) The compound according to any of (1) to (32) above wherein $(R^3R^4N)_m$ is any of dimethylamino group substituted at position 7, diethylamino group substituted at position 7, ethylmethylamino group substituted at position 7, dimethylamino group substituted at position 9, or dimethylamino groups substituted at two positions 7 and 9.

(34) The compound according to any of (1) to (32) above wherein $(R^3R^4N)_m$ is any of the dimethylamino group substituted at position 7, the diethylamino group substituted at position 7, or the ethylmethylamino group substituted at position 7.

(35) The compound according to any of (1) to (32) above wherein $(R^3R^4N)_m$ is the dimethylamino group substituted at position 7.

(36) The compound according to any of (1) to (35) above wherein both $R^1$ and $R^2$ are the alkyl groups having 1 to 6 carbon atoms.

(37) The compound according to any of (1) to (35) above wherein both $R^1$ and $R^2$ are the straight alkyl groups having 2 to 6 carbon atoms.

(38) The compound according to any of (1) to (35) above wherein both $R^1$ and $R^2$ are n-butyl groups.

(39) The compound represented by the general formula (1).

(40) The compound according to any of (1) to (9) or (27) to (38) above wherein the compound represented by the general formula (1B) is the compound represented by the general formula (1).

(41) The compound represented by the general formula (1B) wherein, when the combination of $(A^1, A^2, A^3)$ is (CH$_2$, NH, CH), one or more methylenes which constitute $Z^a$ must be replaced with phenylene having a substitutent. The substitutent(s) in the phenylene having the substitutent are 1 to 4 substitutents selected from the group consisting of alkyl having 1 to 5 carbon atoms, alkoxy having 1 to 5 carbon atoms, nitro group, halogen atom, trifluoromethyl group and —CH$_2$N$^+$R$^{5a}$R$^{6a}$R$^{7a}$, and the substitutents may be the same as or different from one another.

(42) The compound according to (41) above wherein $Z^a$—$(N^+R^{5a}R^{6a}R^{7a})_n$ represents alkyl group having 2 to 10 carbon atoms, substituted with one —$N^+R^{5a}R^{6a}R^{7a}$; $Z^a$ represents a straight methylene chain having 2 to 10 carbon atoms, or a straight methylene chain having 2 to 10 carbon atoms in which one methylene is replaced with phenylene which may have a substitutent, or a straight methylene chain having 2 to 10 carbon atoms in which one methylene is replaced with —O—, or a straight methylene chain having 2 to 10 carbon atoms in which one methylene is replaced with phenylene which may have a substitutent and another methylene is replaced with —O—; and Y represents —NHCS— or —NHCSNH— at para position or meta position.

(43) The compound according to (42) above wherein the combination of $(A^1, A^2, A^3)$ is (CH$_2$, CH(OH), CH), Y represents —NHCSNH— at meta position and $Z^a$ is the following formula (sp-14):

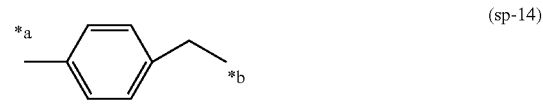

wherein *a binds to Y and *b binds to $N^+R^{5a}R^{6a}R^{7a}$ in the formula (1B).

(44) The compound according to (41) or (42) above wherein the combination of $(A^1, A^2, A^3)$ is (CH$_2$, NH, CH), Y represents —NHCSNH— at meta position and $Z^a$ is any of the following formulae:

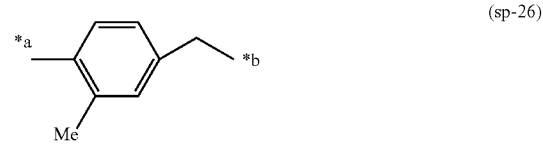

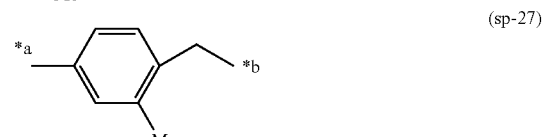

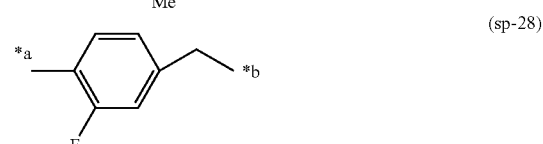

-continued

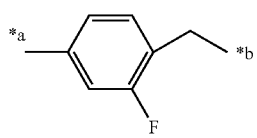 (sp-29)

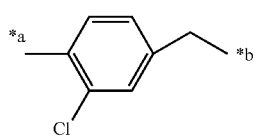 (sp-30)

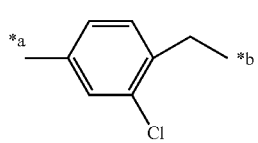 (sp-31)

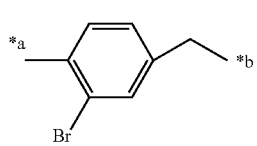 (sp-32)

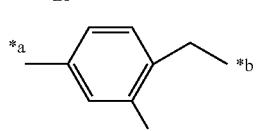 (sp-33)

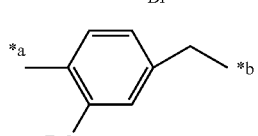 (sp-34)

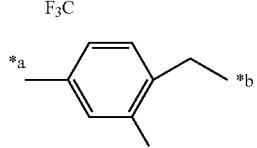 (sp-35)

wherein *a binds to Y and *b binds to $N^+R^{5a}R^{6a}R^{7a}$ in the formula (1B).

(45) The compound according to (44) above wherein $R^1$ and $R^2$ may be the same as or different from each other, and each represents straight alkyl groups having 2 to 6 carbon atoms, and $(R^3R^4N)_m$ represents any of dimethylamino group substituted at position 7, diethylamino group substituted at position 7, ethylmethylamino group substituted at position 7, dimethylamino group substituted at position 9, or dimethylamino groups substituted at two positions 7 and 9.

(46) The compound according to (45) above wherein $(R^3R^4N)_m$ represents any of dimethylamino group substituted at position 7, diethylamino group substituted at position 7, or ethylmethylamino group substituted at position 7, and $N^+R^{5a}R^{6a}R^{7a}$ represents any of 4-t-butylpyridinium, 3-(3-hydroxypropyl)-pyridinium, 3-[2-(methoxycarbonyl)ethyl]-pyridinium, 2-(n-propyl)-pyridinium, 4-phenylquinuclidinium or 1,4-diazabicyclo[2.2.2]octanium groups.

In the formula (1B), the compound which fulfills the conditions 1) to 3) shown below corresponds to the formula (1). The combination of $(A^1, A^2, A^3)$ defined below as the condition, the condition of $Z^a$ and the condition of $N^+R^{5a}R^{6a}R^{7a}$ have been already described as examples of preferable combinations in the formula (1B). $R^1$, $R^2$, $R^3$, $R^4$, Y, m, n, and $X^-$ are common in the formula (1B) and the formula (1). These have been already described as substitutents in the compounds represented by the formula (1B)

1) The combination of $(A^1, A^2, A^3)$ is $(CH_2, NH, CH)$;
2) when one or more methylenes which constitute $Z^a$ are replaced with phenylene which may have a substitutent, the phenylene which may have the substitutent is an unsubstituted phenylene; and
3) when $N^+R^{5a}R^{6a}R^{7a}$ represents pyridinium ring, quinolinium ring or isoquinolinium ring, the pyridinium ring, the quinolinium ring and the isoquinolinium ring may be substituted with one or more groups of cyano, nitro, phenyl, naphthyl, thienyl, pyridyl, cycloalkyl having 3 to 7 carbon atoms, alkoxy having 1 to 5 carbon atoms, carboxy, —$CONH_2$, —$SO_3H$ or —$R^{12}$; the $R^{12}$ represents alkyl group having 1 to 9 carbon atoms or alkenyl group having 2 to 9 carbon atoms; the alkyl group and the alkenyl group in $R^{12}$ may be substituted with one or more groups of phenyl, naphthyl, pyridyl, quinolyl, thienyl, furyl, cycloalkyl having 3 to 7 carbon atoms, cyano, nitro, hydroxy, oxo, thioxo, carboxy, —$CONH_2$ and —$SO_3H$; and further one or more methylenes which constitute the alkyl group and the alkenyl group may be replaced with any of phenylene, thienylene, furylene, cyclohexylene, cyclopentylene, —S—, —$CO_2$—, —NHCO—, —$NR^8$—, and —$N^+W^-R^9R^{10}$—.

In the compound of the present invention, asymmetric centers can be present at $R^{1a}$, $R^{2a}$, $R^x$, $Z^a$ and $(N^+R^{5a}R^{6a}R^{7a})$ in addition to the positions 3, 4 and 5 in the formula (1A). Thus, a plurality of stereoisomers depending on the number of the asymmetric centers can be present. Not only pure stereoisomers but also mixtures of a plurality of optional stereoisomers are included within the scope of the present invention. In the compound of the present invention, a plurality of geometrical isomers can be present depending on types of $R^{1a}$, $R^{2a}$, $R^x$, $Z^a$ and $(NR^{5a}R^{6a}R^{7a})$. Not only pure geometrical isomers but also mixtures of a plurality of optional geometrical isomers are included within the scope of the present invention.

In the compound of the present invention, asymmetric centers can also be present at $R^1$, $R^2$, $R^3$, $R^4$, $Z^a$ and $(N^+R^{5a}R^{6a}R^{7a})$ in addition to the positions 3, 4 and 5 in the formula (1B). Thus, a plurality of stereoisomers depending on the number of the asymmetric centers can be present. Not only pure stereoisomers but also mixtures of a plurality of optional stereoisomers are included within the scope of the present invention. In the compound of the present invention, a plurality of geometrical isomers can be present depending on the types of $Z^a$ and $(N^+R^{5a}R^{6a}R^{7a})$. Not only pure geometrical isomers but also mixtures of a plurality of optional geometrical isomers are included within the scope of the present invention.

In the compound of the present invention, asymmetric centers can also be present at $R^1$, $R^2$, $R^3$, $R^4$, Z and $(N^+R^5R^6R^7)$ in addition to positions 3 and 5 in the formula (1). Thus, a plurality of stereoisomers depending on the number of the asymmetric centers can be present. Not only pure stereoisomers but also mixtures of a plurality of optional stereoisomers are included within the scope of the present invention. In the compound of the present invention, a plurality of geometrical isomers can be present depending on the types of Z and $(N^+R^5R^6R^7)$. Not only pure geometrical isomers but also mixtures of a plurality of optional geometrical isomers are included within the scope of the present invention.

The present invention is also directed to a pharmaceutical composition containing the compound of the present invention represented by the formula (1A), (1B) or (1) as an active component, the pharmaceutical composition in which the pharmaceutical composition is the cholesterol lowering agent, the pharmaceutical composition in which the pharmaceutical composition is the therapeutic agent or the preventive agent for hyperlipemia, arteriosclerosis or syndrome X, the pharmaceutical composition in which the pharmaceutical composition is the therapeutic agent or the preventive agent for hepatic disorders associated with cholestasis, the pharmaceutical composition in which the pharmaceutical composition is the therapeutic agent or the preventive agent for primary biliary cirrhosis or primary sclerosing cholangitis, the pharmaceutical composition in which the pharmaceutical composition is the therapeutic agent or the preventive agent for obesity or fatty liver, and the pharmaceutical composition in which the pharmaceutical composition is the therapeutic agent or the preventive agent for steatohepatitis.

The present invention also relates to pharmaceuticals combining the compound of the present invention represented by the formula (1A), (1B) or (1) with another compound which is an active component of the preventive agent or the therapeutic agent for coronary artery diseases. The pharmaceuticals are effective for the prevention or the treatment of any of hyperlipemia, arteriosclerosis or syndrome X, and may be used for the prevention or the treatment of the coronary artery diseases.

The compound of the present invention represented by the formula (1A), (1B) or (1) is significantly anticipated to act as radical scavenger because the compound is characterized by having the thioamide bond in its molecule. Radicals have potent cytotoxicity, and appear to cause gastrointestinal disease such as inflammatory enteritis in the case of acting upon the gastrointestinal tract to cause the disorder (Thomson A. et al., Dig. Dis., 16, 152-158, 1998). Thiourea has a protective effect on amino acid transporter disorder of small intestine (i.e., inhibition of amino acid absorption) caused by hydroxy radical. Thiourea has been reported to be useful as the radical scavenger (Hayashi K. et al., Scand. J. Gastroenterol., 28, 261-266, 1993). In view of these, it is thought that the compound of the present invention represented by the formula (1A), (1B) or (1) has the action as the radical scavenger which may prevent/treat the gastrointestinal disease such as inflammatory enteritis. The radical scavenging action may be examined by a method in which the compound of the present invention is mixed with a hydroxy radical-generating compound such as hydrogen peroxide solution and t-BuOOH and the residual radical amount is physicochemically or biochemically measured. Another example of the method for examining the action may be a method of placing the compound of the present invention in a model in which small intestine tissue or small intestine epithelial cell line is injured by the hydroxy radical-generating compound, and observing the reduction of injury. As the specific method, Hayashi et al's method (Hayashi K. et al., Scand. J. Gastroenterol., 28, 261-266, 1993) may be exemplified. Therefore, the pharmaceutical composition containing the compound represented by the formula (1A), (1B) or (1) having such an action is also anticipated to exhibit the characteristic feature of the compound represented by the formula (1A), (1B) or (1)

In basic skeletons of the compound represented by the formula (1A), (1B) or (1), 1,4-benzothiazepine skeleton has a basic nitrogen at position 4 which is a vicinal of the asymmetrical center. Thus, an optically active isomer is easily obtained by various optical resolution agents such as camphor sulfonate derivatives and tartrate derivatives. Furthermore, the compound forms a pharmaceutically acceptable salt with an acid due to the presence of the basic nitrogen. Thus, the compound well-soluble in water may be obtained. Therefore, this skeleton is a useful basic skeleton for producing the pharmaceutical products. The compound obtained by introducing the thioamide bond and the quaternary ammonium substituent into the skeleton is a novel compound. When compared with publicly known compounds having such a skeleton, this novel compound exhibits highly potent inhibitory activity for ileal bile acid transporter, high stability so that the compound is not easily metabolized in vivo, and a reduced toxicity to the gastrointestinal tract. By (the aforementioned) test examples, it has been found out that the compound is useful as the cholesterol lowering agent, and further is useful as the pharmaceutical composition for the treatment and the prevention of hyperlipemia, arteriosclerosis and syndrome X. Furthermore, it has been found out that the compound represented by the formula (1A), (1B) or (1) can be combined with the cholesterol lowering agent such as HMG-CoA reductase inhibitor and cholesterol absorption inhibitor, and it has been demonstrated that several combinations thereof have co-administration effects in Test Examples and thus the pharmaceutical composition containing these is useful.

A group of the compounds represented by the formula (1A), (1B) or (1) and having the quaternary ammonium substituent exhibits remarkably low permeability into Caco-2 cells, and is predicted to be poorly absorbed from the intestine. A target molecule of these compounds is supposed to be bile acid transporters that are abundantly present in small intestine, and particularly in an ileum portion thereof. Thus, it is important that the compound is present in the small intestine and particularly in the ileum portion, and it is not necessary that the compound is absorbed in the body. Therefore, it is believed that this group of the compounds having the quaternary ammonium substituent are present mostly in the intestine and acts upon the target molecule at that place, to exhibit the cholesterol lowering effect. A surfactant typified by benzalkonium chloride as a typical example of an organic compound having the quaternary ammonium substituent exhibits cytotoxicity to the gastrointestinal cells. Such cytotoxicity may raise concern of injury on small intestine epithelium which may remarkably affect the absorbability of the co-administered drugs. It has been also found out that an IBAT inhibitor having the quaternary ammonium structure (the compound 5 [Synthetic Example 19]: 1-{4-[4-(3,3-dibutyl-7-dimethylamino-1,1-dioxo-2,3,4,5-tetrahydro-1,4-benzothiazepine-5-yl)phenoxymethyl]benzyl}-4-aza-1-azoniabicyclo[2.2.2]octane chloride which exhibits the strongest activity among the compounds specifically described in WO02/08211) used as a control example in Test Examples of the present invention has the cytotoxicity. Therefore, it is concerned that this compound facilitates the absorbability of the co-administered drug, and thereby increases a concentration of the co-administered drug in blood to cause expression of side effects. When that surfactant is co-administered with the HMG-CoA reductase inhibitor or the fibrate drug, the blood level thereof may increase to cause rhabdomyolysis. When that surfactant is co-administered with ezetimibe, nicotinic acid or the CETP inhibitor, the blood level thereof may increase to cause hepatic toxicity. Such phenomena are considered to be disadvantageous. However, surprisingly, the compound of the present invention represented by the formula (1A), (1B) or (1) having the thioamide bond and the quaternary ammonium substituent does not exhibit the cytotoxicity to Caco-2 cell which is a small intestine epithelial cell line, and is not easily absorbed in vivo, whereby it is anticipated that this compound does not interact with the other drugs. Thus it has been found out that the compound has extremely preferable nature as a drug to be co-administered with drugs for the treatment of the coronary artery diseases and that the compound can be combined with the other cholesterol lowering agents, to thereby complete the present invention.

The compound represented by the formula (1A), (1B) or (1) in the present invention includes acid addition salts. The acid addition salt is preferably the pharmaceutically acceptable salts, and examples thereof includes various publicly known salts, such as hydrochloride salts, hydrobromide salts, sulfate salts, hydrogen sulfate salts, dihydrogen phosphate salts, citrate salts, maleate salts, tartrate salts, fumarate salts, gluconate salts and methanesulfonate salts. The acid addition salt thereof may be obtained by adding an acid component in an amount equivalent to or several times of the compound represented by the formula (1A), (1B) or (1). The acid component to be used may include pharmaceutically acceptable mineral acids or organic acids such as hydrochloric acid, hydrobromic acid, sulfuric acid, hydrogen sulfuric acid, dihydrogen phosphoric acid, citric acid, maleic acid tartaric acid, fumaric acid, gluconic acid and methanesulfonic acid.

It is preferable that the compound represented by the formula (1A), (1B) or (1) or the salt thereof in an effective amount is, if necessary, admixed with a pharmaceutically acceptable carrier, to formulate a pharmaceutical composition. As the pharmaceutically acceptable carrier, excipients, binders such as carboxymethylcellulose, disintegrants, lubricants, additives and the like are exemplified. When the compound represented by the formula (1A), (1B) or (1) is administered to a human, the compound may be orally administered in forms of tablets, powers, granules, capsules, sugar-coated tablets, liquids and syrups. The dosage varies depending on age, body weight and condition of patients, and in general, 0.1 to 500 mg per adult person per day is administered as a single dose or several divided doses. In general, the administration time period may be consecutive several weeks to several months. Both the dosage per day and the administration time period may be increased and decreased depending on the condition of the patient.

Another preferred embodiment of the present invention is a pharmaceutical comprising a combination of the pharmaceutical of the present invention represented by the formula (1A), (1B) or (1), and another pharmaceutical containing as an effective ingredient a compound which is used as a therapeutic agent or a preventive agent for coronary artery disease.

Examples of the combination may include a combination in which each of two or more pharmaceuticals is formulated as a single dose and the pharmaceuticals are administered simultaneously or with an interval of a certain period of time, preferably several hours. In this case, it is preferable to pack respective pharmaceuticals in one package form, although they may also be packaged separately.

It is very preferable that two or more pharmaceuticals are mixed and used as one combined pharmaceutical. The "pharmaceutical" referred to herein may be composed of only the active component or the salt thereof, or may be the pharmaceutical composition to which, if necessary, the pharmaceutically acceptable carrier may be added. When the pharmaceutical is formulated by combining the compound represented by the formula (1A), (1B) or (1) or the salt thereof with the compound for the coronary artery disease, it is preferable that the pharmaceutical is formulated by blending the effective amount of the compound represented by the formula (1A), (1B) or (1) or the salt thereof with the effective amount of the compound for the coronary artery disease. As the pharmaceutically acceptable carrier, excipients, binders such as carboxymethylcellulose, disintegrants, lubricants, additives and the like are exemplified. When such a combination agent is administered to a human, the composition may be orally administered in forms of tablets, powers, granules, capsules, sugar-coated tablets, liquids and syrups. The dosage varies depending on age, body weight and condition of the patients, and in general, 0.1 to 5 g per adult person per day is administered as a single dose or several divided doses. In general, the administration time period may be consecutive several weeks to several months. Both the dosage per day and the administration time period may be increased and decreased depending on the condition of the patient.

The present pharmaceutical composition is characterized in that an adverse effect by drug combination can be substantially avoided. Thus, any drugs usable as the pharmaceutical products may be used by combining with the present pharmaceutical composition, and the drugs usable by combining with the present pharmaceutical composition are preferably the drugs used for the treatment or the prevention of the coronary artery diseases, and more preferably HMG-CoA reductase inhibitors, fibrate drugs, bile acid absorbers, cholesterol absorption inhibitors, CETP inhibitors, nicotinic acid and derivatives thereof, ACAT inhibitors, MTP inhibitors, squalene synthesis inhibitors, PPAR agonists, Liver X receptor (abbreviated hereinbelow as LXR) agonists, Eicosapentaenoic acid (abbreviated hereinbelow as EPA) formulations, phytosterol, phytostanol, angiotensin converting enzyme (abbreviated hereinbelow as ACE) inhibitors, angiotensin II (abbreviated hereinbelow as AT II) receptor inhibitors, viganite, sulfonyl urea, calcium channel inhibitors and diuretic agents. Preferable examples of the HMG-CoA reductase inhibitors may include pravastatin, simvastatin, fluvastatin, lovastatin, atorvastatin, rosuvastatin and pitavastatin. Preferable examples of the fibrate drugs may include phenofibrate, bezafibrate, genfibrozile and chlofibrate. Preferable examples of the bile acid absorber may include cholestyramine, colestipol, colestimide and colesevelam. Preferable examples of the cholesterol absorption inhibitor may include ezetimibe and pamaqueside. Not only nicotinic acid but also acipimox and niceritol may be included as preferable examples. Preferable examples of the CETP inhibitor may include torcetrapib (CP-529414), JTT-705 and CETi. Preferable examples of the squalene synthesis inhibitor may include TAK-475, ER-119884, E-5700 and ER-132781. Preferable examples of the PPAR agonist may include pioglitazone, rosiglitazone, netoglitazone, muraglitazar, tesaglitazar, GW-501516, GW-590735, GW-409544, GW-677954, GW509735, GI-1929, LY-519818, LY-510929, LY-518674, BAY54-9801, GFT-14, GFT-001A, GFT-500, GFT-229 and ONO-5129. Preferable examples of the MTP inhibitor may include implitapide, BMS-201038 and CP-346086. Preferable examples of the ACAT inhibitor may include avasimib, efflucimibe, and CS-505. Preferable examples of the other drugs may include AGI-1067 (CAS RN 216167-82-7), probucol and SB-480848.

Particularly, it is preferable to select one or more from the HMG-CoA reductase inhibitor, the fibrate drug, the bile acid absorber, the cholesterol absorption inhibitor, the CETP inhibitor, the nicotinic acid or the derivative thereof, the ACAT inhibitor, the MTP inhibitor, the squalene synthesis inhibitor, the PPAR agonist, phytosterol, phytostanol, AGI-1067 and probucol. Among others, it is greatly preferable to combine with the HMG-CoA reductase inhibitor. From another standpoint, it is also preferable to combine with the fibrate drug. From still another standpoint, it is also preferable to combine with the bile acid absorber. Alternatively, it is also preferable to combine with the nicotinic acid or the derivative thereof, or it is also preferable to combine with the cholesterol absorption inhibitor. In addition, from still another standpoint, the greatly preferable example may include the combination with both the HMG-CoA reductase inhibitor and the cholesterol absorption inhibitor. Other suitable combinations may include the combinations described in the following 1) to 7):
1) combination with probucol,
2) combination with CETP inhibitor,
3) combination with squalene synthesis inhibitor,
4) combination with MTP inhibitor,
5) combination with ACAT inhibitor,
6) combination with AGI-1067 and
7) combination with LXR stimulator.

If the drug to be combined is the HMG-CoA reductase inhibitor, the dosage thereof to be administered may be 0.1 to 200 mg per adult person per day as a single dose or several divided doses. Preferably, the dosage may be 0.5 to 100 mg as a single dose or several divided doses. As to each of the specific HMG-CoA reductase inhibitors to be combined, it is more preferable that the dosage of pravastatin is 0.5 to 40 mg, the dosage of simvastatin is 2.5 to 80 mg, the dosage of fluvastatin is 0.5 to 40 mg, the dosage of lovastatin is 0.5 to 40 mg, the dosage of atorvastatin is 0.5 to 80 mg, the dosage of rosuvastatin is 0.5 to 40 mg and the dosage of pitavastatin is 0.5 to 4 mg. The statins may be in a form of an appropriate salt, and particularly may be in a form of a calcium salt or a sodium salt. If the drug to be combined is the bile acid absorber, the dosage thereof to be administered may be 0.1 to 15 g, preferably 1 to 10 g and more preferably 1 to 5 g per adult person per day as a single dose or several divided doses. As to each of the specific bile acid absorbers to be combined, 3 to 4 g of cholestyramine, 1 to 2 g of colestipol, 0.5 to 1.5 g of colestimide or 3.5 to 4.5 g of colesevelam may be administered as a single dose or several divided doses. If the drug to be combined is the cholesterol absorption inhibitor, the dosage to be administered may be 0.0001 to 100 mg per adult person per day as a single dose or several divided doses. The dosage may preferably be 0.0005 to 50 mg and more preferably 0.001 to 30 mg as a single dose or several divided doses. If the cholesterol absorption inhibitor to be combined is ezetimibe, 1 to 10 mg of ezetimibe per adult person per day may be administered as a single dose or several divided doses. If the drug to be combined is the fibrate, the dosage to be administered may be 0.01 to 10 g, preferably 0.05 to 5 g and more preferably 0.1 to 3 g per adult person per day as a single dose or several divided doses. If the drug to be combined is the CETP inhibitor, the dosage to be administered may be 0.1 to 2000 mg, preferably 0.5 to 1000 mg and more preferably 1 to 500 mg per adult person per day as a single dose or several divided doses. If the CETP inhibitors is torcetrapib, the dosage to be administered may be 1 to 500 mg, preferably 10 to 250 mg and more preferably 30 to 120 mg per adult person per day as a single dose or several divided doses. If the drug to be combined is the nicotinic acid, the dosage to be administered may be 0.1 to 10 g, more preferably 0.5 to 5 g and still more preferably 0.5 to 3 g per adult person per day as a single dose or several divided doses. If the drug to be combined is the PPAR agonist, the dosage to be administered may be 0.05 to 200 mg, preferably 0.1 to 100 mg and more preferably 0.5 to 50 mg per adult person per day as a single dose or several divided doses. If the drug to be administered is the AGI-1067, the dosage to be administered may be 1 to 1000 mg, preferably 5 to 500 mg and more preferably 10 to 300 mg per adult person per day at a single dose or several divided doses. As to the drugs having other action mechanisms, the amount to be combined may be in accordance with the dosage by which effect may be obtained if the drug is administered alone.

Furthermore, it is possible to combine the compound represented by the formula (1A), (1B) or (1) with a plurality of drugs selected from the aforementioned drugs. The species of the drugs to be combined in this case is preferably two species. Examples of the particularly preferable combination may include the combination of the HMG-CoA reductase inhibitor and the cholesterol absorption inhibitor, the combination of the HMG-CoA reductase inhibitor and the nicotinic acid formulation, the combination of the HMG-CoA reductase inhibitor and a calcium antagonist and the combination of the HMG-CoA reductase inhibitor and the CETP inhibitor. The particularly preferable combinations may be the combination consisting of the compound represented by the formula (1A), (1B) or (1), simvastatin and ezetimibe, the combination consisting of the compound represented by the formula (1A), (1B) or (1), simvastatin and nicotinic acid, the combination consisting of the compound represented by the formula (1A), (1B) or (1), atorvastatin and amlodipine, and the combination consisting of the compound represented by the formula (1A), (1B) or (1), atorvastatin and torcetrapib. In this case, it is also preferable to formulate the drug by appropriately combining the effective amount of the compound represented by the formula (1A), (1B) or (1) with the HMG-CoA reductase inhibitor and the cholesterol absorption inhibitor at the co-administerable dosages.

In order to actually confirm the effect of co-administration of the aforementioned combination, existing animal models may be used. It is preferable that the animal model is the one with which efficacy of each drug can be substantially confirmed when each drug alone is examined. The effective amount of the compound represented by the formula (1A), (1B) or (1) and the effective amounts of the compounds to be combined are administered alone or in combination to model animals. After orally administering once or several times, preferably for several days to 100 days, the effect of coadministration may be confirmed by measuring cholesterol levels in blood or measuring progress levels of arterial sclerosis and comparing the effect of each single drug with the effect of the combination of drugs.

In addition to the method described in Test Examples of the present invention, the effect of the combination of the compound of the formula (1A), (1B) or (1) with the HMG-CoA reductase inhibitor may be confirmed in the following manner. That is, in mice, guinea pigs, hamsters or miniature pigs loaded with cholesterol foods, comparison may be performed as to changes of plasma cholesterol levels before and after the administration of the compounds, or as to increases of low density lipoprotein (LDL) receptor mRNA amount in liver when the combination of the compound with the HMG-CoA reductase inhibitor is administered. In addition to the method described in Test Examples of the present invention, the effect of the combination of the compound of the formula (1A), (1B) or (1) with ezetimibe may be confirmed in the following manner. That is, the compound of the formula (1A), (1B) or (1) and ezetimibe may be co-administered to rats that have been loaded with cholesterol foods, and the changes of cholesterol levels in blood may be examined. Additionally, LDL receptor (LDL-R) knockout mice, apoE knockout mice, LDL-R/apoE knockout mice, apoE*3-Leiden transgenic mice, apoA1 transgenic mice, CETP transgenic mice and WHHL rabbits may also be used as the animal models for testing the co-administration effects.

The pharmaceutical composition of the present invention is characterized by giving no effect on blood levels of the co-administered drugs. In addition to the method described in Test Examples of the present invention, the effect on the blood levels of the co-administered drugs may be confirmed as follows. That is, the effective amount of the compound of the formula (1A), (1B) or (1) and the effective amount of the compound to be combined may be orally administered to the animals, and then the blood levels of the combined drug after the administration may be measured. The levels may be compared with the blood levels when the combined drug alone has been orally administered.

As demonstrated in Test Examples, the pharmaceutical composition of the present invention is characterized in that the composition does not give injury to gastrointestinal cells and that the composition does not facilitate drug permeability on the gastrointestinal cells. That is, the pharmaceutical composition of the present invention does not promote the absorbability of a drug which exerts its effect by being absorbed via the gastrointestinal cells. The present invention is also directed to a pharmaceutical consisting of a combination of the pharmaceutical composition of the present invention and another drug which exerts its effect by being absorbed via the gastrointestinal cells.

Furthermore, for the prevention or the treatment of the coronary artery disease, it is possible to co-administer one or more drugs appropriately selected from the preventive agents or the therapeutic agents for various diseases which occur as complications upon treatment or prevention of the coronary artery disease, for example, psychoactive drugs, sleeping drugs, analgesic agents, antipyretic drugs, anticonvulsive drugs, anti-vertigo drugs, anti-emetic drugs, skeletal muscle agents, ophthalmologic disease therapeutic drugs, anti-pruritus drugs, anemia therapeutic drugs, hemostatic agents, thyroid abnormalities therapeutic drugs, sex hormones, fertility therapeutic drugs, uric acid lowering drugs, immunosuppressant drugs, infectious disease therapeutic drugs, antibacterial drugs, antifungal drugs, antituberculous drugs, antiviral drugs, cardiotonic drugs, angina therapeutic drugs, arrhythmias therapeutic drugs, antihypertensive drugs, pressor drugs, diuretic drugs, cough medicines, expectorant drugs, bronchial asthma therapeutic drugs, bronchodilators, respiratory stimulants, antiulcer drugs, digestion stimulants, liver supporting drugs, biliary tract disease therapeutic drugs, pancreatitis therapeutic drugs, antiflatuents, antidiarrheal drugs, fecal softeners, buccal application drugs, anti-cancer drugs and immunopotentiators. Examples of the psychoactive drugs may include paroxetine hydrochloride, sertraline hydrochloride, fluvoxamine maleic acid, duloxetine hydrochloride, fluoxetine hydrochloride, venlafaxine hydrochloride, mirtazapine, milnacipran hydrochloride, imipramine hydrochloride, maprotiline hydrochloride, sulpiride, alprazolam, diazepam, midazolam, olanzapine, quitiapine, risperidone, and haloperidol. Examples of sleeping drugs may include zopiclone, indiplon, flurazepam, nitrazepam, brotizolam, triazolam and phenobarbital. Examples of the analgesic agents and the antipyretic drugs may include morphine sulfate, pentazocine, acetaminophen and isopropylantipyrine. Examples of the anticonvulsive drugs may include sodium valproate and diazepam. Examples of the anti-vertigo drugs and the anti-emetic drugs may include metoclopramide and domperidone. Examples of skeletal muscle agents may include baclofen and distigmine bromide. Examples of the ophthalmologic disease therapeutic drugs may include betaxolol hydrochloride, isopropyl unoprostone and pilocarpine hydrochloride. Examples of the anti-pruritus drugs may include ketotifen fumarate, crotamiton and toukiinshi. Examples of the anemia therapeutic drugs may include epoetin alpha, epoetin beta, incremin and fesin. Examples of the hemostatic drugs may include carbazochrome sodium sulfonate, transamin and thrombin. Examples of the thyroid abnormalities therapeutic drugs may include thiamazole and liothyronine sodium. Examples of the sex hormones may include male hormone formulations (e.g., testosterone propionate, fluoxymesterone), bromocriptine mesilate, follicular hormone formulations (e.g., estradiol, estradiol benzoate, estradiol dipropionate, estradiol valerate, ethinylestradiol, estriol, estriol acetate benzoate, estriol tripropionate and conjugated estrogen), synthetic estrogen (e.g., mestranol, fosfestrol, estramustine phosphate sodium), and corpus luteum hormone formulations (e.g., progesterone, dydrogesterone, hydroxyprogesterone caproate, medroxyprogesterone acetate, chlormadinoone acetate, allylestrenol, gestonorone caproate, norethisterone). Examples of the fertility therapeutic drugs may include clomifene citrate and chorionic gonadotropin. Examples of the uric acid lowering drugs may include allopurinol and benzbromarone. Examples of the immunosuppressant drugs may include azathioprine, mizoribine, mycophenolate mofetil, cyclosporine and FK506. Examples of antibacterial drugs may include benzylpenicillin potassium, ampicillin, cefazolin sodium, cefotiam hydrochloride, cefoperazon sodium, clindamycin, lincomycin hydrochloride, erythromycin, clarithromycin, doxycycline hydrochloride, minocycline hydrochloride, gentamicin sulfate, amikacin sulfate, norfloxacin, enoxacin, levofloxacin, chloramphenicol, sulfamethoxazol and trimethoprim. Examples of the antifungal drugs may include amphotericin B, miconazole and itraconazole. Examples of the antituberculous drugs may include rifampicin, calcium para-aminosalicylate and ethambutol hydrochloride. Examples of the antiviral drugs may include acyclovir, ganciclovir, ritonavir, interferon-$\alpha$, didanosine and further ribavirin and lamivudine. Examples of the cardiotonic drugs may include digoxin, $\beta$-metildigoxin, digitoxin and denopamine. Examples of the angina therapeutic drugs may include amyl nitrite, nitroglycerin, isosorbide dinitrate, isosorbide mononitrate, alprenolol hydrochloride, bufetolol hydrochloride, bupranolol hydrochloride, oxprenolol hydrochloride, bucumolol hydrochloride, nifedipine, benidipine hydrochloride, diltiazem hydrochloride, verapamil hydrochloride, nisoldipine, nitrendipine, bepridil hydrochloride, efonidipine hydrochloride, amlodipine besilate, trimetazidine hydrochloride, dipyridamole, etafenone hydrochloride, dilazep dihydrochloride, trapidil, nicorandil, carvedilol, propranolol hydrochloride, metoprolol tartrate and atenolol. Examples of the arrhythmias therapeutic drugs may include quinidine sulfate, procainamide hydrochloride, lidocaine, propafenone, propranolol, verapamil hydrochloride, ATP and digoxin. Examples of the antihypertensive drugs may include eutensin, ACE inhibitors (e.g., captopril, enalapril maleate, alacepril, delapril hydrochloride, cilazapril, lisinopril, benazepril hydrochloride, imidapril hydrochloride, temocapril hydrochloride, quinapril hydrochloride, trandolapril, perindopril erbumine), angiotensin II receptor antagonists (e.g., losartan potassium, candesartan cilexetil, valsartan), calcium antagonists (e.g., amlodipine besilate, aranidipine, efonidipine hydrochloride, cilnidipine, nicardipine hydrochloride, nisoldipine, nitrendipine, nifedipine, nilvadipine, barnidipine hydrochloride, felodipine, benidipine hydrochloride, manidipine hydrochloride, diltiazem hydrochloride), beta blockers (e.g., atenolol, bisoprolol fumarate, betaxolol hydrochloride, bevantolol hydrochloride, metoprolol tartrate, acebutolol hydrochloride, celiprolol hydrochloride, nipradilol, tilisolol hydrochloride, nadolol, propranolol hydrochloride, indenolol hydrochloride, carteolol hydrochloride, pindolol, bunitorol hydrochloride, penbutolol sulfate, bopindolol malonate), alpha beta blockers (e.g., amosulalol hydrochloride, arotinolol hydrochloride, carvediolol, labetalol hydrochloride), alpha blockers (e.g., urapidil, terazosin hydrochloride, doxazosin mesilate, bunazosin hydrochloride, prazosin hydrochloride, phentolamine mesylate), sympathetic central depressants (e.g., clonidine hydrochloride, guanfacine hydrochloride, guanabenz acetate, methyldopa), betanidine sulfate, trimetaphan camsilate, Rauwolfia formulations (e.g., reserpine, rescinnamine, alseroxylon), vasodilatory antihypertensive drugs (e.g., hydralazine hydrochloride), nitrate drugs (e.g., nitroglycerin, sodium nitroprusside), and cardiovascular system acting enzyme drugs (e.g., kallidinogenase).

Examples of the pressor drugs may include midodrine hydrochloride, droxidopa, dopamin-HCL and dobutamine-HCL. Examples of the diuretic drugs may include furosemide and trichlormethiazide. Examples of the cough medicines and the expectorant drugs may include bromhexine hydrochloride, carbocisteine, ambroxol hydrochloride, benproperine phosphate and codein phosphate. Examples of the bronchial asthma therapeutic drugs and bronchodilators may include theophylline, procaterol hydrochloride, beclomethasone dipropionate and clenbuterol hydrochloride. Examples of the respiratory stimulants may include doxapram hydrochloride, flumazenil and levallorphan tartrate. Examples of the antiulcer drugs may include cimetidine, ranitidine hydrocholoride, famotidine, omeprazole, lansoprazole, secretin, proglumide, ornoprostil, teprenone, isogladine malate, proglumide, scopolamine butylbromide, metoclopramide, pirenzepine hydrochloride, sodium bicarbonate and dried aluminum hydroxide gel. Examples of the digestion stimulants may include berizym, stomilase, zyma, seven E•P and toughmac E. Examples of the liver supporting drugs may include glutathione, diisopropylamine dichloroacetate and methylmethionine sulfonium chloride, and further Stronger Neo-MinophagenC, aminoethyl sulfonic acid, glucuronate, protoporphyrin disodium, thiopronin, lactulose and proheparum. Examples of the biliary tract disease therapeutic drugs may include flopropione and trepibutone. Examples of the pancreatitis therapeutic drugs may include ulinastatin, citicolin and camostat mesilate. Examples of the antiflatuents and the antidiarrheal drugs may include opium, scopolamine butylbromide, albumin tannate, natural aluminium silicate, berberine chloride and biofermin. Examples of the fecal softeners may include carmelose sodium, dioctyl sodium sulfosuccinate, lactulose, sorbitol, castor oil, senna, bisacodyl, sodium-picosulfate, glycerin, rhubarb and drugs formulating sodium hydrogen carbonate/sodium hydrogen phosphate. Examples of the buccal application drugs may include azulene, povidone iodine, tetracycline hydrochloride, triamcinolone acetonide and despa. Examples of the anti-cancer drugs may include tegafur, carmofur, methotrexate, actinomycin-D, mitomycin-C, daunorubicin hydrochloride, busulfan, cyclophosphamide, paclitaxel, vincristine sulfate, fosfestrol, flutamide and leuprorelin acetate. Examples of the immunopotentiators may include interferon-α, interferon-β, OK-432, and further interferon-α2a, interferon-α2b, peginterferon-α2a, peginterferon-α2b and consensus interferon. (Examples are from, e.g., Tasuku Mizushima, "*Kon-niti no Chiryoyaku* (Today's Therapeutic Medicaments)" 23rd edition, Nankodo, 2001). The preventive drugs and the therapeutic drugs for various complications associated with the diseases caused by arterial sclerosis, and the preventive drugs and the therapeutic drugs for various complications associated with diabetes, and the preventive drugs and the therapeutic drugs for various complications associated with inflammatory diseases, which are combined with the pharmaceutical of the present invention or prepared as the medical mixture with the pharmaceutical of the present invention are not limited thereto.

It is further possible to administer the pharmaceutical of the present invention in combination with transfusion agents, dialysis liquids, displacement liquids and contrast agents frequently administered to the patients with disease caused by arterial sclerosis or diabetes or inflammatory disease. Examples of the transfusion agents may include ringer, and solita T. Examples of the dialysis liquids may include dialysis type artificial kidney reflux liquids. Examples of the displacement liquids may include filtration type and dialysis filtration type supplementary liquids for artificial kidney. Examples of the contrast agents may include iopamidol, iohexyl, iotroxic acid, amidotrizoic acid, iothalamic acid, ioxaglic acid and iotrolan. (Tasuku Mizushima, "*Konniti no Chiryoyaku* (Today's Therapeutic Medicaments)" 23rd edition, Nankodo, 2001). The transfusion agents, the dialysis liquids, the displacement liquids and the contrast agents administered in combination with the pharmaceutical of the present invention are not limited thereto.

EMBODIMENTS OF THE INVENTION

The specific compounds represented by the formula (1A) may include the following compounds and acid addition salts thereof.

Examples of the compounds in which both $R^{1a}$ and $R^{2a}$ are butyl groups, $(R^x)m^a$ is 7-dimethylamino group, the combination of $(A^1, A^2, A^3)$ is $(CH_2, CH(OH), CH)$, $X^-$ is $Br^-$ and the binding position of Y is the meta position may include the compounds described in Table 1 (Table 1-1 to Table 1-159) (E1A0001 to E1A6919, E1U001 to E1U14652, E1C001 to E1C4070). In Table 1, (sp-1) to (sp-44) and (an-1) to (an-407) are the same as the above.

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| Table 1-1 ||||||||||
| Y = NHCS ||| Y = NHCSNH ||| Y = NHCSNH |||
| E1A0001 | sp-1 | an-1 | E1U0001 | sp-1 | an-1 | E1U7327 | sp-27 | an-1 |
| E1A0002 | sp-1 | an-2 | E1U0002 | sp-1 | an-2 | E1U7328 | sp-27 | an-2 |
| E1A0003 | sp-1 | an-3 | E1U0003 | sp-1 | an-3 | E1U7329 | sp-27 | an-3 |
| E1A0004 | sp-1 | an-4 | E1U0004 | sp-1 | an-4 | E1U7330 | sp-27 | an-4 |
| E1A0005 | sp-1 | an-5 | E1U0005 | sp-1 | an-5 | E1U7331 | sp-27 | an-5 |
| E1A0006 | sp-1 | an-6 | E1U0006 | sp-1 | an-6 | E1U7332 | sp-27 | an-6 |
| E1A0007 | sp-1 | an-7 | E1U0007 | sp-1 | an-7 | E1U7333 | sp-27 | an-7 |
| E1A0008 | sp-1 | an-8 | E1U0008 | sp-1 | an-8 | E1U7334 | sp-27 | an-8 |
| E1A0009 | sp-1 | an-9 | E1U0009 | sp-1 | an-9 | E1U7335 | sp-27 | an-9 |
| E1A0010 | sp-1 | an-10 | E1U0010 | sp-1 | an-10 | E1U7336 | sp-27 | an-10 |
| E1A0011 | sp-1 | an-11 | E1U0011 | sp-1 | an-11 | E1U7337 | sp-27 | an-11 |
| E1A0012 | sp-1 | an-12 | E1U0012 | sp-1 | an-12 | E1U7338 | sp-27 | an-12 |
| E1A0013 | sp-1 | an-13 | E1U0013 | sp-1 | an-13 | E1U7339 | sp-27 | an-13 |
| E1A0014 | sp-1 | an-14 | E1U0014 | sp-1 | an-14 | E1U7340 | sp-27 | an-14 |

-continued

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| E1A0015 | sp-1 | an-15 | E1U0015 | sp-1 | an-15 | E1U7341 | sp-27 | an-15 |
| E1A0016 | sp-1 | an-16 | E1U0016 | sp-1 | an-16 | E1U7342 | sp-27 | an-16 |
| E1A0017 | sp-1 | an-17 | E1U0017 | sp-1 | an-17 | E1U7343 | sp-27 | an-17 |
| E1A0018 | sp-1 | an-18 | E1U0018 | sp-1 | an-18 | E1U7344 | sp-27 | an-18 |
| E1A0019 | sp-1 | an-19 | E1U0019 | sp-1 | an-19 | E1U7345 | sp-27 | an-19 |
| E1A0020 | sp-1 | an-20 | E1U0020 | sp-1 | an-20 | E1U7346 | sp-27 | an-20 |
| E1A0021 | sp-1 | an-21 | E1U0021 | sp-1 | an-21 | E1U7347 | sp-27 | an-21 |
| E1A0022 | sp-1 | an-22 | E1U0022 | sp-1 | an-22 | E1U7348 | sp-27 | an-22 |
| E1A0023 | sp-1 | an-23 | E1U0023 | sp-1 | an-23 | E1U7349 | sp-27 | an-23 |
| E1A0024 | sp-1 | an-24 | E1U0024 | sp-1 | an-24 | E1U7350 | sp-27 | an-24 |
| E1A0025 | sp-1 | an-25 | E1U0025 | sp-1 | an-25 | E1U7351 | sp-27 | an-25 |
| E1A0026 | sp-1 | an-26 | E1U0026 | sp-1 | an-26 | E1U7352 | sp-27 | an-26 |
| E1A0027 | sp-1 | an-27 | E1U0027 | sp-1 | an-27 | E1U7353 | sp-27 | an-27 |
| E1A0028 | sp-1 | an-28 | E1U0028 | sp-1 | an-28 | E1U7354 | sp-27 | an-28 |
| E1A0029 | sp-1 | an-29 | E1U0029 | sp-1 | an-29 | E1U7355 | sp-27 | an-29 |
| E1A0030 | sp-1 | an-30 | E1U0030 | sp-1 | an-30 | E1U7356 | sp-27 | an-30 |
| E1A0031 | sp-1 | an-31 | E1U0031 | sp-1 | an-31 | E1U7357 | sp-27 | an-31 |
| E1A0032 | sp-1 | an-32 | E1U0032 | sp-1 | an-32 | E1U7358 | sp-27 | an-32 |
| E1A0033 | sp-1 | an-33 | E1U0033 | sp-1 | an-33 | E1U7359 | sp-27 | an-33 |
| E1A0034 | sp-1 | an-34 | E1U0034 | sp-1 | an-34 | E1U7360 | sp-27 | an-34 |
| E1A0035 | sp-1 | an-35 | E1U0035 | sp-1 | an-35 | E1U7361 | sp-27 | an-35 |
| E1A0036 | sp-1 | an-36 | E1U0036 | sp-1 | an-36 | E1U7362 | sp-27 | an-36 |
| E1A0037 | sp-1 | an-37 | E1U0037 | sp-1 | an-37 | E1U7363 | sp-27 | an-37 |
| E1A0038 | sp-1 | an-38 | E1U0038 | sp-1 | an-38 | E1U7364 | sp-27 | an-38 |
| E1A0039 | sp-1 | an-39 | E1U0039 | sp-1 | an-39 | E1U7365 | sp-27 | an-39 |
| E1A0040 | sp-1 | an-40 | E1U0040 | sp-1 | an-40 | E1U7366 | sp-27 | an-40 |
| E1A0041 | sp-1 | an-41 | E1U0041 | sp-1 | an-41 | E1U7367 | sp-27 | an-41 |
| E1A0042 | sp-1 | an-42 | E1U0042 | sp-1 | an-42 | E1U7368 | sp-27 | an-42 |
| E1A0043 | sp-1 | an-43 | E1U0043 | sp-1 | an-43 | E1U7369 | sp-27 | an-43 |
| E1A0044 | sp-1 | an-44 | E1U0044 | sp-1 | an-44 | E1U7370 | sp-27 | an-44 |
| E1A0045 | sp-1 | an-45 | E1U0045 | sp-1 | an-45 | E1U7371 | sp-27 | an-45 |
| E1A0046 | sp-1 | an-46 | E1U0046 | sp-1 | an-46 | E1U7372 | sp-27 | an-46 |
| E1A0047 | sp-1 | an-47 | E1U0047 | sp-1 | an-47 | E1U7373 | sp-27 | an-47 |
| E1A0048 | sp-1 | an-48 | E1U0048 | sp-1 | an-48 | E1U7374 | sp-27 | an-48 |
| E1A0049 | sp-1 | an-49 | E1U0049 | sp-1 | an-49 | E1U7375 | sp-27 | an-49 |
| E1A0050 | sp-1 | an-50 | E1U0050 | sp-1 | an-50 | E1U7376 | sp-27 | an-50 |
| E1A0051 | sp-1 | an-51 | E1U0051 | sp-1 | an-51 | E1U7377 | sp-27 | an-51 |
| E1A0052 | sp-1 | an-52 | E1U0052 | sp-1 | an-52 | E1U7378 | sp-27 | an-52 |
| E1A0053 | sp-1 | an-53 | E1U0053 | sp-1 | an-53 | E1U7379 | sp-27 | an-53 |
| E1A0054 | sp-1 | an-54 | E1U0054 | sp-1 | an-54 | E1U7380 | sp-27 | an-54 |

Table 1-2

| Y = NHCS | | | Y = NHCSNH | | | Y = NHCSNH | | |
|---|---|---|---|---|---|---|---|---|
| E1A0055 | sp-1 | an-55 | E1U0055 | sp-1 | an-55 | E1U7381 | sp-27 | an-55 |
| E1A0056 | sp-1 | an-56 | E1U0056 | sp-1 | an-56 | E1U7382 | sp-27 | an-56 |
| E1A0057 | sp-1 | an-57 | E1U0057 | sp-1 | an-57 | E1U7383 | sp-27 | an-57 |
| E1A0058 | sp-1 | an-58 | E1U0058 | sp-1 | an-58 | E1U7384 | sp-27 | an-58 |
| E1A0059 | sp-1 | an-59 | E1U0059 | sp-1 | an-59 | E1U7385 | sp-27 | an-59 |
| E1A0060 | sp-1 | an-60 | E1U0060 | sp-1 | an-60 | E1U7386 | sp-27 | an-60 |
| E1A0061 | sp-1 | an-61 | E1U0061 | sp-1 | an-61 | E1U7387 | sp-27 | an-61 |
| E1A0062 | sp-1 | an-62 | E1U0062 | sp-1 | an-62 | E1U7388 | sp-27 | an-62 |
| E1A0063 | sp-1 | an-63 | E1U0063 | sp-1 | an-63 | E1U7389 | sp-27 | an-63 |
| E1A0064 | sp-1 | an-64 | E1U0064 | sp-1 | an-64 | E1U7390 | sp-27 | an-64 |
| E1A0065 | sp-1 | an-65 | E1U0065 | sp-1 | an-65 | E1U7391 | sp-27 | an-65 |
| E1A0066 | sp-1 | an-66 | E1U0066 | sp-1 | an-66 | E1U7392 | sp-27 | an-66 |
| E1A0067 | sp-1 | an-67 | E1U0067 | sp-1 | an-67 | E1U7393 | sp-27 | an-67 |
| E1A0068 | sp-1 | an-68 | E1U0068 | sp-1 | an-68 | E1U7394 | sp-27 | an-68 |
| E1A0069 | sp-1 | an-69 | E1U0069 | sp-1 | an-69 | E1U7395 | sp-27 | an-69 |
| E1A0070 | sp-1 | an-70 | E1U0070 | sp-1 | an-70 | E1U7396 | sp-27 | an-70 |
| E1A0071 | sp-1 | an-71 | E1U0071 | sp-1 | an-71 | E1U7397 | sp-27 | an-71 |
| E1A0072 | sp-1 | an-72 | E1U0072 | sp-1 | an-72 | E1U7398 | sp-27 | an-72 |
| E1A0073 | sp-1 | an-73 | E1U0073 | sp-1 | an-73 | E1U7399 | sp-27 | an-73 |
| E1A0074 | sp-1 | an-74 | E1U0074 | sp-1 | an-74 | E1U7400 | sp-27 | an-74 |
| E1A0075 | sp-1 | an-75 | E1U0075 | sp-1 | an-75 | E1U7401 | sp-27 | an-75 |
| E1A0076 | sp-1 | an-76 | E1U0076 | sp-1 | an-76 | E1U7402 | sp-27 | an-76 |
| E1A0077 | sp-1 | an-77 | E1U0077 | sp-1 | an-77 | E1U7403 | sp-27 | an-77 |
| E1A0078 | sp-1 | an-78 | E1U0078 | sp-1 | an-78 | E1U7404 | sp-27 | an-78 |
| E1A0079 | sp-1 | an-79 | E1U0079 | sp-1 | an-79 | E1U7405 | sp-27 | an-79 |
| E1A0080 | sp-1 | an-80 | E1U0080 | sp-1 | an-80 | E1U7406 | sp-27 | an-80 |
| E1A0081 | sp-1 | an-81 | E1U0081 | sp-1 | an-81 | E1U7407 | sp-27 | an-81 |
| E1A0082 | sp-1 | an-82 | E1U0082 | sp-1 | an-82 | E1U7408 | sp-27 | an-82 |
| E1A0083 | sp-1 | an-83 | E1U0083 | sp-1 | an-83 | E1U7409 | sp-27 | an-83 |
| E1A0084 | sp-1 | an-84 | E1U0084 | sp-1 | an-84 | E1U7410 | sp-27 | an-84 |
| E1A0085 | sp-1 | an-85 | E1U0085 | sp-1 | an-85 | E1U7411 | sp-27 | an-85 |
| E1A0086 | sp-1 | an-86 | E1U0086 | sp-1 | an-86 | E1U7412 | sp-27 | an-86 |
| E1A0087 | sp-1 | an-87 | E1U0087 | sp-1 | an-87 | E1U7413 | sp-27 | an-87 |
| E1A0088 | sp-1 | an-88 | E1U0088 | sp-1 | an-88 | E1U7414 | sp-27 | an-88 |

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| E1A0089 | sp-1 | an-89 | E1U0089 | sp-1 | an-89 | E1U7415 | sp-27 | an-89 |
| E1A0090 | sp-1 | an-90 | E1U0090 | sp-1 | an-90 | E1U7416 | sp-27 | an-90 |
| E1A0091 | sp-1 | an-91 | E1U0091 | sp-1 | an-91 | E1U7417 | sp-27 | an-91 |
| E1A0092 | sp-1 | an-92 | E1U0092 | sp-1 | an-92 | E1U7418 | sp-27 | an-92 |
| E1A0093 | sp-1 | an-93 | E1U0093 | sp-1 | an-93 | E1U7419 | sp-27 | an-93 |
| E1A0094 | sp-1 | an-94 | E1U0094 | sp-1 | an-94 | E1U7420 | sp-27 | an-94 |
| E1A0095 | sp-1 | an-95 | E1U0095 | sp-1 | an-95 | E1U7421 | sp-27 | an-95 |
| E1A0096 | sp-1 | an-96 | E1U0096 | sp-1 | an-96 | E1U7422 | sp-27 | an-96 |
| E1A0097 | sp-1 | an-97 | E1U0097 | sp-1 | an-97 | E1U7423 | sp-27 | an-97 |
| E1A0098 | sp-1 | an-98 | E1U0098 | sp-1 | an-98 | E1U7424 | sp-27 | an-98 |
| E1A0099 | sp-1 | an-99 | E1U0099 | sp-1 | an-99 | E1U7425 | sp-27 | an-99 |
| E1A0100 | sp-1 | an-100 | E1U0100 | sp-1 | an-100 | E1U7426 | sp-27 | an-100 |
| E1A0101 | sp-1 | an-101 | E1U0101 | sp-1 | an-101 | E1U7427 | sp-27 | an-101 |
| E1A0102 | sp-1 | an-102 | E1U0102 | sp-1 | an-102 | E1U7428 | sp-27 | an-102 |
| E1A0103 | sp-1 | an-103 | E1U0103 | sp-1 | an-103 | E1U7429 | sp-27 | an-103 |
| E1A0104 | sp-1 | an-104 | E1U0104 | sp-1 | an-104 | E1U7430 | sp-27 | an-104 |
| E1A0105 | sp-1 | an-105 | E1U0105 | sp-1 | an-105 | E1U7431 | sp-27 | an-105 |
| E1A0106 | sp-1 | an-106 | E1U0106 | sp-1 | an-106 | E1U7432 | sp-27 | an-106 |
| E1A0107 | sp-1 | an-107 | E1U0107 | sp-1 | an-107 | E1U7433 | sp-27 | an-107 |
| E1A0108 | sp-1 | an-108 | E1U0108 | sp-1 | an-108 | E1U7434 | sp-27 | an-108 |

Table 1-3

| Y = NHCS | | | Y = NHCSNH | | | Y = NHCSNH | | |
|---|---|---|---|---|---|---|---|---|
| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
| E1A0109 | sp-1 | an-109 | E1U0109 | sp-1 | an-109 | E1U7435 | sp-27 | an-109 |
| E1A0110 | sp-1 | an-110 | E1U0110 | sp-1 | an-110 | E1U7436 | sp-27 | an-110 |
| E1A0111 | sp-1 | an-111 | E1U0111 | sp-1 | an-111 | E1U7437 | sp-27 | an-111 |
| E1A0112 | sp-1 | an-112 | E1U0112 | sp-1 | an-112 | E1U7438 | sp-27 | an-112 |
| E1A0113 | sp-1 | an-113 | E1U0113 | sp-1 | an-113 | E1U7439 | sp-27 | an-113 |
| E1A0114 | sp-1 | an-114 | E1U0114 | sp-1 | an-114 | E1U7440 | sp-27 | an-114 |
| E1A0115 | sp-1 | an-115 | E1U0115 | sp-1 | an-115 | E1U7441 | sp-27 | an-115 |
| E1A0116 | sp-1 | an-116 | E1U0116 | sp-1 | an-116 | E1U7442 | sp-27 | an-116 |
| E1A0117 | sp-1 | an-117 | E1U0117 | sp-1 | an-117 | E1U7443 | sp-27 | an-117 |
| E1A0118 | sp-1 | an-118 | E1U0118 | sp-1 | an-118 | E1U7444 | sp-27 | an-118 |
| E1A0119 | sp-1 | an-119 | E1U0119 | sp-1 | an-119 | E1U7445 | sp-27 | an-119 |
| E1A0120 | sp-1 | an-120 | E1U0120 | sp-1 | an-120 | E1U7446 | sp-27 | an-120 |
| E1A0121 | sp-1 | an-121 | E1U0121 | sp-1 | an-121 | E1U7447 | sp-27 | an-121 |
| E1A0122 | sp-1 | an-122 | E1U0122 | sp-1 | an-122 | E1U7448 | sp-27 | an-122 |
| E1A0123 | sp-1 | an-123 | E1U0123 | sp-1 | an-123 | E1U7449 | sp-27 | an-123 |
| E1A0124 | sp-1 | an-124 | E1U0124 | sp-1 | an-124 | E1U7450 | sp-27 | an-124 |
| E1A0125 | sp-1 | an-125 | E1U0125 | sp-1 | an-125 | E1U7451 | sp-27 | an-125 |
| E1A0126 | sp-1 | an-126 | E1U0126 | sp-1 | an-126 | E1U7452 | sp-27 | an-126 |
| E1A0127 | sp-1 | an-127 | E1U0127 | sp-1 | an-127 | E1U7453 | sp-27 | an-127 |
| E1A0128 | sp-1 | an-128 | E1U0128 | sp-1 | an-128 | E1U7454 | sp-27 | an-128 |
| E1A0129 | sp-1 | an-129 | E1U0129 | sp-1 | an-129 | E1U7455 | sp-27 | an-129 |
| E1A0130 | sp-1 | an-130 | E1U0130 | sp-1 | an-130 | E1U7456 | sp-27 | an-130 |
| E1A0131 | sp-1 | an-131 | E1U0131 | sp-1 | an-131 | E1U7457 | sp-27 | an-131 |
| E1A0132 | sp-1 | an-132 | E1U0132 | sp-1 | an-132 | E1U7458 | sp-27 | an-132 |
| E1A0133 | sp-1 | an-133 | E1U0133 | sp-1 | an-133 | E1U7459 | sp-27 | an-133 |
| E1A0134 | sp-1 | an-134 | E1U0134 | sp-1 | an-134 | E1U7460 | sp-27 | an-134 |
| E1A0135 | sp-1 | an-135 | E1U0135 | sp-1 | an-135 | E1U7461 | sp-27 | an-135 |
| E1A0136 | sp-1 | an-136 | E1U0136 | sp-1 | an-136 | E1U7462 | sp-27 | an-136 |
| E1A0137 | sp-1 | an-137 | E1U0137 | sp-1 | an-137 | E1U7463 | sp-27 | an-137 |
| E1A0138 | sp-1 | an-138 | E1U0138 | sp-1 | an-138 | E1U7464 | sp-27 | an-138 |
| E1A0139 | sp-1 | an-139 | E1U0139 | sp-1 | an-139 | E1U7465 | sp-27 | an-139 |
| E1A0140 | sp-1 | an-140 | E1U0140 | sp-1 | an-140 | E1U7466 | sp-27 | an-140 |
| E1A0141 | sp-1 | an-141 | E1U0141 | sp-1 | an-141 | E1U7467 | sp-27 | an-141 |
| E1A0142 | sp-1 | an-142 | E1U0142 | sp-1 | an-142 | E1U7468 | sp-27 | an-142 |
| E1A0143 | sp-1 | an-143 | E1U0143 | sp-1 | an-143 | E1U7469 | sp-27 | an-143 |
| E1A0144 | sp-1 | an-144 | E1U0144 | sp-1 | an-144 | E1U7470 | sp-27 | an-144 |
| E1A0145 | sp-1 | an-145 | E1U0145 | sp-1 | an-145 | E1U7471 | sp-27 | an-145 |
| E1A0146 | sp-1 | an-146 | E1U0146 | sp-1 | an-146 | E1U7472 | sp-27 | an-146 |
| E1A0147 | sp-1 | an-147 | E1U0147 | sp-1 | an-147 | E1U7473 | sp-27 | an-147 |
| E1A0148 | sp-1 | an-148 | E1U0148 | sp-1 | an-148 | E1U7474 | sp-27 | an-148 |
| E1A0149 | sp-1 | an-149 | E1U0149 | sp-1 | an-149 | E1U7475 | sp-27 | an-149 |
| E1A0150 | sp-1 | an-150 | E1U0150 | sp-1 | an-150 | E1U7476 | sp-27 | an-150 |
| E1A0151 | sp-1 | an-151 | E1U0151 | sp-1 | an-151 | E1U7477 | sp-27 | an-151 |
| E1A0152 | sp-1 | an-152 | E1U0152 | sp-1 | an-152 | E1U7478 | sp-27 | an-152 |
| E1A0153 | sp-1 | an-153 | E1U0153 | sp-1 | an-153 | E1U7479 | sp-27 | an-153 |
| E1A0154 | sp-1 | an-154 | E1U0154 | sp-1 | an-154 | E1U7480 | sp-27 | an-154 |
| E1A0155 | sp-1 | an-155 | E1U0155 | sp-1 | an-155 | E1U7481 | sp-27 | an-155 |
| E1A0156 | sp-1 | an-156 | E1U0156 | sp-1 | an-156 | E1U7482 | sp-27 | an-156 |
| E1A0157 | sp-1 | an-157 | E1U0157 | sp-1 | an-157 | E1U7483 | sp-27 | an-157 |
| E1A0158 | sp-1 | an-158 | E1U0158 | sp-1 | an-158 | E1U7484 | sp-27 | an-158 |
| E1A0159 | sp-1 | an-159 | E1U0159 | sp-1 | an-159 | E1U7485 | sp-27 | an-159 |
| E1A0160 | sp-1 | an-160 | E1U0160 | sp-1 | an-160 | E1U7486 | sp-27 | an-160 |
| E1A0161 | sp-1 | an-161 | E1U0161 | sp-1 | an-161 | E1U7487 | sp-27 | an-161 |
| E1A0162 | sp-1 | an-162 | E1U0162 | sp-1 | an-162 | E1U7488 | sp-27 | an-162 |

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| | | | | Table 1-4 | | | | |
| | Y = NHCS | | | Y = NHCSNH | | | Y = NHCSNH | |
| E1A0163 | sp-1 | an-163 | E1U0163 | sp-1 | an-163 | E1U7489 | sp-27 | an-163 |
| E1A0164 | sp-1 | an-164 | E1U0164 | sp-1 | an-164 | E1U7490 | sp-27 | an-164 |
| E1A0165 | sp-1 | an-165 | E1U0165 | sp-1 | an-165 | E1U7491 | sp-27 | an-165 |
| E1A0166 | sp-1 | an-166 | E1U0166 | sp-1 | an-166 | E1U7492 | sp-27 | an-166 |
| E1A0167 | sp-1 | an-167 | E1U0167 | sp-1 | an-167 | E1U7493 | sp-27 | an-167 |
| E1A0168 | sp-1 | an-168 | E1U0168 | sp-1 | an-168 | E1U7494 | sp-27 | an-168 |
| E1A0169 | sp-1 | an-169 | E1U0169 | sp-1 | an-169 | E1U7495 | sp-27 | an-169 |
| E1A0170 | sp-1 | an-170 | E1U0170 | sp-1 | an-170 | E1U7496 | sp-27 | an-170 |
| E1A0171 | sp-1 | an-171 | E1U0171 | sp-1 | an-171 | E1U7497 | sp-27 | an-171 |
| E1A0172 | sp-1 | an-172 | E1U0172 | sp-1 | an-172 | E1U7498 | sp-27 | an-172 |
| E1A0173 | sp-1 | an-173 | E1U0173 | sp-1 | an-173 | E1U7499 | sp-27 | an-173 |
| E1A0174 | sp-1 | an-174 | E1U0174 | sp-1 | an-174 | E1U7500 | sp-27 | an-174 |
| E1A0175 | sp-1 | an-175 | E1U0175 | sp-1 | an-175 | E1U7501 | sp-27 | an-175 |
| E1A0176 | sp-1 | an-176 | E1U0176 | sp-1 | an-176 | E1U7502 | sp-27 | an-176 |
| E1A0177 | sp-1 | an-177 | E1U0177 | sp-1 | an-177 | E1U7503 | sp-27 | an-177 |
| E1A0178 | sp-1 | an-178 | E1U0178 | sp-1 | an-178 | E1U7504 | sp-27 | an-178 |
| E1A0179 | sp-1 | an-179 | E1U0179 | sp-1 | an-179 | E1U7505 | sp-27 | an-179 |
| E1A0180 | sp-1 | an-180 | E1U0180 | sp-1 | an-180 | E1U7506 | sp-27 | an-180 |
| E1A0181 | sp-1 | an-181 | E1U0181 | sp-1 | an-181 | E1U7507 | sp-27 | an-181 |
| E1A0182 | sp-1 | an-182 | E1U0182 | sp-1 | an-182 | E1U7508 | sp-27 | an-182 |
| E1A0183 | sp-1 | an-183 | E1U0183 | sp-1 | an-183 | E1U7509 | sp-27 | an-183 |
| E1A0184 | sp-1 | an-184 | E1U0184 | sp-1 | an-184 | E1U7510 | sp-27 | an-184 |
| E1A0185 | sp-1 | an-185 | E1U0185 | sp-1 | an-185 | E1U7511 | sp-27 | an-185 |
| E1A0186 | sp-1 | an-186 | E1U0186 | sp-1 | an-186 | E1U7512 | sp-27 | an-186 |
| E1A0187 | sp-1 | an-187 | E1U0187 | sp-1 | an-187 | E1U7513 | sp-27 | an-187 |
| E1A0188 | sp-1 | an-188 | E1U0188 | sp-1 | an-188 | E1U7514 | sp-27 | an-188 |
| E1A0189 | sp-1 | an-189 | E1U0189 | sp-1 | an-189 | E1U7515 | sp-27 | an-189 |
| E1A0190 | sp-1 | an-190 | E1U0190 | sp-1 | an-190 | E1U7516 | sp-27 | an-190 |
| E1A0191 | sp-1 | an-191 | E1U0191 | sp-1 | an-191 | E1U7517 | sp-27 | an-191 |
| E1A0192 | sp-1 | an-192 | E1U0192 | sp-1 | an-192 | E1U7518 | sp-27 | an-192 |
| E1A0193 | sp-1 | an-193 | E1U0193 | sp-1 | an-193 | E1U7519 | sp-27 | an-193 |
| E1A0194 | sp-1 | an-194 | E1U0194 | sp-1 | an-194 | E1U7520 | sp-27 | an-194 |
| E1A0195 | sp-1 | an-195 | E1U0195 | sp-1 | an-195 | E1U7521 | sp-27 | an-195 |
| E1A0196 | sp-1 | an-196 | E1U0196 | sp-1 | an-196 | E1U7522 | sp-27 | an-196 |
| E1A0197 | sp-1 | an-197 | E1U0197 | sp-1 | an-197 | E1U7523 | sp-27 | an-197 |
| E1A0198 | sp-1 | an-198 | E1U0198 | sp-1 | an-198 | E1U7524 | sp-27 | an-198 |
| E1A0199 | sp-1 | an-199 | E1U0199 | sp-1 | an-199 | E1U7525 | sp-27 | an-199 |
| E1A0200 | sp-1 | an-200 | E1U0200 | sp-1 | an-200 | E1U7526 | sp-27 | an-200 |
| E1A0201 | sp-1 | an-201 | E1U0201 | sp-1 | an-201 | E1U7527 | sp-27 | an-201 |
| E1A0202 | sp-1 | an-202 | E1U0202 | sp-1 | an-202 | E1U7528 | sp-27 | an-202 |
| E1A0203 | sp-1 | an-203 | E1U0203 | sp-1 | an-203 | E1U7529 | sp-27 | an-203 |
| E1A0204 | sp-1 | an-204 | E1U0204 | sp-1 | an-204 | E1U7530 | sp-27 | an-204 |
| E1A0205 | sp-1 | an-205 | E1U0205 | sp-1 | an-205 | E1U7531 | sp-27 | an-205 |
| E1A0206 | sp-1 | an-206 | E1U0206 | sp-1 | an-206 | E1U7532 | sp-27 | an-206 |
| E1A0207 | sp-1 | an-207 | E1U0207 | sp-1 | an-207 | E1U7533 | sp-27 | an-207 |
| E1A0208 | sp-1 | an-208 | E1U0208 | sp-1 | an-208 | E1U7534 | sp-27 | an-208 |
| E1A0209 | sp-1 | an-209 | E1U0209 | sp-1 | an-209 | E1U7535 | sp-27 | an-209 |
| E1A0210 | sp-1 | an-210 | E1U0210 | sp-1 | an-210 | E1U7536 | sp-27 | an-210 |
| E1A0211 | sp-1 | an-211 | E1U0211 | sp-1 | an-211 | E1U7537 | sp-27 | an-211 |
| E1A0212 | sp-1 | an-212 | E1U0212 | sp-1 | an-212 | E1U7538 | sp-27 | an-212 |
| E1A0213 | sp-1 | an-213 | E1U0213 | sp-1 | an-213 | E1U7539 | sp-27 | an-213 |
| E1A0214 | sp-1 | an-214 | E1U0214 | sp-1 | an-214 | E1U7540 | sp-27 | an-214 |
| E1A0215 | sp-1 | an-215 | E1U0215 | sp-1 | an-215 | E1U7541 | sp-27 | an-215 |
| E1A0216 | sp-1 | an-216 | E1U0216 | sp-1 | an-216 | E1U7542 | sp-27 | an-216 |
| | | | | Table 1-5 | | | | |
| | Y = NHCS | | | Y = NHCSNH | | | Y = NHCSNH | |
| E1A0217 | sp-1 | an-217 | E1U0217 | sp-1 | an-217 | E1U7543 | sp-27 | an-217 |
| E1A0218 | sp-1 | an-218 | E1U0218 | sp-1 | an-218 | E1U7544 | sp-27 | an-218 |
| E1A0219 | sp-1 | an-219 | E1U0219 | sp-1 | an-219 | E1U7545 | sp-27 | an-219 |
| E1A0220 | sp-1 | an-220 | E1U0220 | sp-1 | an-220 | E1U7546 | sp-27 | an-220 |
| E1A0221 | sp-1 | an-221 | E1U0221 | sp-1 | an-221 | E1U7547 | sp-27 | an-221 |
| E1A0222 | sp-1 | an-222 | E1U0222 | sp-1 | an-222 | E1U7548 | sp-27 | an-222 |
| E1A0223 | sp-1 | an-223 | E1U0223 | sp-1 | an-223 | E1U7549 | sp-27 | an-223 |
| E1A0224 | sp-1 | an-224 | E1U0224 | sp-1 | an-224 | E1U7550 | sp-27 | an-224 |
| E1A0225 | sp-1 | an-225 | E1U0225 | sp-1 | an-225 | E1U7551 | sp-27 | an-225 |
| E1A0226 | sp-1 | an-226 | E1U0226 | sp-1 | an-226 | E1U7552 | sp-27 | an-226 |
| E1A0227 | sp-1 | an-227 | E1U0227 | sp-1 | an-227 | E1U7553 | sp-27 | an-227 |
| E1A0228 | sp-1 | an-228 | E1U0228 | sp-1 | an-228 | E1U7554 | sp-27 | an-228 |
| E1A0229 | sp-1 | an-229 | E1U0229 | sp-1 | an-229 | E1U7555 | sp-27 | an-229 |
| E1A0230 | sp-1 | an-230 | E1U0230 | sp-1 | an-230 | E1U7556 | sp-27 | an-230 |
| E1A0231 | sp-1 | an-231 | E1U0231 | sp-1 | an-231 | E1U7557 | sp-27 | an-231 |
| E1A0232 | sp-1 | an-232 | E1U0232 | sp-1 | an-232 | E1U7558 | sp-27 | an-232 |

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| E1A0233 | sp-1 | an-233 | E1U0233 | sp-1 | an-233 | E1U7559 | sp-27 | an-233 |
| E1A0234 | sp-1 | an-234 | E1U0234 | sp-1 | an-234 | E1U7560 | sp-27 | an-234 |
| E1A0235 | sp-1 | an-235 | E1U0235 | sp-1 | an-235 | E1U7561 | sp-27 | an-235 |
| E1A0236 | sp-1 | an-236 | E1U0236 | sp-1 | an-236 | E1U7562 | sp-27 | an-236 |
| E1A0237 | sp-1 | an-237 | E1U0237 | sp-1 | an-237 | E1U7563 | sp-27 | an-237 |
| E1A0238 | sp-1 | an-238 | E1U0238 | sp-1 | an-238 | E1U7564 | sp-27 | an-238 |
| E1A0239 | sp-1 | an-239 | E1U0239 | sp-1 | an-239 | E1U7565 | sp-27 | an-239 |
| E1A0240 | sp-1 | an-240 | E1U0240 | sp-1 | an-240 | E1U7566 | sp-27 | an-240 |
| E1A0241 | sp-1 | an-241 | E1U0241 | sp-1 | an-241 | E1U7567 | sp-27 | an-241 |
| E1A0242 | sp-1 | an-242 | E1U0242 | sp-1 | an-242 | E1U7568 | sp-27 | an-242 |
| E1A0243 | sp-1 | an-243 | E1U0243 | sp-1 | an-243 | E1U7569 | sp-27 | an-243 |
| E1A0244 | sp-1 | an-244 | E1U0244 | sp-1 | an-244 | E1U7570 | sp-27 | an-244 |
| E1A0245 | sp-1 | an-245 | E1U0245 | sp-1 | an-245 | E1U7571 | sp-27 | an-245 |
| E1A0246 | sp-1 | an-246 | E1U0246 | sp-1 | an-246 | E1U7572 | sp-27 | an-246 |
| E1A0247 | sp-1 | an-247 | E1U0247 | sp-1 | an-247 | E1U7573 | sp-27 | an-247 |
| E1A0248 | sp-1 | an-248 | E1U0248 | sp-1 | an-248 | E1U7574 | sp-27 | an-248 |
| E1A0249 | sp-1 | an-249 | E1U0249 | sp-1 | an-249 | E1U7575 | sp-27 | an-249 |
| E1A0250 | sp-1 | an-250 | E1U0250 | sp-1 | an-250 | E1U7576 | sp-27 | an-250 |
| E1A0251 | sp-1 | an-251 | E1U0251 | sp-1 | an-251 | E1U7577 | sp-27 | an-251 |
| E1A0252 | sp-1 | an-252 | E1U0252 | sp-1 | an-252 | E1U7578 | sp-27 | an-252 |
| E1A0253 | sp-1 | an-253 | E1U0253 | sp-1 | an-253 | E1U7579 | sp-27 | an-253 |
| E1A0254 | sp-1 | an-254 | E1U0254 | sp-1 | an-254 | E1U7580 | sp-27 | an-254 |
| E1A0255 | sp-1 | an-255 | E1U0255 | sp-1 | an-255 | E1U7581 | sp-27 | an-255 |
| E1A0256 | sp-1 | an-256 | E1U0256 | sp-1 | an-256 | E1U7582 | sp-27 | an-256 |
| E1A0257 | sp-1 | an-257 | E1U0257 | sp-1 | an-257 | E1U7583 | sp-27 | an-257 |
| E1A0258 | sp-1 | an-258 | E1U0258 | sp-1 | an-258 | E1U7584 | sp-27 | an-258 |
| E1A0259 | sp-1 | an-259 | E1U0259 | sp-1 | an-259 | E1U7585 | sp-27 | an-259 |
| E1A0260 | sp-1 | an-260 | E1U0260 | sp-1 | an-260 | E1U7586 | sp-27 | an-260 |
| E1A0261 | sp-1 | an-261 | E1U0261 | sp-1 | an-261 | E1U7587 | sp-27 | an-261 |
| E1A0262 | sp-1 | an-262 | E1U0262 | sp-1 | an-262 | E1U7588 | sp-27 | an-262 |
| E1A0263 | sp-1 | an-263 | E1U0263 | sp-1 | an-263 | E1U7589 | sp-27 | an-263 |
| E1A0264 | sp-1 | an-264 | E1U0264 | sp-1 | an-264 | E1U7590 | sp-27 | an-264 |
| E1A0265 | sp-1 | an-265 | E1U0265 | sp-1 | an-265 | E1U7591 | sp-27 | an-265 |
| E1A0266 | sp-1 | an-266 | E1U0266 | sp-1 | an-266 | E1U7592 | sp-27 | an-266 |
| E1A0267 | sp-1 | an-267 | E1U0267 | sp-1 | an-267 | E1U7593 | sp-27 | an-267 |
| E1A0268 | sp-1 | an-268 | E1U0268 | sp-1 | an-268 | E1U7594 | sp-27 | an-268 |
| E1A0269 | sp-1 | an-269 | E1U0269 | sp-1 | an-269 | E1U7595 | sp-27 | an-269 |
| E1A0270 | sp-1 | an-270 | E1U0270 | sp-1 | an-270 | E1U7596 | sp-27 | an-270 |

Table 1-6

| Y = NHCS | | | Y = NHCSNH | | | Y = NHCSNH | | |
|---|---|---|---|---|---|---|---|---|
| E1A0271 | sp-1 | an-271 | E1U0271 | sp-1 | an-271 | E1U7597 | sp-27 | an-271 |
| E1A0272 | sp-1 | an-272 | E1U0272 | sp-1 | an-272 | E1U7598 | sp-27 | an-272 |
| E1A0273 | sp-1 | an-273 | E1U0273 | sp-1 | an-273 | E1U7599 | sp-27 | an-273 |
| E1A0274 | sp-1 | an-274 | E1U0274 | sp-1 | an-274 | E1U7600 | sp-27 | an-274 |
| E1A0275 | sp-1 | an-275 | E1U0275 | sp-1 | an-275 | E1U7601 | sp-27 | an-275 |
| E1A0276 | sp-1 | an-276 | E1U0276 | sp-1 | an-276 | E1U7602 | sp-27 | an-276 |
| E1A0277 | sp-1 | an-277 | E1U0277 | sp-1 | an-277 | E1U7603 | sp-27 | an-277 |
| E1A0278 | sp-1 | an-278 | E1U0278 | sp-1 | an-278 | E1U7604 | sp-27 | an-278 |
| E1A0279 | sp-1 | an-279 | E1U0279 | sp-1 | an-279 | E1U7605 | sp-27 | an-279 |
| E1A0280 | sp-1 | an-280 | E1U0280 | sp-1 | an-280 | E1U7606 | sp-27 | an-280 |
| E1A0281 | sp-1 | an-281 | E1U0281 | sp-1 | an-281 | E1U7607 | sp-27 | an-281 |
| E1A0282 | sp-1 | an-282 | E1U0282 | sp-1 | an-282 | E1U7608 | sp-27 | an-282 |
| E1A0283 | sp-1 | an-283 | E1U0283 | sp-1 | an-283 | E1U7609 | sp-27 | an-283 |
| E1A0284 | sp-1 | an-284 | E1U0284 | sp-1 | an-284 | E1U7610 | sp-27 | an-284 |
| E1A0285 | sp-1 | an-285 | E1U0285 | sp-1 | an-285 | E1U7611 | sp-27 | an-285 |
| E1A0286 | sp-1 | an-286 | E1U0286 | sp-1 | an-286 | E1U7612 | sp-27 | an-286 |
| E1A0287 | sp-1 | an-287 | E1U0287 | sp-1 | an-287 | E1U7613 | sp-27 | an-287 |
| E1A0288 | sp-1 | an-288 | E1U0288 | sp-1 | an-288 | E1U7614 | sp-27 | an-288 |
| E1A0289 | sp-1 | an-289 | E1U0289 | sp-1 | an-289 | E1U7615 | sp-27 | an-289 |
| E1A0290 | sp-1 | an-290 | E1U0290 | sp-1 | an-290 | E1U7616 | sp-27 | an-290 |
| E1A0291 | sp-1 | an-291 | E1U0291 | sp-1 | an-291 | E1U7617 | sp-27 | an-291 |
| E1A0292 | sp-1 | an-292 | E1U0292 | sp-1 | an-292 | E1U7618 | sp-27 | an-292 |
| E1A0293 | sp-1 | an-293 | E1U0293 | sp-1 | an-293 | E1U7619 | sp-27 | an-293 |
| E1A0294 | sp-1 | an-294 | E1U0294 | sp-1 | an-294 | E1U7620 | sp-27 | an-294 |
| E1A0295 | sp-1 | an-295 | E1U0295 | sp-1 | an-295 | E1U7621 | sp-27 | an-295 |
| E1A0296 | sp-1 | an-296 | E1U0296 | sp-1 | an-296 | E1U7622 | sp-27 | an-296 |
| E1A0297 | sp-1 | an-297 | E1U0297 | sp-1 | an-297 | E1U7623 | sp-27 | an-297 |
| E1A0298 | sp-1 | an-298 | E1U0298 | sp-1 | an-298 | E1U7624 | sp-27 | an-298 |
| E1A0299 | sp-1 | an-299 | E1U0299 | sp-1 | an-299 | E1U7625 | sp-27 | an-299 |
| E1A0300 | sp-1 | an-300 | E1U0300 | sp-1 | an-300 | E1U7626 | sp-27 | an-300 |
| E1A0301 | sp-1 | an-301 | E1U0301 | sp-1 | an-301 | E1U7627 | sp-27 | an-301 |
| E1A0302 | sp-1 | an-302 | E1U0302 | sp-1 | an-302 | E1U7628 | sp-27 | an-302 |
| E1A0303 | sp-1 | an-303 | E1U0303 | sp-1 | an-303 | E1U7629 | sp-27 | an-303 |
| E1A0304 | sp-1 | an-304 | E1U0304 | sp-1 | an-304 | E1U7630 | sp-27 | an-304 |
| E1A0305 | sp-1 | an-305 | E1U0305 | sp-1 | an-305 | E1U7631 | sp-27 | an-305 |
| E1A0306 | sp-1 | an-306 | E1U0306 | sp-1 | an-306 | E1U7632 | sp-27 | an-306 |

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| E1A0307 | sp-1 | an-307 | E1U0307 | sp-1 | an-307 | E1U7633 | sp-27 | an-307 |
| E1A0308 | sp-1 | an-308 | E1U0308 | sp-1 | an-308 | E1U7634 | sp-27 | an-308 |
| E1A0309 | sp-1 | an-309 | E1U0309 | sp-1 | an-309 | E1U7635 | sp-27 | an-309 |
| E1A0310 | sp-1 | an-310 | E1U0310 | sp-1 | an-310 | E1U7636 | sp-27 | an-310 |
| E1A0311 | sp-1 | an-311 | E1U0311 | sp-1 | an-311 | E1U7637 | sp-27 | an-311 |
| E1A0312 | sp-1 | an-312 | E1U0312 | sp-1 | an-312 | E1U7638 | sp-27 | an-312 |
| E1A0313 | sp-1 | an-313 | E1U0313 | sp-1 | an-313 | E1U7639 | sp-27 | an-313 |
| E1A0314 | sp-1 | an-314 | E1U0314 | sp-1 | an-314 | E1U7640 | sp-27 | an-314 |
| E1A0315 | sp-1 | an-315 | E1U0315 | sp-1 | an-315 | E1U7641 | sp-27 | an-315 |
| E1A0316 | sp-1 | an-316 | E1U0316 | sp-1 | an-316 | E1U7642 | sp-27 | an-316 |
| E1A0317 | sp-1 | an-317 | E1U0317 | sp-1 | an-317 | E1U7643 | sp-27 | an-317 |
| E1A0318 | sp-1 | an-318 | E1U0318 | sp-1 | an-318 | E1U7644 | sp-27 | an-318 |
| E1A0319 | sp-1 | an-319 | E1U0319 | sp-1 | an-319 | E1U7645 | sp-27 | an-319 |
| E1A0320 | sp-1 | an-320 | E1U0320 | sp-1 | an-320 | E1U7646 | sp-27 | an-320 |
| E1A0321 | sp-1 | an-321 | E1U0321 | sp-1 | an-321 | E1U7647 | sp-27 | an-321 |
| E1A0322 | sp-1 | an-322 | E1U0322 | sp-1 | an-322 | E1U7648 | sp-27 | an-322 |
| E1A0323 | sp-1 | an-323 | E1U0323 | sp-1 | an-323 | E1U7649 | sp-27 | an-323 |
| E1A0324 | sp-1 | an-324 | E1U0324 | sp-1 | an-324 | E1U7650 | sp-27 | an-324 |

Table 1-7

| Y = NHCS | | | Y = NHCSNH | | | Y = NHCSNH | | |
|---|---|---|---|---|---|---|---|---|
| E1A0325 | sp-1 | an-325 | E1U0325 | sp-1 | an-325 | E1U7651 | sp-27 | an-325 |
| E1A0326 | sp-1 | an-326 | E1U0326 | sp-1 | an-326 | E1U7652 | sp-27 | an-326 |
| E1A0327 | sp-1 | an-327 | E1U0327 | sp-1 | an-327 | E1U7653 | sp-27 | an-327 |
| E1A0328 | sp-1 | an-328 | E1U0328 | sp-1 | an-328 | E1U7654 | sp-27 | an-328 |
| E1A0329 | sp-1 | an-329 | E1U0329 | sp-1 | an-329 | E1U7655 | sp-27 | an-329 |
| E1A0330 | sp-1 | an-330 | E1U0330 | sp-1 | an-330 | E1U7656 | sp-27 | an-330 |
| E1A0331 | sp-1 | an-331 | E1U0331 | sp-1 | an-331 | E1U7657 | sp-27 | an-331 |
| E1A0332 | sp-1 | an-332 | E1U0332 | sp-1 | an-332 | E1U7658 | sp-27 | an-332 |
| E1A0333 | sp-1 | an-333 | E1U0333 | sp-1 | an-333 | E1U7659 | sp-27 | an-333 |
| E1A0334 | sp-1 | an-334 | E1U0334 | sp-1 | an-334 | E1U7660 | sp-27 | an-334 |
| E1A0335 | sp-1 | an-335 | E1U0335 | sp-1 | an-335 | E1U7661 | sp-27 | an-335 |
| E1A0336 | sp-1 | an-336 | E1U0336 | sp-1 | an-336 | E1U7662 | sp-27 | an-336 |
| E1A0337 | sp-1 | an-337 | E1U0337 | sp-1 | an-337 | E1U7663 | sp-27 | an-337 |
| E1A0338 | sp-1 | an-338 | E1U0338 | sp-1 | an-338 | E1U7664 | sp-27 | an-338 |
| E1A0339 | sp-1 | an-339 | E1U0339 | sp-1 | an-339 | E1U7665 | sp-27 | an-339 |
| E1A0340 | sp-1 | an-340 | E1U0340 | sp-1 | an-340 | E1U7666 | sp-27 | an-340 |
| E1A0341 | sp-1 | an-341 | E1U0341 | sp-1 | an-341 | E1U7667 | sp-27 | an-341 |
| E1A0342 | sp-1 | an-342 | E1U0342 | sp-1 | an-342 | E1U7668 | sp-27 | an-342 |
| E1A0343 | sp-1 | an-343 | E1U0343 | sp-1 | an-343 | E1U7669 | sp-27 | an-343 |
| E1A0344 | sp-1 | an-344 | E1U0344 | sp-1 | an-344 | E1U7670 | sp-27 | an-344 |
| E1A0345 | sp-1 | an-345 | E1U0345 | sp-1 | an-345 | E1U7671 | sp-27 | an-345 |
| E1A0346 | sp-1 | an-346 | E1U0346 | sp-1 | an-346 | E1U7672 | sp-27 | an-346 |
| E1A0347 | sp-1 | an-347 | E1U0347 | sp-1 | an-347 | E1U7673 | sp-27 | an-347 |
| E1A0348 | sp-1 | an-348 | E1U0348 | sp-1 | an-348 | E1U7674 | sp-27 | an-348 |
| E1A0349 | sp-1 | an-349 | E1U0349 | sp-1 | an-349 | E1U7675 | sp-27 | an-349 |
| E1A0350 | sp-1 | an-350 | E1U0350 | sp-1 | an-350 | E1U7676 | sp-27 | an-350 |
| E1A0351 | sp-1 | an-351 | E1U0351 | sp-1 | an-351 | E1U7677 | sp-27 | an-351 |
| E1A0352 | sp-1 | an-352 | E1U0352 | sp-1 | an-352 | E1U7678 | sp-27 | an-352 |
| E1A0353 | sp-1 | an-353 | E1U0353 | sp-1 | an-353 | E1U7679 | sp-27 | an-353 |
| E1A0354 | sp-1 | an-354 | E1U0354 | sp-1 | an-354 | E1U7680 | sp-27 | an-354 |
| E1A0355 | sp-1 | an-355 | E1U0355 | sp-1 | an-355 | E1U7681 | sp-27 | an-355 |
| E1A0356 | sp-1 | an-356 | E1U0356 | sp-1 | an-356 | E1U7682 | sp-27 | an-356 |
| E1A0357 | sp-1 | an-357 | E1U0357 | sp-1 | an-357 | E1U7683 | sp-27 | an-357 |
| E1A0358 | sp-1 | an-358 | E1U0358 | sp-1 | an-358 | E1U7684 | sp-27 | an-358 |
| E1A0359 | sp-1 | an-359 | E1U0359 | sp-1 | an-359 | E1U7685 | sp-27 | an-359 |
| E1A0360 | sp-1 | an-360 | E1U0360 | sp-1 | an-360 | E1U7686 | sp-27 | an-360 |
| E1A0361 | sp-1 | an-361 | E1U0361 | sp-1 | an-361 | E1U7687 | sp-27 | an-361 |
| E1A0362 | sp-1 | an-362 | E1U0362 | sp-1 | an-362 | E1U7688 | sp-27 | an-362 |
| E1A0363 | sp-1 | an-363 | E1U0363 | sp-1 | an-363 | E1U7689 | sp-27 | an-363 |
| E1A0364 | sp-1 | an-364 | E1U0364 | sp-1 | an-364 | E1U7690 | sp-27 | an-364 |
| E1A0365 | sp-1 | an-365 | E1U0365 | sp-1 | an-365 | E1U7691 | sp-27 | an-365 |
| E1A0366 | sp-1 | an-366 | E1U0366 | sp-1 | an-366 | E1U7692 | sp-27 | an-366 |
| E1A0367 | sp-1 | an-367 | E1U0367 | sp-1 | an-367 | E1U7693 | sp-27 | an-367 |
| E1A0368 | sp-1 | an-368 | E1U0368 | sp-1 | an-368 | E1U7694 | sp-27 | an-368 |
| E1A0369 | sp-1 | an-369 | E1U0369 | sp-1 | an-369 | E1U7695 | sp-27 | an-369 |
| E1A0370 | sp-1 | an-370 | E1U0370 | sp-1 | an-370 | E1U7696 | sp-27 | an-370 |
| E1A0371 | sp-1 | an-371 | E1U0371 | sp-1 | an-371 | E1U7697 | sp-27 | an-371 |
| E1A0372 | sp-1 | an-372 | E1U0372 | sp-1 | an-372 | E1U7698 | sp-27 | an-372 |
| E1A0373 | sp-1 | an-373 | E1U0373 | sp-1 | an-373 | E1U7699 | sp-27 | an-373 |
| E1A0374 | sp-1 | an-374 | E1U0374 | sp-1 | an-374 | E1U7700 | sp-27 | an-374 |
| E1A0375 | sp-1 | an-375 | E1U0375 | sp-1 | an-375 | E1U7701 | sp-27 | an-375 |
| E1A0376 | sp-1 | an-376 | E1U0376 | sp-1 | an-376 | E1U7702 | sp-27 | an-376 |
| E1A0377 | sp-1 | an-377 | E1U0377 | sp-1 | an-377 | E1U7703 | sp-27 | an-377 |
| E1A0378 | sp-1 | an-378 | E1U0378 | sp-1 | an-378 | E1U7704 | sp-27 | an-378 |

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| \multicolumn{9}{c}{Table 1-8} | | | | | | | | |
| \multicolumn{3}{c}{Y = NHCS} | \multicolumn{3}{c}{Y = NHCSNH} | \multicolumn{3}{c}{Y = NHCSNH} | | | | | | | | |
| E1A0379 | sp-1 | an-379 | E1U0379 | sp-1 | an-379 | E1U7705 | sp-27 | an-379 |
| E1A0380 | sp-1 | an-380 | E1U0380 | sp-1 | an-380 | E1U7706 | sp-27 | an-380 |
| E1A0381 | sp-1 | an-381 | E1U0381 | sp-1 | an-381 | E1U7707 | sp-27 | an-381 |
| E1A0382 | sp-1 | an-382 | E1U0382 | sp-1 | an-382 | E1U7708 | sp-27 | an-382 |
| E1A0383 | sp-1 | an-383 | E1U0383 | sp-1 | an-383 | E1U7709 | sp-27 | an-383 |
| E1A0384 | sp-1 | an-384 | E1U0384 | sp-1 | an-384 | E1U7710 | sp-27 | an-384 |
| E1A0385 | sp-1 | an-385 | E1U0385 | sp-1 | an-385 | E1U7711 | sp-27 | an-385 |
| E1A0386 | sp-1 | an-386 | E1U0386 | sp-1 | an-386 | E1U7712 | sp-27 | an-386 |
| E1A0387 | sp-1 | an-387 | E1U0387 | sp-1 | an-387 | E1U7713 | sp-27 | an-387 |
| E1A0388 | sp-1 | an-388 | E1U0388 | sp-1 | an-388 | E1U7714 | sp-27 | an-388 |
| E1A0389 | sp-1 | an-389 | E1U0389 | sp-1 | an-389 | E1U7715 | sp-27 | an-389 |
| E1A0390 | sp-1 | an-390 | E1U0390 | sp-1 | an-390 | E1U7716 | sp-27 | an-390 |
| E1A0391 | sp-1 | an-391 | E1U0391 | sp-1 | an-391 | E1U7717 | sp-27 | an-391 |
| E1A0392 | sp-1 | an-392 | E1U0392 | sp-1 | an-392 | E1U7718 | sp-27 | an-392 |
| E1A0393 | sp-1 | an-393 | E1U0393 | sp-1 | an-393 | E1U7719 | sp-27 | an-393 |
| E1A0394 | sp-1 | an-394 | E1U0394 | sp-1 | an-394 | E1U7720 | sp-27 | an-394 |
| E1A0395 | sp-1 | an-395 | E1U0395 | sp-1 | an-395 | E1U7721 | sp-27 | an-395 |
| E1A0396 | sp-1 | an-396 | E1U0396 | sp-1 | an-396 | E1U7722 | sp-27 | an-396 |
| E1A0397 | sp-1 | an-397 | E1U0397 | sp-1 | an-397 | E1U7723 | sp-27 | an-397 |
| E1A0398 | sp-1 | an-398 | E1U0398 | sp-1 | an-398 | E1U7724 | sp-27 | an-398 |
| E1A0399 | sp-1 | an-399 | E1U0399 | sp-1 | an-399 | E1U7725 | sp-27 | an-399 |
| E1A0400 | sp-1 | an-400 | E1U0400 | sp-1 | an-400 | E1U7726 | sp-27 | an-400 |
| E1A0401 | sp-1 | an-401 | E1U0401 | sp-1 | an-401 | E1U7727 | sp-27 | an-401 |
| E1A0402 | sp-1 | an-402 | E1U0402 | sp-1 | an-402 | E1U7728 | sp-27 | an-402 |
| E1A0403 | sp-1 | an-403 | E1U0403 | sp-1 | an-403 | E1U7729 | sp-27 | an-403 |
| E1A0404 | sp-1 | an-404 | E1U0404 | sp-1 | an-404 | E1U7730 | sp-27 | an-404 |
| E1A0405 | sp-1 | an-405 | E1U0405 | sp-1 | an-405 | E1U7731 | sp-27 | an-405 |
| E1A0406 | sp-1 | an-406 | E1U0406 | sp-1 | an-406 | E1U7732 | sp-27 | an-406 |
| E1A0407 | sp-1 | an-407 | E1U0407 | sp-1 | an-407 | E1U7733 | sp-27 | an-407 |
| E1A0408 | sp-2 | an-1 | E1U0408 | sp-2 | an-1 | E1U7734 | sp-28 | an-1 |
| E1A0409 | sp-2 | an-2 | E1U0409 | sp-2 | an-2 | E1U7735 | sp-28 | an-2 |
| E1A0410 | sp-2 | an-3 | E1U0410 | sp-2 | an-3 | E1U7736 | sp-28 | an-3 |
| E1A0411 | sp-2 | an-4 | E1U0411 | sp-2 | an-4 | E1U7737 | sp-28 | an-4 |
| E1A0412 | sp-2 | an-5 | E1U0412 | sp-2 | an-5 | E1U7738 | sp-28 | an-5 |
| E1A0413 | sp-2 | an-6 | E1U0413 | sp-2 | an-6 | E1U7739 | sp-28 | an-6 |
| E1A0414 | sp-2 | an-7 | E1U0414 | sp-2 | an-7 | E1U7740 | sp-28 | an-7 |
| E1A0415 | sp-2 | an-8 | E1U0415 | sp-2 | an-8 | E1U7741 | sp-28 | an-8 |
| E1A0416 | sp-2 | an-9 | E1U0416 | sp-2 | an-9 | E1U7742 | sp-28 | an-9 |
| E1A0417 | sp-2 | an-10 | E1U0417 | sp-2 | an-10 | E1U7743 | sp-28 | an-10 |
| E1A0418 | sp-2 | an-11 | E1U0418 | sp-2 | an-11 | E1U7744 | sp-28 | an-11 |
| E1A0419 | sp-2 | an-12 | E1U0419 | sp-2 | an-12 | E1U7745 | sp-28 | an-12 |
| E1A0420 | sp-2 | an-13 | E1U0420 | sp-2 | an-13 | E1U7746 | sp-28 | an-13 |
| E1A0421 | sp-2 | an-14 | E1U0421 | sp-2 | an-14 | E1U7747 | sp-28 | an-14 |
| E1A0422 | sp-2 | an-15 | E1U0422 | sp-2 | an-15 | E1U7748 | sp-28 | an-15 |
| E1A0423 | sp-2 | an-16 | E1U0423 | sp-2 | an-16 | E1U7749 | sp-28 | an-16 |
| E1A0424 | sp-2 | an-17 | E1U0424 | sp-2 | an-17 | E1U7750 | sp-28 | an-17 |
| E1A0425 | sp-2 | an-18 | E1U0425 | sp-2 | an-18 | E1U7751 | sp-28 | an-18 |
| E1A0426 | sp-2 | an-19 | E1U0426 | sp-2 | an-19 | E1U7752 | sp-28 | an-19 |
| E1A0427 | sp-2 | an-20 | E1U0427 | sp-2 | an-20 | E1U7753 | sp-28 | an-20 |
| E1A0428 | sp-2 | an-21 | E1U0428 | sp-2 | an-21 | E1U7754 | sp-28 | an-21 |
| E1A0429 | sp-2 | an-22 | E1U0429 | sp-2 | an-22 | E1U7755 | sp-28 | an-22 |
| E1A0430 | sp-2 | an-23 | E1U0430 | sp-2 | an-23 | E1U7756 | sp-28 | an-23 |
| E1A0431 | sp-2 | an-24 | E1U0431 | sp-2 | an-24 | E1U7757 | sp-28 | an-24 |
| E1A0432 | sp-2 | an-25 | E1U0432 | sp-2 | an-25 | E1U7758 | sp-28 | an-25 |
| \multicolumn{9}{c}{Table 1-9} | | | | | | | | |
| \multicolumn{3}{c}{Y = NHCS} | \multicolumn{3}{c}{Y = NHCSNH} | \multicolumn{3}{c}{Y = NHCSNH} | | | | | | | | |
| E1A0433 | sp-2 | an-26 | E1U0433 | sp-2 | an-26 | E1U7759 | sp-28 | an-26 |
| E1A0434 | sp-2 | an-27 | E1U0434 | sp-2 | an-27 | E1U7760 | sp-28 | an-27 |
| E1A0435 | sp-2 | an-28 | E1U0435 | sp-2 | an-28 | E1U7761 | sp-28 | an-28 |
| E1A0436 | sp-2 | an-29 | E1U0436 | sp-2 | an-29 | E1U7762 | sp-28 | an-29 |
| E1A0437 | sp-2 | an-30 | E1U0437 | sp-2 | an-30 | E1U7763 | sp-28 | an-30 |
| E1A0438 | sp-2 | an-31 | E1U0438 | sp-2 | an-31 | E1U7764 | sp-28 | an-31 |
| E1A0439 | sp-2 | an-32 | E1U0439 | sp-2 | an-32 | E1U7765 | sp-28 | an-32 |
| E1A0440 | sp-2 | an-33 | E1U0440 | sp-2 | an-33 | E1U7766 | sp-28 | an-33 |
| E1A0441 | sp-2 | an-34 | E1U0441 | sp-2 | an-34 | E1U7767 | sp-28 | an-34 |
| E1A0442 | sp-2 | an-35 | E1U0442 | sp-2 | an-35 | E1U7768 | sp-28 | an-35 |
| E1A0443 | sp-2 | an-36 | E1U0443 | sp-2 | an-36 | E1U7769 | sp-28 | an-36 |
| E1A0444 | sp-2 | an-37 | E1U0444 | sp-2 | an-37 | E1U7770 | sp-28 | an-37 |
| E1A0445 | sp-2 | an-38 | E1U0445 | sp-2 | an-38 | E1U7771 | sp-28 | an-38 |
| E1A0446 | sp-2 | an-39 | E1U0446 | sp-2 | an-39 | E1U7772 | sp-28 | an-39 |
| E1A0447 | sp-2 | an-40 | E1U0447 | sp-2 | an-40 | E1U7773 | sp-28 | an-40 |
| E1A0448 | sp-2 | an-41 | E1U0448 | sp-2 | an-41 | E1U7774 | sp-28 | an-41 |

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| E1A0449 | sp-2 | an-42 | E1U0449 | sp-2 | an-42 | E1U7775 | sp-28 | an-42 |
| E1A0450 | sp-2 | an-43 | E1U0450 | sp-2 | an-43 | E1U7776 | sp-28 | an-43 |
| E1A0451 | sp-2 | an-44 | E1U0451 | sp-2 | an-44 | E1U7777 | sp-28 | an-44 |
| E1A0452 | sp-2 | an-45 | E1U0452 | sp-2 | an-45 | E1U7778 | sp-28 | an-45 |
| E1A0453 | sp-2 | an-46 | E1U0453 | sp-2 | an-46 | E1U7779 | sp-28 | an-46 |
| E1A0454 | sp-2 | an-47 | E1U0454 | sp-2 | an-47 | E1U7780 | sp-28 | an-47 |
| E1A0455 | sp-2 | an-48 | E1U0455 | sp-2 | an-48 | E1U7781 | sp-28 | an-48 |
| E1A0456 | sp-2 | an-49 | E1U0456 | sp-2 | an-49 | E1U7782 | sp-28 | an-49 |
| E1A0457 | sp-2 | an-50 | E1U0457 | sp-2 | an-50 | E1U7783 | sp-28 | an-50 |
| E1A0458 | sp-2 | an-51 | E1U0458 | sp-2 | an-51 | E1U7784 | sp-28 | an-51 |
| E1A0459 | sp-2 | an-52 | E1U0459 | sp-2 | an-52 | E1U7785 | sp-28 | an-52 |
| E1A0460 | sp-2 | an-53 | E1U0460 | sp-2 | an-53 | E1U7786 | sp-28 | an-53 |
| E1A0461 | sp-2 | an-54 | E1U0461 | sp-2 | an-54 | E1U7787 | sp-28 | an-54 |
| E1A0462 | sp-2 | an-55 | E1U0462 | sp-2 | an-55 | E1U7788 | sp-28 | an-55 |
| E1A0463 | sp-2 | an-56 | E1U0463 | sp-2 | an-56 | E1U7789 | sp-28 | an-56 |
| E1A0464 | sp-2 | an-57 | E1U0464 | sp-2 | an-57 | E1U7790 | sp-28 | an-57 |
| E1A0465 | sp-2 | an-58 | E1U0465 | sp-2 | an-58 | E1U7791 | sp-28 | an-58 |
| E1A0466 | sp-2 | an-59 | E1U0466 | sp-2 | an-59 | E1U7792 | sp-28 | an-59 |
| E1A0467 | sp-2 | an-60 | E1U0467 | sp-2 | an-60 | E1U7793 | sp-28 | an-60 |
| E1A0468 | sp-2 | an-61 | E1U0468 | sp-2 | an-61 | E1U7794 | sp-28 | an-61 |
| E1A0469 | sp-2 | an-62 | E1U0469 | sp-2 | an-62 | E1U7795 | sp-28 | an-62 |
| E1A0470 | sp-2 | an-63 | E1U0470 | sp-2 | an-63 | E1U7796 | sp-28 | an-63 |
| E1A0471 | sp-2 | an-64 | E1U0471 | sp-2 | an-64 | E1U7797 | sp-28 | an-64 |
| E1A0472 | sp-2 | an-65 | E1U0472 | sp-2 | an-65 | E1U7798 | sp-28 | an-65 |
| E1A0473 | sp-2 | an-66 | E1U0473 | sp-2 | an-66 | E1U7799 | sp-28 | an-66 |
| E1A0474 | sp-2 | an-67 | E1U0474 | sp-2 | an-67 | E1U7800 | sp-28 | an-67 |
| E1A0475 | sp-2 | an-68 | E1U0475 | sp-2 | an-68 | E1U7801 | sp-28 | an-68 |
| E1A0476 | sp-2 | an-69 | E1U0476 | sp-2 | an-69 | E1U7802 | sp-28 | an-69 |
| E1A0477 | sp-2 | an-70 | E1U0477 | sp-2 | an-70 | E1U7803 | sp-28 | an-70 |
| E1A0478 | sp-2 | an-71 | E1U0478 | sp-2 | an-71 | E1U7804 | sp-28 | an-71 |
| E1A0479 | sp-2 | an-72 | E1U0479 | sp-2 | an-72 | E1U7805 | sp-28 | an-72 |
| E1A0480 | sp-2 | an-73 | E1U0480 | sp-2 | an-73 | E1U7806 | sp-28 | an-73 |
| E1A0481 | sp-2 | an-74 | E1U0481 | sp-2 | an-74 | E1U7807 | sp-28 | an-74 |
| E1A0482 | sp-2 | an-75 | E1U0482 | sp-2 | an-75 | E1U7808 | sp-28 | an-75 |
| E1A0483 | sp-2 | an-76 | E1U0483 | sp-2 | an-76 | E1U7809 | sp-28 | an-76 |
| E1A0484 | sp-2 | an-77 | E1U0484 | sp-2 | an-77 | E1U7810 | sp-28 | an-77 |
| E1A0485 | sp-2 | an-78 | E1U0485 | sp-2 | an-78 | E1U7811 | sp-28 | an-78 |
| E1A0486 | sp-2 | an-79 | E1U0486 | sp-2 | an-79 | E1U7812 | sp-28 | an-79 |

Table 1-10

| Y = NHCS | | | Y = NHCSNH | | | Y = NHCSNH | | |
|---|---|---|---|---|---|---|---|---|
| E1A0487 | sp-2 | an-80 | E1U0487 | sp-2 | an-80 | E1U7813 | sp-28 | an-80 |
| E1A0488 | sp-2 | an-81 | E1U0488 | sp-2 | an-81 | E1U7814 | sp-28 | an-81 |
| E1A0489 | sp-2 | an-82 | E1U0489 | sp-2 | an-82 | E1U7815 | sp-28 | an-82 |
| E1A0490 | sp-2 | an-83 | E1U0490 | sp-2 | an-83 | E1U7816 | sp-28 | an-83 |
| E1A0491 | sp-2 | an-84 | E1U0491 | sp-2 | an-84 | E1U7817 | sp-28 | an-84 |
| E1A0492 | sp-2 | an-85 | E1U0492 | sp-2 | an-85 | E1U7818 | sp-28 | an-85 |
| E1A0493 | sp-2 | an-86 | E1U0493 | sp-2 | an-86 | E1U7819 | sp-28 | an-86 |
| E1A0494 | sp-2 | an-87 | E1U0494 | sp-2 | an-87 | E1U7820 | sp-28 | an-87 |
| E1A0495 | sp-2 | an-88 | E1U0495 | sp-2 | an-88 | E1U7821 | sp-28 | an-88 |
| E1A0496 | sp-2 | an-89 | E1U0496 | sp-2 | an-89 | E1U7822 | sp-28 | an-89 |
| E1A0497 | sp-2 | an-90 | E1U0497 | sp-2 | an-90 | E1U7823 | sp-28 | an-90 |
| E1A0498 | sp-2 | an-91 | E1U0498 | sp-2 | an-91 | E1U7824 | sp-28 | an-91 |
| E1A0499 | sp-2 | an-92 | E1U0499 | sp-2 | an-92 | E1U7825 | sp-28 | an-92 |
| E1A0500 | sp-2 | an-93 | E1U0500 | sp-2 | an-93 | E1U7826 | sp-28 | an-93 |
| E1A0501 | sp-2 | an-94 | E1U0501 | sp-2 | an-94 | E1U7827 | sp-28 | an-94 |
| E1A0502 | sp-2 | an-95 | E1U0502 | sp-2 | an-95 | E1U7828 | sp-28 | an-95 |
| E1A0503 | sp-2 | an-96 | E1U0503 | sp-2 | an-96 | E1U7829 | sp-28 | an-96 |
| E1A0504 | sp-2 | an-97 | E1U0504 | sp-2 | an-97 | E1U7830 | sp-28 | an-97 |
| E1A0505 | sp-2 | an-98 | E1U0505 | sp-2 | an-98 | E1U7831 | sp-28 | an-98 |
| E1A0506 | sp-2 | an-99 | E1U0506 | sp-2 | an-99 | E1U7832 | sp-28 | an-99 |
| E1A0507 | sp-2 | an-100 | E1U0507 | sp-2 | an-100 | E1U7833 | sp-28 | an-100 |
| E1A0508 | sp-2 | an-101 | E1U0508 | sp-2 | an-101 | E1U7834 | sp-28 | an-101 |
| E1A0509 | sp-2 | an-102 | E1U0509 | sp-2 | an-102 | E1U7835 | sp-28 | an-102 |
| E1A0510 | sp-2 | an-103 | E1U0510 | sp-2 | an-103 | E1U7836 | sp-28 | an-103 |
| E1A0511 | sp-2 | an-104 | E1U0511 | sp-2 | an-104 | E1U7837 | sp-28 | an-104 |
| E1A0512 | sp-2 | an-105 | E1U0512 | sp-2 | an-105 | E1U7838 | sp-28 | an-105 |
| E1A0513 | sp-2 | an-106 | E1U0513 | sp-2 | an-106 | E1U7839 | sp-28 | an-106 |
| E1A0514 | sp-2 | an-107 | E1U0514 | sp-2 | an-107 | E1U7840 | sp-28 | an-107 |
| E1A0515 | sp-2 | an-108 | E1U0515 | sp-2 | an-108 | E1U7841 | sp-28 | an-108 |
| E1A0516 | sp-2 | an-109 | E1U0516 | sp-2 | an-109 | E1U7842 | sp-28 | an-109 |
| E1A0517 | sp-2 | an-110 | E1U0517 | sp-2 | an-110 | E1U7843 | sp-28 | an-110 |
| E1A0518 | sp-2 | an-111 | E1U0518 | sp-2 | an-111 | E1U7844 | sp-28 | an-111 |
| E1A0519 | sp-2 | an-112 | E1U0519 | sp-2 | an-112 | E1U7845 | sp-28 | an-112 |
| E1A0520 | sp-2 | an-113 | E1U0520 | sp-2 | an-113 | E1U7846 | sp-28 | an-113 |
| E1A0521 | sp-2 | an-114 | E1U0521 | sp-2 | an-114 | E1U7847 | sp-28 | an-114 |
| E1A0522 | sp-2 | an-115 | E1U0522 | sp-2 | an-115 | E1U7848 | sp-28 | an-115 |

-continued

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| E1A0523 | sp-2 | an-116 | E1U0523 | sp-2 | an-116 | E1U7849 | sp-28 | an-116 |
| E1A0524 | sp-2 | an-117 | E1U0524 | sp-2 | an-117 | E1U7850 | sp-28 | an-117 |
| E1A0525 | sp-2 | an-118 | E1U0525 | sp-2 | an-118 | E1U7851 | sp-28 | an-118 |
| E1A0526 | sp-2 | an-119 | E1U0526 | sp-2 | an-119 | E1U7852 | sp-28 | an-119 |
| E1A0527 | sp-2 | an-120 | E1U0527 | sp-2 | an-120 | E1U7853 | sp-28 | an-120 |
| E1A0528 | sp-2 | an-121 | E1U0528 | sp-2 | an-121 | E1U7854 | sp-28 | an-121 |
| E1A0529 | sp-2 | an-122 | E1U0529 | sp-2 | an-122 | E1U7855 | sp-28 | an-122 |
| E1A0530 | sp-2 | an-123 | E1U0530 | sp-2 | an-123 | E1U7856 | sp-28 | an-123 |
| E1A0531 | sp-2 | an-124 | E1U0531 | sp-2 | an-124 | E1U7857 | sp-28 | an-124 |
| E1A0532 | sp-2 | an-125 | E1U0532 | sp-2 | an-125 | E1U7858 | sp-28 | an-125 |
| E1A0533 | sp-2 | an-126 | E1U0533 | sp-2 | an-126 | E1U7859 | sp-28 | an-126 |
| E1A0534 | sp-2 | an-127 | E1U0534 | sp-2 | an-127 | E1U7860 | sp-28 | an-127 |
| E1A0535 | sp-2 | an-128 | E1U0535 | sp-2 | an-128 | E1U7861 | sp-28 | an-128 |
| E1A0536 | sp-2 | an-129 | E1U0536 | sp-2 | an-129 | E1U7862 | sp-28 | an-129 |
| E1A0537 | sp-2 | an-130 | E1U0537 | sp-2 | an-130 | E1U7863 | sp-28 | an-130 |
| E1A0538 | sp-2 | an-131 | E1U0538 | sp-2 | an-131 | E1U7864 | sp-28 | an-131 |
| E1A0539 | sp-2 | an-132 | E1U0539 | sp-2 | an-132 | E1U7865 | sp-28 | an-132 |
| E1A0540 | sp-2 | an-133 | E1U0540 | sp-2 | an-133 | E1U7866 | sp-28 | an-133 |

Table 1-11

| Y = NHCS | | | Y = NHCSNH | | | Y = NHCSNH | | |
|---|---|---|---|---|---|---|---|---|
| E1A0541 | sp-2 | an-134 | E1U0541 | sp-2 | an-134 | E1U7867 | sp-28 | an-134 |
| E1A0542 | sp-2 | an-135 | E1U0542 | sp-2 | an-135 | E1U7868 | sp-28 | an-135 |
| E1A0543 | sp-2 | an-136 | E1U0543 | sp-2 | an-136 | E1U7869 | sp-28 | an-136 |
| E1A0544 | sp-2 | an-137 | E1U0544 | sp-2 | an-137 | E1U7870 | sp-28 | an-137 |
| E1A0545 | sp-2 | an-138 | E1U0545 | sp-2 | an-138 | E1U7871 | sp-28 | an-138 |
| E1A0546 | sp-2 | an-139 | E1U0546 | sp-2 | an-139 | E1U7872 | sp-28 | an-139 |
| E1A0547 | sp-2 | an-140 | E1U0547 | sp-2 | an-140 | E1U7873 | sp-28 | an-140 |
| E1A0548 | sp-2 | an-141 | E1U0548 | sp-2 | an-141 | E1U7874 | sp-28 | an-141 |
| E1A0549 | sp-2 | an-142 | E1U0549 | sp-2 | an-142 | E1U7875 | sp-28 | an-142 |
| E1A0550 | sp-2 | an-143 | E1U0550 | sp-2 | an-143 | E1U7876 | sp-28 | an-143 |
| E1A0551 | sp-2 | an-144 | E1U0551 | sp-2 | an-144 | E1U7877 | sp-28 | an-144 |
| E1A0552 | sp-2 | an-145 | E1U0552 | sp-2 | an-145 | E1U7878 | sp-28 | an-145 |
| E1A0553 | sp-2 | an-146 | E1U0553 | sp-2 | an-146 | E1U7879 | sp-28 | an-146 |
| E1A0554 | sp-2 | an-147 | E1U0554 | sp-2 | an-147 | E1U7880 | sp-28 | an-147 |
| E1A0555 | sp-2 | an-148 | E1U0555 | sp-2 | an-148 | E1U7881 | sp-28 | an-148 |
| E1A0556 | sp-2 | an-149 | E1U0556 | sp-2 | an-149 | E1U7882 | sp-28 | an-149 |
| E1A0557 | sp-2 | an-150 | E1U0557 | sp-2 | an-150 | E1U7883 | sp-28 | an-150 |
| E1A0558 | sp-2 | an-151 | E1U0558 | sp-2 | an-151 | E1U7884 | sp-28 | an-151 |
| E1A0559 | sp-2 | an-152 | E1U0559 | sp-2 | an-152 | E1U7885 | sp-28 | an-152 |
| E1A0560 | sp-2 | an-153 | E1U0560 | sp-2 | an-153 | E1U7886 | sp-28 | an-153 |
| E1A0561 | sp-2 | an-154 | E1U0561 | sp-2 | an-154 | E1U7887 | sp-28 | an-154 |
| E1A0562 | sp-2 | an-155 | E1U0562 | sp-2 | an-155 | E1U7888 | sp-28 | an-155 |
| E1A0563 | sp-2 | an-156 | E1U0563 | sp-2 | an-156 | E1U7889 | sp-28 | an-156 |
| E1A0564 | sp-2 | an-157 | E1U0564 | sp-2 | an-157 | E1U7890 | sp-28 | an-157 |
| E1A0565 | sp-2 | an-158 | E1U0565 | sp-2 | an-158 | E1U7891 | sp-28 | an-158 |
| E1A0566 | sp-2 | an-159 | E1U0566 | sp-2 | an-159 | E1U7892 | sp-28 | an-159 |
| E1A0567 | sp-2 | an-160 | E1U0567 | sp-2 | an-160 | E1U7893 | sp-28 | an-160 |
| E1A0568 | sp-2 | an-161 | E1U0568 | sp-2 | an-161 | E1U7894 | sp-28 | an-161 |
| E1A0569 | sp-2 | an-162 | E1U0569 | sp-2 | an-162 | E1U7895 | sp-28 | an-162 |
| E1A0570 | sp-2 | an-163 | E1U0570 | sp-2 | an-163 | E1U7896 | sp-28 | an-163 |
| E1A0571 | sp-2 | an-164 | E1U0571 | sp-2 | an-164 | E1U7897 | sp-28 | an-164 |
| E1A0572 | sp-2 | an-165 | E1U0572 | sp-2 | an-165 | E1U7898 | sp-28 | an-165 |
| E1A0573 | sp-2 | an-166 | E1U0573 | sp-2 | an-166 | E1U7899 | sp-28 | an-166 |
| E1A0574 | sp-2 | an-167 | E1U0574 | sp-2 | an-167 | E1U7900 | sp-28 | an-167 |
| E1A0575 | sp-2 | an-168 | E1U0575 | sp-2 | an-168 | E1U7901 | sp-28 | an-168 |
| E1A0576 | sp-2 | an-169 | E1U0576 | sp-2 | an-169 | E1U7902 | sp-28 | an-169 |
| E1A0577 | sp-2 | an-170 | E1U0577 | sp-2 | an-170 | E1U7903 | sp-28 | an-170 |
| E1A0578 | sp-2 | an-171 | E1U0578 | sp-2 | an-171 | E1U7904 | sp-28 | an-171 |
| E1A0579 | sp-2 | an-172 | E1U0579 | sp-2 | an-172 | E1U7905 | sp-28 | an-172 |
| E1A0580 | sp-2 | an-173 | E1U0580 | sp-2 | an-173 | E1U7906 | sp-28 | an-173 |
| E1A0581 | sp-2 | an-174 | E1U0581 | sp-2 | an-174 | E1U7907 | sp-28 | an-174 |
| E1A0582 | sp-2 | an-175 | E1U0582 | sp-2 | an-175 | E1U7908 | sp-28 | an-175 |
| E1A0583 | sp-2 | an-176 | E1U0583 | sp-2 | an-176 | E1U7909 | sp-28 | an-176 |
| E1A0584 | sp-2 | an-177 | E1U0584 | sp-2 | an-177 | E1U7910 | sp-28 | an-177 |
| E1A0585 | sp-2 | an-178 | E1U0585 | sp-2 | an-178 | E1U7911 | sp-28 | an-178 |
| E1A0586 | sp-2 | an-179 | E1U0586 | sp-2 | an-179 | E1U7912 | sp-28 | an-179 |
| E1A0587 | sp-2 | an-180 | E1U0587 | sp-2 | an-180 | E1U7913 | sp-28 | an-180 |
| E1A0588 | sp-2 | an-181 | E1U0588 | sp-2 | an-181 | E1U7914 | sp-28 | an-181 |
| E1A0589 | sp-2 | an-182 | E1U0589 | sp-2 | an-182 | E1U7915 | sp-28 | an-182 |
| E1A0590 | sp-2 | an-183 | E1U0590 | sp-2 | an-183 | E1U7916 | sp-28 | an-183 |
| E1A0591 | sp-2 | an-184 | E1U0591 | sp-2 | an-184 | E1U7917 | sp-28 | an-184 |
| E1A0592 | sp-2 | an-185 | E1U0592 | sp-2 | an-185 | E1U7918 | sp-28 | an-185 |
| E1A0593 | sp-2 | an-186 | E1U0593 | sp-2 | an-186 | E1U7919 | sp-28 | an-186 |
| E1A0594 | sp-2 | an-187 | E1U0594 | sp-2 | an-187 | E1U7920 | sp-28 | an-187 |

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| \multicolumn{9}{c}{Table 1-12} |
| \multicolumn{3}{c}{Y = NHCS} | \multicolumn{3}{c}{Y = NHCSNH} | \multicolumn{3}{c}{Y = NHCSNH} |
| E1A0595 | sp-2 | an-188 | E1U0595 | sp-2 | an-188 | E1U7921 | sp-28 | an-188 |
| E1A0596 | sp-2 | an-189 | E1U0596 | sp-2 | an-189 | E1U7922 | sp-28 | an-189 |
| E1A0597 | sp-2 | an-190 | E1U0597 | sp-2 | an-190 | E1U7923 | sp-28 | an-190 |
| E1A0598 | sp-2 | an-191 | E1U0598 | sp-2 | an-191 | E1U7924 | sp-28 | an-191 |
| E1A0599 | sp-2 | an-192 | E1U0599 | sp-2 | an-192 | E1U7925 | sp-28 | an-192 |
| E1A0600 | sp-2 | an-193 | E1U0600 | sp-2 | an-193 | E1U7926 | sp-28 | an-193 |
| E1A0601 | sp-2 | an-194 | E1U0601 | sp-2 | an-194 | E1U7927 | sp-28 | an-194 |
| E1A0602 | sp-2 | an-195 | E1U0602 | sp-2 | an-195 | E1U7928 | sp-28 | an-195 |
| E1A0603 | sp-2 | an-196 | E1U0603 | sp-2 | an-196 | E1U7929 | sp-28 | an-196 |
| E1A0604 | sp-2 | an-197 | E1U0604 | sp-2 | an-197 | E1U7930 | sp-28 | an-197 |
| E1A0605 | sp-2 | an-198 | E1U0605 | sp-2 | an-198 | E1U7931 | sp-28 | an-198 |
| E1A0606 | sp-2 | an-199 | E1U0606 | sp-2 | an-199 | E1U7932 | sp-28 | an-199 |
| E1A0607 | sp-2 | an-200 | E1U0607 | sp-2 | an-200 | E1U7933 | sp-28 | an-200 |
| E1A0608 | sp-2 | an-201 | E1U0608 | sp-2 | an-201 | E1U7934 | sp-28 | an-201 |
| E1A0609 | sp-2 | an-202 | E1U0609 | sp-2 | an-202 | E1U7935 | sp-28 | an-202 |
| E1A0610 | sp-2 | an-203 | E1U0610 | sp-2 | an-203 | E1U7936 | sp-28 | an-203 |
| E1A0611 | sp-2 | an-204 | E1U0611 | sp-2 | an-204 | E1U7937 | sp-28 | an-204 |
| E1A0612 | sp-2 | an-205 | E1U0612 | sp-2 | an-205 | E1U7938 | sp-28 | an-205 |
| E1A0613 | sp-2 | an-206 | E1U0613 | sp-2 | an-206 | E1U7939 | sp-28 | an-206 |
| E1A0614 | sp-2 | an-207 | E1U0614 | sp-2 | an-207 | E1U7940 | sp-28 | an-207 |
| E1A0615 | sp-2 | an-208 | E1U0615 | sp-2 | an-208 | E1U7941 | sp-28 | an-208 |
| E1A0616 | sp-2 | an-209 | E1U0616 | sp-2 | an-209 | E1U7942 | sp-28 | an-209 |
| E1A0617 | sp-2 | an-210 | E1U0617 | sp-2 | an-210 | E1U7943 | sp-28 | an-210 |
| E1A0618 | sp-2 | an-211 | E1U0618 | sp-2 | an-211 | E1U7944 | sp-28 | an-211 |
| E1A0619 | sp-2 | an-212 | E1U0619 | sp-2 | an-212 | E1U7945 | sp-28 | an-212 |
| E1A0620 | sp-2 | an-213 | E1U0620 | sp-2 | an-213 | E1U7946 | sp-28 | an-213 |
| E1A0621 | sp-2 | an-214 | E1U0621 | sp-2 | an-214 | E1U7947 | sp-28 | an-214 |
| E1A0622 | sp-2 | an-215 | E1U0622 | sp-2 | an-215 | E1U7948 | sp-28 | an-215 |
| E1A0623 | sp-2 | an-216 | E1U0623 | sp-2 | an-216 | E1U7949 | sp-28 | an-216 |
| E1A0624 | sp-2 | an-217 | E1U0624 | sp-2 | an-217 | E1U7950 | sp-28 | an-217 |
| E1A0625 | sp-2 | an-218 | E1U0625 | sp-2 | an-218 | E1U7951 | sp-28 | an-218 |
| E1A0626 | sp-2 | an-219 | E1U0626 | sp-2 | an-219 | E1U7952 | sp-28 | an-219 |
| E1A0627 | sp-2 | an-220 | E1U0627 | sp-2 | an-220 | E1U7953 | sp-28 | an-220 |
| E1A0628 | sp-2 | an-221 | E1U0628 | sp-2 | an-221 | E1U7954 | sp-28 | an-221 |
| E1A0629 | sp-2 | an-222 | E1U0629 | sp-2 | an-222 | E1U7955 | sp-28 | an-222 |
| E1A0630 | sp-2 | an-223 | E1U0630 | sp-2 | an-223 | E1U7956 | sp-28 | an-223 |
| E1A0631 | sp-2 | an-224 | E1U0631 | sp-2 | an-224 | E1U7957 | sp-28 | an-224 |
| E1A0632 | sp-2 | an-225 | E1U0632 | sp-2 | an-225 | E1U7958 | sp-28 | an-225 |
| E1A0633 | sp-2 | an-226 | E1U0633 | sp-2 | an-226 | E1U7959 | sp-28 | an-226 |
| E1A0634 | sp-2 | an-227 | E1U0634 | sp-2 | an-227 | E1U7960 | sp-28 | an-227 |
| E1A0635 | sp-2 | an-228 | E1U0635 | sp-2 | an-228 | E1U7961 | sp-28 | an-228 |
| E1A0636 | sp-2 | an-229 | E1U0636 | sp-2 | an-229 | E1U7962 | sp-28 | an-229 |
| E1A0637 | sp-2 | an-230 | E1U0637 | sp-2 | an-230 | E1U7963 | sp-28 | an-230 |
| E1A0638 | sp-2 | an-231 | E1U0638 | sp-2 | an-231 | E1U7964 | sp-28 | an-231 |
| E1A0639 | sp-2 | an-232 | E1U0639 | sp-2 | an-232 | E1U7965 | sp-28 | an-232 |
| E1A0640 | sp-2 | an-233 | E1U0640 | sp-2 | an-233 | E1U7966 | sp-28 | an-233 |
| E1A0641 | sp-2 | an-234 | E1U0641 | sp-2 | an-234 | E1U7967 | sp-28 | an-234 |
| E1A0642 | sp-2 | an-235 | E1U0642 | sp-2 | an-235 | E1U7968 | sp-28 | an-235 |
| E1A0643 | sp-2 | an-236 | E1U0643 | sp-2 | an-236 | E1U7969 | sp-28 | an-236 |
| E1A0644 | sp-2 | an-237 | E1U0644 | sp-2 | an-237 | E1U7970 | sp-28 | an-237 |
| E1A0645 | sp-2 | an-238 | E1U0645 | sp-2 | an-238 | E1U7971 | sp-28 | an-238 |
| E1A0646 | sp-2 | an-239 | E1U0646 | sp-2 | an-239 | E1U7972 | sp-28 | an-239 |
| E1A0647 | sp-2 | an-240 | E1U0647 | sp-2 | an-240 | E1U7973 | sp-28 | an-240 |
| E1A0648 | sp-2 | an-241 | E1U0648 | sp-2 | an-241 | E1U7974 | sp-28 | an-241 |
| \multicolumn{9}{c}{Table 1-13} |
| \multicolumn{3}{c}{Y = NHCS} | \multicolumn{3}{c}{Y = NHCSNH} | \multicolumn{3}{c}{Y = NHCSNH} |
| E1A0649 | sp-2 | an-242 | E1U0649 | sp-2 | an-242 | E1U7975 | sp-28 | an-242 |
| E1A0650 | sp-2 | an-243 | E1U0650 | sp-2 | an-243 | E1U7976 | sp-28 | an-243 |
| E1A0651 | sp-2 | an-244 | E1U0651 | sp-2 | an-244 | E1U7977 | sp-28 | an-244 |
| E1A0652 | sp-2 | an-245 | E1U0652 | sp-2 | an-245 | E1U7978 | sp-28 | an-245 |
| E1A0653 | sp-2 | an-246 | E1U0653 | sp-2 | an-246 | E1U7979 | sp-28 | an-246 |
| E1A0654 | sp-2 | an-247 | E1U0654 | sp-2 | an-247 | E1U7980 | sp-28 | an-247 |
| E1A0655 | sp-2 | an-248 | E1U0655 | sp-2 | an-248 | E1U7981 | sp-28 | an-248 |
| E1A0656 | sp-2 | an-249 | E1U0656 | sp-2 | an-249 | E1U7982 | sp-28 | an-249 |
| E1A0657 | sp-2 | an-250 | E1U0657 | sp-2 | an-250 | E1U7983 | sp-28 | an-250 |
| E1A0658 | sp-2 | an-251 | E1U0658 | sp-2 | an-251 | E1U7984 | sp-28 | an-251 |
| E1A0659 | sp-2 | an-252 | E1U0659 | sp-2 | an-252 | E1U7985 | sp-28 | an-252 |
| E1A0660 | sp-2 | an-253 | E1U0660 | sp-2 | an-253 | E1U7986 | sp-28 | an-253 |
| E1A0661 | sp-2 | an-254 | E1U0661 | sp-2 | an-254 | E1U7987 | sp-28 | an-254 |
| E1A0662 | sp-2 | an-255 | E1U0662 | sp-2 | an-255 | E1U7988 | sp-28 | an-255 |
| E1A0663 | sp-2 | an-256 | E1U0663 | sp-2 | an-256 | E1U7989 | sp-28 | an-256 |
| E1A0664 | sp-2 | an-257 | E1U0664 | sp-2 | an-257 | E1U7990 | sp-28 | an-257 |

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| E1A0665 | sp-2 | an-258 | E1U0665 | sp-2 | an-258 | E1U7991 | sp-28 | an-258 |
| E1A0666 | sp-2 | an-259 | E1U0666 | sp-2 | an-259 | E1U7992 | sp-28 | an-259 |
| E1A0667 | sp-2 | an-260 | E1U0667 | sp-2 | an-260 | E1U7993 | sp-28 | an-260 |
| E1A0668 | sp-2 | an-261 | E1U0668 | sp-2 | an-261 | E1U7994 | sp-28 | an-261 |
| E1A0669 | sp-2 | an-262 | E1U0669 | sp-2 | an-262 | E1U7995 | sp-28 | an-262 |
| E1A0670 | sp-2 | an-263 | E1U0670 | sp-2 | an-263 | E1U7996 | sp-28 | an-263 |
| E1A0671 | sp-2 | an-264 | E1U0671 | sp-2 | an-264 | E1U7997 | sp-28 | an-264 |
| E1A0672 | sp-2 | an-265 | E1U0672 | sp-2 | an-265 | E1U7998 | sp-28 | an-265 |
| E1A0673 | sp-2 | an-266 | E1U0673 | sp-2 | an-266 | E1U7999 | sp-28 | an-266 |
| E1A0674 | sp-2 | an-267 | E1U0674 | sp-2 | an-267 | E1U8000 | sp-28 | an-267 |
| E1A0675 | sp-2 | an-268 | E1U0675 | sp-2 | an-268 | E1U8001 | sp-28 | an-268 |
| E1A0676 | sp-2 | an-269 | E1U0676 | sp-2 | an-269 | E1U8002 | sp-28 | an-269 |
| E1A0677 | sp-2 | an-270 | E1U0677 | sp-2 | an-270 | E1U8003 | sp-28 | an-270 |
| E1A0678 | sp-2 | an-271 | E1U0678 | sp-2 | an-271 | E1U8004 | sp-28 | an-271 |
| E1A0679 | sp-2 | an-272 | E1U0679 | sp-2 | an-272 | E1U8005 | sp-28 | an-272 |
| E1A0680 | sp-2 | an-273 | E1U0680 | sp-2 | an-273 | E1U8006 | sp-28 | an-273 |
| E1A0681 | sp-2 | an-274 | E1U0681 | sp-2 | an-274 | E1U8007 | sp-28 | an-274 |
| E1A0682 | sp-2 | an-275 | E1U0682 | sp-2 | an-275 | E1U8008 | sp-28 | an-275 |
| E1A0683 | sp-2 | an-276 | E1U0683 | sp-2 | an-276 | E1U8009 | sp-28 | an-276 |
| E1A0684 | sp-2 | an-277 | E1U0684 | sp-2 | an-277 | E1U8010 | sp-28 | an-277 |
| E1A0685 | sp-2 | an-278 | E1U0685 | sp-2 | an-278 | E1U8011 | sp-28 | an-278 |
| E1A0686 | sp-2 | an-279 | E1U0686 | sp-2 | an-279 | E1U8012 | sp-28 | an-279 |
| E1A0687 | sp-2 | an-280 | E1U0687 | sp-2 | an-280 | E1U8013 | sp-28 | an-280 |
| E1A0688 | sp-2 | an-281 | E1U0688 | sp-2 | an-281 | E1U8014 | sp-28 | an-281 |
| E1A0689 | sp-2 | an-282 | E1U0689 | sp-2 | an-282 | E1U8015 | sp-28 | an-282 |
| E1A0690 | sp-2 | an-283 | E1U0690 | sp-2 | an-283 | E1U8016 | sp-28 | an-283 |
| E1A0691 | sp-2 | an-284 | E1U0691 | sp-2 | an-284 | E1U8017 | sp-28 | an-284 |
| E1A0692 | sp-2 | an-285 | E1U0692 | sp-2 | an-285 | E1U8018 | sp-28 | an-285 |
| E1A0693 | sp-2 | an-286 | E1U0693 | sp-2 | an-286 | E1U8019 | sp-28 | an-286 |
| E1A0694 | sp-2 | an-287 | E1U0694 | sp-2 | an-287 | E1U8020 | sp-28 | an-287 |
| E1A0695 | sp-2 | an-288 | E1U0695 | sp-2 | an-288 | E1U8021 | sp-28 | an-288 |
| E1A0696 | sp-2 | an-289 | E1U0696 | sp-2 | an-289 | E1U8022 | sp-28 | an-289 |
| E1A0697 | sp-2 | an-290 | E1U0697 | sp-2 | an-290 | E1U8023 | sp-28 | an-290 |
| E1A0698 | sp-2 | an-291 | E1U0698 | sp-2 | an-291 | E1U8024 | sp-28 | an-291 |
| E1A0699 | sp-2 | an-292 | E1U0699 | sp-2 | an-292 | E1U8025 | sp-28 | an-292 |
| E1A0700 | sp-2 | an-293 | E1U0700 | sp-2 | an-293 | E1U8026 | sp-28 | an-293 |
| E1A0701 | sp-2 | an-294 | E1U0701 | sp-2 | an-294 | E1U8027 | sp-28 | an-294 |
| E1A0702 | sp-2 | an-295 | E1U0702 | sp-2 | an-295 | E1U8028 | sp-28 | an-295 |

Table 1-14

| Y = NHCS | | | Y = NHCSNH | | | Y = NHCSNH | | |
|---|---|---|---|---|---|---|---|---|
| E1A0703 | sp-2 | an-296 | E1U0703 | sp-2 | an-296 | E1U8029 | sp-28 | an-296 |
| E1A0704 | sp-2 | an-297 | E1U0704 | sp-2 | an-297 | E1U8030 | sp-28 | an-297 |
| E1A0705 | sp-2 | an-298 | E1U0705 | sp-2 | an-298 | E1U8031 | sp-28 | an-298 |
| E1A0706 | sp-2 | an-299 | E1U0706 | sp-2 | an-299 | E1U8032 | sp-28 | an-299 |
| E1A0707 | sp-2 | an-300 | E1U0707 | sp-2 | an-300 | E1U8033 | sp-28 | an-300 |
| E1A0708 | sp-2 | an-301 | E1U0708 | sp-2 | an-301 | E1U8034 | sp-28 | an-301 |
| E1A0709 | sp-2 | an-302 | E1U0709 | sp-2 | an-302 | E1U8035 | sp-28 | an-302 |
| E1A0710 | sp-2 | an-303 | E1U0710 | sp-2 | an-303 | E1U8036 | sp-28 | an-303 |
| E1A0711 | sp-2 | an-304 | E1U0711 | sp-2 | an-304 | E1U8037 | sp-28 | an-304 |
| E1A0712 | sp-2 | an-305 | E1U0712 | sp-2 | an-305 | E1U8038 | sp-28 | an-305 |
| E1A0713 | sp-2 | an-306 | E1U0713 | sp-2 | an-306 | E1U8039 | sp-28 | an-306 |
| E1A0714 | sp-2 | an-307 | E1U0714 | sp-2 | an-307 | E1U8040 | sp-28 | an-307 |
| E1A0715 | sp-2 | an-308 | E1U0715 | sp-2 | an-308 | E1U8041 | sp-28 | an-308 |
| E1A0716 | sp-2 | an-309 | E1U0716 | sp-2 | an-309 | E1U8042 | sp-28 | an-309 |
| E1A0717 | sp-2 | an-310 | E1U0717 | sp-2 | an-310 | E1U8043 | sp-28 | an-310 |
| E1A0718 | sp-2 | an-311 | E1U0718 | sp-2 | an-311 | E1U8044 | sp-28 | an-311 |
| E1A0719 | sp-2 | an-312 | E1U0719 | sp-2 | an-312 | E1U8045 | sp-28 | an-312 |
| E1A0720 | sp-2 | an-313 | E1U0720 | sp-2 | an-313 | E1U8046 | sp-28 | an-313 |
| E1A0721 | sp-2 | an-314 | E1U0721 | sp-2 | an-314 | E1U8047 | sp-28 | an-314 |
| E1A0722 | sp-2 | an-315 | E1U0722 | sp-2 | an-315 | E1U8048 | sp-28 | an-315 |
| E1A0723 | sp-2 | an-316 | E1U0723 | sp-2 | an-316 | E1U8049 | sp-28 | an-316 |
| E1A0724 | sp-2 | an-317 | E1U0724 | sp-2 | an-317 | E1U8050 | sp-28 | an-317 |
| E1A0725 | sp-2 | an-318 | E1U0725 | sp-2 | an-318 | E1U8051 | sp-28 | an-318 |
| E1A0726 | sp-2 | an-319 | E1U0726 | sp-2 | an-319 | E1U8052 | sp-28 | an-319 |
| E1A0727 | sp-2 | an-320 | E1U0727 | sp-2 | an-320 | E1U8053 | sp-28 | an-320 |
| E1A0728 | sp-2 | an-321 | E1U0728 | sp-2 | an-321 | E1U8054 | sp-28 | an-321 |
| E1A0729 | sp-2 | an-322 | E1U0729 | sp-2 | an-322 | E1U8055 | sp-28 | an-322 |
| E1A0730 | sp-2 | an-323 | E1U0730 | sp-2 | an-323 | E1U8056 | sp-28 | an-323 |
| E1A0731 | sp-2 | an-324 | E1U0731 | sp-2 | an-324 | E1U8057 | sp-28 | an-324 |
| E1A0732 | sp-2 | an-325 | E1U0732 | sp-2 | an-325 | E1U8058 | sp-28 | an-325 |
| E1A0733 | sp-2 | an-326 | E1U0733 | sp-2 | an-326 | E1U8059 | sp-28 | an-326 |
| E1A0734 | sp-2 | an-327 | E1U0734 | sp-2 | an-327 | E1U8060 | sp-28 | an-327 |
| E1A0735 | sp-2 | an-328 | E1U0735 | sp-2 | an-328 | E1U8061 | sp-28 | an-328 |
| E1A0736 | sp-2 | an-329 | E1U0736 | sp-2 | an-329 | E1U8062 | sp-28 | an-329 |
| E1A0737 | sp-2 | an-330 | E1U0737 | sp-2 | an-330 | E1U8063 | sp-28 | an-330 |
| E1A0738 | sp-2 | an-331 | E1U0738 | sp-2 | an-331 | E1U8064 | sp-28 | an-331 |

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| E1A0739 | sp-2 | an-332 | E1U0739 | sp-2 | an-332 | E1U8065 | sp-28 | an-332 |
| E1A0740 | sp-2 | an-333 | E1U0740 | sp-2 | an-333 | E1U8066 | sp-28 | an-333 |
| E1A0741 | sp-2 | an-334 | E1U0741 | sp-2 | an-334 | E1U8067 | sp-28 | an-334 |
| E1A0742 | sp-2 | an-335 | E1U0742 | sp-2 | an-335 | E1U8068 | sp-28 | an-335 |
| E1A0743 | sp-2 | an-336 | E1U0743 | sp-2 | an-336 | E1U8069 | sp-28 | an-336 |
| E1A0744 | sp-2 | an-337 | E1U0744 | sp-2 | an-337 | E1U8070 | sp-28 | an-337 |
| E1A0745 | sp-2 | an-338 | E1U0745 | sp-2 | an-338 | E1U8071 | sp-28 | an-338 |
| E1A0746 | sp-2 | an-339 | E1U0746 | sp-2 | an-339 | E1U8072 | sp-28 | an-339 |
| E1A0747 | sp-2 | an-340 | E1U0747 | sp-2 | an-340 | E1U8073 | sp-28 | an-340 |
| E1A0748 | sp-2 | an-341 | E1U0748 | sp-2 | an-341 | E1U8074 | sp-28 | an-341 |
| E1A0749 | sp-2 | an-342 | E1U0749 | sp-2 | an-342 | E1U8075 | sp-28 | an-342 |
| E1A0750 | sp-2 | an-343 | E1U0750 | sp-2 | an-343 | E1U8076 | sp-28 | an-343 |
| E1A0751 | sp-2 | an-344 | E1U0751 | sp-2 | an-344 | E1U8077 | sp-28 | an-344 |
| E1A0752 | sp-2 | an-345 | E1U0752 | sp-2 | an-345 | E1U8078 | sp-28 | an-345 |
| E1A0753 | sp-2 | an-346 | E1U0753 | sp-2 | an-346 | E1U8079 | sp-28 | an-346 |
| E1A0754 | sp-2 | an-347 | E1U0754 | sp-2 | an-347 | E1U8080 | sp-28 | an-347 |
| E1A0755 | sp-2 | an-348 | E1U0755 | sp-2 | an-348 | E1U8081 | sp-28 | an-348 |
| E1A0756 | sp-2 | an-349 | E1U0756 | sp-2 | an-349 | E1U8082 | sp-28 | an-349 |

Table 1-15

| Y = NHCS | | | Y = NHCSNH | | | Y = NHCSNH | | |
|---|---|---|---|---|---|---|---|---|
| E1A0757 | sp-2 | an-350 | E1U0757 | sp-2 | an-350 | E1U8083 | sp-28 | an-350 |
| E1A0758 | sp-2 | an-351 | E1U0758 | sp-2 | an-351 | E1U8084 | sp-28 | an-351 |
| E1A0759 | sp-2 | an-352 | E1U0759 | sp-2 | an-352 | E1U8085 | sp-28 | an-352 |
| E1A0760 | sp-2 | an-353 | E1U0760 | sp-2 | an-353 | E1U8086 | sp-28 | an-353 |
| E1A0761 | sp-2 | an-354 | E1U0761 | sp-2 | an-354 | E1U8087 | sp-28 | an-354 |
| E1A0762 | sp-2 | an-355 | E1U0762 | sp-2 | an-355 | E1U8088 | sp-28 | an-355 |
| E1A0763 | sp-2 | an-356 | E1U0763 | sp-2 | an-356 | E1U8089 | sp-28 | an-356 |
| E1A0764 | sp-2 | an-357 | E1U0764 | sp-2 | an-357 | E1U8090 | sp-28 | an-357 |
| E1A0765 | sp-2 | an-358 | E1U0765 | sp-2 | an-358 | E1U8091 | sp-28 | an-358 |
| E1A0766 | sp-2 | an-359 | E1U0766 | sp-2 | an-359 | E1U8092 | sp-28 | an-359 |
| E1A0767 | sp-2 | an-360 | E1U0767 | sp-2 | an-360 | E1U8093 | sp-28 | an-360 |
| E1A0768 | sp-2 | an-361 | E1U0768 | sp-2 | an-361 | E1U8094 | sp-28 | an-361 |
| E1A0769 | sp-2 | an-362 | E1U0769 | sp-2 | an-362 | E1U8095 | sp-28 | an-362 |
| E1A0770 | sp-2 | an-363 | E1U0770 | sp-2 | an-363 | E1U8096 | sp-28 | an-363 |
| E1A0771 | sp-2 | an-364 | E1U0771 | sp-2 | an-364 | E1U8097 | sp-28 | an-364 |
| E1A0772 | sp-2 | an-365 | E1U0772 | sp-2 | an-365 | E1U8098 | sp-28 | an-365 |
| E1A0773 | sp-2 | an-366 | E1U0773 | sp-2 | an-366 | E1U8099 | sp-28 | an-366 |
| E1A0774 | sp-2 | an-367 | E1U0774 | sp-2 | an-367 | E1U8100 | sp-28 | an-367 |
| E1A0775 | sp-2 | an-368 | E1U0775 | sp-2 | an-368 | E1U8101 | sp-28 | an-368 |
| E1A0776 | sp-2 | an-369 | E1U0776 | sp-2 | an-369 | E1U8102 | sp-28 | an-369 |
| E1A0777 | sp-2 | an-370 | E1U0777 | sp-2 | an-370 | E1U8103 | sp-28 | an-370 |
| E1A0778 | sp-2 | an-371 | E1U0778 | sp-2 | an-371 | E1U8104 | sp-28 | an-371 |
| E1A0779 | sp-2 | an-372 | E1U0779 | sp-2 | an-372 | E1U8105 | sp-28 | an-372 |
| E1A0780 | sp-2 | an-373 | E1U0780 | sp-2 | an-373 | E1U8106 | sp-28 | an-373 |
| E1A0781 | sp-2 | an-374 | E1U0781 | sp-2 | an-374 | E1U8107 | sp-28 | an-374 |
| E1A0782 | sp-2 | an-375 | E1U0782 | sp-2 | an-375 | E1U8108 | sp-28 | an-375 |
| E1A0783 | sp-2 | an-376 | E1U0783 | sp-2 | an-376 | E1U8109 | sp-28 | an-376 |
| E1A0784 | sp-2 | an-377 | E1U0784 | sp-2 | an-377 | E1U8110 | sp-28 | an-377 |
| E1A0785 | sp-2 | an-378 | E1U0785 | sp-2 | an-378 | E1U8111 | sp-28 | an-378 |
| E1A0786 | sp-2 | an-379 | E1U0786 | sp-2 | an-379 | E1U8112 | sp-28 | an-379 |
| E1A0787 | sp-2 | an-380 | E1U0787 | sp-2 | an-380 | E1U8113 | sp-28 | an-380 |
| E1A0788 | sp-2 | an-381 | E1U0788 | sp-2 | an-381 | E1U8114 | sp-28 | an-381 |
| E1A0789 | sp-2 | an-382 | E1U0789 | sp-2 | an-382 | E1U8115 | sp-28 | an-382 |
| E1A0790 | sp-2 | an-383 | E1U0790 | sp-2 | an-383 | E1U8116 | sp-28 | an-383 |
| E1A0791 | sp-2 | an-384 | E1U0791 | sp-2 | an-384 | E1U8117 | sp-28 | an-384 |
| E1A0792 | sp-2 | an-385 | E1U0792 | sp-2 | an-385 | E1U8118 | sp-28 | an-385 |
| E1A0793 | sp-2 | an-386 | E1U0793 | sp-2 | an-386 | E1U8119 | sp-28 | an-386 |
| E1A0794 | sp-2 | an-387 | E1U0794 | sp-2 | an-387 | E1U8120 | sp-28 | an-387 |
| E1A0795 | sp-2 | an-388 | E1U0795 | sp-2 | an-388 | E1U8121 | sp-28 | an-388 |
| E1A0796 | sp-2 | an-389 | E1U0796 | sp-2 | an-389 | E1U8122 | sp-28 | an-389 |
| E1A0797 | sp-2 | an-390 | E1U0797 | sp-2 | an-390 | E1U8123 | sp-28 | an-390 |
| E1A0798 | sp-2 | an-391 | E1U0798 | sp-2 | an-391 | E1U8124 | sp-28 | an-391 |
| E1A0799 | sp-2 | an-392 | E1U0799 | sp-2 | an-392 | E1U8125 | sp-28 | an-392 |
| E1A0800 | sp-2 | an-393 | E1U0800 | sp-2 | an-393 | E1U8126 | sp-28 | an-393 |
| E1A0801 | sp-2 | an-394 | E1U0801 | sp-2 | an-394 | E1U8127 | sp-28 | an-394 |
| E1A0802 | sp-2 | an-395 | E1U0802 | sp-2 | an-395 | E1U8128 | sp-28 | an-395 |
| E1A0803 | sp-2 | an-396 | E1U0803 | sp-2 | an-396 | E1U8129 | sp-28 | an-396 |
| E1A0804 | sp-2 | an-397 | E1U0804 | sp-2 | an-397 | E1U8130 | sp-28 | an-397 |
| E1A0805 | sp-2 | an-398 | E1U0805 | sp-2 | an-398 | E1U8131 | sp-28 | an-398 |
| E1A0806 | sp-2 | an-399 | E1U0806 | sp-2 | an-399 | E1U8132 | sp-28 | an-399 |
| E1A0807 | sp-2 | an-400 | E1U0807 | sp-2 | an-400 | E1U8133 | sp-28 | an-400 |
| E1A0808 | sp-2 | an-401 | E1U0808 | sp-2 | an-401 | E1U8134 | sp-28 | an-401 |
| E1A0809 | sp-2 | an-402 | E1U0809 | sp-2 | an-402 | E1U8135 | sp-28 | an-402 |
| E1A0810 | sp-2 | an-403 | E1U0810 | sp-2 | an-403 | E1U8136 | sp-28 | an-403 |

-continued

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| | | | | Table 1-16 | | | | |
| | Y = NHCS | | | Y = NHCSNH | | | Y = NHCSNH | |
| E1A0811 | sp-2 | an-404 | E1U0811 | sp-2 | an-404 | E1U8137 | sp-28 | an-404 |
| E1A0812 | sp-2 | an-405 | E1U0812 | sp-2 | an-405 | E1U8138 | sp-28 | an-405 |
| E1A0813 | sp-2 | an-406 | E1U0813 | sp-2 | an-406 | E1U8139 | sp-28 | an-406 |
| E1A0814 | sp-2 | an-407 | E1U0814 | sp-2 | an-407 | E1U8140 | sp-28 | an-407 |
| E1A0815 | sp-3 | an-1 | E1U0815 | sp-3 | an-1 | E1U8141 | sp-29 | an-1 |
| E1A0816 | sp-3 | an-2 | E1U0816 | sp-3 | an-2 | E1U8142 | sp-29 | an-2 |
| E1A0817 | sp-3 | an-3 | E1U0817 | sp-3 | an-3 | E1U8143 | sp-29 | an-3 |
| E1A0818 | sp-3 | an-4 | E1U0818 | sp-3 | an-4 | E1U8144 | sp-29 | an-4 |
| E1A0819 | sp-3 | an-5 | E1U0819 | sp-3 | an-5 | E1U8145 | sp-29 | an-5 |
| E1A0820 | sp-3 | an-6 | E1U0820 | sp-3 | an-6 | E1U8146 | sp-29 | an-6 |
| E1A0821 | sp-3 | an-7 | E1U0821 | sp-3 | an-7 | E1U8147 | sp-29 | an-7 |
| E1A0822 | sp-3 | an-8 | E1U0822 | sp-3 | an-8 | E1U8148 | sp-29 | an-8 |
| E1A0823 | sp-3 | an-9 | E1U0823 | sp-3 | an-9 | E1U8149 | sp-29 | an-9 |
| E1A0824 | sp-3 | an-10 | E1U0824 | sp-3 | an-10 | E1U8150 | sp-29 | an-10 |
| E1A0825 | sp-3 | an-11 | E1U0825 | sp-3 | an-11 | E1U8151 | sp-29 | an-11 |
| E1A0826 | sp-3 | an-12 | E1U0826 | sp-3 | an-12 | E1U8152 | sp-29 | an-12 |
| E1A0827 | sp-3 | an-13 | E1U0827 | sp-3 | an-13 | E1U8153 | sp-29 | an-13 |
| E1A0828 | sp-3 | an-14 | E1U0828 | sp-3 | an-14 | E1U8154 | sp-29 | an-14 |
| E1A0829 | sp-3 | an-15 | E1U0829 | sp-3 | an-15 | E1U8155 | sp-29 | an-15 |
| E1A0830 | sp-3 | an-16 | E1U0830 | sp-3 | an-16 | E1U8156 | sp-29 | an-16 |
| E1A0831 | sp-3 | an-17 | E1U0831 | sp-3 | an-17 | E1U8157 | sp-29 | an-17 |
| E1A0832 | sp-3 | an-18 | E1U0832 | sp-3 | an-18 | E1U8158 | sp-29 | an-18 |
| E1A0833 | sp-3 | an-19 | E1U0833 | sp-3 | an-19 | E1U8159 | sp-29 | an-19 |
| E1A0834 | sp-3 | an-20 | E1U0834 | sp-3 | an-20 | E1U8160 | sp-29 | an-20 |
| E1A0835 | sp-3 | an-21 | E1U0835 | sp-3 | an-21 | E1U8161 | sp-29 | an-21 |
| E1A0836 | sp-3 | an-22 | E1U0836 | sp-3 | an-22 | E1U8162 | sp-29 | an-22 |
| E1A0837 | sp-3 | an-23 | E1U0837 | sp-3 | an-23 | E1U8163 | sp-29 | an-23 |
| E1A0838 | sp-3 | an-24 | E1U0838 | sp-3 | an-24 | E1U8164 | sp-29 | an-24 |
| E1A0839 | sp-3 | an-25 | E1U0839 | sp-3 | an-25 | E1U8165 | sp-29 | an-25 |
| E1A0840 | sp-3 | an-26 | E1U0840 | sp-3 | an-26 | E1U8166 | sp-29 | an-26 |
| E1A0841 | sp-3 | an-27 | E1U0841 | sp-3 | an-27 | E1U8167 | sp-29 | an-27 |
| E1A0842 | sp-3 | an-28 | E1U0842 | sp-3 | an-28 | E1U8168 | sp-29 | an-28 |
| E1A0843 | sp-3 | an-29 | E1U0843 | sp-3 | an-29 | E1U8169 | sp-29 | an-29 |
| E1A0844 | sp-3 | an-30 | E1U0844 | sp-3 | an-30 | E1U8170 | sp-29 | an-30 |
| E1A0845 | sp-3 | an-31 | E1U0845 | sp-3 | an-31 | E1U8171 | sp-29 | an-31 |
| E1A0846 | sp-3 | an-32 | E1U0846 | sp-3 | an-32 | E1U8172 | sp-29 | an-32 |
| E1A0847 | sp-3 | an-33 | E1U0847 | sp-3 | an-33 | E1U8173 | sp-29 | an-33 |
| E1A0848 | sp-3 | an-34 | E1U0848 | sp-3 | an-34 | E1U8174 | sp-29 | an-34 |
| E1A0849 | sp-3 | an-35 | E1U0849 | sp-3 | an-35 | E1U8175 | sp-29 | an-35 |
| E1A0850 | sp-3 | an-36 | E1U0850 | sp-3 | an-36 | E1U8176 | sp-29 | an-36 |
| E1A0851 | sp-3 | an-37 | E1U0851 | sp-3 | an-37 | E1U8177 | sp-29 | an-37 |
| E1A0852 | sp-3 | an-38 | E1U0852 | sp-3 | an-38 | E1U8178 | sp-29 | an-38 |
| E1A0853 | sp-3 | an-39 | E1U0853 | sp-3 | an-39 | E1U8179 | sp-29 | an-39 |
| E1A0854 | sp-3 | an-40 | E1U0854 | sp-3 | an-40 | E1U8180 | sp-29 | an-40 |
| E1A0855 | sp-3 | an-41 | E1U0855 | sp-3 | an-41 | E1U8181 | sp-29 | an-41 |
| E1A0856 | sp-3 | an-42 | E1U0856 | sp-3 | an-42 | E1U8182 | sp-29 | an-42 |
| E1A0857 | sp-3 | an-43 | E1U0857 | sp-3 | an-43 | E1U8183 | sp-29 | an-43 |
| E1A0858 | sp-3 | an-44 | E1U0858 | sp-3 | an-44 | E1U8184 | sp-29 | an-44 |
| E1A0859 | sp-3 | an-45 | E1U0859 | sp-3 | an-45 | E1U8185 | sp-29 | an-45 |
| E1A0860 | sp-3 | an-46 | E1U0860 | sp-3 | an-46 | E1U8186 | sp-29 | an-46 |
| E1A0861 | sp-3 | an-47 | E1U0861 | sp-3 | an-47 | E1U8187 | sp-29 | an-47 |
| E1A0862 | sp-3 | an-48 | E1U0862 | sp-3 | an-48 | E1U8188 | sp-29 | an-48 |
| E1A0863 | sp-3 | an-49 | E1U0863 | sp-3 | an-49 | E1U8189 | sp-29 | an-49 |
| E1A0864 | sp-3 | an-50 | E1U0864 | sp-3 | an-50 | E1U8190 | sp-29 | an-50 |
| | | | | Table 1-17 | | | | |
| | Y = NHCS | | | Y = NHCSNH | | | Y = NHCSNH | |
| E1A0865 | sp-3 | an-51 | E1U0865 | sp-3 | an-51 | E1U8191 | sp-29 | an-51 |
| E1A0866 | sp-3 | an-52 | E1U0866 | sp-3 | an-52 | E1U8192 | sp-29 | an-52 |
| E1A0867 | sp-3 | an-53 | E1U0867 | sp-3 | an-53 | E1U8193 | sp-29 | an-53 |
| E1A0868 | sp-3 | an-54 | E1U0868 | sp-3 | an-54 | E1U8194 | sp-29 | an-54 |
| E1A0869 | sp-3 | an-55 | E1U0869 | sp-3 | an-55 | E1U8195 | sp-29 | an-55 |
| E1A0870 | sp-3 | an-56 | E1U0870 | sp-3 | an-56 | E1U8196 | sp-29 | an-56 |
| E1A0871 | sp-3 | an-57 | E1U0871 | sp-3 | an-57 | E1U8197 | sp-29 | an-57 |
| E1A0872 | sp-3 | an-58 | E1U0872 | sp-3 | an-58 | E1U8198 | sp-29 | an-58 |
| E1A0873 | sp-3 | an-59 | E1U0873 | sp-3 | an-59 | E1U8199 | sp-29 | an-59 |
| E1A0874 | sp-3 | an-60 | E1U0874 | sp-3 | an-60 | E1U8200 | sp-29 | an-60 |
| E1A0875 | sp-3 | an-61 | E1U0875 | sp-3 | an-61 | E1U8201 | sp-29 | an-61 |
| E1A0876 | sp-3 | an-62 | E1U0876 | sp-3 | an-62 | E1U8202 | sp-29 | an-62 |
| E1A0877 | sp-3 | an-63 | E1U0877 | sp-3 | an-63 | E1U8203 | sp-29 | an-63 |
| E1A0878 | sp-3 | an-64 | E1U0878 | sp-3 | an-64 | E1U8204 | sp-29 | an-64 |
| E1A0879 | sp-3 | an-65 | E1U0879 | sp-3 | an-65 | E1U8205 | sp-29 | an-65 |
| E1A0880 | sp-3 | an-66 | E1U0880 | sp-3 | an-66 | E1U8206 | sp-29 | an-66 |

-continued

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| E1A0881 | sp-3 | an-67 | E1U0881 | sp-3 | an-67 | E1U8207 | sp-29 | an-67 |
| E1A0882 | sp-3 | an-68 | E1U0882 | sp-3 | an-68 | E1U8208 | sp-29 | an-68 |
| E1A0883 | sp-3 | an-69 | E1U0883 | sp-3 | an-69 | E1U8209 | sp-29 | an-69 |
| E1A0884 | sp-3 | an-70 | E1U0884 | sp-3 | an-70 | E1U8210 | sp-29 | an-70 |
| E1A0885 | sp-3 | an-71 | E1U0885 | sp-3 | an-71 | E1U8211 | sp-29 | an-71 |
| E1A0886 | sp-3 | an-72 | E1U0886 | sp-3 | an-72 | E1U8212 | sp-29 | an-72 |
| E1A0887 | sp-3 | an-73 | E1U0887 | sp-3 | an-73 | E1U8213 | sp-29 | an-73 |
| E1A0888 | sp-3 | an-74 | E1U0888 | sp-3 | an-74 | E1U8214 | sp-29 | an-74 |
| E1A0889 | sp-3 | an-75 | E1U0889 | sp-3 | an-75 | E1U8215 | sp-29 | an-75 |
| E1A0890 | sp-3 | an-76 | E1U0890 | sp-3 | an-76 | E1U8216 | sp-29 | an-76 |
| E1A0891 | sp-3 | an-77 | E1U0891 | sp-3 | an-77 | E1U8217 | sp-29 | an-77 |
| E1A0892 | sp-3 | an-78 | E1U0892 | sp-3 | an-78 | E1U8218 | sp-29 | an-78 |
| E1A0893 | sp-3 | an-79 | E1U0893 | sp-3 | an-79 | E1U8219 | sp-29 | an-79 |
| E1A0894 | sp-3 | an-80 | E1U0894 | sp-3 | an-80 | E1U8220 | sp-29 | an-80 |
| E1A0895 | sp-3 | an-81 | E1U0895 | sp-3 | an-81 | E1U8221 | sp-29 | an-81 |
| E1A0896 | sp-3 | an-82 | E1U0896 | sp-3 | an-82 | E1U8222 | sp-29 | an-82 |
| E1A0897 | sp-3 | an-83 | E1U0897 | sp-3 | an-83 | E1U8223 | sp-29 | an-83 |
| E1A0898 | sp-3 | an-84 | E1U0898 | sp-3 | an-84 | E1U8224 | sp-29 | an-84 |
| E1A0899 | sp-3 | an-85 | E1U0899 | sp-3 | an-85 | E1U8225 | sp-29 | an-85 |
| E1A0900 | sp-3 | an-86 | E1U0900 | sp-3 | an-86 | E1U8226 | sp-29 | an-86 |
| E1A0901 | sp-3 | an-87 | E1U0901 | sp-3 | an-87 | E1U8227 | sp-29 | an-87 |
| E1A0902 | sp-3 | an-88 | E1U0902 | sp-3 | an-88 | E1U8228 | sp-29 | an-88 |
| E1A0903 | sp-3 | an-89 | E1U0903 | sp-3 | an-89 | E1U8229 | sp-29 | an-89 |
| E1A0904 | sp-3 | an-90 | E1U0904 | sp-3 | an-90 | E1U8230 | sp-29 | an-90 |
| E1A0905 | sp-3 | an-91 | E1U0905 | sp-3 | an-91 | E1U8231 | sp-29 | an-91 |
| E1A0906 | sp-3 | an-92 | E1U0906 | sp-3 | an-92 | E1U8232 | sp-29 | an-92 |
| E1A0907 | sp-3 | an-93 | E1U0907 | sp-3 | an-93 | E1U8233 | sp-29 | an-93 |
| E1A0908 | sp-3 | an-94 | E1U0908 | sp-3 | an-94 | E1U8234 | sp-29 | an-94 |
| E1A0909 | sp-3 | an-95 | E1U0909 | sp-3 | an-95 | E1U8235 | sp-29 | an-95 |
| E1A0910 | sp-3 | an-96 | E1U0910 | sp-3 | an-96 | E1U8236 | sp-29 | an-96 |
| E1A0911 | sp-3 | an-97 | E1U0911 | sp-3 | an-97 | E1U8237 | sp-29 | an-97 |
| E1A0912 | sp-3 | an-98 | E1U0912 | sp-3 | an-98 | E1U8238 | sp-29 | an-98 |
| E1A0913 | sp-3 | an-99 | E1U0913 | sp-3 | an-99 | E1U8239 | sp-29 | an-99 |
| E1A0914 | sp-3 | an-100 | E1U0914 | sp-3 | an-100 | E1U8240 | sp-29 | an-100 |
| E1A0915 | sp-3 | an-101 | E1U0915 | sp-3 | an-101 | E1U8241 | sp-29 | an-101 |
| E1A0916 | sp-3 | an-102 | E1U0916 | sp-3 | an-102 | E1U8242 | sp-29 | an-102 |
| E1A0917 | sp-3 | an-103 | E1U0917 | sp-3 | an-103 | E1U8243 | sp-29 | an-103 |
| E1A0918 | sp-3 | an-104 | E1U0918 | sp-3 | an-104 | E1U8244 | sp-29 | an-104 |

Table 1-18

| Y = NHCS | | | Y = NHCSNH | | | Y = NHCSNH | | |
|---|---|---|---|---|---|---|---|---|
| E1A0919 | sp-3 | an-105 | E1U0919 | sp-3 | an-105 | E1U8245 | sp-29 | an-105 |
| E1A0920 | sp-3 | an-106 | E1U0920 | sp-3 | an-106 | E1U8246 | sp-29 | an-106 |
| E1A0921 | sp-3 | an-107 | E1U0921 | sp-3 | an-107 | E1U8247 | sp-29 | an-107 |
| E1A0922 | sp-3 | an-108 | E1U0922 | sp-3 | an-108 | E1U8248 | sp-29 | an-108 |
| E1A0923 | sp-3 | an-109 | E1U0923 | sp-3 | an-109 | E1U8249 | sp-29 | an-109 |
| E1A0924 | sp-3 | an-110 | E1U0924 | sp-3 | an-110 | E1U8250 | sp-29 | an-110 |
| E1A0925 | sp-3 | an-111 | E1U0925 | sp-3 | an-111 | E1U8251 | sp-29 | an-111 |
| E1A0926 | sp-3 | an-112 | E1U0926 | sp-3 | an-112 | E1U8252 | sp-29 | an-112 |
| E1A0927 | sp-3 | an-113 | E1U0927 | sp-3 | an-113 | E1U8253 | sp-29 | an-113 |
| E1A0928 | sp-3 | an-114 | E1U0928 | sp-3 | an-114 | E1U8254 | sp-29 | an-114 |
| E1A0929 | sp-3 | an-115 | E1U0929 | sp-3 | an-115 | E1U8255 | sp-29 | an-115 |
| E1A0930 | sp-3 | an-116 | E1U0930 | sp-3 | an-116 | E1U8256 | sp-29 | an-116 |
| E1A0931 | sp-3 | an-117 | E1U0931 | sp-3 | an-117 | E1U8257 | sp-29 | an-117 |
| E1A0932 | sp-3 | an-118 | E1U0932 | sp-3 | an-118 | E1U8258 | sp-29 | an-118 |
| E1A0933 | sp-3 | an-119 | E1U0933 | sp-3 | an-119 | E1U8259 | sp-29 | an-119 |
| E1A0934 | sp-3 | an-120 | E1U0934 | sp-3 | an-120 | E1U8260 | sp-29 | an-120 |
| E1A0935 | sp-3 | an-121 | E1U0935 | sp-3 | an-121 | E1U8261 | sp-29 | an-121 |
| E1A0936 | sp-3 | an-122 | E1U0936 | sp-3 | an-122 | E1U8262 | sp-29 | an-122 |
| E1A0937 | sp-3 | an-123 | E1U0937 | sp-3 | an-123 | E1U8263 | sp-29 | an-123 |
| E1A0938 | sp-3 | an-124 | E1U0938 | sp-3 | an-124 | E1U8264 | sp-29 | an-124 |
| E1A0939 | sp-3 | an-125 | E1U0939 | sp-3 | an-125 | E1U8265 | sp-29 | an-125 |
| E1A0940 | sp-3 | an-126 | E1U0940 | sp-3 | an-126 | E1U8266 | sp-29 | an-126 |
| E1A0941 | sp-3 | an-127 | E1U0941 | sp-3 | an-127 | E1U8267 | sp-29 | an-127 |
| E1A0942 | sp-3 | an-128 | E1U0942 | sp-3 | an-128 | E1U8268 | sp-29 | an-128 |
| E1A0943 | sp-3 | an-129 | E1U0943 | sp-3 | an-129 | E1U8269 | sp-29 | an-129 |
| E1A0944 | sp-3 | an-130 | E1U0944 | sp-3 | an-130 | E1U8270 | sp-29 | an-130 |
| E1A0945 | sp-3 | an-131 | E1U0945 | sp-3 | an-131 | E1U8271 | sp-29 | an-131 |
| E1A0946 | sp-3 | an-132 | E1U0946 | sp-3 | an-132 | E1U8272 | sp-29 | an-132 |
| E1A0947 | sp-3 | an-133 | E1U0947 | sp-3 | an-133 | E1U8273 | sp-29 | an-133 |
| E1A0948 | sp-3 | an-134 | E1U0948 | sp-3 | an-134 | E1U8274 | sp-29 | an-134 |
| E1A0949 | sp-3 | an-135 | E1U0949 | sp-3 | an-135 | E1U8275 | sp-29 | an-135 |
| E1A0950 | sp-3 | an-136 | E1U0950 | sp-3 | an-136 | E1U8276 | sp-29 | an-136 |
| E1A0951 | sp-3 | an-137 | E1U0951 | sp-3 | an-137 | E1U8277 | sp-29 | an-137 |
| E1A0952 | sp-3 | an-138 | E1U0952 | sp-3 | an-138 | E1U8278 | sp-29 | an-138 |
| E1A0953 | sp-3 | an-139 | E1U0953 | sp-3 | an-139 | E1U8279 | sp-29 | an-139 |
| E1A0954 | sp-3 | an-140 | E1U0954 | sp-3 | an-140 | E1U8280 | sp-29 | an-140 |

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| E1A0955 | sp-3 | an-141 | E1U0955 | sp-3 | an-141 | E1U8281 | sp-29 | an-141 |
| E1A0956 | sp-3 | an-142 | E1U0956 | sp-3 | an-142 | E1U8282 | sp-29 | an-142 |
| E1A0957 | sp-3 | an-143 | E1U0957 | sp-3 | an-143 | E1U8283 | sp-29 | an-143 |
| E1A0958 | sp-3 | an-144 | E1U0958 | sp-3 | an-144 | E1U8284 | sp-29 | an-144 |
| E1A0959 | sp-3 | an-145 | E1U0959 | sp-3 | an-145 | E1U8285 | sp-29 | an-145 |
| E1A0960 | sp-3 | an-146 | E1U0960 | sp-3 | an-146 | E1U8286 | sp-29 | an-146 |
| E1A0961 | sp-3 | an-147 | E1U0961 | sp-3 | an-147 | E1U8287 | sp-29 | an-147 |
| E1A0962 | sp-3 | an-148 | E1U0962 | sp-3 | an-148 | E1U8288 | sp-29 | an-148 |
| E1A0963 | sp-3 | an-149 | E1U0963 | sp-3 | an-149 | E1U8289 | sp-29 | an-149 |
| E1A0964 | sp-3 | an-150 | E1U0964 | sp-3 | an-150 | E1U8290 | sp-29 | an-150 |
| E1A0965 | sp-3 | an-151 | E1U0965 | sp-3 | an-151 | E1U8291 | sp-29 | an-151 |
| E1A0966 | sp-3 | an-152 | E1U0966 | sp-3 | an-152 | E1U8292 | sp-29 | an-152 |
| E1A0967 | sp-3 | an-153 | E1U0967 | sp-3 | an-153 | E1U8293 | sp-29 | an-153 |
| E1A0968 | sp-3 | an-154 | E1U0968 | sp-3 | an-154 | E1U8294 | sp-29 | an-154 |
| E1A0969 | sp-3 | an-155 | E1U0969 | sp-3 | an-155 | E1U8295 | sp-29 | an-155 |
| E1A0970 | sp-3 | an-156 | E1U0970 | sp-3 | an-156 | E1U8296 | sp-29 | an-156 |
| E1A0971 | sp-3 | an-157 | E1U0971 | sp-3 | an-157 | E1U8297 | sp-29 | an-157 |
| E1A0972 | sp-3 | an-158 | E1U0972 | sp-3 | an-158 | E1U8298 | sp-29 | an-158 |

Table 1-19

| Y = NHCS | | | Y = NHCSNH | | | Y = NHCSNH | | |
|---|---|---|---|---|---|---|---|---|
| E1A0973 | sp-3 | an-159 | E1U0973 | sp-3 | an-159 | E1U8299 | sp-29 | an-159 |
| E1A0974 | sp-3 | an-160 | E1U0974 | sp-3 | an-160 | E1U8300 | sp-29 | an-160 |
| E1A0975 | sp-3 | an-161 | E1U0975 | sp-3 | an-161 | E1U8301 | sp-29 | an-161 |
| E1A0976 | sp-3 | an-162 | E1U0976 | sp-3 | an-162 | E1U8302 | sp-29 | an-162 |
| E1A0977 | sp-3 | an-163 | E1U0977 | sp-3 | an-163 | E1U8303 | sp-29 | an-163 |
| E1A0978 | sp-3 | an-164 | E1U0978 | sp-3 | an-164 | E1U8304 | sp-29 | an-164 |
| E1A0979 | sp-3 | an-165 | E1U0979 | sp-3 | an-165 | E1U8305 | sp-29 | an-165 |
| E1A0980 | sp-3 | an-166 | E1U0980 | sp-3 | an-166 | E1U8306 | sp-29 | an-166 |
| E1A0981 | sp-3 | an-167 | E1U0981 | sp-3 | an-167 | E1U8307 | sp-29 | an-167 |
| E1A0982 | sp-3 | an-168 | E1U0982 | sp-3 | an-168 | E1U8308 | sp-29 | an-168 |
| E1A0983 | sp-3 | an-169 | E1U0983 | sp-3 | an-169 | E1U8309 | sp-29 | an-169 |
| E1A0984 | sp-3 | an-170 | E1U0984 | sp-3 | an-170 | E1U8310 | sp-29 | an-170 |
| E1A0985 | sp-3 | an-171 | E1U0985 | sp-3 | an-171 | E1U8311 | sp-29 | an-171 |
| E1A0986 | sp-3 | an-172 | E1U0986 | sp-3 | an-172 | E1U8312 | sp-29 | an-172 |
| E1A0987 | sp-3 | an-173 | E1U0987 | sp-3 | an-173 | E1U8313 | sp-29 | an-173 |
| E1A0988 | sp-3 | an-174 | E1U0988 | sp-3 | an-174 | E1U8314 | sp-29 | an-174 |
| E1A0989 | sp-3 | an-175 | E1U0989 | sp-3 | an-175 | E1U8315 | sp-29 | an-175 |
| E1A0990 | sp-3 | an-176 | E1U0990 | sp-3 | an-176 | E1U8316 | sp-29 | an-176 |
| E1A0991 | sp-3 | an-177 | E1U0991 | sp-3 | an-177 | E1U8317 | sp-29 | an-177 |
| E1A0992 | sp-3 | an-178 | E1U0992 | sp-3 | an-178 | E1U8318 | sp-29 | an-178 |
| E1A0993 | sp-3 | an-179 | E1U0993 | sp-3 | an-179 | E1U8319 | sp-29 | an-179 |
| E1A0994 | sp-3 | an-180 | E1U0994 | sp-3 | an-180 | E1U8320 | sp-29 | an-180 |
| E1A0995 | sp-3 | an-181 | E1U0995 | sp-3 | an-181 | E1U8321 | sp-29 | an-181 |
| E1A0996 | sp-3 | an-182 | E1U0996 | sp-3 | an-182 | E1U8322 | sp-29 | an-182 |
| E1A0997 | sp-3 | an-183 | E1U0997 | sp-3 | an-183 | E1U8323 | sp-29 | an-183 |
| E1A0998 | sp-3 | an-184 | E1U0998 | sp-3 | an-184 | E1U8324 | sp-29 | an-184 |
| E1A0999 | sp-3 | an-185 | E1U0999 | sp-3 | an-185 | E1U8325 | sp-29 | an-185 |
| E1A1000 | sp-3 | an-186 | E1U1000 | sp-3 | an-186 | E1U8326 | sp-29 | an-186 |
| E1A1001 | sp-3 | an-187 | E1U1001 | sp-3 | an-187 | E1U8327 | sp-29 | an-187 |
| E1A1002 | sp-3 | an-188 | E1U1002 | sp-3 | an-188 | E1U8328 | sp-29 | an-188 |
| E1A1003 | sp-3 | an-189 | E1U1003 | sp-3 | an-189 | E1U8329 | sp-29 | an-189 |
| E1A1004 | sp-3 | an-190 | E1U1004 | sp-3 | an-190 | E1U8330 | sp-29 | an-190 |
| E1A1005 | sp-3 | an-191 | E1U1005 | sp-3 | an-191 | E1U8331 | sp-29 | an-191 |
| E1A1006 | sp-3 | an-192 | E1U1006 | sp-3 | an-192 | E1U8332 | sp-29 | an-192 |
| E1A1007 | sp-3 | an-193 | E1U1007 | sp-3 | an-193 | E1U8333 | sp-29 | an-193 |
| E1A1008 | sp-3 | an-194 | E1U1008 | sp-3 | an-194 | E1U8334 | sp-29 | an-194 |
| E1A1009 | sp-3 | an-195 | E1U1009 | sp-3 | an-195 | E1U8335 | sp-29 | an-195 |
| E1A1010 | sp-3 | an-196 | E1U1010 | sp-3 | an-196 | E1U8336 | sp-29 | an-196 |
| E1A1011 | sp-3 | an-197 | E1U1011 | sp-3 | an-197 | E1U8337 | sp-29 | an-197 |
| E1A1012 | sp-3 | an-198 | E1U1012 | sp-3 | an-198 | E1U8338 | sp-29 | an-198 |
| E1A1013 | sp-3 | an-199 | E1U1013 | sp-3 | an-199 | E1U8339 | sp-29 | an-199 |
| E1A1014 | sp-3 | an-200 | E1U1014 | sp-3 | an-200 | E1U8340 | sp-29 | an-200 |
| E1A1015 | sp-3 | an-201 | E1U1015 | sp-3 | an-201 | E1U8341 | sp-29 | an-201 |
| E1A1016 | sp-3 | an-202 | E1U1016 | sp-3 | an-202 | E1U8342 | sp-29 | an-202 |
| E1A1017 | sp-3 | an-203 | E1U1017 | sp-3 | an-203 | E1U8343 | sp-29 | an-203 |
| E1A1018 | sp-3 | an-204 | E1U1018 | sp-3 | an-204 | E1U8344 | sp-29 | an-204 |
| E1A1019 | sp-3 | an-205 | E1U1019 | sp-3 | an-205 | E1U8345 | sp-29 | an-205 |
| E1A1020 | sp-3 | an-206 | E1U1020 | sp-3 | an-206 | E1U8346 | sp-29 | an-206 |
| E1A1021 | sp-3 | an-207 | E1U1021 | sp-3 | an-207 | E1U8347 | sp-29 | an-207 |
| E1A1022 | sp-3 | an-208 | E1U1022 | sp-3 | an-208 | E1U8348 | sp-29 | an-208 |
| E1A1023 | sp-3 | an-209 | E1U1023 | sp-3 | an-209 | E1U8349 | sp-29 | an-209 |
| E1A1024 | sp-3 | an-210 | E1U1024 | sp-3 | an-210 | E1U8350 | sp-29 | an-210 |
| E1A1025 | sp-3 | an-211 | E1U1025 | sp-3 | an-211 | E1U8351 | sp-29 | an-211 |
| E1A1026 | sp-3 | an-212 | E1U1026 | sp-3 | an-212 | E1U8352 | sp-29 | an-212 |

-continued

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| Table 1-20 ||||||||| 
| Y = NHCS ||| Y = NHCSNH ||| Y = NHCSNH |||
| E1A1027 | sp-3 | an-213 | E1U1027 | sp-3 | an-213 | E1U8353 | sp-29 | an-213 |
| E1A1028 | sp-3 | an-214 | E1U1028 | sp-3 | an-214 | E1U8354 | sp-29 | an-214 |
| E1A1029 | sp-3 | an-215 | E1U1029 | sp-3 | an-215 | E1U8355 | sp-29 | an-215 |
| E1A1030 | sp-3 | an-216 | E1U1030 | sp-3 | an-216 | E1U8356 | sp-29 | an-216 |
| E1A1031 | sp-3 | an-217 | E1U1031 | sp-3 | an-217 | E1U8357 | sp-29 | an-217 |
| E1A1032 | sp-3 | an-218 | E1U1032 | sp-3 | an-218 | E1U8358 | sp-29 | an-218 |
| E1A1033 | sp-3 | an-219 | E1U1033 | sp-3 | an-219 | E1U8359 | sp-29 | an-219 |
| E1A1034 | sp-3 | an-220 | E1U1034 | sp-3 | an-220 | E1U8360 | sp-29 | an-220 |
| E1A1035 | sp-3 | an-221 | E1U1035 | sp-3 | an-221 | E1U8361 | sp-29 | an-221 |
| E1A1036 | sp-3 | an-222 | E1U1036 | sp-3 | an-222 | E1U8362 | sp-29 | an-222 |
| E1A1037 | sp-3 | an-223 | E1U1037 | sp-3 | an-223 | E1U8363 | sp-29 | an-223 |
| E1A1038 | sp-3 | an-224 | E1U1038 | sp-3 | an-224 | E1U8364 | sp-29 | an-224 |
| E1A1039 | sp-3 | an-225 | E1U1039 | sp-3 | an-225 | E1U8365 | sp-29 | an-225 |
| E1A1040 | sp-3 | an-226 | E1U1040 | sp-3 | an-226 | E1U8366 | sp-29 | an-226 |
| E1A1041 | sp-3 | an-227 | E1U1041 | sp-3 | an-227 | E1U8367 | sp-29 | an-227 |
| E1A1042 | sp-3 | an-228 | E1U1042 | sp-3 | an-228 | E1U8368 | sp-29 | an-228 |
| E1A1043 | sp-3 | an-229 | E1U1043 | sp-3 | an-229 | E1U8369 | sp-29 | an-229 |
| E1A1044 | sp-3 | an-230 | E1U1044 | sp-3 | an-230 | E1U8370 | sp-29 | an-230 |
| E1A1045 | sp-3 | an-231 | E1U1045 | sp-3 | an-231 | E1U8371 | sp-29 | an-231 |
| E1A1046 | sp-3 | an-232 | E1U1046 | sp-3 | an-232 | E1U8372 | sp-29 | an-232 |
| E1A1047 | sp-3 | an-233 | E1U1047 | sp-3 | an-233 | E1U8373 | sp-29 | an-233 |
| E1A1048 | sp-3 | an-234 | E1U1048 | sp-3 | an-234 | E1U8374 | sp-29 | an-234 |
| E1A1049 | sp-3 | an-235 | E1U1049 | sp-3 | an-235 | E1U8375 | sp-29 | an-235 |
| E1A1050 | sp-3 | an-236 | E1U1050 | sp-3 | an-236 | E1U8376 | sp-29 | an-236 |
| E1A1051 | sp-3 | an-237 | E1U1051 | sp-3 | an-237 | E1U8377 | sp-29 | an-237 |
| E1A1052 | sp-3 | an-238 | E1U1052 | sp-3 | an-238 | E1U8378 | sp-29 | an-238 |
| E1A1053 | sp-3 | an-239 | E1U1053 | sp-3 | an-239 | E1U8379 | sp-29 | an-239 |
| E1A1054 | sp-3 | an-240 | E1U1054 | sp-3 | an-240 | E1U8380 | sp-29 | an-240 |
| E1A1055 | sp-3 | an-241 | E1U1055 | sp-3 | an-241 | E1U8381 | sp-29 | an-241 |
| E1A1056 | sp-3 | an-242 | E1U1056 | sp-3 | an-242 | E1U8382 | sp-29 | an-242 |
| E1A1057 | sp-3 | an-243 | E1U1057 | sp-3 | an-243 | E1U8383 | sp-29 | an-243 |
| E1A1058 | sp-3 | an-244 | E1U1058 | sp-3 | an-244 | E1U8384 | sp-29 | an-244 |
| E1A1059 | sp-3 | an-245 | E1U1059 | sp-3 | an-245 | E1U8385 | sp-29 | an-245 |
| E1A1060 | sp-3 | an-246 | E1U1060 | sp-3 | an-246 | E1U8386 | sp-29 | an-246 |
| E1A1061 | sp-3 | an-247 | E1U1061 | sp-3 | an-247 | E1U8387 | sp-29 | an-247 |
| E1A1062 | sp-3 | an-248 | E1U1062 | sp-3 | an-248 | E1U8388 | sp-29 | an-248 |
| E1A1063 | sp-3 | an-249 | E1U1063 | sp-3 | an-249 | E1U8389 | sp-29 | an-249 |
| E1A1064 | sp-3 | an-250 | E1U1064 | sp-3 | an-250 | E1U8390 | sp-29 | an-250 |
| E1A1065 | sp-3 | an-251 | E1U1065 | sp-3 | an-251 | E1U8391 | sp-29 | an-251 |
| E1A1066 | sp-3 | an-252 | E1U1066 | sp-3 | an-252 | E1U8392 | sp-29 | an-252 |
| E1A1067 | sp-3 | an-253 | E1U1067 | sp-3 | an-253 | E1U8393 | sp-29 | an-253 |
| E1A1068 | sp-3 | an-254 | E1U1068 | sp-3 | an-254 | E1U8394 | sp-29 | an-254 |
| E1A1069 | sp-3 | an-255 | E1U1069 | sp-3 | an-255 | E1U8395 | sp-29 | an-255 |
| E1A1070 | sp-3 | an-256 | E1U1070 | sp-3 | an-256 | E1U8396 | sp-29 | an-256 |
| E1A1071 | sp-3 | an-257 | E1U1071 | sp-3 | an-257 | E1U8397 | sp-29 | an-257 |
| E1A1072 | sp-3 | an-258 | E1U1072 | sp-3 | an-258 | E1U8398 | sp-29 | an-258 |
| E1A1073 | sp-3 | an-259 | E1U1073 | sp-3 | an-259 | E1U8399 | sp-29 | an-259 |
| E1A1074 | sp-3 | an-260 | E1U1074 | sp-3 | an-260 | E1U8400 | sp-29 | an-260 |
| E1A1075 | sp-3 | an-261 | E1U1075 | sp-3 | an-261 | E1U8401 | sp-29 | an-261 |
| E1A1076 | sp-3 | an-262 | E1U1076 | sp-3 | an-262 | E1U8402 | sp-29 | an-262 |
| E1A1077 | sp-3 | an-263 | E1U1077 | sp-3 | an-263 | E1U8403 | sp-29 | an-263 |
| E1A1078 | sp-3 | an-264 | E1U1078 | sp-3 | an-264 | E1U8404 | sp-29 | an-264 |
| E1A1079 | sp-3 | an-265 | E1U1079 | sp-3 | an-265 | E1U8405 | sp-29 | an-265 |
| E1A1080 | sp-3 | an-266 | E1U1080 | sp-3 | an-266 | E1U8406 | sp-29 | an-266 |
| Table 1-21 |||||||||
| Y = NHCS ||| Y = NHCSNH ||| Y = NHCSNH |||
| E1A1081 | sp-3 | an-267 | E1U1081 | sp-3 | an-267 | E1U8407 | sp-29 | an-267 |
| E1A1082 | sp-3 | an-268 | E1U1082 | sp-3 | an-268 | E1U8408 | sp-29 | an-268 |
| E1A1083 | sp-3 | an-269 | E1U1083 | sp-3 | an-269 | E1U8409 | sp-29 | an-269 |
| E1A1084 | sp-3 | an-270 | E1U1084 | sp-3 | an-270 | E1U8410 | sp-29 | an-270 |
| E1A1085 | sp-3 | an-271 | E1U1085 | sp-3 | an-271 | E1U8411 | sp-29 | an-271 |
| E1A1086 | sp-3 | an-272 | E1U1086 | sp-3 | an-272 | E1U8412 | sp-29 | an-272 |
| E1A1087 | sp-3 | an-273 | E1U1087 | sp-3 | an-273 | E1U8413 | sp-29 | an-273 |
| E1A1088 | sp-3 | an-274 | E1U1088 | sp-3 | an-274 | E1U8414 | sp-29 | an-274 |
| E1A1089 | sp-3 | an-275 | E1U1089 | sp-3 | an-275 | E1U8415 | sp-29 | an-275 |
| E1A1090 | sp-3 | an-276 | E1U1090 | sp-3 | an-276 | E1U8416 | sp-29 | an-276 |
| E1A1091 | sp-3 | an-277 | E1U1091 | sp-3 | an-277 | E1U8417 | sp-29 | an-277 |
| E1A1092 | sp-3 | an-278 | E1U1092 | sp-3 | an-278 | E1U8418 | sp-29 | an-278 |
| E1A1093 | sp-3 | an-279 | E1U1093 | sp-3 | an-279 | E1U8419 | sp-29 | an-279 |
| E1A1094 | sp-3 | an-280 | E1U1094 | sp-3 | an-280 | E1U8420 | sp-29 | an-280 |
| E1A1095 | sp-3 | an-281 | E1U1095 | sp-3 | an-281 | E1U8421 | sp-29 | an-281 |
| E1A1096 | sp-3 | an-282 | E1U1096 | sp-3 | an-282 | E1U8422 | sp-29 | an-282 |

-continued

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| E1A1097 | sp-3 | an-283 | E1U1097 | sp-3 | an-283 | E1U8423 | sp-29 | an-283 |
| E1A1098 | sp-3 | an-284 | E1U1098 | sp-3 | an-284 | E1U8424 | sp-29 | an-284 |
| E1A1099 | sp-3 | an-285 | E1U1099 | sp-3 | an-285 | E1U8425 | sp-29 | an-285 |
| E1A1100 | sp-3 | an-286 | E1U1100 | sp-3 | an-286 | E1U8426 | sp-29 | an-286 |
| E1A1101 | sp-3 | an-287 | E1U1101 | sp-3 | an-287 | E1U8427 | sp-29 | an-287 |
| E1A1102 | sp-3 | an-288 | E1U1102 | sp-3 | an-288 | E1U8428 | sp-29 | an-288 |
| E1A1103 | sp-3 | an-289 | E1U1103 | sp-3 | an-289 | E1U8429 | sp-29 | an-289 |
| E1A1104 | sp-3 | an-290 | E1U1104 | sp-3 | an-290 | E1U8430 | sp-29 | an-290 |
| E1A1105 | sp-3 | an-291 | E1U1105 | sp-3 | an-291 | E1U8431 | sp-29 | an-291 |
| E1A1106 | sp-3 | an-292 | E1U1106 | sp-3 | an-292 | E1U8432 | sp-29 | an-292 |
| E1A1107 | sp-3 | an-293 | E1U1107 | sp-3 | an-293 | E1U8433 | sp-29 | an-293 |
| E1A1108 | sp-3 | an-294 | E1U1108 | sp-3 | an-294 | E1U8434 | sp-29 | an-294 |
| E1A1109 | sp-3 | an-295 | E1U1109 | sp-3 | an-295 | E1U8435 | sp-29 | an-295 |
| E1A1110 | sp-3 | an-296 | E1U1110 | sp-3 | an-296 | E1U8436 | sp-29 | an-296 |
| E1A1111 | sp-3 | an-297 | E1U1111 | sp-3 | an-297 | E1U8437 | sp-29 | an-297 |
| E1A1112 | sp-3 | an-298 | E1U1112 | sp-3 | an-298 | E1U8438 | sp-29 | an-298 |
| E1A1113 | sp-3 | an-299 | E1U1113 | sp-3 | an-299 | E1U8439 | sp-29 | an-299 |
| E1A1114 | sp-3 | an-300 | E1U1114 | sp-3 | an-300 | E1U8440 | sp-29 | an-300 |
| E1A1115 | sp-3 | an-301 | E1U1115 | sp-3 | an-301 | E1U8441 | sp-29 | an-301 |
| E1A1116 | sp-3 | an-302 | E1U1116 | sp-3 | an-302 | E1U8442 | sp-29 | an-302 |
| E1A1117 | sp-3 | an-303 | E1U1117 | sp-3 | an-303 | E1U8443 | sp-29 | an-303 |
| E1A1118 | sp-3 | an-304 | E1U1118 | sp-3 | an-304 | E1U8444 | sp-29 | an-304 |
| E1A1119 | sp-3 | an-305 | E1U1119 | sp-3 | an-305 | E1U8445 | sp-29 | an-305 |
| E1A1120 | sp-3 | an-306 | E1U1120 | sp-3 | an-306 | E1U8446 | sp-29 | an-306 |
| E1A1121 | sp-3 | an-307 | E1U1121 | sp-3 | an-307 | E1U8447 | sp-29 | an-307 |
| E1A1122 | sp-3 | an-308 | E1U1122 | sp-3 | an-308 | E1U8448 | sp-29 | an-308 |
| E1A1123 | sp-3 | an-309 | E1U1123 | sp-3 | an-309 | E1U8449 | sp-29 | an-309 |
| E1A1124 | sp-3 | an-310 | E1U1124 | sp-3 | an-310 | E1U8450 | sp-29 | an-310 |
| E1A1125 | sp-3 | an-311 | E1U1125 | sp-3 | an-311 | E1U8451 | sp-29 | an-311 |
| E1A1126 | sp-3 | an-312 | E1U1126 | sp-3 | an-312 | E1U8452 | sp-29 | an-312 |
| E1A1127 | sp-3 | an-313 | E1U1127 | sp-3 | an-313 | E1U8453 | sp-29 | an-313 |
| E1A1128 | sp-3 | an-314 | E1U1128 | sp-3 | an-314 | E1U8454 | sp-29 | an-314 |
| E1A1129 | sp-3 | an-315 | E1U1129 | sp-3 | an-315 | E1U8455 | sp-29 | an-315 |
| E1A1130 | sp-3 | an-316 | E1U1130 | sp-3 | an-316 | E1U8456 | sp-29 | an-316 |
| E1A1131 | sp-3 | an-317 | E1U1131 | sp-3 | an-317 | E1U8457 | sp-29 | an-317 |
| E1A1132 | sp-3 | an-318 | E1U1132 | sp-3 | an-318 | E1U8458 | sp-29 | an-318 |
| E1A1133 | sp-3 | an-319 | E1U1133 | sp-3 | an-319 | E1U8459 | sp-29 | an-319 |
| E1A1134 | sp-3 | an-320 | E1U1134 | sp-3 | an-320 | E1U8460 | sp-29 | an-320 |

Table 1-22

| Y = NHCS | | | Y = NHCSNH | | | Y = NHCSNH | | |
|---|---|---|---|---|---|---|---|---|
| E1A1135 | sp-3 | an-321 | E1U1135 | sp-3 | an-321 | E1U8461 | sp-29 | an-321 |
| E1A1136 | sp-3 | an-322 | E1U1136 | sp-3 | an-322 | E1U8462 | sp-29 | an-322 |
| E1A1137 | sp-3 | an-323 | E1U1137 | sp-3 | an-323 | E1U8463 | sp-29 | an-323 |
| E1A1138 | sp-3 | an-324 | E1U1138 | sp-3 | an-324 | E1U8464 | sp-29 | an-324 |
| E1A1139 | sp-3 | an-325 | E1U1139 | sp-3 | an-325 | E1U8465 | sp-29 | an-325 |
| E1A1140 | sp-3 | an-326 | E1U1140 | sp-3 | an-326 | E1U8466 | sp-29 | an-326 |
| E1A1141 | sp-3 | an-327 | E1U1141 | sp-3 | an-327 | E1U8467 | sp-29 | an-327 |
| E1A1142 | sp-3 | an-328 | E1U1142 | sp-3 | an-328 | E1U8468 | sp-29 | an-328 |
| E1A1143 | sp-3 | an-329 | E1U1143 | sp-3 | an-329 | E1U8469 | sp-29 | an-329 |
| E1A1144 | sp-3 | an-330 | E1U1144 | sp-3 | an-330 | E1U8470 | sp-29 | an-330 |
| E1A1145 | sp-3 | an-331 | E1U1145 | sp-3 | an-331 | E1U8471 | sp-29 | an-331 |
| E1A1146 | sp-3 | an-332 | E1U1146 | sp-3 | an-332 | E1U8472 | sp-29 | an-332 |
| E1A1147 | sp-3 | an-333 | E1U1147 | sp-3 | an-333 | E1U8473 | sp-29 | an-333 |
| E1A1148 | sp-3 | an-334 | E1U1148 | sp-3 | an-334 | E1U8474 | sp-29 | an-334 |
| E1A1149 | sp-3 | an-335 | E1U1149 | sp-3 | an-335 | E1U8475 | sp-29 | an-335 |
| E1A1150 | sp-3 | an-336 | E1U1150 | sp-3 | an-336 | E1U8476 | sp-29 | an-336 |
| E1A1151 | sp-3 | an-337 | E1U1151 | sp-3 | an-337 | E1U8477 | sp-29 | an-337 |
| E1A1152 | sp-3 | an-338 | E1U1152 | sp-3 | an-338 | E1U8478 | sp-29 | an-338 |
| E1A1153 | sp-3 | an-339 | E1U1153 | sp-3 | an-339 | E1U8479 | sp-29 | an-339 |
| E1A1154 | sp-3 | an-340 | E1U1154 | sp-3 | an-340 | E1U8480 | sp-29 | an-340 |
| E1A1155 | sp-3 | an-341 | E1U1155 | sp-3 | an-341 | E1U8481 | sp-29 | an-341 |
| E1A1156 | sp-3 | an-342 | E1U1156 | sp-3 | an-342 | E1U8482 | sp-29 | an-342 |
| E1A1157 | sp-3 | an-343 | E1U1157 | sp-3 | an-343 | E1U8483 | sp-29 | an-343 |
| E1A1158 | sp-3 | an-344 | E1U1158 | sp-3 | an-344 | E1U8484 | sp-29 | an-344 |
| E1A1159 | sp-3 | an-345 | E1U1159 | sp-3 | an-345 | E1U8485 | sp-29 | an-345 |
| E1A1160 | sp-3 | an-346 | E1U1160 | sp-3 | an-346 | E1U8486 | sp-29 | an-346 |
| E1A1161 | sp-3 | an-347 | E1U1161 | sp-3 | an-347 | E1U8487 | sp-29 | an-347 |
| E1A1162 | sp-3 | an-348 | E1U1162 | sp-3 | an-348 | E1U8488 | sp-29 | an-348 |
| E1A1163 | sp-3 | an-349 | E1U1163 | sp-3 | an-349 | E1U8489 | sp-29 | an-349 |
| E1A1164 | sp-3 | an-350 | E1U1164 | sp-3 | an-350 | E1U8490 | sp-29 | an-350 |
| E1A1165 | sp-3 | an-351 | E1U1165 | sp-3 | an-351 | E1U8491 | sp-29 | an-351 |
| E1A1166 | sp-3 | an-352 | E1U1166 | sp-3 | an-352 | E1U8492 | sp-29 | an-352 |
| E1A1167 | sp-3 | an-353 | E1U1167 | sp-3 | an-353 | E1U8493 | sp-29 | an-353 |
| E1A1168 | sp-3 | an-354 | E1U1168 | sp-3 | an-354 | E1U8494 | sp-29 | an-354 |
| E1A1169 | sp-3 | an-355 | E1U1169 | sp-3 | an-355 | E1U8495 | sp-29 | an-355 |
| E1A1170 | sp-3 | an-356 | E1U1170 | sp-3 | an-356 | E1U8496 | sp-29 | an-356 |

-continued

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| E1A1171 | sp-3 | an-357 | E1U1171 | sp-3 | an-357 | E1U8497 | sp-29 | an-357 |
| E1A1172 | sp-3 | an-358 | E1U1172 | sp-3 | an-358 | E1U8498 | sp-29 | an-358 |
| E1A1173 | sp-3 | an-359 | E1U1173 | sp-3 | an-359 | E1U8499 | sp-29 | an-359 |
| E1A1174 | sp-3 | an-360 | E1U1174 | sp-3 | an-360 | E1U8500 | sp-29 | an-360 |
| E1A1175 | sp-3 | an-361 | E1U1175 | sp-3 | an-361 | E1U8501 | sp-29 | an-361 |
| E1A1176 | sp-3 | an-362 | E1U1176 | sp-3 | an-362 | E1U8502 | sp-29 | an-362 |
| E1A1177 | sp-3 | an-363 | E1U1177 | sp-3 | an-363 | E1U8503 | sp-29 | an-363 |
| E1A1178 | sp-3 | an-364 | E1U1178 | sp-3 | an-364 | E1U8504 | sp-29 | an-364 |
| E1A1179 | sp-3 | an-365 | E1U1179 | sp-3 | an-365 | E1U8505 | sp-29 | an-365 |
| E1A1180 | sp-3 | an-366 | E1U1180 | sp-3 | an-366 | E1U8506 | sp-29 | an-366 |
| E1A1181 | sp-3 | an-367 | E1U1181 | sp-3 | an-367 | E1U8507 | sp-29 | an-367 |
| E1A1182 | sp-3 | an-368 | E1U1182 | sp-3 | an-368 | E1U8508 | sp-29 | an-368 |
| E1A1183 | sp-3 | an-369 | E1U1183 | sp-3 | an-369 | E1U8509 | sp-29 | an-369 |
| E1A1184 | sp-3 | an-370 | E1U1184 | sp-3 | an-370 | E1U8510 | sp-29 | an-370 |
| E1A1185 | sp-3 | an-371 | E1U1185 | sp-3 | an-371 | E1U8511 | sp-29 | an-371 |
| E1A1186 | sp-3 | an-372 | E1U1186 | sp-3 | an-372 | E1U8512 | sp-29 | an-372 |
| E1A1187 | sp-3 | an-373 | E1U1187 | sp-3 | an-373 | E1U8513 | sp-29 | an-373 |
| E1A1188 | sp-3 | an-374 | E1U1188 | sp-3 | an-374 | E1U8514 | sp-29 | an-374 |

Table 1-23

| Y = NHCS | | | Y = NHCSNH | | | Y = NHCSNH | | |
|---|---|---|---|---|---|---|---|---|
| E1A1189 | sp-3 | an-375 | E1U1189 | sp-3 | an-375 | E1U8515 | sp-29 | an-375 |
| E1A1190 | sp-3 | an-376 | E1U1190 | sp-3 | an-376 | E1U8516 | sp-29 | an-376 |
| E1A1191 | sp-3 | an-377 | E1U1191 | sp-3 | an-377 | E1U8517 | sp-29 | an-377 |
| E1A1192 | sp-3 | an-378 | E1U1192 | sp-3 | an-378 | E1U8518 | sp-29 | an-378 |
| E1A1193 | sp-3 | an-379 | E1U1193 | sp-3 | an-379 | E1U8519 | sp-29 | an-379 |
| E1A1194 | sp-3 | an-380 | E1U1194 | sp-3 | an-380 | E1U8520 | sp-29 | an-380 |
| E1A1195 | sp-3 | an-381 | E1U1195 | sp-3 | an-381 | E1U8521 | sp-29 | an-381 |
| E1A1196 | sp-3 | an-382 | E1U1196 | sp-3 | an-382 | E1U8522 | sp-29 | an-382 |
| E1A1197 | sp-3 | an-383 | E1U1197 | sp-3 | an-383 | E1U8523 | sp-29 | an-383 |
| E1A1198 | sp-3 | an-384 | E1U1198 | sp-3 | an-384 | E1U8524 | sp-29 | an-384 |
| E1A1199 | sp-3 | an-385 | E1U1199 | sp-3 | an-385 | E1U8525 | sp-29 | an-385 |
| E1A1200 | sp-3 | an-386 | E1U1200 | sp-3 | an-386 | E1U8526 | sp-29 | an-386 |
| E1A1201 | sp-3 | an-387 | E1U1201 | sp-3 | an-387 | E1U8527 | sp-29 | an-387 |
| E1A1202 | sp-3 | an-388 | E1U1202 | sp-3 | an-388 | E1U8528 | sp-29 | an-388 |
| E1A1203 | sp-3 | an-389 | E1U1203 | sp-3 | an-389 | E1U8529 | sp-29 | an-389 |
| E1A1204 | sp-3 | an-390 | E1U1204 | sp-3 | an-390 | E1U8530 | sp-29 | an-390 |
| E1A1205 | sp-3 | an-391 | E1U1205 | sp-3 | an-391 | E1U8531 | sp-29 | an-391 |
| E1A1206 | sp-3 | an-392 | E1U1206 | sp-3 | an-392 | E1U8532 | sp-29 | an-392 |
| E1A1207 | sp-3 | an-393 | E1U1207 | sp-3 | an-393 | E1U8533 | sp-29 | an-393 |
| E1A1208 | sp-3 | an-394 | E1U1208 | sp-3 | an-394 | E1U8534 | sp-29 | an-394 |
| E1A1209 | sp-3 | an-395 | E1U1209 | sp-3 | an-395 | E1U8535 | sp-29 | an-395 |
| E1A1210 | sp-3 | an-396 | E1U1210 | sp-3 | an-396 | E1U8536 | sp-29 | an-396 |
| E1A1211 | sp-3 | an-397 | E1U1211 | sp-3 | an-397 | E1U8537 | sp-29 | an-397 |
| E1A1212 | sp-3 | an-398 | E1U1212 | sp-3 | an-398 | E1U8538 | sp-29 | an-398 |
| E1A1213 | sp-3 | an-399 | E1U1213 | sp-3 | an-399 | E1U8539 | sp-29 | an-399 |
| E1A1214 | sp-3 | an-400 | E1U1214 | sp-3 | an-400 | E1U8540 | sp-29 | an-400 |
| E1A1215 | sp-3 | an-401 | E1U1215 | sp-3 | an-401 | E1U8541 | sp-29 | an-401 |
| E1A1216 | sp-3 | an-402 | E1U1216 | sp-3 | an-402 | E1U8542 | sp-29 | an-402 |
| E1A1217 | sp-3 | an-403 | E1U1217 | sp-3 | an-403 | E1U8543 | sp-29 | an-403 |
| E1A1218 | sp-3 | an-404 | E1U1218 | sp-3 | an-404 | E1U8544 | sp-29 | an-404 |
| E1A1219 | sp-3 | an-405 | E1U1219 | sp-3 | an-405 | E1U8545 | sp-29 | an-405 |
| E1A1220 | sp-3 | an-406 | E1U1220 | sp-3 | an-406 | E1U8546 | sp-29 | an-406 |
| E1A1221 | sp-3 | an-407 | E1U1221 | sp-3 | an-407 | E1U8547 | sp-29 | an-407 |
| E1A1222 | sp-4 | an-1 | E1U1222 | sp-4 | an-1 | E1U8548 | sp-30 | an-1 |
| E1A1223 | sp-4 | an-2 | E1U1223 | sp-4 | an-2 | E1U8549 | sp-30 | an-2 |
| E1A1224 | sp-4 | an-3 | E1U1224 | sp-4 | an-3 | E1U8550 | sp-30 | an-3 |
| E1A1225 | sp-4 | an-4 | E1U1225 | sp-4 | an-4 | E1U8551 | sp-30 | an-4 |
| E1A1226 | sp-4 | an-5 | E1U1226 | sp-4 | an-5 | E1U8552 | sp-30 | an-5 |
| E1A1227 | sp-4 | an-6 | E1U1227 | sp-4 | an-6 | E1U8553 | sp-30 | an-6 |
| E1A1228 | sp-4 | an-7 | E1U1228 | sp-4 | an-7 | E1U8554 | sp-30 | an-7 |
| E1A1229 | sp-4 | an-8 | E1U1229 | sp-4 | an-8 | E1U8555 | sp-30 | an-8 |
| E1A1230 | sp-4 | an-9 | E1U1230 | sp-4 | an-9 | E1U8556 | sp-30 | an-9 |
| E1A1231 | sp-4 | an-10 | E1U1231 | sp-4 | an-10 | E1U8557 | sp-30 | an-10 |
| E1A1232 | sp-4 | an-11 | E1U1232 | sp-4 | an-11 | E1U8558 | sp-30 | an-11 |
| E1A1233 | sp-4 | an-12 | E1U1233 | sp-4 | an-12 | E1U8559 | sp-30 | an-12 |
| E1A1234 | sp-4 | an-13 | E1U1234 | sp-4 | an-13 | E1U8560 | sp-30 | an-13 |
| E1A1235 | sp-4 | an-14 | E1U1235 | sp-4 | an-14 | E1U8561 | sp-30 | an-14 |
| E1A1236 | sp-4 | an-15 | E1U1236 | sp-4 | an-15 | E1U8562 | sp-30 | an-15 |
| E1A1237 | sp-4 | an-16 | E1U1237 | sp-4 | an-16 | E1U8563 | sp-30 | an-16 |
| E1A1238 | sp-4 | an-17 | E1U1238 | sp-4 | an-17 | E1U8564 | sp-30 | an-17 |
| E1A1239 | sp-4 | an-18 | E1U1239 | sp-4 | an-18 | E1U8565 | sp-30 | an-18 |
| E1A1240 | sp-4 | an-19 | E1U1240 | sp-4 | an-19 | E1U8566 | sp-30 | an-19 |
| E1A1241 | sp-4 | an-20 | E1U1241 | sp-4 | an-20 | E1U8567 | sp-30 | an-20 |
| E1A1242 | sp-4 | an-21 | E1U1242 | sp-4 | an-21 | E1U8568 | sp-30 | an-21 |

-continued

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| Table 1-24 ||||||||||
| Y = NHCS ||| Y = NHCSNH ||| Y = NHCSNH |||
| E1A1243 | sp-4 | an-22 | E1U1243 | sp-4 | an-22 | E1U8569 | sp-30 | an-22 |
| E1A1244 | sp-4 | an-23 | E1U1244 | sp-4 | an-23 | E1U8570 | sp-30 | an-23 |
| E1A1245 | sp-4 | an-24 | E1U1245 | sp-4 | an-24 | E1U8571 | sp-30 | an-24 |
| E1A1246 | sp-4 | an-25 | E1U1246 | sp-4 | an-25 | E1U8572 | sp-30 | an-25 |
| E1A1247 | sp-4 | an-26 | E1U1247 | sp-4 | an-26 | E1U8573 | sp-30 | an-26 |
| E1A1248 | sp-4 | an-27 | E1U1248 | sp-4 | an-27 | E1U8574 | sp-30 | an-27 |
| E1A1249 | sp-4 | an-28 | E1U1249 | sp-4 | an-28 | E1U8575 | sp-30 | an-28 |
| E1A1250 | sp-4 | an-29 | E1U1250 | sp-4 | an-29 | E1U8576 | sp-30 | an-29 |
| E1A1251 | sp-4 | an-30 | E1U1251 | sp-4 | an-30 | E1U8577 | sp-30 | an-30 |
| E1A1252 | sp-4 | an-31 | E1U1252 | sp-4 | an-31 | E1U8578 | sp-30 | an-31 |
| E1A1253 | sp-4 | an-32 | E1U1253 | sp-4 | an-32 | E1U8579 | sp-30 | an-32 |
| E1A1254 | sp-4 | an-33 | E1U1254 | sp-4 | an-33 | E1U8580 | sp-30 | an-33 |
| E1A1255 | sp-4 | an-34 | E1U1255 | sp-4 | an-34 | E1U8581 | sp-30 | an-34 |
| E1A1256 | sp-4 | an-35 | E1U1256 | sp-4 | an-35 | E1U8582 | sp-30 | an-35 |
| E1A1257 | sp-4 | an-36 | E1U1257 | sp-4 | an-36 | E1U8583 | sp-30 | an-36 |
| E1A1258 | sp-4 | an-37 | E1U1258 | sp-4 | an-37 | E1U8584 | sp-30 | an-37 |
| E1A1259 | sp-4 | an-38 | E1U1259 | sp-4 | an-38 | E1U8585 | sp-30 | an-38 |
| E1A1260 | sp-4 | an-39 | E1U1260 | sp-4 | an-39 | E1U8586 | sp-30 | an-39 |
| E1A1261 | sp-4 | an-40 | E1U1261 | sp-4 | an-40 | E1U8587 | sp-30 | an-40 |
| E1A1262 | sp-4 | an-41 | E1U1262 | sp-4 | an-41 | E1U8588 | sp-30 | an-41 |
| E1A1263 | sp-4 | an-42 | E1U1263 | sp-4 | an-42 | E1U8589 | sp-30 | an-42 |
| E1A1264 | sp-4 | an-43 | E1U1264 | sp-4 | an-43 | E1U8590 | sp-30 | an-43 |
| E1A1265 | sp-4 | an-44 | E1U1265 | sp-4 | an-44 | E1U8591 | sp-30 | an-44 |
| E1A1266 | sp-4 | an-45 | E1U1266 | sp-4 | an-45 | E1U8592 | sp-30 | an-45 |
| E1A1267 | sp-4 | an-46 | E1U1267 | sp-4 | an-46 | E1U8593 | sp-30 | an-46 |
| E1A1268 | sp-4 | an-47 | E1U1268 | sp-4 | an-47 | E1U8594 | sp-30 | an-47 |
| E1A1269 | sp-4 | an-48 | E1U1269 | sp-4 | an-48 | E1U8595 | sp-30 | an-48 |
| E1A1270 | sp-4 | an-49 | E1U1270 | sp-4 | an-49 | E1U8596 | sp-30 | an-49 |
| E1A1271 | sp-4 | an-50 | E1U1271 | sp-4 | an-50 | E1U8597 | sp-30 | an-50 |
| E1A1272 | sp-4 | an-51 | E1U1272 | sp-4 | an-51 | E1U8598 | sp-30 | an-51 |
| E1A1273 | sp-4 | an-52 | E1U1273 | sp-4 | an-52 | E1U8599 | sp-30 | an-52 |
| E1A1274 | sp-4 | an-53 | E1U1274 | sp-4 | an-53 | E1U8600 | sp-30 | an-53 |
| E1A1275 | sp-4 | an-54 | E1U1275 | sp-4 | an-54 | E1U8601 | sp-30 | an-54 |
| E1A1276 | sp-4 | an-55 | E1U1276 | sp-4 | an-55 | E1U8602 | sp-30 | an-55 |
| E1A1277 | sp-4 | an-56 | E1U1277 | sp-4 | an-56 | E1U8603 | sp-30 | an-56 |
| E1A1278 | sp-4 | an-57 | E1U1278 | sp-4 | an-57 | E1U8604 | sp-30 | an-57 |
| E1A1279 | sp-4 | an-58 | E1U1279 | sp-4 | an-58 | E1U8605 | sp-30 | an-58 |
| E1A1280 | sp-4 | an-59 | E1U1280 | sp-4 | an-59 | E1U8606 | sp-30 | an-59 |
| E1A1281 | sp-4 | an-60 | E1U1281 | sp-4 | an-60 | E1U8607 | sp-30 | an-60 |
| E1A1282 | sp-4 | an-61 | E1U1282 | sp-4 | an-61 | E1U8608 | sp-30 | an-61 |
| E1A1283 | sp-4 | an-62 | E1U1283 | sp-4 | an-62 | E1U8609 | sp-30 | an-62 |
| E1A1284 | sp-4 | an-63 | E1U1284 | sp-4 | an-63 | E1U8610 | sp-30 | an-63 |
| E1A1285 | sp-4 | an-64 | E1U1285 | sp-4 | an-64 | E1U8611 | sp-30 | an-64 |
| E1A1286 | sp-4 | an-65 | E1U1286 | sp-4 | an-65 | E1U8612 | sp-30 | an-65 |
| E1A1287 | sp-4 | an-66 | E1U1287 | sp-4 | an-66 | E1U8613 | sp-30 | an-66 |
| E1A1288 | sp-4 | an-67 | E1U1288 | sp-4 | an-67 | E1U8614 | sp-30 | an-67 |
| E1A1289 | sp-4 | an-68 | E1U1289 | sp-4 | an-68 | E1U8615 | sp-30 | an-68 |
| E1A1290 | sp-4 | an-69 | E1U1290 | sp-4 | an-69 | E1U8616 | sp-30 | an-69 |
| E1A1291 | sp-4 | an-70 | E1U1291 | sp-4 | an-70 | E1U8617 | sp-30 | an-70 |
| E1A1292 | sp-4 | an-71 | E1U1292 | sp-4 | an-71 | E1U8618 | sp-30 | an-71 |
| E1A1293 | sp-4 | an-72 | E1U1293 | sp-4 | an-72 | E1U8619 | sp-30 | an-72 |
| E1A1294 | sp-4 | an-73 | E1U1294 | sp-4 | an-73 | E1U8620 | sp-30 | an-73 |
| E1A1295 | sp-4 | an-74 | E1U1295 | sp-4 | an-74 | E1U8621 | sp-30 | an-74 |
| E1A1296 | sp-4 | an-75 | E1U1296 | sp-4 | an-75 | E1U8622 | sp-30 | an-75 |
| Table 1-25 ||||||||||
| Y = NHCS ||| Y = NHCSNH ||| Y = NHCSNH |||
| E1A1297 | sp-4 | an-76 | E1U1297 | sp-4 | an-76 | E1U8623 | sp-30 | an-76 |
| E1A1298 | sp-4 | an-77 | E1U1298 | sp-4 | an-77 | E1U8624 | sp-30 | an-77 |
| E1A1299 | sp-4 | an-78 | E1U1299 | sp-4 | an-78 | E1U8625 | sp-30 | an-78 |
| E1A1300 | sp-4 | an-79 | E1U1300 | sp-4 | an-79 | E1U8626 | sp-30 | an-79 |
| E1A1301 | sp-4 | an-80 | E1U1301 | sp-4 | an-80 | E1U8627 | sp-30 | an-80 |
| E1A1302 | sp-4 | an-81 | E1U1302 | sp-4 | an-81 | E1U8628 | sp-30 | an-81 |
| E1A1303 | sp-4 | an-82 | E1U1303 | sp-4 | an-82 | E1U8629 | sp-30 | an-82 |
| E1A1304 | sp-4 | an-83 | E1U1304 | sp-4 | an-83 | E1U8630 | sp-30 | an-83 |
| E1A1305 | sp-4 | an-84 | E1U1305 | sp-4 | an-84 | E1U8631 | sp-30 | an-84 |
| E1A1306 | sp-4 | an-85 | E1U1306 | sp-4 | an-85 | E1U8632 | sp-30 | an-85 |
| E1A1307 | sp-4 | an-86 | E1U1307 | sp-4 | an-86 | E1U8633 | sp-30 | an-86 |
| E1A1308 | sp-4 | an-87 | E1U1308 | sp-4 | an-87 | E1U8634 | sp-30 | an-87 |
| E1A1309 | sp-4 | an-88 | E1U1309 | sp-4 | an-88 | E1U8635 | sp-30 | an-88 |
| E1A1310 | sp-4 | an-89 | E1U1310 | sp-4 | an-89 | E1U8636 | sp-30 | an-89 |
| E1A1311 | sp-4 | an-90 | E1U1311 | sp-4 | an-90 | E1U8637 | sp-30 | an-90 |
| E1A1312 | sp-4 | an-91 | E1U1312 | sp-4 | an-91 | E1U8638 | sp-30 | an-91 |

-continued

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| E1A1313 | sp-4 | an-92 | E1U1313 | sp-4 | an-92 | E1U8639 | sp-30 | an-92 |
| E1A1314 | sp-4 | an-93 | E1U1314 | sp-4 | an-93 | E1U8640 | sp-30 | an-93 |
| E1A1315 | sp-4 | an-94 | E1U1315 | sp-4 | an-94 | E1U8641 | sp-30 | an-94 |
| E1A1316 | sp-4 | an-95 | E1U1316 | sp-4 | an-95 | E1U8642 | sp-30 | an-95 |
| E1A1317 | sp-4 | an-96 | E1U1317 | sp-4 | an-96 | E1U8643 | sp-30 | an-96 |
| E1A1318 | sp-4 | an-97 | E1U1318 | sp-4 | an-97 | E1U8644 | sp-30 | an-97 |
| E1A1319 | sp-4 | an-98 | E1U1319 | sp-4 | an-98 | E1U8645 | sp-30 | an-98 |
| E1A1320 | sp-4 | an-99 | E1U1320 | sp-4 | an-99 | E1U8646 | sp-30 | an-99 |
| E1A1321 | sp-4 | an-100 | E1U1321 | sp-4 | an-100 | E1U8647 | sp-30 | an-100 |
| E1A1322 | sp-4 | an-101 | E1U1322 | sp-4 | an-101 | E1U8648 | sp-30 | an-101 |
| E1A1323 | sp-4 | an-102 | E1U1323 | sp-4 | an-102 | E1U8649 | sp-30 | an-102 |
| E1A1324 | sp-4 | an-103 | E1U1324 | sp-4 | an-103 | E1U8650 | sp-30 | an-103 |
| E1A1325 | sp-4 | an-104 | E1U1325 | sp-4 | an-104 | E1U8651 | sp-30 | an-104 |
| E1A1326 | sp-4 | an-105 | E1U1326 | sp-4 | an-105 | E1U8652 | sp-30 | an-105 |
| E1A1327 | sp-4 | an-106 | E1U1327 | sp-4 | an-106 | E1U8653 | sp-30 | an-106 |
| E1A1328 | sp-4 | an-107 | E1U1328 | sp-4 | an-107 | E1U8654 | sp-30 | an-107 |
| E1A1329 | sp-4 | an-108 | E1U1329 | sp-4 | an-108 | E1U8655 | sp-30 | an-108 |
| E1A1330 | sp-4 | an-109 | E1U1330 | sp-4 | an-109 | E1U8656 | sp-30 | an-109 |
| E1A1331 | sp-4 | an-110 | E1U1331 | sp-4 | an-110 | E1U8657 | sp-30 | an-110 |
| E1A1332 | sp-4 | an-111 | E1U1332 | sp-4 | an-111 | E1U8658 | sp-30 | an-111 |
| E1A1333 | sp-4 | an-112 | E1U1333 | sp-4 | an-112 | E1U8659 | sp-30 | an-112 |
| E1A1334 | sp-4 | an-113 | E1U1334 | sp-4 | an-113 | E1U8660 | sp-30 | an-113 |
| E1A1335 | sp-4 | an-114 | E1U1335 | sp-4 | an-114 | E1U8661 | sp-30 | an-114 |
| E1A1336 | sp-4 | an-115 | E1U1336 | sp-4 | an-115 | E1U8662 | sp-30 | an-115 |
| E1A1337 | sp-4 | an-116 | E1U1337 | sp-4 | an-116 | E1U8663 | sp-30 | an-116 |
| E1A1338 | sp-4 | an-117 | E1U1338 | sp-4 | an-117 | E1U8664 | sp-30 | an-117 |
| E1A1339 | sp-4 | an-118 | E1U1339 | sp-4 | an-118 | E1U8665 | sp-30 | an-118 |
| E1A1340 | sp-4 | an-119 | E1U1340 | sp-4 | an-119 | E1U8666 | sp-30 | an-119 |
| E1A1341 | sp-4 | an-120 | E1U1341 | sp-4 | an-120 | E1U8667 | sp-30 | an-120 |
| E1A1342 | sp-4 | an-121 | E1U1342 | sp-4 | an-121 | E1U8668 | sp-30 | an-121 |
| E1A1343 | sp-4 | an-122 | E1U1343 | sp-4 | an-122 | E1U8669 | sp-30 | an-122 |
| E1A1344 | sp-4 | an-123 | E1U1344 | sp-4 | an-123 | E1U8670 | sp-30 | an-123 |
| E1A1345 | sp-4 | an-124 | E1U1345 | sp-4 | an-124 | E1U8671 | sp-30 | an-124 |
| E1A1346 | sp-4 | an-125 | E1U1346 | sp-4 | an-125 | E1U8672 | sp-30 | an-125 |
| E1A1347 | sp-4 | an-126 | E1U1347 | sp-4 | an-126 | E1U8673 | sp-30 | an-126 |
| E1A1348 | sp-4 | an-127 | E1U1348 | sp-4 | an-127 | E1U8674 | sp-30 | an-127 |
| E1A1349 | sp-4 | an-128 | E1U1349 | sp-4 | an-128 | E1U8675 | sp-30 | an-128 |
| E1A1350 | sp-4 | an-129 | E1U1350 | sp-4 | an-129 | E1U8676 | sp-30 | an-129 |

Table 1-26

| Y = NHCS | | | Y = NHCSNH | | | Y = NHCSNH | | |
|---|---|---|---|---|---|---|---|---|
| E1A1351 | sp-4 | an-130 | E1U1351 | sp-4 | an-130 | E1U8677 | sp-30 | an-130 |
| E1A1352 | sp-4 | an-131 | E1U1352 | sp-4 | an-131 | E1U8678 | sp-30 | an-131 |
| E1A1353 | sp-4 | an-132 | E1U1353 | sp-4 | an-132 | E1U8679 | sp-30 | an-132 |
| E1A1354 | sp-4 | an-133 | E1U1354 | sp-4 | an-133 | E1U8680 | sp-30 | an-133 |
| E1A1355 | sp-4 | an-134 | E1U1355 | sp-4 | an-134 | E1U8681 | sp-30 | an-134 |
| E1A1356 | sp-4 | an-135 | E1U1356 | sp-4 | an-135 | E1U8682 | sp-30 | an-135 |
| E1A1357 | sp-4 | an-136 | E1U1357 | sp-4 | an-136 | E1U8683 | sp-30 | an-136 |
| E1A1358 | sp-4 | an-137 | E1U1358 | sp-4 | an-137 | E1U8684 | sp-30 | an-137 |
| E1A1359 | sp-4 | an-138 | E1U1359 | sp-4 | an-138 | E1U8685 | sp-30 | an-138 |
| E1A1360 | sp-4 | an-139 | E1U1360 | sp-4 | an-139 | E1U8686 | sp-30 | an-139 |
| E1A1361 | sp-4 | an-140 | E1U1361 | sp-4 | an-140 | E1U8687 | sp-30 | an-140 |
| E1A1362 | sp-4 | an-141 | E1U1362 | sp-4 | an-141 | E1U8688 | sp-30 | an-141 |
| E1A1363 | sp-4 | an-142 | E1U1363 | sp-4 | an-142 | E1U8689 | sp-30 | an-142 |
| E1A1364 | sp-4 | an-143 | E1U1364 | sp-4 | an-143 | E1U8690 | sp-30 | an-143 |
| E1A1365 | sp-4 | an-144 | E1U1365 | sp-4 | an-144 | E1U8691 | sp-30 | an-144 |
| E1A1366 | sp-4 | an-145 | E1U1366 | sp-4 | an-145 | E1U8692 | sp-30 | an-145 |
| E1A1367 | sp-4 | an-146 | E1U1367 | sp-4 | an-146 | E1U8693 | sp-30 | an-146 |
| E1A1368 | sp-4 | an-147 | E1U1368 | sp-4 | an-147 | E1U8694 | sp-30 | an-147 |
| E1A1369 | sp-4 | an-148 | E1U1369 | sp-4 | an-148 | E1U8695 | sp-30 | an-148 |
| E1A1370 | sp-4 | an-149 | E1U1370 | sp-4 | an-149 | E1U8696 | sp-30 | an-149 |
| E1A1371 | sp-4 | an-150 | E1U1371 | sp-4 | an-150 | E1U8697 | sp-30 | an-150 |
| E1A1372 | sp-4 | an-151 | E1U1372 | sp-4 | an-151 | E1U8698 | sp-30 | an-151 |
| E1A1373 | sp-4 | an-152 | E1U1373 | sp-4 | an-152 | E1U8699 | sp-30 | an-152 |
| E1A1374 | sp-4 | an-153 | E1U1374 | sp-4 | an-153 | E1U8700 | sp-30 | an-153 |
| E1A1375 | sp-4 | an-154 | E1U1375 | sp-4 | an-154 | E1U8701 | sp-30 | an-154 |
| E1A1376 | sp-4 | an-155 | E1U1376 | sp-4 | an-155 | E1U8702 | sp-30 | an-155 |
| E1A1377 | sp-4 | an-156 | E1U1377 | sp-4 | an-156 | E1U8703 | sp-30 | an-156 |
| E1A1378 | sp-4 | an-157 | E1U1378 | sp-4 | an-157 | E1U8704 | sp-30 | an-157 |
| E1A1379 | sp-4 | an-158 | E1U1379 | sp-4 | an-158 | E1U8705 | sp-30 | an-158 |
| E1A1380 | sp-4 | an-159 | E1U1380 | sp-4 | an-159 | E1U8706 | sp-30 | an-159 |
| E1A1381 | sp-4 | an-160 | E1U1381 | sp-4 | an-160 | E1U8707 | sp-30 | an-160 |
| E1A1382 | sp-4 | an-161 | E1U1382 | sp-4 | an-161 | E1U8708 | sp-30 | an-161 |
| E1A1383 | sp-4 | an-162 | E1U1383 | sp-4 | an-162 | E1U8709 | sp-30 | an-162 |
| E1A1384 | sp-4 | an-163 | E1U1384 | sp-4 | an-163 | E1U8710 | sp-30 | an-163 |
| E1A1385 | sp-4 | an-164 | E1U1385 | sp-4 | an-164 | E1U8711 | sp-30 | an-164 |
| E1A1386 | sp-4 | an-165 | E1U1386 | sp-4 | an-165 | E1U8712 | sp-30 | an-165 |

-continued

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| E1A1387 | sp-4 | an-166 | E1U1387 | sp-4 | an-166 | E1U8713 | sp-30 | an-166 |
| E1A1388 | sp-4 | an-167 | E1U1388 | sp-4 | an-167 | E1U8714 | sp-30 | an-167 |
| E1A1389 | sp-4 | an-168 | E1U1389 | sp-4 | an-168 | E1U8715 | sp-30 | an-168 |
| E1A1390 | sp-4 | an-169 | E1U1390 | sp-4 | an-169 | E1U8716 | sp-30 | an-169 |
| E1A1391 | sp-4 | an-170 | E1U1391 | sp-4 | an-170 | E1U8717 | sp-30 | an-170 |
| E1A1392 | sp-4 | an-171 | E1U1392 | sp-4 | an-171 | E1U8718 | sp-30 | an-171 |
| E1A1393 | sp-4 | an-172 | E1U1393 | sp-4 | an-172 | E1U8719 | sp-30 | an-172 |
| E1A1394 | sp-4 | an-173 | E1U1394 | sp-4 | an-173 | E1U8720 | sp-30 | an-173 |
| E1A1395 | sp-4 | an-174 | E1U1395 | sp-4 | an-174 | E1U8721 | sp-30 | an-174 |
| E1A1396 | sp-4 | an-175 | E1U1396 | sp-4 | an-175 | E1U8722 | sp-30 | an-175 |
| E1A1397 | sp-4 | an-176 | E1U1397 | sp-4 | an-176 | E1U8723 | sp-30 | an-176 |
| E1A1398 | sp-4 | an-177 | E1U1398 | sp-4 | an-177 | E1U8724 | sp-30 | an-177 |
| E1A1399 | sp-4 | an-178 | E1U1399 | sp-4 | an-178 | E1U8725 | sp-30 | an-178 |
| E1A1400 | sp-4 | an-179 | E1U1400 | sp-4 | an-179 | E1U8726 | sp-30 | an-179 |
| E1A1401 | sp-4 | an-180 | E1U1401 | sp-4 | an-180 | E1U8727 | sp-30 | an-180 |
| E1A1402 | sp-4 | an-181 | E1U1402 | sp-4 | an-181 | E1U8728 | sp-30 | an-181 |
| E1A1403 | sp-4 | an-182 | E1U1403 | sp-4 | an-182 | E1U8729 | sp-30 | an-182 |
| E1A1404 | sp-4 | an-183 | E1U1404 | sp-4 | an-183 | E1U8730 | sp-30 | an-183 |

Table 1-27

| Y = NHCS | | | Y = NHCSNH | | | Y = NHCSNH | | |
|---|---|---|---|---|---|---|---|---|
| E1A1405 | sp-4 | an-184 | E1U1405 | sp-4 | an-184 | E1U8731 | sp-30 | an-184 |
| E1A1406 | sp-4 | an-185 | E1U1406 | sp-4 | an-185 | E1U8732 | sp-30 | an-185 |
| E1A1407 | sp-4 | an-186 | E1U1407 | sp-4 | an-186 | E1U8733 | sp-30 | an-186 |
| E1A1408 | sp-4 | an-187 | E1U1408 | sp-4 | an-187 | E1U8734 | sp-30 | an-187 |
| E1A1409 | sp-4 | an-188 | E1U1409 | sp-4 | an-188 | E1U8735 | sp-30 | an-188 |
| E1A1410 | sp-4 | an-189 | E1U1410 | sp-4 | an-189 | E1U8736 | sp-30 | an-189 |
| E1A1411 | sp-4 | an-190 | E1U1411 | sp-4 | an-190 | E1U8737 | sp-30 | an-190 |
| E1A1412 | sp-4 | an-191 | E1U1412 | sp-4 | an-191 | E1U8738 | sp-30 | an-191 |
| E1A1413 | sp-4 | an-192 | E1U1413 | sp-4 | an-192 | E1U8739 | sp-30 | an-192 |
| E1A1414 | sp-4 | an-193 | E1U1414 | sp-4 | an-193 | E1U8740 | sp-30 | an-193 |
| E1A1415 | sp-4 | an-194 | E1U1415 | sp-4 | an-194 | E1U8741 | sp-30 | an-194 |
| E1A1416 | sp-4 | an-195 | E1U1416 | sp-4 | an-195 | E1U8742 | sp-30 | an-195 |
| E1A1417 | sp-4 | an-196 | E1U1417 | sp-4 | an-196 | E1U8743 | sp-30 | an-196 |
| E1A1418 | sp-4 | an-197 | E1U1418 | sp-4 | an-197 | E1U8744 | sp-30 | an-197 |
| E1A1419 | sp-4 | an-198 | E1U1419 | sp-4 | an-198 | E1U8745 | sp-30 | an-198 |
| E1A1420 | sp-4 | an-199 | E1U1420 | sp-4 | an-199 | E1U8746 | sp-30 | an-199 |
| E1A1421 | sp-4 | an-200 | E1U1421 | sp-4 | an-200 | E1U8747 | sp-30 | an-200 |
| E1A1422 | sp-4 | an-201 | E1U1422 | sp-4 | an-201 | E1U8748 | sp-30 | an-201 |
| E1A1423 | sp-4 | an-202 | E1U1423 | sp-4 | an-202 | E1U8749 | sp-30 | an-202 |
| E1A1424 | sp-4 | an-203 | E1U1424 | sp-4 | an-203 | E1U8750 | sp-30 | an-203 |
| E1A1425 | sp-4 | an-204 | E1U1425 | sp-4 | an-204 | E1U8751 | sp-30 | an-204 |
| E1A1426 | sp-4 | an-205 | E1U1426 | sp-4 | an-205 | E1U8752 | sp-30 | an-205 |
| E1A1427 | sp-4 | an-206 | E1U1427 | sp-4 | an-206 | E1U8753 | sp-30 | an-206 |
| E1A1428 | sp-4 | an-207 | E1U1428 | sp-4 | an-207 | E1U8754 | sp-30 | an-207 |
| E1A1429 | sp-4 | an-208 | E1U1429 | sp-4 | an-208 | E1U8755 | sp-30 | an-208 |
| E1A1430 | sp-4 | an-209 | E1U1430 | sp-4 | an-209 | E1U8756 | sp-30 | an-209 |
| E1A1431 | sp-4 | an-210 | E1U1431 | sp-4 | an-210 | E1U8757 | sp-30 | an-210 |
| E1A1432 | sp-4 | an-211 | E1U1432 | sp-4 | an-211 | E1U8758 | sp-30 | an-211 |
| E1A1433 | sp-4 | an-212 | E1U1433 | sp-4 | an-212 | E1U8759 | sp-30 | an-212 |
| E1A1434 | sp-4 | an-213 | E1U1434 | sp-4 | an-213 | E1U8760 | sp-30 | an-213 |
| E1A1435 | sp-4 | an-214 | E1U1435 | sp-4 | an-214 | E1U8761 | sp-30 | an-214 |
| E1A1436 | sp-4 | an-215 | E1U1436 | sp-4 | an-215 | E1U8762 | sp-30 | an-215 |
| E1A1437 | sp-4 | an-216 | E1U1437 | sp-4 | an-216 | E1U8763 | sp-30 | an-216 |
| E1A1438 | sp-4 | an-217 | E1U1438 | sp-4 | an-217 | E1U8764 | sp-30 | an-217 |
| E1A1439 | sp-4 | an-218 | E1U1439 | sp-4 | an-218 | E1U8765 | sp-30 | an-218 |
| E1A1440 | sp-4 | an-219 | E1U1440 | sp-4 | an-219 | E1U8766 | sp-30 | an-219 |
| E1A1441 | sp-4 | an-220 | E1U1441 | sp-4 | an-220 | E1U8767 | sp-30 | an-220 |
| E1A1442 | sp-4 | an-221 | E1U1442 | sp-4 | an-221 | E1U8768 | sp-30 | an-221 |
| E1A1443 | sp-4 | an-222 | E1U1443 | sp-4 | an-222 | E1U8769 | sp-30 | an-222 |
| E1A1444 | sp-4 | an-223 | E1U1444 | sp-4 | an-223 | E1U8770 | sp-30 | an-223 |
| E1A1445 | sp-4 | an-224 | E1U1445 | sp-4 | an-224 | E1U8771 | sp-30 | an-224 |
| E1A1446 | sp-4 | an-225 | E1U1446 | sp-4 | an-225 | E1U8772 | sp-30 | an-225 |
| E1A1447 | sp-4 | an-226 | E1U1447 | sp-4 | an-226 | E1U8773 | sp-30 | an-226 |
| E1A1448 | sp-4 | an-227 | E1U1448 | sp-4 | an-227 | E1U8774 | sp-30 | an-227 |
| E1A1449 | sp-4 | an-228 | E1U1449 | sp-4 | an-228 | E1U8775 | sp-30 | an-228 |
| E1A1450 | sp-4 | an-229 | E1U1450 | sp-4 | an-229 | E1U8776 | sp-30 | an-229 |
| E1A1451 | sp-4 | an-230 | E1U1451 | sp-4 | an-230 | E1U8777 | sp-30 | an-230 |
| E1A1452 | sp-4 | an-231 | E1U1452 | sp-4 | an-231 | E1U8778 | sp-30 | an-231 |
| E1A1453 | sp-4 | an-232 | E1U1453 | sp-4 | an-232 | E1U8779 | sp-30 | an-232 |
| E1A1454 | sp-4 | an-233 | E1U1454 | sp-4 | an-233 | E1U8780 | sp-30 | an-233 |
| E1A1455 | sp-4 | an-234 | E1U1455 | sp-4 | an-234 | E1U8781 | sp-30 | an-234 |
| E1A1456 | sp-4 | an-235 | E1U1456 | sp-4 | an-235 | E1U8782 | sp-30 | an-235 |
| E1A1457 | sp-4 | an-236 | E1U1457 | sp-4 | an-236 | E1U8783 | sp-30 | an-236 |
| E1A1458 | sp-4 | an-237 | E1U1458 | sp-4 | an-237 | E1U8784 | sp-30 | an-237 |

-continued

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| Table 1-28 | | | | | | | | |
| Y = NHCS | | | Y = NHCSNH | | | Y = NHCSNH | | |
| E1A1459 | sp-4 | an-238 | E1U1459 | sp-4 | an-238 | E1U8785 | sp-30 | an-238 |
| E1A1460 | sp-4 | an-239 | E1U1460 | sp-4 | an-239 | E1U8786 | sp-30 | an-239 |
| E1A1461 | sp-4 | an-240 | E1U1461 | sp-4 | an-240 | E1U8787 | sp-30 | an-240 |
| E1A1462 | sp-4 | an-241 | E1U1462 | sp-4 | an-241 | E1U8788 | sp-30 | an-241 |
| E1A1463 | sp-4 | an-242 | E1U1463 | sp-4 | an-242 | E1U8789 | sp-30 | an-242 |
| E1A1464 | sp-4 | an-243 | E1U1464 | sp-4 | an-243 | E1U8790 | sp-30 | an-243 |
| E1A1465 | sp-4 | an-244 | E1U1465 | sp-4 | an-244 | E1U8791 | sp-30 | an-244 |
| E1A1466 | sp-4 | an-245 | E1U1466 | sp-4 | an-245 | E1U8792 | sp-30 | an-245 |
| E1A1467 | sp-4 | an-246 | E1U1467 | sp-4 | an-246 | E1U8793 | sp-30 | an-246 |
| E1A1468 | sp-4 | an-247 | E1U1468 | sp-4 | an-247 | E1U8794 | sp-30 | an-247 |
| E1A1469 | sp-4 | an-248 | E1U1469 | sp-4 | an-248 | E1U8795 | sp-30 | an-248 |
| E1A1470 | sp-4 | an-249 | E1U1470 | sp-4 | an-249 | E1U8796 | sp-30 | an-249 |
| E1A1471 | sp-4 | an-250 | E1U1471 | sp-4 | an-250 | E1U8797 | sp-30 | an-250 |
| E1A1472 | sp-4 | an-251 | E1U1472 | sp-4 | an-251 | E1U8798 | sp-30 | an-251 |
| E1A1473 | sp-4 | an-252 | E1U1473 | sp-4 | an-252 | E1U8799 | sp-30 | an-252 |
| E1A1474 | sp-4 | an-253 | E1U1474 | sp-4 | an-253 | E1U8800 | sp-30 | an-253 |
| E1A1475 | sp-4 | an-254 | E1U1475 | sp-4 | an-254 | E1U8801 | sp-30 | an-254 |
| E1A1476 | sp-4 | an-255 | E1U1476 | sp-4 | an-255 | E1U8802 | sp-30 | an-255 |
| E1A1477 | sp-4 | an-256 | E1U1477 | sp-4 | an-256 | E1U8803 | sp-30 | an-256 |
| E1A1478 | sp-4 | an-257 | E1U1478 | sp-4 | an-257 | E1U8804 | sp-30 | an-257 |
| E1A1479 | sp-4 | an-258 | E1U1479 | sp-4 | an-258 | E1U8805 | sp-30 | an-258 |
| E1A1480 | sp-4 | an-259 | E1U1480 | sp-4 | an-259 | E1U8806 | sp-30 | an-259 |
| E1A1481 | sp-4 | an-260 | E1U1481 | sp-4 | an-260 | E1U8807 | sp-30 | an-260 |
| E1A1482 | sp-4 | an-261 | E1U1482 | sp-4 | an-261 | E1U8808 | sp-30 | an-261 |
| E1A1483 | sp-4 | an-262 | E1U1483 | sp-4 | an-262 | E1U8809 | sp-30 | an-262 |
| E1A1484 | sp-4 | an-263 | E1U1484 | sp-4 | an-263 | E1U8810 | sp-30 | an-263 |
| E1A1485 | sp-4 | an-264 | E1U1485 | sp-4 | an-264 | E1U8811 | sp-30 | an-264 |
| E1A1486 | sp-4 | an-265 | E1U1486 | sp-4 | an-265 | E1U8812 | sp-30 | an-265 |
| E1A1487 | sp-4 | an-266 | E1U1487 | sp-4 | an-266 | E1U8813 | sp-30 | an-266 |
| E1A1488 | sp-4 | an-267 | E1U1488 | sp-4 | an-267 | E1U8814 | sp-30 | an-267 |
| E1A1489 | sp-4 | an-268 | E1U1489 | sp-4 | an-268 | E1U8815 | sp-30 | an-268 |
| E1A1490 | sp-4 | an-269 | E1U1490 | sp-4 | an-269 | E1U8816 | sp-30 | an-269 |
| E1A1491 | sp-4 | an-270 | E1U1491 | sp-4 | an-270 | E1U8817 | sp-30 | an-270 |
| E1A1492 | sp-4 | an-271 | E1U1492 | sp-4 | an-271 | E1U8818 | sp-30 | an-271 |
| E1A1493 | sp-4 | an-272 | E1U1493 | sp-4 | an-272 | E1U8819 | sp-30 | an-272 |
| E1A1494 | sp-4 | an-273 | E1U1494 | sp-4 | an-273 | E1U8820 | sp-30 | an-273 |
| E1A1495 | sp-4 | an-274 | E1U1495 | sp-4 | an-274 | E1U8821 | sp-30 | an-274 |
| E1A1496 | sp-4 | an-275 | E1U1496 | sp-4 | an-275 | E1U8822 | sp-30 | an-275 |
| E1A1497 | sp-4 | an-276 | E1U1497 | sp-4 | an-276 | E1U8823 | sp-30 | an-276 |
| E1A1498 | sp-4 | an-277 | E1U1498 | sp-4 | an-277 | E1U8824 | sp-30 | an-277 |
| E1A1499 | sp-4 | an-278 | E1U1499 | sp-4 | an-278 | E1U8825 | sp-30 | an-278 |
| E1A1500 | sp-4 | an-279 | E1U1500 | sp-4 | an-279 | E1U8826 | sp-30 | an-279 |
| E1A1501 | sp-4 | an-280 | E1U1501 | sp-4 | an-280 | E1U8827 | sp-30 | an-280 |
| E1A1502 | sp-4 | an-281 | E1U1502 | sp-4 | an-281 | E1U8828 | sp-30 | an-281 |
| E1A1503 | sp-4 | an-282 | E1U1503 | sp-4 | an-282 | E1U8829 | sp-30 | an-282 |
| E1A1504 | sp-4 | an-283 | E1U1504 | sp-4 | an-283 | E1U8830 | sp-30 | an-283 |
| E1A1505 | sp-4 | an-284 | E1U1505 | sp-4 | an-284 | E1U8831 | sp-30 | an-284 |
| E1A1506 | sp-4 | an-285 | E1U1506 | sp-4 | an-285 | E1U8832 | sp-30 | an-285 |
| E1A1507 | sp-4 | an-286 | E1U1507 | sp-4 | an-286 | E1U8833 | sp-30 | an-286 |
| E1A1508 | sp-4 | an-287 | E1U1508 | sp-4 | an-287 | E1U8834 | sp-30 | an-287 |
| E1A1509 | sp-4 | an-288 | E1U1509 | sp-4 | an-288 | E1U8835 | sp-30 | an-288 |
| E1A1510 | sp-4 | an-289 | E1U1510 | sp-4 | an-289 | E1U8836 | sp-30 | an-289 |
| E1A1511 | sp-4 | an-290 | E1U1511 | sp-4 | an-290 | E1U8837 | sp-30 | an-290 |
| E1A1512 | sp-4 | an-291 | E1U1512 | sp-4 | an-291 | E1U8838 | sp-30 | an-291 |
| Table 1-29 | | | | | | | | |
| Y = NHCS | | | Y = NHCSNH | | | Y = NHCSNH | | |
| E1A1513 | sp-4 | an-292 | E1U1513 | sp-4 | an-292 | E1U8839 | sp-30 | an-292 |
| E1A1514 | sp-4 | an-293 | E1U1514 | sp-4 | an-293 | E1U8840 | sp-30 | an-293 |
| E1A1515 | sp-4 | an-294 | E1U1515 | sp-4 | an-294 | E1U8841 | sp-30 | an-294 |
| E1A1516 | sp-4 | an-295 | E1U1516 | sp-4 | an-295 | E1U8842 | sp-30 | an-295 |
| E1A1517 | sp-4 | an-296 | E1U1517 | sp-4 | an-296 | E1U8843 | sp-30 | an-296 |
| E1A1518 | sp-4 | an-297 | E1U1518 | sp-4 | an-297 | E1U8844 | sp-30 | an-297 |
| E1A1519 | sp-4 | an-298 | E1U1519 | sp-4 | an-298 | E1U8845 | sp-30 | an-298 |
| E1A1520 | sp-4 | an-299 | E1U1520 | sp-4 | an-299 | E1U8846 | sp-30 | an-299 |
| E1A1521 | sp-4 | an-300 | E1U1521 | sp-4 | an-300 | E1U8847 | sp-30 | an-300 |
| E1A1522 | sp-4 | an-301 | E1U1522 | sp-4 | an-301 | E1U8848 | sp-30 | an-301 |
| E1A1523 | sp-4 | an-302 | E1U1523 | sp-4 | an-302 | E1U8849 | sp-30 | an-302 |
| E1A1524 | sp-4 | an-303 | E1U1524 | sp-4 | an-303 | E1U8850 | sp-30 | an-303 |
| E1A1525 | sp-4 | an-304 | E1U1525 | sp-4 | an-304 | E1U8851 | sp-30 | an-304 |
| E1A1526 | sp-4 | an-305 | E1U1526 | sp-4 | an-305 | E1U8852 | sp-30 | an-305 |
| E1A1527 | sp-4 | an-306 | E1U1527 | sp-4 | an-306 | E1U8853 | sp-30 | an-306 |
| E1A1528 | sp-4 | an-307 | E1U1528 | sp-4 | an-307 | E1U8854 | sp-30 | an-307 |

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| E1A1529 | sp-4 | an-308 | E1U1529 | sp-4 | an-308 | E1U8855 | sp-30 | an-308 |
| E1A1530 | sp-4 | an-309 | E1U1530 | sp-4 | an-309 | E1U8856 | sp-30 | an-309 |
| E1A1531 | sp-4 | an-310 | E1U1531 | sp-4 | an-310 | E1U8857 | sp-30 | an-310 |
| E1A1532 | sp-4 | an-311 | E1U1532 | sp-4 | an-311 | E1U8858 | sp-30 | an-311 |
| E1A1533 | sp-4 | an-312 | E1U1533 | sp-4 | an-312 | E1U8859 | sp-30 | an-312 |
| E1A1534 | sp-4 | an-313 | E1U1534 | sp-4 | an-313 | E1U8860 | sp-30 | an-313 |
| E1A1535 | sp-4 | an-314 | E1U1535 | sp-4 | an-314 | E1U8861 | sp-30 | an-314 |
| E1A1536 | sp-4 | an-315 | E1U1536 | sp-4 | an-315 | E1U8862 | sp-30 | an-315 |
| E1A1537 | sp-4 | an-316 | E1U1537 | sp-4 | an-316 | E1U8863 | sp-30 | an-316 |
| E1A1538 | sp-4 | an-317 | E1U1538 | sp-4 | an-317 | E1U8864 | sp-30 | an-317 |
| E1A1539 | sp-4 | an-318 | E1U1539 | sp-4 | an-318 | E1U8865 | sp-30 | an-318 |
| E1A1540 | sp-4 | an-319 | E1U1540 | sp-4 | an-319 | E1U8866 | sp-30 | an-319 |
| E1A1541 | sp-4 | an-320 | E1U1541 | sp-4 | an-320 | E1U8867 | sp-30 | an-320 |
| E1A1542 | sp-4 | an-321 | E1U1542 | sp-4 | an-321 | E1U8868 | sp-30 | an-321 |
| E1A1543 | sp-4 | an-322 | E1U1543 | sp-4 | an-322 | E1U8869 | sp-30 | an-322 |
| E1A1544 | sp-4 | an-323 | E1U1544 | sp-4 | an-323 | E1U8870 | sp-30 | an-323 |
| E1A1545 | sp-4 | an-324 | E1U1545 | sp-4 | an-324 | E1U8871 | sp-30 | an-324 |
| E1A1546 | sp-4 | an-325 | E1U1546 | sp-4 | an-325 | E1U8872 | sp-30 | an-325 |
| E1A1547 | sp-4 | an-326 | E1U1547 | sp-4 | an-326 | E1U8873 | sp-30 | an-326 |
| E1A1548 | sp-4 | an-327 | E1U1548 | sp-4 | an-327 | E1U8874 | sp-30 | an-327 |
| E1A1549 | sp-4 | an-328 | E1U1549 | sp-4 | an-328 | E1U8875 | sp-30 | an-328 |
| E1A1550 | sp-4 | an-329 | E1U1550 | sp-4 | an-329 | E1U8876 | sp-30 | an-329 |
| E1A1551 | sp-4 | an-330 | E1U1551 | sp-4 | an-330 | E1U8877 | sp-30 | an-330 |
| E1A1552 | sp-4 | an-331 | E1U1552 | sp-4 | an-331 | E1U8878 | sp-30 | an-331 |
| E1A1553 | sp-4 | an-332 | E1U1553 | sp-4 | an-332 | E1U8879 | sp-30 | an-332 |
| E1A1554 | sp-4 | an-333 | E1U1554 | sp-4 | an-333 | E1U8880 | sp-30 | an-333 |
| E1A1555 | sp-4 | an-334 | E1U1555 | sp-4 | an-334 | E1U8881 | sp-30 | an-334 |
| E1A1556 | sp-4 | an-335 | E1U1556 | sp-4 | an-335 | E1U8882 | sp-30 | an-335 |
| E1A1557 | sp-4 | an-336 | E1U1557 | sp-4 | an-336 | E1U8883 | sp-30 | an-336 |
| E1A1558 | sp-4 | an-337 | E1U1558 | sp-4 | an-337 | E1U8884 | sp-30 | an-337 |
| E1A1559 | sp-4 | an-338 | E1U1559 | sp-4 | an-338 | E1U8885 | sp-30 | an-338 |
| E1A1560 | sp-4 | an-339 | E1U1560 | sp-4 | an-339 | E1U8886 | sp-30 | an-339 |
| E1A1561 | sp-4 | an-340 | E1U1561 | sp-4 | an-340 | E1U8887 | sp-30 | an-340 |
| E1A1562 | sp-4 | an-341 | E1U1562 | sp-4 | an-341 | E1U8888 | sp-30 | an-341 |
| E1A1563 | sp-4 | an-342 | E1U1563 | sp-4 | an-342 | E1U8889 | sp-30 | an-342 |
| E1A1564 | sp-4 | an-343 | E1U1564 | sp-4 | an-343 | E1U8890 | sp-30 | an-343 |
| E1A1565 | sp-4 | an-344 | E1U1565 | sp-4 | an-344 | E1U8891 | sp-30 | an-344 |
| E1A1566 | sp-4 | an-345 | E1U1566 | sp-4 | an-345 | E1U8892 | sp-30 | an-345 |

Table 1-30

| Y = NHCS | | | Y = NHCSNH | | | Y = NHCSNH | | |
|---|---|---|---|---|---|---|---|---|
| E1A1567 | sp-4 | an-346 | E1U1567 | sp-4 | an-346 | E1U8893 | sp-30 | an-346 |
| E1A1568 | sp-4 | an-347 | E1U1568 | sp-4 | an-347 | E1U8894 | sp-30 | an-347 |
| E1A1569 | sp-4 | an-348 | E1U1569 | sp-4 | an-348 | E1U8895 | sp-30 | an-348 |
| E1A1570 | sp-4 | an-349 | E1U1570 | sp-4 | an-349 | E1U8896 | sp-30 | an-349 |
| E1A1571 | sp-4 | an-350 | E1U1571 | sp-4 | an-350 | E1U8897 | sp-30 | an-350 |
| E1A1572 | sp-4 | an-351 | E1U1572 | sp-4 | an-351 | E1U8898 | sp-30 | an-351 |
| E1A1573 | sp-4 | an-352 | E1U1573 | sp-4 | an-352 | E1U8899 | sp-30 | an-352 |
| E1A1574 | sp-4 | an-353 | E1U1574 | sp-4 | an-353 | E1U8900 | sp-30 | an-353 |
| E1A1575 | sp-4 | an-354 | E1U1575 | sp-4 | an-354 | E1U8901 | sp-30 | an-354 |
| E1A1576 | sp-4 | an-355 | E1U1576 | sp-4 | an-355 | E1U8902 | sp-30 | an-355 |
| E1A1577 | sp-4 | an-356 | E1U1577 | sp-4 | an-356 | E1U8903 | sp-30 | an-356 |
| E1A1578 | sp-4 | an-357 | E1U1578 | sp-4 | an-357 | E1U8904 | sp-30 | an-357 |
| E1A1579 | sp-4 | an-358 | E1U1579 | sp-4 | an-358 | E1U8905 | sp-30 | an-358 |
| E1A1580 | sp-4 | an-359 | E1U1580 | sp-4 | an-359 | E1U8906 | sp-30 | an-359 |
| E1A1581 | sp-4 | an-360 | E1U1581 | sp-4 | an-360 | E1U8907 | sp-30 | an-360 |
| E1A1582 | sp-4 | an-361 | E1U1582 | sp-4 | an-361 | E1U8908 | sp-30 | an-361 |
| E1A1583 | sp-4 | an-362 | E1U1583 | sp-4 | an-362 | E1U8909 | sp-30 | an-362 |
| E1A1584 | sp-4 | an-363 | E1U1584 | sp-4 | an-363 | E1U8910 | sp-30 | an-363 |
| E1A1585 | sp-4 | an-364 | E1U1585 | sp-4 | an-364 | E1U8911 | sp-30 | an-364 |
| E1A1586 | sp-4 | an-365 | E1U1586 | sp-4 | an-365 | E1U8912 | sp-30 | an-365 |
| E1A1587 | sp-4 | an-366 | E1U1587 | sp-4 | an-366 | E1U8913 | sp-30 | an-366 |
| E1A1588 | sp-4 | an-367 | E1U1588 | sp-4 | an-367 | E1U8914 | sp-30 | an-367 |
| E1A1589 | sp-4 | an-368 | E1U1589 | sp-4 | an-368 | E1U8915 | sp-30 | an-368 |
| E1A1590 | sp-4 | an-369 | E1U1590 | sp-4 | an-369 | E1U8916 | sp-30 | an-369 |
| E1A1591 | sp-4 | an-370 | E1U1591 | sp-4 | an-370 | E1U8917 | sp-30 | an-370 |
| E1A1592 | sp-4 | an-371 | E1U1592 | sp-4 | an-371 | E1U8918 | sp-30 | an-371 |
| E1A1593 | sp-4 | an-372 | E1U1593 | sp-4 | an-372 | E1U8919 | sp-30 | an-372 |
| E1A1594 | sp-4 | an-373 | E1U1594 | sp-4 | an-373 | E1U8920 | sp-30 | an-373 |
| E1A1595 | sp-4 | an-374 | E1U1595 | sp-4 | an-374 | E1U8921 | sp-30 | an-374 |
| E1A1596 | sp-4 | an-375 | E1U1596 | sp-4 | an-375 | E1U8922 | sp-30 | an-375 |
| E1A1597 | sp-4 | an-376 | E1U1597 | sp-4 | an-376 | E1U8923 | sp-30 | an-376 |
| E1A1598 | sp-4 | an-377 | E1U1598 | sp-4 | an-377 | E1U8924 | sp-30 | an-377 |
| E1A1599 | sp-4 | an-378 | E1U1599 | sp-4 | an-378 | E1U8925 | sp-30 | an-378 |
| E1A1600 | sp-4 | an-379 | E1U1600 | sp-4 | an-379 | E1U8926 | sp-30 | an-379 |
| E1A1601 | sp-4 | an-380 | E1U1601 | sp-4 | an-380 | E1U8927 | sp-30 | an-380 |
| E1A1602 | sp-4 | an-381 | E1U1602 | sp-4 | an-381 | E1U8928 | sp-30 | an-381 |

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| E1A1603 | sp-4 | an-382 | E1U1603 | sp-4 | an-382 | E1U8929 | sp-30 | an-382 |
| E1A1604 | sp-4 | an-383 | E1U1604 | sp-4 | an-383 | E1U8930 | sp-30 | an-383 |
| E1A1605 | sp-4 | an-384 | E1U1605 | sp-4 | an-384 | E1U8931 | sp-30 | an-384 |
| E1A1606 | sp-4 | an-385 | E1U1606 | sp-4 | an-385 | E1U8932 | sp-30 | an-385 |
| E1A1607 | sp-4 | an-386 | E1U1607 | sp-4 | an-386 | E1U8933 | sp-30 | an-386 |
| E1A1608 | sp-4 | an-387 | E1U1608 | sp-4 | an-387 | E1U8934 | sp-30 | an-387 |
| E1A1609 | sp-4 | an-388 | E1U1609 | sp-4 | an-388 | E1U8935 | sp-30 | an-388 |
| E1A1610 | sp-4 | an-389 | E1U1610 | sp-4 | an-389 | E1U8936 | sp-30 | an-389 |
| E1A1611 | sp-4 | an-390 | E1U1611 | sp-4 | an-390 | E1U8937 | sp-30 | an-390 |
| E1A1612 | sp-4 | an-391 | E1U1612 | sp-4 | an-391 | E1U8938 | sp-30 | an-391 |
| E1A1613 | sp-4 | an-392 | E1U1613 | sp-4 | an-392 | E1U8939 | sp-30 | an-392 |
| E1A1614 | sp-4 | an-393 | E1U1614 | sp-4 | an-393 | E1U8940 | sp-30 | an-393 |
| E1A1615 | sp-4 | an-394 | E1U1615 | sp-4 | an-394 | E1U8941 | sp-30 | an-394 |
| E1A1616 | sp-4 | an-395 | E1U1616 | sp-4 | an-395 | E1U8942 | sp-30 | an-395 |
| E1A1617 | sp-4 | an-396 | E1U1617 | sp-4 | an-396 | E1U8943 | sp-30 | an-396 |
| E1A1618 | sp-4 | an-397 | E1U1618 | sp-4 | an-397 | E1U8944 | sp-30 | an-397 |
| E1A1619 | sp-4 | an-398 | E1U1619 | sp-4 | an-398 | E1U8945 | sp-30 | an-398 |
| E1A1620 | sp-4 | an-399 | E1U1620 | sp-4 | an-399 | E1U8946 | sp-30 | an-399 |

Table 1-31

| Y = NHCS | | | Y = NHCSNH | | | Y = NHCSNH | | |
|---|---|---|---|---|---|---|---|---|
| E1A1621 | sp-4 | an-400 | E1U1621 | sp-4 | an-400 | E1U8947 | sp-30 | an-400 |
| E1A1622 | sp-4 | an-401 | E1U1622 | sp-4 | an-401 | E1U8948 | sp-30 | an-401 |
| E1A1623 | sp-4 | an-402 | E1U1623 | sp-4 | an-402 | E1U8949 | sp-30 | an-402 |
| E1A1624 | sp-4 | an-403 | E1U1624 | sp-4 | an-403 | E1U8950 | sp-30 | an-403 |
| E1A1625 | sp-4 | an-404 | E1U1625 | sp-4 | an-404 | E1U8951 | sp-30 | an-404 |
| E1A1626 | sp-4 | an-405 | E1U1626 | sp-4 | an-405 | E1U8952 | sp-30 | an-405 |
| E1A1627 | sp-4 | an-406 | E1U1627 | sp-4 | an-406 | E1U8953 | sp-30 | an-406 |
| E1A1628 | sp-4 | an-407 | E1U1628 | sp-4 | an-407 | E1U8954 | sp-30 | an-407 |
| E1A1629 | sp-5 | an-1 | E1U1629 | sp-5 | an-1 | E1U8955 | sp-31 | an-1 |
| E1A1630 | sp-5 | an-2 | E1U1630 | sp-5 | an-2 | E1U8956 | sp-31 | an-2 |
| E1A1631 | sp-5 | an-3 | E1U1631 | sp-5 | an-3 | E1U8957 | sp-31 | an-3 |
| E1A1632 | sp-5 | an-4 | E1U1632 | sp-5 | an-4 | E1U8958 | sp-31 | an-4 |
| E1A1633 | sp-5 | an-5 | E1U1633 | sp-5 | an-5 | E1U8959 | sp-31 | an-5 |
| E1A1634 | sp-5 | an-6 | E1U1634 | sp-5 | an-6 | E1U8960 | sp-31 | an-6 |
| E1A1635 | sp-5 | an-7 | E1U1635 | sp-5 | an-7 | E1U8961 | sp-31 | an-7 |
| E1A1636 | sp-5 | an-8 | E1U1636 | sp-5 | an-8 | E1U8962 | sp-31 | an-8 |
| E1A1637 | sp-5 | an-9 | E1U1637 | sp-5 | an-9 | E1U8963 | sp-31 | an-9 |
| E1A1638 | sp-5 | an-10 | E1U1638 | sp-5 | an-10 | E1U8964 | sp-31 | an-10 |
| E1A1639 | sp-5 | an-11 | E1U1639 | sp-5 | an-11 | E1U8965 | sp-31 | an-11 |
| E1A1640 | sp-5 | an-12 | E1U1640 | sp-5 | an-12 | E1U8966 | sp-31 | an-12 |
| E1A1641 | sp-5 | an-13 | E1U1641 | sp-5 | an-13 | E1U8967 | sp-31 | an-13 |
| E1A1642 | sp-5 | an-14 | E1U1642 | sp-5 | an-14 | E1U8968 | sp-31 | an-14 |
| E1A1643 | sp-5 | an-15 | E1U1643 | sp-5 | an-15 | E1U8969 | sp-31 | an-15 |
| E1A1644 | sp-5 | an-16 | E1U1644 | sp-5 | an-16 | E1U8970 | sp-31 | an-16 |
| E1A1645 | sp-5 | an-17 | E1U1645 | sp-5 | an-17 | E1U8971 | sp-31 | an-17 |
| E1A1646 | sp-5 | an-18 | E1U1646 | sp-5 | an-18 | E1U8972 | sp-31 | an-18 |
| E1A1647 | sp-5 | an-19 | E1U1647 | sp-5 | an-19 | E1U8973 | sp-31 | an-19 |
| E1A1648 | sp-5 | an-20 | E1U1648 | sp-5 | an-20 | E1U8974 | sp-31 | an-20 |
| E1A1649 | sp-5 | an-21 | E1U1649 | sp-5 | an-21 | E1U8975 | sp-31 | an-21 |
| E1A1650 | sp-5 | an-22 | E1U1650 | sp-5 | an-22 | E1U8976 | sp-31 | an-22 |
| E1A1651 | sp-5 | an-23 | E1U1651 | sp-5 | an-23 | E1U8977 | sp-31 | an-23 |
| E1A1652 | sp-5 | an-24 | E1U1652 | sp-5 | an-24 | E1U8978 | sp-31 | an-24 |
| E1A1653 | sp-5 | an-25 | E1U1653 | sp-5 | an-25 | E1U8979 | sp-31 | an-25 |
| E1A1654 | sp-5 | an-26 | E1U1654 | sp-5 | an-26 | E1U8980 | sp-31 | an-26 |
| E1A1655 | sp-5 | an-27 | E1U1655 | sp-5 | an-27 | E1U8981 | sp-31 | an-27 |
| E1A1656 | sp-5 | an-28 | E1U1656 | sp-5 | an-28 | E1U8982 | sp-31 | an-28 |
| E1A1657 | sp-5 | an-29 | E1U1657 | sp-5 | an-29 | E1U8983 | sp-31 | an-29 |
| E1A1658 | sp-5 | an-30 | E1U1658 | sp-5 | an-30 | E1U8984 | sp-31 | an-30 |
| E1A1659 | sp-5 | an-31 | E1U1659 | sp-5 | an-31 | E1U8985 | sp-31 | an-31 |
| E1A1660 | sp-5 | an-32 | E1U1660 | sp-5 | an-32 | E1U8986 | sp-31 | an-32 |
| E1A1661 | sp-5 | an-33 | E1U1661 | sp-5 | an-33 | E1U8987 | sp-31 | an-33 |
| E1A1662 | sp-5 | an-34 | E1U1662 | sp-5 | an-34 | E1U8988 | sp-31 | an-34 |
| E1A1663 | sp-5 | an-35 | E1U1663 | sp-5 | an-35 | E1U8989 | sp-31 | an-35 |
| E1A1664 | sp-5 | an-36 | E1U1664 | sp-5 | an-36 | E1U8990 | sp-31 | an-36 |
| E1A1665 | sp-5 | an-37 | E1U1665 | sp-5 | an-37 | E1U8991 | sp-31 | an-37 |
| E1A1666 | sp-5 | an-38 | E1U1666 | sp-5 | an-38 | E1U8992 | sp-31 | an-38 |
| E1A1667 | sp-5 | an-39 | E1U1667 | sp-5 | an-39 | E1U8993 | sp-31 | an-39 |
| E1A1668 | sp-5 | an-40 | E1U1668 | sp-5 | an-40 | E1U8994 | sp-31 | an-40 |
| E1A1669 | sp-5 | an-41 | E1U1669 | sp-5 | an-41 | E1U8995 | sp-31 | an-41 |
| E1A1670 | sp-5 | an-42 | E1U1670 | sp-5 | an-42 | E1U8996 | sp-31 | an-42 |
| E1A1671 | sp-5 | an-43 | E1U1671 | sp-5 | an-43 | E1U8997 | sp-31 | an-43 |
| E1A1672 | sp-5 | an-44 | E1U1672 | sp-5 | an-44 | E1U8998 | sp-31 | an-44 |
| E1A1673 | sp-5 | an-45 | E1U1673 | sp-5 | an-45 | E1U8999 | sp-31 | an-45 |
| E1A1674 | sp-5 | an-46 | E1U1674 | sp-5 | an-46 | E1U9000 | sp-31 | an-46 |

Table 1-32

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| Y = NHCS | | | Y = NHCSNH | | | Y = NHCSNH | | |
| E1A1675 | sp-5 | an-47 | E1U1675 | sp-5 | an-47 | E1U9001 | sp-31 | an-47 |
| E1A1676 | sp-5 | an-48 | E1U1676 | sp-5 | an-48 | E1U9002 | sp-31 | an-48 |
| E1A1677 | sp-5 | an-49 | E1U1677 | sp-5 | an-49 | E1U9003 | sp-31 | an-49 |
| E1A1678 | sp-5 | an-50 | E1U1678 | sp-5 | an-50 | E1U9004 | sp-31 | an-50 |
| E1A1679 | sp-5 | an-51 | E1U1679 | sp-5 | an-51 | E1U9005 | sp-31 | an-51 |
| E1A1680 | sp-5 | an-52 | E1U1680 | sp-5 | an-52 | E1U9006 | sp-31 | an-52 |
| E1A1681 | sp-5 | an-53 | E1U1681 | sp-5 | an-53 | E1U9007 | sp-31 | an-53 |
| E1A1682 | sp-5 | an-54 | E1U1682 | sp-5 | an-54 | E1U9008 | sp-31 | an-54 |
| E1A1683 | sp-5 | an-55 | E1U1683 | sp-5 | an-55 | E1U9009 | sp-31 | an-55 |
| E1A1684 | sp-5 | an-56 | E1U1684 | sp-5 | an-56 | E1U9010 | sp-31 | an-56 |
| E1A1685 | sp-5 | an-57 | E1U1685 | sp-5 | an-57 | E1U9011 | sp-31 | an-57 |
| E1A1686 | sp-5 | an-58 | E1U1686 | sp-5 | an-58 | E1U9012 | sp-31 | an-58 |
| E1A1687 | sp-5 | an-59 | E1U1687 | sp-5 | an-59 | E1U9013 | sp-31 | an-59 |
| E1A1688 | sp-5 | an-60 | E1U1688 | sp-5 | an-60 | E1U9014 | sp-31 | an-60 |
| E1A1689 | sp-5 | an-61 | E1U1689 | sp-5 | an-61 | E1U9015 | sp-31 | an-61 |
| E1A1690 | sp-5 | an-62 | E1U1690 | sp-5 | an-62 | E1U9016 | sp-31 | an-62 |
| E1A1691 | sp-5 | an-63 | E1U1691 | sp-5 | an-63 | E1U9017 | sp-31 | an-63 |
| E1A1692 | sp-5 | an-64 | E1U1692 | sp-5 | an-64 | E1U9018 | sp-31 | an-64 |
| E1A1693 | sp-5 | an-65 | E1U1693 | sp-5 | an-65 | E1U9019 | sp-31 | an-65 |
| E1A1694 | sp-5 | an-66 | E1U1694 | sp-5 | an-66 | E1U9020 | sp-31 | an-66 |
| E1A1695 | sp-5 | an-67 | E1U1695 | sp-5 | an-67 | E1U9021 | sp-31 | an-67 |
| E1A1696 | sp-5 | an-68 | E1U1696 | sp-5 | an-68 | E1U9022 | sp-31 | an-68 |
| E1A1697 | sp-5 | an-69 | E1U1697 | sp-5 | an-69 | E1U9023 | sp-31 | an-69 |
| E1A1698 | sp-5 | an-70 | E1U1698 | sp-5 | an-70 | E1U9024 | sp-31 | an-70 |
| E1A1699 | sp-5 | an-71 | E1U1699 | sp-5 | an-71 | E1U9025 | sp-31 | an-71 |
| E1A1700 | sp-5 | an-72 | E1U1700 | sp-5 | an-72 | E1U9026 | sp-31 | an-72 |
| E1A1701 | sp-5 | an-73 | E1U1701 | sp-5 | an-73 | E1U9027 | sp-31 | an-73 |
| E1A1702 | sp-5 | an-74 | E1U1702 | sp-5 | an-74 | E1U9028 | sp-31 | an-74 |
| E1A1703 | sp-5 | an-75 | E1U1703 | sp-5 | an-75 | E1U9029 | sp-31 | an-75 |
| E1A1704 | sp-5 | an-76 | E1U1704 | sp-5 | an-76 | E1U9030 | sp-31 | an-76 |
| E1A1705 | sp-5 | an-77 | E1U1705 | sp-5 | an-77 | E1U9031 | sp-31 | an-77 |
| E1A1706 | sp-5 | an-78 | E1U1706 | sp-5 | an-78 | E1U9032 | sp-31 | an-78 |
| E1A1707 | sp-5 | an-79 | E1U1707 | sp-5 | an-79 | E1U9033 | sp-31 | an-79 |
| E1A1708 | sp-5 | an-80 | E1U1708 | sp-5 | an-80 | E1U9034 | sp-31 | an-80 |
| E1A1709 | sp-5 | an-81 | E1U1709 | sp-5 | an-81 | E1U9035 | sp-31 | an-81 |
| E1A1710 | sp-5 | an-82 | E1U1710 | sp-5 | an-82 | E1U9036 | sp-31 | an-82 |
| E1A1711 | sp-5 | an-83 | E1U1711 | sp-5 | an-83 | E1U9037 | sp-31 | an-83 |
| E1A1712 | sp-5 | an-84 | E1U1712 | sp-5 | an-84 | E1U9038 | sp-31 | an-84 |
| E1A1713 | sp-5 | an-85 | E1U1713 | sp-5 | an-85 | E1U9039 | sp-31 | an-85 |
| E1A1714 | sp-5 | an-86 | E1U1714 | sp-5 | an-86 | E1U9040 | sp-31 | an-86 |
| E1A1715 | sp-5 | an-87 | E1U1715 | sp-5 | an-87 | E1U9041 | sp-31 | an-87 |
| E1A1716 | sp-5 | an-88 | E1U1716 | sp-5 | an-88 | E1U9042 | sp-31 | an-88 |
| E1A1717 | sp-5 | an-89 | E1U1717 | sp-5 | an-89 | E1U9043 | sp-31 | an-89 |
| E1A1718 | sp-5 | an-90 | E1U1718 | sp-5 | an-90 | E1U9044 | sp-31 | an-90 |
| E1A1719 | sp-5 | an-91 | E1U1719 | sp-5 | an-91 | E1U9045 | sp-31 | an-91 |
| E1A1720 | sp-5 | an-92 | E1U1720 | sp-5 | an-92 | E1U9046 | sp-31 | an-92 |
| E1A1721 | sp-5 | an-93 | E1U1721 | sp-5 | an-93 | E1U9047 | sp-31 | an-93 |
| E1A1722 | sp-5 | an-94 | E1U1722 | sp-5 | an-94 | E1U9048 | sp-31 | an-94 |
| E1A1723 | sp-5 | an-95 | E1U1723 | sp-5 | an-95 | E1U9049 | sp-31 | an-95 |
| E1A1724 | sp-5 | an-96 | E1U1724 | sp-5 | an-96 | E1U9050 | sp-31 | an-96 |
| E1A1725 | sp-5 | an-97 | E1U1725 | sp-5 | an-97 | E1U9051 | sp-31 | an-97 |
| E1A1726 | sp-5 | an-98 | E1U1726 | sp-5 | an-98 | E1U9052 | sp-31 | an-98 |
| E1A1727 | sp-5 | an-99 | E1U1727 | sp-5 | an-99 | E1U9053 | sp-31 | an-99 |
| E1A1728 | sp-5 | an-100 | E1U1728 | sp-5 | an-100 | E1U9054 | sp-31 | an-100 |

Table 1-33

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| Y = NHCS | | | Y = NHCSNH | | | Y = NHCSNH | | |
| E1A1729 | sp-5 | an-101 | E1U1729 | sp-5 | an-101 | E1U9055 | sp-31 | an-101 |
| E1A1730 | sp-5 | an-102 | E1U1730 | sp-5 | an-102 | E1U9056 | sp-31 | an-102 |
| E1A1731 | sp-5 | an-103 | E1U1731 | sp-5 | an-103 | E1U9057 | sp-31 | an-103 |
| E1A1732 | sp-5 | an-104 | E1U1732 | sp-5 | an-104 | E1U9058 | sp-31 | an-104 |
| E1A1733 | sp-5 | an-105 | E1U1733 | sp-5 | an-105 | E1U9059 | sp-31 | an-105 |
| E1A1734 | sp-5 | an-106 | E1U1734 | sp-5 | an-106 | E1U9060 | sp-31 | an-106 |
| E1A1735 | sp-5 | an-107 | E1U1735 | sp-5 | an-107 | E1U9061 | sp-31 | an-107 |
| E1A1736 | sp-5 | an-108 | E1U1736 | sp-5 | an-108 | E1U9062 | sp-31 | an-108 |
| E1A1737 | sp-5 | an-109 | E1U1737 | sp-5 | an-109 | E1U9063 | sp-31 | an-109 |
| E1A1738 | sp-5 | an-110 | E1U1738 | sp-5 | an-110 | E1U9064 | sp-31 | an-110 |
| E1A1739 | sp-5 | an-111 | E1U1739 | sp-5 | an-111 | E1U9065 | sp-31 | an-111 |
| E1A1740 | sp-5 | an-112 | E1U1740 | sp-5 | an-112 | E1U9066 | sp-31 | an-112 |
| E1A1741 | sp-5 | an-113 | E1U1741 | sp-5 | an-113 | E1U9067 | sp-31 | an-113 |
| E1A1742 | sp-5 | an-114 | E1U1742 | sp-5 | an-114 | E1U9068 | sp-31 | an-114 |
| E1A1743 | sp-5 | an-115 | E1U1743 | sp-5 | an-115 | E1U9069 | sp-31 | an-115 |
| E1A1744 | sp-5 | an-116 | E1U1744 | sp-5 | an-116 | E1U9070 | sp-31 | an-116 |

-continued

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| E1A1745 | sp-5 | an-117 | E1U1745 | sp-5 | an-117 | E1U9071 | sp-31 | an-117 |
| E1A1746 | sp-5 | an-118 | E1U1746 | sp-5 | an-118 | E1U9072 | sp-31 | an-118 |
| E1A1747 | sp-5 | an-119 | E1U1747 | sp-5 | an-119 | E1U9073 | sp-31 | an-119 |
| E1A1748 | sp-5 | an-120 | E1U1748 | sp-5 | an-120 | E1U9074 | sp-31 | an-120 |
| E1A1749 | sp-5 | an-121 | E1U1749 | sp-5 | an-121 | E1U9075 | sp-31 | an-121 |
| E1A1750 | sp-5 | an-122 | E1U1750 | sp-5 | an-122 | E1U9076 | sp-31 | an-122 |
| E1A1751 | sp-5 | an-123 | E1U1751 | sp-5 | an-123 | E1U9077 | sp-31 | an-123 |
| E1A1752 | sp-5 | an-124 | E1U1752 | sp-5 | an-124 | E1U9078 | sp-31 | an-124 |
| E1A1753 | sp-5 | an-125 | E1U1753 | sp-5 | an-125 | E1U9079 | sp-31 | an-125 |
| E1A1754 | sp-5 | an-126 | E1U1754 | sp-5 | an-126 | E1U9080 | sp-31 | an-126 |
| E1A1755 | sp-5 | an-127 | E1U1755 | sp-5 | an-127 | E1U9081 | sp-31 | an-127 |
| E1A1756 | sp-5 | an-128 | E1U1756 | sp-5 | an-128 | E1U9082 | sp-31 | an-128 |
| E1A1757 | sp-5 | an-129 | E1U1757 | sp-5 | an-129 | E1U9083 | sp-31 | an-129 |
| E1A1758 | sp-5 | an-130 | E1U1758 | sp-5 | an-130 | E1U9084 | sp-31 | an-130 |
| E1A1759 | sp-5 | an-131 | E1U1759 | sp-5 | an-131 | E1U9085 | sp-31 | an-131 |
| E1A1760 | sp-5 | an-132 | E1U1760 | sp-5 | an-132 | E1U9086 | sp-31 | an-132 |
| E1A1761 | sp-5 | an-133 | E1U1761 | sp-5 | an-133 | E1U9087 | sp-31 | an-133 |
| E1A1762 | sp-5 | an-134 | E1U1762 | sp-5 | an-134 | E1U9088 | sp-31 | an-134 |
| E1A1763 | sp-5 | an-135 | E1U1763 | sp-5 | an-135 | E1U9089 | sp-31 | an-135 |
| E1A1764 | sp-5 | an-136 | E1U1764 | sp-5 | an-136 | E1U9090 | sp-31 | an-136 |
| E1A1765 | sp-5 | an-137 | E1U1765 | sp-5 | an-137 | E1U9091 | sp-31 | an-137 |
| E1A1766 | sp-5 | an-138 | E1U1766 | sp-5 | an-138 | E1U9092 | sp-31 | an-138 |
| E1A1767 | sp-5 | an-139 | E1U1767 | sp-5 | an-139 | E1U9093 | sp-31 | an-139 |
| E1A1768 | sp-5 | an-140 | E1U1768 | sp-5 | an-140 | E1U9094 | sp-31 | an-140 |
| E1A1769 | sp-5 | an-141 | E1U1769 | sp-5 | an-141 | E1U9095 | sp-31 | an-141 |
| E1A1770 | sp-5 | an-142 | E1U1770 | sp-5 | an-142 | E1U9096 | sp-31 | an-142 |
| E1A1771 | sp-5 | an-143 | E1U1771 | sp-5 | an-143 | E1U9097 | sp-31 | an-143 |
| E1A1772 | sp-5 | an-144 | E1U1772 | sp-5 | an-144 | E1U9098 | sp-31 | an-144 |
| E1A1773 | sp-5 | an-145 | E1U1773 | sp-5 | an-145 | E1U9099 | sp-31 | an-145 |
| E1A1774 | sp-5 | an-146 | E1U1774 | sp-5 | an-146 | E1U9100 | sp-31 | an-146 |
| E1A1775 | sp-5 | an-147 | E1U1775 | sp-5 | an-147 | E1U9101 | sp-31 | an-147 |
| E1A1776 | sp-5 | an-148 | E1U1776 | sp-5 | an-148 | E1U9102 | sp-31 | an-148 |
| E1A1777 | sp-5 | an-149 | E1U1777 | sp-5 | an-149 | E1U9103 | sp-31 | an-149 |
| E1A1778 | sp-5 | an-150 | E1U1778 | sp-5 | an-150 | E1U9104 | sp-31 | an-150 |
| E1A1779 | sp-5 | an-151 | E1U1779 | sp-5 | an-151 | E1U9105 | sp-31 | an-151 |
| E1A1780 | sp-5 | an-152 | E1U1780 | sp-5 | an-152 | E1U9106 | sp-31 | an-152 |
| E1A1781 | sp-5 | an-153 | E1U1781 | sp-5 | an-153 | E1U9107 | sp-31 | an-153 |
| E1A1782 | sp-5 | an-154 | E1U1782 | sp-5 | an-154 | E1U9108 | sp-31 | an-154 |

Table 1-34

| | Y = NHCS | | | Y = NHCSNH | | | Y = NHCSNH | |
|---|---|---|---|---|---|---|---|---|
| E1A1783 | sp-5 | an-155 | E1U1783 | sp-5 | an-155 | E1U9109 | sp-31 | an-155 |
| E1A1784 | sp-5 | an-156 | E1U1784 | sp-5 | an-156 | E1U9110 | sp-31 | an-156 |
| E1A1785 | sp-5 | an-157 | E1U1785 | sp-5 | an-157 | E1U9111 | sp-31 | an-157 |
| E1A1786 | sp-5 | an-158 | E1U1786 | sp-5 | an-158 | E1U9112 | sp-31 | an-158 |
| E1A1787 | sp-5 | an-159 | E1U1787 | sp-5 | an-159 | E1U9113 | sp-31 | an-159 |
| E1A1788 | sp-5 | an-160 | E1U1788 | sp-5 | an-160 | E1U9114 | sp-31 | an-160 |
| E1A1789 | sp-5 | an-161 | E1U1789 | sp-5 | an-161 | E1U9115 | sp-31 | an-161 |
| E1A1790 | sp-5 | an-162 | E1U1790 | sp-5 | an-162 | E1U9116 | sp-31 | an-162 |
| E1A1791 | sp-5 | an-163 | E1U1791 | sp-5 | an-163 | E1U9117 | sp-31 | an-163 |
| E1A1792 | sp-5 | an-164 | E1U1792 | sp-5 | an-164 | E1U9118 | sp-31 | an-164 |
| E1A1793 | sp-5 | an-165 | E1U1793 | sp-5 | an-165 | E1U9119 | sp-31 | an-165 |
| E1A1794 | sp-5 | an-166 | E1U1794 | sp-5 | an-166 | E1U9120 | sp-31 | an-166 |
| E1A1795 | sp-5 | an-167 | E1U1795 | sp-5 | an-167 | E1U9121 | sp-31 | an-167 |
| E1A1796 | sp-5 | an-168 | E1U1796 | sp-5 | an-168 | E1U9122 | sp-31 | an-168 |
| E1A1797 | sp-5 | an-169 | E1U1797 | sp-5 | an-169 | E1U9123 | sp-31 | an-169 |
| E1A1798 | sp-5 | an-170 | E1U1798 | sp-5 | an-170 | E1U9124 | sp-31 | an-170 |
| E1A1799 | sp-5 | an-171 | E1U1799 | sp-5 | an-171 | E1U9125 | sp-31 | an-171 |
| E1A1800 | sp-5 | an-172 | E1U1800 | sp-5 | an-172 | E1U9126 | sp-31 | an-172 |
| E1A1801 | sp-5 | an-173 | E1U1801 | sp-5 | an-173 | E1U9127 | sp-31 | an-173 |
| E1A1802 | sp-5 | an-174 | E1U1802 | sp-5 | an-174 | E1U9128 | sp-31 | an-174 |
| E1A1803 | sp-5 | an-175 | E1U1803 | sp-5 | an-175 | E1U9129 | sp-31 | an-175 |
| E1A1804 | sp-5 | an-176 | E1U1804 | sp-5 | an-176 | E1U9130 | sp-31 | an-176 |
| E1A1805 | sp-5 | an-177 | E1U1805 | sp-5 | an-177 | E1U9131 | sp-31 | an-177 |
| E1A1806 | sp-5 | an-178 | E1U1806 | sp-5 | an-178 | E1U9132 | sp-31 | an-178 |
| E1A1807 | sp-5 | an-179 | E1U1807 | sp-5 | an-179 | E1U9133 | sp-31 | an-179 |
| E1A1808 | sp-5 | an-180 | E1U1808 | sp-5 | an-180 | E1U9134 | sp-31 | an-180 |
| E1A1809 | sp-5 | an-181 | E1U1809 | sp-5 | an-181 | E1U9135 | sp-31 | an-181 |
| E1A1810 | sp-5 | an-182 | E1U1810 | sp-5 | an-182 | E1U9136 | sp-31 | an-182 |
| E1A1811 | sp-5 | an-183 | E1U1811 | sp-5 | an-183 | E1U9137 | sp-31 | an-183 |
| E1A1812 | sp-5 | an-184 | E1U1812 | sp-5 | an-184 | E1U9138 | sp-31 | an-184 |
| E1A1813 | sp-5 | an-185 | E1U1813 | sp-5 | an-185 | E1U9139 | sp-31 | an-185 |
| E1A1814 | sp-5 | an-186 | E1U1814 | sp-5 | an-186 | E1U9140 | sp-31 | an-186 |
| E1A1815 | sp-5 | an-187 | E1U1815 | sp-5 | an-187 | E1U9141 | sp-31 | an-187 |
| E1A1816 | sp-5 | an-188 | E1U1816 | sp-5 | an-188 | E1U9142 | sp-31 | an-188 |
| E1A1817 | sp-5 | an-189 | E1U1817 | sp-5 | an-189 | E1U9143 | sp-31 | an-189 |
| E1A1818 | sp-5 | an-190 | E1U1818 | sp-5 | an-190 | E1U9144 | sp-31 | an-190 |

-continued

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| E1A1819 | sp-5 | an-191 | E1U1819 | sp-5 | an-191 | E1U9145 | sp-31 | an-191 |
| E1A1820 | sp-5 | an-192 | E1U1820 | sp-5 | an-192 | E1U9146 | sp-31 | an-192 |
| E1A1821 | sp-5 | an-193 | E1U1821 | sp-5 | an-193 | E1U9147 | sp-31 | an-193 |
| E1A1822 | sp-5 | an-194 | E1U1822 | sp-5 | an-194 | E1U9148 | sp-31 | an-194 |
| E1A1823 | sp-5 | an-195 | E1U1823 | sp-5 | an-195 | E1U9149 | sp-31 | an-195 |
| E1A1824 | sp-5 | an-196 | E1U1824 | sp-5 | an-196 | E1U9150 | sp-31 | an-196 |
| E1A1825 | sp-5 | an-197 | E1U1825 | sp-5 | an-197 | E1U9151 | sp-31 | an-197 |
| E1A1826 | sp-5 | an-198 | E1U1826 | sp-5 | an-198 | E1U9152 | sp-31 | an-198 |
| E1A1827 | sp-5 | an-199 | E1U1827 | sp-5 | an-199 | E1U9153 | sp-31 | an-199 |
| E1A1828 | sp-5 | an-200 | E1U1828 | sp-5 | an-200 | E1U9154 | sp-31 | an-200 |
| E1A1829 | sp-5 | an-201 | E1U1829 | sp-5 | an-201 | E1U9155 | sp-31 | an-201 |
| E1A1830 | sp-5 | an-202 | E1U1830 | sp-5 | an-202 | E1U9156 | sp-31 | an-202 |
| E1A1831 | sp-5 | an-203 | E1U1831 | sp-5 | an-203 | E1U9157 | sp-31 | an-203 |
| E1A1832 | sp-5 | an-204 | E1U1832 | sp-5 | an-204 | E1U9158 | sp-31 | an-204 |
| E1A1833 | sp-5 | an-205 | E1U1833 | sp-5 | an-205 | E1U9159 | sp-31 | an-205 |
| E1A1834 | sp-5 | an-206 | E1U1834 | sp-5 | an-206 | E1U9160 | sp-31 | an-206 |
| E1A1835 | sp-5 | an-207 | E1U1835 | sp-5 | an-207 | E1U9161 | sp-31 | an-207 |
| E1A1836 | sp-5 | an-208 | E1U1836 | sp-5 | an-208 | E1U9162 | sp-31 | an-208 |

Table 1-35

| Y = NHCS | | | Y = NHCSNH | | | Y = NHCSNH | | |
|---|---|---|---|---|---|---|---|---|
| E1A1837 | sp-5 | an-209 | E1U1837 | sp-5 | an-209 | E1U9163 | sp-31 | an-209 |
| E1A1838 | sp-5 | an-210 | E1U1838 | sp-5 | an-210 | E1U9164 | sp-31 | an-210 |
| E1A1839 | sp-5 | an-211 | E1U1839 | sp-5 | an-211 | E1U9165 | sp-31 | an-211 |
| E1A1840 | sp-5 | an-212 | E1U1840 | sp-5 | an-212 | E1U9166 | sp-31 | an-212 |
| E1A1841 | sp-5 | an-213 | E1U1841 | sp-5 | an-213 | E1U9167 | sp-31 | an-213 |
| E1A1842 | sp-5 | an-214 | E1U1842 | sp-5 | an-214 | E1U9168 | sp-31 | an-214 |
| E1A1843 | sp-5 | an-215 | E1U1843 | sp-5 | an-215 | E1U9169 | sp-31 | an-215 |
| E1A1844 | sp-5 | an-216 | E1U1844 | sp-5 | an-216 | E1U9170 | sp-31 | an-216 |
| E1A1845 | sp-5 | an-217 | E1U1845 | sp-5 | an-217 | E1U9171 | sp-31 | an-217 |
| E1A1846 | sp-5 | an-218 | E1U1846 | sp-5 | an-218 | E1U9172 | sp-31 | an-218 |
| E1A1847 | sp-5 | an-219 | E1U1847 | sp-5 | an-219 | E1U9173 | sp-31 | an-219 |
| E1A1848 | sp-5 | an-220 | E1U1848 | sp-5 | an-220 | E1U9174 | sp-31 | an-220 |
| E1A1849 | sp-5 | an-221 | E1U1849 | sp-5 | an-221 | E1U9175 | sp-31 | an-221 |
| E1A1850 | sp-5 | an-222 | E1U1850 | sp-5 | an-222 | E1U9176 | sp-31 | an-222 |
| E1A1851 | sp-5 | an-223 | E1U1851 | sp-5 | an-223 | E1U9177 | sp-31 | an-223 |
| E1A1852 | sp-5 | an-224 | E1U1852 | sp-5 | an-224 | E1U9178 | sp-31 | an-224 |
| E1A1853 | sp-5 | an-225 | E1U1853 | sp-5 | an-225 | E1U9179 | sp-31 | an-225 |
| E1A1854 | sp-5 | an-226 | E1U1854 | sp-5 | an-226 | E1U9180 | sp-31 | an-226 |
| E1A1855 | sp-5 | an-227 | E1U1855 | sp-5 | an-227 | E1U9181 | sp-31 | an-227 |
| E1A1856 | sp-5 | an-228 | E1U1856 | sp-5 | an-228 | E1U9182 | sp-31 | an-228 |
| E1A1857 | sp-5 | an-229 | E1U1857 | sp-5 | an-229 | E1U9183 | sp-31 | an-229 |
| E1A1858 | sp-5 | an-230 | E1U1858 | sp-5 | an-230 | E1U9184 | sp-31 | an-230 |
| E1A1859 | sp-5 | an-231 | E1U1859 | sp-5 | an-231 | E1U9185 | sp-31 | an-231 |
| E1A1860 | sp-5 | an-232 | E1U1860 | sp-5 | an-232 | E1U9186 | sp-31 | an-232 |
| E1A1861 | sp-5 | an-233 | E1U1861 | sp-5 | an-233 | E1U9187 | sp-31 | an-233 |
| E1A1862 | sp-5 | an-234 | E1U1862 | sp-5 | an-234 | E1U9188 | sp-31 | an-234 |
| E1A1863 | sp-5 | an-235 | E1U1863 | sp-5 | an-235 | E1U9189 | sp-31 | an-235 |
| E1A1864 | sp-5 | an-236 | E1U1864 | sp-5 | an-236 | E1U9190 | sp-31 | an-236 |
| E1A1865 | sp-5 | an-237 | E1U1865 | sp-5 | an-237 | E1U9191 | sp-31 | an-237 |
| E1A1866 | sp-5 | an-238 | E1U1866 | sp-5 | an-238 | E1U9192 | sp-31 | an-238 |
| E1A1867 | sp-5 | an-239 | E1U1867 | sp-5 | an-239 | E1U9193 | sp-31 | an-239 |
| E1A1868 | sp-5 | an-240 | E1U1868 | sp-5 | an-240 | E1U9194 | sp-31 | an-240 |
| E1A1869 | sp-5 | an-241 | E1U1869 | sp-5 | an-241 | E1U9195 | sp-31 | an-241 |
| E1A1870 | sp-5 | an-242 | E1U1870 | sp-5 | an-242 | E1U9196 | sp-31 | an-242 |
| E1A1871 | sp-5 | an-243 | E1U1871 | sp-5 | an-243 | E1U9197 | sp-31 | an-243 |
| E1A1872 | sp-5 | an-244 | E1U1872 | sp-5 | an-244 | E1U9198 | sp-31 | an-244 |
| E1A1873 | sp-5 | an-245 | E1U1873 | sp-5 | an-245 | E1U9199 | sp-31 | an-245 |
| E1A1874 | sp-5 | an-246 | E1U1874 | sp-5 | an-246 | E1U9200 | sp-31 | an-246 |
| E1A1875 | sp-5 | an-247 | E1U1875 | sp-5 | an-247 | E1U9201 | sp-31 | an-247 |
| E1A1876 | sp-5 | an-248 | E1U1876 | sp-5 | an-248 | E1U9202 | sp-31 | an-248 |
| E1A1877 | sp-5 | an-249 | E1U1877 | sp-5 | an-249 | E1U9203 | sp-31 | an-249 |
| E1A1878 | sp-5 | an-250 | E1U1878 | sp-5 | an-250 | E1U9204 | sp-31 | an-250 |
| E1A1879 | sp-5 | an-251 | E1U1879 | sp-5 | an-251 | E1U9205 | sp-31 | an-251 |
| E1A1880 | sp-5 | an-252 | E1U1880 | sp-5 | an-252 | E1U9206 | sp-31 | an-252 |
| E1A1881 | sp-5 | an-253 | E1U1881 | sp-5 | an-253 | E1U9207 | sp-31 | an-253 |
| E1A1882 | sp-5 | an-254 | E1U1882 | sp-5 | an-254 | E1U9208 | sp-31 | an-254 |
| E1A1883 | sp-5 | an-255 | E1U1883 | sp-5 | an-255 | E1U9209 | sp-31 | an-255 |
| E1A1884 | sp-5 | an-256 | E1U1884 | sp-5 | an-256 | E1U9210 | sp-31 | an-256 |
| E1A1885 | sp-5 | an-257 | E1U1885 | sp-5 | an-257 | E1U9211 | sp-31 | an-257 |
| E1A1886 | sp-5 | an-258 | E1U1886 | sp-5 | an-258 | E1U9212 | sp-31 | an-258 |
| E1A1887 | sp-5 | an-259 | E1U1887 | sp-5 | an-259 | E1U9213 | sp-31 | an-259 |
| E1A1888 | sp-5 | an-260 | E1U1888 | sp-5 | an-260 | E1U9214 | sp-31 | an-260 |
| E1A1889 | sp-5 | an-261 | E1U1889 | sp-5 | an-261 | E1U9215 | sp-31 | an-261 |
| E1A1890 | sp-5 | an-262 | E1U1890 | sp-5 | an-262 | E1U9216 | sp-31 | an-262 |

Table 1-36

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| Y = NHCS | | | Y = NHCSNH | | | Y = NHCSNH | | |
| E1A1891 | sp-5 | an-263 | E1U1891 | sp-5 | an-263 | E1U9217 | sp-31 | an-263 |
| E1A1892 | sp-5 | an-264 | E1U1892 | sp-5 | an-264 | E1U9218 | sp-31 | an-264 |
| E1A1893 | sp-5 | an-265 | E1U1893 | sp-5 | an-265 | E1U9219 | sp-31 | an-265 |
| E1A1894 | sp-5 | an-266 | E1U1894 | sp-5 | an-266 | E1U9220 | sp-31 | an-266 |
| E1A1895 | sp-5 | an-267 | E1U1895 | sp-5 | an-267 | E1U9221 | sp-31 | an-267 |
| E1A1896 | sp-5 | an-268 | E1U1896 | sp-5 | an-268 | E1U9222 | sp-31 | an-268 |
| E1A1897 | sp-5 | an-269 | E1U1897 | sp-5 | an-269 | E1U9223 | sp-31 | an-269 |
| E1A1898 | sp-5 | an-270 | E1U1898 | sp-5 | an-270 | E1U9224 | sp-31 | an-270 |
| E1A1899 | sp-5 | an-271 | E1U1899 | sp-5 | an-271 | E1U9225 | sp-31 | an-271 |
| E1A1900 | sp-5 | an-272 | E1U1900 | sp-5 | an-272 | E1U9226 | sp-31 | an-272 |
| E1A1901 | sp-5 | an-273 | E1U1901 | sp-5 | an-273 | E1U9227 | sp-31 | an-273 |
| E1A1902 | sp-5 | an-274 | E1U1902 | sp-5 | an-274 | E1U9228 | sp-31 | an-274 |
| E1A1903 | sp-5 | an-275 | E1U1903 | sp-5 | an-275 | E1U9229 | sp-31 | an-275 |
| E1A1904 | sp-5 | an-276 | E1U1904 | sp-5 | an-276 | E1U9230 | sp-31 | an-276 |
| E1A1905 | sp-5 | an-277 | E1U1905 | sp-5 | an-277 | E1U9231 | sp-31 | an-277 |
| E1A1906 | sp-5 | an-278 | E1U1906 | sp-5 | an-278 | E1U9232 | sp-31 | an-278 |
| E1A1907 | sp-5 | an-279 | E1U1907 | sp-5 | an-279 | E1U9233 | sp-31 | an-279 |
| E1A1908 | sp-5 | an-280 | E1U1908 | sp-5 | an-280 | E1U9234 | sp-31 | an-280 |
| E1A1909 | sp-5 | an-281 | E1U1909 | sp-5 | an-281 | E1U9235 | sp-31 | an-281 |
| E1A1910 | sp-5 | an-282 | E1U1910 | sp-5 | an-282 | E1U9236 | sp-31 | an-282 |
| E1A1911 | sp-5 | an-283 | E1U1911 | sp-5 | an-283 | E1U9237 | sp-31 | an-283 |
| E1A1912 | sp-5 | an-284 | E1U1912 | sp-5 | an-284 | E1U9238 | sp-31 | an-284 |
| E1A1913 | sp-5 | an-285 | E1U1913 | sp-5 | an-285 | E1U9239 | sp-31 | an-285 |
| E1A1914 | sp-5 | an-286 | E1U1914 | sp-5 | an-286 | E1U9240 | sp-31 | an-286 |
| E1A1915 | sp-5 | an-287 | E1U1915 | sp-5 | an-287 | E1U9241 | sp-31 | an-287 |
| E1A1916 | sp-5 | an-288 | E1U1916 | sp-5 | an-288 | E1U9242 | sp-31 | an-288 |
| E1A1917 | sp-5 | an-289 | E1U1917 | sp-5 | an-289 | E1U9243 | sp-31 | an-289 |
| E1A1918 | sp-5 | an-290 | E1U1918 | sp-5 | an-290 | E1U9244 | sp-31 | an-290 |
| E1A1919 | sp-5 | an-291 | E1U1919 | sp-5 | an-291 | E1U9245 | sp-31 | an-291 |
| E1A1920 | sp-5 | an-292 | E1U1920 | sp-5 | an-292 | E1U9246 | sp-31 | an-292 |
| E1A1921 | sp-5 | an-293 | E1U1921 | sp-5 | an-293 | E1U9247 | sp-31 | an-293 |
| E1A1922 | sp-5 | an-294 | E1U1922 | sp-5 | an-294 | E1U9248 | sp-31 | an-294 |
| E1A1923 | sp-5 | an-295 | E1U1923 | sp-5 | an-295 | E1U9249 | sp-31 | an-295 |
| E1A1924 | sp-5 | an-296 | E1U1924 | sp-5 | an-296 | E1U9250 | sp-31 | an-296 |
| E1A1925 | sp-5 | an-297 | E1U1925 | sp-5 | an-297 | E1U9251 | sp-31 | an-297 |
| E1A1926 | sp-5 | an-298 | E1U1926 | sp-5 | an-298 | E1U9252 | sp-31 | an-298 |
| E1A1927 | sp-5 | an-299 | E1U1927 | sp-5 | an-299 | E1U9253 | sp-31 | an-299 |
| E1A1928 | sp-5 | an-300 | E1U1928 | sp-5 | an-300 | E1U9254 | sp-31 | an-300 |
| E1A1929 | sp-5 | an-301 | E1U1929 | sp-5 | an-301 | E1U9255 | sp-31 | an-301 |
| E1A1930 | sp-5 | an-302 | E1U1930 | sp-5 | an-302 | E1U9256 | sp-31 | an-302 |
| E1A1931 | sp-5 | an-303 | E1U1931 | sp-5 | an-303 | E1U9257 | sp-31 | an-303 |
| E1A1932 | sp-5 | an-304 | E1U1932 | sp-5 | an-304 | E1U9258 | sp-31 | an-304 |
| E1A1933 | sp-5 | an-305 | E1U1933 | sp-5 | an-305 | E1U9259 | sp-31 | an-305 |
| E1A1934 | sp-5 | an-306 | E1U1934 | sp-5 | an-306 | E1U9260 | sp-31 | an-306 |
| E1A1935 | sp-5 | an-307 | E1U1935 | sp-5 | an-307 | E1U9261 | sp-31 | an-307 |
| E1A1936 | sp-5 | an-308 | E1U1936 | sp-5 | an-308 | E1U9262 | sp-31 | an-308 |
| E1A1937 | sp-5 | an-309 | E1U1937 | sp-5 | an-309 | E1U9263 | sp-31 | an-309 |
| E1A1938 | sp-5 | an-310 | E1U1938 | sp-5 | an-310 | E1U9264 | sp-31 | an-310 |
| E1A1939 | sp-5 | an-311 | E1U1939 | sp-5 | an-311 | E1U9265 | sp-31 | an-311 |
| E1A1940 | sp-5 | an-312 | E1U1940 | sp-5 | an-312 | E1U9266 | sp-31 | an-312 |
| E1A1941 | sp-5 | an-313 | E1U1941 | sp-5 | an-313 | E1U9267 | sp-31 | an-313 |
| E1A1942 | sp-5 | an-314 | E1U1942 | sp-5 | an-314 | E1U9268 | sp-31 | an-314 |
| E1A1943 | sp-5 | an-315 | E1U1943 | sp-5 | an-315 | E1U9269 | sp-31 | an-315 |
| E1A1944 | sp-5 | an-316 | E1U1944 | sp-5 | an-316 | E1U9270 | sp-31 | an-316 |

Table 1-37

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| Y = NHCS | | | Y = NHCSNH | | | Y = NHCSNH | | |
| E1A1945 | sp-5 | an-317 | E1U1945 | sp-5 | an-317 | E1U9271 | sp-31 | an-317 |
| E1A1946 | sp-5 | an-318 | E1U1946 | sp-5 | an-318 | E1U9272 | sp-31 | an-318 |
| E1A1947 | sp-5 | an-319 | E1U1947 | sp-5 | an-319 | E1U9273 | sp-31 | an-319 |
| E1A1948 | sp-5 | an-320 | E1U1948 | sp-5 | an-320 | E1U9274 | sp-31 | an-320 |
| E1A1949 | sp-5 | an-321 | E1U1949 | sp-5 | an-321 | E1U9275 | sp-31 | an-321 |
| E1A1950 | sp-5 | an-322 | E1U1950 | sp-5 | an-322 | E1U9276 | sp-31 | an-322 |
| E1A1951 | sp-5 | an-323 | E1U1951 | sp-5 | an-323 | E1U9277 | sp-31 | an-323 |
| E1A1952 | sp-5 | an-324 | E1U1952 | sp-5 | an-324 | E1U9278 | sp-31 | an-324 |
| E1A1953 | sp-5 | an-325 | E1U1953 | sp-5 | an-325 | E1U9279 | sp-31 | an-325 |
| E1A1954 | sp-5 | an-326 | E1U1954 | sp-5 | an-326 | E1U9280 | sp-31 | an-326 |
| E1A1955 | sp-5 | an-327 | E1U1955 | sp-5 | an-327 | E1U9281 | sp-31 | an-327 |
| E1A1956 | sp-5 | an-328 | E1U1956 | sp-5 | an-328 | E1U9282 | sp-31 | an-328 |
| E1A1957 | sp-5 | an-329 | E1U1957 | sp-5 | an-329 | E1U9283 | sp-31 | an-329 |
| E1A1958 | sp-5 | an-330 | E1U1958 | sp-5 | an-330 | E1U9284 | sp-31 | an-330 |
| E1A1959 | sp-5 | an-331 | E1U1959 | sp-5 | an-331 | E1U9285 | sp-31 | an-331 |
| E1A1960 | sp-5 | an-332 | E1U1960 | sp-5 | an-332 | E1U9286 | sp-31 | an-332 |

-continued

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| E1A1961 | sp-5 | an-333 | E1U1961 | sp-5 | an-333 | E1U9287 | sp-31 | an-333 |
| E1A1962 | sp-5 | an-334 | E1U1962 | sp-5 | an-334 | E1U9288 | sp-31 | an-334 |
| E1A1963 | sp-5 | an-335 | E1U1963 | sp-5 | an-335 | E1U9289 | sp-31 | an-335 |
| E1A1964 | sp-5 | an-336 | E1U1964 | sp-5 | an-336 | E1U9290 | sp-31 | an-336 |
| E1A1965 | sp-5 | an-337 | E1U1965 | sp-5 | an-337 | E1U9291 | sp-31 | an-337 |
| E1A1966 | sp-5 | an-338 | E1U1966 | sp-5 | an-338 | E1U9292 | sp-31 | an-338 |
| E1A1967 | sp-5 | an-339 | E1U1967 | sp-5 | an-339 | E1U9293 | sp-31 | an-339 |
| E1A1968 | sp-5 | an-340 | E1U1968 | sp-5 | an-340 | E1U9294 | sp-31 | an-340 |
| E1A1969 | sp-5 | an-341 | E1U1969 | sp-5 | an-341 | E1U9295 | sp-31 | an-341 |
| E1A1970 | sp-5 | an-342 | E1U1970 | sp-5 | an-342 | E1U9296 | sp-31 | an-342 |
| E1A1971 | sp-5 | an-343 | E1U1971 | sp-5 | an-343 | E1U9297 | sp-31 | an-343 |
| E1A1972 | sp-5 | an-344 | E1U1972 | sp-5 | an-344 | E1U9298 | sp-31 | an-344 |
| E1A1973 | sp-5 | an-345 | E1U1973 | sp-5 | an-345 | E1U9299 | sp-31 | an-345 |
| E1A1974 | sp-5 | an-346 | E1U1974 | sp-5 | an-346 | E1U9300 | sp-31 | an-346 |
| E1A1975 | sp-5 | an-347 | E1U1975 | sp-5 | an-347 | E1U9301 | sp-31 | an-347 |
| E1A1976 | sp-5 | an-348 | E1U1976 | sp-5 | an-348 | E1U9302 | sp-31 | an-348 |
| E1A1977 | sp-5 | an-349 | E1U1977 | sp-5 | an-349 | E1U9303 | sp-31 | an-349 |
| E1A1978 | sp-5 | an-350 | E1U1978 | sp-5 | an-350 | E1U9304 | sp-31 | an-350 |
| E1A1979 | sp-5 | an-351 | E1U1979 | sp-5 | an-351 | E1U9305 | sp-31 | an-351 |
| E1A1980 | sp-5 | an-352 | E1U1980 | sp-5 | an-352 | E1U9306 | sp-31 | an-352 |
| E1A1981 | sp-5 | an-353 | E1U1981 | sp-5 | an-353 | E1U9307 | sp-31 | an-353 |
| E1A1982 | sp-5 | an-354 | E1U1982 | sp-5 | an-354 | E1U9308 | sp-31 | an-354 |
| E1A1983 | sp-5 | an-355 | E1U1983 | sp-5 | an-355 | E1U9309 | sp-31 | an-355 |
| E1A1984 | sp-5 | an-356 | E1U1984 | sp-5 | an-356 | E1U9310 | sp-31 | an-356 |
| E1A1985 | sp-5 | an-357 | E1U1985 | sp-5 | an-357 | E1U9311 | sp-31 | an-357 |
| E1A1986 | sp-5 | an-358 | E1U1986 | sp-5 | an-358 | E1U9312 | sp-31 | an-358 |
| E1A1987 | sp-5 | an-359 | E1U1987 | sp-5 | an-359 | E1U9313 | sp-31 | an-359 |
| E1A1988 | sp-5 | an-360 | E1U1988 | sp-5 | an-360 | E1U9314 | sp-31 | an-360 |
| E1A1989 | sp-5 | an-361 | E1U1989 | sp-5 | an-361 | E1U9315 | sp-31 | an-361 |
| E1A1990 | sp-5 | an-362 | E1U1990 | sp-5 | an-362 | E1U9316 | sp-31 | an-362 |
| E1A1991 | sp-5 | an-363 | E1U1991 | sp-5 | an-363 | E1U9317 | sp-31 | an-363 |
| E1A1992 | sp-5 | an-364 | E1U1992 | sp-5 | an-364 | E1U9318 | sp-31 | an-364 |
| E1A1993 | sp-5 | an-365 | E1U1993 | sp-5 | an-365 | E1U9319 | sp-31 | an-365 |
| E1A1994 | sp-5 | an-366 | E1U1994 | sp-5 | an-366 | E1U9320 | sp-31 | an-366 |
| E1A1995 | sp-5 | an-367 | E1U1995 | sp-5 | an-367 | E1U9321 | sp-31 | an-367 |
| E1A1996 | sp-5 | an-368 | E1U1996 | sp-5 | an-368 | E1U9322 | sp-31 | an-368 |
| E1A1997 | sp-5 | an-369 | E1U1997 | sp-5 | an-369 | E1U9323 | sp-31 | an-369 |
| E1A1998 | sp-5 | an-370 | E1U1998 | sp-5 | an-370 | E1U9324 | sp-31 | an-370 |

Table 1-38

| Y = NHCS | | | Y = NHCSNH | | | Y = NHCSNH | | |
|---|---|---|---|---|---|---|---|---|
| E1A1999 | sp-5 | an-371 | E1U1999 | sp-5 | an-371 | E1U9325 | sp-31 | an-371 |
| E1A2000 | sp-5 | an-372 | E1U2000 | sp-5 | an-372 | E1U9326 | sp-31 | an-372 |
| E1A2001 | sp-5 | an-373 | E1U2001 | sp-5 | an-373 | E1U9327 | sp-31 | an-373 |
| E1A2002 | sp-5 | an-374 | E1U2002 | sp-5 | an-374 | E1U9328 | sp-31 | an-374 |
| E1A2003 | sp-5 | an-375 | E1U2003 | sp-5 | an-375 | E1U9329 | sp-31 | an-375 |
| E1A2004 | sp-5 | an-376 | E1U2004 | sp-5 | an-376 | E1U9330 | sp-31 | an-376 |
| E1A2005 | sp-5 | an-377 | E1U2005 | sp-5 | an-377 | E1U9331 | sp-31 | an-377 |
| E1A2006 | sp-5 | an-378 | E1U2006 | sp-5 | an-378 | E1U9332 | sp-31 | an-378 |
| E1A2007 | sp-5 | an-379 | E1U2007 | sp-5 | an-379 | E1U9333 | sp-31 | an-379 |
| E1A2008 | sp-5 | an-380 | E1U2008 | sp-5 | an-380 | E1U9334 | sp-31 | an-380 |
| E1A2009 | sp-5 | an-381 | E1U2009 | sp-5 | an-381 | E1U9335 | sp-31 | an-381 |
| E1A2010 | sp-5 | an-382 | E1U2010 | sp-5 | an-382 | E1U9336 | sp-31 | an-382 |
| E1A2011 | sp-5 | an-383 | E1U2011 | sp-5 | an-383 | E1U9337 | sp-31 | an-383 |
| E1A2012 | sp-5 | an-384 | E1U2012 | sp-5 | an-384 | E1U9338 | sp-31 | an-384 |
| E1A2013 | sp-5 | an-385 | E1U2013 | sp-5 | an-385 | E1U9339 | sp-31 | an-385 |
| E1A2014 | sp-5 | an-386 | E1U2014 | sp-5 | an-386 | E1U9340 | sp-31 | an-386 |
| E1A2015 | sp-5 | an-387 | E1U2015 | sp-5 | an-387 | E1U9341 | sp-31 | an-387 |
| E1A2016 | sp-5 | an-388 | E1U2016 | sp-5 | an-388 | E1U9342 | sp-31 | an-388 |
| E1A2017 | sp-5 | an-389 | E1U2017 | sp-5 | an-389 | E1U9343 | sp-31 | an-389 |
| E1A2018 | sp-5 | an-390 | E1U2018 | sp-5 | an-390 | E1U9344 | sp-31 | an-390 |
| E1A2019 | sp-5 | an-391 | E1U2019 | sp-5 | an-391 | E1U9345 | sp-31 | an-391 |
| E1A2020 | sp-5 | an-392 | E1U2020 | sp-5 | an-392 | E1U9346 | sp-31 | an-392 |
| E1A2021 | sp-5 | an-393 | E1U2021 | sp-5 | an-393 | E1U9347 | sp-31 | an-393 |
| E1A2022 | sp-5 | an-394 | E1U2022 | sp-5 | an-394 | E1U9348 | sp-31 | an-394 |
| E1A2023 | sp-5 | an-395 | E1U2023 | sp-5 | an-395 | E1U9349 | sp-31 | an-395 |
| E1A2024 | sp-5 | an-396 | E1U2024 | sp-5 | an-396 | E1U9350 | sp-31 | an-396 |
| E1A2025 | sp-5 | an-397 | E1U2025 | sp-5 | an-397 | E1U9351 | sp-31 | an-397 |
| E1A2026 | sp-5 | an-398 | E1U2026 | sp-5 | an-398 | E1U9352 | sp-31 | an-398 |
| E1A2027 | sp-5 | an-399 | E1U2027 | sp-5 | an-399 | E1U9353 | sp-31 | an-399 |
| E1A2028 | sp-5 | an-400 | E1U2028 | sp-5 | an-400 | E1U9354 | sp-31 | an-400 |
| E1A2029 | sp-5 | an-401 | E1U2029 | sp-5 | an-401 | E1U9355 | sp-31 | an-401 |
| E1A2030 | sp-5 | an-402 | E1U2030 | sp-5 | an-402 | E1U9356 | sp-31 | an-402 |
| E1A2031 | sp-5 | an-403 | E1U2031 | sp-5 | an-403 | E1U9357 | sp-31 | an-403 |
| E1A2032 | sp-5 | an-404 | E1U2032 | sp-5 | an-404 | E1U9358 | sp-31 | an-404 |
| E1A2033 | sp-5 | an-405 | E1U2033 | sp-5 | an-405 | E1U9359 | sp-31 | an-405 |
| E1A2034 | sp-5 | an-406 | E1U2034 | sp-5 | an-406 | E1U9360 | sp-31 | an-406 |

| Ex. No. | $Z^a$ | $N^+R^{5a}R^{6a}R^{7a}$ | Ex. No. | | | Ex. No. | | |
|---|---|---|---|---|---|---|---|---|
| | | | E1U2036 | sp-6 | an-1 | E1U9362 | sp-32 | an-1 |
| E1A2037 | sp-6 | an-2 | E1U2037 | sp-6 | an-2 | E1U9363 | sp-32 | an-2 |
| E1A2038 | sp-6 | an-3 | E1U2038 | sp-6 | an-3 | E1U9364 | sp-32 | an-3 |
| E1A2039 | sp-6 | an-4 | E1U2039 | sp-6 | an-4 | E1U9365 | sp-32 | an-4 |
| E1A2040 | sp-6 | an-5 | E1U2040 | sp-6 | an-5 | E1U9366 | sp-32 | an-5 |
| E1A2041 | sp-6 | an-6 | E1U2041 | sp-6 | an-6 | E1U9367 | sp-32 | an-6 |
| E1A2042 | sp-6 | an-7 | E1U2042 | sp-6 | an-7 | E1U9368 | sp-32 | an-7 |
| E1A2043 | sp-6 | an-8 | E1U2043 | sp-6 | an-8 | E1U9369 | sp-32 | an-8 |
| E1A2044 | sp-6 | an-9 | E1U2044 | sp-6 | an-9 | E1U9370 | sp-32 | an-9 |
| E1A2045 | sp-6 | an-10 | E1U2045 | sp-6 | an-10 | E1U9371 | sp-32 | an-10 |
| E1A2046 | sp-6 | an-11 | E1U2046 | sp-6 | an-11 | E1U9372 | sp-32 | an-11 |
| E1A2047 | sp-6 | an-12 | E1U2047 | sp-6 | an-12 | E1U9373 | sp-32 | an-12 |
| E1A2048 | sp-6 | an-13 | E1U2048 | sp-6 | an-13 | E1U9374 | sp-32 | an-13 |
| E1A2049 | sp-6 | an-14 | E1U2049 | sp-6 | an-14 | E1U9375 | sp-32 | an-14 |
| E1A2050 | sp-6 | an-15 | E1U2050 | sp-6 | an-15 | E1U9376 | sp-32 | an-15 |
| E1A2051 | sp-6 | an-16 | E1U2051 | sp-6 | an-16 | E1U9377 | sp-32 | an-16 |
| E1A2052 | sp-6 | an-17 | E1U2052 | sp-6 | an-17 | E1U9378 | sp-32 | an-17 |

Table 1-39

| Y = NHCS | | | Y = NHCSNH | | | Y = NHCSNH | | |
|---|---|---|---|---|---|---|---|---|
| E1A2053 | sp-6 | an-18 | E1U2053 | sp-6 | an-18 | E1U9379 | sp-32 | an-18 |
| E1A2054 | sp-6 | an-19 | E1U2054 | sp-6 | an-19 | E1U9380 | sp-32 | an-19 |
| E1A2055 | sp-6 | an-20 | E1U2055 | sp-6 | an-20 | E1U9381 | sp-32 | an-20 |
| E1A2056 | sp-6 | an-21 | E1U2056 | sp-6 | an-21 | E1U9382 | sp-32 | an-21 |
| E1A2057 | sp-6 | an-22 | E1U2057 | sp-6 | an-22 | E1U9383 | sp-32 | an-22 |
| E1A2058 | sp-6 | an-23 | E1U2058 | sp-6 | an-23 | E1U9384 | sp-32 | an-23 |
| E1A2059 | sp-6 | an-24 | E1U2059 | sp-6 | an-24 | E1U9385 | sp-32 | an-24 |
| E1A2060 | sp-6 | an-25 | E1U2060 | sp-6 | an-25 | E1U9386 | sp-32 | an-25 |
| E1A2061 | sp-6 | an-26 | E1U2061 | sp-6 | an-26 | E1U9387 | sp-32 | an-26 |
| E1A2062 | sp-6 | an-27 | E1U2062 | sp-6 | an-27 | E1U9388 | sp-32 | an-27 |
| E1A2063 | sp-6 | an-28 | E1U2063 | sp-6 | an-28 | E1U9389 | sp-32 | an-28 |
| E1A2064 | sp-6 | an-29 | E1U2064 | sp-6 | an-29 | E1U9390 | sp-32 | an-29 |
| E1A2065 | sp-6 | an-30 | E1U2065 | sp-6 | an-30 | E1U9391 | sp-32 | an-30 |
| E1A2066 | sp-6 | an-31 | E1U2066 | sp-6 | an-31 | E1U9392 | sp-32 | an-31 |
| E1A2067 | sp-6 | an-32 | E1U2067 | sp-6 | an-32 | E1U9393 | sp-32 | an-32 |
| E1A2068 | sp-6 | an-33 | E1U2068 | sp-6 | an-33 | E1U9394 | sp-32 | an-33 |
| E1A2069 | sp-6 | an-34 | E1U2069 | sp-6 | an-34 | E1U9395 | sp-32 | an-34 |
| E1A2070 | sp-6 | an-35 | E1U2070 | sp-6 | an-35 | E1U9396 | sp-32 | an-35 |
| E1A2071 | sp-6 | an-36 | E1U2071 | sp-6 | an-36 | E1U9397 | sp-32 | an-36 |
| E1A2072 | sp-6 | an-37 | E1U2072 | sp-6 | an-37 | E1U9398 | sp-32 | an-37 |
| E1A2073 | sp-6 | an-38 | E1U2073 | sp-6 | an-38 | E1U9399 | sp-32 | an-38 |
| E1A2074 | sp-6 | an-39 | E1U2074 | sp-6 | an-39 | E1U9400 | sp-32 | an-39 |
| E1A2075 | sp-6 | an-40 | E1U2075 | sp-6 | an-40 | E1U9401 | sp-32 | an-40 |
| E1A2076 | sp-6 | an-41 | E1U2076 | sp-6 | an-41 | E1U9402 | sp-32 | an-41 |
| E1A2077 | sp-6 | an-42 | E1U2077 | sp-6 | an-42 | E1U9403 | sp-32 | an-42 |
| E1A2078 | sp-6 | an-43 | E1U2078 | sp-6 | an-43 | E1U9404 | sp-32 | an-43 |
| E1A2079 | sp-6 | an-44 | E1U2079 | sp-6 | an-44 | E1U9405 | sp-32 | an-44 |
| E1A2080 | sp-6 | an-45 | E1U2080 | sp-6 | an-45 | E1U9406 | sp-32 | an-45 |
| E1A2081 | sp-6 | an-46 | E1U2081 | sp-6 | an-46 | E1U9407 | sp-32 | an-46 |
| E1A2082 | sp-6 | an-47 | E1U2082 | sp-6 | an-47 | E1U9408 | sp-32 | an-47 |
| E1A2083 | sp-6 | an-48 | E1U2083 | sp-6 | an-48 | E1U9409 | sp-32 | an-48 |
| E1A2084 | sp-6 | an-49 | E1U2084 | sp-6 | an-49 | E1U9410 | sp-32 | an-49 |
| E1A2085 | sp-6 | an-50 | E1U2085 | sp-6 | an-50 | E1U9411 | sp-32 | an-50 |
| E1A2086 | sp-6 | an-51 | E1U2086 | sp-6 | an-51 | E1U9412 | sp-32 | an-51 |
| E1A2087 | sp-6 | an-52 | E1U2087 | sp-6 | an-52 | E1U9413 | sp-32 | an-52 |
| E1A2088 | sp-6 | an-53 | E1U2088 | sp-6 | an-53 | E1U9414 | sp-32 | an-53 |
| E1A2089 | sp-6 | an-54 | E1U2089 | sp-6 | an-54 | E1U9415 | sp-32 | an-54 |
| E1A2090 | sp-6 | an-55 | E1U2090 | sp-6 | an-55 | E1U9416 | sp-32 | an-55 |
| E1A2091 | sp-6 | an-56 | E1U2091 | sp-6 | an-56 | E1U9417 | sp-32 | an-56 |
| E1A2092 | sp-6 | an-57 | E1U2092 | sp-6 | an-57 | E1U9418 | sp-32 | an-57 |
| E1A2093 | sp-6 | an-58 | E1U2093 | sp-6 | an-58 | E1U9419 | sp-32 | an-58 |
| E1A2094 | sp-6 | an-59 | E1U2094 | sp-6 | an-59 | E1U9420 | sp-32 | an-59 |
| E1A2095 | sp-6 | an-60 | E1U2095 | sp-6 | an-60 | E1U9421 | sp-32 | an-60 |
| E1A2096 | sp-6 | an-61 | E1U2096 | sp-6 | an-61 | E1U9422 | sp-32 | an-61 |
| E1A2097 | sp-6 | an-62 | E1U2097 | sp-6 | an-62 | E1U9423 | sp-32 | an-62 |
| E1A2098 | sp-6 | an-63 | E1U2098 | sp-6 | an-63 | E1U9424 | sp-32 | an-63 |
| E1A2099 | sp-6 | an-64 | E1U2099 | sp-6 | an-64 | E1U9425 | sp-32 | an-64 |
| E1A2100 | sp-6 | an-65 | E1U2100 | sp-6 | an-65 | E1U9426 | sp-32 | an-65 |
| E1A2101 | sp-6 | an-66 | E1U2101 | sp-6 | an-66 | E1U9427 | sp-32 | an-66 |
| E1A2102 | sp-6 | an-67 | E1U2102 | sp-6 | an-67 | E1U9428 | sp-32 | an-67 |
| E1A2103 | sp-6 | an-68 | E1U2103 | sp-6 | an-68 | E1U9429 | sp-32 | an-68 |
| E1A2104 | sp-6 | an-69 | E1U2104 | sp-6 | an-69 | E1U9430 | sp-32 | an-69 |
| E1A2105 | sp-6 | an-70 | E1U2105 | sp-6 | an-70 | E1U9431 | sp-32 | an-70 |
| E1A2106 | sp-6 | an-71 | E1U2106 | sp-6 | an-71 | E1U9432 | sp-32 | an-71 |

-continued

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| Table 1-40 ||||||||||
| Y = NHCS ||| Y = NHCSNH ||| Y = NHCSNH |||
| E1A2107 | sp-6 | an-72 | E1U2107 | sp-6 | an-72 | E1U9433 | sp-32 | an-72 |
| E1A2108 | sp-6 | an-73 | E1U2108 | sp-6 | an-73 | E1U9434 | sp-32 | an-73 |
| E1A2109 | sp-6 | an-74 | E1U2109 | sp-6 | an-74 | E1U9435 | sp-32 | an-74 |
| E1A2110 | sp-6 | an-75 | E1U2110 | sp-6 | an-75 | E1U9436 | sp-32 | an-75 |
| E1A2111 | sp-6 | an-76 | E1U2111 | sp-6 | an-76 | E1U9437 | sp-32 | an-76 |
| E1A2112 | sp-6 | an-77 | E1U2112 | sp-6 | an-77 | E1U9438 | sp-32 | an-77 |
| E1A2113 | sp-6 | an-78 | E1U2113 | sp-6 | an-78 | E1U9439 | sp-32 | an-78 |
| E1A2114 | sp-6 | an-79 | E1U2114 | sp-6 | an-79 | E1U9440 | sp-32 | an-79 |
| E1A2115 | sp-6 | an-80 | E1U2115 | sp-6 | an-80 | E1U9441 | sp-32 | an-80 |
| E1A2116 | sp-6 | an-81 | E1U2116 | sp-6 | an-81 | E1U9442 | sp-32 | an-81 |
| E1A2117 | sp-6 | an-82 | E1U2117 | sp-6 | an-82 | E1U9443 | sp-32 | an-82 |
| E1A2118 | sp-6 | an-83 | E1U2118 | sp-6 | an-83 | E1U9444 | sp-32 | an-83 |
| E1A2119 | sp-6 | an-84 | E1U2119 | sp-6 | an-84 | E1U9445 | sp-32 | an-84 |
| E1A2120 | sp-6 | an-85 | E1U2120 | sp-6 | an-85 | E1U9446 | sp-32 | an-85 |
| E1A2121 | sp-6 | an-86 | E1U2121 | sp-6 | an-86 | E1U9447 | sp-32 | an-86 |
| E1A2122 | sp-6 | an-87 | E1U2122 | sp-6 | an-87 | E1U9448 | sp-32 | an-87 |
| E1A2123 | sp-6 | an-88 | E1U2123 | sp-6 | an-88 | E1U9449 | sp-32 | an-88 |
| E1A2124 | sp-6 | an-89 | E1U2124 | sp-6 | an-89 | E1U9450 | sp-32 | an-89 |
| E1A2125 | sp-6 | an-90 | E1U2125 | sp-6 | an-90 | E1U9451 | sp-32 | an-90 |
| E1A2126 | sp-6 | an-91 | E1U2126 | sp-6 | an-91 | E1U9452 | sp-32 | an-91 |
| E1A2127 | sp-6 | an-92 | E1U2127 | sp-6 | an-92 | E1U9453 | sp-32 | an-92 |
| E1A2128 | sp-6 | an-93 | E1U2128 | sp-6 | an-93 | E1U9454 | sp-32 | an-93 |
| E1A2129 | sp-6 | an-94 | E1U2129 | sp-6 | an-94 | E1U9455 | sp-32 | an-94 |
| E1A2130 | sp-6 | an-95 | E1U2130 | sp-6 | an-95 | E1U9456 | sp-32 | an-95 |
| E1A2131 | sp-6 | an-96 | E1U2131 | sp-6 | an-96 | E1U9457 | sp-32 | an-96 |
| E1A2132 | sp-6 | an-97 | E1U2132 | sp-6 | an-97 | E1U9458 | sp-32 | an-97 |
| E1A2133 | sp-6 | an-98 | E1U2133 | sp-6 | an-98 | E1U9459 | sp-32 | an-98 |
| E1A2134 | sp-6 | an-99 | E1U2134 | sp-6 | an-99 | E1U9460 | sp-32 | an-99 |
| E1A2135 | sp-6 | an-100 | E1U2135 | sp-6 | an-100 | E1U9461 | sp-32 | an-100 |
| E1A2136 | sp-6 | an-101 | E1U2136 | sp-6 | an-101 | E1U9462 | sp-32 | an-101 |
| E1A2137 | sp-6 | an-102 | E1U2137 | sp-6 | an-102 | E1U9463 | sp-32 | an-102 |
| E1A2138 | sp-6 | an-103 | E1U2138 | sp-6 | an-103 | E1U9464 | sp-32 | an-103 |
| E1A2139 | sp-6 | an-104 | E1U2139 | sp-6 | an-104 | E1U9465 | sp-32 | an-104 |
| E1A2140 | sp-6 | an-105 | E1U2140 | sp-6 | an-105 | E1U9466 | sp-32 | an-105 |
| E1A2141 | sp-6 | an-106 | E1U2141 | sp-6 | an-106 | E1U9467 | sp-32 | an-106 |
| E1A2142 | sp-6 | an-107 | E1U2142 | sp-6 | an-107 | E1U9468 | sp-32 | an-107 |
| E1A2143 | sp-6 | an-108 | E1U2143 | sp-6 | an-108 | E1U9469 | sp-32 | an-108 |
| E1A2144 | sp-6 | an-109 | E1U2144 | sp-6 | an-109 | E1U9470 | sp-32 | an-109 |
| E1A2145 | sp-6 | an-110 | E1U2145 | sp-6 | an-110 | E1U9471 | sp-32 | an-110 |
| E1A2146 | sp-6 | an-111 | E1U2146 | sp-6 | an-111 | E1U9472 | sp-32 | an-111 |
| E1A2147 | sp-6 | an-112 | E1U2147 | sp-6 | an-112 | E1U9473 | sp-32 | an-112 |
| E1A2148 | sp-6 | an-113 | E1U2148 | sp-6 | an-113 | E1U9474 | sp-32 | an-113 |
| E1A2149 | sp-6 | an-114 | E1U2149 | sp-6 | an-114 | E1U9475 | sp-32 | an-114 |
| E1A2150 | sp-6 | an-115 | E1U2150 | sp-6 | an-115 | E1U9476 | sp-32 | an-115 |
| E1A2151 | sp-6 | an-116 | E1U2151 | sp-6 | an-116 | E1U9477 | sp-32 | an-116 |
| E1A2152 | sp-6 | an-117 | E1U2152 | sp-6 | an-117 | E1U9478 | sp-32 | an-117 |
| E1A2153 | sp-6 | an-118 | E1U2153 | sp-6 | an-118 | E1U9479 | sp-32 | an-118 |
| E1A2154 | sp-6 | an-119 | E1U2154 | sp-6 | an-119 | E1U9480 | sp-32 | an-119 |
| E1A2155 | sp-6 | an-120 | E1U2155 | sp-6 | an-120 | E1U9481 | sp-32 | an-120 |
| E1A2156 | sp-6 | an-121 | E1U2156 | sp-6 | an-121 | E1U9482 | sp-32 | an-121 |
| E1A2157 | sp-6 | an-122 | E1U2157 | sp-6 | an-122 | E1U9483 | sp-32 | an-122 |
| E1A2158 | sp-6 | an-123 | E1U2158 | sp-6 | an-123 | E1U9484 | sp-32 | an-123 |
| E1A2159 | sp-6 | an-124 | E1U2159 | sp-6 | an-124 | E1U9485 | sp-32 | an-124 |
| E1A2160 | sp-6 | an-125 | E1U2160 | sp-6 | an-125 | E1U9486 | sp-32 | an-125 |
| Table 1-41 ||||||||||
| Y = NHCS ||| Y = NHCSNH ||| Y = NHCSNH |||
| E1A2161 | sp-6 | an-126 | E1U2161 | sp-6 | an-126 | E1U9487 | sp-32 | an-126 |
| E1A2162 | sp-6 | an-127 | E1U2162 | sp-6 | an-127 | E1U9488 | sp-32 | an-127 |
| E1A2163 | sp-6 | an-128 | E1U2163 | sp-6 | an-128 | E1U9489 | sp-32 | an-128 |
| E1A2164 | sp-6 | an-129 | E1U2164 | sp-6 | an-129 | E1U9490 | sp-32 | an-129 |
| E1A2165 | sp-6 | an-130 | E1U2165 | sp-6 | an-130 | E1U9491 | sp-32 | an-130 |
| E1A2166 | sp-6 | an-131 | E1U2166 | sp-6 | an-131 | E1U9492 | sp-32 | an-131 |
| E1A2167 | sp-6 | an-132 | E1U2167 | sp-6 | an-132 | E1U9493 | sp-32 | an-132 |
| E1A2168 | sp-6 | an-133 | E1U2168 | sp-6 | an-133 | E1U9494 | sp-32 | an-133 |
| E1A2169 | sp-6 | an-134 | E1U2169 | sp-6 | an-134 | E1U9495 | sp-32 | an-134 |
| E1A2170 | sp-6 | an-135 | E1U2170 | sp-6 | an-135 | E1U9496 | sp-32 | an-135 |
| E1A2171 | sp-6 | an-136 | E1U2171 | sp-6 | an-136 | E1U9497 | sp-32 | an-136 |
| E1A2172 | sp-6 | an-137 | E1U2172 | sp-6 | an-137 | E1U9498 | sp-32 | an-137 |
| E1A2173 | sp-6 | an-138 | E1U2173 | sp-6 | an-138 | E1U9499 | sp-32 | an-138 |
| E1A2174 | sp-6 | an-139 | E1U2174 | sp-6 | an-139 | E1U9500 | sp-32 | an-139 |
| E1A2175 | sp-6 | an-140 | E1U2175 | sp-6 | an-140 | E1U9501 | sp-32 | an-140 |
| E1A2176 | sp-6 | an-141 | E1U2176 | sp-6 | an-141 | E1U9502 | sp-32 | an-141 |

-continued

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| E1A2177 | sp-6 | an-142 | E1U2177 | sp-6 | an-142 | E1U9503 | sp-32 | an-142 |
| E1A2178 | sp-6 | an-143 | E1U2178 | sp-6 | an-143 | E1U9504 | sp-32 | an-143 |
| E1A2179 | sp-6 | an-144 | E1U2179 | sp-6 | an-144 | E1U9505 | sp-32 | an-144 |
| E1A2180 | sp-6 | an-145 | E1U2180 | sp-6 | an-145 | E1U9506 | sp-32 | an-145 |
| E1A2181 | sp-6 | an-146 | E1U2181 | sp-6 | an-146 | E1U9507 | sp-32 | an-146 |
| E1A2182 | sp-6 | an-147 | E1U2182 | sp-6 | an-147 | E1U9508 | sp-32 | an-147 |
| E1A2183 | sp-6 | an-148 | E1U2183 | sp-6 | an-148 | E1U9509 | sp-32 | an-148 |
| E1A2184 | sp-6 | an-149 | E1U2184 | sp-6 | an-149 | E1U9510 | sp-32 | an-149 |
| E1A2185 | sp-6 | an-150 | E1U2185 | sp-6 | an-150 | E1U9511 | sp-32 | an-150 |
| E1A2186 | sp-6 | an-151 | E1U2186 | sp-6 | an-151 | E1U9512 | sp-32 | an-151 |
| E1A2187 | sp-6 | an-152 | E1U2187 | sp-6 | an-152 | E1U9513 | sp-32 | an-152 |
| E1A2188 | sp-6 | an-153 | E1U2188 | sp-6 | an-153 | E1U9514 | sp-32 | an-153 |
| E1A2189 | sp-6 | an-154 | E1U2189 | sp-6 | an-154 | E1U9515 | sp-32 | an-154 |
| E1A2190 | sp-6 | an-155 | E1U2190 | sp-6 | an-155 | E1U9516 | sp-32 | an-155 |
| E1A2191 | sp-6 | an-156 | E1U2191 | sp-6 | an-156 | E1U9517 | sp-32 | an-156 |
| E1A2192 | sp-6 | an-157 | E1U2192 | sp-6 | an-157 | E1U9518 | sp-32 | an-157 |
| E1A2193 | sp-6 | an-158 | E1U2193 | sp-6 | an-158 | E1U9519 | sp-32 | an-158 |
| E1A2194 | sp-6 | an-159 | E1U2194 | sp-6 | an-159 | E1U9520 | sp-32 | an-159 |
| E1A2195 | sp-6 | an-160 | E1U2195 | sp-6 | an-160 | E1U9521 | sp-32 | an-160 |
| E1A2196 | sp-6 | an-161 | E1U2196 | sp-6 | an-161 | E1U9522 | sp-32 | an-161 |
| E1A2197 | sp-6 | an-162 | E1U2197 | sp-6 | an-162 | E1U9523 | sp-32 | an-162 |
| E1A2198 | sp-6 | an-163 | E1U2198 | sp-6 | an-163 | E1U9524 | sp-32 | an-163 |
| E1A2199 | sp-6 | an-164 | E1U2199 | sp-6 | an-164 | E1U9525 | sp-32 | an-164 |
| E1A2200 | sp-6 | an-165 | E1U2200 | sp-6 | an-165 | E1U9526 | sp-32 | an-165 |
| E1A2201 | sp-6 | an-166 | E1U2201 | sp-6 | an-166 | E1U9527 | sp-32 | an-166 |
| E1A2202 | sp-6 | an-167 | E1U2202 | sp-6 | an-167 | E1U9528 | sp-32 | an-167 |
| E1A2203 | sp-6 | an-168 | E1U2203 | sp-6 | an-168 | E1U9529 | sp-32 | an-168 |
| E1A2204 | sp-6 | an-169 | E1U2204 | sp-6 | an-169 | E1U9530 | sp-32 | an-169 |
| E1A2205 | sp-6 | an-170 | E1U2205 | sp-6 | an-170 | E1U9531 | sp-32 | an-170 |
| E1A2206 | sp-6 | an-171 | E1U2206 | sp-6 | an-171 | E1U9532 | sp-32 | an-171 |
| E1A2207 | sp-6 | an-172 | E1U2207 | sp-6 | an-172 | E1U9533 | sp-32 | an-172 |
| E1A2208 | sp-6 | an-173 | E1U2208 | sp-6 | an-173 | E1U9534 | sp-32 | an-173 |
| E1A2209 | sp-6 | an-174 | E1U2209 | sp-6 | an-174 | E1U9535 | sp-32 | an-174 |
| E1A2210 | sp-6 | an-175 | E1U2210 | sp-6 | an-175 | E1U9536 | sp-32 | an-175 |
| E1A2211 | sp-6 | an-176 | E1U2211 | sp-6 | an-176 | E1U9537 | sp-32 | an-176 |
| E1A2212 | sp-6 | an-177 | E1U2212 | sp-6 | an-177 | E1U9538 | sp-32 | an-177 |
| E1A2213 | sp-6 | an-178 | E1U2213 | sp-6 | an-178 | E1U9539 | sp-32 | an-178 |
| E1A2214 | sp-6 | an-179 | E1U2214 | sp-6 | an-179 | E1U9540 | sp-32 | an-179 |

Table 1-42

| Y = NHCS | | | Y = NHCSNH | | | Y = NHCSNH | | |
|---|---|---|---|---|---|---|---|---|
| E1A2215 | sp-6 | an-180 | E1U2215 | sp-6 | an-180 | E1U9541 | sp-32 | an-180 |
| E1A2216 | sp-6 | an-181 | E1U2216 | sp-6 | an-181 | E1U9542 | sp-32 | an-181 |
| E1A2217 | sp-6 | an-182 | E1U2217 | sp-6 | an-182 | E1U9543 | sp-32 | an-182 |
| E1A2218 | sp-6 | an-183 | E1U2218 | sp-6 | an-183 | E1U9544 | sp-32 | an-183 |
| E1A2219 | sp-6 | an-184 | E1U2219 | sp-6 | an-184 | E1U9545 | sp-32 | an-184 |
| E1A2220 | sp-6 | an-185 | E1U2220 | sp-6 | an-185 | E1U9546 | sp-32 | an-185 |
| E1A2221 | sp-6 | an-186 | E1U2221 | sp-6 | an-186 | E1U9547 | sp-32 | an-186 |
| E1A2222 | sp-6 | an-187 | E1U2222 | sp-6 | an-187 | E1U9548 | sp-32 | an-187 |
| E1A2223 | sp-6 | an-188 | E1U2223 | sp-6 | an-188 | E1U9549 | sp-32 | an-188 |
| E1A2224 | sp-6 | an-189 | E1U2224 | sp-6 | an-189 | E1U9550 | sp-32 | an-189 |
| E1A2225 | sp-6 | an-190 | E1U2225 | sp-6 | an-190 | E1U9551 | sp-32 | an-190 |
| E1A2226 | sp-6 | an-191 | E1U2226 | sp-6 | an-191 | E1U9552 | sp-32 | an-191 |
| E1A2227 | sp-6 | an-192 | E1U2227 | sp-6 | an-192 | E1U9553 | sp-32 | an-192 |
| E1A2228 | sp-6 | an-193 | E1U2228 | sp-6 | an-193 | E1U9554 | sp-32 | an-193 |
| E1A2229 | sp-6 | an-194 | E1U2229 | sp-6 | an-194 | E1U9555 | sp-32 | an-194 |
| E1A2230 | sp-6 | an-195 | E1U2230 | sp-6 | an-195 | E1U9556 | sp-32 | an-195 |
| E1A2231 | sp-6 | an-196 | E1U2231 | sp-6 | an-196 | E1U9557 | sp-32 | an-196 |
| E1A2232 | sp-6 | an-197 | E1U2232 | sp-6 | an-197 | E1U9558 | sp-32 | an-197 |
| E1A2233 | sp-6 | an-198 | E1U2233 | sp-6 | an-198 | E1U9559 | sp-32 | an-198 |
| E1A2234 | sp-6 | an-199 | E1U2234 | sp-6 | an-199 | E1U9560 | sp-32 | an-199 |
| E1A2235 | sp-6 | an-200 | E1U2235 | sp-6 | an-200 | E1U9561 | sp-32 | an-200 |
| E1A2236 | sp-6 | an-201 | E1U2236 | sp-6 | an-201 | E1U9562 | sp-32 | an-201 |
| E1A2237 | sp-6 | an-202 | E1U2237 | sp-6 | an-202 | E1U9563 | sp-32 | an-202 |
| E1A2238 | sp-6 | an-203 | E1U2238 | sp-6 | an-203 | E1U9564 | sp-32 | an-203 |
| E1A2239 | sp-6 | an-204 | E1U2239 | sp-6 | an-204 | E1U9565 | sp-32 | an-204 |
| E1A2240 | sp-6 | an-205 | E1U2240 | sp-6 | an-205 | E1U9566 | sp-32 | an-205 |
| E1A2241 | sp-6 | an-206 | E1U2241 | sp-6 | an-206 | E1U9567 | sp-32 | an-206 |
| E1A2242 | sp-6 | an-207 | E1U2242 | sp-6 | an-207 | E1U9568 | sp-32 | an-207 |
| E1A2243 | sp-6 | an-208 | E1U2243 | sp-6 | an-208 | E1U9569 | sp-32 | an-208 |
| E1A2244 | sp-6 | an-209 | E1U2244 | sp-6 | an-209 | E1U9570 | sp-32 | an-209 |
| E1A2245 | sp-6 | an-210 | E1U2245 | sp-6 | an-210 | E1U9571 | sp-32 | an-210 |
| E1A2246 | sp-6 | an-211 | E1U2246 | sp-6 | an-211 | E1U9572 | sp-32 | an-211 |
| E1A2247 | sp-6 | an-212 | E1U2247 | sp-6 | an-212 | E1U9573 | sp-32 | an-212 |
| E1A2248 | sp-6 | an-213 | E1U2248 | sp-6 | an-213 | E1U9574 | sp-32 | an-213 |
| E1A2249 | sp-6 | an-214 | E1U2249 | sp-6 | an-214 | E1U9575 | sp-32 | an-214 |
| E1A2250 | sp-6 | an-215 | E1U2250 | sp-6 | an-215 | E1U9576 | sp-32 | an-215 |

-continued

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| E1A2251 | sp-6 | an-216 | E1U2251 | sp-6 | an-216 | E1U9577 | sp-32 | an-216 |
| E1A2252 | sp-6 | an-217 | E1U2252 | sp-6 | an-217 | E1U9578 | sp-32 | an-217 |
| E1A2253 | sp-6 | an-218 | E1U2253 | sp-6 | an-218 | E1U9579 | sp-32 | an-218 |
| E1A2254 | sp-6 | an-219 | E1U2254 | sp-6 | an-219 | E1U9580 | sp-32 | an-219 |
| E1A2255 | sp-6 | an-220 | E1U2255 | sp-6 | an-220 | E1U9581 | sp-32 | an-220 |
| E1A2256 | sp-6 | an-221 | E1U2256 | sp-6 | an-221 | E1U9582 | sp-32 | an-221 |
| E1A2257 | sp-6 | an-222 | E1U2257 | sp-6 | an-222 | E1U9583 | sp-32 | an-222 |
| E1A2258 | sp-6 | an-223 | E1U2258 | sp-6 | an-223 | E1U9584 | sp-32 | an-223 |
| E1A2259 | sp-6 | an-224 | E1U2259 | sp-6 | an-224 | E1U9585 | sp-32 | an-224 |
| E1A2260 | sp-6 | an-225 | E1U2260 | sp-6 | an-225 | E1U9586 | sp-32 | an-225 |
| E1A2261 | sp-6 | an-226 | E1U2261 | sp-6 | an-226 | E1U9587 | sp-32 | an-226 |
| E1A2262 | sp-6 | an-227 | E1U2262 | sp-6 | an-227 | E1U9588 | sp-32 | an-227 |
| E1A2263 | sp-6 | an-228 | E1U2263 | sp-6 | an-228 | E1U9589 | sp-32 | an-228 |
| E1A2264 | sp-6 | an-229 | E1U2264 | sp-6 | an-229 | E1U9590 | sp-32 | an-229 |
| E1A2265 | sp-6 | an-230 | E1U2265 | sp-6 | an-230 | E1U9591 | sp-32 | an-230 |
| E1A2266 | sp-6 | an-231 | E1U2266 | sp-6 | an-231 | E1U9592 | sp-32 | an-231 |
| E1A2267 | sp-6 | an-232 | E1U2267 | sp-6 | an-232 | E1U9593 | sp-32 | an-232 |
| E1A2268 | sp-6 | an-233 | E1U2268 | sp-6 | an-233 | E1U9594 | sp-32 | an-233 |

Table 1-43

| Y = NHCS | | | Y = NHCSNH | | | Y = NHCSNH | | |
|---|---|---|---|---|---|---|---|---|
| E1A2269 | sp-6 | an-234 | E1U2269 | sp-6 | an-234 | E1U9595 | sp-32 | an-234 |
| E1A2270 | sp-6 | an-235 | E1U2270 | sp-6 | an-235 | E1U9596 | sp-32 | an-235 |
| E1A2271 | sp-6 | an-236 | E1U2271 | sp-6 | an-236 | E1U9597 | sp-32 | an-236 |
| E1A2272 | sp-6 | an-237 | E1U2272 | sp-6 | an-237 | E1U9598 | sp-32 | an-237 |
| E1A2273 | sp-6 | an-238 | E1U2273 | sp-6 | an-238 | E1U9599 | sp-32 | an-238 |
| E1A2274 | sp-6 | an-239 | E1U2274 | sp-6 | an-239 | E1U9600 | sp-32 | an-239 |
| E1A2275 | sp-6 | an-240 | E1U2275 | sp-6 | an-240 | E1U9601 | sp-32 | an-240 |
| E1A2276 | sp-6 | an-241 | E1U2276 | sp-6 | an-241 | E1U9602 | sp-32 | an-241 |
| E1A2277 | sp-6 | an-242 | E1U2277 | sp-6 | an-242 | E1U9603 | sp-32 | an-242 |
| E1A2278 | sp-6 | an-243 | E1U2278 | sp-6 | an-243 | E1U9604 | sp-32 | an-243 |
| E1A2279 | sp-6 | an-244 | E1U2279 | sp-6 | an-244 | E1U9605 | sp-32 | an-244 |
| E1A2280 | sp-6 | an-245 | E1U2280 | sp-6 | an-245 | E1U9606 | sp-32 | an-245 |
| E1A2281 | sp-6 | an-246 | E1U2281 | sp-6 | an-246 | E1U9607 | sp-32 | an-246 |
| E1A2282 | sp-6 | an-247 | E1U2282 | sp-6 | an-247 | E1U9608 | sp-32 | an-247 |
| E1A2283 | sp-6 | an-248 | E1U2283 | sp-6 | an-248 | E1U9609 | sp-32 | an-248 |
| E1A2284 | sp-6 | an-249 | E1U2284 | sp-6 | an-249 | E1U9610 | sp-32 | an-249 |
| E1A2285 | sp-6 | an-250 | E1U2285 | sp-6 | an-250 | E1U9611 | sp-32 | an-250 |
| E1A2286 | sp-6 | an-251 | E1U2286 | sp-6 | an-251 | E1U9612 | sp-32 | an-251 |
| E1A2287 | sp-6 | an-252 | E1U2287 | sp-6 | an-252 | E1U9613 | sp-32 | an-252 |
| E1A2288 | sp-6 | an-253 | E1U2288 | sp-6 | an-253 | E1U9614 | sp-32 | an-253 |
| E1A2289 | sp-6 | an-254 | E1U2289 | sp-6 | an-254 | E1U9615 | sp-32 | an-254 |
| E1A2290 | sp-6 | an-255 | E1U2290 | sp-6 | an-255 | E1U9616 | sp-32 | an-255 |
| E1A2291 | sp-6 | an-256 | E1U2291 | sp-6 | an-256 | E1U9617 | sp-32 | an-256 |
| E1A2292 | sp-6 | an-257 | E1U2292 | sp-6 | an-257 | E1U9618 | sp-32 | an-257 |
| E1A2293 | sp-6 | an-258 | E1U2293 | sp-6 | an-258 | E1U9619 | sp-32 | an-258 |
| E1A2294 | sp-6 | an-259 | E1U2294 | sp-6 | an-259 | E1U9620 | sp-32 | an-259 |
| E1A2295 | sp-6 | an-260 | E1U2295 | sp-6 | an-260 | E1U9621 | sp-32 | an-260 |
| E1A2296 | sp-6 | an-261 | E1U2296 | sp-6 | an-261 | E1U9622 | sp-32 | an-261 |
| E1A2297 | sp-6 | an-262 | E1U2297 | sp-6 | an-262 | E1U9623 | sp-32 | an-262 |
| E1A2298 | sp-6 | an-263 | E1U2298 | sp-6 | an-263 | E1U9624 | sp-32 | an-263 |
| E1A2299 | sp-6 | an-264 | E1U2299 | sp-6 | an-264 | E1U9625 | sp-32 | an-264 |
| E1A2300 | sp-6 | an-265 | E1U2300 | sp-6 | an-265 | E1U9626 | sp-32 | an-265 |
| E1A2301 | sp-6 | an-266 | E1U2301 | sp-6 | an-266 | E1U9627 | sp-32 | an-266 |
| E1A2302 | sp-6 | an-267 | E1U2302 | sp-6 | an-267 | E1U9628 | sp-32 | an-267 |
| E1A2303 | sp-6 | an-268 | E1U2303 | sp-6 | an-268 | E1U9629 | sp-32 | an-268 |
| E1A2304 | sp-6 | an-269 | E1U2304 | sp-6 | an-269 | E1U9630 | sp-32 | an-269 |
| E1A2305 | sp-6 | an-270 | E1U2305 | sp-6 | an-270 | E1U9631 | sp-32 | an-270 |
| E1A2306 | sp-6 | an-271 | E1U2306 | sp-6 | an-271 | E1U9632 | sp-32 | an-271 |
| E1A2307 | sp-6 | an-272 | E1U2307 | sp-6 | an-272 | E1U9633 | sp-32 | an-272 |
| E1A2308 | sp-6 | an-273 | E1U2308 | sp-6 | an-273 | E1U9634 | sp-32 | an-273 |
| E1A2309 | sp-6 | an-274 | E1U2309 | sp-6 | an-274 | E1U9635 | sp-32 | an-274 |
| E1A2310 | sp-6 | an-275 | E1U2310 | sp-6 | an-275 | E1U9636 | sp-32 | an-275 |
| E1A2311 | sp-6 | an-276 | E1U2311 | sp-6 | an-276 | E1U9637 | sp-32 | an-276 |
| E1A2312 | sp-6 | an-277 | E1U2312 | sp-6 | an-277 | E1U9638 | sp-32 | an-277 |
| E1A2313 | sp-6 | an-278 | E1U2313 | sp-6 | an-278 | E1U9639 | sp-32 | an-278 |
| E1A2314 | sp-6 | an-279 | E1U2314 | sp-6 | an-279 | E1U9640 | sp-32 | an-279 |
| E1A2315 | sp-6 | an-280 | E1U2315 | sp-6 | an-280 | E1U9641 | sp-32 | an-280 |
| E1A2316 | sp-6 | an-281 | E1U2316 | sp-6 | an-281 | E1U9642 | sp-32 | an-281 |
| E1A2317 | sp-6 | an-282 | E1U2317 | sp-6 | an-282 | E1U9643 | sp-32 | an-282 |
| E1A2318 | sp-6 | an-283 | E1U2318 | sp-6 | an-283 | E1U9644 | sp-32 | an-283 |
| E1A2319 | sp-6 | an-284 | E1U2319 | sp-6 | an-284 | E1U9645 | sp-32 | an-284 |
| E1A2320 | sp-6 | an-285 | E1U2320 | sp-6 | an-285 | E1U9646 | sp-32 | an-285 |
| E1A2321 | sp-6 | an-286 | E1U2321 | sp-6 | an-286 | E1U9647 | sp-32 | an-286 |
| E1A2322 | sp-6 | an-287 | E1U2322 | sp-6 | an-287 | E1U9648 | sp-32 | an-287 |

-continued

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| Table 1-44 ||||||||| 
| Y = NHCS ||| Y = NHCSNH ||| Y = NHCSNH |||
| E1A2323 | sp-6 | an-288 | E1U2323 | sp-6 | an-288 | E1U9649 | sp-32 | an-288 |
| E1A2324 | sp-6 | an-289 | E1U2324 | sp-6 | an-289 | E1U9650 | sp-32 | an-289 |
| E1A2325 | sp-6 | an-290 | E1U2325 | sp-6 | an-290 | E1U9651 | sp-32 | an-290 |
| E1A2326 | sp-6 | an-291 | E1U2326 | sp-6 | an-291 | E1U9652 | sp-32 | an-291 |
| E1A2327 | sp-6 | an-292 | E1U2327 | sp-6 | an-292 | E1U9653 | sp-32 | an-292 |
| E1A2328 | sp-6 | an-293 | E1U2328 | sp-6 | an-293 | E1U9654 | sp-32 | an-293 |
| E1A2329 | sp-6 | an-294 | E1U2329 | sp-6 | an-294 | E1U9655 | sp-32 | an-294 |
| E1A2330 | sp-6 | an-295 | E1U2330 | sp-6 | an-295 | E1U9656 | sp-32 | an-295 |
| E1A2331 | sp-6 | an-296 | E1U2331 | sp-6 | an-296 | E1U9657 | sp-32 | an-296 |
| E1A2332 | sp-6 | an-297 | E1U2332 | sp-6 | an-297 | E1U9658 | sp-32 | an-297 |
| E1A2333 | sp-6 | an-298 | E1U2333 | sp-6 | an-298 | E1U9659 | sp-32 | an-298 |
| E1A2334 | sp-6 | an-299 | E1U2334 | sp-6 | an-299 | E1U9660 | sp-32 | an-299 |
| E1A2335 | sp-6 | an-300 | E1U2335 | sp-6 | an-300 | E1U9661 | sp-32 | an-300 |
| E1A2336 | sp-6 | an-301 | E1U2336 | sp-6 | an-301 | E1U9662 | sp-32 | an-301 |
| E1A2337 | sp-6 | an-302 | E1U2337 | sp-6 | an-302 | E1U9663 | sp-32 | an-302 |
| E1A2338 | sp-6 | an-303 | E1U2338 | sp-6 | an-303 | E1U9664 | sp-32 | an-303 |
| E1A2339 | sp-6 | an-304 | E1U2339 | sp-6 | an-304 | E1U9665 | sp-32 | an-304 |
| E1A2340 | sp-6 | an-305 | E1U2340 | sp-6 | an-305 | E1U9666 | sp-32 | an-305 |
| E1A2341 | sp-6 | an-306 | E1U2341 | sp-6 | an-306 | E1U9667 | sp-32 | an-306 |
| E1A2342 | sp-6 | an-307 | E1U2342 | sp-6 | an-307 | E1U9668 | sp-32 | an-307 |
| E1A2343 | sp-6 | an-308 | E1U2343 | sp-6 | an-308 | E1U9669 | sp-32 | an-308 |
| E1A2344 | sp-6 | an-309 | E1U2344 | sp-6 | an-309 | E1U9670 | sp-32 | an-309 |
| E1A2345 | sp-6 | an-310 | E1U2345 | sp-6 | an-310 | E1U9671 | sp-32 | an-310 |
| E1A2346 | sp-6 | an-311 | E1U2346 | sp-6 | an-311 | E1U9672 | sp-32 | an-311 |
| E1A2347 | sp-6 | an-312 | E1U2347 | sp-6 | an-312 | E1U9673 | sp-32 | an-312 |
| E1A2348 | sp-6 | an-313 | E1U2348 | sp-6 | an-313 | E1U9674 | sp-32 | an-313 |
| E1A2349 | sp-6 | an-314 | E1U2349 | sp-6 | an-314 | E1U9675 | sp-32 | an-314 |
| E1A2350 | sp-6 | an-315 | E1U2350 | sp-6 | an-315 | E1U9676 | sp-32 | an-315 |
| E1A2351 | sp-6 | an-316 | E1U2351 | sp-6 | an-316 | E1U9677 | sp-32 | an-316 |
| E1A2352 | sp-6 | an-317 | E1U2352 | sp-6 | an-317 | E1U9678 | sp-32 | an-317 |
| E1A2353 | sp-6 | an-318 | E1U2353 | sp-6 | an-318 | E1U9679 | sp-32 | an-318 |
| E1A2354 | sp-6 | an-319 | E1U2354 | sp-6 | an-319 | E1U9680 | sp-32 | an-319 |
| E1A2355 | sp-6 | an-320 | E1U2355 | sp-6 | an-320 | E1U9681 | sp-32 | an-320 |
| E1A2356 | sp-6 | an-321 | E1U2356 | sp-6 | an-321 | E1U9682 | sp-32 | an-321 |
| E1A2357 | sp-6 | an-322 | E1U2357 | sp-6 | an-322 | E1U9683 | sp-32 | an-322 |
| E1A2358 | sp-6 | an-323 | E1U2358 | sp-6 | an-323 | E1U9684 | sp-32 | an-323 |
| E1A2359 | sp-6 | an-324 | E1U2359 | sp-6 | an-324 | E1U9685 | sp-32 | an-324 |
| E1A2360 | sp-6 | an-325 | E1U2360 | sp-6 | an-325 | E1U9686 | sp-32 | an-325 |
| E1A2361 | sp-6 | an-326 | E1U2361 | sp-6 | an-326 | E1U9687 | sp-32 | an-326 |
| E1A2362 | sp-6 | an-327 | E1U2362 | sp-6 | an-327 | E1U9688 | sp-32 | an-327 |
| E1A2363 | sp-6 | an-328 | E1U2363 | sp-6 | an-328 | E1U9689 | sp-32 | an-328 |
| E1A2364 | sp-6 | an-329 | E1U2364 | sp-6 | an-329 | E1U9690 | sp-32 | an-329 |
| E1A2365 | sp-6 | an-330 | E1U2365 | sp-6 | an-330 | E1U9691 | sp-32 | an-330 |
| E1A2366 | sp-6 | an-331 | E1U2366 | sp-6 | an-331 | E1U9692 | sp-32 | an-331 |
| E1A2367 | sp-6 | an-332 | E1U2367 | sp-6 | an-332 | E1U9693 | sp-32 | an-332 |
| E1A2368 | sp-6 | an-333 | E1U2368 | sp-6 | an-333 | E1U9694 | sp-32 | an-333 |
| E1A2369 | sp-6 | an-334 | E1U2369 | sp-6 | an-334 | E1U9695 | sp-32 | an-334 |
| E1A2370 | sp-6 | an-335 | E1U2370 | sp-6 | an-335 | E1U9696 | sp-32 | an-335 |
| E1A2371 | sp-6 | an-336 | E1U2371 | sp-6 | an-336 | E1U9697 | sp-32 | an-336 |
| E1A2372 | sp-6 | an-337 | E1U2372 | sp-6 | an-337 | E1U9698 | sp-32 | an-337 |
| E1A2373 | sp-6 | an-338 | E1U2373 | sp-6 | an-338 | E1U9699 | sp-32 | an-338 |
| E1A2374 | sp-6 | an-339 | E1U2374 | sp-6 | an-339 | E1U9700 | sp-32 | an-339 |
| E1A2375 | sp-6 | an-340 | E1U2375 | sp-6 | an-340 | E1U9701 | sp-32 | an-340 |
| E1A2376 | sp-6 | an-341 | E1U2376 | sp-6 | an-341 | E1U9702 | sp-32 | an-341 |
| Table 1-45 ||||||||| 
| Y = NHCS ||| Y = NHCSNH ||| Y = NHCSNH |||
| E1A2377 | sp-6 | an-342 | E1U2377 | sp-6 | an-342 | E1U9703 | sp-32 | an-342 |
| E1A2378 | sp-6 | an-343 | E1U2378 | sp-6 | an-343 | E1U9704 | sp-32 | an-343 |
| E1A2379 | sp-6 | an-344 | E1U2379 | sp-6 | an-344 | E1U9705 | sp-32 | an-344 |
| E1A2380 | sp-6 | an-345 | E1U2380 | sp-6 | an-345 | E1U9706 | sp-32 | an-345 |
| E1A2381 | sp-6 | an-346 | E1U2381 | sp-6 | an-346 | E1U9707 | sp-32 | an-346 |
| E1A2382 | sp-6 | an-347 | E1U2382 | sp-6 | an-347 | E1U9708 | sp-32 | an-347 |
| E1A2383 | sp-6 | an-348 | E1U2383 | sp-6 | an-348 | E1U9709 | sp-32 | an-348 |
| E1A2384 | sp-6 | an-349 | E1U2384 | sp-6 | an-349 | E1U9710 | sp-32 | an-349 |
| E1A2385 | sp-6 | an-350 | E1U2385 | sp-6 | an-350 | E1U9711 | sp-32 | an-350 |
| E1A2386 | sp-6 | an-351 | E1U2386 | sp-6 | an-351 | E1U9712 | sp-32 | an-351 |
| E1A2387 | sp-6 | an-352 | E1U2387 | sp-6 | an-352 | E1U9713 | sp-32 | an-352 |
| E1A2388 | sp-6 | an-353 | E1U2388 | sp-6 | an-353 | E1U9714 | sp-32 | an-353 |
| E1A2389 | sp-6 | an-354 | E1U2389 | sp-6 | an-354 | E1U9715 | sp-32 | an-354 |
| E1A2390 | sp-6 | an-355 | E1U2390 | sp-6 | an-355 | E1U9716 | sp-32 | an-355 |
| E1A2391 | sp-6 | an-356 | E1U2391 | sp-6 | an-356 | E1U9717 | sp-32 | an-356 |
| E1A2392 | sp-6 | an-357 | E1U2392 | sp-6 | an-357 | E1U9718 | sp-32 | an-357 |

-continued

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| E1A2393 | sp-6 | an-358 | E1U2393 | sp-6 | an-358 | E1U9719 | sp-32 | an-358 |
| E1A2394 | sp-6 | an-359 | E1U2394 | sp-6 | an-359 | E1U9720 | sp-32 | an-359 |
| E1A2395 | sp-6 | an-360 | E1U2395 | sp-6 | an-360 | E1U9721 | sp-32 | an-360 |
| E1A2396 | sp-6 | an-361 | E1U2396 | sp-6 | an-361 | E1U9722 | sp-32 | an-361 |
| E1A2397 | sp-6 | an-362 | E1U2397 | sp-6 | an-362 | E1U9723 | sp-32 | an-362 |
| E1A2398 | sp-6 | an-363 | E1U2398 | sp-6 | an-363 | E1U9724 | sp-32 | an-363 |
| E1A2399 | sp-6 | an-364 | E1U2399 | sp-6 | an-364 | E1U9725 | sp-32 | an-364 |
| E1A2400 | sp-6 | an-365 | E1U2400 | sp-6 | an-365 | E1U9726 | sp-32 | an-365 |
| E1A2401 | sp-6 | an-366 | E1U2401 | sp-6 | an-366 | E1U9727 | sp-32 | an-366 |
| E1A2402 | sp-6 | an-367 | E1U2402 | sp-6 | an-367 | E1U9728 | sp-32 | an-367 |
| E1A2403 | sp-6 | an-368 | E1U2403 | sp-6 | an-368 | E1U9729 | sp-32 | an-368 |
| E1A2404 | sp-6 | an-369 | E1U2404 | sp-6 | an-369 | E1U9730 | sp-32 | an-369 |
| E1A2405 | sp-6 | an-370 | E1U2405 | sp-6 | an-370 | E1U9731 | sp-32 | an-370 |
| E1A2406 | sp-6 | an-371 | E1U2406 | sp-6 | an-371 | E1U9732 | sp-32 | an-371 |
| E1A2407 | sp-6 | an-372 | E1U2407 | sp-6 | an-372 | E1U9733 | sp-32 | an-372 |
| E1A2408 | sp-6 | an-373 | E1U2408 | sp-6 | an-373 | E1U9734 | sp-32 | an-373 |
| E1A2409 | sp-6 | an-374 | E1U2409 | sp-6 | an-374 | E1U9735 | sp-32 | an-374 |
| E1A2410 | sp-6 | an-375 | E1U2410 | sp-6 | an-375 | E1U9736 | sp-32 | an-375 |
| E1A2411 | sp-6 | an-376 | E1U2411 | sp-6 | an-376 | E1U9737 | sp-32 | an-376 |
| E1A2412 | sp-6 | an-377 | E1U2412 | sp-6 | an-377 | E1U9738 | sp-32 | an-377 |
| E1A2413 | sp-6 | an-378 | E1U2413 | sp-6 | an-378 | E1U9739 | sp-32 | an-378 |
| E1A2414 | sp-6 | an-379 | E1U2414 | sp-6 | an-379 | E1U9740 | sp-32 | an-379 |
| E1A2415 | sp-6 | an-380 | E1U2415 | sp-6 | an-380 | E1U9741 | sp-32 | an-380 |
| E1A2416 | sp-6 | an-381 | E1U2416 | sp-6 | an-381 | E1U9742 | sp-32 | an-381 |
| E1A2417 | sp-6 | an-382 | E1U2417 | sp-6 | an-382 | E1U9743 | sp-32 | an-382 |
| E1A2418 | sp-6 | an-383 | E1U2418 | sp-6 | an-383 | E1U9744 | sp-32 | an-383 |
| E1A2419 | sp-6 | an-384 | E1U2419 | sp-6 | an-384 | E1U9745 | sp-32 | an-384 |
| E1A2420 | sp-6 | an-385 | E1U2420 | sp-6 | an-385 | E1U9746 | sp-32 | an-385 |
| E1A2421 | sp-6 | an-386 | E1U2421 | sp-6 | an-386 | E1U9747 | sp-32 | an-386 |
| E1A2422 | sp-6 | an-387 | E1U2422 | sp-6 | an-387 | E1U9748 | sp-32 | an-387 |
| E1A2423 | sp-6 | an-388 | E1U2423 | sp-6 | an-388 | E1U9749 | sp-32 | an-388 |
| E1A2424 | sp-6 | an-389 | E1U2424 | sp-6 | an-389 | E1U9750 | sp-32 | an-389 |
| E1A2425 | sp-6 | an-390 | E1U2425 | sp-6 | an-390 | E1U9751 | sp-32 | an-390 |
| E1A2426 | sp-6 | an-391 | E1U2426 | sp-6 | an-391 | E1U9752 | sp-32 | an-391 |
| E1A2427 | sp-6 | an-392 | E1U2427 | sp-6 | an-392 | E1U9753 | sp-32 | an-392 |
| E1A2428 | sp-6 | an-393 | E1U2428 | sp-6 | an-393 | E1U9754 | sp-32 | an-393 |
| E1A2429 | sp-6 | an-394 | E1U2429 | sp-6 | an-394 | E1U9755 | sp-32 | an-394 |
| E1A2430 | sp-6 | an-395 | E1U2430 | sp-6 | an-395 | E1U9756 | sp-32 | an-395 |

Table 1-46

| Y = NHCS | | | Y = NHCSNH | | | Y = NHCSNH | | |
|---|---|---|---|---|---|---|---|---|
| E1A2431 | sp-6 | an-396 | E1U2431 | sp-6 | an-396 | E1U9757 | sp-32 | an-396 |
| E1A2432 | sp-6 | an-397 | E1U2432 | sp-6 | an-397 | E1U9758 | sp-32 | an-397 |
| E1A2433 | sp-6 | an-398 | E1U2433 | sp-6 | an-398 | E1U9759 | sp-32 | an-398 |
| E1A2434 | sp-6 | an-399 | E1U2434 | sp-6 | an-399 | E1U9760 | sp-32 | an-399 |
| E1A2435 | sp-6 | an-400 | E1U2435 | sp-6 | an-400 | E1U9761 | sp-32 | an-400 |
| E1A2436 | sp-6 | an-401 | E1U2436 | sp-6 | an-401 | E1U9762 | sp-32 | an-401 |
| E1A2437 | sp-6 | an-402 | E1U2437 | sp-6 | an-402 | E1U9763 | sp-32 | an-402 |
| E1A2438 | sp-6 | an-403 | E1U2438 | sp-6 | an-403 | E1U9764 | sp-32 | an-403 |
| E1A2439 | sp-6 | an-404 | E1U2439 | sp-6 | an-404 | E1U9765 | sp-32 | an-404 |
| E1A2440 | sp-6 | an-405 | E1U2440 | sp-6 | an-405 | E1U9766 | sp-32 | an-405 |
| E1A2441 | sp-6 | an-406 | E1U2441 | sp-6 | an-406 | E1U9767 | sp-32 | an-406 |
| E1A2442 | sp-6 | an-407 | E1U2442 | sp-6 | an-407 | E1U9768 | sp-32 | an-407 |
| E1A2443 | sp-7 | an-1 | E1U2443 | sp-7 | an-1 | E1U9769 | sp-33 | an-1 |
| E1A2444 | sp-7 | an-2 | E1U2444 | sp-7 | an-2 | E1U9770 | sp-33 | an-2 |
| E1A2445 | sp-7 | an-3 | E1U2445 | sp-7 | an-3 | E1U9771 | sp-33 | an-3 |
| E1A2446 | sp-7 | an-4 | E1U2446 | sp-7 | an-4 | E1U9772 | sp-33 | an-4 |
| E1A2447 | sp-7 | an-5 | E1U2447 | sp-7 | an-5 | E1U9773 | sp-33 | an-5 |
| E1A2448 | sp-7 | an-6 | E1U2448 | sp-7 | an-6 | E1U9774 | sp-33 | an-6 |
| E1A2449 | sp-7 | an-7 | E1U2449 | sp-7 | an-7 | E1U9775 | sp-33 | an-7 |
| E1A2450 | sp-7 | an-8 | E1U2450 | sp-7 | an-8 | E1U9776 | sp-33 | an-8 |
| E1A2451 | sp-7 | an-9 | E1U2451 | sp-7 | an-9 | E1U9777 | sp-33 | an-9 |
| E1A2452 | sp-7 | an-10 | E1U2452 | sp-7 | an-10 | E1U9778 | sp-33 | an-10 |
| E1A2453 | sp-7 | an-11 | E1U2453 | sp-7 | an-11 | E1U9779 | sp-33 | an-11 |
| E1A2454 | sp-7 | an-12 | E1U2454 | sp-7 | an-12 | E1U9780 | sp-33 | an-12 |
| E1A2455 | sp-7 | an-13 | E1U2455 | sp-7 | an-13 | E1U9781 | sp-33 | an-13 |
| E1A2456 | sp-7 | an-14 | E1U2456 | sp-7 | an-14 | E1U9782 | sp-33 | an-14 |
| E1A2457 | sp-7 | an-15 | E1U2457 | sp-7 | an-15 | E1U9783 | sp-33 | an-15 |
| E1A2458 | sp-7 | an-16 | E1U2458 | sp-7 | an-16 | E1U9784 | sp-33 | an-16 |
| E1A2459 | sp-7 | an-17 | E1U2459 | sp-7 | an-17 | E1U9785 | sp-33 | an-17 |
| E1A2460 | sp-7 | an-18 | E1U2460 | sp-7 | an-18 | E1U9786 | sp-33 | an-18 |
| E1A2461 | sp-7 | an-19 | E1U2461 | sp-7 | an-19 | E1U9787 | sp-33 | an-19 |
| E1A2462 | sp-7 | an-20 | E1U2462 | sp-7 | an-20 | E1U9788 | sp-33 | an-20 |
| E1A2463 | sp-7 | an-21 | E1U2463 | sp-7 | an-21 | E1U9789 | sp-33 | an-21 |
| E1A2464 | sp-7 | an-22 | E1U2464 | sp-7 | an-22 | E1U9790 | sp-33 | an-22 |
| E1A2465 | sp-7 | an-23 | E1U2465 | sp-7 | an-23 | E1U9791 | sp-33 | an-23 |
| E1A2466 | sp-7 | an-24 | E1U2466 | sp-7 | an-24 | E1U9792 | sp-33 | an-24 |

-continued

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| E1A2467 | sp-7 | an-25 | E1U2467 | sp-7 | an-25 | E1U9793 | sp-33 | an-25 |
| E1A2468 | sp-7 | an-26 | E1U2468 | sp-7 | an-26 | E1U9794 | sp-33 | an-26 |
| E1A2469 | sp-7 | an-27 | E1U2469 | sp-7 | an-27 | E1U9795 | sp-33 | an-27 |
| E1A2470 | sp-7 | an-28 | E1U2470 | sp-7 | an-28 | E1U9796 | sp-33 | an-28 |
| E1A2471 | sp-7 | an-29 | E1U2471 | sp-7 | an-29 | E1U9797 | sp-33 | an-29 |
| E1A2472 | sp-7 | an-30 | E1U2472 | sp-7 | an-30 | E1U9798 | sp-33 | an-30 |
| E1A2473 | sp-7 | an-31 | E1U2473 | sp-7 | an-31 | E1U9799 | sp-33 | an-31 |
| E1A2474 | sp-7 | an-32 | E1U2474 | sp-7 | an-32 | E1U9800 | sp-33 | an-32 |
| E1A2475 | sp-7 | an-33 | E1U2475 | sp-7 | an-33 | E1U9801 | sp-33 | an-33 |
| E1A2476 | sp-7 | an-34 | E1U2476 | sp-7 | an-34 | E1U9802 | sp-33 | an-34 |
| E1A2477 | sp-7 | an-35 | E1U2477 | sp-7 | an-35 | E1U9803 | sp-33 | an-35 |
| E1A2478 | sp-7 | an-36 | E1U2478 | sp-7 | an-36 | E1U9804 | sp-33 | an-36 |
| E1A2479 | sp-7 | an-37 | E1U2479 | sp-7 | an-37 | E1U9805 | sp-33 | an-37 |
| E1A2480 | sp-7 | an-38 | E1U2480 | sp-7 | an-38 | E1U9806 | sp-33 | an-38 |
| E1A2481 | sp-7 | an-39 | E1U2481 | sp-7 | an-39 | E1U9807 | sp-33 | an-39 |
| E1A2482 | sp-7 | an-40 | E1U2482 | sp-7 | an-40 | E1U9808 | sp-33 | an-40 |
| E1A2483 | sp-7 | an-41 | E1U2483 | sp-7 | an-41 | E1U9809 | sp-33 | an-41 |
| E1A2484 | sp-7 | an-42 | E1U2484 | sp-7 | an-42 | E1U9810 | sp-33 | an-42 |

Table 1-47

| Y = NHCS | | | Y = NHCSNH | | | Y = NHCSNH | | |
|---|---|---|---|---|---|---|---|---|
| E1A2485 | sp-7 | an-43 | E1U2485 | sp-7 | an-43 | E1U9811 | sp-33 | an-43 |
| E1A2486 | sp-7 | an-44 | E1U2486 | sp-7 | an-44 | E1U9812 | sp-33 | an-44 |
| E1A2487 | sp-7 | an-45 | E1U2487 | sp-7 | an-45 | E1U9813 | sp-33 | an-45 |
| E1A2488 | sp-7 | an-46 | E1U2488 | sp-7 | an-46 | E1U9814 | sp-33 | an-46 |
| E1A2489 | sp-7 | an-47 | E1U2489 | sp-7 | an-47 | E1U9815 | sp-33 | an-47 |
| E1A2490 | sp-7 | an-48 | E1U2490 | sp-7 | an-48 | E1U9816 | sp-33 | an-48 |
| E1A2491 | sp-7 | an-49 | E1U2491 | sp-7 | an-49 | E1U9817 | sp-33 | an-49 |
| E1A2492 | sp-7 | an-50 | E1U2492 | sp-7 | an-50 | E1U9818 | sp-33 | an-50 |
| E1A2493 | sp-7 | an-51 | E1U2493 | sp-7 | an-51 | E1U9819 | sp-33 | an-51 |
| E1A2494 | sp-7 | an-52 | E1U2494 | sp-7 | an-52 | E1U9820 | sp-33 | an-52 |
| E1A2495 | sp-7 | an-53 | E1U2495 | sp-7 | an-53 | E1U9821 | sp-33 | an-53 |
| E1A2496 | sp-7 | an-54 | E1U2496 | sp-7 | an-54 | E1U9822 | sp-33 | an-54 |
| E1A2497 | sp-7 | an-55 | E1U2497 | sp-7 | an-55 | E1U9823 | sp-33 | an-55 |
| E1A2498 | sp-7 | an-56 | E1U2498 | sp-7 | an-56 | E1U9824 | sp-33 | an-56 |
| E1A2499 | sp-7 | an-57 | E1U2499 | sp-7 | an-57 | E1U9825 | sp-33 | an-57 |
| E1A2500 | sp-7 | an-58 | E1U2500 | sp-7 | an-58 | E1U9826 | sp-33 | an-58 |
| E1A2501 | sp-7 | an-59 | E1U2501 | sp-7 | an-59 | E1U9827 | sp-33 | an-59 |
| E1A2502 | sp-7 | an-60 | E1U2502 | sp-7 | an-60 | E1U9828 | sp-33 | an-60 |
| E1A2503 | sp-7 | an-61 | E1U2503 | sp-7 | an-61 | E1U9829 | sp-33 | an-61 |
| E1A2504 | sp-7 | an-62 | E1U2504 | sp-7 | an-62 | E1U9830 | sp-33 | an-62 |
| E1A2505 | sp-7 | an-63 | E1U2505 | sp-7 | an-63 | E1U9831 | sp-33 | an-63 |
| E1A2506 | sp-7 | an-64 | E1U2506 | sp-7 | an-64 | E1U9832 | sp-33 | an-64 |
| E1A2507 | sp-7 | an-65 | E1U2507 | sp-7 | an-65 | E1U9833 | sp-33 | an-65 |
| E1A2508 | sp-7 | an-66 | E1U2508 | sp-7 | an-66 | E1U9834 | sp-33 | an-66 |
| E1A2509 | sp-7 | an-67 | E1U2509 | sp-7 | an-67 | E1U9835 | sp-33 | an-67 |
| E1A2510 | sp-7 | an-68 | E1U2510 | sp-7 | an-68 | E1U9836 | sp-33 | an-68 |
| E1A2511 | sp-7 | an-69 | E1U2511 | sp-7 | an-69 | E1U9837 | sp-33 | an-69 |
| E1A2512 | sp-7 | an-70 | E1U2512 | sp-7 | an-70 | E1U9838 | sp-33 | an-70 |
| E1A2513 | sp-7 | an-71 | E1U2513 | sp-7 | an-71 | E1U9839 | sp-33 | an-71 |
| E1A2514 | sp-7 | an-72 | E1U2514 | sp-7 | an-72 | E1U9840 | sp-33 | an-72 |
| E1A2515 | sp-7 | an-73 | E1U2515 | sp-7 | an-73 | E1U9841 | sp-33 | an-73 |
| E1A2516 | sp-7 | an-74 | E1U2516 | sp-7 | an-74 | E1U9842 | sp-33 | an-74 |
| E1A2517 | sp-7 | an-75 | E1U2517 | sp-7 | an-75 | E1U9843 | sp-33 | an-75 |
| E1A2518 | sp-7 | an-76 | E1U2518 | sp-7 | an-76 | E1U9844 | sp-33 | an-76 |
| E1A2519 | sp-7 | an-77 | E1U2519 | sp-7 | an-77 | E1U9845 | sp-33 | an-77 |
| E1A2520 | sp-7 | an-78 | E1U2520 | sp-7 | an-78 | E1U9846 | sp-33 | an-78 |
| E1A2521 | sp-7 | an-79 | E1U2521 | sp-7 | an-79 | E1U9847 | sp-33 | an-79 |
| E1A2522 | sp-7 | an-80 | E1U2522 | sp-7 | an-80 | E1U9848 | sp-33 | an-80 |
| E1A2523 | sp-7 | an-81 | E1U2523 | sp-7 | an-81 | E1U9849 | sp-33 | an-81 |
| E1A2524 | sp-7 | an-82 | E1U2524 | sp-7 | an-82 | E1U9850 | sp-33 | an-82 |
| E1A2525 | sp-7 | an-83 | E1U2525 | sp-7 | an-83 | E1U9851 | sp-33 | an-83 |
| E1A2526 | sp-7 | an-84 | E1U2526 | sp-7 | an-84 | E1U9852 | sp-33 | an-84 |
| E1A2527 | sp-7 | an-85 | E1U2527 | sp-7 | an-85 | E1U9853 | sp-33 | an-85 |
| E1A2528 | sp-7 | an-86 | E1U2528 | sp-7 | an-86 | E1U9854 | sp-33 | an-86 |
| E1A2529 | sp-7 | an-87 | E1U2529 | sp-7 | an-87 | E1U9855 | sp-33 | an-87 |
| E1A2530 | sp-7 | an-88 | E1U2530 | sp-7 | an-88 | E1U9856 | sp-33 | an-88 |
| E1A2531 | sp-7 | an-89 | E1U2531 | sp-7 | an-89 | E1U9857 | sp-33 | an-89 |
| E1A2532 | sp-7 | an-90 | E1U2532 | sp-7 | an-90 | E1U9858 | sp-33 | an-90 |
| E1A2533 | sp-7 | an-91 | E1U2533 | sp-7 | an-91 | E1U9859 | sp-33 | an-91 |
| E1A2534 | sp-7 | an-92 | E1U2534 | sp-7 | an-92 | E1U9860 | sp-33 | an-92 |
| E1A2535 | sp-7 | an-93 | E1U2535 | sp-7 | an-93 | E1U9861 | sp-33 | an-93 |
| E1A2536 | sp-7 | an-94 | E1U2536 | sp-7 | an-94 | E1U9862 | sp-33 | an-94 |
| E1A2537 | sp-7 | an-95 | E1U2537 | sp-7 | an-95 | E1U9863 | sp-33 | an-95 |
| E1A2538 | sp-7 | an-96 | E1U2538 | sp-7 | an-96 | E1U9864 | sp-33 | an-96 |

-continued

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| | | | | Table 1-48 | | | | |
| | Y = NHCS | | | Y = NHCSNH | | | Y = NHCSNH | |
| E1A2539 | sp-7 | an-97 | E1U2539 | sp-7 | an-97 | E1U9865 | sp-33 | an-97 |
| E1A2540 | sp-7 | an-98 | E1U2540 | sp-7 | an-98 | E1U9866 | sp-33 | an-98 |
| E1A2541 | sp-7 | an-99 | E1U2541 | sp-7 | an-99 | E1U9867 | sp-33 | an-99 |
| E1A2542 | sp-7 | an-100 | E1U2542 | sp-7 | an-100 | E1U9868 | sp-33 | an-100 |
| E1A2543 | sp-7 | an-101 | E1U2543 | sp-7 | an-101 | E1U9869 | sp-33 | an-101 |
| E1A2544 | sp-7 | an-102 | E1U2544 | sp-7 | an-102 | E1U9870 | sp-33 | an-102 |
| E1A2545 | sp-7 | an-103 | E1U2545 | sp-7 | an-103 | E1U9871 | sp-33 | an-103 |
| E1A2546 | sp-7 | an-104 | E1U2546 | sp-7 | an-104 | E1U9872 | sp-33 | an-104 |
| E1A2547 | sp-7 | an-105 | E1U2547 | sp-7 | an-105 | E1U9873 | sp-33 | an-105 |
| E1A2548 | sp-7 | an-106 | E1U2548 | sp-7 | an-106 | E1U9874 | sp-33 | an-106 |
| E1A2549 | sp-7 | an-107 | E1U2549 | sp-7 | an-107 | E1U9875 | sp-33 | an-107 |
| E1A2550 | sp-7 | an-108 | E1U2550 | sp-7 | an-108 | E1U9876 | sp-33 | an-108 |
| E1A2551 | sp-7 | an-109 | E1U2551 | sp-7 | an-109 | E1U9877 | sp-33 | an-109 |
| E1A2552 | sp-7 | an-110 | E1U2552 | sp-7 | an-110 | E1U9878 | sp-33 | an-110 |
| E1A2553 | sp-7 | an-111 | E1U2553 | sp-7 | an-111 | E1U9879 | sp-33 | an-111 |
| E1A2554 | sp-7 | an-112 | E1U2554 | sp-7 | an-112 | E1U9880 | sp-33 | an-112 |
| E1A2555 | sp-7 | an-113 | E1U2555 | sp-7 | an-113 | E1U9881 | sp-33 | an-113 |
| E1A2556 | sp-7 | an-114 | E1U2556 | sp-7 | an-114 | E1U9882 | sp-33 | an-114 |
| E1A2557 | sp-7 | an-115 | E1U2557 | sp-7 | an-115 | E1U9883 | sp-33 | an-115 |
| E1A2558 | sp-7 | an-116 | E1U2558 | sp-7 | an-116 | E1U9884 | sp-33 | an-116 |
| E1A2559 | sp-7 | an-117 | E1U2559 | sp-7 | an-117 | E1U9885 | sp-33 | an-117 |
| E1A2560 | sp-7 | an-118 | E1U2560 | sp-7 | an-118 | E1U9886 | sp-33 | an-118 |
| E1A2561 | sp-7 | an-119 | E1U2561 | sp-7 | an-119 | E1U9887 | sp-33 | an-119 |
| E1A2562 | sp-7 | an-120 | E1U2562 | sp-7 | an-120 | E1U9888 | sp-33 | an-120 |
| E1A2563 | sp-7 | an-121 | E1U2563 | sp-7 | an-121 | E1U9889 | sp-33 | an-121 |
| E1A2564 | sp-7 | an-122 | E1U2564 | sp-7 | an-122 | E1U9890 | sp-33 | an-122 |
| E1A2565 | sp-7 | an-123 | E1U2565 | sp-7 | an-123 | E1U9891 | sp-33 | an-123 |
| E1A2566 | sp-7 | an-124 | E1U2566 | sp-7 | an-124 | E1U9892 | sp-33 | an-124 |
| E1A2567 | sp-7 | an-125 | E1U2567 | sp-7 | an-125 | E1U9893 | sp-33 | an-125 |
| E1A2568 | sp-7 | an-126 | E1U2568 | sp-7 | an-126 | E1U9894 | sp-33 | an-126 |
| E1A2569 | sp-7 | an-127 | E1U2569 | sp-7 | an-127 | E1U9895 | sp-33 | an-127 |
| E1A2570 | sp-7 | an-128 | E1U2570 | sp-7 | an-128 | E1U9896 | sp-33 | an-128 |
| E1A2571 | sp-7 | an-129 | E1U2571 | sp-7 | an-129 | E1U9897 | sp-33 | an-129 |
| E1A2572 | sp-7 | an-130 | E1U2572 | sp-7 | an-130 | E1U9898 | sp-33 | an-130 |
| E1A2573 | sp-7 | an-131 | E1U2573 | sp-7 | an-131 | E1U9899 | sp-33 | an-131 |
| E1A2574 | sp-7 | an-132 | E1U2574 | sp-7 | an-132 | E1U9900 | sp-33 | an-132 |
| E1A2575 | sp-7 | an-133 | E1U2575 | sp-7 | an-133 | E1U9901 | sp-33 | an-133 |
| E1A2576 | sp-7 | an-134 | E1U2576 | sp-7 | an-134 | E1U9902 | sp-33 | an-134 |
| E1A2577 | sp-7 | an-135 | E1U2577 | sp-7 | an-135 | E1U9903 | sp-33 | an-135 |
| E1A2578 | sp-7 | an-136 | E1U2578 | sp-7 | an-136 | E1U9904 | sp-33 | an-136 |
| E1A2579 | sp-7 | an-137 | E1U2579 | sp-7 | an-137 | E1U9905 | sp-33 | an-137 |
| E1A2580 | sp-7 | an-138 | E1U2580 | sp-7 | an-138 | E1U9906 | sp-33 | an-138 |
| E1A2581 | sp-7 | an-139 | E1U2581 | sp-7 | an-139 | E1U9907 | sp-33 | an-139 |
| E1A2582 | sp-7 | an-140 | E1U2582 | sp-7 | an-140 | E1U9908 | sp-33 | an-140 |
| E1A2583 | sp-7 | an-141 | E1U2583 | sp-7 | an-141 | E1U9909 | sp-33 | an-141 |
| E1A2584 | sp-7 | an-142 | E1U2584 | sp-7 | an-142 | E1U9910 | sp-33 | an-142 |
| E1A2585 | sp-7 | an-143 | E1U2585 | sp-7 | an-143 | E1U9911 | sp-33 | an-143 |
| E1A2586 | sp-7 | an-144 | E1U2586 | sp-7 | an-144 | E1U9912 | sp-33 | an-144 |
| E1A2587 | sp-7 | an-145 | E1U2587 | sp-7 | an-145 | E1U9913 | sp-33 | an-145 |
| E1A2588 | sp-7 | an-146 | E1U2588 | sp-7 | an-146 | E1U9914 | sp-33 | an-146 |
| E1A2589 | sp-7 | an-147 | E1U2589 | sp-7 | an-147 | E1U9915 | sp-33 | an-147 |
| E1A2590 | sp-7 | an-148 | E1U2590 | sp-7 | an-148 | E1U9916 | sp-33 | an-148 |
| E1A2591 | sp-7 | an-149 | E1U2591 | sp-7 | an-149 | E1U9917 | sp-33 | an-149 |
| E1A2592 | sp-7 | an-150 | E1U2592 | sp-7 | an-150 | E1U9918 | sp-33 | an-150 |
| | | | | Table 1-49 | | | | |
| | Y = NHCS | | | Y = NHCSNH | | | Y = NHCSNH | |
| E1A2593 | sp-7 | an-151 | E1U2593 | sp-7 | an-151 | E1U9919 | sp-33 | an-151 |
| E1A2594 | sp-7 | an-152 | E1U2594 | sp-7 | an-152 | E1U9920 | sp-33 | an-152 |
| E1A2595 | sp-7 | an-153 | E1U2595 | sp-7 | an-153 | E1U9921 | sp-33 | an-153 |
| E1A2596 | sp-7 | an-154 | E1U2596 | sp-7 | an-154 | E1U9922 | sp-33 | an-154 |
| E1A2597 | sp-7 | an-155 | E1U2597 | sp-7 | an-155 | E1U9923 | sp-33 | an-155 |
| E1A2598 | sp-7 | an-156 | E1U2598 | sp-7 | an-156 | E1U9924 | sp-33 | an-156 |
| E1A2599 | sp-7 | an-157 | E1U2599 | sp-7 | an-157 | E1U9925 | sp-33 | an-157 |
| E1A2600 | sp-7 | an-158 | E1U2600 | sp-7 | an-158 | E1U9926 | sp-33 | an-158 |
| E1A2601 | sp-7 | an-159 | E1U2601 | sp-7 | an-159 | E1U9927 | sp-33 | an-159 |
| E1A2602 | sp-7 | an-160 | E1U2602 | sp-7 | an-160 | E1U9928 | sp-33 | an-160 |
| E1A2603 | sp-7 | an-161 | E1U2603 | sp-7 | an-161 | E1U9929 | sp-33 | an-161 |
| E1A2604 | sp-7 | an-162 | E1U2604 | sp-7 | an-162 | E1U9930 | sp-33 | an-162 |
| E1A2605 | sp-7 | an-163 | E1U2605 | sp-7 | an-163 | E1U9931 | sp-33 | an-163 |
| E1A2606 | sp-7 | an-164 | E1U2606 | sp-7 | an-164 | E1U9932 | sp-33 | an-164 |
| E1A2607 | sp-7 | an-165 | E1U2607 | sp-7 | an-165 | E1U9933 | sp-33 | an-165 |
| E1A2608 | sp-7 | an-166 | E1U2608 | sp-7 | an-166 | E1U9934 | sp-33 | an-166 |

-continued

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| E1A2609 | sp-7 | an-167 | E1U2609 | sp-7 | an-167 | E1U9935 | sp-33 | an-167 |
| E1A2610 | sp-7 | an-168 | E1U2610 | sp-7 | an-168 | E1U9936 | sp-33 | an-168 |
| E1A2611 | sp-7 | an-169 | E1U2611 | sp-7 | an-169 | E1U9937 | sp-33 | an-169 |
| E1A2612 | sp-7 | an-170 | E1U2612 | sp-7 | an-170 | E1U9938 | sp-33 | an-170 |
| E1A2613 | sp-7 | an-171 | E1U2613 | sp-7 | an-171 | E1U9939 | sp-33 | an-171 |
| E1A2614 | sp-7 | an-172 | E1U2614 | sp-7 | an-172 | E1U9940 | sp-33 | an-172 |
| E1A2615 | sp-7 | an-173 | E1U2615 | sp-7 | an-173 | E1U9941 | sp-33 | an-173 |
| E1A2616 | sp-7 | an-174 | E1U2616 | sp-7 | an-174 | E1U9942 | sp-33 | an-174 |
| E1A2617 | sp-7 | an-175 | E1U2617 | sp-7 | an-175 | E1U9943 | sp-33 | an-175 |
| E1A2618 | sp-7 | an-176 | E1U2618 | sp-7 | an-176 | E1U9944 | sp-33 | an-176 |
| E1A2619 | sp-7 | an-177 | E1U2619 | sp-7 | an-177 | E1U9945 | sp-33 | an-177 |
| E1A2620 | sp-7 | an-178 | E1U2620 | sp-7 | an-178 | E1U9946 | sp-33 | an-178 |
| E1A2621 | sp-7 | an-179 | E1U2621 | sp-7 | an-179 | E1U9947 | sp-33 | an-179 |
| E1A2622 | sp-7 | an-180 | E1U2622 | sp-7 | an-180 | E1U9948 | sp-33 | an-180 |
| E1A2623 | sp-7 | an-181 | E1U2623 | sp-7 | an-181 | E1U9949 | sp-33 | an-181 |
| E1A2624 | sp-7 | an-182 | E1U2624 | sp-7 | an-182 | E1U9950 | sp-33 | an-182 |
| E1A2625 | sp-7 | an-183 | E1U2625 | sp-7 | an-183 | E1U9951 | sp-33 | an-183 |
| E1A2626 | sp-7 | an-184 | E1U2626 | sp-7 | an-184 | E1U9952 | sp-33 | an-184 |
| E1A2627 | sp-7 | an-185 | E1U2627 | sp-7 | an-185 | E1U9953 | sp-33 | an-185 |
| E1A2628 | sp-7 | an-186 | E1U2628 | sp-7 | an-186 | E1U9954 | sp-33 | an-186 |
| E1A2629 | sp-7 | an-187 | E1U2629 | sp-7 | an-187 | E1U9955 | sp-33 | an-187 |
| E1A2630 | sp-7 | an-188 | E1U2630 | sp-7 | an-188 | E1U9956 | sp-33 | an-188 |
| E1A2631 | sp-7 | an-189 | E1U2631 | sp-7 | an-189 | E1U9957 | sp-33 | an-189 |
| E1A2632 | sp-7 | an-190 | E1U2632 | sp-7 | an-190 | E1U9958 | sp-33 | an-190 |
| E1A2633 | sp-7 | an-191 | E1U2633 | sp-7 | an-191 | E1U9959 | sp-33 | an-191 |
| E1A2634 | sp-7 | an-192 | E1U2634 | sp-7 | an-192 | E1U9960 | sp-33 | an-192 |
| E1A2635 | sp-7 | an-193 | E1U2635 | sp-7 | an-193 | E1U9961 | sp-33 | an-193 |
| E1A2636 | sp-7 | an-194 | E1U2636 | sp-7 | an-194 | E1U9962 | sp-33 | an-194 |
| E1A2637 | sp-7 | an-195 | E1U2637 | sp-7 | an-195 | E1U9963 | sp-33 | an-195 |
| E1A2638 | sp-7 | an-196 | E1U2638 | sp-7 | an-196 | E1U9964 | sp-33 | an-196 |
| E1A2639 | sp-7 | an-197 | E1U2639 | sp-7 | an-197 | E1U9965 | sp-33 | an-197 |
| E1A2640 | sp-7 | an-198 | E1U2640 | sp-7 | an-198 | E1U9966 | sp-33 | an-198 |
| E1A2641 | sp-7 | an-199 | E1U2641 | sp-7 | an-199 | E1U9967 | sp-33 | an-199 |
| E1A2642 | sp-7 | an-200 | E1U2642 | sp-7 | an-200 | E1U9968 | sp-33 | an-200 |
| E1A2643 | sp-7 | an-201 | E1U2643 | sp-7 | an-201 | E1U9969 | sp-33 | an-201 |
| E1A2644 | sp-7 | an-202 | E1U2644 | sp-7 | an-202 | E1U9970 | sp-33 | an-202 |
| E1A2645 | sp-7 | an-203 | E1U2645 | sp-7 | an-203 | E1U9971 | sp-33 | an-203 |
| E1A2646 | sp-7 | an-204 | E1U2646 | sp-7 | an-204 | E1U9972 | sp-33 | an-204 |

Table 1-50

| Y = NHCS | | | Y = NHCSNH | | | Y = NHCSNH | | |
|---|---|---|---|---|---|---|---|---|
| E1A2647 | sp-7 | an-205 | E1U2647 | sp-7 | an-205 | E1U9973 | sp-33 | an-205 |
| E1A2648 | sp-7 | an-206 | E1U2648 | sp-7 | an-206 | E1U9974 | sp-33 | an-206 |
| E1A2649 | sp-7 | an-207 | E1U2649 | sp-7 | an-207 | E1U9975 | sp-33 | an-207 |
| E1A2650 | sp-7 | an-208 | E1U2650 | sp-7 | an-208 | E1U9976 | sp-33 | an-208 |
| E1A2651 | sp-7 | an-209 | E1U2651 | sp-7 | an-209 | E1U9977 | sp-33 | an-209 |
| E1A2652 | sp-7 | an-210 | E1U2652 | sp-7 | an-210 | E1U9978 | sp-33 | an-210 |
| E1A2653 | sp-7 | an-211 | E1U2653 | sp-7 | an-211 | E1U9979 | sp-33 | an-211 |
| E1A2654 | sp-7 | an-212 | E1U2654 | sp-7 | an-212 | E1U9980 | sp-33 | an-212 |
| E1A2655 | sp-7 | an-213 | E1U2655 | sp-7 | an-213 | E1U9981 | sp-33 | an-213 |
| E1A2656 | sp-7 | an-214 | E1U2656 | sp-7 | an-214 | E1U9982 | sp-33 | an-214 |
| E1A2657 | sp-7 | an-215 | E1U2657 | sp-7 | an-215 | E1U9983 | sp-33 | an-215 |
| E1A2658 | sp-7 | an-216 | E1U2658 | sp-7 | an-216 | E1U9984 | sp-33 | an-216 |
| E1A2659 | sp-7 | an-217 | E1U2659 | sp-7 | an-217 | E1U9985 | sp-33 | an-217 |
| E1A2660 | sp-7 | an-218 | E1U2660 | sp-7 | an-218 | E1U9986 | sp-33 | an-218 |
| E1A2661 | sp-7 | an-219 | E1U2661 | sp-7 | an-219 | E1U9987 | sp-33 | an-219 |
| E1A2662 | sp-7 | an-220 | E1U2662 | sp-7 | an-220 | E1U9988 | sp-33 | an-220 |
| E1A2663 | sp-7 | an-221 | E1U2663 | sp-7 | an-221 | E1U9989 | sp-33 | an-221 |
| E1A2664 | sp-7 | an-222 | E1U2664 | sp-7 | an-222 | E1U9990 | sp-33 | an-222 |
| E1A2665 | sp-7 | an-223 | E1U2665 | sp-7 | an-223 | E1U9991 | sp-33 | an-223 |
| E1A2666 | sp-7 | an-224 | E1U2666 | sp-7 | an-224 | E1U9992 | sp-33 | an-224 |
| E1A2667 | sp-7 | an-225 | E1U2667 | sp-7 | an-225 | E1U9993 | sp-33 | an-225 |
| E1A2668 | sp-7 | an-226 | E1U2668 | sp-7 | an-226 | E1U9994 | sp-33 | an-226 |
| E1A2669 | sp-7 | an-227 | E1U2669 | sp-7 | an-227 | E1U9995 | sp-33 | an-227 |
| E1A2670 | sp-7 | an-228 | E1U2670 | sp-7 | an-228 | E1U9996 | sp-33 | an-228 |
| E1A2671 | sp-7 | an-229 | E1U2671 | sp-7 | an-229 | E1U9997 | sp-33 | an-229 |
| E1A2672 | sp-7 | an-230 | E1U2672 | sp-7 | an-230 | E1U9998 | sp-33 | an-230 |
| E1A2673 | sp-7 | an-231 | E1U2673 | sp-7 | an-231 | E1U9999 | sp-33 | an-231 |
| E1A2674 | sp-7 | an-232 | E1U2674 | sp-7 | an-232 | E1U10000 | sp-33 | an-232 |
| E1A2675 | sp-7 | an-233 | E1U2675 | sp-7 | an-233 | E1U10001 | sp-33 | an-233 |
| E1A2676 | sp-7 | an-234 | E1U2676 | sp-7 | an-234 | E1U10002 | sp-33 | an-234 |
| E1A2677 | sp-7 | an-235 | E1U2677 | sp-7 | an-235 | E1U10003 | sp-33 | an-235 |
| E1A2678 | sp-7 | an-236 | E1U2678 | sp-7 | an-236 | E1U10004 | sp-33 | an-236 |
| E1A2679 | sp-7 | an-237 | E1U2679 | sp-7 | an-237 | E1U10005 | sp-33 | an-237 |
| E1A2680 | sp-7 | an-238 | E1U2680 | sp-7 | an-238 | E1U10006 | sp-33 | an-238 |
| E1A2681 | sp-7 | an-239 | E1U2681 | sp-7 | an-239 | E1U10007 | sp-33 | an-239 |
| E1A2682 | sp-7 | an-240 | E1U2682 | sp-7 | an-240 | E1U10008 | sp-33 | an-240 |

-continued

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| E1A2683 | sp-7 | an-241 | E1U2683 | sp-7 | an-241 | E1U10009 | sp-33 | an-241 |
| E1A2684 | sp-7 | an-242 | E1U2684 | sp-7 | an-242 | E1U10010 | sp-33 | an-242 |
| E1A2685 | sp-7 | an-243 | E1U2685 | sp-7 | an-243 | E1U10011 | sp-33 | an-243 |
| E1A2686 | sp-7 | an-244 | E1U2686 | sp-7 | an-244 | E1U10012 | sp-33 | an-244 |
| E1A2687 | sp-7 | an-245 | E1U2687 | sp-7 | an-245 | E1U10013 | sp-33 | an-245 |
| E1A2688 | sp-7 | an-246 | E1U2688 | sp-7 | an-246 | E1U10014 | sp-33 | an-246 |
| E1A2689 | sp-7 | an-247 | E1U2689 | sp-7 | an-247 | E1U10015 | sp-33 | an-247 |
| E1A2690 | sp-7 | an-248 | E1U2690 | sp-7 | an-248 | E1U10016 | sp-33 | an-248 |
| E1A2691 | sp-7 | an-249 | E1U2691 | sp-7 | an-249 | E1U10017 | sp-33 | an-249 |
| E1A2692 | sp-7 | an-250 | E1U2692 | sp-7 | an-250 | E1U10018 | sp-33 | an-250 |
| E1A2693 | sp-7 | an-251 | E1U2693 | sp-7 | an-251 | E1U10019 | sp-33 | an-251 |
| E1A2694 | sp-7 | an-252 | E1U2694 | sp-7 | an-252 | E1U10020 | sp-33 | an-252 |
| E1A2695 | sp-7 | an-253 | E1U2695 | sp-7 | an-253 | E1U10021 | sp-33 | an-253 |
| E1A2696 | sp-7 | an-254 | E1U2696 | sp-7 | an-254 | E1U10022 | sp-33 | an-254 |
| E1A2697 | sp-7 | an-255 | E1U2697 | sp-7 | an-255 | E1U10023 | sp-33 | an-255 |
| E1A2698 | sp-7 | an-256 | E1U2698 | sp-7 | an-256 | E1U10024 | sp-33 | an-256 |
| E1A2699 | sp-7 | an-257 | E1U2699 | sp-7 | an-257 | E1U10025 | sp-33 | an-257 |
| E1A2700 | sp-7 | an-258 | E1U2700 | sp-7 | an-258 | E1U10026 | sp-33 | an-258 |

Table 1-51

| Y = NHCS | | | Y = NHCSNH | | | Y = NHCSNH | | |
|---|---|---|---|---|---|---|---|---|
| E1A2701 | sp-7 | an-259 | E1U2701 | sp-7 | an-259 | E1U10027 | sp-33 | an-259 |
| E1A2702 | sp-7 | an-260 | E1U2702 | sp-7 | an-260 | E1U10028 | sp-33 | an-260 |
| E1A2703 | sp-7 | an-261 | E1U2703 | sp-7 | an-261 | E1U10029 | sp-33 | an-261 |
| E1A2704 | sp-7 | an-262 | E1U2704 | sp-7 | an-262 | E1U10030 | sp-33 | an-262 |
| E1A2705 | sp-7 | an-263 | E1U2705 | sp-7 | an-263 | E1U10031 | sp-33 | an-263 |
| E1A2706 | sp-7 | an-264 | E1U2706 | sp-7 | an-264 | E1U10032 | sp-33 | an-264 |
| E1A2707 | sp-7 | an-265 | E1U2707 | sp-7 | an-265 | E1U10033 | sp-33 | an-265 |
| E1A2708 | sp-7 | an-266 | E1U2708 | sp-7 | an-266 | E1U10034 | sp-33 | an-266 |
| E1A2709 | sp-7 | an-267 | E1U2709 | sp-7 | an-267 | E1U10035 | sp-33 | an-267 |
| E1A2710 | sp-7 | an-268 | E1U2710 | sp-7 | an-268 | E1U10036 | sp-33 | an-268 |
| E1A2711 | sp-7 | an-269 | E1U2711 | sp-7 | an-269 | E1U10037 | sp-33 | an-269 |
| E1A2712 | sp-7 | an-270 | E1U2712 | sp-7 | an-270 | E1U10038 | sp-33 | an-270 |
| E1A2713 | sp-7 | an-271 | E1U2713 | sp-7 | an-271 | E1U10039 | sp-33 | an-271 |
| E1A2714 | sp-7 | an-272 | E1U2714 | sp-7 | an-272 | E1U10040 | sp-33 | an-272 |
| E1A2715 | sp-7 | an-273 | E1U2715 | sp-7 | an-273 | E1U10041 | sp-33 | an-273 |
| E1A2716 | sp-7 | an-274 | E1U2716 | sp-7 | an-274 | E1U10042 | sp-33 | an-274 |
| E1A2717 | sp-7 | an-275 | E1U2717 | sp-7 | an-275 | E1U10043 | sp-33 | an-275 |
| E1A2718 | sp-7 | an-276 | E1U2718 | sp-7 | an-276 | E1U10044 | sp-33 | an-276 |
| E1A2719 | sp-7 | an-277 | E1U2719 | sp-7 | an-277 | E1U10045 | sp-33 | an-277 |
| E1A2720 | sp-7 | an-278 | E1U2720 | sp-7 | an-278 | E1U10046 | sp-33 | an-278 |
| E1A2721 | sp-7 | an-279 | E1U2721 | sp-7 | an-279 | E1U10047 | sp-33 | an-279 |
| E1A2722 | sp-7 | an-280 | E1U2722 | sp-7 | an-280 | E1U10048 | sp-33 | an-280 |
| E1A2723 | sp-7 | an-281 | E1U2723 | sp-7 | an-281 | E1U10049 | sp-33 | an-281 |
| E1A2724 | sp-7 | an-282 | E1U2724 | sp-7 | an-282 | E1U10050 | sp-33 | an-282 |
| E1A2725 | sp-7 | an-283 | E1U2725 | sp-7 | an-283 | E1U10051 | sp-33 | an-283 |
| E1A2726 | sp-7 | an-284 | E1U2726 | sp-7 | an-284 | E1U10052 | sp-33 | an-284 |
| E1A2727 | sp-7 | an-285 | E1U2727 | sp-7 | an-285 | E1U10053 | sp-33 | an-285 |
| E1A2728 | sp-7 | an-286 | E1U2728 | sp-7 | an-286 | E1U10054 | sp-33 | an-286 |
| E1A2729 | sp-7 | an-287 | E1U2729 | sp-7 | an-287 | E1U10055 | sp-33 | an-287 |
| E1A2730 | sp-7 | an-288 | E1U2730 | sp-7 | an-288 | E1U10056 | sp-33 | an-288 |
| E1A2731 | sp-7 | an-289 | E1U2731 | sp-7 | an-289 | E1U10057 | sp-33 | an-289 |
| E1A2732 | sp-7 | an-290 | E1U2732 | sp-7 | an-290 | E1U10058 | sp-33 | an-290 |
| E1A2733 | sp-7 | an-291 | E1U2733 | sp-7 | an-291 | E1U10059 | sp-33 | an-291 |
| E1A2734 | sp-7 | an-292 | E1U2734 | sp-7 | an-292 | E1U10060 | sp-33 | an-292 |
| E1A2735 | sp-7 | an-293 | E1U2735 | sp-7 | an-293 | E1U10061 | sp-33 | an-293 |
| E1A2736 | sp-7 | an-294 | E1U2736 | sp-7 | an-294 | E1U10062 | sp-33 | an-294 |
| E1A2737 | sp-7 | an-295 | E1U2737 | sp-7 | an-295 | E1U10063 | sp-33 | an-295 |
| E1A2738 | sp-7 | an-296 | E1U2738 | sp-7 | an-296 | E1U10064 | sp-33 | an-296 |
| E1A2739 | sp-7 | an-297 | E1U2739 | sp-7 | an-297 | E1U10065 | sp-33 | an-297 |
| E1A2740 | sp-7 | an-298 | E1U2740 | sp-7 | an-298 | E1U10066 | sp-33 | an-298 |
| E1A2741 | sp-7 | an-299 | E1U2741 | sp-7 | an-299 | E1U10067 | sp-33 | an-299 |
| E1A2742 | sp-7 | an-300 | E1U2742 | sp-7 | an-300 | E1U10068 | sp-33 | an-300 |
| E1A2743 | sp-7 | an-301 | E1U2743 | sp-7 | an-301 | E1U10069 | sp-33 | an-301 |
| E1A2744 | sp-7 | an-302 | E1U2744 | sp-7 | an-302 | E1U10070 | sp-33 | an-302 |
| E1A2745 | sp-7 | an-303 | E1U2745 | sp-7 | an-303 | E1U10071 | sp-33 | an-303 |
| E1A2746 | sp-7 | an-304 | E1U2746 | sp-7 | an-304 | E1U10072 | sp-33 | an-304 |
| E1A2747 | sp-7 | an-305 | E1U2747 | sp-7 | an-305 | E1U10073 | sp-33 | an-305 |
| E1A2748 | sp-7 | an-306 | E1U2748 | sp-7 | an-306 | E1U10074 | sp-33 | an-306 |
| E1A2749 | sp-7 | an-307 | E1U2749 | sp-7 | an-307 | E1U10075 | sp-33 | an-307 |
| E1A2750 | sp-7 | an-308 | E1U2750 | sp-7 | an-308 | E1U10076 | sp-33 | an-308 |
| E1A2751 | sp-7 | an-309 | E1U2751 | sp-7 | an-309 | E1U10077 | sp-33 | an-309 |
| E1A2752 | sp-7 | an-310 | E1U2752 | sp-7 | an-310 | E1U10078 | sp-33 | an-310 |
| E1A2753 | sp-7 | an-311 | E1U2753 | sp-7 | an-311 | E1U10079 | sp-33 | an-311 |
| E1A2754 | sp-7 | an-312 | E1U2754 | sp-7 | an-312 | E1U10080 | sp-33 | an-312 |

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| | | | | Table 1-52 | | | | |
| | Y = NHCS | | | Y = NHCSNH | | | Y = NHCSNH | |
| E1A2755 | sp-7 | an-313 | E1U2755 | sp-7 | an-313 | E1U10081 | sp-33 | an-313 |
| E1A2756 | sp-7 | an-314 | E1U2756 | sp-7 | an-314 | E1U10082 | sp-33 | an-314 |
| E1A2757 | sp-7 | an-315 | E1U2757 | sp-7 | an-315 | E1U10083 | sp-33 | an-315 |
| E1A2758 | sp-7 | an-316 | E1U2758 | sp-7 | an-316 | E1U10084 | sp-33 | an-316 |
| E1A2759 | sp-7 | an-317 | E1U2759 | sp-7 | an-317 | E1U10085 | sp-33 | an-317 |
| E1A2760 | sp-7 | an-318 | E1U2760 | sp-7 | an-318 | E1U10086 | sp-33 | an-318 |
| E1A2761 | sp-7 | an-319 | E1U2761 | sp-7 | an-319 | E1U10087 | sp-33 | an-319 |
| E1A2762 | sp-7 | an-320 | E1U2762 | sp-7 | an-320 | E1U10088 | sp-33 | an-320 |
| E1A2763 | sp-7 | an-321 | E1U2763 | sp-7 | an-321 | E1U10089 | sp-33 | an-321 |
| E1A2764 | sp-7 | an-322 | E1U2764 | sp-7 | an-322 | E1U10090 | sp-33 | an-322 |
| E1A2765 | sp-7 | an-323 | E1U2765 | sp-7 | an-323 | E1U10091 | sp-33 | an-323 |
| E1A2766 | sp-7 | an-324 | E1U2766 | sp-7 | an-324 | E1U10092 | sp-33 | an-324 |
| E1A2767 | sp-7 | an-325 | E1U2767 | sp-7 | an-325 | E1U10093 | sp-33 | an-325 |
| E1A2768 | sp-7 | an-326 | E1U2768 | sp-7 | an-326 | E1U10094 | sp-33 | an-326 |
| E1A2769 | sp-7 | an-327 | E1U2769 | sp-7 | an-327 | E1U10095 | sp-33 | an-327 |
| E1A2770 | sp-7 | an-328 | E1U2770 | sp-7 | an-328 | E1U10096 | sp-33 | an-328 |
| E1A2771 | sp-7 | an-329 | E1U2771 | sp-7 | an-329 | E1U10097 | sp-33 | an-329 |
| E1A2772 | sp-7 | an-330 | E1U2772 | sp-7 | an-330 | E1U10098 | sp-33 | an-330 |
| E1A2773 | sp-7 | an-331 | E1U2773 | sp-7 | an-331 | E1U10099 | sp-33 | an-331 |
| E1A2774 | sp-7 | an-332 | E1U2774 | sp-7 | an-332 | E1U10100 | sp-33 | an-332 |
| E1A2775 | sp-7 | an-333 | E1U2775 | sp-7 | an-333 | E1U10101 | sp-33 | an-333 |
| E1A2776 | sp-7 | an-334 | E1U2776 | sp-7 | an-334 | E1U10102 | sp-33 | an-334 |
| E1A2777 | sp-7 | an-335 | E1U2777 | sp-7 | an-335 | E1U10103 | sp-33 | an-335 |
| E1A2778 | sp-7 | an-336 | E1U2778 | sp-7 | an-336 | E1U10104 | sp-33 | an-336 |
| E1A2779 | sp-7 | an-337 | E1U2779 | sp-7 | an-337 | E1U10105 | sp-33 | an-337 |
| E1A2780 | sp-7 | an-338 | E1U2780 | sp-7 | an-338 | E1U10106 | sp-33 | an-338 |
| E1A2781 | sp-7 | an-339 | E1U2781 | sp-7 | an-339 | E1U10107 | sp-33 | an-339 |
| E1A2782 | sp-7 | an-340 | E1U2782 | sp-7 | an-340 | E1U10108 | sp-33 | an-340 |
| E1A2783 | sp-7 | an-341 | E1U2783 | sp-7 | an-341 | E1U10109 | sp-33 | an-341 |
| E1A2784 | sp-7 | an-342 | E1U2784 | sp-7 | an-342 | E1U10110 | sp-33 | an-342 |
| E1A2785 | sp-7 | an-343 | E1U2785 | sp-7 | an-343 | E1U10111 | sp-33 | an-343 |
| E1A2786 | sp-7 | an-344 | E1U2786 | sp-7 | an-344 | E1U10112 | sp-33 | an-344 |
| E1A2787 | sp-7 | an-345 | E1U2787 | sp-7 | an-345 | E1U10113 | sp-33 | an-345 |
| E1A2788 | sp-7 | an-346 | E1U2788 | sp-7 | an-346 | E1U10114 | sp-33 | an-346 |
| E1A2789 | sp-7 | an-347 | E1U2789 | sp-7 | an-347 | E1U10115 | sp-33 | an-347 |
| E1A2790 | sp-7 | an-348 | E1U2790 | sp-7 | an-348 | E1U10116 | sp-33 | an-348 |
| E1A2791 | sp-7 | an-349 | E1U2791 | sp-7 | an-349 | E1U10117 | sp-33 | an-349 |
| E1A2792 | sp-7 | an-350 | E1U2792 | sp-7 | an-350 | E1U10118 | sp-33 | an-350 |
| E1A2793 | sp-7 | an-351 | E1U2793 | sp-7 | an-351 | E1U10119 | sp-33 | an-351 |
| E1A2794 | sp-7 | an-352 | E1U2794 | sp-7 | an-352 | E1U10120 | sp-33 | an-352 |
| E1A2795 | sp-7 | an-353 | E1U2795 | sp-7 | an-353 | E1U10121 | sp-33 | an-353 |
| E1A2796 | sp-7 | an-354 | E1U2796 | sp-7 | an-354 | E1U10122 | sp-33 | an-354 |
| E1A2797 | sp-7 | an-355 | E1U2797 | sp-7 | an-355 | E1U10123 | sp-33 | an-355 |
| E1A2798 | sp-7 | an-356 | E1U2798 | sp-7 | an-356 | E1U10124 | sp-33 | an-356 |
| E1A2799 | sp-7 | an-357 | E1U2799 | sp-7 | an-357 | E1U10125 | sp-33 | an-357 |
| E1A2800 | sp-7 | an-358 | E1U2800 | sp-7 | an-358 | E1U10126 | sp-33 | an-358 |
| E1A2801 | sp-7 | an-359 | E1U2801 | sp-7 | an-359 | E1U10127 | sp-33 | an-359 |
| E1A2802 | sp-7 | an-360 | E1U2802 | sp-7 | an-360 | E1U10128 | sp-33 | an-360 |
| E1A2803 | sp-7 | an-361 | E1U2803 | sp-7 | an-361 | E1U10129 | sp-33 | an-361 |
| E1A2804 | sp-7 | an-362 | E1U2804 | sp-7 | an-362 | E1U10130 | sp-33 | an-362 |
| E1A2805 | sp-7 | an-363 | E1U2805 | sp-7 | an-363 | E1U10131 | sp-33 | an-363 |
| E1A2806 | sp-7 | an-364 | E1U2806 | sp-7 | an-364 | E1U10132 | sp-33 | an-364 |
| E1A2807 | sp-7 | an-365 | E1U2807 | sp-7 | an-365 | E1U10133 | sp-33 | an-365 |
| E1A2808 | sp-7 | an-366 | E1U2808 | sp-7 | an-366 | E1U10134 | sp-33 | an-366 |
| | | | | Table 1-53 | | | | |
| | Y = NHCS | | | Y = NHCSNH | | | Y = NHCSNH | |
| E1A2809 | sp-7 | an-367 | E1U2809 | sp-7 | an-367 | E1U10135 | sp-33 | an-367 |
| E1A2810 | sp-7 | an-368 | E1U2810 | sp-7 | an-368 | E1U10136 | sp-33 | an-368 |
| E1A2811 | sp-7 | an-369 | E1U2811 | sp-7 | an-369 | E1U10137 | sp-33 | an-369 |
| E1A2812 | sp-7 | an-370 | E1U2812 | sp-7 | an-370 | E1U10138 | sp-33 | an-370 |
| E1A2813 | sp-7 | an-371 | E1U2813 | sp-7 | an-371 | E1U10139 | sp-33 | an-371 |
| E1A2814 | sp-7 | an-372 | E1U2814 | sp-7 | an-372 | E1U10140 | sp-33 | an-372 |
| E1A2815 | sp-7 | an-373 | E1U2815 | sp-7 | an-373 | E1U10141 | sp-33 | an-373 |
| E1A2816 | sp-7 | an-374 | E1U2816 | sp-7 | an-374 | E1U10142 | sp-33 | an-374 |
| E1A2817 | sp-7 | an-375 | E1U2817 | sp-7 | an-375 | E1U10143 | sp-33 | an-375 |
| E1A2818 | sp-7 | an-376 | E1U2818 | sp-7 | an-376 | E1U10144 | sp-33 | an-376 |
| E1A2819 | sp-7 | an-377 | E1U2819 | sp-7 | an-377 | E1U10145 | sp-33 | an-377 |
| E1A2820 | sp-7 | an-378 | E1U2820 | sp-7 | an-378 | E1U10146 | sp-33 | an-378 |
| E1A2821 | sp-7 | an-379 | E1U2821 | sp-7 | an-379 | E1U10147 | sp-33 | an-379 |
| E1A2822 | sp-7 | an-380 | E1U2822 | sp-7 | an-380 | E1U10148 | sp-33 | an-380 |
| E1A2823 | sp-7 | an-381 | E1U2823 | sp-7 | an-381 | E1U10149 | sp-33 | an-381 |
| E1A2824 | sp-7 | an-382 | E1U2824 | sp-7 | an-382 | E1U10150 | sp-33 | an-382 |

-continued

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| E1A2825 | sp-7 | an-383 | E1U2825 | sp-7 | an-383 | E1U10151 | sp-33 | an-383 |
| E1A2826 | sp-7 | an-384 | E1U2826 | sp-7 | an-384 | E1U10152 | sp-33 | an-384 |
| E1A2827 | sp-7 | an-385 | E1U2827 | sp-7 | an-385 | E1U10153 | sp-33 | an-385 |
| E1A2828 | sp-7 | an-386 | E1U2828 | sp-7 | an-386 | E1U10154 | sp-33 | an-386 |
| E1A2829 | sp-7 | an-387 | E1U2829 | sp-7 | an-387 | E1U10155 | sp-33 | an-387 |
| E1A2830 | sp-7 | an-388 | E1U2830 | sp-7 | an-388 | E1U10156 | sp-33 | an-388 |
| E1A2831 | sp-7 | an-389 | E1U2831 | sp-7 | an-389 | E1U10157 | sp-33 | an-389 |
| E1A2832 | sp-7 | an-390 | E1U2832 | sp-7 | an-390 | E1U10158 | sp-33 | an-390 |
| E1A2833 | sp-7 | an-391 | E1U2833 | sp-7 | an-391 | E1U10159 | sp-33 | an-391 |
| E1A2834 | sp-7 | an-392 | E1U2834 | sp-7 | an-392 | E1U10160 | sp-33 | an-392 |
| E1A2835 | sp-7 | an-393 | E1U2835 | sp-7 | an-393 | E1U10161 | sp-33 | an-393 |
| E1A2836 | sp-7 | an-394 | E1U2836 | sp-7 | an-394 | E1U10162 | sp-33 | an-394 |
| E1A2837 | sp-7 | an-395 | E1U2837 | sp-7 | an-395 | E1U10163 | sp-33 | an-395 |
| E1A2838 | sp-7 | an-396 | E1U2838 | sp-7 | an-396 | E1U10164 | sp-33 | an-396 |
| E1A2839 | sp-7 | an-397 | E1U2839 | sp-7 | an-397 | E1U10165 | sp-33 | an-397 |
| E1A2840 | sp-7 | an-398 | E1U2840 | sp-7 | an-398 | E1U10166 | sp-33 | an-398 |
| E1A2841 | sp-7 | an-399 | E1U2841 | sp-7 | an-399 | E1U10167 | sp-33 | an-399 |
| E1A2842 | sp-7 | an-400 | E1U2842 | sp-7 | an-400 | E1U10168 | sp-33 | an-400 |
| E1A2843 | sp-7 | an-401 | E1U2843 | sp-7 | an-401 | E1U10169 | sp-33 | an-401 |
| E1A2844 | sp-7 | an-402 | E1U2844 | sp-7 | an-402 | E1U10170 | sp-33 | an-402 |
| E1A2845 | sp-7 | an-403 | E1U2845 | sp-7 | an-403 | E1U10171 | sp-33 | an-403 |
| E1A2846 | sp-7 | an-404 | E1U2846 | sp-7 | an-404 | E1U10172 | sp-33 | an-404 |
| E1A2847 | sp-7 | an-405 | E1U2847 | sp-7 | an-405 | E1U10173 | sp-33 | an-405 |
| E1A2848 | sp-7 | an-406 | E1U2848 | sp-7 | an-406 | E1U10174 | sp-33 | an-406 |
| E1A2849 | sp-7 | an-407 | E1U2849 | sp-7 | an-407 | E1U10175 | sp-33 | an-407 |
| E1A2850 | sp-8 | an-1 | E1U2850 | sp-8 | an-1 | E1U10176 | sp-34 | an-1 |
| E1A2851 | sp-8 | an-2 | E1U2851 | sp-8 | an-2 | E1U10177 | sp-34 | an-2 |
| E1A2852 | sp-8 | an-3 | E1U2852 | sp-8 | an-3 | E1U10178 | sp-34 | an-3 |
| E1A2853 | sp-8 | an-4 | E1U2853 | sp-8 | an-4 | E1U10179 | sp-34 | an-4 |
| E1A2854 | sp-8 | an-5 | E1U2854 | sp-8 | an-5 | E1U10180 | sp-34 | an-5 |
| E1A2855 | sp-8 | an-6 | E1U2855 | sp-8 | an-6 | E1U10181 | sp-34 | an-6 |
| E1A2856 | sp-8 | an-7 | E1U2856 | sp-8 | an-7 | E1U10182 | sp-34 | an-7 |
| E1A2857 | sp-8 | an-8 | E1U2857 | sp-8 | an-8 | E1U10183 | sp-34 | an-8 |
| E1A2858 | sp-8 | an-9 | E1U2858 | sp-8 | an-9 | E1U10184 | sp-34 | an-9 |
| E1A2859 | sp-8 | an-10 | E1U2859 | sp-8 | an-10 | E1U10185 | sp-34 | an-10 |
| E1A2860 | sp-8 | an-11 | E1U2860 | sp-8 | an-11 | E1U10186 | sp-34 | an-11 |
| E1A2861 | sp-8 | an-12 | E1U2861 | sp-8 | an-12 | E1U10187 | sp-34 | an-12 |
| E1A2862 | sp-8 | an-13 | E1U2862 | sp-8 | an-13 | E1U10188 | sp-34 | an-13 |

Table 1-54

| Y = NHCS | | | Y = NHCSNH | | | Y = NHCSNH | | |
|---|---|---|---|---|---|---|---|---|
| E1A2863 | sp-8 | an-14 | E1U2863 | sp-8 | an-14 | E1U10189 | sp-34 | an-14 |
| E1A2864 | sp-8 | an-15 | E1U2864 | sp-8 | an-15 | E1U10190 | sp-34 | an-15 |
| E1A2865 | sp-8 | an-16 | E1U2865 | sp-8 | an-16 | E1U10191 | sp-34 | an-16 |
| E1A2866 | sp-8 | an-17 | E1U2866 | sp-8 | an-17 | E1U10192 | sp-34 | an-17 |
| E1A2867 | sp-8 | an-18 | E1U2867 | sp-8 | an-18 | E1U10193 | sp-34 | an-18 |
| E1A2868 | sp-8 | an-19 | E1U2868 | sp-8 | an-19 | E1U10194 | sp-34 | an-19 |
| E1A2869 | sp-8 | an-20 | E1U2869 | sp-8 | an-20 | E1U10195 | sp-34 | an-20 |
| E1A2870 | sp-8 | an-21 | E1U2870 | sp-8 | an-21 | E1U10196 | sp-34 | an-21 |
| E1A2871 | sp-8 | an-22 | E1U2871 | sp-8 | an-22 | E1U10197 | sp-34 | an-22 |
| E1A2872 | sp-8 | an-23 | E1U2872 | sp-8 | an-23 | E1U10198 | sp-34 | an-23 |
| E1A2873 | sp-8 | an-24 | E1U2873 | sp-8 | an-24 | E1U10199 | sp-34 | an-24 |
| E1A2874 | sp-8 | an-25 | E1U2874 | sp-8 | an-25 | E1U10200 | sp-34 | an-25 |
| E1A2875 | sp-8 | an-26 | E1U2875 | sp-8 | an-26 | E1U10201 | sp-34 | an-26 |
| E1A2876 | sp-8 | an-27 | E1U2876 | sp-8 | an-27 | E1U10202 | sp-34 | an-27 |
| E1A2877 | sp-8 | an-28 | E1U2877 | sp-8 | an-28 | E1U10203 | sp-34 | an-28 |
| E1A2878 | sp-8 | an-29 | E1U2878 | sp-8 | an-29 | E1U10204 | sp-34 | an-29 |
| E1A2879 | sp-8 | an-30 | E1U2879 | sp-8 | an-30 | E1U10205 | sp-34 | an-30 |
| E1A2880 | sp-8 | an-31 | E1U2880 | sp-8 | an-31 | E1U10206 | sp-34 | an-31 |
| E1A2881 | sp-8 | an-32 | E1U2881 | sp-8 | an-32 | E1U10207 | sp-34 | an-32 |
| E1A2882 | sp-8 | an-33 | E1U2882 | sp-8 | an-33 | E1U10208 | sp-34 | an-33 |
| E1A2883 | sp-8 | an-34 | E1U2883 | sp-8 | an-34 | E1U10209 | sp-34 | an-34 |
| E1A2884 | sp-8 | an-35 | E1U2884 | sp-8 | an-35 | E1U10210 | sp-34 | an-35 |
| E1A2885 | sp-8 | an-36 | E1U2885 | sp-8 | an-36 | E1U10211 | sp-34 | an-36 |
| E1A2886 | sp-8 | an-37 | E1U2886 | sp-8 | an-37 | E1U10212 | sp-34 | an-37 |
| E1A2887 | sp-8 | an-38 | E1U2887 | sp-8 | an-38 | E1U10213 | sp-34 | an-38 |
| E1A2888 | sp-8 | an-39 | E1U2888 | sp-8 | an-39 | E1U10214 | sp-34 | an-39 |
| E1A2889 | sp-8 | an-40 | E1U2889 | sp-8 | an-40 | E1U10215 | sp-34 | an-40 |
| E1A2890 | sp-8 | an-41 | E1U2890 | sp-8 | an-41 | E1U10216 | sp-34 | an-41 |
| E1A2891 | sp-8 | an-42 | E1U2891 | sp-8 | an-42 | E1U10217 | sp-34 | an-42 |
| E1A2892 | sp-8 | an-43 | E1U2892 | sp-8 | an-43 | E1U10218 | sp-34 | an-43 |
| E1A2893 | sp-8 | an-44 | E1U2893 | sp-8 | an-44 | E1U10219 | sp-34 | an-44 |
| E1A2894 | sp-8 | an-45 | E1U2894 | sp-8 | an-45 | E1U10220 | sp-34 | an-45 |
| E1A2895 | sp-8 | an-46 | E1U2895 | sp-8 | an-46 | E1U10221 | sp-34 | an-46 |
| E1A2896 | sp-8 | an-47 | E1U2896 | sp-8 | an-47 | E1U10222 | sp-34 | an-47 |
| E1A2897 | sp-8 | an-48 | E1U2897 | sp-8 | an-48 | E1U10223 | sp-34 | an-48 |
| E1A2898 | sp-8 | an-49 | E1U2898 | sp-8 | an-49 | E1U10224 | sp-34 | an-49 |

-continued

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| E1A2899 | sp-8 | an-50 | E1U2899 | sp-8 | an-50 | E1U10225 | sp-34 | an-50 |
| E1A2900 | sp-8 | an-51 | E1U2900 | sp-8 | an-51 | E1U10226 | sp-34 | an-51 |
| E1A2901 | sp-8 | an-52 | E1U2901 | sp-8 | an-52 | E1U10227 | sp-34 | an-52 |
| E1A2902 | sp-8 | an-53 | E1U2902 | sp-8 | an-53 | E1U10228 | sp-34 | an-53 |
| E1A2903 | sp-8 | an-54 | E1U2903 | sp-8 | an-54 | E1U10229 | sp-34 | an-54 |
| E1A2904 | sp-8 | an-55 | E1U2904 | sp-8 | an-55 | E1U10230 | sp-34 | an-55 |
| E1A2905 | sp-8 | an-56 | E1U2905 | sp-8 | an-56 | E1U10231 | sp-34 | an-56 |
| E1A2906 | sp-8 | an-57 | E1U2906 | sp-8 | an-57 | E1U10232 | sp-34 | an-57 |
| E1A2907 | sp-8 | an-58 | E1U2907 | sp-8 | an-58 | E1U10233 | sp-34 | an-58 |
| E1A2908 | sp-8 | an-59 | E1U2908 | sp-8 | an-59 | E1U10234 | sp-34 | an-59 |
| E1A2909 | sp-8 | an-60 | E1U2909 | sp-8 | an-60 | E1U10235 | sp-34 | an-60 |
| E1A2910 | sp-8 | an-61 | E1U2910 | sp-8 | an-61 | E1U10236 | sp-34 | an-61 |
| E1A2911 | sp-8 | an-62 | E1U2911 | sp-8 | an-62 | E1U10237 | sp-34 | an-62 |
| E1A2912 | sp-8 | an-63 | E1U2912 | sp-8 | an-63 | E1U10238 | sp-34 | an-63 |
| E1A2913 | sp-8 | an-64 | E1U2913 | sp-8 | an-64 | E1U10239 | sp-34 | an-64 |
| E1A2914 | sp-8 | an-65 | E1U2914 | sp-8 | an-65 | E1U10240 | sp-34 | an-65 |
| E1A2915 | sp-8 | an-66 | E1U2915 | sp-8 | an-66 | E1U10241 | sp-34 | an-66 |
| E1A2916 | sp-8 | an-67 | E1U2916 | sp-8 | an-67 | E1U10242 | sp-34 | an-67 |

Table 1-55

| Y = NHCS | | | Y = NHCSNH | | | Y = NHCSNH | | |
|---|---|---|---|---|---|---|---|---|
| E1A2917 | sp-8 | an-68 | E1U2917 | sp-8 | an-68 | E1U10243 | sp-34 | an-68 |
| E1A2918 | sp-8 | an-69 | E1U2918 | sp-8 | an-69 | E1U10244 | sp-34 | an-69 |
| E1A2919 | sp-8 | an-70 | E1U2919 | sp-8 | an-70 | E1U10245 | sp-34 | an-70 |
| E1A2920 | sp-8 | an-71 | E1U2920 | sp-8 | an-71 | E1U10246 | sp-34 | an-71 |
| E1A2921 | sp-8 | an-72 | E1U2921 | sp-8 | an-72 | E1U10247 | sp-34 | an-72 |
| E1A2922 | sp-8 | an-73 | E1U2922 | sp-8 | an-73 | E1U10248 | sp-34 | an-73 |
| E1A2923 | sp-8 | an-74 | E1U2923 | sp-8 | an-74 | E1U10249 | sp-34 | an-74 |
| E1A2924 | sp-8 | an-75 | E1U2924 | sp-8 | an-75 | E1U10250 | sp-34 | an-75 |
| E1A2925 | sp-8 | an-76 | E1U2925 | sp-8 | an-76 | E1U10251 | sp-34 | an-76 |
| E1A2926 | sp-8 | an-77 | E1U2926 | sp-8 | an-77 | E1U10252 | sp-34 | an-77 |
| E1A2927 | sp-8 | an-78 | E1U2927 | sp-8 | an-78 | E1U10253 | sp-34 | an-78 |
| E1A2928 | sp-8 | an-79 | E1U2928 | sp-8 | an-79 | E1U10254 | sp-34 | an-79 |
| E1A2929 | sp-8 | an-80 | E1U2929 | sp-8 | an-80 | E1U10255 | sp-34 | an-80 |
| E1A2930 | sp-8 | an-81 | E1U2930 | sp-8 | an-81 | E1U10256 | sp-34 | an-81 |
| E1A2931 | sp-8 | an-82 | E1U2931 | sp-8 | an-82 | E1U10257 | sp-34 | an-82 |
| E1A2932 | sp-8 | an-83 | E1U2932 | sp-8 | an-83 | E1U10258 | sp-34 | an-83 |
| E1A2933 | sp-8 | an-84 | E1U2933 | sp-8 | an-84 | E1U10259 | sp-34 | an-84 |
| E1A2934 | sp-8 | an-85 | E1U2934 | sp-8 | an-85 | E1U10260 | sp-34 | an-85 |
| E1A2935 | sp-8 | an-86 | E1U2935 | sp-8 | an-86 | E1U10261 | sp-34 | an-86 |
| E1A2936 | sp-8 | an-87 | E1U2936 | sp-8 | an-87 | E1U10262 | sp-34 | an-87 |
| E1A2937 | sp-8 | an-88 | E1U2937 | sp-8 | an-88 | E1U10263 | sp-34 | an-88 |
| E1A2938 | sp-8 | an-89 | E1U2938 | sp-8 | an-89 | E1U10264 | sp-34 | an-89 |
| E1A2939 | sp-8 | an-90 | E1U2939 | sp-8 | an-90 | E1U10265 | sp-34 | an-90 |
| E1A2940 | sp-8 | an-91 | E1U2940 | sp-8 | an-91 | E1U10266 | sp-34 | an-91 |
| E1A2941 | sp-8 | an-92 | E1U2941 | sp-8 | an-92 | E1U10267 | sp-34 | an-92 |
| E1A2942 | sp-8 | an-93 | E1U2942 | sp-8 | an-93 | E1U10268 | sp-34 | an-93 |
| E1A2943 | sp-8 | an-94 | E1U2943 | sp-8 | an-94 | E1U10269 | sp-34 | an-94 |
| E1A2944 | sp-8 | an-95 | E1U2944 | sp-8 | an-95 | E1U10270 | sp-34 | an-95 |
| E1A2945 | sp-8 | an-96 | E1U2945 | sp-8 | an-96 | E1U10271 | sp-34 | an-96 |
| E1A2946 | sp-8 | an-97 | E1U2946 | sp-8 | an-97 | E1U10272 | sp-34 | an-97 |
| E1A2947 | sp-8 | an-98 | E1U2947 | sp-8 | an-98 | E1U10273 | sp-34 | an-98 |
| E1A2948 | sp-8 | an-99 | E1U2948 | sp-8 | an-99 | E1U10274 | sp-34 | an-99 |
| E1A2949 | sp-8 | an-100 | E1U2949 | sp-8 | an-100 | E1U10275 | sp-34 | an-100 |
| E1A2950 | sp-8 | an-101 | E1U2950 | sp-8 | an-101 | E1U10276 | sp-34 | an-101 |
| E1A2951 | sp-8 | an-102 | E1U2951 | sp-8 | an-102 | E1U10277 | sp-34 | an-102 |
| E1A2952 | sp-8 | an-103 | E1U2952 | sp-8 | an-103 | E1U10278 | sp-34 | an-103 |
| E1A2953 | sp-8 | an-104 | E1U2953 | sp-8 | an-104 | E1U10279 | sp-34 | an-104 |
| E1A2954 | sp-8 | an-105 | E1U2954 | sp-8 | an-105 | E1U10280 | sp-34 | an-105 |
| E1A2955 | sp-8 | an-106 | E1U2955 | sp-8 | an-106 | E1U10281 | sp-34 | an-106 |
| E1A2956 | sp-8 | an-107 | E1U2956 | sp-8 | an-107 | E1U10282 | sp-34 | an-107 |
| E1A2957 | sp-8 | an-108 | E1U2957 | sp-8 | an-108 | E1U10283 | sp-34 | an-108 |
| E1A2958 | sp-8 | an-109 | E1U2958 | sp-8 | an-109 | E1U10284 | sp-34 | an-109 |
| E1A2959 | sp-8 | an-110 | E1U2959 | sp-8 | an-110 | E1U10285 | sp-34 | an-110 |
| E1A2960 | sp-8 | an-111 | E1U2960 | sp-8 | an-111 | E1U10286 | sp-34 | an-111 |
| E1A2961 | sp-8 | an-112 | E1U2961 | sp-8 | an-112 | E1U10287 | sp-34 | an-112 |
| E1A2962 | sp-8 | an-113 | E1U2962 | sp-8 | an-113 | E1U10288 | sp-34 | an-113 |
| E1A2963 | sp-8 | an-114 | E1U2963 | sp-8 | an-114 | E1U10289 | sp-34 | an-114 |
| E1A2964 | sp-8 | an-115 | E1U2964 | sp-8 | an-115 | E1U10290 | sp-34 | an-115 |
| E1A2965 | sp-8 | an-116 | E1U2965 | sp-8 | an-116 | E1U10291 | sp-34 | an-116 |
| E1A2966 | sp-8 | an-117 | E1U2966 | sp-8 | an-117 | E1U10292 | sp-34 | an-117 |
| E1A2967 | sp-8 | an-118 | E1U2967 | sp-8 | an-118 | E1U10293 | sp-34 | an-118 |
| E1A2968 | sp-8 | an-119 | E1U2968 | sp-8 | an-119 | E1U10294 | sp-34 | an-119 |
| E1A2969 | sp-8 | an-120 | E1U2969 | sp-8 | an-120 | E1U10295 | sp-34 | an-120 |
| E1A2970 | sp-8 | an-121 | E1U2970 | sp-8 | an-121 | E1U10296 | sp-34 | an-121 |

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| Table 1-56 ||||||||||

| Y = NHCS ||| Y = NHCSNH ||| Y = NHCSNH |||
|---|---|---|---|---|---|---|---|---|
| E1A2971 | sp-8 | an-122 | E1U2971 | sp-8 | an-122 | E1U10297 | sp-34 | an-122 |
| E1A2972 | sp-8 | an-123 | E1U2972 | sp-8 | an-123 | E1U10298 | sp-34 | an-123 |
| E1A2973 | sp-8 | an-124 | E1U2973 | sp-8 | an-124 | E1U10299 | sp-34 | an-124 |
| E1A2974 | sp-8 | an-125 | E1U2974 | sp-8 | an-125 | E1U10300 | sp-34 | an-125 |
| E1A2975 | sp-8 | an-126 | E1U2975 | sp-8 | an-126 | E1U10301 | sp-34 | an-126 |
| E1A2976 | sp-8 | an-127 | E1U2976 | sp-8 | an-127 | E1U10302 | sp-34 | an-127 |
| E1A2977 | sp-8 | an-128 | E1U2977 | sp-8 | an-128 | E1U10303 | sp-34 | an-128 |
| E1A2978 | sp-8 | an-129 | E1U2978 | sp-8 | an-129 | E1U10304 | sp-34 | an-129 |
| E1A2979 | sp-8 | an-130 | E1U2979 | sp-8 | an-130 | E1U10305 | sp-34 | an-130 |
| E1A2980 | sp-8 | an-131 | E1U2980 | sp-8 | an-131 | E1U10306 | sp-34 | an-131 |
| E1A2981 | sp-8 | an-132 | E1U2981 | sp-8 | an-132 | E1U10307 | sp-34 | an-132 |
| E1A2982 | sp-8 | an-133 | E1U2982 | sp-8 | an-133 | E1U10308 | sp-34 | an-133 |
| E1A2983 | sp-8 | an-134 | E1U2983 | sp-8 | an-134 | E1U10309 | sp-34 | an-134 |
| E1A2984 | sp-8 | an-135 | E1U2984 | sp-8 | an-135 | E1U10310 | sp-34 | an-135 |
| E1A2985 | sp-8 | an-136 | E1U2985 | sp-8 | an-136 | E1U10311 | sp-34 | an-136 |
| E1A2986 | sp-8 | an-137 | E1U2986 | sp-8 | an-137 | E1U10312 | sp-34 | an-137 |
| E1A2987 | sp-8 | an-138 | E1U2987 | sp-8 | an-138 | E1U10313 | sp-34 | an-138 |
| E1A2988 | sp-8 | an-139 | E1U2988 | sp-8 | an-139 | E1U10314 | sp-34 | an-139 |
| E1A2989 | sp-8 | an-140 | E1U2989 | sp-8 | an-140 | E1U10315 | sp-34 | an-140 |
| E1A2990 | sp-8 | an-141 | E1U2990 | sp-8 | an-141 | E1U10316 | sp-34 | an-141 |
| E1A2991 | sp-8 | an-142 | E1U2991 | sp-8 | an-142 | E1U10317 | sp-34 | an-142 |
| E1A2992 | sp-8 | an-143 | E1U2992 | sp-8 | an-143 | E1U10318 | sp-34 | an-143 |
| E1A2993 | sp-8 | an-144 | E1U2993 | sp-8 | an-144 | E1U10319 | sp-34 | an-144 |
| E1A2994 | sp-8 | an-145 | E1U2994 | sp-8 | an-145 | E1U10320 | sp-34 | an-145 |
| E1A2995 | sp-8 | an-146 | E1U2995 | sp-8 | an-146 | E1U10321 | sp-34 | an-146 |
| E1A2996 | sp-8 | an-147 | E1U2996 | sp-8 | an-147 | E1U10322 | sp-34 | an-147 |
| E1A2997 | sp-8 | an-148 | E1U2997 | sp-8 | an-148 | E1U10323 | sp-34 | an-148 |
| E1A2998 | sp-8 | an-149 | E1U2998 | sp-8 | an-149 | E1U10324 | sp-34 | an-149 |
| E1A2999 | sp-8 | an-150 | E1U2999 | sp-8 | an-150 | E1U10325 | sp-34 | an-150 |
| E1A3000 | sp-8 | an-151 | E1U3000 | sp-8 | an-151 | E1U10326 | sp-34 | an-151 |
| E1A3001 | sp-8 | an-152 | E1U3001 | sp-8 | an-152 | E1U10327 | sp-34 | an-152 |
| E1A3002 | sp-8 | an-153 | E1U3002 | sp-8 | an-153 | E1U10328 | sp-34 | an-153 |
| E1A3003 | sp-8 | an-154 | E1U3003 | sp-8 | an-154 | E1U10329 | sp-34 | an-154 |
| E1A3004 | sp-8 | an-155 | E1U3004 | sp-8 | an-155 | E1U10330 | sp-34 | an-155 |
| E1A3005 | sp-8 | an-156 | E1U3005 | sp-8 | an-156 | E1U10331 | sp-34 | an-156 |
| E1A3006 | sp-8 | an-157 | E1U3006 | sp-8 | an-157 | E1U10332 | sp-34 | an-157 |
| E1A3007 | sp-8 | an-158 | E1U3007 | sp-8 | an-158 | E1U10333 | sp-34 | an-158 |
| E1A3008 | sp-8 | an-159 | E1U3008 | sp-8 | an-159 | E1U10334 | sp-34 | an-159 |
| E1A3009 | sp-8 | an-160 | E1U3009 | sp-8 | an-160 | E1U10335 | sp-34 | an-160 |
| E1A3010 | sp-8 | an-161 | E1U3010 | sp-8 | an-161 | E1U10336 | sp-34 | an-161 |
| E1A3011 | sp-8 | an-162 | E1U3011 | sp-8 | an-162 | E1U10337 | sp-34 | an-162 |
| E1A3012 | sp-8 | an-163 | E1U3012 | sp-8 | an-163 | E1U10338 | sp-34 | an-163 |
| E1A3013 | sp-8 | an-164 | E1U3013 | sp-8 | an-164 | E1U10339 | sp-34 | an-164 |
| E1A3014 | sp-8 | an-165 | E1U3014 | sp-8 | an-165 | E1U10340 | sp-34 | an-165 |
| E1A3015 | sp-8 | an-166 | E1U3015 | sp-8 | an-166 | E1U10341 | sp-34 | an-166 |
| E1A3016 | sp-8 | an-167 | E1U3016 | sp-8 | an-167 | E1U10342 | sp-34 | an-167 |
| E1A3017 | sp-8 | an-168 | E1U3017 | sp-8 | an-168 | E1U10343 | sp-34 | an-168 |
| E1A3018 | sp-8 | an-169 | E1U3018 | sp-8 | an-169 | E1U10344 | sp-34 | an-169 |
| E1A3019 | sp-8 | an-170 | E1U3019 | sp-8 | an-170 | E1U10345 | sp-34 | an-170 |
| E1A3020 | sp-8 | an-171 | E1U3020 | sp-8 | an-171 | E1U10346 | sp-34 | an-171 |
| E1A3021 | sp-8 | an-172 | E1U3021 | sp-8 | an-172 | E1U10347 | sp-34 | an-172 |
| E1A3022 | sp-8 | an-173 | E1U3022 | sp-8 | an-173 | E1U10348 | sp-34 | an-173 |
| E1A3023 | sp-8 | an-174 | E1U3023 | sp-8 | an-174 | E1U10349 | sp-34 | an-174 |
| E1A3024 | sp-8 | an-175 | E1U3024 | sp-8 | an-175 | E1U10350 | sp-34 | an-175 |

Table 1-57

| Y = NHCS ||| Y = NHCSNH ||| Y = NHCSNH |||
|---|---|---|---|---|---|---|---|---|
| E1A3025 | sp-8 | an-176 | E1U3025 | sp-8 | an-176 | E1U10351 | sp-34 | an-176 |
| E1A3026 | sp-8 | an-177 | E1U3026 | sp-8 | an-177 | E1U10352 | sp-34 | an-177 |
| E1A3027 | sp-8 | an-178 | E1U3027 | sp-8 | an-178 | E1U10353 | sp-34 | an-178 |
| E1A3028 | sp-8 | an-179 | E1U3028 | sp-8 | an-179 | E1U10354 | sp-34 | an-179 |
| E1A3029 | sp-8 | an-180 | E1U3029 | sp-8 | an-180 | E1U10355 | sp-34 | an-180 |
| E1A3030 | sp-8 | an-181 | E1U3030 | sp-8 | an-181 | E1U10356 | sp-34 | an-181 |
| E1A3031 | sp-8 | an-182 | E1U3031 | sp-8 | an-182 | E1U10357 | sp-34 | an-182 |
| E1A3032 | sp-8 | an-183 | E1U3032 | sp-8 | an-183 | E1U10358 | sp-34 | an-183 |
| E1A3033 | sp-8 | an-184 | E1U3033 | sp-8 | an-184 | E1U10359 | sp-34 | an-184 |
| E1A3034 | sp-8 | an-185 | E1U3034 | sp-8 | an-185 | E1U10360 | sp-34 | an-185 |
| E1A3035 | sp-8 | an-186 | E1U3035 | sp-8 | an-186 | E1U10361 | sp-34 | an-186 |
| E1A3036 | sp-8 | an-187 | E1U3036 | sp-8 | an-187 | E1U10362 | sp-34 | an-187 |
| E1A3037 | sp-8 | an-188 | E1U3037 | sp-8 | an-188 | E1U10363 | sp-34 | an-188 |
| E1A3038 | sp-8 | an-189 | E1U3038 | sp-8 | an-189 | E1U10364 | sp-34 | an-189 |
| E1A3039 | sp-8 | an-190 | E1U3039 | sp-8 | an-190 | E1U10365 | sp-34 | an-190 |
| E1A3040 | sp-8 | an-191 | E1U3040 | sp-8 | an-191 | E1U10366 | sp-34 | an-191 |

-continued

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| E1A3041 | sp-8 | an-192 | E1U3041 | sp-8 | an-192 | E1U10367 | sp-34 | an-192 |
| E1A3042 | sp-8 | an-193 | E1U3042 | sp-8 | an-193 | E1U10368 | sp-34 | an-193 |
| E1A3043 | sp-8 | an-194 | E1U3043 | sp-8 | an-194 | E1U10369 | sp-34 | an-194 |
| E1A3044 | sp-8 | an-195 | E1U3044 | sp-8 | an-195 | E1U10370 | sp-34 | an-195 |
| E1A3045 | sp-8 | an-196 | E1U3045 | sp-8 | an-196 | E1U10371 | sp-34 | an-196 |
| E1A3046 | sp-8 | an-197 | E1U3046 | sp-8 | an-197 | E1U10372 | sp-34 | an-197 |
| E1A3047 | sp-8 | an-198 | E1U3047 | sp-8 | an-198 | E1U10373 | sp-34 | an-198 |
| E1A3048 | sp-8 | an-199 | E1U3048 | sp-8 | an-199 | E1U10374 | sp-34 | an-199 |
| E1A3049 | sp-8 | an-200 | E1U3049 | sp-8 | an-200 | E1U10375 | sp-34 | an-200 |
| E1A3050 | sp-8 | an-201 | E1U3050 | sp-8 | an-201 | E1U10376 | sp-34 | an-201 |
| E1A3051 | sp-8 | an-202 | E1U3051 | sp-8 | an-202 | E1U10377 | sp-34 | an-202 |
| E1A3052 | sp-8 | an-203 | E1U3052 | sp-8 | an-203 | E1U10378 | sp-34 | an-203 |
| E1A3053 | sp-8 | an-204 | E1U3053 | sp-8 | an-204 | E1U10379 | sp-34 | an-204 |
| E1A3054 | sp-8 | an-205 | E1U3054 | sp-8 | an-205 | E1U10380 | sp-34 | an-205 |
| E1A3055 | sp-8 | an-206 | E1U3055 | sp-8 | an-206 | E1U10381 | sp-34 | an-206 |
| E1A3056 | sp-8 | an-207 | E1U3056 | sp-8 | an-207 | E1U10382 | sp-34 | an-207 |
| E1A3057 | sp-8 | an-208 | E1U3057 | sp-8 | an-208 | E1U10383 | sp-34 | an-208 |
| E1A3058 | sp-8 | an-209 | E1U3058 | sp-8 | an-209 | E1U10384 | sp-34 | an-209 |
| E1A3059 | sp-8 | an-210 | E1U3059 | sp-8 | an-210 | E1U10385 | sp-34 | an-210 |
| E1A3060 | sp-8 | an-211 | E1U3060 | sp-8 | an-211 | E1U10386 | sp-34 | an-211 |
| E1A3061 | sp-8 | an-212 | E1U3061 | sp-8 | an-212 | E1U10387 | sp-34 | an-212 |
| E1A3062 | sp-8 | an-213 | E1U3062 | sp-8 | an-213 | E1U10388 | sp-34 | an-213 |
| E1A3063 | sp-8 | an-214 | E1U3063 | sp-8 | an-214 | E1U10389 | sp-34 | an-214 |
| E1A3064 | sp-8 | an-215 | E1U3064 | sp-8 | an-215 | E1U10390 | sp-34 | an-215 |
| E1A3065 | sp-8 | an-216 | E1U3065 | sp-8 | an-216 | E1U10391 | sp-34 | an-216 |
| E1A3066 | sp-8 | an-217 | E1U3066 | sp-8 | an-217 | E1U10392 | sp-34 | an-217 |
| E1A3067 | sp-8 | an-218 | E1U3067 | sp-8 | an-218 | E1U10393 | sp-34 | an-218 |
| E1A3068 | sp-8 | an-219 | E1U3068 | sp-8 | an-219 | E1U10394 | sp-34 | an-219 |
| E1A3069 | sp-8 | an-220 | E1U3069 | sp-8 | an-220 | E1U10395 | sp-34 | an-220 |
| E1A3070 | sp-8 | an-221 | E1U3070 | sp-8 | an-221 | E1U10396 | sp-34 | an-221 |
| E1A3071 | sp-8 | an-222 | E1U3071 | sp-8 | an-222 | E1U10397 | sp-34 | an-222 |
| E1A3072 | sp-8 | an-223 | E1U3072 | sp-8 | an-223 | E1U10398 | sp-34 | an-223 |
| E1A3073 | sp-8 | an-224 | E1U3073 | sp-8 | an-224 | E1U10399 | sp-34 | an-224 |
| E1A3074 | sp-8 | an-225 | E1U3074 | sp-8 | an-225 | E1U10400 | sp-34 | an-225 |
| E1A3075 | sp-8 | an-226 | E1U3075 | sp-8 | an-226 | E1U10401 | sp-34 | an-226 |
| E1A3076 | sp-8 | an-227 | E1U3076 | sp-8 | an-227 | E1U10402 | sp-34 | an-227 |
| E1A3077 | sp-8 | an-228 | E1U3077 | sp-8 | an-228 | E1U10403 | sp-34 | an-228 |
| E1A3078 | sp-8 | an-229 | E1U3078 | sp-8 | an-229 | E1U10404 | sp-34 | an-229 |

Table 1-58

| Y = NHCS | | | Y = NHCSNH | | | Y = NHCSNH | | |
|---|---|---|---|---|---|---|---|---|
| E1A3079 | sp-8 | an-230 | E1U3079 | sp-8 | an-230 | E1U10405 | sp-34 | an-230 |
| E1A3080 | sp-8 | an-231 | E1U3080 | sp-8 | an-231 | E1U10406 | sp-34 | an-231 |
| E1A3081 | sp-8 | an-232 | E1U3081 | sp-8 | an-232 | E1U10407 | sp-34 | an-232 |
| E1A3082 | sp-8 | an-233 | E1U3082 | sp-8 | an-233 | E1U10408 | sp-34 | an-233 |
| E1A3083 | sp-8 | an-234 | E1U3083 | sp-8 | an-234 | E1U10409 | sp-34 | an-234 |
| E1A3084 | sp-8 | an-235 | E1U3084 | sp-8 | an-235 | E1U10410 | sp-34 | an-235 |
| E1A3085 | sp-8 | an-236 | E1U3085 | sp-8 | an-236 | E1U10411 | sp-34 | an-236 |
| E1A3086 | sp-8 | an-237 | E1U3086 | sp-8 | an-237 | E1U10412 | sp-34 | an-237 |
| E1A3087 | sp-8 | an-238 | E1U3087 | sp-8 | an-238 | E1U10413 | sp-34 | an-238 |
| E1A3088 | sp-8 | an-239 | E1U3088 | sp-8 | an-239 | E1U10414 | sp-34 | an-239 |
| E1A3089 | sp-8 | an-240 | E1U3089 | sp-8 | an-240 | E1U10415 | sp-34 | an-240 |
| E1A3090 | sp-8 | an-241 | E1U3090 | sp-8 | an-241 | E1U10416 | sp-34 | an-241 |
| E1A3091 | sp-8 | an-242 | E1U3091 | sp-8 | an-242 | E1U10417 | sp-34 | an-242 |
| E1A3092 | sp-8 | an-243 | E1U3092 | sp-8 | an-243 | E1U10418 | sp-34 | an-243 |
| E1A3093 | sp-8 | an-244 | E1U3093 | sp-8 | an-244 | E1U10419 | sp-34 | an-244 |
| E1A3094 | sp-8 | an-245 | E1U3094 | sp-8 | an-245 | E1U10420 | sp-34 | an-245 |
| E1A3095 | sp-8 | an-246 | E1U3095 | sp-8 | an-246 | E1U10421 | sp-34 | an-246 |
| E1A3096 | sp-8 | an-247 | E1U3096 | sp-8 | an-247 | E1U10422 | sp-34 | an-247 |
| E1A3097 | sp-8 | an-248 | E1U3097 | sp-8 | an-248 | E1U10423 | sp-34 | an-248 |
| E1A3098 | sp-8 | an-249 | E1U3098 | sp-8 | an-249 | E1U10424 | sp-34 | an-249 |
| E1A3099 | sp-8 | an-250 | E1U3099 | sp-8 | an-250 | E1U10425 | sp-34 | an-250 |
| E1A3100 | sp-8 | an-251 | E1U3100 | sp-8 | an-251 | E1U10426 | sp-34 | an-251 |
| E1A3101 | sp-8 | an-252 | E1U3101 | sp-8 | an-252 | E1U10427 | sp-34 | an-252 |
| E1A3102 | sp-8 | an-253 | E1U3102 | sp-8 | an-253 | E1U10428 | sp-34 | an-253 |
| E1A3103 | sp-8 | an-254 | E1U3103 | sp-8 | an-254 | E1U10429 | sp-34 | an-254 |
| E1A3104 | sp-8 | an-255 | E1U3104 | sp-8 | an-255 | E1U10430 | sp-34 | an-255 |
| E1A3105 | sp-8 | an-256 | E1U3105 | sp-8 | an-256 | E1U10431 | sp-34 | an-256 |
| E1A3106 | sp-8 | an-257 | E1U3106 | sp-8 | an-257 | E1U10432 | sp-34 | an-257 |
| E1A3107 | sp-8 | an-258 | E1U3107 | sp-8 | an-258 | E1U10433 | sp-34 | an-258 |
| E1A3108 | sp-8 | an-259 | E1U3108 | sp-8 | an-259 | E1U10434 | sp-34 | an-259 |
| E1A3109 | sp-8 | an-260 | E1U3109 | sp-8 | an-260 | E1U10435 | sp-34 | an-260 |
| E1A3110 | sp-8 | an-261 | E1U3110 | sp-8 | an-261 | E1U10436 | sp-34 | an-261 |
| E1A3111 | sp-8 | an-262 | E1U3111 | sp-8 | an-262 | E1U10437 | sp-34 | an-262 |
| E1A3112 | sp-8 | an-263 | E1U3112 | sp-8 | an-263 | E1U10438 | sp-34 | an-263 |
| E1A3113 | sp-8 | an-264 | E1U3113 | sp-8 | an-264 | E1U10439 | sp-34 | an-264 |
| E1A3114 | sp-8 | an-265 | E1U3114 | sp-8 | an-265 | E1U10440 | sp-34 | an-265 |

-continued

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| E1A3115 | sp-8 | an-266 | E1U3115 | sp-8 | an-266 | E1U10441 | sp-34 | an-266 |
| E1A3116 | sp-8 | an-267 | E1U3116 | sp-8 | an-267 | E1U10442 | sp-34 | an-267 |
| E1A3117 | sp-8 | an-268 | E1U3117 | sp-8 | an-268 | E1U10443 | sp-34 | an-268 |
| E1A3118 | sp-8 | an-269 | E1U3118 | sp-8 | an-269 | E1U10444 | sp-34 | an-269 |
| E1A3119 | sp-8 | an-270 | E1U3119 | sp-8 | an-270 | E1U10445 | sp-34 | an-270 |
| E1A3120 | sp-8 | an-271 | E1U3120 | sp-8 | an-271 | E1U10446 | sp-34 | an-271 |
| E1A3121 | sp-8 | an-272 | E1U3121 | sp-8 | an-272 | E1U10447 | sp-34 | an-272 |
| E1A3122 | sp-8 | an-273 | E1U3122 | sp-8 | an-273 | E1U10448 | sp-34 | an-273 |
| E1A3123 | sp-8 | an-274 | E1U3123 | sp-8 | an-274 | E1U10449 | sp-34 | an-274 |
| E1A3124 | sp-8 | an-275 | E1U3124 | sp-8 | an-275 | E1U10450 | sp-34 | an-275 |
| E1A3125 | sp-8 | an-276 | E1U3125 | sp-8 | an-276 | E1U10451 | sp-34 | an-276 |
| E1A3126 | sp-8 | an-277 | E1U3126 | sp-8 | an-277 | E1U10452 | sp-34 | an-277 |
| E1A3127 | sp-8 | an-278 | E1U3127 | sp-8 | an-278 | E1U10453 | sp-34 | an-278 |
| E1A3128 | sp-8 | an-279 | E1U3128 | sp-8 | an-279 | E1U10454 | sp-34 | an-279 |
| E1A3129 | sp-8 | an-280 | E1U3129 | sp-8 | an-280 | E1U10455 | sp-34 | an-280 |
| E1A3130 | sp-8 | an-281 | E1U3130 | sp-8 | an-281 | E1U10456 | sp-34 | an-281 |
| E1A3131 | sp-8 | an-282 | E1U3131 | sp-8 | an-282 | E1U10457 | sp-34 | an-282 |
| E1A3132 | sp-8 | an-283 | E1U3132 | sp-8 | an-283 | E1U10458 | sp-34 | an-283 |

Table 1-59

| Y = NHCS | | | Y = NHCSNH | | | Y = NHCSNH | | |
|---|---|---|---|---|---|---|---|---|
| E1A3133 | sp-8 | an-284 | E1U3133 | sp-8 | an-284 | E1U10459 | sp-34 | an-284 |
| E1A3134 | sp-8 | an-285 | E1U3134 | sp-8 | an-285 | E1U10460 | sp-34 | an-285 |
| E1A3135 | sp-8 | an-286 | E1U3135 | sp-8 | an-286 | E1U10461 | sp-34 | an-286 |
| E1A3136 | sp-8 | an-287 | E1U3136 | sp-8 | an-287 | E1U10462 | sp-34 | an-287 |
| E1A3137 | sp-8 | an-288 | E1U3137 | sp-8 | an-288 | E1U10463 | sp-34 | an-288 |
| E1A3138 | sp-8 | an-289 | E1U3138 | sp-8 | an-289 | E1U10464 | sp-34 | an-289 |
| E1A3139 | sp-8 | an-290 | E1U3139 | sp-8 | an-290 | E1U10465 | sp-34 | an-290 |
| E1A3140 | sp-8 | an-291 | E1U3140 | sp-8 | an-291 | E1U10466 | sp-34 | an-291 |
| E1A3141 | sp-8 | an-292 | E1U3141 | sp-8 | an-292 | E1U10467 | sp-34 | an-292 |
| E1A3142 | sp-8 | an-293 | E1U3142 | sp-8 | an-293 | E1U10468 | sp-34 | an-293 |
| E1A3143 | sp-8 | an-294 | E1U3143 | sp-8 | an-294 | E1U10469 | sp-34 | an-294 |
| E1A3144 | sp-8 | an-295 | E1U3144 | sp-8 | an-295 | E1U10470 | sp-34 | an-295 |
| E1A3145 | sp-8 | an-296 | E1U3145 | sp-8 | an-296 | E1U10471 | sp-34 | an-296 |
| E1A3146 | sp-8 | an-297 | E1U3146 | sp-8 | an-297 | E1U10472 | sp-34 | an-297 |
| E1A3147 | sp-8 | an-298 | E1U3147 | sp-8 | an-298 | E1U10473 | sp-34 | an-298 |
| E1A3148 | sp-8 | an-299 | E1U3148 | sp-8 | an-299 | E1U10474 | sp-34 | an-299 |
| E1A3149 | sp-8 | an-300 | E1U3149 | sp-8 | an-300 | E1U10475 | sp-34 | an-300 |
| E1A3150 | sp-8 | an-301 | E1U3150 | sp-8 | an-301 | E1U10476 | sp-34 | an-301 |
| E1A3151 | sp-8 | an-302 | E1U3151 | sp-8 | an-302 | E1U10477 | sp-34 | an-302 |
| E1A3152 | sp-8 | an-303 | E1U3152 | sp-8 | an-303 | E1U10478 | sp-34 | an-303 |
| E1A3153 | sp-8 | an-304 | E1U3153 | sp-8 | an-304 | E1U10479 | sp-34 | an-304 |
| E1A3154 | sp-8 | an-305 | E1U3154 | sp-8 | an-305 | E1U10480 | sp-34 | an-305 |
| E1A3155 | sp-8 | an-306 | E1U3155 | sp-8 | an-306 | E1U10481 | sp-34 | an-306 |
| E1A3156 | sp-8 | an-307 | E1U3156 | sp-8 | an-307 | E1U10482 | sp-34 | an-307 |
| E1A3157 | sp-8 | an-308 | E1U3157 | sp-8 | an-308 | E1U10483 | sp-34 | an-308 |
| E1A3158 | sp-8 | an-309 | E1U3158 | sp-8 | an-309 | E1U10484 | sp-34 | an-309 |
| E1A3159 | sp-8 | an-310 | E1U3159 | sp-8 | an-310 | E1U10485 | sp-34 | an-310 |
| E1A3160 | sp-8 | an-311 | E1U3160 | sp-8 | an-311 | E1U10486 | sp-34 | an-311 |
| E1A3161 | sp-8 | an-312 | E1U3161 | sp-8 | an-312 | E1U10487 | sp-34 | an-312 |
| E1A3162 | sp-8 | an-313 | E1U3162 | sp-8 | an-313 | E1U10488 | sp-34 | an-313 |
| E1A3163 | sp-8 | an-314 | E1U3163 | sp-8 | an-314 | E1U10489 | sp-34 | an-314 |
| E1A3164 | sp-8 | an-315 | E1U3164 | sp-8 | an-315 | E1U10490 | sp-34 | an-315 |
| E1A3165 | sp-8 | an-316 | E1U3165 | sp-8 | an-316 | E1U10491 | sp-34 | an-316 |
| E1A3166 | sp-8 | an-317 | E1U3166 | sp-8 | an-317 | E1U10492 | sp-34 | an-317 |
| E1A3167 | sp-8 | an-318 | E1U3167 | sp-8 | an-318 | E1U10493 | sp-34 | an-318 |
| E1A3168 | sp-8 | an-319 | E1U3168 | sp-8 | an-319 | E1U10494 | sp-34 | an-319 |
| E1A3169 | sp-8 | an-320 | E1U3169 | sp-8 | an-320 | E1U10495 | sp-34 | an-320 |
| E1A3170 | sp-8 | an-321 | E1U3170 | sp-8 | an-321 | E1U10496 | sp-34 | an-321 |
| E1A3171 | sp-8 | an-322 | E1U3171 | sp-8 | an-322 | E1U10497 | sp-34 | an-322 |
| E1A3172 | sp-8 | an-323 | E1U3172 | sp-8 | an-323 | E1U10498 | sp-34 | an-323 |
| E1A3173 | sp-8 | an-324 | E1U3173 | sp-8 | an-324 | E1U10499 | sp-34 | an-324 |
| E1A3174 | sp-8 | an-325 | E1U3174 | sp-8 | an-325 | E1U10500 | sp-34 | an-325 |
| E1A3175 | sp-8 | an-326 | E1U3175 | sp-8 | an-326 | E1U10501 | sp-34 | an-326 |
| E1A3176 | sp-8 | an-327 | E1U3176 | sp-8 | an-327 | E1U10502 | sp-34 | an-327 |
| E1A3177 | sp-8 | an-328 | E1U3177 | sp-8 | an-328 | E1U10503 | sp-34 | an-328 |
| E1A3178 | sp-8 | an-329 | E1U3178 | sp-8 | an-329 | E1U10504 | sp-34 | an-329 |
| E1A3179 | sp-8 | an-330 | E1U3179 | sp-8 | an-330 | E1U10505 | sp-34 | an-330 |
| E1A3180 | sp-8 | an-331 | E1U3180 | sp-8 | an-331 | E1U10506 | sp-34 | an-331 |
| E1A3181 | sp-8 | an-332 | E1U3181 | sp-8 | an-332 | E1U10507 | sp-34 | an-332 |
| E1A3182 | sp-8 | an-333 | E1U3182 | sp-8 | an-333 | E1U10508 | sp-34 | an-333 |
| E1A3183 | sp-8 | an-334 | E1U3183 | sp-8 | an-334 | E1U10509 | sp-34 | an-334 |
| E1A3184 | sp-8 | an-335 | E1U3184 | sp-8 | an-335 | E1U10510 | sp-34 | an-335 |
| E1A3185 | sp-8 | an-336 | E1U3185 | sp-8 | an-336 | E1U10511 | sp-34 | an-336 |
| E1A3186 | sp-8 | an-337 | E1U3186 | sp-8 | an-337 | E1U10512 | sp-34 | an-337 |

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| Table 1-60 | | | | | | | | |
| Y = NHCS | | | Y = NHCSNH | | | Y = NHCSNH | | |
| E1A3187 | sp-8 | an-338 | E1U3187 | sp-8 | an-338 | E1U10513 | sp-34 | an-338 |
| E1A3188 | sp-8 | an-339 | E1U3188 | sp-8 | an-339 | E1U10514 | sp-34 | an-339 |
| E1A3189 | sp-8 | an-340 | E1U3189 | sp-8 | an-340 | E1U10515 | sp-34 | an-340 |
| E1A3190 | sp-8 | an-341 | E1U3190 | sp-8 | an-341 | E1U10516 | sp-34 | an-341 |
| E1A3191 | sp-8 | an-342 | E1U3191 | sp-8 | an-342 | E1U10517 | sp-34 | an-342 |
| E1A3192 | sp-8 | an-343 | E1U3192 | sp-8 | an-343 | E1U10518 | sp-34 | an-343 |
| E1A3193 | sp-8 | an-344 | E1U3193 | sp-8 | an-344 | E1U10519 | sp-34 | an-344 |
| E1A3194 | sp-8 | an-345 | E1U3194 | sp-8 | an-345 | E1U10520 | sp-34 | an-345 |
| E1A3195 | sp-8 | an-346 | E1U3195 | sp-8 | an-346 | E1U10521 | sp-34 | an-346 |
| E1A3196 | sp-8 | an-347 | E1U3196 | sp-8 | an-347 | E1U10522 | sp-34 | an-347 |
| E1A3197 | sp-8 | an-348 | E1U3197 | sp-8 | an-348 | E1U10523 | sp-34 | an-348 |
| E1A3198 | sp-8 | an-349 | E1U3198 | sp-8 | an-349 | E1U10524 | sp-34 | an-349 |
| E1A3199 | sp-8 | an-350 | E1U3199 | sp-8 | an-350 | E1U10525 | sp-34 | an-350 |
| E1A3200 | sp-8 | an-351 | E1U3200 | sp-8 | an-351 | E1U10526 | sp-34 | an-351 |
| E1A3201 | sp-8 | an-352 | E1U3201 | sp-8 | an-352 | E1U10527 | sp-34 | an-352 |
| E1A3202 | sp-8 | an-353 | E1U3202 | sp-8 | an-353 | E1U10528 | sp-34 | an-353 |
| E1A3203 | sp-8 | an-354 | E1U3203 | sp-8 | an-354 | E1U10529 | sp-34 | an-354 |
| E1A3204 | sp-8 | an-355 | E1U3204 | sp-8 | an-355 | E1U10530 | sp-34 | an-355 |
| E1A3205 | sp-8 | an-356 | E1U3205 | sp-8 | an-356 | E1U10531 | sp-34 | an-356 |
| E1A3206 | sp-8 | an-357 | E1U3206 | sp-8 | an-357 | E1U10532 | sp-34 | an-357 |
| E1A3207 | sp-8 | an-358 | E1U3207 | sp-8 | an-358 | E1U10533 | sp-34 | an-358 |
| E1A3208 | sp-8 | an-359 | E1U3208 | sp-8 | an-359 | E1U10534 | sp-34 | an-359 |
| E1A3209 | sp-8 | an-360 | E1U3209 | sp-8 | an-360 | E1U10535 | sp-34 | an-360 |
| E1A3210 | sp-8 | an-361 | E1U3210 | sp-8 | an-361 | E1U10536 | sp-34 | an-361 |
| E1A3211 | sp-8 | an-362 | E1U3211 | sp-8 | an-362 | E1U10537 | sp-34 | an-362 |
| E1A3212 | sp-8 | an-363 | E1U3212 | sp-8 | an-363 | E1U10538 | sp-34 | an-363 |
| E1A3213 | sp-8 | an-364 | E1U3213 | sp-8 | an-364 | E1U10539 | sp-34 | an-364 |
| E1A3214 | sp-8 | an-365 | E1U3214 | sp-8 | an-365 | E1U10540 | sp-34 | an-365 |
| E1A3215 | sp-8 | an-366 | E1U3215 | sp-8 | an-366 | E1U10541 | sp-34 | an-366 |
| E1A3216 | sp-8 | an-367 | E1U3216 | sp-8 | an-367 | E1U10542 | sp-34 | an-367 |
| E1A3217 | sp-8 | an-368 | E1U3217 | sp-8 | an-368 | E1U10543 | sp-34 | an-368 |
| E1A3218 | sp-8 | an-369 | E1U3218 | sp-8 | an-369 | E1U10544 | sp-34 | an-369 |
| E1A3219 | sp-8 | an-370 | E1U3219 | sp-8 | an-370 | E1U10545 | sp-34 | an-370 |
| E1A3220 | sp-8 | an-371 | E1U3220 | sp-8 | an-371 | E1U10546 | sp-34 | an-371 |
| E1A3221 | sp-8 | an-372 | E1U3221 | sp-8 | an-372 | E1U10547 | sp-34 | an-372 |
| E1A3222 | sp-8 | an-373 | E1U3222 | sp-8 | an-373 | E1U10548 | sp-34 | an-373 |
| E1A3223 | sp-8 | an-374 | E1U3223 | sp-8 | an-374 | E1U10549 | sp-34 | an-374 |
| E1A3224 | sp-8 | an-375 | E1U3224 | sp-8 | an-375 | E1U10550 | sp-34 | an-375 |
| E1A3225 | sp-8 | an-376 | E1U3225 | sp-8 | an-376 | E1U10551 | sp-34 | an-376 |
| E1A3226 | sp-8 | an-377 | E1U3226 | sp-8 | an-377 | E1U10552 | sp-34 | an-377 |
| E1A3227 | sp-8 | an-378 | E1U3227 | sp-8 | an-378 | E1U10553 | sp-34 | an-378 |
| E1A3228 | sp-8 | an-379 | E1U3228 | sp-8 | an-379 | E1U10554 | sp-34 | an-379 |
| E1A3229 | sp-8 | an-380 | E1U3229 | sp-8 | an-380 | E1U10555 | sp-34 | an-380 |
| E1A3230 | sp-8 | an-381 | E1U3230 | sp-8 | an-381 | E1U10556 | sp-34 | an-381 |
| E1A3231 | sp-8 | an-382 | E1U3231 | sp-8 | an-382 | E1U10557 | sp-34 | an-382 |
| E1A3232 | sp-8 | an-383 | E1U3232 | sp-8 | an-383 | E1U10558 | sp-34 | an-383 |
| E1A3233 | sp-8 | an-384 | E1U3233 | sp-8 | an-384 | E1U10559 | sp-34 | an-384 |
| E1A3234 | sp-8 | an-385 | E1U3234 | sp-8 | an-385 | E1U10560 | sp-34 | an-385 |
| E1A3235 | sp-8 | an-386 | E1U3235 | sp-8 | an-386 | E1U10561 | sp-34 | an-386 |
| E1A3236 | sp-8 | an-387 | E1U3236 | sp-8 | an-387 | E1U10562 | sp-34 | an-387 |
| E1A3237 | sp-8 | an-388 | E1U3237 | sp-8 | an-388 | E1U10563 | sp-34 | an-388 |
| E1A3238 | sp-8 | an-389 | E1U3238 | sp-8 | an-389 | E1U10564 | sp-34 | an-389 |
| E1A3239 | sp-8 | an-390 | E1U3239 | sp-8 | an-390 | E1U10565 | sp-34 | an-390 |
| E1A3240 | sp-8 | an-391 | E1U3240 | sp-8 | an-391 | E1U10566 | sp-34 | an-391 |
| Table 1-61 | | | | | | | | |
| Y = NHCS | | | Y = NHCSNH | | | Y = NHCSNH | | |
| E1A3241 | sp-8 | an-392 | E1U3241 | sp-8 | an-392 | E1U10567 | sp-34 | an-392 |
| E1A3242 | sp-8 | an-393 | E1U3242 | sp-8 | an-393 | E1U10568 | sp-34 | an-393 |
| E1A3243 | sp-8 | an-394 | E1U3243 | sp-8 | an-394 | E1U10569 | sp-34 | an-394 |
| E1A3244 | sp-8 | an-395 | E1U3244 | sp-8 | an-395 | E1U10570 | sp-34 | an-395 |
| E1A3245 | sp-8 | an-396 | E1U3245 | sp-8 | an-396 | E1U10571 | sp-34 | an-396 |
| E1A3246 | sp-8 | an-397 | E1U3246 | sp-8 | an-397 | E1U10572 | sp-34 | an-397 |
| E1A3247 | sp-8 | an-398 | E1U3247 | sp-8 | an-398 | E1U10573 | sp-34 | an-398 |
| E1A3248 | sp-8 | an-399 | E1U3248 | sp-8 | an-399 | E1U10574 | sp-34 | an-399 |
| E1A3249 | sp-8 | an-400 | E1U3249 | sp-8 | an-400 | E1U10575 | sp-34 | an-400 |
| E1A3250 | sp-8 | an-401 | E1U3250 | sp-8 | an-401 | E1U10576 | sp-34 | an-401 |
| E1A3251 | sp-8 | an-402 | E1U3251 | sp-8 | an-402 | E1U10577 | sp-34 | an-402 |
| E1A3252 | sp-8 | an-403 | E1U3252 | sp-8 | an-403 | E1U10578 | sp-34 | an-403 |
| E1A3253 | sp-8 | an-404 | E1U3253 | sp-8 | an-404 | E1U10579 | sp-34 | an-404 |
| E1A3254 | sp-8 | an-405 | E1U3254 | sp-8 | an-405 | E1U10580 | sp-34 | an-405 |
| E1A3255 | sp-8 | an-406 | E1U3255 | sp-8 | an-406 | E1U10581 | sp-34 | an-406 |
| E1A3256 | sp-8 | an-407 | E1U3256 | sp-8 | an-407 | E1U10582 | sp-34 | an-407 |

-continued

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| E1A3257 | sp-9 | an-1 | E1U3257 | sp-9 | an-1 | E1U10583 | sp-35 | an-1 |
| E1A3258 | sp-9 | an-2 | E1U3258 | sp-9 | an-2 | E1U10584 | sp-35 | an-2 |
| E1A3259 | sp-9 | an-3 | E1U3259 | sp-9 | an-3 | E1U10585 | sp-35 | an-3 |
| E1A3260 | sp-9 | an-4 | E1U3260 | sp-9 | an-4 | E1U10586 | sp-35 | an-4 |
| E1A3261 | sp-9 | an-5 | E1U3261 | sp-9 | an-5 | E1U10587 | sp-35 | an-5 |
| E1A3262 | sp-9 | an-6 | E1U3262 | sp-9 | an-6 | E1U10588 | sp-35 | an-6 |
| E1A3263 | sp-9 | an-7 | E1U3263 | sp-9 | an-7 | E1U10589 | sp-35 | an-7 |
| E1A3264 | sp-9 | an-8 | E1U3264 | sp-9 | an-8 | E1U10590 | sp-35 | an-8 |
| E1A3265 | sp-9 | an-9 | E1U3265 | sp-9 | an-9 | E1U10591 | sp-35 | an-9 |
| E1A3266 | sp-9 | an-10 | E1U3266 | sp-9 | an-10 | E1U10592 | sp-35 | an-10 |
| E1A3267 | sp-9 | an-11 | E1U3267 | sp-9 | an-11 | E1U10593 | sp-35 | an-11 |
| E1A3268 | sp-9 | an-12 | E1U3268 | sp-9 | an-12 | E1U10594 | sp-35 | an-12 |
| E1A3269 | sp-9 | an-13 | E1U3269 | sp-9 | an-13 | E1U10595 | sp-35 | an-13 |
| E1A3270 | sp-9 | an-14 | E1U3270 | sp-9 | an-14 | E1U10596 | sp-35 | an-14 |
| E1A3271 | sp-9 | an-15 | E1U3271 | sp-9 | an-15 | E1U10597 | sp-35 | an-15 |
| E1A3272 | sp-9 | an-16 | E1U3272 | sp-9 | an-16 | E1U10598 | sp-35 | an-16 |
| E1A3273 | sp-9 | an-17 | E1U3273 | sp-9 | an-17 | E1U10599 | sp-35 | an-17 |
| E1A3274 | sp-9 | an-18 | E1U3274 | sp-9 | an-18 | E1U10600 | sp-35 | an-18 |
| E1A3275 | sp-9 | an-19 | E1U3275 | sp-9 | an-19 | E1U10601 | sp-35 | an-19 |
| E1A3276 | sp-9 | an-20 | E1U3276 | sp-9 | an-20 | E1U10602 | sp-35 | an-20 |
| E1A3277 | sp-9 | an-21 | E1U3277 | sp-9 | an-21 | E1U10603 | sp-35 | an-21 |
| E1A3278 | sp-9 | an-22 | E1U3278 | sp-9 | an-22 | E1U10604 | sp-35 | an-22 |
| E1A3279 | sp-9 | an-23 | E1U3279 | sp-9 | an-23 | E1U10605 | sp-35 | an-23 |
| E1A3280 | sp-9 | an-24 | E1U3280 | sp-9 | an-24 | E1U10606 | sp-35 | an-24 |
| E1A3281 | sp-9 | an-25 | E1U3281 | sp-9 | an-25 | E1U10607 | sp-35 | an-25 |
| E1A3282 | sp-9 | an-26 | E1U3282 | sp-9 | an-26 | E1U10608 | sp-35 | an-26 |
| E1A3283 | sp-9 | an-27 | E1U3283 | sp-9 | an-27 | E1U10609 | sp-35 | an-27 |
| E1A3284 | sp-9 | an-28 | E1U3284 | sp-9 | an-28 | E1U10610 | sp-35 | an-28 |
| E1A3285 | sp-9 | an-29 | E1U3285 | sp-9 | an-29 | E1U10611 | sp-35 | an-29 |
| E1A3286 | sp-9 | an-30 | E1U3286 | sp-9 | an-30 | E1U10612 | sp-35 | an-30 |
| E1A3287 | sp-9 | an-31 | E1U3287 | sp-9 | an-31 | E1U10613 | sp-35 | an-31 |
| E1A3288 | sp-9 | an-32 | E1U3288 | sp-9 | an-32 | E1U10614 | sp-35 | an-32 |
| E1A3289 | sp-9 | an-33 | E1U3289 | sp-9 | an-33 | E1U10615 | sp-35 | an-33 |
| E1A3290 | sp-9 | an-34 | E1U3290 | sp-9 | an-34 | E1U10616 | sp-35 | an-34 |
| E1A3291 | sp-9 | an-35 | E1U3291 | sp-9 | an-35 | E1U10617 | sp-35 | an-35 |
| E1A3292 | sp-9 | an-36 | E1U3292 | sp-9 | an-36 | E1U10618 | sp-35 | an-36 |
| E1A3293 | sp-9 | an-37 | E1U3293 | sp-9 | an-37 | E1U10619 | sp-35 | an-37 |
| E1A3294 | sp-9 | an-38 | E1U3294 | sp-9 | an-38 | E1U10620 | sp-35 | an-38 |

Table 1-62

| Y = NHCS | | | Y = NHCSNH | | | Y = NHCSNH | | |
|---|---|---|---|---|---|---|---|---|
| E1A3295 | sp-9 | an-39 | E1U3295 | sp-9 | an-39 | E1U10621 | sp-35 | an-39 |
| E1A3296 | sp-9 | an-40 | E1U3296 | sp-9 | an-40 | E1U10622 | sp-35 | an-40 |
| E1A3297 | sp-9 | an-41 | E1U3297 | sp-9 | an-41 | E1U10623 | sp-35 | an-41 |
| E1A3298 | sp-9 | an-42 | E1U3298 | sp-9 | an-42 | E1U10624 | sp-35 | an-42 |
| E1A3299 | sp-9 | an-43 | E1U3299 | sp-9 | an-43 | E1U10625 | sp-35 | an-43 |
| E1A3300 | sp-9 | an-44 | E1U3300 | sp-9 | an-44 | E1U10626 | sp-35 | an-44 |
| E1A3301 | sp-9 | an-45 | E1U3301 | sp-9 | an-45 | E1U10627 | sp-35 | an-45 |
| E1A3302 | sp-9 | an-46 | E1U3302 | sp-9 | an-46 | E1U10628 | sp-35 | an-46 |
| E1A3303 | sp-9 | an-47 | E1U3303 | sp-9 | an-47 | E1U10629 | sp-35 | an-47 |
| E1A3304 | sp-9 | an-48 | E1U3304 | sp-9 | an-48 | E1U10630 | sp-35 | an-48 |
| E1A3305 | sp-9 | an-49 | E1U3305 | sp-9 | an-49 | E1U10631 | sp-35 | an-49 |
| E1A3306 | sp-9 | an-50 | E1U3306 | sp-9 | an-50 | E1U10632 | sp-35 | an-50 |
| E1A3307 | sp-9 | an-51 | E1U3307 | sp-9 | an-51 | E1U10633 | sp-35 | an-51 |
| E1A3308 | sp-9 | an-52 | E1U3308 | sp-9 | an-52 | E1U10634 | sp-35 | an-52 |
| E1A3309 | sp-9 | an-53 | E1U3309 | sp-9 | an-53 | E1U10635 | sp-35 | an-53 |
| E1A3310 | sp-9 | an-54 | E1U3310 | sp-9 | an-54 | E1U10636 | sp-35 | an-54 |
| E1A3311 | sp-9 | an-55 | E1U3311 | sp-9 | an-55 | E1U10637 | sp-35 | an-55 |
| E1A3312 | sp-9 | an-56 | E1U3312 | sp-9 | an-56 | E1U10638 | sp-35 | an-56 |
| E1A3313 | sp-9 | an-57 | E1U3313 | sp-9 | an-57 | E1U10639 | sp-35 | an-57 |
| E1A3314 | sp-9 | an-58 | E1U3314 | sp-9 | an-58 | E1U10640 | sp-35 | an-58 |
| E1A3315 | sp-9 | an-59 | E1U3315 | sp-9 | an-59 | E1U10641 | sp-35 | an-59 |
| E1A3316 | sp-9 | an-60 | E1U3316 | sp-9 | an-60 | E1U10642 | sp-35 | an-60 |
| E1A3317 | sp-9 | an-61 | E1U3317 | sp-9 | an-61 | E1U10643 | sp-35 | an-61 |
| E1A3318 | sp-9 | an-62 | E1U3318 | sp-9 | an-62 | E1U10644 | sp-35 | an-62 |
| E1A3319 | sp-9 | an-63 | E1U3319 | sp-9 | an-63 | E1U10645 | sp-35 | an-63 |
| E1A3320 | sp-9 | an-64 | E1U3320 | sp-9 | an-64 | E1U10646 | sp-35 | an-64 |
| E1A3321 | sp-9 | an-65 | E1U3321 | sp-9 | an-65 | E1U10647 | sp-35 | an-65 |
| E1A3322 | sp-9 | an-66 | E1U3322 | sp-9 | an-66 | E1U10648 | sp-35 | an-66 |
| E1A3323 | sp-9 | an-67 | E1U3323 | sp-9 | an-67 | E1U10649 | sp-35 | an-67 |
| E1A3324 | sp-9 | an-68 | E1U3324 | sp-9 | an-68 | E1U10650 | sp-35 | an-68 |
| E1A3325 | sp-9 | an-69 | E1U3325 | sp-9 | an-69 | E1U10651 | sp-35 | an-69 |
| E1A3326 | sp-9 | an-70 | E1U3326 | sp-9 | an-70 | E1U10652 | sp-35 | an-70 |
| E1A3327 | sp-9 | an-71 | E1U3327 | sp-9 | an-71 | E1U10653 | sp-35 | an-71 |
| E1A3328 | sp-9 | an-72 | E1U3328 | sp-9 | an-72 | E1U10654 | sp-35 | an-72 |
| E1A3329 | sp-9 | an-73 | E1U3329 | sp-9 | an-73 | E1U10655 | sp-35 | an-73 |
| E1A3330 | sp-9 | an-74 | E1U3330 | sp-9 | an-74 | E1U10656 | sp-35 | an-74 |

-continued

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| E1A3331 | sp-9 | an-75 | E1U3331 | sp-9 | an-75 | E1U10657 | sp-35 | an-75 |
| E1A3332 | sp-9 | an-76 | E1U3332 | sp-9 | an-76 | E1U10658 | sp-35 | an-76 |
| E1A3333 | sp-9 | an-77 | E1U3333 | sp-9 | an-77 | E1U10659 | sp-35 | an-77 |
| E1A3334 | sp-9 | an-78 | E1U3334 | sp-9 | an-78 | E1U10660 | sp-35 | an-78 |
| E1A3335 | sp-9 | an-79 | E1U3335 | sp-9 | an-79 | E1U10661 | sp-35 | an-79 |
| E1A3336 | sp-9 | an-80 | E1U3336 | sp-9 | an-80 | E1U10662 | sp-35 | an-80 |
| E1A3337 | sp-9 | an-81 | E1U3337 | sp-9 | an-81 | E1U10663 | sp-35 | an-81 |
| E1A3338 | sp-9 | an-82 | E1U3338 | sp-9 | an-82 | E1U10664 | sp-35 | an-82 |
| E1A3339 | sp-9 | an-83 | E1U3339 | sp-9 | an-83 | E1U10665 | sp-35 | an-83 |
| E1A3340 | sp-9 | an-84 | E1U3340 | sp-9 | an-84 | E1U10666 | sp-35 | an-84 |
| E1A3341 | sp-9 | an-85 | E1U3341 | sp-9 | an-85 | E1U10667 | sp-35 | an-85 |
| E1A3342 | sp-9 | an-86 | E1U3342 | sp-9 | an-86 | E1U10668 | sp-35 | an-86 |
| E1A3343 | sp-9 | an-87 | E1U3343 | sp-9 | an-87 | E1U10669 | sp-35 | an-87 |
| E1A3344 | sp-9 | an-88 | E1U3344 | sp-9 | an-88 | E1U10670 | sp-35 | an-88 |
| E1A3345 | sp-9 | an-89 | E1U3345 | sp-9 | an-89 | E1U10671 | sp-35 | an-89 |
| E1A3346 | sp-9 | an-90 | E1U3346 | sp-9 | an-90 | E1U10672 | sp-35 | an-90 |
| E1A3347 | sp-9 | an-91 | E1U3347 | sp-9 | an-91 | E1U10673 | sp-35 | an-91 |
| E1A3348 | sp-9 | an-92 | E1U3348 | sp-9 | an-92 | E1U10674 | sp-35 | an-92 |

Table 1-63

| Y = NHCS | | | Y = NHCSNH | | | Y = NHCSNH | | |
|---|---|---|---|---|---|---|---|---|
| E1A3349 | sp-9 | an-93 | E1U3349 | sp-9 | an-93 | E1U10675 | sp-35 | an-93 |
| E1A3350 | sp-9 | an-94 | E1U3350 | sp-9 | an-94 | E1U10676 | sp-35 | an-94 |
| E1A3351 | sp-9 | an-95 | E1U3351 | sp-9 | an-95 | E1U10677 | sp-35 | an-95 |
| E1A3352 | sp-9 | an-96 | E1U3352 | sp-9 | an-96 | E1U10678 | sp-35 | an-96 |
| E1A3353 | sp-9 | an-97 | E1U3353 | sp-9 | an-97 | E1U10679 | sp-35 | an-97 |
| E1A3354 | sp-9 | an-98 | E1U3354 | sp-9 | an-98 | E1U10680 | sp-35 | an-98 |
| E1A3355 | sp-9 | an-99 | E1U3355 | sp-9 | an-99 | E1U10681 | sp-35 | an-99 |
| E1A3356 | sp-9 | an-100 | E1U3356 | sp-9 | an-100 | E1U10682 | sp-35 | an-100 |
| E1A3357 | sp-9 | an-101 | E1U3357 | sp-9 | an-101 | E1U10683 | sp-35 | an-101 |
| E1A3358 | sp-9 | an-102 | E1U3358 | sp-9 | an-102 | E1U10684 | sp-35 | an-102 |
| E1A3359 | sp-9 | an-103 | E1U3359 | sp-9 | an-103 | E1U10685 | sp-35 | an-103 |
| E1A3360 | sp-9 | an-104 | E1U3360 | sp-9 | an-104 | E1U10686 | sp-35 | an-104 |
| E1A3361 | sp-9 | an-105 | E1U3361 | sp-9 | an-105 | E1U10687 | sp-35 | an-105 |
| E1A3362 | sp-9 | an-106 | E1U3362 | sp-9 | an-106 | E1U10688 | sp-35 | an-106 |
| E1A3363 | sp-9 | an-107 | E1U3363 | sp-9 | an-107 | E1U10689 | sp-35 | an-107 |
| E1A3364 | sp-9 | an-108 | E1U3364 | sp-9 | an-108 | E1U10690 | sp-35 | an-108 |
| E1A3365 | sp-9 | an-109 | E1U3365 | sp-9 | an-109 | E1U10691 | sp-35 | an-109 |
| E1A3366 | sp-9 | an-110 | E1U3366 | sp-9 | an-110 | E1U10692 | sp-35 | an-110 |
| E1A3367 | sp-9 | an-111 | E1U3367 | sp-9 | an-111 | E1U10693 | sp-35 | an-111 |
| E1A3368 | sp-9 | an-112 | E1U3368 | sp-9 | an-112 | E1U10694 | sp-35 | an-112 |
| E1A3369 | sp-9 | an-113 | E1U3369 | sp-9 | an-113 | E1U10695 | sp-35 | an-113 |
| E1A3370 | sp-9 | an-114 | E1U3370 | sp-9 | an-114 | E1U10696 | sp-35 | an-114 |
| E1A3371 | sp-9 | an-115 | E1U3371 | sp-9 | an-115 | E1U10697 | sp-35 | an-115 |
| E1A3372 | sp-9 | an-116 | E1U3372 | sp-9 | an-116 | E1U10698 | sp-35 | an-116 |
| E1A3373 | sp-9 | an-117 | E1U3373 | sp-9 | an-117 | E1U10699 | sp-35 | an-117 |
| E1A3374 | sp-9 | an-118 | E1U3374 | sp-9 | an-118 | E1U10700 | sp-35 | an-118 |
| E1A3375 | sp-9 | an-119 | E1U3375 | sp-9 | an-119 | E1U10701 | sp-35 | an-119 |
| E1A3376 | sp-9 | an-120 | E1U3376 | sp-9 | an-120 | E1U10702 | sp-35 | an-120 |
| E1A3377 | sp-9 | an-121 | E1U3377 | sp-9 | an-121 | E1U10703 | sp-35 | an-121 |
| E1A3378 | sp-9 | an-122 | E1U3378 | sp-9 | an-122 | E1U10704 | sp-35 | an-122 |
| E1A3379 | sp-9 | an-123 | E1U3379 | sp-9 | an-123 | E1U10705 | sp-35 | an-123 |
| E1A3380 | sp-9 | an-124 | E1U3380 | sp-9 | an-124 | E1U10706 | sp-35 | an-124 |
| E1A3381 | sp-9 | an-125 | E1U3381 | sp-9 | an-125 | E1U10707 | sp-35 | an-125 |
| E1A3382 | sp-9 | an-126 | E1U3382 | sp-9 | an-126 | E1U10708 | sp-35 | an-126 |
| E1A3383 | sp-9 | an-127 | E1U3383 | sp-9 | an-127 | E1U10709 | sp-35 | an-127 |
| E1A3384 | sp-9 | an-128 | E1U3384 | sp-9 | an-128 | E1U10710 | sp-35 | an-128 |
| E1A3385 | sp-9 | an-129 | E1U3385 | sp-9 | an-129 | E1U10711 | sp-35 | an-129 |
| E1A3386 | sp-9 | an-130 | E1U3386 | sp-9 | an-130 | E1U10712 | sp-35 | an-130 |
| E1A3387 | sp-9 | an-131 | E1U3387 | sp-9 | an-131 | E1U10713 | sp-35 | an-131 |
| E1A3388 | sp-9 | an-132 | E1U3388 | sp-9 | an-132 | E1U10714 | sp-35 | an-132 |
| E1A3389 | sp-9 | an-133 | E1U3389 | sp-9 | an-133 | E1U10715 | sp-35 | an-133 |
| E1A3390 | sp-9 | an-134 | E1U3390 | sp-9 | an-134 | E1U10716 | sp-35 | an-134 |
| E1A3391 | sp-9 | an-135 | E1U3391 | sp-9 | an-135 | E1U10717 | sp-35 | an-135 |
| E1A3392 | sp-9 | an-136 | E1U3392 | sp-9 | an-136 | E1U10718 | sp-35 | an-136 |
| E1A3393 | sp-9 | an-137 | E1U3393 | sp-9 | an-137 | E1U10719 | sp-35 | an-137 |
| E1A3394 | sp-9 | an-138 | E1U3394 | sp-9 | an-138 | E1U10720 | sp-35 | an-138 |
| E1A3395 | sp-9 | an-139 | E1U3395 | sp-9 | an-139 | E1U10721 | sp-35 | an-139 |
| E1A3396 | sp-9 | an-140 | E1U3396 | sp-9 | an-140 | E1U10722 | sp-35 | an-140 |
| E1A3397 | sp-9 | an-141 | E1U3397 | sp-9 | an-141 | E1U10723 | sp-35 | an-141 |
| E1A3398 | sp-9 | an-142 | E1U3398 | sp-9 | an-142 | E1U10724 | sp-35 | an-142 |
| E1A3399 | sp-9 | an-143 | E1U3399 | sp-9 | an-143 | E1U10725 | sp-35 | an-143 |
| E1A3400 | sp-9 | an-144 | E1U3400 | sp-9 | an-144 | E1U10726 | sp-35 | an-144 |
| E1A3401 | sp-9 | an-145 | E1U3401 | sp-9 | an-145 | E1U10727 | sp-35 | an-145 |
| E1A3402 | sp-9 | an-146 | E1U3402 | sp-9 | an-146 | E1U10728 | sp-35 | an-146 |

-continued

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| Table 1-64 ||||||||| 
| Y = NHCS ||| Y = NHCSNH ||| Y = NHCSNH |||
| E1A3403 | sp-9 | an-147 | E1U3403 | sp-9 | an-147 | E1U10729 | sp-35 | an-147 |
| E1A3404 | sp-9 | an-148 | E1U3404 | sp-9 | an-148 | E1U10730 | sp-35 | an-148 |
| E1A3405 | sp-9 | an-149 | E1U3405 | sp-9 | an-149 | E1U10731 | sp-35 | an-149 |
| E1A3406 | sp-9 | an-150 | E1U3406 | sp-9 | an-150 | E1U10732 | sp-35 | an-150 |
| E1A3407 | sp-9 | an-151 | E1U3407 | sp-9 | an-151 | E1U10733 | sp-35 | an-151 |
| E1A3408 | sp-9 | an-152 | E1U3408 | sp-9 | an-152 | E1U10734 | sp-35 | an-152 |
| E1A3409 | sp-9 | an-153 | E1U3409 | sp-9 | an-153 | E1U10735 | sp-35 | an-153 |
| E1A3410 | sp-9 | an-154 | E1U3410 | sp-9 | an-154 | E1U10736 | sp-35 | an-154 |
| E1A3411 | sp-9 | an-155 | E1U3411 | sp-9 | an-155 | E1U10737 | sp-35 | an-155 |
| E1A3412 | sp-9 | an-156 | E1U3412 | sp-9 | an-156 | E1U10738 | sp-35 | an-156 |
| E1A3413 | sp-9 | an-157 | E1U3413 | sp-9 | an-157 | E1U10739 | sp-35 | an-157 |
| E1A3414 | sp-9 | an-158 | E1U3414 | sp-9 | an-158 | E1U10740 | sp-35 | an-158 |
| E1A3415 | sp-9 | an-159 | E1U3415 | sp-9 | an-159 | E1U10741 | sp-35 | an-159 |
| E1A3416 | sp-9 | an-160 | E1U3416 | sp-9 | an-160 | E1U10742 | sp-35 | an-160 |
| E1A3417 | sp-9 | an-161 | E1U3417 | sp-9 | an-161 | E1U10743 | sp-35 | an-161 |
| E1A3418 | sp-9 | an-162 | E1U3418 | sp-9 | an-162 | E1U10744 | sp-35 | an-162 |
| E1A3419 | sp-9 | an-163 | E1U3419 | sp-9 | an-163 | E1U10745 | sp-35 | an-163 |
| E1A3420 | sp-9 | an-164 | E1U3420 | sp-9 | an-164 | E1U10746 | sp-35 | an-164 |
| E1A3421 | sp-9 | an-165 | E1U3421 | sp-9 | an-165 | E1U10747 | sp-35 | an-165 |
| E1A3422 | sp-9 | an-166 | E1U3422 | sp-9 | an-166 | E1U10748 | sp-35 | an-166 |
| E1A3423 | sp-9 | an-167 | E1U3423 | sp-9 | an-167 | E1U10749 | sp-35 | an-167 |
| E1A3424 | sp-9 | an-168 | E1U3424 | sp-9 | an-168 | E1U10750 | sp-35 | an-168 |
| E1A3425 | sp-9 | an-169 | E1U3425 | sp-9 | an-169 | E1U10751 | sp-35 | an-169 |
| E1A3426 | sp-9 | an-170 | E1U3426 | sp-9 | an-170 | E1U10752 | sp-35 | an-170 |
| E1A3427 | sp-9 | an-171 | E1U3427 | sp-9 | an-171 | E1U10753 | sp-35 | an-171 |
| E1A3428 | sp-9 | an-172 | E1U3428 | sp-9 | an-172 | E1U10754 | sp-35 | an-172 |
| E1A3429 | sp-9 | an-173 | E1U3429 | sp-9 | an-173 | E1U10755 | sp-35 | an-173 |
| E1A3430 | sp-9 | an-174 | E1U3430 | sp-9 | an-174 | E1U10756 | sp-35 | an-174 |
| E1A3431 | sp-9 | an-175 | E1U3431 | sp-9 | an-175 | E1U10757 | sp-35 | an-175 |
| E1A3432 | sp-9 | an-176 | E1U3432 | sp-9 | an-176 | E1U10758 | sp-35 | an-176 |
| E1A3433 | sp-9 | an-177 | E1U3433 | sp-9 | an-177 | E1U10759 | sp-35 | an-177 |
| E1A3434 | sp-9 | an-178 | E1U3434 | sp-9 | an-178 | E1U10760 | sp-35 | an-178 |
| E1A3435 | sp-9 | an-179 | E1U3435 | sp-9 | an-179 | E1U10761 | sp-35 | an-179 |
| E1A3436 | sp-9 | an-180 | E1U3436 | sp-9 | an-180 | E1U10762 | sp-35 | an-180 |
| E1A3437 | sp-9 | an-181 | E1U3437 | sp-9 | an-181 | E1U10763 | sp-35 | an-181 |
| E1A3438 | sp-9 | an-182 | E1U3438 | sp-9 | an-182 | E1U10764 | sp-35 | an-182 |
| E1A3439 | sp-9 | an-183 | E1U3439 | sp-9 | an-183 | E1U10765 | sp-35 | an-183 |
| E1A3440 | sp-9 | an-184 | E1U3440 | sp-9 | an-184 | E1U10766 | sp-35 | an-184 |
| E1A3441 | sp-9 | an-185 | E1U3441 | sp-9 | an-185 | E1U10767 | sp-35 | an-185 |
| E1A3442 | sp-9 | an-186 | E1U3442 | sp-9 | an-186 | E1U10768 | sp-35 | an-186 |
| E1A3443 | sp-9 | an-187 | E1U3443 | sp-9 | an-187 | E1U10769 | sp-35 | an-187 |
| E1A3444 | sp-9 | an-188 | E1U3444 | sp-9 | an-188 | E1U10770 | sp-35 | an-188 |
| E1A3445 | sp-9 | an-189 | E1U3445 | sp-9 | an-189 | E1U10771 | sp-35 | an-189 |
| E1A3446 | sp-9 | an-190 | E1U3446 | sp-9 | an-190 | E1U10772 | sp-35 | an-190 |
| E1A3447 | sp-9 | an-191 | E1U3447 | sp-9 | an-191 | E1U10773 | sp-35 | an-191 |
| E1A3448 | sp-9 | an-192 | E1U3448 | sp-9 | an-192 | E1U10774 | sp-35 | an-192 |
| E1A3449 | sp-9 | an-193 | E1U3449 | sp-9 | an-193 | E1U10775 | sp-35 | an-193 |
| E1A3450 | sp-9 | an-194 | E1U3450 | sp-9 | an-194 | E1U10776 | sp-35 | an-194 |
| E1A3451 | sp-9 | an-195 | E1U3451 | sp-9 | an-195 | E1U10777 | sp-35 | an-195 |
| E1A3452 | sp-9 | an-196 | E1U3452 | sp-9 | an-196 | E1U10778 | sp-35 | an-196 |
| E1A3453 | sp-9 | an-197 | E1U3453 | sp-9 | an-197 | E1U10779 | sp-35 | an-197 |
| E1A3454 | sp-9 | an-198 | E1U3454 | sp-9 | an-198 | E1U10780 | sp-35 | an-198 |
| E1A3455 | sp-9 | an-199 | E1U3455 | sp-9 | an-199 | E1U10781 | sp-35 | an-199 |
| E1A3456 | sp-9 | an-200 | E1U3456 | sp-9 | an-200 | E1U10782 | sp-35 | an-200 |
| Table 1-65 |||||||||
| Y = NHCS ||| Y = NHCSNH ||| Y = NHCSNH |||
| E1A3457 | sp-9 | an-201 | E1U3457 | sp-9 | an-201 | E1U10783 | sp-35 | an-201 |
| E1A3458 | sp-9 | an-202 | E1U3458 | sp-9 | an-202 | E1U10784 | sp-35 | an-202 |
| E1A3459 | sp-9 | an-203 | E1U3459 | sp-9 | an-203 | E1U10785 | sp-35 | an-203 |
| E1A3460 | sp-9 | an-204 | E1U3460 | sp-9 | an-204 | E1U10786 | sp-35 | an-204 |
| E1A3461 | sp-9 | an-205 | E1U3461 | sp-9 | an-205 | E1U10787 | sp-35 | an-205 |
| E1A3462 | sp-9 | an-206 | E1U3462 | sp-9 | an-206 | E1U10788 | sp-35 | an-206 |
| E1A3463 | sp-9 | an-207 | E1U3463 | sp-9 | an-207 | E1U10789 | sp-35 | an-207 |
| E1A3464 | sp-9 | an-208 | E1U3464 | sp-9 | an-208 | E1U10790 | sp-35 | an-208 |
| E1A3465 | sp-9 | an-209 | E1U3465 | sp-9 | an-209 | E1U10791 | sp-35 | an-209 |
| E1A3466 | sp-9 | an-210 | E1U3466 | sp-9 | an-210 | E1U10792 | sp-35 | an-210 |
| E1A3467 | sp-9 | an-211 | E1U3467 | sp-9 | an-211 | E1U10793 | sp-35 | an-211 |
| E1A3468 | sp-9 | an-212 | E1U3468 | sp-9 | an-212 | E1U10794 | sp-35 | an-212 |
| E1A3469 | sp-9 | an-213 | E1U3469 | sp-9 | an-213 | E1U10795 | sp-35 | an-213 |
| E1A3470 | sp-9 | an-214 | E1U3470 | sp-9 | an-214 | E1U10796 | sp-35 | an-214 |
| E1A3471 | sp-9 | an-215 | E1U3471 | sp-9 | an-215 | E1U10797 | sp-35 | an-215 |
| E1A3472 | sp-9 | an-216 | E1U3472 | sp-9 | an-216 | E1U10798 | sp-35 | an-216 |

-continued

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| E1A3473 | sp-9 | an-217 | E1U3473 | sp-9 | an-217 | E1U10799 | sp-35 | an-217 |
| E1A3474 | sp-9 | an-218 | E1U3474 | sp-9 | an-218 | E1U10800 | sp-35 | an-218 |
| E1A3475 | sp-9 | an-219 | E1U3475 | sp-9 | an-219 | E1U10801 | sp-35 | an-219 |
| E1A3476 | sp-9 | an-220 | E1U3476 | sp-9 | an-220 | E1U10802 | sp-35 | an-220 |
| E1A3477 | sp-9 | an-221 | E1U3477 | sp-9 | an-221 | E1U10803 | sp-35 | an-221 |
| E1A3478 | sp-9 | an-222 | E1U3478 | sp-9 | an-222 | E1U10804 | sp-35 | an-222 |
| E1A3479 | sp-9 | an-223 | E1U3479 | sp-9 | an-223 | E1U10805 | sp-35 | an-223 |
| E1A3480 | sp-9 | an-224 | E1U3480 | sp-9 | an-224 | E1U10806 | sp-35 | an-224 |
| E1A3481 | sp-9 | an-225 | E1U3481 | sp-9 | an-225 | E1U10807 | sp-35 | an-225 |
| E1A3482 | sp-9 | an-226 | E1U3482 | sp-9 | an-226 | E1U10808 | sp-35 | an-226 |
| E1A3483 | sp-9 | an-227 | E1U3483 | sp-9 | an-227 | E1U10809 | sp-35 | an-227 |
| E1A3484 | sp-9 | an-228 | E1U3484 | sp-9 | an-228 | E1U10810 | sp-35 | an-228 |
| E1A3485 | sp-9 | an-229 | E1U3485 | sp-9 | an-229 | E1U10811 | sp-35 | an-229 |
| E1A3486 | sp-9 | an-230 | E1U3486 | sp-9 | an-230 | E1U10812 | sp-35 | an-230 |
| E1A3487 | sp-9 | an-231 | E1U3487 | sp-9 | an-231 | E1U10813 | sp-35 | an-231 |
| E1A3488 | sp-9 | an-232 | E1U3488 | sp-9 | an-232 | E1U10814 | sp-35 | an-232 |
| E1A3489 | sp-9 | an-233 | E1U3489 | sp-9 | an-233 | E1U10815 | sp-35 | an-233 |
| E1A3490 | sp-9 | an-234 | E1U3490 | sp-9 | an-234 | E1U10816 | sp-35 | an-234 |
| E1A3491 | sp-9 | an-235 | E1U3491 | sp-9 | an-235 | E1U10817 | sp-35 | an-235 |
| E1A3492 | sp-9 | an-236 | E1U3492 | sp-9 | an-236 | E1U10818 | sp-35 | an-236 |
| E1A3493 | sp-9 | an-237 | E1U3493 | sp-9 | an-237 | E1U10819 | sp-35 | an-237 |
| E1A3494 | sp-9 | an-238 | E1U3494 | sp-9 | an-238 | E1U10820 | sp-35 | an-238 |
| E1A3495 | sp-9 | an-239 | E1U3495 | sp-9 | an-239 | E1U10821 | sp-35 | an-239 |
| E1A3496 | sp-9 | an-240 | E1U3496 | sp-9 | an-240 | E1U10822 | sp-35 | an-240 |
| E1A3497 | sp-9 | an-241 | E1U3497 | sp-9 | an-241 | E1U10823 | sp-35 | an-241 |
| E1A3498 | sp-9 | an-242 | E1U3498 | sp-9 | an-242 | E1U10824 | sp-35 | an-242 |
| E1A3499 | sp-9 | an-243 | E1U3499 | sp-9 | an-243 | E1U10825 | sp-35 | an-243 |
| E1A3500 | sp-9 | an-244 | E1U3500 | sp-9 | an-244 | E1U10826 | sp-35 | an-244 |
| E1A3501 | sp-9 | an-245 | E1U3501 | sp-9 | an-245 | E1U10827 | sp-35 | an-245 |
| E1A3502 | sp-9 | an-246 | E1U3502 | sp-9 | an-246 | E1U10828 | sp-35 | an-246 |
| E1A3503 | sp-9 | an-247 | E1U3503 | sp-9 | an-247 | E1U10829 | sp-35 | an-247 |
| E1A3504 | sp-9 | an-248 | E1U3504 | sp-9 | an-248 | E1U10830 | sp-35 | an-248 |
| E1A3505 | sp-9 | an-249 | E1U3505 | sp-9 | an-249 | E1U10831 | sp-35 | an-249 |
| E1A3506 | sp-9 | an-250 | E1U3506 | sp-9 | an-250 | E1U10832 | sp-35 | an-250 |
| E1A3507 | sp-9 | an-251 | E1U3507 | sp-9 | an-251 | E1U10833 | sp-35 | an-251 |
| E1A3508 | sp-9 | an-252 | E1U3508 | sp-9 | an-252 | E1U10834 | sp-35 | an-252 |
| E1A3509 | sp-9 | an-253 | E1U3509 | sp-9 | an-253 | E1U10835 | sp-35 | an-253 |
| E1A3510 | sp-9 | an-254 | E1U3510 | sp-9 | an-254 | E1U10836 | sp-35 | an-254 |

Table 1-66

| Y = NHCS | | | Y = NHCSNH | | | Y = NHCSNH | | |
|---|---|---|---|---|---|---|---|---|
| E1A3511 | sp-9 | an-255 | E1U3511 | sp-9 | an-255 | E1U10837 | sp-35 | an-255 |
| E1A3512 | sp-9 | an-256 | E1U3512 | sp-9 | an-256 | E1U10838 | sp-35 | an-256 |
| E1A3513 | sp-9 | an-257 | E1U3513 | sp-9 | an-257 | E1U10839 | sp-35 | an-257 |
| E1A3514 | sp-9 | an-258 | E1U3514 | sp-9 | an-258 | E1U10840 | sp-35 | an-258 |
| E1A3515 | sp-9 | an-259 | E1U3515 | sp-9 | an-259 | E1U10841 | sp-35 | an-259 |
| E1A3516 | sp-9 | an-260 | E1U3516 | sp-9 | an-260 | E1U10842 | sp-35 | an-260 |
| E1A3517 | sp-9 | an-261 | E1U3517 | sp-9 | an-261 | E1U10843 | sp-35 | an-261 |
| E1A3518 | sp-9 | an-262 | E1U3518 | sp-9 | an-262 | E1U10844 | sp-35 | an-262 |
| E1A3519 | sp-9 | an-263 | E1U3519 | sp-9 | an-263 | E1U10845 | sp-35 | an-263 |
| E1A3520 | sp-9 | an-264 | E1U3520 | sp-9 | an-264 | E1U10846 | sp-35 | an-264 |
| E1A3521 | sp-9 | an-265 | E1U3521 | sp-9 | an-265 | E1U10847 | sp-35 | an-265 |
| E1A3522 | sp-9 | an-266 | E1U3522 | sp-9 | an-266 | E1U10848 | sp-35 | an-266 |
| E1A3523 | sp-9 | an-267 | E1U3523 | sp-9 | an-267 | E1U10849 | sp-35 | an-267 |
| E1A3524 | sp-9 | an-268 | E1U3524 | sp-9 | an-268 | E1U10850 | sp-35 | an-268 |
| E1A3525 | sp-9 | an-269 | E1U3525 | sp-9 | an-269 | E1U10851 | sp-35 | an-269 |
| E1A3526 | sp-9 | an-270 | E1U3526 | sp-9 | an-270 | E1U10852 | sp-35 | an-270 |
| E1A3527 | sp-9 | an-271 | E1U3527 | sp-9 | an-271 | E1U10853 | sp-35 | an-271 |
| E1A3528 | sp-9 | an-272 | E1U3528 | sp-9 | an-272 | E1U10854 | sp-35 | an-272 |
| E1A3529 | sp-9 | an-273 | E1U3529 | sp-9 | an-273 | E1U10855 | sp-35 | an-273 |
| E1A3530 | sp-9 | an-274 | E1U3530 | sp-9 | an-274 | E1U10856 | sp-35 | an-274 |
| E1A3531 | sp-9 | an-275 | E1U3531 | sp-9 | an-275 | E1U10857 | sp-35 | an-275 |
| E1A3532 | sp-9 | an-276 | E1U3532 | sp-9 | an-276 | E1U10858 | sp-35 | an-276 |
| E1A3533 | sp-9 | an-277 | E1U3533 | sp-9 | an-277 | E1U10859 | sp-35 | an-277 |
| E1A3534 | sp-9 | an-278 | E1U3534 | sp-9 | an-278 | E1U10860 | sp-35 | an-278 |
| E1A3535 | sp-9 | an-279 | E1U3535 | sp-9 | an-279 | E1U10861 | sp-35 | an-279 |
| E1A3536 | sp-9 | an-280 | E1U3536 | sp-9 | an-280 | E1U10862 | sp-35 | an-280 |
| E1A3537 | sp-9 | an-281 | E1U3537 | sp-9 | an-281 | E1U10863 | sp-35 | an-281 |
| E1A3538 | sp-9 | an-282 | E1U3538 | sp-9 | an-282 | E1U10864 | sp-35 | an-282 |
| E1A3539 | sp-9 | an-283 | E1U3539 | sp-9 | an-283 | E1U10865 | sp-35 | an-283 |
| E1A3540 | sp-9 | an-284 | E1U3540 | sp-9 | an-284 | E1U10866 | sp-35 | an-284 |
| E1A3541 | sp-9 | an-285 | E1U3541 | sp-9 | an-285 | E1U10867 | sp-35 | an-285 |
| E1A3542 | sp-9 | an-286 | E1U3542 | sp-9 | an-286 | E1U10868 | sp-35 | an-286 |
| E1A3543 | sp-9 | an-287 | E1U3543 | sp-9 | an-287 | E1U10869 | sp-35 | an-287 |
| E1A3544 | sp-9 | an-288 | E1U3544 | sp-9 | an-288 | E1U10870 | sp-35 | an-288 |
| E1A3545 | sp-9 | an-289 | E1U3545 | sp-9 | an-289 | E1U10871 | sp-35 | an-289 |
| E1A3546 | sp-9 | an-290 | E1U3546 | sp-9 | an-290 | E1U10872 | sp-35 | an-290 |

-continued

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| E1A3547 | sp-9 | an-291 | E1U3547 | sp-9 | an-291 | E1U10873 | sp-35 | an-291 |
| E1A3548 | sp-9 | an-292 | E1U3548 | sp-9 | an-292 | E1U10874 | sp-35 | an-292 |
| E1A3549 | sp-9 | an-293 | E1U3549 | sp-9 | an-293 | E1U10875 | sp-35 | an-293 |
| E1A3550 | sp-9 | an-294 | E1U3550 | sp-9 | an-294 | E1U10876 | sp-35 | an-294 |
| E1A3551 | sp-9 | an-295 | E1U3551 | sp-9 | an-295 | E1U10877 | sp-35 | an-295 |
| E1A3552 | sp-9 | an-296 | E1U3552 | sp-9 | an-296 | E1U10878 | sp-35 | an-296 |
| E1A3553 | sp-9 | an-297 | E1U3553 | sp-9 | an-297 | E1U10879 | sp-35 | an-297 |
| E1A3554 | sp-9 | an-298 | E1U3554 | sp-9 | an-298 | E1U10880 | sp-35 | an-298 |
| E1A3555 | sp-9 | an-299 | E1U3555 | sp-9 | an-299 | E1U10881 | sp-35 | an-299 |
| E1A3556 | sp-9 | an-300 | E1U3556 | sp-9 | an-300 | E1U10882 | sp-35 | an-300 |
| E1A3557 | sp-9 | an-301 | E1U3557 | sp-9 | an-301 | E1U10883 | sp-35 | an-301 |
| E1A3558 | sp-9 | an-302 | E1U3558 | sp-9 | an-302 | E1U10884 | sp-35 | an-302 |
| E1A3559 | sp-9 | an-303 | E1U3559 | sp-9 | an-303 | E1U10885 | sp-35 | an-303 |
| E1A3560 | sp-9 | an-304 | E1U3560 | sp-9 | an-304 | E1U10886 | sp-35 | an-304 |
| E1A3561 | sp-9 | an-305 | E1U3561 | sp-9 | an-305 | E1U10887 | sp-35 | an-305 |
| E1A3562 | sp-9 | an-306 | E1U3562 | sp-9 | an-306 | E1U10888 | sp-35 | an-306 |
| E1A3563 | sp-9 | an-307 | E1U3563 | sp-9 | an-307 | E1U10889 | sp-35 | an-307 |
| E1A3564 | sp-9 | an-308 | E1U3564 | sp-9 | an-308 | E1U10890 | sp-35 | an-308 |

Table 1-67

| Y = NHCS | | | Y = NHCSNH | | | Y = NHCSNH | | |
|---|---|---|---|---|---|---|---|---|
| E1A3565 | sp-9 | an-309 | E1U3565 | sp-9 | an-309 | E1U10891 | sp-35 | an-309 |
| E1A3566 | sp-9 | an-310 | E1U3566 | sp-9 | an-310 | E1U10892 | sp-35 | an-310 |
| E1A3567 | sp-9 | an-311 | E1U3567 | sp-9 | an-311 | E1U10893 | sp-35 | an-311 |
| E1A3568 | sp-9 | an-312 | E1U3568 | sp-9 | an-312 | E1U10894 | sp-35 | an-312 |
| E1A3569 | sp-9 | an-313 | E1U3569 | sp-9 | an-313 | E1U10895 | sp-35 | an-313 |
| E1A3570 | sp-9 | an-314 | E1U3570 | sp-9 | an-314 | E1U10896 | sp-35 | an-314 |
| E1A3571 | sp-9 | an-315 | E1U3571 | sp-9 | an-315 | E1U10897 | sp-35 | an-315 |
| E1A3572 | sp-9 | an-316 | E1U3572 | sp-9 | an-316 | E1U10898 | sp-35 | an-316 |
| E1A3573 | sp-9 | an-317 | E1U3573 | sp-9 | an-317 | E1U10899 | sp-35 | an-317 |
| E1A3574 | sp-9 | an-318 | E1U3574 | sp-9 | an-318 | E1U10900 | sp-35 | an-318 |
| E1A3575 | sp-9 | an-319 | E1U3575 | sp-9 | an-319 | E1U10901 | sp-35 | an-319 |
| E1A3576 | sp-9 | an-320 | E1U3576 | sp-9 | an-320 | E1U10902 | sp-35 | an-320 |
| E1A3577 | sp-9 | an-321 | E1U3577 | sp-9 | an-321 | E1U10903 | sp-35 | an-321 |
| E1A3578 | sp-9 | an-322 | E1U3578 | sp-9 | an-322 | E1U10904 | sp-35 | an-322 |
| E1A3579 | sp-9 | an-323 | E1U3579 | sp-9 | an-323 | E1U10905 | sp-35 | an-323 |
| E1A3580 | sp-9 | an-324 | E1U3580 | sp-9 | an-324 | E1U10906 | sp-35 | an-324 |
| E1A3581 | sp-9 | an-325 | E1U3581 | sp-9 | an-325 | E1U10907 | sp-35 | an-325 |
| E1A3582 | sp-9 | an-326 | E1U3582 | sp-9 | an-326 | E1U10908 | sp-35 | an-326 |
| E1A3583 | sp-9 | an-327 | E1U3583 | sp-9 | an-327 | E1U10909 | sp-35 | an-327 |
| E1A3584 | sp-9 | an-328 | E1U3584 | sp-9 | an-328 | E1U10910 | sp-35 | an-328 |
| E1A3585 | sp-9 | an-329 | E1U3585 | sp-9 | an-329 | E1U10911 | sp-35 | an-329 |
| E1A3586 | sp-9 | an-330 | E1U3586 | sp-9 | an-330 | E1U10912 | sp-35 | an-330 |
| E1A3587 | sp-9 | an-331 | E1U3587 | sp-9 | an-331 | E1U10913 | sp-35 | an-331 |
| E1A3588 | sp-9 | an-332 | E1U3588 | sp-9 | an-332 | E1U10914 | sp-35 | an-332 |
| E1A3589 | sp-9 | an-333 | E1U3589 | sp-9 | an-333 | E1U10915 | sp-35 | an-333 |
| E1A3590 | sp-9 | an-334 | E1U3590 | sp-9 | an-334 | E1U10916 | sp-35 | an-334 |
| E1A3591 | sp-9 | an-335 | E1U3591 | sp-9 | an-335 | E1U10917 | sp-35 | an-335 |
| E1A3592 | sp-9 | an-336 | E1U3592 | sp-9 | an-336 | E1U10918 | sp-35 | an-336 |
| E1A3593 | sp-9 | an-337 | E1U3593 | sp-9 | an-337 | E1U10919 | sp-35 | an-337 |
| E1A3594 | sp-9 | an-338 | E1U3594 | sp-9 | an-338 | E1U10920 | sp-35 | an-338 |
| E1A3595 | sp-9 | an-339 | E1U3595 | sp-9 | an-339 | E1U10921 | sp-35 | an-339 |
| E1A3596 | sp-9 | an-340 | E1U3596 | sp-9 | an-340 | E1U10922 | sp-35 | an-340 |
| E1A3597 | sp-9 | an-341 | E1U3597 | sp-9 | an-341 | E1U10923 | sp-35 | an-341 |
| E1A3598 | sp-9 | an-342 | E1U3598 | sp-9 | an-342 | E1U10924 | sp-35 | an-342 |
| E1A3599 | sp-9 | an-343 | E1U3599 | sp-9 | an-343 | E1U10925 | sp-35 | an-343 |
| E1A3600 | sp-9 | an-344 | E1U3600 | sp-9 | an-344 | E1U10926 | sp-35 | an-344 |
| E1A3601 | sp-9 | an-345 | E1U3601 | sp-9 | an-345 | E1U10927 | sp-35 | an-345 |
| E1A3602 | sp-9 | an-346 | E1U3602 | sp-9 | an-346 | E1U10928 | sp-35 | an-346 |
| E1A3603 | sp-9 | an-347 | E1U3603 | sp-9 | an-347 | E1U10929 | sp-35 | an-347 |
| E1A3604 | sp-9 | an-348 | E1U3604 | sp-9 | an-348 | E1U10930 | sp-35 | an-348 |
| E1A3605 | sp-9 | an-349 | E1U3605 | sp-9 | an-349 | E1U10931 | sp-35 | an-349 |
| E1A3606 | sp-9 | an-350 | E1U3606 | sp-9 | an-350 | E1U10932 | sp-35 | an-350 |
| E1A3607 | sp-9 | an-351 | E1U3607 | sp-9 | an-351 | E1U10933 | sp-35 | an-351 |
| E1A3608 | sp-9 | an-352 | E1U3608 | sp-9 | an-352 | E1U10934 | sp-35 | an-352 |
| E1A3609 | sp-9 | an-353 | E1U3609 | sp-9 | an-353 | E1U10935 | sp-35 | an-353 |
| E1A3610 | sp-9 | an-354 | E1U3610 | sp-9 | an-354 | E1U10936 | sp-35 | an-354 |
| E1A3611 | sp-9 | an-355 | E1U3611 | sp-9 | an-355 | E1U10937 | sp-35 | an-355 |
| E1A3612 | sp-9 | an-356 | E1U3612 | sp-9 | an-356 | E1U10938 | sp-35 | an-356 |
| E1A3613 | sp-9 | an-357 | E1U3613 | sp-9 | an-357 | E1U10939 | sp-35 | an-357 |
| E1A3614 | sp-9 | an-358 | E1U3614 | sp-9 | an-358 | E1U10940 | sp-35 | an-358 |
| E1A3615 | sp-9 | an-359 | E1U3615 | sp-9 | an-359 | E1U10941 | sp-35 | an-359 |
| E1A3616 | sp-9 | an-360 | E1U3616 | sp-9 | an-360 | E1U10942 | sp-35 | an-360 |
| E1A3617 | sp-9 | an-361 | E1U3617 | sp-9 | an-361 | E1U10943 | sp-35 | an-361 |
| E1A3618 | sp-9 | an-362 | E1U3618 | sp-9 | an-362 | E1U10944 | sp-35 | an-362 |

-continued

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| Table 1-68 ||||||||| 
| Y = NHCS ||| Y = NHCSNH ||| Y = NHCSNH |||
| E1A3619 | sp-9 | an-363 | E1U3619 | sp-9 | an-363 | E1U10945 | sp-35 | an-363 |
| E1A3620 | sp-9 | an-364 | E1U3620 | sp-9 | an-364 | E1U10946 | sp-35 | an-364 |
| E1A3621 | sp-9 | an-365 | E1U3621 | sp-9 | an-365 | E1U10947 | sp-35 | an-365 |
| E1A3622 | sp-9 | an-366 | E1U3622 | sp-9 | an-366 | E1U10948 | sp-35 | an-366 |
| E1A3623 | sp-9 | an-367 | E1U3623 | sp-9 | an-367 | E1U10949 | sp-35 | an-367 |
| E1A3624 | sp-9 | an-368 | E1U3624 | sp-9 | an-368 | E1U10950 | sp-35 | an-368 |
| E1A3625 | sp-9 | an-369 | E1U3625 | sp-9 | an-369 | E1U10951 | sp-35 | an-369 |
| E1A3626 | sp-9 | an-370 | E1U3626 | sp-9 | an-370 | E1U10952 | sp-35 | an-370 |
| E1A3627 | sp-9 | an-371 | E1U3627 | sp-9 | an-371 | E1U10953 | sp-35 | an-371 |
| E1A3628 | sp-9 | an-372 | E1U3628 | sp-9 | an-372 | E1U10954 | sp-35 | an-372 |
| E1A3629 | sp-9 | an-373 | E1U3629 | sp-9 | an-373 | E1U10955 | sp-35 | an-373 |
| E1A3630 | sp-9 | an-374 | E1U3630 | sp-9 | an-374 | E1U10956 | sp-35 | an-374 |
| E1A3631 | sp-9 | an-375 | E1U3631 | sp-9 | an-375 | E1U10957 | sp-35 | an-375 |
| E1A3632 | sp-9 | an-376 | E1U3632 | sp-9 | an-376 | E1U10958 | sp-35 | an-376 |
| E1A3633 | sp-9 | an-377 | E1U3633 | sp-9 | an-377 | E1U10959 | sp-35 | an-377 |
| E1A3634 | sp-9 | an-378 | E1U3634 | sp-9 | an-378 | E1U10960 | sp-35 | an-378 |
| E1A3635 | sp-9 | an-379 | E1U3635 | sp-9 | an-379 | E1U10961 | sp-35 | an-379 |
| E1A3636 | sp-9 | an-380 | E1U3636 | sp-9 | an-380 | E1U10962 | sp-35 | an-380 |
| E1A3637 | sp-9 | an-381 | E1U3637 | sp-9 | an-381 | E1U10963 | sp-35 | an-381 |
| E1A3638 | sp-9 | an-382 | E1U3638 | sp-9 | an-382 | E1U10964 | sp-35 | an-382 |
| E1A3639 | sp-9 | an-383 | E1U3639 | sp-9 | an-383 | E1U10965 | sp-35 | an-383 |
| E1A3640 | sp-9 | an-384 | E1U3640 | sp-9 | an-384 | E1U10966 | sp-35 | an-384 |
| E1A3641 | sp-9 | an-385 | E1U3641 | sp-9 | an-385 | E1U10967 | sp-35 | an-385 |
| E1A3642 | sp-9 | an-386 | E1U3642 | sp-9 | an-386 | E1U10968 | sp-35 | an-386 |
| E1A3643 | sp-9 | an-387 | E1U3643 | sp-9 | an-387 | E1U10969 | sp-35 | an-387 |
| E1A3644 | sp-9 | an-388 | E1U3644 | sp-9 | an-388 | E1U10970 | sp-35 | an-388 |
| E1A3645 | sp-9 | an-389 | E1U3645 | sp-9 | an-389 | E1U10971 | sp-35 | an-389 |
| E1A3646 | sp-9 | an-390 | E1U3646 | sp-9 | an-390 | E1U10972 | sp-35 | an-390 |
| E1A3647 | sp-9 | an-391 | E1U3647 | sp-9 | an-391 | E1U10973 | sp-35 | an-391 |
| E1A3648 | sp-9 | an-392 | E1U3648 | sp-9 | an-392 | E1U10974 | sp-35 | an-392 |
| E1A3649 | sp-9 | an-393 | E1U3649 | sp-9 | an-393 | E1U10975 | sp-35 | an-393 |
| E1A3650 | sp-9 | an-394 | E1U3650 | sp-9 | an-394 | E1U10976 | sp-35 | an-394 |
| E1A3651 | sp-9 | an-395 | E1U3651 | sp-9 | an-395 | E1U10977 | sp-35 | an-395 |
| E1A3652 | sp-9 | an-396 | E1U3652 | sp-9 | an-396 | E1U10978 | sp-35 | an-396 |
| E1A3653 | sp-9 | an-397 | E1U3653 | sp-9 | an-397 | E1U10979 | sp-35 | an-397 |
| E1A3654 | sp-9 | an-398 | E1U3654 | sp-9 | an-398 | E1U10980 | sp-35 | an-398 |
| E1A3655 | sp-9 | an-399 | E1U3655 | sp-9 | an-399 | E1U10981 | sp-35 | an-399 |
| E1A3656 | sp-9 | an-400 | E1U3656 | sp-9 | an-400 | E1U10982 | sp-35 | an-400 |
| E1A3657 | sp-9 | an-401 | E1U3657 | sp-9 | an-401 | E1U10983 | sp-35 | an-401 |
| E1A3658 | sp-9 | an-402 | E1U3658 | sp-9 | an-402 | E1U10984 | sp-35 | an-402 |
| E1A3659 | sp-9 | an-403 | E1U3659 | sp-9 | an-403 | E1U10985 | sp-35 | an-403 |
| E1A3660 | sp-9 | an-404 | E1U3660 | sp-9 | an-404 | E1U10986 | sp-35 | an-404 |
| E1A3661 | sp-9 | an-405 | E1U3661 | sp-9 | an-405 | E1U10987 | sp-35 | an-405 |
| E1A3662 | sp-9 | an-406 | E1U3662 | sp-9 | an-406 | E1U10988 | sp-35 | an-406 |
| E1A3663 | sp-9 | an-407 | E1U3663 | sp-9 | an-407 | E1U10989 | sp-35 | an-407 |
| E1A3664 | sp-10 | an-1 | E1U3664 | sp-12 | an-1 | E1U10990 | sp-36 | an-1 |
| E1A3665 | sp-10 | an-2 | E1U3665 | sp-12 | an-2 | E1U10991 | sp-36 | an-2 |
| E1A3666 | sp-10 | an-3 | E1U3666 | sp-12 | an-3 | E1U10992 | sp-36 | an-3 |
| E1A3667 | sp-10 | an-4 | E1U3667 | sp-12 | an-4 | E1U10993 | sp-36 | an-4 |
| E1A3668 | sp-10 | an-5 | E1U3668 | sp-12 | an-5 | E1U10994 | sp-36 | an-5 |
| E1A3669 | sp-10 | an-6 | E1U3669 | sp-12 | an-6 | E1U10995 | sp-36 | an-6 |
| E1A3670 | sp-10 | an-7 | E1U3670 | sp-12 | an-7 | E1U10996 | sp-36 | an-7 |
| E1A3671 | sp-10 | an-8 | E1U3671 | sp-12 | an-8 | E1U10997 | sp-36 | an-8 |
| E1A3672 | sp-10 | an-9 | E1U3672 | sp-12 | an-9 | E1U10998 | sp-36 | an-9 |
| Table 1-69 |||||||||
| Y = NHCS ||| Y = NHCSNH ||| Y = NHCSNH |||
| E1A3673 | sp-10 | an-10 | E1U3673 | sp-12 | an-10 | E1U10999 | sp-36 | an-10 |
| E1A3674 | sp-10 | an-11 | E1U3674 | sp-12 | an-11 | E1U11000 | sp-36 | an-11 |
| E1A3675 | sp-10 | an-12 | E1U3675 | sp-12 | an-12 | E1U11001 | sp-36 | an-12 |
| E1A3676 | sp-10 | an-13 | E1U3676 | sp-12 | an-13 | E1U11002 | sp-36 | an-13 |
| E1A3677 | sp-10 | an-14 | E1U3677 | sp-12 | an-14 | E1U11003 | sp-36 | an-14 |
| E1A3678 | sp-10 | an-15 | E1U3678 | sp-12 | an-15 | E1U11004 | sp-36 | an-15 |
| E1A3679 | sp-10 | an-16 | E1U3679 | sp-12 | an-16 | E1U11005 | sp-36 | an-16 |
| E1A3680 | sp-10 | an-17 | E1U3680 | sp-12 | an-17 | E1U11006 | sp-36 | an-17 |
| E1A3681 | sp-10 | an-18 | E1U3681 | sp-12 | an-18 | E1U11007 | sp-36 | an-18 |
| E1A3682 | sp-10 | an-19 | E1U3682 | sp-12 | an-19 | E1U11008 | sp-36 | an-19 |
| E1A3683 | sp-10 | an-20 | E1U3683 | sp-12 | an-20 | E1U11009 | sp-36 | an-20 |
| E1A3684 | sp-10 | an-21 | E1U3684 | sp-12 | an-21 | E1U11010 | sp-36 | an-21 |
| E1A3685 | sp-10 | an-22 | E1U3685 | sp-12 | an-22 | E1U11011 | sp-36 | an-22 |
| E1A3686 | sp-10 | an-23 | E1U3686 | sp-12 | an-23 | E1U11012 | sp-36 | an-23 |
| E1A3687 | sp-10 | an-24 | E1U3687 | sp-12 | an-24 | E1U11013 | sp-36 | an-24 |
| E1A3688 | sp-10 | an-25 | E1U3688 | sp-12 | an-25 | E1U11014 | sp-36 | an-25 |

-continued

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| E1A3689 | sp-10 | an-26 | E1U3689 | sp-12 | an-26 | E1U11015 | sp-36 | an-26 |
| E1A3690 | sp-10 | an-27 | E1U3690 | sp-12 | an-27 | E1U11016 | sp-36 | an-27 |
| E1A3691 | sp-10 | an-28 | E1U3691 | sp-12 | an-28 | E1U11017 | sp-36 | an-28 |
| E1A3692 | sp-10 | an-29 | E1U3692 | sp-12 | an-29 | E1U11018 | sp-36 | an-29 |
| E1A3693 | sp-10 | an-30 | E1U3693 | sp-12 | an-30 | E1U11019 | sp-36 | an-30 |
| E1A3694 | sp-10 | an-31 | E1U3694 | sp-12 | an-31 | E1U11020 | sp-36 | an-31 |
| E1A3695 | sp-10 | an-32 | E1U3695 | sp-12 | an-32 | E1U11021 | sp-36 | an-32 |
| E1A3696 | sp-10 | an-33 | E1U3696 | sp-12 | an-33 | E1U11022 | sp-36 | an-33 |
| E1A3697 | sp-10 | an-34 | E1U3697 | sp-12 | an-34 | E1U11023 | sp-36 | an-34 |
| E1A3698 | sp-10 | an-35 | E1U3698 | sp-12 | an-35 | E1U11024 | sp-36 | an-35 |
| E1A3699 | sp-10 | an-36 | E1U3699 | sp-12 | an-36 | E1U11025 | sp-36 | an-36 |
| E1A3700 | sp-10 | an-37 | E1U3700 | sp-12 | an-37 | E1U11026 | sp-36 | an-37 |
| E1A3701 | sp-10 | an-38 | E1U3701 | sp-12 | an-38 | E1U11027 | sp-36 | an-38 |
| E1A3702 | sp-10 | an-39 | E1U3702 | sp-12 | an-39 | E1U11028 | sp-36 | an-39 |
| E1A3703 | sp-10 | an-40 | E1U3703 | sp-12 | an-40 | E1U11029 | sp-36 | an-40 |
| E1A3704 | sp-10 | an-41 | E1U3704 | sp-12 | an-41 | E1U11030 | sp-36 | an-41 |
| E1A3705 | sp-10 | an-42 | E1U3705 | sp-12 | an-42 | E1U11031 | sp-36 | an-42 |
| E1A3706 | sp-10 | an-43 | E1U3706 | sp-12 | an-43 | E1U11032 | sp-36 | an-43 |
| E1A3707 | sp-10 | an-44 | E1U3707 | sp-12 | an-44 | E1U11033 | sp-36 | an-44 |
| E1A3708 | sp-10 | an-45 | E1U3708 | sp-12 | an-45 | E1U11034 | sp-36 | an-45 |
| E1A3709 | sp-10 | an-46 | E1U3709 | sp-12 | an-46 | E1U11035 | sp-36 | an-46 |
| E1A3710 | sp-10 | an-47 | E1U3710 | sp-12 | an-47 | E1U11036 | sp-36 | an-47 |
| E1A3711 | sp-10 | an-48 | E1U3711 | sp-12 | an-48 | E1U11037 | sp-36 | an-48 |
| E1A3712 | sp-10 | an-49 | E1U3712 | sp-12 | an-49 | E1U11038 | sp-36 | an-49 |
| E1A3713 | sp-10 | an-50 | E1U3713 | sp-12 | an-50 | E1U11039 | sp-36 | an-50 |
| E1A3714 | sp-10 | an-51 | E1U3714 | sp-12 | an-51 | E1U11040 | sp-36 | an-51 |
| E1A3715 | sp-10 | an-52 | E1U3715 | sp-12 | an-52 | E1U11041 | sp-36 | an-52 |
| E1A3716 | sp-10 | an-53 | E1U3716 | sp-12 | an-53 | E1U11042 | sp-36 | an-53 |
| E1A3717 | sp-10 | an-54 | E1U3717 | sp-12 | an-54 | E1U11043 | sp-36 | an-54 |
| E1A3718 | sp-10 | an-55 | E1U3718 | sp-12 | an-55 | E1U11044 | sp-36 | an-55 |
| E1A3719 | sp-10 | an-56 | E1U3719 | sp-12 | an-56 | E1U11045 | sp-36 | an-56 |
| E1A3720 | sp-10 | an-57 | E1U3720 | sp-12 | an-57 | E1U11046 | sp-36 | an-57 |
| E1A3721 | sp-10 | an-58 | E1U3721 | sp-12 | an-58 | E1U11047 | sp-36 | an-58 |
| E1A3722 | sp-10 | an-59 | E1U3722 | sp-12 | an-59 | E1U11048 | sp-36 | an-59 |
| E1A3723 | sp-10 | an-60 | E1U3723 | sp-12 | an-60 | E1U11049 | sp-36 | an-60 |
| E1A3724 | sp-10 | an-61 | E1U3724 | sp-12 | an-61 | E1U11050 | sp-36 | an-61 |
| E1A3725 | sp-10 | an-62 | E1U3725 | sp-12 | an-62 | E1U11051 | sp-36 | an-62 |
| E1A3726 | sp-10 | an-63 | E1U3726 | sp-12 | an-63 | E1U11052 | sp-36 | an-63 |

Table 1-70

| Y = NHCS | | | Y = NHCSNH | | | Y = NHCSNH | | |
|---|---|---|---|---|---|---|---|---|
| E1A3727 | sp-10 | an-64 | E1U3727 | sp-12 | an-64 | E1U11053 | sp-36 | an-64 |
| E1A3728 | sp-10 | an-65 | E1U3728 | sp-12 | an-65 | E1U11054 | sp-36 | an-65 |
| E1A3729 | sp-10 | an-66 | E1U3729 | sp-12 | an-66 | E1U11055 | sp-36 | an-66 |
| E1A3730 | sp-10 | an-67 | E1U3730 | sp-12 | an-67 | E1U11056 | sp-36 | an-67 |
| E1A3731 | sp-10 | an-68 | E1U3731 | sp-12 | an-68 | E1U11057 | sp-36 | an-68 |
| E1A3732 | sp-10 | an-69 | E1U3732 | sp-12 | an-69 | E1U11058 | sp-36 | an-69 |
| E1A3733 | sp-10 | an-70 | E1U3733 | sp-12 | an-70 | E1U11059 | sp-36 | an-70 |
| E1A3734 | sp-10 | an-71 | E1U3734 | sp-12 | an-71 | E1U11060 | sp-36 | an-71 |
| E1A3735 | sp-10 | an-72 | E1U3735 | sp-12 | an-72 | E1U11061 | sp-36 | an-72 |
| E1A3736 | sp-10 | an-73 | E1U3736 | sp-12 | an-73 | E1U11062 | sp-36 | an-73 |
| E1A3737 | sp-10 | an-74 | E1U3737 | sp-12 | an-74 | E1U11063 | sp-36 | an-74 |
| E1A3738 | sp-10 | an-75 | E1U3738 | sp-12 | an-75 | E1U11064 | sp-36 | an-75 |
| E1A3739 | sp-10 | an-76 | E1U3739 | sp-12 | an-76 | E1U11065 | sp-36 | an-76 |
| E1A3740 | sp-10 | an-77 | E1U3740 | sp-12 | an-77 | E1U11066 | sp-36 | an-77 |
| E1A3741 | sp-10 | an-78 | E1U3741 | sp-12 | an-78 | E1U11067 | sp-36 | an-78 |
| E1A3742 | sp-10 | an-79 | E1U3742 | sp-12 | an-79 | E1U11068 | sp-36 | an-79 |
| E1A3743 | sp-10 | an-80 | E1U3743 | sp-12 | an-80 | E1U11069 | sp-36 | an-80 |
| E1A3744 | sp-10 | an-81 | E1U3744 | sp-12 | an-81 | E1U11070 | sp-36 | an-81 |
| E1A3745 | sp-10 | an-82 | E1U3745 | sp-12 | an-82 | E1U11071 | sp-36 | an-82 |
| E1A3746 | sp-10 | an-83 | E1U3746 | sp-12 | an-83 | E1U11072 | sp-36 | an-83 |
| E1A3747 | sp-10 | an-84 | E1U3747 | sp-12 | an-84 | E1U11073 | sp-36 | an-84 |
| E1A3748 | sp-10 | an-85 | E1U3748 | sp-12 | an-85 | E1U11074 | sp-36 | an-85 |
| E1A3749 | sp-10 | an-86 | E1U3749 | sp-12 | an-86 | E1U11075 | sp-36 | an-86 |
| E1A3750 | sp-10 | an-87 | E1U3750 | sp-12 | an-87 | E1U11076 | sp-36 | an-87 |
| E1A3751 | sp-10 | an-88 | E1U3751 | sp-12 | an-88 | E1U11077 | sp-36 | an-88 |
| E1A3752 | sp-10 | an-89 | E1U3752 | sp-12 | an-89 | E1U11078 | sp-36 | an-89 |
| E1A3753 | sp-10 | an-90 | E1U3753 | sp-12 | an-90 | E1U11079 | sp-36 | an-90 |
| E1A3754 | sp-10 | an-91 | E1U3754 | sp-12 | an-91 | E1U11080 | sp-36 | an-91 |
| E1A3755 | sp-10 | an-92 | E1U3755 | sp-12 | an-92 | E1U11081 | sp-36 | an-92 |
| E1A3756 | sp-10 | an-93 | E1U3756 | sp-12 | an-93 | E1U11082 | sp-36 | an-93 |
| E1A3757 | sp-10 | an-94 | E1U3757 | sp-12 | an-94 | E1U11083 | sp-36 | an-94 |
| E1A3758 | sp-10 | an-95 | E1U3758 | sp-12 | an-95 | E1U11084 | sp-36 | an-95 |
| E1A3759 | sp-10 | an-96 | E1U3759 | sp-12 | an-96 | E1U11085 | sp-36 | an-96 |
| E1A3760 | sp-10 | an-97 | E1U3760 | sp-12 | an-97 | E1U11086 | sp-36 | an-97 |
| E1A3761 | sp-10 | an-98 | E1U3761 | sp-12 | an-98 | E1U11087 | sp-36 | an-98 |
| E1A3762 | sp-10 | an-99 | E1U3762 | sp-12 | an-99 | E1U11088 | sp-36 | an-99 |

-continued

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| E1A3763 | sp-10 | an-100 | E1U3763 | sp-12 | an-100 | E1U11089 | sp-36 | an-100 |
| E1A3764 | sp-10 | an-101 | E1U3764 | sp-12 | an-101 | E1U11090 | sp-36 | an-101 |
| E1A3765 | sp-10 | an-102 | E1U3765 | sp-12 | an-102 | E1U11091 | sp-36 | an-102 |
| E1A3766 | sp-10 | an-103 | E1U3766 | sp-12 | an-103 | E1U11092 | sp-36 | an-103 |
| E1A3767 | sp-10 | an-104 | E1U3767 | sp-12 | an-104 | E1U11093 | sp-36 | an-104 |
| E1A3768 | sp-10 | an-105 | E1U3768 | sp-12 | an-105 | E1U11094 | sp-36 | an-105 |
| E1A3769 | sp-10 | an-106 | E1U3769 | sp-12 | an-106 | E1U11095 | sp-36 | an-106 |
| E1A3770 | sp-10 | an-107 | E1U3770 | sp-12 | an-107 | E1U11096 | sp-36 | an-107 |
| E1A3771 | sp-10 | an-108 | E1U3771 | sp-12 | an-108 | E1U11097 | sp-36 | an-108 |
| E1A3772 | sp-10 | an-109 | E1U3772 | sp-12 | an-109 | E1U11098 | sp-36 | an-109 |
| E1A3773 | sp-10 | an-110 | E1U3773 | sp-12 | an-110 | E1U11099 | sp-36 | an-110 |
| E1A3774 | sp-10 | an-111 | E1U3774 | sp-12 | an-111 | E1U11100 | sp-36 | an-111 |
| E1A3775 | sp-10 | an-112 | E1U3775 | sp-12 | an-112 | E1U11101 | sp-36 | an-112 |
| E1A3776 | sp-10 | an-113 | E1U3776 | sp-12 | an-113 | E1U11102 | sp-36 | an-113 |
| E1A3777 | sp-10 | an-114 | E1U3777 | sp-12 | an-114 | E1U11103 | sp-36 | an-114 |
| E1A3778 | sp-10 | an-115 | E1U3778 | sp-12 | an-115 | E1U11104 | sp-36 | an-115 |
| E1A3779 | sp-10 | an-116 | E1U3779 | sp-12 | an-116 | E1U11105 | sp-36 | an-116 |
| E1A3780 | sp-10 | an-117 | E1U3780 | sp-12 | an-117 | E1U11106 | sp-36 | an-117 |

Table 1-71

| Y = NHCS | | | Y = NHCSNH | | | Y = NHCSNH | | |
|---|---|---|---|---|---|---|---|---|
| E1A3781 | sp-10 | an-118 | E1U3781 | sp-12 | an-118 | E1U11107 | sp-36 | an-118 |
| E1A3782 | sp-10 | an-119 | E1U3782 | sp-12 | an-119 | E1U11108 | sp-36 | an-119 |
| E1A3783 | sp-10 | an-120 | E1U3783 | sp-12 | an-120 | E1U11109 | sp-36 | an-120 |
| E1A3784 | sp-10 | an-121 | E1U3784 | sp-12 | an-121 | E1U11110 | sp-36 | an-121 |
| E1A3785 | sp-10 | an-122 | E1U3785 | sp-12 | an-122 | E1U11111 | sp-36 | an-122 |
| E1A3786 | sp-10 | an-123 | E1U3786 | sp-12 | an-123 | E1U11112 | sp-36 | an-123 |
| E1A3787 | sp-10 | an-124 | E1U3787 | sp-12 | an-124 | E1U11113 | sp-36 | an-124 |
| E1A3788 | sp-10 | an-125 | E1U3788 | sp-12 | an-125 | E1U11114 | sp-36 | an-125 |
| E1A3789 | sp-10 | an-126 | E1U3789 | sp-12 | an-126 | E1U11115 | sp-36 | an-126 |
| E1A3790 | sp-10 | an-127 | E1U3790 | sp-12 | an-127 | E1U11116 | sp-36 | an-127 |
| E1A3791 | sp-10 | an-128 | E1U3791 | sp-12 | an-128 | E1U11117 | sp-36 | an-128 |
| E1A3792 | sp-10 | an-129 | E1U3792 | sp-12 | an-129 | E1U11118 | sp-36 | an-129 |
| E1A3793 | sp-10 | an-130 | E1U3793 | sp-12 | an-130 | E1U11119 | sp-36 | an-130 |
| E1A3794 | sp-10 | an-131 | E1U3794 | sp-12 | an-131 | E1U11120 | sp-36 | an-131 |
| E1A3795 | sp-10 | an-132 | E1U3795 | sp-12 | an-132 | E1U11121 | sp-36 | an-132 |
| E1A3796 | sp-10 | an-133 | E1U3796 | sp-12 | an-133 | E1U11122 | sp-36 | an-133 |
| E1A3797 | sp-10 | an-134 | E1U3797 | sp-12 | an-134 | E1U11123 | sp-36 | an-134 |
| E1A3798 | sp-10 | an-135 | E1U3798 | sp-12 | an-135 | E1U11124 | sp-36 | an-135 |
| E1A3799 | sp-10 | an-136 | E1U3799 | sp-12 | an-136 | E1U11125 | sp-36 | an-136 |
| E1A3800 | sp-10 | an-137 | E1U3800 | sp-12 | an-137 | E1U11126 | sp-36 | an-137 |
| E1A3801 | sp-10 | an-138 | E1U3801 | sp-12 | an-138 | E1U11127 | sp-36 | an-138 |
| E1A3802 | sp-10 | an-139 | E1U3802 | sp-12 | an-139 | E1U11128 | sp-36 | an-139 |
| E1A3803 | sp-10 | an-140 | E1U3803 | sp-12 | an-140 | E1U11129 | sp-36 | an-140 |
| E1A3804 | sp-10 | an-141 | E1U3804 | sp-12 | an-141 | E1U11130 | sp-36 | an-141 |
| E1A3805 | sp-10 | an-142 | E1U3805 | sp-12 | an-142 | E1U11131 | sp-36 | an-142 |
| E1A3806 | sp-10 | an-143 | E1U3806 | sp-12 | an-143 | E1U11132 | sp-36 | an-143 |
| E1A3807 | sp-10 | an-144 | E1U3807 | sp-12 | an-144 | E1U11133 | sp-36 | an-144 |
| E1A3808 | sp-10 | an-145 | E1U3808 | sp-12 | an-145 | E1U11134 | sp-36 | an-145 |
| E1A3809 | sp-10 | an-146 | E1U3809 | sp-12 | an-146 | E1U11135 | sp-36 | an-146 |
| E1A3810 | sp-10 | an-147 | E1U3810 | sp-12 | an-147 | E1U11136 | sp-36 | an-147 |
| E1A3811 | sp-10 | an-148 | E1U3811 | sp-12 | an-148 | E1U11137 | sp-36 | an-148 |
| E1A3812 | sp-10 | an-149 | E1U3812 | sp-12 | an-149 | E1U11138 | sp-36 | an-149 |
| E1A3813 | sp-10 | an-150 | E1U3813 | sp-12 | an-150 | E1U11139 | sp-36 | an-150 |
| E1A3814 | sp-10 | an-151 | E1U3814 | sp-12 | an-151 | E1U11140 | sp-36 | an-151 |
| E1A3815 | sp-10 | an-152 | E1U3815 | sp-12 | an-152 | E1U11141 | sp-36 | an-152 |
| E1A3816 | sp-10 | an-153 | E1U3816 | sp-12 | an-153 | E1U11142 | sp-36 | an-153 |
| E1A3817 | sp-10 | an-154 | E1U3817 | sp-12 | an-154 | E1U11143 | sp-36 | an-154 |
| E1A3818 | sp-10 | an-155 | E1U3818 | sp-12 | an-155 | E1U11144 | sp-36 | an-155 |
| E1A3819 | sp-10 | an-156 | E1U3819 | sp-12 | an-156 | E1U11145 | sp-36 | an-156 |
| E1A3820 | sp-10 | an-157 | E1U3820 | sp-12 | an-157 | E1U11146 | sp-36 | an-157 |
| E1A3821 | sp-10 | an-158 | E1U3821 | sp-12 | an-158 | E1U11147 | sp-36 | an-158 |
| E1A3822 | sp-10 | an-159 | E1U3822 | sp-12 | an-159 | E1U11148 | sp-36 | an-159 |
| E1A3823 | sp-10 | an-160 | E1U3823 | sp-12 | an-160 | E1U11149 | sp-36 | an-160 |
| E1A3824 | sp-10 | an-161 | E1U3824 | sp-12 | an-161 | E1U11150 | sp-36 | an-161 |
| E1A3825 | sp-10 | an-162 | E1U3825 | sp-12 | an-162 | E1U11151 | sp-36 | an-162 |
| E1A3826 | sp-10 | an-163 | E1U3826 | sp-12 | an-163 | E1U11152 | sp-36 | an-163 |
| E1A3827 | sp-10 | an-164 | E1U3827 | sp-12 | an-164 | E1U11153 | sp-36 | an-164 |
| E1A3828 | sp-10 | an-165 | E1U3828 | sp-12 | an-165 | E1U11154 | sp-36 | an-165 |
| E1A3829 | sp-10 | an-166 | E1U3829 | sp-12 | an-166 | E1U11155 | sp-36 | an-166 |
| E1A3830 | sp-10 | an-167 | E1U3830 | sp-12 | an-167 | E1U11156 | sp-36 | an-167 |
| E1A3831 | sp-10 | an-168 | E1U3831 | sp-12 | an-168 | E1U11157 | sp-36 | an-168 |
| E1A3832 | sp-10 | an-169 | E1U3832 | sp-12 | an-169 | E1U11158 | sp-36 | an-169 |
| E1A3833 | sp-10 | an-170 | E1U3833 | sp-12 | an-170 | E1U11159 | sp-36 | an-170 |
| E1A3834 | sp-10 | an-171 | E1U3834 | sp-12 | an-171 | E1U11160 | sp-36 | an-171 |

Table 1-72

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| Y = NHCS | | | Y = NHCSNH | | | Y = NHCSNH | | |
| E1A3835 | sp-10 | an-172 | E1U3835 | sp-12 | an-172 | E1U11161 | sp-36 | an-172 |
| E1A3836 | sp-10 | an-173 | E1U3836 | sp-12 | an-173 | E1U11162 | sp-36 | an-173 |
| E1A3837 | sp-10 | an-174 | E1U3837 | sp-12 | an-174 | E1U11163 | sp-36 | an-174 |
| E1A3838 | sp-10 | an-175 | E1U3838 | sp-12 | an-175 | E1U11164 | sp-36 | an-175 |
| E1A3839 | sp-10 | an-176 | E1U3839 | sp-12 | an-176 | E1U11165 | sp-36 | an-176 |
| E1A3840 | sp-10 | an-177 | E1U3840 | sp-12 | an-177 | E1U11166 | sp-36 | an-177 |
| E1A3841 | sp-10 | an-178 | E1U3841 | sp-12 | an-178 | E1U11167 | sp-36 | an-178 |
| E1A3842 | sp-10 | an-179 | E1U3842 | sp-12 | an-179 | E1U11168 | sp-36 | an-179 |
| E1A3843 | sp-10 | an-180 | E1U3843 | sp-12 | an-180 | E1U11169 | sp-36 | an-180 |
| E1A3844 | sp-10 | an-181 | E1U3844 | sp-12 | an-181 | E1U11170 | sp-36 | an-181 |
| E1A3845 | sp-10 | an-182 | E1U3845 | sp-12 | an-182 | E1U11171 | sp-36 | an-182 |
| E1A3846 | sp-10 | an-183 | E1U3846 | sp-12 | an-183 | E1U11172 | sp-36 | an-183 |
| E1A3847 | sp-10 | an-184 | E1U3847 | sp-12 | an-184 | E1U11173 | sp-36 | an-184 |
| E1A3848 | sp-10 | an-185 | E1U3848 | sp-12 | an-185 | E1U11174 | sp-36 | an-185 |
| E1A3849 | sp-10 | an-186 | E1U3849 | sp-12 | an-186 | E1U11175 | sp-36 | an-186 |
| E1A3850 | sp-10 | an-187 | E1U3850 | sp-12 | an-187 | E1U11176 | sp-36 | an-187 |
| E1A3851 | sp-10 | an-188 | E1U3851 | sp-12 | an-188 | E1U11177 | sp-36 | an-188 |
| E1A3852 | sp-10 | an-189 | E1U3852 | sp-12 | an-189 | E1U11178 | sp-36 | an-189 |
| E1A3853 | sp-10 | an-190 | E1U3853 | sp-12 | an-190 | E1U11179 | sp-36 | an-190 |
| E1A3854 | sp-10 | an-191 | E1U3854 | sp-12 | an-191 | E1U11180 | sp-36 | an-191 |
| E1A3855 | sp-10 | an-192 | E1U3855 | sp-12 | an-192 | E1U11181 | sp-36 | an-192 |
| E1A3856 | sp-10 | an-193 | E1U3856 | sp-12 | an-193 | E1U11182 | sp-36 | an-193 |
| E1A3857 | sp-10 | an-194 | E1U3857 | sp-12 | an-194 | E1U11183 | sp-36 | an-194 |
| E1A3858 | sp-10 | an-195 | E1U3858 | sp-12 | an-195 | E1U11184 | sp-36 | an-195 |
| E1A3859 | sp-10 | an-196 | E1U3859 | sp-12 | an-196 | E1U11185 | sp-36 | an-196 |
| E1A3860 | sp-10 | an-197 | E1U3860 | sp-12 | an-197 | E1U11186 | sp-36 | an-197 |
| E1A3861 | sp-10 | an-198 | E1U3861 | sp-12 | an-198 | E1U11187 | sp-36 | an-198 |
| E1A3862 | sp-10 | an-199 | E1U3862 | sp-12 | an-199 | E1U11188 | sp-36 | an-199 |
| E1A3863 | sp-10 | an-200 | E1U3863 | sp-12 | an-200 | E1U11189 | sp-36 | an-200 |
| E1A3864 | sp-10 | an-201 | E1U3864 | sp-12 | an-201 | E1U11190 | sp-36 | an-201 |
| E1A3865 | sp-10 | an-202 | E1U3865 | sp-12 | an-202 | E1U11191 | sp-36 | an-202 |
| E1A3866 | sp-10 | an-203 | E1U3866 | sp-12 | an-203 | E1U11192 | sp-36 | an-203 |
| E1A3867 | sp-10 | an-204 | E1U3867 | sp-12 | an-204 | E1U11193 | sp-36 | an-204 |
| E1A3868 | sp-10 | an-205 | E1U3868 | sp-12 | an-205 | E1U11194 | sp-36 | an-205 |
| E1A3869 | sp-10 | an-206 | E1U3869 | sp-12 | an-206 | E1U11195 | sp-36 | an-206 |
| E1A3870 | sp-10 | an-207 | E1U3870 | sp-12 | an-207 | E1U11196 | sp-36 | an-207 |
| E1A3871 | sp-10 | an-208 | E1U3871 | sp-12 | an-208 | E1U11197 | sp-36 | an-208 |
| E1A3872 | sp-10 | an-209 | E1U3872 | sp-12 | an-209 | E1U11198 | sp-36 | an-209 |
| E1A3873 | sp-10 | an-210 | E1U3873 | sp-12 | an-210 | E1U11199 | sp-36 | an-210 |
| E1A3874 | sp-10 | an-211 | E1U3874 | sp-12 | an-211 | E1U11200 | sp-36 | an-211 |
| E1A3875 | sp-10 | an-212 | E1U3875 | sp-12 | an-212 | E1U11201 | sp-36 | an-212 |
| E1A3876 | sp-10 | an-213 | E1U3876 | sp-12 | an-213 | E1U11202 | sp-36 | an-213 |
| E1A3877 | sp-10 | an-214 | E1U3877 | sp-12 | an-214 | E1U11203 | sp-36 | an-214 |
| E1A3878 | sp-10 | an-215 | E1U3878 | sp-12 | an-215 | E1U11204 | sp-36 | an-215 |
| E1A3879 | sp-10 | an-216 | E1U3879 | sp-12 | an-216 | E1U11205 | sp-36 | an-216 |
| E1A3880 | sp-10 | an-217 | E1U3880 | sp-12 | an-217 | E1U11206 | sp-36 | an-217 |
| E1A3881 | sp-10 | an-218 | E1U3881 | sp-12 | an-218 | E1U11207 | sp-36 | an-218 |
| E1A3882 | sp-10 | an-219 | E1U3882 | sp-12 | an-219 | E1U11208 | sp-36 | an-219 |
| E1A3883 | sp-10 | an-220 | E1U3883 | sp-12 | an-220 | E1U11209 | sp-36 | an-220 |
| E1A3884 | sp-10 | an-221 | E1U3884 | sp-12 | an-221 | E1U11210 | sp-36 | an-221 |
| E1A3885 | sp-10 | an-222 | E1U3885 | sp-12 | an-222 | E1U11211 | sp-36 | an-222 |
| E1A3886 | sp-10 | an-223 | E1U3886 | sp-12 | an-223 | E1U11212 | sp-36 | an-223 |
| E1A3887 | sp-10 | an-224 | E1U3887 | sp-12 | an-224 | E1U11213 | sp-36 | an-224 |
| E1A3888 | sp-10 | an-225 | E1U3888 | sp-12 | an-225 | E1U11214 | sp-36 | an-225 |

Table 1-73

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| Y = NHCS | | | Y = NHCSNH | | | Y = NHCSNH | | |
| E1A3889 | sp-10 | an-226 | E1U3889 | sp-12 | an-226 | E1U11215 | sp-36 | an-226 |
| E1A3890 | sp-10 | an-227 | E1U3890 | sp-12 | an-227 | E1U11216 | sp-36 | an-227 |
| E1A3891 | sp-10 | an-228 | E1U3891 | sp-12 | an-228 | E1U11217 | sp-36 | an-228 |
| E1A3892 | sp-10 | an-229 | E1U3892 | sp-12 | an-229 | E1U11218 | sp-36 | an-229 |
| E1A3893 | sp-10 | an-230 | E1U3893 | sp-12 | an-230 | E1U11219 | sp-36 | an-230 |
| E1A3894 | sp-10 | an-231 | E1U3894 | sp-12 | an-231 | E1U11220 | sp-36 | an-231 |
| E1A3895 | sp-10 | an-232 | E1U3895 | sp-12 | an-232 | E1U11221 | sp-36 | an-232 |
| E1A3896 | sp-10 | an-233 | E1U3896 | sp-12 | an-233 | E1U11222 | sp-36 | an-233 |
| E1A3897 | sp-10 | an-234 | E1U3897 | sp-12 | an-234 | E1U11223 | sp-36 | an-234 |
| E1A3898 | sp-10 | an-235 | E1U3898 | sp-12 | an-235 | E1U11224 | sp-36 | an-235 |
| E1A3899 | sp-10 | an-236 | E1U3899 | sp-12 | an-236 | E1U11225 | sp-36 | an-236 |
| E1A3900 | sp-10 | an-237 | E1U3900 | sp-12 | an-237 | E1U11226 | sp-36 | an-237 |
| E1A3901 | sp-10 | an-238 | E1U3901 | sp-12 | an-238 | E1U11227 | sp-36 | an-238 |
| E1A3902 | sp-10 | an-239 | E1U3902 | sp-12 | an-239 | E1U11228 | sp-36 | an-239 |
| E1A3903 | sp-10 | an-240 | E1U3903 | sp-12 | an-240 | E1U11229 | sp-36 | an-240 |
| E1A3904 | sp-10 | an-241 | E1U3904 | sp-12 | an-241 | E1U11230 | sp-36 | an-241 |

-continued

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| E1A3905 | sp-10 | an-242 | E1U3905 | sp-12 | an-242 | E1U11231 | sp-36 | an-242 |
| E1A3906 | sp-10 | an-243 | E1U3906 | sp-12 | an-243 | E1U11232 | sp-36 | an-243 |
| E1A3907 | sp-10 | an-244 | E1U3907 | sp-12 | an-244 | E1U11233 | sp-36 | an-244 |
| E1A3908 | sp-10 | an-245 | E1U3908 | sp-12 | an-245 | E1U11234 | sp-36 | an-245 |
| E1A3909 | sp-10 | an-246 | E1U3909 | sp-12 | an-246 | E1U11235 | sp-36 | an-246 |
| E1A3910 | sp-10 | an-247 | E1U3910 | sp-12 | an-247 | E1U11236 | sp-36 | an-247 |
| E1A3911 | sp-10 | an-248 | E1U3911 | sp-12 | an-248 | E1U11237 | sp-36 | an-248 |
| E1A3912 | sp-10 | an-249 | E1U3912 | sp-12 | an-249 | E1U11238 | sp-36 | an-249 |
| E1A3913 | sp-10 | an-250 | E1U3913 | sp-12 | an-250 | E1U11239 | sp-36 | an-250 |
| E1A3914 | sp-10 | an-251 | E1U3914 | sp-12 | an-251 | E1U11240 | sp-36 | an-251 |
| E1A3915 | sp-10 | an-252 | E1U3915 | sp-12 | an-252 | E1U11241 | sp-36 | an-252 |
| E1A3916 | sp-10 | an-253 | E1U3916 | sp-12 | an-253 | E1U11242 | sp-36 | an-253 |
| E1A3917 | sp-10 | an-254 | E1U3917 | sp-12 | an-254 | E1U11243 | sp-36 | an-254 |
| E1A3918 | sp-10 | an-255 | E1U3918 | sp-12 | an-255 | E1U11244 | sp-36 | an-255 |
| E1A3919 | sp-10 | an-256 | E1U3919 | sp-12 | an-256 | E1U11245 | sp-36 | an-256 |
| E1A3920 | sp-10 | an-257 | E1U3920 | sp-12 | an-257 | E1U11246 | sp-36 | an-257 |
| E1A3921 | sp-10 | an-258 | E1U3921 | sp-12 | an-258 | E1U11247 | sp-36 | an-258 |
| E1A3922 | sp-10 | an-259 | E1U3922 | sp-12 | an-259 | E1U11248 | sp-36 | an-259 |
| E1A3923 | sp-10 | an-260 | E1U3923 | sp-12 | an-260 | E1U11249 | sp-36 | an-260 |
| E1A3924 | sp-10 | an-261 | E1U3924 | sp-12 | an-261 | E1U11250 | sp-36 | an-261 |
| E1A3925 | sp-10 | an-262 | E1U3925 | sp-12 | an-262 | E1U11251 | sp-36 | an-262 |
| E1A3926 | sp-10 | an-263 | E1U3926 | sp-12 | an-263 | E1U11252 | sp-36 | an-263 |
| E1A3927 | sp-10 | an-264 | E1U3927 | sp-12 | an-264 | E1U11253 | sp-36 | an-264 |
| E1A3928 | sp-10 | an-265 | E1U3928 | sp-12 | an-265 | E1U11254 | sp-36 | an-265 |
| E1A3929 | sp-10 | an-266 | E1U3929 | sp-12 | an-266 | E1U11255 | sp-36 | an-266 |
| E1A3930 | sp-10 | an-267 | E1U3930 | sp-12 | an-267 | E1U11256 | sp-36 | an-267 |
| E1A3931 | sp-10 | an-268 | E1U3931 | sp-12 | an-268 | E1U11257 | sp-36 | an-268 |
| E1A3932 | sp-10 | an-269 | E1U3932 | sp-12 | an-269 | E1U11258 | sp-36 | an-269 |
| E1A3933 | sp-10 | an-270 | E1U3933 | sp-12 | an-270 | E1U11259 | sp-36 | an-270 |
| E1A3934 | sp-10 | an-271 | E1U3934 | sp-12 | an-271 | E1U11260 | sp-36 | an-271 |
| E1A3935 | sp-10 | an-272 | E1U3935 | sp-12 | an-272 | E1U11261 | sp-36 | an-272 |
| E1A3936 | sp-10 | an-273 | E1U3936 | sp-12 | an-273 | E1U11262 | sp-36 | an-273 |
| E1A3937 | sp-10 | an-274 | E1U3937 | sp-12 | an-274 | E1U11263 | sp-36 | an-274 |
| E1A3938 | sp-10 | an-275 | E1U3938 | sp-12 | an-275 | E1U11264 | sp-36 | an-275 |
| E1A3939 | sp-10 | an-276 | E1U3939 | sp-12 | an-276 | E1U11265 | sp-36 | an-276 |
| E1A3940 | sp-10 | an-277 | E1U3940 | sp-12 | an-277 | E1U11266 | sp-36 | an-277 |
| E1A3941 | sp-10 | an-278 | E1U3941 | sp-12 | an-278 | E1U11267 | sp-36 | an-278 |
| E1A3942 | sp-10 | an-279 | E1U3942 | sp-12 | an-279 | E1U11268 | sp-36 | an-279 |

Table 1-74

| | Y = NHCS | | | Y = NHCSNH | | | Y = NHCSNH | |
|---|---|---|---|---|---|---|---|---|
| E1A3943 | sp-10 | an-280 | E1U3943 | sp-12 | an-280 | E1U11269 | sp-36 | an-280 |
| E1A3944 | sp-10 | an-281 | E1U3944 | sp-12 | an-281 | E1U11270 | sp-36 | an-281 |
| E1A3945 | sp-10 | an-282 | E1U3945 | sp-12 | an-282 | E1U11271 | sp-36 | an-282 |
| E1A3946 | sp-10 | an-283 | E1U3946 | sp-12 | an-283 | E1U11272 | sp-36 | an-283 |
| E1A3947 | sp-10 | an-284 | E1U3947 | sp-12 | an-284 | E1U11273 | sp-36 | an-284 |
| E1A3948 | sp-10 | an-285 | E1U3948 | sp-12 | an-285 | E1U11274 | sp-36 | an-285 |
| E1A3949 | sp-10 | an-286 | E1U3949 | sp-12 | an-286 | E1U11275 | sp-36 | an-286 |
| E1A3950 | sp-10 | an-287 | E1U3950 | sp-12 | an-287 | E1U11276 | sp-36 | an-287 |
| E1A3951 | sp-10 | an-288 | E1U3951 | sp-12 | an-288 | E1U11277 | sp-36 | an-288 |
| E1A3952 | sp-10 | an-289 | E1U3952 | sp-12 | an-289 | E1U11278 | sp-36 | an-289 |
| E1A3953 | sp-10 | an-290 | E1U3953 | sp-12 | an-290 | E1U11279 | sp-36 | an-290 |
| E1A3954 | sp-10 | an-291 | E1U3954 | sp-12 | an-291 | E1U11280 | sp-36 | an-291 |
| E1A3955 | sp-10 | an-292 | E1U3955 | sp-12 | an-292 | E1U11281 | sp-36 | an-292 |
| E1A3956 | sp-10 | an-293 | E1U3956 | sp-12 | an-293 | E1U11282 | sp-36 | an-293 |
| E1A3957 | sp-10 | an-294 | E1U3957 | sp-12 | an-294 | E1U11283 | sp-36 | an-294 |
| E1A3958 | sp-10 | an-295 | E1U3958 | sp-12 | an-295 | E1U11284 | sp-36 | an-295 |
| E1A3959 | sp-10 | an-296 | E1U3959 | sp-12 | an-296 | E1U11285 | sp-36 | an-296 |
| E1A3960 | sp-10 | an-297 | E1U3960 | sp-12 | an-297 | E1U11286 | sp-36 | an-297 |
| E1A3961 | sp-10 | an-298 | E1U3961 | sp-12 | an-298 | E1U11287 | sp-36 | an-298 |
| E1A3962 | sp-10 | an-299 | E1U3962 | sp-12 | an-299 | E1U11288 | sp-36 | an-299 |
| E1A3963 | sp-10 | an-300 | E1U3963 | sp-12 | an-300 | E1U11289 | sp-36 | an-300 |
| E1A3964 | sp-10 | an-301 | E1U3964 | sp-12 | an-301 | E1U11290 | sp-36 | an-301 |
| E1A3965 | sp-10 | an-302 | E1U3965 | sp-12 | an-302 | E1U11291 | sp-36 | an-302 |
| E1A3966 | sp-10 | an-303 | E1U3966 | sp-12 | an-303 | E1U11292 | sp-36 | an-303 |
| E1A3967 | sp-10 | an-304 | E1U3967 | sp-12 | an-304 | E1U11293 | sp-36 | an-304 |
| E1A3968 | sp-10 | an-305 | E1U3968 | sp-12 | an-305 | E1U11294 | sp-36 | an-305 |
| E1A3969 | sp-10 | an-306 | E1U3969 | sp-12 | an-306 | E1U11295 | sp-36 | an-306 |
| E1A3970 | sp-10 | an-307 | E1U3970 | sp-12 | an-307 | E1U11296 | sp-36 | an-307 |
| E1A3971 | sp-10 | an-308 | E1U3971 | sp-12 | an-308 | E1U11297 | sp-36 | an-308 |
| E1A3972 | sp-10 | an-309 | E1U3972 | sp-12 | an-309 | E1U11298 | sp-36 | an-309 |
| E1A3973 | sp-10 | an-310 | E1U3973 | sp-12 | an-310 | E1U11299 | sp-36 | an-310 |
| E1A3974 | sp-10 | an-311 | E1U3974 | sp-12 | an-311 | E1U11300 | sp-36 | an-311 |
| E1A3975 | sp-10 | an-312 | E1U3975 | sp-12 | an-312 | E1U11301 | sp-36 | an-312 |
| E1A3976 | sp-10 | an-313 | E1U3976 | sp-12 | an-313 | E1U11302 | sp-36 | an-313 |
| E1A3977 | sp-10 | an-314 | E1U3977 | sp-12 | an-314 | E1U11303 | sp-36 | an-314 |
| E1A3978 | sp-10 | an-315 | E1U3978 | sp-12 | an-315 | E1U11304 | sp-36 | an-315 |

-continued

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| E1A3979 | sp-10 | an-316 | E1U3979 | sp-12 | an-316 | E1U11305 | sp-36 | an-316 |
| E1A3980 | sp-10 | an-317 | E1U3980 | sp-12 | an-317 | E1U11306 | sp-36 | an-317 |
| E1A3981 | sp-10 | an-318 | E1U3981 | sp-12 | an-318 | E1U11307 | sp-36 | an-318 |
| E1A3982 | sp-10 | an-319 | E1U3982 | sp-12 | an-319 | E1U11308 | sp-36 | an-319 |
| E1A3983 | sp-10 | an-320 | E1U3983 | sp-12 | an-320 | E1U11309 | sp-36 | an-320 |
| E1A3984 | sp-10 | an-321 | E1U3984 | sp-12 | an-321 | E1U11310 | sp-36 | an-321 |
| E1A3985 | sp-10 | an-322 | E1U3985 | sp-12 | an-322 | E1U11311 | sp-36 | an-322 |
| E1A3986 | sp-10 | an-323 | E1U3986 | sp-12 | an-323 | E1U11312 | sp-36 | an-323 |
| E1A3987 | sp-10 | an-324 | E1U3987 | sp-12 | an-324 | E1U11313 | sp-36 | an-324 |
| E1A3988 | sp-10 | an-325 | E1U3988 | sp-12 | an-325 | E1U11314 | sp-36 | an-325 |
| E1A3989 | sp-10 | an-326 | E1U3989 | sp-12 | an-326 | E1U11315 | sp-36 | an-326 |
| E1A3990 | sp-10 | an-327 | E1U3990 | sp-12 | an-327 | E1U11316 | sp-36 | an-327 |
| E1A3991 | sp-10 | an-328 | E1U3991 | sp-12 | an-328 | E1U11317 | sp-36 | an-328 |
| E1A3992 | sp-10 | an-329 | E1U3992 | sp-12 | an-329 | E1U11318 | sp-36 | an-329 |
| E1A3993 | sp-10 | an-330 | E1U3993 | sp-12 | an-330 | E1U11319 | sp-36 | an-330 |
| E1A3994 | sp-10 | an-331 | E1U3994 | sp-12 | an-331 | E1U11320 | sp-36 | an-331 |
| E1A3995 | sp-10 | an-332 | E1U3995 | sp-12 | an-332 | E1U11321 | sp-36 | an-332 |
| E1A3996 | sp-10 | an-333 | E1U3996 | sp-12 | an-333 | E1U11322 | sp-36 | an-333 |

Table 1-75

| Y = NHCS | | | Y = NHCSNH | | | Y = NHCSNH | | |
|---|---|---|---|---|---|---|---|---|
| E1A3997 | sp-10 | an-334 | E1U3997 | sp-12 | an-334 | E1U11323 | sp-36 | an-334 |
| E1A3998 | sp-10 | an-335 | E1U3998 | sp-12 | an-335 | E1U11324 | sp-36 | an-335 |
| E1A3999 | sp-10 | an-336 | E1U3999 | sp-12 | an-336 | E1U11325 | sp-36 | an-336 |
| E1A4000 | sp-10 | an-337 | E1U4000 | sp-12 | an-337 | E1U11326 | sp-36 | an-337 |
| E1A4001 | sp-10 | an-338 | E1U4001 | sp-12 | an-338 | E1U11327 | sp-36 | an-338 |
| E1A4002 | sp-10 | an-339 | E1U4002 | sp-12 | an-339 | E1U11328 | sp-36 | an-339 |
| E1A4003 | sp-10 | an-340 | E1U4003 | sp-12 | an-340 | E1U11329 | sp-36 | an-340 |
| E1A4004 | sp-10 | an-341 | E1U4004 | sp-12 | an-341 | E1U11330 | sp-36 | an-341 |
| E1A4005 | sp-10 | an-342 | E1U4005 | sp-12 | an-342 | E1U11331 | sp-36 | an-342 |
| E1A4006 | sp-10 | an-343 | E1U4006 | sp-12 | an-343 | E1U11332 | sp-36 | an-343 |
| E1A4007 | sp-10 | an-344 | E1U4007 | sp-12 | an-344 | E1U11333 | sp-36 | an-344 |
| E1A4008 | sp-10 | an-345 | E1U4008 | sp-12 | an-345 | E1U11334 | sp-36 | an-345 |
| E1A4009 | sp-10 | an-346 | E1U4009 | sp-12 | an-346 | E1U11335 | sp-36 | an-346 |
| E1A4010 | sp-10 | an-347 | E1U4010 | sp-12 | an-347 | E1U11336 | sp-36 | an-347 |
| E1A4011 | sp-10 | an-348 | E1U4011 | sp-12 | an-348 | E1U11337 | sp-36 | an-348 |
| E1A4012 | sp-10 | an-349 | E1U4012 | sp-12 | an-349 | E1U11338 | sp-36 | an-349 |
| E1A4013 | sp-10 | an-350 | E1U4013 | sp-12 | an-350 | E1U11339 | sp-36 | an-350 |
| E1A4014 | sp-10 | an-351 | E1U4014 | sp-12 | an-351 | E1U11340 | sp-36 | an-351 |
| E1A4015 | sp-10 | an-352 | E1U4015 | sp-12 | an-352 | E1U11341 | sp-36 | an-352 |
| E1A4016 | sp-10 | an-353 | E1U4016 | sp-12 | an-353 | E1U11342 | sp-36 | an-353 |
| E1A4017 | sp-10 | an-354 | E1U4017 | sp-12 | an-354 | E1U11343 | sp-36 | an-354 |
| E1A4018 | sp-10 | an-355 | E1U4018 | sp-12 | an-355 | E1U11344 | sp-36 | an-355 |
| E1A4019 | sp-10 | an-356 | E1U4019 | sp-12 | an-356 | E1U11345 | sp-36 | an-356 |
| E1A4020 | sp-10 | an-357 | E1U4020 | sp-12 | an-357 | E1U11346 | sp-36 | an-357 |
| E1A4021 | sp-10 | an-358 | E1U4021 | sp-12 | an-358 | E1U11347 | sp-36 | an-358 |
| E1A4022 | sp-10 | an-359 | E1U4022 | sp-12 | an-359 | E1U11348 | sp-36 | an-359 |
| E1A4023 | sp-10 | an-360 | E1U4023 | sp-12 | an-360 | E1U11349 | sp-36 | an-360 |
| E1A4024 | sp-10 | an-361 | E1U4024 | sp-12 | an-361 | E1U11350 | sp-36 | an-361 |
| E1A4025 | sp-10 | an-362 | E1U4025 | sp-12 | an-362 | E1U11351 | sp-36 | an-362 |
| E1A4026 | sp-10 | an-363 | E1U4026 | sp-12 | an-363 | E1U11352 | sp-36 | an-363 |
| E1A4027 | sp-10 | an-364 | E1U4027 | sp-12 | an-364 | E1U11353 | sp-36 | an-364 |
| E1A4028 | sp-10 | an-365 | E1U4028 | sp-12 | an-365 | E1U11354 | sp-36 | an-365 |
| E1A4029 | sp-10 | an-366 | E1U4029 | sp-12 | an-366 | E1U11355 | sp-36 | an-366 |
| E1A4030 | sp-10 | an-367 | E1U4030 | sp-12 | an-367 | E1U11356 | sp-36 | an-367 |
| E1A4031 | sp-10 | an-368 | E1U4031 | sp-12 | an-368 | E1U11357 | sp-36 | an-368 |
| E1A4032 | sp-10 | an-369 | E1U4032 | sp-12 | an-369 | E1U11358 | sp-36 | an-369 |
| E1A4033 | sp-10 | an-370 | E1U4033 | sp-12 | an-370 | E1U11359 | sp-36 | an-370 |
| E1A4034 | sp-10 | an-371 | E1U4034 | sp-12 | an-371 | E1U11360 | sp-36 | an-371 |
| E1A4035 | sp-10 | an-372 | E1U4035 | sp-12 | an-372 | E1U11361 | sp-36 | an-372 |
| E1A4036 | sp-10 | an-373 | E1U4036 | sp-12 | an-373 | E1U11362 | sp-36 | an-373 |
| E1A4037 | sp-10 | an-374 | E1U4037 | sp-12 | an-374 | E1U11363 | sp-36 | an-374 |
| E1A4038 | sp-10 | an-375 | E1U4038 | sp-12 | an-375 | E1U11364 | sp-36 | an-375 |
| E1A4039 | sp-10 | an-376 | E1U4039 | sp-12 | an-376 | E1U11365 | sp-36 | an-376 |
| E1A4040 | sp-10 | an-377 | E1U4040 | sp-12 | an-377 | E1U11366 | sp-36 | an-377 |
| E1A4041 | sp-10 | an-378 | E1U4041 | sp-12 | an-378 | E1U11367 | sp-36 | an-378 |
| E1A4042 | sp-10 | an-379 | E1U4042 | sp-12 | an-379 | E1U11368 | sp-36 | an-379 |
| E1A4043 | sp-10 | an-380 | E1U4043 | sp-12 | an-380 | E1U11369 | sp-36 | an-380 |
| E1A4044 | sp-10 | an-381 | E1U4044 | sp-12 | an-381 | E1U11370 | sp-36 | an-381 |
| E1A4045 | sp-10 | an-382 | E1U4045 | sp-12 | an-382 | E1U11371 | sp-36 | an-382 |
| E1A4046 | sp-10 | an-383 | E1U4046 | sp-12 | an-383 | E1U11372 | sp-36 | an-383 |
| E1A4047 | sp-10 | an-384 | E1U4047 | sp-12 | an-384 | E1U11373 | sp-36 | an-384 |
| E1A4048 | sp-10 | an-385 | E1U4048 | sp-12 | an-385 | E1U11374 | sp-36 | an-385 |
| E1A4049 | sp-10 | an-386 | E1U4049 | sp-12 | an-386 | E1U11375 | sp-36 | an-386 |
| E1A4050 | sp-10 | an-387 | E1U4050 | sp-12 | an-387 | E1U11376 | sp-36 | an-387 |

-continued

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|

Table 1-76

| Y = NHCS | | | Y = NHCSNH | | | Y = NHCSNH | | |
|---|---|---|---|---|---|---|---|---|
| E1A4051 | sp-10 | an-388 | E1U4051 | sp-12 | an-388 | E1U11377 | sp-36 | an-388 |
| E1A4052 | sp-10 | an-389 | E1U4052 | sp-12 | an-389 | E1U11378 | sp-36 | an-389 |
| E1A4053 | sp-10 | an-390 | E1U4053 | sp-12 | an-390 | E1U11379 | sp-36 | an-390 |
| E1A4054 | sp-10 | an-391 | E1U4054 | sp-12 | an-391 | E1U11380 | sp-36 | an-391 |
| E1A4055 | sp-10 | an-392 | E1U4055 | sp-12 | an-392 | E1U11381 | sp-36 | an-392 |
| E1A4056 | sp-10 | an-393 | E1U4056 | sp-12 | an-393 | E1U11382 | sp-36 | an-393 |
| E1A4057 | sp-10 | an-394 | E1U4057 | sp-12 | an-394 | E1U11383 | sp-36 | an-394 |
| E1A4058 | sp-10 | an-395 | E1U4058 | sp-12 | an-395 | E1U11384 | sp-36 | an-395 |
| E1A4059 | sp-10 | an-396 | E1U4059 | sp-12 | an-396 | E1U11385 | sp-36 | an-396 |
| E1A4060 | sp-10 | an-397 | E1U4060 | sp-12 | an-397 | E1U11386 | sp-36 | an-397 |
| E1A4061 | sp-10 | an-398 | E1U4061 | sp-12 | an-398 | E1U11387 | sp-36 | an-398 |
| E1A4062 | sp-10 | an-399 | E1U4062 | sp-12 | an-399 | E1U11388 | sp-36 | an-399 |
| E1A4063 | sp-10 | an-400 | E1U4063 | sp-12 | an-400 | E1U11389 | sp-36 | an-400 |
| E1A4064 | sp-10 | an-401 | E1U4064 | sp-12 | an-401 | E1U11390 | sp-36 | an-401 |
| E1A4065 | sp-10 | an-402 | E1U4065 | sp-12 | an-402 | E1U11391 | sp-36 | an-402 |
| E1A4066 | sp-10 | an-403 | E1U4066 | sp-12 | an-403 | E1U11392 | sp-36 | an-403 |
| E1A4067 | sp-10 | an-404 | E1U4067 | sp-12 | an-404 | E1U11393 | sp-36 | an-404 |
| E1A4068 | sp-10 | an-405 | E1U4068 | sp-12 | an-405 | E1U11394 | sp-36 | an-405 |
| E1A4069 | sp-10 | an-406 | E1U4069 | sp-12 | an-406 | E1U11395 | sp-36 | an-406 |
| E1A4070 | sp-10 | an-407 | E1U4070 | sp-12 | an-407 | E1U11396 | sp-36 | an-407 |
| E1A4071 | sp-14 | an-1 | E1U4071 | sp-13 | an-1 | E1U11397 | sp-37 | an-1 |
| E1A4072 | sp-14 | an-2 | E1U4072 | sp-13 | an-2 | E1U11398 | sp-37 | an-2 |
| E1A4073 | sp-14 | an-3 | E1U4073 | sp-13 | an-3 | E1U11399 | sp-37 | an-3 |
| E1A4074 | sp-14 | an-4 | E1U4074 | sp-13 | an-4 | E1U11400 | sp-37 | an-4 |
| E1A4075 | sp-14 | an-5 | E1U4075 | sp-13 | an-5 | E1U11401 | sp-37 | an-5 |
| E1A4076 | sp-14 | an-6 | E1U4076 | sp-13 | an-6 | E1U11402 | sp-37 | an-6 |
| E1A4077 | sp-14 | an-7 | E1U4077 | sp-13 | an-7 | E1U11403 | sp-37 | an-7 |
| E1A4078 | sp-14 | an-8 | E1U4078 | sp-13 | an-8 | E1U11404 | sp-37 | an-8 |
| E1A4079 | sp-14 | an-9 | E1U4079 | sp-13 | an-9 | E1U11405 | sp-37 | an-9 |
| E1A4080 | sp-14 | an-10 | E1U4080 | sp-13 | an-10 | E1U11406 | sp-37 | an-10 |
| E1A4081 | sp-14 | an-11 | E1U4081 | sp-13 | an-11 | E1U11407 | sp-37 | an-11 |
| E1A4082 | sp-14 | an-12 | E1U4082 | sp-13 | an-12 | E1U11408 | sp-37 | an-12 |
| E1A4083 | sp-14 | an-13 | E1U4083 | sp-13 | an-13 | E1U11409 | sp-37 | an-13 |
| E1A4084 | sp-14 | an-14 | E1U4084 | sp-13 | an-14 | E1U11410 | sp-37 | an-14 |
| E1A4085 | sp-14 | an-15 | E1U4085 | sp-13 | an-15 | E1U11411 | sp-37 | an-15 |
| E1A4086 | sp-14 | an-16 | E1U4086 | sp-13 | an-16 | E1U11412 | sp-37 | an-16 |
| E1A4087 | sp-14 | an-17 | E1U4087 | sp-13 | an-17 | E1U11413 | sp-37 | an-17 |
| E1A4088 | sp-14 | an-18 | E1U4088 | sp-13 | an-18 | E1U11414 | sp-37 | an-18 |
| E1A4089 | sp-14 | an-19 | E1U4089 | sp-13 | an-19 | E1U11415 | sp-37 | an-19 |
| E1A4090 | sp-14 | an-20 | E1U4090 | sp-13 | an-20 | E1U11416 | sp-37 | an-20 |
| E1A4091 | sp-14 | an-21 | E1U4091 | sp-13 | an-21 | E1U11417 | sp-37 | an-21 |
| E1A4092 | sp-14 | an-22 | E1U4092 | sp-13 | an-22 | E1U11418 | sp-37 | an-22 |
| E1A4093 | sp-14 | an-23 | E1U4093 | sp-13 | an-23 | E1U11419 | sp-37 | an-23 |
| E1A4094 | sp-14 | an-24 | E1U4094 | sp-13 | an-24 | E1U11420 | sp-37 | an-24 |
| E1A4095 | sp-14 | an-25 | E1U4095 | sp-13 | an-25 | E1U11421 | sp-37 | an-25 |
| E1A4096 | sp-14 | an-26 | E1U4096 | sp-13 | an-26 | E1U11422 | sp-37 | an-26 |
| E1A4097 | sp-14 | an-27 | E1U4097 | sp-13 | an-27 | E1U11423 | sp-37 | an-27 |
| E1A4098 | sp-14 | an-28 | E1U4098 | sp-13 | an-28 | E1U11424 | sp-37 | an-28 |
| E1A4099 | sp-14 | an-29 | E1U4099 | sp-13 | an-29 | E1U11425 | sp-37 | an-29 |
| E1A4100 | sp-14 | an-30 | E1U4100 | sp-13 | an-30 | E1U11426 | sp-37 | an-30 |
| E1A4101 | sp-14 | an-31 | E1U4101 | sp-13 | an-31 | E1U11427 | sp-37 | an-31 |
| E1A4102 | sp-14 | an-32 | E1U4102 | sp-13 | an-32 | E1U11428 | sp-37 | an-32 |
| E1A4103 | sp-14 | an-33 | E1U4103 | sp-13 | an-33 | E1U11429 | sp-37 | an-33 |
| E1A4104 | sp-14 | an-34 | E1U4104 | sp-13 | an-34 | E1U11430 | sp-37 | an-34 |

Table 1-77

| Y = NHCS | | | Y = NHCSNH | | | Y = NHCSNH | | |
|---|---|---|---|---|---|---|---|---|
| E1A4105 | sp-14 | an-35 | E1U4105 | sp-13 | an-35 | E1U11431 | sp-37 | an-35 |
| E1A4106 | sp-14 | an-36 | E1U4106 | sp-13 | an-36 | E1U11432 | sp-37 | an-36 |
| E1A4107 | sp-14 | an-37 | E1U4107 | sp-13 | an-37 | E1U11433 | sp-37 | an-37 |
| E1A4108 | sp-14 | an-38 | E1U4108 | sp-13 | an-38 | E1U11434 | sp-37 | an-38 |
| E1A4109 | sp-14 | an-39 | E1U4109 | sp-13 | an-39 | E1U11435 | sp-37 | an-39 |
| E1A4110 | sp-14 | an-40 | E1U4110 | sp-13 | an-40 | E1U11436 | sp-37 | an-40 |
| E1A4111 | sp-14 | an-41 | E1U4111 | sp-13 | an-41 | E1U11437 | sp-37 | an-41 |
| E1A4112 | sp-14 | an-42 | E1U4112 | sp-13 | an-42 | E1U11438 | sp-37 | an-42 |
| E1A4113 | sp-14 | an-43 | E1U4113 | sp-13 | an-43 | E1U11439 | sp-37 | an-43 |
| E1A4114 | sp-14 | an-44 | E1U4114 | sp-13 | an-44 | E1U11440 | sp-37 | an-44 |
| E1A4115 | sp-14 | an-45 | E1U4115 | sp-13 | an-45 | E1U11441 | sp-37 | an-45 |
| E1A4116 | sp-14 | an-46 | E1U4116 | sp-13 | an-46 | E1U11442 | sp-37 | an-46 |
| E1A4117 | sp-14 | an-47 | E1U4117 | sp-13 | an-47 | E1U11443 | sp-37 | an-47 |
| E1A4118 | sp-14 | an-48 | E1U4118 | sp-13 | an-48 | E1U11444 | sp-37 | an-48 |
| E1A4119 | sp-14 | an-49 | E1U4119 | sp-13 | an-49 | E1U11445 | sp-37 | an-49 |
| E1A4120 | sp-14 | an-50 | E1U4120 | sp-13 | an-50 | E1U11446 | sp-37 | an-50 |

-continued

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| E1A4121 | sp-14 | an-51 | E1U4121 | sp-13 | an-51 | E1U11447 | sp-37 | an-51 |
| E1A4122 | sp-14 | an-52 | E1U4122 | sp-13 | an-52 | E1U11448 | sp-37 | an-52 |
| E1A4123 | sp-14 | an-53 | E1U4123 | sp-13 | an-53 | E1U11449 | sp-37 | an-53 |
| E1A4124 | sp-14 | an-54 | E1U4124 | sp-13 | an-54 | E1U11450 | sp-37 | an-54 |
| E1A4125 | sp-14 | an-55 | E1U4125 | sp-13 | an-55 | E1U11451 | sp-37 | an-55 |
| E1A4126 | sp-14 | an-56 | E1U4126 | sp-13 | an-56 | E1U11452 | sp-37 | an-56 |
| E1A4127 | sp-14 | an-57 | E1U4127 | sp-13 | an-57 | E1U11453 | sp-37 | an-57 |
| E1A4128 | sp-14 | an-58 | E1U4128 | sp-13 | an-58 | E1U11454 | sp-37 | an-58 |
| E1A4129 | sp-14 | an-59 | E1U4129 | sp-13 | an-59 | E1U11455 | sp-37 | an-59 |
| E1A4130 | sp-14 | an-60 | E1U4130 | sp-13 | an-60 | E1U11456 | sp-37 | an-60 |
| E1A4131 | sp-14 | an-61 | E1U4131 | sp-13 | an-61 | E1U11457 | sp-37 | an-61 |
| E1A4132 | sp-14 | an-62 | E1U4132 | sp-13 | an-62 | E1U11458 | sp-37 | an-62 |
| E1A4133 | sp-14 | an-63 | E1U4133 | sp-13 | an-63 | E1U11459 | sp-37 | an-63 |
| E1A4134 | sp-14 | an-64 | E1U4134 | sp-13 | an-64 | E1U11460 | sp-37 | an-64 |
| E1A4135 | sp-14 | an-65 | E1U4135 | sp-13 | an-65 | E1U11461 | sp-37 | an-65 |
| E1A4136 | sp-14 | an-66 | E1U4136 | sp-13 | an-66 | E1U11462 | sp-37 | an-66 |
| E1A4137 | sp-14 | an-67 | E1U4137 | sp-13 | an-67 | E1U11463 | sp-37 | an-67 |
| E1A4138 | sp-14 | an-68 | E1U4138 | sp-13 | an-68 | E1U11464 | sp-37 | an-68 |
| E1A4139 | sp-14 | an-69 | E1U4139 | sp-13 | an-69 | E1U11465 | sp-37 | an-69 |
| E1A4140 | sp-14 | an-70 | E1U4140 | sp-13 | an-70 | E1U11466 | sp-37 | an-70 |
| E1A4141 | sp-14 | an-71 | E1U4141 | sp-13 | an-71 | E1U11467 | sp-37 | an-71 |
| E1A4142 | sp-14 | an-72 | E1U4142 | sp-13 | an-72 | E1U11468 | sp-37 | an-72 |
| E1A4143 | sp-14 | an-73 | E1U4143 | sp-13 | an-73 | E1U11469 | sp-37 | an-73 |
| E1A4144 | sp-14 | an-74 | E1U4144 | sp-13 | an-74 | E1U11470 | sp-37 | an-74 |
| E1A4145 | sp-14 | an-75 | E1U4145 | sp-13 | an-75 | E1U11471 | sp-37 | an-75 |
| E1A4146 | sp-14 | an-76 | E1U4146 | sp-13 | an-76 | E1U11472 | sp-37 | an-76 |
| E1A4147 | sp-14 | an-77 | E1U4147 | sp-13 | an-77 | E1U11473 | sp-37 | an-77 |
| E1A4148 | sp-14 | an-78 | E1U4148 | sp-13 | an-78 | E1U11474 | sp-37 | an-78 |
| E1A4149 | sp-14 | an-79 | E1U4149 | sp-13 | an-79 | E1U11475 | sp-37 | an-79 |
| E1A4150 | sp-14 | an-80 | E1U4150 | sp-13 | an-80 | E1U11476 | sp-37 | an-80 |
| E1A4151 | sp-14 | an-81 | E1U4151 | sp-13 | an-81 | E1U11477 | sp-37 | an-81 |
| E1A4152 | sp-14 | an-82 | E1U4152 | sp-13 | an-82 | E1U11478 | sp-37 | an-82 |
| E1A4153 | sp-14 | an-83 | E1U4153 | sp-13 | an-83 | E1U11479 | sp-37 | an-83 |
| E1A4154 | sp-14 | an-84 | E1U4154 | sp-13 | an-84 | E1U11480 | sp-37 | an-84 |
| E1A4155 | sp-14 | an-85 | E1U4155 | sp-13 | an-85 | E1U11481 | sp-37 | an-85 |
| E1A4156 | sp-14 | an-86 | E1U4156 | sp-13 | an-86 | E1U11482 | sp-37 | an-86 |
| E1A4157 | sp-14 | an-87 | E1U4157 | sp-13 | an-87 | E1U11483 | sp-37 | an-87 |
| E1A4158 | sp-14 | an-88 | E1U4158 | sp-13 | an-88 | E1U11484 | sp-37 | an-88 |

Table 1-78

| Y = NHCS | | | Y = NHCSNH | | | Y = NHCSNH | | |
|---|---|---|---|---|---|---|---|---|
| E1A4159 | sp-14 | an-89 | E1U4159 | sp-13 | an-89 | E1U11485 | sp-37 | an-89 |
| E1A4160 | sp-14 | an-90 | E1U4160 | sp-13 | an-90 | E1U11486 | sp-37 | an-90 |
| E1A4161 | sp-14 | an-91 | E1U4161 | sp-13 | an-91 | E1U11487 | sp-37 | an-91 |
| E1A4162 | sp-14 | an-92 | E1U4162 | sp-13 | an-92 | E1U11488 | sp-37 | an-92 |
| E1A4163 | sp-14 | an-93 | E1U4163 | sp-13 | an-93 | E1U11489 | sp-37 | an-93 |
| E1A4164 | sp-14 | an-94 | E1U4164 | sp-13 | an-94 | E1U11490 | sp-37 | an-94 |
| E1A4165 | sp-14 | an-95 | E1U4165 | sp-13 | an-95 | E1U11491 | sp-37 | an-95 |
| E1A4166 | sp-14 | an-96 | E1U4166 | sp-13 | an-96 | E1U11492 | sp-37 | an-96 |
| E1A4167 | sp-14 | an-97 | E1U4167 | sp-13 | an-97 | E1U11493 | sp-37 | an-97 |
| E1A4168 | sp-14 | an-98 | E1U4168 | sp-13 | an-98 | E1U11494 | sp-37 | an-98 |
| E1A4169 | sp-14 | an-99 | E1U4169 | sp-13 | an-99 | E1U11495 | sp-37 | an-99 |
| E1A4170 | sp-14 | an-100 | E1U4170 | sp-13 | an-100 | E1U11496 | sp-37 | an-100 |
| E1A4171 | sp-14 | an-101 | E1U4171 | sp-13 | an-101 | E1U11497 | sp-37 | an-101 |
| E1A4172 | sp-14 | an-102 | E1U4172 | sp-13 | an-102 | E1U11498 | sp-37 | an-102 |
| E1A4173 | sp-14 | an-103 | E1U4173 | sp-13 | an-103 | E1U11499 | sp-37 | an-103 |
| E1A4174 | sp-14 | an-104 | E1U4174 | sp-13 | an-104 | E1U11500 | sp-37 | an-104 |
| E1A4175 | sp-14 | an-105 | E1U4175 | sp-13 | an-105 | E1U11501 | sp-37 | an-105 |
| E1A4176 | sp-14 | an-106 | E1U4176 | sp-13 | an-106 | E1U11502 | sp-37 | an-106 |
| E1A4177 | sp-14 | an-107 | E1U4177 | sp-13 | an-107 | E1U11503 | sp-37 | an-107 |
| E1A4178 | sp-14 | an-108 | E1U4178 | sp-13 | an-108 | E1U11504 | sp-37 | an-108 |
| E1A4179 | sp-14 | an-109 | E1U4179 | sp-13 | an-109 | E1U11505 | sp-37 | an-109 |
| E1A4180 | sp-14 | an-110 | E1U4180 | sp-13 | an-110 | E1U11506 | sp-37 | an-110 |
| E1A4181 | sp-14 | an-111 | E1U4181 | sp-13 | an-111 | E1U11507 | sp-37 | an-111 |
| E1A4182 | sp-14 | an-112 | E1U4182 | sp-13 | an-112 | E1U11508 | sp-37 | an-112 |
| E1A4183 | sp-14 | an-113 | E1U4183 | sp-13 | an-113 | E1U11509 | sp-37 | an-113 |
| E1A4184 | sp-14 | an-114 | E1U4184 | sp-13 | an-114 | E1U11510 | sp-37 | an-114 |
| E1A4185 | sp-14 | an-115 | E1U4185 | sp-13 | an-115 | E1U11511 | sp-37 | an-115 |
| E1A4186 | sp-14 | an-116 | E1U4186 | sp-13 | an-116 | E1U11512 | sp-37 | an-116 |
| E1A4187 | sp-14 | an-117 | E1U4187 | sp-13 | an-117 | E1U11513 | sp-37 | an-117 |
| E1A4188 | sp-14 | an-118 | E1U4188 | sp-13 | an-118 | E1U11514 | sp-37 | an-118 |
| E1A4189 | sp-14 | an-119 | E1U4189 | sp-13 | an-119 | E1U11515 | sp-37 | an-119 |
| E1A4190 | sp-14 | an-120 | E1U4190 | sp-13 | an-120 | E1U11516 | sp-37 | an-120 |
| E1A4191 | sp-14 | an-121 | E1U4191 | sp-13 | an-121 | E1U11517 | sp-37 | an-121 |
| E1A4192 | sp-14 | an-122 | E1U4192 | sp-13 | an-122 | E1U11518 | sp-37 | an-122 |
| E1A4193 | sp-14 | an-123 | E1U4193 | sp-13 | an-123 | E1U11519 | sp-37 | an-123 |
| E1A4194 | sp-14 | an-124 | E1U4194 | sp-13 | an-124 | E1U11520 | sp-37 | an-124 |

-continued

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| E1A4195 | sp-14 | an-125 | E1U4195 | sp-13 | an-125 | E1U11521 | sp-37 | an-125 |
| E1A4196 | sp-14 | an-126 | E1U4196 | sp-13 | an-126 | E1U11522 | sp-37 | an-126 |
| E1A4197 | sp-14 | an-127 | E1U4197 | sp-13 | an-127 | E1U11523 | sp-37 | an-127 |
| E1A4198 | sp-14 | an-128 | E1U4198 | sp-13 | an-128 | E1U11524 | sp-37 | an-128 |
| E1A4199 | sp-14 | an-129 | E1U4199 | sp-13 | an-129 | E1U11525 | sp-37 | an-129 |
| E1A4200 | sp-14 | an-130 | E1U4200 | sp-13 | an-130 | E1U11526 | sp-37 | an-130 |
| E1A4201 | sp-14 | an-131 | E1U4201 | sp-13 | an-131 | E1U11527 | sp-37 | an-131 |
| E1A4202 | sp-14 | an-132 | E1U4202 | sp-13 | an-132 | E1U11528 | sp-37 | an-132 |
| E1A4203 | sp-14 | an-133 | E1U4203 | sp-13 | an-133 | E1U11529 | sp-37 | an-133 |
| E1A4204 | sp-14 | an-134 | E1U4204 | sp-13 | an-134 | E1U11530 | sp-37 | an-134 |
| E1A4205 | sp-14 | an-135 | E1U4205 | sp-13 | an-135 | E1U11531 | sp-37 | an-135 |
| E1A4206 | sp-14 | an-136 | E1U4206 | sp-13 | an-136 | E1U11532 | sp-37 | an-136 |
| E1A4207 | sp-14 | an-137 | E1U4207 | sp-13 | an-137 | E1U11533 | sp-37 | an-137 |
| E1A4208 | sp-14 | an-138 | E1U4208 | sp-13 | an-138 | E1U11534 | sp-37 | an-138 |
| E1A4209 | sp-14 | an-139 | E1U4209 | sp-13 | an-139 | E1U11535 | sp-37 | an-139 |
| E1A4210 | sp-14 | an-140 | E1U4210 | sp-13 | an-140 | E1U11536 | sp-37 | an-140 |
| E1A4211 | sp-14 | an-141 | E1U4211 | sp-13 | an-141 | E1U11537 | sp-37 | an-141 |
| E1A4212 | sp-14 | an-142 | E1U4212 | sp-13 | an-142 | E1U11538 | sp-37 | an-142 |

Table 1-79

| Y = NHCS | | | Y = NHCSNH | | | Y = NHCSNH | | |
|---|---|---|---|---|---|---|---|---|
| E1A4213 | sp-14 | an-143 | E1U4213 | sp-13 | an-143 | E1U11539 | sp-37 | an-143 |
| E1A4214 | sp-14 | an-144 | E1U4214 | sp-13 | an-144 | E1U11540 | sp-37 | an-144 |
| E1A4215 | sp-14 | an-145 | E1U4215 | sp-13 | an-145 | E1U11541 | sp-37 | an-145 |
| E1A4216 | sp-14 | an-146 | E1U4216 | sp-13 | an-146 | E1U11542 | sp-37 | an-146 |
| E1A4217 | sp-14 | an-147 | E1U4217 | sp-13 | an-147 | E1U11543 | sp-37 | an-147 |
| E1A4218 | sp-14 | an-148 | E1U4218 | sp-13 | an-148 | E1U11544 | sp-37 | an-148 |
| E1A4219 | sp-14 | an-149 | E1U4219 | sp-13 | an-149 | E1U11545 | sp-37 | an-149 |
| E1A4220 | sp-14 | an-150 | E1U4220 | sp-13 | an-150 | E1U11546 | sp-37 | an-150 |
| E1A4221 | sp-14 | an-151 | E1U4221 | sp-13 | an-151 | E1U11547 | sp-37 | an-151 |
| E1A4222 | sp-14 | an-152 | E1U4222 | sp-13 | an-152 | E1U11548 | sp-37 | an-152 |
| E1A4223 | sp-14 | an-153 | E1U4223 | sp-13 | an-153 | E1U11549 | sp-37 | an-153 |
| E1A4224 | sp-14 | an-154 | E1U4224 | sp-13 | an-154 | E1U11550 | sp-37 | an-154 |
| E1A4225 | sp-14 | an-155 | E1U4225 | sp-13 | an-155 | E1U11551 | sp-37 | an-155 |
| E1A4226 | sp-14 | an-156 | E1U4226 | sp-13 | an-156 | E1U11552 | sp-37 | an-156 |
| E1A4227 | sp-14 | an-157 | E1U4227 | sp-13 | an-157 | E1U11553 | sp-37 | an-157 |
| E1A4228 | sp-14 | an-158 | E1U4228 | sp-13 | an-158 | E1U11554 | sp-37 | an-158 |
| E1A4229 | sp-14 | an-159 | E1U4229 | sp-13 | an-159 | E1U11555 | sp-37 | an-159 |
| E1A4230 | sp-14 | an-160 | E1U4230 | sp-13 | an-160 | E1U11556 | sp-37 | an-160 |
| E1A4231 | sp-14 | an-161 | E1U4231 | sp-13 | an-161 | E1U11557 | sp-37 | an-161 |
| E1A4232 | sp-14 | an-162 | E1U4232 | sp-13 | an-162 | E1U11558 | sp-37 | an-162 |
| E1A4233 | sp-14 | an-163 | E1U4233 | sp-13 | an-163 | E1U11559 | sp-37 | an-163 |
| E1A4234 | sp-14 | an-164 | E1U4234 | sp-13 | an-164 | E1U11560 | sp-37 | an-164 |
| E1A4235 | sp-14 | an-165 | E1U4235 | sp-13 | an-165 | E1U11561 | sp-37 | an-165 |
| E1A4236 | sp-14 | an-166 | E1U4236 | sp-13 | an-166 | E1U11562 | sp-37 | an-166 |
| E1A4237 | sp-14 | an-167 | E1U4237 | sp-13 | an-167 | E1U11563 | sp-37 | an-167 |
| E1A4238 | sp-14 | an-168 | E1U4238 | sp-13 | an-168 | E1U11564 | sp-37 | an-168 |
| E1A4239 | sp-14 | an-169 | E1U4239 | sp-13 | an-169 | E1U11565 | sp-37 | an-169 |
| E1A4240 | sp-14 | an-170 | E1U4240 | sp-13 | an-170 | E1U11566 | sp-37 | an-170 |
| E1A4241 | sp-14 | an-171 | E1U4241 | sp-13 | an-171 | E1U11567 | sp-37 | an-171 |
| E1A4242 | sp-14 | an-172 | E1U4242 | sp-13 | an-172 | E1U11568 | sp-37 | an-172 |
| E1A4243 | sp-14 | an-173 | E1U4243 | sp-13 | an-173 | E1U11569 | sp-37 | an-173 |
| E1A4244 | sp-14 | an-174 | E1U4244 | sp-13 | an-174 | E1U11570 | sp-37 | an-174 |
| E1A4245 | sp-14 | an-175 | E1U4245 | sp-13 | an-175 | E1U11571 | sp-37 | an-175 |
| E1A4246 | sp-14 | an-176 | E1U4246 | sp-13 | an-176 | E1U11572 | sp-37 | an-176 |
| E1A4247 | sp-14 | an-177 | E1U4247 | sp-13 | an-177 | E1U11573 | sp-37 | an-177 |
| E1A4248 | sp-14 | an-178 | E1U4248 | sp-13 | an-178 | E1U11574 | sp-37 | an-178 |
| E1A4249 | sp-14 | an-179 | E1U4249 | sp-13 | an-179 | E1U11575 | sp-37 | an-179 |
| E1A4250 | sp-14 | an-180 | E1U4250 | sp-13 | an-180 | E1U11576 | sp-37 | an-180 |
| E1A4251 | sp-14 | an-181 | E1U4251 | sp-13 | an-181 | E1U11577 | sp-37 | an-181 |
| E1A4252 | sp-14 | an-182 | E1U4252 | sp-13 | an-182 | E1U11578 | sp-37 | an-182 |
| E1A4253 | sp-14 | an-183 | E1U4253 | sp-13 | an-183 | E1U11579 | sp-37 | an-183 |
| E1A4254 | sp-14 | an-184 | E1U4254 | sp-13 | an-184 | E1U11580 | sp-37 | an-184 |
| E1A4255 | sp-14 | an-185 | E1U4255 | sp-13 | an-185 | E1U11581 | sp-37 | an-185 |
| E1A4256 | sp-14 | an-186 | E1U4256 | sp-13 | an-186 | E1U11582 | sp-37 | an-186 |
| E1A4257 | sp-14 | an-187 | E1U4257 | sp-13 | an-187 | E1U11583 | sp-37 | an-187 |
| E1A4258 | sp-14 | an-188 | E1U4258 | sp-13 | an-188 | E1U11584 | sp-37 | an-188 |
| E1A4259 | sp-14 | an-189 | E1U4259 | sp-13 | an-189 | E1U11585 | sp-37 | an-189 |
| E1A4260 | sp-14 | an-190 | E1U4260 | sp-13 | an-190 | E1U11586 | sp-37 | an-190 |
| E1A4261 | sp-14 | an-191 | E1U4261 | sp-13 | an-191 | E1U11587 | sp-37 | an-191 |
| E1A4262 | sp-14 | an-192 | E1U4262 | sp-13 | an-192 | E1U11588 | sp-37 | an-192 |
| E1A4263 | sp-14 | an-193 | E1U4263 | sp-13 | an-193 | E1U11589 | sp-37 | an-193 |
| E1A4264 | sp-14 | an-194 | E1U4264 | sp-13 | an-194 | E1U11590 | sp-37 | an-194 |
| E1A4265 | sp-14 | an-195 | E1U4265 | sp-13 | an-195 | E1U11591 | sp-37 | an-195 |
| E1A4266 | sp-14 | an-196 | E1U4266 | sp-13 | an-196 | E1U11592 | sp-37 | an-196 |

-continued

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| Table 1-80 ||||||||||
| Y = NHCS ||| Y = NHCSNH ||| Y = NHCSNH |||
| E1A4267 | sp-14 | an-197 | E1U4267 | sp-13 | an-197 | E1U11593 | sp-37 | an-197 |
| E1A4268 | sp-14 | an-198 | E1U4268 | sp-13 | an-198 | E1U11594 | sp-37 | an-198 |
| E1A4269 | sp-14 | an-199 | E1U4269 | sp-13 | an-199 | E1U11595 | sp-37 | an-199 |
| E1A4270 | sp-14 | an-200 | E1U4270 | sp-13 | an-200 | E1U11596 | sp-37 | an-200 |
| E1A4271 | sp-14 | an-201 | E1U4271 | sp-13 | an-201 | E1U11597 | sp-37 | an-201 |
| E1A4272 | sp-14 | an-202 | E1U4272 | sp-13 | an-202 | E1U11598 | sp-37 | an-202 |
| E1A4273 | sp-14 | an-203 | E1U4273 | sp-13 | an-203 | E1U11599 | sp-37 | an-203 |
| E1A4274 | sp-14 | an-204 | E1U4274 | sp-13 | an-204 | E1U11600 | sp-37 | an-204 |
| E1A4275 | sp-14 | an-205 | E1U4275 | sp-13 | an-205 | E1U11601 | sp-37 | an-205 |
| E1A4276 | sp-14 | an-206 | E1U4276 | sp-13 | an-206 | E1U11602 | sp-37 | an-206 |
| E1A4277 | sp-14 | an-207 | E1U4277 | sp-13 | an-207 | E1U11603 | sp-37 | an-207 |
| E1A4278 | sp-14 | an-208 | E1U4278 | sp-13 | an-208 | E1U11604 | sp-37 | an-208 |
| E1A4279 | sp-14 | an-209 | E1U4279 | sp-13 | an-209 | E1U11605 | sp-37 | an-209 |
| E1A4280 | sp-14 | an-210 | E1U4280 | sp-13 | an-210 | E1U11606 | sp-37 | an-210 |
| E1A4281 | sp-14 | an-211 | E1U4281 | sp-13 | an-211 | E1U11607 | sp-37 | an-211 |
| E1A4282 | sp-14 | an-212 | E1U4282 | sp-13 | an-212 | E1U11608 | sp-37 | an-212 |
| E1A4283 | sp-14 | an-213 | E1U4283 | sp-13 | an-213 | E1U11609 | sp-37 | an-213 |
| E1A4284 | sp-14 | an-214 | E1U4284 | sp-13 | an-214 | E1U11610 | sp-37 | an-214 |
| E1A4285 | sp-14 | an-215 | E1U4285 | sp-13 | an-215 | E1U11611 | sp-37 | an-215 |
| E1A4286 | sp-14 | an-216 | E1U4286 | sp-13 | an-216 | E1U11612 | sp-37 | an-216 |
| E1A4287 | sp-14 | an-217 | E1U4287 | sp-13 | an-217 | E1U11613 | sp-37 | an-217 |
| E1A4288 | sp-14 | an-218 | E1U4288 | sp-13 | an-218 | E1U11614 | sp-37 | an-218 |
| E1A4289 | sp-14 | an-219 | E1U4289 | sp-13 | an-219 | E1U11615 | sp-37 | an-219 |
| E1A4290 | sp-14 | an-220 | E1U4290 | sp-13 | an-220 | E1U11616 | sp-37 | an-220 |
| E1A4291 | sp-14 | an-221 | E1U4291 | sp-13 | an-221 | E1U11617 | sp-37 | an-221 |
| E1A4292 | sp-14 | an-222 | E1U4292 | sp-13 | an-222 | E1U11618 | sp-37 | an-222 |
| E1A4293 | sp-14 | an-223 | E1U4293 | sp-13 | an-223 | E1U11619 | sp-37 | an-223 |
| E1A4294 | sp-14 | an-224 | E1U4294 | sp-13 | an-224 | E1U11620 | sp-37 | an-224 |
| E1A4295 | sp-14 | an-225 | E1U4295 | sp-13 | an-225 | E1U11621 | sp-37 | an-225 |
| E1A4296 | sp-14 | an-226 | E1U4296 | sp-13 | an-226 | E1U11622 | sp-37 | an-226 |
| E1A4297 | sp-14 | an-227 | E1U4297 | sp-13 | an-227 | E1U11623 | sp-37 | an-227 |
| E1A4298 | sp-14 | an-228 | E1U4298 | sp-13 | an-228 | E1U11624 | sp-37 | an-228 |
| E1A4299 | sp-14 | an-229 | E1U4299 | sp-13 | an-229 | E1U11625 | sp-37 | an-229 |
| E1A4300 | sp-14 | an-230 | E1U4300 | sp-13 | an-230 | E1U11626 | sp-37 | an-230 |
| E1A4301 | sp-14 | an-231 | E1U4301 | sp-13 | an-231 | E1U11627 | sp-37 | an-231 |
| E1A4302 | sp-14 | an-232 | E1U4302 | sp-13 | an-232 | E1U11628 | sp-37 | an-232 |
| E1A4303 | sp-14 | an-233 | E1U4303 | sp-13 | an-233 | E1U11629 | sp-37 | an-233 |
| E1A4304 | sp-14 | an-234 | E1U4304 | sp-13 | an-234 | E1U11630 | sp-37 | an-234 |
| E1A4305 | sp-14 | an-235 | E1U4305 | sp-13 | an-235 | E1U11631 | sp-37 | an-235 |
| E1A4306 | sp-14 | an-236 | E1U4306 | sp-13 | an-236 | E1U11632 | sp-37 | an-236 |
| E1A4307 | sp-14 | an-237 | E1U4307 | sp-13 | an-237 | E1U11633 | sp-37 | an-237 |
| E1A4308 | sp-14 | an-238 | E1U4308 | sp-13 | an-238 | E1U11634 | sp-37 | an-238 |
| E1A4309 | sp-14 | an-239 | E1U4309 | sp-13 | an-239 | E1U11635 | sp-37 | an-239 |
| E1A4310 | sp-14 | an-240 | E1U4310 | sp-13 | an-240 | E1U11636 | sp-37 | an-240 |
| E1A4311 | sp-14 | an-241 | E1U4311 | sp-13 | an-241 | E1U11637 | sp-37 | an-241 |
| E1A4312 | sp-14 | an-242 | E1U4312 | sp-13 | an-242 | E1U11638 | sp-37 | an-242 |
| E1A4313 | sp-14 | an-243 | E1U4313 | sp-13 | an-243 | E1U11639 | sp-37 | an-243 |
| E1A4314 | sp-14 | an-244 | E1U4314 | sp-13 | an-244 | E1U11640 | sp-37 | an-244 |
| E1A4315 | sp-14 | an-245 | E1U4315 | sp-13 | an-245 | E1U11641 | sp-37 | an-245 |
| E1A4316 | sp-14 | an-246 | E1U4316 | sp-13 | an-246 | E1U11642 | sp-37 | an-246 |
| E1A4317 | sp-14 | an-247 | E1U4317 | sp-13 | an-247 | E1U11643 | sp-37 | an-247 |
| E1A4318 | sp-14 | an-248 | E1U4318 | sp-13 | an-248 | E1U11644 | sp-37 | an-248 |
| E1A4319 | sp-14 | an-249 | E1U4319 | sp-13 | an-249 | E1U11645 | sp-37 | an-249 |
| E1A4320 | sp-14 | an-250 | E1U4320 | sp-13 | an-250 | E1U11646 | sp-37 | an-250 |
| Table 1-81 ||||||||||
| Y = NHCS ||| Y = NHCSNH ||| Y = NHCSNH |||
| E1A4321 | sp-14 | an-251 | E1U4321 | sp-13 | an-251 | E1U11647 | sp-37 | an-251 |
| E1A4322 | sp-14 | an-252 | E1U4322 | sp-13 | an-252 | E1U11648 | sp-37 | an-252 |
| E1A4323 | sp-14 | an-253 | E1U4323 | sp-13 | an-253 | E1U11649 | sp-37 | an-253 |
| E1A4324 | sp-14 | an-254 | E1U4324 | sp-13 | an-254 | E1U11650 | sp-37 | an-254 |
| E1A4325 | sp-14 | an-255 | E1U4325 | sp-13 | an-255 | E1U11651 | sp-37 | an-255 |
| E1A4326 | sp-14 | an-256 | E1U4326 | sp-13 | an-256 | E1U11652 | sp-37 | an-256 |
| E1A4327 | sp-14 | an-257 | E1U4327 | sp-13 | an-257 | E1U11653 | sp-37 | an-257 |
| E1A4328 | sp-14 | an-258 | E1U4328 | sp-13 | an-258 | E1U11654 | sp-37 | an-258 |
| E1A4329 | sp-14 | an-259 | E1U4329 | sp-13 | an-259 | E1U11655 | sp-37 | an-259 |
| E1A4330 | sp-14 | an-260 | E1U4330 | sp-13 | an-260 | E1U11656 | sp-37 | an-260 |
| E1A4331 | sp-14 | an-261 | E1U4331 | sp-13 | an-261 | E1U11657 | sp-37 | an-261 |
| E1A4332 | sp-14 | an-262 | E1U4332 | sp-13 | an-262 | E1U11658 | sp-37 | an-262 |
| E1A4333 | sp-14 | an-263 | E1U4333 | sp-13 | an-263 | E1U11659 | sp-37 | an-263 |
| E1A4334 | sp-14 | an-264 | E1U4334 | sp-13 | an-264 | E1U11660 | sp-37 | an-264 |
| E1A4335 | sp-14 | an-265 | E1U4335 | sp-13 | an-265 | E1U11661 | sp-37 | an-265 |
| E1A4336 | sp-14 | an-266 | E1U4336 | sp-13 | an-266 | E1U11662 | sp-37 | an-266 |

-continued

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| E1A4337 | sp-14 | an-267 | E1U4337 | sp-13 | an-267 | E1U11663 | sp-37 | an-267 |
| E1A4338 | sp-14 | an-268 | E1U4338 | sp-13 | an-268 | E1U11664 | sp-37 | an-268 |
| E1A4339 | sp-14 | an-269 | E1U4339 | sp-13 | an-269 | E1U11665 | sp-37 | an-269 |
| E1A4340 | sp-14 | an-270 | E1U4340 | sp-13 | an-270 | E1U11666 | sp-37 | an-270 |
| E1A4341 | sp-14 | an-271 | E1U4341 | sp-13 | an-271 | E1U11667 | sp-37 | an-271 |
| E1A4342 | sp-14 | an-272 | E1U4342 | sp-13 | an-272 | E1U11668 | sp-37 | an-272 |
| E1A4343 | sp-14 | an-273 | E1U4343 | sp-13 | an-273 | E1U11669 | sp-37 | an-273 |
| E1A4344 | sp-14 | an-274 | E1U4344 | sp-13 | an-274 | E1U11670 | sp-37 | an-274 |
| E1A4345 | sp-14 | an-275 | E1U4345 | sp-13 | an-275 | E1U11671 | sp-37 | an-275 |
| E1A4346 | sp-14 | an-276 | E1U4346 | sp-13 | an-276 | E1U11672 | sp-37 | an-276 |
| E1A4347 | sp-14 | an-277 | E1U4347 | sp-13 | an-277 | E1U11673 | sp-37 | an-277 |
| E1A4348 | sp-14 | an-278 | E1U4348 | sp-13 | an-278 | E1U11674 | sp-37 | an-278 |
| E1A4349 | sp-14 | an-279 | E1U4349 | sp-13 | an-279 | E1U11675 | sp-37 | an-279 |
| E1A4350 | sp-14 | an-280 | E1U4350 | sp-13 | an-280 | E1U11676 | sp-37 | an-280 |
| E1A4351 | sp-14 | an-281 | E1U4351 | sp-13 | an-281 | E1U11677 | sp-37 | an-281 |
| E1A4352 | sp-14 | an-282 | E1U4352 | sp-13 | an-282 | E1U11678 | sp-37 | an-282 |
| E1A4353 | sp-14 | an-283 | E1U4353 | sp-13 | an-283 | E1U11679 | sp-37 | an-283 |
| E1A4354 | sp-14 | an-284 | E1U4354 | sp-13 | an-284 | E1U11680 | sp-37 | an-284 |
| E1A4355 | sp-14 | an-285 | E1U4355 | sp-13 | an-285 | E1U11681 | sp-37 | an-285 |
| E1A4356 | sp-14 | an-286 | E1U4356 | sp-13 | an-286 | E1U11682 | sp-37 | an-286 |
| E1A4357 | sp-14 | an-287 | E1U4357 | sp-13 | an-287 | E1U11683 | sp-37 | an-287 |
| E1A4358 | sp-14 | an-288 | E1U4358 | sp-13 | an-288 | E1U11684 | sp-37 | an-288 |
| E1A4359 | sp-14 | an-289 | E1U4359 | sp-13 | an-289 | E1U11685 | sp-37 | an-289 |
| E1A4360 | sp-14 | an-290 | E1U4360 | sp-13 | an-290 | E1U11686 | sp-37 | an-290 |
| E1A4361 | sp-14 | an-291 | E1U4361 | sp-13 | an-291 | E1U11687 | sp-37 | an-291 |
| E1A4362 | sp-14 | an-292 | E1U4362 | sp-13 | an-292 | E1U11688 | sp-37 | an-292 |
| E1A4363 | sp-14 | an-293 | E1U4363 | sp-13 | an-293 | E1U11689 | sp-37 | an-293 |
| E1A4364 | sp-14 | an-294 | E1U4364 | sp-13 | an-294 | E1U11690 | sp-37 | an-294 |
| E1A4365 | sp-14 | an-295 | E1U4365 | sp-13 | an-295 | E1U11691 | sp-37 | an-295 |
| E1A4366 | sp-14 | an-296 | E1U4366 | sp-13 | an-296 | E1U11692 | sp-37 | an-296 |
| E1A4367 | sp-14 | an-297 | E1U4367 | sp-13 | an-297 | E1U11693 | sp-37 | an-297 |
| E1A4368 | sp-14 | an-298 | E1U4368 | sp-13 | an-298 | E1U11694 | sp-37 | an-298 |
| E1A4369 | sp-14 | an-299 | E1U4369 | sp-13 | an-299 | E1U11695 | sp-37 | an-299 |
| E1A4370 | sp-14 | an-300 | E1U4370 | sp-13 | an-300 | E1U11696 | sp-37 | an-300 |
| E1A4371 | sp-14 | an-301 | E1U4371 | sp-13 | an-301 | E1U11697 | sp-37 | an-301 |
| E1A4372 | sp-14 | an-302 | E1U4372 | sp-13 | an-302 | E1U11698 | sp-37 | an-302 |
| E1A4373 | sp-14 | an-303 | E1U4373 | sp-13 | an-303 | E1U11699 | sp-37 | an-303 |
| E1A4374 | sp-14 | an-304 | E1U4374 | sp-13 | an-304 | E1U11700 | sp-37 | an-304 |

Table 1-82

| Y = NHCS | | | Y = NHCSNH | | | Y = NHCSNH | | |
|---|---|---|---|---|---|---|---|---|
| E1A4375 | sp-14 | an-305 | E1U4375 | sp-13 | an-305 | E1U11701 | sp-37 | an-305 |
| E1A4376 | sp-14 | an-306 | E1U4376 | sp-13 | an-306 | E1U11702 | sp-37 | an-306 |
| E1A4377 | sp-14 | an-307 | E1U4377 | sp-13 | an-307 | E1U11703 | sp-37 | an-307 |
| E1A4378 | sp-14 | an-308 | E1U4378 | sp-13 | an-308 | E1U11704 | sp-37 | an-308 |
| E1A4379 | sp-14 | an-309 | E1U4379 | sp-13 | an-309 | E1U11705 | sp-37 | an-309 |
| E1A4380 | sp-14 | an-310 | E1U4380 | sp-13 | an-310 | E1U11706 | sp-37 | an-310 |
| E1A4381 | sp-14 | an-311 | E1U4381 | sp-13 | an-311 | E1U11707 | sp-37 | an-311 |
| E1A4382 | sp-14 | an-312 | E1U4382 | sp-13 | an-312 | E1U11708 | sp-37 | an-312 |
| E1A4383 | sp-14 | an-313 | E1U4383 | sp-13 | an-313 | E1U11709 | sp-37 | an-313 |
| E1A4384 | sp-14 | an-314 | E1U4384 | sp-13 | an-314 | E1U11710 | sp-37 | an-314 |
| E1A4385 | sp-14 | an-315 | E1U4385 | sp-13 | an-315 | E1U11711 | sp-37 | an-315 |
| E1A4386 | sp-14 | an-316 | E1U4386 | sp-13 | an-316 | E1U11712 | sp-37 | an-316 |
| E1A4387 | sp-14 | an-317 | E1U4387 | sp-13 | an-317 | E1U11713 | sp-37 | an-317 |
| E1A4388 | sp-14 | an-318 | E1U4388 | sp-13 | an-318 | E1U11714 | sp-37 | an-318 |
| E1A4389 | sp-14 | an-319 | E1U4389 | sp-13 | an-319 | E1U11715 | sp-37 | an-319 |
| E1A4390 | sp-14 | an-320 | E1U4390 | sp-13 | an-320 | E1U11716 | sp-37 | an-320 |
| E1A4391 | sp-14 | an-321 | E1U4391 | sp-13 | an-321 | E1U11717 | sp-37 | an-321 |
| E1A4392 | sp-14 | an-322 | E1U4392 | sp-13 | an-322 | E1U11718 | sp-37 | an-322 |
| E1A4393 | sp-14 | an-323 | E1U4393 | sp-13 | an-323 | E1U11719 | sp-37 | an-323 |
| E1A4394 | sp-14 | an-324 | E1U4394 | sp-13 | an-324 | E1U11720 | sp-37 | an-324 |
| E1A4395 | sp-14 | an-325 | E1U4395 | sp-13 | an-325 | E1U11721 | sp-37 | an-325 |
| E1A4396 | sp-14 | an-326 | E1U4396 | sp-13 | an-326 | E1U11722 | sp-37 | an-326 |
| E1A4397 | sp-14 | an-327 | E1U4397 | sp-13 | an-327 | E1U11723 | sp-37 | an-327 |
| E1A4398 | sp-14 | an-328 | E1U4398 | sp-13 | an-328 | E1U11724 | sp-37 | an-328 |
| E1A4399 | sp-14 | an-329 | E1U4399 | sp-13 | an-329 | E1U11725 | sp-37 | an-329 |
| E1A4400 | sp-14 | an-330 | E1U4400 | sp-13 | an-330 | E1U11726 | sp-37 | an-330 |
| E1A4401 | sp-14 | an-331 | E1U4401 | sp-13 | an-331 | E1U11727 | sp-37 | an-331 |
| E1A4402 | sp-14 | an-332 | E1U4402 | sp-13 | an-332 | E1U11728 | sp-37 | an-332 |
| E1A4403 | sp-14 | an-333 | E1U4403 | sp-13 | an-333 | E1U11729 | sp-37 | an-333 |
| E1A4404 | sp-14 | an-334 | E1U4404 | sp-13 | an-334 | E1U11730 | sp-37 | an-334 |
| E1A4405 | sp-14 | an-335 | E1U4405 | sp-13 | an-335 | E1U11731 | sp-37 | an-335 |
| E1A4406 | sp-14 | an-336 | E1U4406 | sp-13 | an-336 | E1U11732 | sp-37 | an-336 |
| E1A4407 | sp-14 | an-337 | E1U4407 | sp-13 | an-337 | E1U11733 | sp-37 | an-337 |
| E1A4408 | sp-14 | an-338 | E1U4408 | sp-13 | an-338 | E1U11734 | sp-37 | an-338 |
| E1A4409 | sp-14 | an-339 | E1U4409 | sp-13 | an-339 | E1U11735 | sp-37 | an-339 |
| E1A4410 | sp-14 | an-340 | E1U4410 | sp-13 | an-340 | E1U11736 | sp-37 | an-340 |

-continued

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| E1A4411 | sp-14 | an-341 | E1U4411 | sp-13 | an-341 | E1U11737 | sp-37 | an-341 |
| E1A4412 | sp-14 | an-342 | E1U4412 | sp-13 | an-342 | E1U11738 | sp-37 | an-342 |
| E1A4413 | sp-14 | an-343 | E1U4413 | sp-13 | an-343 | E1U11739 | sp-37 | an-343 |
| E1A4414 | sp-14 | an-344 | E1U4414 | sp-13 | an-344 | E1U11740 | sp-37 | an-344 |
| E1A4415 | sp-14 | an-345 | E1U4415 | sp-13 | an-345 | E1U11741 | sp-37 | an-345 |
| E1A4416 | sp-14 | an-346 | E1U4416 | sp-13 | an-346 | E1U11742 | sp-37 | an-346 |
| E1A4417 | sp-14 | an-347 | E1U4417 | sp-13 | an-347 | E1U11743 | sp-37 | an-347 |
| E1A4418 | sp-14 | an-348 | E1U4418 | sp-13 | an-348 | E1U11744 | sp-37 | an-348 |
| E1A4419 | sp-14 | an-349 | E1U4419 | sp-13 | an-349 | E1U11745 | sp-37 | an-349 |
| E1A4420 | sp-14 | an-350 | E1U4420 | sp-13 | an-350 | E1U11746 | sp-37 | an-350 |
| E1A4421 | sp-14 | an-351 | E1U4421 | sp-13 | an-351 | E1U11747 | sp-37 | an-351 |
| E1A4422 | sp-14 | an-352 | E1U4422 | sp-13 | an-352 | E1U11748 | sp-37 | an-352 |
| E1A4423 | sp-14 | an-353 | E1U4423 | sp-13 | an-353 | E1U11749 | sp-37 | an-353 |
| E1A4424 | sp-14 | an-354 | E1U4424 | sp-13 | an-354 | E1U11750 | sp-37 | an-354 |
| E1A4425 | sp-14 | an-355 | E1U4425 | sp-13 | an-355 | E1U11751 | sp-37 | an-355 |
| E1A4426 | sp-14 | an-356 | E1U4426 | sp-13 | an-356 | E1U11752 | sp-37 | an-356 |
| E1A4427 | sp-14 | an-357 | E1U4427 | sp-13 | an-357 | E1U11753 | sp-37 | an-357 |
| E1A4428 | sp-14 | an-358 | E1U4428 | sp-13 | an-358 | E1U11754 | sp-37 | an-358 |

Table 1-83

| Y = NHCS | | | Y = NHCSNH | | | Y = NHCSNH | | |
|---|---|---|---|---|---|---|---|---|
| E1A4429 | sp-14 | an-359 | E1U4429 | sp-13 | an-359 | E1U11755 | sp-37 | an-359 |
| E1A4430 | sp-14 | an-360 | E1U4430 | sp-13 | an-360 | E1U11756 | sp-37 | an-360 |
| E1A4431 | sp-14 | an-361 | E1U4431 | sp-13 | an-361 | E1U11757 | sp-37 | an-361 |
| E1A4432 | sp-14 | an-362 | E1U4432 | sp-13 | an-362 | E1U11758 | sp-37 | an-362 |
| E1A4433 | sp-14 | an-363 | E1U4433 | sp-13 | an-363 | E1U11759 | sp-37 | an-363 |
| E1A4434 | sp-14 | an-364 | E1U4434 | sp-13 | an-364 | E1U11760 | sp-37 | an-364 |
| E1A4435 | sp-14 | an-365 | E1U4435 | sp-13 | an-365 | E1U11761 | sp-37 | an-365 |
| E1A4436 | sp-14 | an-366 | E1U4436 | sp-13 | an-366 | E1U11762 | sp-37 | an-366 |
| E1A4437 | sp-14 | an-367 | E1U4437 | sp-13 | an-367 | E1U11763 | sp-37 | an-367 |
| E1A4438 | sp-14 | an-368 | E1U4438 | sp-13 | an-368 | E1U11764 | sp-37 | an-368 |
| E1A4439 | sp-14 | an-369 | E1U4439 | sp-13 | an-369 | E1U11765 | sp-37 | an-369 |
| E1A4440 | sp-14 | an-370 | E1U4440 | sp-13 | an-370 | E1U11766 | sp-37 | an-370 |
| E1A4441 | sp-14 | an-371 | E1U4441 | sp-13 | an-371 | E1U11767 | sp-37 | an-371 |
| E1A4442 | sp-14 | an-372 | E1U4442 | sp-13 | an-372 | E1U11768 | sp-37 | an-372 |
| E1A4443 | sp-14 | an-373 | E1U4443 | sp-13 | an-373 | E1U11769 | sp-37 | an-373 |
| E1A4444 | sp-14 | an-374 | E1U4444 | sp-13 | an-374 | E1U11770 | sp-37 | an-374 |
| E1A4445 | sp-14 | an-375 | E1U4445 | sp-13 | an-375 | E1U11771 | sp-37 | an-375 |
| E1A4446 | sp-14 | an-376 | E1U4446 | sp-13 | an-376 | E1U11772 | sp-37 | an-376 |
| E1A4447 | sp-14 | an-377 | E1U4447 | sp-13 | an-377 | E1U11773 | sp-37 | an-377 |
| E1A4448 | sp-14 | an-378 | E1U4448 | sp-13 | an-378 | E1U11774 | sp-37 | an-378 |
| E1A4449 | sp-14 | an-379 | E1U4449 | sp-13 | an-379 | E1U11775 | sp-37 | an-379 |
| E1A4450 | sp-14 | an-380 | E1U4450 | sp-13 | an-380 | E1U11776 | sp-37 | an-380 |
| E1A4451 | sp-14 | an-381 | E1U4451 | sp-13 | an-381 | E1U11777 | sp-37 | an-381 |
| E1A4452 | sp-14 | an-382 | E1U4452 | sp-13 | an-382 | E1U11778 | sp-37 | an-382 |
| E1A4453 | sp-14 | an-383 | E1U4453 | sp-13 | an-383 | E1U11779 | sp-37 | an-383 |
| E1A4454 | sp-14 | an-384 | E1U4454 | sp-13 | an-384 | E1U11780 | sp-37 | an-384 |
| E1A4455 | sp-14 | an-385 | E1U4455 | sp-13 | an-385 | E1U11781 | sp-37 | an-385 |
| E1A4456 | sp-14 | an-386 | E1U4456 | sp-13 | an-386 | E1U11782 | sp-37 | an-386 |
| E1A4457 | sp-14 | an-387 | E1U4457 | sp-13 | an-387 | E1U11783 | sp-37 | an-387 |
| E1A4458 | sp-14 | an-388 | E1U4458 | sp-13 | an-388 | E1U11784 | sp-37 | an-388 |
| E1A4459 | sp-14 | an-389 | E1U4459 | sp-13 | an-389 | E1U11785 | sp-37 | an-389 |
| E1A4460 | sp-14 | an-390 | E1U4460 | sp-13 | an-390 | E1U11786 | sp-37 | an-390 |
| E1A4461 | sp-14 | an-391 | E1U4461 | sp-13 | an-391 | E1U11787 | sp-37 | an-391 |
| E1A4462 | sp-14 | an-392 | E1U4462 | sp-13 | an-392 | E1U11788 | sp-37 | an-392 |
| E1A4463 | sp-14 | an-393 | E1U4463 | sp-13 | an-393 | E1U11789 | sp-37 | an-393 |
| E1A4464 | sp-14 | an-394 | E1U4464 | sp-13 | an-394 | E1U11790 | sp-37 | an-394 |
| E1A4465 | sp-14 | an-395 | E1U4465 | sp-13 | an-395 | E1U11791 | sp-37 | an-395 |
| E1A4466 | sp-14 | an-396 | E1U4466 | sp-13 | an-396 | E1U11792 | sp-37 | an-396 |
| E1A4467 | sp-14 | an-397 | E1U4467 | sp-13 | an-397 | E1U11793 | sp-37 | an-397 |
| E1A4468 | sp-14 | an-398 | E1U4468 | sp-13 | an-398 | E1U11794 | sp-37 | an-398 |
| E1A4469 | sp-14 | an-399 | E1U4469 | sp-13 | an-399 | E1U11795 | sp-37 | an-399 |
| E1A4470 | sp-14 | an-400 | E1U4470 | sp-13 | an-400 | E1U11796 | sp-37 | an-400 |
| E1A4471 | sp-14 | an-401 | E1U4471 | sp-13 | an-401 | E1U11797 | sp-37 | an-401 |
| E1A4472 | sp-14 | an-402 | E1U4472 | sp-13 | an-402 | E1U11798 | sp-37 | an-402 |
| E1A4473 | sp-14 | an-403 | E1U4473 | sp-13 | an-403 | E1U11799 | sp-37 | an-403 |
| E1A4474 | sp-14 | an-404 | E1U4474 | sp-13 | an-404 | E1U11800 | sp-37 | an-404 |
| E1A4475 | sp-14 | an-405 | E1U4475 | sp-13 | an-405 | E1U11801 | sp-37 | an-405 |
| E1A4476 | sp-14 | an-406 | E1U4476 | sp-13 | an-406 | E1U11802 | sp-37 | an-406 |
| E1A4477 | sp-14 | an-407 | E1U4477 | sp-13 | an-407 | E1U11803 | sp-37 | an-407 |
| E1A4478 | sp-15 | an-1 | E1U4478 | sp-14 | an-1 | E1U11804 | sp-38 | an-1 |
| E1A4479 | sp-15 | an-2 | E1U4479 | sp-14 | an-2 | E1U11805 | sp-38 | an-2 |
| E1A4480 | sp-15 | an-3 | E1U4480 | sp-14 | an-3 | E1U11806 | sp-38 | an-3 |
| E1A4481 | sp-15 | an-4 | E1U4481 | sp-14 | an-4 | E1U11807 | sp-38 | an-4 |
| E1A4482 | sp-15 | an-5 | E1U4482 | sp-14 | an-5 | E1U11808 | sp-38 | an-5 |

-continued

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| | | | | Table 1-84 | | | | |
| | Y = NHCS | | | Y = NHCSNH | | | Y = NHCSNH | |
| E1A4483 | sp-15 | an-6 | E1U4483 | sp-14 | an-6 | E1U11809 | sp-38 | an-6 |
| E1A4484 | sp-15 | an-7 | E1U4484 | sp-14 | an-7 | E1U11810 | sp-38 | an-7 |
| E1A4485 | sp-15 | an-8 | E1U4485 | sp-14 | an-8 | E1U11811 | sp-38 | an-8 |
| E1A4486 | sp-15 | an-9 | E1U4486 | sp-14 | an-9 | E1U11812 | sp-38 | an-9 |
| E1A4487 | sp-15 | an-10 | E1U4487 | sp-14 | an-10 | E1U11813 | sp-38 | an-10 |
| E1A4488 | sp-15 | an-11 | E1U4488 | sp-14 | an-11 | E1U11814 | sp-38 | an-11 |
| E1A4489 | sp-15 | an-12 | E1U4489 | sp-14 | an-12 | E1U11815 | sp-38 | an-12 |
| E1A4490 | sp-15 | an-13 | E1U4490 | sp-14 | an-13 | E1U11816 | sp-38 | an-13 |
| E1A4491 | sp-15 | an-14 | E1U4491 | sp-14 | an-14 | E1U11817 | sp-38 | an-14 |
| E1A4492 | sp-15 | an-15 | E1U4492 | sp-14 | an-15 | E1U11818 | sp-38 | an-15 |
| E1A4493 | sp-15 | an-16 | E1U4493 | sp-14 | an-16 | E1U11819 | sp-38 | an-16 |
| E1A4494 | sp-15 | an-17 | E1U4494 | sp-14 | an-17 | E1U11820 | sp-38 | an-17 |
| E1A4495 | sp-15 | an-18 | E1U4495 | sp-14 | an-18 | E1U11821 | sp-38 | an-18 |
| E1A4496 | sp-15 | an-19 | E1U4496 | sp-14 | an-19 | E1U11822 | sp-38 | an-19 |
| E1A4497 | sp-15 | an-20 | E1U4497 | sp-14 | an-20 | E1U11823 | sp-38 | an-20 |
| E1A4498 | sp-15 | an-21 | E1U4498 | sp-14 | an-21 | E1U11824 | sp-38 | an-21 |
| E1A4499 | sp-15 | an-22 | E1U4499 | sp-14 | an-22 | E1U11825 | sp-38 | an-22 |
| E1A4500 | sp-15 | an-23 | E1U4500 | sp-14 | an-23 | E1U11826 | sp-38 | an-23 |
| E1A4501 | sp-15 | an-24 | E1U4501 | sp-14 | an-24 | E1U11827 | sp-38 | an-24 |
| E1A4502 | sp-15 | an-25 | E1U4502 | sp-14 | an-25 | E1U11828 | sp-38 | an-25 |
| E1A4503 | sp-15 | an-26 | E1U4503 | sp-14 | an-26 | E1U11829 | sp-38 | an-26 |
| E1A4504 | sp-15 | an-27 | E1U4504 | sp-14 | an-27 | E1U11830 | sp-38 | an-27 |
| E1A4505 | sp-15 | an-28 | E1U4505 | sp-14 | an-28 | E1U11831 | sp-38 | an-28 |
| E1A4506 | sp-15 | an-29 | E1U4506 | sp-14 | an-29 | E1U11832 | sp-38 | an-29 |
| E1A4507 | sp-15 | an-30 | E1U4507 | sp-14 | an-30 | E1U11833 | sp-38 | an-30 |
| E1A4508 | sp-15 | an-31 | E1U4508 | sp-14 | an-31 | E1U11834 | sp-38 | an-31 |
| E1A4509 | sp-15 | an-32 | E1U4509 | sp-14 | an-32 | E1U11835 | sp-38 | an-32 |
| E1A4510 | sp-15 | an-33 | E1U4510 | sp-14 | an-33 | E1U11836 | sp-38 | an-33 |
| E1A4511 | sp-15 | an-34 | E1U4511 | sp-14 | an-34 | E1U11837 | sp-38 | an-34 |
| E1A4512 | sp-15 | an-35 | E1U4512 | sp-14 | an-35 | E1U11838 | sp-38 | an-35 |
| E1A4513 | sp-15 | an-36 | E1U4513 | sp-14 | an-36 | E1U11839 | sp-38 | an-36 |
| E1A4514 | sp-15 | an-37 | E1U4514 | sp-14 | an-37 | E1U11840 | sp-38 | an-37 |
| E1A4515 | sp-15 | an-38 | E1U4515 | sp-14 | an-38 | E1U11841 | sp-38 | an-38 |
| E1A4516 | sp-15 | an-39 | E1U4516 | sp-14 | an-39 | E1U11842 | sp-38 | an-39 |
| E1A4517 | sp-15 | an-40 | E1U4517 | sp-14 | an-40 | E1U11843 | sp-38 | an-40 |
| E1A4518 | sp-15 | an-41 | E1U4518 | sp-14 | an-41 | E1U11844 | sp-38 | an-41 |
| E1A4519 | sp-15 | an-42 | E1U4519 | sp-14 | an-42 | E1U11845 | sp-38 | an-42 |
| E1A4520 | sp-15 | an-43 | E1U4520 | sp-14 | an-43 | E1U11846 | sp-38 | an-43 |
| E1A4521 | sp-15 | an-44 | E1U4521 | sp-14 | an-44 | E1U11847 | sp-38 | an-44 |
| E1A4522 | sp-15 | an-45 | E1U4522 | sp-14 | an-45 | E1U11848 | sp-38 | an-45 |
| E1A4523 | sp-15 | an-46 | E1U4523 | sp-14 | an-46 | E1U11849 | sp-38 | an-46 |
| E1A4524 | sp-15 | an-47 | E1U4524 | sp-14 | an-47 | E1U11850 | sp-38 | an-47 |
| E1A4525 | sp-15 | an-48 | E1U4525 | sp-14 | an-48 | E1U11851 | sp-38 | an-48 |
| E1A4526 | sp-15 | an-49 | E1U4526 | sp-14 | an-49 | E1U11852 | sp-38 | an-49 |
| E1A4527 | sp-15 | an-50 | E1U4527 | sp-14 | an-50 | E1U11853 | sp-38 | an-50 |
| E1A4528 | sp-15 | an-51 | E1U4528 | sp-14 | an-51 | E1U11854 | sp-38 | an-51 |
| E1A4529 | sp-15 | an-52 | E1U4529 | sp-14 | an-52 | E1U11855 | sp-38 | an-52 |
| E1A4530 | sp-15 | an-53 | E1U4530 | sp-14 | an-53 | E1U11856 | sp-38 | an-53 |
| E1A4531 | sp-15 | an-54 | E1U4531 | sp-14 | an-54 | E1U11857 | sp-38 | an-54 |
| E1A4532 | sp-15 | an-55 | E1U4532 | sp-14 | an-55 | E1U11858 | sp-38 | an-55 |
| E1A4533 | sp-15 | an-56 | E1U4533 | sp-14 | an-56 | E1U11859 | sp-38 | an-56 |
| E1A4534 | sp-15 | an-57 | E1U4534 | sp-14 | an-57 | E1U11860 | sp-38 | an-57 |
| E1A4535 | sp-15 | an-58 | E1U4535 | sp-14 | an-58 | E1U11861 | sp-38 | an-58 |
| E1A4536 | sp-15 | an-59 | E1U4536 | sp-14 | an-59 | E1U11862 | sp-38 | an-59 |
| | | | | Table 1-85 | | | | |
| | Y = NHCS | | | Y = NHCSNH | | | Y = NHCSNH | |
| E1A4537 | sp-15 | an-60 | E1U4537 | sp-14 | an-60 | E1U11863 | sp-38 | an-60 |
| E1A4538 | sp-15 | an-61 | E1U4538 | sp-14 | an-61 | E1U11864 | sp-38 | an-61 |
| E1A4539 | sp-15 | an-62 | E1U4539 | sp-14 | an-62 | E1U11865 | sp-38 | an-62 |
| E1A4540 | sp-15 | an-63 | E1U4540 | sp-14 | an-63 | E1U11866 | sp-38 | an-63 |
| E1A4541 | sp-15 | an-64 | E1U4541 | sp-14 | an-64 | E1U11867 | sp-38 | an-64 |
| E1A4542 | sp-15 | an-65 | E1U4542 | sp-14 | an-65 | E1U11868 | sp-38 | an-65 |
| E1A4543 | sp-15 | an-66 | E1U4543 | sp-14 | an-66 | E1U11869 | sp-38 | an-66 |
| E1A4544 | sp-15 | an-67 | E1U4544 | sp-14 | an-67 | E1U11870 | sp-38 | an-67 |
| E1A4545 | sp-15 | an-68 | E1U4545 | sp-14 | an-68 | E1U11871 | sp-38 | an-68 |
| E1A4546 | sp-15 | an-69 | E1U4546 | sp-14 | an-69 | E1U11872 | sp-38 | an-69 |
| E1A4547 | sp-15 | an-70 | E1U4547 | sp-14 | an-70 | E1U11873 | sp-38 | an-70 |
| E1A4548 | sp-15 | an-71 | E1U4548 | sp-14 | an-71 | E1U11874 | sp-38 | an-71 |
| E1A4549 | sp-15 | an-72 | E1U4549 | sp-14 | an-72 | E1U11875 | sp-38 | an-72 |
| E1A4550 | sp-15 | an-73 | E1U4550 | sp-14 | an-73 | E1U11876 | sp-38 | an-73 |
| E1A4551 | sp-15 | an-74 | E1U4551 | sp-14 | an-74 | E1U11877 | sp-38 | an-74 |
| E1A4552 | sp-15 | an-75 | E1U4552 | sp-14 | an-75 | E1U11878 | sp-38 | an-75 |

-continued

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| E1A4553 | sp-15 | an-76 | E1U4553 | sp-14 | an-76 | E1U11879 | sp-38 | an-76 |
| E1A4554 | sp-15 | an-77 | E1U4554 | sp-14 | an-77 | E1U11880 | sp-38 | an-77 |
| E1A4555 | sp-15 | an-78 | E1U4555 | sp-14 | an-78 | E1U11881 | sp-38 | an-78 |
| E1A4556 | sp-15 | an-79 | E1U4556 | sp-14 | an-79 | E1U11882 | sp-38 | an-79 |
| E1A4557 | sp-15 | an-80 | E1U4557 | sp-14 | an-80 | E1U11883 | sp-38 | an-80 |
| E1A4558 | sp-15 | an-81 | E1U4558 | sp-14 | an-81 | E1U11884 | sp-38 | an-81 |
| E1A4559 | sp-15 | an-82 | E1U4559 | sp-14 | an-82 | E1U11885 | sp-38 | an-82 |
| E1A4560 | sp-15 | an-83 | E1U4560 | sp-14 | an-83 | E1U11886 | sp-38 | an-83 |
| E1A4561 | sp-15 | an-84 | E1U4561 | sp-14 | an-84 | E1U11887 | sp-38 | an-84 |
| E1A4562 | sp-15 | an-85 | E1U4562 | sp-14 | an-85 | E1U11888 | sp-38 | an-85 |
| E1A4563 | sp-15 | an-86 | E1U4563 | sp-14 | an-86 | E1U11889 | sp-38 | an-86 |
| E1A4564 | sp-15 | an-87 | E1U4564 | sp-14 | an-87 | E1U11890 | sp-38 | an-87 |
| E1A4565 | sp-15 | an-88 | E1U4565 | sp-14 | an-88 | E1U11891 | sp-38 | an-88 |
| E1A4566 | sp-15 | an-89 | E1U4566 | sp-14 | an-89 | E1U11892 | sp-38 | an-89 |
| E1A4567 | sp-15 | an-90 | E1U4567 | sp-14 | an-90 | E1U11893 | sp-38 | an-90 |
| E1A4568 | sp-15 | an-91 | E1U4568 | sp-14 | an-91 | E1U11894 | sp-38 | an-91 |
| E1A4569 | sp-15 | an-92 | E1U4569 | sp-14 | an-92 | E1U11895 | sp-38 | an-92 |
| E1A4570 | sp-15 | an-93 | E1U4570 | sp-14 | an-93 | E1U11896 | sp-38 | an-93 |
| E1A4571 | sp-15 | an-94 | E1U4571 | sp-14 | an-94 | E1U11897 | sp-38 | an-94 |
| E1A4572 | sp-15 | an-95 | E1U4572 | sp-14 | an-95 | E1U11898 | sp-38 | an-95 |
| E1A4573 | sp-15 | an-96 | E1U4573 | sp-14 | an-96 | E1U11899 | sp-38 | an-96 |
| E1A4574 | sp-15 | an-97 | E1U4574 | sp-14 | an-97 | E1U11900 | sp-38 | an-97 |
| E1A4575 | sp-15 | an-98 | E1U4575 | sp-14 | an-98 | E1U11901 | sp-38 | an-98 |
| E1A4576 | sp-15 | an-99 | E1U4576 | sp-14 | an-99 | E1U11902 | sp-38 | an-99 |
| E1A4577 | sp-15 | an-100 | E1U4577 | sp-14 | an-100 | E1U11903 | sp-38 | an-100 |
| E1A4578 | sp-15 | an-101 | E1U4578 | sp-14 | an-101 | E1U11904 | sp-38 | an-101 |
| E1A4579 | sp-15 | an-102 | E1U4579 | sp-14 | an-102 | E1U11905 | sp-38 | an-102 |
| E1A4580 | sp-15 | an-103 | E1U4580 | sp-14 | an-103 | E1U11906 | sp-38 | an-103 |
| E1A4581 | sp-15 | an-104 | E1U4581 | sp-14 | an-104 | E1U11907 | sp-38 | an-104 |
| E1A4582 | sp-15 | an-105 | E1U4582 | sp-14 | an-105 | E1U11908 | sp-38 | an-105 |
| E1A4583 | sp-15 | an-106 | E1U4583 | sp-14 | an-106 | E1U11909 | sp-38 | an-106 |
| E1A4584 | sp-15 | an-107 | E1U4584 | sp-14 | an-107 | E1U11910 | sp-38 | an-107 |
| E1A4585 | sp-15 | an-108 | E1U4585 | sp-14 | an-108 | E1U11911 | sp-38 | an-108 |
| E1A4586 | sp-15 | an-109 | E1U4586 | sp-14 | an-109 | E1U11912 | sp-38 | an-109 |
| E1A4587 | sp-15 | an-110 | E1U4587 | sp-14 | an-110 | E1U11913 | sp-38 | an-110 |
| E1A4588 | sp-15 | an-111 | E1U4588 | sp-14 | an-111 | E1U11914 | sp-38 | an-111 |
| E1A4589 | sp-15 | an-112 | E1U4589 | sp-14 | an-112 | E1U11915 | sp-38 | an-112 |
| E1A4590 | sp-15 | an-113 | E1U4590 | sp-14 | an-113 | E1U11916 | sp-38 | an-113 |

Table 1-86

| Y = NHCS | | | Y = NHCSNH | | | Y = NHCSNH | | |
|---|---|---|---|---|---|---|---|---|
| E1A4591 | sp-15 | an-114 | E1U4591 | sp-14 | an-114 | E1U11917 | sp-38 | an-114 |
| E1A4592 | sp-15 | an-115 | E1U4592 | sp-14 | an-115 | E1U11918 | sp-38 | an-115 |
| E1A4593 | sp-15 | an-116 | E1U4593 | sp-14 | an-116 | E1U11919 | sp-38 | an-116 |
| E1A4594 | sp-15 | an-117 | E1U4594 | sp-14 | an-117 | E1U11920 | sp-38 | an-117 |
| E1A4595 | sp-15 | an-118 | E1U4595 | sp-14 | an-118 | E1U11921 | sp-38 | an-118 |
| E1A4596 | sp-15 | an-119 | E1U4596 | sp-14 | an-119 | E1U11922 | sp-38 | an-119 |
| E1A4597 | sp-15 | an-120 | E1U4597 | sp-14 | an-120 | E1U11923 | sp-38 | an-120 |
| E1A4598 | sp-15 | an-121 | E1U4598 | sp-14 | an-121 | E1U11924 | sp-38 | an-121 |
| E1A4599 | sp-15 | an-122 | E1U4599 | sp-14 | an-122 | E1U11925 | sp-38 | an-122 |
| E1A4600 | sp-15 | an-123 | E1U4600 | sp-14 | an-123 | E1U11926 | sp-38 | an-123 |
| E1A4601 | sp-15 | an-124 | E1U4601 | sp-14 | an-124 | E1U11927 | sp-38 | an-124 |
| E1A4602 | sp-15 | an-125 | E1U4602 | sp-14 | an-125 | E1U11928 | sp-38 | an-125 |
| E1A4603 | sp-15 | an-126 | E1U4603 | sp-14 | an-126 | E1U11929 | sp-38 | an-126 |
| E1A4604 | sp-15 | an-127 | E1U4604 | sp-14 | an-127 | E1U11930 | sp-38 | an-127 |
| E1A4605 | sp-15 | an-128 | E1U4605 | sp-14 | an-128 | E1U11931 | sp-38 | an-128 |
| E1A4606 | sp-15 | an-129 | E1U4606 | sp-14 | an-129 | E1U11932 | sp-38 | an-129 |
| E1A4607 | sp-15 | an-130 | E1U4607 | sp-14 | an-130 | E1U11933 | sp-38 | an-130 |
| E1A4608 | sp-15 | an-131 | E1U4608 | sp-14 | an-131 | E1U11934 | sp-38 | an-131 |
| E1A4609 | sp-15 | an-132 | E1U4609 | sp-14 | an-132 | E1U11935 | sp-38 | an-132 |
| E1A4610 | sp-15 | an-133 | E1U4610 | sp-14 | an-133 | E1U11936 | sp-38 | an-133 |
| E1A4611 | sp-15 | an-134 | E1U4611 | sp-14 | an-134 | E1U11937 | sp-38 | an-134 |
| E1A4612 | sp-15 | an-135 | E1U4612 | sp-14 | an-135 | E1U11938 | sp-38 | an-135 |
| E1A4613 | sp-15 | an-136 | E1U4613 | sp-14 | an-136 | E1U11939 | sp-38 | an-136 |
| E1A4614 | sp-15 | an-137 | E1U4614 | sp-14 | an-137 | E1U11940 | sp-38 | an-137 |
| E1A4615 | sp-15 | an-138 | E1U4615 | sp-14 | an-138 | E1U11941 | sp-38 | an-138 |
| E1A4616 | sp-15 | an-139 | E1U4616 | sp-14 | an-139 | E1U11942 | sp-38 | an-139 |
| E1A4617 | sp-15 | an-140 | E1U4617 | sp-14 | an-140 | E1U11943 | sp-38 | an-140 |
| E1A4618 | sp-15 | an-141 | E1U4618 | sp-14 | an-141 | E1U11944 | sp-38 | an-141 |
| E1A4619 | sp-15 | an-142 | E1U4619 | sp-14 | an-142 | E1U11945 | sp-38 | an-142 |
| E1A4620 | sp-15 | an-143 | E1U4620 | sp-14 | an-143 | E1U11946 | sp-38 | an-143 |
| E1A4621 | sp-15 | an-144 | E1U4621 | sp-14 | an-144 | E1U11947 | sp-38 | an-144 |
| E1A4622 | sp-15 | an-145 | E1U4622 | sp-14 | an-145 | E1U11948 | sp-38 | an-145 |
| E1A4623 | sp-15 | an-146 | E1U4623 | sp-14 | an-146 | E1U11949 | sp-38 | an-146 |
| E1A4624 | sp-15 | an-147 | E1U4624 | sp-14 | an-147 | E1U11950 | sp-38 | an-147 |
| E1A4625 | sp-15 | an-148 | E1U4625 | sp-14 | an-148 | E1U11951 | sp-38 | an-148 |
| E1A4626 | sp-15 | an-149 | E1U4626 | sp-14 | an-149 | E1U11952 | sp-38 | an-149 |

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| E1A4627 | sp-15 | an-150 | E1U4627 | sp-14 | an-150 | E1U11953 | sp-38 | an-150 |
| E1A4628 | sp-15 | an-151 | E1U4628 | sp-14 | an-151 | E1U11954 | sp-38 | an-151 |
| E1A4629 | sp-15 | an-152 | E1U4629 | sp-14 | an-152 | E1U11955 | sp-38 | an-152 |
| E1A4630 | sp-15 | an-153 | E1U4630 | sp-14 | an-153 | E1U11956 | sp-38 | an-153 |
| E1A4631 | sp-15 | an-154 | E1U4631 | sp-14 | an-154 | E1U11957 | sp-38 | an-154 |
| E1A4632 | sp-15 | an-155 | E1U4632 | sp-14 | an-155 | E1U11958 | sp-38 | an-155 |
| E1A4633 | sp-15 | an-156 | E1U4633 | sp-14 | an-156 | E1U11959 | sp-38 | an-156 |
| E1A4634 | sp-15 | an-157 | E1U4634 | sp-14 | an-157 | E1U11960 | sp-38 | an-157 |
| E1A4635 | sp-15 | an-158 | E1U4635 | sp-14 | an-158 | E1U11961 | sp-38 | an-158 |
| E1A4636 | sp-15 | an-159 | E1U4636 | sp-14 | an-159 | E1U11962 | sp-38 | an-159 |
| E1A4637 | sp-15 | an-160 | E1U4637 | sp-14 | an-160 | E1U11963 | sp-38 | an-160 |
| E1A4638 | sp-15 | an-161 | E1U4638 | sp-14 | an-161 | E1U11964 | sp-38 | an-161 |
| E1A4639 | sp-15 | an-162 | E1U4639 | sp-14 | an-162 | E1U11965 | sp-38 | an-162 |
| E1A4640 | sp-15 | an-163 | E1U4640 | sp-14 | an-163 | E1U11966 | sp-38 | an-163 |
| E1A4641 | sp-15 | an-164 | E1U4641 | sp-14 | an-164 | E1U11967 | sp-38 | an-164 |
| E1A4642 | sp-15 | an-165 | E1U4642 | sp-14 | an-165 | E1U11968 | sp-38 | an-165 |
| E1A4643 | sp-15 | an-166 | E1U4643 | sp-14 | an-166 | E1U11969 | sp-38 | an-166 |
| E1A4644 | sp-15 | an-167 | E1U4644 | sp-14 | an-167 | E1U11970 | sp-38 | an-167 |

Table 1-87

| Y = NHCS | | | Y = NHCSNH | | | Y = NHCSNH | | |
|---|---|---|---|---|---|---|---|---|
| E1A4645 | sp-15 | an-168 | E1U4645 | sp-14 | an-168 | E1U11971 | sp-38 | an-168 |
| E1A4646 | sp-15 | an-169 | E1U4646 | sp-14 | an-169 | E1U11972 | sp-38 | an-169 |
| E1A4647 | sp-15 | an-170 | E1U4647 | sp-14 | an-170 | E1U11973 | sp-38 | an-170 |
| E1A4648 | sp-15 | an-171 | E1U4648 | sp-14 | an-171 | E1U11974 | sp-38 | an-171 |
| E1A4649 | sp-15 | an-172 | E1U4649 | sp-14 | an-172 | E1U11975 | sp-38 | an-172 |
| E1A4650 | sp-15 | an-173 | E1U4650 | sp-14 | an-173 | E1U11976 | sp-38 | an-173 |
| E1A4651 | sp-15 | an-174 | E1U4651 | sp-14 | an-174 | E1U11977 | sp-38 | an-174 |
| E1A4652 | sp-15 | an-175 | E1U4652 | sp-14 | an-175 | E1U11978 | sp-38 | an-175 |
| E1A4653 | sp-15 | an-176 | E1U4653 | sp-14 | an-176 | E1U11979 | sp-38 | an-176 |
| E1A4654 | sp-15 | an-177 | E1U4654 | sp-14 | an-177 | E1U11980 | sp-38 | an-177 |
| E1A4655 | sp-15 | an-178 | E1U4655 | sp-14 | an-178 | E1U11981 | sp-38 | an-178 |
| E1A4656 | sp-15 | an-179 | E1U4656 | sp-14 | an-179 | E1U11982 | sp-38 | an-179 |
| E1A4657 | sp-15 | an-180 | E1U4657 | sp-14 | an-180 | E1U11983 | sp-38 | an-180 |
| E1A4658 | sp-15 | an-181 | E1U4658 | sp-14 | an-181 | E1U11984 | sp-38 | an-181 |
| E1A4659 | sp-15 | an-182 | E1U4659 | sp-14 | an-182 | E1U11985 | sp-38 | an-182 |
| E1A4660 | sp-15 | an-183 | E1U4660 | sp-14 | an-183 | E1U11986 | sp-38 | an-183 |
| E1A4661 | sp-15 | an-184 | E1U4661 | sp-14 | an-184 | E1U11987 | sp-38 | an-184 |
| E1A4662 | sp-15 | an-185 | E1U4662 | sp-14 | an-185 | E1U11988 | sp-38 | an-185 |
| E1A4663 | sp-15 | an-186 | E1U4663 | sp-14 | an-186 | E1U11989 | sp-38 | an-186 |
| E1A4664 | sp-15 | an-187 | E1U4664 | sp-14 | an-187 | E1U11990 | sp-38 | an-187 |
| E1A4665 | sp-15 | an-188 | E1U4665 | sp-14 | an-188 | E1U11991 | sp-38 | an-188 |
| E1A4666 | sp-15 | an-189 | E1U4666 | sp-14 | an-189 | E1U11992 | sp-38 | an-189 |
| E1A4667 | sp-15 | an-190 | E1U4667 | sp-14 | an-190 | E1U11993 | sp-38 | an-190 |
| E1A4668 | sp-15 | an-191 | E1U4668 | sp-14 | an-191 | E1U11994 | sp-38 | an-191 |
| E1A4669 | sp-15 | an-192 | E1U4669 | sp-14 | an-192 | E1U11995 | sp-38 | an-192 |
| E1A4670 | sp-15 | an-193 | E1U4670 | sp-14 | an-193 | E1U11996 | sp-38 | an-193 |
| E1A4671 | sp-15 | an-194 | E1U4671 | sp-14 | an-194 | E1U11997 | sp-38 | an-194 |
| E1A4672 | sp-15 | an-195 | E1U4672 | sp-14 | an-195 | E1U11998 | sp-38 | an-195 |
| E1A4673 | sp-15 | an-196 | E1U4673 | sp-14 | an-196 | E1U11999 | sp-38 | an-196 |
| E1A4674 | sp-15 | an-197 | E1U4674 | sp-14 | an-197 | E1U12000 | sp-38 | an-197 |
| E1A4675 | sp-15 | an-198 | E1U4675 | sp-14 | an-198 | E1U12001 | sp-38 | an-198 |
| E1A4676 | sp-15 | an-199 | E1U4676 | sp-14 | an-199 | E1U12002 | sp-38 | an-199 |
| E1A4677 | sp-15 | an-200 | E1U4677 | sp-14 | an-200 | E1U12003 | sp-38 | an-200 |
| E1A4678 | sp-15 | an-201 | E1U4678 | sp-14 | an-201 | E1U12004 | sp-38 | an-201 |
| E1A4679 | sp-15 | an-202 | E1U4679 | sp-14 | an-202 | E1U12005 | sp-38 | an-202 |
| E1A4680 | sp-15 | an-203 | E1U4680 | sp-14 | an-203 | E1U12006 | sp-38 | an-203 |
| E1A4681 | sp-15 | an-204 | E1U4681 | sp-14 | an-204 | E1U12007 | sp-38 | an-204 |
| E1A4682 | sp-15 | an-205 | E1U4682 | sp-14 | an-205 | E1U12008 | sp-38 | an-205 |
| E1A4683 | sp-15 | an-206 | E1U4683 | sp-14 | an-206 | E1U12009 | sp-38 | an-206 |
| E1A4684 | sp-15 | an-207 | E1U4684 | sp-14 | an-207 | E1U12010 | sp-38 | an-207 |
| E1A4685 | sp-15 | an-208 | E1U4685 | sp-14 | an-208 | E1U12011 | sp-38 | an-208 |
| E1A4686 | sp-15 | an-209 | E1U4686 | sp-14 | an-209 | E1U12012 | sp-38 | an-209 |
| E1A4687 | sp-15 | an-210 | E1U4687 | sp-14 | an-210 | E1U12013 | sp-38 | an-210 |
| E1A4688 | sp-15 | an-211 | E1U4688 | sp-14 | an-211 | E1U12014 | sp-38 | an-211 |
| E1A4689 | sp-15 | an-212 | E1U4689 | sp-14 | an-212 | E1U12015 | sp-38 | an-212 |
| E1A4690 | sp-15 | an-213 | E1U4690 | sp-14 | an-213 | E1U12016 | sp-38 | an-213 |
| E1A4691 | sp-15 | an-214 | E1U4691 | sp-14 | an-214 | E1U12017 | sp-38 | an-214 |
| E1A4692 | sp-15 | an-215 | E1U4692 | sp-14 | an-215 | E1U12018 | sp-38 | an-215 |
| E1A4693 | sp-15 | an-216 | E1U4693 | sp-14 | an-216 | E1U12019 | sp-38 | an-216 |
| E1A4694 | sp-15 | an-217 | E1U4694 | sp-14 | an-217 | E1U12020 | sp-38 | an-217 |
| E1A4695 | sp-15 | an-218 | E1U4695 | sp-14 | an-218 | E1U12021 | sp-38 | an-218 |
| E1A4696 | sp-15 | an-219 | E1U4696 | sp-14 | an-219 | E1U12022 | sp-38 | an-219 |
| E1A4697 | sp-15 | an-220 | E1U4697 | sp-14 | an-220 | E1U12023 | sp-38 | an-220 |
| E1A4698 | sp-15 | an-221 | E1U4698 | sp-14 | an-221 | E1U12024 | sp-38 | an-221 |

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| Table 1-88 ||||||||| 
| Y = NHCS ||| Y = NHCSNH ||| Y = NHCSNH |||
| E1A4699 | sp-15 | an-222 | E1U4699 | sp-14 | an-222 | E1U12025 | sp-38 | an-222 |
| E1A4700 | sp-15 | an-223 | E1U4700 | sp-14 | an-223 | E1U12026 | sp-38 | an-223 |
| E1A4701 | sp-15 | an-224 | E1U4701 | sp-14 | an-224 | E1U12027 | sp-38 | an-224 |
| E1A4702 | sp-15 | an-225 | E1U4702 | sp-14 | an-225 | E1U12028 | sp-38 | an-225 |
| E1A4703 | sp-15 | an-226 | E1U4703 | sp-14 | an-226 | E1U12029 | sp-38 | an-226 |
| E1A4704 | sp-15 | an-227 | E1U4704 | sp-14 | an-227 | E1U12030 | sp-38 | an-227 |
| E1A4705 | sp-15 | an-228 | E1U4705 | sp-14 | an-228 | E1U12031 | sp-38 | an-228 |
| E1A4706 | sp-15 | an-229 | E1U4706 | sp-14 | an-229 | E1U12032 | sp-38 | an-229 |
| E1A4707 | sp-15 | an-230 | E1U4707 | sp-14 | an-230 | E1U12033 | sp-38 | an-230 |
| E1A4708 | sp-15 | an-231 | E1U4708 | sp-14 | an-231 | E1U12034 | sp-38 | an-231 |
| E1A4709 | sp-15 | an-232 | E1U4709 | sp-14 | an-232 | E1U12035 | sp-38 | an-232 |
| E1A4710 | sp-15 | an-233 | E1U4710 | sp-14 | an-233 | E1U12036 | sp-38 | an-233 |
| E1A4711 | sp-15 | an-234 | E1U4711 | sp-14 | an-234 | E1U12037 | sp-38 | an-234 |
| E1A4712 | sp-15 | an-235 | E1U4712 | sp-14 | an-235 | E1U12038 | sp-38 | an-235 |
| E1A4713 | sp-15 | an-236 | E1U4713 | sp-14 | an-236 | E1U12039 | sp-38 | an-236 |
| E1A4714 | sp-15 | an-237 | E1U4714 | sp-14 | an-237 | E1U12040 | sp-38 | an-237 |
| E1A4715 | sp-15 | an-238 | E1U4715 | sp-14 | an-238 | E1U12041 | sp-38 | an-238 |
| E1A4716 | sp-15 | an-239 | E1U4716 | sp-14 | an-239 | E1U12042 | sp-38 | an-239 |
| E1A4717 | sp-15 | an-240 | E1U4717 | sp-14 | an-240 | E1U12043 | sp-38 | an-240 |
| E1A4718 | sp-15 | an-241 | E1U4718 | sp-14 | an-241 | E1U12044 | sp-38 | an-241 |
| E1A4719 | sp-15 | an-242 | E1U4719 | sp-14 | an-242 | E1U12045 | sp-38 | an-242 |
| E1A4720 | sp-15 | an-243 | E1U4720 | sp-14 | an-243 | E1U12046 | sp-38 | an-243 |
| E1A4721 | sp-15 | an-244 | E1U4721 | sp-14 | an-244 | E1U12047 | sp-38 | an-244 |
| E1A4722 | sp-15 | an-245 | E1U4722 | sp-14 | an-245 | E1U12048 | sp-38 | an-245 |
| E1A4723 | sp-15 | an-246 | E1U4723 | sp-14 | an-246 | E1U12049 | sp-38 | an-246 |
| E1A4724 | sp-15 | an-247 | E1U4724 | sp-14 | an-247 | E1U12050 | sp-38 | an-247 |
| E1A4725 | sp-15 | an-248 | E1U4725 | sp-14 | an-248 | E1U12051 | sp-38 | an-248 |
| E1A4726 | sp-15 | an-249 | E1U4726 | sp-14 | an-249 | E1U12052 | sp-38 | an-249 |
| E1A4727 | sp-15 | an-250 | E1U4727 | sp-14 | an-250 | E1U12053 | sp-38 | an-250 |
| E1A4728 | sp-15 | an-251 | E1U4728 | sp-14 | an-251 | E1U12054 | sp-38 | an-251 |
| E1A4729 | sp-15 | an-252 | E1U4729 | sp-14 | an-252 | E1U12055 | sp-38 | an-252 |
| E1A4730 | sp-15 | an-253 | E1U4730 | sp-14 | an-253 | E1U12056 | sp-38 | an-253 |
| E1A4731 | sp-15 | an-254 | E1U4731 | sp-14 | an-254 | E1U12057 | sp-38 | an-254 |
| E1A4732 | sp-15 | an-255 | E1U4732 | sp-14 | an-255 | E1U12058 | sp-38 | an-255 |
| E1A4733 | sp-15 | an-256 | E1U4733 | sp-14 | an-256 | E1U12059 | sp-38 | an-256 |
| E1A4734 | sp-15 | an-257 | E1U4734 | sp-14 | an-257 | E1U12060 | sp-38 | an-257 |
| E1A4735 | sp-15 | an-258 | E1U4735 | sp-14 | an-258 | E1U12061 | sp-38 | an-258 |
| E1A4736 | sp-15 | an-259 | E1U4736 | sp-14 | an-259 | E1U12062 | sp-38 | an-259 |
| E1A4737 | sp-15 | an-260 | E1U4737 | sp-14 | an-260 | E1U12063 | sp-38 | an-260 |
| E1A4738 | sp-15 | an-261 | E1U4738 | sp-14 | an-261 | E1U12064 | sp-38 | an-261 |
| E1A4739 | sp-15 | an-262 | E1U4739 | sp-14 | an-262 | E1U12065 | sp-38 | an-262 |
| E1A4740 | sp-15 | an-263 | E1U4740 | sp-14 | an-263 | E1U12066 | sp-38 | an-263 |
| E1A4741 | sp-15 | an-264 | E1U4741 | sp-14 | an-264 | E1U12067 | sp-38 | an-264 |
| E1A4742 | sp-15 | an-265 | E1U4742 | sp-14 | an-265 | E1U12068 | sp-38 | an-265 |
| E1A4743 | sp-15 | an-266 | E1U4743 | sp-14 | an-266 | E1U12069 | sp-38 | an-266 |
| E1A4744 | sp-15 | an-267 | E1U4744 | sp-14 | an-267 | E1U12070 | sp-38 | an-267 |
| E1A4745 | sp-15 | an-268 | E1U4745 | sp-14 | an-268 | E1U12071 | sp-38 | an-268 |
| E1A4746 | sp-15 | an-269 | E1U4746 | sp-14 | an-269 | E1U12072 | sp-38 | an-269 |
| E1A4747 | sp-15 | an-270 | E1U4747 | sp-14 | an-270 | E1U12073 | sp-38 | an-270 |
| E1A4748 | sp-15 | an-271 | E1U4748 | sp-14 | an-271 | E1U12074 | sp-38 | an-271 |
| E1A4749 | sp-15 | an-272 | E1U4749 | sp-14 | an-272 | E1U12075 | sp-38 | an-272 |
| E1A4750 | sp-15 | an-273 | E1U4750 | sp-14 | an-273 | E1U12076 | sp-38 | an-273 |
| E1A4751 | sp-15 | an-274 | E1U4751 | sp-14 | an-274 | E1U12077 | sp-38 | an-274 |
| E1A4752 | sp-15 | an-275 | E1U4752 | sp-14 | an-275 | E1U12078 | sp-38 | an-275 |
| Table 1-89 |||||||||
| Y = NHCS ||| Y = NHCSNH ||| Y = NHCSNH |||
| E1A4753 | sp-15 | an-276 | E1U4753 | sp-14 | an-276 | E1U12079 | sp-38 | an-276 |
| E1A4754 | sp-15 | an-277 | E1U4754 | sp-14 | an-277 | E1U12080 | sp-38 | an-277 |
| E1A4755 | sp-15 | an-278 | E1U4755 | sp-14 | an-278 | E1U12081 | sp-38 | an-278 |
| E1A4756 | sp-15 | an-279 | E1U4756 | sp-14 | an-279 | E1U12082 | sp-38 | an-279 |
| E1A4757 | sp-15 | an-280 | E1U4757 | sp-14 | an-280 | E1U12083 | sp-38 | an-280 |
| E1A4758 | sp-15 | an-281 | E1U4758 | sp-14 | an-281 | E1U12084 | sp-38 | an-281 |
| E1A4759 | sp-15 | an-282 | E1U4759 | sp-14 | an-282 | E1U12085 | sp-38 | an-282 |
| E1A4760 | sp-15 | an-283 | E1U4760 | sp-14 | an-283 | E1U12086 | sp-38 | an-283 |
| E1A4761 | sp-15 | an-284 | E1U4761 | sp-14 | an-284 | E1U12087 | sp-38 | an-284 |
| E1A4762 | sp-15 | an-285 | E1U4762 | sp-14 | an-285 | E1U12088 | sp-38 | an-285 |
| E1A4763 | sp-15 | an-286 | E1U4763 | sp-14 | an-286 | E1U12089 | sp-38 | an-286 |
| E1A4764 | sp-15 | an-287 | E1U4764 | sp-14 | an-287 | E1U12090 | sp-38 | an-287 |
| E1A4765 | sp-15 | an-288 | E1U4765 | sp-14 | an-288 | E1U12091 | sp-38 | an-288 |
| E1A4766 | sp-15 | an-289 | E1U4766 | sp-14 | an-289 | E1U12092 | sp-38 | an-289 |
| E1A4767 | sp-15 | an-290 | E1U4767 | sp-14 | an-290 | E1U12093 | sp-38 | an-290 |
| E1A4768 | sp-15 | an-291 | E1U4768 | sp-14 | an-291 | E1U12094 | sp-38 | an-291 |

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| E1A4769 | sp-15 | an-292 | E1U4769 | sp-14 | an-292 | E1U12095 | sp-38 | an-292 |
| E1A4770 | sp-15 | an-293 | E1U4770 | sp-14 | an-293 | E1U12096 | sp-38 | an-293 |
| E1A4771 | sp-15 | an-294 | E1U4771 | sp-14 | an-294 | E1U12097 | sp-38 | an-294 |
| E1A4772 | sp-15 | an-295 | E1U4772 | sp-14 | an-295 | E1U12098 | sp-38 | an-295 |
| E1A4773 | sp-15 | an-296 | E1U4773 | sp-14 | an-296 | E1U12099 | sp-38 | an-296 |
| E1A4774 | sp-15 | an-297 | E1U4774 | sp-14 | an-297 | E1U12100 | sp-38 | an-297 |
| E1A4775 | sp-15 | an-298 | E1U4775 | sp-14 | an-298 | E1U12101 | sp-38 | an-298 |
| E1A4776 | sp-15 | an-299 | E1U4776 | sp-14 | an-299 | E1U12102 | sp-38 | an-299 |
| E1A4777 | sp-15 | an-300 | E1U4777 | sp-14 | an-300 | E1U12103 | sp-38 | an-300 |
| E1A4778 | sp-15 | an-301 | E1U4778 | sp-14 | an-301 | E1U12104 | sp-38 | an-301 |
| E1A4779 | sp-15 | an-302 | E1U4779 | sp-14 | an-302 | E1U12105 | sp-38 | an-302 |
| E1A4780 | sp-15 | an-303 | E1U4780 | sp-14 | an-303 | E1U12106 | sp-38 | an-303 |
| E1A4781 | sp-15 | an-304 | E1U4781 | sp-14 | an-304 | E1U12107 | sp-38 | an-304 |
| E1A4782 | sp-15 | an-305 | E1U4782 | sp-14 | an-305 | E1U12108 | sp-38 | an-305 |
| E1A4783 | sp-15 | an-306 | E1U4783 | sp-14 | an-306 | E1U12109 | sp-38 | an-306 |
| E1A4784 | sp-15 | an-307 | E1U4784 | sp-14 | an-307 | E1U12110 | sp-38 | an-307 |
| E1A4785 | sp-15 | an-308 | E1U4785 | sp-14 | an-308 | E1U12111 | sp-38 | an-308 |
| E1A4786 | sp-15 | an-309 | E1U4786 | sp-14 | an-309 | E1U12112 | sp-38 | an-309 |
| E1A4787 | sp-15 | an-310 | E1U4787 | sp-14 | an-310 | E1U12113 | sp-38 | an-310 |
| E1A4788 | sp-15 | an-311 | E1U4788 | sp-14 | an-311 | E1U12114 | sp-38 | an-311 |
| E1A4789 | sp-15 | an-312 | E1U4789 | sp-14 | an-312 | E1U12115 | sp-38 | an-312 |
| E1A4790 | sp-15 | an-313 | E1U4790 | sp-14 | an-313 | E1U12116 | sp-38 | an-313 |
| E1A4791 | sp-15 | an-314 | E1U4791 | sp-14 | an-314 | E1U12117 | sp-38 | an-314 |
| E1A4792 | sp-15 | an-315 | E1U4792 | sp-14 | an-315 | E1U12118 | sp-38 | an-315 |
| E1A4793 | sp-15 | an-316 | E1U4793 | sp-14 | an-316 | E1U12119 | sp-38 | an-316 |
| E1A4794 | sp-15 | an-317 | E1U4794 | sp-14 | an-317 | E1U12120 | sp-38 | an-317 |
| E1A4795 | sp-15 | an-318 | E1U4795 | sp-14 | an-318 | E1U12121 | sp-38 | an-318 |
| E1A4796 | sp-15 | an-319 | E1U4796 | sp-14 | an-319 | E1U12122 | sp-38 | an-319 |
| E1A4797 | sp-15 | an-320 | E1U4797 | sp-14 | an-320 | E1U12123 | sp-38 | an-320 |
| E1A4798 | sp-15 | an-321 | E1U4798 | sp-14 | an-321 | E1U12124 | sp-38 | an-321 |
| E1A4799 | sp-15 | an-322 | E1U4799 | sp-14 | an-322 | E1U12125 | sp-38 | an-322 |
| E1A4800 | sp-15 | an-323 | E1U4800 | sp-14 | an-323 | E1U12126 | sp-38 | an-323 |
| E1A4801 | sp-15 | an-324 | E1U4801 | sp-14 | an-324 | E1U12127 | sp-38 | an-324 |
| E1A4802 | sp-15 | an-325 | E1U4802 | sp-14 | an-325 | E1U12128 | sp-38 | an-325 |
| E1A4803 | sp-15 | an-326 | E1U4803 | sp-14 | an-326 | E1U12129 | sp-38 | an-326 |
| E1A4804 | sp-15 | an-327 | E1U4804 | sp-14 | an-327 | E1U12130 | sp-38 | an-327 |
| E1A4805 | sp-15 | an-328 | E1U4805 | sp-14 | an-328 | E1U12131 | sp-38 | an-328 |
| E1A4806 | sp-15 | an-329 | E1U4806 | sp-14 | an-329 | E1U12132 | sp-38 | an-329 |

Table 1-90

| Y = NHCS | | | Y = NHCSNH | | | Y = NHCSNH | | |
|---|---|---|---|---|---|---|---|---|
| E1A4807 | sp-15 | an-330 | E1U4807 | sp-14 | an-330 | E1U12133 | sp-38 | an-330 |
| E1A4808 | sp-15 | an-331 | E1U4808 | sp-14 | an-331 | E1U12134 | sp-38 | an-331 |
| E1A4809 | sp-15 | an-332 | E1U4809 | sp-14 | an-332 | E1U12135 | sp-38 | an-332 |
| E1A4810 | sp-15 | an-333 | E1U4810 | sp-14 | an-333 | E1U12136 | sp-38 | an-333 |
| E1A4811 | sp-15 | an-334 | E1U4811 | sp-14 | an-334 | E1U12137 | sp-38 | an-334 |
| E1A4812 | sp-15 | an-335 | E1U4812 | sp-14 | an-335 | E1U12138 | sp-38 | an-335 |
| E1A4813 | sp-15 | an-336 | E1U4813 | sp-14 | an-336 | E1U12139 | sp-38 | an-336 |
| E1A4814 | sp-15 | an-337 | E1U4814 | sp-14 | an-337 | E1U12140 | sp-38 | an-337 |
| E1A4815 | sp-15 | an-338 | E1U4815 | sp-14 | an-338 | E1U12141 | sp-38 | an-338 |
| E1A4816 | sp-15 | an-339 | E1U4816 | sp-14 | an-339 | E1U12142 | sp-38 | an-339 |
| E1A4817 | sp-15 | an-340 | E1U4817 | sp-14 | an-340 | E1U12143 | sp-38 | an-340 |
| E1A4818 | sp-15 | an-341 | E1U4818 | sp-14 | an-341 | E1U12144 | sp-38 | an-341 |
| E1A4819 | sp-15 | an-342 | E1U4819 | sp-14 | an-342 | E1U12145 | sp-38 | an-342 |
| E1A4820 | sp-15 | an-343 | E1U4820 | sp-14 | an-343 | E1U12146 | sp-38 | an-343 |
| E1A4821 | sp-15 | an-344 | E1U4821 | sp-14 | an-344 | E1U12147 | sp-38 | an-344 |
| E1A4822 | sp-15 | an-345 | E1U4822 | sp-14 | an-345 | E1U12148 | sp-38 | an-345 |
| E1A4823 | sp-15 | an-346 | E1U4823 | sp-14 | an-346 | E1U12149 | sp-38 | an-346 |
| E1A4824 | sp-15 | an-347 | E1U4824 | sp-14 | an-347 | E1U12150 | sp-38 | an-347 |
| E1A4825 | sp-15 | an-348 | E1U4825 | sp-14 | an-348 | E1U12151 | sp-38 | an-348 |
| E1A4826 | sp-15 | an-349 | E1U4826 | sp-14 | an-349 | E1U12152 | sp-38 | an-349 |
| E1A4827 | sp-15 | an-350 | E1U4827 | sp-14 | an-350 | E1U12153 | sp-38 | an-350 |
| E1A4828 | sp-15 | an-351 | E1U4828 | sp-14 | an-351 | E1U12154 | sp-38 | an-351 |
| E1A4829 | sp-15 | an-352 | E1U4829 | sp-14 | an-352 | E1U12155 | sp-38 | an-352 |
| E1A4830 | sp-15 | an-353 | E1U4830 | sp-14 | an-353 | E1U12156 | sp-38 | an-353 |
| E1A4831 | sp-15 | an-354 | E1U4831 | sp-14 | an-354 | E1U12157 | sp-38 | an-354 |
| E1A4832 | sp-15 | an-355 | E1U4832 | sp-14 | an-355 | E1U12158 | sp-38 | an-355 |
| E1A4833 | sp-15 | an-356 | E1U4833 | sp-14 | an-356 | E1U12159 | sp-38 | an-356 |
| E1A4834 | sp-15 | an-357 | E1U4834 | sp-14 | an-357 | E1U12160 | sp-38 | an-357 |
| E1A4835 | sp-15 | an-358 | E1U4835 | sp-14 | an-358 | E1U12161 | sp-38 | an-358 |
| E1A4836 | sp-15 | an-359 | E1U4836 | sp-14 | an-359 | E1U12162 | sp-38 | an-359 |
| E1A4837 | sp-15 | an-360 | E1U4837 | sp-14 | an-360 | E1U12163 | sp-38 | an-360 |
| E1A4838 | sp-15 | an-361 | E1U4838 | sp-14 | an-361 | E1U12164 | sp-38 | an-361 |
| E1A4839 | sp-15 | an-362 | E1U4839 | sp-14 | an-362 | E1U12165 | sp-38 | an-362 |
| E1A4840 | sp-15 | an-363 | E1U4840 | sp-14 | an-363 | E1U12166 | sp-38 | an-363 |
| E1A4841 | sp-15 | an-364 | E1U4841 | sp-14 | an-364 | E1U12167 | sp-38 | an-364 |
| E1A4842 | sp-15 | an-365 | E1U4842 | sp-14 | an-365 | E1U12168 | sp-38 | an-365 |

-continued

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| E1A4843 | sp-15 | an-366 | E1U4843 | sp-14 | an-366 | E1U12169 | sp-38 | an-366 |
| E1A4844 | sp-15 | an-367 | E1U4844 | sp-14 | an-367 | E1U12170 | sp-38 | an-367 |
| E1A4845 | sp-15 | an-368 | E1U4845 | sp-14 | an-368 | E1U12171 | sp-38 | an-368 |
| E1A4846 | sp-15 | an-369 | E1U4846 | sp-14 | an-369 | E1U12172 | sp-38 | an-369 |
| E1A4847 | sp-15 | an-370 | E1U4847 | sp-14 | an-370 | E1U12173 | sp-38 | an-370 |
| E1A4848 | sp-15 | an-371 | E1U4848 | sp-14 | an-371 | E1U12174 | sp-38 | an-371 |
| E1A4849 | sp-15 | an-372 | E1U4849 | sp-14 | an-372 | E1U12175 | sp-38 | an-372 |
| E1A4850 | sp-15 | an-373 | E1U4850 | sp-14 | an-373 | E1U12176 | sp-38 | an-373 |
| E1A4851 | sp-15 | an-374 | E1U4851 | sp-14 | an-374 | E1U12177 | sp-38 | an-374 |
| E1A4852 | sp-15 | an-375 | E1U4852 | sp-14 | an-375 | E1U12178 | sp-38 | an-375 |
| E1A4853 | sp-15 | an-376 | E1U4853 | sp-14 | an-376 | E1U12179 | sp-38 | an-376 |
| E1A4854 | sp-15 | an-377 | E1U4854 | sp-14 | an-377 | E1U12180 | sp-38 | an-377 |
| E1A4855 | sp-15 | an-378 | E1U4855 | sp-14 | an-378 | E1U12181 | sp-38 | an-378 |
| E1A4856 | sp-15 | an-379 | E1U4856 | sp-14 | an-379 | E1U12182 | sp-38 | an-379 |
| E1A4857 | sp-15 | an-380 | E1U4857 | sp-14 | an-380 | E1U12183 | sp-38 | an-380 |
| E1A4858 | sp-15 | an-381 | E1U4858 | sp-14 | an-381 | E1U12184 | sp-38 | an-381 |
| E1A4859 | sp-15 | an-382 | E1U4859 | sp-14 | an-382 | E1U12185 | sp-38 | an-382 |
| E1A4860 | sp-15 | an-383 | E1U4860 | sp-14 | an-383 | E1U12186 | sp-38 | an-383 |

Table 1-91

| Y = NHCS | | | Y = NHCSNH | | | Y = NHCSNH | | |
|---|---|---|---|---|---|---|---|---|
| E1A4861 | sp-15 | an-384 | E1U4861 | sp-14 | an-384 | E1U12187 | sp-38 | an-384 |
| E1A4862 | sp-15 | an-385 | E1U4862 | sp-14 | an-385 | E1U12188 | sp-38 | an-385 |
| E1A4863 | sp-15 | an-386 | E1U4863 | sp-14 | an-386 | E1U12189 | sp-38 | an-386 |
| E1A4864 | sp-15 | an-387 | E1U4864 | sp-14 | an-387 | E1U12190 | sp-38 | an-387 |
| E1A4865 | sp-15 | an-388 | E1U4865 | sp-14 | an-388 | E1U12191 | sp-38 | an-388 |
| E1A4866 | sp-15 | an-389 | E1U4866 | sp-14 | an-389 | E1U12192 | sp-38 | an-389 |
| E1A4867 | sp-15 | an-390 | E1U4867 | sp-14 | an-390 | E1U12193 | sp-38 | an-390 |
| E1A4868 | sp-15 | an-391 | E1U4868 | sp-14 | an-391 | E1U12194 | sp-38 | an-391 |
| E1A4869 | sp-15 | an-392 | E1U4869 | sp-14 | an-392 | E1U12195 | sp-38 | an-392 |
| E1A4870 | sp-15 | an-393 | E1U4870 | sp-14 | an-393 | E1U12196 | sp-38 | an-393 |
| E1A4871 | sp-15 | an-394 | E1U4871 | sp-14 | an-394 | E1U12197 | sp-38 | an-394 |
| E1A4872 | sp-15 | an-395 | E1U4872 | sp-14 | an-395 | E1U12198 | sp-38 | an-395 |
| E1A4873 | sp-15 | an-396 | E1U4873 | sp-14 | an-396 | E1U12199 | sp-38 | an-396 |
| E1A4874 | sp-15 | an-397 | E1U4874 | sp-14 | an-397 | E1U12200 | sp-38 | an-397 |
| E1A4875 | sp-15 | an-398 | E1U4875 | sp-14 | an-398 | E1U12201 | sp-38 | an-398 |
| E1A4876 | sp-15 | an-399 | E1U4876 | sp-14 | an-399 | E1U12202 | sp-38 | an-399 |
| E1A4877 | sp-15 | an-400 | E1U4877 | sp-14 | an-400 | E1U12203 | sp-38 | an-400 |
| E1A4878 | sp-15 | an-401 | E1U4878 | sp-14 | an-401 | E1U12204 | sp-38 | an-401 |
| E1A4879 | sp-15 | an-402 | E1U4879 | sp-14 | an-402 | E1U12205 | sp-38 | an-402 |
| E1A4880 | sp-15 | an-403 | E1U4880 | sp-14 | an-403 | E1U12206 | sp-38 | an-403 |
| E1A4881 | sp-15 | an-404 | E1U4881 | sp-14 | an-404 | E1U12207 | sp-38 | an-404 |
| E1A4882 | sp-15 | an-405 | E1U4882 | sp-14 | an-405 | E1U12208 | sp-38 | an-405 |
| E1A4883 | sp-15 | an-406 | E1U4883 | sp-14 | an-406 | E1U12209 | sp-38 | an-406 |
| E1A4884 | sp-15 | an-407 | E1U4884 | sp-14 | an-407 | E1U12210 | sp-38 | an-407 |
| E1A4885 | sp-16 | an-1 | E1U4885 | sp-17 | an-1 | E1U12211 | sp-39 | an-1 |
| E1A4886 | sp-16 | an-2 | E1U4886 | sp-17 | an-2 | E1U12212 | sp-39 | an-2 |
| E1A4887 | sp-16 | an-3 | E1U4887 | sp-17 | an-3 | E1U12213 | sp-39 | an-3 |
| E1A4888 | sp-16 | an-4 | E1U4888 | sp-17 | an-4 | E1U12214 | sp-39 | an-4 |
| E1A4889 | sp-16 | an-5 | E1U4889 | sp-17 | an-5 | E1U12215 | sp-39 | an-5 |
| E1A4890 | sp-16 | an-6 | E1U4890 | sp-17 | an-6 | E1U12216 | sp-39 | an-6 |
| E1A4891 | sp-16 | an-7 | E1U4891 | sp-17 | an-7 | E1U12217 | sp-39 | an-7 |
| E1A4892 | sp-16 | an-8 | E1U4892 | sp-17 | an-8 | E1U12218 | sp-39 | an-8 |
| E1A4893 | sp-16 | an-9 | E1U4893 | sp-17 | an-9 | E1U12219 | sp-39 | an-9 |
| E1A4894 | sp-16 | an-10 | E1U4894 | sp-17 | an-10 | E1U12220 | sp-39 | an-10 |
| E1A4895 | sp-16 | an-11 | E1U4895 | sp-17 | an-11 | E1U12221 | sp-39 | an-11 |
| E1A4896 | sp-16 | an-12 | E1U4896 | sp-17 | an-12 | E1U12222 | sp-39 | an-12 |
| E1A4897 | sp-16 | an-13 | E1U4897 | sp-17 | an-13 | E1U12223 | sp-39 | an-13 |
| E1A4898 | sp-16 | an-14 | E1U4898 | sp-17 | an-14 | E1U12224 | sp-39 | an-14 |
| E1A4899 | sp-16 | an-15 | E1U4899 | sp-17 | an-15 | E1U12225 | sp-39 | an-15 |
| E1A4900 | sp-16 | an-16 | E1U4900 | sp-17 | an-16 | E1U12226 | sp-39 | an-16 |
| E1A4901 | sp-16 | an-17 | E1U4901 | sp-17 | an-17 | E1U12227 | sp-39 | an-17 |
| E1A4902 | sp-16 | an-18 | E1U4902 | sp-17 | an-18 | E1U12228 | sp-39 | an-18 |
| E1A4903 | sp-16 | an-19 | E1U4903 | sp-17 | an-19 | E1U12229 | sp-39 | an-19 |
| E1A4904 | sp-16 | an-20 | E1U4904 | sp-17 | an-20 | E1U12230 | sp-39 | an-20 |
| E1A4905 | sp-16 | an-21 | E1U4905 | sp-17 | an-21 | E1U12231 | sp-39 | an-21 |
| E1A4906 | sp-16 | an-22 | E1U4906 | sp-17 | an-22 | E1U12232 | sp-39 | an-22 |
| E1A4907 | sp-16 | an-23 | E1U4907 | sp-17 | an-23 | E1U12233 | sp-39 | an-23 |
| E1A4908 | sp-16 | an-24 | E1U4908 | sp-17 | an-24 | E1U12234 | sp-39 | an-24 |
| E1A4909 | sp-16 | an-25 | E1U4909 | sp-17 | an-25 | E1U12235 | sp-39 | an-25 |
| E1A4910 | sp-16 | an-26 | E1U4910 | sp-17 | an-26 | E1U12236 | sp-39 | an-26 |
| E1A4911 | sp-16 | an-27 | E1U4911 | sp-17 | an-27 | E1U12237 | sp-39 | an-27 |
| E1A4912 | sp-16 | an-28 | E1U4912 | sp-17 | an-28 | E1U12238 | sp-39 | an-28 |
| E1A4913 | sp-16 | an-29 | E1U4913 | sp-17 | an-29 | E1U12239 | sp-39 | an-29 |
| E1A4914 | sp-16 | an-30 | E1U4914 | sp-17 | an-30 | E1U12240 | sp-39 | an-30 |

Table 1-92

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| Y = NHCS | | | Y = NHCSNH | | | Y = NHCSNH | | |
| E1A4915 | sp-16 | an-31 | E1U4915 | sp-17 | an-31 | E1U12241 | sp-39 | an-31 |
| E1A4916 | sp-16 | an-32 | E1U4916 | sp-17 | an-32 | E1U12242 | sp-39 | an-32 |
| E1A4917 | sp-16 | an-33 | E1U4917 | sp-17 | an-33 | E1U12243 | sp-39 | an-33 |
| E1A4918 | sp-16 | an-34 | E1U4918 | sp-17 | an-34 | E1U12244 | sp-39 | an-34 |
| E1A4919 | sp-16 | an-35 | E1U4919 | sp-17 | an-35 | E1U12245 | sp-39 | an-35 |
| E1A4920 | sp-16 | an-36 | E1U4920 | sp-17 | an-36 | E1U12246 | sp-39 | an-36 |
| E1A4921 | sp-16 | an-37 | E1U4921 | sp-17 | an-37 | E1U12247 | sp-39 | an-37 |
| E1A4922 | sp-16 | an-38 | E1U4922 | sp-17 | an-38 | E1U12248 | sp-39 | an-38 |
| E1A4923 | sp-16 | an-39 | E1U4923 | sp-17 | an-39 | E1U12249 | sp-39 | an-39 |
| E1A4924 | sp-16 | an-40 | E1U4924 | sp-17 | an-40 | E1U12250 | sp-39 | an-40 |
| E1A4925 | sp-16 | an-41 | E1U4925 | sp-17 | an-41 | E1U12251 | sp-39 | an-41 |
| E1A4926 | sp-16 | an-42 | E1U4926 | sp-17 | an-42 | E1U12252 | sp-39 | an-42 |
| E1A4927 | sp-16 | an-43 | E1U4927 | sp-17 | an-43 | E1U12253 | sp-39 | an-43 |
| E1A4928 | sp-16 | an-44 | E1U4928 | sp-17 | an-44 | E1U12254 | sp-39 | an-44 |
| E1A4929 | sp-16 | an-45 | E1U4929 | sp-17 | an-45 | E1U12255 | sp-39 | an-45 |
| E1A4930 | sp-16 | an-46 | E1U4930 | sp-17 | an-46 | E1U12256 | sp-39 | an-46 |
| E1A4931 | sp-16 | an-47 | E1U4931 | sp-17 | an-47 | E1U12257 | sp-39 | an-47 |
| E1A4932 | sp-16 | an-48 | E1U4932 | sp-17 | an-48 | E1U12258 | sp-39 | an-48 |
| E1A4933 | sp-16 | an-49 | E1U4933 | sp-17 | an-49 | E1U12259 | sp-39 | an-49 |
| E1A4934 | sp-16 | an-50 | E1U4934 | sp-17 | an-50 | E1U12260 | sp-39 | an-50 |
| E1A4935 | sp-16 | an-51 | E1U4935 | sp-17 | an-51 | E1U12261 | sp-39 | an-51 |
| E1A4936 | sp-16 | an-52 | E1U4936 | sp-17 | an-52 | E1U12262 | sp-39 | an-52 |
| E1A4937 | sp-16 | an-53 | E1U4937 | sp-17 | an-53 | E1U12263 | sp-39 | an-53 |
| E1A4938 | sp-16 | an-54 | E1U4938 | sp-17 | an-54 | E1U12264 | sp-39 | an-54 |
| E1A4939 | sp-16 | an-55 | E1U4939 | sp-17 | an-55 | E1U12265 | sp-39 | an-55 |
| E1A4940 | sp-16 | an-56 | E1U4940 | sp-17 | an-56 | E1U12266 | sp-39 | an-56 |
| E1A4941 | sp-16 | an-57 | E1U4941 | sp-17 | an-57 | E1U12267 | sp-39 | an-57 |
| E1A4942 | sp-16 | an-58 | E1U4942 | sp-17 | an-58 | E1U12268 | sp-39 | an-58 |
| E1A4943 | sp-16 | an-59 | E1U4943 | sp-17 | an-59 | E1U12269 | sp-39 | an-59 |
| E1A4944 | sp-16 | an-60 | E1U4944 | sp-17 | an-60 | E1U12270 | sp-39 | an-60 |
| E1A4945 | sp-16 | an-61 | E1U4945 | sp-17 | an-61 | E1U12271 | sp-39 | an-61 |
| E1A4946 | sp-16 | an-62 | E1U4946 | sp-17 | an-62 | E1U12272 | sp-39 | an-62 |
| E1A4947 | sp-16 | an-63 | E1U4947 | sp-17 | an-63 | E1U12273 | sp-39 | an-63 |
| E1A4948 | sp-16 | an-64 | E1U4948 | sp-17 | an-64 | E1U12274 | sp-39 | an-64 |
| E1A4949 | sp-16 | an-65 | E1U4949 | sp-17 | an-65 | E1U12275 | sp-39 | an-65 |
| E1A4950 | sp-16 | an-66 | E1U4950 | sp-17 | an-66 | E1U12276 | sp-39 | an-66 |
| E1A4951 | sp-16 | an-67 | E1U4951 | sp-17 | an-67 | E1U12277 | sp-39 | an-67 |
| E1A4952 | sp-16 | an-68 | E1U4952 | sp-17 | an-68 | E1U12278 | sp-39 | an-68 |
| E1A4953 | sp-16 | an-69 | E1U4953 | sp-17 | an-69 | E1U12279 | sp-39 | an-69 |
| E1A4954 | sp-16 | an-70 | E1U4954 | sp-17 | an-70 | E1U12280 | sp-39 | an-70 |
| E1A4955 | sp-16 | an-71 | E1U4955 | sp-17 | an-71 | E1U12281 | sp-39 | an-71 |
| E1A4956 | sp-16 | an-72 | E1U4956 | sp-17 | an-72 | E1U12282 | sp-39 | an-72 |
| E1A4957 | sp-16 | an-73 | E1U4957 | sp-17 | an-73 | E1U12283 | sp-39 | an-73 |
| E1A4958 | sp-16 | an-74 | E1U4958 | sp-17 | an-74 | E1U12284 | sp-39 | an-74 |
| E1A4959 | sp-16 | an-75 | E1U4959 | sp-17 | an-75 | E1U12285 | sp-39 | an-75 |
| E1A4960 | sp-16 | an-76 | E1U4960 | sp-17 | an-76 | E1U12286 | sp-39 | an-76 |
| E1A4961 | sp-16 | an-77 | E1U4961 | sp-17 | an-77 | E1U12287 | sp-39 | an-77 |
| E1A4962 | sp-16 | an-78 | E1U4962 | sp-17 | an-78 | E1U12288 | sp-39 | an-78 |
| E1A4963 | sp-16 | an-79 | E1U4963 | sp-17 | an-79 | E1U12289 | sp-39 | an-79 |
| E1A4964 | sp-16 | an-80 | E1U4964 | sp-17 | an-80 | E1U12290 | sp-39 | an-80 |
| E1A4965 | sp-16 | an-81 | E1U4965 | sp-17 | an-81 | E1U12291 | sp-39 | an-81 |
| E1A4966 | sp-16 | an-82 | E1U4966 | sp-17 | an-82 | E1U12292 | sp-39 | an-82 |
| E1A4967 | sp-16 | an-83 | E1U4967 | sp-17 | an-83 | E1U12293 | sp-39 | an-83 |
| E1A4968 | sp-16 | an-84 | E1U4968 | sp-17 | an-84 | E1U12294 | sp-39 | an-84 |

Table 1-93

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| Y = NHCS | | | Y = NHCSNH | | | Y = NHCSNH | | |
| E1A4969 | sp-16 | an-85 | E1U4969 | sp-17 | an-85 | E1U12295 | sp-39 | an-85 |
| E1A4970 | sp-16 | an-86 | E1U4970 | sp-17 | an-86 | E1U12296 | sp-39 | an-86 |
| E1A4971 | sp-16 | an-87 | E1U4971 | sp-17 | an-87 | E1U12297 | sp-39 | an-87 |
| E1A4972 | sp-16 | an-88 | E1U4972 | sp-17 | an-88 | E1U12298 | sp-39 | an-88 |
| E1A4973 | sp-16 | an-89 | E1U4973 | sp-17 | an-89 | E1U12299 | sp-39 | an-89 |
| E1A4974 | sp-16 | an-90 | E1U4974 | sp-17 | an-90 | E1U12300 | sp-39 | an-90 |
| E1A4975 | sp-16 | an-91 | E1U4975 | sp-17 | an-91 | E1U12301 | sp-39 | an-91 |
| E1A4976 | sp-16 | an-92 | E1U4976 | sp-17 | an-92 | E1U12302 | sp-39 | an-92 |
| E1A4977 | sp-16 | an-93 | E1U4977 | sp-17 | an-93 | E1U12303 | sp-39 | an-93 |
| E1A4978 | sp-16 | an-94 | E1U4978 | sp-17 | an-94 | E1U12304 | sp-39 | an-94 |
| E1A4979 | sp-16 | an-95 | E1U4979 | sp-17 | an-95 | E1U12305 | sp-39 | an-95 |
| E1A4980 | sp-16 | an-96 | E1U4980 | sp-17 | an-96 | E1U12306 | sp-39 | an-96 |
| E1A4981 | sp-16 | an-97 | E1U4981 | sp-17 | an-97 | E1U12307 | sp-39 | an-97 |
| E1A4982 | sp-16 | an-98 | E1U4982 | sp-17 | an-98 | E1U12308 | sp-39 | an-98 |
| E1A4983 | sp-16 | an-99 | E1U4983 | sp-17 | an-99 | E1U12309 | sp-39 | an-99 |
| E1A4984 | sp-16 | an-100 | E1U4984 | sp-17 | an-100 | E1U12310 | sp-39 | an-100 |

-continued

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| E1A4985 | sp-16 | an-101 | E1U4985 | sp-17 | an-101 | E1U12311 | sp-39 | an-101 |
| E1A4986 | sp-16 | an-102 | E1U4986 | sp-17 | an-102 | E1U12312 | sp-39 | an-102 |
| E1A4987 | sp-16 | an-103 | E1U4987 | sp-17 | an-103 | E1U12313 | sp-39 | an-103 |
| E1A4988 | sp-16 | an-104 | E1U4988 | sp-17 | an-104 | E1U12314 | sp-39 | an-104 |
| E1A4989 | sp-16 | an-105 | E1U4989 | sp-17 | an-105 | E1U12315 | sp-39 | an-105 |
| E1A4990 | sp-16 | an-106 | E1U4990 | sp-17 | an-106 | E1U12316 | sp-39 | an-106 |
| E1A4991 | sp-16 | an-107 | E1U4991 | sp-17 | an-107 | E1U12317 | sp-39 | an-107 |
| E1A4992 | sp-16 | an-108 | E1U4992 | sp-17 | an-108 | E1U12318 | sp-39 | an-108 |
| E1A4993 | sp-16 | an-109 | E1U4993 | sp-17 | an-109 | E1U12319 | sp-39 | an-109 |
| E1A4994 | sp-16 | an-110 | E1U4994 | sp-17 | an-110 | E1U12320 | sp-39 | an-110 |
| E1A4995 | sp-16 | an-111 | E1U4995 | sp-17 | an-111 | E1U12321 | sp-39 | an-111 |
| E1A4996 | sp-16 | an-112 | E1U4996 | sp-17 | an-112 | E1U12322 | sp-39 | an-112 |
| E1A4997 | sp-16 | an-113 | E1U4997 | sp-17 | an-113 | E1U12323 | sp-39 | an-113 |
| E1A4998 | sp-16 | an-114 | E1U4998 | sp-17 | an-114 | E1U12324 | sp-39 | an-114 |
| E1A4999 | sp-16 | an-115 | E1U4999 | sp-17 | an-115 | E1U12325 | sp-39 | an-115 |
| E1A5000 | sp-16 | an-116 | E1U5000 | sp-17 | an-116 | E1U12326 | sp-39 | an-116 |
| E1A5001 | sp-16 | an-117 | E1U5001 | sp-17 | an-117 | E1U12327 | sp-39 | an-117 |
| E1A5002 | sp-16 | an-118 | E1U5002 | sp-17 | an-118 | E1U12328 | sp-39 | an-118 |
| E1A5003 | sp-16 | an-119 | E1U5003 | sp-17 | an-119 | E1U12329 | sp-39 | an-119 |
| E1A5004 | sp-16 | an-120 | E1U5004 | sp-17 | an-120 | E1U12330 | sp-39 | an-120 |
| E1A5005 | sp-16 | an-121 | E1U5005 | sp-17 | an-121 | E1U12331 | sp-39 | an-121 |
| E1A5006 | sp-16 | an-122 | E1U5006 | sp-17 | an-122 | E1U12332 | sp-39 | an-122 |
| E1A5007 | sp-16 | an-123 | E1U5007 | sp-17 | an-123 | E1U12333 | sp-39 | an-123 |
| E1A5008 | sp-16 | an-124 | E1U5008 | sp-17 | an-124 | E1U12334 | sp-39 | an-124 |
| E1A5009 | sp-16 | an-125 | E1U5009 | sp-17 | an-125 | E1U12335 | sp-39 | an-125 |
| E1A5010 | sp-16 | an-126 | E1U5010 | sp-17 | an-126 | E1U12336 | sp-39 | an-126 |
| E1A5011 | sp-16 | an-127 | E1U5011 | sp-17 | an-127 | E1U12337 | sp-39 | an-127 |
| E1A5012 | sp-16 | an-128 | E1U5012 | sp-17 | an-128 | E1U12338 | sp-39 | an-128 |
| E1A5013 | sp-16 | an-129 | E1U5013 | sp-17 | an-129 | E1U12339 | sp-39 | an-129 |
| E1A5014 | sp-16 | an-130 | E1U5014 | sp-17 | an-130 | E1U12340 | sp-39 | an-130 |
| E1A5015 | sp-16 | an-131 | E1U5015 | sp-17 | an-131 | E1U12341 | sp-39 | an-131 |
| E1A5016 | sp-16 | an-132 | E1U5016 | sp-17 | an-132 | E1U12342 | sp-39 | an-132 |
| E1A5017 | sp-16 | an-133 | E1U5017 | sp-17 | an-133 | E1U12343 | sp-39 | an-133 |
| E1A5018 | sp-16 | an-134 | E1U5018 | sp-17 | an-134 | E1U12344 | sp-39 | an-134 |
| E1A5019 | sp-16 | an-135 | E1U5019 | sp-17 | an-135 | E1U12345 | sp-39 | an-135 |
| E1A5020 | sp-16 | an-136 | E1U5020 | sp-17 | an-136 | E1U12346 | sp-39 | an-136 |
| E1A5021 | sp-16 | an-137 | E1U5021 | sp-17 | an-137 | E1U12347 | sp-39 | an-137 |
| E1A5022 | sp-16 | an-138 | E1U5022 | sp-17 | an-138 | E1U12348 | sp-39 | an-138 |

Table 1-94

| Y = NHCS | | | Y = NHCSNH | | | Y = NHCSNH | | |
|---|---|---|---|---|---|---|---|---|
| E1A5023 | sp-16 | an-139 | E1U5023 | sp-17 | an-139 | E1U12349 | sp-39 | an-139 |
| E1A5024 | sp-16 | an-140 | E1U5024 | sp-17 | an-140 | E1U12350 | sp-39 | an-140 |
| E1A5025 | sp-16 | an-141 | E1U5025 | sp-17 | an-141 | E1U12351 | sp-39 | an-141 |
| E1A5026 | sp-16 | an-142 | E1U5026 | sp-17 | an-142 | E1U12352 | sp-39 | an-142 |
| E1A5027 | sp-16 | an-143 | E1U5027 | sp-17 | an-143 | E1U12353 | sp-39 | an-143 |
| E1A5028 | sp-16 | an-144 | E1U5028 | sp-17 | an-144 | E1U12354 | sp-39 | an-144 |
| E1A5029 | sp-16 | an-145 | E1U5029 | sp-17 | an-145 | E1U12355 | sp-39 | an-145 |
| E1A5030 | sp-16 | an-146 | E1U5030 | sp-17 | an-146 | E1U12356 | sp-39 | an-146 |
| E1A5031 | sp-16 | an-147 | E1U5031 | sp-17 | an-147 | E1U12357 | sp-39 | an-147 |
| E1A5032 | sp-16 | an-148 | E1U5032 | sp-17 | an-148 | E1U12358 | sp-39 | an-148 |
| E1A5033 | sp-16 | an-149 | E1U5033 | sp-17 | an-149 | E1U12359 | sp-39 | an-149 |
| E1A5034 | sp-16 | an-150 | E1U5034 | sp-17 | an-150 | E1U12360 | sp-39 | an-150 |
| E1A5035 | sp-16 | an-151 | E1U5035 | sp-17 | an-151 | E1U12361 | sp-39 | an-151 |
| E1A5036 | sp-16 | an-152 | E1U5036 | sp-17 | an-152 | E1U12362 | sp-39 | an-152 |
| E1A5037 | sp-16 | an-153 | E1U5037 | sp-17 | an-153 | E1U12363 | sp-39 | an-153 |
| E1A5038 | sp-16 | an-154 | E1U5038 | sp-17 | an-154 | E1U12364 | sp-39 | an-154 |
| E1A5039 | sp-16 | an-155 | E1U5039 | sp-17 | an-155 | E1U12365 | sp-39 | an-155 |
| E1A5040 | sp-16 | an-156 | E1U5040 | sp-17 | an-156 | E1U12366 | sp-39 | an-156 |
| E1A5041 | sp-16 | an-157 | E1U5041 | sp-17 | an-157 | E1U12367 | sp-39 | an-157 |
| E1A5042 | sp-16 | an-158 | E1U5042 | sp-17 | an-158 | E1U12368 | sp-39 | an-158 |
| E1A5043 | sp-16 | an-159 | E1U5043 | sp-17 | an-159 | E1U12369 | sp-39 | an-159 |
| E1A5044 | sp-16 | an-160 | E1U5044 | sp-17 | an-160 | E1U12370 | sp-39 | an-160 |
| E1A5045 | sp-16 | an-161 | E1U5045 | sp-17 | an-161 | E1U12371 | sp-39 | an-161 |
| E1A5046 | sp-16 | an-162 | E1U5046 | sp-17 | an-162 | E1U12372 | sp-39 | an-162 |
| E1A5047 | sp-16 | an-163 | E1U5047 | sp-17 | an-163 | E1U12373 | sp-39 | an-163 |
| E1A5048 | sp-16 | an-164 | E1U5048 | sp-17 | an-164 | E1U12374 | sp-39 | an-164 |
| E1A5049 | sp-16 | an-165 | E1U5049 | sp-17 | an-165 | E1U12375 | sp-39 | an-165 |
| E1A5050 | sp-16 | an-166 | E1U5050 | sp-17 | an-166 | E1U12376 | sp-39 | an-166 |
| E1A5051 | sp-16 | an-167 | E1U5051 | sp-17 | an-167 | E1U12377 | sp-39 | an-167 |
| E1A5052 | sp-16 | an-168 | E1U5052 | sp-17 | an-168 | E1U12378 | sp-39 | an-168 |
| E1A5053 | sp-16 | an-169 | E1U5053 | sp-17 | an-169 | E1U12379 | sp-39 | an-169 |
| E1A5054 | sp-16 | an-170 | E1U5054 | sp-17 | an-170 | E1U12380 | sp-39 | an-170 |
| E1A5055 | sp-16 | an-171 | E1U5055 | sp-17 | an-171 | E1U12381 | sp-39 | an-171 |
| E1A5056 | sp-16 | an-172 | E1U5056 | sp-17 | an-172 | E1U12382 | sp-39 | an-172 |
| E1A5057 | sp-16 | an-173 | E1U5057 | sp-17 | an-173 | E1U12383 | sp-39 | an-173 |
| E1A5058 | sp-16 | an-174 | E1U5058 | sp-17 | an-174 | E1U12384 | sp-39 | an-174 |

-continued

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| E1A5059 | sp-16 | an-175 | E1U5059 | sp-17 | an-175 | E1U12385 | sp-39 | an-175 |
| E1A5060 | sp-16 | an-176 | E1U5060 | sp-17 | an-176 | E1U12386 | sp-39 | an-176 |
| E1A5061 | sp-16 | an-177 | E1U5061 | sp-17 | an-177 | E1U12387 | sp-39 | an-177 |
| E1A5062 | sp-16 | an-178 | E1U5062 | sp-17 | an-178 | E1U12388 | sp-39 | an-178 |
| E1A5063 | sp-16 | an-179 | E1U5063 | sp-17 | an-179 | E1U12389 | sp-39 | an-179 |
| E1A5064 | sp-16 | an-180 | E1U5064 | sp-17 | an-180 | E1U12390 | sp-39 | an-180 |
| E1A5065 | sp-16 | an-181 | E1U5065 | sp-17 | an-181 | E1U12391 | sp-39 | an-181 |
| E1A5066 | sp-16 | an-182 | E1U5066 | sp-17 | an-182 | E1U12392 | sp-39 | an-182 |
| E1A5067 | sp-16 | an-183 | E1U5067 | sp-17 | an-183 | E1U12393 | sp-39 | an-183 |
| E1A5068 | sp-16 | an-184 | E1U5068 | sp-17 | an-184 | E1U12394 | sp-39 | an-184 |
| E1A5069 | sp-16 | an-185 | E1U5069 | sp-17 | an-185 | E1U12395 | sp-39 | an-185 |
| E1A5070 | sp-16 | an-186 | E1U5070 | sp-17 | an-186 | E1U12396 | sp-39 | an-186 |
| E1A5071 | sp-16 | an-187 | E1U5071 | sp-17 | an-187 | E1U12397 | sp-39 | an-187 |
| E1A5072 | sp-16 | an-188 | E1U5072 | sp-17 | an-188 | E1U12398 | sp-39 | an-188 |
| E1A5073 | sp-16 | an-189 | E1U5073 | sp-17 | an-189 | E1U12399 | sp-39 | an-189 |
| E1A5074 | sp-16 | an-190 | E1U5074 | sp-17 | an-190 | E1U12400 | sp-39 | an-190 |
| E1A5075 | sp-16 | an-191 | E1U5075 | sp-17 | an-191 | E1U12401 | sp-39 | an-191 |
| E1A5076 | sp-16 | an-192 | E1U5076 | sp-17 | an-192 | E1U12402 | sp-39 | an-192 |

Table 1-95

| Y = NHCS | | | Y = NHCSNH | | | Y = NHCSNH | | |
|---|---|---|---|---|---|---|---|---|
| E1A5077 | sp-16 | an-193 | E1U5077 | sp-17 | an-193 | E1U12403 | sp-39 | an-193 |
| E1A5078 | sp-16 | an-194 | E1U5078 | sp-17 | an-194 | E1U12404 | sp-39 | an-194 |
| E1A5079 | sp-16 | an-195 | E1U5079 | sp-17 | an-195 | E1U12405 | sp-39 | an-195 |
| E1A5080 | sp-16 | an-196 | E1U5080 | sp-17 | an-196 | E1U12406 | sp-39 | an-196 |
| E1A5081 | sp-16 | an-197 | E1U5081 | sp-17 | an-197 | E1U12407 | sp-39 | an-197 |
| E1A5082 | sp-16 | an-198 | E1U5082 | sp-17 | an-198 | E1U12408 | sp-39 | an-198 |
| E1A5083 | sp-16 | an-199 | E1U5083 | sp-17 | an-199 | E1U12409 | sp-39 | an-199 |
| E1A5084 | sp-16 | an-200 | E1U5084 | sp-17 | an-200 | E1U12410 | sp-39 | an-200 |
| E1A5085 | sp-16 | an-201 | E1U5085 | sp-17 | an-201 | E1U12411 | sp-39 | an-201 |
| E1A5086 | sp-16 | an-202 | E1U5086 | sp-17 | an-202 | E1U12412 | sp-39 | an-202 |
| E1A5087 | sp-16 | an-203 | E1U5087 | sp-17 | an-203 | E1U12413 | sp-39 | an-203 |
| E1A5088 | sp-16 | an-204 | E1U5088 | sp-17 | an-204 | E1U12414 | sp-39 | an-204 |
| E1A5089 | sp-16 | an-205 | E1U5089 | sp-17 | an-205 | E1U12415 | sp-39 | an-205 |
| E1A5090 | sp-16 | an-206 | E1U5090 | sp-17 | an-206 | E1U12416 | sp-39 | an-206 |
| E1A5091 | sp-16 | an-207 | E1U5091 | sp-17 | an-207 | E1U12417 | sp-39 | an-207 |
| E1A5092 | sp-16 | an-208 | E1U5092 | sp-17 | an-208 | E1U12418 | sp-39 | an-208 |
| E1A5093 | sp-16 | an-209 | E1U5093 | sp-17 | an-209 | E1U12419 | sp-39 | an-209 |
| E1A5094 | sp-16 | an-210 | E1U5094 | sp-17 | an-210 | E1U12420 | sp-39 | an-210 |
| E1A5095 | sp-16 | an-211 | E1U5095 | sp-17 | an-211 | E1U12421 | sp-39 | an-211 |
| E1A5096 | sp-16 | an-212 | E1U5096 | sp-17 | an-212 | E1U12422 | sp-39 | an-212 |
| E1A5097 | sp-16 | an-213 | E1U5097 | sp-17 | an-213 | E1U12423 | sp-39 | an-213 |
| E1A5098 | sp-16 | an-214 | E1U5098 | sp-17 | an-214 | E1U12424 | sp-39 | an-214 |
| E1A5099 | sp-16 | an-215 | E1U5099 | sp-17 | an-215 | E1U12425 | sp-39 | an-215 |
| E1A5100 | sp-16 | an-216 | E1U5100 | sp-17 | an-216 | E1U12426 | sp-39 | an-216 |
| E1A5101 | sp-16 | an-217 | E1U5101 | sp-17 | an-217 | E1U12427 | sp-39 | an-217 |
| E1A5102 | sp-16 | an-218 | E1U5102 | sp-17 | an-218 | E1U12428 | sp-39 | an-218 |
| E1A5103 | sp-16 | an-219 | E1U5103 | sp-17 | an-219 | E1U12429 | sp-39 | an-219 |
| E1A5104 | sp-16 | an-220 | E1U5104 | sp-17 | an-220 | E1U12430 | sp-39 | an-220 |
| E1A5105 | sp-16 | an-221 | E1U5105 | sp-17 | an-221 | E1U12431 | sp-39 | an-221 |
| E1A5106 | sp-16 | an-222 | E1U5106 | sp-17 | an-222 | E1U12432 | sp-39 | an-222 |
| E1A5107 | sp-16 | an-223 | E1U5107 | sp-17 | an-223 | E1U12433 | sp-39 | an-223 |
| E1A5108 | sp-16 | an-224 | E1U5108 | sp-17 | an-224 | E1U12434 | sp-39 | an-224 |
| E1A5109 | sp-16 | an-225 | E1U5109 | sp-17 | an-225 | E1U12435 | sp-39 | an-225 |
| E1A5110 | sp-16 | an-226 | E1U5110 | sp-17 | an-226 | E1U12436 | sp-39 | an-226 |
| E1A5111 | sp-16 | an-227 | E1U5111 | sp-17 | an-227 | E1U12437 | sp-39 | an-227 |
| E1A5112 | sp-16 | an-228 | E1U5112 | sp-17 | an-228 | E1U12438 | sp-39 | an-228 |
| E1A5113 | sp-16 | an-229 | E1U5113 | sp-17 | an-229 | E1U12439 | sp-39 | an-229 |
| E1A5114 | sp-16 | an-230 | E1U5114 | sp-17 | an-230 | E1U12440 | sp-39 | an-230 |
| E1A5115 | sp-16 | an-231 | E1U5115 | sp-17 | an-231 | E1U12441 | sp-39 | an-231 |
| E1A5116 | sp-16 | an-232 | E1U5116 | sp-17 | an-232 | E1U12442 | sp-39 | an-232 |
| E1A5117 | sp-16 | an-233 | E1U5117 | sp-17 | an-233 | E1U12443 | sp-39 | an-233 |
| E1A5118 | sp-16 | an-234 | E1U5118 | sp-17 | an-234 | E1U12444 | sp-39 | an-234 |
| E1A5119 | sp-16 | an-235 | E1U5119 | sp-17 | an-235 | E1U12445 | sp-39 | an-235 |
| E1A5120 | sp-16 | an-236 | E1U5120 | sp-17 | an-236 | E1U12446 | sp-39 | an-236 |
| E1A5121 | sp-16 | an-237 | E1U5121 | sp-17 | an-237 | E1U12447 | sp-39 | an-237 |
| E1A5122 | sp-16 | an-238 | E1U5122 | sp-17 | an-238 | E1U12448 | sp-39 | an-238 |
| E1A5123 | sp-16 | an-239 | E1U5123 | sp-17 | an-239 | E1U12449 | sp-39 | an-239 |
| E1A5124 | sp-16 | an-240 | E1U5124 | sp-17 | an-240 | E1U12450 | sp-39 | an-240 |
| E1A5125 | sp-16 | an-241 | E1U5125 | sp-17 | an-241 | E1U12451 | sp-39 | an-241 |
| E1A5126 | sp-16 | an-242 | E1U5126 | sp-17 | an-242 | E1U12452 | sp-39 | an-242 |
| E1A5127 | sp-16 | an-243 | E1U5127 | sp-17 | an-243 | E1U12453 | sp-39 | an-243 |
| E1A5128 | sp-16 | an-244 | E1U5128 | sp-17 | an-244 | E1U12454 | sp-39 | an-244 |
| E1A5129 | sp-16 | an-245 | E1U5129 | sp-17 | an-245 | E1U12455 | sp-39 | an-245 |
| E1A5130 | sp-16 | an-246 | E1U5130 | sp-17 | an-246 | E1U12456 | sp-39 | an-246 |

-continued

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| | | | | Table 1-96 | | | | |
| | Y = NHCS | | | Y = NHCSNH | | | Y = NHCSNH | |
| E1A5131 | sp-16 | an-247 | E1U5131 | sp-17 | an-247 | E1U12457 | sp-39 | an-247 |
| E1A5132 | sp-16 | an-248 | E1U5132 | sp-17 | an-248 | E1U12458 | sp-39 | an-248 |
| E1A5133 | sp-16 | an-249 | E1U5133 | sp-17 | an-249 | E1U12459 | sp-39 | an-249 |
| E1A5134 | sp-16 | an-250 | E1U5134 | sp-17 | an-250 | E1U12460 | sp-39 | an-250 |
| E1A5135 | sp-16 | an-251 | E1U5135 | sp-17 | an-251 | E1U12461 | sp-39 | an-251 |
| E1A5136 | sp-16 | an-252 | E1U5136 | sp-17 | an-252 | E1U12462 | sp-39 | an-252 |
| E1A5137 | sp-16 | an-253 | E1U5137 | sp-17 | an-253 | E1U12463 | sp-39 | an-253 |
| E1A5138 | sp-16 | an-254 | E1U5138 | sp-17 | an-254 | E1U12464 | sp-39 | an-254 |
| E1A5139 | sp-16 | an-255 | E1U5139 | sp-17 | an-255 | E1U12465 | sp-39 | an-255 |
| E1A5140 | sp-16 | an-256 | E1U5140 | sp-17 | an-256 | E1U12466 | sp-39 | an-256 |
| E1A5141 | sp-16 | an-257 | E1U5141 | sp-17 | an-257 | E1U12467 | sp-39 | an-257 |
| E1A5142 | sp-16 | an-258 | E1U5142 | sp-17 | an-258 | E1U12468 | sp-39 | an-258 |
| E1A5143 | sp-16 | an-259 | E1U5143 | sp-17 | an-259 | E1U12469 | sp-39 | an-259 |
| E1A5144 | sp-16 | an-260 | E1U5144 | sp-17 | an-260 | E1U12470 | sp-39 | an-260 |
| E1A5145 | sp-16 | an-261 | E1U5145 | sp-17 | an-261 | E1U12471 | sp-39 | an-261 |
| E1A5146 | sp-16 | an-262 | E1U5146 | sp-17 | an-262 | E1U12472 | sp-39 | an-262 |
| E1A5147 | sp-16 | an-263 | E1U5147 | sp-17 | an-263 | E1U12473 | sp-39 | an-263 |
| E1A5148 | sp-16 | an-264 | E1U5148 | sp-17 | an-264 | E1U12474 | sp-39 | an-264 |
| E1A5149 | sp-16 | an-265 | E1U5149 | sp-17 | an-265 | E1U12475 | sp-39 | an-265 |
| E1A5150 | sp-16 | an-266 | E1U5150 | sp-17 | an-266 | E1U12476 | sp-39 | an-266 |
| E1A5151 | sp-16 | an-267 | E1U5151 | sp-17 | an-267 | E1U12477 | sp-39 | an-267 |
| E1A5152 | sp-16 | an-268 | E1U5152 | sp-17 | an-268 | E1U12478 | sp-39 | an-268 |
| E1A5153 | sp-16 | an-269 | E1U5153 | sp-17 | an-269 | E1U12479 | sp-39 | an-269 |
| E1A5154 | sp-16 | an-270 | E1U5154 | sp-17 | an-270 | E1U12480 | sp-39 | an-270 |
| E1A5155 | sp-16 | an-271 | E1U5155 | sp-17 | an-271 | E1U12481 | sp-39 | an-271 |
| E1A5156 | sp-16 | an-272 | E1U5156 | sp-17 | an-272 | E1U12482 | sp-39 | an-272 |
| E1A5157 | sp-16 | an-273 | E1U5157 | sp-17 | an-273 | E1U12483 | sp-39 | an-273 |
| E1A5158 | sp-16 | an-274 | E1U5158 | sp-17 | an-274 | E1U12484 | sp-39 | an-274 |
| E1A5159 | sp-16 | an-275 | E1U5159 | sp-17 | an-275 | E1U12485 | sp-39 | an-275 |
| E1A5160 | sp-16 | an-276 | E1U5160 | sp-17 | an-276 | E1U12486 | sp-39 | an-276 |
| E1A5161 | sp-16 | an-277 | E1U5161 | sp-17 | an-277 | E1U12487 | sp-39 | an-277 |
| E1A5162 | sp-16 | an-278 | E1U5162 | sp-17 | an-278 | E1U12488 | sp-39 | an-278 |
| E1A5163 | sp-16 | an-279 | E1U5163 | sp-17 | an-279 | E1U12489 | sp-39 | an-279 |
| E1A5164 | sp-16 | an-280 | E1U5164 | sp-17 | an-280 | E1U12490 | sp-39 | an-280 |
| E1A5165 | sp-16 | an-281 | E1U5165 | sp-17 | an-281 | E1U12491 | sp-39 | an-281 |
| E1A5166 | sp-16 | an-282 | E1U5166 | sp-17 | an-282 | E1U12492 | sp-39 | an-282 |
| E1A5167 | sp-16 | an-283 | E1U5167 | sp-17 | an-283 | E1U12493 | sp-39 | an-283 |
| E1A5168 | sp-16 | an-284 | E1U5168 | sp-17 | an-284 | E1U12494 | sp-39 | an-284 |
| E1A5169 | sp-16 | an-285 | E1U5169 | sp-17 | an-285 | E1U12495 | sp-39 | an-285 |
| E1A5170 | sp-16 | an-286 | E1U5170 | sp-17 | an-286 | E1U12496 | sp-39 | an-286 |
| E1A5171 | sp-16 | an-287 | E1U5171 | sp-17 | an-287 | E1U12497 | sp-39 | an-287 |
| E1A5172 | sp-16 | an-288 | E1U5172 | sp-17 | an-288 | E1U12498 | sp-39 | an-288 |
| E1A5173 | sp-16 | an-289 | E1U5173 | sp-17 | an-289 | E1U12499 | sp-39 | an-289 |
| E1A5174 | sp-16 | an-290 | E1U5174 | sp-17 | an-290 | E1U12500 | sp-39 | an-290 |
| E1A5175 | sp-16 | an-291 | E1U5175 | sp-17 | an-291 | E1U12501 | sp-39 | an-291 |
| E1A5176 | sp-16 | an-292 | E1U5176 | sp-17 | an-292 | E1U12502 | sp-39 | an-292 |
| E1A5177 | sp-16 | an-293 | E1U5177 | sp-17 | an-293 | E1U12503 | sp-39 | an-293 |
| E1A5178 | sp-16 | an-294 | E1U5178 | sp-17 | an-294 | E1U12504 | sp-39 | an-294 |
| E1A5179 | sp-16 | an-295 | E1U5179 | sp-17 | an-295 | E1U12505 | sp-39 | an-295 |
| E1A5180 | sp-16 | an-296 | E1U5180 | sp-17 | an-296 | E1U12506 | sp-39 | an-296 |
| E1A5181 | sp-16 | an-297 | E1U5181 | sp-17 | an-297 | E1U12507 | sp-39 | an-297 |
| E1A5182 | sp-16 | an-298 | E1U5182 | sp-17 | an-298 | E1U12508 | sp-39 | an-298 |
| E1A5183 | sp-16 | an-299 | E1U5183 | sp-17 | an-299 | E1U12509 | sp-39 | an-299 |
| E1A5184 | sp-16 | an-300 | E1U5184 | sp-17 | an-300 | E1U12510 | sp-39 | an-300 |
| | | | | Table 1-97 | | | | |
| | Y = NHCS | | | Y = NHCSNH | | | Y = NHCSNH | |
| E1A5185 | sp-16 | an-301 | E1U5185 | sp-17 | an-301 | E1U12511 | sp-39 | an-301 |
| E1A5186 | sp-16 | an-302 | E1U5186 | sp-17 | an-302 | E1U12512 | sp-39 | an-302 |
| E1A5187 | sp-16 | an-303 | E1U5187 | sp-17 | an-303 | E1U12513 | sp-39 | an-303 |
| E1A5188 | sp-16 | an-304 | E1U5188 | sp-17 | an-304 | E1U12514 | sp-39 | an-304 |
| E1A5189 | sp-16 | an-305 | E1U5189 | sp-17 | an-305 | E1U12515 | sp-39 | an-305 |
| E1A5190 | sp-16 | an-306 | E1U5190 | sp-17 | an-306 | E1U12516 | sp-39 | an-306 |
| E1A5191 | sp-16 | an-307 | E1U5191 | sp-17 | an-307 | E1U12517 | sp-39 | an-307 |
| E1A5192 | sp-16 | an-308 | E1U5192 | sp-17 | an-308 | E1U12518 | sp-39 | an-308 |
| E1A5193 | sp-16 | an-309 | E1U5193 | sp-17 | an-309 | E1U12519 | sp-39 | an-309 |
| E1A5194 | sp-16 | an-310 | E1U5194 | sp-17 | an-310 | E1U12520 | sp-39 | an-310 |
| E1A5195 | sp-16 | an-311 | E1U5195 | sp-17 | an-311 | E1U12521 | sp-39 | an-311 |
| E1A5196 | sp-16 | an-312 | E1U5196 | sp-17 | an-312 | E1U12522 | sp-39 | an-312 |
| E1A5197 | sp-16 | an-313 | E1U5197 | sp-17 | an-313 | E1U12523 | sp-39 | an-313 |
| E1A5198 | sp-16 | an-314 | E1U5198 | sp-17 | an-314 | E1U12524 | sp-39 | an-314 |
| E1A5199 | sp-16 | an-315 | E1U5199 | sp-17 | an-315 | E1U12525 | sp-39 | an-315 |
| E1A5200 | sp-16 | an-316 | E1U5200 | sp-17 | an-316 | E1U12526 | sp-39 | an-316 |

-continued

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| E1A5201 | sp-16 | an-317 | E1U5201 | sp-17 | an-317 | E1U12527 | sp-39 | an-317 |
| E1A5202 | sp-16 | an-318 | E1U5202 | sp-17 | an-318 | E1U12528 | sp-39 | an-318 |
| E1A5203 | sp-16 | an-319 | E1U5203 | sp-17 | an-319 | E1U12529 | sp-39 | an-319 |
| E1A5204 | sp-16 | an-320 | E1U5204 | sp-17 | an-320 | E1U12530 | sp-39 | an-320 |
| E1A5205 | sp-16 | an-321 | E1U5205 | sp-17 | an-321 | E1U12531 | sp-39 | an-321 |
| E1A5206 | sp-16 | an-322 | E1U5206 | sp-17 | an-322 | E1U12532 | sp-39 | an-322 |
| E1A5207 | sp-16 | an-323 | E1U5207 | sp-17 | an-323 | E1U12533 | sp-39 | an-323 |
| E1A5208 | sp-16 | an-324 | E1U5208 | sp-17 | an-324 | E1U12534 | sp-39 | an-324 |
| E1A5209 | sp-16 | an-325 | E1U5209 | sp-17 | an-325 | E1U12535 | sp-39 | an-325 |
| E1A5210 | sp-16 | an-326 | E1U5210 | sp-17 | an-326 | E1U12536 | sp-39 | an-326 |
| E1A5211 | sp-16 | an-327 | E1U5211 | sp-17 | an-327 | E1U12537 | sp-39 | an-327 |
| E1A5212 | sp-16 | an-328 | E1U5212 | sp-17 | an-328 | E1U12538 | sp-39 | an-328 |
| E1A5213 | sp-16 | an-329 | E1U5213 | sp-17 | an-329 | E1U12539 | sp-39 | an-329 |
| E1A5214 | sp-16 | an-330 | E1U5214 | sp-17 | an-330 | E1U12540 | sp-39 | an-330 |
| E1A5215 | sp-16 | an-331 | E1U5215 | sp-17 | an-331 | E1U12541 | sp-39 | an-331 |
| E1A5216 | sp-16 | an-332 | E1U5216 | sp-17 | an-332 | E1U12542 | sp-39 | an-332 |
| E1A5217 | sp-16 | an-333 | E1U5217 | sp-17 | an-333 | E1U12543 | sp-39 | an-333 |
| E1A5218 | sp-16 | an-334 | E1U5218 | sp-17 | an-334 | E1U12544 | sp-39 | an-334 |
| E1A5219 | sp-16 | an-335 | E1U5219 | sp-17 | an-335 | E1U12545 | sp-39 | an-335 |
| E1A5220 | sp-16 | an-336 | E1U5220 | sp-17 | an-336 | E1U12546 | sp-39 | an-336 |
| E1A5221 | sp-16 | an-337 | E1U5221 | sp-17 | an-337 | E1U12547 | sp-39 | an-337 |
| E1A5222 | sp-16 | an-338 | E1U5222 | sp-17 | an-338 | E1U12548 | sp-39 | an-338 |
| E1A5223 | sp-16 | an-339 | E1U5223 | sp-17 | an-339 | E1U12549 | sp-39 | an-339 |
| E1A5224 | sp-16 | an-340 | E1U5224 | sp-17 | an-340 | E1U12550 | sp-39 | an-340 |
| E1A5225 | sp-16 | an-341 | E1U5225 | sp-17 | an-341 | E1U12551 | sp-39 | an-341 |
| E1A5226 | sp-16 | an-342 | E1U5226 | sp-17 | an-342 | E1U12552 | sp-39 | an-342 |
| E1A5227 | sp-16 | an-343 | E1U5227 | sp-17 | an-343 | E1U12553 | sp-39 | an-343 |
| E1A5228 | sp-16 | an-344 | E1U5228 | sp-17 | an-344 | E1U12554 | sp-39 | an-344 |
| E1A5229 | sp-16 | an-345 | E1U5229 | sp-17 | an-345 | E1U12555 | sp-39 | an-345 |
| E1A5230 | sp-16 | an-346 | E1U5230 | sp-17 | an-346 | E1U12556 | sp-39 | an-346 |
| E1A5231 | sp-16 | an-347 | E1U5231 | sp-17 | an-347 | E1U12557 | sp-39 | an-347 |
| E1A5232 | sp-16 | an-348 | E1U5232 | sp-17 | an-348 | E1U12558 | sp-39 | an-348 |
| E1A5233 | sp-16 | an-349 | E1U5233 | sp-17 | an-349 | E1U12559 | sp-39 | an-349 |
| E1A5234 | sp-16 | an-350 | E1U5234 | sp-17 | an-350 | E1U12560 | sp-39 | an-350 |
| E1A5235 | sp-16 | an-351 | E1U5235 | sp-17 | an-351 | E1U12561 | sp-39 | an-351 |
| E1A5236 | sp-16 | an-352 | E1U5236 | sp-17 | an-352 | E1U12562 | sp-39 | an-352 |
| E1A5237 | sp-16 | an-353 | E1U5237 | sp-17 | an-353 | E1U12563 | sp-39 | an-353 |
| E1A5238 | sp-16 | an-354 | E1U5238 | sp-17 | an-354 | E1U12564 | sp-39 | an-354 |

Table 1-98

| Y = NHCS | | | Y = NHCSNH | | | Y = NHCSNH | | |
|---|---|---|---|---|---|---|---|---|
| E1A5239 | sp-16 | an-355 | E1U5239 | sp-17 | an-355 | E1U12565 | sp-39 | an-355 |
| E1A5240 | sp-16 | an-356 | E1U5240 | sp-17 | an-356 | E1U12566 | sp-39 | an-356 |
| E1A5241 | sp-16 | an-357 | E1U5241 | sp-17 | an-357 | E1U12567 | sp-39 | an-357 |
| E1A5242 | sp-16 | an-358 | E1U5242 | sp-17 | an-358 | E1U12568 | sp-39 | an-358 |
| E1A5243 | sp-16 | an-359 | E1U5243 | sp-17 | an-359 | E1U12569 | sp-39 | an-359 |
| E1A5244 | sp-16 | an-360 | E1U5244 | sp-17 | an-360 | E1U12570 | sp-39 | an-360 |
| E1A5245 | sp-16 | an-361 | E1U5245 | sp-17 | an-361 | E1U12571 | sp-39 | an-361 |
| E1A5246 | sp-16 | an-362 | E1U5246 | sp-17 | an-362 | E1U12572 | sp-39 | an-362 |
| E1A5247 | sp-16 | an-363 | E1U5247 | sp-17 | an-363 | E1U12573 | sp-39 | an-363 |
| E1A5248 | sp-16 | an-364 | E1U5248 | sp-17 | an-364 | E1U12574 | sp-39 | an-364 |
| E1A5249 | sp-16 | an-365 | E1U5249 | sp-17 | an-365 | E1U12575 | sp-39 | an-365 |
| E1A5250 | sp-16 | an-366 | E1U5250 | sp-17 | an-366 | E1U12576 | sp-39 | an-366 |
| E1A5251 | sp-16 | an-367 | E1U5251 | sp-17 | an-367 | E1U12577 | sp-39 | an-367 |
| E1A5252 | sp-16 | an-368 | E1U5252 | sp-17 | an-368 | E1U12578 | sp-39 | an-368 |
| E1A5253 | sp-16 | an-369 | E1U5253 | sp-17 | an-369 | E1U12579 | sp-39 | an-369 |
| E1A5254 | sp-16 | an-370 | E1U5254 | sp-17 | an-370 | E1U12580 | sp-39 | an-370 |
| E1A5255 | sp-16 | an-371 | E1U5255 | sp-17 | an-371 | E1U12581 | sp-39 | an-371 |
| E1A5256 | sp-16 | an-372 | E1U5256 | sp-17 | an-372 | E1U12582 | sp-39 | an-372 |
| E1A5257 | sp-16 | an-373 | E1U5257 | sp-17 | an-373 | E1U12583 | sp-39 | an-373 |
| E1A5258 | sp-16 | an-374 | E1U5258 | sp-17 | an-374 | E1U12584 | sp-39 | an-374 |
| E1A5259 | sp-16 | an-375 | E1U5259 | sp-17 | an-375 | E1U12585 | sp-39 | an-375 |
| E1A5260 | sp-16 | an-376 | E1U5260 | sp-17 | an-376 | E1U12586 | sp-39 | an-376 |
| E1A5261 | sp-16 | an-377 | E1U5261 | sp-17 | an-377 | E1U12587 | sp-39 | an-377 |
| E1A5262 | sp-16 | an-378 | E1U5262 | sp-17 | an-378 | E1U12588 | sp-39 | an-378 |
| E1A5263 | sp-16 | an-379 | E1U5263 | sp-17 | an-379 | E1U12589 | sp-39 | an-379 |
| E1A5264 | sp-16 | an-380 | E1U5264 | sp-17 | an-380 | E1U12590 | sp-39 | an-380 |
| E1A5265 | sp-16 | an-381 | E1U5265 | sp-17 | an-381 | E1U12591 | sp-39 | an-381 |
| E1A5266 | sp-16 | an-382 | E1U5266 | sp-17 | an-382 | E1U12592 | sp-39 | an-382 |
| E1A5267 | sp-16 | an-383 | E1U5267 | sp-17 | an-383 | E1U12593 | sp-39 | an-383 |
| E1A5268 | sp-16 | an-384 | E1U5268 | sp-17 | an-384 | E1U12594 | sp-39 | an-384 |
| E1A5269 | sp-16 | an-385 | E1U5269 | sp-17 | an-385 | E1U12595 | sp-39 | an-385 |
| E1A5270 | sp-16 | an-386 | E1U5270 | sp-17 | an-386 | E1U12596 | sp-39 | an-386 |
| E1A5271 | sp-16 | an-387 | E1U5271 | sp-17 | an-387 | E1U12597 | sp-39 | an-387 |
| E1A5272 | sp-16 | an-388 | E1U5272 | sp-17 | an-388 | E1U12598 | sp-39 | an-388 |
| E1A5273 | sp-16 | an-389 | E1U5273 | sp-17 | an-389 | E1U12599 | sp-39 | an-389 |
| E1A5274 | sp-16 | an-390 | E1U5274 | sp-17 | an-390 | E1U12600 | sp-39 | an-390 |

-continued

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| E1A5275 | sp-16 | an-391 | E1U5275 | sp-17 | an-391 | E1U12601 | sp-39 | an-391 |
| E1A5276 | sp-16 | an-392 | E1U5276 | sp-17 | an-392 | E1U12602 | sp-39 | an-392 |
| E1A5277 | sp-16 | an-393 | E1U5277 | sp-17 | an-393 | E1U12603 | sp-39 | an-393 |
| E1A5278 | sp-16 | an-394 | E1U5278 | sp-17 | an-394 | E1U12604 | sp-39 | an-394 |
| E1A5279 | sp-16 | an-395 | E1U5279 | sp-17 | an-395 | E1U12605 | sp-39 | an-395 |
| E1A5280 | sp-16 | an-396 | E1U5280 | sp-17 | an-396 | E1U12606 | sp-39 | an-396 |
| E1A5281 | sp-16 | an-397 | E1U5281 | sp-17 | an-397 | E1U12607 | sp-39 | an-397 |
| E1A5282 | sp-16 | an-398 | E1U5282 | sp-17 | an-398 | E1U12608 | sp-39 | an-398 |
| E1A5283 | sp-16 | an-399 | E1U5283 | sp-17 | an-399 | E1U12609 | sp-39 | an-399 |
| E1A5284 | sp-16 | an-400 | E1U5284 | sp-17 | an-400 | E1U12610 | sp-39 | an-400 |
| E1A5285 | sp-16 | an-401 | E1U5285 | sp-17 | an-401 | E1U12611 | sp-39 | an-401 |
| E1A5286 | sp-16 | an-402 | E1U5286 | sp-17 | an-402 | E1U12612 | sp-39 | an-402 |
| E1A5287 | sp-16 | an-403 | E1U5287 | sp-17 | an-403 | E1U12613 | sp-39 | an-403 |
| E1A5288 | sp-16 | an-404 | E1U5288 | sp-17 | an-404 | E1U12614 | sp-39 | an-404 |
| E1A5289 | sp-16 | an-405 | E1U5289 | sp-17 | an-405 | E1U12615 | sp-39 | an-405 |
| E1A5290 | sp-16 | an-406 | E1U5290 | sp-17 | an-406 | E1U12616 | sp-39 | an-406 |
| E1A5291 | sp-16 | an-407 | E1U5291 | sp-17 | an-407 | E1U12617 | sp-39 | an-407 |
| E1A5292 | sp-18 | an-1 | E1U5292 | sp-20 | an-1 | E1U12618 | sp-40 | an-1 |

Table 1-99

| Y = NHCS | | | Y = NHCSNH | | | Y = NHCSNH | | |
|---|---|---|---|---|---|---|---|---|
| E1A5293 | sp-18 | an-2 | E1U5293 | sp-20 | an-2 | E1U12619 | sp-40 | an-2 |
| E1A5294 | sp-18 | an-3 | E1U5294 | sp-20 | an-3 | E1U12620 | sp-40 | an-3 |
| E1A5295 | sp-18 | an-4 | E1U5295 | sp-20 | an-4 | E1U12621 | sp-40 | an-4 |
| E1A5296 | sp-18 | an-5 | E1U5296 | sp-20 | an-5 | E1U12622 | sp-40 | an-5 |
| E1A5297 | sp-18 | an-6 | E1U5297 | sp-20 | an-6 | E1U12623 | sp-40 | an-6 |
| E1A5298 | sp-18 | an-7 | E1U5298 | sp-20 | an-7 | E1U12624 | sp-40 | an-7 |
| E1A5299 | sp-18 | an-8 | E1U5299 | sp-20 | an-8 | E1U12625 | sp-40 | an-8 |
| E1A5300 | sp-18 | an-9 | E1U5300 | sp-20 | an-9 | E1U12626 | sp-40 | an-9 |
| E1A5301 | sp-18 | an-10 | E1U5301 | sp-20 | an-10 | E1U12627 | sp-40 | an-10 |
| E1A5302 | sp-18 | an-11 | E1U5302 | sp-20 | an-11 | E1U12628 | sp-40 | an-11 |
| E1A5303 | sp-18 | an-12 | E1U5303 | sp-20 | an-12 | E1U12629 | sp-40 | an-12 |
| E1A5304 | sp-18 | an-13 | E1U5304 | sp-20 | an-13 | E1U12630 | sp-40 | an-13 |
| E1A5305 | sp-18 | an-14 | E1U5305 | sp-20 | an-14 | E1U12631 | sp-40 | an-14 |
| E1A5306 | sp-18 | an-15 | E1U5306 | sp-20 | an-15 | E1U12632 | sp-40 | an-15 |
| E1A5307 | sp-18 | an-16 | E1U5307 | sp-20 | an-16 | E1U12633 | sp-40 | an-16 |
| E1A5308 | sp-18 | an-17 | E1U5308 | sp-20 | an-17 | E1U12634 | sp-40 | an-17 |
| E1A5309 | sp-18 | an-18 | E1U5309 | sp-20 | an-18 | E1U12635 | sp-40 | an-18 |
| E1A5310 | sp-18 | an-19 | E1U5310 | sp-20 | an-19 | E1U12636 | sp-40 | an-19 |
| E1A5311 | sp-18 | an-20 | E1U5311 | sp-20 | an-20 | E1U12637 | sp-40 | an-20 |
| E1A5312 | sp-18 | an-21 | E1U5312 | sp-20 | an-21 | E1U12638 | sp-40 | an-21 |
| E1A5313 | sp-18 | an-22 | E1U5313 | sp-20 | an-22 | E1U12639 | sp-40 | an-22 |
| E1A5314 | sp-18 | an-23 | E1U5314 | sp-20 | an-23 | E1U12640 | sp-40 | an-23 |
| E1A5315 | sp-18 | an-24 | E1U5315 | sp-20 | an-24 | E1U12641 | sp-40 | an-24 |
| E1A5316 | sp-18 | an-25 | E1U5316 | sp-20 | an-25 | E1U12642 | sp-40 | an-25 |
| E1A5317 | sp-18 | an-26 | E1U5317 | sp-20 | an-26 | E1U12643 | sp-40 | an-26 |
| E1A5318 | sp-18 | an-27 | E1U5318 | sp-20 | an-27 | E1U12644 | sp-40 | an-27 |
| E1A5319 | sp-18 | an-28 | E1U5319 | sp-20 | an-28 | E1U12645 | sp-40 | an-28 |
| E1A5320 | sp-18 | an-29 | E1U5320 | sp-20 | an-29 | E1U12646 | sp-40 | an-29 |
| E1A5321 | sp-18 | an-30 | E1U5321 | sp-20 | an-30 | E1U12647 | sp-40 | an-30 |
| E1A5322 | sp-18 | an-31 | E1U5322 | sp-20 | an-31 | E1U12648 | sp-40 | an-31 |
| E1A5323 | sp-18 | an-32 | E1U5323 | sp-20 | an-32 | E1U12649 | sp-40 | an-32 |
| E1A5324 | sp-18 | an-33 | E1U5324 | sp-20 | an-33 | E1U12650 | sp-40 | an-33 |
| E1A5325 | sp-18 | an-34 | E1U5325 | sp-20 | an-34 | E1U12651 | sp-40 | an-34 |
| E1A5326 | sp-18 | an-35 | E1U5326 | sp-20 | an-35 | E1U12652 | sp-40 | an-35 |
| E1A5327 | sp-18 | an-36 | E1U5327 | sp-20 | an-36 | E1U12653 | sp-40 | an-36 |
| E1A5328 | sp-18 | an-37 | E1U5328 | sp-20 | an-37 | E1U12654 | sp-40 | an-37 |
| E1A5329 | sp-18 | an-38 | E1U5329 | sp-20 | an-38 | E1U12655 | sp-40 | an-38 |
| E1A5330 | sp-18 | an-39 | E1U5330 | sp-20 | an-39 | E1U12656 | sp-40 | an-39 |
| E1A5331 | sp-18 | an-40 | E1U5331 | sp-20 | an-40 | E1U12657 | sp-40 | an-40 |
| E1A5332 | sp-18 | an-41 | E1U5332 | sp-20 | an-41 | E1U12658 | sp-40 | an-41 |
| E1A5333 | sp-18 | an-42 | E1U5333 | sp-20 | an-42 | E1U12659 | sp-40 | an-42 |
| E1A5334 | sp-18 | an-43 | E1U5334 | sp-20 | an-43 | E1U12660 | sp-40 | an-43 |
| E1A5335 | sp-18 | an-44 | E1U5335 | sp-20 | an-44 | E1U12661 | sp-40 | an-44 |
| E1A5336 | sp-18 | an-45 | E1U5336 | sp-20 | an-45 | E1U12662 | sp-40 | an-45 |
| E1A5337 | sp-18 | an-46 | E1U5337 | sp-20 | an-46 | E1U12663 | sp-40 | an-46 |
| E1A5338 | sp-18 | an-47 | E1U5338 | sp-20 | an-47 | E1U12664 | sp-40 | an-47 |
| E1A5339 | sp-18 | an-48 | E1U5339 | sp-20 | an-48 | E1U12665 | sp-40 | an-48 |
| E1A5340 | sp-18 | an-49 | E1U5340 | sp-20 | an-49 | E1U12666 | sp-40 | an-49 |
| E1A5341 | sp-18 | an-50 | E1U5341 | sp-20 | an-50 | E1U12667 | sp-40 | an-50 |
| E1A5342 | sp-18 | an-51 | E1U5342 | sp-20 | an-51 | E1U12668 | sp-40 | an-51 |
| E1A5343 | sp-18 | an-52 | E1U5343 | sp-20 | an-52 | E1U12669 | sp-40 | an-52 |
| E1A5344 | sp-18 | an-53 | E1U5344 | sp-20 | an-53 | E1U12670 | sp-40 | an-53 |
| E1A5345 | sp-18 | an-54 | E1U5345 | sp-20 | an-54 | E1U12671 | sp-40 | an-54 |
| E1A5346 | sp-18 | an-55 | E1U5346 | sp-20 | an-55 | E1U12672 | sp-40 | an-55 |

-continued

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| Table 1-100 ||||||||| 
| Y = NHCS ||| Y = NHCSNH ||| Y = NHCSNH |||
| E1A5347 | sp-18 | an-56 | E1U5347 | sp-20 | an-56 | E1U12673 | sp-40 | an-56 |
| E1A5348 | sp-18 | an-57 | E1U5348 | sp-20 | an-57 | E1U12674 | sp-40 | an-57 |
| E1A5349 | sp-18 | an-58 | E1U5349 | sp-20 | an-58 | E1U12675 | sp-40 | an-58 |
| E1A5350 | sp-18 | an-59 | E1U5350 | sp-20 | an-59 | E1U12676 | sp-40 | an-59 |
| E1A5351 | sp-18 | an-60 | E1U5351 | sp-20 | an-60 | E1U12677 | sp-40 | an-60 |
| E1A5352 | sp-18 | an-61 | E1U5352 | sp-20 | an-61 | E1U12678 | sp-40 | an-61 |
| E1A5353 | sp-18 | an-62 | E1U5353 | sp-20 | an-62 | E1U12679 | sp-40 | an-62 |
| E1A5354 | sp-18 | an-63 | E1U5354 | sp-20 | an-63 | E1U12680 | sp-40 | an-63 |
| E1A5355 | sp-18 | an-64 | E1U5355 | sp-20 | an-64 | E1U12681 | sp-40 | an-64 |
| E1A5356 | sp-18 | an-65 | E1U5356 | sp-20 | an-65 | E1U12682 | sp-40 | an-65 |
| E1A5357 | sp-18 | an-66 | E1U5357 | sp-20 | an-66 | E1U12683 | sp-40 | an-66 |
| E1A5358 | sp-18 | an-67 | E1U5358 | sp-20 | an-67 | E1U12684 | sp-40 | an-67 |
| E1A5359 | sp-18 | an-68 | E1U5359 | sp-20 | an-68 | E1U12685 | sp-40 | an-68 |
| E1A5360 | sp-18 | an-69 | E1U5360 | sp-20 | an-69 | E1U12686 | sp-40 | an-69 |
| E1A5361 | sp-18 | an-70 | E1U5361 | sp-20 | an-70 | E1U12687 | sp-40 | an-70 |
| E1A5362 | sp-18 | an-71 | E1U5362 | sp-20 | an-71 | E1U12688 | sp-40 | an-71 |
| E1A5363 | sp-18 | an-72 | E1U5363 | sp-20 | an-72 | E1U12689 | sp-40 | an-72 |
| E1A5364 | sp-18 | an-73 | E1U5364 | sp-20 | an-73 | E1U12690 | sp-40 | an-73 |
| E1A5365 | sp-18 | an-74 | E1U5365 | sp-20 | an-74 | E1U12691 | sp-40 | an-74 |
| E1A5366 | sp-18 | an-75 | E1U5366 | sp-20 | an-75 | E1U12692 | sp-40 | an-75 |
| E1A5367 | sp-18 | an-76 | E1U5367 | sp-20 | an-76 | E1U12693 | sp-40 | an-76 |
| E1A5368 | sp-18 | an-77 | E1U5368 | sp-20 | an-77 | E1U12694 | sp-40 | an-77 |
| E1A5369 | sp-18 | an-78 | E1U5369 | sp-20 | an-78 | E1U12695 | sp-40 | an-78 |
| E1A5370 | sp-18 | an-79 | E1U5370 | sp-20 | an-79 | E1U12696 | sp-40 | an-79 |
| E1A5371 | sp-18 | an-80 | E1U5371 | sp-20 | an-80 | E1U12697 | sp-40 | an-80 |
| E1A5372 | sp-18 | an-81 | E1U5372 | sp-20 | an-81 | E1U12698 | sp-40 | an-81 |
| E1A5373 | sp-18 | an-82 | E1U5373 | sp-20 | an-82 | E1U12699 | sp-40 | an-82 |
| E1A5374 | sp-18 | an-83 | E1U5374 | sp-20 | an-83 | E1U12700 | sp-40 | an-83 |
| E1A5375 | sp-18 | an-84 | E1U5375 | sp-20 | an-84 | E1U12701 | sp-40 | an-84 |
| E1A5376 | sp-18 | an-85 | E1U5376 | sp-20 | an-85 | E1U12702 | sp-40 | an-85 |
| E1A5377 | sp-18 | an-86 | E1U5377 | sp-20 | an-86 | E1U12703 | sp-40 | an-86 |
| E1A5378 | sp-18 | an-87 | E1U5378 | sp-20 | an-87 | E1U12704 | sp-40 | an-87 |
| E1A5379 | sp-18 | an-88 | E1U5379 | sp-20 | an-88 | E1U12705 | sp-40 | an-88 |
| E1A5380 | sp-18 | an-89 | E1U5380 | sp-20 | an-89 | E1U12706 | sp-40 | an-89 |
| E1A5381 | sp-18 | an-90 | E1U5381 | sp-20 | an-90 | E1U12707 | sp-40 | an-90 |
| E1A5382 | sp-18 | an-91 | E1U5382 | sp-20 | an-91 | E1U12708 | sp-40 | an-91 |
| E1A5383 | sp-18 | an-92 | E1U5383 | sp-20 | an-92 | E1U12709 | sp-40 | an-92 |
| E1A5384 | sp-18 | an-93 | E1U5384 | sp-20 | an-93 | E1U12710 | sp-40 | an-93 |
| E1A5385 | sp-18 | an-94 | E1U5385 | sp-20 | an-94 | E1U12711 | sp-40 | an-94 |
| E1A5386 | sp-18 | an-95 | E1U5386 | sp-20 | an-95 | E1U12712 | sp-40 | an-95 |
| E1A5387 | sp-18 | an-96 | E1U5387 | sp-20 | an-96 | E1U12713 | sp-40 | an-96 |
| E1A5388 | sp-18 | an-97 | E1U5388 | sp-20 | an-97 | E1U12714 | sp-40 | an-97 |
| E1A5389 | sp-18 | an-98 | E1U5389 | sp-20 | an-98 | E1U12715 | sp-40 | an-98 |
| E1A5390 | sp-18 | an-99 | E1U5390 | sp-20 | an-99 | E1U12716 | sp-40 | an-99 |
| E1A5391 | sp-18 | an-100 | E1U5391 | sp-20 | an-100 | E1U12717 | sp-40 | an-100 |
| E1A5392 | sp-18 | an-101 | E1U5392 | sp-20 | an-101 | E1U12718 | sp-40 | an-101 |
| E1A5393 | sp-18 | an-102 | E1U5393 | sp-20 | an-102 | E1U12719 | sp-40 | an-102 |
| E1A5394 | sp-18 | an-103 | E1U5394 | sp-20 | an-103 | E1U12720 | sp-40 | an-103 |
| E1A5395 | sp-18 | an-104 | E1U5395 | sp-20 | an-104 | E1U12721 | sp-40 | an-104 |
| E1A5396 | sp-18 | an-105 | E1U5396 | sp-20 | an-105 | E1U12722 | sp-40 | an-105 |
| E1A5397 | sp-18 | an-106 | E1U5397 | sp-20 | an-106 | E1U12723 | sp-40 | an-106 |
| E1A5398 | sp-18 | an-107 | E1U5398 | sp-20 | an-107 | E1U12724 | sp-40 | an-107 |
| E1A5399 | sp-18 | an-108 | E1U5399 | sp-20 | an-108 | E1U12725 | sp-40 | an-108 |
| E1A5400 | sp-18 | an-109 | E1U5400 | sp-20 | an-109 | E1U12726 | sp-40 | an-109 |
| Table 1-101 |||||||||
| Y = NHCS ||| Y = NHCSNH ||| Y = NHCSNH |||
| E1A5401 | sp-18 | an-110 | E1U5401 | sp-20 | an-110 | E1U12727 | sp-40 | an-110 |
| E1A5402 | sp-18 | an-111 | E1U5402 | sp-20 | an-111 | E1U12728 | sp-40 | an-111 |
| E1A5403 | sp-18 | an-112 | E1U5403 | sp-20 | an-112 | E1U12729 | sp-40 | an-112 |
| E1A5404 | sp-18 | an-113 | E1U5404 | sp-20 | an-113 | E1U12730 | sp-40 | an-113 |
| E1A5405 | sp-18 | an-114 | E1U5405 | sp-20 | an-114 | E1U12731 | sp-40 | an-114 |
| E1A5406 | sp-18 | an-115 | E1U5406 | sp-20 | an-115 | E1U12732 | sp-40 | an-115 |
| E1A5407 | sp-18 | an-116 | E1U5407 | sp-20 | an-116 | E1U12733 | sp-40 | an-116 |
| E1A5408 | sp-18 | an-117 | E1U5408 | sp-20 | an-117 | E1U12734 | sp-40 | an-117 |
| E1A5409 | sp-18 | an-118 | E1U5409 | sp-20 | an-118 | E1U12735 | sp-40 | an-118 |
| E1A5410 | sp-18 | an-119 | E1U5410 | sp-20 | an-119 | E1U12736 | sp-40 | an-119 |
| E1A5411 | sp-18 | an-120 | E1U5411 | sp-20 | an-120 | E1U12737 | sp-40 | an-120 |
| E1A5412 | sp-18 | an-121 | E1U5412 | sp-20 | an-121 | E1U12738 | sp-40 | an-121 |
| E1A5413 | sp-18 | an-122 | E1U5413 | sp-20 | an-122 | E1U12739 | sp-40 | an-122 |
| E1A5414 | sp-18 | an-123 | E1U5414 | sp-20 | an-123 | E1U12740 | sp-40 | an-123 |
| E1A5415 | sp-18 | an-124 | E1U5415 | sp-20 | an-124 | E1U12741 | sp-40 | an-124 |
| E1A5416 | sp-18 | an-125 | E1U5416 | sp-20 | an-125 | E1U12742 | sp-40 | an-125 |

-continued

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| E1A5417 | sp-18 | an-126 | E1U5417 | sp-20 | an-126 | E1U12743 | sp-40 | an-126 |
| E1A5418 | sp-18 | an-127 | E1U5418 | sp-20 | an-127 | E1U12744 | sp-40 | an-127 |
| E1A5419 | sp-18 | an-128 | E1U5419 | sp-20 | an-128 | E1U12745 | sp-40 | an-128 |
| E1A5420 | sp-18 | an-129 | E1U5420 | sp-20 | an-129 | E1U12746 | sp-40 | an-129 |
| E1A5421 | sp-18 | an-130 | E1U5421 | sp-20 | an-130 | E1U12747 | sp-40 | an-130 |
| E1A5422 | sp-18 | an-131 | E1U5422 | sp-20 | an-131 | E1U12748 | sp-40 | an-131 |
| E1A5423 | sp-18 | an-132 | E1U5423 | sp-20 | an-132 | E1U12749 | sp-40 | an-132 |
| E1A5424 | sp-18 | an-133 | E1U5424 | sp-20 | an-133 | E1U12750 | sp-40 | an-133 |
| E1A5425 | sp-18 | an-134 | E1U5425 | sp-20 | an-134 | E1U12751 | sp-40 | an-134 |
| E1A5426 | sp-18 | an-135 | E1U5426 | sp-20 | an-135 | E1U12752 | sp-40 | an-135 |
| E1A5427 | sp-18 | an-136 | E1U5427 | sp-20 | an-136 | E1U12753 | sp-40 | an-136 |
| E1A5428 | sp-18 | an-137 | E1U5428 | sp-20 | an-137 | E1U12754 | sp-40 | an-137 |
| E1A5429 | sp-18 | an-138 | E1U5429 | sp-20 | an-138 | E1U12755 | sp-40 | an-138 |
| E1A5430 | sp-18 | an-139 | E1U5430 | sp-20 | an-139 | E1U12756 | sp-40 | an-139 |
| E1A5431 | sp-18 | an-140 | E1U5431 | sp-20 | an-140 | E1U12757 | sp-40 | an-140 |
| E1A5432 | sp-18 | an-141 | E1U5432 | sp-20 | an-141 | E1U12758 | sp-40 | an-141 |
| E1A5433 | sp-18 | an-142 | E1U5433 | sp-20 | an-142 | E1U12759 | sp-40 | an-142 |
| E1A5434 | sp-18 | an-143 | E1U5434 | sp-20 | an-143 | E1U12760 | sp-40 | an-143 |
| E1A5435 | sp-18 | an-144 | E1U5435 | sp-20 | an-144 | E1U12761 | sp-40 | an-144 |
| E1A5436 | sp-18 | an-145 | E1U5436 | sp-20 | an-145 | E1U12762 | sp-40 | an-145 |
| E1A5437 | sp-18 | an-146 | E1U5437 | sp-20 | an-146 | E1U12763 | sp-40 | an-146 |
| E1A5438 | sp-18 | an-147 | E1U5438 | sp-20 | an-147 | E1U12764 | sp-40 | an-147 |
| E1A5439 | sp-18 | an-148 | E1U5439 | sp-20 | an-148 | E1U12765 | sp-40 | an-148 |
| E1A5440 | sp-18 | an-149 | E1U5440 | sp-20 | an-149 | E1U12766 | sp-40 | an-149 |
| E1A5441 | sp-18 | an-150 | E1U5441 | sp-20 | an-150 | E1U12767 | sp-40 | an-150 |
| E1A5442 | sp-18 | an-151 | E1U5442 | sp-20 | an-151 | E1U12768 | sp-40 | an-151 |
| E1A5443 | sp-18 | an-152 | E1U5443 | sp-20 | an-152 | E1U12769 | sp-40 | an-152 |
| E1A5444 | sp-18 | an-153 | E1U5444 | sp-20 | an-153 | E1U12770 | sp-40 | an-153 |
| E1A5445 | sp-18 | an-154 | E1U5445 | sp-20 | an-154 | E1U12771 | sp-40 | an-154 |
| E1A5446 | sp-18 | an-155 | E1U5446 | sp-20 | an-155 | E1U12772 | sp-40 | an-155 |
| E1A5447 | sp-18 | an-156 | E1U5447 | sp-20 | an-156 | E1U12773 | sp-40 | an-156 |
| E1A5448 | sp-18 | an-157 | E1U5448 | sp-20 | an-157 | E1U12774 | sp-40 | an-157 |
| E1A5449 | sp-18 | an-158 | E1U5449 | sp-20 | an-158 | E1U12775 | sp-40 | an-158 |
| E1A5450 | sp-18 | an-159 | E1U5450 | sp-20 | an-159 | E1U12776 | sp-40 | an-159 |
| E1A5451 | sp-18 | an-160 | E1U5451 | sp-20 | an-160 | E1U12777 | sp-40 | an-160 |
| E1A5452 | sp-18 | an-161 | E1U5452 | sp-20 | an-161 | E1U12778 | sp-40 | an-161 |
| E1A5453 | sp-18 | an-162 | E1U5453 | sp-20 | an-162 | E1U12779 | sp-40 | an-162 |
| E1A5454 | sp-18 | an-163 | E1U5454 | sp-20 | an-163 | E1U12780 | sp-40 | an-163 |

Table 1-102

| Y = NHCS | | | Y = NHCSNH | | | Y = NHCSNH | | |
|---|---|---|---|---|---|---|---|---|
| E1A5455 | sp-18 | an-164 | E1U5455 | sp-20 | an-164 | E1U12781 | sp-40 | an-164 |
| E1A5456 | sp-18 | an-165 | E1U5456 | sp-20 | an-165 | E1U12782 | sp-40 | an-165 |
| E1A5457 | sp-18 | an-166 | E1U5457 | sp-20 | an-166 | E1U12783 | sp-40 | an-166 |
| E1A5458 | sp-18 | an-167 | E1U5458 | sp-20 | an-167 | E1U12784 | sp-40 | an-167 |
| E1A5459 | sp-18 | an-168 | E1U5459 | sp-20 | an-168 | E1U12785 | sp-40 | an-168 |
| E1A5460 | sp-18 | an-169 | E1U5460 | sp-20 | an-169 | E1U12786 | sp-40 | an-169 |
| E1A5461 | sp-18 | an-170 | E1U5461 | sp-20 | an-170 | E1U12787 | sp-40 | an-170 |
| E1A5462 | sp-18 | an-171 | E1U5462 | sp-20 | an-171 | E1U12788 | sp-40 | an-171 |
| E1A5463 | sp-18 | an-172 | E1U5463 | sp-20 | an-172 | E1U12789 | sp-40 | an-172 |
| E1A5464 | sp-18 | an-173 | E1U5464 | sp-20 | an-173 | E1U12790 | sp-40 | an-173 |
| E1A5465 | sp-18 | an-174 | E1U5465 | sp-20 | an-174 | E1U12791 | sp-40 | an-174 |
| E1A5466 | sp-18 | an-175 | E1U5466 | sp-20 | an-175 | E1U12792 | sp-40 | an-175 |
| E1A5467 | sp-18 | an-176 | E1U5467 | sp-20 | an-176 | E1U12793 | sp-40 | an-176 |
| E1A5468 | sp-18 | an-177 | E1U5468 | sp-20 | an-177 | E1U12794 | sp-40 | an-177 |
| E1A5469 | sp-18 | an-178 | E1U5469 | sp-20 | an-178 | E1U12795 | sp-40 | an-178 |
| E1A5470 | sp-18 | an-179 | E1U5470 | sp-20 | an-179 | E1U12796 | sp-40 | an-179 |
| E1A5471 | sp-18 | an-180 | E1U5471 | sp-20 | an-180 | E1U12797 | sp-40 | an-180 |
| E1A5472 | sp-18 | an-181 | E1U5472 | sp-20 | an-181 | E1U12798 | sp-40 | an-181 |
| E1A5473 | sp-18 | an-182 | E1U5473 | sp-20 | an-182 | E1U12799 | sp-40 | an-182 |
| E1A5474 | sp-18 | an-183 | E1U5474 | sp-20 | an-183 | E1U12800 | sp-40 | an-183 |
| E1A5475 | sp-18 | an-184 | E1U5475 | sp-20 | an-184 | E1U12801 | sp-40 | an-184 |
| E1A5476 | sp-18 | an-185 | E1U5476 | sp-20 | an-185 | E1U12802 | sp-40 | an-185 |
| E1A5477 | sp-18 | an-186 | E1U5477 | sp-20 | an-186 | E1U12803 | sp-40 | an-186 |
| E1A5478 | sp-18 | an-187 | E1U5478 | sp-20 | an-187 | E1U12804 | sp-40 | an-187 |
| E1A5479 | sp-18 | an-188 | E1U5479 | sp-20 | an-188 | E1U12805 | sp-40 | an-188 |
| E1A5480 | sp-18 | an-189 | E1U5480 | sp-20 | an-189 | E1U12806 | sp-40 | an-189 |
| E1A5481 | sp-18 | an-190 | E1U5481 | sp-20 | an-190 | E1U12807 | sp-40 | an-190 |
| E1A5482 | sp-18 | an-191 | E1U5482 | sp-20 | an-191 | E1U12808 | sp-40 | an-191 |
| E1A5483 | sp-18 | an-192 | E1U5483 | sp-20 | an-192 | E1U12809 | sp-40 | an-192 |
| E1A5484 | sp-18 | an-193 | E1U5484 | sp-20 | an-193 | E1U12810 | sp-40 | an-193 |
| E1A5485 | sp-18 | an-194 | E1U5485 | sp-20 | an-194 | E1U12811 | sp-40 | an-194 |
| E1A5486 | sp-18 | an-195 | E1U5486 | sp-20 | an-195 | E1U12812 | sp-40 | an-195 |
| E1A5487 | sp-18 | an-196 | E1U5487 | sp-20 | an-196 | E1U12813 | sp-40 | an-196 |
| E1A5488 | sp-18 | an-197 | E1U5488 | sp-20 | an-197 | E1U12814 | sp-40 | an-197 |
| E1A5489 | sp-18 | an-198 | E1U5489 | sp-20 | an-198 | E1U12815 | sp-40 | an-198 |
| E1A5490 | sp-18 | an-199 | E1U5490 | sp-20 | an-199 | E1U12816 | sp-40 | an-199 |

-continued

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| E1A5491 | sp-18 | an-200 | E1U5491 | sp-20 | an-200 | E1U12817 | sp-40 | an-200 |
| E1A5492 | sp-18 | an-201 | E1U5492 | sp-20 | an-201 | E1U12818 | sp-40 | an-201 |
| E1A5493 | sp-18 | an-202 | E1U5493 | sp-20 | an-202 | E1U12819 | sp-40 | an-202 |
| E1A5494 | sp-18 | an-203 | E1U5494 | sp-20 | an-203 | E1U12820 | sp-40 | an-203 |
| E1A5495 | sp-18 | an-204 | E1U5495 | sp-20 | an-204 | E1U12821 | sp-40 | an-204 |
| E1A5496 | sp-18 | an-205 | E1U5496 | sp-20 | an-205 | E1U12822 | sp-40 | an-205 |
| E1A5497 | sp-18 | an-206 | E1U5497 | sp-20 | an-206 | E1U12823 | sp-40 | an-206 |
| E1A5498 | sp-18 | an-207 | E1U5498 | sp-20 | an-207 | E1U12824 | sp-40 | an-207 |
| E1A5499 | sp-18 | an-208 | E1U5499 | sp-20 | an-208 | E1U12825 | sp-40 | an-208 |
| E1A5500 | sp-18 | an-209 | E1U5500 | sp-20 | an-209 | E1U12826 | sp-40 | an-209 |
| E1A5501 | sp-18 | an-210 | E1U5501 | sp-20 | an-210 | E1U12827 | sp-40 | an-210 |
| E1A5502 | sp-18 | an-211 | E1U5502 | sp-20 | an-211 | E1U12828 | sp-40 | an-211 |
| E1A5503 | sp-18 | an-212 | E1U5503 | sp-20 | an-212 | E1U12829 | sp-40 | an-212 |
| E1A5504 | sp-18 | an-213 | E1U5504 | sp-20 | an-213 | E1U12830 | sp-40 | an-213 |
| E1A5505 | sp-18 | an-214 | E1U5505 | sp-20 | an-214 | E1U12831 | sp-40 | an-214 |
| E1A5506 | sp-18 | an-215 | E1U5506 | sp-20 | an-215 | E1U12832 | sp-40 | an-215 |
| E1A5507 | sp-18 | an-216 | E1U5507 | sp-20 | an-216 | E1U12833 | sp-40 | an-216 |
| E1A5508 | sp-18 | an-217 | E1U5508 | sp-20 | an-217 | E1U12834 | sp-40 | an-217 |

Table 1-103

| Y = NHCS | | | Y = NHCSNH | | | Y = NHCSNH | | |
|---|---|---|---|---|---|---|---|---|
| E1A5509 | sp-18 | an-218 | E1U5509 | sp-20 | an-218 | E1U12835 | sp-40 | an-218 |
| E1A5510 | sp-18 | an-219 | E1U5510 | sp-20 | an-219 | E1U12836 | sp-40 | an-219 |
| E1A5511 | sp-18 | an-220 | E1U5511 | sp-20 | an-220 | E1U12837 | sp-40 | an-220 |
| E1A5512 | sp-18 | an-221 | E1U5512 | sp-20 | an-221 | E1U12838 | sp-40 | an-221 |
| E1A5513 | sp-18 | an-222 | E1U5513 | sp-20 | an-222 | E1U12839 | sp-40 | an-222 |
| E1A5514 | sp-18 | an-223 | E1U5514 | sp-20 | an-223 | E1U12840 | sp-40 | an-223 |
| E1A5515 | sp-18 | an-224 | E1U5515 | sp-20 | an-224 | E1U12841 | sp-40 | an-224 |
| E1A5516 | sp-18 | an-225 | E1U5516 | sp-20 | an-225 | E1U12842 | sp-40 | an-225 |
| E1A5517 | sp-18 | an-226 | E1U5517 | sp-20 | an-226 | E1U12843 | sp-40 | an-226 |
| E1A5518 | sp-18 | an-227 | E1U5518 | sp-20 | an-227 | E1U12844 | sp-40 | an-227 |
| E1A5519 | sp-18 | an-228 | E1U5519 | sp-20 | an-228 | E1U12845 | sp-40 | an-228 |
| E1A5520 | sp-18 | an-229 | E1U5520 | sp-20 | an-229 | E1U12846 | sp-40 | an-229 |
| E1A5521 | sp-18 | an-230 | E1U5521 | sp-20 | an-230 | E1U12847 | sp-40 | an-230 |
| E1A5522 | sp-18 | an-231 | E1U5522 | sp-20 | an-231 | E1U12848 | sp-40 | an-231 |
| E1A5523 | sp-18 | an-232 | E1U5523 | sp-20 | an-232 | E1U12849 | sp-40 | an-232 |
| E1A5524 | sp-18 | an-233 | E1U5524 | sp-20 | an-233 | E1U12850 | sp-40 | an-233 |
| E1A5525 | sp-18 | an-234 | E1U5525 | sp-20 | an-234 | E1U12851 | sp-40 | an-234 |
| E1A5526 | sp-18 | an-235 | E1U5526 | sp-20 | an-235 | E1U12852 | sp-40 | an-235 |
| E1A5527 | sp-18 | an-236 | E1U5527 | sp-20 | an-236 | E1U12853 | sp-40 | an-236 |
| E1A5528 | sp-18 | an-237 | E1U5528 | sp-20 | an-237 | E1U12854 | sp-40 | an-237 |
| E1A5529 | sp-18 | an-238 | E1U5529 | sp-20 | an-238 | E1U12855 | sp-40 | an-238 |
| E1A5530 | sp-18 | an-239 | E1U5530 | sp-20 | an-239 | E1U12856 | sp-40 | an-239 |
| E1A5531 | sp-18 | an-240 | E1U5531 | sp-20 | an-240 | E1U12857 | sp-40 | an-240 |
| E1A5532 | sp-18 | an-241 | E1U5532 | sp-20 | an-241 | E1U12858 | sp-40 | an-241 |
| E1A5533 | sp-18 | an-242 | E1U5533 | sp-20 | an-242 | E1U12859 | sp-40 | an-242 |
| E1A5534 | sp-18 | an-243 | E1U5534 | sp-20 | an-243 | E1U12860 | sp-40 | an-243 |
| E1A5535 | sp-18 | an-244 | E1U5535 | sp-20 | an-244 | E1U12861 | sp-40 | an-244 |
| E1A5536 | sp-18 | an-245 | E1U5536 | sp-20 | an-245 | E1U12862 | sp-40 | an-245 |
| E1A5537 | sp-18 | an-246 | E1U5537 | sp-20 | an-246 | E1U12863 | sp-40 | an-246 |
| E1A5538 | sp-18 | an-247 | E1U5538 | sp-20 | an-247 | E1U12864 | sp-40 | an-247 |
| E1A5539 | sp-18 | an-248 | E1U5539 | sp-20 | an-248 | E1U12865 | sp-40 | an-248 |
| E1A5540 | sp-18 | an-249 | E1U5540 | sp-20 | an-249 | E1U12866 | sp-40 | an-249 |
| E1A5541 | sp-18 | an-250 | E1U5541 | sp-20 | an-250 | E1U12867 | sp-40 | an-250 |
| E1A5542 | sp-18 | an-251 | E1U5542 | sp-20 | an-251 | E1U12868 | sp-40 | an-251 |
| E1A5543 | sp-18 | an-252 | E1U5543 | sp-20 | an-252 | E1U12869 | sp-40 | an-252 |
| E1A5544 | sp-18 | an-253 | E1U5544 | sp-20 | an-253 | E1U12870 | sp-40 | an-253 |
| E1A5545 | sp-18 | an-254 | E1U5545 | sp-20 | an-254 | E1U12871 | sp-40 | an-254 |
| E1A5546 | sp-18 | an-255 | E1U5546 | sp-20 | an-255 | E1U12872 | sp-40 | an-255 |
| E1A5547 | sp-18 | an-256 | E1U5547 | sp-20 | an-256 | E1U12873 | sp-40 | an-256 |
| E1A5548 | sp-18 | an-257 | E1U5548 | sp-20 | an-257 | E1U12874 | sp-40 | an-257 |
| E1A5549 | sp-18 | an-258 | E1U5549 | sp-20 | an-258 | E1U12875 | sp-40 | an-258 |
| E1A5550 | sp-18 | an-259 | E1U5550 | sp-20 | an-259 | E1U12876 | sp-40 | an-259 |
| E1A5551 | sp-18 | an-260 | E1U5551 | sp-20 | an-260 | E1U12877 | sp-40 | an-260 |
| E1A5552 | sp-18 | an-261 | E1U5552 | sp-20 | an-261 | E1U12878 | sp-40 | an-261 |
| E1A5553 | sp-18 | an-262 | E1U5553 | sp-20 | an-262 | E1U12879 | sp-40 | an-262 |
| E1A5554 | sp-18 | an-263 | E1U5554 | sp-20 | an-263 | E1U12880 | sp-40 | an-263 |
| E1A5555 | sp-18 | an-264 | E1U5555 | sp-20 | an-264 | E1U12881 | sp-40 | an-264 |
| E1A5556 | sp-18 | an-265 | E1U5556 | sp-20 | an-265 | E1U12882 | sp-40 | an-265 |
| E1A5557 | sp-18 | an-266 | E1U5557 | sp-20 | an-266 | E1U12883 | sp-40 | an-266 |
| E1A5558 | sp-18 | an-267 | E1U5558 | sp-20 | an-267 | E1U12884 | sp-40 | an-267 |
| E1A5559 | sp-18 | an-268 | E1U5559 | sp-20 | an-268 | E1U12885 | sp-40 | an-268 |
| E1A5560 | sp-18 | an-269 | E1U5560 | sp-20 | an-269 | E1U12886 | sp-40 | an-269 |
| E1A5561 | sp-18 | an-270 | E1U5561 | sp-20 | an-270 | E1U12887 | sp-40 | an-270 |
| E1A5562 | sp-18 | an-271 | E1U5562 | sp-20 | an-271 | E1U12888 | sp-40 | an-271 |

Table 1-104

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| Y = NHCS | | | Y = NHCSNH | | | Y = NHCSNH | | |
| E1A5563 | sp-18 | an-272 | E1U5563 | sp-20 | an-272 | E1U12889 | sp-40 | an-272 |
| E1A5564 | sp-18 | an-273 | E1U5564 | sp-20 | an-273 | E1U12890 | sp-40 | an-273 |
| E1A5565 | sp-18 | an-274 | E1U5565 | sp-20 | an-274 | E1U12891 | sp-40 | an-274 |
| E1A5566 | sp-18 | an-275 | E1U5566 | sp-20 | an-275 | E1U12892 | sp-40 | an-275 |
| E1A5567 | sp-18 | an-276 | E1U5567 | sp-20 | an-276 | E1U12893 | sp-40 | an-276 |
| E1A5568 | sp-18 | an-277 | E1U5568 | sp-20 | an-277 | E1U12894 | sp-40 | an-277 |
| E1A5569 | sp-18 | an-278 | E1U5569 | sp-20 | an-278 | E1U12895 | sp-40 | an-278 |
| E1A5570 | sp-18 | an-279 | E1U5570 | sp-20 | an-279 | E1U12896 | sp-40 | an-279 |
| E1A5571 | sp-18 | an-280 | E1U5571 | sp-20 | an-280 | E1U12897 | sp-40 | an-280 |
| E1A5572 | sp-18 | an-281 | E1U5572 | sp-20 | an-281 | E1U12898 | sp-40 | an-281 |
| E1A5573 | sp-18 | an-282 | E1U5573 | sp-20 | an-282 | E1U12899 | sp-40 | an-282 |
| E1A5574 | sp-18 | an-283 | E1U5574 | sp-20 | an-283 | E1U12900 | sp-40 | an-283 |
| E1A5575 | sp-18 | an-284 | E1U5575 | sp-20 | an-284 | E1U12901 | sp-40 | an-284 |
| E1A5576 | sp-18 | an-285 | E1U5576 | sp-20 | an-285 | E1U12902 | sp-40 | an-285 |
| E1A5577 | sp-18 | an-286 | E1U5577 | sp-20 | an-286 | E1U12903 | sp-40 | an-286 |
| E1A5578 | sp-18 | an-287 | E1U5578 | sp-20 | an-287 | E1U12904 | sp-40 | an-287 |
| E1A5579 | sp-18 | an-288 | E1U5579 | sp-20 | an-288 | E1U12905 | sp-40 | an-288 |
| E1A5580 | sp-18 | an-289 | E1U5580 | sp-20 | an-289 | E1U12906 | sp-40 | an-289 |
| E1A5581 | sp-18 | an-290 | E1U5581 | sp-20 | an-290 | E1U12907 | sp-40 | an-290 |
| E1A5582 | sp-18 | an-291 | E1U5582 | sp-20 | an-291 | E1U12908 | sp-40 | an-291 |
| E1A5583 | sp-18 | an-292 | E1U5583 | sp-20 | an-292 | E1U12909 | sp-40 | an-292 |
| E1A5584 | sp-18 | an-293 | E1U5584 | sp-20 | an-293 | E1U12910 | sp-40 | an-293 |
| E1A5585 | sp-18 | an-294 | E1U5585 | sp-20 | an-294 | E1U12911 | sp-40 | an-294 |
| E1A5586 | sp-18 | an-295 | E1U5586 | sp-20 | an-295 | E1U12912 | sp-40 | an-295 |
| E1A5587 | sp-18 | an-296 | E1U5587 | sp-20 | an-296 | E1U12913 | sp-40 | an-296 |
| E1A5588 | sp-18 | an-297 | E1U5588 | sp-20 | an-297 | E1U12914 | sp-40 | an-297 |
| E1A5589 | sp-18 | an-298 | E1U5589 | sp-20 | an-298 | E1U12915 | sp-40 | an-298 |
| E1A5590 | sp-18 | an-299 | E1U5590 | sp-20 | an-299 | E1U12916 | sp-40 | an-299 |
| E1A5591 | sp-18 | an-300 | E1U5591 | sp-20 | an-300 | E1U12917 | sp-40 | an-300 |
| E1A5592 | sp-18 | an-301 | E1U5592 | sp-20 | an-301 | E1U12918 | sp-40 | an-301 |
| E1A5593 | sp-18 | an-302 | E1U5593 | sp-20 | an-302 | E1U12919 | sp-40 | an-302 |
| E1A5594 | sp-18 | an-303 | E1U5594 | sp-20 | an-303 | E1U12920 | sp-40 | an-303 |
| E1A5595 | sp-18 | an-304 | E1U5595 | sp-20 | an-304 | E1U12921 | sp-40 | an-304 |
| E1A5596 | sp-18 | an-305 | E1U5596 | sp-20 | an-305 | E1U12922 | sp-40 | an-305 |
| E1A5597 | sp-18 | an-306 | E1U5597 | sp-20 | an-306 | E1U12923 | sp-40 | an-306 |
| E1A5598 | sp-18 | an-307 | E1U5598 | sp-20 | an-307 | E1U12924 | sp-40 | an-307 |
| E1A5599 | sp-18 | an-308 | E1U5599 | sp-20 | an-308 | E1U12925 | sp-40 | an-308 |
| E1A5600 | sp-18 | an-309 | E1U5600 | sp-20 | an-309 | E1U12926 | sp-40 | an-309 |
| E1A5601 | sp-18 | an-310 | E1U5601 | sp-20 | an-310 | E1U12927 | sp-40 | an-310 |
| E1A5602 | sp-18 | an-311 | E1U5602 | sp-20 | an-311 | E1U12928 | sp-40 | an-311 |
| E1A5603 | sp-18 | an-312 | E1U5603 | sp-20 | an-312 | E1U12929 | sp-40 | an-312 |
| E1A5604 | sp-18 | an-313 | E1U5604 | sp-20 | an-313 | E1U12930 | sp-40 | an-313 |
| E1A5605 | sp-18 | an-314 | E1U5605 | sp-20 | an-314 | E1U12931 | sp-40 | an-314 |
| E1A5606 | sp-18 | an-315 | E1U5606 | sp-20 | an-315 | E1U12932 | sp-40 | an-315 |
| E1A5607 | sp-18 | an-316 | E1U5607 | sp-20 | an-316 | E1U12933 | sp-40 | an-316 |
| E1A5608 | sp-18 | an-317 | E1U5608 | sp-20 | an-317 | E1U12934 | sp-40 | an-317 |
| E1A5609 | sp-18 | an-318 | E1U5609 | sp-20 | an-318 | E1U12935 | sp-40 | an-318 |
| E1A5610 | sp-18 | an-319 | E1U5610 | sp-20 | an-319 | E1U12936 | sp-40 | an-319 |
| E1A5611 | sp-18 | an-320 | E1U5611 | sp-20 | an-320 | E1U12937 | sp-40 | an-320 |
| E1A5612 | sp-18 | an-321 | E1U5612 | sp-20 | an-321 | E1U12938 | sp-40 | an-321 |
| E1A5613 | sp-18 | an-322 | E1U5613 | sp-20 | an-322 | E1U12939 | sp-40 | an-322 |
| E1A5614 | sp-18 | an-323 | E1U5614 | sp-20 | an-323 | E1U12940 | sp-40 | an-323 |
| E1A5615 | sp-18 | an-324 | E1U5615 | sp-20 | an-324 | E1U12941 | sp-40 | an-324 |
| E1A5616 | sp-18 | an-325 | E1U5616 | sp-20 | an-325 | E1U12942 | sp-40 | an-325 |

Table 1-105

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| Y = NHCS | | | Y = NHCSNH | | | Y = NHCSNH | | |
| E1A5617 | sp-18 | an-326 | E1U5617 | sp-20 | an-326 | E1U12943 | sp-40 | an-326 |
| E1A5618 | sp-18 | an-327 | E1U5618 | sp-20 | an-327 | E1U12944 | sp-40 | an-327 |
| E1A5619 | sp-18 | an-328 | E1U5619 | sp-20 | an-328 | E1U12945 | sp-40 | an-328 |
| E1A5620 | sp-18 | an-329 | E1U5620 | sp-20 | an-329 | E1U12946 | sp-40 | an-329 |
| E1A5621 | sp-18 | an-330 | E1U5621 | sp-20 | an-330 | E1U12947 | sp-40 | an-330 |
| E1A5622 | sp-18 | an-331 | E1U5622 | sp-20 | an-331 | E1U12948 | sp-40 | an-331 |
| E1A5623 | sp-18 | an-332 | E1U5623 | sp-20 | an-332 | E1U12949 | sp-40 | an-332 |
| E1A5624 | sp-18 | an-333 | E1U5624 | sp-20 | an-333 | E1U12950 | sp-40 | an-333 |
| E1A5625 | sp-18 | an-334 | E1U5625 | sp-20 | an-334 | E1U12951 | sp-40 | an-334 |
| E1A5626 | sp-18 | an-335 | E1U5626 | sp-20 | an-335 | E1U12952 | sp-40 | an-335 |
| E1A5627 | sp-18 | an-336 | E1U5627 | sp-20 | an-336 | E1U12953 | sp-40 | an-336 |
| E1A5628 | sp-18 | an-337 | E1U5628 | sp-20 | an-337 | E1U12954 | sp-40 | an-337 |
| E1A5629 | sp-18 | an-338 | E1U5629 | sp-20 | an-338 | E1U12955 | sp-40 | an-338 |
| E1A5630 | sp-18 | an-339 | E1U5630 | sp-20 | an-339 | E1U12956 | sp-40 | an-339 |
| E1A5631 | sp-18 | an-340 | E1U5631 | sp-20 | an-340 | E1U12957 | sp-40 | an-340 |
| E1A5632 | sp-18 | an-341 | E1U5632 | sp-20 | an-341 | E1U12958 | sp-40 | an-341 |

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| E1A5633 | sp-18 | an-342 | E1U5633 | sp-20 | an-342 | E1U12959 | sp-40 | an-342 |
| E1A5634 | sp-18 | an-343 | E1U5634 | sp-20 | an-343 | E1U12960 | sp-40 | an-343 |
| E1A5635 | sp-18 | an-344 | E1U5635 | sp-20 | an-344 | E1U12961 | sp-40 | an-344 |
| E1A5636 | sp-18 | an-345 | E1U5636 | sp-20 | an-345 | E1U12962 | sp-40 | an-345 |
| E1A5637 | sp-18 | an-346 | E1U5637 | sp-20 | an-346 | E1U12963 | sp-40 | an-346 |
| E1A5638 | sp-18 | an-347 | E1U5638 | sp-20 | an-347 | E1U12964 | sp-40 | an-347 |
| E1A5639 | sp-18 | an-348 | E1U5639 | sp-20 | an-348 | E1U12965 | sp-40 | an-348 |
| E1A5640 | sp-18 | an-349 | E1U5640 | sp-20 | an-349 | E1U12966 | sp-40 | an-349 |
| E1A5641 | sp-18 | an-350 | E1U5641 | sp-20 | an-350 | E1U12967 | sp-40 | an-350 |
| E1A5642 | sp-18 | an-351 | E1U5642 | sp-20 | an-351 | E1U12968 | sp-40 | an-351 |
| E1A5643 | sp-18 | an-352 | E1U5643 | sp-20 | an-352 | E1U12969 | sp-40 | an-352 |
| E1A5644 | sp-18 | an-353 | E1U5644 | sp-20 | an-353 | E1U12970 | sp-40 | an-353 |
| E1A5645 | sp-18 | an-354 | E1U5645 | sp-20 | an-354 | E1U12971 | sp-40 | an-354 |
| E1A5646 | sp-18 | an-355 | E1U5646 | sp-20 | an-355 | E1U12972 | sp-40 | an-355 |
| E1A5647 | sp-18 | an-356 | E1U5647 | sp-20 | an-356 | E1U12973 | sp-40 | an-356 |
| E1A5648 | sp-18 | an-357 | E1U5648 | sp-20 | an-357 | E1U12974 | sp-40 | an-357 |
| E1A5649 | sp-18 | an-358 | E1U5649 | sp-20 | an-358 | E1U12975 | sp-40 | an-358 |
| E1A5650 | sp-18 | an-359 | E1U5650 | sp-20 | an-359 | E1U12976 | sp-40 | an-359 |
| E1A5651 | sp-18 | an-360 | E1U5651 | sp-20 | an-360 | E1U12977 | sp-40 | an-360 |
| E1A5652 | sp-18 | an-361 | E1U5652 | sp-20 | an-361 | E1U12978 | sp-40 | an-361 |
| E1A5653 | sp-18 | an-362 | E1U5653 | sp-20 | an-362 | E1U12979 | sp-40 | an-362 |
| E1A5654 | sp-18 | an-363 | E1U5654 | sp-20 | an-363 | E1U12980 | sp-40 | an-363 |
| E1A5655 | sp-18 | an-364 | E1U5655 | sp-20 | an-364 | E1U12981 | sp-40 | an-364 |
| E1A5656 | sp-18 | an-365 | E1U5656 | sp-20 | an-365 | E1U12982 | sp-40 | an-365 |
| E1A5657 | sp-18 | an-366 | E1U5657 | sp-20 | an-366 | E1U12983 | sp-40 | an-366 |
| E1A5658 | sp-18 | an-367 | E1U5658 | sp-20 | an-367 | E1U12984 | sp-40 | an-367 |
| E1A5659 | sp-18 | an-368 | E1U5659 | sp-20 | an-368 | E1U12985 | sp-40 | an-368 |
| E1A5660 | sp-18 | an-369 | E1U5660 | sp-20 | an-369 | E1U12986 | sp-40 | an-369 |
| E1A5661 | sp-18 | an-370 | E1U5661 | sp-20 | an-370 | E1U12987 | sp-40 | an-370 |
| E1A5662 | sp-18 | an-371 | E1U5662 | sp-20 | an-371 | E1U12988 | sp-40 | an-371 |
| E1A5663 | sp-18 | an-372 | E1U5663 | sp-20 | an-372 | E1U12989 | sp-40 | an-372 |
| E1A5664 | sp-18 | an-373 | E1U5664 | sp-20 | an-373 | E1U12990 | sp-40 | an-373 |
| E1A5665 | sp-18 | an-374 | E1U5665 | sp-20 | an-374 | E1U12991 | sp-40 | an-374 |
| E1A5666 | sp-18 | an-375 | E1U5666 | sp-20 | an-375 | E1U12992 | sp-40 | an-375 |
| E1A5667 | sp-18 | an-376 | E1U5667 | sp-20 | an-376 | E1U12993 | sp-40 | an-376 |
| E1A5668 | sp-18 | an-377 | E1U5668 | sp-20 | an-377 | E1U12994 | sp-40 | an-377 |
| E1A5669 | sp-18 | an-378 | E1U5669 | sp-20 | an-378 | E1U12995 | sp-40 | an-378 |
| E1A5670 | sp-18 | an-379 | E1U5670 | sp-20 | an-379 | E1U12996 | sp-40 | an-379 |

Table 1-106

| Y = NHCS | | | Y = NHCSNH | | | Y = NHCSNH | | |
|---|---|---|---|---|---|---|---|---|
| E1A5671 | sp-18 | an-380 | E1U5671 | sp-20 | an-380 | E1U12997 | sp-40 | an-380 |
| E1A5672 | sp-18 | an-381 | E1U5672 | sp-20 | an-381 | E1U12998 | sp-40 | an-381 |
| E1A5673 | sp-18 | an-382 | E1U5673 | sp-20 | an-382 | E1U12999 | sp-40 | an-382 |
| E1A5674 | sp-18 | an-383 | E1U5674 | sp-20 | an-383 | E1U13000 | sp-40 | an-383 |
| E1A5675 | sp-18 | an-384 | E1U5675 | sp-20 | an-384 | E1U13001 | sp-40 | an-384 |
| E1A5676 | sp-18 | an-385 | E1U5676 | sp-20 | an-385 | E1U13002 | sp-40 | an-385 |
| E1A5677 | sp-18 | an-386 | E1U5677 | sp-20 | an-386 | E1U13003 | sp-40 | an-386 |
| E1A5678 | sp-18 | an-387 | E1U5678 | sp-20 | an-387 | E1U13004 | sp-40 | an-387 |
| E1A5679 | sp-18 | an-388 | E1U5679 | sp-20 | an-388 | E1U13005 | sp-40 | an-388 |
| E1A5680 | sp-18 | an-389 | E1U5680 | sp-20 | an-389 | E1U13006 | sp-40 | an-389 |
| E1A5681 | sp-18 | an-390 | E1U5681 | sp-20 | an-390 | E1U13007 | sp-40 | an-390 |
| E1A5682 | sp-18 | an-391 | E1U5682 | sp-20 | an-391 | E1U13008 | sp-40 | an-391 |
| E1A5683 | sp-18 | an-392 | E1U5683 | sp-20 | an-392 | E1U13009 | sp-40 | an-392 |
| E1A5684 | sp-18 | an-393 | E1U5684 | sp-20 | an-393 | E1U13010 | sp-40 | an-393 |
| E1A5685 | sp-18 | an-394 | E1U5685 | sp-20 | an-394 | E1U13011 | sp-40 | an-394 |
| E1A5686 | sp-18 | an-395 | E1U5686 | sp-20 | an-395 | E1U13012 | sp-40 | an-395 |
| E1A5687 | sp-18 | an-396 | E1U5687 | sp-20 | an-396 | E1U13013 | sp-40 | an-396 |
| E1A5688 | sp-18 | an-397 | E1U5688 | sp-20 | an-397 | E1U13014 | sp-40 | an-397 |
| E1A5689 | sp-18 | an-398 | E1U5689 | sp-20 | an-398 | E1U13015 | sp-40 | an-398 |
| E1A5690 | sp-18 | an-399 | E1U5690 | sp-20 | an-399 | E1U13016 | sp-40 | an-399 |
| E1A5691 | sp-18 | an-400 | E1U5691 | sp-20 | an-400 | E1U13017 | sp-40 | an-400 |
| E1A5692 | sp-18 | an-401 | E1U5692 | sp-20 | an-401 | E1U13018 | sp-40 | an-401 |
| E1A5693 | sp-18 | an-402 | E1U5693 | sp-20 | an-402 | E1U13019 | sp-40 | an-402 |
| E1A5694 | sp-18 | an-403 | E1U5694 | sp-20 | an-403 | E1U13020 | sp-40 | an-403 |
| E1A5695 | sp-18 | an-404 | E1U5695 | sp-20 | an-404 | E1U13021 | sp-40 | an-404 |
| E1A5696 | sp-18 | an-405 | E1U5696 | sp-20 | an-405 | E1U13022 | sp-40 | an-405 |
| E1A5697 | sp-18 | an-406 | E1U5697 | sp-20 | an-406 | E1U13023 | sp-40 | an-406 |
| E1A5698 | sp-18 | an-407 | E1U5698 | sp-20 | an-407 | E1U13024 | sp-40 | an-407 |
| E1A5699 | sp-19 | an-1 | E1U5699 | sp-23 | an-1 | E1U13025 | sp-41 | an-1 |
| E1A5700 | sp-19 | an-2 | E1U5700 | sp-23 | an-2 | E1U13026 | sp-41 | an-2 |
| E1A5701 | sp-19 | an-3 | E1U5701 | sp-23 | an-3 | E1U13027 | sp-41 | an-3 |
| E1A5702 | sp-19 | an-4 | E1U5702 | sp-23 | an-4 | E1U13028 | sp-41 | an-4 |
| E1A5703 | sp-19 | an-5 | E1U5703 | sp-23 | an-5 | E1U13029 | sp-41 | an-5 |
| E1A5704 | sp-19 | an-6 | E1U5704 | sp-23 | an-6 | E1U13030 | sp-41 | an-6 |
| E1A5705 | sp-19 | an-7 | E1U5705 | sp-23 | an-7 | E1U13031 | sp-41 | an-7 |
| E1A5706 | sp-19 | an-8 | E1U5706 | sp-23 | an-8 | E1U13032 | sp-41 | an-8 |

-continued

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| E1A5707 | sp-19 | an-9 | E1U5707 | sp-23 | an-9 | E1U13033 | sp-41 | an-9 |
| E1A5708 | sp-19 | an-10 | E1U5708 | sp-23 | an-10 | E1U13034 | sp-41 | an-10 |
| E1A5709 | sp-19 | an-11 | E1U5709 | sp-23 | an-11 | E1U13035 | sp-41 | an-11 |
| E1A5710 | sp-19 | an-12 | E1U5710 | sp-23 | an-12 | E1U13036 | sp-41 | an-12 |
| E1A5711 | sp-19 | an-13 | E1U5711 | sp-23 | an-13 | E1U13037 | sp-41 | an-13 |
| E1A5712 | sp-19 | an-14 | E1U5712 | sp-23 | an-14 | E1U13038 | sp-41 | an-14 |
| E1A5713 | sp-19 | an-15 | E1U5713 | sp-23 | an-15 | E1U13039 | sp-41 | an-15 |
| E1A5714 | sp-19 | an-16 | E1U5714 | sp-23 | an-16 | E1U13040 | sp-41 | an-16 |
| E1A5715 | sp-19 | an-17 | E1U5715 | sp-23 | an-17 | E1U13041 | sp-41 | an-17 |
| E1A5716 | sp-19 | an-18 | E1U5716 | sp-23 | an-18 | E1U13042 | sp-41 | an-18 |
| E1A5717 | sp-19 | an-19 | E1U5717 | sp-23 | an-19 | E1U13043 | sp-41 | an-19 |
| E1A5718 | sp-19 | an-20 | E1U5718 | sp-23 | an-20 | E1U13044 | sp-41 | an-20 |
| E1A5719 | sp-19 | an-21 | E1U5719 | sp-23 | an-21 | E1U13045 | sp-41 | an-21 |
| E1A5720 | sp-19 | an-22 | E1U5720 | sp-23 | an-22 | E1U13046 | sp-41 | an-22 |
| E1A5721 | sp-19 | an-23 | E1U5721 | sp-23 | an-23 | E1U13047 | sp-41 | an-23 |
| E1A5722 | sp-19 | an-24 | E1U5722 | sp-23 | an-24 | E1U13048 | sp-41 | an-24 |
| E1A5723 | sp-19 | an-25 | E1U5723 | sp-23 | an-25 | E1U13049 | sp-41 | an-25 |
| E1A5724 | sp-19 | an-26 | E1U5724 | sp-23 | an-26 | E1U13050 | sp-41 | an-26 |

Table 1-107

| Y = NHCS | | | Y = NHCSNH | | | Y = NHCSNH | | |
|---|---|---|---|---|---|---|---|---|
| E1A5725 | sp-19 | an-27 | E1U5725 | sp-23 | an-27 | E1U13051 | sp-41 | an-27 |
| E1A5726 | sp-19 | an-28 | E1U5726 | sp-23 | an-28 | E1U13052 | sp-41 | an-28 |
| E1A5727 | sp-19 | an-29 | E1U5727 | sp-23 | an-29 | E1U13053 | sp-41 | an-29 |
| E1A5728 | sp-19 | an-30 | E1U5728 | sp-23 | an-30 | E1U13054 | sp-41 | an-30 |
| E1A5729 | sp-19 | an-31 | E1U5729 | sp-23 | an-31 | E1U13055 | sp-41 | an-31 |
| E1A5730 | sp-19 | an-32 | E1U5730 | sp-23 | an-32 | E1U13056 | sp-41 | an-32 |
| E1A5731 | sp-19 | an-33 | E1U5731 | sp-23 | an-33 | E1U13057 | sp-41 | an-33 |
| E1A5732 | sp-19 | an-34 | E1U5732 | sp-23 | an-34 | E1U13058 | sp-41 | an-34 |
| E1A5733 | sp-19 | an-35 | E1U5733 | sp-23 | an-35 | E1U13059 | sp-41 | an-35 |
| E1A5734 | sp-19 | an-36 | E1U5734 | sp-23 | an-36 | E1U13060 | sp-41 | an-36 |
| E1A5735 | sp-19 | an-37 | E1U5735 | sp-23 | an-37 | E1U13061 | sp-41 | an-37 |
| E1A5736 | sp-19 | an-38 | E1U5736 | sp-23 | an-38 | E1U13062 | sp-41 | an-38 |
| E1A5737 | sp-19 | an-39 | E1U5737 | sp-23 | an-39 | E1U13063 | sp-41 | an-39 |
| E1A5738 | sp-19 | an-40 | E1U5738 | sp-23 | an-40 | E1U13064 | sp-41 | an-40 |
| E1A5739 | sp-19 | an-41 | E1U5739 | sp-23 | an-41 | E1U13065 | sp-41 | an-41 |
| E1A5740 | sp-19 | an-42 | E1U5740 | sp-23 | an-42 | E1U13066 | sp-41 | an-42 |
| E1A5741 | sp-19 | an-43 | E1U5741 | sp-23 | an-43 | E1U13067 | sp-41 | an-43 |
| E1A5742 | sp-19 | an-44 | E1U5742 | sp-23 | an-44 | E1U13068 | sp-41 | an-44 |
| E1A5743 | sp-19 | an-45 | E1U5743 | sp-23 | an-45 | E1U13069 | sp-41 | an-45 |
| E1A5744 | sp-19 | an-46 | E1U5744 | sp-23 | an-46 | E1U13070 | sp-41 | an-46 |
| E1A5745 | sp-19 | an-47 | E1U5745 | sp-23 | an-47 | E1U13071 | sp-41 | an-47 |
| E1A5746 | sp-19 | an-48 | E1U5746 | sp-23 | an-48 | E1U13072 | sp-41 | an-48 |
| E1A5747 | sp-19 | an-49 | E1U5747 | sp-23 | an-49 | E1U13073 | sp-41 | an-49 |
| E1A5748 | sp-19 | an-50 | E1U5748 | sp-23 | an-50 | E1U13074 | sp-41 | an-50 |
| E1A5749 | sp-19 | an-51 | E1U5749 | sp-23 | an-51 | E1U13075 | sp-41 | an-51 |
| E1A5750 | sp-19 | an-52 | E1U5750 | sp-23 | an-52 | E1U13076 | sp-41 | an-52 |
| E1A5751 | sp-19 | an-53 | E1U5751 | sp-23 | an-53 | E1U13077 | sp-41 | an-53 |
| E1A5752 | sp-19 | an-54 | E1U5752 | sp-23 | an-54 | E1U13078 | sp-41 | an-54 |
| E1A5753 | sp-19 | an-55 | E1U5753 | sp-23 | an-55 | E1U13079 | sp-41 | an-55 |
| E1A5754 | sp-19 | an-56 | E1U5754 | sp-23 | an-56 | E1U13080 | sp-41 | an-56 |
| E1A5755 | sp-19 | an-57 | E1U5755 | sp-23 | an-57 | E1U13081 | sp-41 | an-57 |
| E1A5756 | sp-19 | an-58 | E1U5756 | sp-23 | an-58 | E1U13082 | sp-41 | an-58 |
| E1A5757 | sp-19 | an-59 | E1U5757 | sp-23 | an-59 | E1U13083 | sp-41 | an-59 |
| E1A5758 | sp-19 | an-60 | E1U5758 | sp-23 | an-60 | E1U13084 | sp-41 | an-60 |
| E1A5759 | sp-19 | an-61 | E1U5759 | sp-23 | an-61 | E1U13085 | sp-41 | an-61 |
| E1A5760 | sp-19 | an-62 | E1U5760 | sp-23 | an-62 | E1U13086 | sp-41 | an-62 |
| E1A5761 | sp-19 | an-63 | E1U5761 | sp-23 | an-63 | E1U13087 | sp-41 | an-63 |
| E1A5762 | sp-19 | an-64 | E1U5762 | sp-23 | an-64 | E1U13088 | sp-41 | an-64 |
| E1A5763 | sp-19 | an-65 | E1U5763 | sp-23 | an-65 | E1U13089 | sp-41 | an-65 |
| E1A5764 | sp-19 | an-66 | E1U5764 | sp-23 | an-66 | E1U13090 | sp-41 | an-66 |
| E1A5765 | sp-19 | an-67 | E1U5765 | sp-23 | an-67 | E1U13091 | sp-41 | an-67 |
| E1A5766 | sp-19 | an-68 | E1U5766 | sp-23 | an-68 | E1U13092 | sp-41 | an-68 |
| E1A5767 | sp-19 | an-69 | E1U5767 | sp-23 | an-69 | E1U13093 | sp-41 | an-69 |
| E1A5768 | sp-19 | an-70 | E1U5768 | sp-23 | an-70 | E1U13094 | sp-41 | an-70 |
| E1A5769 | sp-19 | an-71 | E1U5769 | sp-23 | an-71 | E1U13095 | sp-41 | an-71 |
| E1A5770 | sp-19 | an-72 | E1U5770 | sp-23 | an-72 | E1U13096 | sp-41 | an-72 |
| E1A5771 | sp-19 | an-73 | E1U5771 | sp-23 | an-73 | E1U13097 | sp-41 | an-73 |
| E1A5772 | sp-19 | an-74 | E1U5772 | sp-23 | an-74 | E1U13098 | sp-41 | an-74 |
| E1A5773 | sp-19 | an-75 | E1U5773 | sp-23 | an-75 | E1U13099 | sp-41 | an-75 |
| E1A5774 | sp-19 | an-76 | E1U5774 | sp-23 | an-76 | E1U13100 | sp-41 | an-76 |
| E1A5775 | sp-19 | an-77 | E1U5775 | sp-23 | an-77 | E1U13101 | sp-41 | an-77 |
| E1A5776 | sp-19 | an-78 | E1U5776 | sp-23 | an-78 | E1U13102 | sp-41 | an-78 |
| E1A5777 | sp-19 | an-79 | E1U5777 | sp-23 | an-79 | E1U13103 | sp-41 | an-79 |
| E1A5778 | sp-19 | an-80 | E1U5778 | sp-23 | an-80 | E1U13104 | sp-41 | an-80 |

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| | | | | Table 1-108 | | | | |
| | Y = NHCS | | | Y = NHCSNH | | | Y = NHCSNH | |
| E1A5779 | sp-19 | an-81 | E1U5779 | sp-23 | an-81 | E1U13105 | sp-41 | an-81 |
| E1A5780 | sp-19 | an-82 | E1U5780 | sp-23 | an-82 | E1U13106 | sp-41 | an-82 |
| E1A5781 | sp-19 | an-83 | E1U5781 | sp-23 | an-83 | E1U13107 | sp-41 | an-83 |
| E1A5782 | sp-19 | an-84 | E1U5782 | sp-23 | an-84 | E1U13108 | sp-41 | an-84 |
| E1A5783 | sp-19 | an-85 | E1U5783 | sp-23 | an-85 | E1U13109 | sp-41 | an-85 |
| E1A5784 | sp-19 | an-86 | E1U5784 | sp-23 | an-86 | E1U13110 | sp-41 | an-86 |
| E1A5785 | sp-19 | an-87 | E1U5785 | sp-23 | an-87 | E1U13111 | sp-41 | an-87 |
| E1A5786 | sp-19 | an-88 | E1U5786 | sp-23 | an-88 | E1U13112 | sp-41 | an-88 |
| E1A5787 | sp-19 | an-89 | E1U5787 | sp-23 | an-89 | E1U13113 | sp-41 | an-89 |
| E1A5788 | sp-19 | an-90 | E1U5788 | sp-23 | an-90 | E1U13114 | sp-41 | an-90 |
| E1A5789 | sp-19 | an-91 | E1U5789 | sp-23 | an-91 | E1U13115 | sp-41 | an-91 |
| E1A5790 | sp-19 | an-92 | E1U5790 | sp-23 | an-92 | E1U13116 | sp-41 | an-92 |
| E1A5791 | sp-19 | an-93 | E1U5791 | sp-23 | an-93 | E1U13117 | sp-41 | an-93 |
| E1A5792 | sp-19 | an-94 | E1U5792 | sp-23 | an-94 | E1U13118 | sp-41 | an-94 |
| E1A5793 | sp-19 | an-95 | E1U5793 | sp-23 | an-95 | E1U13119 | sp-41 | an-95 |
| E1A5794 | sp-19 | an-96 | E1U5794 | sp-23 | an-96 | E1U13120 | sp-41 | an-96 |
| E1A5795 | sp-19 | an-97 | E1U5795 | sp-23 | an-97 | E1U13121 | sp-41 | an-97 |
| E1A5796 | sp-19 | an-98 | E1U5796 | sp-23 | an-98 | E1U13122 | sp-41 | an-98 |
| E1A5797 | sp-19 | an-99 | E1U5797 | sp-23 | an-99 | E1U13123 | sp-41 | an-99 |
| E1A5798 | sp-19 | an-100 | E1U5798 | sp-23 | an-100 | E1U13124 | sp-41 | an-100 |
| E1A5799 | sp-19 | an-101 | E1U5799 | sp-23 | an-101 | E1U13125 | sp-41 | an-101 |
| E1A5800 | sp-19 | an-102 | E1U5800 | sp-23 | an-102 | E1U13126 | sp-41 | an-102 |
| E1A5801 | sp-19 | an-103 | E1U5801 | sp-23 | an-103 | E1U13127 | sp-41 | an-103 |
| E1A5802 | sp-19 | an-104 | E1U5802 | sp-23 | an-104 | E1U13128 | sp-41 | an-104 |
| E1A5803 | sp-19 | an-105 | E1U5803 | sp-23 | an-105 | E1U13129 | sp-41 | an-105 |
| E1A5804 | sp-19 | an-106 | E1U5804 | sp-23 | an-106 | E1U13130 | sp-41 | an-106 |
| E1A5805 | sp-19 | an-107 | E1U5805 | sp-23 | an-107 | E1U13131 | sp-41 | an-107 |
| E1A5806 | sp-19 | an-108 | E1U5806 | sp-23 | an-108 | E1U13132 | sp-41 | an-108 |
| E1A5807 | sp-19 | an-109 | E1U5807 | sp-23 | an-109 | E1U13133 | sp-41 | an-109 |
| E1A5808 | sp-19 | an-110 | E1U5808 | sp-23 | an-110 | E1U13134 | sp-41 | an-110 |
| E1A5809 | sp-19 | an-111 | E1U5809 | sp-23 | an-111 | E1U13135 | sp-41 | an-111 |
| E1A5810 | sp-19 | an-112 | E1U5810 | sp-23 | an-112 | E1U13136 | sp-41 | an-112 |
| E1A5811 | sp-19 | an-113 | E1U5811 | sp-23 | an-113 | E1U13137 | sp-41 | an-113 |
| E1A5812 | sp-19 | an-114 | E1U5812 | sp-23 | an-114 | E1U13138 | sp-41 | an-114 |
| E1A5813 | sp-19 | an-115 | E1U5813 | sp-23 | an-115 | E1U13139 | sp-41 | an-115 |
| E1A5814 | sp-19 | an-116 | E1U5814 | sp-23 | an-116 | E1U13140 | sp-41 | an-116 |
| E1A5815 | sp-19 | an-117 | E1U5815 | sp-23 | an-117 | E1U13141 | sp-41 | an-117 |
| E1A5816 | sp-19 | an-118 | E1U5816 | sp-23 | an-118 | E1U13142 | sp-41 | an-118 |
| E1A5817 | sp-19 | an-119 | E1U5817 | sp-23 | an-119 | E1U13143 | sp-41 | an-119 |
| E1A5818 | sp-19 | an-120 | E1U5818 | sp-23 | an-120 | E1U13144 | sp-41 | an-120 |
| E1A5819 | sp-19 | an-121 | E1U5819 | sp-23 | an-121 | E1U13145 | sp-41 | an-121 |
| E1A5820 | sp-19 | an-122 | E1U5820 | sp-23 | an-122 | E1U13146 | sp-41 | an-122 |
| E1A5821 | sp-19 | an-123 | E1U5821 | sp-23 | an-123 | E1U13147 | sp-41 | an-123 |
| E1A5822 | sp-19 | an-124 | E1U5822 | sp-23 | an-124 | E1U13148 | sp-41 | an-124 |
| E1A5823 | sp-19 | an-125 | E1U5823 | sp-23 | an-125 | E1U13149 | sp-41 | an-125 |
| E1A5824 | sp-19 | an-126 | E1U5824 | sp-23 | an-126 | E1U13150 | sp-41 | an-126 |
| E1A5825 | sp-19 | an-127 | E1U5825 | sp-23 | an-127 | E1U13151 | sp-41 | an-127 |
| E1A5826 | sp-19 | an-128 | E1U5826 | sp-23 | an-128 | E1U13152 | sp-41 | an-128 |
| E1A5827 | sp-19 | an-129 | E1U5827 | sp-23 | an-129 | E1U13153 | sp-41 | an-129 |
| E1A5828 | sp-19 | an-130 | E1U5828 | sp-23 | an-130 | E1U13154 | sp-41 | an-130 |
| E1A5829 | sp-19 | an-131 | E1U5829 | sp-23 | an-131 | E1U13155 | sp-41 | an-131 |
| E1A5830 | sp-19 | an-132 | E1U5830 | sp-23 | an-132 | E1U13156 | sp-41 | an-132 |
| E1A5831 | sp-19 | an-133 | E1U5831 | sp-23 | an-133 | E1U13157 | sp-41 | an-133 |
| E1A5832 | sp-19 | an-134 | E1U5832 | sp-23 | an-134 | E1U13158 | sp-41 | an-134 |
| | | | | Table 1-109 | | | | |
| | Y = NHCS | | | Y = NHCSNH | | | Y = NHCSNH | |
| E1A5833 | sp-19 | an-135 | E1U5833 | sp-23 | an-135 | E1U13159 | sp-41 | an-135 |
| E1A5834 | sp-19 | an-136 | E1U5834 | sp-23 | an-136 | E1U13160 | sp-41 | an-136 |
| E1A5835 | sp-19 | an-137 | E1U5835 | sp-23 | an-137 | E1U13161 | sp-41 | an-137 |
| E1A5836 | sp-19 | an-138 | E1U5836 | sp-23 | an-138 | E1U13162 | sp-41 | an-138 |
| E1A5837 | sp-19 | an-139 | E1U5837 | sp-23 | an-139 | E1U13163 | sp-41 | an-139 |
| E1A5838 | sp-19 | an-140 | E1U5838 | sp-23 | an-140 | E1U13164 | sp-41 | an-140 |
| E1A5839 | sp-19 | an-141 | E1U5839 | sp-23 | an-141 | E1U13165 | sp-41 | an-141 |
| E1A5840 | sp-19 | an-142 | E1U5840 | sp-23 | an-142 | E1U13166 | sp-41 | an-142 |
| E1A5841 | sp-19 | an-143 | E1U5841 | sp-23 | an-143 | E1U13167 | sp-41 | an-143 |
| E1A5842 | sp-19 | an-144 | E1U5842 | sp-23 | an-144 | E1U13168 | sp-41 | an-144 |
| E1A5843 | sp-19 | an-145 | E1U5843 | sp-23 | an-145 | E1U13169 | sp-41 | an-145 |
| E1A5844 | sp-19 | an-146 | E1U5844 | sp-23 | an-146 | E1U13170 | sp-41 | an-146 |
| E1A5845 | sp-19 | an-147 | E1U5845 | sp-23 | an-147 | E1U13171 | sp-41 | an-147 |
| E1A5846 | sp-19 | an-148 | E1U5846 | sp-23 | an-148 | E1U13172 | sp-41 | an-148 |
| E1A5847 | sp-19 | an-149 | E1U5847 | sp-23 | an-149 | E1U13173 | sp-41 | an-149 |
| E1A5848 | sp-19 | an-150 | E1U5848 | sp-23 | an-150 | E1U13174 | sp-41 | an-150 |

-continued

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| E1A5849 | sp-19 | an-151 | E1U5849 | sp-23 | an-151 | E1U13175 | sp-41 | an-151 |
| E1A5850 | sp-19 | an-152 | E1U5850 | sp-23 | an-152 | E1U13176 | sp-41 | an-152 |
| E1A5851 | sp-19 | an-153 | E1U5851 | sp-23 | an-153 | E1U13177 | sp-41 | an-153 |
| E1A5852 | sp-19 | an-154 | E1U5852 | sp-23 | an-154 | E1U13178 | sp-41 | an-154 |
| E1A5853 | sp-19 | an-155 | E1U5853 | sp-23 | an-155 | E1U13179 | sp-41 | an-155 |
| E1A5854 | sp-19 | an-156 | E1U5854 | sp-23 | an-156 | E1U13180 | sp-41 | an-156 |
| E1A5855 | sp-19 | an-157 | E1U5855 | sp-23 | an-157 | E1U13181 | sp-41 | an-157 |
| E1A5856 | sp-19 | an-158 | E1U5856 | sp-23 | an-158 | E1U13182 | sp-41 | an-158 |
| E1A5857 | sp-19 | an-159 | E1U5857 | sp-23 | an-159 | E1U13183 | sp-41 | an-159 |
| E1A5858 | sp-19 | an-160 | E1U5858 | sp-23 | an-160 | E1U13184 | sp-41 | an-160 |
| E1A5859 | sp-19 | an-161 | E1U5859 | sp-23 | an-161 | E1U13185 | sp-41 | an-161 |
| E1A5860 | sp-19 | an-162 | E1U5860 | sp-23 | an-162 | E1U13186 | sp-41 | an-162 |
| E1A5861 | sp-19 | an-163 | E1U5861 | sp-23 | an-163 | E1U13187 | sp-41 | an-163 |
| E1A5862 | sp-19 | an-164 | E1U5862 | sp-23 | an-164 | E1U13188 | sp-41 | an-164 |
| E1A5863 | sp-19 | an-165 | E1U5863 | sp-23 | an-165 | E1U13189 | sp-41 | an-165 |
| E1A5864 | sp-19 | an-166 | E1U5864 | sp-23 | an-166 | E1U13190 | sp-41 | an-166 |
| E1A5865 | sp-19 | an-167 | E1U5865 | sp-23 | an-167 | E1U13191 | sp-41 | an-167 |
| E1A5866 | sp-19 | an-168 | E1U5866 | sp-23 | an-168 | E1U13192 | sp-41 | an-168 |
| E1A5867 | sp-19 | an-169 | E1U5867 | sp-23 | an-169 | E1U13193 | sp-41 | an-169 |
| E1A5868 | sp-19 | an-170 | E1U5868 | sp-23 | an-170 | E1U13194 | sp-41 | an-170 |
| E1A5869 | sp-19 | an-171 | E1U5869 | sp-23 | an-171 | E1U13195 | sp-41 | an-171 |
| E1A5870 | sp-19 | an-172 | E1U5870 | sp-23 | an-172 | E1U13196 | sp-41 | an-172 |
| E1A5871 | sp-19 | an-173 | E1U5871 | sp-23 | an-173 | E1U13197 | sp-41 | an-173 |
| E1A5872 | sp-19 | an-174 | E1U5872 | sp-23 | an-174 | E1U13198 | sp-41 | an-174 |
| E1A5873 | sp-19 | an-175 | E1U5873 | sp-23 | an-175 | E1U13199 | sp-41 | an-175 |
| E1A5874 | sp-19 | an-176 | E1U5874 | sp-23 | an-176 | E1U13200 | sp-41 | an-176 |
| E1A5875 | sp-19 | an-177 | E1U5875 | sp-23 | an-177 | E1U13201 | sp-41 | an-177 |
| E1A5876 | sp-19 | an-178 | E1U5876 | sp-23 | an-178 | E1U13202 | sp-41 | an-178 |
| E1A5877 | sp-19 | an-179 | E1U5877 | sp-23 | an-179 | E1U13203 | sp-41 | an-179 |
| E1A5878 | sp-19 | an-180 | E1U5878 | sp-23 | an-180 | E1U13204 | sp-41 | an-180 |
| E1A5879 | sp-19 | an-181 | E1U5879 | sp-23 | an-181 | E1U13205 | sp-41 | an-181 |
| E1A5880 | sp-19 | an-182 | E1U5880 | sp-23 | an-182 | E1U13206 | sp-41 | an-182 |
| E1A5881 | sp-19 | an-183 | E1U5881 | sp-23 | an-183 | E1U13207 | sp-41 | an-183 |
| E1A5882 | sp-19 | an-184 | E1U5882 | sp-23 | an-184 | E1U13208 | sp-41 | an-184 |
| E1A5883 | sp-19 | an-185 | E1U5883 | sp-23 | an-185 | E1U13209 | sp-41 | an-185 |
| E1A5884 | sp-19 | an-186 | E1U5884 | sp-23 | an-186 | E1U13210 | sp-41 | an-186 |
| E1A5885 | sp-19 | an-187 | E1U5885 | sp-23 | an-187 | E1U13211 | sp-41 | an-187 |
| E1A5886 | sp-19 | an-188 | E1U5886 | sp-23 | an-188 | E1U13212 | sp-41 | an-188 |

Table 1-110

| Y = NHCS | | | Y = NHCSNH | | | Y = NHCSNH | | |
|---|---|---|---|---|---|---|---|---|
| E1A5887 | sp-19 | an-189 | E1U5887 | sp-23 | an-189 | E1U13213 | sp-41 | an-189 |
| E1A5888 | sp-19 | an-190 | E1U5888 | sp-23 | an-190 | E1U13214 | sp-41 | an-190 |
| E1A5889 | sp-19 | an-191 | E1U5889 | sp-23 | an-191 | E1U13215 | sp-41 | an-191 |
| E1A5890 | sp-19 | an-192 | E1U5890 | sp-23 | an-192 | E1U13216 | sp-41 | an-192 |
| E1A5891 | sp-19 | an-193 | E1U5891 | sp-23 | an-193 | E1U13217 | sp-41 | an-193 |
| E1A5892 | sp-19 | an-194 | E1U5892 | sp-23 | an-194 | E1U13218 | sp-41 | an-194 |
| E1A5893 | sp-19 | an-195 | E1U5893 | sp-23 | an-195 | E1U13219 | sp-41 | an-195 |
| E1A5894 | sp-19 | an-196 | E1U5894 | sp-23 | an-196 | E1U13220 | sp-41 | an-196 |
| E1A5895 | sp-19 | an-197 | E1U5895 | sp-23 | an-197 | E1U13221 | sp-41 | an-197 |
| E1A5896 | sp-19 | an-198 | E1U5896 | sp-23 | an-198 | E1U13222 | sp-41 | an-198 |
| E1A5897 | sp-19 | an-199 | E1U5897 | sp-23 | an-199 | E1U13223 | sp-41 | an-199 |
| E1A5898 | sp-19 | an-200 | E1U5898 | sp-23 | an-200 | E1U13224 | sp-41 | an-200 |
| E1A5899 | sp-19 | an-201 | E1U5899 | sp-23 | an-201 | E1U13225 | sp-41 | an-201 |
| E1A5900 | sp-19 | an-202 | E1U5900 | sp-23 | an-202 | E1U13226 | sp-41 | an-202 |
| E1A5901 | sp-19 | an-203 | E1U5901 | sp-23 | an-203 | E1U13227 | sp-41 | an-203 |
| E1A5902 | sp-19 | an-204 | E1U5902 | sp-23 | an-204 | E1U13228 | sp-41 | an-204 |
| E1A5903 | sp-19 | an-205 | E1U5903 | sp-23 | an-205 | E1U13229 | sp-41 | an-205 |
| E1A5904 | sp-19 | an-206 | E1U5904 | sp-23 | an-206 | E1U13230 | sp-41 | an-206 |
| E1A5905 | sp-19 | an-207 | E1U5905 | sp-23 | an-207 | E1U13231 | sp-41 | an-207 |
| E1A5906 | sp-19 | an-208 | E1U5906 | sp-23 | an-208 | E1U13232 | sp-41 | an-208 |
| E1A5907 | sp-19 | an-209 | E1U5907 | sp-23 | an-209 | E1U13233 | sp-41 | an-209 |
| E1A5908 | sp-19 | an-210 | E1U5908 | sp-23 | an-210 | E1U13234 | sp-41 | an-210 |
| E1A5909 | sp-19 | an-211 | E1U5909 | sp-23 | an-211 | E1U13235 | sp-41 | an-211 |
| E1A5910 | sp-19 | an-212 | E1U5910 | sp-23 | an-212 | E1U13236 | sp-41 | an-212 |
| E1A5911 | sp-19 | an-213 | E1U5911 | sp-23 | an-213 | E1U13237 | sp-41 | an-213 |
| E1A5912 | sp-19 | an-214 | E1U5912 | sp-23 | an-214 | E1U13238 | sp-41 | an-214 |
| E1A5913 | sp-19 | an-215 | E1U5913 | sp-23 | an-215 | E1U13239 | sp-41 | an-215 |
| E1A5914 | sp-19 | an-216 | E1U5914 | sp-23 | an-216 | E1U13240 | sp-41 | an-216 |
| E1A5915 | sp-19 | an-217 | E1U5915 | sp-23 | an-217 | E1U13241 | sp-41 | an-217 |
| E1A5916 | sp-19 | an-218 | E1U5916 | sp-23 | an-218 | E1U13242 | sp-41 | an-218 |
| E1A5917 | sp-19 | an-219 | E1U5917 | sp-23 | an-219 | E1U13243 | sp-41 | an-219 |
| E1A5918 | sp-19 | an-220 | E1U5918 | sp-23 | an-220 | E1U13244 | sp-41 | an-220 |
| E1A5919 | sp-19 | an-221 | E1U5919 | sp-23 | an-221 | E1U13245 | sp-41 | an-221 |
| E1A5920 | sp-19 | an-222 | E1U5920 | sp-23 | an-222 | E1U13246 | sp-41 | an-222 |
| E1A5921 | sp-19 | an-223 | E1U5921 | sp-23 | an-223 | E1U13247 | sp-41 | an-223 |
| E1A5922 | sp-19 | an-224 | E1U5922 | sp-23 | an-224 | E1U13248 | sp-41 | an-224 |

-continued

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| E1A5923 | sp-19 | an-225 | E1U5923 | sp-23 | an-225 | E1U13249 | sp-41 | an-225 |
| E1A5924 | sp-19 | an-226 | E1U5924 | sp-23 | an-226 | E1U13250 | sp-41 | an-226 |
| E1A5925 | sp-19 | an-227 | E1U5925 | sp-23 | an-227 | E1U13251 | sp-41 | an-227 |
| E1A5926 | sp-19 | an-228 | E1U5926 | sp-23 | an-228 | E1U13252 | sp-41 | an-228 |
| E1A5927 | sp-19 | an-229 | E1U5927 | sp-23 | an-229 | E1U13253 | sp-41 | an-229 |
| E1A5928 | sp-19 | an-230 | E1U5928 | sp-23 | an-230 | E1U13254 | sp-41 | an-230 |
| E1A5929 | sp-19 | an-231 | E1U5929 | sp-23 | an-231 | E1U13255 | sp-41 | an-231 |
| E1A5930 | sp-19 | an-232 | E1U5930 | sp-23 | an-232 | E1U13256 | sp-41 | an-232 |
| E1A5931 | sp-19 | an-233 | E1U5931 | sp-23 | an-233 | E1U13257 | sp-41 | an-233 |
| E1A5932 | sp-19 | an-234 | E1U5932 | sp-23 | an-234 | E1U13258 | sp-41 | an-234 |
| E1A5933 | sp-19 | an-235 | E1U5933 | sp-23 | an-235 | E1U13259 | sp-41 | an-235 |
| E1A5934 | sp-19 | an-236 | E1U5934 | sp-23 | an-236 | E1U13260 | sp-41 | an-236 |
| E1A5935 | sp-19 | an-237 | E1U5935 | sp-23 | an-237 | E1U13261 | sp-41 | an-237 |
| E1A5936 | sp-19 | an-238 | E1U5936 | sp-23 | an-238 | E1U13262 | sp-41 | an-238 |
| E1A5937 | sp-19 | an-239 | E1U5937 | sp-23 | an-239 | E1U13263 | sp-41 | an-239 |
| E1A5938 | sp-19 | an-240 | E1U5938 | sp-23 | an-240 | E1U13264 | sp-41 | an-240 |
| E1A5939 | sp-19 | an-241 | E1U5939 | sp-23 | an-241 | E1U13265 | sp-41 | an-241 |
| E1A5940 | sp-19 | an-242 | E1U5940 | sp-23 | an-242 | E1U13266 | sp-41 | an-242 |

Table 1-111

| Y = NHCS | | | Y = NHCSNH | | | Y = NHCSNH | | |
|---|---|---|---|---|---|---|---|---|
| E1A5941 | sp-19 | an-243 | E1U5941 | sp-23 | an-243 | E1U13267 | sp-41 | an-243 |
| E1A5942 | sp-19 | an-244 | E1U5942 | sp-23 | an-244 | E1U13268 | sp-41 | an-244 |
| E1A5943 | sp-19 | an-245 | E1U5943 | sp-23 | an-245 | E1U13269 | sp-41 | an-245 |
| E1A5944 | sp-19 | an-246 | E1U5944 | sp-23 | an-246 | E1U13270 | sp-41 | an-246 |
| E1A5945 | sp-19 | an-247 | E1U5945 | sp-23 | an-247 | E1U13271 | sp-41 | an-247 |
| E1A5946 | sp-19 | an-248 | E1U5946 | sp-23 | an-248 | E1U13272 | sp-41 | an-248 |
| E1A5947 | sp-19 | an-249 | E1U5947 | sp-23 | an-249 | E1U13273 | sp-41 | an-249 |
| E1A5948 | sp-19 | an-250 | E1U5948 | sp-23 | an-250 | E1U13274 | sp-41 | an-250 |
| E1A5949 | sp-19 | an-251 | E1U5949 | sp-23 | an-251 | E1U13275 | sp-41 | an-251 |
| E1A5950 | sp-19 | an-252 | E1U5950 | sp-23 | an-252 | E1U13276 | sp-41 | an-252 |
| E1A5951 | sp-19 | an-253 | E1U5951 | sp-23 | an-253 | E1U13277 | sp-41 | an-253 |
| E1A5952 | sp-19 | an-254 | E1U5952 | sp-23 | an-254 | E1U13278 | sp-41 | an-254 |
| E1A5953 | sp-19 | an-255 | E1U5953 | sp-23 | an-255 | E1U13279 | sp-41 | an-255 |
| E1A5954 | sp-19 | an-256 | E1U5954 | sp-23 | an-256 | E1U13280 | sp-41 | an-256 |
| E1A5955 | sp-19 | an-257 | E1U5955 | sp-23 | an-257 | E1U13281 | sp-41 | an-257 |
| E1A5956 | sp-19 | an-258 | E1U5956 | sp-23 | an-258 | E1U13282 | sp-41 | an-258 |
| E1A5957 | sp-19 | an-259 | E1U5957 | sp-23 | an-259 | E1U13283 | sp-41 | an-259 |
| E1A5958 | sp-19 | an-260 | E1U5958 | sp-23 | an-260 | E1U13284 | sp-41 | an-260 |
| E1A5959 | sp-19 | an-261 | E1U5959 | sp-23 | an-261 | E1U13285 | sp-41 | an-261 |
| E1A5960 | sp-19 | an-262 | E1U5960 | sp-23 | an-262 | E1U13286 | sp-41 | an-262 |
| E1A5961 | sp-19 | an-263 | E1U5961 | sp-23 | an-263 | E1U13287 | sp-41 | an-263 |
| E1A5962 | sp-19 | an-264 | E1U5962 | sp-23 | an-264 | E1U13288 | sp-41 | an-264 |
| E1A5963 | sp-19 | an-265 | E1U5963 | sp-23 | an-265 | E1U13289 | sp-41 | an-265 |
| E1A5964 | sp-19 | an-266 | E1U5964 | sp-23 | an-266 | E1U13290 | sp-41 | an-266 |
| E1A5965 | sp-19 | an-267 | E1U5965 | sp-23 | an-267 | E1U13291 | sp-41 | an-267 |
| E1A5966 | sp-19 | an-268 | E1U5966 | sp-23 | an-268 | E1U13292 | sp-41 | an-268 |
| E1A5967 | sp-19 | an-269 | E1U5967 | sp-23 | an-269 | E1U13293 | sp-41 | an-269 |
| E1A5968 | sp-19 | an-270 | E1U5968 | sp-23 | an-270 | E1U13294 | sp-41 | an-270 |
| E1A5969 | sp-19 | an-271 | E1U5969 | sp-23 | an-271 | E1U13295 | sp-41 | an-271 |
| E1A5970 | sp-19 | an-272 | E1U5970 | sp-23 | an-272 | E1U13296 | sp-41 | an-272 |
| E1A5971 | sp-19 | an-273 | E1U5971 | sp-23 | an-273 | E1U13297 | sp-41 | an-273 |
| E1A5972 | sp-19 | an-274 | E1U5972 | sp-23 | an-274 | E1U13298 | sp-41 | an-274 |
| E1A5973 | sp-19 | an-275 | E1U5973 | sp-23 | an-275 | E1U13299 | sp-41 | an-275 |
| E1A5974 | sp-19 | an-276 | E1U5974 | sp-23 | an-276 | E1U13300 | sp-41 | an-276 |
| E1A5975 | sp-19 | an-277 | E1U5975 | sp-23 | an-277 | E1U13301 | sp-41 | an-277 |
| E1A5976 | sp-19 | an-278 | E1U5976 | sp-23 | an-278 | E1U13302 | sp-41 | an-278 |
| E1A5977 | sp-19 | an-279 | E1U5977 | sp-23 | an-279 | E1U13303 | sp-41 | an-279 |
| E1A5978 | sp-19 | an-280 | E1U5978 | sp-23 | an-280 | E1U13304 | sp-41 | an-280 |
| E1A5979 | sp-19 | an-281 | E1U5979 | sp-23 | an-281 | E1U13305 | sp-41 | an-281 |
| E1A5980 | sp-19 | an-282 | E1U5980 | sp-23 | an-282 | E1U13306 | sp-41 | an-282 |
| E1A5981 | sp-19 | an-283 | E1U5981 | sp-23 | an-283 | E1U13307 | sp-41 | an-283 |
| E1A5982 | sp-19 | an-284 | E1U5982 | sp-23 | an-284 | E1U13308 | sp-41 | an-284 |
| E1A5983 | sp-19 | an-285 | E1U5983 | sp-23 | an-285 | E1U13309 | sp-41 | an-285 |
| E1A5984 | sp-19 | an-286 | E1U5984 | sp-23 | an-286 | E1U13310 | sp-41 | an-286 |
| E1A5985 | sp-19 | an-287 | E1U5985 | sp-23 | an-287 | E1U13311 | sp-41 | an-287 |
| E1A5986 | sp-19 | an-288 | E1U5986 | sp-23 | an-288 | E1U13312 | sp-41 | an-288 |
| E1A5987 | sp-19 | an-289 | E1U5987 | sp-23 | an-289 | E1U13313 | sp-41 | an-289 |
| E1A5988 | sp-19 | an-290 | E1U5988 | sp-23 | an-290 | E1U13314 | sp-41 | an-290 |
| E1A5989 | sp-19 | an-291 | E1U5989 | sp-23 | an-291 | E1U13315 | sp-41 | an-291 |
| E1A5990 | sp-19 | an-292 | E1U5990 | sp-23 | an-292 | E1U13316 | sp-41 | an-292 |
| E1A5991 | sp-19 | an-293 | E1U5991 | sp-23 | an-293 | E1U13317 | sp-41 | an-293 |
| E1A5992 | sp-19 | an-294 | E1U5992 | sp-23 | an-294 | E1U13318 | sp-41 | an-294 |
| E1A5993 | sp-19 | an-295 | E1U5993 | sp-23 | an-295 | E1U13319 | sp-41 | an-295 |
| E1A5994 | sp-19 | an-296 | E1U5994 | sp-23 | an-296 | E1U13320 | sp-41 | an-296 |

-continued

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| Table 1-112 ||||||||||
| Y = NHCS ||| Y = NHCSNH ||| Y = NHCSNH |||
| E1A5995 | sp-19 | an-297 | E1U5995 | sp-23 | an-297 | E1U13321 | sp-41 | an-297 |
| E1A5996 | sp-19 | an-298 | E1U5996 | sp-23 | an-298 | E1U13322 | sp-41 | an-298 |
| E1A5997 | sp-19 | an-299 | E1U5997 | sp-23 | an-299 | E1U13323 | sp-41 | an-299 |
| E1A5998 | sp-19 | an-300 | E1U5998 | sp-23 | an-300 | E1U13324 | sp-41 | an-300 |
| E1A5999 | sp-19 | an-301 | E1U5999 | sp-23 | an-301 | E1U13325 | sp-41 | an-301 |
| E1A6000 | sp-19 | an-302 | E1U6000 | sp-23 | an-302 | E1U13326 | sp-41 | an-302 |
| E1A6001 | sp-19 | an-303 | E1U6001 | sp-23 | an-303 | E1U13327 | sp-41 | an-303 |
| E1A6002 | sp-19 | an-304 | E1U6002 | sp-23 | an-304 | E1U13328 | sp-41 | an-304 |
| E1A6003 | sp-19 | an-305 | E1U6003 | sp-23 | an-305 | E1U13329 | sp-41 | an-305 |
| E1A6004 | sp-19 | an-306 | E1U6004 | sp-23 | an-306 | E1U13330 | sp-41 | an-306 |
| E1A6005 | sp-19 | an-307 | E1U6005 | sp-23 | an-307 | E1U13331 | sp-41 | an-307 |
| E1A6006 | sp-19 | an-308 | E1U6006 | sp-23 | an-308 | E1U13332 | sp-41 | an-308 |
| E1A6007 | sp-19 | an-309 | E1U6007 | sp-23 | an-309 | E1U13333 | sp-41 | an-309 |
| E1A6008 | sp-19 | an-310 | E1U6008 | sp-23 | an-310 | E1U13334 | sp-41 | an-310 |
| E1A6009 | sp-19 | an-311 | E1U6009 | sp-23 | an-311 | E1U13335 | sp-41 | an-311 |
| E1A6010 | sp-19 | an-312 | E1U6010 | sp-23 | an-312 | E1U13336 | sp-41 | an-312 |
| E1A6011 | sp-19 | an-313 | E1U6011 | sp-23 | an-313 | E1U13337 | sp-41 | an-313 |
| E1A6012 | sp-19 | an-314 | E1U6012 | sp-23 | an-314 | E1U13338 | sp-41 | an-314 |
| E1A6013 | sp-19 | an-315 | E1U6013 | sp-23 | an-315 | E1U13339 | sp-41 | an-315 |
| E1A6014 | sp-19 | an-316 | E1U6014 | sp-23 | an-316 | E1U13340 | sp-41 | an-316 |
| E1A6015 | sp-19 | an-317 | E1U6015 | sp-23 | an-317 | E1U13341 | sp-41 | an-317 |
| E1A6016 | sp-19 | an-318 | E1U6016 | sp-23 | an-318 | E1U13342 | sp-41 | an-318 |
| E1A6017 | sp-19 | an-319 | E1U6017 | sp-23 | an-319 | E1U13343 | sp-41 | an-319 |
| E1A6018 | sp-19 | an-320 | E1U6018 | sp-23 | an-320 | E1U13344 | sp-41 | an-320 |
| E1A6019 | sp-19 | an-321 | E1U6019 | sp-23 | an-321 | E1U13345 | sp-41 | an-321 |
| E1A6020 | sp-19 | an-322 | E1U6020 | sp-23 | an-322 | E1U13346 | sp-41 | an-322 |
| E1A6021 | sp-19 | an-323 | E1U6021 | sp-23 | an-323 | E1U13347 | sp-41 | an-323 |
| E1A6022 | sp-19 | an-324 | E1U6022 | sp-23 | an-324 | E1U13348 | sp-41 | an-324 |
| E1A6023 | sp-19 | an-325 | E1U6023 | sp-23 | an-325 | E1U13349 | sp-41 | an-325 |
| E1A6024 | sp-19 | an-326 | E1U6024 | sp-23 | an-326 | E1U13350 | sp-41 | an-326 |
| E1A6025 | sp-19 | an-327 | E1U6025 | sp-23 | an-327 | E1U13351 | sp-41 | an-327 |
| E1A6026 | sp-19 | an-328 | E1U6026 | sp-23 | an-328 | E1U13352 | sp-41 | an-328 |
| E1A6027 | sp-19 | an-329 | E1U6027 | sp-23 | an-329 | E1U13353 | sp-41 | an-329 |
| E1A6028 | sp-19 | an-330 | E1U6028 | sp-23 | an-330 | E1U13354 | sp-41 | an-330 |
| E1A6029 | sp-19 | an-331 | E1U6029 | sp-23 | an-331 | E1U13355 | sp-41 | an-331 |
| E1A6030 | sp-19 | an-332 | E1U6030 | sp-23 | an-332 | E1U13356 | sp-41 | an-332 |
| E1A6031 | sp-19 | an-333 | E1U6031 | sp-23 | an-333 | E1U13357 | sp-41 | an-333 |
| E1A6032 | sp-19 | an-334 | E1U6032 | sp-23 | an-334 | E1U13358 | sp-41 | an-334 |
| E1A6033 | sp-19 | an-335 | E1U6033 | sp-23 | an-335 | E1U13359 | sp-41 | an-335 |
| E1A6034 | sp-19 | an-336 | E1U6034 | sp-23 | an-336 | E1U13360 | sp-41 | an-336 |
| E1A6035 | sp-19 | an-337 | E1U6035 | sp-23 | an-337 | E1U13361 | sp-41 | an-337 |
| E1A6036 | sp-19 | an-338 | E1U6036 | sp-23 | an-338 | E1U13362 | sp-41 | an-338 |
| E1A6037 | sp-19 | an-339 | E1U6037 | sp-23 | an-339 | E1U13363 | sp-41 | an-339 |
| E1A6038 | sp-19 | an-340 | E1U6038 | sp-23 | an-340 | E1U13364 | sp-41 | an-340 |
| E1A6039 | sp-19 | an-341 | E1U6039 | sp-23 | an-341 | E1U13365 | sp-41 | an-341 |
| E1A6040 | sp-19 | an-342 | E1U6040 | sp-23 | an-342 | E1U13366 | sp-41 | an-342 |
| E1A6041 | sp-19 | an-343 | E1U6041 | sp-23 | an-343 | E1U13367 | sp-41 | an-343 |
| E1A6042 | sp-19 | an-344 | E1U6042 | sp-23 | an-344 | E1U13368 | sp-41 | an-344 |
| E1A6043 | sp-19 | an-345 | E1U6043 | sp-23 | an-345 | E1U13369 | sp-41 | an-345 |
| E1A6044 | sp-19 | an-346 | E1U6044 | sp-23 | an-346 | E1U13370 | sp-41 | an-346 |
| E1A6045 | sp-19 | an-347 | E1U6045 | sp-23 | an-347 | E1U13371 | sp-41 | an-347 |
| E1A6046 | sp-19 | an-348 | E1U6046 | sp-23 | an-348 | E1U13372 | sp-41 | an-348 |
| E1A6047 | sp-19 | an-349 | E1U6047 | sp-23 | an-349 | E1U13373 | sp-41 | an-349 |
| E1A6048 | sp-19 | an-350 | E1U6048 | sp-23 | an-350 | E1U13374 | sp-41 | an-350 |
| Table 1-113 ||||||||||
| Y = NHCS ||| Y = NHCSNH ||| Y = NHCSNH |||
| E1A6049 | sp-19 | an-351 | E1U6049 | sp-23 | an-351 | E1U13375 | sp-41 | an-351 |
| E1A6050 | sp-19 | an-352 | E1U6050 | sp-23 | an-352 | E1U13376 | sp-41 | an-352 |
| E1A6051 | sp-19 | an-353 | E1U6051 | sp-23 | an-353 | E1U13377 | sp-41 | an-353 |
| E1A6052 | sp-19 | an-354 | E1U6052 | sp-23 | an-354 | E1U13378 | sp-41 | an-354 |
| E1A6053 | sp-19 | an-355 | E1U6053 | sp-23 | an-355 | E1U13379 | sp-41 | an-355 |
| E1A6054 | sp-19 | an-356 | E1U6054 | sp-23 | an-356 | E1U13380 | sp-41 | an-356 |
| E1A6055 | sp-19 | an-357 | E1U6055 | sp-23 | an-357 | E1U13381 | sp-41 | an-357 |
| E1A6056 | sp-19 | an-358 | E1U6056 | sp-23 | an-358 | E1U13382 | sp-41 | an-358 |
| E1A6057 | sp-19 | an-359 | E1U6057 | sp-23 | an-359 | E1U13383 | sp-41 | an-359 |
| E1A6058 | sp-19 | an-360 | E1U6058 | sp-23 | an-360 | E1U13384 | sp-41 | an-360 |
| E1A6059 | sp-19 | an-361 | E1U6059 | sp-23 | an-361 | E1U13385 | sp-41 | an-361 |
| E1A6060 | sp-19 | an-362 | E1U6060 | sp-23 | an-362 | E1U13386 | sp-41 | an-362 |
| E1A6061 | sp-19 | an-363 | E1U6061 | sp-23 | an-363 | E1U13387 | sp-41 | an-363 |
| E1A6062 | sp-19 | an-364 | E1U6062 | sp-23 | an-364 | E1U13388 | sp-41 | an-364 |
| E1A6063 | sp-19 | an-365 | E1U6063 | sp-23 | an-365 | E1U13389 | sp-41 | an-365 |
| E1A6064 | sp-19 | an-366 | E1U6064 | sp-23 | an-366 | E1U13390 | sp-41 | an-366 |

-continued

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| E1A6065 | sp-19 | an-367 | E1U6065 | sp-23 | an-367 | E1U13391 | sp-41 | an-367 |
| E1A6066 | sp-19 | an-368 | E1U6066 | sp-23 | an-368 | E1U13392 | sp-41 | an-368 |
| E1A6067 | sp-19 | an-369 | E1U6067 | sp-23 | an-369 | E1U13393 | sp-41 | an-369 |
| E1A6068 | sp-19 | an-370 | E1U6068 | sp-23 | an-370 | E1U13394 | sp-41 | an-370 |
| E1A6069 | sp-19 | an-371 | E1U6069 | sp-23 | an-371 | E1U13395 | sp-41 | an-371 |
| E1A6070 | sp-19 | an-372 | E1U6070 | sp-23 | an-372 | E1U13396 | sp-41 | an-372 |
| E1A6071 | sp-19 | an-373 | E1U6071 | sp-23 | an-373 | E1U13397 | sp-41 | an-373 |
| E1A6072 | sp-19 | an-374 | E1U6072 | sp-23 | an-374 | E1U13398 | sp-41 | an-374 |
| E1A6073 | sp-19 | an-375 | E1U6073 | sp-23 | an-375 | E1U13399 | sp-41 | an-375 |
| E1A6074 | sp-19 | an-376 | E1U6074 | sp-23 | an-376 | E1U13400 | sp-41 | an-376 |
| E1A6075 | sp-19 | an-377 | E1U6075 | sp-23 | an-377 | E1U13401 | sp-41 | an-377 |
| E1A6076 | sp-19 | an-378 | E1U6076 | sp-23 | an-378 | E1U13402 | sp-41 | an-378 |
| E1A6077 | sp-19 | an-379 | E1U6077 | sp-23 | an-379 | E1U13403 | sp-41 | an-379 |
| E1A6078 | sp-19 | an-380 | E1U6078 | sp-23 | an-380 | E1U13404 | sp-41 | an-380 |
| E1A6079 | sp-19 | an-381 | E1U6079 | sp-23 | an-381 | E1U13405 | sp-41 | an-381 |
| E1A6080 | sp-19 | an-382 | E1U6080 | sp-23 | an-382 | E1U13406 | sp-41 | an-382 |
| E1A6081 | sp-19 | an-383 | E1U6081 | sp-23 | an-383 | E1U13407 | sp-41 | an-383 |
| E1A6082 | sp-19 | an-384 | E1U6082 | sp-23 | an-384 | E1U13408 | sp-41 | an-384 |
| E1A6083 | sp-19 | an-385 | E1U6083 | sp-23 | an-385 | E1U13409 | sp-41 | an-385 |
| E1A6084 | sp-19 | an-386 | E1U6084 | sp-23 | an-386 | E1U13410 | sp-41 | an-386 |
| E1A6085 | sp-19 | an-387 | E1U6085 | sp-23 | an-387 | E1U13411 | sp-41 | an-387 |
| E1A6086 | sp-19 | an-388 | E1U6086 | sp-23 | an-388 | E1U13412 | sp-41 | an-388 |
| E1A6087 | sp-19 | an-389 | E1U6087 | sp-23 | an-389 | E1U13413 | sp-41 | an-389 |
| E1A6088 | sp-19 | an-390 | E1U6088 | sp-23 | an-390 | E1U13414 | sp-41 | an-390 |
| E1A6089 | sp-19 | an-391 | E1U6089 | sp-23 | an-391 | E1U13415 | sp-41 | an-391 |
| E1A6090 | sp-19 | an-392 | E1U6090 | sp-23 | an-392 | E1U13416 | sp-41 | an-392 |
| E1A6091 | sp-19 | an-393 | E1U6091 | sp-23 | an-393 | E1U13417 | sp-41 | an-393 |
| E1A6092 | sp-19 | an-394 | E1U6092 | sp-23 | an-394 | E1U13418 | sp-41 | an-394 |
| E1A6093 | sp-19 | an-395 | E1U6093 | sp-23 | an-395 | E1U13419 | sp-41 | an-395 |
| E1A6094 | sp-19 | an-396 | E1U6094 | sp-23 | an-396 | E1U13420 | sp-41 | an-396 |
| E1A6095 | sp-19 | an-397 | E1U6095 | sp-23 | an-397 | E1U13421 | sp-41 | an-397 |
| E1A6096 | sp-19 | an-398 | E1U6096 | sp-23 | an-398 | E1U13422 | sp-41 | an-398 |
| E1A6097 | sp-19 | an-399 | E1U6097 | sp-23 | an-399 | E1U13423 | sp-41 | an-399 |
| E1A6098 | sp-19 | an-400 | E1U6098 | sp-23 | an-400 | E1U13424 | sp-41 | an-400 |
| E1A6099 | sp-19 | an-401 | E1U6099 | sp-23 | an-401 | E1U13425 | sp-41 | an-401 |
| E1A6100 | sp-19 | an-402 | E1U6100 | sp-23 | an-402 | E1U13426 | sp-41 | an-402 |
| E1A6101 | sp-19 | an-403 | E1U6101 | sp-23 | an-403 | E1U13427 | sp-41 | an-403 |
| E1A6102 | sp-19 | an-404 | E1U6102 | sp-23 | an-404 | E1U13428 | sp-41 | an-404 |

Table 1-114

| Y = NHCS | | | Y = NHCSNH | | | Y = NHCSNH | | |
|---|---|---|---|---|---|---|---|---|
| E1A6103 | sp-19 | an-405 | E1U6103 | sp-23 | an-405 | E1U13429 | sp-41 | an-405 |
| E1A6104 | sp-19 | an-406 | E1U6104 | sp-23 | an-406 | E1U13430 | sp-41 | an-406 |
| E1A6105 | sp-19 | an-407 | E1U6105 | sp-23 | an-407 | E1U13431 | sp-41 | an-407 |
| E1A6106 | sp-21 | an-1 | E1U6106 | sp-24 | an-1 | E1U13432 | sp-42 | an-1 |
| E1A6107 | sp-21 | an-2 | E1U6107 | sp-24 | an-2 | E1U13433 | sp-42 | an-2 |
| E1A6108 | sp-21 | an-3 | E1U6108 | sp-24 | an-3 | E1U13434 | sp-42 | an-3 |
| E1A6109 | sp-21 | an-4 | E1U6109 | sp-24 | an-4 | E1U13435 | sp-42 | an-4 |
| E1A6110 | sp-21 | an-5 | E1U6110 | sp-24 | an-5 | E1U13436 | sp-42 | an-5 |
| E1A6111 | sp-21 | an-6 | E1U6111 | sp-24 | an-6 | E1U13437 | sp-42 | an-6 |
| E1A6112 | sp-21 | an-7 | E1U6112 | sp-24 | an-7 | E1U13438 | sp-42 | an-7 |
| E1A6113 | sp-21 | an-8 | E1U6113 | sp-24 | an-8 | E1U13439 | sp-42 | an-8 |
| E1A6114 | sp-21 | an-9 | E1U6114 | sp-24 | an-9 | E1U13440 | sp-42 | an-9 |
| E1A6115 | sp-21 | an-10 | E1U6115 | sp-24 | an-10 | E1U13441 | sp-42 | an-10 |
| E1A6116 | sp-21 | an-11 | E1U6116 | sp-24 | an-11 | E1U13442 | sp-42 | an-11 |
| E1A6117 | sp-21 | an-12 | E1U6117 | sp-24 | an-12 | E1U13443 | sp-42 | an-12 |
| E1A6118 | sp-21 | an-13 | E1U6118 | sp-24 | an-13 | E1U13444 | sp-42 | an-13 |
| E1A6119 | sp-21 | an-14 | E1U6119 | sp-24 | an-14 | E1U13445 | sp-42 | an-14 |
| E1A6120 | sp-21 | an-15 | E1U6120 | sp-24 | an-15 | E1U13446 | sp-42 | an-15 |
| E1A6121 | sp-21 | an-16 | E1U6121 | sp-24 | an-16 | E1U13447 | sp-42 | an-16 |
| E1A6122 | sp-21 | an-17 | E1U6122 | sp-24 | an-17 | E1U13448 | sp-42 | an-17 |
| E1A6123 | sp-21 | an-18 | E1U6123 | sp-24 | an-18 | E1U13449 | sp-42 | an-18 |
| E1A6124 | sp-21 | an-19 | E1U6124 | sp-24 | an-19 | E1U13450 | sp-42 | an-19 |
| E1A6125 | sp-21 | an-20 | E1U6125 | sp-24 | an-20 | E1U13451 | sp-42 | an-20 |
| E1A6126 | sp-21 | an-21 | E1U6126 | sp-24 | an-21 | E1U13452 | sp-42 | an-21 |
| E1A6127 | sp-21 | an-22 | E1U6127 | sp-24 | an-22 | E1U13453 | sp-42 | an-22 |
| E1A6128 | sp-21 | an-23 | E1U6128 | sp-24 | an-23 | E1U13454 | sp-42 | an-23 |
| E1A6129 | sp-21 | an-24 | E1U6129 | sp-24 | an-24 | E1U13455 | sp-42 | an-24 |
| E1A6130 | sp-21 | an-25 | E1U6130 | sp-24 | an-25 | E1U13456 | sp-42 | an-25 |
| E1A6131 | sp-21 | an-26 | E1U6131 | sp-24 | an-26 | E1U13457 | sp-42 | an-26 |
| E1A6132 | sp-21 | an-27 | E1U6132 | sp-24 | an-27 | E1U13458 | sp-42 | an-27 |
| E1A6133 | sp-21 | an-28 | E1U6133 | sp-24 | an-28 | E1U13459 | sp-42 | an-28 |
| E1A6134 | sp-21 | an-29 | E1U6134 | sp-24 | an-29 | E1U13460 | sp-42 | an-29 |
| E1A6135 | sp-21 | an-30 | E1U6135 | sp-24 | an-30 | E1U13461 | sp-42 | an-30 |
| E1A6136 | sp-21 | an-31 | E1U6136 | sp-24 | an-31 | E1U13462 | sp-42 | an-31 |
| E1A6137 | sp-21 | an-32 | E1U6137 | sp-24 | an-32 | E1U13463 | sp-42 | an-32 |
| E1A6138 | sp-21 | an-33 | E1U6138 | sp-24 | an-33 | E1U13464 | sp-42 | an-33 |

-continued

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| E1A6139 | sp-21 | an-34 | E1U6139 | sp-24 | an-34 | E1U13465 | sp-42 | an-34 |
| E1A6140 | sp-21 | an-35 | E1U6140 | sp-24 | an-35 | E1U13466 | sp-42 | an-35 |
| E1A6141 | sp-21 | an-36 | E1U6141 | sp-24 | an-36 | E1U13467 | sp-42 | an-36 |
| E1A6142 | sp-21 | an-37 | E1U6142 | sp-24 | an-37 | E1U13468 | sp-42 | an-37 |
| E1A6143 | sp-21 | an-38 | E1U6143 | sp-24 | an-38 | E1U13469 | sp-42 | an-38 |
| E1A6144 | sp-21 | an-39 | E1U6144 | sp-24 | an-39 | E1U13470 | sp-42 | an-39 |
| E1A6145 | sp-21 | an-40 | E1U6145 | sp-24 | an-40 | E1U13471 | sp-42 | an-40 |
| E1A6146 | sp-21 | an-41 | E1U6146 | sp-24 | an-41 | E1U13472 | sp-42 | an-41 |
| E1A6147 | sp-21 | an-42 | E1U6147 | sp-24 | an-42 | E1U13473 | sp-42 | an-42 |
| E1A6148 | sp-21 | an-43 | E1U6148 | sp-24 | an-43 | E1U13474 | sp-42 | an-43 |
| E1A6149 | sp-21 | an-44 | E1U6149 | sp-24 | an-44 | E1U13475 | sp-42 | an-44 |
| E1A6150 | sp-21 | an-45 | E1U6150 | sp-24 | an-45 | E1U13476 | sp-42 | an-45 |
| E1A6151 | sp-21 | an-46 | E1U6151 | sp-24 | an-46 | E1U13477 | sp-42 | an-46 |
| E1A6152 | sp-21 | an-47 | E1U6152 | sp-24 | an-47 | E1U13478 | sp-42 | an-47 |
| E1A6153 | sp-21 | an-48 | E1U6153 | sp-24 | an-48 | E1U13479 | sp-42 | an-48 |
| E1A6154 | sp-21 | an-49 | E1U6154 | sp-24 | an-49 | E1U13480 | sp-42 | an-49 |
| E1A6155 | sp-21 | an-50 | E1U6155 | sp-24 | an-50 | E1U13481 | sp-42 | an-50 |
| E1A6156 | sp-21 | an-51 | E1U6156 | sp-24 | an-51 | E1U13482 | sp-42 | an-51 |

Table 1-115

| Y = NHCS | | | Y = NHCSNH | | | Y = NHCSNH | | |
|---|---|---|---|---|---|---|---|---|
| E1A6157 | sp-21 | an-52 | E1U6157 | sp-24 | an-52 | E1U13483 | sp-42 | an-52 |
| E1A6158 | sp-21 | an-53 | E1U6158 | sp-24 | an-53 | E1U13484 | sp-42 | an-53 |
| E1A6159 | sp-21 | an-54 | E1U6159 | sp-24 | an-54 | E1U13485 | sp-42 | an-54 |
| E1A6160 | sp-21 | an-55 | E1U6160 | sp-24 | an-55 | E1U13486 | sp-42 | an-55 |
| E1A6161 | sp-21 | an-56 | E1U6161 | sp-24 | an-56 | E1U13487 | sp-42 | an-56 |
| E1A6162 | sp-21 | an-57 | E1U6162 | sp-24 | an-57 | E1U13488 | sp-42 | an-57 |
| E1A6163 | sp-21 | an-58 | E1U6163 | sp-24 | an-58 | E1U13489 | sp-42 | an-58 |
| E1A6164 | sp-21 | an-59 | E1U6164 | sp-24 | an-59 | E1U13490 | sp-42 | an-59 |
| E1A6165 | sp-21 | an-60 | E1U6165 | sp-24 | an-60 | E1U13491 | sp-42 | an-60 |
| E1A6166 | sp-21 | an-61 | E1U6166 | sp-24 | an-61 | E1U13492 | sp-42 | an-61 |
| E1A6167 | sp-21 | an-62 | E1U6167 | sp-24 | an-62 | E1U13493 | sp-42 | an-62 |
| E1A6168 | sp-21 | an-63 | E1U6168 | sp-24 | an-63 | E1U13494 | sp-42 | an-63 |
| E1A6169 | sp-21 | an-64 | E1U6169 | sp-24 | an-64 | E1U13495 | sp-42 | an-64 |
| E1A6170 | sp-21 | an-65 | E1U6170 | sp-24 | an-65 | E1U13496 | sp-42 | an-65 |
| E1A6171 | sp-21 | an-66 | E1U6171 | sp-24 | an-66 | E1U13497 | sp-42 | an-66 |
| E1A6172 | sp-21 | an-67 | E1U6172 | sp-24 | an-67 | E1U13498 | sp-42 | an-67 |
| E1A6173 | sp-21 | an-68 | E1U6173 | sp-24 | an-68 | E1U13499 | sp-42 | an-68 |
| E1A6174 | sp-21 | an-69 | E1U6174 | sp-24 | an-69 | E1U13500 | sp-42 | an-69 |
| E1A6175 | sp-21 | an-70 | E1U6175 | sp-24 | an-70 | E1U13501 | sp-42 | an-70 |
| E1A6176 | sp-21 | an-71 | E1U6176 | sp-24 | an-71 | E1U13502 | sp-42 | an-71 |
| E1A6177 | sp-21 | an-72 | E1U6177 | sp-24 | an-72 | E1U13503 | sp-42 | an-72 |
| E1A6178 | sp-21 | an-73 | E1U6178 | sp-24 | an-73 | E1U13504 | sp-42 | an-73 |
| E1A6179 | sp-21 | an-74 | E1U6179 | sp-24 | an-74 | E1U13505 | sp-42 | an-74 |
| E1A6180 | sp-21 | an-75 | E1U6180 | sp-24 | an-75 | E1U13506 | sp-42 | an-75 |
| E1A6181 | sp-21 | an-76 | E1U6181 | sp-24 | an-76 | E1U13507 | sp-42 | an-76 |
| E1A6182 | sp-21 | an-77 | E1U6182 | sp-24 | an-77 | E1U13508 | sp-42 | an-77 |
| E1A6183 | sp-21 | an-78 | E1U6183 | sp-24 | an-78 | E1U13509 | sp-42 | an-78 |
| E1A6184 | sp-21 | an-79 | E1U6184 | sp-24 | an-79 | E1U13510 | sp-42 | an-79 |
| E1A6185 | sp-21 | an-80 | E1U6185 | sp-24 | an-80 | E1U13511 | sp-42 | an-80 |
| E1A6186 | sp-21 | an-81 | E1U6186 | sp-24 | an-81 | E1U13512 | sp-42 | an-81 |
| E1A6187 | sp-21 | an-82 | E1U6187 | sp-24 | an-82 | E1U13513 | sp-42 | an-82 |
| E1A6188 | sp-21 | an-83 | E1U6188 | sp-24 | an-83 | E1U13514 | sp-42 | an-83 |
| E1A6189 | sp-21 | an-84 | E1U6189 | sp-24 | an-84 | E1U13515 | sp-42 | an-84 |
| E1A6190 | sp-21 | an-85 | E1U6190 | sp-24 | an-85 | E1U13516 | sp-42 | an-85 |
| E1A6191 | sp-21 | an-86 | E1U6191 | sp-24 | an-86 | E1U13517 | sp-42 | an-86 |
| E1A6192 | sp-21 | an-87 | E1U6192 | sp-24 | an-87 | E1U13518 | sp-42 | an-87 |
| E1A6193 | sp-21 | an-88 | E1U6193 | sp-24 | an-88 | E1U13519 | sp-42 | an-88 |
| E1A6194 | sp-21 | an-89 | E1U6194 | sp-24 | an-89 | E1U13520 | sp-42 | an-89 |
| E1A6195 | sp-21 | an-90 | E1U6195 | sp-24 | an-90 | E1U13521 | sp-42 | an-90 |
| E1A6196 | sp-21 | an-91 | E1U6196 | sp-24 | an-91 | E1U13522 | sp-42 | an-91 |
| E1A6197 | sp-21 | an-92 | E1U6197 | sp-24 | an-92 | E1U13523 | sp-42 | an-92 |
| E1A6198 | sp-21 | an-93 | E1U6198 | sp-24 | an-93 | E1U13524 | sp-42 | an-93 |
| E1A6199 | sp-21 | an-94 | E1U6199 | sp-24 | an-94 | E1U13525 | sp-42 | an-94 |
| E1A6200 | sp-21 | an-95 | E1U6200 | sp-24 | an-95 | E1U13526 | sp-42 | an-95 |
| E1A6201 | sp-21 | an-96 | E1U6201 | sp-24 | an-96 | E1U13527 | sp-42 | an-96 |
| E1A6202 | sp-21 | an-97 | E1U6202 | sp-24 | an-97 | E1U13528 | sp-42 | an-97 |
| E1A6203 | sp-21 | an-98 | E1U6203 | sp-24 | an-98 | E1U13529 | sp-42 | an-98 |
| E1A6204 | sp-21 | an-99 | E1U6204 | sp-24 | an-99 | E1U13530 | sp-42 | an-99 |
| E1A6205 | sp-21 | an-100 | E1U6205 | sp-24 | an-100 | E1U13531 | sp-42 | an-100 |
| E1A6206 | sp-21 | an-101 | E1U6206 | sp-24 | an-101 | E1U13532 | sp-42 | an-101 |
| E1A6207 | sp-21 | an-102 | E1U6207 | sp-24 | an-102 | E1U13533 | sp-42 | an-102 |
| E1A6208 | sp-21 | an-103 | E1U6208 | sp-24 | an-103 | E1U13534 | sp-42 | an-103 |
| E1A6209 | sp-21 | an-104 | E1U6209 | sp-24 | an-104 | E1U13535 | sp-42 | an-104 |
| E1A6210 | sp-21 | an-105 | E1U6210 | sp-24 | an-105 | E1U13536 | sp-42 | an-105 |

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| Table 1-116 | | | | | | | | |
| Y = NHCS | | | Y = NHCSNH | | | Y = NHCSNH | | |
| E1A6211 | sp-21 | an-106 | E1U6211 | sp-24 | an-106 | E1U13537 | sp-42 | an-106 |
| E1A6212 | sp-21 | an-107 | E1U6212 | sp-24 | an-107 | E1U13538 | sp-42 | an-107 |
| E1A6213 | sp-21 | an-108 | E1U6213 | sp-24 | an-108 | E1U13539 | sp-42 | an-108 |
| E1A6214 | sp-21 | an-109 | E1U6214 | sp-24 | an-109 | E1U13540 | sp-42 | an-109 |
| E1A6215 | sp-21 | an-110 | E1U6215 | sp-24 | an-110 | E1U13541 | sp-42 | an-110 |
| E1A6216 | sp-21 | an-111 | E1U6216 | sp-24 | an-111 | E1U13542 | sp-42 | an-111 |
| E1A6217 | sp-21 | an-112 | E1U6217 | sp-24 | an-112 | E1U13543 | sp-42 | an-112 |
| E1A6218 | sp-21 | an-113 | E1U6218 | sp-24 | an-113 | E1U13544 | sp-42 | an-113 |
| E1A6219 | sp-21 | an-114 | E1U6219 | sp-24 | an-114 | E1U13545 | sp-42 | an-114 |
| E1A6220 | sp-21 | an-115 | E1U6220 | sp-24 | an-115 | E1U13546 | sp-42 | an-115 |
| E1A6221 | sp-21 | an-116 | E1U6221 | sp-24 | an-116 | E1U13547 | sp-42 | an-116 |
| E1A6222 | sp-21 | an-117 | E1U6222 | sp-24 | an-117 | E1U13548 | sp-42 | an-117 |
| E1A6223 | sp-21 | an-118 | E1U6223 | sp-24 | an-118 | E1U13549 | sp-42 | an-118 |
| E1A6224 | sp-21 | an-119 | E1U6224 | sp-24 | an-119 | E1U13550 | sp-42 | an-119 |
| E1A6225 | sp-21 | an-120 | E1U6225 | sp-24 | an-120 | E1U13551 | sp-42 | an-120 |
| E1A6226 | sp-21 | an-121 | E1U6226 | sp-24 | an-121 | E1U13552 | sp-42 | an-121 |
| E1A6227 | sp-21 | an-122 | E1U6227 | sp-24 | an-122 | E1U13553 | sp-42 | an-122 |
| E1A6228 | sp-21 | an-123 | E1U6228 | sp-24 | an-123 | E1U13554 | sp-42 | an-123 |
| E1A6229 | sp-21 | an-124 | E1U6229 | sp-24 | an-124 | E1U13555 | sp-42 | an-124 |
| E1A6230 | sp-21 | an-125 | E1U6230 | sp-24 | an-125 | E1U13556 | sp-42 | an-125 |
| E1A6231 | sp-21 | an-126 | E1U6231 | sp-24 | an-126 | E1U13557 | sp-42 | an-126 |
| E1A6232 | sp-21 | an-127 | E1U6232 | sp-24 | an-127 | E1U13558 | sp-42 | an-127 |
| E1A6233 | sp-21 | an-128 | E1U6233 | sp-24 | an-128 | E1U13559 | sp-42 | an-128 |
| E1A6234 | sp-21 | an-129 | E1U6234 | sp-24 | an-129 | E1U13560 | sp-42 | an-129 |
| E1A6235 | sp-21 | an-130 | E1U6235 | sp-24 | an-130 | E1U13561 | sp-42 | an-130 |
| E1A6236 | sp-21 | an-131 | E1U6236 | sp-24 | an-131 | E1U13562 | sp-42 | an-131 |
| E1A6237 | sp-21 | an-132 | E1U6237 | sp-24 | an-132 | E1U13563 | sp-42 | an-132 |
| E1A6238 | sp-21 | an-133 | E1U6238 | sp-24 | an-133 | E1U13564 | sp-42 | an-133 |
| E1A6239 | sp-21 | an-134 | E1U6239 | sp-24 | an-134 | E1U13565 | sp-42 | an-134 |
| E1A6240 | sp-21 | an-135 | E1U6240 | sp-24 | an-135 | E1U13566 | sp-42 | an-135 |
| E1A6241 | sp-21 | an-136 | E1U6241 | sp-24 | an-136 | E1U13567 | sp-42 | an-136 |
| E1A6242 | sp-21 | an-137 | E1U6242 | sp-24 | an-137 | E1U13568 | sp-42 | an-137 |
| E1A6243 | sp-21 | an-138 | E1U6243 | sp-24 | an-138 | E1U13569 | sp-42 | an-138 |
| E1A6244 | sp-21 | an-139 | E1U6244 | sp-24 | an-139 | E1U13570 | sp-42 | an-139 |
| E1A6245 | sp-21 | an-140 | E1U6245 | sp-24 | an-140 | E1U13571 | sp-42 | an-140 |
| E1A6246 | sp-21 | an-141 | E1U6246 | sp-24 | an-141 | E1U13572 | sp-42 | an-141 |
| E1A6247 | sp-21 | an-142 | E1U6247 | sp-24 | an-142 | E1U13573 | sp-42 | an-142 |
| E1A6248 | sp-21 | an-143 | E1U6248 | sp-24 | an-143 | E1U13574 | sp-42 | an-143 |
| E1A6249 | sp-21 | an-144 | E1U6249 | sp-24 | an-144 | E1U13575 | sp-42 | an-144 |
| E1A6250 | sp-21 | an-145 | E1U6250 | sp-24 | an-145 | E1U13576 | sp-42 | an-145 |
| E1A6251 | sp-21 | an-146 | E1U6251 | sp-24 | an-146 | E1U13577 | sp-42 | an-146 |
| E1A6252 | sp-21 | an-147 | E1U6252 | sp-24 | an-147 | E1U13578 | sp-42 | an-147 |
| E1A6253 | sp-21 | an-148 | E1U6253 | sp-24 | an-148 | E1U13579 | sp-42 | an-148 |
| E1A6254 | sp-21 | an-149 | E1U6254 | sp-24 | an-149 | E1U13580 | sp-42 | an-149 |
| E1A6255 | sp-21 | an-150 | E1U6255 | sp-24 | an-150 | E1U13581 | sp-42 | an-150 |
| E1A6256 | sp-21 | an-151 | E1U6256 | sp-24 | an-151 | E1U13582 | sp-42 | an-151 |
| E1A6257 | sp-21 | an-152 | E1U6257 | sp-24 | an-152 | E1U13583 | sp-42 | an-152 |
| E1A6258 | sp-21 | an-153 | E1U6258 | sp-24 | an-153 | E1U13584 | sp-42 | an-153 |
| E1A6259 | sp-21 | an-154 | E1U6259 | sp-24 | an-154 | E1U13585 | sp-42 | an-154 |
| E1A6260 | sp-21 | an-155 | E1U6260 | sp-24 | an-155 | E1U13586 | sp-42 | an-155 |
| E1A6261 | sp-21 | an-156 | E1U6261 | sp-24 | an-156 | E1U13587 | sp-42 | an-156 |
| E1A6262 | sp-21 | an-157 | E1U6262 | sp-24 | an-157 | E1U13588 | sp-42 | an-157 |
| E1A6263 | sp-21 | an-158 | E1U6263 | sp-24 | an-158 | E1U13589 | sp-42 | an-158 |
| E1A6264 | sp-21 | an-159 | E1U6264 | sp-24 | an-159 | E1U13590 | sp-42 | an-159 |
| Table 1-117 | | | | | | | | |
| Y = NHCS | | | Y = NHCSNH | | | Y = NHCSNH | | |
| E1A6265 | sp-21 | an-160 | E1U6265 | sp-24 | an-160 | E1U13591 | sp-42 | an-160 |
| E1A6266 | sp-21 | an-161 | E1U6266 | sp-24 | an-161 | E1U13592 | sp-42 | an-161 |
| E1A6267 | sp-21 | an-162 | E1U6267 | sp-24 | an-162 | E1U13593 | sp-42 | an-162 |
| E1A6268 | sp-21 | an-163 | E1U6268 | sp-24 | an-163 | E1U13594 | sp-42 | an-163 |
| E1A6269 | sp-21 | an-164 | E1U6269 | sp-24 | an-164 | E1U13595 | sp-42 | an-164 |
| E1A6270 | sp-21 | an-165 | E1U6270 | sp-24 | an-165 | E1U13596 | sp-42 | an-165 |
| E1A6271 | sp-21 | an-166 | E1U6271 | sp-24 | an-166 | E1U13597 | sp-42 | an-166 |
| E1A6272 | sp-21 | an-167 | E1U6272 | sp-24 | an-167 | E1U13598 | sp-42 | an-167 |
| E1A6273 | sp-21 | an-168 | E1U6273 | sp-24 | an-168 | E1U13599 | sp-42 | an-168 |
| E1A6274 | sp-21 | an-169 | E1U6274 | sp-24 | an-169 | E1U13600 | sp-42 | an-169 |
| E1A6275 | sp-21 | an-170 | E1U6275 | sp-24 | an-170 | E1U13601 | sp-42 | an-170 |
| E1A6276 | sp-21 | an-171 | E1U6276 | sp-24 | an-171 | E1U13602 | sp-42 | an-171 |
| E1A6277 | sp-21 | an-172 | E1U6277 | sp-24 | an-172 | E1U13603 | sp-42 | an-172 |
| E1A6278 | sp-21 | an-173 | E1U6278 | sp-24 | an-173 | E1U13604 | sp-42 | an-173 |
| E1A6279 | sp-21 | an-174 | E1U6279 | sp-24 | an-174 | E1U13605 | sp-42 | an-174 |
| E1A6280 | sp-21 | an-175 | E1U6280 | sp-24 | an-175 | E1U13606 | sp-42 | an-175 |

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| E1A6281 | sp-21 | an-176 | E1U6281 | sp-24 | an-176 | E1U13607 | sp-42 | an-176 |
| E1A6282 | sp-21 | an-177 | E1U6282 | sp-24 | an-177 | E1U13608 | sp-42 | an-177 |
| E1A6283 | sp-21 | an-178 | E1U6283 | sp-24 | an-178 | E1U13609 | sp-42 | an-178 |
| E1A6284 | sp-21 | an-179 | E1U6284 | sp-24 | an-179 | E1U13610 | sp-42 | an-179 |
| E1A6285 | sp-21 | an-180 | E1U6285 | sp-24 | an-180 | E1U13611 | sp-42 | an-180 |
| E1A6286 | sp-21 | an-181 | E1U6286 | sp-24 | an-181 | E1U13612 | sp-42 | an-181 |
| E1A6287 | sp-21 | an-182 | E1U6287 | sp-24 | an-182 | E1U13613 | sp-42 | an-182 |
| E1A6288 | sp-21 | an-183 | E1U6288 | sp-24 | an-183 | E1U13614 | sp-42 | an-183 |
| E1A6289 | sp-21 | an-184 | E1U6289 | sp-24 | an-184 | E1U13615 | sp-42 | an-184 |
| E1A6290 | sp-21 | an-185 | E1U6290 | sp-24 | an-185 | E1U13616 | sp-42 | an-185 |
| E1A6291 | sp-21 | an-186 | E1U6291 | sp-24 | an-186 | E1U13617 | sp-42 | an-186 |
| E1A6292 | sp-21 | an-187 | E1U6292 | sp-24 | an-187 | E1U13618 | sp-42 | an-187 |
| E1A6293 | sp-21 | an-188 | E1U6293 | sp-24 | an-188 | E1U13619 | sp-42 | an-188 |
| E1A6294 | sp-21 | an-189 | E1U6294 | sp-24 | an-189 | E1U13620 | sp-42 | an-189 |
| E1A6295 | sp-21 | an-190 | E1U6295 | sp-24 | an-190 | E1U13621 | sp-42 | an-190 |
| E1A6296 | sp-21 | an-191 | E1U6296 | sp-24 | an-191 | E1U13622 | sp-42 | an-191 |
| E1A6297 | sp-21 | an-192 | E1U6297 | sp-24 | an-192 | E1U13623 | sp-42 | an-192 |
| E1A6298 | sp-21 | an-193 | E1U6298 | sp-24 | an-193 | E1U13624 | sp-42 | an-193 |
| E1A6299 | sp-21 | an-194 | E1U6299 | sp-24 | an-194 | E1U13625 | sp-42 | an-194 |
| E1A6300 | sp-21 | an-195 | E1U6300 | sp-24 | an-195 | E1U13626 | sp-42 | an-195 |
| E1A6301 | sp-21 | an-196 | E1U6301 | sp-24 | an-196 | E1U13627 | sp-42 | an-196 |
| E1A6302 | sp-21 | an-197 | E1U6302 | sp-24 | an-197 | E1U13628 | sp-42 | an-197 |
| E1A6303 | sp-21 | an-198 | E1U6303 | sp-24 | an-198 | E1U13629 | sp-42 | an-198 |
| E1A6304 | sp-21 | an-199 | E1U6304 | sp-24 | an-199 | E1U13630 | sp-42 | an-199 |
| E1A6305 | sp-21 | an-200 | E1U6305 | sp-24 | an-200 | E1U13631 | sp-42 | an-200 |
| E1A6306 | sp-21 | an-201 | E1U6306 | sp-24 | an-201 | E1U13632 | sp-42 | an-201 |
| E1A6307 | sp-21 | an-202 | E1U6307 | sp-24 | an-202 | E1U13633 | sp-42 | an-202 |
| E1A6308 | sp-21 | an-203 | E1U6308 | sp-24 | an-203 | E1U13634 | sp-42 | an-203 |
| E1A6309 | sp-21 | an-204 | E1U6309 | sp-24 | an-204 | E1U13635 | sp-42 | an-204 |
| E1A6310 | sp-21 | an-205 | E1U6310 | sp-24 | an-205 | E1U13636 | sp-42 | an-205 |
| E1A6311 | sp-21 | an-206 | E1U6311 | sp-24 | an-206 | E1U13637 | sp-42 | an-206 |
| E1A6312 | sp-21 | an-207 | E1U6312 | sp-24 | an-207 | E1U13638 | sp-42 | an-207 |
| E1A6313 | sp-21 | an-208 | E1U6313 | sp-24 | an-208 | E1U13639 | sp-42 | an-208 |
| E1A6314 | sp-21 | an-209 | E1U6314 | sp-24 | an-209 | E1U13640 | sp-42 | an-209 |
| E1A6315 | sp-21 | an-210 | E1U6315 | sp-24 | an-210 | E1U13641 | sp-42 | an-210 |
| E1A6316 | sp-21 | an-211 | E1U6316 | sp-24 | an-211 | E1U13642 | sp-42 | an-211 |
| E1A6317 | sp-21 | an-212 | E1U6317 | sp-24 | an-212 | E1U13643 | sp-42 | an-212 |
| E1A6318 | sp-21 | an-213 | E1U6318 | sp-24 | an-213 | E1U13644 | sp-42 | an-213 |

Table 1-118

| Y = NHCS | | | Y = NHCSNH | | | Y = NHCSNH | | |
|---|---|---|---|---|---|---|---|---|
| E1A6319 | sp-21 | an-214 | E1U6319 | sp-24 | an-214 | E1U13645 | sp-42 | an-214 |
| E1A6320 | sp-21 | an-215 | E1U6320 | sp-24 | an-215 | E1U13646 | sp-42 | an-215 |
| E1A6321 | sp-21 | an-216 | E1U6321 | sp-24 | an-216 | E1U13647 | sp-42 | an-216 |
| E1A6322 | sp-21 | an-217 | E1U6322 | sp-24 | an-217 | E1U13648 | sp-42 | an-217 |
| E1A6323 | sp-21 | an-218 | E1U6323 | sp-24 | an-218 | E1U13649 | sp-42 | an-218 |
| E1A6324 | sp-21 | an-219 | E1U6324 | sp-24 | an-219 | E1U13650 | sp-42 | an-219 |
| E1A6325 | sp-21 | an-220 | E1U6325 | sp-24 | an-220 | E1U13651 | sp-42 | an-220 |
| E1A6326 | sp-21 | an-221 | E1U6326 | sp-24 | an-221 | E1U13652 | sp-42 | an-221 |
| E1A6327 | sp-21 | an-222 | E1U6327 | sp-24 | an-222 | E1U13653 | sp-42 | an-222 |
| E1A6328 | sp-21 | an-223 | E1U6328 | sp-24 | an-223 | E1U13654 | sp-42 | an-223 |
| E1A6329 | sp-21 | an-224 | E1U6329 | sp-24 | an-224 | E1U13655 | sp-42 | an-224 |
| E1A6330 | sp-21 | an-225 | E1U6330 | sp-24 | an-225 | E1U13656 | sp-42 | an-225 |
| E1A6331 | sp-21 | an-226 | E1U6331 | sp-24 | an-226 | E1U13657 | sp-42 | an-226 |
| E1A6332 | sp-21 | an-227 | E1U6332 | sp-24 | an-227 | E1U13658 | sp-42 | an-227 |
| E1A6333 | sp-21 | an-228 | E1U6333 | sp-24 | an-228 | E1U13659 | sp-42 | an-228 |
| E1A6334 | sp-21 | an-229 | E1U6334 | sp-24 | an-229 | E1U13660 | sp-42 | an-229 |
| E1A6335 | sp-21 | an-230 | E1U6335 | sp-24 | an-230 | E1U13661 | sp-42 | an-230 |
| E1A6336 | sp-21 | an-231 | E1U6336 | sp-24 | an-231 | E1U13662 | sp-42 | an-231 |
| E1A6337 | sp-21 | an-232 | E1U6337 | sp-24 | an-232 | E1U13663 | sp-42 | an-232 |
| E1A6338 | sp-21 | an-233 | E1U6338 | sp-24 | an-233 | E1U13664 | sp-42 | an-233 |
| E1A6339 | sp-21 | an-234 | E1U6339 | sp-24 | an-234 | E1U13665 | sp-42 | an-234 |
| E1A6340 | sp-21 | an-235 | E1U6340 | sp-24 | an-235 | E1U13666 | sp-42 | an-235 |
| E1A6341 | sp-21 | an-236 | E1U6341 | sp-24 | an-236 | E1U13667 | sp-42 | an-236 |
| E1A6342 | sp-21 | an-237 | E1U6342 | sp-24 | an-237 | E1U13668 | sp-42 | an-237 |
| E1A6343 | sp-21 | an-238 | E1U6343 | sp-24 | an-238 | E1U13669 | sp-42 | an-238 |
| E1A6344 | sp-21 | an-239 | E1U6344 | sp-24 | an-239 | E1U13670 | sp-42 | an-239 |
| E1A6345 | sp-21 | an-240 | E1U6345 | sp-24 | an-240 | E1U13671 | sp-42 | an-240 |
| E1A6346 | sp-21 | an-241 | E1U6346 | sp-24 | an-241 | E1U13672 | sp-42 | an-241 |
| E1A6347 | sp-21 | an-242 | E1U6347 | sp-24 | an-242 | E1U13673 | sp-42 | an-242 |
| E1A6348 | sp-21 | an-243 | E1U6348 | sp-24 | an-243 | E1U13674 | sp-42 | an-243 |
| E1A6349 | sp-21 | an-244 | E1U6349 | sp-24 | an-244 | E1U13675 | sp-42 | an-244 |
| E1A6350 | sp-21 | an-245 | E1U6350 | sp-24 | an-245 | E1U13676 | sp-42 | an-245 |
| E1A6351 | sp-21 | an-246 | E1U6351 | sp-24 | an-246 | E1U13677 | sp-42 | an-246 |
| E1A6352 | sp-21 | an-247 | E1U6352 | sp-24 | an-247 | E1U13678 | sp-42 | an-247 |
| E1A6353 | sp-21 | an-248 | E1U6353 | sp-24 | an-248 | E1U13679 | sp-42 | an-248 |
| E1A6354 | sp-21 | an-249 | E1U6354 | sp-24 | an-249 | E1U13680 | sp-42 | an-249 |

-continued

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| E1A6355 | sp-21 | an-250 | E1U6355 | sp-24 | an-250 | E1U13681 | sp-42 | an-250 |
| E1A6356 | sp-21 | an-251 | E1U6356 | sp-24 | an-251 | E1U13682 | sp-42 | an-251 |
| E1A6357 | sp-21 | an-252 | E1U6357 | sp-24 | an-252 | E1U13683 | sp-42 | an-252 |
| E1A6358 | sp-21 | an-253 | E1U6358 | sp-24 | an-253 | E1U13684 | sp-42 | an-253 |
| E1A6359 | sp-21 | an-254 | E1U6359 | sp-24 | an-254 | E1U13685 | sp-42 | an-254 |
| E1A6360 | sp-21 | an-255 | E1U6360 | sp-24 | an-255 | E1U13686 | sp-42 | an-255 |
| E1A6361 | sp-21 | an-256 | E1U6361 | sp-24 | an-256 | E1U13687 | sp-42 | an-256 |
| E1A6362 | sp-21 | an-257 | E1U6362 | sp-24 | an-257 | E1U13688 | sp-42 | an-257 |
| E1A6363 | sp-21 | an-258 | E1U6363 | sp-24 | an-258 | E1U13689 | sp-42 | an-258 |
| E1A6364 | sp-21 | an-259 | E1U6364 | sp-24 | an-259 | E1U13690 | sp-42 | an-259 |
| E1A6365 | sp-21 | an-260 | E1U6365 | sp-24 | an-260 | E1U13691 | sp-42 | an-260 |
| E1A6366 | sp-21 | an-261 | E1U6366 | sp-24 | an-261 | E1U13692 | sp-42 | an-261 |
| E1A6367 | sp-21 | an-262 | E1U6367 | sp-24 | an-262 | E1U13693 | sp-42 | an-262 |
| E1A6368 | sp-21 | an-263 | E1U6368 | sp-24 | an-263 | E1U13694 | sp-42 | an-263 |
| E1A6369 | sp-21 | an-264 | E1U6369 | sp-24 | an-264 | E1U13695 | sp-42 | an-264 |
| E1A6370 | sp-21 | an-265 | E1U6370 | sp-24 | an-265 | E1U13696 | sp-42 | an-265 |
| E1A6371 | sp-21 | an-266 | E1U6371 | sp-24 | an-266 | E1U13697 | sp-42 | an-266 |
| E1A6372 | sp-21 | an-267 | E1U6372 | sp-24 | an-267 | E1U13698 | sp-42 | an-267 |

Table 1-119

| Y = NHCS | | | Y = NHCSNH | | | Y = NHCSNH | | |
|---|---|---|---|---|---|---|---|---|
| E1A6373 | sp-21 | an-268 | E1U6373 | sp-24 | an-268 | E1U13699 | sp-42 | an-268 |
| E1A6374 | sp-21 | an-269 | E1U6374 | sp-24 | an-269 | E1U13700 | sp-42 | an-269 |
| E1A6375 | sp-21 | an-270 | E1U6375 | sp-24 | an-270 | E1U13701 | sp-42 | an-270 |
| E1A6376 | sp-21 | an-271 | E1U6376 | sp-24 | an-271 | E1U13702 | sp-42 | an-271 |
| E1A6377 | sp-21 | an-272 | E1U6377 | sp-24 | an-272 | E1U13703 | sp-42 | an-272 |
| E1A6378 | sp-21 | an-273 | E1U6378 | sp-24 | an-273 | E1U13704 | sp-42 | an-273 |
| E1A6379 | sp-21 | an-274 | E1U6379 | sp-24 | an-274 | E1U13705 | sp-42 | an-274 |
| E1A6380 | sp-21 | an-275 | E1U6380 | sp-24 | an-275 | E1U13706 | sp-42 | an-275 |
| E1A6381 | sp-21 | an-276 | E1U6381 | sp-24 | an-276 | E1U13707 | sp-42 | an-276 |
| E1A6382 | sp-21 | an-277 | E1U6382 | sp-24 | an-277 | E1U13708 | sp-42 | an-277 |
| E1A6383 | sp-21 | an-278 | E1U6383 | sp-24 | an-278 | E1U13709 | sp-42 | an-278 |
| E1A6384 | sp-21 | an-279 | E1U6384 | sp-24 | an-279 | E1U13710 | sp-42 | an-279 |
| E1A6385 | sp-21 | an-280 | E1U6385 | sp-24 | an-280 | E1U13711 | sp-42 | an-280 |
| E1A6386 | sp-21 | an-281 | E1U6386 | sp-24 | an-281 | E1U13712 | sp-42 | an-281 |
| E1A6387 | sp-21 | an-282 | E1U6387 | sp-24 | an-282 | E1U13713 | sp-42 | an-282 |
| E1A6388 | sp-21 | an-283 | E1U6388 | sp-24 | an-283 | E1U13714 | sp-42 | an-283 |
| E1A6389 | sp-21 | an-284 | E1U6389 | sp-24 | an-284 | E1U13715 | sp-42 | an-284 |
| E1A6390 | sp-21 | an-285 | E1U6390 | sp-24 | an-285 | E1U13716 | sp-42 | an-285 |
| E1A6391 | sp-21 | an-286 | E1U6391 | sp-24 | an-286 | E1U13717 | sp-42 | an-286 |
| E1A6392 | sp-21 | an-287 | E1U6392 | sp-24 | an-287 | E1U13718 | sp-42 | an-287 |
| E1A6393 | sp-21 | an-288 | E1U6393 | sp-24 | an-288 | E1U13719 | sp-42 | an-288 |
| E1A6394 | sp-21 | an-289 | E1U6394 | sp-24 | an-289 | E1U13720 | sp-42 | an-289 |
| E1A6395 | sp-21 | an-290 | E1U6395 | sp-24 | an-290 | E1U13721 | sp-42 | an-290 |
| E1A6396 | sp-21 | an-291 | E1U6396 | sp-24 | an-291 | E1U13722 | sp-42 | an-291 |
| E1A6397 | sp-21 | an-292 | E1U6397 | sp-24 | an-292 | E1U13723 | sp-42 | an-292 |
| E1A6398 | sp-21 | an-293 | E1U6398 | sp-24 | an-293 | E1U13724 | sp-42 | an-293 |
| E1A6399 | sp-21 | an-294 | E1U6399 | sp-24 | an-294 | E1U13725 | sp-42 | an-294 |
| E1A6400 | sp-21 | an-295 | E1U6400 | sp-24 | an-295 | E1U13726 | sp-42 | an-295 |
| E1A6401 | sp-21 | an-296 | E1U6401 | sp-24 | an-296 | E1U13727 | sp-42 | an-296 |
| E1A6402 | sp-21 | an-297 | E1U6402 | sp-24 | an-297 | E1U13728 | sp-42 | an-297 |
| E1A6403 | sp-21 | an-298 | E1U6403 | sp-24 | an-298 | E1U13729 | sp-42 | an-298 |
| E1A6404 | sp-21 | an-299 | E1U6404 | sp-24 | an-299 | E1U13730 | sp-42 | an-299 |
| E1A6405 | sp-21 | an-300 | E1U6405 | sp-24 | an-300 | E1U13731 | sp-42 | an-300 |
| E1A6406 | sp-21 | an-301 | E1U6406 | sp-24 | an-301 | E1U13732 | sp-42 | an-301 |
| E1A6407 | sp-21 | an-302 | E1U6407 | sp-24 | an-302 | E1U13733 | sp-42 | an-302 |
| E1A6408 | sp-21 | an-303 | E1U6408 | sp-24 | an-303 | E1U13734 | sp-42 | an-303 |
| E1A6409 | sp-21 | an-304 | E1U6409 | sp-24 | an-304 | E1U13735 | sp-42 | an-304 |
| E1A6410 | sp-21 | an-305 | E1U6410 | sp-24 | an-305 | E1U13736 | sp-42 | an-305 |
| E1A6411 | sp-21 | an-306 | E1U6411 | sp-24 | an-306 | E1U13737 | sp-42 | an-306 |
| E1A6412 | sp-21 | an-307 | E1U6412 | sp-24 | an-307 | E1U13738 | sp-42 | an-307 |
| E1A6413 | sp-21 | an-308 | E1U6413 | sp-24 | an-308 | E1U13739 | sp-42 | an-308 |
| E1A6414 | sp-21 | an-309 | E1U6414 | sp-24 | an-309 | E1U13740 | sp-42 | an-309 |
| E1A6415 | sp-21 | an-310 | E1U6415 | sp-24 | an-310 | E1U13741 | sp-42 | an-310 |
| E1A6416 | sp-21 | an-311 | E1U6416 | sp-24 | an-311 | E1U13742 | sp-42 | an-311 |
| E1A6417 | sp-21 | an-312 | E1U6417 | sp-24 | an-312 | E1U13743 | sp-42 | an-312 |
| E1A6418 | sp-21 | an-313 | E1U6418 | sp-24 | an-313 | E1U13744 | sp-42 | an-313 |
| E1A6419 | sp-21 | an-314 | E1U6419 | sp-24 | an-314 | E1U13745 | sp-42 | an-314 |
| E1A6420 | sp-21 | an-315 | E1U6420 | sp-24 | an-315 | E1U13746 | sp-42 | an-315 |
| E1A6421 | sp-21 | an-316 | E1U6421 | sp-24 | an-316 | E1U13747 | sp-42 | an-316 |
| E1A6422 | sp-21 | an-317 | E1U6422 | sp-24 | an-317 | E1U13748 | sp-42 | an-317 |
| E1A6423 | sp-21 | an-318 | E1U6423 | sp-24 | an-318 | E1U13749 | sp-42 | an-318 |
| E1A6424 | sp-21 | an-319 | E1U6424 | sp-24 | an-319 | E1U13750 | sp-42 | an-319 |
| E1A6425 | sp-21 | an-320 | E1U6425 | sp-24 | an-320 | E1U13751 | sp-42 | an-320 |
| E1A6426 | sp-21 | an-321 | E1U6426 | sp-24 | an-321 | E1U13752 | sp-42 | an-321 |

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| Table 1-120 ||||||||||

| Y = NHCS | | | Y = NHCSNH | | | Y = NHCSNH | | |
|---|---|---|---|---|---|---|---|---|
| E1A6427 | sp-21 | an-322 | E1U6427 | sp-24 | an-322 | E1U13753 | sp-42 | an-322 |
| E1A6428 | sp-21 | an-323 | E1U6428 | sp-24 | an-323 | E1U13754 | sp-42 | an-323 |
| E1A6429 | sp-21 | an-324 | E1U6429 | sp-24 | an-324 | E1U13755 | sp-42 | an-324 |
| E1A6430 | sp-21 | an-325 | E1U6430 | sp-24 | an-325 | E1U13756 | sp-42 | an-325 |
| E1A6431 | sp-21 | an-326 | E1U6431 | sp-24 | an-326 | E1U13757 | sp-42 | an-326 |
| E1A6432 | sp-21 | an-327 | E1U6432 | sp-24 | an-327 | E1U13758 | sp-42 | an-327 |
| E1A6433 | sp-21 | an-328 | E1U6433 | sp-24 | an-328 | E1U13759 | sp-42 | an-328 |
| E1A6434 | sp-21 | an-329 | E1U6434 | sp-24 | an-329 | E1U13760 | sp-42 | an-329 |
| E1A6435 | sp-21 | an-330 | E1U6435 | sp-24 | an-330 | E1U13761 | sp-42 | an-330 |
| E1A6436 | sp-21 | an-331 | E1U6436 | sp-24 | an-331 | E1U13762 | sp-42 | an-331 |
| E1A6437 | sp-21 | an-332 | E1U6437 | sp-24 | an-332 | E1U13763 | sp-42 | an-332 |
| E1A6438 | sp-21 | an-333 | E1U6438 | sp-24 | an-333 | E1U13764 | sp-42 | an-333 |
| E1A6439 | sp-21 | an-334 | E1U6439 | sp-24 | an-334 | E1U13765 | sp-42 | an-334 |
| E1A6440 | sp-21 | an-335 | E1U6440 | sp-24 | an-335 | E1U13766 | sp-42 | an-335 |
| E1A6441 | sp-21 | an-336 | E1U6441 | sp-24 | an-336 | E1U13767 | sp-42 | an-336 |
| E1A6442 | sp-21 | an-337 | E1U6442 | sp-24 | an-337 | E1U13768 | sp-42 | an-337 |
| E1A6443 | sp-21 | an-338 | E1U6443 | sp-24 | an-338 | E1U13769 | sp-42 | an-338 |
| E1A6444 | sp-21 | an-339 | E1U6444 | sp-24 | an-339 | E1U13770 | sp-42 | an-339 |
| E1A6445 | sp-21 | an-340 | E1U6445 | sp-24 | an-340 | E1U13771 | sp-42 | an-340 |
| E1A6446 | sp-21 | an-341 | E1U6446 | sp-24 | an-341 | E1U13772 | sp-42 | an-341 |
| E1A6447 | sp-21 | an-342 | E1U6447 | sp-24 | an-342 | E1U13773 | sp-42 | an-342 |
| E1A6448 | sp-21 | an-343 | E1U6448 | sp-24 | an-343 | E1U13774 | sp-42 | an-343 |
| E1A6449 | sp-21 | an-344 | E1U6449 | sp-24 | an-344 | E1U13775 | sp-42 | an-344 |
| E1A6450 | sp-21 | an-345 | E1U6450 | sp-24 | an-345 | E1U13776 | sp-42 | an-345 |
| E1A6451 | sp-21 | an-346 | E1U6451 | sp-24 | an-346 | E1U13777 | sp-42 | an-346 |
| E1A6452 | sp-21 | an-347 | E1U6452 | sp-24 | an-347 | E1U13778 | sp-42 | an-347 |
| E1A6453 | sp-21 | an-348 | E1U6453 | sp-24 | an-348 | E1U13779 | sp-42 | an-348 |
| E1A6454 | sp-21 | an-349 | E1U6454 | sp-24 | an-349 | E1U13780 | sp-42 | an-349 |
| E1A6455 | sp-21 | an-350 | E1U6455 | sp-24 | an-350 | E1U13781 | sp-42 | an-350 |
| E1A6456 | sp-21 | an-351 | E1U6456 | sp-24 | an-351 | E1U13782 | sp-42 | an-351 |
| E1A6457 | sp-21 | an-352 | E1U6457 | sp-24 | an-352 | E1U13783 | sp-42 | an-352 |
| E1A6458 | sp-21 | an-353 | E1U6458 | sp-24 | an-353 | E1U13784 | sp-42 | an-353 |
| E1A6459 | sp-21 | an-354 | E1U6459 | sp-24 | an-354 | E1U13785 | sp-42 | an-354 |
| E1A6460 | sp-21 | an-355 | E1U6460 | sp-24 | an-355 | E1U13786 | sp-42 | an-355 |
| E1A6461 | sp-21 | an-356 | E1U6461 | sp-24 | an-356 | E1U13787 | sp-42 | an-356 |
| E1A6462 | sp-21 | an-357 | E1U6462 | sp-24 | an-357 | E1U13788 | sp-42 | an-357 |
| E1A6463 | sp-21 | an-358 | E1U6463 | sp-24 | an-358 | E1U13789 | sp-42 | an-358 |
| E1A6464 | sp-21 | an-359 | E1U6464 | sp-24 | an-359 | E1U13790 | sp-42 | an-359 |
| E1A6465 | sp-21 | an-360 | E1U6465 | sp-24 | an-360 | E1U13791 | sp-42 | an-360 |
| E1A6466 | sp-21 | an-361 | E1U6466 | sp-24 | an-361 | E1U13792 | sp-42 | an-361 |
| E1A6467 | sp-21 | an-362 | E1U6467 | sp-24 | an-362 | E1U13793 | sp-42 | an-362 |
| E1A6468 | sp-21 | an-363 | E1U6468 | sp-24 | an-363 | E1U13794 | sp-42 | an-363 |
| E1A6469 | sp-21 | an-364 | E1U6469 | sp-24 | an-364 | E1U13795 | sp-42 | an-364 |
| E1A6470 | sp-21 | an-365 | E1U6470 | sp-24 | an-365 | E1U13796 | sp-42 | an-365 |
| E1A6471 | sp-21 | an-366 | E1U6471 | sp-24 | an-366 | E1U13797 | sp-42 | an-366 |
| E1A6472 | sp-21 | an-367 | E1U6472 | sp-24 | an-367 | E1U13798 | sp-42 | an-367 |
| E1A6473 | sp-21 | an-368 | E1U6473 | sp-24 | an-368 | E1U13799 | sp-42 | an-368 |
| E1A6474 | sp-21 | an-369 | E1U6474 | sp-24 | an-369 | E1U13800 | sp-42 | an-369 |
| E1A6475 | sp-21 | an-370 | E1U6475 | sp-24 | an-370 | E1U13801 | sp-42 | an-370 |
| E1A6476 | sp-21 | an-371 | E1U6476 | sp-24 | an-371 | E1U13802 | sp-42 | an-371 |
| E1A6477 | sp-21 | an-372 | E1U6477 | sp-24 | an-372 | E1U13803 | sp-42 | an-372 |
| E1A6478 | sp-21 | an-373 | E1U6478 | sp-24 | an-373 | E1U13804 | sp-42 | an-373 |
| E1A6479 | sp-21 | an-374 | E1U6479 | sp-24 | an-374 | E1U13805 | sp-42 | an-374 |
| E1A6480 | sp-21 | an-375 | E1U6480 | sp-24 | an-375 | E1U13806 | sp-42 | an-375 |
| Table 1-121 ||||||||||

| Y = NHCS | | | Y = NHCSNH | | | Y = NHCSNH | | |
|---|---|---|---|---|---|---|---|---|
| E1A6481 | sp-21 | an-376 | E1U6481 | sp-24 | an-376 | E1U13807 | sp-42 | an-376 |
| E1A6482 | sp-21 | an-377 | E1U6482 | sp-24 | an-377 | E1U13808 | sp-42 | an-377 |
| E1A6483 | sp-21 | an-378 | E1U6483 | sp-24 | an-378 | E1U13809 | sp-42 | an-378 |
| E1A6484 | sp-21 | an-379 | E1U6484 | sp-24 | an-379 | E1U13810 | sp-42 | an-379 |
| E1A6485 | sp-21 | an-380 | E1U6485 | sp-24 | an-380 | E1U13811 | sp-42 | an-380 |
| E1A6486 | sp-21 | an-381 | E1U6486 | sp-24 | an-381 | E1U13812 | sp-42 | an-381 |
| E1A6487 | sp-21 | an-382 | E1U6487 | sp-24 | an-382 | E1U13813 | sp-42 | an-382 |
| E1A6488 | sp-21 | an-383 | E1U6488 | sp-24 | an-383 | E1U13814 | sp-42 | an-383 |
| E1A6489 | sp-21 | an-384 | E1U6489 | sp-24 | an-384 | E1U13815 | sp-42 | an-384 |
| E1A6490 | sp-21 | an-385 | E1U6490 | sp-24 | an-385 | E1U13816 | sp-42 | an-385 |
| E1A6491 | sp-21 | an-386 | E1U6491 | sp-24 | an-386 | E1U13817 | sp-42 | an-386 |
| E1A6492 | sp-21 | an-387 | E1U6492 | sp-24 | an-387 | E1U13818 | sp-42 | an-387 |
| E1A6493 | sp-21 | an-388 | E1U6493 | sp-24 | an-388 | E1U13819 | sp-42 | an-388 |
| E1A6494 | sp-21 | an-389 | E1U6494 | sp-24 | an-389 | E1U13820 | sp-42 | an-389 |
| E1A6495 | sp-21 | an-390 | E1U6495 | sp-24 | an-390 | E1U13821 | sp-42 | an-390 |
| E1A6496 | sp-21 | an-391 | E1U6496 | sp-24 | an-391 | E1U13822 | sp-42 | an-391 |

-continued

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| E1A6497 | sp-21 | an-392 | E1U6497 | sp-24 | an-392 | E1U13823 | sp-42 | an-392 |
| E1A6498 | sp-21 | an-393 | E1U6498 | sp-24 | an-393 | E1U13824 | sp-42 | an-393 |
| E1A6499 | sp-21 | an-394 | E1U6499 | sp-24 | an-394 | E1U13825 | sp-42 | an-394 |
| E1A6500 | sp-21 | an-395 | E1U6500 | sp-24 | an-395 | E1U13826 | sp-42 | an-395 |
| E1A6501 | sp-21 | an-396 | E1U6501 | sp-24 | an-396 | E1U13827 | sp-42 | an-396 |
| E1A6502 | sp-21 | an-397 | E1U6502 | sp-24 | an-397 | E1U13828 | sp-42 | an-397 |
| E1A6503 | sp-21 | an-398 | E1U6503 | sp-24 | an-398 | E1U13829 | sp-42 | an-398 |
| E1A6504 | sp-21 | an-399 | E1U6504 | sp-24 | an-399 | E1U13830 | sp-42 | an-399 |
| E1A6505 | sp-21 | an-400 | E1U6505 | sp-24 | an-400 | E1U13831 | sp-42 | an-400 |
| E1A6506 | sp-21 | an-401 | E1U6506 | sp-24 | an-401 | E1U13832 | sp-42 | an-401 |
| E1A6507 | sp-21 | an-402 | E1U6507 | sp-24 | an-402 | E1U13833 | sp-42 | an-402 |
| E1A6508 | sp-21 | an-403 | E1U6508 | sp-24 | an-403 | E1U13834 | sp-42 | an-403 |
| E1A6509 | sp-21 | an-404 | E1U6509 | sp-24 | an-404 | E1U13835 | sp-42 | an-404 |
| E1A6510 | sp-21 | an-405 | E1U6510 | sp-24 | an-405 | E1U13836 | sp-42 | an-405 |
| E1A6511 | sp-21 | an-406 | E1U6511 | sp-24 | an-406 | E1U13837 | sp-42 | an-406 |
| E1A6512 | sp-21 | an-407 | E1U6512 | sp-24 | an-407 | E1U13838 | sp-42 | an-407 |
| E1A6513 | sp-22 | an-1 | E1U6513 | sp-25 | an-1 | E1U13839 | sp-43 | an-1 |
| E1A6514 | sp-22 | an-2 | E1U6514 | sp-25 | an-2 | E1U13840 | sp-43 | an-2 |
| E1A6515 | sp-22 | an-3 | E1U6515 | sp-25 | an-3 | E1U13841 | sp-43 | an-3 |
| E1A6516 | sp-22 | an-4 | E1U6516 | sp-25 | an-4 | E1U13842 | sp-43 | an-4 |
| E1A6517 | sp-22 | an-5 | E1U6517 | sp-25 | an-5 | E1U13843 | sp-43 | an-5 |
| E1A6518 | sp-22 | an-6 | E1U6518 | sp-25 | an-6 | E1U13844 | sp-43 | an-6 |
| E1A6519 | sp-22 | an-7 | E1U6519 | sp-25 | an-7 | E1U13845 | sp-43 | an-7 |
| E1A6520 | sp-22 | an-8 | E1U6520 | sp-25 | an-8 | E1U13846 | sp-43 | an-8 |
| E1A6521 | sp-22 | an-9 | E1U6521 | sp-25 | an-9 | E1U13847 | sp-43 | an-9 |
| E1A6522 | sp-22 | an-10 | E1U6522 | sp-25 | an-10 | E1U13848 | sp-43 | an-10 |
| E1A6523 | sp-22 | an-11 | E1U6523 | sp-25 | an-11 | E1U13849 | sp-43 | an-11 |
| E1A6524 | sp-22 | an-12 | E1U6524 | sp-25 | an-12 | E1U13850 | sp-43 | an-12 |
| E1A6525 | sp-22 | an-13 | E1U6525 | sp-25 | an-13 | E1U13851 | sp-43 | an-13 |
| E1A6526 | sp-22 | an-14 | E1U6526 | sp-25 | an-14 | E1U13852 | sp-43 | an-14 |
| E1A6527 | sp-22 | an-15 | E1U6527 | sp-25 | an-15 | E1U13853 | sp-43 | an-15 |
| E1A6528 | sp-22 | an-16 | E1U6528 | sp-25 | an-16 | E1U13854 | sp-43 | an-16 |
| E1A6529 | sp-22 | an-17 | E1U6529 | sp-25 | an-17 | E1U13855 | sp-43 | an-17 |
| E1A6530 | sp-22 | an-18 | E1U6530 | sp-25 | an-18 | E1U13856 | sp-43 | an-18 |
| E1A6531 | sp-22 | an-19 | E1U6531 | sp-25 | an-19 | E1U13857 | sp-43 | an-19 |
| E1A6532 | sp-22 | an-20 | E1U6532 | sp-25 | an-20 | E1U13858 | sp-43 | an-20 |
| E1A6533 | sp-22 | an-21 | E1U6533 | sp-25 | an-21 | E1U13859 | sp-43 | an-21 |
| E1A6534 | sp-22 | an-22 | E1U6534 | sp-25 | an-22 | E1U13860 | sp-43 | an-22 |

Table 1-122

| Y = NHCS | | | Y = NHCSNH | | | Y = NHCSNH | | |
|---|---|---|---|---|---|---|---|---|
| E1A6535 | sp-22 | an-23 | E1U6535 | sp-25 | an-23 | E1U13861 | sp-43 | an-23 |
| E1A6536 | sp-22 | an-24 | E1U6536 | sp-25 | an-24 | E1U13862 | sp-43 | an-24 |
| E1A6537 | sp-22 | an-25 | E1U6537 | sp-25 | an-25 | E1U13863 | sp-43 | an-25 |
| E1A6538 | sp-22 | an-26 | E1U6538 | sp-25 | an-26 | E1U13864 | sp-43 | an-26 |
| E1A6539 | sp-22 | an-27 | E1U6539 | sp-25 | an-27 | E1U13865 | sp-43 | an-27 |
| E1A6540 | sp-22 | an-28 | E1U6540 | sp-25 | an-28 | E1U13866 | sp-43 | an-28 |
| E1A6541 | sp-22 | an-29 | E1U6541 | sp-25 | an-29 | E1U13867 | sp-43 | an-29 |
| E1A6542 | sp-22 | an-30 | E1U6542 | sp-25 | an-30 | E1U13868 | sp-43 | an-30 |
| E1A6543 | sp-22 | an-31 | E1U6543 | sp-25 | an-31 | E1U13869 | sp-43 | an-31 |
| E1A6544 | sp-22 | an-32 | E1U6544 | sp-25 | an-32 | E1U13870 | sp-43 | an-32 |
| E1A6545 | sp-22 | an-33 | E1U6545 | sp-25 | an-33 | E1U13871 | sp-43 | an-33 |
| E1A6546 | sp-22 | an-34 | E1U6546 | sp-25 | an-34 | E1U13872 | sp-43 | an-34 |
| E1A6547 | sp-22 | an-35 | E1U6547 | sp-25 | an-35 | E1U13873 | sp-43 | an-35 |
| E1A6548 | sp-22 | an-36 | E1U6548 | sp-25 | an-36 | E1U13874 | sp-43 | an-36 |
| E1A6549 | sp-22 | an-37 | E1U6549 | sp-25 | an-37 | E1U13875 | sp-43 | an-37 |
| E1A6550 | sp-22 | an-38 | E1U6550 | sp-25 | an-38 | E1U13876 | sp-43 | an-38 |
| E1A6551 | sp-22 | an-39 | E1U6551 | sp-25 | an-39 | E1U13877 | sp-43 | an-39 |
| E1A6552 | sp-22 | an-40 | E1U6552 | sp-25 | an-40 | E1U13878 | sp-43 | an-40 |
| E1A6553 | sp-22 | an-41 | E1U6553 | sp-25 | an-41 | E1U13879 | sp-43 | an-41 |
| E1A6554 | sp-22 | an-42 | E1U6554 | sp-25 | an-42 | E1U13880 | sp-43 | an-42 |
| E1A6555 | sp-22 | an-43 | E1U6555 | sp-25 | an-43 | E1U13881 | sp-43 | an-43 |
| E1A6556 | sp-22 | an-44 | E1U6556 | sp-25 | an-44 | E1U13882 | sp-43 | an-44 |
| E1A6557 | sp-22 | an-45 | E1U6557 | sp-25 | an-45 | E1U13883 | sp-43 | an-45 |
| E1A6558 | sp-22 | an-46 | E1U6558 | sp-25 | an-46 | E1U13884 | sp-43 | an-46 |
| E1A6559 | sp-22 | an-47 | E1U6559 | sp-25 | an-47 | E1U13885 | sp-43 | an-47 |
| E1A6560 | sp-22 | an-48 | E1U6560 | sp-25 | an-48 | E1U13886 | sp-43 | an-48 |
| E1A6561 | sp-22 | an-49 | E1U6561 | sp-25 | an-49 | E1U13887 | sp-43 | an-49 |
| E1A6562 | sp-22 | an-50 | E1U6562 | sp-25 | an-50 | E1U13888 | sp-43 | an-50 |
| E1A6563 | sp-22 | an-51 | E1U6563 | sp-25 | an-51 | E1U13889 | sp-43 | an-51 |
| E1A6564 | sp-22 | an-52 | E1U6564 | sp-25 | an-52 | E1U13890 | sp-43 | an-52 |
| E1A6565 | sp-22 | an-53 | E1U6565 | sp-25 | an-53 | E1U13891 | sp-43 | an-53 |
| E1A6566 | sp-22 | an-54 | E1U6566 | sp-25 | an-54 | E1U13892 | sp-43 | an-54 |
| E1A6567 | sp-22 | an-55 | E1U6567 | sp-25 | an-55 | E1U13893 | sp-43 | an-55 |
| E1A6568 | sp-22 | an-56 | E1U6568 | sp-25 | an-56 | E1U13894 | sp-43 | an-56 |
| E1A6569 | sp-22 | an-57 | E1U6569 | sp-25 | an-57 | E1U13895 | sp-43 | an-57 |
| E1A6570 | sp-22 | an-58 | E1U6570 | sp-25 | an-58 | E1U13896 | sp-43 | an-58 |

-continued

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| E1A6571 | sp-22 | an-59 | E1U6571 | sp-25 | an-59 | E1U13897 | sp-43 | an-59 |
| E1A6572 | sp-22 | an-60 | E1U6572 | sp-25 | an-60 | E1U13898 | sp-43 | an-60 |
| E1A6573 | sp-22 | an-61 | E1U6573 | sp-25 | an-61 | E1U13899 | sp-43 | an-61 |
| E1A6574 | sp-22 | an-62 | E1U6574 | sp-25 | an-62 | E1U13900 | sp-43 | an-62 |
| E1A6575 | sp-22 | an-63 | E1U6575 | sp-25 | an-63 | E1U13901 | sp-43 | an-63 |
| E1A6576 | sp-22 | an-64 | E1U6576 | sp-25 | an-64 | E1U13902 | sp-43 | an-64 |
| E1A6577 | sp-22 | an-65 | E1U6577 | sp-25 | an-65 | E1U13903 | sp-43 | an-65 |
| E1A6578 | sp-22 | an-66 | E1U6578 | sp-25 | an-66 | E1U13904 | sp-43 | an-66 |
| E1A6579 | sp-22 | an-67 | E1U6579 | sp-25 | an-67 | E1U13905 | sp-43 | an-67 |
| E1A6580 | sp-22 | an-68 | E1U6580 | sp-25 | an-68 | E1U13906 | sp-43 | an-68 |
| E1A6581 | sp-22 | an-69 | E1U6581 | sp-25 | an-69 | E1U13907 | sp-43 | an-69 |
| E1A6582 | sp-22 | an-70 | E1U6582 | sp-25 | an-70 | E1U13908 | sp-43 | an-70 |
| E1A6583 | sp-22 | an-71 | E1U6583 | sp-25 | an-71 | E1U13909 | sp-43 | an-71 |
| E1A6584 | sp-22 | an-72 | E1U6584 | sp-25 | an-72 | E1U13910 | sp-43 | an-72 |
| E1A6585 | sp-22 | an-73 | E1U6585 | sp-25 | an-73 | E1U13911 | sp-43 | an-73 |
| E1A6586 | sp-22 | an-74 | E1U6586 | sp-25 | an-74 | E1U13912 | sp-43 | an-74 |
| E1A6587 | sp-22 | an-75 | E1U6587 | sp-25 | an-75 | E1U13913 | sp-43 | an-75 |
| E1A6588 | sp-22 | an-76 | E1U6588 | sp-25 | an-76 | E1U13914 | sp-43 | an-76 |

Table 1-123

| Y = NHCS | | | Y = NHCSNH | | | Y = NHCSNH | | |
|---|---|---|---|---|---|---|---|---|
| E1A6589 | sp-22 | an-77 | E1U6589 | sp-25 | an-77 | E1U13915 | sp-43 | an-77 |
| E1A6590 | sp-22 | an-78 | E1U6590 | sp-25 | an-78 | E1U13916 | sp-43 | an-78 |
| E1A6591 | sp-22 | an-79 | E1U6591 | sp-25 | an-79 | E1U13917 | sp-43 | an-79 |
| E1A6592 | sp-22 | an-80 | E1U6592 | sp-25 | an-80 | E1U13918 | sp-43 | an-80 |
| E1A6593 | sp-22 | an-81 | E1U6593 | sp-25 | an-81 | E1U13919 | sp-43 | an-81 |
| E1A6594 | sp-22 | an-82 | E1U6594 | sp-25 | an-82 | E1U13920 | sp-43 | an-82 |
| E1A6595 | sp-22 | an-83 | E1U6595 | sp-25 | an-83 | E1U13921 | sp-43 | an-83 |
| E1A6596 | sp-22 | an-84 | E1U6596 | sp-25 | an-84 | E1U13922 | sp-43 | an-84 |
| E1A6597 | sp-22 | an-85 | E1U6597 | sp-25 | an-85 | E1U13923 | sp-43 | an-85 |
| E1A6598 | sp-22 | an-86 | E1U6598 | sp-25 | an-86 | E1U13924 | sp-43 | an-86 |
| E1A6599 | sp-22 | an-87 | E1U6599 | sp-25 | an-87 | E1U13925 | sp-43 | an-87 |
| E1A6600 | sp-22 | an-88 | E1U6600 | sp-25 | an-88 | E1U13926 | sp-43 | an-88 |
| E1A6601 | sp-22 | an-89 | E1U6601 | sp-25 | an-89 | E1U13927 | sp-43 | an-89 |
| E1A6602 | sp-22 | an-90 | E1U6602 | sp-25 | an-90 | E1U13928 | sp-43 | an-90 |
| E1A6603 | sp-22 | an-91 | E1U6603 | sp-25 | an-91 | E1U13929 | sp-43 | an-91 |
| E1A6604 | sp-22 | an-92 | E1U6604 | sp-25 | an-92 | E1U13930 | sp-43 | an-92 |
| E1A6605 | sp-22 | an-93 | E1U6605 | sp-25 | an-93 | E1U13931 | sp-43 | an-93 |
| E1A6606 | sp-22 | an-94 | E1U6606 | sp-25 | an-94 | E1U13932 | sp-43 | an-94 |
| E1A6607 | sp-22 | an-95 | E1U6607 | sp-25 | an-95 | E1U13933 | sp-43 | an-95 |
| E1A6608 | sp-22 | an-96 | E1U6608 | sp-25 | an-96 | E1U13934 | sp-43 | an-96 |
| E1A6609 | sp-22 | an-97 | E1U6609 | sp-25 | an-97 | E1U13935 | sp-43 | an-97 |
| E1A6610 | sp-22 | an-98 | E1U6610 | sp-25 | an-98 | E1U13936 | sp-43 | an-98 |
| E1A6611 | sp-22 | an-99 | E1U6611 | sp-25 | an-99 | E1U13937 | sp-43 | an-99 |
| E1A6612 | sp-22 | an-100 | E1U6612 | sp-25 | an-100 | E1U13938 | sp-43 | an-100 |
| E1A6613 | sp-22 | an-101 | E1U6613 | sp-25 | an-101 | E1U13939 | sp-43 | an-101 |
| E1A6614 | sp-22 | an-102 | E1U6614 | sp-25 | an-102 | E1U13940 | sp-43 | an-102 |
| E1A6615 | sp-22 | an-103 | E1U6615 | sp-25 | an-103 | E1U13941 | sp-43 | an-103 |
| E1A6616 | sp-22 | an-104 | E1U6616 | sp-25 | an-104 | E1U13942 | sp-43 | an-104 |
| E1A6617 | sp-22 | an-105 | E1U6617 | sp-25 | an-105 | E1U13943 | sp-43 | an-105 |
| E1A6618 | sp-22 | an-106 | E1U6618 | sp-25 | an-106 | E1U13944 | sp-43 | an-106 |
| E1A6619 | sp-22 | an-107 | E1U6619 | sp-25 | an-107 | E1U13945 | sp-43 | an-107 |
| E1A6620 | sp-22 | an-108 | E1U6620 | sp-25 | an-108 | E1U13946 | sp-43 | an-108 |
| E1A6621 | sp-22 | an-109 | E1U6621 | sp-25 | an-109 | E1U13947 | sp-43 | an-109 |
| E1A6622 | sp-22 | an-110 | E1U6622 | sp-25 | an-110 | E1U13948 | sp-43 | an-110 |
| E1A6623 | sp-22 | an-111 | E1U6623 | sp-25 | an-111 | E1U13949 | sp-43 | an-111 |
| E1A6624 | sp-22 | an-112 | E1U6624 | sp-25 | an-112 | E1U13950 | sp-43 | an-112 |
| E1A6625 | sp-22 | an-113 | E1U6625 | sp-25 | an-113 | E1U13951 | sp-43 | an-113 |
| E1A6626 | sp-22 | an-114 | E1U6626 | sp-25 | an-114 | E1U13952 | sp-43 | an-114 |
| E1A6627 | sp-22 | an-115 | E1U6627 | sp-25 | an-115 | E1U13953 | sp-43 | an-115 |
| E1A6628 | sp-22 | an-116 | E1U6628 | sp-25 | an-116 | E1U13954 | sp-43 | an-116 |
| E1A6629 | sp-22 | an-117 | E1U6629 | sp-25 | an-117 | E1U13955 | sp-43 | an-117 |
| E1A6630 | sp-22 | an-118 | E1U6630 | sp-25 | an-118 | E1U13956 | sp-43 | an-118 |
| E1A6631 | sp-22 | an-119 | E1U6631 | sp-25 | an-119 | E1U13957 | sp-43 | an-119 |
| E1A6632 | sp-22 | an-120 | E1U6632 | sp-25 | an-120 | E1U13958 | sp-43 | an-120 |
| E1A6633 | sp-22 | an-121 | E1U6633 | sp-25 | an-121 | E1U13959 | sp-43 | an-121 |
| E1A6634 | sp-22 | an-122 | E1U6634 | sp-25 | an-122 | E1U13960 | sp-43 | an-122 |
| E1A6635 | sp-22 | an-123 | E1U6635 | sp-25 | an-123 | E1U13961 | sp-43 | an-123 |
| E1A6636 | sp-22 | an-124 | E1U6636 | sp-25 | an-124 | E1U13962 | sp-43 | an-124 |
| E1A6637 | sp-22 | an-125 | E1U6637 | sp-25 | an-125 | E1U13963 | sp-43 | an-125 |
| E1A6638 | sp-22 | an-126 | E1U6638 | sp-25 | an-126 | E1U13964 | sp-43 | an-126 |
| E1A6639 | sp-22 | an-127 | E1U6639 | sp-25 | an-127 | E1U13965 | sp-43 | an-127 |
| E1A6640 | sp-22 | an-128 | E1U6640 | sp-25 | an-128 | E1U13966 | sp-43 | an-128 |
| E1A6641 | sp-22 | an-129 | E1U6641 | sp-25 | an-129 | E1U13967 | sp-43 | an-129 |
| E1A6642 | sp-22 | an-130 | E1U6642 | sp-25 | an-130 | E1U13968 | sp-43 | an-130 |

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| Table 1-124 ||||||||||
| Y = NHCS ||| Y = NHCSNH ||| Y = NHCSNH |||
| E1A6643 | sp-22 | an-131 | E1U6643 | sp-25 | an-131 | E1U13969 | sp-43 | an-131 |
| E1A6644 | sp-22 | an-132 | E1U6644 | sp-25 | an-132 | E1U13970 | sp-43 | an-132 |
| E1A6645 | sp-22 | an-133 | E1U6645 | sp-25 | an-133 | E1U13971 | sp-43 | an-133 |
| E1A6646 | sp-22 | an-134 | E1U6646 | sp-25 | an-134 | E1U13972 | sp-43 | an-134 |
| E1A6647 | sp-22 | an-135 | E1U6647 | sp-25 | an-135 | E1U13973 | sp-43 | an-135 |
| E1A6648 | sp-22 | an-136 | E1U6648 | sp-25 | an-136 | E1U13974 | sp-43 | an-136 |
| E1A6649 | sp-22 | an-137 | E1U6649 | sp-25 | an-137 | E1U13975 | sp-43 | an-137 |
| E1A6650 | sp-22 | an-138 | E1U6650 | sp-25 | an-138 | E1U13976 | sp-43 | an-138 |
| E1A6651 | sp-22 | an-139 | E1U6651 | sp-25 | an-139 | E1U13977 | sp-43 | an-139 |
| E1A6652 | sp-22 | an-140 | E1U6652 | sp-25 | an-140 | E1U13978 | sp-43 | an-140 |
| E1A6653 | sp-22 | an-141 | E1U6653 | sp-25 | an-141 | E1U13979 | sp-43 | an-141 |
| E1A6654 | sp-22 | an-142 | E1U6654 | sp-25 | an-142 | E1U13980 | sp-43 | an-142 |
| E1A6655 | sp-22 | an-143 | E1U6655 | sp-25 | an-143 | E1U13981 | sp-43 | an-143 |
| E1A6656 | sp-22 | an-144 | E1U6656 | sp-25 | an-144 | E1U13982 | sp-43 | an-144 |
| E1A6657 | sp-22 | an-145 | E1U6657 | sp-25 | an-145 | E1U13983 | sp-43 | an-145 |
| E1A6658 | sp-22 | an-146 | E1U6658 | sp-25 | an-146 | E1U13984 | sp-43 | an-146 |
| E1A6659 | sp-22 | an-147 | E1U6659 | sp-25 | an-147 | E1U13985 | sp-43 | an-147 |
| E1A6660 | sp-22 | an-148 | E1U6660 | sp-25 | an-148 | E1U13986 | sp-43 | an-148 |
| E1A6661 | sp-22 | an-149 | E1U6661 | sp-25 | an-149 | E1U13987 | sp-43 | an-149 |
| E1A6662 | sp-22 | an-150 | E1U6662 | sp-25 | an-150 | E1U13988 | sp-43 | an-150 |
| E1A6663 | sp-22 | an-151 | E1U6663 | sp-25 | an-151 | E1U13989 | sp-43 | an-151 |
| E1A6664 | sp-22 | an-152 | E1U6664 | sp-25 | an-152 | E1U13990 | sp-43 | an-152 |
| E1A6665 | sp-22 | an-153 | E1U6665 | sp-25 | an-153 | E1U13991 | sp-43 | an-153 |
| E1A6666 | sp-22 | an-154 | E1U6666 | sp-25 | an-154 | E1U13992 | sp-43 | an-154 |
| E1A6667 | sp-22 | an-155 | E1U6667 | sp-25 | an-155 | E1U13993 | sp-43 | an-155 |
| E1A6668 | sp-22 | an-156 | E1U6668 | sp-25 | an-156 | E1U13994 | sp-43 | an-156 |
| E1A6669 | sp-22 | an-157 | E1U6669 | sp-25 | an-157 | E1U13995 | sp-43 | an-157 |
| E1A6670 | sp-22 | an-158 | E1U6670 | sp-25 | an-158 | E1U13996 | sp-43 | an-158 |
| E1A6671 | sp-22 | an-159 | E1U6671 | sp-25 | an-159 | E1U13997 | sp-43 | an-159 |
| E1A6672 | sp-22 | an-160 | E1U6672 | sp-25 | an-160 | E1U13998 | sp-43 | an-160 |
| E1A6673 | sp-22 | an-161 | E1U6673 | sp-25 | an-161 | E1U13999 | sp-43 | an-161 |
| E1A6674 | sp-22 | an-162 | E1U6674 | sp-25 | an-162 | E1U14000 | sp-43 | an-162 |
| E1A6675 | sp-22 | an-163 | E1U6675 | sp-25 | an-163 | E1U14001 | sp-43 | an-163 |
| E1A6676 | sp-22 | an-164 | E1U6676 | sp-25 | an-164 | E1U14002 | sp-43 | an-164 |
| E1A6677 | sp-22 | an-165 | E1U6677 | sp-25 | an-165 | E1U14003 | sp-43 | an-165 |
| E1A6678 | sp-22 | an-166 | E1U6678 | sp-25 | an-166 | E1U14004 | sp-43 | an-166 |
| E1A6679 | sp-22 | an-167 | E1U6679 | sp-25 | an-167 | E1U14005 | sp-43 | an-167 |
| E1A6680 | sp-22 | an-168 | E1U6680 | sp-25 | an-168 | E1U14006 | sp-43 | an-168 |
| E1A6681 | sp-22 | an-169 | E1U6681 | sp-25 | an-169 | E1U14007 | sp-43 | an-169 |
| E1A6682 | sp-22 | an-170 | E1U6682 | sp-25 | an-170 | E1U14008 | sp-43 | an-170 |
| E1A6683 | sp-22 | an-171 | E1U6683 | sp-25 | an-171 | E1U14009 | sp-43 | an-171 |
| E1A6684 | sp-22 | an-172 | E1U6684 | sp-25 | an-172 | E1U14010 | sp-43 | an-172 |
| E1A6685 | sp-22 | an-173 | E1U6685 | sp-25 | an-173 | E1U14011 | sp-43 | an-173 |
| E1A6686 | sp-22 | an-174 | E1U6686 | sp-25 | an-174 | E1U14012 | sp-43 | an-174 |
| E1A6687 | sp-22 | an-175 | E1U6687 | sp-25 | an-175 | E1U14013 | sp-43 | an-175 |
| E1A6688 | sp-22 | an-176 | E1U6688 | sp-25 | an-176 | E1U14014 | sp-43 | an-176 |
| E1A6689 | sp-22 | an-177 | E1U6689 | sp-25 | an-177 | E1U14015 | sp-43 | an-177 |
| E1A6690 | sp-22 | an-178 | E1U6690 | sp-25 | an-178 | E1U14016 | sp-43 | an-178 |
| E1A6691 | sp-22 | an-179 | E1U6691 | sp-25 | an-179 | E1U14017 | sp-43 | an-179 |
| E1A6692 | sp-22 | an-180 | E1U6692 | sp-25 | an-180 | E1U14018 | sp-43 | an-180 |
| E1A6693 | sp-22 | an-181 | E1U6693 | sp-25 | an-181 | E1U14019 | sp-43 | an-181 |
| E1A6694 | sp-22 | an-182 | E1U6694 | sp-25 | an-182 | E1U14020 | sp-43 | an-182 |
| E1A6695 | sp-22 | an-183 | E1U6695 | sp-25 | an-183 | E1U14021 | sp-43 | an-183 |
| E1A6696 | sp-22 | an-184 | E1U6696 | sp-25 | an-184 | E1U14022 | sp-43 | an-184 |
| Table 1-125 ||||||||||
| Y = NHCS ||| Y = NHCSNH ||| Y = NHCSNH |||
| E1A6697 | sp-22 | an-185 | E1U6697 | sp-25 | an-185 | E1U14023 | sp-43 | an-185 |
| E1A6698 | sp-22 | an-186 | E1U6698 | sp-25 | an-186 | E1U14024 | sp-43 | an-186 |
| E1A6699 | sp-22 | an-187 | E1U6699 | sp-25 | an-187 | E1U14025 | sp-43 | an-187 |
| E1A6700 | sp-22 | an-188 | E1U6700 | sp-25 | an-188 | E1U14026 | sp-43 | an-188 |
| E1A6701 | sp-22 | an-189 | E1U6701 | sp-25 | an-189 | E1U14027 | sp-43 | an-189 |
| E1A6702 | sp-22 | an-190 | E1U6702 | sp-25 | an-190 | E1U14028 | sp-43 | an-190 |
| E1A6703 | sp-22 | an-191 | E1U6703 | sp-25 | an-191 | E1U14029 | sp-43 | an-191 |
| E1A6704 | sp-22 | an-192 | E1U6704 | sp-25 | an-192 | E1U14030 | sp-43 | an-192 |
| E1A6705 | sp-22 | an-193 | E1U6705 | sp-25 | an-193 | E1U14031 | sp-43 | an-193 |
| E1A6706 | sp-22 | an-194 | E1U6706 | sp-25 | an-194 | E1U14032 | sp-43 | an-194 |
| E1A6707 | sp-22 | an-195 | E1U6707 | sp-25 | an-195 | E1U14033 | sp-43 | an-195 |
| E1A6708 | sp-22 | an-196 | E1U6708 | sp-25 | an-196 | E1U14034 | sp-43 | an-196 |
| E1A6709 | sp-22 | an-197 | E1U6709 | sp-25 | an-197 | E1U14035 | sp-43 | an-197 |
| E1A6710 | sp-22 | an-198 | E1U6710 | sp-25 | an-198 | E1U14036 | sp-43 | an-198 |
| E1A6711 | sp-22 | an-199 | E1U6711 | sp-25 | an-199 | E1U14037 | sp-43 | an-199 |
| E1A6712 | sp-22 | an-200 | E1U6712 | sp-25 | an-200 | E1U14038 | sp-43 | an-200 |

-continued

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| E1A6713 | sp-22 | an-201 | E1U6713 | sp-25 | an-201 | E1U14039 | sp-43 | an-201 |
| E1A6714 | sp-22 | an-202 | E1U6714 | sp-25 | an-202 | E1U14040 | sp-43 | an-202 |
| E1A6715 | sp-22 | an-203 | E1U6715 | sp-25 | an-203 | E1U14041 | sp-43 | an-203 |
| E1A6716 | sp-22 | an-204 | E1U6716 | sp-25 | an-204 | E1U14042 | sp-43 | an-204 |
| E1A6717 | sp-22 | an-205 | E1U6717 | sp-25 | an-205 | E1U14043 | sp-43 | an-205 |
| E1A6718 | sp-22 | an-206 | E1U6718 | sp-25 | an-206 | E1U14044 | sp-43 | an-206 |
| E1A6719 | sp-22 | an-207 | E1U6719 | sp-25 | an-207 | E1U14045 | sp-43 | an-207 |
| E1A6720 | sp-22 | an-208 | E1U6720 | sp-25 | an-208 | E1U14046 | sp-43 | an-208 |
| E1A6721 | sp-22 | an-209 | E1U6721 | sp-25 | an-209 | E1U14047 | sp-43 | an-209 |
| E1A6722 | sp-22 | an-210 | E1U6722 | sp-25 | an-210 | E1U14048 | sp-43 | an-210 |
| E1A6723 | sp-22 | an-211 | E1U6723 | sp-25 | an-211 | E1U14049 | sp-43 | an-211 |
| E1A6724 | sp-22 | an-212 | E1U6724 | sp-25 | an-212 | E1U14050 | sp-43 | an-212 |
| E1A6725 | sp-22 | an-213 | E1U6725 | sp-25 | an-213 | E1U14051 | sp-43 | an-213 |
| E1A6726 | sp-22 | an-214 | E1U6726 | sp-25 | an-214 | E1U14052 | sp-43 | an-214 |
| E1A6727 | sp-22 | an-215 | E1U6727 | sp-25 | an-215 | E1U14053 | sp-43 | an-215 |
| E1A6728 | sp-22 | an-216 | E1U6728 | sp-25 | an-216 | E1U14054 | sp-43 | an-216 |
| E1A6729 | sp-22 | an-217 | E1U6729 | sp-25 | an-217 | E1U14055 | sp-43 | an-217 |
| E1A6730 | sp-22 | an-218 | E1U6730 | sp-25 | an-218 | E1U14056 | sp-43 | an-218 |
| E1A6731 | sp-22 | an-219 | E1U6731 | sp-25 | an-219 | E1U14057 | sp-43 | an-219 |
| E1A6732 | sp-22 | an-220 | E1U6732 | sp-25 | an-220 | E1U14058 | sp-43 | an-220 |
| E1A6733 | sp-22 | an-221 | E1U6733 | sp-25 | an-221 | E1U14059 | sp-43 | an-221 |
| E1A6734 | sp-22 | an-222 | E1U6734 | sp-25 | an-222 | E1U14060 | sp-43 | an-222 |
| E1A6735 | sp-22 | an-223 | E1U6735 | sp-25 | an-223 | E1U14061 | sp-43 | an-223 |
| E1A6736 | sp-22 | an-224 | E1U6736 | sp-25 | an-224 | E1U14062 | sp-43 | an-224 |
| E1A6737 | sp-22 | an-225 | E1U6737 | sp-25 | an-225 | E1U14063 | sp-43 | an-225 |
| E1A6738 | sp-22 | an-226 | E1U6738 | sp-25 | an-226 | E1U14064 | sp-43 | an-226 |
| E1A6739 | sp-22 | an-227 | E1U6739 | sp-25 | an-227 | E1U14065 | sp-43 | an-227 |
| E1A6740 | sp-22 | an-228 | E1U6740 | sp-25 | an-228 | E1U14066 | sp-43 | an-228 |
| E1A6741 | sp-22 | an-229 | E1U6741 | sp-25 | an-229 | E1U14067 | sp-43 | an-229 |
| E1A6742 | sp-22 | an-230 | E1U6742 | sp-25 | an-230 | E1U14068 | sp-43 | an-230 |
| E1A6743 | sp-22 | an-231 | E1U6743 | sp-25 | an-231 | E1U14069 | sp-43 | an-231 |
| E1A6744 | sp-22 | an-232 | E1U6744 | sp-25 | an-232 | E1U14070 | sp-43 | an-232 |
| E1A6745 | sp-22 | an-233 | E1U6745 | sp-25 | an-233 | E1U14071 | sp-43 | an-233 |
| E1A6746 | sp-22 | an-234 | E1U6746 | sp-25 | an-234 | E1U14072 | sp-43 | an-234 |
| E1A6747 | sp-22 | an-235 | E1U6747 | sp-25 | an-235 | E1U14073 | sp-43 | an-235 |
| E1A6748 | sp-22 | an-236 | E1U6748 | sp-25 | an-236 | E1U14074 | sp-43 | an-236 |
| E1A6749 | sp-22 | an-237 | E1U6749 | sp-25 | an-237 | E1U14075 | sp-43 | an-237 |
| E1A6750 | sp-22 | an-238 | E1U6750 | sp-25 | an-238 | E1U14076 | sp-43 | an-238 |

Table 1-126

| Y = NHCS | | | Y = NHCSNH | | | Y = NHCSNH | | |
|---|---|---|---|---|---|---|---|---|
| E1A6751 | sp-22 | an-239 | E1U6751 | sp-25 | an-239 | E1U14077 | sp-43 | an-239 |
| E1A6752 | sp-22 | an-240 | E1U6752 | sp-25 | an-240 | E1U14078 | sp-43 | an-240 |
| E1A6753 | sp-22 | an-241 | E1U6753 | sp-25 | an-241 | E1U14079 | sp-43 | an-241 |
| E1A6754 | sp-22 | an-242 | E1U6754 | sp-25 | an-242 | E1U14080 | sp-43 | an-242 |
| E1A6755 | sp-22 | an-243 | E1U6755 | sp-25 | an-243 | E1U14081 | sp-43 | an-243 |
| E1A6756 | sp-22 | an-244 | E1U6756 | sp-25 | an-244 | E1U14082 | sp-43 | an-244 |
| E1A6757 | sp-22 | an-245 | E1U6757 | sp-25 | an-245 | E1U14083 | sp-43 | an-245 |
| E1A6758 | sp-22 | an-246 | E1U6758 | sp-25 | an-246 | E1U14084 | sp-43 | an-246 |
| E1A6759 | sp-22 | an-247 | E1U6759 | sp-25 | an-247 | E1U14085 | sp-43 | an-247 |
| E1A6760 | sp-22 | an-248 | E1U6760 | sp-25 | an-248 | E1U14086 | sp-43 | an-248 |
| E1A6761 | sp-22 | an-249 | E1U6761 | sp-25 | an-249 | E1U14087 | sp-43 | an-249 |
| E1A6762 | sp-22 | an-250 | E1U6762 | sp-25 | an-250 | E1U14088 | sp-43 | an-250 |
| E1A6763 | sp-22 | an-251 | E1U6763 | sp-25 | an-251 | E1U14089 | sp-43 | an-251 |
| E1A6764 | sp-22 | an-252 | E1U6764 | sp-25 | an-252 | E1U14090 | sp-43 | an-252 |
| E1A6765 | sp-22 | an-253 | E1U6765 | sp-25 | an-253 | E1U14091 | sp-43 | an-253 |
| E1A6766 | sp-22 | an-254 | E1U6766 | sp-25 | an-254 | E1U14092 | sp-43 | an-254 |
| E1A6767 | sp-22 | an-255 | E1U6767 | sp-25 | an-255 | E1U14093 | sp-43 | an-255 |
| E1A6768 | sp-22 | an-256 | E1U6768 | sp-25 | an-256 | E1U14094 | sp-43 | an-256 |
| E1A6769 | sp-22 | an-257 | E1U6769 | sp-25 | an-257 | E1U14095 | sp-43 | an-257 |
| E1A6770 | sp-22 | an-258 | E1U6770 | sp-25 | an-258 | E1U14096 | sp-43 | an-258 |
| E1A6771 | sp-22 | an-259 | E1U6771 | sp-25 | an-259 | E1U14097 | sp-43 | an-259 |
| E1A6772 | sp-22 | an-260 | E1U6772 | sp-25 | an-260 | E1U14098 | sp-43 | an-260 |
| E1A6773 | sp-22 | an-261 | E1U6773 | sp-25 | an-261 | E1U14099 | sp-43 | an-261 |
| E1A6774 | sp-22 | an-262 | E1U6774 | sp-25 | an-262 | E1U14100 | sp-43 | an-262 |
| E1A6775 | sp-22 | an-263 | E1U6775 | sp-25 | an-263 | E1U14101 | sp-43 | an-263 |
| E1A6776 | sp-22 | an-264 | E1U6776 | sp-25 | an-264 | E1U14102 | sp-43 | an-264 |
| E1A6777 | sp-22 | an-265 | E1U6777 | sp-25 | an-265 | E1U14103 | sp-43 | an-265 |
| E1A6778 | sp-22 | an-266 | E1U6778 | sp-25 | an-266 | E1U14104 | sp-43 | an-266 |
| E1A6779 | sp-22 | an-267 | E1U6779 | sp-25 | an-267 | E1U14105 | sp-43 | an-267 |
| E1A6780 | sp-22 | an-268 | E1U6780 | sp-25 | an-268 | E1U14106 | sp-43 | an-268 |
| E1A6781 | sp-22 | an-269 | E1U6781 | sp-25 | an-269 | E1U14107 | sp-43 | an-269 |
| E1A6782 | sp-22 | an-270 | E1U6782 | sp-25 | an-270 | E1U14108 | sp-43 | an-270 |
| E1A6783 | sp-22 | an-271 | E1U6783 | sp-25 | an-271 | E1U14109 | sp-43 | an-271 |
| E1A6784 | sp-22 | an-272 | E1U6784 | sp-25 | an-272 | E1U14110 | sp-43 | an-272 |
| E1A6785 | sp-22 | an-273 | E1U6785 | sp-25 | an-273 | E1U14111 | sp-43 | an-273 |
| E1A6786 | sp-22 | an-274 | E1U6786 | sp-25 | an-274 | E1U14112 | sp-43 | an-274 |

-continued

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| E1A6787 | sp-22 | an-275 | E1U6787 | sp-25 | an-275 | E1U14113 | sp-43 | an-275 |
| E1A6788 | sp-22 | an-276 | E1U6788 | sp-25 | an-276 | E1U14114 | sp-43 | an-276 |
| E1A6789 | sp-22 | an-277 | E1U6789 | sp-25 | an-277 | E1U14115 | sp-43 | an-277 |
| E1A6790 | sp-22 | an-278 | E1U6790 | sp-25 | an-278 | E1U14116 | sp-43 | an-278 |
| E1A6791 | sp-22 | an-279 | E1U6791 | sp-25 | an-279 | E1U14117 | sp-43 | an-279 |
| E1A6792 | sp-22 | an-280 | E1U6792 | sp-25 | an-280 | E1U14118 | sp-43 | an-280 |
| E1A6793 | sp-22 | an-281 | E1U6793 | sp-25 | an-281 | E1U14119 | sp-43 | an-281 |
| E1A6794 | sp-22 | an-282 | E1U6794 | sp-25 | an-282 | E1U14120 | sp-43 | an-282 |
| E1A6795 | sp-22 | an-283 | E1U6795 | sp-25 | an-283 | E1U14121 | sp-43 | an-283 |
| E1A6796 | sp-22 | an-284 | E1U6796 | sp-25 | an-284 | E1U14122 | sp-43 | an-284 |
| E1A6797 | sp-22 | an-285 | E1U6797 | sp-25 | an-285 | E1U14123 | sp-43 | an-285 |
| E1A6798 | sp-22 | an-286 | E1U6798 | sp-25 | an-286 | E1U14124 | sp-43 | an-286 |
| E1A6799 | sp-22 | an-287 | E1U6799 | sp-25 | an-287 | E1U14125 | sp-43 | an-287 |
| E1A6800 | sp-22 | an-288 | E1U6800 | sp-25 | an-288 | E1U14126 | sp-43 | an-288 |
| E1A6801 | sp-22 | an-289 | E1U6801 | sp-25 | an-289 | E1U14127 | sp-43 | an-289 |
| E1A6802 | sp-22 | an-290 | E1U6802 | sp-25 | an-290 | E1U14128 | sp-43 | an-290 |
| E1A6803 | sp-22 | an-291 | E1U6803 | sp-25 | an-291 | E1U14129 | sp-43 | an-291 |
| E1A6804 | sp-22 | an-292 | E1U6804 | sp-25 | an-292 | E1U14130 | sp-43 | an-292 |

Table 1-127

| Y = NHCS | | | Y = NHCSNH | | | Y = NHCSNH | | |
|---|---|---|---|---|---|---|---|---|
| E1A6805 | sp-22 | an-293 | E1U6805 | sp-25 | an-293 | E1U14131 | sp-43 | an-293 |
| E1A6806 | sp-22 | an-294 | E1U6806 | sp-25 | an-294 | E1U14132 | sp-43 | an-294 |
| E1A6807 | sp-22 | an-295 | E1U6807 | sp-25 | an-295 | E1U14133 | sp-43 | an-295 |
| E1A6808 | sp-22 | an-296 | E1U6808 | sp-25 | an-296 | E1U14134 | sp-43 | an-296 |
| E1A6809 | sp-22 | an-297 | E1U6809 | sp-25 | an-297 | E1U14135 | sp-43 | an-297 |
| E1A6810 | sp-22 | an-298 | E1U6810 | sp-25 | an-298 | E1U14136 | sp-43 | an-298 |
| E1A6811 | sp-22 | an-299 | E1U6811 | sp-25 | an-299 | E1U14137 | sp-43 | an-299 |
| E1A6812 | sp-22 | an-300 | E1U6812 | sp-25 | an-300 | E1U14138 | sp-43 | an-300 |
| E1A6813 | sp-22 | an-301 | E1U6813 | sp-25 | an-301 | E1U14139 | sp-43 | an-301 |
| E1A6814 | sp-22 | an-302 | E1U6814 | sp-25 | an-302 | E1U14140 | sp-43 | an-302 |
| E1A6815 | sp-22 | an-303 | E1U6815 | sp-25 | an-303 | E1U14141 | sp-43 | an-303 |
| E1A6816 | sp-22 | an-304 | E1U6816 | sp-25 | an-304 | E1U14142 | sp-43 | an-304 |
| E1A6817 | sp-22 | an-305 | E1U6817 | sp-25 | an-305 | E1U14143 | sp-43 | an-305 |
| E1A6818 | sp-22 | an-306 | E1U6818 | sp-25 | an-306 | E1U14144 | sp-43 | an-306 |
| E1A6819 | sp-22 | an-307 | E1U6819 | sp-25 | an-307 | E1U14145 | sp-43 | an-307 |
| E1A6820 | sp-22 | an-308 | E1U6820 | sp-25 | an-308 | E1U14146 | sp-43 | an-308 |
| E1A6821 | sp-22 | an-309 | E1U6821 | sp-25 | an-309 | E1U14147 | sp-43 | an-309 |
| E1A6822 | sp-22 | an-310 | E1U6822 | sp-25 | an-310 | E1U14148 | sp-43 | an-310 |
| E1A6823 | sp-22 | an-311 | E1U6823 | sp-25 | an-311 | E1U14149 | sp-43 | an-311 |
| E1A6824 | sp-22 | an-312 | E1U6824 | sp-25 | an-312 | E1U14150 | sp-43 | an-312 |
| E1A6825 | sp-22 | an-313 | E1U6825 | sp-25 | an-313 | E1U14151 | sp-43 | an-313 |
| E1A6826 | sp-22 | an-314 | E1U6826 | sp-25 | an-314 | E1U14152 | sp-43 | an-314 |
| E1A6827 | sp-22 | an-315 | E1U6827 | sp-25 | an-315 | E1U14153 | sp-43 | an-315 |
| E1A6828 | sp-22 | an-316 | E1U6828 | sp-25 | an-316 | E1U14154 | sp-43 | an-316 |
| E1A6829 | sp-22 | an-317 | E1U6829 | sp-25 | an-317 | E1U14155 | sp-43 | an-317 |
| E1A6830 | sp-22 | an-318 | E1U6830 | sp-25 | an-318 | E1U14156 | sp-43 | an-318 |
| E1A6831 | sp-22 | an-319 | E1U6831 | sp-25 | an-319 | E1U14157 | sp-43 | an-319 |
| E1A6832 | sp-22 | an-320 | E1U6832 | sp-25 | an-320 | E1U14158 | sp-43 | an-320 |
| E1A6833 | sp-22 | an-321 | E1U6833 | sp-25 | an-321 | E1U14159 | sp-43 | an-321 |
| E1A6834 | sp-22 | an-322 | E1U6834 | sp-25 | an-322 | E1U14160 | sp-43 | an-322 |
| E1A6835 | sp-22 | an-323 | E1U6835 | sp-25 | an-323 | E1U14161 | sp-43 | an-323 |
| E1A6836 | sp-22 | an-324 | E1U6836 | sp-25 | an-324 | E1U14162 | sp-43 | an-324 |
| E1A6837 | sp-22 | an-325 | E1U6837 | sp-25 | an-325 | E1U14163 | sp-43 | an-325 |
| E1A6838 | sp-22 | an-326 | E1U6838 | sp-25 | an-326 | E1U14164 | sp-43 | an-326 |
| E1A6839 | sp-22 | an-327 | E1U6839 | sp-25 | an-327 | E1U14165 | sp-43 | an-327 |
| E1A6840 | sp-22 | an-328 | E1U6840 | sp-25 | an-328 | E1U14166 | sp-43 | an-328 |
| E1A6841 | sp-22 | an-329 | E1U6841 | sp-25 | an-329 | E1U14167 | sp-43 | an-329 |
| E1A6842 | sp-22 | an-330 | E1U6842 | sp-25 | an-330 | E1U14168 | sp-43 | an-330 |
| E1A6843 | sp-22 | an-331 | E1U6843 | sp-25 | an-331 | E1U14169 | sp-43 | an-331 |
| E1A6844 | sp-22 | an-332 | E1U6844 | sp-25 | an-332 | E1U14170 | sp-43 | an-332 |
| E1A6845 | sp-22 | an-333 | E1U6845 | sp-25 | an-333 | E1U14171 | sp-43 | an-333 |
| E1A6846 | sp-22 | an-334 | E1U6846 | sp-25 | an-334 | E1U14172 | sp-43 | an-334 |
| E1A6847 | sp-22 | an-335 | E1U6847 | sp-25 | an-335 | E1U14173 | sp-43 | an-335 |
| E1A6848 | sp-22 | an-336 | E1U6848 | sp-25 | an-336 | E1U14174 | sp-43 | an-336 |
| E1A6849 | sp-22 | an-337 | E1U6849 | sp-25 | an-337 | E1U14175 | sp-43 | an-337 |
| E1A6850 | sp-22 | an-338 | E1U6850 | sp-25 | an-338 | E1U14176 | sp-43 | an-338 |
| E1A6851 | sp-22 | an-339 | E1U6851 | sp-25 | an-339 | E1U14177 | sp-43 | an-339 |
| E1A6852 | sp-22 | an-340 | E1U6852 | sp-25 | an-340 | E1U14178 | sp-43 | an-340 |
| E1A6853 | sp-22 | an-341 | E1U6853 | sp-25 | an-341 | E1U14179 | sp-43 | an-341 |
| E1A6854 | sp-22 | an-342 | E1U6854 | sp-25 | an-342 | E1U14180 | sp-43 | an-342 |
| E1A6855 | sp-22 | an-343 | E1U6855 | sp-25 | an-343 | E1U14181 | sp-43 | an-343 |
| E1A6856 | sp-22 | an-344 | E1U6856 | sp-25 | an-344 | E1U14182 | sp-43 | an-344 |
| E1A6857 | sp-22 | an-345 | E1U6857 | sp-25 | an-345 | E1U14183 | sp-43 | an-345 |
| E1A6858 | sp-22 | an-346 | E1U6858 | sp-25 | an-346 | E1U14184 | sp-43 | an-346 |

-continued

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| | | | | Table 1-128 | | | | |
| | Y = NHCS | | | Y = NHCSNH | | | Y = NHCSNH | |
| E1A6859 | sp-22 | an-347 | E1U6859 | sp-25 | an-347 | E1U14185 | sp-43 | an-347 |
| E1A6860 | sp-22 | an-348 | E1U6860 | sp-25 | an-348 | E1U14186 | sp-43 | an-348 |
| E1A6861 | sp-22 | an-349 | E1U6861 | sp-25 | an-349 | E1U14187 | sp-43 | an-349 |
| E1A6862 | sp-22 | an-350 | E1U6862 | sp-25 | an-350 | E1U14188 | sp-43 | an-350 |
| E1A6863 | sp-22 | an-351 | E1U6863 | sp-25 | an-351 | E1U14189 | sp-43 | an-351 |
| E1A6864 | sp-22 | an-352 | E1U6864 | sp-25 | an-352 | E1U14190 | sp-43 | an-352 |
| E1A6865 | sp-22 | an-353 | E1U6865 | sp-25 | an-353 | E1U14191 | sp-43 | an-353 |
| E1A6866 | sp-22 | an-354 | E1U6866 | sp-25 | an-354 | E1U14192 | sp-43 | an-354 |
| E1A6867 | sp-22 | an-355 | E1U6867 | sp-25 | an-355 | E1U14193 | sp-43 | an-355 |
| E1A6868 | sp-22 | an-356 | E1U6868 | sp-25 | an-356 | E1U14194 | sp-43 | an-356 |
| E1A6869 | sp-22 | an-357 | E1U6869 | sp-25 | an-357 | E1U14195 | sp-43 | an-357 |
| E1A6870 | sp-22 | an-358 | E1U6870 | sp-25 | an-358 | E1U14196 | sp-43 | an-358 |
| E1A6871 | sp-22 | an-359 | E1U6871 | sp-25 | an-359 | E1U14197 | sp-43 | an-359 |
| E1A6872 | sp-22 | an-360 | E1U6872 | sp-25 | an-360 | E1U14198 | sp-43 | an-360 |
| E1A6873 | sp-22 | an-361 | E1U6873 | sp-25 | an-361 | E1U14199 | sp-43 | an-361 |
| E1A6874 | sp-22 | an-362 | E1U6874 | sp-25 | an-362 | E1U14200 | sp-43 | an-362 |
| E1A6875 | sp-22 | an-363 | E1U6875 | sp-25 | an-363 | E1U14201 | sp-43 | an-363 |
| E1A6876 | sp-22 | an-364 | E1U6876 | sp-25 | an-364 | E1U14202 | sp-43 | an-364 |
| E1A6877 | sp-22 | an-365 | E1U6877 | sp-25 | an-365 | E1U14203 | sp-43 | an-365 |
| E1A6878 | sp-22 | an-366 | E1U6878 | sp-25 | an-366 | E1U14204 | sp-43 | an-366 |
| E1A6879 | sp-22 | an-367 | E1U6879 | sp-25 | an-367 | E1U14205 | sp-43 | an-367 |
| E1A6880 | sp-22 | an-368 | E1U6880 | sp-25 | an-368 | E1U14206 | sp-43 | an-368 |
| E1A6881 | sp-22 | an-369 | E1U6881 | sp-25 | an-369 | E1U14207 | sp-43 | an-369 |
| E1A6882 | sp-22 | an-370 | E1U6882 | sp-25 | an-370 | E1U14208 | sp-43 | an-370 |
| E1A6883 | sp-22 | an-371 | E1U6883 | sp-25 | an-371 | E1U14209 | sp-43 | an-371 |
| E1A6884 | sp-22 | an-372 | E1U6884 | sp-25 | an-372 | E1U14210 | sp-43 | an-372 |
| E1A6885 | sp-22 | an-373 | E1U6885 | sp-25 | an-373 | E1U14211 | sp-43 | an-373 |
| E1A6886 | sp-22 | an-374 | E1U6886 | sp-25 | an-374 | E1U14212 | sp-43 | an-374 |
| E1A6887 | sp-22 | an-375 | E1U6887 | sp-25 | an-375 | E1U14213 | sp-43 | an-375 |
| E1A6888 | sp-22 | an-376 | E1U6888 | sp-25 | an-376 | E1U14214 | sp-43 | an-376 |
| E1A6889 | sp-22 | an-377 | E1U6889 | sp-25 | an-377 | E1U14215 | sp-43 | an-377 |
| E1A6890 | sp-22 | an-378 | E1U6890 | sp-25 | an-378 | E1U14216 | sp-43 | an-378 |
| E1A6891 | sp-22 | an-379 | E1U6891 | sp-25 | an-379 | E1U14217 | sp-43 | an-379 |
| E1A6892 | sp-22 | an-380 | E1U6892 | sp-25 | an-380 | E1U14218 | sp-43 | an-380 |
| E1A6893 | sp-22 | an-381 | E1U6893 | sp-25 | an-381 | E1U14219 | sp-43 | an-381 |
| E1A6894 | sp-22 | an-382 | E1U6894 | sp-25 | an-382 | E1U14220 | sp-43 | an-382 |
| E1A6895 | sp-22 | an-383 | E1U6895 | sp-25 | an-383 | E1U14221 | sp-43 | an-383 |
| E1A6896 | sp-22 | an-384 | E1U6896 | sp-25 | an-384 | E1U14222 | sp-43 | an-384 |
| E1A6897 | sp-22 | an-385 | E1U6897 | sp-25 | an-385 | E1U14223 | sp-43 | an-385 |
| E1A6898 | sp-22 | an-386 | E1U6898 | sp-25 | an-386 | E1U14224 | sp-43 | an-386 |
| E1A6899 | sp-22 | an-387 | E1U6899 | sp-25 | an-387 | E1U14225 | sp-43 | an-387 |
| E1A6900 | sp-22 | an-388 | E1U6900 | sp-25 | an-388 | E1U14226 | sp-43 | an-388 |
| E1A6901 | sp-22 | an-389 | E1U6901 | sp-25 | an-389 | E1U14227 | sp-43 | an-389 |
| E1A6902 | sp-22 | an-390 | E1U6902 | sp-25 | an-390 | E1U14228 | sp-43 | an-390 |
| E1A6903 | sp-22 | an-391 | E1U6903 | sp-25 | an-391 | E1U14229 | sp-43 | an-391 |
| E1A6904 | sp-22 | an-392 | E1U6904 | sp-25 | an-392 | E1U14230 | sp-43 | an-392 |
| E1A6905 | sp-22 | an-393 | E1U6905 | sp-25 | an-393 | E1U14231 | sp-43 | an-393 |
| E1A6906 | sp-22 | an-394 | E1U6906 | sp-25 | an-394 | E1U14232 | sp-43 | an-394 |
| E1A6907 | sp-22 | an-395 | E1U6907 | sp-25 | an-395 | E1U14233 | sp-43 | an-395 |
| E1A6908 | sp-22 | an-396 | E1U6908 | sp-25 | an-396 | E1U14234 | sp-43 | an-396 |
| E1A6909 | sp-22 | an-397 | E1U6909 | sp-25 | an-397 | E1U14235 | sp-43 | an-397 |
| E1A6910 | sp-22 | an-398 | E1U6910 | sp-25 | an-398 | E1U14236 | sp-43 | an-398 |
| E1A6911 | sp-22 | an-399 | E1U6911 | sp-25 | an-399 | E1U14237 | sp-43 | an-399 |
| E1A6912 | sp-22 | an-400 | E1U6912 | sp-25 | an-400 | E1U14238 | sp-43 | an-400 |
| | | | | Table 1-129 | | | | |
| | Y = NHCS | | | Y = NHCSNH | | | Y = NHCSNH | |
| E1A6913 | sp-22 | an-401 | E1U6913 | sp-25 | an-401 | E1U14239 | sp-43 | an-401 |
| E1A6914 | sp-22 | an-402 | E1U6914 | sp-25 | an-402 | E1U14240 | sp-43 | an-402 |
| E1A6915 | sp-22 | an-403 | E1U6915 | sp-25 | an-403 | E1U14241 | sp-43 | an-403 |
| E1A6916 | sp-22 | an-404 | E1U6916 | sp-25 | an-404 | E1U14242 | sp-43 | an-404 |
| E1A6917 | sp-22 | an-405 | E1U6917 | sp-25 | an-405 | E1U14243 | sp-43 | an-405 |
| E1A6918 | sp-22 | an-406 | E1U6918 | sp-25 | an-406 | E1U14244 | sp-43 | an-406 |
| E1A6919 | sp-22 | an-407 | E1U6919 | sp-25 | an-407 | E1U14245 | sp-43 | an-407 |
| | | | E1U6920 | sp-26 | an-1 | E1U14246 | sp-44 | an-1 |
| | Y = NHCSO | | E1U6921 | sp-26 | an-2 | E1U14247 | sp-44 | an-2 |
| E1C0001 | sp-1 | an-1 | E1U6922 | sp-26 | an-3 | E1U14248 | sp-44 | an-3 |
| E1C0002 | sp-1 | an-2 | E1U6923 | sp-26 | an-4 | E1U14249 | sp-44 | an-4 |
| E1C0003 | sp-1 | an-3 | E1U6924 | sp-26 | an-5 | E1U14250 | sp-44 | an-5 |
| E1C0004 | sp-1 | an-4 | E1U6925 | sp-26 | an-6 | E1U14251 | sp-44 | an-6 |
| E1C0005 | sp-1 | an-5 | E1U6926 | sp-26 | an-7 | E1U14252 | sp-44 | an-7 |
| E1C0006 | sp-1 | an-6 | E1U6927 | sp-26 | an-8 | E1U14253 | sp-44 | an-8 |

-continued

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| E1C0007 | sp-1 | an-7 | E1U6928 | sp-26 | an-9 | E1U14254 | sp-44 | an-9 |
| E1C0008 | sp-1 | an-8 | E1U6929 | sp-26 | an-10 | E1U14255 | sp-44 | an-10 |
| E1C0009 | sp-1 | an-9 | E1U6930 | sp-26 | an-11 | E1U14256 | sp-44 | an-11 |
| E1C0010 | sp-1 | an-10 | E1U6931 | sp-26 | an-12 | E1U14257 | sp-44 | an-12 |
| E1C0011 | sp-1 | an-11 | E1U6932 | sp-26 | an-13 | E1U14258 | sp-44 | an-13 |
| E1C0012 | sp-1 | an-12 | E1U6933 | sp-26 | an-14 | E1U14259 | sp-44 | an-14 |
| E1C0013 | sp-1 | an-13 | E1U6934 | sp-26 | an-15 | E1U14260 | sp-44 | an-15 |
| E1C0014 | sp-1 | an-14 | E1U6935 | sp-26 | an-16 | E1U14261 | sp-44 | an-16 |
| E1C0015 | sp-1 | an-15 | E1U6936 | sp-26 | an-17 | E1U14262 | sp-44 | an-17 |
| E1C0016 | sp-1 | an-16 | E1U6937 | sp-26 | an-18 | E1U14263 | sp-44 | an-18 |
| E1C0017 | sp-1 | an-17 | E1U6938 | sp-26 | an-19 | E1U14264 | sp-44 | an-19 |
| E1C0018 | sp-1 | an-18 | E1U6939 | sp-26 | an-20 | E1U14265 | sp-44 | an-20 |
| E1C0019 | sp-1 | an-19 | E1U6940 | sp-26 | an-21 | E1U14266 | sp-44 | an-21 |
| E1C0020 | sp-1 | an-20 | E1U6941 | sp-26 | an-22 | E1U14267 | sp-44 | an-22 |
| E1C0021 | sp-1 | an-21 | E1U6942 | sp-26 | an-23 | E1U14268 | sp-44 | an-23 |
| E1C0022 | sp-1 | an-22 | E1U6943 | sp-26 | an-24 | E1U14269 | sp-44 | an-24 |
| E1C0023 | sp-1 | an-23 | E1U6944 | sp-26 | an-25 | E1U14270 | sp-44 | an-25 |
| E1C0024 | sp-1 | an-24 | E1U6945 | sp-26 | an-26 | E1U14271 | sp-44 | an-26 |
| E1C0025 | sp-1 | an-25 | E1U6946 | sp-26 | an-27 | E1U14272 | sp-44 | an-27 |
| E1C0026 | sp-1 | an-26 | E1U6947 | sp-26 | an-28 | E1U14273 | sp-44 | an-28 |
| E1C0027 | sp-1 | an-27 | E1U6948 | sp-26 | an-29 | E1U14274 | sp-44 | an-29 |
| E1C0028 | sp-1 | an-28 | E1U6949 | sp-26 | an-30 | E1U14275 | sp-44 | an-30 |
| E1C0029 | sp-1 | an-29 | E1U6950 | sp-26 | an-31 | E1U14276 | sp-44 | an-31 |
| E1C0030 | sp-1 | an-30 | E1U6951 | sp-26 | an-32 | E1U14277 | sp-44 | an-32 |
| E1C0031 | sp-1 | an-31 | E1U6952 | sp-26 | an-33 | E1U14278 | sp-44 | an-33 |
| E1C0032 | sp-1 | an-32 | E1U6953 | sp-26 | an-34 | E1U14279 | sp-44 | an-34 |
| E1C0033 | sp-1 | an-33 | E1U6954 | sp-26 | an-35 | E1U14280 | sp-44 | an-35 |
| E1C0034 | sp-1 | an-34 | E1U6955 | sp-26 | an-36 | E1U14281 | sp-44 | an-36 |
| E1C0035 | sp-1 | an-35 | E1U6956 | sp-26 | an-37 | E1U14282 | sp-44 | an-37 |
| E1C0036 | sp-1 | an-36 | E1U6957 | sp-26 | an-38 | E1U14283 | sp-44 | an-38 |
| E1C0037 | sp-1 | an-37 | E1U6958 | sp-26 | an-39 | E1U14284 | sp-44 | an-39 |
| E1C0038 | sp-1 | an-38 | E1U6959 | sp-26 | an-40 | E1U14285 | sp-44 | an-40 |
| E1C0039 | sp-1 | an-39 | E1U6960 | sp-26 | an-41 | E1U14286 | sp-44 | an-41 |
| E1C0040 | sp-1 | an-40 | E1U6961 | sp-26 | an-42 | E1U14287 | sp-44 | an-42 |
| E1C0041 | sp-1 | an-41 | E1U6962 | sp-26 | an-43 | E1U14288 | sp-44 | an-43 |
| E1C0042 | sp-1 | an-42 | E1U6963 | sp-26 | an-44 | E1U14289 | sp-44 | an-44 |
| E1C0043 | sp-1 | an-43 | E1U6964 | sp-26 | an-45 | E1U14290 | sp-44 | an-45 |
| E1C0044 | sp-1 | an-44 | E1U6965 | sp-26 | an-46 | E1U14291 | sp-44 | an-46 |
| E1C0045 | sp-1 | an-45 | E1U6966 | sp-26 | an-47 | E1U14292 | sp-44 | an-47 |

Table 1-130

| Y = NHCSO | | | Y = NHCSNH | | | Y = NHCSNH | | |
|---|---|---|---|---|---|---|---|---|
| E1C0046 | sp-1 | an-46 | E1U6967 | sp-26 | an-48 | E1U14293 | sp-44 | an-48 |
| E1C0047 | sp-1 | an-47 | E1U6968 | sp-26 | an-49 | E1U14294 | sp-44 | an-49 |
| E1C0048 | sp-1 | an-48 | E1U6969 | sp-26 | an-50 | E1U14295 | sp-44 | an-50 |
| E1C0049 | sp-1 | an-49 | E1U6970 | sp-26 | an-51 | E1U14296 | sp-44 | an-51 |
| E1C0050 | sp-1 | an-50 | E1U6971 | sp-26 | an-52 | E1U14297 | sp-44 | an-52 |
| E1C0051 | sp-1 | an-51 | E1U6972 | sp-26 | an-53 | E1U14298 | sp-44 | an-53 |
| E1C0052 | sp-1 | an-52 | E1U6973 | sp-26 | an-54 | E1U14299 | sp-44 | an-54 |
| E1C0053 | sp-1 | an-53 | E1U6974 | sp-26 | an-55 | E1U14300 | sp-44 | an-55 |
| E1C0054 | sp-1 | an-54 | E1U6975 | sp-26 | an-56 | E1U14301 | sp-44 | an-56 |
| E1C0055 | sp-1 | an-55 | E1U6976 | sp-26 | an-57 | E1U14302 | sp-44 | an-57 |
| E1C0056 | sp-1 | an-56 | E1U6977 | sp-26 | an-58 | E1U14303 | sp-44 | an-58 |
| E1C0057 | sp-1 | an-57 | E1U6978 | sp-26 | an-59 | E1U14304 | sp-44 | an-59 |
| E1C0058 | sp-1 | an-58 | E1U6979 | sp-26 | an-60 | E1U14305 | sp-44 | an-60 |
| E1C0059 | sp-1 | an-59 | E1U6980 | sp-26 | an-61 | E1U14306 | sp-44 | an-61 |
| E1C0060 | sp-1 | an-60 | E1U6981 | sp-26 | an-62 | E1U14307 | sp-44 | an-62 |
| E1C0061 | sp-1 | an-61 | E1U6982 | sp-26 | an-63 | E1U14308 | sp-44 | an-63 |
| E1C0062 | sp-1 | an-62 | E1U6983 | sp-26 | an-64 | E1U14309 | sp-44 | an-64 |
| E1C0063 | sp-1 | an-63 | E1U6984 | sp-26 | an-65 | E1U14310 | sp-44 | an-65 |
| E1C0064 | sp-1 | an-64 | E1U6985 | sp-26 | an-66 | E1U14311 | sp-44 | an-66 |
| E1C0065 | sp-1 | an-65 | E1U6986 | sp-26 | an-67 | E1U14312 | sp-44 | an-67 |
| E1C0066 | sp-1 | an-66 | E1U6987 | sp-26 | an-68 | E1U14313 | sp-44 | an-68 |
| E1C0067 | sp-1 | an-67 | E1U6988 | sp-26 | an-69 | E1U14314 | sp-44 | an-69 |
| E1C0068 | sp-1 | an-68 | E1U6989 | sp-26 | an-70 | E1U14315 | sp-44 | an-70 |
| E1C0069 | sp-1 | an-69 | E1U6990 | sp-26 | an-71 | E1U14316 | sp-44 | an-71 |
| E1C0070 | sp-1 | an-70 | E1U6991 | sp-26 | an-72 | E1U14317 | sp-44 | an-72 |
| E1C0071 | sp-1 | an-71 | E1U6992 | sp-26 | an-73 | E1U14318 | sp-44 | an-73 |
| E1C0072 | sp-1 | an-72 | E1U6993 | sp-26 | an-74 | E1U14319 | sp-44 | an-74 |
| E1C0073 | sp-1 | an-73 | E1U6994 | sp-26 | an-75 | E1U14320 | sp-44 | an-75 |
| E1C0074 | sp-1 | an-74 | E1U6995 | sp-26 | an-76 | E1U14321 | sp-44 | an-76 |
| E1C0075 | sp-1 | an-75 | E1U6996 | sp-26 | an-77 | E1U14322 | sp-44 | an-77 |
| E1C0076 | sp-1 | an-76 | E1U6997 | sp-26 | an-78 | E1U14323 | sp-44 | an-78 |
| E1C0077 | sp-1 | an-77 | E1U6998 | sp-26 | an-79 | E1U14324 | sp-44 | an-79 |
| E1C0078 | sp-1 | an-78 | E1U6999 | sp-26 | an-80 | E1U14325 | sp-44 | an-80 |
| E1C0079 | sp-1 | an-79 | E1U7000 | sp-26 | an-81 | E1U14326 | sp-44 | an-81 |
| E1C0080 | sp-1 | an-80 | E1U7001 | sp-26 | an-82 | E1U14327 | sp-44 | an-82 |

-continued

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| E1C0081 | sp-1 | an-81 | E1U7002 | sp-26 | an-83 | E1U14328 | sp-44 | an-83 |
| E1C0082 | sp-1 | an-82 | E1U7003 | sp-26 | an-84 | E1U14329 | sp-44 | an-84 |
| E1C0083 | sp-1 | an-83 | E1U7004 | sp-26 | an-85 | E1U14330 | sp-44 | an-85 |
| E1C0084 | sp-1 | an-84 | E1U7005 | sp-26 | an-86 | E1U14331 | sp-44 | an-86 |
| E1C0085 | sp-1 | an-85 | E1U7006 | sp-26 | an-87 | E1U14332 | sp-44 | an-87 |
| E1C0086 | sp-1 | an-86 | E1U7007 | sp-26 | an-88 | E1U14333 | sp-44 | an-88 |
| E1C0087 | sp-1 | an-87 | E1U7008 | sp-26 | an-89 | E1U14334 | sp-44 | an-89 |
| E1C0088 | sp-1 | an-88 | E1U7009 | sp-26 | an-90 | E1U14335 | sp-44 | an-90 |
| E1C0089 | sp-1 | an-89 | E1U7010 | sp-26 | an-91 | E1U14336 | sp-44 | an-91 |
| E1C0090 | sp-1 | an-90 | E1U7011 | sp-26 | an-92 | E1U14337 | sp-44 | an-92 |
| E1C0091 | sp-1 | an-91 | E1U7012 | sp-26 | an-93 | E1U14338 | sp-44 | an-93 |
| E1C0092 | sp-1 | an-92 | E1U7013 | sp-26 | an-94 | E1U14339 | sp-44 | an-94 |
| E1C0093 | sp-1 | an-93 | E1U7014 | sp-26 | an-95 | E1U14340 | sp-44 | an-95 |
| E1C0094 | sp-1 | an-94 | E1U7015 | sp-26 | an-96 | E1U14341 | sp-44 | an-96 |
| E1C0095 | sp-1 | an-95 | E1U7016 | sp-26 | an-97 | E1U14342 | sp-44 | an-97 |
| E1C0096 | sp-1 | an-96 | E1U7017 | sp-26 | an-98 | E1U14343 | sp-44 | an-98 |
| E1C0097 | sp-1 | an-97 | E1U7018 | sp-26 | an-99 | E1U14344 | sp-44 | an-99 |
| E1C0098 | sp-1 | an-98 | E1U7019 | sp-26 | an-100 | E1U14345 | sp-44 | an-100 |
| E1C0099 | sp-1 | an-99 | E1U7020 | sp-26 | an-101 | E1U14346 | sp-44 | an-101 |

Table 1-131

| Y = NHCSO | | | Y = NHCSNH | | | Y = NHCSNH | | |
|---|---|---|---|---|---|---|---|---|
| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
| E1C0100 | sp-1 | an-100 | E1U7021 | sp-26 | an-102 | E1U14347 | sp-44 | an-102 |
| E1C0101 | sp-1 | an-101 | E1U7022 | sp-26 | an-103 | E1U14348 | sp-44 | an-103 |
| E1C0102 | sp-1 | an-102 | E1U7023 | sp-26 | an-104 | E1U14349 | sp-44 | an-104 |
| E1C0103 | sp-1 | an-103 | E1U7024 | sp-26 | an-105 | E1U14350 | sp-44 | an-105 |
| E1C0104 | sp-1 | an-104 | E1U7025 | sp-26 | an-106 | E1U14351 | sp-44 | an-106 |
| E1C0105 | sp-1 | an-105 | E1U7026 | sp-26 | an-107 | E1U14352 | sp-44 | an-107 |
| E1C0106 | sp-1 | an-106 | E1U7027 | sp-26 | an-108 | E1U14353 | sp-44 | an-108 |
| E1C0107 | sp-1 | an-107 | E1U7028 | sp-26 | an-109 | E1U14354 | sp-44 | an-109 |
| E1C0108 | sp-1 | an-108 | E1U7029 | sp-26 | an-110 | E1U14355 | sp-44 | an-110 |
| E1C0109 | sp-1 | an-109 | E1U7030 | sp-26 | an-111 | E1U14356 | sp-44 | an-111 |
| E1C0110 | sp-1 | an-110 | E1U7031 | sp-26 | an-112 | E1U14357 | sp-44 | an-112 |
| E1C0111 | sp-1 | an-111 | E1U7032 | sp-26 | an-113 | E1U14358 | sp-44 | an-113 |
| E1C0112 | sp-1 | an-112 | E1U7033 | sp-26 | an-114 | E1U14359 | sp-44 | an-114 |
| E1C0113 | sp-1 | an-113 | E1U7034 | sp-26 | an-115 | E1U14360 | sp-44 | an-115 |
| E1C0114 | sp-1 | an-114 | E1U7035 | sp-26 | an-116 | E1U14361 | sp-44 | an-116 |
| E1C0115 | sp-1 | an-115 | E1U7036 | sp-26 | an-117 | E1U14362 | sp-44 | an-117 |
| E1C0116 | sp-1 | an-116 | E1U7037 | sp-26 | an-118 | E1U14363 | sp-44 | an-118 |
| E1C0117 | sp-1 | an-117 | E1U7038 | sp-26 | an-119 | E1U14364 | sp-44 | an-119 |
| E1C0118 | sp-1 | an-118 | E1U7039 | sp-26 | an-120 | E1U14365 | sp-44 | an-120 |
| E1C0119 | sp-1 | an-119 | E1U7040 | sp-26 | an-121 | E1U14366 | sp-44 | an-121 |
| E1C0120 | sp-1 | an-120 | E1U7041 | sp-26 | an-122 | E1U14367 | sp-44 | an-122 |
| E1C0121 | sp-1 | an-121 | E1U7042 | sp-26 | an-123 | E1U14368 | sp-44 | an-123 |
| E1C0122 | sp-1 | an-122 | E1U7043 | sp-26 | an-124 | E1U14369 | sp-44 | an-124 |
| E1C0123 | sp-1 | an-123 | E1U7044 | sp-26 | an-125 | E1U14370 | sp-44 | an-125 |
| E1C0124 | sp-1 | an-124 | E1U7045 | sp-26 | an-126 | E1U14371 | sp-44 | an-126 |
| E1C0125 | sp-1 | an-125 | E1U7046 | sp-26 | an-127 | E1U14372 | sp-44 | an-127 |
| E1C0126 | sp-1 | an-126 | E1U7047 | sp-26 | an-128 | E1U14373 | sp-44 | an-128 |
| E1C0127 | sp-1 | an-127 | E1U7048 | sp-26 | an-129 | E1U14374 | sp-44 | an-129 |
| E1C0128 | sp-1 | an-128 | E1U7049 | sp-26 | an-130 | E1U14375 | sp-44 | an-130 |
| E1C0129 | sp-1 | an-129 | E1U7050 | sp-26 | an-131 | E1U14376 | sp-44 | an-131 |
| E1C0130 | sp-1 | an-130 | E1U7051 | sp-26 | an-132 | E1U14377 | sp-44 | an-132 |
| E1C0131 | sp-1 | an-131 | E1U7052 | sp-26 | an-133 | E1U14378 | sp-44 | an-133 |
| E1C0132 | sp-1 | an-132 | E1U7053 | sp-26 | an-134 | E1U14379 | sp-44 | an-134 |
| E1C0133 | sp-1 | an-133 | E1U7054 | sp-26 | an-135 | E1U14380 | sp-44 | an-135 |
| E1C0134 | sp-1 | an-134 | E1U7055 | sp-26 | an-136 | E1U14381 | sp-44 | an-136 |
| E1C0135 | sp-1 | an-135 | E1U7056 | sp-26 | an-137 | E1U14382 | sp-44 | an-137 |
| E1C0136 | sp-1 | an-136 | E1U7057 | sp-26 | an-138 | E1U14383 | sp-44 | an-138 |
| E1C0137 | sp-1 | an-137 | E1U7058 | sp-26 | an-139 | E1U14384 | sp-44 | an-139 |
| E1C0138 | sp-1 | an-138 | E1U7059 | sp-26 | an-140 | E1U14385 | sp-44 | an-140 |
| E1C0139 | sp-1 | an-139 | E1U7060 | sp-26 | an-141 | E1U14386 | sp-44 | an-141 |
| E1C0140 | sp-1 | an-140 | E1U7061 | sp-26 | an-142 | E1U14387 | sp-44 | an-142 |
| E1C0141 | sp-1 | an-141 | E1U7062 | sp-26 | an-143 | E1U14388 | sp-44 | an-143 |
| E1C0142 | sp-1 | an-142 | E1U7063 | sp-26 | an-144 | E1U14389 | sp-44 | an-144 |
| E1C0143 | sp-1 | an-143 | E1U7064 | sp-26 | an-145 | E1U14390 | sp-44 | an-145 |
| E1C0144 | sp-1 | an-144 | E1U7065 | sp-26 | an-146 | E1U14391 | sp-44 | an-146 |
| E1C0145 | sp-1 | an-145 | E1U7066 | sp-26 | an-147 | E1U14392 | sp-44 | an-147 |
| E1C0146 | sp-1 | an-146 | E1U7067 | sp-26 | an-148 | E1U14393 | sp-44 | an-148 |
| E1C0147 | sp-1 | an-147 | E1U7068 | sp-26 | an-149 | E1U14394 | sp-44 | an-149 |
| E1C0148 | sp-1 | an-148 | E1U7069 | sp-26 | an-150 | E1U14395 | sp-44 | an-150 |
| E1C0149 | sp-1 | an-149 | E1U7070 | sp-26 | an-151 | E1U14396 | sp-44 | an-151 |
| E1C0150 | sp-1 | an-150 | E1U7071 | sp-26 | an-152 | E1U14397 | sp-44 | an-152 |
| E1C0151 | sp-1 | an-151 | E1U7072 | sp-26 | an-153 | E1U14398 | sp-44 | an-153 |
| E1C0152 | sp-1 | an-152 | E1U7073 | sp-26 | an-154 | E1U14399 | sp-44 | an-154 |
| E1C0153 | sp-1 | an-153 | E1U7074 | sp-26 | an-155 | E1U14400 | sp-44 | an-155 |

-continued

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| | | | | Table 1-132 | | | | |
| | Y = NHCSO | | | Y = NHCSNH | | | Y = NHCSNH | |
| E1C0154 | sp-1 | an-154 | E1U7075 | sp-26 | an-156 | E1U14401 | sp-44 | an-156 |
| E1C0155 | sp-1 | an-155 | E1U7076 | sp-26 | an-157 | E1U14402 | sp-44 | an-157 |
| E1C0156 | sp-1 | an-156 | E1U7077 | sp-26 | an-158 | E1U14403 | sp-44 | an-158 |
| E1C0157 | sp-1 | an-157 | E1U7078 | sp-26 | an-159 | E1U14404 | sp-44 | an-159 |
| E1C0158 | sp-1 | an-158 | E1U7079 | sp-26 | an-160 | E1U14405 | sp-44 | an-160 |
| E1C0159 | sp-1 | an-159 | E1U7080 | sp-26 | an-161 | E1U14406 | sp-44 | an-161 |
| E1C0160 | sp-1 | an-160 | E1U7081 | sp-26 | an-162 | E1U14407 | sp-44 | an-162 |
| E1C0161 | sp-1 | an-161 | E1U7082 | sp-26 | an-163 | E1U14408 | sp-44 | an-163 |
| E1C0162 | sp-1 | an-162 | E1U7083 | sp-26 | an-164 | E1U14409 | sp-44 | an-164 |
| E1C0163 | sp-1 | an-163 | E1U7084 | sp-26 | an-165 | E1U14410 | sp-44 | an-165 |
| E1C0164 | sp-1 | an-164 | E1U7085 | sp-26 | an-166 | E1U14411 | sp-44 | an-166 |
| E1C0165 | sp-1 | an-165 | E1U7086 | sp-26 | an-167 | E1U14412 | sp-44 | an-167 |
| E1C0166 | sp-1 | an-166 | E1U7087 | sp-26 | an-168 | E1U14413 | sp-44 | an-168 |
| E1C0167 | sp-1 | an-167 | E1U7088 | sp-26 | an-169 | E1U14414 | sp-44 | an-169 |
| E1C0168 | sp-1 | an-168 | E1U7089 | sp-26 | an-170 | E1U14415 | sp-44 | an-170 |
| E1C0169 | sp-1 | an-169 | E1U7090 | sp-26 | an-171 | E1U14416 | sp-44 | an-171 |
| E1C0170 | sp-1 | an-170 | E1U7091 | sp-26 | an-172 | E1U14417 | sp-44 | an-172 |
| E1C0171 | sp-1 | an-171 | E1U7092 | sp-26 | an-173 | E1U14418 | sp-44 | an-173 |
| E1C0172 | sp-1 | an-172 | E1U7093 | sp-26 | an-174 | E1U14419 | sp-44 | an-174 |
| E1C0173 | sp-1 | an-173 | E1U7094 | sp-26 | an-175 | E1U14420 | sp-44 | an-175 |
| E1C0174 | sp-1 | an-174 | E1U7095 | sp-26 | an-176 | E1U14421 | sp-44 | an-176 |
| E1C0175 | sp-1 | an-175 | E1U7096 | sp-26 | an-177 | E1U14422 | sp-44 | an-177 |
| E1C0176 | sp-1 | an-176 | E1U7097 | sp-26 | an-178 | E1U14423 | sp-44 | an-178 |
| E1C0177 | sp-1 | an-177 | E1U7098 | sp-26 | an-179 | E1U14424 | sp-44 | an-179 |
| E1C0178 | sp-1 | an-178 | E1U7099 | sp-26 | an-180 | E1U14425 | sp-44 | an-180 |
| E1C0179 | sp-1 | an-179 | E1U7100 | sp-26 | an-181 | E1U14426 | sp-44 | an-181 |
| E1C0180 | sp-1 | an-180 | E1U7101 | sp-26 | an-182 | E1U14427 | sp-44 | an-182 |
| E1C0181 | sp-1 | an-181 | E1U7102 | sp-26 | an-183 | E1U14428 | sp-44 | an-183 |
| E1C0182 | sp-1 | an-182 | E1U7103 | sp-26 | an-184 | E1U14429 | sp-44 | an-184 |
| E1C0183 | sp-1 | an-183 | E1U7104 | sp-26 | an-185 | E1U14430 | sp-44 | an-185 |
| E1C0184 | sp-1 | an-184 | E1U7105 | sp-26 | an-186 | E1U14431 | sp-44 | an-186 |
| E1C0185 | sp-1 | an-185 | E1U7106 | sp-26 | an-187 | E1U14432 | sp-44 | an-187 |
| E1C0186 | sp-1 | an-186 | E1U7107 | sp-26 | an-188 | E1U14433 | sp-44 | an-188 |
| E1C0187 | sp-1 | an-187 | E1U7108 | sp-26 | an-189 | E1U14434 | sp-44 | an-189 |
| E1C0188 | sp-1 | an-188 | E1U7109 | sp-26 | an-190 | E1U14435 | sp-44 | an-190 |
| E1C0189 | sp-1 | an-189 | E1U7110 | sp-26 | an-191 | E1U14436 | sp-44 | an-191 |
| E1C0190 | sp-1 | an-190 | E1U7111 | sp-26 | an-192 | E1U14437 | sp-44 | an-192 |
| E1C0191 | sp-1 | an-191 | E1U7112 | sp-26 | an-193 | E1U14438 | sp-44 | an-193 |
| E1C0192 | sp-1 | an-192 | E1U7113 | sp-26 | an-194 | E1U14439 | sp-44 | an-194 |
| E1C0193 | sp-1 | an-193 | E1U7114 | sp-26 | an-195 | E1U14440 | sp-44 | an-195 |
| E1C0194 | sp-1 | an-194 | E1U7115 | sp-26 | an-196 | E1U14441 | sp-44 | an-196 |
| E1C0195 | sp-1 | an-195 | E1U7116 | sp-26 | an-197 | E1U14442 | sp-44 | an-197 |
| E1C0196 | sp-1 | an-196 | E1U7117 | sp-26 | an-198 | E1U14443 | sp-44 | an-198 |
| E1C0197 | sp-1 | an-197 | E1U7118 | sp-26 | an-199 | E1U14444 | sp-44 | an-199 |
| E1C0198 | sp-1 | an-198 | E1U7119 | sp-26 | an-200 | E1U14445 | sp-44 | an-200 |
| E1C0199 | sp-1 | an-199 | E1U7120 | sp-26 | an-201 | E1U14446 | sp-44 | an-201 |
| E1C0200 | sp-1 | an-200 | E1U7121 | sp-26 | an-202 | E1U14447 | sp-44 | an-202 |
| E1C0201 | sp-1 | an-201 | E1U7122 | sp-26 | an-203 | E1U14448 | sp-44 | an-203 |
| E1C0202 | sp-1 | an-202 | E1U7123 | sp-26 | an-204 | E1U14449 | sp-44 | an-204 |
| E1C0203 | sp-1 | an-203 | E1U7124 | sp-26 | an-205 | E1U14450 | sp-44 | an-205 |
| E1C0204 | sp-1 | an-204 | E1U7125 | sp-26 | an-206 | E1U14451 | sp-44 | an-206 |
| E1C0205 | sp-1 | an-205 | E1U7126 | sp-26 | an-207 | E1U14452 | sp-44 | an-207 |
| E1C0206 | sp-1 | an-206 | E1U7127 | sp-26 | an-208 | E1U14453 | sp-44 | an-208 |
| E1C0207 | sp-1 | an-207 | E1U7128 | sp-26 | an-209 | E1U14454 | sp-44 | an-209 |
| | | | | Table 1-133 | | | | |
| | Y = NHCSO | | | Y = NHCSNH | | | Y = NHCSNH | |
| E1C0208 | sp-1 | an-208 | E1U7129 | sp-26 | an-210 | E1U14455 | sp-44 | an-210 |
| E1C0209 | sp-1 | an-209 | E1U7130 | sp-26 | an-211 | E1U14456 | sp-44 | an-211 |
| E1C0210 | sp-1 | an-210 | E1U7131 | sp-26 | an-212 | E1U14457 | sp-44 | an-212 |
| E1C0211 | sp-1 | an-211 | E1U7132 | sp-26 | an-213 | E1U14458 | sp-44 | an-213 |
| E1C0212 | sp-1 | an-212 | E1U7133 | sp-26 | an-214 | E1U14459 | sp-44 | an-214 |
| E1C0213 | sp-1 | an-213 | E1U7134 | sp-26 | an-215 | E1U14460 | sp-44 | an-215 |
| E1C0214 | sp-1 | an-214 | E1U7135 | sp-26 | an-216 | E1U14461 | sp-44 | an-216 |
| E1C0215 | sp-1 | an-215 | E1U7136 | sp-26 | an-217 | E1U14462 | sp-44 | an-217 |
| E1C0216 | sp-1 | an-216 | E1U7137 | sp-26 | an-218 | E1U14463 | sp-44 | an-218 |
| E1C0217 | sp-1 | an-217 | E1U7138 | sp-26 | an-219 | E1U14464 | sp-44 | an-219 |
| E1C0218 | sp-1 | an-218 | E1U7139 | sp-26 | an-220 | E1U14465 | sp-44 | an-220 |
| E1C0219 | sp-1 | an-219 | E1U7140 | sp-26 | an-221 | E1U14466 | sp-44 | an-221 |
| E1C0220 | sp-1 | an-220 | E1U7141 | sp-26 | an-222 | E1U14467 | sp-44 | an-222 |
| E1C0221 | sp-1 | an-221 | E1U7142 | sp-26 | an-223 | E1U14468 | sp-44 | an-223 |
| E1C0222 | sp-1 | an-222 | E1U7143 | sp-26 | an-224 | E1U14469 | sp-44 | an-224 |
| E1C0223 | sp-1 | an-223 | E1U7144 | sp-26 | an-225 | E1U14470 | sp-44 | an-225 |

-continued

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| E1C0224 | sp-1 | an-224 | E1U7145 | sp-26 | an-226 | E1U14471 | sp-44 | an-226 |
| E1C0225 | sp-1 | an-225 | E1U7146 | sp-26 | an-227 | E1U14472 | sp-44 | an-227 |
| E1C0226 | sp-1 | an-226 | E1U7147 | sp-26 | an-228 | E1U14473 | sp-44 | an-228 |
| E1C0227 | sp-1 | an-227 | E1U7148 | sp-26 | an-229 | E1U14474 | sp-44 | an-229 |
| E1C0228 | sp-1 | an-228 | E1U7149 | sp-26 | an-230 | E1U14475 | sp-44 | an-230 |
| E1C0229 | sp-1 | an-229 | E1U7150 | sp-26 | an-231 | E1U14476 | sp-44 | an-231 |
| E1C0230 | sp-1 | an-230 | E1U7151 | sp-26 | an-232 | E1U14477 | sp-44 | an-232 |
| E1C0231 | sp-1 | an-231 | E1U7152 | sp-26 | an-233 | E1U14478 | sp-44 | an-233 |
| E1C0232 | sp-1 | an-232 | E1U7153 | sp-26 | an-234 | E1U14479 | sp-44 | an-234 |
| E1C0233 | sp-1 | an-233 | E1U7154 | sp-26 | an-235 | E1U14480 | sp-44 | an-235 |
| E1C0234 | sp-1 | an-234 | E1U7155 | sp-26 | an-236 | E1U14481 | sp-44 | an-236 |
| E1C0235 | sp-1 | an-235 | E1U7156 | sp-26 | an-237 | E1U14482 | sp-44 | an-237 |
| E1C0236 | sp-1 | an-236 | E1U7157 | sp-26 | an-238 | E1U14483 | sp-44 | an-238 |
| E1C0237 | sp-1 | an-237 | E1U7158 | sp-26 | an-239 | E1U14484 | sp-44 | an-239 |
| E1C0238 | sp-1 | an-238 | E1U7159 | sp-26 | an-240 | E1U14485 | sp-44 | an-240 |
| E1C0239 | sp-1 | an-239 | E1U7160 | sp-26 | an-241 | E1U14486 | sp-44 | an-241 |
| E1C0240 | sp-1 | an-240 | E1U7161 | sp-26 | an-242 | E1U14487 | sp-44 | an-242 |
| E1C0241 | sp-1 | an-241 | E1U7162 | sp-26 | an-243 | E1U14488 | sp-44 | an-243 |
| E1C0242 | sp-1 | an-242 | E1U7163 | sp-26 | an-244 | E1U14489 | sp-44 | an-244 |
| E1C0243 | sp-1 | an-243 | E1U7164 | sp-26 | an-245 | E1U14490 | sp-44 | an-245 |
| E1C0244 | sp-1 | an-244 | E1U7165 | sp-26 | an-246 | E1U14491 | sp-44 | an-246 |
| E1C0245 | sp-1 | an-245 | E1U7166 | sp-26 | an-247 | E1U14492 | sp-44 | an-247 |
| E1C0246 | sp-1 | an-246 | E1U7167 | sp-26 | an-248 | E1U14493 | sp-44 | an-248 |
| E1C0247 | sp-1 | an-247 | E1U7168 | sp-26 | an-249 | E1U14494 | sp-44 | an-249 |
| E1C0248 | sp-1 | an-248 | E1U7169 | sp-26 | an-250 | E1U14495 | sp-44 | an-250 |
| E1C0249 | sp-1 | an-249 | E1U7170 | sp-26 | an-251 | E1U14496 | sp-44 | an-251 |
| E1C0250 | sp-1 | an-250 | E1U7171 | sp-26 | an-252 | E1U14497 | sp-44 | an-252 |
| E1C0251 | sp-1 | an-251 | E1U7172 | sp-26 | an-253 | E1U14498 | sp-44 | an-253 |
| E1C0252 | sp-1 | an-252 | E1U7173 | sp-26 | an-254 | E1U14499 | sp-44 | an-254 |
| E1C0253 | sp-1 | an-253 | E1U7174 | sp-26 | an-255 | E1U14500 | sp-44 | an-255 |
| E1C0254 | sp-1 | an-254 | E1U7175 | sp-26 | an-256 | E1U14501 | sp-44 | an-256 |
| E1C0255 | sp-1 | an-255 | E1U7176 | sp-26 | an-257 | E1U14502 | sp-44 | an-257 |
| E1C0256 | sp-1 | an-256 | E1U7177 | sp-26 | an-258 | E1U14503 | sp-44 | an-258 |
| E1C0257 | sp-1 | an-257 | E1U7178 | sp-26 | an-259 | E1U14504 | sp-44 | an-259 |
| E1C0258 | sp-1 | an-258 | E1U7179 | sp-26 | an-260 | E1U14505 | sp-44 | an-260 |
| E1C0259 | sp-1 | an-259 | E1U7180 | sp-26 | an-261 | E1U14506 | sp-44 | an-261 |
| E1C0260 | sp-1 | an-260 | E1U7181 | sp-26 | an-262 | E1U14507 | sp-44 | an-262 |
| E1C0261 | sp-1 | an-261 | E1U7182 | sp-26 | an-263 | E1U14508 | sp-44 | an-263 |

Table 1-134

| | Y = NHCSO | | | Y = NHCSNH | | | Y = NHCSNH | |
|---|---|---|---|---|---|---|---|---|
| E1C0262 | sp-1 | an-262 | E1U7183 | sp-26 | an-264 | E1U14509 | sp-44 | an-264 |
| E1C0263 | sp-1 | an-263 | E1U7184 | sp-26 | an-265 | E1U14510 | sp-44 | an-265 |
| E1C0264 | sp-1 | an-264 | E1U7185 | sp-26 | an-266 | E1U14511 | sp-44 | an-266 |
| E1C0265 | sp-1 | an-265 | E1U7186 | sp-26 | an-267 | E1U14512 | sp-44 | an-267 |
| E1C0266 | sp-1 | an-266 | E1U7187 | sp-26 | an-268 | E1U14513 | sp-44 | an-268 |
| E1C0267 | sp-1 | an-267 | E1U7188 | sp-26 | an-269 | E1U14514 | sp-44 | an-269 |
| E1C0268 | sp-1 | an-268 | E1U7189 | sp-26 | an-270 | E1U14515 | sp-44 | an-270 |
| E1C0269 | sp-1 | an-269 | E1U7190 | sp-26 | an-271 | E1U14516 | sp-44 | an-271 |
| E1C0270 | sp-1 | an-270 | E1U7191 | sp-26 | an-272 | E1U14517 | sp-44 | an-272 |
| E1C0271 | sp-1 | an-271 | E1U7192 | sp-26 | an-273 | E1U14518 | sp-44 | an-273 |
| E1C0272 | sp-1 | an-272 | E1U7193 | sp-26 | an-274 | E1U14519 | sp-44 | an-274 |
| E1C0273 | sp-1 | an-273 | E1U7194 | sp-26 | an-275 | E1U14520 | sp-44 | an-275 |
| E1C0274 | sp-1 | an-274 | E1U7195 | sp-26 | an-276 | E1U14521 | sp-44 | an-276 |
| E1C0275 | sp-1 | an-275 | E1U7196 | sp-26 | an-277 | E1U14522 | sp-44 | an-277 |
| E1C0276 | sp-1 | an-276 | E1U7197 | sp-26 | an-278 | E1U14523 | sp-44 | an-278 |
| E1C0277 | sp-1 | an-277 | E1U7198 | sp-26 | an-279 | E1U14524 | sp-44 | an-279 |
| E1C0278 | sp-1 | an-278 | E1U7199 | sp-26 | an-280 | E1U14525 | sp-44 | an-280 |
| E1C0279 | sp-1 | an-279 | E1U7200 | sp-26 | an-281 | E1U14526 | sp-44 | an-281 |
| E1C0280 | sp-1 | an-280 | E1U7201 | sp-26 | an-282 | E1U14527 | sp-44 | an-282 |
| E1C0281 | sp-1 | an-281 | E1U7202 | sp-26 | an-283 | E1U14528 | sp-44 | an-283 |
| E1C0282 | sp-1 | an-282 | E1U7203 | sp-26 | an-284 | E1U14529 | sp-44 | an-284 |
| E1C0283 | sp-1 | an-283 | E1U7204 | sp-26 | an-285 | E1U14530 | sp-44 | an-285 |
| E1C0284 | sp-1 | an-284 | E1U7205 | sp-26 | an-286 | E1U14531 | sp-44 | an-286 |
| E1C0285 | sp-1 | an-285 | E1U7206 | sp-26 | an-287 | E1U14532 | sp-44 | an-287 |
| E1C0286 | sp-1 | an-286 | E1U7207 | sp-26 | an-288 | E1U14533 | sp-44 | an-288 |
| E1C0287 | sp-1 | an-287 | E1U7208 | sp-26 | an-289 | E1U14534 | sp-44 | an-289 |
| E1C0288 | sp-1 | an-288 | E1U7209 | sp-26 | an-290 | E1U14535 | sp-44 | an-290 |
| E1C0289 | sp-1 | an-289 | E1U7210 | sp-26 | an-291 | E1U14536 | sp-44 | an-291 |
| E1C0290 | sp-1 | an-290 | E1U7211 | sp-26 | an-292 | E1U14537 | sp-44 | an-292 |
| E1C0291 | sp-1 | an-291 | E1U7212 | sp-26 | an-293 | E1U14538 | sp-44 | an-293 |
| E1C0292 | sp-1 | an-292 | E1U7213 | sp-26 | an-294 | E1U14539 | sp-44 | an-294 |
| E1C0293 | sp-1 | an-293 | E1U7214 | sp-26 | an-295 | E1U14540 | sp-44 | an-295 |
| E1C0294 | sp-1 | an-294 | E1U7215 | sp-26 | an-296 | E1U14541 | sp-44 | an-296 |
| E1C0295 | sp-1 | an-295 | E1U7216 | sp-26 | an-297 | E1U14542 | sp-44 | an-297 |
| E1C0296 | sp-1 | an-296 | E1U7217 | sp-26 | an-298 | E1U14543 | sp-44 | an-298 |
| E1C0297 | sp-1 | an-297 | E1U7218 | sp-26 | an-299 | E1U14544 | sp-44 | an-299 |

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| E1C0298 | sp-1 | an-298 | E1U7219 | sp-26 | an-300 | E1U14545 | sp-44 | an-300 |
| E1C0299 | sp-1 | an-299 | E1U7220 | sp-26 | an-301 | E1U14546 | sp-44 | an-301 |
| E1C0300 | sp-1 | an-300 | E1U7221 | sp-26 | an-302 | E1U14547 | sp-44 | an-302 |
| E1C0301 | sp-1 | an-301 | E1U7222 | sp-26 | an-303 | E1U14548 | sp-44 | an-303 |
| E1C0302 | sp-1 | an-302 | E1U7223 | sp-26 | an-304 | E1U14549 | sp-44 | an-304 |
| E1C0303 | sp-1 | an-303 | E1U7224 | sp-26 | an-305 | E1U14550 | sp-44 | an-305 |
| E1C0304 | sp-1 | an-304 | E1U7225 | sp-26 | an-306 | E1U14551 | sp-44 | an-306 |
| E1C0305 | sp-1 | an-305 | E1U7226 | sp-26 | an-307 | E1U14552 | sp-44 | an-307 |
| E1C0306 | sp-1 | an-306 | E1U7227 | sp-26 | an-308 | E1U14553 | sp-44 | an-308 |
| E1C0307 | sp-1 | an-307 | E1U7228 | sp-26 | an-309 | E1U14554 | sp-44 | an-309 |
| E1C0308 | sp-1 | an-308 | E1U7229 | sp-26 | an-310 | E1U14555 | sp-44 | an-310 |
| E1C0309 | sp-1 | an-309 | E1U7230 | sp-26 | an-311 | E1U14556 | sp-44 | an-311 |
| E1C0310 | sp-1 | an-310 | E1U7231 | sp-26 | an-312 | E1U14557 | sp-44 | an-312 |
| E1C0311 | sp-1 | an-311 | E1U7232 | sp-26 | an-313 | E1U14558 | sp-44 | an-313 |
| E1C0312 | sp-1 | an-312 | E1U7233 | sp-26 | an-314 | E1U14559 | sp-44 | an-314 |
| E1C0313 | sp-1 | an-313 | E1U7234 | sp-26 | an-315 | E1U14560 | sp-44 | an-315 |
| E1C0314 | sp-1 | an-314 | E1U7235 | sp-26 | an-316 | E1U14561 | sp-44 | an-316 |
| E1C0315 | sp-1 | an-315 | E1U7236 | sp-26 | an-317 | E1U14562 | sp-44 | an-317 |

Table 1-135

| Y = NHCSO | | | Y = NHCSNH | | | Y = NHCSNH | | |
|---|---|---|---|---|---|---|---|---|
| E1C0316 | sp-1 | an-316 | E1U7237 | sp-26 | an-318 | E1U14563 | sp-44 | an-318 |
| E1C0317 | sp-1 | an-317 | E1U7238 | sp-26 | an-319 | E1U14564 | sp-44 | an-319 |
| E1C0318 | sp-1 | an-318 | E1U7239 | sp-26 | an-320 | E1U14565 | sp-44 | an-320 |
| E1C0319 | sp-1 | an-319 | E1U7240 | sp-26 | an-321 | E1U14566 | sp-44 | an-321 |
| E1C0320 | sp-1 | an-320 | E1U7241 | sp-26 | an-322 | E1U14567 | sp-44 | an-322 |
| E1C0321 | sp-1 | an-321 | E1U7242 | sp-26 | an-323 | E1U14568 | sp-44 | an-323 |
| E1C0322 | sp-1 | an-322 | E1U7243 | sp-26 | an-324 | E1U14569 | sp-44 | an-324 |
| E1C0323 | sp-1 | an-323 | E1U7244 | sp-26 | an-325 | E1U14570 | sp-44 | an-325 |
| E1C0324 | sp-1 | an-324 | E1U7245 | sp-26 | an-326 | E1U14571 | sp-44 | an-326 |
| E1C0325 | sp-1 | an-325 | E1U7246 | sp-26 | an-327 | E1U14572 | sp-44 | an-327 |
| E1C0326 | sp-1 | an-326 | E1U7247 | sp-26 | an-328 | E1U14573 | sp-44 | an-328 |
| E1C0327 | sp-1 | an-327 | E1U7248 | sp-26 | an-329 | E1U14574 | sp-44 | an-329 |
| E1C0328 | sp-1 | an-328 | E1U7249 | sp-26 | an-330 | E1U14575 | sp-44 | an-330 |
| E1C0329 | sp-1 | an-329 | E1U7250 | sp-26 | an-331 | E1U14576 | sp-44 | an-331 |
| E1C0330 | sp-1 | an-330 | E1U7251 | sp-26 | an-332 | E1U14577 | sp-44 | an-332 |
| E1C0331 | sp-1 | an-331 | E1U7252 | sp-26 | an-333 | E1U14578 | sp-44 | an-333 |
| E1C0332 | sp-1 | an-332 | E1U7253 | sp-26 | an-334 | E1U14579 | sp-44 | an-334 |
| E1C0333 | sp-1 | an-333 | E1U7254 | sp-26 | an-335 | E1U14580 | sp-44 | an-335 |
| E1C0334 | sp-1 | an-334 | E1U7255 | sp-26 | an-336 | E1U14581 | sp-44 | an-336 |
| E1C0335 | sp-1 | an-335 | E1U7256 | sp-26 | an-337 | E1U14582 | sp-44 | an-337 |
| E1C0336 | sp-1 | an-336 | E1U7257 | sp-26 | an-338 | E1U14583 | sp-44 | an-338 |
| E1C0337 | sp-1 | an-337 | E1U7258 | sp-26 | an-339 | E1U14584 | sp-44 | an-339 |
| E1C0338 | sp-1 | an-338 | E1U7259 | sp-26 | an-340 | E1U14585 | sp-44 | an-340 |
| E1C0339 | sp-1 | an-339 | E1U7260 | sp-26 | an-341 | E1U14586 | sp-44 | an-341 |
| E1C0340 | sp-1 | an-340 | E1U7261 | sp-26 | an-342 | E1U14587 | sp-44 | an-342 |
| E1C0341 | sp-1 | an-341 | E1U7262 | sp-26 | an-343 | E1U14588 | sp-44 | an-343 |
| E1C0342 | sp-1 | an-342 | E1U7263 | sp-26 | an-344 | E1U14589 | sp-44 | an-344 |
| E1C0343 | sp-1 | an-343 | E1U7264 | sp-26 | an-345 | E1U14590 | sp-44 | an-345 |
| E1C0344 | sp-1 | an-344 | E1U7265 | sp-26 | an-346 | E1U14591 | sp-44 | an-346 |
| E1C0345 | sp-1 | an-345 | E1U7266 | sp-26 | an-347 | E1U14592 | sp-44 | an-347 |
| E1C0346 | sp-1 | an-346 | E1U7267 | sp-26 | an-348 | E1U14593 | sp-44 | an-348 |
| E1C0347 | sp-1 | an-347 | E1U7268 | sp-26 | an-349 | E1U14594 | sp-44 | an-349 |
| E1C0348 | sp-1 | an-348 | E1U7269 | sp-26 | an-350 | E1U14595 | sp-44 | an-350 |
| E1C0349 | sp-1 | an-349 | E1U7270 | sp-26 | an-351 | E1U14596 | sp-44 | an-351 |
| E1C0350 | sp-1 | an-350 | E1U7271 | sp-26 | an-352 | E1U14597 | sp-44 | an-352 |
| E1C0351 | sp-1 | an-351 | E1U7272 | sp-26 | an-353 | E1U14598 | sp-44 | an-353 |
| E1C0352 | sp-1 | an-352 | E1U7273 | sp-26 | an-354 | E1U14599 | sp-44 | an-354 |
| E1C0353 | sp-1 | an-353 | E1U7274 | sp-26 | an-355 | E1U14600 | sp-44 | an-355 |
| E1C0354 | sp-1 | an-354 | E1U7275 | sp-26 | an-356 | E1U14601 | sp-44 | an-356 |
| E1C0355 | sp-1 | an-355 | E1U7276 | sp-26 | an-357 | E1U14602 | sp-44 | an-357 |
| E1C0356 | sp-1 | an-356 | E1U7277 | sp-26 | an-358 | E1U14603 | sp-44 | an-358 |
| E1C0357 | sp-1 | an-357 | E1U7278 | sp-26 | an-359 | E1U14604 | sp-44 | an-359 |
| E1C0358 | sp-1 | an-358 | E1U7279 | sp-26 | an-360 | E1U14605 | sp-44 | an-360 |
| E1C0359 | sp-1 | an-359 | E1U7280 | sp-26 | an-361 | E1U14606 | sp-44 | an-361 |
| E1C0360 | sp-1 | an-360 | E1U7281 | sp-26 | an-362 | E1U14607 | sp-44 | an-362 |
| E1C0361 | sp-1 | an-361 | E1U7282 | sp-26 | an-363 | E1U14608 | sp-44 | an-363 |
| E1C0362 | sp-1 | an-362 | E1U7283 | sp-26 | an-364 | E1U14609 | sp-44 | an-364 |
| E1C0363 | sp-1 | an-363 | E1U7284 | sp-26 | an-365 | E1U14610 | sp-44 | an-365 |
| E1C0364 | sp-1 | an-364 | E1U7285 | sp-26 | an-366 | E1U14611 | sp-44 | an-366 |
| E1C0365 | sp-1 | an-365 | E1U7286 | sp-26 | an-367 | E1U14612 | sp-44 | an-367 |
| E1C0366 | sp-1 | an-366 | E1U7287 | sp-26 | an-368 | E1U14613 | sp-44 | an-368 |
| E1C0367 | sp-1 | an-367 | E1U7288 | sp-26 | an-369 | E1U14614 | sp-44 | an-369 |
| E1C0368 | sp-1 | an-368 | E1U7289 | sp-26 | an-370 | E1U14615 | sp-44 | an-370 |
| E1C0369 | sp-1 | an-369 | E1U7290 | sp-26 | an-371 | E1U14616 | sp-44 | an-371 |

Table 1-136

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| Y = NHCSO | | | Y = NHCSNH | | | Y = NHCSNH | | |
| E1C0370 | sp-1 | an-370 | E1U7291 | sp-26 | an-372 | E1U14617 | sp-44 | an-372 |
| E1C0371 | sp-1 | an-371 | E1U7292 | sp-26 | an-373 | E1U14618 | sp-44 | an-373 |
| E1C0372 | sp-1 | an-372 | E1U7293 | sp-26 | an-374 | E1U14619 | sp-44 | an-374 |
| E1C0373 | sp-1 | an-373 | E1U7294 | sp-26 | an-375 | E1U14620 | sp-44 | an-375 |
| E1C0374 | sp-1 | an-374 | E1U7295 | sp-26 | an-376 | E1U14621 | sp-44 | an-376 |
| E1C0375 | sp-1 | an-375 | E1U7296 | sp-26 | an-377 | E1U14622 | sp-44 | an-377 |
| E1C0376 | sp-1 | an-376 | E1U7297 | sp-26 | an-378 | E1U14623 | sp-44 | an-378 |
| E1C0377 | sp-1 | an-377 | E1U7298 | sp-26 | an-379 | E1U14624 | sp-44 | an-379 |
| E1C0378 | sp-1 | an-378 | E1U7299 | sp-26 | an-380 | E1U14625 | sp-44 | an-380 |
| E1C0379 | sp-1 | an-379 | E1U7300 | sp-26 | an-381 | E1U14626 | sp-44 | an-381 |
| E1C0380 | sp-1 | an-380 | E1U7301 | sp-26 | an-382 | E1U14627 | sp-44 | an-382 |
| E1C0381 | sp-1 | an-381 | E1U7302 | sp-26 | an-383 | E1U14628 | sp-44 | an-383 |
| E1C0382 | sp-1 | an-382 | E1U7303 | sp-26 | an-384 | E1U14629 | sp-44 | an-384 |
| E1C0383 | sp-1 | an-383 | E1U7304 | sp-26 | an-385 | E1U14630 | sp-44 | an-385 |
| E1C0384 | sp-1 | an-384 | E1U7305 | sp-26 | an-386 | E1U14631 | sp-44 | an-386 |
| E1C0385 | sp-1 | an-385 | E1U7306 | sp-26 | an-387 | E1U14632 | sp-44 | an-387 |
| E1C0386 | sp-1 | an-386 | E1U7307 | sp-26 | an-388 | E1U14633 | sp-44 | an-388 |
| E1C0387 | sp-1 | an-387 | E1U7308 | sp-26 | an-389 | E1U14634 | sp-44 | an-389 |
| E1C0388 | sp-1 | an-388 | E1U7309 | sp-26 | an-390 | E1U14635 | sp-44 | an-390 |
| E1C0389 | sp-1 | an-389 | E1U7310 | sp-26 | an-391 | E1U14636 | sp-44 | an-391 |
| E1C0390 | sp-1 | an-390 | E1U7311 | sp-26 | an-392 | E1U14637 | sp-44 | an-392 |
| E1C0391 | sp-1 | an-391 | E1U7312 | sp-26 | an-393 | E1U14638 | sp-44 | an-393 |
| E1C0392 | sp-1 | an-392 | E1U7313 | sp-26 | an-394 | E1U14639 | sp-44 | an-394 |
| E1C0393 | sp-1 | an-393 | E1U7314 | sp-26 | an-395 | E1U14640 | sp-44 | an-395 |
| E1C0394 | sp-1 | an-394 | E1U7315 | sp-26 | an-396 | E1U14641 | sp-44 | an-396 |
| E1C0395 | sp-1 | an-395 | E1U7316 | sp-26 | an-397 | E1U14642 | sp-44 | an-397 |
| E1C0396 | sp-1 | an-396 | E1U7317 | sp-26 | an-398 | E1U14643 | sp-44 | an-398 |
| E1C0397 | sp-1 | an-397 | E1U7318 | sp-26 | an-399 | E1U14644 | sp-44 | an-399 |
| E1C0398 | sp-1 | an-398 | E1U7319 | sp-26 | an-400 | E1U14645 | sp-44 | an-400 |
| E1C0399 | sp-1 | an-399 | E1U7320 | sp-26 | an-401 | E1U14646 | sp-44 | an-401 |
| E1C0400 | sp-1 | an-400 | E1U7321 | sp-26 | an-402 | E1U14647 | sp-44 | an-402 |
| E1C0401 | sp-1 | an-401 | E1U7322 | sp-26 | an-403 | E1U14648 | sp-44 | an-403 |
| E1C0402 | sp-1 | an-402 | E1U7323 | sp-26 | an-404 | E1U14649 | sp-44 | an-404 |
| E1C0403 | sp-1 | an-403 | E1U7324 | sp-26 | an-405 | E1U14650 | sp-44 | an-405 |
| E1C0404 | sp-1 | an-404 | E1U7325 | sp-26 | an-406 | E1U14651 | sp-44 | an-406 |
| E1C0405 | sp-1 | an-405 | E1U7326 | sp-26 | an-407 | E1U14652 | sp-44 | an-407 |
| E1C0406 | sp-1 | an-406 | | | | | | |
| E1C0407 | sp-1 | an-407 | Y = NHCSO | | | Y = NHCSO | | |
| E1C0408 | sp-2 | an-1 | E1C1629 | sp-5 | an-1 | E1C2850 | sp-8 | an-1 |
| E1C0409 | sp-2 | an-2 | E1C1630 | sp-5 | an-2 | E1C2851 | sp-8 | an-2 |
| E1C0410 | sp-2 | an-3 | E1C1631 | sp-5 | an-3 | E1C2852 | sp-8 | an-3 |
| E1C0411 | sp-2 | an-4 | E1C1632 | sp-5 | an-4 | E1C2853 | sp-8 | an-4 |
| E1C0412 | sp-2 | an-5 | E1C1633 | sp-5 | an-5 | E1C2854 | sp-8 | an-5 |
| E1C0413 | sp-2 | an-6 | E1C1634 | sp-5 | an-6 | E1C2855 | sp-8 | an-6 |
| E1C0414 | sp-2 | an-7 | E1C1635 | sp-5 | an-7 | E1C2856 | sp-8 | an-7 |
| E1C0415 | sp-2 | an-8 | E1C1636 | sp-5 | an-8 | E1C2857 | sp-8 | an-8 |
| E1C0416 | sp-2 | an-9 | E1C1637 | sp-5 | an-9 | E1C2858 | sp-8 | an-9 |
| E1C0417 | sp-2 | an-10 | E1C1638 | sp-5 | an-10 | E1C2859 | sp-8 | an-10 |
| E1C0418 | sp-2 | an-11 | E1C1639 | sp-5 | an-11 | E1C2860 | sp-8 | an-11 |
| E1C0419 | sp-2 | an-12 | E1C1640 | sp-5 | an-12 | E1C2861 | sp-8 | an-12 |
| E1C0420 | sp-2 | an-13 | E1C1641 | sp-5 | an-13 | E1C2862 | sp-8 | an-13 |
| E1C0421 | sp-2 | an-14 | E1C1642 | sp-5 | an-14 | E1C2863 | sp-8 | an-14 |
| E1C0422 | sp-2 | an-15 | E1C1643 | sp-5 | an-15 | E1C2864 | sp-8 | an-15 |
| E1C0423 | sp-2 | an-16 | E1C1644 | sp-5 | an-16 | E1C2865 | sp-8 | an-16 |

Table 1-137

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| Y = NHCSO | | | Y = NHCSO | | | Y = NHCSO | | |
| E1C0424 | sp-2 | an-17 | E1C1645 | sp-5 | an-17 | E1C2866 | sp-8 | an-17 |
| E1C0425 | sp-2 | an-18 | E1C1646 | sp-5 | an-18 | E1C2867 | sp-8 | an-18 |
| E1C0426 | sp-2 | an-19 | E1C1647 | sp-5 | an-19 | E1C2868 | sp-8 | an-19 |
| E1C0427 | sp-2 | an-20 | E1C1648 | sp-5 | an-20 | E1C2869 | sp-8 | an-20 |
| E1C0428 | sp-2 | an-21 | E1C1649 | sp-5 | an-21 | E1C2870 | sp-8 | an-21 |
| E1C0429 | sp-2 | an-22 | E1C1650 | sp-5 | an-22 | E1C2871 | sp-8 | an-22 |
| E1C0430 | sp-2 | an-23 | E1C1651 | sp-5 | an-23 | E1C2872 | sp-8 | an-23 |
| E1C0431 | sp-2 | an-24 | E1C1652 | sp-5 | an-24 | E1C2873 | sp-8 | an-24 |
| E1C0432 | sp-2 | an-25 | E1C1653 | sp-5 | an-25 | E1C2874 | sp-8 | an-25 |
| E1C0433 | sp-2 | an-26 | E1C1654 | sp-5 | an-26 | E1C2875 | sp-8 | an-26 |
| E1C0434 | sp-2 | an-27 | E1C1655 | sp-5 | an-27 | E1C2876 | sp-8 | an-27 |
| E1C0435 | sp-2 | an-28 | E1C1656 | sp-5 | an-28 | E1C2877 | sp-8 | an-28 |
| E1C0436 | sp-2 | an-29 | E1C1657 | sp-5 | an-29 | E1C2878 | sp-8 | an-29 |
| E1C0437 | sp-2 | an-30 | E1C1658 | sp-5 | an-30 | E1C2879 | sp-8 | an-30 |
| E1C0438 | sp-2 | an-31 | E1C1659 | sp-5 | an-31 | E1C2880 | sp-8 | an-31 |

-continued

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| E1C0439 | sp-2 | an-32 | E1C1660 | sp-5 | an-32 | E1C2881 | sp-8 | an-32 |
| E1C0440 | sp-2 | an-33 | E1C1661 | sp-5 | an-33 | E1C2882 | sp-8 | an-33 |
| E1C0441 | sp-2 | an-34 | E1C1662 | sp-5 | an-34 | E1C2883 | sp-8 | an-34 |
| E1C0442 | sp-2 | an-35 | E1C1663 | sp-5 | an-35 | E1C2884 | sp-8 | an-35 |
| E1C0443 | sp-2 | an-36 | E1C1664 | sp-5 | an-36 | E1C2885 | sp-8 | an-36 |
| E1C0444 | sp-2 | an-37 | E1C1665 | sp-5 | an-37 | E1C2886 | sp-8 | an-37 |
| E1C0445 | sp-2 | an-38 | E1C1666 | sp-5 | an-38 | E1C2887 | sp-8 | an-38 |
| E1C0446 | sp-2 | an-39 | E1C1667 | sp-5 | an-39 | E1C2888 | sp-8 | an-39 |
| E1C0447 | sp-2 | an-40 | E1C1668 | sp-5 | an-40 | E1C2889 | sp-8 | an-40 |
| E1C0448 | sp-2 | an-41 | E1C1669 | sp-5 | an-41 | E1C2890 | sp-8 | an-41 |
| E1C0449 | sp-2 | an-42 | E1C1670 | sp-5 | an-42 | E1C2891 | sp-8 | an-42 |
| E1C0450 | sp-2 | an-43 | E1C1671 | sp-5 | an-43 | E1C2892 | sp-8 | an-43 |
| E1C0451 | sp-2 | an-44 | E1C1672 | sp-5 | an-44 | E1C2893 | sp-8 | an-44 |
| E1C0452 | sp-2 | an-45 | E1C1673 | sp-5 | an-45 | E1C2894 | sp-8 | an-45 |
| E1C0453 | sp-2 | an-46 | E1C1674 | sp-5 | an-46 | E1C2895 | sp-8 | an-46 |
| E1C0454 | sp-2 | an-47 | E1C1675 | sp-5 | an-47 | E1C2896 | sp-8 | an-47 |
| E1C0455 | sp-2 | an-48 | E1C1676 | sp-5 | an-48 | E1C2897 | sp-8 | an-48 |
| E1C0456 | sp-2 | an-49 | E1C1677 | sp-5 | an-49 | E1C2898 | sp-8 | an-49 |
| E1C0457 | sp-2 | an-50 | E1C1678 | sp-5 | an-50 | E1C2899 | sp-8 | an-50 |
| E1C0458 | sp-2 | an-51 | E1C1679 | sp-5 | an-51 | E1C2900 | sp-8 | an-51 |
| E1C0459 | sp-2 | an-52 | E1C1680 | sp-5 | an-52 | E1C2901 | sp-8 | an-52 |
| E1C0460 | sp-2 | an-53 | E1C1681 | sp-5 | an-53 | E1C2902 | sp-8 | an-53 |
| E1C0461 | sp-2 | an-54 | E1C1682 | sp-5 | an-54 | E1C2903 | sp-8 | an-54 |
| E1C0462 | sp-2 | an-55 | E1C1683 | sp-5 | an-55 | E1C2904 | sp-8 | an-55 |
| E1C0463 | sp-2 | an-56 | E1C1684 | sp-5 | an-56 | E1C2905 | sp-8 | an-56 |
| E1C0464 | sp-2 | an-57 | E1C1685 | sp-5 | an-57 | E1C2906 | sp-8 | an-57 |
| E1C0465 | sp-2 | an-58 | E1C1686 | sp-5 | an-58 | E1C2907 | sp-8 | an-58 |
| E1C0466 | sp-2 | an-59 | E1C1687 | sp-5 | an-59 | E1C2908 | sp-8 | an-59 |
| E1C0467 | sp-2 | an-60 | E1C1688 | sp-5 | an-60 | E1C2909 | sp-8 | an-60 |
| E1C0468 | sp-2 | an-61 | E1C1689 | sp-5 | an-61 | E1C2910 | sp-8 | an-61 |
| E1C0469 | sp-2 | an-62 | E1C1690 | sp-5 | an-62 | E1C2911 | sp-8 | an-62 |
| E1C0470 | sp-2 | an-63 | E1C1691 | sp-5 | an-63 | E1C2912 | sp-8 | an-63 |
| E1C0471 | sp-2 | an-64 | E1C1692 | sp-5 | an-64 | E1C2913 | sp-8 | an-64 |
| E1C0472 | sp-2 | an-65 | E1C1693 | sp-5 | an-65 | E1C2914 | sp-8 | an-65 |
| E1C0473 | sp-2 | an-66 | E1C1694 | sp-5 | an-66 | E1C2915 | sp-8 | an-66 |
| E1C0474 | sp-2 | an-67 | E1C1695 | sp-5 | an-67 | E1C2916 | sp-8 | an-67 |
| E1C0475 | sp-2 | an-68 | E1C1696 | sp-5 | an-68 | E1C2917 | sp-8 | an-68 |
| E1C0476 | sp-2 | an-69 | E1C1697 | sp-5 | an-69 | E1C2918 | sp-8 | an-69 |
| E1C0477 | sp-2 | an-70 | E1C1698 | sp-5 | an-70 | E1C2919 | sp-8 | an-70 |

Table 1-138

| Y = NHCSO | | | Y = NHCSO | | | Y = NHCSO | | |
|---|---|---|---|---|---|---|---|---|
| E1C0478 | sp-2 | an-71 | E1C1699 | sp-5 | an-71 | E1C2920 | sp-8 | an-71 |
| E1C0479 | sp-2 | an-72 | E1C1700 | sp-5 | an-72 | E1C2921 | sp-8 | an-72 |
| E1C0480 | sp-2 | an-73 | E1C1701 | sp-5 | an-73 | E1C2922 | sp-8 | an-73 |
| E1C0481 | sp-2 | an-74 | E1C1702 | sp-5 | an-74 | E1C2923 | sp-8 | an-74 |
| E1C0482 | sp-2 | an-75 | E1C1703 | sp-5 | an-75 | E1C2924 | sp-8 | an-75 |
| E1C0483 | sp-2 | an-76 | E1C1704 | sp-5 | an-76 | E1C2925 | sp-8 | an-76 |
| E1C0484 | sp-2 | an-77 | E1C1705 | sp-5 | an-77 | E1C2926 | sp-8 | an-77 |
| E1C0485 | sp-2 | an-78 | E1C1706 | sp-5 | an-78 | E1C2927 | sp-8 | an-78 |
| E1C0486 | sp-2 | an-79 | E1C1707 | sp-5 | an-79 | E1C2928 | sp-8 | an-79 |
| E1C0487 | sp-2 | an-80 | E1C1708 | sp-5 | an-80 | E1C2929 | sp-8 | an-80 |
| E1C0488 | sp-2 | an-81 | E1C1709 | sp-5 | an-81 | E1C2930 | sp-8 | an-81 |
| E1C0489 | sp-2 | an-82 | E1C1710 | sp-5 | an-82 | E1C2931 | sp-8 | an-82 |
| E1C0490 | sp-2 | an-83 | E1C1711 | sp-5 | an-83 | E1C2932 | sp-8 | an-83 |
| E1C0491 | sp-2 | an-84 | E1C1712 | sp-5 | an-84 | E1C2933 | sp-8 | an-84 |
| E1C0492 | sp-2 | an-85 | E1C1713 | sp-5 | an-85 | E1C2934 | sp-8 | an-85 |
| E1C0493 | sp-2 | an-86 | E1C1714 | sp-5 | an-86 | E1C2935 | sp-8 | an-86 |
| E1C0494 | sp-2 | an-87 | E1C1715 | sp-5 | an-87 | E1C2936 | sp-8 | an-87 |
| E1C0495 | sp-2 | an-88 | E1C1716 | sp-5 | an-88 | E1C2937 | sp-8 | an-88 |
| E1C0496 | sp-2 | an-89 | E1C1717 | sp-5 | an-89 | E1C2938 | sp-8 | an-89 |
| E1C0497 | sp-2 | an-90 | E1C1718 | sp-5 | an-90 | E1C2939 | sp-8 | an-90 |
| E1C0498 | sp-2 | an-91 | E1C1719 | sp-5 | an-91 | E1C2940 | sp-8 | an-91 |
| E1C0499 | sp-2 | an-92 | E1C1720 | sp-5 | an-92 | E1C2941 | sp-8 | an-92 |
| E1C0500 | sp-2 | an-93 | E1C1721 | sp-5 | an-93 | E1C2942 | sp-8 | an-93 |
| E1C0501 | sp-2 | an-94 | E1C1722 | sp-5 | an-94 | E1C2943 | sp-8 | an-94 |
| E1C0502 | sp-2 | an-95 | E1C1723 | sp-5 | an-95 | E1C2944 | sp-8 | an-95 |
| E1C0503 | sp-2 | an-96 | E1C1724 | sp-5 | an-96 | E1C2945 | sp-8 | an-96 |
| E1C0504 | sp-2 | an-97 | E1C1725 | sp-5 | an-97 | E1C2946 | sp-8 | an-97 |
| E1C0505 | sp-2 | an-98 | E1C1726 | sp-5 | an-98 | E1C2947 | sp-8 | an-98 |
| E1C0506 | sp-2 | an-99 | E1C1727 | sp-5 | an-99 | E1C2948 | sp-8 | an-99 |
| E1C0507 | sp-2 | an-100 | E1C1728 | sp-5 | an-100 | E1C2949 | sp-8 | an-100 |
| E1C0508 | sp-2 | an-101 | E1C1729 | sp-5 | an-101 | E1C2950 | sp-8 | an-101 |
| E1C0509 | sp-2 | an-102 | E1C1730 | sp-5 | an-102 | E1C2951 | sp-8 | an-102 |
| E1C0510 | sp-2 | an-103 | E1C1731 | sp-5 | an-103 | E1C2952 | sp-8 | an-103 |
| E1C0511 | sp-2 | an-104 | E1C1732 | sp-5 | an-104 | E1C2953 | sp-8 | an-104 |
| E1C0512 | sp-2 | an-105 | E1C1733 | sp-5 | an-105 | E1C2954 | sp-8 | an-105 |

-continued

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| E1C0513 | sp-2 | an-106 | E1C1734 | sp-5 | an-106 | E1C2955 | sp-8 | an-106 |
| E1C0514 | sp-2 | an-107 | E1C1735 | sp-5 | an-107 | E1C2956 | sp-8 | an-107 |
| E1C0515 | sp-2 | an-108 | E1C1736 | sp-5 | an-108 | E1C2957 | sp-8 | an-108 |
| E1C0516 | sp-2 | an-109 | E1C1737 | sp-5 | an-109 | E1C2958 | sp-8 | an-109 |
| E1C0517 | sp-2 | an-110 | E1C1738 | sp-5 | an-110 | E1C2959 | sp-8 | an-110 |
| E1C0518 | sp-2 | an-111 | E1C1739 | sp-5 | an-111 | E1C2960 | sp-8 | an-111 |
| E1C0519 | sp-2 | an-112 | E1C1740 | sp-5 | an-112 | E1C2961 | sp-8 | an-112 |
| E1C0520 | sp-2 | an-113 | E1C1741 | sp-5 | an-113 | E1C2962 | sp-8 | an-113 |
| E1C0521 | sp-2 | an-114 | E1C1742 | sp-5 | an-114 | E1C2963 | sp-8 | an-114 |
| E1C0522 | sp-2 | an-115 | E1C1743 | sp-5 | an-115 | E1C2964 | sp-8 | an-115 |
| E1C0523 | sp-2 | an-116 | E1C1744 | sp-5 | an-116 | E1C2965 | sp-8 | an-116 |
| E1C0524 | sp-2 | an-117 | E1C1745 | sp-5 | an-117 | E1C2966 | sp-8 | an-117 |
| E1C0525 | sp-2 | an-118 | E1C1746 | sp-5 | an-118 | E1C2967 | sp-8 | an-118 |
| E1C0526 | sp-2 | an-119 | E1C1747 | sp-5 | an-119 | E1C2968 | sp-8 | an-119 |
| E1C0527 | sp-2 | an-120 | E1C1748 | sp-5 | an-120 | E1C2969 | sp-8 | an-120 |
| E1C0528 | sp-2 | an-121 | E1C1749 | sp-5 | an-121 | E1C2970 | sp-8 | an-121 |
| E1C0529 | sp-2 | an-122 | E1C1750 | sp-5 | an-122 | E1C2971 | sp-8 | an-122 |
| E1C0530 | sp-2 | an-123 | E1C1751 | sp-5 | an-123 | E1C2972 | sp-8 | an-123 |
| E1C0531 | sp-2 | an-124 | E1C1752 | sp-5 | an-124 | E1C2973 | sp-8 | an-124 |

Table 1-139

| Y = NHCSO | | | Y = NHCSO | | | Y = NHCSO | | |
|---|---|---|---|---|---|---|---|---|
| E1C0532 | sp-2 | an-125 | E1C1753 | sp-5 | an-125 | E1C2974 | sp-8 | an-125 |
| E1C0533 | sp-2 | an-126 | E1C1754 | sp-5 | an-126 | E1C2975 | sp-8 | an-126 |
| E1C0534 | sp-2 | an-127 | E1C1755 | sp-5 | an-127 | E1C2976 | sp-8 | an-127 |
| E1C0535 | sp-2 | an-128 | E1C1756 | sp-5 | an-128 | E1C2977 | sp-8 | an-128 |
| E1C0536 | sp-2 | an-129 | E1C1757 | sp-5 | an-129 | E1C2978 | sp-8 | an-129 |
| E1C0537 | sp-2 | an-130 | E1C1758 | sp-5 | an-130 | E1C2979 | sp-8 | an-130 |
| E1C0538 | sp-2 | an-131 | E1C1759 | sp-5 | an-131 | E1C2980 | sp-8 | an-131 |
| E1C0539 | sp-2 | an-132 | E1C1760 | sp-5 | an-132 | E1C2981 | sp-8 | an-132 |
| E1C0540 | sp-2 | an-133 | E1C1761 | sp-5 | an-133 | E1C2982 | sp-8 | an-133 |
| E1C0541 | sp-2 | an-134 | E1C1762 | sp-5 | an-134 | E1C2983 | sp-8 | an-134 |
| E1C0542 | sp-2 | an-135 | E1C1763 | sp-5 | an-135 | E1C2984 | sp-8 | an-135 |
| E1C0543 | sp-2 | an-136 | E1C1764 | sp-5 | an-136 | E1C2985 | sp-8 | an-136 |
| E1C0544 | sp-2 | an-137 | E1C1765 | sp-5 | an-137 | E1C2986 | sp-8 | an-137 |
| E1C0545 | sp-2 | an-138 | E1C1766 | sp-5 | an-138 | E1C2987 | sp-8 | an-138 |
| E1C0546 | sp-2 | an-139 | E1C1767 | sp-5 | an-139 | E1C2988 | sp-8 | an-139 |
| E1C0547 | sp-2 | an-140 | E1C1768 | sp-5 | an-140 | E1C2989 | sp-8 | an-140 |
| E1C0548 | sp-2 | an-141 | E1C1769 | sp-5 | an-141 | E1C2990 | sp-8 | an-141 |
| E1C0549 | sp-2 | an-142 | E1C1770 | sp-5 | an-142 | E1C2991 | sp-8 | an-142 |
| E1C0550 | sp-2 | an-143 | E1C1771 | sp-5 | an-143 | E1C2992 | sp-8 | an-143 |
| E1C0551 | sp-2 | an-144 | E1C1772 | sp-5 | an-144 | E1C2993 | sp-8 | an-144 |
| E1C0552 | sp-2 | an-145 | E1C1773 | sp-5 | an-145 | E1C2994 | sp-8 | an-145 |
| E1C0553 | sp-2 | an-146 | E1C1774 | sp-5 | an-146 | E1C2995 | sp-8 | an-146 |
| E1C0554 | sp-2 | an-147 | E1C1775 | sp-5 | an-147 | E1C2996 | sp-8 | an-147 |
| E1C0555 | sp-2 | an-148 | E1C1776 | sp-5 | an-148 | E1C2997 | sp-8 | an-148 |
| E1C0556 | sp-2 | an-149 | E1C1777 | sp-5 | an-149 | E1C2998 | sp-8 | an-149 |
| E1C0557 | sp-2 | an-150 | E1C1778 | sp-5 | an-150 | E1C2999 | sp-8 | an-150 |
| E1C0558 | sp-2 | an-151 | E1C1779 | sp-5 | an-151 | E1C3000 | sp-8 | an-151 |
| E1C0559 | sp-2 | an-152 | E1C1780 | sp-5 | an-152 | E1C3001 | sp-8 | an-152 |
| E1C0560 | sp-2 | an-153 | E1C1781 | sp-5 | an-153 | E1C3002 | sp-8 | an-153 |
| E1C0561 | sp-2 | an-154 | E1C1782 | sp-5 | an-154 | E1C3003 | sp-8 | an-154 |
| E1C0562 | sp-2 | an-155 | E1C1783 | sp-5 | an-155 | E1C3004 | sp-8 | an-155 |
| E1C0563 | sp-2 | an-156 | E1C1784 | sp-5 | an-156 | E1C3005 | sp-8 | an-156 |
| E1C0564 | sp-2 | an-157 | E1C1785 | sp-5 | an-157 | E1C3006 | sp-8 | an-157 |
| E1C0565 | sp-2 | an-158 | E1C1786 | sp-5 | an-158 | E1C3007 | sp-8 | an-158 |
| E1C0566 | sp-2 | an-159 | E1C1787 | sp-5 | an-159 | E1C3008 | sp-8 | an-159 |
| E1C0567 | sp-2 | an-160 | E1C1788 | sp-5 | an-160 | E1C3009 | sp-8 | an-160 |
| E1C0568 | sp-2 | an-161 | E1C1789 | sp-5 | an-161 | E1C3010 | sp-8 | an-161 |
| E1C0569 | sp-2 | an-162 | E1C1790 | sp-5 | an-162 | E1C3011 | sp-8 | an-162 |
| E1C0570 | sp-2 | an-163 | E1C1791 | sp-5 | an-163 | E1C3012 | sp-8 | an-163 |
| E1C0571 | sp-2 | an-164 | E1C1792 | sp-5 | an-164 | E1C3013 | sp-8 | an-164 |
| E1C0572 | sp-2 | an-165 | E1C1793 | sp-5 | an-165 | E1C3014 | sp-8 | an-165 |
| E1C0573 | sp-2 | an-166 | E1C1794 | sp-5 | an-166 | E1C3015 | sp-8 | an-166 |
| E1C0574 | sp-2 | an-167 | E1C1795 | sp-5 | an-167 | E1C3016 | sp-8 | an-167 |
| E1C0575 | sp-2 | an-168 | E1C1796 | sp-5 | an-168 | E1C3017 | sp-8 | an-168 |
| E1C0576 | sp-2 | an-169 | E1C1797 | sp-5 | an-169 | E1C3018 | sp-8 | an-169 |
| E1C0577 | sp-2 | an-170 | E1C1798 | sp-5 | an-170 | E1C3019 | sp-8 | an-170 |
| E1C0578 | sp-2 | an-171 | E1C1799 | sp-5 | an-171 | E1C3020 | sp-8 | an-171 |
| E1C0579 | sp-2 | an-172 | E1C1800 | sp-5 | an-172 | E1C3021 | sp-8 | an-172 |
| E1C0580 | sp-2 | an-173 | E1C1801 | sp-5 | an-173 | E1C3022 | sp-8 | an-173 |
| E1C0581 | sp-2 | an-174 | E1C1802 | sp-5 | an-174 | E1C3023 | sp-8 | an-174 |
| E1C0582 | sp-2 | an-175 | E1C1803 | sp-5 | an-175 | E1C3024 | sp-8 | an-175 |
| E1C0583 | sp-2 | an-176 | E1C1804 | sp-5 | an-176 | E1C3025 | sp-8 | an-176 |
| E1C0584 | sp-2 | an-177 | E1C1805 | sp-5 | an-177 | E1C3026 | sp-8 | an-177 |
| E1C0585 | sp-2 | an-178 | E1C1806 | sp-5 | an-178 | E1C3027 | sp-8 | an-178 |

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| Table 1-140 ||||||||| 
| Y = NHCSO ||| Y = NHCSO ||| Y = NHCSO |||
| E1C0586 | sp-2 | an-179 | E1C1807 | sp-5 | an-179 | E1C3028 | sp-8 | an-179 |
| E1C0587 | sp-2 | an-180 | E1C1808 | sp-5 | an-180 | E1C3029 | sp-8 | an-180 |
| E1C0588 | sp-2 | an-181 | E1C1809 | sp-5 | an-181 | E1C3030 | sp-8 | an-181 |
| E1C0589 | sp-2 | an-182 | E1C1810 | sp-5 | an-182 | E1C3031 | sp-8 | an-182 |
| E1C0590 | sp-2 | an-183 | E1C1811 | sp-5 | an-183 | E1C3032 | sp-8 | an-183 |
| E1C0591 | sp-2 | an-184 | E1C1812 | sp-5 | an-184 | E1C3033 | sp-8 | an-184 |
| E1C0592 | sp-2 | an-185 | E1C1813 | sp-5 | an-185 | E1C3034 | sp-8 | an-185 |
| E1C0593 | sp-2 | an-186 | E1C1814 | sp-5 | an-186 | E1C3035 | sp-8 | an-186 |
| E1C0594 | sp-2 | an-187 | E1C1815 | sp-5 | an-187 | E1C3036 | sp-8 | an-187 |
| E1C0595 | sp-2 | an-188 | E1C1816 | sp-5 | an-188 | E1C3037 | sp-8 | an-188 |
| E1C0596 | sp-2 | an-189 | E1C1817 | sp-5 | an-189 | E1C3038 | sp-8 | an-189 |
| E1C0597 | sp-2 | an-190 | E1C1818 | sp-5 | an-190 | E1C3039 | sp-8 | an-190 |
| E1C0598 | sp-2 | an-191 | E1C1819 | sp-5 | an-191 | E1C3040 | sp-8 | an-191 |
| E1C0599 | sp-2 | an-192 | E1C1820 | sp-5 | an-192 | E1C3041 | sp-8 | an-192 |
| E1C0600 | sp-2 | an-193 | E1C1821 | sp-5 | an-193 | E1C3042 | sp-8 | an-193 |
| E1C0601 | sp-2 | an-194 | E1C1822 | sp-5 | an-194 | E1C3043 | sp-8 | an-194 |
| E1C0602 | sp-2 | an-195 | E1C1823 | sp-5 | an-195 | E1C3044 | sp-8 | an-195 |
| E1C0603 | sp-2 | an-196 | E1C1824 | sp-5 | an-196 | E1C3045 | sp-8 | an-196 |
| E1C0604 | sp-2 | an-197 | E1C1825 | sp-5 | an-197 | E1C3046 | sp-8 | an-197 |
| E1C0605 | sp-2 | an-198 | E1C1826 | sp-5 | an-198 | E1C3047 | sp-8 | an-198 |
| E1C0606 | sp-2 | an-199 | E1C1827 | sp-5 | an-199 | E1C3048 | sp-8 | an-199 |
| E1C0607 | sp-2 | an-200 | E1C1828 | sp-5 | an-200 | E1C3049 | sp-8 | an-200 |
| E1C0608 | sp-2 | an-201 | E1C1829 | sp-5 | an-201 | E1C3050 | sp-8 | an-201 |
| E1C0609 | sp-2 | an-202 | E1C1830 | sp-5 | an-202 | E1C3051 | sp-8 | an-202 |
| E1C0610 | sp-2 | an-203 | E1C1831 | sp-5 | an-203 | E1C3052 | sp-8 | an-203 |
| E1C0611 | sp-2 | an-204 | E1C1832 | sp-5 | an-204 | E1C3053 | sp-8 | an-204 |
| E1C0612 | sp-2 | an-205 | E1C1833 | sp-5 | an-205 | E1C3054 | sp-8 | an-205 |
| E1C0613 | sp-2 | an-206 | E1C1834 | sp-5 | an-206 | E1C3055 | sp-8 | an-206 |
| E1C0614 | sp-2 | an-207 | E1C1835 | sp-5 | an-207 | E1C3056 | sp-8 | an-207 |
| E1C0615 | sp-2 | an-208 | E1C1836 | sp-5 | an-208 | E1C3057 | sp-8 | an-208 |
| E1C0616 | sp-2 | an-209 | E1C1837 | sp-5 | an-209 | E1C3058 | sp-8 | an-209 |
| E1C0617 | sp-2 | an-210 | E1C1838 | sp-5 | an-210 | E1C3059 | sp-8 | an-210 |
| E1C0618 | sp-2 | an-211 | E1C1839 | sp-5 | an-211 | E1C3060 | sp-8 | an-211 |
| E1C0619 | sp-2 | an-212 | E1C1840 | sp-5 | an-212 | E1C3061 | sp-8 | an-212 |
| E1C0620 | sp-2 | an-213 | E1C1841 | sp-5 | an-213 | E1C3062 | sp-8 | an-213 |
| E1C0621 | sp-2 | an-214 | E1C1842 | sp-5 | an-214 | E1C3063 | sp-8 | an-214 |
| E1C0622 | sp-2 | an-215 | E1C1843 | sp-5 | an-215 | E1C3064 | sp-8 | an-215 |
| E1C0623 | sp-2 | an-216 | E1C1844 | sp-5 | an-216 | E1C3065 | sp-8 | an-216 |
| E1C0624 | sp-2 | an-217 | E1C1845 | sp-5 | an-217 | E1C3066 | sp-8 | an-217 |
| E1C0625 | sp-2 | an-218 | E1C1846 | sp-5 | an-218 | E1C3067 | sp-8 | an-218 |
| E1C0626 | sp-2 | an-219 | E1C1847 | sp-5 | an-219 | E1C3068 | sp-8 | an-219 |
| E1C0627 | sp-2 | an-220 | E1C1848 | sp-5 | an-220 | E1C3069 | sp-8 | an-220 |
| E1C0628 | sp-2 | an-221 | E1C1849 | sp-5 | an-221 | E1C3070 | sp-8 | an-221 |
| E1C0629 | sp-2 | an-222 | E1C1850 | sp-5 | an-222 | E1C3071 | sp-8 | an-222 |
| E1C0630 | sp-2 | an-223 | E1C1851 | sp-5 | an-223 | E1C3072 | sp-8 | an-223 |
| E1C0631 | sp-2 | an-224 | E1C1852 | sp-5 | an-224 | E1C3073 | sp-8 | an-224 |
| E1C0632 | sp-2 | an-225 | E1C1853 | sp-5 | an-225 | E1C3074 | sp-8 | an-225 |
| E1C0633 | sp-2 | an-226 | E1C1854 | sp-5 | an-226 | E1C3075 | sp-8 | an-226 |
| E1C0634 | sp-2 | an-227 | E1C1855 | sp-5 | an-227 | E1C3076 | sp-8 | an-227 |
| E1C0635 | sp-2 | an-228 | E1C1856 | sp-5 | an-228 | E1C3077 | sp-8 | an-228 |
| E1C0636 | sp-2 | an-229 | E1C1857 | sp-5 | an-229 | E1C3078 | sp-8 | an-229 |
| E1C0637 | sp-2 | an-230 | E1C1858 | sp-5 | an-230 | E1C3079 | sp-8 | an-230 |
| E1C0638 | sp-2 | an-231 | E1C1859 | sp-5 | an-231 | E1C3080 | sp-8 | an-231 |
| E1C0639 | sp-2 | an-232 | E1C1860 | sp-5 | an-232 | E1C3081 | sp-8 | an-232 |
| Table 1-141 ||||||||| 
| Y = NHCSO ||| Y = NHCSO ||| Y = NHCSO |||
| E1C0640 | sp-2 | an-233 | E1C1861 | sp-5 | an-233 | E1C3082 | sp-8 | an-233 |
| E1C0641 | sp-2 | an-234 | E1C1862 | sp-5 | an-234 | E1C3083 | sp-8 | an-234 |
| E1C0642 | sp-2 | an-235 | E1C1863 | sp-5 | an-235 | E1C3084 | sp-8 | an-235 |
| E1C0643 | sp-2 | an-236 | E1C1864 | sp-5 | an-236 | E1C3085 | sp-8 | an-236 |
| E1C0644 | sp-2 | an-237 | E1C1865 | sp-5 | an-237 | E1C3086 | sp-8 | an-237 |
| E1C0645 | sp-2 | an-238 | E1C1866 | sp-5 | an-238 | E1C3087 | sp-8 | an-238 |
| E1C0646 | sp-2 | an-239 | E1C1867 | sp-5 | an-239 | E1C3088 | sp-8 | an-239 |
| E1C0647 | sp-2 | an-240 | E1C1868 | sp-5 | an-240 | E1C3089 | sp-8 | an-240 |
| E1C0648 | sp-2 | an-241 | E1C1869 | sp-5 | an-241 | E1C3090 | sp-8 | an-241 |
| E1C0649 | sp-2 | an-242 | E1C1870 | sp-5 | an-242 | E1C3091 | sp-8 | an-242 |
| E1C0650 | sp-2 | an-243 | E1C1871 | sp-5 | an-243 | E1C3092 | sp-8 | an-243 |
| E1C0651 | sp-2 | an-244 | E1C1872 | sp-5 | an-244 | E1C3093 | sp-8 | an-244 |
| E1C0652 | sp-2 | an-245 | E1C1873 | sp-5 | an-245 | E1C3094 | sp-8 | an-245 |
| E1C0653 | sp-2 | an-246 | E1C1874 | sp-5 | an-246 | E1C3095 | sp-8 | an-246 |
| E1C0654 | sp-2 | an-247 | E1C1875 | sp-5 | an-247 | E1C3096 | sp-8 | an-247 |
| E1C0655 | sp-2 | an-248 | E1C1876 | sp-5 | an-248 | E1C3097 | sp-8 | an-248 |

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| E1C0656 | sp-2 | an-249 | E1C1877 | sp-5 | an-249 | E1C3098 | sp-8 | an-249 |
| E1C0657 | sp-2 | an-250 | E1C1878 | sp-5 | an-250 | E1C3099 | sp-8 | an-250 |
| E1C0658 | sp-2 | an-251 | E1C1879 | sp-5 | an-251 | E1C3100 | sp-8 | an-251 |
| E1C0659 | sp-2 | an-252 | E1C1880 | sp-5 | an-252 | E1C3101 | sp-8 | an-252 |
| E1C0660 | sp-2 | an-253 | E1C1881 | sp-5 | an-253 | E1C3102 | sp-8 | an-253 |
| E1C0661 | sp-2 | an-254 | E1C1882 | sp-5 | an-254 | E1C3103 | sp-8 | an-254 |
| E1C0662 | sp-2 | an-255 | E1C1883 | sp-5 | an-255 | E1C3104 | sp-8 | an-255 |
| E1C0663 | sp-2 | an-256 | E1C1884 | sp-5 | an-256 | E1C3105 | sp-8 | an-256 |
| E1C0664 | sp-2 | an-257 | E1C1885 | sp-5 | an-257 | E1C3106 | sp-8 | an-257 |
| E1C0665 | sp-2 | an-258 | E1C1886 | sp-5 | an-258 | E1C3107 | sp-8 | an-258 |
| E1C0666 | sp-2 | an-259 | E1C1887 | sp-5 | an-259 | E1C3108 | sp-8 | an-259 |
| E1C0667 | sp-2 | an-260 | E1C1888 | sp-5 | an-260 | E1C3109 | sp-8 | an-260 |
| E1C0668 | sp-2 | an-261 | E1C1889 | sp-5 | an-261 | E1C3110 | sp-8 | an-261 |
| E1C0669 | sp-2 | an-262 | E1C1890 | sp-5 | an-262 | E1C3111 | sp-8 | an-262 |
| E1C0670 | sp-2 | an-263 | E1C1891 | sp-5 | an-263 | E1C3112 | sp-8 | an-263 |
| E1C0671 | sp-2 | an-264 | E1C1892 | sp-5 | an-264 | E1C3113 | sp-8 | an-264 |
| E1C0672 | sp-2 | an-265 | E1C1893 | sp-5 | an-265 | E1C3114 | sp-8 | an-265 |
| E1C0673 | sp-2 | an-266 | E1C1894 | sp-5 | an-266 | E1C3115 | sp-8 | an-266 |
| E1C0674 | sp-2 | an-267 | E1C1895 | sp-5 | an-267 | E1C3116 | sp-8 | an-267 |
| E1C0675 | sp-2 | an-268 | E1C1896 | sp-5 | an-268 | E1C3117 | sp-8 | an-268 |
| E1C0676 | sp-2 | an-269 | E1C1897 | sp-5 | an-269 | E1C3118 | sp-8 | an-269 |
| E1C0677 | sp-2 | an-270 | E1C1898 | sp-5 | an-270 | E1C3119 | sp-8 | an-270 |
| E1C0678 | sp-2 | an-271 | E1C1899 | sp-5 | an-271 | E1C3120 | sp-8 | an-271 |
| E1C0679 | sp-2 | an-272 | E1C1900 | sp-5 | an-272 | E1C3121 | sp-8 | an-272 |
| E1C0680 | sp-2 | an-273 | E1C1901 | sp-5 | an-273 | E1C3122 | sp-8 | an-273 |
| E1C0681 | sp-2 | an-274 | E1C1902 | sp-5 | an-274 | E1C3123 | sp-8 | an-274 |
| E1C0682 | sp-2 | an-275 | E1C1903 | sp-5 | an-275 | E1C3124 | sp-8 | an-275 |
| E1C0683 | sp-2 | an-276 | E1C1904 | sp-5 | an-276 | E1C3125 | sp-8 | an-276 |
| E1C0684 | sp-2 | an-277 | E1C1905 | sp-5 | an-277 | E1C3126 | sp-8 | an-277 |
| E1C0685 | sp-2 | an-278 | E1C1906 | sp-5 | an-278 | E1C3127 | sp-8 | an-278 |
| E1C0686 | sp-2 | an-279 | E1C1907 | sp-5 | an-279 | E1C3128 | sp-8 | an-279 |
| E1C0687 | sp-2 | an-280 | E1C1908 | sp-5 | an-280 | E1C3129 | sp-8 | an-280 |
| E1C0688 | sp-2 | an-281 | E1C1909 | sp-5 | an-281 | E1C3130 | sp-8 | an-281 |
| E1C0689 | sp-2 | an-282 | E1C1910 | sp-5 | an-282 | E1C3131 | sp-8 | an-282 |
| E1C0690 | sp-2 | an-283 | E1C1911 | sp-5 | an-283 | E1C3132 | sp-8 | an-283 |
| E1C0691 | sp-2 | an-284 | E1C1912 | sp-5 | an-284 | E1C3133 | sp-8 | an-284 |
| E1C0692 | sp-2 | an-285 | E1C1913 | sp-5 | an-285 | E1C3134 | sp-8 | an-285 |
| E1C0693 | sp-2 | an-286 | E1C1914 | sp-5 | an-286 | E1C3135 | sp-8 | an-286 |

Table 1-142

| Y = NHCSO | | | Y = NHCSO | | | Y = NHCSO | | |
|---|---|---|---|---|---|---|---|---|
| E1C0694 | sp-2 | an-287 | E1C1915 | sp-5 | an-287 | E1C3136 | sp-8 | an-287 |
| E1C0695 | sp-2 | an-288 | E1C1916 | sp-5 | an-288 | E1C3137 | sp-8 | an-288 |
| E1C0696 | sp-2 | an-289 | E1C1917 | sp-5 | an-289 | E1C3138 | sp-8 | an-289 |
| E1C0697 | sp-2 | an-290 | E1C1918 | sp-5 | an-290 | E1C3139 | sp-8 | an-290 |
| E1C0698 | sp-2 | an-291 | E1C1919 | sp-5 | an-291 | E1C3140 | sp-8 | an-291 |
| E1C0699 | sp-2 | an-292 | E1C1920 | sp-5 | an-292 | E1C3141 | sp-8 | an-292 |
| E1C0700 | sp-2 | an-293 | E1C1921 | sp-5 | an-293 | E1C3142 | sp-8 | an-293 |
| E1C0701 | sp-2 | an-294 | E1C1922 | sp-5 | an-294 | E1C3143 | sp-8 | an-294 |
| E1C0702 | sp-2 | an-295 | E1C1923 | sp-5 | an-295 | E1C3144 | sp-8 | an-295 |
| E1C0703 | sp-2 | an-296 | E1C1924 | sp-5 | an-296 | E1C3145 | sp-8 | an-296 |
| E1C0704 | sp-2 | an-297 | E1C1925 | sp-5 | an-297 | E1C3146 | sp-8 | an-297 |
| E1C0705 | sp-2 | an-298 | E1C1926 | sp-5 | an-298 | E1C3147 | sp-8 | an-298 |
| E1C0706 | sp-2 | an-299 | E1C1927 | sp-5 | an-299 | E1C3148 | sp-8 | an-299 |
| E1C0707 | sp-2 | an-300 | E1C1928 | sp-5 | an-300 | E1C3149 | sp-8 | an-300 |
| E1C0708 | sp-2 | an-301 | E1C1929 | sp-5 | an-301 | E1C3150 | sp-8 | an-301 |
| E1C0709 | sp-2 | an-302 | E1C1930 | sp-5 | an-302 | E1C3151 | sp-8 | an-302 |
| E1C0710 | sp-2 | an-303 | E1C1931 | sp-5 | an-303 | E1C3152 | sp-8 | an-303 |
| E1C0711 | sp-2 | an-304 | E1C1932 | sp-5 | an-304 | E1C3153 | sp-8 | an-304 |
| E1C0712 | sp-2 | an-305 | E1C1933 | sp-5 | an-305 | E1C3154 | sp-8 | an-305 |
| E1C0713 | sp-2 | an-306 | E1C1934 | sp-5 | an-306 | E1C3155 | sp-8 | an-306 |
| E1C0714 | sp-2 | an-307 | E1C1935 | sp-5 | an-307 | E1C3156 | sp-8 | an-307 |
| E1C0715 | sp-2 | an-308 | E1C1936 | sp-5 | an-308 | E1C3157 | sp-8 | an-308 |
| E1C0716 | sp-2 | an-309 | E1C1937 | sp-5 | an-309 | E1C3158 | sp-8 | an-309 |
| E1C0717 | sp-2 | an-310 | E1C1938 | sp-5 | an-310 | E1C3159 | sp-8 | an-310 |
| E1C0718 | sp-2 | an-311 | E1C1939 | sp-5 | an-311 | E1C3160 | sp-8 | an-311 |
| E1C0719 | sp-2 | an-312 | E1C1940 | sp-5 | an-312 | E1C3161 | sp-8 | an-312 |
| E1C0720 | sp-2 | an-313 | E1C1941 | sp-5 | an-313 | E1C3162 | sp-8 | an-313 |
| E1C0721 | sp-2 | an-314 | E1C1942 | sp-5 | an-314 | E1C3163 | sp-8 | an-314 |
| E1C0722 | sp-2 | an-315 | E1C1943 | sp-5 | an-315 | E1C3164 | sp-8 | an-315 |
| E1C0723 | sp-2 | an-316 | E1C1944 | sp-5 | an-316 | E1C3165 | sp-8 | an-316 |
| E1C0724 | sp-2 | an-317 | E1C1945 | sp-5 | an-317 | E1C3166 | sp-8 | an-317 |
| E1C0725 | sp-2 | an-318 | E1C1946 | sp-5 | an-318 | E1C3167 | sp-8 | an-318 |
| E1C0726 | sp-2 | an-319 | E1C1947 | sp-5 | an-319 | E1C3168 | sp-8 | an-319 |
| E1C0727 | sp-2 | an-320 | E1C1948 | sp-5 | an-320 | E1C3169 | sp-8 | an-320 |
| E1C0728 | sp-2 | an-321 | E1C1949 | sp-5 | an-321 | E1C3170 | sp-8 | an-321 |
| E1C0729 | sp-2 | an-322 | E1C1950 | sp-5 | an-322 | E1C3171 | sp-8 | an-322 |

-continued

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| E1C0730 | sp-2 | an-323 | E1C1951 | sp-5 | an-323 | E1C3172 | sp-8 | an-323 |
| E1C0731 | sp-2 | an-324 | E1C1952 | sp-5 | an-324 | E1C3173 | sp-8 | an-324 |
| E1C0732 | sp-2 | an-325 | E1C1953 | sp-5 | an-325 | E1C3174 | sp-8 | an-325 |
| E1C0733 | sp-2 | an-326 | E1C1954 | sp-5 | an-326 | E1C3175 | sp-8 | an-326 |
| E1C0734 | sp-2 | an-327 | E1C1955 | sp-5 | an-327 | E1C3176 | sp-8 | an-327 |
| E1C0735 | sp-2 | an-328 | E1C1956 | sp-5 | an-328 | E1C3177 | sp-8 | an-328 |
| E1C0736 | sp-2 | an-329 | E1C1957 | sp-5 | an-329 | E1C3178 | sp-8 | an-329 |
| E1C0737 | sp-2 | an-330 | E1C1958 | sp-5 | an-330 | E1C3179 | sp-8 | an-330 |
| E1C0738 | sp-2 | an-331 | E1C1959 | sp-5 | an-331 | E1C3180 | sp-8 | an-331 |
| E1C0739 | sp-2 | an-332 | E1C1960 | sp-5 | an-332 | E1C3181 | sp-8 | an-332 |
| E1C0740 | sp-2 | an-333 | E1C1961 | sp-5 | an-333 | E1C3182 | sp-8 | an-333 |
| E1C0741 | sp-2 | an-334 | E1C1962 | sp-5 | an-334 | E1C3183 | sp-8 | an-334 |
| E1C0742 | sp-2 | an-335 | E1C1963 | sp-5 | an-335 | E1C3184 | sp-8 | an-335 |
| E1C0743 | sp-2 | an-336 | E1C1964 | sp-5 | an-336 | E1C3185 | sp-8 | an-336 |
| E1C0744 | sp-2 | an-337 | E1C1965 | sp-5 | an-337 | E1C3186 | sp-8 | an-337 |
| E1C0745 | sp-2 | an-338 | E1C1966 | sp-5 | an-338 | E1C3187 | sp-8 | an-338 |
| E1C0746 | sp-2 | an-339 | E1C1967 | sp-5 | an-339 | E1C3188 | sp-8 | an-339 |
| E1C0747 | sp-2 | an-340 | E1C1968 | sp-5 | an-340 | E1C3189 | sp-8 | an-340 |

Table 1-143

| Y = NHCSO | | | Y = NHCSO | | | Y = NHCSO | | |
|---|---|---|---|---|---|---|---|---|
| E1C0748 | sp-2 | an-341 | E1C1969 | sp-5 | an-341 | E1C3190 | sp-8 | an-341 |
| E1C0749 | sp-2 | an-342 | E1C1970 | sp-5 | an-342 | E1C3191 | sp-8 | an-342 |
| E1C0750 | sp-2 | an-343 | E1C1971 | sp-5 | an-343 | E1C3192 | sp-8 | an-343 |
| E1C0751 | sp-2 | an-344 | E1C1972 | sp-5 | an-344 | E1C3193 | sp-8 | an-344 |
| E1C0752 | sp-2 | an-345 | E1C1973 | sp-5 | an-345 | E1C3194 | sp-8 | an-345 |
| E1C0753 | sp-2 | an-346 | E1C1974 | sp-5 | an-346 | E1C3195 | sp-8 | an-346 |
| E1C0754 | sp-2 | an-347 | E1C1975 | sp-5 | an-347 | E1C3196 | sp-8 | an-347 |
| E1C0755 | sp-2 | an-348 | E1C1976 | sp-5 | an-348 | E1C3197 | sp-8 | an-348 |
| E1C0756 | sp-2 | an-349 | E1C1977 | sp-5 | an-349 | E1C3198 | sp-8 | an-349 |
| E1C0757 | sp-2 | an-350 | E1C1978 | sp-5 | an-350 | E1C3199 | sp-8 | an-350 |
| E1C0758 | sp-2 | an-351 | E1C1979 | sp-5 | an-351 | E1C3200 | sp-8 | an-351 |
| E1C0759 | sp-2 | an-352 | E1C1980 | sp-5 | an-352 | E1C3201 | sp-8 | an-352 |
| E1C0760 | sp-2 | an-353 | E1C1981 | sp-5 | an-353 | E1C3202 | sp-8 | an-353 |
| E1C0761 | sp-2 | an-354 | E1C1982 | sp-5 | an-354 | E1C3203 | sp-8 | an-354 |
| E1C0762 | sp-2 | an-355 | E1C1983 | sp-5 | an-355 | E1C3204 | sp-8 | an-355 |
| E1C0763 | sp-2 | an-356 | E1C1984 | sp-5 | an-356 | E1C3205 | sp-8 | an-356 |
| E1C0764 | sp-2 | an-357 | E1C1985 | sp-5 | an-357 | E1C3206 | sp-8 | an-357 |
| E1C0765 | sp-2 | an-358 | E1C1986 | sp-5 | an-358 | E1C3207 | sp-8 | an-358 |
| E1C0766 | sp-2 | an-359 | E1C1987 | sp-5 | an-359 | E1C3208 | sp-8 | an-359 |
| E1C0767 | sp-2 | an-360 | E1C1988 | sp-5 | an-360 | E1C3209 | sp-8 | an-360 |
| E1C0768 | sp-2 | an-361 | E1C1989 | sp-5 | an-361 | E1C3210 | sp-8 | an-361 |
| E1C0769 | sp-2 | an-362 | E1C1990 | sp-5 | an-362 | E1C3211 | sp-8 | an-362 |
| E1C0770 | sp-2 | an-363 | E1C1991 | sp-5 | an-363 | E1C3212 | sp-8 | an-363 |
| E1C0771 | sp-2 | an-364 | E1C1992 | sp-5 | an-364 | E1C3213 | sp-8 | an-364 |
| E1C0772 | sp-2 | an-365 | E1C1993 | sp-5 | an-365 | E1C3214 | sp-8 | an-365 |
| E1C0773 | sp-2 | an-366 | E1C1994 | sp-5 | an-366 | E1C3215 | sp-8 | an-366 |
| E1C0774 | sp-2 | an-367 | E1C1995 | sp-5 | an-367 | E1C3216 | sp-8 | an-367 |
| E1C0775 | sp-2 | an-368 | E1C1996 | sp-5 | an-368 | E1C3217 | sp-8 | an-368 |
| E1C0776 | sp-2 | an-369 | E1C1997 | sp-5 | an-369 | E1C3218 | sp-8 | an-369 |
| E1C0777 | sp-2 | an-370 | E1C1998 | sp-5 | an-370 | E1C3219 | sp-8 | an-370 |
| E1C0778 | sp-2 | an-371 | E1C1999 | sp-5 | an-371 | E1C3220 | sp-8 | an-371 |
| E1C0779 | sp-2 | an-372 | E1C2000 | sp-5 | an-372 | E1C3221 | sp-8 | an-372 |
| E1C0780 | sp-2 | an-373 | E1C2001 | sp-5 | an-373 | E1C3222 | sp-8 | an-373 |
| E1C0781 | sp-2 | an-374 | E1C2002 | sp-5 | an-374 | E1C3223 | sp-8 | an-374 |
| E1C0782 | sp-2 | an-375 | E1C2003 | sp-5 | an-375 | E1C3224 | sp-8 | an-375 |
| E1C0783 | sp-2 | an-376 | E1C2004 | sp-5 | an-376 | E1C3225 | sp-8 | an-376 |
| E1C0784 | sp-2 | an-377 | E1C2005 | sp-5 | an-377 | E1C3226 | sp-8 | an-377 |
| E1C0785 | sp-2 | an-378 | E1C2006 | sp-5 | an-378 | E1C3227 | sp-8 | an-378 |
| E1C0786 | sp-2 | an-379 | E1C2007 | sp-5 | an-379 | E1C3228 | sp-8 | an-379 |
| E1C0787 | sp-2 | an-380 | E1C2008 | sp-5 | an-380 | E1C3229 | sp-8 | an-380 |
| E1C0788 | sp-2 | an-381 | E1C2009 | sp-5 | an-381 | E1C3230 | sp-8 | an-381 |
| E1C0789 | sp-2 | an-382 | E1C2010 | sp-5 | an-382 | E1C3231 | sp-8 | an-382 |
| E1C0790 | sp-2 | an-383 | E1C2011 | sp-5 | an-383 | E1C3232 | sp-8 | an-383 |
| E1C0791 | sp-2 | an-384 | E1C2012 | sp-5 | an-384 | E1C3233 | sp-8 | an-384 |
| E1C0792 | sp-2 | an-385 | E1C2013 | sp-5 | an-385 | E1C3234 | sp-8 | an-385 |
| E1C0793 | sp-2 | an-386 | E1C2014 | sp-5 | an-386 | E1C3235 | sp-8 | an-386 |
| E1C0794 | sp-2 | an-387 | E1C2015 | sp-5 | an-387 | E1C3236 | sp-8 | an-387 |
| E1C0795 | sp-2 | an-388 | E1C2016 | sp-5 | an-388 | E1C3237 | sp-8 | an-388 |
| E1C0796 | sp-2 | an-389 | E1C2017 | sp-5 | an-389 | E1C3238 | sp-8 | an-389 |
| E1C0797 | sp-2 | an-390 | E1C2018 | sp-5 | an-390 | E1C3239 | sp-8 | an-390 |
| E1C0798 | sp-2 | an-391 | E1C2019 | sp-5 | an-391 | E1C3240 | sp-8 | an-391 |
| E1C0799 | sp-2 | an-392 | E1C2020 | sp-5 | an-392 | E1C3241 | sp-8 | an-392 |
| E1C0800 | sp-2 | an-393 | E1C2021 | sp-5 | an-393 | E1C3242 | sp-8 | an-393 |
| E1C0801 | sp-2 | an-394 | E1C2022 | sp-5 | an-394 | E1C3243 | sp-8 | an-394 |

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| \multicolumn{9}{c}{Table 1-144} |||||||||
| \multicolumn{3}{c}{Y = NHCSO} | \multicolumn{3}{c}{Y = NHCSO} | \multicolumn{3}{c}{Y = NHCSO} |||
| E1C0802 | sp-2 | an-395 | E1C2023 | sp-5 | an-395 | E1C3244 | sp-8 | an-395 |
| E1C0803 | sp-2 | an-396 | E1C2024 | sp-5 | an-396 | E1C3245 | sp-8 | an-396 |
| E1C0804 | sp-2 | an-397 | E1C2025 | sp-5 | an-397 | E1C3246 | sp-8 | an-397 |
| E1C0805 | sp-2 | an-398 | E1C2026 | sp-5 | an-398 | E1C3247 | sp-8 | an-398 |
| E1C0806 | sp-2 | an-399 | E1C2027 | sp-5 | an-399 | E1C3248 | sp-8 | an-399 |
| E1C0807 | sp-2 | an-400 | E1C2028 | sp-5 | an-400 | E1C3249 | sp-8 | an-400 |
| E1C0808 | sp-2 | an-401 | E1C2029 | sp-5 | an-401 | E1C3250 | sp-8 | an-401 |
| E1C0809 | sp-2 | an-402 | E1C2030 | sp-5 | an-402 | E1C3251 | sp-8 | an-402 |
| E1C0810 | sp-2 | an-403 | E1C2031 | sp-5 | an-403 | E1C3252 | sp-8 | an-403 |
| E1C0811 | sp-2 | an-404 | E1C2032 | sp-5 | an-404 | E1C3253 | sp-8 | an-404 |
| E1C0812 | sp-2 | an-405 | E1C2033 | sp-5 | an-405 | E1C3254 | sp-8 | an-405 |
| E1C0813 | sp-2 | an-406 | E1C2034 | sp-5 | an-406 | E1C3255 | sp-8 | an-406 |
| E1C0814 | sp-2 | an-407 | E1C2035 | sp-5 | an-407 | E1C3256 | sp-8 | an-407 |
| E1C0815 | sp-3 | an-1 | E1C2036 | sp-6 | an-1 | E1C3257 | sp-9 | an-1 |
| E1C0816 | sp-3 | an-2 | E1C2037 | sp-6 | an-2 | E1C3258 | sp-9 | an-2 |
| E1C0817 | sp-3 | an-3 | E1C2038 | sp-6 | an-3 | E1C3259 | sp-9 | an-3 |
| E1C0818 | sp-3 | an-4 | E1C2039 | sp-6 | an-4 | E1C3260 | sp-9 | an-4 |
| E1C0819 | sp-3 | an-5 | E1C2040 | sp-6 | an-5 | E1C3261 | sp-9 | an-5 |
| E1C0820 | sp-3 | an-6 | E1C2041 | sp-6 | an-6 | E1C3262 | sp-9 | an-6 |
| E1C0821 | sp-3 | an-7 | E1C2042 | sp-6 | an-7 | E1C3263 | sp-9 | an-7 |
| E1C0822 | sp-3 | an-8 | E1C2043 | sp-6 | an-8 | E1C3264 | sp-9 | an-8 |
| E1C0823 | sp-3 | an-9 | E1C2044 | sp-6 | an-9 | E1C3265 | sp-9 | an-9 |
| E1C0824 | sp-3 | an-10 | E1C2045 | sp-6 | an-10 | E1C3266 | sp-9 | an-10 |
| E1C0825 | sp-3 | an-11 | E1C2046 | sp-6 | an-11 | E1C3267 | sp-9 | an-11 |
| E1C0826 | sp-3 | an-12 | E1C2047 | sp-6 | an-12 | E1C3268 | sp-9 | an-12 |
| E1C0827 | sp-3 | an-13 | E1C2048 | sp-6 | an-13 | E1C3269 | sp-9 | an-13 |
| E1C0828 | sp-3 | an-14 | E1C2049 | sp-6 | an-14 | E1C3270 | sp-9 | an-14 |
| E1C0829 | sp-3 | an-15 | E1C2050 | sp-6 | an-15 | E1C3271 | sp-9 | an-15 |
| E1C0830 | sp-3 | an-16 | E1C2051 | sp-6 | an-16 | E1C3272 | sp-9 | an-16 |
| E1C0831 | sp-3 | an-17 | E1C2052 | sp-6 | an-17 | E1C3273 | sp-9 | an-17 |
| E1C0832 | sp-3 | an-18 | E1C2053 | sp-6 | an-18 | E1C3274 | sp-9 | an-18 |
| E1C0833 | sp-3 | an-19 | E1C2054 | sp-6 | an-19 | E1C3275 | sp-9 | an-19 |
| E1C0834 | sp-3 | an-20 | E1C2055 | sp-6 | an-20 | E1C3276 | sp-9 | an-20 |
| E1C0835 | sp-3 | an-21 | E1C2056 | sp-6 | an-21 | E1C3277 | sp-9 | an-21 |
| E1C0836 | sp-3 | an-22 | E1C2057 | sp-6 | an-22 | E1C3278 | sp-9 | an-22 |
| E1C0837 | sp-3 | an-23 | E1C2058 | sp-6 | an-23 | E1C3279 | sp-9 | an-23 |
| E1C0838 | sp-3 | an-24 | E1C2059 | sp-6 | an-24 | E1C3280 | sp-9 | an-24 |
| E1C0839 | sp-3 | an-25 | E1C2060 | sp-6 | an-25 | E1C3281 | sp-9 | an-25 |
| E1C0840 | sp-3 | an-26 | E1C2061 | sp-6 | an-26 | E1C3282 | sp-9 | an-26 |
| E1C0841 | sp-3 | an-27 | E1C2062 | sp-6 | an-27 | E1C3283 | sp-9 | an-27 |
| E1C0842 | sp-3 | an-28 | E1C2063 | sp-6 | an-28 | E1C3284 | sp-9 | an-28 |
| E1C0843 | sp-3 | an-29 | E1C2064 | sp-6 | an-29 | E1C3285 | sp-9 | an-29 |
| E1C0844 | sp-3 | an-30 | E1C2065 | sp-6 | an-30 | E1C3286 | sp-9 | an-30 |
| E1C0845 | sp-3 | an-31 | E1C2066 | sp-6 | an-31 | E1C3287 | sp-9 | an-31 |
| E1C0846 | sp-3 | an-32 | E1C2067 | sp-6 | an-32 | E1C3288 | sp-9 | an-32 |
| E1C0847 | sp-3 | an-33 | E1C2068 | sp-6 | an-33 | E1C3289 | sp-9 | an-33 |
| E1C0848 | sp-3 | an-34 | E1C2069 | sp-6 | an-34 | E1C3290 | sp-9 | an-34 |
| E1C0849 | sp-3 | an-35 | E1C2070 | sp-6 | an-35 | E1C3291 | sp-9 | an-35 |
| E1C0850 | sp-3 | an-36 | E1C2071 | sp-6 | an-36 | E1C3292 | sp-9 | an-36 |
| E1C0851 | sp-3 | an-37 | E1C2072 | sp-6 | an-37 | E1C3293 | sp-9 | an-37 |
| E1C0852 | sp-3 | an-38 | E1C2073 | sp-6 | an-38 | E1C3294 | sp-9 | an-38 |
| E1C0853 | sp-3 | an-39 | E1C2074 | sp-6 | an-39 | E1C3295 | sp-9 | an-39 |
| E1C0854 | sp-3 | an-40 | E1C2075 | sp-6 | an-40 | E1C3296 | sp-9 | an-40 |
| E1C0855 | sp-3 | an-41 | E1C2076 | sp-6 | an-41 | E1C3297 | sp-9 | an-41 |
| \multicolumn{9}{c}{Table 1-145} |||||||||
| \multicolumn{3}{c}{Y = NHCSO} | \multicolumn{3}{c}{Y = NHCSO} | \multicolumn{3}{c}{Y = NHCSO} |||
| E1C0856 | sp-3 | an-42 | E1C2077 | sp-6 | an-42 | E1C3298 | sp-9 | an-42 |
| E1C0857 | sp-3 | an-43 | E1C2078 | sp-6 | an-43 | E1C3299 | sp-9 | an-43 |
| E1C0858 | sp-3 | an-44 | E1C2079 | sp-6 | an-44 | E1C3300 | sp-9 | an-44 |
| E1C0859 | sp-3 | an-45 | E1C2080 | sp-6 | an-45 | E1C3301 | sp-9 | an-45 |
| E1C0860 | sp-3 | an-46 | E1C2081 | sp-6 | an-46 | E1C3302 | sp-9 | an-46 |
| E1C0861 | sp-3 | an-47 | E1C2082 | sp-6 | an-47 | E1C3303 | sp-9 | an-47 |
| E1C0862 | sp-3 | an-48 | E1C2083 | sp-6 | an-48 | E1C3304 | sp-9 | an-48 |
| E1C0863 | sp-3 | an-49 | E1C2084 | sp-6 | an-49 | E1C3305 | sp-9 | an-49 |
| E1C0864 | sp-3 | an-50 | E1C2085 | sp-6 | an-50 | E1C3306 | sp-9 | an-50 |
| E1C0865 | sp-3 | an-51 | E1C2086 | sp-6 | an-51 | E1C3307 | sp-9 | an-51 |
| E1C0866 | sp-3 | an-52 | E1C2087 | sp-6 | an-52 | E1C3308 | sp-9 | an-52 |
| E1C0867 | sp-3 | an-53 | E1C2088 | sp-6 | an-53 | E1C3309 | sp-9 | an-53 |
| E1C0868 | sp-3 | an-54 | E1C2089 | sp-6 | an-54 | E1C3310 | sp-9 | an-54 |
| E1C0869 | sp-3 | an-55 | E1C2090 | sp-6 | an-55 | E1C3311 | sp-9 | an-55 |
| E1C0870 | sp-3 | an-56 | E1C2091 | sp-6 | an-56 | E1C3312 | sp-9 | an-56 |
| E1C0871 | sp-3 | an-57 | E1C2092 | sp-6 | an-57 | E1C3313 | sp-9 | an-57 |

-continued

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| E1C0872 | sp-3 | an-58 | E1C2093 | sp-6 | an-58 | E1C3314 | sp-9 | an-58 |
| E1C0873 | sp-3 | an-59 | E1C2094 | sp-6 | an-59 | E1C3315 | sp-9 | an-59 |
| E1C0874 | sp-3 | an-60 | E1C2095 | sp-6 | an-60 | E1C3316 | sp-9 | an-60 |
| E1C0875 | sp-3 | an-61 | E1C2096 | sp-6 | an-61 | E1C3317 | sp-9 | an-61 |
| E1C0876 | sp-3 | an-62 | E1C2097 | sp-6 | an-62 | E1C3318 | sp-9 | an-62 |
| E1C0877 | sp-3 | an-63 | E1C2098 | sp-6 | an-63 | E1C3319 | sp-9 | an-63 |
| E1C0878 | sp-3 | an-64 | E1C2099 | sp-6 | an-64 | E1C3320 | sp-9 | an-64 |
| E1C0879 | sp-3 | an-65 | E1C2100 | sp-6 | an-65 | E1C3321 | sp-9 | an-65 |
| E1C0880 | sp-3 | an-66 | E1C2101 | sp-6 | an-66 | E1C3322 | sp-9 | an-66 |
| E1C0881 | sp-3 | an-67 | E1C2102 | sp-6 | an-67 | E1C3323 | sp-9 | an-67 |
| E1C0882 | sp-3 | an-68 | E1C2103 | sp-6 | an-68 | E1C3324 | sp-9 | an-68 |
| E1C0883 | sp-3 | an-69 | E1C2104 | sp-6 | an-69 | E1C3325 | sp-9 | an-69 |
| E1C0884 | sp-3 | an-70 | E1C2105 | sp-6 | an-70 | E1C3326 | sp-9 | an-70 |
| E1C0885 | sp-3 | an-71 | E1C2106 | sp-6 | an-71 | E1C3327 | sp-9 | an-71 |
| E1C0886 | sp-3 | an-72 | E1C2107 | sp-6 | an-72 | E1C3328 | sp-9 | an-72 |
| E1C0887 | sp-3 | an-73 | E1C2108 | sp-6 | an-73 | E1C3329 | sp-9 | an-73 |
| E1C0888 | sp-3 | an-74 | E1C2109 | sp-6 | an-74 | E1C3330 | sp-9 | an-74 |
| E1C0889 | sp-3 | an-75 | E1C2110 | sp-6 | an-75 | E1C3331 | sp-9 | an-75 |
| E1C0890 | sp-3 | an-76 | E1C2111 | sp-6 | an-76 | E1C3332 | sp-9 | an-76 |
| E1C0891 | sp-3 | an-77 | E1C2112 | sp-6 | an-77 | E1C3333 | sp-9 | an-77 |
| E1C0892 | sp-3 | an-78 | E1C2113 | sp-6 | an-78 | E1C3334 | sp-9 | an-78 |
| E1C0893 | sp-3 | an-79 | E1C2114 | sp-6 | an-79 | E1C3335 | sp-9 | an-79 |
| E1C0894 | sp-3 | an-80 | E1C2115 | sp-6 | an-80 | E1C3336 | sp-9 | an-80 |
| E1C0895 | sp-3 | an-81 | E1C2116 | sp-6 | an-81 | E1C3337 | sp-9 | an-81 |
| E1C0896 | sp-3 | an-82 | E1C2117 | sp-6 | an-82 | E1C3338 | sp-9 | an-82 |
| E1C0897 | sp-3 | an-83 | E1C2118 | sp-6 | an-83 | E1C3339 | sp-9 | an-83 |
| E1C0898 | sp-3 | an-84 | E1C2119 | sp-6 | an-84 | E1C3340 | sp-9 | an-84 |
| E1C0899 | sp-3 | an-85 | E1C2120 | sp-6 | an-85 | E1C3341 | sp-9 | an-85 |
| E1C0900 | sp-3 | an-86 | E1C2121 | sp-6 | an-86 | E1C3342 | sp-9 | an-86 |
| E1C0901 | sp-3 | an-87 | E1C2122 | sp-6 | an-87 | E1C3343 | sp-9 | an-87 |
| E1C0902 | sp-3 | an-88 | E1C2123 | sp-6 | an-88 | E1C3344 | sp-9 | an-88 |
| E1C0903 | sp-3 | an-89 | E1C2124 | sp-6 | an-89 | E1C3345 | sp-9 | an-89 |
| E1C0904 | sp-3 | an-90 | E1C2125 | sp-6 | an-90 | E1C3346 | sp-9 | an-90 |
| E1C0905 | sp-3 | an-91 | E1C2126 | sp-6 | an-91 | E1C3347 | sp-9 | an-91 |
| E1C0906 | sp-3 | an-92 | E1C2127 | sp-6 | an-92 | E1C3348 | sp-9 | an-92 |
| E1C0907 | sp-3 | an-93 | E1C2128 | sp-6 | an-93 | E1C3349 | sp-9 | an-93 |
| E1C0908 | sp-3 | an-94 | E1C2129 | sp-6 | an-94 | E1C3350 | sp-9 | an-94 |
| E1C0909 | sp-3 | an-95 | E1C2130 | sp-6 | an-95 | E1C3351 | sp-9 | an-95 |

Table 1-146

| Y = NHCSO | | | Y = NHCSO | | | Y = NHCSO | | |
|---|---|---|---|---|---|---|---|---|
| E1C0910 | sp-3 | an-96 | E1C2131 | sp-6 | an-96 | E1C3352 | sp-9 | an-96 |
| E1C0911 | sp-3 | an-97 | E1C2132 | sp-6 | an-97 | E1C3353 | sp-9 | an-97 |
| E1C0912 | sp-3 | an-98 | E1C2133 | sp-6 | an-98 | E1C3354 | sp-9 | an-98 |
| E1C0913 | sp-3 | an-99 | E1C2134 | sp-6 | an-99 | E1C3355 | sp-9 | an-99 |
| E1C0914 | sp-3 | an-100 | E1C2135 | sp-6 | an-100 | E1C3356 | sp-9 | an-100 |
| E1C0915 | sp-3 | an-101 | E1C2136 | sp-6 | an-101 | E1C3357 | sp-9 | an-101 |
| E1C0916 | sp-3 | an-102 | E1C2137 | sp-6 | an-102 | E1C3358 | sp-9 | an-102 |
| E1C0917 | sp-3 | an-103 | E1C2138 | sp-6 | an-103 | E1C3359 | sp-9 | an-103 |
| E1C0918 | sp-3 | an-104 | E1C2139 | sp-6 | an-104 | E1C3360 | sp-9 | an-104 |
| E1C0919 | sp-3 | an-105 | E1C2140 | sp-6 | an-105 | E1C3361 | sp-9 | an-105 |
| E1C0920 | sp-3 | an-106 | E1C2141 | sp-6 | an-106 | E1C3362 | sp-9 | an-106 |
| E1C0921 | sp-3 | an-107 | E1C2142 | sp-6 | an-107 | E1C3363 | sp-9 | an-107 |
| E1C0922 | sp-3 | an-108 | E1C2143 | sp-6 | an-108 | E1C3364 | sp-9 | an-108 |
| E1C0923 | sp-3 | an-109 | E1C2144 | sp-6 | an-109 | E1C3365 | sp-9 | an-109 |
| E1C0924 | sp-3 | an-110 | E1C2145 | sp-6 | an-110 | E1C3366 | sp-9 | an-110 |
| E1C0925 | sp-3 | an-111 | E1C2146 | sp-6 | an-111 | E1C3367 | sp-9 | an-111 |
| E1C0926 | sp-3 | an-112 | E1C2147 | sp-6 | an-112 | E1C3368 | sp-9 | an-112 |
| E1C0927 | sp-3 | an-113 | E1C2148 | sp-6 | an-113 | E1C3369 | sp-9 | an-113 |
| E1C0928 | sp-3 | an-114 | E1C2149 | sp-6 | an-114 | E1C3370 | sp-9 | an-114 |
| E1C0929 | sp-3 | an-115 | E1C2150 | sp-6 | an-115 | E1C3371 | sp-9 | an-115 |
| E1C0930 | sp-3 | an-116 | E1C2151 | sp-6 | an-116 | E1C3372 | sp-9 | an-116 |
| E1C0931 | sp-3 | an-117 | E1C2152 | sp-6 | an-117 | E1C3373 | sp-9 | an-117 |
| E1C0932 | sp-3 | an-118 | E1C2153 | sp-6 | an-118 | E1C3374 | sp-9 | an-118 |
| E1C0933 | sp-3 | an-119 | E1C2154 | sp-6 | an-119 | E1C3375 | sp-9 | an-119 |
| E1C0934 | sp-3 | an-120 | E1C2155 | sp-6 | an-120 | E1C3376 | sp-9 | an-120 |
| E1C0935 | sp-3 | an-121 | E1C2156 | sp-6 | an-121 | E1C3377 | sp-9 | an-121 |
| E1C0936 | sp-3 | an-122 | E1C2157 | sp-6 | an-122 | E1C3378 | sp-9 | an-122 |
| E1C0937 | sp-3 | an-123 | E1C2158 | sp-6 | an-123 | E1C3379 | sp-9 | an-123 |
| E1C0938 | sp-3 | an-124 | E1C2159 | sp-6 | an-124 | E1C3380 | sp-9 | an-124 |
| E1C0939 | sp-3 | an-125 | E1C2160 | sp-6 | an-125 | E1C3381 | sp-9 | an-125 |
| E1C0940 | sp-3 | an-126 | E1C2161 | sp-6 | an-126 | E1C3382 | sp-9 | an-126 |
| E1C0941 | sp-3 | an-127 | E1C2162 | sp-6 | an-127 | E1C3383 | sp-9 | an-127 |
| E1C0942 | sp-3 | an-128 | E1C2163 | sp-6 | an-128 | E1C3384 | sp-9 | an-128 |
| E1C0943 | sp-3 | an-129 | E1C2164 | sp-6 | an-129 | E1C3385 | sp-9 | an-129 |
| E1C0944 | sp-3 | an-130 | E1C2165 | sp-6 | an-130 | E1C3386 | sp-9 | an-130 |
| E1C0945 | sp-3 | an-131 | E1C2166 | sp-6 | an-131 | E1C3387 | sp-9 | an-131 |

-continued

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| E1C0946 | sp-3 | an-132 | E1C2167 | sp-6 | an-132 | E1C3388 | sp-9 | an-132 |
| E1C0947 | sp-3 | an-133 | E1C2168 | sp-6 | an-133 | E1C3389 | sp-9 | an-133 |
| E1C0948 | sp-3 | an-134 | E1C2169 | sp-6 | an-134 | E1C3390 | sp-9 | an-134 |
| E1C0949 | sp-3 | an-135 | E1C2170 | sp-6 | an-135 | E1C3391 | sp-9 | an-135 |
| E1C0950 | sp-3 | an-136 | E1C2171 | sp-6 | an-136 | E1C3392 | sp-9 | an-136 |
| E1C0951 | sp-3 | an-137 | E1C2172 | sp-6 | an-137 | E1C3393 | sp-9 | an-137 |
| E1C0952 | sp-3 | an-138 | E1C2173 | sp-6 | an-138 | E1C3394 | sp-9 | an-138 |
| E1C0953 | sp-3 | an-139 | E1C2174 | sp-6 | an-139 | E1C3395 | sp-9 | an-139 |
| E1C0954 | sp-3 | an-140 | E1C2175 | sp-6 | an-140 | E1C3396 | sp-9 | an-140 |
| E1C0955 | sp-3 | an-141 | E1C2176 | sp-6 | an-141 | E1C3397 | sp-9 | an-141 |
| E1C0956 | sp-3 | an-142 | E1C2177 | sp-6 | an-142 | E1C3398 | sp-9 | an-142 |
| E1C0957 | sp-3 | an-143 | E1C2178 | sp-6 | an-143 | E1C3399 | sp-9 | an-143 |
| E1C0958 | sp-3 | an-144 | E1C2179 | sp-6 | an-144 | E1C3400 | sp-9 | an-144 |
| E1C0959 | sp-3 | an-145 | E1C2180 | sp-6 | an-145 | E1C3401 | sp-9 | an-145 |
| E1C0960 | sp-3 | an-146 | E1C2181 | sp-6 | an-146 | E1C3402 | sp-9 | an-146 |
| E1C0961 | sp-3 | an-147 | E1C2182 | sp-6 | an-147 | E1C3403 | sp-9 | an-147 |
| E1C0962 | sp-3 | an-148 | E1C2183 | sp-6 | an-148 | E1C3404 | sp-9 | an-148 |
| E1C0963 | sp-3 | an-149 | E1C2184 | sp-6 | an-149 | E1C3405 | sp-9 | an-149 |

Table 1-147

| Y = NHCSO | | | Y = NHCSO | | | Y = NHCSO | | |
|---|---|---|---|---|---|---|---|---|
| E1C0964 | sp-3 | an-150 | E1C2185 | sp-6 | an-150 | E1C3406 | sp-9 | an-150 |
| E1C0965 | sp-3 | an-151 | E1C2186 | sp-6 | an-151 | E1C3407 | sp-9 | an-151 |
| E1C0966 | sp-3 | an-152 | E1C2187 | sp-6 | an-152 | E1C3408 | sp-9 | an-152 |
| E1C0967 | sp-3 | an-153 | E1C2188 | sp-6 | an-153 | E1C3409 | sp-9 | an-153 |
| E1C0968 | sp-3 | an-154 | E1C2189 | sp-6 | an-154 | E1C3410 | sp-9 | an-154 |
| E1C0969 | sp-3 | an-155 | E1C2190 | sp-6 | an-155 | E1C3411 | sp-9 | an-155 |
| E1C0970 | sp-3 | an-156 | E1C2191 | sp-6 | an-156 | E1C3412 | sp-9 | an-156 |
| E1C0971 | sp-3 | an-157 | E1C2192 | sp-6 | an-157 | E1C3413 | sp-9 | an-157 |
| E1C0972 | sp-3 | an-158 | E1C2193 | sp-6 | an-158 | E1C3414 | sp-9 | an-158 |
| E1C0973 | sp-3 | an-159 | E1C2194 | sp-6 | an-159 | E1C3415 | sp-9 | an-159 |
| E1C0974 | sp-3 | an-160 | E1C2195 | sp-6 | an-160 | E1C3416 | sp-9 | an-160 |
| E1C0975 | sp-3 | an-161 | E1C2196 | sp-6 | an-161 | E1C3417 | sp-9 | an-161 |
| E1C0976 | sp-3 | an-162 | E1C2197 | sp-6 | an-162 | E1C3418 | sp-9 | an-162 |
| E1C0977 | sp-3 | an-163 | E1C2198 | sp-6 | an-163 | E1C3419 | sp-9 | an-163 |
| E1C0978 | sp-3 | an-164 | E1C2199 | sp-6 | an-164 | E1C3420 | sp-9 | an-164 |
| E1C0979 | sp-3 | an-165 | E1C2200 | sp-6 | an-165 | E1C3421 | sp-9 | an-165 |
| E1C0980 | sp-3 | an-166 | E1C2201 | sp-6 | an-166 | E1C3422 | sp-9 | an-166 |
| E1C0981 | sp-3 | an-167 | E1C2202 | sp-6 | an-167 | E1C3423 | sp-9 | an-167 |
| E1C0982 | sp-3 | an-168 | E1C2203 | sp-6 | an-168 | E1C3424 | sp-9 | an-168 |
| E1C0983 | sp-3 | an-169 | E1C2204 | sp-6 | an-169 | E1C3425 | sp-9 | an-169 |
| E1C0984 | sp-3 | an-170 | E1C2205 | sp-6 | an-170 | E1C3426 | sp-9 | an-170 |
| E1C0985 | sp-3 | an-171 | E1C2206 | sp-6 | an-171 | E1C3427 | sp-9 | an-171 |
| E1C0986 | sp-3 | an-172 | E1C2207 | sp-6 | an-172 | E1C3428 | sp-9 | an-172 |
| E1C0987 | sp-3 | an-173 | E1C2208 | sp-6 | an-173 | E1C3429 | sp-9 | an-173 |
| E1C0988 | sp-3 | an-174 | E1C2209 | sp-6 | an-174 | E1C3430 | sp-9 | an-174 |
| E1C0989 | sp-3 | an-175 | E1C2210 | sp-6 | an-175 | E1C3431 | sp-9 | an-175 |
| E1C0990 | sp-3 | an-176 | E1C2211 | sp-6 | an-176 | E1C3432 | sp-9 | an-176 |
| E1C0991 | sp-3 | an-177 | E1C2212 | sp-6 | an-177 | E1C3433 | sp-9 | an-177 |
| E1C0992 | sp-3 | an-178 | E1C2213 | sp-6 | an-178 | E1C3434 | sp-9 | an-178 |
| E1C0993 | sp-3 | an-179 | E1C2214 | sp-6 | an-179 | E1C3435 | sp-9 | an-179 |
| E1C0994 | sp-3 | an-180 | E1C2215 | sp-6 | an-180 | E1C3436 | sp-9 | an-180 |
| E1C0995 | sp-3 | an-181 | E1C2216 | sp-6 | an-181 | E1C3437 | sp-9 | an-181 |
| E1C0996 | sp-3 | an-182 | E1C2217 | sp-6 | an-182 | E1C3438 | sp-9 | an-182 |
| E1C0997 | sp-3 | an-183 | E1C2218 | sp-6 | an-183 | E1C3439 | sp-9 | an-183 |
| E1C0998 | sp-3 | an-184 | E1C2219 | sp-6 | an-184 | E1C3440 | sp-9 | an-184 |
| E1C0999 | sp-3 | an-185 | E1C2220 | sp-6 | an-185 | E1C3441 | sp-9 | an-185 |
| E1C1000 | sp-3 | an-186 | E1C2221 | sp-6 | an-186 | E1C3442 | sp-9 | an-186 |
| E1C1001 | sp-3 | an-187 | E1C2222 | sp-6 | an-187 | E1C3443 | sp-9 | an-187 |
| E1C1002 | sp-3 | an-188 | E1C2223 | sp-6 | an-188 | E1C3444 | sp-9 | an-188 |
| E1C1003 | sp-3 | an-189 | E1C2224 | sp-6 | an-189 | E1C3445 | sp-9 | an-189 |
| E1C1004 | sp-3 | an-190 | E1C2225 | sp-6 | an-190 | E1C3446 | sp-9 | an-190 |
| E1C1005 | sp-3 | an-191 | E1C2226 | sp-6 | an-191 | E1C3447 | sp-9 | an-191 |
| E1C1006 | sp-3 | an-192 | E1C2227 | sp-6 | an-192 | E1C3448 | sp-9 | an-192 |
| E1C1007 | sp-3 | an-193 | E1C2228 | sp-6 | an-193 | E1C3449 | sp-9 | an-193 |
| E1C1008 | sp-3 | an-194 | E1C2229 | sp-6 | an-194 | E1C3450 | sp-9 | an-194 |
| E1C1009 | sp-3 | an-195 | E1C2230 | sp-6 | an-195 | E1C3451 | sp-9 | an-195 |
| E1C1010 | sp-3 | an-196 | E1C2231 | sp-6 | an-196 | E1C3452 | sp-9 | an-196 |
| E1C1011 | sp-3 | an-197 | E1C2232 | sp-6 | an-197 | E1C3453 | sp-9 | an-197 |
| E1C1012 | sp-3 | an-198 | E1C2233 | sp-6 | an-198 | E1C3454 | sp-9 | an-198 |
| E1C1013 | sp-3 | an-199 | E1C2234 | sp-6 | an-199 | E1C3455 | sp-9 | an-199 |
| E1C1014 | sp-3 | an-200 | E1C2235 | sp-6 | an-200 | E1C3456 | sp-9 | an-200 |
| E1C1015 | sp-3 | an-201 | E1C2236 | sp-6 | an-201 | E1C3457 | sp-9 | an-201 |
| E1C1016 | sp-3 | an-202 | E1C2237 | sp-6 | an-202 | E1C3458 | sp-9 | an-202 |
| E1C1017 | sp-3 | an-203 | E1C2238 | sp-6 | an-203 | E1C3459 | sp-9 | an-203 |

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| Table 1-148 ||||||||| 
| Y = NHCSO ||| Y = NHCSO ||| Y = NHCSO |||
| E1C1018 | sp-3 | an-204 | E1C2239 | sp-6 | an-204 | E1C3460 | sp-9 | an-204 |
| E1C1019 | sp-3 | an-205 | E1C2240 | sp-6 | an-205 | E1C3461 | sp-9 | an-205 |
| E1C1020 | sp-3 | an-206 | E1C2241 | sp-6 | an-206 | E1C3462 | sp-9 | an-206 |
| E1C1021 | sp-3 | an-207 | E1C2242 | sp-6 | an-207 | E1C3463 | sp-9 | an-207 |
| E1C1022 | sp-3 | an-208 | E1C2243 | sp-6 | an-208 | E1C3464 | sp-9 | an-208 |
| E1C1023 | sp-3 | an-209 | E1C2244 | sp-6 | an-209 | E1C3465 | sp-9 | an-209 |
| E1C1024 | sp-3 | an-210 | E1C2245 | sp-6 | an-210 | E1C3466 | sp-9 | an-210 |
| E1C1025 | sp-3 | an-211 | E1C2246 | sp-6 | an-211 | E1C3467 | sp-9 | an-211 |
| E1C1026 | sp-3 | an-212 | E1C2247 | sp-6 | an-212 | E1C3468 | sp-9 | an-212 |
| E1C1027 | sp-3 | an-213 | E1C2248 | sp-6 | an-213 | E1C3469 | sp-9 | an-213 |
| E1C1028 | sp-3 | an-214 | E1C2249 | sp-6 | an-214 | E1C3470 | sp-9 | an-214 |
| E1C1029 | sp-3 | an-215 | E1C2250 | sp-6 | an-215 | E1C3471 | sp-9 | an-215 |
| E1C1030 | sp-3 | an-216 | E1C2251 | sp-6 | an-216 | E1C3472 | sp-9 | an-216 |
| E1C1031 | sp-3 | an-217 | E1C2252 | sp-6 | an-217 | E1C3473 | sp-9 | an-217 |
| E1C1032 | sp-3 | an-218 | E1C2253 | sp-6 | an-218 | E1C3474 | sp-9 | an-218 |
| E1C1033 | sp-3 | an-219 | E1C2254 | sp-6 | an-219 | E1C3475 | sp-9 | an-219 |
| E1C1034 | sp-3 | an-220 | E1C2255 | sp-6 | an-220 | E1C3476 | sp-9 | an-220 |
| E1C1035 | sp-3 | an-221 | E1C2256 | sp-6 | an-221 | E1C3477 | sp-9 | an-221 |
| E1C1036 | sp-3 | an-222 | E1C2257 | sp-6 | an-222 | E1C3478 | sp-9 | an-222 |
| E1C1037 | sp-3 | an-223 | E1C2258 | sp-6 | an-223 | E1C3479 | sp-9 | an-223 |
| E1C1038 | sp-3 | an-224 | E1C2259 | sp-6 | an-224 | E1C3480 | sp-9 | an-224 |
| E1C1039 | sp-3 | an-225 | E1C2260 | sp-6 | an-225 | E1C3481 | sp-9 | an-225 |
| E1C1040 | sp-3 | an-226 | E1C2261 | sp-6 | an-226 | E1C3482 | sp-9 | an-226 |
| E1C1041 | sp-3 | an-227 | E1C2262 | sp-6 | an-227 | E1C3483 | sp-9 | an-227 |
| E1C1042 | sp-3 | an-228 | E1C2263 | sp-6 | an-228 | E1C3484 | sp-9 | an-228 |
| E1C1043 | sp-3 | an-229 | E1C2264 | sp-6 | an-229 | E1C3485 | sp-9 | an-229 |
| E1C1044 | sp-3 | an-230 | E1C2265 | sp-6 | an-230 | E1C3486 | sp-9 | an-230 |
| E1C1045 | sp-3 | an-231 | E1C2266 | sp-6 | an-231 | E1C3487 | sp-9 | an-231 |
| E1C1046 | sp-3 | an-232 | E1C2267 | sp-6 | an-232 | E1C3488 | sp-9 | an-232 |
| E1C1047 | sp-3 | an-233 | E1C2268 | sp-6 | an-233 | E1C3489 | sp-9 | an-233 |
| E1C1048 | sp-3 | an-234 | E1C2269 | sp-6 | an-234 | E1C3490 | sp-9 | an-234 |
| E1C1049 | sp-3 | an-235 | E1C2270 | sp-6 | an-235 | E1C3491 | sp-9 | an-235 |
| E1C1050 | sp-3 | an-236 | E1C2271 | sp-6 | an-236 | E1C3492 | sp-9 | an-236 |
| E1C1051 | sp-3 | an-237 | E1C2272 | sp-6 | an-237 | E1C3493 | sp-9 | an-237 |
| E1C1052 | sp-3 | an-238 | E1C2273 | sp-6 | an-238 | E1C3494 | sp-9 | an-238 |
| E1C1053 | sp-3 | an-239 | E1C2274 | sp-6 | an-239 | E1C3495 | sp-9 | an-239 |
| E1C1054 | sp-3 | an-240 | E1C2275 | sp-6 | an-240 | E1C3496 | sp-9 | an-240 |
| E1C1055 | sp-3 | an-241 | E1C2276 | sp-6 | an-241 | E1C3497 | sp-9 | an-241 |
| E1C1056 | sp-3 | an-242 | E1C2277 | sp-6 | an-242 | E1C3498 | sp-9 | an-242 |
| E1C1057 | sp-3 | an-243 | E1C2278 | sp-6 | an-243 | E1C3499 | sp-9 | an-243 |
| E1C1058 | sp-3 | an-244 | E1C2279 | sp-6 | an-244 | E1C3500 | sp-9 | an-244 |
| E1C1059 | sp-3 | an-245 | E1C2280 | sp-6 | an-245 | E1C3501 | sp-9 | an-245 |
| E1C1060 | sp-3 | an-246 | E1C2281 | sp-6 | an-246 | E1C3502 | sp-9 | an-246 |
| E1C1061 | sp-3 | an-247 | E1C2282 | sp-6 | an-247 | E1C3503 | sp-9 | an-247 |
| E1C1062 | sp-3 | an-248 | E1C2283 | sp-6 | an-248 | E1C3504 | sp-9 | an-248 |
| E1C1063 | sp-3 | an-249 | E1C2284 | sp-6 | an-249 | E1C3505 | sp-9 | an-249 |
| E1C1064 | sp-3 | an-250 | E1C2285 | sp-6 | an-250 | E1C3506 | sp-9 | an-250 |
| E1C1065 | sp-3 | an-251 | E1C2286 | sp-6 | an-251 | E1C3507 | sp-9 | an-251 |
| E1C1066 | sp-3 | an-252 | E1C2287 | sp-6 | an-252 | E1C3508 | sp-9 | an-252 |
| E1C1067 | sp-3 | an-253 | E1C2288 | sp-6 | an-253 | E1C3509 | sp-9 | an-253 |
| E1C1068 | sp-3 | an-254 | E1C2289 | sp-6 | an-254 | E1C3510 | sp-9 | an-254 |
| E1C1069 | sp-3 | an-255 | E1C2290 | sp-6 | an-255 | E1C3511 | sp-9 | an-255 |
| E1C1070 | sp-3 | an-256 | E1C2291 | sp-6 | an-256 | E1C3512 | sp-9 | an-256 |
| E1C1071 | sp-3 | an-257 | E1C2292 | sp-6 | an-257 | E1C3513 | sp-9 | an-257 |
| Table 1-149 |||||||||
| Y = NHCSO ||| Y = NHCSO ||| Y = NHCSO |||
| E1C1072 | sp-3 | an-258 | E1C2293 | sp-6 | an-258 | E1C3514 | sp-9 | an-258 |
| E1C1073 | sp-3 | an-259 | E1C2294 | sp-6 | an-259 | E1C3515 | sp-9 | an-259 |
| E1C1074 | sp-3 | an-260 | E1C2295 | sp-6 | an-260 | E1C3516 | sp-9 | an-260 |
| E1C1075 | sp-3 | an-261 | E1C2296 | sp-6 | an-261 | E1C3517 | sp-9 | an-261 |
| E1C1076 | sp-3 | an-262 | E1C2297 | sp-6 | an-262 | E1C3518 | sp-9 | an-262 |
| E1C1077 | sp-3 | an-263 | E1C2298 | sp-6 | an-263 | E1C3519 | sp-9 | an-263 |
| E1C1078 | sp-3 | an-264 | E1C2299 | sp-6 | an-264 | E1C3520 | sp-9 | an-264 |
| E1C1079 | sp-3 | an-265 | E1C2300 | sp-6 | an-265 | E1C3521 | sp-9 | an-265 |
| E1C1080 | sp-3 | an-266 | E1C2301 | sp-6 | an-266 | E1C3522 | sp-9 | an-266 |
| E1C1081 | sp-3 | an-267 | E1C2302 | sp-6 | an-267 | E1C3523 | sp-9 | an-267 |
| E1C1082 | sp-3 | an-268 | E1C2303 | sp-6 | an-268 | E1C3524 | sp-9 | an-268 |
| E1C1083 | sp-3 | an-269 | E1C2304 | sp-6 | an-269 | E1C3525 | sp-9 | an-269 |
| E1C1084 | sp-3 | an-270 | E1C2305 | sp-6 | an-270 | E1C3526 | sp-9 | an-270 |
| E1C1085 | sp-3 | an-271 | E1C2306 | sp-6 | an-271 | E1C3527 | sp-9 | an-271 |
| E1C1086 | sp-3 | an-272 | E1C2307 | sp-6 | an-272 | E1C3528 | sp-9 | an-272 |
| E1C1087 | sp-3 | an-273 | E1C2308 | sp-6 | an-273 | E1C3529 | sp-9 | an-273 |

-continued

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| E1C1088 | sp-3 | an-274 | E1C2309 | sp-6 | an-274 | E1C3530 | sp-9 | an-274 |
| E1C1089 | sp-3 | an-275 | E1C2310 | sp-6 | an-275 | E1C3531 | sp-9 | an-275 |
| E1C1090 | sp-3 | an-276 | E1C2311 | sp-6 | an-276 | E1C3532 | sp-9 | an-276 |
| E1C1091 | sp-3 | an-277 | E1C2312 | sp-6 | an-277 | E1C3533 | sp-9 | an-277 |
| E1C1092 | sp-3 | an-278 | E1C2313 | sp-6 | an-278 | E1C3534 | sp-9 | an-278 |
| E1C1093 | sp-3 | an-279 | E1C2314 | sp-6 | an-279 | E1C3535 | sp-9 | an-279 |
| E1C1094 | sp-3 | an-280 | E1C2315 | sp-6 | an-280 | E1C3536 | sp-9 | an-280 |
| E1C1095 | sp-3 | an-281 | E1C2316 | sp-6 | an-281 | E1C3537 | sp-9 | an-281 |
| E1C1096 | sp-3 | an-282 | E1C2317 | sp-6 | an-282 | E1C3538 | sp-9 | an-282 |
| E1C1097 | sp-3 | an-283 | E1C2318 | sp-6 | an-283 | E1C3539 | sp-9 | an-283 |
| E1C1098 | sp-3 | an-284 | E1C2319 | sp-6 | an-284 | E1C3540 | sp-9 | an-284 |
| E1C1099 | sp-3 | an-285 | E1C2320 | sp-6 | an-285 | E1C3541 | sp-9 | an-285 |
| E1C1100 | sp-3 | an-286 | E1C2321 | sp-6 | an-286 | E1C3542 | sp-9 | an-286 |
| E1C1101 | sp-3 | an-287 | E1C2322 | sp-6 | an-287 | E1C3543 | sp-9 | an-287 |
| E1C1102 | sp-3 | an-288 | E1C2323 | sp-6 | an-288 | E1C3544 | sp-9 | an-288 |
| E1C1103 | sp-3 | an-289 | E1C2324 | sp-6 | an-289 | E1C3545 | sp-9 | an-289 |
| E1C1104 | sp-3 | an-290 | E1C2325 | sp-6 | an-290 | E1C3546 | sp-9 | an-290 |
| E1C1105 | sp-3 | an-291 | E1C2326 | sp-6 | an-291 | E1C3547 | sp-9 | an-291 |
| E1C1106 | sp-3 | an-292 | E1C2327 | sp-6 | an-292 | E1C3548 | sp-9 | an-292 |
| E1C1107 | sp-3 | an-293 | E1C2328 | sp-6 | an-293 | E1C3549 | sp-9 | an-293 |
| E1C1108 | sp-3 | an-294 | E1C2329 | sp-6 | an-294 | E1C3550 | sp-9 | an-294 |
| E1C1109 | sp-3 | an-295 | E1C2330 | sp-6 | an-295 | E1C3551 | sp-9 | an-295 |
| E1C1110 | sp-3 | an-296 | E1C2331 | sp-6 | an-296 | E1C3552 | sp-9 | an-296 |
| E1C1111 | sp-3 | an-297 | E1C2332 | sp-6 | an-297 | E1C3553 | sp-9 | an-297 |
| E1C1112 | sp-3 | an-298 | E1C2333 | sp-6 | an-298 | E1C3554 | sp-9 | an-298 |
| E1C1113 | sp-3 | an-299 | E1C2334 | sp-6 | an-299 | E1C3555 | sp-9 | an-299 |
| E1C1114 | sp-3 | an-300 | E1C2335 | sp-6 | an-300 | E1C3556 | sp-9 | an-300 |
| E1C1115 | sp-3 | an-301 | E1C2336 | sp-6 | an-301 | E1C3557 | sp-9 | an-301 |
| E1C1116 | sp-3 | an-302 | E1C2337 | sp-6 | an-302 | E1C3558 | sp-9 | an-302 |
| E1C1117 | sp-3 | an-303 | E1C2338 | sp-6 | an-303 | E1C3559 | sp-9 | an-303 |
| E1C1118 | sp-3 | an-304 | E1C2339 | sp-6 | an-304 | E1C3560 | sp-9 | an-304 |
| E1C1119 | sp-3 | an-305 | E1C2340 | sp-6 | an-305 | E1C3561 | sp-9 | an-305 |
| E1C1120 | sp-3 | an-306 | E1C2341 | sp-6 | an-306 | E1C3562 | sp-9 | an-306 |
| E1C1121 | sp-3 | an-307 | E1C2342 | sp-6 | an-307 | E1C3563 | sp-9 | an-307 |
| E1C1122 | sp-3 | an-308 | E1C2343 | sp-6 | an-308 | E1C3564 | sp-9 | an-308 |
| E1C1123 | sp-3 | an-309 | E1C2344 | sp-6 | an-309 | E1C3565 | sp-9 | an-309 |
| E1C1124 | sp-3 | an-310 | E1C2345 | sp-6 | an-310 | E1C3566 | sp-9 | an-310 |
| E1C1125 | sp-3 | an-311 | E1C2346 | sp-6 | an-311 | E1C3567 | sp-9 | an-311 |

Table 1-150

| Y = NHCSO | | | Y = NHCSO | | | Y = NHCSO | | |
|---|---|---|---|---|---|---|---|---|
| E1C1126 | sp-3 | an-312 | E1C2347 | sp-6 | an-312 | E1C3568 | sp-9 | an-312 |
| E1C1127 | sp-3 | an-313 | E1C2348 | sp-6 | an-313 | E1C3569 | sp-9 | an-313 |
| E1C1128 | sp-3 | an-314 | E1C2349 | sp-6 | an-314 | E1C3570 | sp-9 | an-314 |
| E1C1129 | sp-3 | an-315 | E1C2350 | sp-6 | an-315 | E1C3571 | sp-9 | an-315 |
| E1C1130 | sp-3 | an-316 | E1C2351 | sp-6 | an-316 | E1C3572 | sp-9 | an-316 |
| E1C1131 | sp-3 | an-317 | E1C2352 | sp-6 | an-317 | E1C3573 | sp-9 | an-317 |
| E1C1132 | sp-3 | an-318 | E1C2353 | sp-6 | an-318 | E1C3574 | sp-9 | an-318 |
| E1C1133 | sp-3 | an-319 | E1C2354 | sp-6 | an-319 | E1C3575 | sp-9 | an-319 |
| E1C1134 | sp-3 | an-320 | E1C2355 | sp-6 | an-320 | E1C3576 | sp-9 | an-320 |
| E1C1135 | sp-3 | an-321 | E1C2356 | sp-6 | an-321 | E1C3577 | sp-9 | an-321 |
| E1C1136 | sp-3 | an-322 | E1C2357 | sp-6 | an-322 | E1C3578 | sp-9 | an-322 |
| E1C1137 | sp-3 | an-323 | E1C2358 | sp-6 | an-323 | E1C3579 | sp-9 | an-323 |
| E1C1138 | sp-3 | an-324 | E1C2359 | sp-6 | an-324 | E1C3580 | sp-9 | an-324 |
| E1C1139 | sp-3 | an-325 | E1C2360 | sp-6 | an-325 | E1C3581 | sp-9 | an-325 |
| E1C1140 | sp-3 | an-326 | E1C2361 | sp-6 | an-326 | E1C3582 | sp-9 | an-326 |
| E1C1141 | sp-3 | an-327 | E1C2362 | sp-6 | an-327 | E1C3583 | sp-9 | an-327 |
| E1C1142 | sp-3 | an-328 | E1C2363 | sp-6 | an-328 | E1C3584 | sp-9 | an-328 |
| E1C1143 | sp-3 | an-329 | E1C2364 | sp-6 | an-329 | E1C3585 | sp-9 | an-329 |
| E1C1144 | sp-3 | an-330 | E1C2365 | sp-6 | an-330 | E1C3586 | sp-9 | an-330 |
| E1C1145 | sp-3 | an-331 | E1C2366 | sp-6 | an-331 | E1C3587 | sp-9 | an-331 |
| E1C1146 | sp-3 | an-332 | E1C2367 | sp-6 | an-332 | E1C3588 | sp-9 | an-332 |
| E1C1147 | sp-3 | an-333 | E1C2368 | sp-6 | an-333 | E1C3589 | sp-9 | an-333 |
| E1C1148 | sp-3 | an-334 | E1C2369 | sp-6 | an-334 | E1C3590 | sp-9 | an-334 |
| E1C1149 | sp-3 | an-335 | E1C2370 | sp-6 | an-335 | E1C3591 | sp-9 | an-335 |
| E1C1150 | sp-3 | an-336 | E1C2371 | sp-6 | an-336 | E1C3592 | sp-9 | an-336 |
| E1C1151 | sp-3 | an-337 | E1C2372 | sp-6 | an-337 | E1C3593 | sp-9 | an-337 |
| E1C1152 | sp-3 | an-338 | E1C2373 | sp-6 | an-338 | E1C3594 | sp-9 | an-338 |
| E1C1153 | sp-3 | an-339 | E1C2374 | sp-6 | an-339 | E1C3595 | sp-9 | an-339 |
| E1C1154 | sp-3 | an-340 | E1C2375 | sp-6 | an-340 | E1C3596 | sp-9 | an-340 |
| E1C1155 | sp-3 | an-341 | E1C2376 | sp-6 | an-341 | E1C3597 | sp-9 | an-341 |
| E1C1156 | sp-3 | an-342 | E1C2377 | sp-6 | an-342 | E1C3598 | sp-9 | an-342 |
| E1C1157 | sp-3 | an-343 | E1C2378 | sp-6 | an-343 | E1C3599 | sp-9 | an-343 |
| E1C1158 | sp-3 | an-344 | E1C2379 | sp-6 | an-344 | E1C3600 | sp-9 | an-344 |
| E1C1159 | sp-3 | an-345 | E1C2380 | sp-6 | an-345 | E1C3601 | sp-9 | an-345 |
| E1C1160 | sp-3 | an-346 | E1C2381 | sp-6 | an-346 | E1C3602 | sp-9 | an-346 |
| E1C1161 | sp-3 | an-347 | E1C2382 | sp-6 | an-347 | E1C3603 | sp-9 | an-347 |

-continued

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| E1C1162 | sp-3 | an-348 | E1C2383 | sp-6 | an-348 | E1C3604 | sp-9 | an-348 |
| E1C1163 | sp-3 | an-349 | E1C2384 | sp-6 | an-349 | E1C3605 | sp-9 | an-349 |
| E1C1164 | sp-3 | an-350 | E1C2385 | sp-6 | an-350 | E1C3606 | sp-9 | an-350 |
| E1C1165 | sp-3 | an-351 | E1C2386 | sp-6 | an-351 | E1C3607 | sp-9 | an-351 |
| E1C1166 | sp-3 | an-352 | E1C2387 | sp-6 | an-352 | E1C3608 | sp-9 | an-352 |
| E1C1167 | sp-3 | an-353 | E1C2388 | sp-6 | an-353 | E1C3609 | sp-9 | an-353 |
| E1C1168 | sp-3 | an-354 | E1C2389 | sp-6 | an-354 | E1C3610 | sp-9 | an-354 |
| E1C1169 | sp-3 | an-355 | E1C2390 | sp-6 | an-355 | E1C3611 | sp-9 | an-355 |
| E1C1170 | sp-3 | an-356 | E1C2391 | sp-6 | an-356 | E1C3612 | sp-9 | an-356 |
| E1C1171 | sp-3 | an-357 | E1C2392 | sp-6 | an-357 | E1C3613 | sp-9 | an-357 |
| E1C1172 | sp-3 | an-358 | E1C2393 | sp-6 | an-358 | E1C3614 | sp-9 | an-358 |
| E1C1173 | sp-3 | an-359 | E1C2394 | sp-6 | an-359 | E1C3615 | sp-9 | an-359 |
| E1C1174 | sp-3 | an-360 | E1C2395 | sp-6 | an-360 | E1C3616 | sp-9 | an-360 |
| E1C1175 | sp-3 | an-361 | E1C2396 | sp-6 | an-361 | E1C3617 | sp-9 | an-361 |
| E1C1176 | sp-3 | an-362 | E1C2397 | sp-6 | an-362 | E1C3618 | sp-9 | an-362 |
| E1C1177 | sp-3 | an-363 | E1C2398 | sp-6 | an-363 | E1C3619 | sp-9 | an-363 |
| E1C1178 | sp-3 | an-364 | E1C2399 | sp-6 | an-364 | E1C3620 | sp-9 | an-364 |
| E1C1179 | sp-3 | an-365 | E1C2400 | sp-6 | an-365 | E1C3621 | sp-9 | an-365 |

Table 1-151

| Y = NHCSO | | | Y = NHCSO | | | Y = NHCSO | | |
|---|---|---|---|---|---|---|---|---|
| E1C1180 | sp-3 | an-366 | E1C2401 | sp-6 | an-366 | E1C3622 | sp-9 | an-366 |
| E1C1181 | sp-3 | an-367 | E1C2402 | sp-6 | an-367 | E1C3623 | sp-9 | an-367 |
| E1C1182 | sp-3 | an-368 | E1C2403 | sp-6 | an-368 | E1C3624 | sp-9 | an-368 |
| E1C1183 | sp-3 | an-369 | E1C2404 | sp-6 | an-369 | E1C3625 | sp-9 | an-369 |
| E1C1184 | sp-3 | an-370 | E1C2405 | sp-6 | an-370 | E1C3626 | sp-9 | an-370 |
| E1C1185 | sp-3 | an-371 | E1C2406 | sp-6 | an-371 | E1C3627 | sp-9 | an-371 |
| E1C1186 | sp-3 | an-372 | E1C2407 | sp-6 | an-372 | E1C3628 | sp-9 | an-372 |
| E1C1187 | sp-3 | an-373 | E1C2408 | sp-6 | an-373 | E1C3629 | sp-9 | an-373 |
| E1C1188 | sp-3 | an-374 | E1C2409 | sp-6 | an-374 | E1C3630 | sp-9 | an-374 |
| E1C1189 | sp-3 | an-375 | E1C2410 | sp-6 | an-375 | E1C3631 | sp-9 | an-375 |
| E1C1190 | sp-3 | an-376 | E1C2411 | sp-6 | an-376 | E1C3632 | sp-9 | an-376 |
| E1C1191 | sp-3 | an-377 | E1C2412 | sp-6 | an-377 | E1C3633 | sp-9 | an-377 |
| E1C1192 | sp-3 | an-378 | E1C2413 | sp-6 | an-378 | E1C3634 | sp-9 | an-378 |
| E1C1193 | sp-3 | an-379 | E1C2414 | sp-6 | an-379 | E1C3635 | sp-9 | an-379 |
| E1C1194 | sp-3 | an-380 | E1C2415 | sp-6 | an-380 | E1C3636 | sp-9 | an-380 |
| E1C1195 | sp-3 | an-381 | E1C2416 | sp-6 | an-381 | E1C3637 | sp-9 | an-381 |
| E1C1196 | sp-3 | an-382 | E1C2417 | sp-6 | an-382 | E1C3638 | sp-9 | an-382 |
| E1C1197 | sp-3 | an-383 | E1C2418 | sp-6 | an-383 | E1C3639 | sp-9 | an-383 |
| E1C1198 | sp-3 | an-384 | E1C2419 | sp-6 | an-384 | E1C3640 | sp-9 | an-384 |
| E1C1199 | sp-3 | an-385 | E1C2420 | sp-6 | an-385 | E1C3641 | sp-9 | an-385 |
| E1C1200 | sp-3 | an-386 | E1C2421 | sp-6 | an-386 | E1C3642 | sp-9 | an-386 |
| E1C1201 | sp-3 | an-387 | E1C2422 | sp-6 | an-387 | E1C3643 | sp-9 | an-387 |
| E1C1202 | sp-3 | an-388 | E1C2423 | sp-6 | an-388 | E1C3644 | sp-9 | an-388 |
| E1C1203 | sp-3 | an-389 | E1C2424 | sp-6 | an-389 | E1C3645 | sp-9 | an-389 |
| E1C1204 | sp-3 | an-390 | E1C2425 | sp-6 | an-390 | E1C3646 | sp-9 | an-390 |
| E1C1205 | sp-3 | an-391 | E1C2426 | sp-6 | an-391 | E1C3647 | sp-9 | an-391 |
| E1C1206 | sp-3 | an-392 | E1C2427 | sp-6 | an-392 | E1C3648 | sp-9 | an-392 |
| E1C1207 | sp-3 | an-393 | E1C2428 | sp-6 | an-393 | E1C3649 | sp-9 | an-393 |
| E1C1208 | sp-3 | an-394 | E1C2429 | sp-6 | an-394 | E1C3650 | sp-9 | an-394 |
| E1C1209 | sp-3 | an-395 | E1C2430 | sp-6 | an-395 | E1C3651 | sp-9 | an-395 |
| E1C1210 | sp-3 | an-396 | E1C2431 | sp-6 | an-396 | E1C3652 | sp-9 | an-396 |
| E1C1211 | sp-3 | an-397 | E1C2432 | sp-6 | an-397 | E1C3653 | sp-9 | an-397 |
| E1C1212 | sp-3 | an-398 | E1C2433 | sp-6 | an-398 | E1C3654 | sp-9 | an-398 |
| E1C1213 | sp-3 | an-399 | E1C2434 | sp-6 | an-399 | E1C3655 | sp-9 | an-399 |
| E1C1214 | sp-3 | an-400 | E1C2435 | sp-6 | an-400 | E1C3656 | sp-9 | an-400 |
| E1C1215 | sp-3 | an-401 | E1C2436 | sp-6 | an-401 | E1C3657 | sp-9 | an-401 |
| E1C1216 | sp-3 | an-402 | E1C2437 | sp-6 | an-402 | E1C3658 | sp-9 | an-402 |
| E1C1217 | sp-3 | an-403 | E1C2438 | sp-6 | an-403 | E1C3659 | sp-9 | an-403 |
| E1C1218 | sp-3 | an-404 | E1C2439 | sp-6 | an-404 | E1C3660 | sp-9 | an-404 |
| E1C1219 | sp-3 | an-405 | E1C2440 | sp-6 | an-405 | E1C3661 | sp-9 | an-405 |
| E1C1220 | sp-3 | an-406 | E1C2441 | sp-6 | an-406 | E1C3662 | sp-9 | an-406 |
| E1C1221 | sp-3 | an-407 | E1C2442 | sp-6 | an-407 | E1C3663 | sp-9 | an-407 |
| E1C1222 | sp-4 | an-1 | E1C2443 | sp-7 | an-1 | E1C3664 | sp-11 | an-1 |
| E1C1223 | sp-4 | an-2 | E1C2444 | sp-7 | an-2 | E1C3665 | sp-11 | an-2 |
| E1C1224 | sp-4 | an-3 | E1C2445 | sp-7 | an-3 | E1C3666 | sp-11 | an-3 |
| E1C1225 | sp-4 | an-4 | E1C2446 | sp-7 | an-4 | E1C3667 | sp-11 | an-4 |
| E1C1226 | sp-4 | an-5 | E1C2447 | sp-7 | an-5 | E1C3668 | sp-11 | an-5 |
| E1C1227 | sp-4 | an-6 | E1C2448 | sp-7 | an-6 | E1C3669 | sp-11 | an-6 |
| E1C1228 | sp-4 | an-7 | E1C2449 | sp-7 | an-7 | E1C3670 | sp-11 | an-7 |
| E1C1229 | sp-4 | an-8 | E1C2450 | sp-7 | an-8 | E1C3671 | sp-11 | an-8 |
| E1C1230 | sp-4 | an-9 | E1C2451 | sp-7 | an-9 | E1C3672 | sp-11 | an-9 |
| E1C1231 | sp-4 | an-10 | E1C2452 | sp-7 | an-10 | E1C3673 | sp-11 | an-10 |
| E1C1232 | sp-4 | an-11 | E1C2453 | sp-7 | an-11 | E1C3674 | sp-11 | an-11 |
| E1C1233 | sp-4 | an-12 | E1C2454 | sp-7 | an-12 | E1C3675 | sp-11 | an-12 |

-continued

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| Table 1-152 ||||||||||
| Y = NHCSO ||| Y = NHCSO ||| Y = NHCSO |||
| E1C1234 | sp-4 | an-13 | E1C2455 | sp-7 | an-13 | E1C3676 | sp-11 | an-13 |
| E1C1235 | sp-4 | an-14 | E1C2456 | sp-7 | an-14 | E1C3677 | sp-11 | an-14 |
| E1C1236 | sp-4 | an-15 | E1C2457 | sp-7 | an-15 | E1C3678 | sp-11 | an-15 |
| E1C1237 | sp-4 | an-16 | E1C2458 | sp-7 | an-16 | E1C3679 | sp-11 | an-16 |
| E1C1238 | sp-4 | an-17 | E1C2459 | sp-7 | an-17 | E1C3680 | sp-11 | an-17 |
| E1C1239 | sp-4 | an-18 | E1C2460 | sp-7 | an-18 | E1C3681 | sp-11 | an-18 |
| E1C1240 | sp-4 | an-19 | E1C2461 | sp-7 | an-19 | E1C3682 | sp-11 | an-19 |
| E1C1241 | sp-4 | an-20 | E1C2462 | sp-7 | an-20 | E1C3683 | sp-11 | an-20 |
| E1C1242 | sp-4 | an-21 | E1C2463 | sp-7 | an-21 | E1C3684 | sp-11 | an-21 |
| E1C1243 | sp-4 | an-22 | E1C2464 | sp-7 | an-22 | E1C3685 | sp-11 | an-22 |
| E1C1244 | sp-4 | an-23 | E1C2465 | sp-7 | an-23 | E1C3686 | sp-11 | an-23 |
| E1C1245 | sp-4 | an-24 | E1C2466 | sp-7 | an-24 | E1C3687 | sp-11 | an-24 |
| E1C1246 | sp-4 | an-25 | E1C2467 | sp-7 | an-25 | E1C3688 | sp-11 | an-25 |
| E1C1247 | sp-4 | an-26 | E1C2468 | sp-7 | an-26 | E1C3689 | sp-11 | an-26 |
| E1C1248 | sp-4 | an-27 | E1C2469 | sp-7 | an-27 | E1C3690 | sp-11 | an-27 |
| E1C1249 | sp-4 | an-28 | E1C2470 | sp-7 | an-28 | E1C3691 | sp-11 | an-28 |
| E1C1250 | sp-4 | an-29 | E1C2471 | sp-7 | an-29 | E1C3692 | sp-11 | an-29 |
| E1C1251 | sp-4 | an-30 | E1C2472 | sp-7 | an-30 | E1C3693 | sp-11 | an-30 |
| E1C1252 | sp-4 | an-31 | E1C2473 | sp-7 | an-31 | E1C3694 | sp-11 | an-31 |
| E1C1253 | sp-4 | an-32 | E1C2474 | sp-7 | an-32 | E1C3695 | sp-11 | an-32 |
| E1C1254 | sp-4 | an-33 | E1C2475 | sp-7 | an-33 | E1C3696 | sp-11 | an-33 |
| E1C1255 | sp-4 | an-34 | E1C2476 | sp-7 | an-34 | E1C3697 | sp-11 | an-34 |
| E1C1256 | sp-4 | an-35 | E1C2477 | sp-7 | an-35 | E1C3698 | sp-11 | an-35 |
| E1C1257 | sp-4 | an-36 | E1C2478 | sp-7 | an-36 | E1C3699 | sp-11 | an-36 |
| E1C1258 | sp-4 | an-37 | E1C2479 | sp-7 | an-37 | E1C3700 | sp-11 | an-37 |
| E1C1259 | sp-4 | an-38 | E1C2480 | sp-7 | an-38 | E1C3701 | sp-11 | an-38 |
| E1C1260 | sp-4 | an-39 | E1C2481 | sp-7 | an-39 | E1C3702 | sp-11 | an-39 |
| E1C1261 | sp-4 | an-40 | E1C2482 | sp-7 | an-40 | E1C3703 | sp-11 | an-40 |
| E1C1262 | sp-4 | an-41 | E1C2483 | sp-7 | an-41 | E1C3704 | sp-11 | an-41 |
| E1C1263 | sp-4 | an-42 | E1C2484 | sp-7 | an-42 | E1C3705 | sp-11 | an-42 |
| E1C1264 | sp-4 | an-43 | E1C2485 | sp-7 | an-43 | E1C3706 | sp-11 | an-43 |
| E1C1265 | sp-4 | an-44 | E1C2486 | sp-7 | an-44 | E1C3707 | sp-11 | an-44 |
| E1C1266 | sp-4 | an-45 | E1C2487 | sp-7 | an-45 | E1C3708 | sp-11 | an-45 |
| E1C1267 | sp-4 | an-46 | E1C2488 | sp-7 | an-46 | E1C3709 | sp-11 | an-46 |
| E1C1268 | sp-4 | an-47 | E1C2489 | sp-7 | an-47 | E1C3710 | sp-11 | an-47 |
| E1C1269 | sp-4 | an-48 | E1C2490 | sp-7 | an-48 | E1C3711 | sp-11 | an-48 |
| E1C1270 | sp-4 | an-49 | E1C2491 | sp-7 | an-49 | E1C3712 | sp-11 | an-49 |
| E1C1271 | sp-4 | an-50 | E1C2492 | sp-7 | an-50 | E1C3713 | sp-11 | an-50 |
| E1C1272 | sp-4 | an-51 | E1C2493 | sp-7 | an-51 | E1C3714 | sp-11 | an-51 |
| E1C1273 | sp-4 | an-52 | E1C2494 | sp-7 | an-52 | E1C3715 | sp-11 | an-52 |
| E1C1274 | sp-4 | an-53 | E1C2495 | sp-7 | an-53 | E1C3716 | sp-11 | an-53 |
| E1C1275 | sp-4 | an-54 | E1C2496 | sp-7 | an-54 | E1C3717 | sp-11 | an-54 |
| E1C1276 | sp-4 | an-55 | E1C2497 | sp-7 | an-55 | E1C3718 | sp-11 | an-55 |
| E1C1277 | sp-4 | an-56 | E1C2498 | sp-7 | an-56 | E1C3719 | sp-11 | an-56 |
| E1C1278 | sp-4 | an-57 | E1C2499 | sp-7 | an-57 | E1C3720 | sp-11 | an-57 |
| E1C1279 | sp-4 | an-58 | E1C2500 | sp-7 | an-58 | E1C3721 | sp-11 | an-58 |
| E1C1280 | sp-4 | an-59 | E1C2501 | sp-7 | an-59 | E1C3722 | sp-11 | an-59 |
| E1C1281 | sp-4 | an-60 | E1C2502 | sp-7 | an-60 | E1C3723 | sp-11 | an-60 |
| E1C1282 | sp-4 | an-61 | E1C2503 | sp-7 | an-61 | E1C3724 | sp-11 | an-61 |
| E1C1283 | sp-4 | an-62 | E1C2504 | sp-7 | an-62 | E1C3725 | sp-11 | an-62 |
| E1C1284 | sp-4 | an-63 | E1C2505 | sp-7 | an-63 | E1C3726 | sp-11 | an-63 |
| E1C1285 | sp-4 | an-64 | E1C2506 | sp-7 | an-64 | E1C3727 | sp-11 | an-64 |
| E1C1286 | sp-4 | an-65 | E1C2507 | sp-7 | an-65 | E1C3728 | sp-11 | an-65 |
| E1C1287 | sp-4 | an-66 | E1C2508 | sp-7 | an-66 | E1C3729 | sp-11 | an-66 |
| Table 1-153 ||||||||||
| Y = NHCSO ||| Y = NHCSO ||| Y = NHCSO |||
| E1C1288 | sp-4 | an-67 | E1C2509 | sp-7 | an-67 | E1C3730 | sp-11 | an-67 |
| E1C1289 | sp-4 | an-68 | E1C2510 | sp-7 | an-68 | E1C3731 | sp-11 | an-68 |
| E1C1290 | sp-4 | an-69 | E1C2511 | sp-7 | an-69 | E1C3732 | sp-11 | an-69 |
| E1C1291 | sp-4 | an-70 | E1C2512 | sp-7 | an-70 | E1C3733 | sp-11 | an-70 |
| E1C1292 | sp-4 | an-71 | E1C2513 | sp-7 | an-71 | E1C3734 | sp-11 | an-71 |
| E1C1293 | sp-4 | an-72 | E1C2514 | sp-7 | an-72 | E1C3735 | sp-11 | an-72 |
| E1C1294 | sp-4 | an-73 | E1C2515 | sp-7 | an-73 | E1C3736 | sp-11 | an-73 |
| E1C1295 | sp-4 | an-74 | E1C2516 | sp-7 | an-74 | E1C3737 | sp-11 | an-74 |
| E1C1296 | sp-4 | an-75 | E1C2517 | sp-7 | an-75 | E1C3738 | sp-11 | an-75 |
| E1C1297 | sp-4 | an-76 | E1C2518 | sp-7 | an-76 | E1C3739 | sp-11 | an-76 |
| E1C1298 | sp-4 | an-77 | E1C2519 | sp-7 | an-77 | E1C3740 | sp-11 | an-77 |
| E1C1299 | sp-4 | an-78 | E1C2520 | sp-7 | an-78 | E1C3741 | sp-11 | an-78 |
| E1C1300 | sp-4 | an-79 | E1C2521 | sp-7 | an-79 | E1C3742 | sp-11 | an-79 |
| E1C1301 | sp-4 | an-80 | E1C2522 | sp-7 | an-80 | E1C3743 | sp-11 | an-80 |
| E1C1302 | sp-4 | an-81 | E1C2523 | sp-7 | an-81 | E1C3744 | sp-11 | an-81 |
| E1C1303 | sp-4 | an-82 | E1C2524 | sp-7 | an-82 | E1C3745 | sp-11 | an-82 |

-continued

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| E1C1304 | sp-4 | an-83 | E1C2525 | sp-7 | an-83 | E1C3746 | sp-11 | an-83 |
| E1C1305 | sp-4 | an-84 | E1C2526 | sp-7 | an-84 | E1C3747 | sp-11 | an-84 |
| E1C1306 | sp-4 | an-85 | E1C2527 | sp-7 | an-85 | E1C3748 | sp-11 | an-85 |
| E1C1307 | sp-4 | an-86 | E1C2528 | sp-7 | an-86 | E1C3749 | sp-11 | an-86 |
| E1C1308 | sp-4 | an-87 | E1C2529 | sp-7 | an-87 | E1C3750 | sp-11 | an-87 |
| E1C1309 | sp-4 | an-88 | E1C2530 | sp-7 | an-88 | E1C3751 | sp-11 | an-88 |
| E1C1310 | sp-4 | an-89 | E1C2531 | sp-7 | an-89 | E1C3752 | sp-11 | an-89 |
| E1C1311 | sp-4 | an-90 | E1C2532 | sp-7 | an-90 | E1C3753 | sp-11 | an-90 |
| E1C1312 | sp-4 | an-91 | E1C2533 | sp-7 | an-91 | E1C3754 | sp-11 | an-91 |
| E1C1313 | sp-4 | an-92 | E1C2534 | sp-7 | an-92 | E1C3755 | sp-11 | an-92 |
| E1C1314 | sp-4 | an-93 | E1C2535 | sp-7 | an-93 | E1C3756 | sp-11 | an-93 |
| E1C1315 | sp-4 | an-94 | E1C2536 | sp-7 | an-94 | E1C3757 | sp-11 | an-94 |
| E1C1316 | sp-4 | an-95 | E1C2537 | sp-7 | an-95 | E1C3758 | sp-11 | an-95 |
| E1C1317 | sp-4 | an-96 | E1C2538 | sp-7 | an-96 | E1C3759 | sp-11 | an-96 |
| E1C1318 | sp-4 | an-97 | E1C2539 | sp-7 | an-97 | E1C3760 | sp-11 | an-97 |
| E1C1319 | sp-4 | an-98 | E1C2540 | sp-7 | an-98 | E1C3761 | sp-11 | an-98 |
| E1C1320 | sp-4 | an-99 | E1C2541 | sp-7 | an-99 | E1C3762 | sp-11 | an-99 |
| E1C1321 | sp-4 | an-100 | E1C2542 | sp-7 | an-100 | E1C3763 | sp-11 | an-100 |
| E1C1322 | sp-4 | an-101 | E1C2543 | sp-7 | an-101 | E1C3764 | sp-11 | an-101 |
| E1C1323 | sp-4 | an-102 | E1C2544 | sp-7 | an-102 | E1C3765 | sp-11 | an-102 |
| E1C1324 | sp-4 | an-103 | E1C2545 | sp-7 | an-103 | E1C3766 | sp-11 | an-103 |
| E1C1325 | sp-4 | an-104 | E1C2546 | sp-7 | an-104 | E1C3767 | sp-11 | an-104 |
| E1C1326 | sp-4 | an-105 | E1C2547 | sp-7 | an-105 | E1C3768 | sp-11 | an-105 |
| E1C1327 | sp-4 | an-106 | E1C2548 | sp-7 | an-106 | E1C3769 | sp-11 | an-106 |
| E1C1328 | sp-4 | an-107 | E1C2549 | sp-7 | an-107 | E1C3770 | sp-11 | an-107 |
| E1C1329 | sp-4 | an-108 | E1C2550 | sp-7 | an-108 | E1C3771 | sp-11 | an-108 |
| E1C1330 | sp-4 | an-109 | E1C2551 | sp-7 | an-109 | E1C3772 | sp-11 | an-109 |
| E1C1331 | sp-4 | an-110 | E1C2552 | sp-7 | an-110 | E1C3773 | sp-11 | an-110 |
| E1C1332 | sp-4 | an-111 | E1C2553 | sp-7 | an-111 | E1C3774 | sp-11 | an-111 |
| E1C1333 | sp-4 | an-112 | E1C2554 | sp-7 | an-112 | E1C3775 | sp-11 | an-112 |
| E1C1334 | sp-4 | an-113 | E1C2555 | sp-7 | an-113 | E1C3776 | sp-11 | an-113 |
| E1C1335 | sp-4 | an-114 | E1C2556 | sp-7 | an-114 | E1C3777 | sp-11 | an-114 |
| E1C1336 | sp-4 | an-115 | E1C2557 | sp-7 | an-115 | E1C3778 | sp-11 | an-115 |
| E1C1337 | sp-4 | an-116 | E1C2558 | sp-7 | an-116 | E1C3779 | sp-11 | an-116 |
| E1C1338 | sp-4 | an-117 | E1C2559 | sp-7 | an-117 | E1C3780 | sp-11 | an-117 |
| E1C1339 | sp-4 | an-118 | E1C2560 | sp-7 | an-118 | E1C3781 | sp-11 | an-118 |
| E1C1340 | sp-4 | an-119 | E1C2561 | sp-7 | an-119 | E1C3782 | sp-11 | an-119 |
| E1C1341 | sp-4 | an-120 | E1C2562 | sp-7 | an-120 | E1C3783 | sp-11 | an-120 |

Table 1-154

| Y = NHCSO | | | Y = NHCSO | | | Y = NHCSO | | |
|---|---|---|---|---|---|---|---|---|
| E1C1342 | sp-4 | an-121 | E1C2563 | sp-7 | an-121 | E1C3784 | sp-11 | an-121 |
| E1C1343 | sp-4 | an-122 | E1C2564 | sp-7 | an-122 | E1C3785 | sp-11 | an-122 |
| E1C1344 | sp-4 | an-123 | E1C2565 | sp-7 | an-123 | E1C3786 | sp-11 | an-123 |
| E1C1345 | sp-4 | an-124 | E1C2566 | sp-7 | an-124 | E1C3787 | sp-11 | an-124 |
| E1C1346 | sp-4 | an-125 | E1C2567 | sp-7 | an-125 | E1C3788 | sp-11 | an-125 |
| E1C1347 | sp-4 | an-126 | E1C2568 | sp-7 | an-126 | E1C3789 | sp-11 | an-126 |
| E1C1348 | sp-4 | an-127 | E1C2569 | sp-7 | an-127 | E1C3790 | sp-11 | an-127 |
| E1C1349 | sp-4 | an-128 | E1C2570 | sp-7 | an-128 | E1C3791 | sp-11 | an-128 |
| E1C1350 | sp-4 | an-129 | E1C2571 | sp-7 | an-129 | E1C3792 | sp-11 | an-129 |
| E1C1351 | sp-4 | an-130 | E1C2572 | sp-7 | an-130 | E1C3793 | sp-11 | an-130 |
| E1C1352 | sp-4 | an-131 | E1C2573 | sp-7 | an-131 | E1C3794 | sp-11 | an-131 |
| E1C1353 | sp-4 | an-132 | E1C2574 | sp-7 | an-132 | E1C3795 | sp-11 | an-132 |
| E1C1354 | sp-4 | an-133 | E1C2575 | sp-7 | an-133 | E1C3796 | sp-11 | an-133 |
| E1C1355 | sp-4 | an-134 | E1C2576 | sp-7 | an-134 | E1C3797 | sp-11 | an-134 |
| E1C1356 | sp-4 | an-135 | E1C2577 | sp-7 | an-135 | E1C3798 | sp-11 | an-135 |
| E1C1357 | sp-4 | an-136 | E1C2578 | sp-7 | an-136 | E1C3799 | sp-11 | an-136 |
| E1C1358 | sp-4 | an-137 | E1C2579 | sp-7 | an-137 | E1C3800 | sp-11 | an-137 |
| E1C1359 | sp-4 | an-138 | E1C2580 | sp-7 | an-138 | E1C3801 | sp-11 | an-138 |
| E1C1360 | sp-4 | an-139 | E1C2581 | sp-7 | an-139 | E1C3802 | sp-11 | an-139 |
| E1C1361 | sp-4 | an-140 | E1C2582 | sp-7 | an-140 | E1C3803 | sp-11 | an-140 |
| E1C1362 | sp-4 | an-141 | E1C2583 | sp-7 | an-141 | E1C3804 | sp-11 | an-141 |
| E1C1363 | sp-4 | an-142 | E1C2584 | sp-7 | an-142 | E1C3805 | sp-11 | an-142 |
| E1C1364 | sp-4 | an-143 | E1C2585 | sp-7 | an-143 | E1C3806 | sp-11 | an-143 |
| E1C1365 | sp-4 | an-144 | E1C2586 | sp-7 | an-144 | E1C3807 | sp-11 | an-144 |
| E1C1366 | sp-4 | an-145 | E1C2587 | sp-7 | an-145 | E1C3808 | sp-11 | an-145 |
| E1C1367 | sp-4 | an-146 | E1C2588 | sp-7 | an-146 | E1C3809 | sp-11 | an-146 |
| E1C1368 | sp-4 | an-147 | E1C2589 | sp-7 | an-147 | E1C3810 | sp-11 | an-147 |
| E1C1369 | sp-4 | an-148 | E1C2590 | sp-7 | an-148 | E1C3811 | sp-11 | an-148 |
| E1C1370 | sp-4 | an-149 | E1C2591 | sp-7 | an-149 | E1C3812 | sp-11 | an-149 |
| E1C1371 | sp-4 | an-150 | E1C2592 | sp-7 | an-150 | E1C3813 | sp-11 | an-150 |
| E1C1372 | sp-4 | an-151 | E1C2593 | sp-7 | an-151 | E1C3814 | sp-11 | an-151 |
| E1C1373 | sp-4 | an-152 | E1C2594 | sp-7 | an-152 | E1C3815 | sp-11 | an-152 |
| E1C1374 | sp-4 | an-153 | E1C2595 | sp-7 | an-153 | E1C3816 | sp-11 | an-153 |
| E1C1375 | sp-4 | an-154 | E1C2596 | sp-7 | an-154 | E1C3817 | sp-11 | an-154 |
| E1C1376 | sp-4 | an-155 | E1C2597 | sp-7 | an-155 | E1C3818 | sp-11 | an-155 |
| E1C1377 | sp-4 | an-156 | E1C2598 | sp-7 | an-156 | E1C3819 | sp-11 | an-156 |

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| E1C1378 | sp-4 | an-157 | E1C2599 | sp-7 | an-157 | E1C3820 | sp-11 | an-157 |
| E1C1379 | sp-4 | an-158 | E1C2600 | sp-7 | an-158 | E1C3821 | sp-11 | an-158 |
| E1C1380 | sp-4 | an-159 | E1C2601 | sp-7 | an-159 | E1C3822 | sp-11 | an-159 |
| E1C1381 | sp-4 | an-160 | E1C2602 | sp-7 | an-160 | E1C3823 | sp-11 | an-160 |
| E1C1382 | sp-4 | an-161 | E1C2603 | sp-7 | an-161 | E1C3824 | sp-11 | an-161 |
| E1C1383 | sp-4 | an-162 | E1C2604 | sp-7 | an-162 | E1C3825 | sp-11 | an-162 |
| E1C1384 | sp-4 | an-163 | E1C2605 | sp-7 | an-163 | E1C3826 | sp-11 | an-163 |
| E1C1385 | sp-4 | an-164 | E1C2606 | sp-7 | an-164 | E1C3827 | sp-11 | an-164 |
| E1C1386 | sp-4 | an-165 | E1C2607 | sp-7 | an-165 | E1C3828 | sp-11 | an-165 |
| E1C1387 | sp-4 | an-166 | E1C2608 | sp-7 | an-166 | E1C3829 | sp-11 | an-166 |
| E1C1388 | sp-4 | an-167 | E1C2609 | sp-7 | an-167 | E1C3830 | sp-11 | an-167 |
| E1C1389 | sp-4 | an-168 | E1C2610 | sp-7 | an-168 | E1C3831 | sp-11 | an-168 |
| E1C1390 | sp-4 | an-169 | E1C2611 | sp-7 | an-169 | E1C3832 | sp-11 | an-169 |
| E1C1391 | sp-4 | an-170 | E1C2612 | sp-7 | an-170 | E1C3833 | sp-11 | an-170 |
| E1C1392 | sp-4 | an-171 | E1C2613 | sp-7 | an-171 | E1C3834 | sp-11 | an-171 |
| E1C1393 | sp-4 | an-172 | E1C2614 | sp-7 | an-172 | E1C3835 | sp-11 | an-172 |
| E1C1394 | sp-4 | an-173 | E1C2615 | sp-7 | an-173 | E1C3836 | sp-11 | an-173 |
| E1C1395 | sp-4 | an-174 | E1C2616 | sp-7 | an-174 | E1C3837 | sp-11 | an-174 |

Table 1-155

| Y = NHCSO | | | Y = NHCSO | | | Y = NHCSO | | |
|---|---|---|---|---|---|---|---|---|
| E1C1396 | sp-4 | an-175 | E1C2617 | sp-7 | an-175 | E1C3838 | sp-11 | an-175 |
| E1C1397 | sp-4 | an-176 | E1C2618 | sp-7 | an-176 | E1C3839 | sp-11 | an-176 |
| E1C1398 | sp-4 | an-177 | E1C2619 | sp-7 | an-177 | E1C3840 | sp-11 | an-177 |
| E1C1399 | sp-4 | an-178 | E1C2620 | sp-7 | an-178 | E1C3841 | sp-11 | an-178 |
| E1C1400 | sp-4 | an-179 | E1C2621 | sp-7 | an-179 | E1C3842 | sp-11 | an-179 |
| E1C1401 | sp-4 | an-180 | E1C2622 | sp-7 | an-180 | E1C3843 | sp-11 | an-180 |
| E1C1402 | sp-4 | an-181 | E1C2623 | sp-7 | an-181 | E1C3844 | sp-11 | an-181 |
| E1C1403 | sp-4 | an-182 | E1C2624 | sp-7 | an-182 | E1C3845 | sp-11 | an-182 |
| E1C1404 | sp-4 | an-183 | E1C2625 | sp-7 | an-183 | E1C3846 | sp-11 | an-183 |
| E1C1405 | sp-4 | an-184 | E1C2626 | sp-7 | an-184 | E1C3847 | sp-11 | an-184 |
| E1C1406 | sp-4 | an-185 | E1C2627 | sp-7 | an-185 | E1C3848 | sp-11 | an-185 |
| E1C1407 | sp-4 | an-186 | E1C2628 | sp-7 | an-186 | E1C3849 | sp-11 | an-186 |
| E1C1408 | sp-4 | an-187 | E1C2629 | sp-7 | an-187 | E1C3850 | sp-11 | an-187 |
| E1C1409 | sp-4 | an-188 | E1C2630 | sp-7 | an-188 | E1C3851 | sp-11 | an-188 |
| E1C1410 | sp-4 | an-189 | E1C2631 | sp-7 | an-189 | E1C3852 | sp-11 | an-189 |
| E1C1411 | sp-4 | an-190 | E1C2632 | sp-7 | an-190 | E1C3853 | sp-11 | an-190 |
| E1C1412 | sp-4 | an-191 | E1C2633 | sp-7 | an-191 | E1C3854 | sp-11 | an-191 |
| E1C1413 | sp-4 | an-192 | E1C2634 | sp-7 | an-192 | E1C3855 | sp-11 | an-192 |
| E1C1414 | sp-4 | an-193 | E1C2635 | sp-7 | an-193 | E1C3856 | sp-11 | an-193 |
| E1C1415 | sp-4 | an-194 | E1C2636 | sp-7 | an-194 | E1C3857 | sp-11 | an-194 |
| E1C1416 | sp-4 | an-195 | E1C2637 | sp-7 | an-195 | E1C3858 | sp-11 | an-195 |
| E1C1417 | sp-4 | an-196 | E1C2638 | sp-7 | an-196 | E1C3859 | sp-11 | an-196 |
| E1C1418 | sp-4 | an-197 | E1C2639 | sp-7 | an-197 | E1C3860 | sp-11 | an-197 |
| E1C1419 | sp-4 | an-198 | E1C2640 | sp-7 | an-198 | E1C3861 | sp-11 | an-198 |
| E1C1420 | sp-4 | an-199 | E1C2641 | sp-7 | an-199 | E1C3862 | sp-11 | an-199 |
| E1C1421 | sp-4 | an-200 | E1C2642 | sp-7 | an-200 | E1C3863 | sp-11 | an-200 |
| E1C1422 | sp-4 | an-201 | E1C2643 | sp-7 | an-201 | E1C3864 | sp-11 | an-201 |
| E1C1423 | sp-4 | an-202 | E1C2644 | sp-7 | an-202 | E1C3865 | sp-11 | an-202 |
| E1C1424 | sp-4 | an-203 | E1C2645 | sp-7 | an-203 | E1C3866 | sp-11 | an-203 |
| E1C1425 | sp-4 | an-204 | E1C2646 | sp-7 | an-204 | E1C3867 | sp-11 | an-204 |
| E1C1426 | sp-4 | an-205 | E1C2647 | sp-7 | an-205 | E1C3868 | sp-11 | an-205 |
| E1C1427 | sp-4 | an-206 | E1C2648 | sp-7 | an-206 | E1C3869 | sp-11 | an-206 |
| E1C1428 | sp-4 | an-207 | E1C2649 | sp-7 | an-207 | E1C3870 | sp-11 | an-207 |
| E1C1429 | sp-4 | an-208 | E1C2650 | sp-7 | an-208 | E1C3871 | sp-11 | an-208 |
| E1C1430 | sp-4 | an-209 | E1C2651 | sp-7 | an-209 | E1C3872 | sp-11 | an-209 |
| E1C1431 | sp-4 | an-210 | E1C2652 | sp-7 | an-210 | E1C3873 | sp-11 | an-210 |
| E1C1432 | sp-4 | an-211 | E1C2653 | sp-7 | an-211 | E1C3874 | sp-11 | an-211 |
| E1C1433 | sp-4 | an-212 | E1C2654 | sp-7 | an-212 | E1C3875 | sp-11 | an-212 |
| E1C1434 | sp-4 | an-213 | E1C2655 | sp-7 | an-213 | E1C3876 | sp-11 | an-213 |
| E1C1435 | sp-4 | an-214 | E1C2656 | sp-7 | an-214 | E1C3877 | sp-11 | an-214 |
| E1C1436 | sp-4 | an-215 | E1C2657 | sp-7 | an-215 | E1C3878 | sp-11 | an-215 |
| E1C1437 | sp-4 | an-216 | E1C2658 | sp-7 | an-216 | E1C3879 | sp-11 | an-216 |
| E1C1438 | sp-4 | an-217 | E1C2659 | sp-7 | an-217 | E1C3880 | sp-11 | an-217 |
| E1C1439 | sp-4 | an-218 | E1C2660 | sp-7 | an-218 | E1C3881 | sp-11 | an-218 |
| E1C1440 | sp-4 | an-219 | E1C2661 | sp-7 | an-219 | E1C3882 | sp-11 | an-219 |
| E1C1441 | sp-4 | an-220 | E1C2662 | sp-7 | an-220 | E1C3883 | sp-11 | an-220 |
| E1C1442 | sp-4 | an-221 | E1C2663 | sp-7 | an-221 | E1C3884 | sp-11 | an-221 |
| E1C1443 | sp-4 | an-222 | E1C2664 | sp-7 | an-222 | E1C3885 | sp-11 | an-222 |
| E1C1444 | sp-4 | an-223 | E1C2665 | sp-7 | an-223 | E1C3886 | sp-11 | an-223 |
| E1C1445 | sp-4 | an-224 | E1C2666 | sp-7 | an-224 | E1C3887 | sp-11 | an-224 |
| E1C1446 | sp-4 | an-225 | E1C2667 | sp-7 | an-225 | E1C3888 | sp-11 | an-225 |
| E1C1447 | sp-4 | an-226 | E1C2668 | sp-7 | an-226 | E1C3889 | sp-11 | an-226 |
| E1C1448 | sp-4 | an-227 | E1C2669 | sp-7 | an-227 | E1C3890 | sp-11 | an-227 |
| E1C1449 | sp-4 | an-228 | E1C2670 | sp-7 | an-228 | E1C3891 | sp-11 | an-228 |

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| Table 1-156 ||||||||| 
| Y = NHCSO ||| Y = NHCSO ||| Y = NHCSO |||
| E1C1450 | sp-4 | an-229 | E1C2671 | sp-7 | an-229 | E1C3892 | sp-11 | an-229 |
| E1C1451 | sp-4 | an-230 | E1C2672 | sp-7 | an-230 | E1C3893 | sp-11 | an-230 |
| E1C1452 | sp-4 | an-231 | E1C2673 | sp-7 | an-231 | E1C3894 | sp-11 | an-231 |
| E1C1453 | sp-4 | an-232 | E1C2674 | sp-7 | an-232 | E1C3895 | sp-11 | an-232 |
| E1C1454 | sp-4 | an-233 | E1C2675 | sp-7 | an-233 | E1C3896 | sp-11 | an-233 |
| E1C1455 | sp-4 | an-234 | E1C2676 | sp-7 | an-234 | E1C3897 | sp-11 | an-234 |
| E1C1456 | sp-4 | an-235 | E1C2677 | sp-7 | an-235 | E1C3898 | sp-11 | an-235 |
| E1C1457 | sp-4 | an-236 | E1C2678 | sp-7 | an-236 | E1C3899 | sp-11 | an-236 |
| E1C1458 | sp-4 | an-237 | E1C2679 | sp-7 | an-237 | E1C3900 | sp-11 | an-237 |
| E1C1459 | sp-4 | an-238 | E1C2680 | sp-7 | an-238 | E1C3901 | sp-11 | an-238 |
| E1C1460 | sp-4 | an-239 | E1C2681 | sp-7 | an-239 | E1C3902 | sp-11 | an-239 |
| E1C1461 | sp-4 | an-240 | E1C2682 | sp-7 | an-240 | E1C3903 | sp-11 | an-240 |
| E1C1462 | sp-4 | an-241 | E1C2683 | sp-7 | an-241 | E1C3904 | sp-11 | an-241 |
| E1C1463 | sp-4 | an-242 | E1C2684 | sp-7 | an-242 | E1C3905 | sp-11 | an-242 |
| E1C1464 | sp-4 | an-243 | E1C2685 | sp-7 | an-243 | E1C3906 | sp-11 | an-243 |
| E1C1465 | sp-4 | an-244 | E1C2686 | sp-7 | an-244 | E1C3907 | sp-11 | an-244 |
| E1C1466 | sp-4 | an-245 | E1C2687 | sp-7 | an-245 | E1C3908 | sp-11 | an-245 |
| E1C1467 | sp-4 | an-246 | E1C2688 | sp-7 | an-246 | E1C3909 | sp-11 | an-246 |
| E1C1468 | sp-4 | an-247 | E1C2689 | sp-7 | an-247 | E1C3910 | sp-11 | an-247 |
| E1C1469 | sp-4 | an-248 | E1C2690 | sp-7 | an-248 | E1C3911 | sp-11 | an-248 |
| E1C1470 | sp-4 | an-249 | E1C2691 | sp-7 | an-249 | E1C3912 | sp-11 | an-249 |
| E1C1471 | sp-4 | an-250 | E1C2692 | sp-7 | an-250 | E1C3913 | sp-11 | an-250 |
| E1C1472 | sp-4 | an-251 | E1C2693 | sp-7 | an-251 | E1C3914 | sp-11 | an-251 |
| E1C1473 | sp-4 | an-252 | E1C2694 | sp-7 | an-252 | E1C3915 | sp-11 | an-252 |
| E1C1474 | sp-4 | an-253 | E1C2695 | sp-7 | an-253 | E1C3916 | sp-11 | an-253 |
| E1C1475 | sp-4 | an-254 | E1C2696 | sp-7 | an-254 | E1C3917 | sp-11 | an-254 |
| E1C1476 | sp-4 | an-255 | E1C2697 | sp-7 | an-255 | E1C3918 | sp-11 | an-255 |
| E1C1477 | sp-4 | an-256 | E1C2698 | sp-7 | an-256 | E1C3919 | sp-11 | an-256 |
| E1C1478 | sp-4 | an-257 | E1C2699 | sp-7 | an-257 | E1C3920 | sp-11 | an-257 |
| E1C1479 | sp-4 | an-258 | E1C2700 | sp-7 | an-258 | E1C3921 | sp-11 | an-258 |
| E1C1480 | sp-4 | an-259 | E1C2701 | sp-7 | an-259 | E1C3922 | sp-11 | an-259 |
| E1C1481 | sp-4 | an-260 | E1C2702 | sp-7 | an-260 | E1C3923 | sp-11 | an-260 |
| E1C1482 | sp-4 | an-261 | E1C2703 | sp-7 | an-261 | E1C3924 | sp-11 | an-261 |
| E1C1483 | sp-4 | an-262 | E1C2704 | sp-7 | an-262 | E1C3925 | sp-11 | an-262 |
| E1C1484 | sp-4 | an-263 | E1C2705 | sp-7 | an-263 | E1C3926 | sp-11 | an-263 |
| E1C1485 | sp-4 | an-264 | E1C2706 | sp-7 | an-264 | E1C3927 | sp-11 | an-264 |
| E1C1486 | sp-4 | an-265 | E1C2707 | sp-7 | an-265 | E1C3928 | sp-11 | an-265 |
| E1C1487 | sp-4 | an-266 | E1C2708 | sp-7 | an-266 | E1C3929 | sp-11 | an-266 |
| E1C1488 | sp-4 | an-267 | E1C2709 | sp-7 | an-267 | E1C3930 | sp-11 | an-267 |
| E1C1489 | sp-4 | an-268 | E1C2710 | sp-7 | an-268 | E1C3931 | sp-11 | an-268 |
| E1C1490 | sp-4 | an-269 | E1C2711 | sp-7 | an-269 | E1C3932 | sp-11 | an-269 |
| E1C1491 | sp-4 | an-270 | E1C2712 | sp-7 | an-270 | E1C3933 | sp-11 | an-270 |
| E1C1492 | sp-4 | an-271 | E1C2713 | sp-7 | an-271 | E1C3934 | sp-11 | an-271 |
| E1C1493 | sp-4 | an-272 | E1C2714 | sp-7 | an-272 | E1C3935 | sp-11 | an-272 |
| E1C1494 | sp-4 | an-273 | E1C2715 | sp-7 | an-273 | E1C3936 | sp-11 | an-273 |
| E1C1495 | sp-4 | an-274 | E1C2716 | sp-7 | an-274 | E1C3937 | sp-11 | an-274 |
| E1C1496 | sp-4 | an-275 | E1C2717 | sp-7 | an-275 | E1C3938 | sp-11 | an-275 |
| E1C1497 | sp-4 | an-276 | E1C2718 | sp-7 | an-276 | E1C3939 | sp-11 | an-276 |
| E1C1498 | sp-4 | an-277 | E1C2719 | sp-7 | an-277 | E1C3940 | sp-11 | an-277 |
| E1C1499 | sp-4 | an-278 | E1C2720 | sp-7 | an-278 | E1C3941 | sp-11 | an-278 |
| E1C1500 | sp-4 | an-279 | E1C2721 | sp-7 | an-279 | E1C3942 | sp-11 | an-279 |
| E1C1501 | sp-4 | an-280 | E1C2722 | sp-7 | an-280 | E1C3943 | sp-11 | an-280 |
| E1C1502 | sp-4 | an-281 | E1C2723 | sp-7 | an-281 | E1C3944 | sp-11 | an-281 |
| E1C1503 | sp-4 | an-282 | E1C2724 | sp-7 | an-282 | E1C3945 | sp-11 | an-282 |
| Table 1-157 |||||||||
| Y = NHCSO ||| Y = NHCSO ||| Y = NHCSO |||
| E1C1504 | sp-4 | an-283 | E1C2725 | sp-7 | an-283 | E1C3946 | sp-11 | an-283 |
| E1C1505 | sp-4 | an-284 | E1C2726 | sp-7 | an-284 | E1C3947 | sp-11 | an-284 |
| E1C1506 | sp-4 | an-285 | E1C2727 | sp-7 | an-285 | E1C3948 | sp-11 | an-285 |
| E1C1507 | sp-4 | an-286 | E1C2728 | sp-7 | an-286 | E1C3949 | sp-11 | an-286 |
| E1C1508 | sp-4 | an-287 | E1C2729 | sp-7 | an-287 | E1C3950 | sp-11 | an-287 |
| E1C1509 | sp-4 | an-288 | E1C2730 | sp-7 | an-288 | E1C3951 | sp-11 | an-288 |
| E1C1510 | sp-4 | an-289 | E1C2731 | sp-7 | an-289 | E1C3952 | sp-11 | an-289 |
| E1C1511 | sp-4 | an-290 | E1C2732 | sp-7 | an-290 | E1C3953 | sp-11 | an-290 |
| E1C1512 | sp-4 | an-291 | E1C2733 | sp-7 | an-291 | E1C3954 | sp-11 | an-291 |
| E1C1513 | sp-4 | an-292 | E1C2734 | sp-7 | an-292 | E1C3955 | sp-11 | an-292 |
| E1C1514 | sp-4 | an-293 | E1C2735 | sp-7 | an-293 | E1C3956 | sp-11 | an-293 |
| E1C1515 | sp-4 | an-294 | E1C2736 | sp-7 | an-294 | E1C3957 | sp-11 | an-294 |
| E1C1516 | sp-4 | an-295 | E1C2737 | sp-7 | an-295 | E1C3958 | sp-11 | an-295 |
| E1C1517 | sp-4 | an-296 | E1C2738 | sp-7 | an-296 | E1C3959 | sp-11 | an-296 |
| E1C1518 | sp-4 | an-297 | E1C2739 | sp-7 | an-297 | E1C3960 | sp-11 | an-297 |
| E1C1519 | sp-4 | an-298 | E1C2740 | sp-7 | an-298 | E1C3961 | sp-11 | an-298 |

-continued

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| E1C1520 | sp-4 | an-299 | E1C2741 | sp-7 | an-299 | E1C3962 | sp-11 | an-299 |
| E1C1521 | sp-4 | an-300 | E1C2742 | sp-7 | an-300 | E1C3963 | sp-11 | an-300 |
| E1C1522 | sp-4 | an-301 | E1C2743 | sp-7 | an-301 | E1C3964 | sp-11 | an-301 |
| E1C1523 | sp-4 | an-302 | E1C2744 | sp-7 | an-302 | E1C3965 | sp-11 | an-302 |
| E1C1524 | sp-4 | an-303 | E1C2745 | sp-7 | an-303 | E1C3966 | sp-11 | an-303 |
| E1C1525 | sp-4 | an-304 | E1C2746 | sp-7 | an-304 | E1C3967 | sp-11 | an-304 |
| E1C1526 | sp-4 | an-305 | E1C2747 | sp-7 | an-305 | E1C3968 | sp-11 | an-305 |
| E1C1527 | sp-4 | an-306 | E1C2748 | sp-7 | an-306 | E1C3969 | sp-11 | an-306 |
| E1C1528 | sp-4 | an-307 | E1C2749 | sp-7 | an-307 | E1C3970 | sp-11 | an-307 |
| E1C1529 | sp-4 | an-308 | E1C2750 | sp-7 | an-308 | E1C3971 | sp-11 | an-308 |
| E1C1530 | sp-4 | an-309 | E1C2751 | sp-7 | an-309 | E1C3972 | sp-11 | an-309 |
| E1C1531 | sp-4 | an-310 | E1C2752 | sp-7 | an-310 | E1C3973 | sp-11 | an-310 |
| E1C1532 | sp-4 | an-311 | E1C2753 | sp-7 | an-311 | E1C3974 | sp-11 | an-311 |
| E1C1533 | sp-4 | an-312 | E1C2754 | sp-7 | an-312 | E1C3975 | sp-11 | an-312 |
| E1C1534 | sp-4 | an-313 | E1C2755 | sp-7 | an-313 | E1C3976 | sp-11 | an-313 |
| E1C1535 | sp-4 | an-314 | E1C2756 | sp-7 | an-314 | E1C3977 | sp-11 | an-314 |
| E1C1536 | sp-4 | an-315 | E1C2757 | sp-7 | an-315 | E1C3978 | sp-11 | an-315 |
| E1C1537 | sp-4 | an-316 | E1C2758 | sp-7 | an-316 | E1C3979 | sp-11 | an-316 |
| E1C1538 | sp-4 | an-317 | E1C2759 | sp-7 | an-317 | E1C3980 | sp-11 | an-317 |
| E1C1539 | sp-4 | an-318 | E1C2760 | sp-7 | an-318 | E1C3981 | sp-11 | an-318 |
| E1C1540 | sp-4 | an-319 | E1C2761 | sp-7 | an-319 | E1C3982 | sp-11 | an-319 |
| E1C1541 | sp-4 | an-320 | E1C2762 | sp-7 | an-320 | E1C3983 | sp-11 | an-320 |
| E1C1542 | sp-4 | an-321 | E1C2763 | sp-7 | an-321 | E1C3984 | sp-11 | an-321 |
| E1C1543 | sp-4 | an-322 | E1C2764 | sp-7 | an-322 | E1C3985 | sp-11 | an-322 |
| E1C1544 | sp-4 | an-323 | E1C2765 | sp-7 | an-323 | E1C3986 | sp-11 | an-323 |
| E1C1545 | sp-4 | an-324 | E1C2766 | sp-7 | an-324 | E1C3987 | sp-11 | an-324 |
| E1C1546 | sp-4 | an-325 | E1C2767 | sp-7 | an-325 | E1C3988 | sp-11 | an-325 |
| E1C1547 | sp-4 | an-326 | E1C2768 | sp-7 | an-326 | E1C3989 | sp-11 | an-326 |
| E1C1548 | sp-4 | an-327 | E1C2769 | sp-7 | an-327 | E1C3990 | sp-11 | an-327 |
| E1C1549 | sp-4 | an-328 | E1C2770 | sp-7 | an-328 | E1C3991 | sp-11 | an-328 |
| E1C1550 | sp-4 | an-329 | E1C2771 | sp-7 | an-329 | E1C3992 | sp-11 | an-329 |
| E1C1551 | sp-4 | an-330 | E1C2772 | sp-7 | an-330 | E1C3993 | sp-11 | an-330 |
| E1C1552 | sp-4 | an-331 | E1C2773 | sp-7 | an-331 | E1C3994 | sp-11 | an-331 |
| E1C1553 | sp-4 | an-332 | E1C2774 | sp-7 | an-332 | E1C3995 | sp-11 | an-332 |
| E1C1554 | sp-4 | an-333 | E1C2775 | sp-7 | an-333 | E1C3996 | sp-11 | an-333 |
| E1C1555 | sp-4 | an-334 | E1C2776 | sp-7 | an-334 | E1C3997 | sp-11 | an-334 |
| E1C1556 | sp-4 | an-335 | E1C2777 | sp-7 | an-335 | E1C3998 | sp-11 | an-335 |
| E1C1557 | sp-4 | an-336 | E1C2778 | sp-7 | an-336 | E1C3999 | sp-11 | an-336 |

Table 1-158

| Y = NHCSO | | | Y = NHCSO | | | Y = NHCSO | | |
|---|---|---|---|---|---|---|---|---|
| E1C1558 | sp-4 | an-337 | E1C2779 | sp-7 | an-337 | E1C4000 | sp-11 | an-337 |
| E1C1559 | sp-4 | an-338 | E1C2780 | sp-7 | an-338 | E1C4001 | sp-11 | an-338 |
| E1C1560 | sp-4 | an-339 | E1C2781 | sp-7 | an-339 | E1C4002 | sp-11 | an-339 |
| E1C1561 | sp-4 | an-340 | E1C2782 | sp-7 | an-340 | E1C4003 | sp-11 | an-340 |
| E1C1562 | sp-4 | an-341 | E1C2783 | sp-7 | an-341 | E1C4004 | sp-11 | an-341 |
| E1C1563 | sp-4 | an-342 | E1C2784 | sp-7 | an-342 | E1C4005 | sp-11 | an-342 |
| E1C1564 | sp-4 | an-343 | E1C2785 | sp-7 | an-343 | E1C4006 | sp-11 | an-343 |
| E1C1565 | sp-4 | an-344 | E1C2786 | sp-7 | an-344 | E1C4007 | sp-11 | an-344 |
| E1C1566 | sp-4 | an-345 | E1C2787 | sp-7 | an-345 | E1C4008 | sp-11 | an-345 |
| E1C1567 | sp-4 | an-346 | E1C2788 | sp-7 | an-346 | E1C4009 | sp-11 | an-346 |
| E1C1568 | sp-4 | an-347 | E1C2789 | sp-7 | an-347 | E1C4010 | sp-11 | an-347 |
| E1C1569 | sp-4 | an-348 | E1C2790 | sp-7 | an-348 | E1C4011 | sp-11 | an-348 |
| E1C1570 | sp-4 | an-349 | E1C2791 | sp-7 | an-349 | E1C4012 | sp-11 | an-349 |
| E1C1571 | sp-4 | an-350 | E1C2792 | sp-7 | an-350 | E1C4013 | sp-11 | an-350 |
| E1C1572 | sp-4 | an-351 | E1C2793 | sp-7 | an-351 | E1C4014 | sp-11 | an-351 |
| E1C1573 | sp-4 | an-352 | E1C2794 | sp-7 | an-352 | E1C4015 | sp-11 | an-352 |
| E1C1574 | sp-4 | an-353 | E1C2795 | sp-7 | an-353 | E1C4016 | sp-11 | an-353 |
| E1C1575 | sp-4 | an-354 | E1C2796 | sp-7 | an-354 | E1C4017 | sp-11 | an-354 |
| E1C1576 | sp-4 | an-355 | E1C2797 | sp-7 | an-355 | E1C4018 | sp-11 | an-355 |
| E1C1577 | sp-4 | an-356 | E1C2798 | sp-7 | an-356 | E1C4019 | sp-11 | an-356 |
| E1C1578 | sp-4 | an-357 | E1C2799 | sp-7 | an-357 | E1C4020 | sp-11 | an-357 |
| E1C1579 | sp-4 | an-358 | E1C2800 | sp-7 | an-358 | E1C4021 | sp-11 | an-358 |
| E1C1580 | sp-4 | an-359 | E1C2801 | sp-7 | an-359 | E1C4022 | sp-11 | an-359 |
| E1C1581 | sp-4 | an-360 | E1C2802 | sp-7 | an-360 | E1C4023 | sp-11 | an-360 |
| E1C1582 | sp-4 | an-361 | E1C2803 | sp-7 | an-361 | E1C4024 | sp-11 | an-361 |
| E1C1583 | sp-4 | an-362 | E1C2804 | sp-7 | an-362 | E1C4025 | sp-11 | an-362 |
| E1C1584 | sp-4 | an-363 | E1C2805 | sp-7 | an-363 | E1C4026 | sp-11 | an-363 |
| E1C1585 | sp-4 | an-364 | E1C2806 | sp-7 | an-364 | E1C4027 | sp-11 | an-364 |
| E1C1586 | sp-4 | an-365 | E1C2807 | sp-7 | an-365 | E1C4028 | sp-11 | an-365 |
| E1C1587 | sp-4 | an-366 | E1C2808 | sp-7 | an-366 | E1C4029 | sp-11 | an-366 |
| E1C1588 | sp-4 | an-367 | E1C2809 | sp-7 | an-367 | E1C4030 | sp-11 | an-367 |
| E1C1589 | sp-4 | an-368 | E1C2810 | sp-7 | an-368 | E1C4031 | sp-11 | an-368 |
| E1C1590 | sp-4 | an-369 | E1C2811 | sp-7 | an-369 | E1C4032 | sp-11 | an-369 |
| E1C1591 | sp-4 | an-370 | E1C2812 | sp-7 | an-370 | E1C4033 | sp-11 | an-370 |
| E1C1592 | sp-4 | an-371 | E1C2813 | sp-7 | an-371 | E1C4034 | sp-11 | an-371 |
| E1C1593 | sp-4 | an-372 | E1C2814 | sp-7 | an-372 | E1C4035 | sp-11 | an-372 |

-continued

| Ex. No. | $Z^a$ | $N^+R^{5a}R^{6a}R^{7a}$ | Ex. No. | $Z^a$ | $N^+R^{5a}R^{6a}R^{7a}$ | Ex. No. | $Z^a$ | $N^+R^{5a}R^{6a}R^{7a}$ |
|---|---|---|---|---|---|---|---|---|
| E1C1594 | sp-4 | an-373 | E1C2815 | sp-7 | an-373 | E1C4036 | sp-11 | an-373 |
| E1C1595 | sp-4 | an-374 | E1C2816 | sp-7 | an-374 | E1C4037 | sp-11 | an-374 |
| E1C1596 | sp-4 | an-375 | E1C2817 | sp-7 | an-375 | E1C4038 | sp-11 | an-375 |
| E1C1597 | sp-4 | an-376 | E1C2818 | sp-7 | an-376 | E1C4039 | sp-11 | an-376 |
| E1C1598 | sp-4 | an-377 | E1C2819 | sp-7 | an-377 | E1C4040 | sp-11 | an-377 |
| E1C1599 | sp-4 | an-378 | E1C2820 | sp-7 | an-378 | E1C4041 | sp-11 | an-378 |
| E1C1600 | sp-4 | an-379 | E1C2821 | sp-7 | an-379 | E1C4042 | sp-11 | an-379 |
| E1C1601 | sp-4 | an-380 | E1C2822 | sp-7 | an-380 | E1C4043 | sp-11 | an-380 |
| E1C1602 | sp-4 | an-381 | E1C2823 | sp-7 | an-381 | E1C4044 | sp-11 | an-381 |
| E1C1603 | sp-4 | an-382 | E1C2824 | sp-7 | an-382 | E1C4045 | sp-11 | an-382 |
| E1C1604 | sp-4 | an-383 | E1C2825 | sp-7 | an-383 | E1C4046 | sp-11 | an-383 |
| E1C1605 | sp-4 | an-384 | E1C2826 | sp-7 | an-384 | E1C4047 | sp-11 | an-384 |
| E1C1606 | sp-4 | an-385 | E1C2827 | sp-7 | an-385 | E1C4048 | sp-11 | an-385 |
| E1C1607 | sp-4 | an-386 | E1C2828 | sp-7 | an-386 | E1C4049 | sp-11 | an-386 |
| E1C1608 | sp-4 | an-387 | E1C2829 | sp-7 | an-387 | E1C4050 | sp-11 | an-387 |
| E1C1609 | sp-4 | an-388 | E1C2830 | sp-7 | an-388 | E1C4051 | sp-11 | an-388 |
| E1C1610 | sp-4 | an-389 | E1C2831 | sp-7 | an-389 | E1C4052 | sp-11 | an-389 |
| E1C1611 | sp-4 | an-390 | E1C2832 | sp-7 | an-390 | E1C4053 | sp-11 | an-390 |

Table 1-159

| Y = NHCSO | | | Y = NHCSO | | | Y = NHCSO | | |
|---|---|---|---|---|---|---|---|---|
| E1C1612 | sp-4 | an-391 | E1C2833 | sp-7 | an-391 | E1C4054 | sp-11 | an-391 |
| E1C1613 | sp-4 | an-392 | E1C2834 | sp-7 | an-392 | E1C4055 | sp-11 | an-392 |
| E1C1614 | sp-4 | an-393 | E1C2835 | sp-7 | an-393 | E1C4056 | sp-11 | an-393 |
| E1C1615 | sp-4 | an-394 | E1C2836 | sp-7 | an-394 | E1C4057 | sp-11 | an-394 |
| E1C1616 | sp-4 | an-395 | E1C2837 | sp-7 | an-395 | E1C4058 | sp-11 | an-395 |
| E1C1617 | sp-4 | an-396 | E1C2838 | sp-7 | an-396 | E1C4059 | sp-11 | an-396 |
| E1C1618 | sp-4 | an-397 | E1C2839 | sp-7 | an-397 | E1C4060 | sp-11 | an-397 |
| E1C1619 | sp-4 | an-398 | E1C2840 | sp-7 | an-398 | E1C4061 | sp-11 | an-398 |
| E1C1620 | sp-4 | an-399 | E1C2841 | sp-7 | an-399 | E1C4062 | sp-11 | an-399 |
| E1C1621 | sp-4 | an-400 | E1C2842 | sp-7 | an-400 | E1C4063 | sp-11 | an-400 |
| E1C1622 | sp-4 | an-401 | E1C2843 | sp-7 | an-401 | E1C4064 | sp-11 | an-401 |
| E1C1623 | sp-4 | an-402 | E1C2844 | sp-7 | an-402 | E1C4065 | sp-11 | an-402 |
| E1C1624 | sp-4 | an-403 | E1C2845 | sp-7 | an-403 | E1C4066 | sp-11 | an-403 |
| E1C1625 | sp-4 | an-404 | E1C2846 | sp-7 | an-404 | E1C4067 | sp-11 | an-404 |
| E1C1626 | sp-4 | an-405 | E1C2847 | sp-7 | an-405 | E1C4068 | sp-11 | an-405 |
| E1C1627 | sp-4 | an-406 | E1C2848 | sp-7 | an-406 | E1C4069 | sp-11 | an-406 |
| E1C1628 | sp-4 | an-407 | E1C2849 | sp-7 | an-407 | E1C4070 | sp-11 | an-407 |

Further examples are the compounds (E2A0001 to E2A6919, E2U0001 to E2U14652, E2C0001 to E2C4070) in which the binding position of Y has been changed to the para position in the compounds (E1A0001 to E1A6919, E1U0001 to E1U14652, E1C0001 to E1C4070) described in Table 1 (Table 1-1 to Table 1-159). For example, it is meant herein that the compound E1A0001 has been changed to the compound E2A0001, and the same meaning is also applied to the subsequent compounds.

Further examples are the compounds (E3A0001 to E3A6919, E3U0001 to E3U14652, E3C0001 to E3C4070) in which $(R^x)m^a$ has been changed to 7-diethylamino group in the compounds (E1A0001 to E1A6919, E1U0001 to E1U14652, E1C0001 to E1C4070) described in Table 1.

Further examples are the compounds (E4A0001 to E4A6919, E4U0001 to E4U14652, E4C0001 to E4C4070) in which $(R^x)m^a$ has been changed to 7-ethylmethylamino group in the compounds (E1A0001 to E1A6919, E1U0001 to E1U14652, E1C0001 to E1C4070) described in Table 1.

Further examples are the compounds (E5A0001 to E5A6919, E5U0001 to E5U14652, E5C0001 to E5C4070) in which $(R^x)m^a$ has been changed to 9-dimethylamino group in the compounds (E1A0001 to E1A6919, E1U0001 to E1U14652, E1C0001 to E1C4070) described in Table 1.

Further examples are the compounds (E6A0001 to E6A6919, E6U0001 to E6U14652, E6C0001 to E6C4070) in which $(R^x)m^a$ has been changed to 7,9-bis(dimethylamino) group in the compounds (E1A0001 to E1A6919, E1U0001 to E1U14652, E1C0001 to E1C4070) described in Table 1.

Further examples are the compounds (E7A0001 to E7A6919, E7U0001 to E7U14652, E7C0001 to E7C4070) in which both $R^{1a}$ and $R^{2a}$ have been changed to propyl groups in the compounds (E1A0001 to E1A6919, E1U0001 to E1U14652, E1C0001 to E1C4070) described in Table 1.

Further examples are the compounds (E8A0001 to E8A6919, E8U0001 to E8U14652, E8C0001 to E8C4070) in which both $R^{1a}$ and $R^{2a}$ have been changed to pentyl groups in the compounds (E1A0001 to E1A6919, E1U0001 to E1U14652, E1C0001 to E1C4070) described in Table 1.

Further examples are the compounds (E9A0001 to E9A6919, E9U0001 to E9U14652, E9C0001 to E9C4070) in which both $R^{1a}$ and $R^{2a}$ have been changed to hexyl groups in the compounds (E1A0001 to E1A6919, E1U0001 to E1U14652, E1C0001 to E1C4070) described in Table 1.

Further examples are the compounds (E10A0001 to E10A6919, E10U0001 to E10U14652, E10C0001 to E10C4070) in which $R^{1a}$ has been changed to ethyl group in the compounds (E1A0001 to E1A6919, E1U0001 to E1U14652, E1C0001 to E1C4070) described in Table 1.

Further examples are the compounds (E11A0001 to E11A6919, E11U0001 to E11U14652, E11C0001 to E11C4070) in which $(R^x)m^a$ has been changed to 7,8-dimethoxy group in the compounds (E1A0001 to E1A6919, E1U0001 to E1U14652, E1C0001 to E1C4070) described in Table 1.

Further examples are the compounds (E12A0001 to E12A6919, E12U0001 to E12U14652, E12C0001 to E12C4070) in which the combination of $(A^1, A^2, A^3)$ has been changed to (CH$_2$, NH, CH) in the compounds (E1A0001 to E1A6919, E1U0001 to E1U14652, E1C0001 to E1C4070) described in Table 1.

Further examples are the compounds (E13A0001 to E13A6919, E13U0001 to E13U14652, E13C0001 to E13C4070) in which the combination of (A$^1$, A$^2$, A$^3$) has been changed to (NH, CH(OH), CH) in the compounds (E1A0001 to E1A6919, E1U0001 to E1U14652, E1C0001 to E1C4070) described in Table 1.

Further examples are the compounds (E14A0001 to E14A6919, E14U0001 to E14U14652, E14C0001 to E14C4070) in which the combination of (A$^1$, A$^2$, A$^3$) has been changed to (CH$_2$, CH$_2$, N) in the compounds (E1A0001 to E1A6919, E1U0001 to E1U14652, E1C0001 to E1C4070) described in Table 1.

Further examples are the compounds (E15A0001 to E15A6919, E15U0001 to E15U14652, E15C0001 to E15C4070) in which the combination of (A$^1$, A$^2$, A$^3$) has been changed to (CH$_2$, NH, CH) and (R$^x$)m$^a$ has been changed to 7,8-dimethoxy group in the compounds (E1A0001 to E1A6919, E1U0001 to E1U14652, E1C0001 to E1C4070) described in Table 1.

Further examples are the compounds (E16A0001 to E16A6919, E16U0001 to E16U14652, E16C0001 to E16C4070) in which the combination of (A$^1$, A$^2$, A$^3$) has been changed to (NH, CH(OH), CH) and (R$^x$)m$^a$ has been changed to 7,8-dimethoxy group in the compounds (E1A0001 to E1A6919, E1U0001 to E1U14652, E1C0001 to E1C4070) described in Table 1.

Further examples are the compounds (E17A0001 to E17A6919, E17U0001 to E17U14652, E17C0001 to E17C4070) in which the combination of (A$^1$, A$^2$, A$^3$) has been changed to (CH$_2$, CH$_2$, N) and (R$^x$)m$^a$ has been changed to 7,8-dimethoxy group in the compounds (E1A0001 to E1A6919, E1U001 to E1U14652, E1C0001 to E1C4070) described in Table 1.

Further examples are the compounds (E18A0001 to E18A6919, E18U0001 to E18U14652, E18C0001 to E18C4070) in which the combination of (A$^1$, A$^2$, A$^3$) has been changed to (CH$_2$, NH, CH) and (R$^x$)m$^a$ has been changed to 7,9-bis(dimethylamino) group in the compounds (E1A0001 to E1A6919, E1U0001 to E1U14652, E1C0001 to E1C4070) described in Table 1.

Further examples are the compounds (E19A0001 to E19A6919, E19U0001 to E19U14652, E19C0001 to E19C4070) in which the combination of (A$^1$, A$^2$, A$^3$) has been changed to (NH, CH(OH), CH) and (R$^x$)m$^a$ has been changed to 7,9-bis(dimethylamino) group in the compounds (E1A0001 to E1A6919, E1U0001 to E1U14652, E1C0001 to E1C4070) described in Table 1.

Further examples are the compounds (E20A0001 to E20A6919, E20U0001 to E20U14652, E20C0001 to E20C4070) in which the combination of (A$^1$, A$^2$, A$^3$) has been changed to (CH$_2$, CH$_2$, N) and (R$^x$)m$^a$ has been changed to 7,9-bis(dimethylamino) group in the compounds (E1A0001 to E1A6919, E1U0001 to E1U14652, E1C0001 to E1C4070) described in Table 1.

Examples of the specific compounds represented by the formula (1) may include the following compounds and acid addition salts thereof.

Examples of the compounds in which both R$^1$ and R$^2$ are butyl groups, (R$^3$R$^4$N)$_m$ is 7-dimethylamino group, X$^-$ is Br$^-$ and the binding position of Y is the meta position may include the compounds described in Table 2 (1A0001 to 1A6681, 1U0001 to 1U6681, 1C0001 to 1C3930). In Table 2, (sp-1) to (sp-25) and (an-1) to (an-393) are the same as the above.

| Ex. No. | Z | N$^+$R$^5$R$^6$R$^7$ | Ex. No. | Z | N$^+$R$^5$R$^6$R$^7$ | Ex. No. | Z | N$^+$R$^5$R$^6$R$^7$ |
|---|---|---|---|---|---|---|---|---|
| Table 2-1 ||||||||||
| Y = NHCS ||| Y = NHCSNH ||| Y = NHCSO |||
| 1A0001 | sp-1 | an-1 | 1U0001 | sp-1 | an-1 | 1C0001 | sp-1 | an-1 |
| 1A0002 | sp-1 | an-2 | 1U0002 | sp-1 | an-2 | 1C0002 | sp-1 | an-2 |
| 1A0003 | sp-1 | an-3 | 1U0003 | sp-1 | an-3 | 1C0003 | sp-1 | an-3 |
| 1A0004 | sp-1 | an-4 | 1U0004 | sp-1 | an-4 | 1C0004 | sp-1 | an-4 |
| 1A0005 | sp-1 | an-5 | 1U0005 | sp-1 | an-5 | 1C0005 | sp-1 | an-5 |
| 1A0006 | sp-1 | an-6 | 1U0006 | sp-1 | an-6 | 1C0006 | sp-1 | an-6 |
| 1A0007 | sp-1 | an-7 | 1U0007 | sp-1 | an-7 | 1C0007 | sp-1 | an-7 |
| 1A0008 | sp-1 | an-8 | 1U0008 | sp-1 | an-8 | 1C0008 | sp-1 | an-8 |
| 1A0009 | sp-1 | an-9 | 1U0009 | sp-1 | an-9 | 1C0009 | sp-1 | an-9 |
| 1A0010 | sp-1 | an-10 | 1U0010 | sp-1 | an-10 | 1C0010 | sp-1 | an-10 |
| 1A0011 | sp-1 | an-11 | 1U0011 | sp-1 | an-11 | 1C0011 | sp-1 | an-11 |
| 1A0012 | sp-1 | an-12 | 1U0012 | sp-1 | an-12 | 1C0012 | sp-1 | an-12 |
| 1A0013 | sp-1 | an-13 | 1U0013 | sp-1 | an-13 | 1C0013 | sp-1 | an-13 |
| 1A0014 | sp-1 | an-14 | 1U0014 | sp-1 | an-14 | 1C0014 | sp-1 | an-14 |
| 1A0015 | sp-1 | an-15 | 1U0015 | sp-1 | an-15 | 1C0015 | sp-1 | an-15 |
| 1A0016 | sp-1 | an-16 | 1U0016 | sp-1 | an-16 | 1C0016 | sp-1 | an-16 |
| 1A0017 | sp-1 | an-17 | 1U0017 | sp-1 | an-17 | 1C0017 | sp-1 | an-17 |
| 1A0018 | sp-1 | an-18 | 1U0018 | sp-1 | an-18 | 1C0018 | sp-1 | an-18 |
| 1A0019 | sp-1 | an-19 | 1U0019 | sp-1 | an-19 | 1C0019 | sp-1 | an-19 |
| 1A0020 | sp-1 | an-20 | 1U0020 | sp-1 | an-20 | 1C0020 | sp-1 | an-20 |
| 1A0021 | sp-1 | an-21 | 1U0021 | sp-1 | an-21 | 1C0021 | sp-1 | an-21 |
| 1A0022 | sp-1 | an-22 | 1U0022 | sp-1 | an-22 | 1C0022 | sp-1 | an-22 |
| 1A0023 | sp-1 | an-23 | 1U0023 | sp-1 | an-23 | 1C0023 | sp-1 | an-23 |
| 1A0024 | sp-1 | an-24 | 1U0024 | sp-1 | an-24 | 1C0024 | sp-1 | an-24 |
| 1A0025 | sp-1 | an-25 | 1U0025 | sp-1 | an-25 | 1C0025 | sp-1 | an-25 |
| 1A0026 | sp-1 | an-26 | 1U0026 | sp-1 | an-26 | 1C0026 | sp-1 | an-26 |
| 1A0027 | sp-1 | an-27 | 1U0027 | sp-1 | an-27 | 1C0027 | sp-1 | an-27 |
| 1A0028 | sp-1 | an-28 | 1U0028 | sp-1 | an-28 | 1C0028 | sp-1 | an-28 |
| 1A0029 | sp-1 | an-29 | 1U0029 | sp-1 | an-29 | 1C0029 | sp-1 | an-29 |
| 1A0030 | sp-1 | an-30 | 1U0030 | sp-1 | an-30 | 1C0030 | sp-1 | an-30 |
| 1A0031 | sp-1 | an-31 | 1U0031 | sp-1 | an-31 | 1C0031 | sp-1 | an-31 |
| 1A0032 | sp-1 | an-32 | 1U0032 | sp-1 | an-32 | 1C0032 | sp-1 | an-32 |

-continued

| Ex. No. | Z | $N^+R^5R^6R^7$ | Ex. No. | Z | $N^+R^5R^6R^7$ | Ex. No. | Z | $N^+R^5R^6R^7$ |
|---|---|---|---|---|---|---|---|---|
| 1A0033 | sp-1 | an-33 | 1U0033 | sp-1 | an-33 | 1C0033 | sp-1 | an-33 |
| 1A0034 | sp-1 | an-34 | 1U0034 | sp-1 | an-34 | 1C0034 | sp-1 | an-34 |
| 1A0035 | sp-1 | an-35 | 1U0035 | sp-1 | an-35 | 1C0035 | sp-1 | an-35 |
| 1A0036 | sp-1 | an-36 | 1U0036 | sp-1 | an-36 | 1C0036 | sp-1 | an-36 |
| 1A0037 | sp-1 | an-37 | 1U0037 | sp-1 | an-37 | 1C0037 | sp-1 | an-37 |
| 1A0038 | sp-1 | an-38 | 1U0038 | sp-1 | an-38 | 1C0038 | sp-1 | an-38 |
| 1A0039 | sp-1 | an-39 | 1U0039 | sp-1 | an-39 | 1C0039 | sp-1 | an-39 |
| 1A0040 | sp-1 | an-40 | 1U0040 | sp-1 | an-40 | 1C0040 | sp-1 | an-40 |
| 1A0041 | sp-1 | an-41 | 1U0041 | sp-1 | an-41 | 1C0041 | sp-1 | an-41 |
| 1A0042 | sp-1 | an-42 | 1U0042 | sp-1 | an-42 | 1C0042 | sp-1 | an-42 |
| 1A0043 | sp-1 | an-43 | 1U0043 | sp-1 | an-43 | 1C0043 | sp-1 | an-43 |
| 1A0044 | sp-1 | an-44 | 1U0044 | sp-1 | an-44 | 1C0044 | sp-1 | an-44 |
| 1A0045 | sp-1 | an-45 | 1U0045 | sp-1 | an-45 | 1C0045 | sp-1 | an-45 |
| 1A0046 | sp-1 | an-46 | 1U0046 | sp-1 | an-46 | 1C0046 | sp-1 | an-46 |
| 1A0047 | sp-1 | an-47 | 1U0047 | sp-1 | an-47 | 1C0047 | sp-1 | an-47 |
| 1A0048 | sp-1 | an-48 | 1U0048 | sp-1 | an-48 | 1C0048 | sp-1 | an-48 |
| 1A0049 | sp-1 | an-49 | 1U0049 | sp-1 | an-49 | 1C0049 | sp-1 | an-49 |
| 1A0050 | sp-1 | an-50 | 1U0050 | sp-1 | an-50 | 1C0050 | sp-1 | an-50 |
| 1A0051 | sp-1 | an-51 | 1U0051 | sp-1 | an-51 | 1C0051 | sp-1 | an-51 |
| 1A0052 | sp-1 | an-52 | 1U0052 | sp-1 | an-52 | 1C0052 | sp-1 | an-52 |
| 1A0053 | sp-1 | an-53 | 1U0053 | sp-1 | an-53 | 1C0053 | sp-1 | an-53 |
| 1A0054 | sp-1 | an-54 | 1U0054 | sp-1 | an-54 | 1C0054 | sp-1 | an-54 |
| 1A0055 | sp-1 | an-55 | 1U0055 | sp-1 | an-55 | 1C0055 | sp-1 | an-55 |
| 1A0056 | sp-1 | an-56 | 1U0056 | sp-1 | an-56 | 1C0056 | sp-1 | an-56 |

Table 2-2

| Y = NHCS | | | Y = NHCSNH | | | Y = NHCSO | | |
|---|---|---|---|---|---|---|---|---|
| 1A0057 | sp-1 | an-57 | 1U0057 | sp-1 | an-57 | 1C0057 | sp-1 | an-57 |
| 1A0058 | sp-1 | an-58 | 1U0058 | sp-1 | an-58 | 1C0058 | sp-1 | an-58 |
| 1A0059 | sp-1 | an-59 | 1U0059 | sp-1 | an-59 | 1C0059 | sp-1 | an-59 |
| 1A0060 | sp-1 | an-60 | 1U0060 | sp-1 | an-60 | 1C0060 | sp-1 | an-60 |
| 1A0061 | sp-1 | an-61 | 1U0061 | sp-1 | an-61 | 1C0061 | sp-1 | an-61 |
| 1A0062 | sp-1 | an-62 | 1U0062 | sp-1 | an-62 | 1C0062 | sp-1 | an-62 |
| 1A0063 | sp-1 | an-63 | 1U0063 | sp-1 | an-63 | 1C0063 | sp-1 | an-63 |
| 1A0064 | sp-1 | an-64 | 1U0064 | sp-1 | an-64 | 1C0064 | sp-1 | an-64 |
| 1A0065 | sp-1 | an-65 | 1U0065 | sp-1 | an-65 | 1C0065 | sp-1 | an-65 |
| 1A0066 | sp-1 | an-66 | 1U0066 | sp-1 | an-66 | 1C0066 | sp-1 | an-66 |
| 1A0067 | sp-1 | an-67 | 1U0067 | sp-1 | an-67 | 1C0067 | sp-1 | an-67 |
| 1A0068 | sp-1 | an-68 | 1U0068 | sp-1 | an-68 | 1C0068 | sp-1 | an-68 |
| 1A0069 | sp-1 | an-69 | 1U0069 | sp-1 | an-69 | 1C0069 | sp-1 | an-69 |
| 1A0070 | sp-1 | an-70 | 1U0070 | sp-1 | an-70 | 1C0070 | sp-1 | an-70 |
| 1A0071 | sp-1 | an-71 | 1U0071 | sp-1 | an-71 | 1C0071 | sp-1 | an-71 |
| 1A0072 | sp-1 | an-72 | 1U0072 | sp-1 | an-72 | 1C0072 | sp-1 | an-72 |
| 1A0073 | sp-1 | an-73 | 1U0073 | sp-1 | an-73 | 1C0073 | sp-1 | an-73 |
| 1A0074 | sp-1 | an-74 | 1U0074 | sp-1 | an-74 | 1C0074 | sp-1 | an-74 |
| 1A0075 | sp-1 | an-75 | 1U0075 | sp-1 | an-75 | 1C0075 | sp-1 | an-75 |
| 1A0076 | sp-1 | an-76 | 1U0076 | sp-1 | an-76 | 1C0076 | sp-1 | an-76 |
| 1A0077 | sp-1 | an-77 | 1U0077 | sp-1 | an-77 | 1C0077 | sp-1 | an-77 |
| 1A0078 | sp-1 | an-78 | 1U0078 | sp-1 | an-78 | 1C0078 | sp-1 | an-78 |
| 1A0079 | sp-1 | an-79 | 1U0079 | sp-1 | an-79 | 1C0079 | sp-1 | an-79 |
| 1A0080 | sp-1 | an-80 | 1U0080 | sp-1 | an-80 | 1C0080 | sp-1 | an-80 |
| 1A0081 | sp-1 | an-81 | 1U0081 | sp-1 | an-81 | 1C0081 | sp-1 | an-81 |
| 1A0082 | sp-1 | an-82 | 1U0082 | sp-1 | an-82 | 1C0082 | sp-1 | an-82 |
| 1A0083 | sp-1 | an-83 | 1U0083 | sp-1 | an-83 | 1C0083 | sp-1 | an-83 |
| 1A0084 | sp-1 | an-84 | 1U0084 | sp-1 | an-84 | 1C0084 | sp-1 | an-84 |
| 1A0085 | sp-1 | an-85 | 1U0085 | sp-1 | an-85 | 1C0085 | sp-1 | an-85 |
| 1A0086 | sp-1 | an-86 | 1U0086 | sp-1 | an-86 | 1C0086 | sp-1 | an-86 |
| 1A0087 | sp-1 | an-87 | 1U0087 | sp-1 | an-87 | 1C0087 | sp-1 | an-87 |
| 1A0088 | sp-1 | an-88 | 1U0088 | sp-1 | an-88 | 1C0088 | sp-1 | an-88 |
| 1A0089 | sp-1 | an-89 | 1U0089 | sp-1 | an-89 | 1C0089 | sp-1 | an-89 |
| 1A0090 | sp-1 | an-90 | 1U0090 | sp-1 | an-90 | 1C0090 | sp-1 | an-90 |
| 1A0091 | sp-1 | an-91 | 1U0091 | sp-1 | an-91 | 1C0091 | sp-1 | an-91 |
| 1A0092 | sp-1 | an-92 | 1U0092 | sp-1 | an-92 | 1C0092 | sp-1 | an-92 |
| 1A0093 | sp-1 | an-93 | 1U0093 | sp-1 | an-93 | 1C0093 | sp-1 | an-93 |
| 1A0094 | sp-1 | an-94 | 1U0094 | sp-1 | an-94 | 1C0094 | sp-1 | an-94 |
| 1A0095 | sp-1 | an-95 | 1U0095 | sp-1 | an-95 | 1C0095 | sp-1 | an-95 |
| 1A0096 | sp-1 | an-96 | 1U0096 | sp-1 | an-96 | 1C0096 | sp-1 | an-96 |
| 1A0097 | sp-1 | an-97 | 1U0097 | sp-1 | an-97 | 1C0097 | sp-1 | an-97 |
| 1A0098 | sp-1 | an-98 | 1U0098 | sp-1 | an-98 | 1C0098 | sp-1 | an-98 |
| 1A0099 | sp-1 | an-99 | 1U0099 | sp-1 | an-99 | 1C0099 | sp-1 | an-99 |
| 1A0100 | sp-1 | an-100 | 1U0100 | sp-1 | an-100 | 1C0100 | sp-1 | an-100 |
| 1A0101 | sp-1 | an-101 | 1U0101 | sp-1 | an-101 | 1C0101 | sp-1 | an-101 |
| 1A0102 | sp-1 | an-102 | 1U0102 | sp-1 | an-102 | 1C0102 | sp-1 | an-102 |
| 1A0103 | sp-1 | an-103 | 1U0103 | sp-1 | an-103 | 1C0103 | sp-1 | an-103 |
| 1A0104 | sp-1 | an-104 | 1U0104 | sp-1 | an-104 | 1C0104 | sp-1 | an-104 |
| 1A0105 | sp-1 | an-105 | 1U0105 | sp-1 | an-105 | 1C0105 | sp-1 | an-105 |
| 1A0106 | sp-1 | an-106 | 1U0106 | sp-1 | an-106 | 1C0106 | sp-1 | an-106 |

| Ex. No. | Z | N⁺R⁵R⁶R⁷ | Ex. No. | Z | N⁺R⁵R⁶R⁷ | Ex. No. | Z | N⁺R⁵R⁶R⁷ |
|---|---|---|---|---|---|---|---|---|
| 1A0107 | sp-1 | an-107 | 1U0107 | sp-1 | an-107 | 1C0107 | sp-1 | an-107 |
| 1A0108 | sp-1 | an-108 | 1U0108 | sp-1 | an-108 | 1C0108 | sp-1 | an-108 |
| 1A0109 | sp-1 | an-109 | 1U0109 | sp-1 | an-109 | 1C0109 | sp-1 | an-109 |
| 1A0110 | sp-1 | an-110 | 1U0110 | sp-1 | an-110 | 1C0110 | sp-1 | an-110 |
| 1A0111 | sp-1 | an-111 | 1U0111 | sp-1 | an-111 | 1C0111 | sp-1 | an-111 |
| 1A0112 | sp-1 | an-112 | 1U0112 | sp-1 | an-112 | 1C0112 | sp-1 | an-112 |

Table 2-3

| Y = NHCS | | | Y = NHCSNH | | | Y = NHCSO | | |
|---|---|---|---|---|---|---|---|---|
| 1A0113 | sp-1 | an-113 | 1U0113 | sp-1 | an-113 | 1C0113 | sp-1 | an-113 |
| 1A0114 | sp-1 | an-114 | 1U0114 | sp-1 | an-114 | 1C0114 | sp-1 | an-114 |
| 1A0115 | sp-1 | an-115 | 1U0115 | sp-1 | an-115 | 1C0115 | sp-1 | an-115 |
| 1A0116 | sp-1 | an-116 | 1U0116 | sp-1 | an-116 | 1C0116 | sp-1 | an-116 |
| 1A0117 | sp-1 | an-117 | 1U0117 | sp-1 | an-117 | 1C0117 | sp-1 | an-117 |
| 1A0118 | sp-1 | an-118 | 1U0118 | sp-1 | an-118 | 1C0118 | sp-1 | an-118 |
| 1A0119 | sp-1 | an-119 | 1U0119 | sp-1 | an-119 | 1C0119 | sp-1 | an-119 |
| 1A0120 | sp-1 | an-120 | 1U0120 | sp-1 | an-120 | 1C0120 | sp-1 | an-120 |
| 1A0121 | sp-1 | an-121 | 1U0121 | sp-1 | an-121 | 1C0121 | sp-1 | an-121 |
| 1A0122 | sp-1 | an-122 | 1U0122 | sp-1 | an-122 | 1C0122 | sp-1 | an-122 |
| 1A0123 | sp-1 | an-123 | 1U0123 | sp-1 | an-123 | 1C0123 | sp-1 | an-123 |
| 1A0124 | sp-1 | an-124 | 1U0124 | sp-1 | an-124 | 1C0124 | sp-1 | an-124 |
| 1A0125 | sp-1 | an-125 | 1U0125 | sp-1 | an-125 | 1C0125 | sp-1 | an-125 |
| 1A0126 | sp-1 | an-126 | 1U0126 | sp-1 | an-126 | 1C0126 | sp-1 | an-126 |
| 1A0127 | sp-1 | an-127 | 1U0127 | sp-1 | an-127 | 1C0127 | sp-1 | an-127 |
| 1A0128 | sp-1 | an-128 | 1U0128 | sp-1 | an-128 | 1C0128 | sp-1 | an-128 |
| 1A0129 | sp-1 | an-129 | 1U0129 | sp-1 | an-129 | 1C0129 | sp-1 | an-129 |
| 1A0130 | sp-1 | an-130 | 1U0130 | sp-1 | an-130 | 1C0130 | sp-1 | an-130 |
| 1A0131 | sp-1 | an-131 | 1U0131 | sp-1 | an-131 | 1C0131 | sp-1 | an-131 |
| 1A0132 | sp-1 | an-132 | 1U0132 | sp-1 | an-132 | 1C0132 | sp-1 | an-132 |
| 1A0133 | sp-1 | an-133 | 1U0133 | sp-1 | an-133 | 1C0133 | sp-1 | an-133 |
| 1A0134 | sp-1 | an-134 | 1U0134 | sp-1 | an-134 | 1C0134 | sp-1 | an-134 |
| 1A0135 | sp-1 | an-135 | 1U0135 | sp-1 | an-135 | 1C0135 | sp-1 | an-135 |
| 1A0136 | sp-1 | an-136 | 1U0136 | sp-1 | an-136 | 1C0136 | sp-1 | an-136 |
| 1A0137 | sp-1 | an-137 | 1U0137 | sp-1 | an-137 | 1C0137 | sp-1 | an-137 |
| 1A0138 | sp-1 | an-138 | 1U0138 | sp-1 | an-138 | 1C0138 | sp-1 | an-138 |
| 1A0139 | sp-1 | an-139 | 1U0139 | sp-1 | an-139 | 1C0139 | sp-1 | an-139 |
| 1A0140 | sp-1 | an-140 | 1U0140 | sp-1 | an-140 | 1C0140 | sp-1 | an-140 |
| 1A0141 | sp-1 | an-141 | 1U0141 | sp-1 | an-141 | 1C0141 | sp-1 | an-141 |
| 1A0142 | sp-1 | an-142 | 1U0142 | sp-1 | an-142 | 1C0142 | sp-1 | an-142 |
| 1A0143 | sp-1 | an-143 | 1U0143 | sp-1 | an-143 | 1C0143 | sp-1 | an-143 |
| 1A0144 | sp-1 | an-144 | 1U0144 | sp-1 | an-144 | 1C0144 | sp-1 | an-144 |
| 1A0145 | sp-1 | an-145 | 1U0145 | sp-1 | an-145 | 1C0145 | sp-1 | an-145 |
| 1A0146 | sp-1 | an-146 | 1U0146 | sp-1 | an-146 | 1C0146 | sp-1 | an-146 |
| 1A0147 | sp-1 | an-147 | 1U0147 | sp-1 | an-147 | 1C0147 | sp-1 | an-147 |
| 1A0148 | sp-1 | an-148 | 1U0148 | sp-1 | an-148 | 1C0148 | sp-1 | an-148 |
| 1A0149 | sp-1 | an-149 | 1U0149 | sp-1 | an-149 | 1C0149 | sp-1 | an-149 |
| 1A0150 | sp-1 | an-150 | 1U0150 | sp-1 | an-150 | 1C0150 | sp-1 | an-150 |
| 1A0151 | sp-1 | an-151 | 1U0151 | sp-1 | an-151 | 1C0151 | sp-1 | an-151 |
| 1A0152 | sp-1 | an-152 | 1U0152 | sp-1 | an-152 | 1C0152 | sp-1 | an-152 |
| 1A0153 | sp-1 | an-153 | 1U0153 | sp-1 | an-153 | 1C0153 | sp-1 | an-153 |
| 1A0154 | sp-1 | an-154 | 1U0154 | sp-1 | an-154 | 1C0154 | sp-1 | an-154 |
| 1A0155 | sp-1 | an-155 | 1U0155 | sp-1 | an-155 | 1C0155 | sp-1 | an-155 |
| 1A0156 | sp-1 | an-156 | 1U0156 | sp-1 | an-156 | 1C0156 | sp-1 | an-156 |
| 1A0157 | sp-1 | an-157 | 1U0157 | sp-1 | an-157 | 1C0157 | sp-1 | an-157 |
| 1A0158 | sp-1 | an-158 | 1U0158 | sp-1 | an-158 | 1C0158 | sp-1 | an-158 |
| 1A0159 | sp-1 | an-159 | 1U0159 | sp-1 | an-159 | 1C0159 | sp-1 | an-159 |
| 1A0160 | sp-1 | an-160 | 1U0160 | sp-1 | an-160 | 1C0160 | sp-1 | an-160 |
| 1A0161 | sp-1 | an-161 | 1U0161 | sp-1 | an-161 | 1C0161 | sp-1 | an-161 |
| 1A0162 | sp-1 | an-162 | 1U0162 | sp-1 | an-162 | 1C0162 | sp-1 | an-162 |
| 1A0163 | sp-1 | an-163 | 1U0163 | sp-1 | an-163 | 1C0163 | sp-1 | an-163 |
| 1A0164 | sp-1 | an-164 | 1U0164 | sp-1 | an-164 | 1C0164 | sp-1 | an-164 |
| 1A0165 | sp-1 | an-165 | 1U0165 | sp-1 | an-165 | 1C0165 | sp-1 | an-165 |
| 1A0166 | sp-1 | an-166 | 1U0166 | sp-1 | an-166 | 1C0166 | sp-1 | an-166 |
| 1A0167 | sp-1 | an-167 | 1U0167 | sp-1 | an-167 | 1C0167 | sp-1 | an-167 |
| 1A0168 | sp-1 | an-168 | 1U0168 | sp-1 | an-168 | 1C0168 | sp-1 | an-168 |

Table 2-4

| Y = NHCS | | | Y = NHCSNH | | | Y = NHCSO | | |
|---|---|---|---|---|---|---|---|---|
| 1A0169 | sp-1 | an-169 | 1U0169 | sp-1 | an-169 | 1C0169 | sp-1 | an-169 |
| 1A0170 | sp-1 | an-170 | 1U0170 | sp-1 | an-170 | 1C0170 | sp-1 | an-170 |
| 1A0171 | sp-1 | an-171 | 1U0171 | sp-1 | an-171 | 1C0171 | sp-1 | an-171 |
| 1A0172 | sp-1 | an-172 | 1U0172 | sp-1 | an-172 | 1C0172 | sp-1 | an-172 |
| 1A0173 | sp-1 | an-173 | 1U0173 | sp-1 | an-173 | 1C0173 | sp-1 | an-173 |
| 1A0174 | sp-1 | an-174 | 1U0174 | sp-1 | an-174 | 1C0174 | sp-1 | an-174 |
| 1A0175 | sp-1 | an-175 | 1U0175 | sp-1 | an-175 | 1C0175 | sp-1 | an-175 |
| 1A0176 | sp-1 | an-176 | 1U0176 | sp-1 | an-176 | 1C0176 | sp-1 | an-176 |

-continued

| Ex. No. | Z | N⁺R⁵R⁶R⁷ | Ex. No. | Z | N⁺R⁵R⁶R⁷ | Ex. No. | Z | N⁺R⁵R⁶R⁷ |
|---|---|---|---|---|---|---|---|---|
| 1A0177 | sp-1 | an-177 | 1U0177 | sp-1 | an-177 | 1C0177 | sp-1 | an-177 |
| 1A0178 | sp-1 | an-178 | 1U0178 | sp-1 | an-178 | 1C0178 | sp-1 | an-178 |
| 1A0179 | sp-1 | an-179 | 1U0179 | sp-1 | an-179 | 1C0179 | sp-1 | an-179 |
| 1A0180 | sp-1 | an-180 | 1U0180 | sp-1 | an-180 | 1C0180 | sp-1 | an-180 |
| 1A0181 | sp-1 | an-181 | 1U0181 | sp-1 | an-181 | 1C0181 | sp-1 | an-181 |
| 1A0182 | sp-1 | an-182 | 1U0182 | sp-1 | an-182 | 1C0182 | sp-1 | an-182 |
| 1A0183 | sp-1 | an-183 | 1U0183 | sp-1 | an-183 | 1C0183 | sp-1 | an-183 |
| 1A0184 | sp-1 | an-184 | 1U0184 | sp-1 | an-184 | 1C0184 | sp-1 | an-184 |
| 1A0185 | sp-1 | an-185 | 1U0185 | sp-1 | an-185 | 1C0185 | sp-1 | an-185 |
| 1A0186 | sp-1 | an-186 | 1U0186 | sp-1 | an-186 | 1C0186 | sp-1 | an-186 |
| 1A0187 | sp-1 | an-187 | 1U0187 | sp-1 | an-187 | 1C0187 | sp-1 | an-187 |
| 1A0188 | sp-1 | an-188 | 1U0188 | sp-1 | an-188 | 1C0188 | sp-1 | an-188 |
| 1A0189 | sp-1 | an-189 | 1U0189 | sp-1 | an-189 | 1C0189 | sp-1 | an-189 |
| 1A0190 | sp-1 | an-190 | 1U0190 | sp-1 | an-190 | 1C0190 | sp-1 | an-190 |
| 1A0191 | sp-1 | an-191 | 1U0191 | sp-1 | an-191 | 1C0191 | sp-1 | an-191 |
| 1A0192 | sp-1 | an-192 | 1U0192 | sp-1 | an-192 | 1C0192 | sp-1 | an-192 |
| 1A0193 | sp-1 | an-193 | 1U0193 | sp-1 | an-193 | 1C0193 | sp-1 | an-193 |
| 1A0194 | sp-1 | an-194 | 1U0194 | sp-1 | an-194 | 1C0194 | sp-1 | an-194 |
| 1A0195 | sp-1 | an-195 | 1U0195 | sp-1 | an-195 | 1C0195 | sp-1 | an-195 |
| 1A0196 | sp-1 | an-196 | 1U0196 | sp-1 | an-196 | 1C0196 | sp-1 | an-196 |
| 1A0197 | sp-1 | an-197 | 1U0197 | sp-1 | an-197 | 1C0197 | sp-1 | an-197 |
| 1A0198 | sp-1 | an-198 | 1U0198 | sp-1 | an-198 | 1C0198 | sp-1 | an-198 |
| 1A0199 | sp-1 | an-199 | 1U0199 | sp-1 | an-199 | 1C0199 | sp-1 | an-199 |
| 1A0200 | sp-1 | an-200 | 1U0200 | sp-1 | an-200 | 1C0200 | sp-1 | an-200 |
| 1A0201 | sp-1 | an-201 | 1U0201 | sp-1 | an-201 | 1C0201 | sp-1 | an-201 |
| 1A0202 | sp-1 | an-202 | 1U0202 | sp-1 | an-202 | 1C0202 | sp-1 | an-202 |
| 1A0203 | sp-1 | an-203 | 1U0203 | sp-1 | an-203 | 1C0203 | sp-1 | an-203 |
| 1A0204 | sp-1 | an-204 | 1U0204 | sp-1 | an-204 | 1C0204 | sp-1 | an-204 |
| 1A0205 | sp-1 | an-205 | 1U0205 | sp-1 | an-205 | 1C0205 | sp-1 | an-205 |
| 1A0206 | sp-1 | an-206 | 1U0206 | sp-1 | an-206 | 1C0206 | sp-1 | an-206 |
| 1A0207 | sp-1 | an-207 | 1U0207 | sp-1 | an-207 | 1C0207 | sp-1 | an-207 |
| 1A0208 | sp-1 | an-208 | 1U0208 | sp-1 | an-208 | 1C0208 | sp-1 | an-208 |
| 1A0209 | sp-1 | an-209 | 1U0209 | sp-1 | an-209 | 1C0209 | sp-1 | an-209 |
| 1A0210 | sp-1 | an-210 | 1U0210 | sp-1 | an-210 | 1C0210 | sp-1 | an-210 |
| 1A0211 | sp-1 | an-211 | 1U0211 | sp-1 | an-211 | 1C0211 | sp-1 | an-211 |
| 1A0212 | sp-1 | an-212 | 1U0212 | sp-1 | an-212 | 1C0212 | sp-1 | an-212 |
| 1A0213 | sp-1 | an-213 | 1U0213 | sp-1 | an-213 | 1C0213 | sp-1 | an-213 |
| 1A0214 | sp-1 | an-214 | 1U0214 | sp-1 | an-214 | 1C0214 | sp-1 | an-214 |
| 1A0215 | sp-1 | an-215 | 1U0215 | sp-1 | an-215 | 1C0215 | sp-1 | an-215 |
| 1A0216 | sp-1 | an-216 | 1U0216 | sp-1 | an-216 | 1C0216 | sp-1 | an-216 |
| 1A0217 | sp-1 | an-217 | 1U0217 | sp-1 | an-217 | 1C0217 | sp-1 | an-217 |
| 1A0218 | sp-1 | an-218 | 1U0218 | sp-1 | an-218 | 1C0218 | sp-1 | an-218 |
| 1A0219 | sp-1 | an-219 | 1U0219 | sp-1 | an-219 | 1C0219 | sp-1 | an-219 |
| 1A0220 | sp-1 | an-220 | 1U0220 | sp-1 | an-220 | 1C0220 | sp-1 | an-220 |
| 1A0221 | sp-1 | an-221 | 1U0221 | sp-1 | an-221 | 1C0221 | sp-1 | an-221 |
| 1A0222 | sp-1 | an-222 | 1U0222 | sp-1 | an-222 | 1C0222 | sp-1 | an-222 |
| 1A0223 | sp-1 | an-223 | 1U0223 | sp-1 | an-223 | 1C0223 | sp-1 | an-223 |
| 1A0224 | sp-1 | an-224 | 1U0224 | sp-1 | an-224 | 1C0224 | sp-1 | an-224 |

Table 2-5

| Y = NHCS | | | Y = NHCSNH | | | Y = NHCSO | | |
|---|---|---|---|---|---|---|---|---|
| 1A0225 | sp-1 | an-225 | 1U0225 | sp-1 | an-225 | 1C0225 | sp-1 | an-225 |
| 1A0226 | sp-1 | an-226 | 1U0226 | sp-1 | an-226 | 1C0226 | sp-1 | an-226 |
| 1A0227 | sp-1 | an-227 | 1U0227 | sp-1 | an-227 | 1C0227 | sp-1 | an-227 |
| 1A0228 | sp-1 | an-228 | 1U0228 | sp-1 | an-228 | 1C0228 | sp-1 | an-228 |
| 1A0229 | sp-1 | an-229 | 1U0229 | sp-1 | an-229 | 1C0229 | sp-1 | an-229 |
| 1A0230 | sp-1 | an-230 | 1U0230 | sp-1 | an-230 | 1C0230 | sp-1 | an-230 |
| 1A0231 | sp-1 | an-231 | 1U0231 | sp-1 | an-231 | 1C0231 | sp-1 | an-231 |
| 1A0232 | sp-1 | an-232 | 1U0232 | sp-1 | an-232 | 1C0232 | sp-1 | an-232 |
| 1A0233 | sp-1 | an-233 | 1U0233 | sp-1 | an-233 | 1C0233 | sp-1 | an-233 |
| 1A0234 | sp-1 | an-234 | 1U0234 | sp-1 | an-234 | 1C0234 | sp-1 | an-234 |
| 1A0235 | sp-1 | an-235 | 1U0235 | sp-1 | an-235 | 1C0235 | sp-1 | an-235 |
| 1A0236 | sp-1 | an-236 | 1U0236 | sp-1 | an-236 | 1C0236 | sp-1 | an-236 |
| 1A0237 | sp-1 | an-237 | 1U0237 | sp-1 | an-237 | 1C0237 | sp-1 | an-237 |
| 1A0238 | sp-1 | an-238 | 1U0238 | sp-1 | an-238 | 1C0238 | sp-1 | an-238 |
| 1A0239 | sp-1 | an-239 | 1U0239 | sp-1 | an-239 | 1C0239 | sp-1 | an-239 |
| 1A0240 | sp-1 | an-240 | 1U0240 | sp-1 | an-240 | 1C0240 | sp-1 | an-240 |
| 1A0241 | sp-1 | an-241 | 1U0241 | sp-1 | an-241 | 1C0241 | sp-1 | an-241 |
| 1A0242 | sp-1 | an-242 | 1U0242 | sp-1 | an-242 | 1C0242 | sp-1 | an-242 |
| 1A0243 | sp-1 | an-243 | 1U0243 | sp-1 | an-243 | 1C0243 | sp-1 | an-243 |
| 1A0244 | sp-1 | an-244 | 1U0244 | sp-1 | an-244 | 1C0244 | sp-1 | an-244 |
| 1A0245 | sp-1 | an-245 | 1U0245 | sp-1 | an-245 | 1C0245 | sp-1 | an-245 |
| 1A0246 | sp-1 | an-246 | 1U0246 | sp-1 | an-246 | 1C0246 | sp-1 | an-246 |
| 1A0247 | sp-1 | an-247 | 1U0247 | sp-1 | an-247 | 1C0247 | sp-1 | an-247 |
| 1A0248 | sp-1 | an-248 | 1U0248 | sp-1 | an-248 | 1C0248 | sp-1 | an-248 |
| 1A0249 | sp-1 | an-249 | 1U0249 | sp-1 | an-249 | 1C0249 | sp-1 | an-249 |
| 1A0250 | sp-1 | an-250 | 1U0250 | sp-1 | an-250 | 1C0250 | sp-1 | an-250 |

-continued

| Ex. No. | Z | N⁺R⁵R⁶R⁷ | Ex. No. | Z | N⁺R⁵R⁶R⁷ | Ex. No. | Z | N⁺R⁵R⁶R⁷ |
|---|---|---|---|---|---|---|---|---|
| 1A0251 | sp-1 | an-251 | 1U0251 | sp-1 | an-251 | 1C0251 | sp-1 | an-251 |
| 1A0252 | sp-1 | an-252 | 1U0252 | sp-1 | an-252 | 1C0252 | sp-1 | an-252 |
| 1A0253 | sp-1 | an-253 | 1U0253 | sp-1 | an-253 | 1C0253 | sp-1 | an-253 |
| 1A0254 | sp-1 | an-254 | 1U0254 | sp-1 | an-254 | 1C0254 | sp-1 | an-254 |
| 1A0255 | sp-1 | an-255 | 1U0255 | sp-1 | an-255 | 1C0255 | sp-1 | an-255 |
| 1A0256 | sp-1 | an-256 | 1U0256 | sp-1 | an-256 | 1C0256 | sp-1 | an-256 |
| 1A0257 | sp-1 | an-257 | 1U0257 | sp-1 | an-257 | 1C0257 | sp-1 | an-257 |
| 1A0258 | sp-1 | an-258 | 1U0258 | sp-1 | an-258 | 1C0258 | sp-1 | an-258 |
| 1A0259 | sp-1 | an-259 | 1U0259 | sp-1 | an-259 | 1C0259 | sp-1 | an-259 |
| 1A0260 | sp-1 | an-260 | 1U0260 | sp-1 | an-260 | 1C0260 | sp-1 | an-260 |
| 1A0261 | sp-1 | an-261 | 1U0261 | sp-1 | an-261 | 1C0261 | sp-1 | an-261 |
| 1A0262 | sp-1 | an-262 | 1U0262 | sp-1 | an-262 | 1C0262 | sp-1 | an-262 |
| 1A0263 | sp-1 | an-263 | 1U0263 | sp-1 | an-263 | 1C0263 | sp-1 | an-263 |
| 1A0264 | sp-1 | an-264 | 1U0264 | sp-1 | an-264 | 1C0264 | sp-1 | an-264 |
| 1A0265 | sp-1 | an-265 | 1U0265 | sp-1 | an-265 | 1C0265 | sp-1 | an-265 |
| 1A0266 | sp-1 | an-266 | 1U0266 | sp-1 | an-266 | 1C0266 | sp-1 | an-266 |
| 1A0267 | sp-1 | an-267 | 1U0267 | sp-1 | an-267 | 1C0267 | sp-1 | an-267 |
| 1A0268 | sp-1 | an-268 | 1U0268 | sp-1 | an-268 | 1C0268 | sp-1 | an-268 |
| 1A0269 | sp-1 | an-269 | 1U0269 | sp-1 | an-269 | 1C0269 | sp-1 | an-269 |
| 1A0270 | sp-1 | an-270 | 1U0270 | sp-1 | an-270 | 1C0270 | sp-1 | an-270 |
| 1A0271 | sp-1 | an-271 | 1U0271 | sp-1 | an-271 | 1C0271 | sp-1 | an-271 |
| 1A0272 | sp-1 | an-272 | 1U0272 | sp-1 | an-272 | 1C0272 | sp-1 | an-272 |
| 1A0273 | sp-1 | an-273 | 1U0273 | sp-1 | an-273 | 1C0273 | sp-1 | an-273 |
| 1A0274 | sp-1 | an-274 | 1U0274 | sp-1 | an-274 | 1C0274 | sp-1 | an-274 |
| 1A0275 | sp-1 | an-275 | 1U0275 | sp-1 | an-275 | 1C0275 | sp-1 | an-275 |
| 1A0276 | sp-1 | an-276 | 1U0276 | sp-1 | an-276 | 1C0276 | sp-1 | an-276 |
| 1A0277 | sp-1 | an-277 | 1U0277 | sp-1 | an-277 | 1C0277 | sp-1 | an-277 |
| 1A0278 | sp-1 | an-278 | 1U0278 | sp-1 | an-278 | 1C0278 | sp-1 | an-278 |
| 1A0279 | sp-1 | an-279 | 1U0279 | sp-1 | an-279 | 1C0279 | sp-1 | an-279 |
| 1A0280 | sp-1 | an-280 | 1U0280 | sp-1 | an-280 | 1C0280 | sp-1 | an-280 |

Table 2-6

| Y = NHCS | | | Y = NHCSNH | | | Y = NHCSO | | |
|---|---|---|---|---|---|---|---|---|
| 1A0281 | sp-1 | an-281 | 1U0281 | sp-1 | an-281 | 1C0281 | sp-1 | an-281 |
| 1A0282 | sp-1 | an-282 | 1U0282 | sp-1 | an-282 | 1C0282 | sp-1 | an-282 |
| 1A0283 | sp-1 | an-283 | 1U0283 | sp-1 | an-283 | 1C0283 | sp-1 | an-283 |
| 1A0284 | sp-1 | an-284 | 1U0284 | sp-1 | an-284 | 1C0284 | sp-1 | an-284 |
| 1A0285 | sp-1 | an-285 | 1U0285 | sp-1 | an-285 | 1C0285 | sp-1 | an-285 |
| 1A0286 | sp-1 | an-286 | 1U0286 | sp-1 | an-286 | 1C0286 | sp-1 | an-286 |
| 1A0287 | sp-1 | an-287 | 1U0287 | sp-1 | an-287 | 1C0287 | sp-1 | an-287 |
| 1A0288 | sp-1 | an-288 | 1U0288 | sp-1 | an-288 | 1C0288 | sp-1 | an-288 |
| 1A0289 | sp-1 | an-289 | 1U0289 | sp-1 | an-289 | 1C0289 | sp-1 | an-289 |
| 1A0290 | sp-1 | an-290 | 1U0290 | sp-1 | an-290 | 1C0290 | sp-1 | an-290 |
| 1A0291 | sp-1 | an-291 | 1U0291 | sp-1 | an-291 | 1C0291 | sp-1 | an-291 |
| 1A0292 | sp-1 | an-292 | 1U0292 | sp-1 | an-292 | 1C0292 | sp-1 | an-292 |
| 1A0293 | sp-1 | an-293 | 1U0293 | sp-1 | an-293 | 1C0293 | sp-1 | an-293 |
| 1A0294 | sp-1 | an-294 | 1U0294 | sp-1 | an-294 | 1C0294 | sp-1 | an-294 |
| 1A0295 | sp-1 | an-295 | 1U0295 | sp-1 | an-295 | 1C0295 | sp-1 | an-295 |
| 1A0296 | sp-1 | an-296 | 1U0296 | sp-1 | an-296 | 1C0296 | sp-1 | an-296 |
| 1A0297 | sp-1 | an-297 | 1U0297 | sp-1 | an-297 | 1C0297 | sp-1 | an-297 |
| 1A0298 | sp-1 | an-298 | 1U0298 | sp-1 | an-298 | 1C0298 | sp-1 | an-298 |
| 1A0299 | sp-1 | an-299 | 1U0299 | sp-1 | an-299 | 1C0299 | sp-1 | an-299 |
| 1A0300 | sp-1 | an-300 | 1U0300 | sp-1 | an-300 | 1C0300 | sp-1 | an-300 |
| 1A0301 | sp-1 | an-301 | 1U0301 | sp-1 | an-301 | 1C0301 | sp-1 | an-301 |
| 1A0302 | sp-1 | an-302 | 1U0302 | sp-1 | an-302 | 1C0302 | sp-1 | an-302 |
| 1A0303 | sp-1 | an-303 | 1U0303 | sp-1 | an-303 | 1C0303 | sp-1 | an-303 |
| 1A0304 | sp-1 | an-304 | 1U0304 | sp-1 | an-304 | 1C0304 | sp-1 | an-304 |
| 1A0305 | sp-1 | an-305 | 1U0305 | sp-1 | an-305 | 1C0305 | sp-1 | an-305 |
| 1A0306 | sp-1 | an-306 | 1U0306 | sp-1 | an-306 | 1C0306 | sp-1 | an-306 |
| 1A0307 | sp-1 | an-307 | 1U0307 | sp-1 | an-307 | 1C0307 | sp-1 | an-307 |
| 1A0308 | sp-1 | an-308 | 1U0308 | sp-1 | an-308 | 1C0308 | sp-1 | an-308 |
| 1A0309 | sp-1 | an-309 | 1U0309 | sp-1 | an-309 | 1C0309 | sp-1 | an-309 |
| 1A0310 | sp-1 | an-310 | 1U0310 | sp-1 | an-310 | 1C0310 | sp-1 | an-310 |
| 1A0311 | sp-1 | an-311 | 1U0311 | sp-1 | an-311 | 1C0311 | sp-1 | an-311 |
| 1A0312 | sp-1 | an-312 | 1U0312 | sp-1 | an-312 | 1C0312 | sp-1 | an-312 |
| 1A0313 | sp-1 | an-313 | 1U0313 | sp-1 | an-313 | 1C0313 | sp-1 | an-313 |
| 1A0314 | sp-1 | an-314 | 1U0314 | sp-1 | an-314 | 1C0314 | sp-1 | an-314 |
| 1A0315 | sp-1 | an-315 | 1U0315 | sp-1 | an-315 | 1C0315 | sp-1 | an-315 |
| 1A0316 | sp-1 | an-316 | 1U0316 | sp-1 | an-316 | 1C0316 | sp-1 | an-316 |
| 1A0317 | sp-1 | an-317 | 1U0317 | sp-1 | an-317 | 1C0317 | sp-1 | an-317 |
| 1A0318 | sp-1 | an-318 | 1U0318 | sp-1 | an-318 | 1C0318 | sp-1 | an-318 |
| 1A0319 | sp-1 | an-319 | 1U0319 | sp-1 | an-319 | 1C0319 | sp-1 | an-319 |
| 1A0320 | sp-1 | an-320 | 1U0320 | sp-1 | an-320 | 1C0320 | sp-1 | an-320 |
| 1A0321 | sp-1 | an-321 | 1U0321 | sp-1 | an-321 | 1C0321 | sp-1 | an-321 |
| 1A0322 | sp-1 | an-322 | 1U0322 | sp-1 | an-322 | 1C0322 | sp-1 | an-322 |
| 1A0323 | sp-1 | an-323 | 1U0323 | sp-1 | an-323 | 1C0323 | sp-1 | an-323 |
| 1A0324 | sp-1 | an-324 | 1U0324 | sp-1 | an-324 | 1C0324 | sp-1 | an-324 |

| Ex. No. | Z | $N^+R^5R^6R^7$ | Ex. No. | Z | $N^+R^5R^6R^7$ | Ex. No. | Z | $N^+R^5R^6R^7$ |
|---|---|---|---|---|---|---|---|---|
| 1A0325 | sp-1 | an-325 | 1U0325 | sp-1 | an-325 | 1C0325 | sp-1 | an-325 |
| 1A0326 | sp-1 | an-326 | 1U0326 | sp-1 | an-326 | 1C0326 | sp-1 | an-326 |
| 1A0327 | sp-1 | an-327 | 1U0327 | sp-1 | an-327 | 1C0327 | sp-1 | an-327 |
| 1A0328 | sp-1 | an-328 | 1U0328 | sp-1 | an-328 | 1C0328 | sp-1 | an-328 |
| 1A0329 | sp-1 | an-329 | 1U0329 | sp-1 | an-329 | 1C0329 | sp-1 | an-329 |
| 1A0330 | sp-1 | an-330 | 1U0330 | sp-1 | an-330 | 1C0330 | sp-1 | an-330 |
| 1A0331 | sp-1 | an-331 | 1U0331 | sp-1 | an-331 | 1C0331 | sp-1 | an-331 |
| 1A0332 | sp-1 | an-332 | 1U0332 | sp-1 | an-332 | 1C0332 | sp-1 | an-332 |
| 1A0333 | sp-1 | an-333 | 1U0333 | sp-1 | an-333 | 1C0333 | sp-1 | an-333 |
| 1A0334 | sp-1 | an-334 | 1U0334 | sp-1 | an-334 | 1C0334 | sp-1 | an-334 |
| 1A0335 | sp-1 | an-335 | 1U0335 | sp-1 | an-335 | 1C0335 | sp-1 | an-335 |
| 1A0336 | sp-1 | an-336 | 1U0336 | sp-1 | an-336 | 1C0336 | sp-1 | an-336 |

Table 2-7

| Y = NHCS | | | Y = NHCSNH | | | Y = NHCSO | | |
|---|---|---|---|---|---|---|---|---|
| 1A0337 | sp-1 | an-337 | 1U0337 | sp-1 | an-337 | 1C0337 | sp-1 | an-337 |
| 1A0338 | sp-1 | an-338 | 1U0338 | sp-1 | an-338 | 1C0338 | sp-1 | an-338 |
| 1A0339 | sp-1 | an-339 | 1U0339 | sp-1 | an-339 | 1C0339 | sp-1 | an-339 |
| 1A0340 | sp-1 | an-340 | 1U0340 | sp-1 | an-340 | 1C0340 | sp-1 | an-340 |
| 1A0341 | sp-1 | an-341 | 1U0341 | sp-1 | an-341 | 1C0341 | sp-1 | an-341 |
| 1A0342 | sp-1 | an-342 | 1U0342 | sp-1 | an-342 | 1C0342 | sp-1 | an-342 |
| 1A0343 | sp-1 | an-343 | 1U0343 | sp-1 | an-343 | 1C0343 | sp-1 | an-343 |
| 1A0344 | sp-1 | an-344 | 1U0344 | sp-1 | an-344 | 1C0344 | sp-1 | an-344 |
| 1A0345 | sp-1 | an-345 | 1U0345 | sp-1 | an-345 | 1C0345 | sp-1 | an-345 |
| 1A0346 | sp-1 | an-346 | 1U0346 | sp-1 | an-346 | 1C0346 | sp-1 | an-346 |
| 1A0347 | sp-1 | an-347 | 1U0347 | sp-1 | an-347 | 1C0347 | sp-1 | an-347 |
| 1A0348 | sp-1 | an-348 | 1U0348 | sp-1 | an-348 | 1C0348 | sp-1 | an-348 |
| 1A0349 | sp-1 | an-349 | 1U0349 | sp-1 | an-349 | 1C0349 | sp-1 | an-349 |
| 1A0350 | sp-1 | an-350 | 1U0350 | sp-1 | an-350 | 1C0350 | sp-1 | an-350 |
| 1A0351 | sp-1 | an-351 | 1U0351 | sp-1 | an-351 | 1C0351 | sp-1 | an-351 |
| 1A0352 | sp-1 | an-352 | 1U0352 | sp-1 | an-352 | 1C0352 | sp-1 | an-352 |
| 1A0353 | sp-1 | an-353 | 1U0353 | sp-1 | an-353 | 1C0353 | sp-1 | an-353 |
| 1A0354 | sp-1 | an-354 | 1U0354 | sp-1 | an-354 | 1C0354 | sp-1 | an-354 |
| 1A0355 | sp-1 | an-355 | 1U0355 | sp-1 | an-355 | 1C0355 | sp-1 | an-355 |
| 1A0356 | sp-1 | an-356 | 1U0356 | sp-1 | an-356 | 1C0356 | sp-1 | an-356 |
| 1A0357 | sp-1 | an-357 | 1U0357 | sp-1 | an-357 | 1C0357 | sp-1 | an-357 |
| 1A0358 | sp-1 | an-358 | 1U0358 | sp-1 | an-358 | 1C0358 | sp-1 | an-358 |
| 1A0359 | sp-1 | an-359 | 1U0359 | sp-1 | an-359 | 1C0359 | sp-1 | an-359 |
| 1A0360 | sp-1 | an-360 | 1U0360 | sp-1 | an-360 | 1C0360 | sp-1 | an-360 |
| 1A0361 | sp-1 | an-361 | 1U0361 | sp-1 | an-361 | 1C0361 | sp-1 | an-361 |
| 1A0362 | sp-1 | an-362 | 1U0362 | sp-1 | an-362 | 1C0362 | sp-1 | an-362 |
| 1A0363 | sp-1 | an-363 | 1U0363 | sp-1 | an-363 | 1C0363 | sp-1 | an-363 |
| 1A0364 | sp-1 | an-364 | 1U0364 | sp-1 | an-364 | 1C0364 | sp-1 | an-364 |
| 1A0365 | sp-1 | an-365 | 1U0365 | sp-1 | an-365 | 1C0365 | sp-1 | an-365 |
| 1A0366 | sp-1 | an-366 | 1U0366 | sp-1 | an-366 | 1C0366 | sp-1 | an-366 |
| 1A0367 | sp-1 | an-367 | 1U0367 | sp-1 | an-367 | 1C0367 | sp-1 | an-367 |
| 1A0368 | sp-1 | an-368 | 1U0368 | sp-1 | an-368 | 1C0368 | sp-1 | an-368 |
| 1A0369 | sp-1 | an-369 | 1U0369 | sp-1 | an-369 | 1C0369 | sp-1 | an-369 |
| 1A0370 | sp-1 | an-370 | 1U0370 | sp-1 | an-370 | 1C0370 | sp-1 | an-370 |
| 1A0371 | sp-1 | an-371 | 1U0371 | sp-1 | an-371 | 1C0371 | sp-1 | an-371 |
| 1A0372 | sp-1 | an-372 | 1U0372 | sp-1 | an-372 | 1C0372 | sp-1 | an-372 |
| 1A0373 | sp-1 | an-373 | 1U0373 | sp-1 | an-373 | 1C0373 | sp-1 | an-373 |
| 1A0374 | sp-1 | an-374 | 1U0374 | sp-1 | an-374 | 1C0374 | sp-1 | an-374 |
| 1A0375 | sp-1 | an-375 | 1U0375 | sp-1 | an-375 | 1C0375 | sp-1 | an-375 |
| 1A0376 | sp-1 | an-376 | 1U0376 | sp-1 | an-376 | 1C0376 | sp-1 | an-376 |
| 1A0377 | sp-1 | an-377 | 1U0377 | sp-1 | an-377 | 1C0377 | sp-1 | an-377 |
| 1A0378 | sp-2 | an-1 | 1U0378 | sp-2 | an-1 | 1C0378 | sp-2 | an-1 |
| 1A0379 | sp-2 | an-2 | 1U0379 | sp-2 | an-2 | 1C0379 | sp-2 | an-2 |
| 1A0380 | sp-2 | an-3 | 1U0380 | sp-2 | an-3 | 1C0380 | sp-2 | an-3 |
| 1A0381 | sp-2 | an-4 | 1U0381 | sp-2 | an-4 | 1C0381 | sp-2 | an-4 |
| 1A0382 | sp-2 | an-5 | 1U0382 | sp-2 | an-5 | 1C0382 | sp-2 | an-5 |
| 1A0383 | sp-2 | an-6 | 1U0383 | sp-2 | an-6 | 1C0383 | sp-2 | an-6 |
| 1A0384 | sp-2 | an-7 | 1U0384 | sp-2 | an-7 | 1C0384 | sp-2 | an-7 |
| 1A0385 | sp-2 | an-8 | 1U0385 | sp-2 | an-8 | 1C0385 | sp-2 | an-8 |
| 1A0386 | sp-2 | an-9 | 1U0386 | sp-2 | an-9 | 1C0386 | sp-2 | an-9 |
| 1A0387 | sp-2 | an-10 | 1U0387 | sp-2 | an-10 | 1C0387 | sp-2 | an-10 |
| 1A0388 | sp-2 | an-11 | 1U0388 | sp-2 | an-11 | 1C0388 | sp-2 | an-11 |
| 1A0389 | sp-2 | an-12 | 1U0389 | sp-2 | an-12 | 1C0389 | sp-2 | an-12 |
| 1A0390 | sp-2 | an-13 | 1U0390 | sp-2 | an-13 | 1C0390 | sp-2 | an-13 |
| 1A0391 | sp-2 | an-14 | 1U0391 | sp-2 | an-14 | 1C0391 | sp-2 | an-14 |
| 1A0392 | sp-2 | an-15 | 1U0392 | sp-2 | an-15 | 1C0392 | sp-2 | an-15 |

Table 2-8

| Y = NHCS | | | Y = NHCSNH | | | Y = NHCSO | | |
|---|---|---|---|---|---|---|---|---|
| 1A0393 | sp-2 | an-16 | 1U0393 | sp-2 | an-16 | 1C0393 | sp-2 | an-16 |
| 1A0394 | sp-2 | an-17 | 1U0394 | sp-2 | an-17 | 1C0394 | sp-2 | an-17 |

-continued

| Ex. No. | Z | N+R5R6R7 | Ex. No. | Z | N+R5R6R7 | Ex. No. | Z | N+R5R6R7 |
|---|---|---|---|---|---|---|---|---|
| 1A0395 | sp-2 | an-18 | 1U0395 | sp-2 | an-18 | 1C0395 | sp-2 | an-18 |
| 1A0396 | sp-2 | an-19 | 1U0396 | sp-2 | an-19 | 1C0396 | sp-2 | an-19 |
| 1A0397 | sp-2 | an-20 | 1U0397 | sp-2 | an-20 | 1C0397 | sp-2 | an-20 |
| 1A0398 | sp-2 | an-21 | 1U0398 | sp-2 | an-21 | 1C0398 | sp-2 | an-21 |
| 1A0399 | sp-2 | an-22 | 1U0399 | sp-2 | an-22 | 1C0399 | sp-2 | an-22 |
| 1A0400 | sp-2 | an-23 | 1U0400 | sp-2 | an-23 | 1C0400 | sp-2 | an-23 |
| 1A0401 | sp-2 | an-24 | 1U0401 | sp-2 | an-24 | 1C0401 | sp-2 | an-24 |
| 1A0402 | sp-2 | an-25 | 1U0402 | sp-2 | an-25 | 1C0402 | sp-2 | an-25 |
| 1A0403 | sp-2 | an-26 | 1U0403 | sp-2 | an-26 | 1C0403 | sp-2 | an-26 |
| 1A0404 | sp-2 | an-27 | 1U0404 | sp-2 | an-27 | 1C0404 | sp-2 | an-27 |
| 1A0405 | sp-2 | an-28 | 1U0405 | sp-2 | an-28 | 1C0405 | sp-2 | an-28 |
| 1A0406 | sp-2 | an-29 | 1U0406 | sp-2 | an-29 | 1C0406 | sp-2 | an-29 |
| 1A0407 | sp-2 | an-30 | 1U0407 | sp-2 | an-30 | 1C0407 | sp-2 | an-30 |
| 1A0408 | sp-2 | an-31 | 1U0408 | sp-2 | an-31 | 1C0408 | sp-2 | an-31 |
| 1A0409 | sp-2 | an-32 | 1U0409 | sp-2 | an-32 | 1C0409 | sp-2 | an-32 |
| 1A0410 | sp-2 | an-33 | 1U0410 | sp-2 | an-33 | 1C0410 | sp-2 | an-33 |
| 1A0411 | sp-2 | an-34 | 1U0411 | sp-2 | an-34 | 1C0411 | sp-2 | an-34 |
| 1A0412 | sp-2 | an-35 | 1U0412 | sp-2 | an-35 | 1C0412 | sp-2 | an-35 |
| 1A0413 | sp-2 | an-36 | 1U0413 | sp-2 | an-36 | 1C0413 | sp-2 | an-36 |
| 1A0414 | sp-2 | an-37 | 1U0414 | sp-2 | an-37 | 1C0414 | sp-2 | an-37 |
| 1A0415 | sp-2 | an-38 | 1U0415 | sp-2 | an-38 | 1C0415 | sp-2 | an-38 |
| 1A0416 | sp-2 | an-39 | 1U0416 | sp-2 | an-39 | 1C0416 | sp-2 | an-39 |
| 1A0417 | sp-2 | an-40 | 1U0417 | sp-2 | an-40 | 1C0417 | sp-2 | an-40 |
| 1A0418 | sp-2 | an-41 | 1U0418 | sp-2 | an-41 | 1C0418 | sp-2 | an-41 |
| 1A0419 | sp-2 | an-42 | 1U0419 | sp-2 | an-42 | 1C0419 | sp-2 | an-42 |
| 1A0420 | sp-2 | an-43 | 1U0420 | sp-2 | an-43 | 1C0420 | sp-2 | an-43 |
| 1A0421 | sp-2 | an-44 | 1U0421 | sp-2 | an-44 | 1C0421 | sp-2 | an-44 |
| 1A0422 | sp-2 | an-45 | 1U0422 | sp-2 | an-45 | 1C0422 | sp-2 | an-45 |
| 1A0423 | sp-2 | an-46 | 1U0423 | sp-2 | an-46 | 1C0423 | sp-2 | an-46 |
| 1A0424 | sp-2 | an-47 | 1U0424 | sp-2 | an-47 | 1C0424 | sp-2 | an-47 |
| 1A0425 | sp-2 | an-48 | 1U0425 | sp-2 | an-48 | 1C0425 | sp-2 | an-48 |
| 1A0426 | sp-2 | an-49 | 1U0426 | sp-2 | an-49 | 1C0426 | sp-2 | an-49 |
| 1A0427 | sp-2 | an-50 | 1U0427 | sp-2 | an-50 | 1C0427 | sp-2 | an-50 |
| 1A0428 | sp-2 | an-51 | 1U0428 | sp-2 | an-51 | 1C0428 | sp-2 | an-51 |
| 1A0429 | sp-2 | an-52 | 1U0429 | sp-2 | an-52 | 1C0429 | sp-2 | an-52 |
| 1A0430 | sp-2 | an-53 | 1U0430 | sp-2 | an-53 | 1C0430 | sp-2 | an-53 |
| 1A0431 | sp-2 | an-54 | 1U0431 | sp-2 | an-54 | 1C0431 | sp-2 | an-54 |
| 1A0432 | sp-2 | an-55 | 1U0432 | sp-2 | an-55 | 1C0432 | sp-2 | an-55 |
| 1A0433 | sp-2 | an-56 | 1U0433 | sp-2 | an-56 | 1C0433 | sp-2 | an-56 |
| 1A0434 | sp-2 | an-57 | 1U0434 | sp-2 | an-57 | 1C0434 | sp-2 | an-57 |
| 1A0435 | sp-2 | an-58 | 1U0435 | sp-2 | an-58 | 1C0435 | sp-2 | an-58 |
| 1A0436 | sp-2 | an-59 | 1U0436 | sp-2 | an-59 | 1C0436 | sp-2 | an-59 |
| 1A0437 | sp-2 | an-60 | 1U0437 | sp-2 | an-60 | 1C0437 | sp-2 | an-60 |
| 1A0438 | sp-2 | an-61 | 1U0438 | sp-2 | an-61 | 1C0438 | sp-2 | an-61 |
| 1A0439 | sp-2 | an-62 | 1U0439 | sp-2 | an-62 | 1C0439 | sp-2 | an-62 |
| 1A0440 | sp-2 | an-63 | 1U0440 | sp-2 | an-63 | 1C0440 | sp-2 | an-63 |
| 1A0441 | sp-2 | an-64 | 1U0441 | sp-2 | an-64 | 1C0441 | sp-2 | an-64 |
| 1A0442 | sp-2 | an-65 | 1U0442 | sp-2 | an-65 | 1C0442 | sp-2 | an-65 |
| 1A0443 | sp-2 | an-66 | 1U0443 | sp-2 | an-66 | 1C0443 | sp-2 | an-66 |
| 1A0444 | sp-2 | an-67 | 1U0444 | sp-2 | an-67 | 1C0444 | sp-2 | an-67 |
| 1A0445 | sp-2 | an-68 | 1U0445 | sp-2 | an-68 | 1C0445 | sp-2 | an-68 |
| 1A0446 | sp-2 | an-69 | 1U0446 | sp-2 | an-69 | 1C0446 | sp-2 | an-69 |
| 1A0447 | sp-2 | an-70 | 1U0447 | sp-2 | an-70 | 1C0447 | sp-2 | an-70 |
| 1A0448 | sp-2 | an-71 | 1U0448 | sp-2 | an-71 | 1C0448 | sp-2 | an-71 |

Table 2-9

| Y = NHCS | | | Y = NHCSNH | | | Y = NHCSO | | |
|---|---|---|---|---|---|---|---|---|
| 1A0449 | sp-2 | an-72 | 1U0449 | sp-2 | an-72 | 1C0449 | sp-2 | an-72 |
| 1A0450 | sp-2 | an-73 | 1U0450 | sp-2 | an-73 | 1C0450 | sp-2 | an-73 |
| 1A0451 | sp-2 | an-74 | 1U0451 | sp-2 | an-74 | 1C0451 | sp-2 | an-74 |
| 1A0452 | sp-2 | an-75 | 1U0452 | sp-2 | an-75 | 1C0452 | sp-2 | an-75 |
| 1A0453 | sp-2 | an-76 | 1U0453 | sp-2 | an-76 | 1C0453 | sp-2 | an-76 |
| 1A0454 | sp-2 | an-77 | 1U0454 | sp-2 | an-77 | 1C0454 | sp-2 | an-77 |
| 1A0455 | sp-2 | an-78 | 1U0455 | sp-2 | an-78 | 1C0455 | sp-2 | an-78 |
| 1A0456 | sp-2 | an-79 | 1U0456 | sp-2 | an-79 | 1C0456 | sp-2 | an-79 |
| 1A0457 | sp-2 | an-80 | 1U0457 | sp-2 | an-80 | 1C0457 | sp-2 | an-80 |
| 1A0458 | sp-2 | an-81 | 1U0458 | sp-2 | an-81 | 1C0458 | sp-2 | an-81 |
| 1A0459 | sp-2 | an-82 | 1U0459 | sp-2 | an-82 | 1C0459 | sp-2 | an-82 |
| 1A0460 | sp-2 | an-83 | 1U0460 | sp-2 | an-83 | 1C0460 | sp-2 | an-83 |
| 1A0461 | sp-2 | an-84 | 1U0461 | sp-2 | an-84 | 1C0461 | sp-2 | an-84 |
| 1A0462 | sp-2 | an-85 | 1U0462 | sp-2 | an-85 | 1C0462 | sp-2 | an-85 |
| 1A0463 | sp-2 | an-86 | 1U0463 | sp-2 | an-86 | 1C0463 | sp-2 | an-86 |
| 1A0464 | sp-2 | an-87 | 1U0464 | sp-2 | an-87 | 1C0464 | sp-2 | an-87 |
| 1A0465 | sp-2 | an-88 | 1U0465 | sp-2 | an-88 | 1C0465 | sp-2 | an-88 |
| 1A0466 | sp-2 | an-89 | 1U0466 | sp-2 | an-89 | 1C0466 | sp-2 | an-89 |
| 1A0467 | sp-2 | an-90 | 1U0467 | sp-2 | an-90 | 1C0467 | sp-2 | an-90 |
| 1A0468 | sp-2 | an-91 | 1U0468 | sp-2 | an-91 | 1C0468 | sp-2 | an-91 |

-continued

| Ex. No. | Z | N⁺R⁵R⁶R⁷ | Ex. No. | Z | N⁺R⁵R⁶R⁷ | Ex. No. | Z | N⁺R⁵R⁶R⁷ |
|---|---|---|---|---|---|---|---|---|
| 1A0469 | sp-2 | an-92 | 1U0469 | sp-2 | an-92 | 1C0469 | sp-2 | an-92 |
| 1A0470 | sp-2 | an-93 | 1U0470 | sp-2 | an-93 | 1C0470 | sp-2 | an-93 |
| 1A0471 | sp-2 | an-94 | 1U0471 | sp-2 | an-94 | 1C0471 | sp-2 | an-94 |
| 1A0472 | sp-2 | an-95 | 1U0472 | sp-2 | an-95 | 1C0472 | sp-2 | an-95 |
| 1A0473 | sp-2 | an-96 | 1U0473 | sp-2 | an-96 | 1C0473 | sp-2 | an-96 |
| 1A0474 | sp-2 | an-97 | 1U0474 | sp-2 | an-97 | 1C0474 | sp-2 | an-97 |
| 1A0475 | sp-2 | an-98 | 1U0475 | sp-2 | an-98 | 1C0475 | sp-2 | an-98 |
| 1A0476 | sp-2 | an-99 | 1U0476 | sp-2 | an-99 | 1C0476 | sp-2 | an-99 |
| 1A0477 | sp-2 | an-100 | 1U0477 | sp-2 | an-100 | 1C0477 | sp-2 | an-100 |
| 1A0478 | sp-2 | an-101 | 1U0478 | sp-2 | an-101 | 1C0478 | sp-2 | an-101 |
| 1A0479 | sp-2 | an-102 | 1U0479 | sp-2 | an-102 | 1C0479 | sp-2 | an-102 |
| 1A0480 | sp-2 | an-103 | 1U0480 | sp-2 | an-103 | 1C0480 | sp-2 | an-103 |
| 1A0481 | sp-2 | an-104 | 1U0481 | sp-2 | an-104 | 1C0481 | sp-2 | an-104 |
| 1A0482 | sp-2 | an-105 | 1U0482 | sp-2 | an-105 | 1C0482 | sp-2 | an-105 |
| 1A0483 | sp-2 | an-106 | 1U0483 | sp-2 | an-106 | 1C0483 | sp-2 | an-106 |
| 1A0484 | sp-2 | an-107 | 1U0484 | sp-2 | an-107 | 1C0484 | sp-2 | an-107 |
| 1A0485 | sp-2 | an-108 | 1U0485 | sp-2 | an-108 | 1C0485 | sp-2 | an-108 |
| 1A0486 | sp-2 | an-109 | 1U0486 | sp-2 | an-109 | 1C0486 | sp-2 | an-109 |
| 1A0487 | sp-2 | an-110 | 1U0487 | sp-2 | an-110 | 1C0487 | sp-2 | an-110 |
| 1A0488 | sp-2 | an-111 | 1U0488 | sp-2 | an-111 | 1C0488 | sp-2 | an-111 |
| 1A0489 | sp-2 | an-112 | 1U0489 | sp-2 | an-112 | 1C0489 | sp-2 | an-112 |
| 1A0490 | sp-2 | an-113 | 1U0490 | sp-2 | an-113 | 1C0490 | sp-2 | an-113 |
| 1A0491 | sp-2 | an-114 | 1U0491 | sp-2 | an-114 | 1C0491 | sp-2 | an-114 |
| 1A0492 | sp-2 | an-115 | 1U0492 | sp-2 | an-115 | 1C0492 | sp-2 | an-115 |
| 1A0493 | sp-2 | an-116 | 1U0493 | sp-2 | an-116 | 1C0493 | sp-2 | an-116 |
| 1A0494 | sp-2 | an-117 | 1U0494 | sp-2 | an-117 | 1C0494 | sp-2 | an-117 |
| 1A0495 | sp-2 | an-118 | 1U0495 | sp-2 | an-118 | 1C0495 | sp-2 | an-118 |
| 1A0496 | sp-2 | an-119 | 1U0496 | sp-2 | an-119 | 1C0496 | sp-2 | an-119 |
| 1A0497 | sp-2 | an-120 | 1U0497 | sp-2 | an-120 | 1C0497 | sp-2 | an-120 |
| 1A0498 | sp-2 | an-121 | 1U0498 | sp-2 | an-121 | 1C0498 | sp-2 | an-121 |
| 1A0499 | sp-2 | an-122 | 1U0499 | sp-2 | an-122 | 1C0499 | sp-2 | an-122 |
| 1A0500 | sp-2 | an-123 | 1U0500 | sp-2 | an-123 | 1C0500 | sp-2 | an-123 |
| 1A0501 | sp-2 | an-124 | 1U0501 | sp-2 | an-124 | 1C0501 | sp-2 | an-124 |
| 1A0502 | sp-2 | an-125 | 1U0502 | sp-2 | an-125 | 1C0502 | sp-2 | an-125 |
| 1A0503 | sp-2 | an-126 | 1U0503 | sp-2 | an-126 | 1C0503 | sp-2 | an-126 |
| 1A0504 | sp-2 | an-127 | 1U0504 | sp-2 | an-127 | 1C0504 | sp-2 | an-127 |

Table 2-10

| Y = NHCS | | | Y = NHCSNH | | | Y = NHCSO | | |
|---|---|---|---|---|---|---|---|---|
| 1A0505 | sp-2 | an-128 | 1U0505 | sp-2 | an-128 | 1C0505 | sp-2 | an-128 |
| 1A0506 | sp-2 | an-129 | 1U0506 | sp-2 | an-129 | 1C0506 | sp-2 | an-129 |
| 1A0507 | sp-2 | an-130 | 1U0507 | sp-2 | an-130 | 1C0507 | sp-2 | an-130 |
| 1A0508 | sp-2 | an-131 | 1U0508 | sp-2 | an-131 | 1C0508 | sp-2 | an-131 |
| 1A0509 | sp-2 | an-132 | 1U0509 | sp-2 | an-132 | 1C0509 | sp-2 | an-132 |
| 1A0510 | sp-2 | an-133 | 1U0510 | sp-2 | an-133 | 1C0510 | sp-2 | an-133 |
| 1A0511 | sp-2 | an-134 | 1U0511 | sp-2 | an-134 | 1C0511 | sp-2 | an-134 |
| 1A0512 | sp-2 | an-135 | 1U0512 | sp-2 | an-135 | 1C0512 | sp-2 | an-135 |
| 1A0513 | sp-2 | an-136 | 1U0513 | sp-2 | an-136 | 1C0513 | sp-2 | an-136 |
| 1A0514 | sp-2 | an-137 | 1U0514 | sp-2 | an-137 | 1C0514 | sp-2 | an-137 |
| 1A0515 | sp-2 | an-138 | 1U0515 | sp-2 | an-138 | 1C0515 | sp-2 | an-138 |
| 1A0516 | sp-2 | an-139 | 1U0516 | sp-2 | an-139 | 1C0516 | sp-2 | an-139 |
| 1A0517 | sp-2 | an-140 | 1U0517 | sp-2 | an-140 | 1C0517 | sp-2 | an-140 |
| 1A0518 | sp-2 | an-141 | 1U0518 | sp-2 | an-141 | 1C0518 | sp-2 | an-141 |
| 1A0519 | sp-2 | an-142 | 1U0519 | sp-2 | an-142 | 1C0519 | sp-2 | an-142 |
| 1A0520 | sp-2 | an-143 | 1U0520 | sp-2 | an-143 | 1C0520 | sp-2 | an-143 |
| 1A0521 | sp-2 | an-144 | 1U0521 | sp-2 | an-144 | 1C0521 | sp-2 | an-144 |
| 1A0522 | sp-2 | an-145 | 1U0522 | sp-2 | an-145 | 1C0522 | sp-2 | an-145 |
| 1A0523 | sp-2 | an-146 | 1U0523 | sp-2 | an-146 | 1C0523 | sp-2 | an-146 |
| 1A0524 | sp-2 | an-147 | 1U0524 | sp-2 | an-147 | 1C0524 | sp-2 | an-147 |
| 1A0525 | sp-2 | an-148 | 1U0525 | sp-2 | an-148 | 1C0525 | sp-2 | an-148 |
| 1A0526 | sp-2 | an-149 | 1U0526 | sp-2 | an-149 | 1C0526 | sp-2 | an-149 |
| 1A0527 | sp-2 | an-150 | 1U0527 | sp-2 | an-150 | 1C0527 | sp-2 | an-150 |
| 1A0528 | sp-2 | an-151 | 1U0528 | sp-2 | an-151 | 1C0528 | sp-2 | an-151 |
| 1A0529 | sp-2 | an-152 | 1U0529 | sp-2 | an-152 | 1C0529 | sp-2 | an-152 |
| 1A0530 | sp-2 | an-153 | 1U0530 | sp-2 | an-153 | 1C0530 | sp-2 | an-153 |
| 1A0531 | sp-2 | an-154 | 1U0531 | sp-2 | an-154 | 1C0531 | sp-2 | an-154 |
| 1A0532 | sp-2 | an-155 | 1U0532 | sp-2 | an-155 | 1C0532 | sp-2 | an-155 |
| 1A0533 | sp-2 | an-156 | 1U0533 | sp-2 | an-156 | 1C0533 | sp-2 | an-156 |
| 1A0534 | sp-2 | an-157 | 1U0534 | sp-2 | an-157 | 1C0534 | sp-2 | an-157 |
| 1A0535 | sp-2 | an-158 | 1U0535 | sp-2 | an-158 | 1C0535 | sp-2 | an-158 |
| 1A0536 | sp-2 | an-159 | 1U0536 | sp-2 | an-159 | 1C0536 | sp-2 | an-159 |
| 1A0537 | sp-2 | an-160 | 1U0537 | sp-2 | an-160 | 1C0537 | sp-2 | an-160 |
| 1A0538 | sp-2 | an-161 | 1U0538 | sp-2 | an-161 | 1C0538 | sp-2 | an-161 |
| 1A0539 | sp-2 | an-162 | 1U0539 | sp-2 | an-162 | 1C0539 | sp-2 | an-162 |
| 1A0540 | sp-2 | an-163 | 1U0540 | sp-2 | an-163 | 1C0540 | sp-2 | an-163 |
| 1A0541 | sp-2 | an-164 | 1U0541 | sp-2 | an-164 | 1C0541 | sp-2 | an-164 |
| 1A0542 | sp-2 | an-165 | 1U0542 | sp-2 | an-165 | 1C0542 | sp-2 | an-165 |

| Ex. No. | Z | N⁺R⁵R⁶R⁷ | Ex. No. | Z | N⁺R⁵R⁶R⁷ | Ex. No. | Z | N⁺R⁵R⁶R⁷ |
|---|---|---|---|---|---|---|---|---|
| 1A0543 | sp-2 | an-166 | 1U0543 | sp-2 | an-166 | 1C0543 | sp-2 | an-166 |
| 1A0544 | sp-2 | an-167 | 1U0544 | sp-2 | an-167 | 1C0544 | sp-2 | an-167 |
| 1A0545 | sp-2 | an-168 | 1U0545 | sp-2 | an-168 | 1C0545 | sp-2 | an-168 |
| 1A0546 | sp-2 | an-169 | 1U0546 | sp-2 | an-169 | 1C0546 | sp-2 | an-169 |
| 1A0547 | sp-2 | an-170 | 1U0547 | sp-2 | an-170 | 1C0547 | sp-2 | an-170 |
| 1A0548 | sp-2 | an-171 | 1U0548 | sp-2 | an-171 | 1C0548 | sp-2 | an-171 |
| 1A0549 | sp-2 | an-172 | 1U0549 | sp-2 | an-172 | 1C0549 | sp-2 | an-172 |
| 1A0550 | sp-2 | an-173 | 1U0550 | sp-2 | an-173 | 1C0550 | sp-2 | an-173 |
| 1A0551 | sp-2 | an-174 | 1U0551 | sp-2 | an-174 | 1C0551 | sp-2 | an-174 |
| 1A0552 | sp-2 | an-175 | 1U0552 | sp-2 | an-175 | 1C0552 | sp-2 | an-175 |
| 1A0553 | sp-2 | an-176 | 1U0553 | sp-2 | an-176 | 1C0553 | sp-2 | an-176 |
| 1A0554 | sp-2 | an-177 | 1U0554 | sp-2 | an-177 | 1C0554 | sp-2 | an-177 |
| 1A0555 | sp-2 | an-178 | 1U0555 | sp-2 | an-178 | 1C0555 | sp-2 | an-178 |
| 1A0556 | sp-2 | an-179 | 1U0556 | sp-2 | an-179 | 1C0556 | sp-2 | an-179 |
| 1A0557 | sp-2 | an-180 | 1U0557 | sp-2 | an-180 | 1C0557 | sp-2 | an-180 |
| 1A0558 | sp-2 | an-181 | 1U0558 | sp-2 | an-181 | 1C0558 | sp-2 | an-181 |
| 1A0559 | sp-2 | an-182 | 1U0559 | sp-2 | an-182 | 1C0559 | sp-2 | an-182 |
| 1A0560 | sp-2 | an-183 | 1U0560 | sp-2 | an-183 | 1C0560 | sp-2 | an-183 |

Table 2-11

| Y = NHCS | | | Y = NHCSNH | | | Y = NHCSO | | |
|---|---|---|---|---|---|---|---|---|
| 1A0561 | sp-2 | an-184 | 1U0561 | sp-2 | an-184 | 1C0561 | sp-2 | an-184 |
| 1A0562 | sp-2 | an-185 | 1U0562 | sp-2 | an-185 | 1C0562 | sp-2 | an-185 |
| 1A0563 | sp-2 | an-186 | 1U0563 | sp-2 | an-186 | 1C0563 | sp-2 | an-186 |
| 1A0564 | sp-2 | an-187 | 1U0564 | sp-2 | an-187 | 1C0564 | sp-2 | an-187 |
| 1A0565 | sp-2 | an-188 | 1U0565 | sp-2 | an-188 | 1C0565 | sp-2 | an-188 |
| 1A0566 | sp-2 | an-189 | 1U0566 | sp-2 | an-189 | 1C0566 | sp-2 | an-189 |
| 1A0567 | sp-2 | an-190 | 1U0567 | sp-2 | an-190 | 1C0567 | sp-2 | an-190 |
| 1A0568 | sp-2 | an-191 | 1U0568 | sp-2 | an-191 | 1C0568 | sp-2 | an-191 |
| 1A0569 | sp-2 | an-192 | 1U0569 | sp-2 | an-192 | 1C0569 | sp-2 | an-192 |
| 1A0570 | sp-2 | an-193 | 1U0570 | sp-2 | an-193 | 1C0570 | sp-2 | an-193 |
| 1A0571 | sp-2 | an-194 | 1U0571 | sp-2 | an-194 | 1C0571 | sp-2 | an-194 |
| 1A0572 | sp-2 | an-195 | 1U0572 | sp-2 | an-195 | 1C0572 | sp-2 | an-195 |
| 1A0573 | sp-2 | an-196 | 1U0573 | sp-2 | an-196 | 1C0573 | sp-2 | an-196 |
| 1A0574 | sp-2 | an-197 | 1U0574 | sp-2 | an-197 | 1C0574 | sp-2 | an-197 |
| 1A0575 | sp-2 | an-198 | 1U0575 | sp-2 | an-198 | 1C0575 | sp-2 | an-198 |
| 1A0576 | sp-2 | an-199 | 1U0576 | sp-2 | an-199 | 1C0576 | sp-2 | an-199 |
| 1A0577 | sp-2 | an-200 | 1U0577 | sp-2 | an-200 | 1C0577 | sp-2 | an-200 |
| 1A0578 | sp-2 | an-201 | 1U0578 | sp-2 | an-201 | 1C0578 | sp-2 | an-201 |
| 1A0579 | sp-2 | an-202 | 1U0579 | sp-2 | an-202 | 1C0579 | sp-2 | an-202 |
| 1A0580 | sp-2 | an-203 | 1U0580 | sp-2 | an-203 | 1C0580 | sp-2 | an-203 |
| 1A0581 | sp-2 | an-204 | 1U0581 | sp-2 | an-204 | 1C0581 | sp-2 | an-204 |
| 1A0582 | sp-2 | an-205 | 1U0582 | sp-2 | an-205 | 1C0582 | sp-2 | an-205 |
| 1A0583 | sp-2 | an-206 | 1U0583 | sp-2 | an-206 | 1C0583 | sp-2 | an-206 |
| 1A0584 | sp-2 | an-207 | 1U0584 | sp-2 | an-207 | 1C0584 | sp-2 | an-207 |
| 1A0585 | sp-2 | an-208 | 1U0585 | sp-2 | an-208 | 1C0585 | sp-2 | an-208 |
| 1A0586 | sp-2 | an-209 | 1U0586 | sp-2 | an-209 | 1C0586 | sp-2 | an-209 |
| 1A0587 | sp-2 | an-210 | 1U0587 | sp-2 | an-210 | 1C0587 | sp-2 | an-210 |
| 1A0588 | sp-2 | an-211 | 1U0588 | sp-2 | an-211 | 1C0588 | sp-2 | an-211 |
| 1A0589 | sp-2 | an-212 | 1U0589 | sp-2 | an-212 | 1C0589 | sp-2 | an-212 |
| 1A0590 | sp-2 | an-213 | 1U0590 | sp-2 | an-213 | 1C0590 | sp-2 | an-213 |
| 1A0591 | sp-2 | an-214 | 1U0591 | sp-2 | an-214 | 1C0591 | sp-2 | an-214 |
| 1A0592 | sp-2 | an-215 | 1U0592 | sp-2 | an-215 | 1C0592 | sp-2 | an-215 |
| 1A0593 | sp-2 | an-216 | 1U0593 | sp-2 | an-216 | 1C0593 | sp-2 | an-216 |
| 1A0594 | sp-2 | an-217 | 1U0594 | sp-2 | an-217 | 1C0594 | sp-2 | an-217 |
| 1A0595 | sp-2 | an-218 | 1U0595 | sp-2 | an-218 | 1C0595 | sp-2 | an-218 |
| 1A0596 | sp-2 | an-219 | 1U0596 | sp-2 | an-219 | 1C0596 | sp-2 | an-219 |
| 1A0597 | sp-2 | an-220 | 1U0597 | sp-2 | an-220 | 1C0597 | sp-2 | an-220 |
| 1A0598 | sp-2 | an-221 | 1U0598 | sp-2 | an-221 | 1C0598 | sp-2 | an-221 |
| 1A0599 | sp-2 | an-222 | 1U0599 | sp-2 | an-222 | 1C0599 | sp-2 | an-222 |
| 1A0600 | sp-2 | an-223 | 1U0600 | sp-2 | an-223 | 1C0600 | sp-2 | an-223 |
| 1A0601 | sp-2 | an-224 | 1U0601 | sp-2 | an-224 | 1C0601 | sp-2 | an-224 |
| 1A0602 | sp-2 | an-225 | 1U0602 | sp-2 | an-225 | 1C0602 | sp-2 | an-225 |
| 1A0603 | sp-2 | an-226 | 1U0603 | sp-2 | an-226 | 1C0603 | sp-2 | an-226 |
| 1A0604 | sp-2 | an-227 | 1U0604 | sp-2 | an-227 | 1C0604 | sp-2 | an-227 |
| 1A0605 | sp-2 | an-228 | 1U0605 | sp-2 | an-228 | 1C0605 | sp-2 | an-228 |
| 1A0606 | sp-2 | an-229 | 1U0606 | sp-2 | an-229 | 1C0606 | sp-2 | an-229 |
| 1A0607 | sp-2 | an-230 | 1U0607 | sp-2 | an-230 | 1C0607 | sp-2 | an-230 |
| 1A0608 | sp-2 | an-231 | 1U0608 | sp-2 | an-231 | 1C0608 | sp-2 | an-231 |
| 1A0609 | sp-2 | an-232 | 1U0609 | sp-2 | an-232 | 1C0609 | sp-2 | an-232 |
| 1A0610 | sp-2 | an-233 | 1U0610 | sp-2 | an-233 | 1C0610 | sp-2 | an-233 |
| 1A0611 | sp-2 | an-234 | 1U0611 | sp-2 | an-234 | 1C0611 | sp-2 | an-234 |
| 1A0612 | sp-2 | an-235 | 1U0612 | sp-2 | an-235 | 1C0612 | sp-2 | an-235 |
| 1A0613 | sp-2 | an-236 | 1U0613 | sp-2 | an-236 | 1C0613 | sp-2 | an-236 |
| 1A0614 | sp-2 | an-237 | 1U0614 | sp-2 | an-237 | 1C0614 | sp-2 | an-237 |
| 1A0615 | sp-2 | an-238 | 1U0615 | sp-2 | an-238 | 1C0615 | sp-2 | an-238 |
| 1A0616 | sp-2 | an-239 | 1U0616 | sp-2 | an-239 | 1C0616 | sp-2 | an-239 |

| Ex. No. | Z | N⁺R⁵R⁶R⁷ | Ex. No. | Z | N⁺R⁵R⁶R⁷ | Ex. No. | Z | N⁺R⁵R⁶R⁷ |
|---|---|---|---|---|---|---|---|---|
| | Table 2-12 |||||||||

| Y = NHCS ||| Y = NHCSNH ||| Y = NHCSO |||
|---|---|---|---|---|---|---|---|---|
| 1A0617 | sp-2 | an-240 | 1U0617 | sp-2 | an-240 | 1C0617 | sp-2 | an-240 |
| 1A0618 | sp-2 | an-241 | 1U0618 | sp-2 | an-241 | 1C0618 | sp-2 | an-241 |
| 1A0619 | sp-2 | an-242 | 1U0619 | sp-2 | an-242 | 1C0619 | sp-2 | an-242 |
| 1A0620 | sp-2 | an-243 | 1U0620 | sp-2 | an-243 | 1C0620 | sp-2 | an-243 |
| 1A0621 | sp-2 | an-244 | 1U0621 | sp-2 | an-244 | 1C0621 | sp-2 | an-244 |
| 1A0622 | sp-2 | an-245 | 1U0622 | sp-2 | an-245 | 1C0622 | sp-2 | an-245 |
| 1A0623 | sp-2 | an-246 | 1U0623 | sp-2 | an-246 | 1C0623 | sp-2 | an-246 |
| 1A0624 | sp-2 | an-247 | 1U0624 | sp-2 | an-247 | 1C0624 | sp-2 | an-247 |
| 1A0625 | sp-2 | an-248 | 1U0625 | sp-2 | an-248 | 1C0625 | sp-2 | an-248 |
| 1A0626 | sp-2 | an-249 | 1U0626 | sp-2 | an-249 | 1C0626 | sp-2 | an-249 |
| 1A0627 | sp-2 | an-250 | 1U0627 | sp-2 | an-250 | 1C0627 | sp-2 | an-250 |
| 1A0628 | sp-2 | an-251 | 1U0628 | sp-2 | an-251 | 1C0628 | sp-2 | an-251 |
| 1A0629 | sp-2 | an-252 | 1U0629 | sp-2 | an-252 | 1C0629 | sp-2 | an-252 |
| 1A0630 | sp-2 | an-253 | 1U0630 | sp-2 | an-253 | 1C0630 | sp-2 | an-253 |
| 1A0631 | sp-2 | an-254 | 1U0631 | sp-2 | an-254 | 1C0631 | sp-2 | an-254 |
| 1A0632 | sp-2 | an-255 | 1U0632 | sp-2 | an-255 | 1C0632 | sp-2 | an-255 |
| 1A0633 | sp-2 | an-256 | 1U0633 | sp-2 | an-256 | 1C0633 | sp-2 | an-256 |
| 1A0634 | sp-2 | an-257 | 1U0634 | sp-2 | an-257 | 1C0634 | sp-2 | an-257 |
| 1A0635 | sp-2 | an-258 | 1U0635 | sp-2 | an-258 | 1C0635 | sp-2 | an-258 |
| 1A0636 | sp-2 | an-259 | 1U0636 | sp-2 | an-259 | 1C0636 | sp-2 | an-259 |
| 1A0637 | sp-2 | an-260 | 1U0637 | sp-2 | an-260 | 1C0637 | sp-2 | an-260 |
| 1A0638 | sp-2 | an-261 | 1U0638 | sp-2 | an-261 | 1C0638 | sp-2 | an-261 |
| 1A0639 | sp-2 | an-262 | 1U0639 | sp-2 | an-262 | 1C0639 | sp-2 | an-262 |
| 1A0640 | sp-2 | an-263 | 1U0640 | sp-2 | an-263 | 1C0640 | sp-2 | an-263 |
| 1A0641 | sp-2 | an-264 | 1U0641 | sp-2 | an-264 | 1C0641 | sp-2 | an-264 |
| 1A0642 | sp-2 | an-265 | 1U0642 | sp-2 | an-265 | 1C0642 | sp-2 | an-265 |
| 1A0643 | sp-2 | an-266 | 1U0643 | sp-2 | an-266 | 1C0643 | sp-2 | an-266 |
| 1A0644 | sp-2 | an-267 | 1U0644 | sp-2 | an-267 | 1C0644 | sp-2 | an-267 |
| 1A0645 | sp-2 | an-268 | 1U0645 | sp-2 | an-268 | 1C0645 | sp-2 | an-268 |
| 1A0646 | sp-2 | an-269 | 1U0646 | sp-2 | an-269 | 1C0646 | sp-2 | an-269 |
| 1A0647 | sp-2 | an-270 | 1U0647 | sp-2 | an-270 | 1C0647 | sp-2 | an-270 |
| 1A0648 | sp-2 | an-271 | 1U0648 | sp-2 | an-271 | 1C0648 | sp-2 | an-271 |
| 1A0649 | sp-2 | an-272 | 1U0649 | sp-2 | an-272 | 1C0649 | sp-2 | an-272 |
| 1A0650 | sp-2 | an-273 | 1U0650 | sp-2 | an-273 | 1C0650 | sp-2 | an-273 |
| 1A0651 | sp-2 | an-274 | 1U0651 | sp-2 | an-274 | 1C0651 | sp-2 | an-274 |
| 1A0652 | sp-2 | an-275 | 1U0652 | sp-2 | an-275 | 1C0652 | sp-2 | an-275 |
| 1A0653 | sp-2 | an-276 | 1U0653 | sp-2 | an-276 | 1C0653 | sp-2 | an-276 |
| 1A0654 | sp-2 | an-277 | 1U0654 | sp-2 | an-277 | 1C0654 | sp-2 | an-277 |
| 1A0655 | sp-2 | an-278 | 1U0655 | sp-2 | an-278 | 1C0655 | sp-2 | an-278 |
| 1A0656 | sp-2 | an-279 | 1U0656 | sp-2 | an-279 | 1C0656 | sp-2 | an-279 |
| 1A0657 | sp-2 | an-280 | 1U0657 | sp-2 | an-280 | 1C0657 | sp-2 | an-280 |
| 1A0658 | sp-2 | an-281 | 1U0658 | sp-2 | an-281 | 1C0658 | sp-2 | an-281 |
| 1A0659 | sp-2 | an-282 | 1U0659 | sp-2 | an-282 | 1C0659 | sp-2 | an-282 |
| 1A0660 | sp-2 | an-283 | 1U0660 | sp-2 | an-283 | 1C0660 | sp-2 | an-283 |
| 1A0661 | sp-2 | an-284 | 1U0661 | sp-2 | an-284 | 1C0661 | sp-2 | an-284 |
| 1A0662 | sp-2 | an-285 | 1U0662 | sp-2 | an-285 | 1C0662 | sp-2 | an-285 |
| 1A0663 | sp-2 | an-286 | 1U0663 | sp-2 | an-286 | 1C0663 | sp-2 | an-286 |
| 1A0664 | sp-2 | an-287 | 1U0664 | sp-2 | an-287 | 1C0664 | sp-2 | an-287 |
| 1A0665 | sp-2 | an-288 | 1U0665 | sp-2 | an-288 | 1C0665 | sp-2 | an-288 |
| 1A0666 | sp-2 | an-289 | 1U0666 | sp-2 | an-289 | 1C0666 | sp-2 | an-289 |
| 1A0667 | sp-2 | an-290 | 1U0667 | sp-2 | an-290 | 1C0667 | sp-2 | an-290 |
| 1A0668 | sp-2 | an-291 | 1U0668 | sp-2 | an-291 | 1C0668 | sp-2 | an-291 |
| 1A0669 | sp-2 | an-292 | 1U0669 | sp-2 | an-292 | 1C0669 | sp-2 | an-292 |
| 1A0670 | sp-2 | an-293 | 1U0670 | sp-2 | an-293 | 1C0670 | sp-2 | an-293 |
| 1A0671 | sp-2 | an-294 | 1U0671 | sp-2 | an-294 | 1C0671 | sp-2 | an-294 |
| 1A0672 | sp-2 | an-295 | 1U0672 | sp-2 | an-295 | 1C0672 | sp-2 | an-295 |
| | Table 2-13 |||||||||

| Y = NHCS ||| Y = NHCSNH ||| Y = NHCSO |||
|---|---|---|---|---|---|---|---|---|
| 1A0673 | sp-2 | an-296 | 1U0673 | sp-2 | an-296 | 1C0673 | sp-2 | an-296 |
| 1A0674 | sp-2 | an-297 | 1U0674 | sp-2 | an-297 | 1C0674 | sp-2 | an-297 |
| 1A0675 | sp-2 | an-298 | 1U0675 | sp-2 | an-298 | 1C0675 | sp-2 | an-298 |
| 1A0676 | sp-2 | an-299 | 1U0676 | sp-2 | an-299 | 1C0676 | sp-2 | an-299 |
| 1A0677 | sp-2 | an-300 | 1U0677 | sp-2 | an-300 | 1C0677 | sp-2 | an-300 |
| 1A0678 | sp-2 | an-301 | 1U0678 | sp-2 | an-301 | 1C0678 | sp-2 | an-301 |
| 1A0679 | sp-2 | an-302 | 1U0679 | sp-2 | an-302 | 1C0679 | sp-2 | an-302 |
| 1A0680 | sp-2 | an-303 | 1U0680 | sp-2 | an-303 | 1C0680 | sp-2 | an-303 |
| 1A0681 | sp-2 | an-304 | 1U0681 | sp-2 | an-304 | 1C0681 | sp-2 | an-304 |
| 1A0682 | sp-2 | an-305 | 1U0682 | sp-2 | an-305 | 1C0682 | sp-2 | an-305 |
| 1A0683 | sp-2 | an-306 | 1U0683 | sp-2 | an-306 | 1C0683 | sp-2 | an-306 |
| 1A0684 | sp-2 | an-307 | 1U0684 | sp-2 | an-307 | 1C0684 | sp-2 | an-307 |
| 1A0685 | sp-2 | an-308 | 1U0685 | sp-2 | an-308 | 1C0685 | sp-2 | an-308 |
| 1A0686 | sp-2 | an-309 | 1U0686 | sp-2 | an-309 | 1C0686 | sp-2 | an-309 |

-continued

| Ex. No. | Z | N⁺R⁵R⁶R⁷ | Ex. No. | Z | N⁺R⁵R⁶R⁷ | Ex. No. | Z | N⁺R⁵R⁶R⁷ |
|---|---|---|---|---|---|---|---|---|
| 1A0687 | sp-2 | an-310 | 1U0687 | sp-2 | an-310 | 1C0687 | sp-2 | an-310 |
| 1A0688 | sp-2 | an-311 | 1U0688 | sp-2 | an-311 | 1C0688 | sp-2 | an-311 |
| 1A0689 | sp-2 | an-312 | 1U0689 | sp-2 | an-312 | 1C0689 | sp-2 | an-312 |
| 1A0690 | sp-2 | an-313 | 1U0690 | sp-2 | an-313 | 1C0690 | sp-2 | an-313 |
| 1A0691 | sp-2 | an-314 | 1U0691 | sp-2 | an-314 | 1C0691 | sp-2 | an-314 |
| 1A0692 | sp-2 | an-315 | 1U0692 | sp-2 | an-315 | 1C0692 | sp-2 | an-315 |
| 1A0693 | sp-2 | an-316 | 1U0693 | sp-2 | an-316 | 1C0693 | sp-2 | an-316 |
| 1A0694 | sp-2 | an-317 | 1U0694 | sp-2 | an-317 | 1C0694 | sp-2 | an-317 |
| 1A0695 | sp-2 | an-318 | 1U0695 | sp-2 | an-318 | 1C0695 | sp-2 | an-318 |
| 1A0696 | sp-2 | an-319 | 1U0696 | sp-2 | an-319 | 1C0696 | sp-2 | an-319 |
| 1A0697 | sp-2 | an-320 | 1U0697 | sp-2 | an-320 | 1C0697 | sp-2 | an-320 |
| 1A0698 | sp-2 | an-321 | 1U0698 | sp-2 | an-321 | 1C0698 | sp-2 | an-321 |
| 1A0699 | sp-2 | an-322 | 1U0699 | sp-2 | an-322 | 1C0699 | sp-2 | an-322 |
| 1A0700 | sp-2 | an-323 | 1U0700 | sp-2 | an-323 | 1C0700 | sp-2 | an-323 |
| 1A0701 | sp-2 | an-324 | 1U0701 | sp-2 | an-324 | 1C0701 | sp-2 | an-324 |
| 1A0702 | sp-2 | an-325 | 1U0702 | sp-2 | an-325 | 1C0702 | sp-2 | an-325 |
| 1A0703 | sp-2 | an-326 | 1U0703 | sp-2 | an-326 | 1C0703 | sp-2 | an-326 |
| 1A0704 | sp-2 | an-327 | 1U0704 | sp-2 | an-327 | 1C0704 | sp-2 | an-327 |
| 1A0705 | sp-2 | an-328 | 1U0705 | sp-2 | an-328 | 1C0705 | sp-2 | an-328 |
| 1A0706 | sp-2 | an-329 | 1U0706 | sp-2 | an-329 | 1C0706 | sp-2 | an-329 |
| 1A0707 | sp-2 | an-330 | 1U0707 | sp-2 | an-330 | 1C0707 | sp-2 | an-330 |
| 1A0708 | sp-2 | an-331 | 1U0708 | sp-2 | an-331 | 1C0708 | sp-2 | an-331 |
| 1A0709 | sp-2 | an-332 | 1U0709 | sp-2 | an-332 | 1C0709 | sp-2 | an-332 |
| 1A0710 | sp-2 | an-333 | 1U0710 | sp-2 | an-333 | 1C0710 | sp-2 | an-333 |
| 1A0711 | sp-2 | an-334 | 1U0711 | sp-2 | an-334 | 1C0711 | sp-2 | an-334 |
| 1A0712 | sp-2 | an-335 | 1U0712 | sp-2 | an-335 | 1C0712 | sp-2 | an-335 |
| 1A0713 | sp-2 | an-336 | 1U0713 | sp-2 | an-336 | 1C0713 | sp-2 | an-336 |
| 1A0714 | sp-2 | an-337 | 1U0714 | sp-2 | an-337 | 1C0714 | sp-2 | an-337 |
| 1A0715 | sp-2 | an-338 | 1U0715 | sp-2 | an-338 | 1C0715 | sp-2 | an-338 |
| 1A0716 | sp-2 | an-339 | 1U0716 | sp-2 | an-339 | 1C0716 | sp-2 | an-339 |
| 1A0717 | sp-2 | an-340 | 1U0717 | sp-2 | an-340 | 1C0717 | sp-2 | an-340 |
| 1A0718 | sp-2 | an-341 | 1U0718 | sp-2 | an-341 | 1C0718 | sp-2 | an-341 |
| 1A0719 | sp-2 | an-342 | 1U0719 | sp-2 | an-342 | 1C0719 | sp-2 | an-342 |
| 1A0720 | sp-2 | an-343 | 1U0720 | sp-2 | an-343 | 1C0720 | sp-2 | an-343 |
| 1A0721 | sp-2 | an-344 | 1U0721 | sp-2 | an-344 | 1C0721 | sp-2 | an-344 |
| 1A0722 | sp-2 | an-345 | 1U0722 | sp-2 | an-345 | 1C0722 | sp-2 | an-345 |
| 1A0723 | sp-2 | an-346 | 1U0723 | sp-2 | an-346 | 1C0723 | sp-2 | an-346 |
| 1A0724 | sp-2 | an-347 | 1U0724 | sp-2 | an-347 | 1C0724 | sp-2 | an-347 |
| 1A0725 | sp-2 | an-348 | 1U0725 | sp-2 | an-348 | 1C0725 | sp-2 | an-348 |
| 1A0726 | sp-2 | an-349 | 1U0726 | sp-2 | an-349 | 1C0726 | sp-2 | an-349 |
| 1A0727 | sp-2 | an-350 | 1U0727 | sp-2 | an-350 | 1C0727 | sp-2 | an-350 |
| 1A0728 | sp-2 | an-351 | 1U0728 | sp-2 | an-351 | 1C0728 | sp-2 | an-351 |

Table 2-14

| Y = NHCS | | | Y = NHCSNH | | | Y = NHCSO | | |
|---|---|---|---|---|---|---|---|---|
| 1A0729 | sp-2 | an-352 | 1U0729 | sp-2 | an-352 | 1C0729 | sp-2 | an-352 |
| 1A0730 | sp-2 | an-353 | 1U0730 | sp-2 | an-353 | 1C0730 | sp-2 | an-353 |
| 1A0731 | sp-2 | an-354 | 1U0731 | sp-2 | an-354 | 1C0731 | sp-2 | an-354 |
| 1A0732 | sp-2 | an-355 | 1U0732 | sp-2 | an-355 | 1C0732 | sp-2 | an-355 |
| 1A0733 | sp-2 | an-356 | 1U0733 | sp-2 | an-356 | 1C0733 | sp-2 | an-356 |
| 1A0734 | sp-2 | an-357 | 1U0734 | sp-2 | an-357 | 1C0734 | sp-2 | an-357 |
| 1A0735 | sp-2 | an-358 | 1U0735 | sp-2 | an-358 | 1C0735 | sp-2 | an-358 |
| 1A0736 | sp-2 | an-359 | 1U0736 | sp-2 | an-359 | 1C0736 | sp-2 | an-359 |
| 1A0737 | sp-2 | an-360 | 1U0737 | sp-2 | an-360 | 1C0737 | sp-2 | an-360 |
| 1A0738 | sp-2 | an-361 | 1U0738 | sp-2 | an-361 | 1C0738 | sp-2 | an-361 |
| 1A0739 | sp-2 | an-362 | 1U0739 | sp-2 | an-362 | 1C0739 | sp-2 | an-362 |
| 1A0740 | sp-2 | an-363 | 1U0740 | sp-2 | an-363 | 1C0740 | sp-2 | an-363 |
| 1A0741 | sp-2 | an-364 | 1U0741 | sp-2 | an-364 | 1C0741 | sp-2 | an-364 |
| 1A0742 | sp-2 | an-365 | 1U0742 | sp-2 | an-365 | 1C0742 | sp-2 | an-365 |
| 1A0743 | sp-2 | an-366 | 1U0743 | sp-2 | an-366 | 1C0743 | sp-2 | an-366 |
| 1A0744 | sp-2 | an-367 | 1U0744 | sp-2 | an-367 | 1C0744 | sp-2 | an-367 |
| 1A0745 | sp-2 | an-368 | 1U0745 | sp-2 | an-368 | 1C0745 | sp-2 | an-368 |
| 1A0746 | sp-2 | an-369 | 1U0746 | sp-2 | an-369 | 1C0746 | sp-2 | an-369 |
| 1A0747 | sp-2 | an-370 | 1U0747 | sp-2 | an-370 | 1C0747 | sp-2 | an-370 |
| 1A0748 | sp-2 | an-371 | 1U0748 | sp-2 | an-371 | 1C0748 | sp-2 | an-371 |
| 1A0749 | sp-2 | an-372 | 1U0749 | sp-2 | an-372 | 1C0749 | sp-2 | an-372 |
| 1A0750 | sp-2 | an-373 | 1U0750 | sp-2 | an-373 | 1C0750 | sp-2 | an-373 |
| 1A0751 | sp-2 | an-374 | 1U0751 | sp-2 | an-374 | 1C0751 | sp-2 | an-374 |
| 1A0752 | sp-2 | an-375 | 1U0752 | sp-2 | an-375 | 1C0752 | sp-2 | an-375 |
| 1A0753 | sp-2 | an-376 | 1U0753 | sp-2 | an-376 | 1C0753 | sp-2 | an-376 |
| 1A0754 | sp-2 | an-377 | 1U0754 | sp-2 | an-377 | 1C0754 | sp-2 | an-377 |
| 1A0755 | sp-3 | an-1 | 1U0755 | sp-3 | an-1 | 1C0755 | sp-3 | an-1 |
| 1A0756 | sp-3 | an-2 | 1U0756 | sp-3 | an-2 | 1C0756 | sp-3 | an-2 |
| 1A0757 | sp-3 | an-3 | 1U0757 | sp-3 | an-3 | 1C0757 | sp-3 | an-3 |
| 1A0758 | sp-3 | an-4 | 1U0758 | sp-3 | an-4 | 1C0758 | sp-3 | an-4 |
| 1A0759 | sp-3 | an-5 | 1U0759 | sp-3 | an-5 | 1C0759 | sp-3 | an-5 |
| 1A0760 | sp-3 | an-6 | 1U0760 | sp-3 | an-6 | 1C0760 | sp-3 | an-6 |

| Ex. No. | Z | N⁺R⁵R⁶R⁷ | Ex. No. | Z | N⁺R⁵R⁶R⁷ | Ex. No. | Z | N⁺R⁵R⁶R⁷ |
|---|---|---|---|---|---|---|---|---|
| 1A0761 | sp-3 | an-7 | 1U0761 | sp-3 | an-7 | 1C0761 | sp-3 | an-7 |
| 1A0762 | sp-3 | an-8 | 1U0762 | sp-3 | an-8 | 1C0762 | sp-3 | an-8 |
| 1A0763 | sp-3 | an-9 | 1U0763 | sp-3 | an-9 | 1C0763 | sp-3 | an-9 |
| 1A0764 | sp-3 | an-10 | 1U0764 | sp-3 | an-10 | 1C0764 | sp-3 | an-10 |
| 1A0765 | sp-3 | an-11 | 1U0765 | sp-3 | an-11 | 1C0765 | sp-3 | an-11 |
| 1A0766 | sp-3 | an-12 | 1U0766 | sp-3 | an-12 | 1C0766 | sp-3 | an-12 |
| 1A0767 | sp-3 | an-13 | 1U0767 | sp-3 | an-13 | 1C0767 | sp-3 | an-13 |
| 1A0768 | sp-3 | an-14 | 1U0768 | sp-3 | an-14 | 1C0768 | sp-3 | an-14 |
| 1A0769 | sp-3 | an-15 | 1U0769 | sp-3 | an-15 | 1C0769 | sp-3 | an-15 |
| 1A0770 | sp-3 | an-16 | 1U0770 | sp-3 | an-16 | 1C0770 | sp-3 | an-16 |
| 1A0771 | sp-3 | an-17 | 1U0771 | sp-3 | an-17 | 1C0771 | sp-3 | an-17 |
| 1A0772 | sp-3 | an-18 | 1U0772 | sp-3 | an-18 | 1C0772 | sp-3 | an-18 |
| 1A0773 | sp-3 | an-19 | 1U0773 | sp-3 | an-19 | 1C0773 | sp-3 | an-19 |
| 1A0774 | sp-3 | an-20 | 1U0774 | sp-3 | an-20 | 1C0774 | sp-3 | an-20 |
| 1A0775 | sp-3 | an-21 | 1U0775 | sp-3 | an-21 | 1C0775 | sp-3 | an-21 |
| 1A0776 | sp-3 | an-22 | 1U0776 | sp-3 | an-22 | 1C0776 | sp-3 | an-22 |
| 1A0777 | sp-3 | an-23 | 1U0777 | sp-3 | an-23 | 1C0777 | sp-3 | an-23 |
| 1A0778 | sp-3 | an-24 | 1U0778 | sp-3 | an-24 | 1C0778 | sp-3 | an-24 |
| 1A0779 | sp-3 | an-25 | 1U0779 | sp-3 | an-25 | 1C0779 | sp-3 | an-25 |
| 1A0780 | sp-3 | an-26 | 1U0780 | sp-3 | an-26 | 1C0780 | sp-3 | an-26 |
| 1A0781 | sp-3 | an-27 | 1U0781 | sp-3 | an-27 | 1C0781 | sp-3 | an-27 |
| 1A0782 | sp-3 | an-28 | 1U0782 | sp-3 | an-28 | 1C0782 | sp-3 | an-28 |
| 1A0783 | sp-3 | an-29 | 1U0783 | sp-3 | an-29 | 1C0783 | sp-3 | an-29 |
| 1A0784 | sp-3 | an-30 | 1U0784 | sp-3 | an-30 | 1C0784 | sp-3 | an-30 |

Table 2-15

| Y = NHCS | | | Y = NHCSNH | | | Y = NHCSO | | |
|---|---|---|---|---|---|---|---|---|
| 1A0785 | sp-3 | an-31 | 1U0785 | sp-3 | an-31 | 1C0785 | sp-3 | an-31 |
| 1A0786 | sp-3 | an-32 | 1U0786 | sp-3 | an-32 | 1C0786 | sp-3 | an-32 |
| 1A0787 | sp-3 | an-33 | 1U0787 | sp-3 | an-33 | 1C0787 | sp-3 | an-33 |
| 1A0788 | sp-3 | an-34 | 1U0788 | sp-3 | an-34 | 1C0788 | sp-3 | an-34 |
| 1A0789 | sp-3 | an-35 | 1U0789 | sp-3 | an-35 | 1C0789 | sp-3 | an-35 |
| 1A0790 | sp-3 | an-36 | 1U0790 | sp-3 | an-36 | 1C0790 | sp-3 | an-36 |
| 1A0791 | sp-3 | an-37 | 1U0791 | sp-3 | an-37 | 1C0791 | sp-3 | an-37 |
| 1A0792 | sp-3 | an-38 | 1U0792 | sp-3 | an-38 | 1C0792 | sp-3 | an-38 |
| 1A0793 | sp-3 | an-39 | 1U0793 | sp-3 | an-39 | 1C0793 | sp-3 | an-39 |
| 1A0794 | sp-3 | an-40 | 1U0794 | sp-3 | an-40 | 1C0794 | sp-3 | an-40 |
| 1A0795 | sp-3 | an-41 | 1U0795 | sp-3 | an-41 | 1C0795 | sp-3 | an-41 |
| 1A0796 | sp-3 | an-42 | 1U0796 | sp-3 | an-42 | 1C0796 | sp-3 | an-42 |
| 1A0797 | sp-3 | an-43 | 1U0797 | sp-3 | an-43 | 1C0797 | sp-3 | an-43 |
| 1A0798 | sp-3 | an-44 | 1U0798 | sp-3 | an-44 | 1C0798 | sp-3 | an-44 |
| 1A0799 | sp-3 | an-45 | 1U0799 | sp-3 | an-45 | 1C0799 | sp-3 | an-45 |
| 1A0800 | sp-3 | an-46 | 1U0800 | sp-3 | an-46 | 1C0800 | sp-3 | an-46 |
| 1A0801 | sp-3 | an-47 | 1U0801 | sp-3 | an-47 | 1C0801 | sp-3 | an-47 |
| 1A0802 | sp-3 | an-48 | 1U0802 | sp-3 | an-48 | 1C0802 | sp-3 | an-48 |
| 1A0803 | sp-3 | an-49 | 1U0803 | sp-3 | an-49 | 1C0803 | sp-3 | an-49 |
| 1A0804 | sp-3 | an-50 | 1U0804 | sp-3 | an-50 | 1C0804 | sp-3 | an-50 |
| 1A0805 | sp-3 | an-51 | 1U0805 | sp-3 | an-51 | 1C0805 | sp-3 | an-51 |
| 1A0806 | sp-3 | an-52 | 1U0806 | sp-3 | an-52 | 1C0806 | sp-3 | an-52 |
| 1A0807 | sp-3 | an-53 | 1U0807 | sp-3 | an-53 | 1C0807 | sp-3 | an-53 |
| 1A0808 | sp-3 | an-54 | 1U0808 | sp-3 | an-54 | 1C0808 | sp-3 | an-54 |
| 1A0809 | sp-3 | an-55 | 1U0809 | sp-3 | an-55 | 1C0809 | sp-3 | an-55 |
| 1A0810 | sp-3 | an-56 | 1U0810 | sp-3 | an-56 | 1C0810 | sp-3 | an-56 |
| 1A0811 | sp-3 | an-57 | 1U0811 | sp-3 | an-57 | 1C0811 | sp-3 | an-57 |
| 1A0812 | sp-3 | an-58 | 1U0812 | sp-3 | an-58 | 1C0812 | sp-3 | an-58 |
| 1A0813 | sp-3 | an-59 | 1U0813 | sp-3 | an-59 | 1C0813 | sp-3 | an-59 |
| 1A0814 | sp-3 | an-60 | 1U0814 | sp-3 | an-60 | 1C0814 | sp-3 | an-60 |
| 1A0815 | sp-3 | an-61 | 1U0815 | sp-3 | an-61 | 1C0815 | sp-3 | an-61 |
| 1A0816 | sp-3 | an-62 | 1U0816 | sp-3 | an-62 | 1C0816 | sp-3 | an-62 |
| 1A0817 | sp-3 | an-63 | 1U0817 | sp-3 | an-63 | 1C0817 | sp-3 | an-63 |
| 1A0818 | sp-3 | an-64 | 1U0818 | sp-3 | an-64 | 1C0818 | sp-3 | an-64 |
| 1A0819 | sp-3 | an-65 | 1U0819 | sp-3 | an-65 | 1C0819 | sp-3 | an-65 |
| 1A0820 | sp-3 | an-66 | 1U0820 | sp-3 | an-66 | 1C0820 | sp-3 | an-66 |
| 1A0821 | sp-3 | an-67 | 1U0821 | sp-3 | an-67 | 1C0821 | sp-3 | an-67 |
| 1A0822 | sp-3 | an-68 | 1U0822 | sp-3 | an-68 | 1C0822 | sp-3 | an-68 |
| 1A0823 | sp-3 | an-69 | 1U0823 | sp-3 | an-69 | 1C0823 | sp-3 | an-69 |
| 1A0824 | sp-3 | an-70 | 1U0824 | sp-3 | an-70 | 1C0824 | sp-3 | an-70 |
| 1A0825 | sp-3 | an-71 | 1U0825 | sp-3 | an-71 | 1C0825 | sp-3 | an-71 |
| 1A0826 | sp-3 | an-72 | 1U0826 | sp-3 | an-72 | 1C0826 | sp-3 | an-72 |
| 1A0827 | sp-3 | an-73 | 1U0827 | sp-3 | an-73 | 1C0827 | sp-3 | an-73 |
| 1A0828 | sp-3 | an-74 | 1U0828 | sp-3 | an-74 | 1C0828 | sp-3 | an-74 |
| 1A0829 | sp-3 | an-75 | 1U0829 | sp-3 | an-75 | 1C0829 | sp-3 | an-75 |
| 1A0830 | sp-3 | an-76 | 1U0830 | sp-3 | an-76 | 1C0830 | sp-3 | an-76 |
| 1A0831 | sp-3 | an-77 | 1U0831 | sp-3 | an-77 | 1C0831 | sp-3 | an-77 |
| 1A0832 | sp-3 | an-78 | 1U0832 | sp-3 | an-78 | 1C0832 | sp-3 | an-78 |
| 1A0833 | sp-3 | an-79 | 1U0833 | sp-3 | an-79 | 1C0833 | sp-3 | an-79 |
| 1A0834 | sp-3 | an-80 | 1U0834 | sp-3 | an-80 | 1C0834 | sp-3 | an-80 |

-continued

| Ex. No. | Z | N⁺R⁵R⁶R⁷ | Ex. No. | Z | N⁺R⁵R⁶R⁷ | Ex. No. | Z | N⁺R⁵R⁶R⁷ |
|---|---|---|---|---|---|---|---|---|
| 1A0835 | sp-3 | an-81 | 1U0835 | sp-3 | an-81 | 1C0835 | sp-3 | an-81 |
| 1A0836 | sp-3 | an-82 | 1U0836 | sp-3 | an-82 | 1C0836 | sp-3 | an-82 |
| 1A0837 | sp-3 | an-83 | 1U0837 | sp-3 | an-83 | 1C0837 | sp-3 | an-83 |
| 1A0838 | sp-3 | an-84 | 1U0838 | sp-3 | an-84 | 1C0838 | sp-3 | an-84 |
| 1A0839 | sp-3 | an-85 | 1U0839 | sp-3 | an-85 | 1C0839 | sp-3 | an-85 |
| 1A0840 | sp-3 | an-86 | 1U0840 | sp-3 | an-86 | 1C0840 | sp-3 | an-86 |

Table 2-16

| Y = NHCS | | | Y = NHCSNH | | | Y = NHCSO | | |
|---|---|---|---|---|---|---|---|---|
| 1A0841 | sp-3 | an-87 | 1U0841 | sp-3 | an-87 | 1C0841 | sp-3 | an-87 |
| 1A0842 | sp-3 | an-88 | 1U0842 | sp-3 | an-88 | 1C0842 | sp-3 | an-88 |
| 1A0843 | sp-3 | an-89 | 1U0843 | sp-3 | an-89 | 1C0843 | sp-3 | an-89 |
| 1A0844 | sp-3 | an-90 | 1U0844 | sp-3 | an-90 | 1C0844 | sp-3 | an-90 |
| 1A0845 | sp-3 | an-91 | 1U0845 | sp-3 | an-91 | 1C0845 | sp-3 | an-91 |
| 1A0846 | sp-3 | an-92 | 1U0846 | sp-3 | an-92 | 1C0846 | sp-3 | an-92 |
| 1A0847 | sp-3 | an-93 | 1U0847 | sp-3 | an-93 | 1C0847 | sp-3 | an-93 |
| 1A0848 | sp-3 | an-94 | 1U0848 | sp-3 | an-94 | 1C0848 | sp-3 | an-94 |
| 1A0849 | sp-3 | an-95 | 1U0849 | sp-3 | an-95 | 1C0849 | sp-3 | an-95 |
| 1A0850 | sp-3 | an-96 | 1U0850 | sp-3 | an-96 | 1C0850 | sp-3 | an-96 |
| 1A0851 | sp-3 | an-97 | 1U0851 | sp-3 | an-97 | 1C0851 | sp-3 | an-97 |
| 1A0852 | sp-3 | an-98 | 1U0852 | sp-3 | an-98 | 1C0852 | sp-3 | an-98 |
| 1A0853 | sp-3 | an-99 | 1U0853 | sp-3 | an-99 | 1C0853 | sp-3 | an-99 |
| 1A0854 | sp-3 | an-100 | 1U0854 | sp-3 | an-100 | 1C0854 | sp-3 | an-100 |
| 1A0855 | sp-3 | an-101 | 1U0855 | sp-3 | an-101 | 1C0855 | sp-3 | an-101 |
| 1A0856 | sp-3 | an-102 | 1U0856 | sp-3 | an-102 | 1C0856 | sp-3 | an-102 |
| 1A0857 | sp-3 | an-103 | 1U0857 | sp-3 | an-103 | 1C0857 | sp-3 | an-103 |
| 1A0858 | sp-3 | an-104 | 1U0858 | sp-3 | an-104 | 1C0858 | sp-3 | an-104 |
| 1A0859 | sp-3 | an-105 | 1U0859 | sp-3 | an-105 | 1C0859 | sp-3 | an-105 |
| 1A0860 | sp-3 | an-106 | 1U0860 | sp-3 | an-106 | 1C0860 | sp-3 | an-106 |
| 1A0861 | sp-3 | an-107 | 1U0861 | sp-3 | an-107 | 1C0861 | sp-3 | an-107 |
| 1A0862 | sp-3 | an-108 | 1U0862 | sp-3 | an-108 | 1C0862 | sp-3 | an-108 |
| 1A0863 | sp-3 | an-109 | 1U0863 | sp-3 | an-109 | 1C0863 | sp-3 | an-109 |
| 1A0864 | sp-3 | an-110 | 1U0864 | sp-3 | an-110 | 1C0864 | sp-3 | an-110 |
| 1A0865 | sp-3 | an-111 | 1U0865 | sp-3 | an-111 | 1C0865 | sp-3 | an-111 |
| 1A0866 | sp-3 | an-112 | 1U0866 | sp-3 | an-112 | 1C0866 | sp-3 | an-112 |
| 1A0867 | sp-3 | an-113 | 1U0867 | sp-3 | an-113 | 1C0867 | sp-3 | an-113 |
| 1A0868 | sp-3 | an-114 | 1U0868 | sp-3 | an-114 | 1C0868 | sp-3 | an-114 |
| 1A0869 | sp-3 | an-115 | 1U0869 | sp-3 | an-115 | 1C0869 | sp-3 | an-115 |
| 1A0870 | sp-3 | an-116 | 1U0870 | sp-3 | an-116 | 1C0870 | sp-3 | an-116 |
| 1A0871 | sp-3 | an-117 | 1U0871 | sp-3 | an-117 | 1C0871 | sp-3 | an-117 |
| 1A0872 | sp-3 | an-118 | 1U0872 | sp-3 | an-118 | 1C0872 | sp-3 | an-118 |
| 1A0873 | sp-3 | an-119 | 1U0873 | sp-3 | an-119 | 1C0873 | sp-3 | an-119 |
| 1A0874 | sp-3 | an-120 | 1U0874 | sp-3 | an-120 | 1C0874 | sp-3 | an-120 |
| 1A0875 | sp-3 | an-121 | 1U0875 | sp-3 | an-121 | 1C0875 | sp-3 | an-121 |
| 1A0876 | sp-3 | an-122 | 1U0876 | sp-3 | an-122 | 1C0876 | sp-3 | an-122 |
| 1A0877 | sp-3 | an-123 | 1U0877 | sp-3 | an-123 | 1C0877 | sp-3 | an-123 |
| 1A0878 | sp-3 | an-124 | 1U0878 | sp-3 | an-124 | 1C0878 | sp-3 | an-124 |
| 1A0879 | sp-3 | an-125 | 1U0879 | sp-3 | an-125 | 1C0879 | sp-3 | an-125 |
| 1A0880 | sp-3 | an-126 | 1U0880 | sp-3 | an-126 | 1C0880 | sp-3 | an-126 |
| 1A0881 | sp-3 | an-127 | 1U0881 | sp-3 | an-127 | 1C0881 | sp-3 | an-127 |
| 1A0882 | sp-3 | an-128 | 1U0882 | sp-3 | an-128 | 1C0882 | sp-3 | an-128 |
| 1A0883 | sp-3 | an-129 | 1U0883 | sp-3 | an-129 | 1C0883 | sp-3 | an-129 |
| 1A0884 | sp-3 | an-130 | 1U0884 | sp-3 | an-130 | 1C0884 | sp-3 | an-130 |
| 1A0885 | sp-3 | an-131 | 1U0885 | sp-3 | an-131 | 1C0885 | sp-3 | an-131 |
| 1A0886 | sp-3 | an-132 | 1U0886 | sp-3 | an-132 | 1C0886 | sp-3 | an-132 |
| 1A0887 | sp-3 | an-133 | 1U0887 | sp-3 | an-133 | 1C0887 | sp-3 | an-133 |
| 1A0888 | sp-3 | an-134 | 1U0888 | sp-3 | an-134 | 1C0888 | sp-3 | an-134 |
| 1A0889 | sp-3 | an-135 | 1U0889 | sp-3 | an-135 | 1C0889 | sp-3 | an-135 |
| 1A0890 | sp-3 | an-136 | 1U0890 | sp-3 | an-136 | 1C0890 | sp-3 | an-136 |
| 1A0891 | sp-3 | an-137 | 1U0891 | sp-3 | an-137 | 1C0891 | sp-3 | an-137 |
| 1A0892 | sp-3 | an-138 | 1U0892 | sp-3 | an-138 | 1C0892 | sp-3 | an-138 |
| 1A0893 | sp-3 | an-139 | 1U0893 | sp-3 | an-139 | 1C0893 | sp-3 | an-139 |
| 1A0894 | sp-3 | an-140 | 1U0894 | sp-3 | an-140 | 1C0894 | sp-3 | an-140 |
| 1A0895 | sp-3 | an-141 | 1U0895 | sp-3 | an-141 | 1C0895 | sp-3 | an-141 |
| 1A0896 | sp-3 | an-142 | 1U0896 | sp-3 | an-142 | 1C0896 | sp-3 | an-142 |

Table 2-17

| Y = NHCS | | | Y = NHCSNH | | | Y = NHCSO | | |
|---|---|---|---|---|---|---|---|---|
| 1A0897 | sp-3 | an-143 | 1U0897 | sp-3 | an-143 | 1C0897 | sp-3 | an-143 |
| 1A0898 | sp-3 | an-144 | 1U0898 | sp-3 | an-144 | 1C0898 | sp-3 | an-144 |
| 1A0899 | sp-3 | an-145 | 1U0899 | sp-3 | an-145 | 1C0899 | sp-3 | an-145 |
| 1A0900 | sp-3 | an-146 | 1U0900 | sp-3 | an-146 | 1C0900 | sp-3 | an-146 |
| 1A0901 | sp-3 | an-147 | 1U0901 | sp-3 | an-147 | 1C0901 | sp-3 | an-147 |
| 1A0902 | sp-3 | an-148 | 1U0902 | sp-3 | an-148 | 1C0902 | sp-3 | an-148 |
| 1A0903 | sp-3 | an-149 | 1U0903 | sp-3 | an-149 | 1C0903 | sp-3 | an-149 |
| 1A0904 | sp-3 | an-150 | 1U0904 | sp-3 | an-150 | 1C0904 | sp-3 | an-150 |

| Ex. No. | Z | $N^+R^5R^6R^7$ | Ex. No. | Z | $N^+R^5R^6R^7$ | Ex. No. | Z | $N^+R^5R^6R^7$ |
|---|---|---|---|---|---|---|---|---|
| 1A0905 | sp-3 | an-151 | 1U0905 | sp-3 | an-151 | 1C0905 | sp-3 | an-151 |
| 1A0906 | sp-3 | an-152 | 1U0906 | sp-3 | an-152 | 1C0906 | sp-3 | an-152 |
| 1A0907 | sp-3 | an-153 | 1U0907 | sp-3 | an-153 | 1C0907 | sp-3 | an-153 |
| 1A0908 | sp-3 | an-154 | 1U0908 | sp-3 | an-154 | 1C0908 | sp-3 | an-154 |
| 1A0909 | sp-3 | an-155 | 1U0909 | sp-3 | an-155 | 1C0909 | sp-3 | an-155 |
| 1A0910 | sp-3 | an-156 | 1U0910 | sp-3 | an-156 | 1C0910 | sp-3 | an-156 |
| 1A0911 | sp-3 | an-157 | 1U0911 | sp-3 | an-157 | 1C0911 | sp-3 | an-157 |
| 1A0912 | sp-3 | an-158 | 1U0912 | sp-3 | an-158 | 1C0912 | sp-3 | an-158 |
| 1A0913 | sp-3 | an-159 | 1U0913 | sp-3 | an-159 | 1C0913 | sp-3 | an-159 |
| 1A0914 | sp-3 | an-160 | 1U0914 | sp-3 | an-160 | 1C0914 | sp-3 | an-160 |
| 1A0915 | sp-3 | an-161 | 1U0915 | sp-3 | an-161 | 1C0915 | sp-3 | an-161 |
| 1A0916 | sp-3 | an-162 | 1U0916 | sp-3 | an-162 | 1C0916 | sp-3 | an-162 |
| 1A0917 | sp-3 | an-163 | 1U0917 | sp-3 | an-163 | 1C0917 | sp-3 | an-163 |
| 1A0918 | sp-3 | an-164 | 1U0918 | sp-3 | an-164 | 1C0918 | sp-3 | an-164 |
| 1A0919 | sp-3 | an-165 | 1U0919 | sp-3 | an-165 | 1C0919 | sp-3 | an-165 |
| 1A0920 | sp-3 | an-166 | 1U0920 | sp-3 | an-166 | 1C0920 | sp-3 | an-166 |
| 1A0921 | sp-3 | an-167 | 1U0921 | sp-3 | an-167 | 1C0921 | sp-3 | an-167 |
| 1A0922 | sp-3 | an-168 | 1U0922 | sp-3 | an-168 | 1C0922 | sp-3 | an-168 |
| 1A0923 | sp-3 | an-169 | 1U0923 | sp-3 | an-169 | 1C0923 | sp-3 | an-169 |
| 1A0924 | sp-3 | an-170 | 1U0924 | sp-3 | an-170 | 1C0924 | sp-3 | an-170 |
| 1A0925 | sp-3 | an-171 | 1U0925 | sp-3 | an-171 | 1C0925 | sp-3 | an-171 |
| 1A0926 | sp-3 | an-172 | 1U0926 | sp-3 | an-172 | 1C0926 | sp-3 | an-172 |
| 1A0927 | sp-3 | an-173 | 1U0927 | sp-3 | an-173 | 1C0927 | sp-3 | an-173 |
| 1A0928 | sp-3 | an-174 | 1U0928 | sp-3 | an-174 | 1C0928 | sp-3 | an-174 |
| 1A0929 | sp-3 | an-175 | 1U0929 | sp-3 | an-175 | 1C0929 | sp-3 | an-175 |
| 1A0930 | sp-3 | an-176 | 1U0930 | sp-3 | an-176 | 1C0930 | sp-3 | an-176 |
| 1A0931 | sp-3 | an-177 | 1U0931 | sp-3 | an-177 | 1C0931 | sp-3 | an-177 |
| 1A0932 | sp-3 | an-178 | 1U0932 | sp-3 | an-178 | 1C0932 | sp-3 | an-178 |
| 1A0933 | sp-3 | an-179 | 1U0933 | sp-3 | an-179 | 1C0933 | sp-3 | an-179 |
| 1A0934 | sp-3 | an-180 | 1U0934 | sp-3 | an-180 | 1C0934 | sp-3 | an-180 |
| 1A0935 | sp-3 | an-181 | 1U0935 | sp-3 | an-181 | 1C0935 | sp-3 | an-181 |
| 1A0936 | sp-3 | an-182 | 1U0936 | sp-3 | an-182 | 1C0936 | sp-3 | an-182 |
| 1A0937 | sp-3 | an-183 | 1U0937 | sp-3 | an-183 | 1C0937 | sp-3 | an-183 |
| 1A0938 | sp-3 | an-184 | 1U0938 | sp-3 | an-184 | 1C0938 | sp-3 | an-184 |
| 1A0939 | sp-3 | an-185 | 1U0939 | sp-3 | an-185 | 1C0939 | sp-3 | an-185 |
| 1A0940 | sp-3 | an-186 | 1U0940 | sp-3 | an-186 | 1C0940 | sp-3 | an-186 |
| 1A0941 | sp-3 | an-187 | 1U0941 | sp-3 | an-187 | 1C0941 | sp-3 | an-187 |
| 1A0942 | sp-3 | an-188 | 1U0942 | sp-3 | an-188 | 1C0942 | sp-3 | an-188 |
| 1A0943 | sp-3 | an-189 | 1U0943 | sp-3 | an-189 | 1C0943 | sp-3 | an-189 |
| 1A0944 | sp-3 | an-190 | 1U0944 | sp-3 | an-190 | 1C0944 | sp-3 | an-190 |
| 1A0945 | sp-3 | an-191 | 1U0945 | sp-3 | an-191 | 1C0945 | sp-3 | an-191 |
| 1A0946 | sp-3 | an-192 | 1U0946 | sp-3 | an-192 | 1C0946 | sp-3 | an-192 |
| 1A0947 | sp-3 | an-193 | 1U0947 | sp-3 | an-193 | 1C0947 | sp-3 | an-193 |
| 1A0948 | sp-3 | an-194 | 1U0948 | sp-3 | an-194 | 1C0948 | sp-3 | an-194 |
| 1A0949 | sp-3 | an-195 | 1U0949 | sp-3 | an-195 | 1C0949 | sp-3 | an-195 |
| 1A0950 | sp-3 | an-196 | 1U0950 | sp-3 | an-196 | 1C0950 | sp-3 | an-196 |
| 1A0951 | sp-3 | an-197 | 1U0951 | sp-3 | an-197 | 1C0951 | sp-3 | an-197 |
| 1A0952 | sp-3 | an-198 | 1U0952 | sp-3 | an-198 | 1C0952 | sp-3 | an-198 |

Table 2-18

| Y = NHCS | | | Y = NHCSNH | | | Y = NHCSO | | |
|---|---|---|---|---|---|---|---|---|
| 1A0953 | sp-3 | an-199 | 1U0953 | sp-3 | an-199 | 1C0953 | sp-3 | an-199 |
| 1A0954 | sp-3 | an-200 | 1U0954 | sp-3 | an-200 | 1C0954 | sp-3 | an-200 |
| 1A0955 | sp-3 | an-201 | 1U0955 | sp-3 | an-201 | 1C0955 | sp-3 | an-201 |
| 1A0956 | sp-3 | an-202 | 1U0956 | sp-3 | an-202 | 1C0956 | sp-3 | an-202 |
| 1A0957 | sp-3 | an-203 | 1U0957 | sp-3 | an-203 | 1C0957 | sp-3 | an-203 |
| 1A0958 | sp-3 | an-204 | 1U0958 | sp-3 | an-204 | 1C0958 | sp-3 | an-204 |
| 1A0959 | sp-3 | an-205 | 1U0959 | sp-3 | an-205 | 1C0959 | sp-3 | an-205 |
| 1A0960 | sp-3 | an-206 | 1U0960 | sp-3 | an-206 | 1C0960 | sp-3 | an-206 |
| 1A0961 | sp-3 | an-207 | 1U0961 | sp-3 | an-207 | 1C0961 | sp-3 | an-207 |
| 1A0962 | sp-3 | an-208 | 1U0962 | sp-3 | an-208 | 1C0962 | sp-3 | an-208 |
| 1A0963 | sp-3 | an-209 | 1U0963 | sp-3 | an-209 | 1C0963 | sp-3 | an-209 |
| 1A0964 | sp-3 | an-210 | 1U0964 | sp-3 | an-210 | 1C0964 | sp-3 | an-210 |
| 1A0965 | sp-3 | an-211 | 1U0965 | sp-3 | an-211 | 1C0965 | sp-3 | an-211 |
| 1A0966 | sp-3 | an-212 | 1U0966 | sp-3 | an-212 | 1C0966 | sp-3 | an-212 |
| 1A0967 | sp-3 | an-213 | 1U0967 | sp-3 | an-213 | 1C0967 | sp-3 | an-213 |
| 1A0968 | sp-3 | an-214 | 1U0968 | sp-3 | an-214 | 1C0968 | sp-3 | an-214 |
| 1A0969 | sp-3 | an-215 | 1U0969 | sp-3 | an-215 | 1C0969 | sp-3 | an-215 |
| 1A0970 | sp-3 | an-216 | 1U0970 | sp-3 | an-216 | 1C0970 | sp-3 | an-216 |
| 1A0971 | sp-3 | an-217 | 1U0971 | sp-3 | an-217 | 1C0971 | sp-3 | an-217 |
| 1A0972 | sp-3 | an-218 | 1U0972 | sp-3 | an-218 | 1C0972 | sp-3 | an-218 |
| 1A0973 | sp-3 | an-219 | 1U0973 | sp-3 | an-219 | 1C0973 | sp-3 | an-219 |
| 1A0974 | sp-3 | an-220 | 1U0974 | sp-3 | an-220 | 1C0974 | sp-3 | an-220 |
| 1A0975 | sp-3 | an-221 | 1U0975 | sp-3 | an-221 | 1C0975 | sp-3 | an-221 |
| 1A0976 | sp-3 | an-222 | 1U0976 | sp-3 | an-222 | 1C0976 | sp-3 | an-222 |
| 1A0977 | sp-3 | an-223 | 1U0977 | sp-3 | an-223 | 1C0977 | sp-3 | an-223 |
| 1A0978 | sp-3 | an-224 | 1U0978 | sp-3 | an-224 | 1C0978 | sp-3 | an-224 |

-continued

| Ex. No. | Z | N⁺R⁵R⁶R⁷ | Ex. No. | Z | N⁺R⁵R⁶R⁷ | Ex. No. | Z | N⁺R⁵R⁶R⁷ |
|---|---|---|---|---|---|---|---|---|
| 1A0979 | sp-3 | an-225 | 1U0979 | sp-3 | an-225 | 1C0979 | sp-3 | an-225 |
| 1A0980 | sp-3 | an-226 | 1U0980 | sp-3 | an-226 | 1C0980 | sp-3 | an-226 |
| 1A0981 | sp-3 | an-227 | 1U0981 | sp-3 | an-227 | 1C0981 | sp-3 | an-227 |
| 1A0982 | sp-3 | an-228 | 1U0982 | sp-3 | an-228 | 1C0982 | sp-3 | an-228 |
| 1A0983 | sp-3 | an-229 | 1U0983 | sp-3 | an-229 | 1C0983 | sp-3 | an-229 |
| 1A0984 | sp-3 | an-230 | 1U0984 | sp-3 | an-230 | 1C0984 | sp-3 | an-230 |
| 1A0985 | sp-3 | an-231 | 1U0985 | sp-3 | an-231 | 1C0985 | sp-3 | an-231 |
| 1A0986 | sp-3 | an-232 | 1U0986 | sp-3 | an-232 | 1C0986 | sp-3 | an-232 |
| 1A0987 | sp-3 | an-233 | 1U0987 | sp-3 | an-233 | 1C0987 | sp-3 | an-233 |
| 1A0988 | sp-3 | an-234 | 1U0988 | sp-3 | an-234 | 1C0988 | sp-3 | an-234 |
| 1A0989 | sp-3 | an-235 | 1U0989 | sp-3 | an-235 | 1C0989 | sp-3 | an-235 |
| 1A0990 | sp-3 | an-236 | 1U0990 | sp-3 | an-236 | 1C0990 | sp-3 | an-236 |
| 1A0991 | sp-3 | an-237 | 1U0991 | sp-3 | an-237 | 1C0991 | sp-3 | an-237 |
| 1A0992 | sp-3 | an-238 | 1U0992 | sp-3 | an-238 | 1C0992 | sp-3 | an-238 |
| 1A0993 | sp-3 | an-239 | 1U0993 | sp-3 | an-239 | 1C0993 | sp-3 | an-239 |
| 1A0994 | sp-3 | an-240 | 1U0994 | sp-3 | an-240 | 1C0994 | sp-3 | an-240 |
| 1A0995 | sp-3 | an-241 | 1U0995 | sp-3 | an-241 | 1C0995 | sp-3 | an-241 |
| 1A0996 | sp-3 | an-242 | 1U0996 | sp-3 | an-242 | 1C0996 | sp-3 | an-242 |
| 1A0997 | sp-3 | an-243 | 1U0997 | sp-3 | an-243 | 1C0997 | sp-3 | an-243 |
| 1A0998 | sp-3 | an-244 | 1U0998 | sp-3 | an-244 | 1C0998 | sp-3 | an-244 |
| 1A0999 | sp-3 | an-245 | 1U0999 | sp-3 | an-245 | 1C0999 | sp-3 | an-245 |
| 1A1000 | sp-3 | an-246 | 1U1000 | sp-3 | an-246 | 1C1000 | sp-3 | an-246 |
| 1A1001 | sp-3 | an-247 | 1U1001 | sp-3 | an-247 | 1C1001 | sp-3 | an-247 |
| 1A1002 | sp-3 | an-248 | 1U1002 | sp-3 | an-248 | 1C1002 | sp-3 | an-248 |
| 1A1003 | sp-3 | an-249 | 1U1003 | sp-3 | an-249 | 1C1003 | sp-3 | an-249 |
| 1A1004 | sp-3 | an-250 | 1U1004 | sp-3 | an-250 | 1C1004 | sp-3 | an-250 |
| 1A1005 | sp-3 | an-251 | 1U1005 | sp-3 | an-251 | 1C1005 | sp-3 | an-251 |
| 1A1006 | sp-3 | an-252 | 1U1006 | sp-3 | an-252 | 1C1006 | sp-3 | an-252 |
| 1A1007 | sp-3 | an-253 | 1U1007 | sp-3 | an-253 | 1C1007 | sp-3 | an-253 |
| 1A1008 | sp-3 | an-254 | 1U1008 | sp-3 | an-254 | 1C1008 | sp-3 | an-254 |

Table 2-19

| Y = NHCS | | | Y = NHCSNH | | | Y = NHCSO | | |
|---|---|---|---|---|---|---|---|---|
| 1A1009 | sp-3 | an-255 | 1U1009 | sp-3 | an-255 | 1C1009 | sp-3 | an-255 |
| 1A1010 | sp-3 | an-256 | 1U1010 | sp-3 | an-256 | 1C1010 | sp-3 | an-256 |
| 1A1011 | sp-3 | an-257 | 1U1011 | sp-3 | an-257 | 1C1011 | sp-3 | an-257 |
| 1A1012 | sp-3 | an-258 | 1U1012 | sp-3 | an-258 | 1C1012 | sp-3 | an-258 |
| 1A1013 | sp-3 | an-259 | 1U1013 | sp-3 | an-259 | 1C1013 | sp-3 | an-259 |
| 1A1014 | sp-3 | an-260 | 1U1014 | sp-3 | an-260 | 1C1014 | sp-3 | an-260 |
| 1A1015 | sp-3 | an-261 | 1U1015 | sp-3 | an-261 | 1C1015 | sp-3 | an-261 |
| 1A1016 | sp-3 | an-262 | 1U1016 | sp-3 | an-262 | 1C1016 | sp-3 | an-262 |
| 1A1017 | sp-3 | an-263 | 1U1017 | sp-3 | an-263 | 1C1017 | sp-3 | an-263 |
| 1A1018 | sp-3 | an-264 | 1U1018 | sp-3 | an-264 | 1C1018 | sp-3 | an-264 |
| 1A1019 | sp-3 | an-265 | 1U1019 | sp-3 | an-265 | 1C1019 | sp-3 | an-265 |
| 1A1020 | sp-3 | an-266 | 1U1020 | sp-3 | an-266 | 1C1020 | sp-3 | an-266 |
| 1A1021 | sp-3 | an-267 | 1U1021 | sp-3 | an-267 | 1C1021 | sp-3 | an-267 |
| 1A1022 | sp-3 | an-268 | 1U1022 | sp-3 | an-268 | 1C1022 | sp-3 | an-268 |
| 1A1023 | sp-3 | an-269 | 1U1023 | sp-3 | an-269 | 1C1023 | sp-3 | an-269 |
| 1A1024 | sp-3 | an-270 | 1U1024 | sp-3 | an-270 | 1C1024 | sp-3 | an-270 |
| 1A1025 | sp-3 | an-271 | 1U1025 | sp-3 | an-271 | 1C1025 | sp-3 | an-271 |
| 1A1026 | sp-3 | an-272 | 1U1026 | sp-3 | an-272 | 1C1026 | sp-3 | an-272 |
| 1A1027 | sp-3 | an-273 | 1U1027 | sp-3 | an-273 | 1C1027 | sp-3 | an-273 |
| 1A1028 | sp-3 | an-274 | 1U1028 | sp-3 | an-274 | 1C1028 | sp-3 | an-274 |
| 1A1029 | sp-3 | an-275 | 1U1029 | sp-3 | an-275 | 1C1029 | sp-3 | an-275 |
| 1A1030 | sp-3 | an-276 | 1U1030 | sp-3 | an-276 | 1C1030 | sp-3 | an-276 |
| 1A1031 | sp-3 | an-277 | 1U1031 | sp-3 | an-277 | 1C1031 | sp-3 | an-277 |
| 1A1032 | sp-3 | an-278 | 1U1032 | sp-3 | an-278 | 1C1032 | sp-3 | an-278 |
| 1A1033 | sp-3 | an-279 | 1U1033 | sp-3 | an-279 | 1C1033 | sp-3 | an-279 |
| 1A1034 | sp-3 | an-280 | 1U1034 | sp-3 | an-280 | 1C1034 | sp-3 | an-280 |
| 1A1035 | sp-3 | an-281 | 1U1035 | sp-3 | an-281 | 1C1035 | sp-3 | an-281 |
| 1A1036 | sp-3 | an-282 | 1U1036 | sp-3 | an-282 | 1C1036 | sp-3 | an-282 |
| 1A1037 | sp-3 | an-283 | 1U1037 | sp-3 | an-283 | 1C1037 | sp-3 | an-283 |
| 1A1038 | sp-3 | an-284 | 1U1038 | sp-3 | an-284 | 1C1038 | sp-3 | an-284 |
| 1A1039 | sp-3 | an-285 | 1U1039 | sp-3 | an-285 | 1C1039 | sp-3 | an-285 |
| 1A1040 | sp-3 | an-286 | 1U1040 | sp-3 | an-286 | 1C1040 | sp-3 | an-286 |
| 1A1041 | sp-3 | an-287 | 1U1041 | sp-3 | an-287 | 1C1041 | sp-3 | an-287 |
| 1A1042 | sp-3 | an-288 | 1U1042 | sp-3 | an-288 | 1C1042 | sp-3 | an-288 |
| 1A1043 | sp-3 | an-289 | 1U1043 | sp-3 | an-289 | 1C1043 | sp-3 | an-289 |
| 1A1044 | sp-3 | an-290 | 1U1044 | sp-3 | an-290 | 1C1044 | sp-3 | an-290 |
| 1A1045 | sp-3 | an-291 | 1U1045 | sp-3 | an-291 | 1C1045 | sp-3 | an-291 |
| 1A1046 | sp-3 | an-292 | 1U1046 | sp-3 | an-292 | 1C1046 | sp-3 | an-292 |
| 1A1047 | sp-3 | an-293 | 1U1047 | sp-3 | an-293 | 1C1047 | sp-3 | an-293 |
| 1A1048 | sp-3 | an-294 | 1U1048 | sp-3 | an-294 | 1C1048 | sp-3 | an-294 |
| 1A1049 | sp-3 | an-295 | 1U1049 | sp-3 | an-295 | 1C1049 | sp-3 | an-295 |
| 1A1050 | sp-3 | an-296 | 1U1050 | sp-3 | an-296 | 1C1050 | sp-3 | an-296 |
| 1A1051 | sp-3 | an-297 | 1U1051 | sp-3 | an-297 | 1C1051 | sp-3 | an-297 |
| 1A1052 | sp-3 | an-298 | 1U1052 | sp-3 | an-298 | 1C1052 | sp-3 | an-298 |

-continued

| Ex. No. | Z | N⁺R⁵R⁶R⁷ | Ex. No. | Z | N⁺R⁵R⁶R⁷ | Ex. No. | Z | N⁺R⁵R⁶R⁷ |
|---|---|---|---|---|---|---|---|---|
| 1A1053 | sp-3 | an-299 | 1U1053 | sp-3 | an-299 | 1C1053 | sp-3 | an-299 |
| 1A1054 | sp-3 | an-300 | 1U1054 | sp-3 | an-300 | 1C1054 | sp-3 | an-300 |
| 1A1055 | sp-3 | an-301 | 1U1055 | sp-3 | an-301 | 1C1055 | sp-3 | an-301 |
| 1A1056 | sp-3 | an-302 | 1U1056 | sp-3 | an-302 | 1C1056 | sp-3 | an-302 |
| 1A1057 | sp-3 | an-303 | 1U1057 | sp-3 | an-303 | 1C1057 | sp-3 | an-303 |
| 1A1058 | sp-3 | an-304 | 1U1058 | sp-3 | an-304 | 1C1058 | sp-3 | an-304 |
| 1A1059 | sp-3 | an-305 | 1U1059 | sp-3 | an-305 | 1C1059 | sp-3 | an-305 |
| 1A1060 | sp-3 | an-306 | 1U1060 | sp-3 | an-306 | 1C1060 | sp-3 | an-306 |
| 1A1061 | sp-3 | an-307 | 1U1061 | sp-3 | an-307 | 1C1061 | sp-3 | an-307 |
| 1A1062 | sp-3 | an-308 | 1U1062 | sp-3 | an-308 | 1C1062 | sp-3 | an-308 |
| 1A1063 | sp-3 | an-309 | 1U1063 | sp-3 | an-309 | 1C1063 | sp-3 | an-309 |
| 1A1064 | sp-3 | an-310 | 1U1064 | sp-3 | an-310 | 1C1064 | sp-3 | an-310 |

Table 2-20

| Y = NHCS | | | Y = NHCSNH | | | Y = NHCSO | | |
|---|---|---|---|---|---|---|---|---|
| 1A1065 | sp-3 | an-311 | 1U1065 | sp-3 | an-311 | 1C1065 | sp-3 | an-311 |
| 1A1066 | sp-3 | an-312 | 1U1066 | sp-3 | an-312 | 1C1066 | sp-3 | an-312 |
| 1A1067 | sp-3 | an-313 | 1U1067 | sp-3 | an-313 | 1C1067 | sp-3 | an-313 |
| 1A1068 | sp-3 | an-314 | 1U1068 | sp-3 | an-314 | 1C1068 | sp-3 | an-314 |
| 1A1069 | sp-3 | an-315 | 1U1069 | sp-3 | an-315 | 1C1069 | sp-3 | an-315 |
| 1A1070 | sp-3 | an-316 | 1U1070 | sp-3 | an-316 | 1C1070 | sp-3 | an-316 |
| 1A1071 | sp-3 | an-317 | 1U1071 | sp-3 | an-317 | 1C1071 | sp-3 | an-317 |
| 1A1072 | sp-3 | an-318 | 1U1072 | sp-3 | an-318 | 1C1072 | sp-3 | an-318 |
| 1A1073 | sp-3 | an-319 | 1U1073 | sp-3 | an-319 | 1C1073 | sp-3 | an-319 |
| 1A1074 | sp-3 | an-320 | 1U1074 | sp-3 | an-320 | 1C1074 | sp-3 | an-320 |
| 1A1075 | sp-3 | an-321 | 1U1075 | sp-3 | an-321 | 1C1075 | sp-3 | an-321 |
| 1A1076 | sp-3 | an-322 | 1U1076 | sp-3 | an-322 | 1C1076 | sp-3 | an-322 |
| 1A1077 | sp-3 | an-323 | 1U1077 | sp-3 | an-323 | 1C1077 | sp-3 | an-323 |
| 1A1078 | sp-3 | an-324 | 1U1078 | sp-3 | an-324 | 1C1078 | sp-3 | an-324 |
| 1A1079 | sp-3 | an-325 | 1U1079 | sp-3 | an-325 | 1C1079 | sp-3 | an-325 |
| 1A1080 | sp-3 | an-326 | 1U1080 | sp-3 | an-326 | 1C1080 | sp-3 | an-326 |
| 1A1081 | sp-3 | an-327 | 1U1081 | sp-3 | an-327 | 1C1081 | sp-3 | an-327 |
| 1A1082 | sp-3 | an-328 | 1U1082 | sp-3 | an-328 | 1C1082 | sp-3 | an-328 |
| 1A1083 | sp-3 | an-329 | 1U1083 | sp-3 | an-329 | 1C1083 | sp-3 | an-329 |
| 1A1084 | sp-3 | an-330 | 1U1084 | sp-3 | an-330 | 1C1084 | sp-3 | an-330 |
| 1A1085 | sp-3 | an-331 | 1U1085 | sp-3 | an-331 | 1C1085 | sp-3 | an-331 |
| 1A1086 | sp-3 | an-332 | 1U1086 | sp-3 | an-332 | 1C1086 | sp-3 | an-332 |
| 1A1087 | sp-3 | an-333 | 1U1087 | sp-3 | an-333 | 1C1087 | sp-3 | an-333 |
| 1A1088 | sp-3 | an-334 | 1U1088 | sp-3 | an-334 | 1C1088 | sp-3 | an-334 |
| 1A1089 | sp-3 | an-335 | 1U1089 | sp-3 | an-335 | 1C1089 | sp-3 | an-335 |
| 1A1090 | sp-3 | an-336 | 1U1090 | sp-3 | an-336 | 1C1090 | sp-3 | an-336 |
| 1A1091 | sp-3 | an-337 | 1U1091 | sp-3 | an-337 | 1C1091 | sp-3 | an-337 |
| 1A1092 | sp-3 | an-338 | 1U1092 | sp-3 | an-338 | 1C1092 | sp-3 | an-338 |
| 1A1093 | sp-3 | an-339 | 1U1093 | sp-3 | an-339 | 1C1093 | sp-3 | an-339 |
| 1A1094 | sp-3 | an-340 | 1U1094 | sp-3 | an-340 | 1C1094 | sp-3 | an-340 |
| 1A1095 | sp-3 | an-341 | 1U1095 | sp-3 | an-341 | 1C1095 | sp-3 | an-341 |
| 1A1096 | sp-3 | an-342 | 1U1096 | sp-3 | an-342 | 1C1096 | sp-3 | an-342 |
| 1A1097 | sp-3 | an-343 | 1U1097 | sp-3 | an-343 | 1C1097 | sp-3 | an-343 |
| 1A1098 | sp-3 | an-344 | 1U1098 | sp-3 | an-344 | 1C1098 | sp-3 | an-344 |
| 1A1099 | sp-3 | an-345 | 1U1099 | sp-3 | an-345 | 1C1099 | sp-3 | an-345 |
| 1A1100 | sp-3 | an-346 | 1U1100 | sp-3 | an-346 | 1C1100 | sp-3 | an-346 |
| 1A1101 | sp-3 | an-347 | 1U1101 | sp-3 | an-347 | 1C1101 | sp-3 | an-347 |
| 1A1102 | sp-3 | an-348 | 1U1102 | sp-3 | an-348 | 1C1102 | sp-3 | an-348 |
| 1A1103 | sp-3 | an-349 | 1U1103 | sp-3 | an-349 | 1C1103 | sp-3 | an-349 |
| 1A1104 | sp-3 | an-350 | 1U1104 | sp-3 | an-350 | 1C1104 | sp-3 | an-350 |
| 1A1105 | sp-3 | an-351 | 1U1105 | sp-3 | an-351 | 1C1105 | sp-3 | an-351 |
| 1A1106 | sp-3 | an-352 | 1U1106 | sp-3 | an-352 | 1C1106 | sp-3 | an-352 |
| 1A1107 | sp-3 | an-353 | 1U1107 | sp-3 | an-353 | 1C1107 | sp-3 | an-353 |
| 1A1108 | sp-3 | an-354 | 1U1108 | sp-3 | an-354 | 1C1108 | sp-3 | an-354 |
| 1A1109 | sp-3 | an-355 | 1U1109 | sp-3 | an-355 | 1C1109 | sp-3 | an-355 |
| 1A1110 | sp-3 | an-356 | 1U1110 | sp-3 | an-356 | 1C1110 | sp-3 | an-356 |
| 1A1111 | sp-3 | an-357 | 1U1111 | sp-3 | an-357 | 1C1111 | sp-3 | an-357 |
| 1A1112 | sp-3 | an-358 | 1U1112 | sp-3 | an-358 | 1C1112 | sp-3 | an-358 |
| 1A1113 | sp-3 | an-359 | 1U1113 | sp-3 | an-359 | 1C1113 | sp-3 | an-359 |
| 1A1114 | sp-3 | an-360 | 1U1114 | sp-3 | an-360 | 1C1114 | sp-3 | an-360 |
| 1A1115 | sp-3 | an-361 | 1U1115 | sp-3 | an-361 | 1C1115 | sp-3 | an-361 |
| 1A1116 | sp-3 | an-362 | 1U1116 | sp-3 | an-362 | 1C1116 | sp-3 | an-362 |
| 1A1117 | sp-3 | an-363 | 1U1117 | sp-3 | an-363 | 1C1117 | sp-3 | an-363 |
| 1A1118 | sp-3 | an-364 | 1U1118 | sp-3 | an-364 | 1C1118 | sp-3 | an-364 |
| 1A1119 | sp-3 | an-365 | 1U1119 | sp-3 | an-365 | 1C1119 | sp-3 | an-365 |
| 1A1120 | sp-3 | an-366 | 1U1120 | sp-3 | an-366 | 1C1120 | sp-3 | an-366 |

Table 2-21

| Y = NHCS | | | Y = NHCSNH | | | Y = NHCSO | | |
|---|---|---|---|---|---|---|---|---|
| 1A1121 | sp-3 | an-367 | 1U1121 | sp-3 | an-367 | 1C1121 | sp-3 | an-367 |
| 1A1122 | sp-3 | an-368 | 1U1122 | sp-3 | an-368 | 1C1122 | sp-3 | an-368 |

-continued

| Ex. No. | Z | N+R5R6R7 | Ex. No. | Z | N+R5R6R7 | Ex. No. | Z | N+R5R6R7 |
|---|---|---|---|---|---|---|---|---|
| 1A1123 | sp-3 | an-369 | 1U1123 | sp-3 | an-369 | 1C1123 | sp-3 | an-369 |
| 1A1124 | sp-3 | an-370 | 1U1124 | sp-3 | an-370 | 1C1124 | sp-3 | an-370 |
| 1A1125 | sp-3 | an-371 | 1U1125 | sp-3 | an-371 | 1C1125 | sp-3 | an-371 |
| 1A1126 | sp-3 | an-372 | 1U1126 | sp-3 | an-372 | 1C1126 | sp-3 | an-372 |
| 1A1127 | sp-3 | an-373 | 1U1127 | sp-3 | an-373 | 1C1127 | sp-3 | an-373 |
| 1A1128 | sp-3 | an-374 | 1U1128 | sp-3 | an-374 | 1C1128 | sp-3 | an-374 |
| 1A1129 | sp-3 | an-375 | 1U1129 | sp-3 | an-375 | 1C1129 | sp-3 | an-375 |
| 1A1130 | sp-3 | an-376 | 1U1130 | sp-3 | an-376 | 1C1130 | sp-3 | an-376 |
| 1A1131 | sp-3 | an-377 | 1U1131 | sp-3 | an-377 | 1C1131 | sp-3 | an-377 |
| 1A1132 | sp-4 | an-1 | 1U1132 | sp-4 | an-1 | 1C1132 | sp-4 | an-1 |
| 1A1133 | sp-4 | an-2 | 1U1133 | sp-4 | an-2 | 1C1133 | sp-4 | an-2 |
| 1A1134 | sp-4 | an-3 | 1U1134 | sp-4 | an-3 | 1C1134 | sp-4 | an-3 |
| 1A1135 | sp-4 | an-4 | 1U1135 | sp-4 | an-4 | 1C1135 | sp-4 | an-4 |
| 1A1136 | sp-4 | an-5 | 1U1136 | sp-4 | an-5 | 1C1136 | sp-4 | an-5 |
| 1A1137 | sp-4 | an-6 | 1U1137 | sp-4 | an-6 | 1C1137 | sp-4 | an-6 |
| 1A1138 | sp-4 | an-7 | 1U1138 | sp-4 | an-7 | 1C1138 | sp-4 | an-7 |
| 1A1139 | sp-4 | an-8 | 1U1139 | sp-4 | an-8 | 1C1139 | sp-4 | an-8 |
| 1A1140 | sp-4 | an-9 | 1U1140 | sp-4 | an-9 | 1C1140 | sp-4 | an-9 |
| 1A1141 | sp-4 | an-10 | 1U1141 | sp-4 | an-10 | 1C1141 | sp-4 | an-10 |
| 1A1142 | sp-4 | an-11 | 1U1142 | sp-4 | an-11 | 1C1142 | sp-4 | an-11 |
| 1A1143 | sp-4 | an-12 | 1U1143 | sp-4 | an-12 | 1C1143 | sp-4 | an-12 |
| 1A1144 | sp-4 | an-13 | 1U1144 | sp-4 | an-13 | 1C1144 | sp-4 | an-13 |
| 1A1145 | sp-4 | an-14 | 1U1145 | sp-4 | an-14 | 1C1145 | sp-4 | an-14 |
| 1A1146 | sp-4 | an-15 | 1U1146 | sp-4 | an-15 | 1C1146 | sp-4 | an-15 |
| 1A1147 | sp-4 | an-16 | 1U1147 | sp-4 | an-16 | 1C1147 | sp-4 | an-16 |
| 1A1148 | sp-4 | an-17 | 1U1148 | sp-4 | an-17 | 1C1148 | sp-4 | an-17 |
| 1A1149 | sp-4 | an-18 | 1U1149 | sp-4 | an-18 | 1C1149 | sp-4 | an-18 |
| 1A1150 | sp-4 | an-19 | 1U1150 | sp-4 | an-19 | 1C1150 | sp-4 | an-19 |
| 1A1151 | sp-4 | an-20 | 1U1151 | sp-4 | an-20 | 1C1151 | sp-4 | an-20 |
| 1A1152 | sp-4 | an-21 | 1U1152 | sp-4 | an-21 | 1C1152 | sp-4 | an-21 |
| 1A1153 | sp-4 | an-22 | 1U1153 | sp-4 | an-22 | 1C1153 | sp-4 | an-22 |
| 1A1154 | sp-4 | an-23 | 1U1154 | sp-4 | an-23 | 1C1154 | sp-4 | an-23 |
| 1A1155 | sp-4 | an-24 | 1U1155 | sp-4 | an-24 | 1C1155 | sp-4 | an-24 |
| 1A1156 | sp-4 | an-25 | 1U1156 | sp-4 | an-25 | 1C1156 | sp-4 | an-25 |
| 1A1157 | sp-4 | an-26 | 1U1157 | sp-4 | an-26 | 1C1157 | sp-4 | an-26 |
| 1A1158 | sp-4 | an-27 | 1U1158 | sp-4 | an-27 | 1C1158 | sp-4 | an-27 |
| 1A1159 | sp-4 | an-28 | 1U1159 | sp-4 | an-28 | 1C1159 | sp-4 | an-28 |
| 1A1160 | sp-4 | an-29 | 1U1160 | sp-4 | an-29 | 1C1160 | sp-4 | an-29 |
| 1A1161 | sp-4 | an-30 | 1U1161 | sp-4 | an-30 | 1C1161 | sp-4 | an-30 |
| 1A1162 | sp-4 | an-31 | 1U1162 | sp-4 | an-31 | 1C1162 | sp-4 | an-31 |
| 1A1163 | sp-4 | an-32 | 1U1163 | sp-4 | an-32 | 1C1163 | sp-4 | an-32 |
| 1A1164 | sp-4 | an-33 | 1U1164 | sp-4 | an-33 | 1C1164 | sp-4 | an-33 |
| 1A1165 | sp-4 | an-34 | 1U1165 | sp-4 | an-34 | 1C1165 | sp-4 | an-34 |
| 1A1166 | sp-4 | an-35 | 1U1166 | sp-4 | an-35 | 1C1166 | sp-4 | an-35 |
| 1A1167 | sp-4 | an-36 | 1U1167 | sp-4 | an-36 | 1C1167 | sp-4 | an-36 |
| 1A1168 | sp-4 | an-37 | 1U1168 | sp-4 | an-37 | 1C1168 | sp-4 | an-37 |
| 1A1169 | sp-4 | an-38 | 1U1169 | sp-4 | an-38 | 1C1169 | sp-4 | an-38 |
| 1A1170 | sp-4 | an-39 | 1U1170 | sp-4 | an-39 | 1C1170 | sp-4 | an-39 |
| 1A1171 | sp-4 | an-40 | 1U1171 | sp-4 | an-40 | 1C1171 | sp-4 | an-40 |
| 1A1172 | sp-4 | an-41 | 1U1172 | sp-4 | an-41 | 1C1172 | sp-4 | an-41 |
| 1A1173 | sp-4 | an-42 | 1U1173 | sp-4 | an-42 | 1C1173 | sp-4 | an-42 |
| 1A1174 | sp-4 | an-43 | 1U1174 | sp-4 | an-43 | 1C1174 | sp-4 | an-43 |
| 1A1175 | sp-4 | an-44 | 1U1175 | sp-4 | an-44 | 1C1175 | sp-4 | an-44 |
| 1A1176 | sp-4 | an-45 | 1U1176 | sp-4 | an-45 | 1C1176 | sp-4 | an-45 |

Table 2-22

| Y = NHCS | | | Y = NHCSNH | | | Y = NHCSO | | |
|---|---|---|---|---|---|---|---|---|
| 1A1177 | sp-4 | an-46 | 1U1177 | sp-4 | an-46 | 1C1177 | sp-4 | an-46 |
| 1A1178 | sp-4 | an-47 | 1U1178 | sp-4 | an-47 | 1C1178 | sp-4 | an-47 |
| 1A1179 | sp-4 | an-48 | 1U1179 | sp-4 | an-48 | 1C1179 | sp-4 | an-48 |
| 1A1180 | sp-4 | an-49 | 1U1180 | sp-4 | an-49 | 1C1180 | sp-4 | an-49 |
| 1A1181 | sp-4 | an-50 | 1U1181 | sp-4 | an-50 | 1C1181 | sp-4 | an-50 |
| 1A1182 | sp-4 | an-51 | 1U1182 | sp-4 | an-51 | 1C1182 | sp-4 | an-51 |
| 1A1183 | sp-4 | an-52 | 1U1183 | sp-4 | an-52 | 1C1183 | sp-4 | an-52 |
| 1A1184 | sp-4 | an-53 | 1U1184 | sp-4 | an-53 | 1C1184 | sp-4 | an-53 |
| 1A1185 | sp-4 | an-54 | 1U1185 | sp-4 | an-54 | 1C1185 | sp-4 | an-54 |
| 1A1186 | sp-4 | an-55 | 1U1186 | sp-4 | an-55 | 1C1186 | sp-4 | an-55 |
| 1A1187 | sp-4 | an-56 | 1U1187 | sp-4 | an-56 | 1C1187 | sp-4 | an-56 |
| 1A1188 | sp-4 | an-57 | 1U1188 | sp-4 | an-57 | 1C1188 | sp-4 | an-57 |
| 1A1189 | sp-4 | an-58 | 1U1189 | sp-4 | an-58 | 1C1189 | sp-4 | an-58 |
| 1A1190 | sp-4 | an-59 | 1U1190 | sp-4 | an-59 | 1C1190 | sp-4 | an-59 |
| 1A1191 | sp-4 | an-60 | 1U1191 | sp-4 | an-60 | 1C1191 | sp-4 | an-60 |
| 1A1192 | sp-4 | an-61 | 1U1192 | sp-4 | an-61 | 1C1192 | sp-4 | an-61 |
| 1A1193 | sp-4 | an-62 | 1U1193 | sp-4 | an-62 | 1C1193 | sp-4 | an-62 |
| 1A1194 | sp-4 | an-63 | 1U1194 | sp-4 | an-63 | 1C1194 | sp-4 | an-63 |
| 1A1195 | sp-4 | an-64 | 1U1195 | sp-4 | an-64 | 1C1195 | sp-4 | an-64 |
| 1A1196 | sp-4 | an-65 | 1U1196 | sp-4 | an-65 | 1C1196 | sp-4 | an-65 |

-continued

| Ex. No. | Z | $N^+R^5R^6R^7$ | Ex. No. | Z | $N^+R^5R^6R^7$ | Ex. No. | Z | $N^+R^5R^6R^7$ |
|---|---|---|---|---|---|---|---|---|
| 1A1197 | sp-4 | an-66 | 1U1197 | sp-4 | an-66 | 1C1197 | sp-4 | an-66 |
| 1A1198 | sp-4 | an-67 | 1U1198 | sp-4 | an-67 | 1C1198 | sp-4 | an-67 |
| 1A1199 | sp-4 | an-68 | 1U1199 | sp-4 | an-68 | 1C1199 | sp-4 | an-68 |
| 1A1200 | sp-4 | an-69 | 1U1200 | sp-4 | an-69 | 1C1200 | sp-4 | an-69 |
| 1A1201 | sp-4 | an-70 | 1U1201 | sp-4 | an-70 | 1C1201 | sp-4 | an-70 |
| 1A1202 | sp-4 | an-71 | 1U1202 | sp-4 | an-71 | 1C1202 | sp-4 | an-71 |
| 1A1203 | sp-4 | an-72 | 1U1203 | sp-4 | an-72 | 1C1203 | sp-4 | an-72 |
| 1A1204 | sp-4 | an-73 | 1U1204 | sp-4 | an-73 | 1C1204 | sp-4 | an-73 |
| 1A1205 | sp-4 | an-74 | 1U1205 | sp-4 | an-74 | 1C1205 | sp-4 | an-74 |
| 1A1206 | sp-4 | an-75 | 1U1206 | sp-4 | an-75 | 1C1206 | sp-4 | an-75 |
| 1A1207 | sp-4 | an-76 | 1U1207 | sp-4 | an-76 | 1C1207 | sp-4 | an-76 |
| 1A1208 | sp-4 | an-77 | 1U1208 | sp-4 | an-77 | 1C1208 | sp-4 | an-77 |
| 1A1209 | sp-4 | an-78 | 1U1209 | sp-4 | an-78 | 1C1209 | sp-4 | an-78 |
| 1A1210 | sp-4 | an-79 | 1U1210 | sp-4 | an-79 | 1C1210 | sp-4 | an-79 |
| 1A1211 | sp-4 | an-80 | 1U1211 | sp-4 | an-80 | 1C1211 | sp-4 | an-80 |
| 1A1212 | sp-4 | an-81 | 1U1212 | sp-4 | an-81 | 1C1212 | sp-4 | an-81 |
| 1A1213 | sp-4 | an-82 | 1U1213 | sp-4 | an-82 | 1C1213 | sp-4 | an-82 |
| 1A1214 | sp-4 | an-83 | 1U1214 | sp-4 | an-83 | 1C1214 | sp-4 | an-83 |
| 1A1215 | sp-4 | an-84 | 1U1215 | sp-4 | an-84 | 1C1215 | sp-4 | an-84 |
| 1A1216 | sp-4 | an-85 | 1U1216 | sp-4 | an-85 | 1C1216 | sp-4 | an-85 |
| 1A1217 | sp-4 | an-86 | 1U1217 | sp-4 | an-86 | 1C1217 | sp-4 | an-86 |
| 1A1218 | sp-4 | an-87 | 1U1218 | sp-4 | an-87 | 1C1218 | sp-4 | an-87 |
| 1A1219 | sp-4 | an-88 | 1U1219 | sp-4 | an-88 | 1C1219 | sp-4 | an-88 |
| 1A1220 | sp-4 | an-89 | 1U1220 | sp-4 | an-89 | 1C1220 | sp-4 | an-89 |
| 1A1221 | sp-4 | an-90 | 1U1221 | sp-4 | an-90 | 1C1221 | sp-4 | an-90 |
| 1A1222 | sp-4 | an-91 | 1U1222 | sp-4 | an-91 | 1C1222 | sp-4 | an-91 |
| 1A1223 | sp-4 | an-92 | 1U1223 | sp-4 | an-92 | 1C1223 | sp-4 | an-92 |
| 1A1224 | sp-4 | an-93 | 1U1224 | sp-4 | an-93 | 1C1224 | sp-4 | an-93 |
| 1A1225 | sp-4 | an-94 | 1U1225 | sp-4 | an-94 | 1C1225 | sp-4 | an-94 |
| 1A1226 | sp-4 | an-95 | 1U1226 | sp-4 | an-95 | 1C1226 | sp-4 | an-95 |
| 1A1227 | sp-4 | an-96 | 1U1227 | sp-4 | an-96 | 1C1227 | sp-4 | an-96 |
| 1A1228 | sp-4 | an-97 | 1U1228 | sp-4 | an-97 | 1C1228 | sp-4 | an-97 |
| 1A1229 | sp-4 | an-98 | 1U1229 | sp-4 | an-98 | 1C1229 | sp-4 | an-98 |
| 1A1230 | sp-4 | an-99 | 1U1230 | sp-4 | an-99 | 1C1230 | sp-4 | an-99 |
| 1A1231 | sp-4 | an-100 | 1U1231 | sp-4 | an-100 | 1C1231 | sp-4 | an-100 |
| 1A1232 | sp-4 | an-101 | 1U1232 | sp-4 | an-101 | 1C1232 | sp-4 | an-101 |

Table 2-23

| Y = NHCS | | | Y = NHCSNH | | | Y = NHCSO | | |
|---|---|---|---|---|---|---|---|---|
| 1A1233 | sp-4 | an-102 | 1U1233 | sp-4 | an-102 | 1C1233 | sp-4 | an-102 |
| 1A1234 | sp-4 | an-103 | 1U1234 | sp-4 | an-103 | 1C1234 | sp-4 | an-103 |
| 1A1235 | sp-4 | an-104 | 1U1235 | sp-4 | an-104 | 1C1235 | sp-4 | an-104 |
| 1A1236 | sp-4 | an-105 | 1U1236 | sp-4 | an-105 | 1C1236 | sp-4 | an-105 |
| 1A1237 | sp-4 | an-106 | 1U1237 | sp-4 | an-106 | 1C1237 | sp-4 | an-106 |
| 1A1238 | sp-4 | an-107 | 1U1238 | sp-4 | an-107 | 1C1238 | sp-4 | an-107 |
| 1A1239 | sp-4 | an-108 | 1U1239 | sp-4 | an-108 | 1C1239 | sp-4 | an-108 |
| 1A1240 | sp-4 | an-109 | 1U1240 | sp-4 | an-109 | 1C1240 | sp-4 | an-109 |
| 1A1241 | sp-4 | an-110 | 1U1241 | sp-4 | an-110 | 1C1241 | sp-4 | an-110 |
| 1A1242 | sp-4 | an-111 | 1U1242 | sp-4 | an-111 | 1C1242 | sp-4 | an-111 |
| 1A1243 | sp-4 | an-112 | 1U1243 | sp-4 | an-112 | 1C1243 | sp-4 | an-112 |
| 1A1244 | sp-4 | an-113 | 1U1244 | sp-4 | an-113 | 1C1244 | sp-4 | an-113 |
| 1A1245 | sp-4 | an-114 | 1U1245 | sp-4 | an-114 | 1C1245 | sp-4 | an-114 |
| 1A1246 | sp-4 | an-115 | 1U1246 | sp-4 | an-115 | 1C1246 | sp-4 | an-115 |
| 1A1247 | sp-4 | an-116 | 1U1247 | sp-4 | an-116 | 1C1247 | sp-4 | an-116 |
| 1A1248 | sp-4 | an-117 | 1U1248 | sp-4 | an-117 | 1C1248 | sp-4 | an-117 |
| 1A1249 | sp-4 | an-118 | 1U1249 | sp-4 | an-118 | 1C1249 | sp-4 | an-118 |
| 1A1250 | sp-4 | an-119 | 1U1250 | sp-4 | an-119 | 1C1250 | sp-4 | an-119 |
| 1A1251 | sp-4 | an-120 | 1U1251 | sp-4 | an-120 | 1C1251 | sp-4 | an-120 |
| 1A1252 | sp-4 | an-121 | 1U1252 | sp-4 | an-121 | 1C1252 | sp-4 | an-121 |
| 1A1253 | sp-4 | an-122 | 1U1253 | sp-4 | an-122 | 1C1253 | sp-4 | an-122 |
| 1A1254 | sp-4 | an-123 | 1U1254 | sp-4 | an-123 | 1C1254 | sp-4 | an-123 |
| 1A1255 | sp-4 | an-124 | 1U1255 | sp-4 | an-124 | 1C1255 | sp-4 | an-124 |
| 1A1256 | sp-4 | an-125 | 1U1256 | sp-4 | an-125 | 1C1256 | sp-4 | an-125 |
| 1A1257 | sp-4 | an-126 | 1U1257 | sp-4 | an-126 | 1C1257 | sp-4 | an-126 |
| 1A1258 | sp-4 | an-127 | 1U1258 | sp-4 | an-127 | 1C1258 | sp-4 | an-127 |
| 1A1259 | sp-4 | an-128 | 1U1259 | sp-4 | an-128 | 1C1259 | sp-4 | an-128 |
| 1A1260 | sp-4 | an-129 | 1U1260 | sp-4 | an-129 | 1C1260 | sp-4 | an-129 |
| 1A1261 | sp-4 | an-130 | 1U1261 | sp-4 | an-130 | 1C1261 | sp-4 | an-130 |
| 1A1262 | sp-4 | an-131 | 1U1262 | sp-4 | an-131 | 1C1262 | sp-4 | an-131 |
| 1A1263 | sp-4 | an-132 | 1U1263 | sp-4 | an-132 | 1C1263 | sp-4 | an-132 |
| 1A1264 | sp-4 | an-133 | 1U1264 | sp-4 | an-133 | 1C1264 | sp-4 | an-133 |
| 1A1265 | sp-4 | an-134 | 1U1265 | sp-4 | an-134 | 1C1265 | sp-4 | an-134 |
| 1A1266 | sp-4 | an-135 | 1U1266 | sp-4 | an-135 | 1C1266 | sp-4 | an-135 |
| 1A1267 | sp-4 | an-136 | 1U1267 | sp-4 | an-136 | 1C1267 | sp-4 | an-136 |
| 1A1268 | sp-4 | an-137 | 1U1268 | sp-4 | an-137 | 1C1268 | sp-4 | an-137 |
| 1A1269 | sp-4 | an-138 | 1U1269 | sp-4 | an-138 | 1C1269 | sp-4 | an-138 |
| 1A1270 | sp-4 | an-139 | 1U1270 | sp-4 | an-139 | 1C1270 | sp-4 | an-139 |

-continued

| Ex. No. | Z | $N^+R^5R^6R^7$ | Ex. No. | Z | $N^+R^5R^6R^7$ | Ex. No. | Z | $N^+R^5R^6R^7$ |
|---|---|---|---|---|---|---|---|---|
| 1A1271 | sp-4 | an-140 | 1U1271 | sp-4 | an-140 | 1C1271 | sp-4 | an-140 |
| 1A1272 | sp-4 | an-141 | 1U1272 | sp-4 | an-141 | 1C1272 | sp-4 | an-141 |
| 1A1273 | sp-4 | an-142 | 1U1273 | sp-4 | an-142 | 1C1273 | sp-4 | an-142 |
| 1A1274 | sp-4 | an-143 | 1U1274 | sp-4 | an-143 | 1C1274 | sp-4 | an-143 |
| 1A1275 | sp-4 | an-144 | 1U1275 | sp-4 | an-144 | 1C1275 | sp-4 | an-144 |
| 1A1276 | sp-4 | an-145 | 1U1276 | sp-4 | an-145 | 1C1276 | sp-4 | an-145 |
| 1A1277 | sp-4 | an-146 | 1U1277 | sp-4 | an-146 | 1C1277 | sp-4 | an-146 |
| 1A1278 | sp-4 | an-147 | 1U1278 | sp-4 | an-147 | 1C1278 | sp-4 | an-147 |
| 1A1279 | sp-4 | an-148 | 1U1279 | sp-4 | an-148 | 1C1279 | sp-4 | an-148 |
| 1A1280 | sp-4 | an-149 | 1U1280 | sp-4 | an-149 | 1C1280 | sp-4 | an-149 |
| 1A1281 | sp-4 | an-150 | 1U1281 | sp-4 | an-150 | 1C1281 | sp-4 | an-150 |
| 1A1282 | sp-4 | an-151 | 1U1282 | sp-4 | an-151 | 1C1282 | sp-4 | an-151 |
| 1A1283 | sp-4 | an-152 | 1U1283 | sp-4 | an-152 | 1C1283 | sp-4 | an-152 |
| 1A1284 | sp-4 | an-153 | 1U1284 | sp-4 | an-153 | 1C1284 | sp-4 | an-153 |
| 1A1285 | sp-4 | an-154 | 1U1285 | sp-4 | an-154 | 1C1285 | sp-4 | an-154 |
| 1A1286 | sp-4 | an-155 | 1U1286 | sp-4 | an-155 | 1C1286 | sp-4 | an-155 |
| 1A1287 | sp-4 | an-156 | 1U1287 | sp-4 | an-156 | 1C1287 | sp-4 | an-156 |
| 1A1288 | sp-4 | an-157 | 1U1288 | sp-4 | an-157 | 1C1288 | sp-4 | an-157 |

Table 2-24

| Y = NHCS | | | Y = NHCSNH | | | Y = NHCSO | | |
|---|---|---|---|---|---|---|---|---|
| 1A1289 | sp-4 | an-158 | 1U1289 | sp-4 | an-158 | 1C1289 | sp-4 | an-158 |
| 1A1290 | sp-4 | an-159 | 1U1290 | sp-4 | an-159 | 1C1290 | sp-4 | an-159 |
| 1A1291 | sp-4 | an-160 | 1U1291 | sp-4 | an-160 | 1C1291 | sp-4 | an-160 |
| 1A1292 | sp-4 | an-161 | 1U1292 | sp-4 | an-161 | 1C1292 | sp-4 | an-161 |
| 1A1293 | sp-4 | an-162 | 1U1293 | sp-4 | an-162 | 1C1293 | sp-4 | an-162 |
| 1A1294 | sp-4 | an-163 | 1U1294 | sp-4 | an-163 | 1C1294 | sp-4 | an-163 |
| 1A1295 | sp-4 | an-164 | 1U1295 | sp-4 | an-164 | 1C1295 | sp-4 | an-164 |
| 1A1296 | sp-4 | an-165 | 1U1296 | sp-4 | an-165 | 1C1296 | sp-4 | an-165 |
| 1A1297 | sp-4 | an-166 | 1U1297 | sp-4 | an-166 | 1C1297 | sp-4 | an-166 |
| 1A1298 | sp-4 | an-167 | 1U1298 | sp-4 | an-167 | 1C1298 | sp-4 | an-167 |
| 1A1299 | sp-4 | an-168 | 1U1299 | sp-4 | an-168 | 1C1299 | sp-4 | an-168 |
| 1A1300 | sp-4 | an-169 | 1U1300 | sp-4 | an-169 | 1C1300 | sp-4 | an-169 |
| 1A1301 | sp-4 | an-170 | 1U1301 | sp-4 | an-170 | 1C1301 | sp-4 | an-170 |
| 1A1302 | sp-4 | an-171 | 1U1302 | sp-4 | an-171 | 1C1302 | sp-4 | an-171 |
| 1A1303 | sp-4 | an-172 | 1U1303 | sp-4 | an-172 | 1C1303 | sp-4 | an-172 |
| 1A1304 | sp-4 | an-173 | 1U1304 | sp-4 | an-173 | 1C1304 | sp-4 | an-173 |
| 1A1305 | sp-4 | an-174 | 1U1305 | sp-4 | an-174 | 1C1305 | sp-4 | an-174 |
| 1A1306 | sp-4 | an-175 | 1U1306 | sp-4 | an-175 | 1C1306 | sp-4 | an-175 |
| 1A1307 | sp-4 | an-176 | 1U1307 | sp-4 | an-176 | 1C1307 | sp-4 | an-176 |
| 1A1308 | sp-4 | an-177 | 1U1308 | sp-4 | an-177 | 1C1308 | sp-4 | an-177 |
| 1A1309 | sp-4 | an-178 | 1U1309 | sp-4 | an-178 | 1C1309 | sp-4 | an-178 |
| 1A1310 | sp-4 | an-179 | 1U1310 | sp-4 | an-179 | 1C1310 | sp-4 | an-179 |
| 1A1311 | sp-4 | an-180 | 1U1311 | sp-4 | an-180 | 1C1311 | sp-4 | an-180 |
| 1A1312 | sp-4 | an-181 | 1U1312 | sp-4 | an-181 | 1C1312 | sp-4 | an-181 |
| 1A1313 | sp-4 | an-182 | 1U1313 | sp-4 | an-182 | 1C1313 | sp-4 | an-182 |
| 1A1314 | sp-4 | an-183 | 1U1314 | sp-4 | an-183 | 1C1314 | sp-4 | an-183 |
| 1A1315 | sp-4 | an-184 | 1U1315 | sp-4 | an-184 | 1C1315 | sp-4 | an-184 |
| 1A1316 | sp-4 | an-185 | 1U1316 | sp-4 | an-185 | 1C1316 | sp-4 | an-185 |
| 1A1317 | sp-4 | an-186 | 1U1317 | sp-4 | an-186 | 1C1317 | sp-4 | an-186 |
| 1A1318 | sp-4 | an-187 | 1U1318 | sp-4 | an-187 | 1C1318 | sp-4 | an-187 |
| 1A1319 | sp-4 | an-188 | 1U1319 | sp-4 | an-188 | 1C1319 | sp-4 | an-188 |
| 1A1320 | sp-4 | an-189 | 1U1320 | sp-4 | an-189 | 1C1320 | sp-4 | an-189 |
| 1A1321 | sp-4 | an-190 | 1U1321 | sp-4 | an-190 | 1C1321 | sp-4 | an-190 |
| 1A1322 | sp-4 | an-191 | 1U1322 | sp-4 | an-191 | 1C1322 | sp-4 | an-191 |
| 1A1323 | sp-4 | an-192 | 1U1323 | sp-4 | an-192 | 1C1323 | sp-4 | an-192 |
| 1A1324 | sp-4 | an-193 | 1U1324 | sp-4 | an-193 | 1C1324 | sp-4 | an-193 |
| 1A1325 | sp-4 | an-194 | 1U1325 | sp-4 | an-194 | 1C1325 | sp-4 | an-194 |
| 1A1326 | sp-4 | an-195 | 1U1326 | sp-4 | an-195 | 1C1326 | sp-4 | an-195 |
| 1A1327 | sp-4 | an-196 | 1U1327 | sp-4 | an-196 | 1C1327 | sp-4 | an-196 |
| 1A1328 | sp-4 | an-197 | 1U1328 | sp-4 | an-197 | 1C1328 | sp-4 | an-197 |
| 1A1329 | sp-4 | an-198 | 1U1329 | sp-4 | an-198 | 1C1329 | sp-4 | an-198 |
| 1A1330 | sp-4 | an-199 | 1U1330 | sp-4 | an-199 | 1C1330 | sp-4 | an-199 |
| 1A1331 | sp-4 | an-200 | 1U1331 | sp-4 | an-200 | 1C1331 | sp-4 | an-200 |
| 1A1332 | sp-4 | an-201 | 1U1332 | sp-4 | an-201 | 1C1332 | sp-4 | an-201 |
| 1A1333 | sp-4 | an-202 | 1U1333 | sp-4 | an-202 | 1C1333 | sp-4 | an-202 |
| 1A1334 | sp-4 | an-203 | 1U1334 | sp-4 | an-203 | 1C1334 | sp-4 | an-203 |
| 1A1335 | sp-4 | an-204 | 1U1335 | sp-4 | an-204 | 1C1335 | sp-4 | an-204 |
| 1A1336 | sp-4 | an-205 | 1U1336 | sp-4 | an-205 | 1C1336 | sp-4 | an-205 |
| 1A1337 | sp-4 | an-206 | 1U1337 | sp-4 | an-206 | 1C1337 | sp-4 | an-206 |
| 1A1338 | sp-4 | an-207 | 1U1338 | sp-4 | an-207 | 1C1338 | sp-4 | an-207 |
| 1A1339 | sp-4 | an-208 | 1U1339 | sp-4 | an-208 | 1C1339 | sp-4 | an-208 |
| 1A1340 | sp-4 | an-209 | 1U1340 | sp-4 | an-209 | 1C1340 | sp-4 | an-209 |
| 1A1341 | sp-4 | an-210 | 1U1341 | sp-4 | an-210 | 1C1341 | sp-4 | an-210 |
| 1A1342 | sp-4 | an-211 | 1U1342 | sp-4 | an-211 | 1C1342 | sp-4 | an-211 |
| 1A1343 | sp-4 | an-212 | 1U1343 | sp-4 | an-212 | 1C1343 | sp-4 | an-212 |
| 1A1344 | sp-4 | an-213 | 1U1344 | sp-4 | an-213 | 1C1344 | sp-4 | an-213 |

-continued

| Ex. No. | Z | $N^+R^5R^6R^7$ | Ex. No. | Z | $N^+R^5R^6R^7$ | Ex. No. | Z | $N^+R^5R^6R^7$ |
|---|---|---|---|---|---|---|---|---|

Table 2-25

| Y = NHCS | | | Y = NHCSNH | | | Y = NHCSO | | |
|---|---|---|---|---|---|---|---|---|
| 1A1345 | sp-4 | an-214 | 1U1345 | sp-4 | an-214 | 1C1345 | sp-4 | an-214 |
| 1A1346 | sp-4 | an-215 | 1U1346 | sp-4 | an-215 | 1C1346 | sp-4 | an-215 |
| 1A1347 | sp-4 | an-216 | 1U1347 | sp-4 | an-216 | 1C1347 | sp-4 | an-216 |
| 1A1348 | sp-4 | an-217 | 1U1348 | sp-4 | an-217 | 1C1348 | sp-4 | an-217 |
| 1A1349 | sp-4 | an-218 | 1U1349 | sp-4 | an-218 | 1C1349 | sp-4 | an-218 |
| 1A1350 | sp-4 | an-219 | 1U1350 | sp-4 | an-219 | 1C1350 | sp-4 | an-219 |
| 1A1351 | sp-4 | an-220 | 1U1351 | sp-4 | an-220 | 1C1351 | sp-4 | an-220 |
| 1A1352 | sp-4 | an-221 | 1U1352 | sp-4 | an-221 | 1C1352 | sp-4 | an-221 |
| 1A1353 | sp-4 | an-222 | 1U1353 | sp-4 | an-222 | 1C1353 | sp-4 | an-222 |
| 1A1354 | sp-4 | an-223 | 1U1354 | sp-4 | an-223 | 1C1354 | sp-4 | an-223 |
| 1A1355 | sp-4 | an-224 | 1U1355 | sp-4 | an-224 | 1C1355 | sp-4 | an-224 |
| 1A1356 | sp-4 | an-225 | 1U1356 | sp-4 | an-225 | 1C1356 | sp-4 | an-225 |
| 1A1357 | sp-4 | an-226 | 1U1357 | sp-4 | an-226 | 1C1357 | sp-4 | an-226 |
| 1A1358 | sp-4 | an-227 | 1U1358 | sp-4 | an-227 | 1C1358 | sp-4 | an-227 |
| 1A1359 | sp-4 | an-228 | 1U1359 | sp-4 | an-228 | 1C1359 | sp-4 | an-228 |
| 1A1360 | sp-4 | an-229 | 1U1360 | sp-4 | an-229 | 1C1360 | sp-4 | an-229 |
| 1A1361 | sp-4 | an-230 | 1U1361 | sp-4 | an-230 | 1C1361 | sp-4 | an-230 |
| 1A1362 | sp-4 | an-231 | 1U1362 | sp-4 | an-231 | 1C1362 | sp-4 | an-231 |
| 1A1363 | sp-4 | an-232 | 1U1363 | sp-4 | an-232 | 1C1363 | sp-4 | an-232 |
| 1A1364 | sp-4 | an-233 | 1U1364 | sp-4 | an-233 | 1C1364 | sp-4 | an-233 |
| 1A1365 | sp-4 | an-234 | 1U1365 | sp-4 | an-234 | 1C1365 | sp-4 | an-234 |
| 1A1366 | sp-4 | an-235 | 1U1366 | sp-4 | an-235 | 1C1366 | sp-4 | an-235 |
| 1A1367 | sp-4 | an-236 | 1U1367 | sp-4 | an-236 | 1C1367 | sp-4 | an-236 |
| 1A1368 | sp-4 | an-237 | 1U1368 | sp-4 | an-237 | 1C1368 | sp-4 | an-237 |
| 1A1369 | sp-4 | an-238 | 1U1369 | sp-4 | an-238 | 1C1369 | sp-4 | an-238 |
| 1A1370 | sp-4 | an-239 | 1U1370 | sp-4 | an-239 | 1C1370 | sp-4 | an-239 |
| 1A1371 | sp-4 | an-240 | 1U1371 | sp-4 | an-240 | 1C1371 | sp-4 | an-240 |
| 1A1372 | sp-4 | an-241 | 1U1372 | sp-4 | an-241 | 1C1372 | sp-4 | an-241 |
| 1A1373 | sp-4 | an-242 | 1U1373 | sp-4 | an-242 | 1C1373 | sp-4 | an-242 |
| 1A1374 | sp-4 | an-243 | 1U1374 | sp-4 | an-243 | 1C1374 | sp-4 | an-243 |
| 1A1375 | sp-4 | an-244 | 1U1375 | sp-4 | an-244 | 1C1375 | sp-4 | an-244 |
| 1A1376 | sp-4 | an-245 | 1U1376 | sp-4 | an-245 | 1C1376 | sp-4 | an-245 |
| 1A1377 | sp-4 | an-246 | 1U1377 | sp-4 | an-246 | 1C1377 | sp-4 | an-246 |
| 1A1378 | sp-4 | an-247 | 1U1378 | sp-4 | an-247 | 1C1378 | sp-4 | an-247 |
| 1A1379 | sp-4 | an-248 | 1U1379 | sp-4 | an-248 | 1C1379 | sp-4 | an-248 |
| 1A1380 | sp-4 | an-249 | 1U1380 | sp-4 | an-249 | 1C1380 | sp-4 | an-249 |
| 1A1381 | sp-4 | an-250 | 1U1381 | sp-4 | an-250 | 1C1381 | sp-4 | an-250 |
| 1A1382 | sp-4 | an-251 | 1U1382 | sp-4 | an-251 | 1C1382 | sp-4 | an-251 |
| 1A1383 | sp-4 | an-252 | 1U1383 | sp-4 | an-252 | 1C1383 | sp-4 | an-252 |
| 1A1384 | sp-4 | an-253 | 1U1384 | sp-4 | an-253 | 1C1384 | sp-4 | an-253 |
| 1A1385 | sp-4 | an-254 | 1U1385 | sp-4 | an-254 | 1C1385 | sp-4 | an-254 |
| 1A1386 | sp-4 | an-255 | 1U1386 | sp-4 | an-255 | 1C1386 | sp-4 | an-255 |
| 1A1387 | sp-4 | an-256 | 1U1387 | sp-4 | an-256 | 1C1387 | sp-4 | an-256 |
| 1A1388 | sp-4 | an-257 | 1U1388 | sp-4 | an-257 | 1C1388 | sp-4 | an-257 |
| 1A1389 | sp-4 | an-258 | 1U1389 | sp-4 | an-258 | 1C1389 | sp-4 | an-258 |
| 1A1390 | sp-4 | an-259 | 1U1390 | sp-4 | an-259 | 1C1390 | sp-4 | an-259 |
| 1A1391 | sp-4 | an-260 | 1U1391 | sp-4 | an-260 | 1C1391 | sp-4 | an-260 |
| 1A1392 | sp-4 | an-261 | 1U1392 | sp-4 | an-261 | 1C1392 | sp-4 | an-261 |
| 1A1393 | sp-4 | an-262 | 1U1393 | sp-4 | an-262 | 1C1393 | sp-4 | an-262 |
| 1A1394 | sp-4 | an-263 | 1U1394 | sp-4 | an-263 | 1C1394 | sp-4 | an-263 |
| 1A1395 | sp-4 | an-264 | 1U1395 | sp-4 | an-264 | 1C1395 | sp-4 | an-264 |
| 1A1396 | sp-4 | an-265 | 1U1396 | sp-4 | an-265 | 1C1396 | sp-4 | an-265 |
| 1A1397 | sp-4 | an-266 | 1U1397 | sp-4 | an-266 | 1C1397 | sp-4 | an-266 |
| 1A1398 | sp-4 | an-267 | 1U1398 | sp-4 | an-267 | 1C1398 | sp-4 | an-267 |
| 1A1399 | sp-4 | an-268 | 1U1399 | sp-4 | an-268 | 1C1399 | sp-4 | an-268 |
| 1A1400 | sp-4 | an-269 | 1U1400 | sp-4 | an-269 | 1C1400 | sp-4 | an-269 |

Table 2-26

| Y = NHCS | | | Y = NHCSNH | | | Y = NHCSO | | |
|---|---|---|---|---|---|---|---|---|
| 1A1401 | sp-4 | an-270 | 1U1401 | sp-4 | an-270 | 1C1401 | sp-4 | an-270 |
| 1A1402 | sp-4 | an-271 | 1U1402 | sp-4 | an-271 | 1C1402 | sp-4 | an-271 |
| 1A1403 | sp-4 | an-272 | 1U1403 | sp-4 | an-272 | 1C1403 | sp-4 | an-272 |
| 1A1404 | sp-4 | an-273 | 1U1404 | sp-4 | an-273 | 1C1404 | sp-4 | an-273 |
| 1A1405 | sp-4 | an-274 | 1U1405 | sp-4 | an-274 | 1C1405 | sp-4 | an-274 |
| 1A1406 | sp-4 | an-275 | 1U1406 | sp-4 | an-275 | 1C1406 | sp-4 | an-275 |
| 1A1407 | sp-4 | an-276 | 1U1407 | sp-4 | an-276 | 1C1407 | sp-4 | an-276 |
| 1A1408 | sp-4 | an-277 | 1U1408 | sp-4 | an-277 | 1C1408 | sp-4 | an-277 |
| 1A1409 | sp-4 | an-278 | 1U1409 | sp-4 | an-278 | 1C1409 | sp-4 | an-278 |
| 1A1410 | sp-4 | an-279 | 1U1410 | sp-4 | an-279 | 1C1410 | sp-4 | an-279 |
| 1A1411 | sp-4 | an-280 | 1U1411 | sp-4 | an-280 | 1C1411 | sp-4 | an-280 |
| 1A1412 | sp-4 | an-281 | 1U1412 | sp-4 | an-281 | 1C1412 | sp-4 | an-281 |
| 1A1413 | sp-4 | an-282 | 1U1413 | sp-4 | an-282 | 1C1413 | sp-4 | an-282 |
| 1A1414 | sp-4 | an-283 | 1U1414 | sp-4 | an-283 | 1C1414 | sp-4 | an-283 |

-continued

| Ex. No. | Z | N⁺R⁵R⁶R⁷ | Ex. No. | Z | N⁺R⁵R⁶R⁷ | Ex. No. | Z | N⁺R⁵R⁶R⁷ |
|---|---|---|---|---|---|---|---|---|
| 1A1415 | sp-4 | an-284 | 1U1415 | sp-4 | an-284 | 1C1415 | sp-4 | an-284 |
| 1A1416 | sp-4 | an-285 | 1U1416 | sp-4 | an-285 | 1C1416 | sp-4 | an-285 |
| 1A1417 | sp-4 | an-286 | 1U1417 | sp-4 | an-286 | 1C1417 | sp-4 | an-286 |
| 1A1418 | sp-4 | an-287 | 1U1418 | sp-4 | an-287 | 1C1418 | sp-4 | an-287 |
| 1A1419 | sp-4 | an-288 | 1U1419 | sp-4 | an-288 | 1C1419 | sp-4 | an-288 |
| 1A1420 | sp-4 | an-289 | 1U1420 | sp-4 | an-289 | 1C1420 | sp-4 | an-289 |
| 1A1421 | sp-4 | an-290 | 1U1421 | sp-4 | an-290 | 1C1421 | sp-4 | an-290 |
| 1A1422 | sp-4 | an-291 | 1U1422 | sp-4 | an-291 | 1C1422 | sp-4 | an-291 |
| 1A1423 | sp-4 | an-292 | 1U1423 | sp-4 | an-292 | 1C1423 | sp-4 | an-292 |
| 1A1424 | sp-4 | an-293 | 1U1424 | sp-4 | an-293 | 1C1424 | sp-4 | an-293 |
| 1A1425 | sp-4 | an-294 | 1U1425 | sp-4 | an-294 | 1C1425 | sp-4 | an-294 |
| 1A1426 | sp-4 | an-295 | 1U1426 | sp-4 | an-295 | 1C1426 | sp-4 | an-295 |
| 1A1427 | sp-4 | an-296 | 1U1427 | sp-4 | an-296 | 1C1427 | sp-4 | an-296 |
| 1A1428 | sp-4 | an-297 | 1U1428 | sp-4 | an-297 | 1C1428 | sp-4 | an-297 |
| 1A1429 | sp-4 | an-298 | 1U1429 | sp-4 | an-298 | 1C1429 | sp-4 | an-298 |
| 1A1430 | sp-4 | an-299 | 1U1430 | sp-4 | an-299 | 1C1430 | sp-4 | an-299 |
| 1A1431 | sp-4 | an-300 | 1U1431 | sp-4 | an-300 | 1C1431 | sp-4 | an-300 |
| 1A1432 | sp-4 | an-301 | 1U1432 | sp-4 | an-301 | 1C1432 | sp-4 | an-301 |
| 1A1433 | sp-4 | an-302 | 1U1433 | sp-4 | an-302 | 1C1433 | sp-4 | an-302 |
| 1A1434 | sp-4 | an-303 | 1U1434 | sp-4 | an-303 | 1C1434 | sp-4 | an-303 |
| 1A1435 | sp-4 | an-304 | 1U1435 | sp-4 | an-304 | 1C1435 | sp-4 | an-304 |
| 1A1436 | sp-4 | an-305 | 1U1436 | sp-4 | an-305 | 1C1436 | sp-4 | an-305 |
| 1A1437 | sp-4 | an-306 | 1U1437 | sp-4 | an-306 | 1C1437 | sp-4 | an-306 |
| 1A1438 | sp-4 | an-307 | 1U1438 | sp-4 | an-307 | 1C1438 | sp-4 | an-307 |
| 1A1439 | sp-4 | an-308 | 1U1439 | sp-4 | an-308 | 1C1439 | sp-4 | an-308 |
| 1A1440 | sp-4 | an-309 | 1U1440 | sp-4 | an-309 | 1C1440 | sp-4 | an-309 |
| 1A1441 | sp-4 | an-310 | 1U1441 | sp-4 | an-310 | 1C1441 | sp-4 | an-310 |
| 1A1442 | sp-4 | an-311 | 1U1442 | sp-4 | an-311 | 1C1442 | sp-4 | an-311 |
| 1A1443 | sp-4 | an-312 | 1U1443 | sp-4 | an-312 | 1C1443 | sp-4 | an-312 |
| 1A1444 | sp-4 | an-313 | 1U1444 | sp-4 | an-313 | 1C1444 | sp-4 | an-313 |
| 1A1445 | sp-4 | an-314 | 1U1445 | sp-4 | an-314 | 1C1445 | sp-4 | an-314 |
| 1A1446 | sp-4 | an-315 | 1U1446 | sp-4 | an-315 | 1C1446 | sp-4 | an-315 |
| 1A1447 | sp-4 | an-316 | 1U1447 | sp-4 | an-316 | 1C1447 | sp-4 | an-316 |
| 1A1448 | sp-4 | an-317 | 1U1448 | sp-4 | an-317 | 1C1448 | sp-4 | an-317 |
| 1A1449 | sp-4 | an-318 | 1U1449 | sp-4 | an-318 | 1C1449 | sp-4 | an-318 |
| 1A1450 | sp-4 | an-319 | 1U1450 | sp-4 | an-319 | 1C1450 | sp-4 | an-319 |
| 1A1451 | sp-4 | an-320 | 1U1451 | sp-4 | an-320 | 1C1451 | sp-4 | an-320 |
| 1A1452 | sp-4 | an-321 | 1U1452 | sp-4 | an-321 | 1C1452 | sp-4 | an-321 |
| 1A1453 | sp-4 | an-322 | 1U1453 | sp-4 | an-322 | 1C1453 | sp-4 | an-322 |
| 1A1454 | sp-4 | an-323 | 1U1454 | sp-4 | an-323 | 1C1454 | sp-4 | an-323 |
| 1A1455 | sp-4 | an-324 | 1U1455 | sp-4 | an-324 | 1C1455 | sp-4 | an-324 |
| 1A1456 | sp-4 | an-325 | 1U1456 | sp-4 | an-325 | 1C1456 | sp-4 | an-325 |

Table 2-27

| | Y = NHCS | | | Y = NHCSNH | | | Y = NHCSO | |
|---|---|---|---|---|---|---|---|---|
| 1A1457 | sp-4 | an-326 | 1U1457 | sp-4 | an-326 | 1C1457 | sp-4 | an-326 |
| 1A1458 | sp-4 | an-327 | 1U1458 | sp-4 | an-327 | 1C1458 | sp-4 | an-327 |
| 1A1459 | sp-4 | an-328 | 1U1459 | sp-4 | an-328 | 1C1459 | sp-4 | an-328 |
| 1A1460 | sp-4 | an-329 | 1U1460 | sp-4 | an-329 | 1C1460 | sp-4 | an-329 |
| 1A1461 | sp-4 | an-330 | 1U1461 | sp-4 | an-330 | 1C1461 | sp-4 | an-330 |
| 1A1462 | sp-4 | an-331 | 1U1462 | sp-4 | an-331 | 1C1462 | sp-4 | an-331 |
| 1A1463 | sp-4 | an-332 | 1U1463 | sp-4 | an-332 | 1C1463 | sp-4 | an-332 |
| 1A1464 | sp-4 | an-333 | 1U1464 | sp-4 | an-333 | 1C1464 | sp-4 | an-333 |
| 1A1465 | sp-4 | an-334 | 1U1465 | sp-4 | an-334 | 1C1465 | sp-4 | an-334 |
| 1A1466 | sp-4 | an-335 | 1U1466 | sp-4 | an-335 | 1C1466 | sp-4 | an-335 |
| 1A1467 | sp-4 | an-336 | 1U1467 | sp-4 | an-336 | 1C1467 | sp-4 | an-336 |
| 1A1468 | sp-4 | an-337 | 1U1468 | sp-4 | an-337 | 1C1468 | sp-4 | an-337 |
| 1A1469 | sp-4 | an-338 | 1U1469 | sp-4 | an-338 | 1C1469 | sp-4 | an-338 |
| 1A1470 | sp-4 | an-339 | 1U1470 | sp-4 | an-339 | 1C1470 | sp-4 | an-339 |
| 1A1471 | sp-4 | an-340 | 1U1471 | sp-4 | an-340 | 1C1471 | sp-4 | an-340 |
| 1A1472 | sp-4 | an-341 | 1U1472 | sp-4 | an-341 | 1C1472 | sp-4 | an-341 |
| 1A1473 | sp-4 | an-342 | 1U1473 | sp-4 | an-342 | 1C1473 | sp-4 | an-342 |
| 1A1474 | sp-4 | an-343 | 1U1474 | sp-4 | an-343 | 1C1474 | sp-4 | an-343 |
| 1A1475 | sp-4 | an-344 | 1U1475 | sp-4 | an-344 | 1C1475 | sp-4 | an-344 |
| 1A1476 | sp-4 | an-345 | 1U1476 | sp-4 | an-345 | 1C1476 | sp-4 | an-345 |
| 1A1477 | sp-4 | an-346 | 1U1477 | sp-4 | an-346 | 1C1477 | sp-4 | an-346 |
| 1A1478 | sp-4 | an-347 | 1U1478 | sp-4 | an-347 | 1C1478 | sp-4 | an-347 |
| 1A1479 | sp-4 | an-348 | 1U1479 | sp-4 | an-348 | 1C1479 | sp-4 | an-348 |
| 1A1480 | sp-4 | an-349 | 1U1480 | sp-4 | an-349 | 1C1480 | sp-4 | an-349 |
| 1A1481 | sp-4 | an-350 | 1U1481 | sp-4 | an-350 | 1C1481 | sp-4 | an-350 |
| 1A1482 | sp-4 | an-351 | 1U1482 | sp-4 | an-351 | 1C1482 | sp-4 | an-351 |
| 1A1483 | sp-4 | an-352 | 1U1483 | sp-4 | an-352 | 1C1483 | sp-4 | an-352 |
| 1A1484 | sp-4 | an-353 | 1U1484 | sp-4 | an-353 | 1C1484 | sp-4 | an-353 |
| 1A1485 | sp-4 | an-354 | 1U1485 | sp-4 | an-354 | 1C1485 | sp-4 | an-354 |
| 1A1486 | sp-4 | an-355 | 1U1486 | sp-4 | an-355 | 1C1486 | sp-4 | an-355 |
| 1A1487 | sp-4 | an-356 | 1U1487 | sp-4 | an-356 | 1C1487 | sp-4 | an-356 |
| 1A1488 | sp-4 | an-357 | 1U1488 | sp-4 | an-357 | 1C1488 | sp-4 | an-357 |

| Ex. No. | Z | N+R5R6R7 | Ex. No. | Z | N+R5R6R7 | Ex. No. | Z | N+R5R6R7 |
|---|---|---|---|---|---|---|---|---|
| 1A1489 | sp-4 | an-358 | 1U1489 | sp-4 | an-358 | 1C1489 | sp-4 | an-358 |
| 1A1490 | sp-4 | an-359 | 1U1490 | sp-4 | an-359 | 1C1490 | sp-4 | an-359 |
| 1A1491 | sp-4 | an-360 | 1U1491 | sp-4 | an-360 | 1C1491 | sp-4 | an-360 |
| 1A1492 | sp-4 | an-361 | 1U1492 | sp-4 | an-361 | 1C1492 | sp-4 | an-361 |
| 1A1493 | sp-4 | an-362 | 1U1493 | sp-4 | an-362 | 1C1493 | sp-4 | an-362 |
| 1A1494 | sp-4 | an-363 | 1U1494 | sp-4 | an-363 | 1C1494 | sp-4 | an-363 |
| 1A1495 | sp-4 | an-364 | 1U1495 | sp-4 | an-364 | 1C1495 | sp-4 | an-364 |
| 1A1496 | sp-4 | an-365 | 1U1496 | sp-4 | an-365 | 1C1496 | sp-4 | an-365 |
| 1A1497 | sp-4 | an-366 | 1U1497 | sp-4 | an-366 | 1C1497 | sp-4 | an-366 |
| 1A1498 | sp-4 | an-367 | 1U1498 | sp-4 | an-367 | 1C1498 | sp-4 | an-367 |
| 1A1499 | sp-4 | an-368 | 1U1499 | sp-4 | an-368 | 1C1499 | sp-4 | an-368 |
| 1A1500 | sp-4 | an-369 | 1U1500 | sp-4 | an-369 | 1C1500 | sp-4 | an-369 |
| 1A1501 | sp-4 | an-370 | 1U1501 | sp-4 | an-370 | 1C1501 | sp-4 | an-370 |
| 1A1502 | sp-4 | an-371 | 1U1502 | sp-4 | an-371 | 1C1502 | sp-4 | an-371 |
| 1A1503 | sp-4 | an-372 | 1U1503 | sp-4 | an-372 | 1C1503 | sp-4 | an-372 |
| 1A1504 | sp-4 | an-373 | 1U1504 | sp-4 | an-373 | 1C1504 | sp-4 | an-373 |
| 1A1505 | sp-4 | an-374 | 1U1505 | sp-4 | an-374 | 1C1505 | sp-4 | an-374 |
| 1A1506 | sp-4 | an-375 | 1U1506 | sp-4 | an-375 | 1C1506 | sp-4 | an-375 |
| 1A1507 | sp-4 | an-376 | 1U1507 | sp-4 | an-376 | 1C1507 | sp-4 | an-376 |
| 1A1508 | sp-4 | an-377 | 1U1508 | sp-4 | an-377 | 1C1508 | sp-4 | an-377 |
| 1A1509 | sp-5 | an-1 | 1U1509 | sp-5 | an-1 | 1C1509 | sp-5 | an-1 |
| 1A1510 | sp-5 | an-2 | 1U1510 | sp-5 | an-2 | 1C1510 | sp-5 | an-2 |
| 1A1511 | sp-5 | an-3 | 1U1511 | sp-5 | an-3 | 1C1511 | sp-5 | an-3 |
| 1A1512 | sp-5 | an-4 | 1U1512 | sp-5 | an-4 | 1C1512 | sp-5 | an-4 |

Table 2-28

| Y = NHCS | | | Y = NHCSNH | | | Y = NHCSO | | |
|---|---|---|---|---|---|---|---|---|
| 1A1513 | sp-5 | an-5 | 1U1513 | sp-5 | an-5 | 1C1513 | sp-5 | an-5 |
| 1A1514 | sp-5 | an-6 | 1U1514 | sp-5 | an-6 | 1C1514 | sp-5 | an-6 |
| 1A1515 | sp-5 | an-7 | 1U1515 | sp-5 | an-7 | 1C1515 | sp-5 | an-7 |
| 1A1516 | sp-5 | an-8 | 1U1516 | sp-5 | an-8 | 1C1516 | sp-5 | an-8 |
| 1A1517 | sp-5 | an-9 | 1U1517 | sp-5 | an-9 | 1C1517 | sp-5 | an-9 |
| 1A1518 | sp-5 | an-10 | 1U1518 | sp-5 | an-10 | 1C1518 | sp-5 | an-10 |
| 1A1519 | sp-5 | an-11 | 1U1519 | sp-5 | an-11 | 1C1519 | sp-5 | an-11 |
| 1A1520 | sp-5 | an-12 | 1U1520 | sp-5 | an-12 | 1C1520 | sp-5 | an-12 |
| 1A1521 | sp-5 | an-13 | 1U1521 | sp-5 | an-13 | 1C1521 | sp-5 | an-13 |
| 1A1522 | sp-5 | an-14 | 1U1522 | sp-5 | an-14 | 1C1522 | sp-5 | an-14 |
| 1A1523 | sp-5 | an-15 | 1U1523 | sp-5 | an-15 | 1C1523 | sp-5 | an-15 |
| 1A1524 | sp-5 | an-16 | 1U1524 | sp-5 | an-16 | 1C1524 | sp-5 | an-16 |
| 1A1525 | sp-5 | an-17 | 1U1525 | sp-5 | an-17 | 1C1525 | sp-5 | an-17 |
| 1A1526 | sp-5 | an-18 | 1U1526 | sp-5 | an-18 | 1C1526 | sp-5 | an-18 |
| 1A1527 | sp-5 | an-19 | 1U1527 | sp-5 | an-19 | 1C1527 | sp-5 | an-19 |
| 1A1528 | sp-5 | an-20 | 1U1528 | sp-5 | an-20 | 1C1528 | sp-5 | an-20 |
| 1A1529 | sp-5 | an-21 | 1U1529 | sp-5 | an-21 | 1C1529 | sp-5 | an-21 |
| 1A1530 | sp-5 | an-22 | 1U1530 | sp-5 | an-22 | 1C1530 | sp-5 | an-22 |
| 1A1531 | sp-5 | an-23 | 1U1531 | sp-5 | an-23 | 1C1531 | sp-5 | an-23 |
| 1A1532 | sp-5 | an-24 | 1U1532 | sp-5 | an-24 | 1C1532 | sp-5 | an-24 |
| 1A1533 | sp-5 | an-25 | 1U1533 | sp-5 | an-25 | 1C1533 | sp-5 | an-25 |
| 1A1534 | sp-5 | an-26 | 1U1534 | sp-5 | an-26 | 1C1534 | sp-5 | an-26 |
| 1A1535 | sp-5 | an-27 | 1U1535 | sp-5 | an-27 | 1C1535 | sp-5 | an-27 |
| 1A1536 | sp-5 | an-28 | 1U1536 | sp-5 | an-28 | 1C1536 | sp-5 | an-28 |
| 1A1537 | sp-5 | an-29 | 1U1537 | sp-5 | an-29 | 1C1537 | sp-5 | an-29 |
| 1A1538 | sp-5 | an-30 | 1U1538 | sp-5 | an-30 | 1C1538 | sp-5 | an-30 |
| 1A1539 | sp-5 | an-31 | 1U1539 | sp-5 | an-31 | 1C1539 | sp-5 | an-31 |
| 1A1540 | sp-5 | an-32 | 1U1540 | sp-5 | an-32 | 1C1540 | sp-5 | an-32 |
| 1A1541 | sp-5 | an-33 | 1U1541 | sp-5 | an-33 | 1C1541 | sp-5 | an-33 |
| 1A1542 | sp-5 | an-34 | 1U1542 | sp-5 | an-34 | 1C1542 | sp-5 | an-34 |
| 1A1543 | sp-5 | an-35 | 1U1543 | sp-5 | an-35 | 1C1543 | sp-5 | an-35 |
| 1A1544 | sp-5 | an-36 | 1U1544 | sp-5 | an-36 | 1C1544 | sp-5 | an-36 |
| 1A1545 | sp-5 | an-37 | 1U1545 | sp-5 | an-37 | 1C1545 | sp-5 | an-37 |
| 1A1546 | sp-5 | an-38 | 1U1546 | sp-5 | an-38 | 1C1546 | sp-5 | an-38 |
| 1A1547 | sp-5 | an-39 | 1U1547 | sp-5 | an-39 | 1C1547 | sp-5 | an-39 |
| 1A1548 | sp-5 | an-40 | 1U1548 | sp-5 | an-40 | 1C1548 | sp-5 | an-40 |
| 1A1549 | sp-5 | an-41 | 1U1549 | sp-5 | an-41 | 1C1549 | sp-5 | an-41 |
| 1A1550 | sp-5 | an-42 | 1U1550 | sp-5 | an-42 | 1C1550 | sp-5 | an-42 |
| 1A1551 | sp-5 | an-43 | 1U1551 | sp-5 | an-43 | 1C1551 | sp-5 | an-43 |
| 1A1552 | sp-5 | an-44 | 1U1552 | sp-5 | an-44 | 1C1552 | sp-5 | an-44 |
| 1A1553 | sp-5 | an-45 | 1U1553 | sp-5 | an-45 | 1C1553 | sp-5 | an-45 |
| 1A1554 | sp-5 | an-46 | 1U1554 | sp-5 | an-46 | 1C1554 | sp-5 | an-46 |
| 1A1555 | sp-5 | an-47 | 1U1555 | sp-5 | an-47 | 1C1555 | sp-5 | an-47 |
| 1A1556 | sp-5 | an-48 | 1U1556 | sp-5 | an-48 | 1C1556 | sp-5 | an-48 |
| 1A1557 | sp-5 | an-49 | 1U1557 | sp-5 | an-49 | 1C1557 | sp-5 | an-49 |
| 1A1558 | sp-5 | an-50 | 1U1558 | sp-5 | an-50 | 1C1558 | sp-5 | an-50 |
| 1A1559 | sp-5 | an-51 | 1U1559 | sp-5 | an-51 | 1C1559 | sp-5 | an-51 |
| 1A1560 | sp-5 | an-52 | 1U1560 | sp-5 | an-52 | 1C1560 | sp-5 | an-52 |
| 1A1561 | sp-5 | an-53 | 1U1561 | sp-5 | an-53 | 1C1561 | sp-5 | an-53 |
| 1A1562 | sp-5 | an-54 | 1U1562 | sp-5 | an-54 | 1C1562 | sp-5 | an-54 |

-continued

| Ex. No. | Z | N⁺R⁵R⁶R⁷ | Ex. No. | Z | N⁺R⁵R⁶R⁷ | Ex. No. | Z | N⁺R⁵R⁶R⁷ |
|---|---|---|---|---|---|---|---|---|
| 1A1563 | sp-5 | an-55 | 1U1563 | sp-5 | an-55 | 1C1563 | sp-5 | an-55 |
| 1A1564 | sp-5 | an-56 | 1U1564 | sp-5 | an-56 | 1C1564 | sp-5 | an-56 |
| 1A1565 | sp-5 | an-57 | 1U1565 | sp-5 | an-57 | 1C1565 | sp-5 | an-57 |
| 1A1566 | sp-5 | an-58 | 1U1566 | sp-5 | an-58 | 1C1566 | sp-5 | an-58 |
| 1A1567 | sp-5 | an-59 | 1U1567 | sp-5 | an-59 | 1C1567 | sp-5 | an-59 |
| 1A1568 | sp-5 | an-60 | 1U1568 | sp-5 | an-60 | 1C1568 | sp-5 | an-60 |

Table 2-29

| Y = NHCS | | | Y = NHCSNH | | | Y = NHCSO | | |
|---|---|---|---|---|---|---|---|---|
| 1A1569 | sp-5 | an-61 | 1U1569 | sp-5 | an-61 | 1C1569 | sp-5 | an-61 |
| 1A1570 | sp-5 | an-62 | 1U1570 | sp-5 | an-62 | 1C1570 | sp-5 | an-62 |
| 1A1571 | sp-5 | an-63 | 1U1571 | sp-5 | an-63 | 1C1571 | sp-5 | an-63 |
| 1A1572 | sp-5 | an-64 | 1U1572 | sp-5 | an-64 | 1C1572 | sp-5 | an-64 |
| 1A1573 | sp-5 | an-65 | 1U1573 | sp-5 | an-65 | 1C1573 | sp-5 | an-65 |
| 1A1574 | sp-5 | an-66 | 1U1574 | sp-5 | an-66 | 1C1574 | sp-5 | an-66 |
| 1A1575 | sp-5 | an-67 | 1U1575 | sp-5 | an-67 | 1C1575 | sp-5 | an-67 |
| 1A1576 | sp-5 | an-68 | 1U1576 | sp-5 | an-68 | 1C1576 | sp-5 | an-68 |
| 1A1577 | sp-5 | an-69 | 1U1577 | sp-5 | an-69 | 1C1577 | sp-5 | an-69 |
| 1A1578 | sp-5 | an-70 | 1U1578 | sp-5 | an-70 | 1C1578 | sp-5 | an-70 |
| 1A1579 | sp-5 | an-71 | 1U1579 | sp-5 | an-71 | 1C1579 | sp-5 | an-71 |
| 1A1580 | sp-5 | an-72 | 1U1580 | sp-5 | an-72 | 1C1580 | sp-5 | an-72 |
| 1A1581 | sp-5 | an-73 | 1U1581 | sp-5 | an-73 | 1C1581 | sp-5 | an-73 |
| 1A1582 | sp-5 | an-74 | 1U1582 | sp-5 | an-74 | 1C1582 | sp-5 | an-74 |
| 1A1583 | sp-5 | an-75 | 1U1583 | sp-5 | an-75 | 1C1583 | sp-5 | an-75 |
| 1A1584 | sp-5 | an-76 | 1U1584 | sp-5 | an-76 | 1C1584 | sp-5 | an-76 |
| 1A1585 | sp-5 | an-77 | 1U1585 | sp-5 | an-77 | 1C1585 | sp-5 | an-77 |
| 1A1586 | sp-5 | an-78 | 1U1586 | sp-5 | an-78 | 1C1586 | sp-5 | an-78 |
| 1A1587 | sp-5 | an-79 | 1U1587 | sp-5 | an-79 | 1C1587 | sp-5 | an-79 |
| 1A1588 | sp-5 | an-80 | 1U1588 | sp-5 | an-80 | 1C1588 | sp-5 | an-80 |
| 1A1589 | sp-5 | an-81 | 1U1589 | sp-5 | an-81 | 1C1589 | sp-5 | an-81 |
| 1A1590 | sp-5 | an-82 | 1U1590 | sp-5 | an-82 | 1C1590 | sp-5 | an-82 |
| 1A1591 | sp-5 | an-83 | 1U1591 | sp-5 | an-83 | 1C1591 | sp-5 | an-83 |
| 1A1592 | sp-5 | an-84 | 1U1592 | sp-5 | an-84 | 1C1592 | sp-5 | an-84 |
| 1A1593 | sp-5 | an-85 | 1U1593 | sp-5 | an-85 | 1C1593 | sp-5 | an-85 |
| 1A1594 | sp-5 | an-86 | 1U1594 | sp-5 | an-86 | 1C1594 | sp-5 | an-86 |
| 1A1595 | sp-5 | an-87 | 1U1595 | sp-5 | an-87 | 1C1595 | sp-5 | an-87 |
| 1A1596 | sp-5 | an-88 | 1U1596 | sp-5 | an-88 | 1C1596 | sp-5 | an-88 |
| 1A1597 | sp-5 | an-89 | 1U1597 | sp-5 | an-89 | 1C1597 | sp-5 | an-89 |
| 1A1598 | sp-5 | an-90 | 1U1598 | sp-5 | an-90 | 1C1598 | sp-5 | an-90 |
| 1A1599 | sp-5 | an-91 | 1U1599 | sp-5 | an-91 | 1C1599 | sp-5 | an-91 |
| 1A1600 | sp-5 | an-92 | 1U1600 | sp-5 | an-92 | 1C1600 | sp-5 | an-92 |
| 1A1601 | sp-5 | an-93 | 1U1601 | sp-5 | an-93 | 1C1601 | sp-5 | an-93 |
| 1A1602 | sp-5 | an-94 | 1U1602 | sp-5 | an-94 | 1C1602 | sp-5 | an-94 |
| 1A1603 | sp-5 | an-95 | 1U1603 | sp-5 | an-95 | 1C1603 | sp-5 | an-95 |
| 1A1604 | sp-5 | an-96 | 1U1604 | sp-5 | an-96 | 1C1604 | sp-5 | an-96 |
| 1A1605 | sp-5 | an-97 | 1U1605 | sp-5 | an-97 | 1C1605 | sp-5 | an-97 |
| 1A1606 | sp-5 | an-98 | 1U1606 | sp-5 | an-98 | 1C1606 | sp-5 | an-98 |
| 1A1607 | sp-5 | an-99 | 1U1607 | sp-5 | an-99 | 1C1607 | sp-5 | an-99 |
| 1A1608 | sp-5 | an-100 | 1U1608 | sp-5 | an-100 | 1C1608 | sp-5 | an-100 |
| 1A1609 | sp-5 | an-101 | 1U1609 | sp-5 | an-101 | 1C1609 | sp-5 | an-101 |
| 1A1610 | sp-5 | an-102 | 1U1610 | sp-5 | an-102 | 1C1610 | sp-5 | an-102 |
| 1A1611 | sp-5 | an-103 | 1U1611 | sp-5 | an-103 | 1C1611 | sp-5 | an-103 |
| 1A1612 | sp-5 | an-104 | 1U1612 | sp-5 | an-104 | 1C1612 | sp-5 | an-104 |
| 1A1613 | sp-5 | an-105 | 1U1613 | sp-5 | an-105 | 1C1613 | sp-5 | an-105 |
| 1A1614 | sp-5 | an-106 | 1U1614 | sp-5 | an-106 | 1C1614 | sp-5 | an-106 |
| 1A1615 | sp-5 | an-107 | 1U1615 | sp-5 | an-107 | 1C1615 | sp-5 | an-107 |
| 1A1616 | sp-5 | an-108 | 1U1616 | sp-5 | an-108 | 1C1616 | sp-5 | an-108 |
| 1A1617 | sp-5 | an-109 | 1U1617 | sp-5 | an-109 | 1C1617 | sp-5 | an-109 |
| 1A1618 | sp-5 | an-110 | 1U1618 | sp-5 | an-110 | 1C1618 | sp-5 | an-110 |
| 1A1619 | sp-5 | an-111 | 1U1619 | sp-5 | an-111 | 1C1619 | sp-5 | an-111 |
| 1A1620 | sp-5 | an-112 | 1U1620 | sp-5 | an-112 | 1C1620 | sp-5 | an-112 |
| 1A1621 | sp-5 | an-113 | 1U1621 | sp-5 | an-113 | 1C1621 | sp-5 | an-113 |
| 1A1622 | sp-5 | an-114 | 1U1622 | sp-5 | an-114 | 1C1622 | sp-5 | an-114 |
| 1A1623 | sp-5 | an-115 | 1U1623 | sp-5 | an-115 | 1C1623 | sp-5 | an-115 |
| 1A1624 | sp-5 | an-116 | 1U1624 | sp-5 | an-116 | 1C1624 | sp-5 | an-116 |

Table 2-30

| Y = NHCS | | | Y = NHCSNH | | | Y = NHCSO | | |
|---|---|---|---|---|---|---|---|---|
| 1A1625 | sp-5 | an-117 | 1U1625 | sp-5 | an-117 | 1C1625 | sp-5 | an-117 |
| 1A1626 | sp-5 | an-118 | 1U1626 | sp-5 | an-118 | 1C1626 | sp-5 | an-118 |
| 1A1627 | sp-5 | an-119 | 1U1627 | sp-5 | an-119 | 1C1627 | sp-5 | an-119 |
| 1A1628 | sp-5 | an-120 | 1U1628 | sp-5 | an-120 | 1C1628 | sp-5 | an-120 |
| 1A1629 | sp-5 | an-121 | 1U1629 | sp-5 | an-121 | 1C1629 | sp-5 | an-121 |
| 1A1630 | sp-5 | an-122 | 1U1630 | sp-5 | an-122 | 1C1630 | sp-5 | an-122 |
| 1A1631 | sp-5 | an-123 | 1U1631 | sp-5 | an-123 | 1C1631 | sp-5 | an-123 |
| 1A1632 | sp-5 | an-124 | 1U1632 | sp-5 | an-124 | 1C1632 | sp-5 | an-124 |

-continued

| Ex. No. | Z | N⁺R⁵R⁶R⁷ | Ex. No. | Z | N⁺R⁵R⁶R⁷ | Ex. No. | Z | N⁺R⁵R⁶R⁷ |
|---|---|---|---|---|---|---|---|---|
| 1A1633 | sp-5 | an-125 | 1U1633 | sp-5 | an-125 | 1C1633 | sp-5 | an-125 |
| 1A1634 | sp-5 | an-126 | 1U1634 | sp-5 | an-126 | 1C1634 | sp-5 | an-126 |
| 1A1635 | sp-5 | an-127 | 1U1635 | sp-5 | an-127 | 1C1635 | sp-5 | an-127 |
| 1A1636 | sp-5 | an-128 | 1U1636 | sp-5 | an-128 | 1C1636 | sp-5 | an-128 |
| 1A1637 | sp-5 | an-129 | 1U1637 | sp-5 | an-129 | 1C1637 | sp-5 | an-129 |
| 1A1638 | sp-5 | an-130 | 1U1638 | sp-5 | an-130 | 1C1638 | sp-5 | an-130 |
| 1A1639 | sp-5 | an-131 | 1U1639 | sp-5 | an-131 | 1C1639 | sp-5 | an-131 |
| 1A1640 | sp-5 | an-132 | 1U1640 | sp-5 | an-132 | 1C1640 | sp-5 | an-132 |
| 1A1641 | sp-5 | an-133 | 1U1641 | sp-5 | an-133 | 1C1641 | sp-5 | an-133 |
| 1A1642 | sp-5 | an-134 | 1U1642 | sp-5 | an-134 | 1C1642 | sp-5 | an-134 |
| 1A1643 | sp-5 | an-135 | 1U1643 | sp-5 | an-135 | 1C1643 | sp-5 | an-135 |
| 1A1644 | sp-5 | an-136 | 1U1644 | sp-5 | an-136 | 1C1644 | sp-5 | an-136 |
| 1A1645 | sp-5 | an-137 | 1U1645 | sp-5 | an-137 | 1C1645 | sp-5 | an-137 |
| 1A1646 | sp-5 | an-138 | 1U1646 | sp-5 | an-138 | 1C1646 | sp-5 | an-138 |
| 1A1647 | sp-5 | an-139 | 1U1647 | sp-5 | an-139 | 1C1647 | sp-5 | an-139 |
| 1A1648 | sp-5 | an-140 | 1U1648 | sp-5 | an-140 | 1C1648 | sp-5 | an-140 |
| 1A1649 | sp-5 | an-141 | 1U1649 | sp-5 | an-141 | 1C1649 | sp-5 | an-141 |
| 1A1650 | sp-5 | an-142 | 1U1650 | sp-5 | an-142 | 1C1650 | sp-5 | an-142 |
| 1A1651 | sp-5 | an-143 | 1U1651 | sp-5 | an-143 | 1C1651 | sp-5 | an-143 |
| 1A1652 | sp-5 | an-144 | 1U1652 | sp-5 | an-144 | 1C1652 | sp-5 | an-144 |
| 1A1653 | sp-5 | an-145 | 1U1653 | sp-5 | an-145 | 1C1653 | sp-5 | an-145 |
| 1A1654 | sp-5 | an-146 | 1U1654 | sp-5 | an-146 | 1C1654 | sp-5 | an-146 |
| 1A1655 | sp-5 | an-147 | 1U1655 | sp-5 | an-147 | 1C1655 | sp-5 | an-147 |
| 1A1656 | sp-5 | an-148 | 1U1656 | sp-5 | an-148 | 1C1656 | sp-5 | an-148 |
| 1A1657 | sp-5 | an-149 | 1U1657 | sp-5 | an-149 | 1C1657 | sp-5 | an-149 |
| 1A1658 | sp-5 | an-150 | 1U1658 | sp-5 | an-150 | 1C1658 | sp-5 | an-150 |
| 1A1659 | sp-5 | an-151 | 1U1659 | sp-5 | an-151 | 1C1659 | sp-5 | an-151 |
| 1A1660 | sp-5 | an-152 | 1U1660 | sp-5 | an-152 | 1C1660 | sp-5 | an-152 |
| 1A1661 | sp-5 | an-153 | 1U1661 | sp-5 | an-153 | 1C1661 | sp-5 | an-153 |
| 1A1662 | sp-5 | an-154 | 1U1662 | sp-5 | an-154 | 1C1662 | sp-5 | an-154 |
| 1A1663 | sp-5 | an-155 | 1U1663 | sp-5 | an-155 | 1C1663 | sp-5 | an-155 |
| 1A1664 | sp-5 | an-156 | 1U1664 | sp-5 | an-156 | 1C1664 | sp-5 | an-156 |
| 1A1665 | sp-5 | an-157 | 1U1665 | sp-5 | an-157 | 1C1665 | sp-5 | an-157 |
| 1A1666 | sp-5 | an-158 | 1U1666 | sp-5 | an-158 | 1C1666 | sp-5 | an-158 |
| 1A1667 | sp-5 | an-159 | 1U1667 | sp-5 | an-159 | 1C1667 | sp-5 | an-159 |
| 1A1668 | sp-5 | an-160 | 1U1668 | sp-5 | an-160 | 1C1668 | sp-5 | an-160 |
| 1A1669 | sp-5 | an-161 | 1U1669 | sp-5 | an-161 | 1C1669 | sp-5 | an-161 |
| 1A1670 | sp-5 | an-162 | 1U1670 | sp-5 | an-162 | 1C1670 | sp-5 | an-162 |
| 1A1671 | sp-5 | an-163 | 1U1671 | sp-5 | an-163 | 1C1671 | sp-5 | an-163 |
| 1A1672 | sp-5 | an-164 | 1U1672 | sp-5 | an-164 | 1C1672 | sp-5 | an-164 |
| 1A1673 | sp-5 | an-165 | 1U1673 | sp-5 | an-165 | 1C1673 | sp-5 | an-165 |
| 1A1674 | sp-5 | an-166 | 1U1674 | sp-5 | an-166 | 1C1674 | sp-5 | an-166 |
| 1A1675 | sp-5 | an-167 | 1U1675 | sp-5 | an-167 | 1C1675 | sp-5 | an-167 |
| 1A1676 | sp-5 | an-168 | 1U1676 | sp-5 | an-168 | 1C1676 | sp-5 | an-168 |
| 1A1677 | sp-5 | an-169 | 1U1677 | sp-5 | an-169 | 1C1677 | sp-5 | an-169 |
| 1A1678 | sp-5 | an-170 | 1U1678 | sp-5 | an-170 | 1C1678 | sp-5 | an-170 |
| 1A1679 | sp-5 | an-171 | 1U1679 | sp-5 | an-171 | 1C1679 | sp-5 | an-171 |
| 1A1680 | sp-5 | an-172 | 1U1680 | sp-5 | an-172 | 1C1680 | sp-5 | an-172 |

Table 2-31

| Y = NHCS | | | Y = NHCSNH | | | Y = NHCSO | | |
|---|---|---|---|---|---|---|---|---|
| 1A1681 | sp-5 | an-173 | 1U1681 | sp-5 | an-173 | 1C1681 | sp-5 | an-173 |
| 1A1682 | sp-5 | an-174 | 1U1682 | sp-5 | an-174 | 1C1682 | sp-5 | an-174 |
| 1A1683 | sp-5 | an-175 | 1U1683 | sp-5 | an-175 | 1C1683 | sp-5 | an-175 |
| 1A1684 | sp-5 | an-176 | 1U1684 | sp-5 | an-176 | 1C1684 | sp-5 | an-176 |
| 1A1685 | sp-5 | an-177 | 1U1685 | sp-5 | an-177 | 1C1685 | sp-5 | an-177 |
| 1A1686 | sp-5 | an-178 | 1U1686 | sp-5 | an-178 | 1C1686 | sp-5 | an-178 |
| 1A1687 | sp-5 | an-179 | 1U1687 | sp-5 | an-179 | 1C1687 | sp-5 | an-179 |
| 1A1688 | sp-5 | an-180 | 1U1688 | sp-5 | an-180 | 1C1688 | sp-5 | an-180 |
| 1A1689 | sp-5 | an-181 | 1U1689 | sp-5 | an-181 | 1C1689 | sp-5 | an-181 |
| 1A1690 | sp-5 | an-182 | 1U1690 | sp-5 | an-182 | 1C1690 | sp-5 | an-182 |
| 1A1691 | sp-5 | an-183 | 1U1691 | sp-5 | an-183 | 1C1691 | sp-5 | an-183 |
| 1A1692 | sp-5 | an-184 | 1U1692 | sp-5 | an-184 | 1C1692 | sp-5 | an-184 |
| 1A1693 | sp-5 | an-185 | 1U1693 | sp-5 | an-185 | 1C1693 | sp-5 | an-185 |
| 1A1694 | sp-5 | an-186 | 1U1694 | sp-5 | an-186 | 1C1694 | sp-5 | an-186 |
| 1A1695 | sp-5 | an-187 | 1U1695 | sp-5 | an-187 | 1C1695 | sp-5 | an-187 |
| 1A1696 | sp-5 | an-188 | 1U1696 | sp-5 | an-188 | 1C1696 | sp-5 | an-188 |
| 1A1697 | sp-5 | an-189 | 1U1697 | sp-5 | an-189 | 1C1697 | sp-5 | an-189 |
| 1A1698 | sp-5 | an-190 | 1U1698 | sp-5 | an-190 | 1C1698 | sp-5 | an-190 |
| 1A1699 | sp-5 | an-191 | 1U1699 | sp-5 | an-191 | 1C1699 | sp-5 | an-191 |
| 1A1700 | sp-5 | an-192 | 1U1700 | sp-5 | an-192 | 1C1700 | sp-5 | an-192 |
| 1A1701 | sp-5 | an-193 | 1U1701 | sp-5 | an-193 | 1C1701 | sp-5 | an-193 |
| 1A1702 | sp-5 | an-194 | 1U1702 | sp-5 | an-194 | 1C1702 | sp-5 | an-194 |
| 1A1703 | sp-5 | an-195 | 1U1703 | sp-5 | an-195 | 1C1703 | sp-5 | an-195 |
| 1A1704 | sp-5 | an-196 | 1U1704 | sp-5 | an-196 | 1C1704 | sp-5 | an-196 |
| 1A1705 | sp-5 | an-197 | 1U1705 | sp-5 | an-197 | 1C1705 | sp-5 | an-197 |
| 1A1706 | sp-5 | an-198 | 1U1706 | sp-5 | an-198 | 1C1706 | sp-5 | an-198 |

-continued

| Ex. No. | Z | N⁺R⁵R⁶R⁷ | Ex. No. | Z | N⁺R⁵R⁶R⁷ | Ex. No. | Z | N⁺R⁵R⁶R⁷ |
|---|---|---|---|---|---|---|---|---|
| 1A1707 | sp-5 | an-199 | 1U1707 | sp-5 | an-199 | 1C1707 | sp-5 | an-199 |
| 1A1708 | sp-5 | an-200 | 1U1708 | sp-5 | an-200 | 1C1708 | sp-5 | an-200 |
| 1A1709 | sp-5 | an-201 | 1U1709 | sp-5 | an-201 | 1C1709 | sp-5 | an-201 |
| 1A1710 | sp-5 | an-202 | 1U1710 | sp-5 | an-202 | 1C1710 | sp-5 | an-202 |
| 1A1711 | sp-5 | an-203 | 1U1711 | sp-5 | an-203 | 1C1711 | sp-5 | an-203 |
| 1A1712 | sp-5 | an-204 | 1U1712 | sp-5 | an-204 | 1C1712 | sp-5 | an-204 |
| 1A1713 | sp-5 | an-205 | 1U1713 | sp-5 | an-205 | 1C1713 | sp-5 | an-205 |
| 1A1714 | sp-5 | an-206 | 1U1714 | sp-5 | an-206 | 1C1714 | sp-5 | an-206 |
| 1A1715 | sp-5 | an-207 | 1U1715 | sp-5 | an-207 | 1C1715 | sp-5 | an-207 |
| 1A1716 | sp-5 | an-208 | 1U1716 | sp-5 | an-208 | 1C1716 | sp-5 | an-208 |
| 1A1717 | sp-5 | an-209 | 1U1717 | sp-5 | an-209 | 1C1717 | sp-5 | an-209 |
| 1A1718 | sp-5 | an-210 | 1U1718 | sp-5 | an-210 | 1C1718 | sp-5 | an-210 |
| 1A1719 | sp-5 | an-211 | 1U1719 | sp-5 | an-211 | 1C1719 | sp-5 | an-211 |
| 1A1720 | sp-5 | an-212 | 1U1720 | sp-5 | an-212 | 1C1720 | sp-5 | an-212 |
| 1A1721 | sp-5 | an-213 | 1U1721 | sp-5 | an-213 | 1C1721 | sp-5 | an-213 |
| 1A1722 | sp-5 | an-214 | 1U1722 | sp-5 | an-214 | 1C1722 | sp-5 | an-214 |
| 1A1723 | sp-5 | an-215 | 1U1723 | sp-5 | an-215 | 1C1723 | sp-5 | an-215 |
| 1A1724 | sp-5 | an-216 | 1U1724 | sp-5 | an-216 | 1C1724 | sp-5 | an-216 |
| 1A1725 | sp-5 | an-217 | 1U1725 | sp-5 | an-217 | 1C1725 | sp-5 | an-217 |
| 1A1726 | sp-5 | an-218 | 1U1726 | sp-5 | an-218 | 1C1726 | sp-5 | an-218 |
| 1A1727 | sp-5 | an-219 | 1U1727 | sp-5 | an-219 | 1C1727 | sp-5 | an-219 |
| 1A1728 | sp-5 | an-220 | 1U1728 | sp-5 | an-220 | 1C1728 | sp-5 | an-220 |
| 1A1729 | sp-5 | an-221 | 1U1729 | sp-5 | an-221 | 1C1729 | sp-5 | an-221 |
| 1A1730 | sp-5 | an-222 | 1U1730 | sp-5 | an-222 | 1C1730 | sp-5 | an-222 |
| 1A1731 | sp-5 | an-223 | 1U1731 | sp-5 | an-223 | 1C1731 | sp-5 | an-223 |
| 1A1732 | sp-5 | an-224 | 1U1732 | sp-5 | an-224 | 1C1732 | sp-5 | an-224 |
| 1A1733 | sp-5 | an-225 | 1U1733 | sp-5 | an-225 | 1C1733 | sp-5 | an-225 |
| 1A1734 | sp-5 | an-226 | 1U1734 | sp-5 | an-226 | 1C1734 | sp-5 | an-226 |
| 1A1735 | sp-5 | an-227 | 1U1735 | sp-5 | an-227 | 1C1735 | sp-5 | an-227 |
| 1A1736 | sp-5 | an-228 | 1U1736 | sp-5 | an-228 | 1C1736 | sp-5 | an-228 |

Table 2-32

| | Y = NHCS | | | Y = NHCSNH | | | Y = NHCSO | |
|---|---|---|---|---|---|---|---|---|
| 1A1737 | sp-5 | an-229 | 1U1737 | sp-5 | an-229 | 1C1737 | sp-5 | an-229 |
| 1A1738 | sp-5 | an-230 | 1U1738 | sp-5 | an-230 | 1C1738 | sp-5 | an-230 |
| 1A1739 | sp-5 | an-231 | 1U1739 | sp-5 | an-231 | 1C1739 | sp-5 | an-231 |
| 1A1740 | sp-5 | an-232 | 1U1740 | sp-5 | an-232 | 1C1740 | sp-5 | an-232 |
| 1A1741 | sp-5 | an-233 | 1U1741 | sp-5 | an-233 | 1C1741 | sp-5 | an-233 |
| 1A1742 | sp-5 | an-234 | 1U1742 | sp-5 | an-234 | 1C1742 | sp-5 | an-234 |
| 1A1743 | sp-5 | an-235 | 1U1743 | sp-5 | an-235 | 1C1743 | sp-5 | an-235 |
| 1A1744 | sp-5 | an-236 | 1U1744 | sp-5 | an-236 | 1C1744 | sp-5 | an-236 |
| 1A1745 | sp-5 | an-237 | 1U1745 | sp-5 | an-237 | 1C1745 | sp-5 | an-237 |
| 1A1746 | sp-5 | an-238 | 1U1746 | sp-5 | an-238 | 1C1746 | sp-5 | an-238 |
| 1A1747 | sp-5 | an-239 | 1U1747 | sp-5 | an-239 | 1C1747 | sp-5 | an-239 |
| 1A1748 | sp-5 | an-240 | 1U1748 | sp-5 | an-240 | 1C1748 | sp-5 | an-240 |
| 1A1749 | sp-5 | an-241 | 1U1749 | sp-5 | an-241 | 1C1749 | sp-5 | an-241 |
| 1A1750 | sp-5 | an-242 | 1U1750 | sp-5 | an-242 | 1C1750 | sp-5 | an-242 |
| 1A1751 | sp-5 | an-243 | 1U1751 | sp-5 | an-243 | 1C1751 | sp-5 | an-243 |
| 1A1752 | sp-5 | an-244 | 1U1752 | sp-5 | an-244 | 1C1752 | sp-5 | an-244 |
| 1A1753 | sp-5 | an-245 | 1U1753 | sp-5 | an-245 | 1C1753 | sp-5 | an-245 |
| 1A1754 | sp-5 | an-246 | 1U1754 | sp-5 | an-246 | 1C1754 | sp-5 | an-246 |
| 1A1755 | sp-5 | an-247 | 1U1755 | sp-5 | an-247 | 1C1755 | sp-5 | an-247 |
| 1A1756 | sp-5 | an-248 | 1U1756 | sp-5 | an-248 | 1C1756 | sp-5 | an-248 |
| 1A1757 | sp-5 | an-249 | 1U1757 | sp-5 | an-249 | 1C1757 | sp-5 | an-249 |
| 1A1758 | sp-5 | an-250 | 1U1758 | sp-5 | an-250 | 1C1758 | sp-5 | an-250 |
| 1A1759 | sp-5 | an-251 | 1U1759 | sp-5 | an-251 | 1C1759 | sp-5 | an-251 |
| 1A1760 | sp-5 | an-252 | 1U1760 | sp-5 | an-252 | 1C1760 | sp-5 | an-252 |
| 1A1761 | sp-5 | an-253 | 1U1761 | sp-5 | an-253 | 1C1761 | sp-5 | an-253 |
| 1A1762 | sp-5 | an-254 | 1U1762 | sp-5 | an-254 | 1C1762 | sp-5 | an-254 |
| 1A1763 | sp-5 | an-255 | 1U1763 | sp-5 | an-255 | 1C1763 | sp-5 | an-255 |
| 1A1764 | sp-5 | an-256 | 1U1764 | sp-5 | an-256 | 1C1764 | sp-5 | an-256 |
| 1A1765 | sp-5 | an-257 | 1U1765 | sp-5 | an-257 | 1C1765 | sp-5 | an-257 |
| 1A1766 | sp-5 | an-258 | 1U1766 | sp-5 | an-258 | 1C1766 | sp-5 | an-258 |
| 1A1767 | sp-5 | an-259 | 1U1767 | sp-5 | an-259 | 1C1767 | sp-5 | an-259 |
| 1A1768 | sp-5 | an-260 | 1U1768 | sp-5 | an-260 | 1C1768 | sp-5 | an-260 |
| 1A1769 | sp-5 | an-261 | 1U1769 | sp-5 | an-261 | 1C1769 | sp-5 | an-261 |
| 1A1770 | sp-5 | an-262 | 1U1770 | sp-5 | an-262 | 1C1770 | sp-5 | an-262 |
| 1A1771 | sp-5 | an-263 | 1U1771 | sp-5 | an-263 | 1C1771 | sp-5 | an-263 |
| 1A1772 | sp-5 | an-264 | 1U1772 | sp-5 | an-264 | 1C1772 | sp-5 | an-264 |
| 1A1773 | sp-5 | an-265 | 1U1773 | sp-5 | an-265 | 1C1773 | sp-5 | an-265 |
| 1A1774 | sp-5 | an-266 | 1U1774 | sp-5 | an-266 | 1C1774 | sp-5 | an-266 |
| 1A1775 | sp-5 | an-267 | 1U1775 | sp-5 | an-267 | 1C1775 | sp-5 | an-267 |
| 1A1776 | sp-5 | an-268 | 1U1776 | sp-5 | an-268 | 1C1776 | sp-5 | an-268 |
| 1A1777 | sp-5 | an-269 | 1U1777 | sp-5 | an-269 | 1C1777 | sp-5 | an-269 |
| 1A1778 | sp-5 | an-270 | 1U1778 | sp-5 | an-270 | 1C1778 | sp-5 | an-270 |
| 1A1779 | sp-5 | an-271 | 1U1779 | sp-5 | an-271 | 1C1779 | sp-5 | an-271 |
| 1A1780 | sp-5 | an-272 | 1U1780 | sp-5 | an-272 | 1C1780 | sp-5 | an-272 |

-continued

| Ex. No. | Z | N+R5R6R7 | Ex. No. | Z | N+R5R6R7 | Ex. No. | Z | N+R5R6R7 |
|---|---|---|---|---|---|---|---|---|
| 1A1781 | sp-5 | an-273 | 1U1781 | sp-5 | an-273 | 1C1781 | sp-5 | an-273 |
| 1A1782 | sp-5 | an-274 | 1U1782 | sp-5 | an-274 | 1C1782 | sp-5 | an-274 |
| 1A1783 | sp-5 | an-275 | 1U1783 | sp-5 | an-275 | 1C1783 | sp-5 | an-275 |
| 1A1784 | sp-5 | an-276 | 1U1784 | sp-5 | an-276 | 1C1784 | sp-5 | an-276 |
| 1A1785 | sp-5 | an-277 | 1U1785 | sp-5 | an-277 | 1C1785 | sp-5 | an-277 |
| 1A1786 | sp-5 | an-278 | 1U1786 | sp-5 | an-278 | 1C1786 | sp-5 | an-278 |
| 1A1787 | sp-5 | an-279 | 1U1787 | sp-5 | an-279 | 1C1787 | sp-5 | an-279 |
| 1A1788 | sp-5 | an-280 | 1U1788 | sp-5 | an-280 | 1C1788 | sp-5 | an-280 |
| 1A1789 | sp-5 | an-281 | 1U1789 | sp-5 | an-281 | 1C1789 | sp-5 | an-281 |
| 1A1790 | sp-5 | an-282 | 1U1790 | sp-5 | an-282 | 1C1790 | sp-5 | an-282 |
| 1A1791 | sp-5 | an-283 | 1U1791 | sp-5 | an-283 | 1C1791 | sp-5 | an-283 |
| 1A1792 | sp-5 | an-284 | 1U1792 | sp-5 | an-284 | 1C1792 | sp-5 | an-284 |

Table 2-33

| Y = NHCS | | | Y = NHCSNH | | | Y = NHCSO | | |
|---|---|---|---|---|---|---|---|---|
| 1A1793 | sp-5 | an-285 | 1U1793 | sp-5 | an-285 | 1C1793 | sp-5 | an-285 |
| 1A1794 | sp-5 | an-286 | 1U1794 | sp-5 | an-286 | 1C1794 | sp-5 | an-286 |
| 1A1795 | sp-5 | an-287 | 1U1795 | sp-5 | an-287 | 1C1795 | sp-5 | an-287 |
| 1A1796 | sp-5 | an-288 | 1U1796 | sp-5 | an-288 | 1C1796 | sp-5 | an-288 |
| 1A1797 | sp-5 | an-289 | 1U1797 | sp-5 | an-289 | 1C1797 | sp-5 | an-289 |
| 1A1798 | sp-5 | an-290 | 1U1798 | sp-5 | an-290 | 1C1798 | sp-5 | an-290 |
| 1A1799 | sp-5 | an-291 | 1U1799 | sp-5 | an-291 | 1C1799 | sp-5 | an-291 |
| 1A1800 | sp-5 | an-292 | 1U1800 | sp-5 | an-292 | 1C1800 | sp-5 | an-292 |
| 1A1801 | sp-5 | an-293 | 1U1801 | sp-5 | an-293 | 1C1801 | sp-5 | an-293 |
| 1A1802 | sp-5 | an-294 | 1U1802 | sp-5 | an-294 | 1C1802 | sp-5 | an-294 |
| 1A1803 | sp-5 | an-295 | 1U1803 | sp-5 | an-295 | 1C1803 | sp-5 | an-295 |
| 1A1804 | sp-5 | an-296 | 1U1804 | sp-5 | an-296 | 1C1804 | sp-5 | an-296 |
| 1A1805 | sp-5 | an-297 | 1U1805 | sp-5 | an-297 | 1C1805 | sp-5 | an-297 |
| 1A1806 | sp-5 | an-298 | 1U1806 | sp-5 | an-298 | 1C1806 | sp-5 | an-298 |
| 1A1807 | sp-5 | an-299 | 1U1807 | sp-5 | an-299 | 1C1807 | sp-5 | an-299 |
| 1A1808 | sp-5 | an-300 | 1U1808 | sp-5 | an-300 | 1C1808 | sp-5 | an-300 |
| 1A1809 | sp-5 | an-301 | 1U1809 | sp-5 | an-301 | 1C1809 | sp-5 | an-301 |
| 1A1810 | sp-5 | an-302 | 1U1810 | sp-5 | an-302 | 1C1810 | sp-5 | an-302 |
| 1A1811 | sp-5 | an-303 | 1U1811 | sp-5 | an-303 | 1C1811 | sp-5 | an-303 |
| 1A1812 | sp-5 | an-304 | 1U1812 | sp-5 | an-304 | 1C1812 | sp-5 | an-304 |
| 1A1813 | sp-5 | an-305 | 1U1813 | sp-5 | an-305 | 1C1813 | sp-5 | an-305 |
| 1A1814 | sp-5 | an-306 | 1U1814 | sp-5 | an-306 | 1C1814 | sp-5 | an-306 |
| 1A1815 | sp-5 | an-307 | 1U1815 | sp-5 | an-307 | 1C1815 | sp-5 | an-307 |
| 1A1816 | sp-5 | an-308 | 1U1816 | sp-5 | an-308 | 1C1816 | sp-5 | an-308 |
| 1A1817 | sp-5 | an-309 | 1U1817 | sp-5 | an-309 | 1C1817 | sp-5 | an-309 |
| 1A1818 | sp-5 | an-310 | 1U1818 | sp-5 | an-310 | 1C1818 | sp-5 | an-310 |
| 1A1819 | sp-5 | an-311 | 1U1819 | sp-5 | an-311 | 1C1819 | sp-5 | an-311 |
| 1A1820 | sp-5 | an-312 | 1U1820 | sp-5 | an-312 | 1C1820 | sp-5 | an-312 |
| 1A1821 | sp-5 | an-313 | 1U1821 | sp-5 | an-313 | 1C1821 | sp-5 | an-313 |
| 1A1822 | sp-5 | an-314 | 1U1822 | sp-5 | an-314 | 1C1822 | sp-5 | an-314 |
| 1A1823 | sp-5 | an-315 | 1U1823 | sp-5 | an-315 | 1C1823 | sp-5 | an-315 |
| 1A1824 | sp-5 | an-316 | 1U1824 | sp-5 | an-316 | 1C1824 | sp-5 | an-316 |
| 1A1825 | sp-5 | an-317 | 1U1825 | sp-5 | an-317 | 1C1825 | sp-5 | an-317 |
| 1A1826 | sp-5 | an-318 | 1U1826 | sp-5 | an-318 | 1C1826 | sp-5 | an-318 |
| 1A1827 | sp-5 | an-319 | 1U1827 | sp-5 | an-319 | 1C1827 | sp-5 | an-319 |
| 1A1828 | sp-5 | an-320 | 1U1828 | sp-5 | an-320 | 1C1828 | sp-5 | an-320 |
| 1A1829 | sp-5 | an-321 | 1U1829 | sp-5 | an-321 | 1C1829 | sp-5 | an-321 |
| 1A1830 | sp-5 | an-322 | 1U1830 | sp-5 | an-322 | 1C1830 | sp-5 | an-322 |
| 1A1831 | sp-5 | an-323 | 1U1831 | sp-5 | an-323 | 1C1831 | sp-5 | an-323 |
| 1A1832 | sp-5 | an-324 | 1U1832 | sp-5 | an-324 | 1C1832 | sp-5 | an-324 |
| 1A1833 | sp-5 | an-325 | 1U1833 | sp-5 | an-325 | 1C1833 | sp-5 | an-325 |
| 1A1834 | sp-5 | an-326 | 1U1834 | sp-5 | an-326 | 1C1834 | sp-5 | an-326 |
| 1A1835 | sp-5 | an-327 | 1U1835 | sp-5 | an-327 | 1C1835 | sp-5 | an-327 |
| 1A1836 | sp-5 | an-328 | 1U1836 | sp-5 | an-328 | 1C1836 | sp-5 | an-328 |
| 1A1837 | sp-5 | an-329 | 1U1837 | sp-5 | an-329 | 1C1837 | sp-5 | an-329 |
| 1A1838 | sp-5 | an-330 | 1U1838 | sp-5 | an-330 | 1C1838 | sp-5 | an-330 |
| 1A1839 | sp-5 | an-331 | 1U1839 | sp-5 | an-331 | 1C1839 | sp-5 | an-331 |
| 1A1840 | sp-5 | an-332 | 1U1840 | sp-5 | an-332 | 1C1840 | sp-5 | an-332 |
| 1A1841 | sp-5 | an-333 | 1U1841 | sp-5 | an-333 | 1C1841 | sp-5 | an-333 |
| 1A1842 | sp-5 | an-334 | 1U1842 | sp-5 | an-334 | 1C1842 | sp-5 | an-334 |
| 1A1843 | sp-5 | an-335 | 1U1843 | sp-5 | an-335 | 1C1843 | sp-5 | an-335 |
| 1A1844 | sp-5 | an-336 | 1U1844 | sp-5 | an-336 | 1C1844 | sp-5 | an-336 |
| 1A1845 | sp-5 | an-337 | 1U1845 | sp-5 | an-337 | 1C1845 | sp-5 | an-337 |
| 1A1846 | sp-5 | an-338 | 1U1846 | sp-5 | an-338 | 1C1846 | sp-5 | an-338 |
| 1A1847 | sp-5 | an-339 | 1U1847 | sp-5 | an-339 | 1C1847 | sp-5 | an-339 |
| 1A1848 | sp-5 | an-340 | 1U1848 | sp-5 | an-340 | 1C1848 | sp-5 | an-340 |

Table 2-34

| Y = NHCS | | | Y = NHCSNH | | | Y = NHCSO | | |
|---|---|---|---|---|---|---|---|---|
| 1A1849 | sp-5 | an-341 | 1U1849 | sp-5 | an-341 | 1C1849 | sp-5 | an-341 |
| 1A1850 | sp-5 | an-342 | 1U1850 | sp-5 | an-342 | 1C1850 | sp-5 | an-342 |

| Ex. No. | Z | N⁺R⁵R⁶R⁷ | Ex. No. | Z | N⁺R⁵R⁶R⁷ | Ex. No. | Z | N⁺R⁵R⁶R⁷ |
|---|---|---|---|---|---|---|---|---|
| 1A1851 | sp-5 | an-343 | 1U1851 | sp-5 | an-343 | 1C1851 | sp-5 | an-343 |
| 1A1852 | sp-5 | an-344 | 1U1852 | sp-5 | an-344 | 1C1852 | sp-5 | an-344 |
| 1A1853 | sp-5 | an-345 | 1U1853 | sp-5 | an-345 | 1C1853 | sp-5 | an-345 |
| 1A1854 | sp-5 | an-346 | 1U1854 | sp-5 | an-346 | 1C1854 | sp-5 | an-346 |
| 1A1855 | sp-5 | an-347 | 1U1855 | sp-5 | an-347 | 1C1855 | sp-5 | an-347 |
| 1A1856 | sp-5 | an-348 | 1U1856 | sp-5 | an-348 | 1C1856 | sp-5 | an-348 |
| 1A1857 | sp-5 | an-349 | 1U1857 | sp-5 | an-349 | 1C1857 | sp-5 | an-349 |
| 1A1858 | sp-5 | an-350 | 1U1858 | sp-5 | an-350 | 1C1858 | sp-5 | an-350 |
| 1A1859 | sp-5 | an-351 | 1U1859 | sp-5 | an-351 | 1C1859 | sp-5 | an-351 |
| 1A1860 | sp-5 | an-352 | 1U1860 | sp-5 | an-352 | 1C1860 | sp-5 | an-352 |
| 1A1861 | sp-5 | an-353 | 1U1861 | sp-5 | an-353 | 1C1861 | sp-5 | an-353 |
| 1A1862 | sp-5 | an-354 | 1U1862 | sp-5 | an-354 | 1C1862 | sp-5 | an-354 |
| 1A1863 | sp-5 | an-355 | 1U1863 | sp-5 | an-355 | 1C1863 | sp-5 | an-355 |
| 1A1864 | sp-5 | an-356 | 1U1864 | sp-5 | an-356 | 1C1864 | sp-5 | an-356 |
| 1A1865 | sp-5 | an-357 | 1U1865 | sp-5 | an-357 | 1C1865 | sp-5 | an-357 |
| 1A1866 | sp-5 | an-358 | 1U1866 | sp-5 | an-358 | 1C1866 | sp-5 | an-358 |
| 1A1867 | sp-5 | an-359 | 1U1867 | sp-5 | an-359 | 1C1867 | sp-5 | an-359 |
| 1A1868 | sp-5 | an-360 | 1U1868 | sp-5 | an-360 | 1C1868 | sp-5 | an-360 |
| 1A1869 | sp-5 | an-361 | 1U1869 | sp-5 | an-361 | 1C1869 | sp-5 | an-361 |
| 1A1870 | sp-5 | an-362 | 1U1870 | sp-5 | an-362 | 1C1870 | sp-5 | an-362 |
| 1A1871 | sp-5 | an-363 | 1U1871 | sp-5 | an-363 | 1C1871 | sp-5 | an-363 |
| 1A1872 | sp-5 | an-364 | 1U1872 | sp-5 | an-364 | 1C1872 | sp-5 | an-364 |
| 1A1873 | sp-5 | an-365 | 1U1873 | sp-5 | an-365 | 1C1873 | sp-5 | an-365 |
| 1A1874 | sp-5 | an-366 | 1U1874 | sp-5 | an-366 | 1C1874 | sp-5 | an-366 |
| 1A1875 | sp-5 | an-367 | 1U1875 | sp-5 | an-367 | 1C1875 | sp-5 | an-367 |
| 1A1876 | sp-5 | an-368 | 1U1876 | sp-5 | an-368 | 1C1876 | sp-5 | an-368 |
| 1A1877 | sp-5 | an-369 | 1U1877 | sp-5 | an-369 | 1C1877 | sp-5 | an-369 |
| 1A1878 | sp-5 | an-370 | 1U1878 | sp-5 | an-370 | 1C1878 | sp-5 | an-370 |
| 1A1879 | sp-5 | an-371 | 1U1879 | sp-5 | an-371 | 1C1879 | sp-5 | an-371 |
| 1A1880 | sp-5 | an-372 | 1U1880 | sp-5 | an-372 | 1C1880 | sp-5 | an-372 |
| 1A1881 | sp-5 | an-373 | 1U1881 | sp-5 | an-373 | 1C1881 | sp-5 | an-373 |
| 1A1882 | sp-5 | an-374 | 1U1882 | sp-5 | an-374 | 1C1882 | sp-5 | an-374 |
| 1A1883 | sp-5 | an-375 | 1U1883 | sp-5 | an-375 | 1C1883 | sp-5 | an-375 |
| 1A1884 | sp-5 | an-376 | 1U1884 | sp-5 | an-376 | 1C1884 | sp-5 | an-376 |
| 1A1885 | sp-5 | an-377 | 1U1885 | sp-5 | an-377 | 1C1885 | sp-5 | an-377 |
| 1A1886 | sp-6 | an-1 | 1U1886 | sp-6 | an-1 | 1C1886 | sp-6 | an-1 |
| 1A1887 | sp-6 | an-2 | 1U1887 | sp-6 | an-2 | 1C1887 | sp-6 | an-2 |
| 1A1888 | sp-6 | an-3 | 1U1888 | sp-6 | an-3 | 1C1888 | sp-6 | an-3 |
| 1A1889 | sp-6 | an-4 | 1U1889 | sp-6 | an-4 | 1C1889 | sp-6 | an-4 |
| 1A1890 | sp-6 | an-5 | 1U1890 | sp-6 | an-5 | 1C1890 | sp-6 | an-5 |
| 1A1891 | sp-6 | an-6 | 1U1891 | sp-6 | an-6 | 1C1891 | sp-6 | an-6 |
| 1A1892 | sp-6 | an-7 | 1U1892 | sp-6 | an-7 | 1C1892 | sp-6 | an-7 |
| 1A1893 | sp-6 | an-8 | 1U1893 | sp-6 | an-8 | 1C1893 | sp-6 | an-8 |
| 1A1894 | sp-6 | an-9 | 1U1894 | sp-6 | an-9 | 1C1894 | sp-6 | an-9 |
| 1A1895 | sp-6 | an-10 | 1U1895 | sp-6 | an-10 | 1C1895 | sp-6 | an-10 |
| 1A1896 | sp-6 | an-11 | 1U1896 | sp-6 | an-11 | 1C1896 | sp-6 | an-11 |
| 1A1897 | sp-6 | an-12 | 1U1897 | sp-6 | an-12 | 1C1897 | sp-6 | an-12 |
| 1A1898 | sp-6 | an-13 | 1U1898 | sp-6 | an-13 | 1C1898 | sp-6 | an-13 |
| 1A1899 | sp-6 | an-14 | 1U1899 | sp-6 | an-14 | 1C1899 | sp-6 | an-14 |
| 1A1900 | sp-6 | an-15 | 1U1900 | sp-6 | an-15 | 1C1900 | sp-6 | an-15 |
| 1A1901 | sp-6 | an-16 | 1U1901 | sp-6 | an-16 | 1C1901 | sp-6 | an-16 |
| 1A1902 | sp-6 | an-17 | 1U1902 | sp-6 | an-17 | 1C1902 | sp-6 | an-17 |
| 1A1903 | sp-6 | an-18 | 1U1903 | sp-6 | an-18 | 1C1903 | sp-6 | an-18 |
| 1A1904 | sp-6 | an-19 | 1U1904 | sp-6 | an-19 | 1C1904 | sp-6 | an-19 |

Table 2-35

| Y = NHCS | | | Y = NHCSNH | | | Y = NHCSO | | |
|---|---|---|---|---|---|---|---|---|
| 1A1905 | sp-6 | an-20 | 1U1905 | sp-6 | an-20 | 1C1905 | sp-6 | an-20 |
| 1A1906 | sp-6 | an-21 | 1U1906 | sp-6 | an-21 | 1C1906 | sp-6 | an-21 |
| 1A1907 | sp-6 | an-22 | 1U1907 | sp-6 | an-22 | 1C1907 | sp-6 | an-22 |
| 1A1908 | sp-6 | an-23 | 1U1908 | sp-6 | an-23 | 1C1908 | sp-6 | an-23 |
| 1A1909 | sp-6 | an-24 | 1U1909 | sp-6 | an-24 | 1C1909 | sp-6 | an-24 |
| 1A1910 | sp-6 | an-25 | 1U1910 | sp-6 | an-25 | 1C1910 | sp-6 | an-25 |
| 1A1911 | sp-6 | an-26 | 1U1911 | sp-6 | an-26 | 1C1911 | sp-6 | an-26 |
| 1A1912 | sp-6 | an-27 | 1U1912 | sp-6 | an-27 | 1C1912 | sp-6 | an-27 |
| 1A1913 | sp-6 | an-28 | 1U1913 | sp-6 | an-28 | 1C1913 | sp-6 | an-28 |
| 1A1914 | sp-6 | an-29 | 1U1914 | sp-6 | an-29 | 1C1914 | sp-6 | an-29 |
| 1A1915 | sp-6 | an-30 | 1U1915 | sp-6 | an-30 | 1C1915 | sp-6 | an-30 |
| 1A1916 | sp-6 | an-31 | 1U1916 | sp-6 | an-31 | 1C1916 | sp-6 | an-31 |
| 1A1917 | sp-6 | an-32 | 1U1917 | sp-6 | an-32 | 1C1917 | sp-6 | an-32 |
| 1A1918 | sp-6 | an-33 | 1U1918 | sp-6 | an-33 | 1C1918 | sp-6 | an-33 |
| 1A1919 | sp-6 | an-34 | 1U1919 | sp-6 | an-34 | 1C1919 | sp-6 | an-34 |
| 1A1920 | sp-6 | an-35 | 1U1920 | sp-6 | an-35 | 1C1920 | sp-6 | an-35 |
| 1A1921 | sp-6 | an-36 | 1U1921 | sp-6 | an-36 | 1C1921 | sp-6 | an-36 |
| 1A1922 | sp-6 | an-37 | 1U1922 | sp-6 | an-37 | 1C1922 | sp-6 | an-37 |
| 1A1923 | sp-6 | an-38 | 1U1923 | sp-6 | an-38 | 1C1923 | sp-6 | an-38 |
| 1A1924 | sp-6 | an-39 | 1U1924 | sp-6 | an-39 | 1C1924 | sp-6 | an-39 |

| Ex. No. | Z | N⁺R⁵R⁶R⁷ | Ex. No. | Z | N⁺R⁵R⁶R⁷ | Ex. No. | Z | N⁺R⁵R⁶R⁷ |
|---|---|---|---|---|---|---|---|---|
| 1A1925 | sp-6 | an-40 | 1U1925 | sp-6 | an-40 | 1C1925 | sp-6 | an-40 |
| 1A1926 | sp-6 | an-41 | 1U1926 | sp-6 | an-41 | 1C1926 | sp-6 | an-41 |
| 1A1927 | sp-6 | an-42 | 1U1927 | sp-6 | an-42 | 1C1927 | sp-6 | an-42 |
| 1A1928 | sp-6 | an-43 | 1U1928 | sp-6 | an-43 | 1C1928 | sp-6 | an-43 |
| 1A1929 | sp-6 | an-44 | 1U1929 | sp-6 | an-44 | 1C1929 | sp-6 | an-44 |
| 1A1930 | sp-6 | an-45 | 1U1930 | sp-6 | an-45 | 1C1930 | sp-6 | an-45 |
| 1A1931 | sp-6 | an-46 | 1U1931 | sp-6 | an-46 | 1C1931 | sp-6 | an-46 |
| 1A1932 | sp-6 | an-47 | 1U1932 | sp-6 | an-47 | 1C1932 | sp-6 | an-47 |
| 1A1933 | sp-6 | an-48 | 1U1933 | sp-6 | an-48 | 1C1933 | sp-6 | an-48 |
| 1A1934 | sp-6 | an-49 | 1U1934 | sp-6 | an-49 | 1C1934 | sp-6 | an-49 |
| 1A1935 | sp-6 | an-50 | 1U1935 | sp-6 | an-50 | 1C1935 | sp-6 | an-50 |
| 1A1936 | sp-6 | an-51 | 1U1936 | sp-6 | an-51 | 1C1936 | sp-6 | an-51 |
| 1A1937 | sp-6 | an-52 | 1U1937 | sp-6 | an-52 | 1C1937 | sp-6 | an-52 |
| 1A1938 | sp-6 | an-53 | 1U1938 | sp-6 | an-53 | 1C1938 | sp-6 | an-53 |
| 1A1939 | sp-6 | an-54 | 1U1939 | sp-6 | an-54 | 1C1939 | sp-6 | an-54 |
| 1A1940 | sp-6 | an-55 | 1U1940 | sp-6 | an-55 | 1C1940 | sp-6 | an-55 |
| 1A1941 | sp-6 | an-56 | 1U1941 | sp-6 | an-56 | 1C1941 | sp-6 | an-56 |
| 1A1942 | sp-6 | an-57 | 1U1942 | sp-6 | an-57 | 1C1942 | sp-6 | an-57 |
| 1A1943 | sp-6 | an-58 | 1U1943 | sp-6 | an-58 | 1C1943 | sp-6 | an-58 |
| 1A1944 | sp-6 | an-59 | 1U1944 | sp-6 | an-59 | 1C1944 | sp-6 | an-59 |
| 1A1945 | sp-6 | an-60 | 1U1945 | sp-6 | an-60 | 1C1945 | sp-6 | an-60 |
| 1A1946 | sp-6 | an-61 | 1U1946 | sp-6 | an-61 | 1C1946 | sp-6 | an-61 |
| 1A1947 | sp-6 | an-62 | 1U1947 | sp-6 | an-62 | 1C1947 | sp-6 | an-62 |
| 1A1948 | sp-6 | an-63 | 1U1948 | sp-6 | an-63 | 1C1948 | sp-6 | an-63 |
| 1A1949 | sp-6 | an-64 | 1U1949 | sp-6 | an-64 | 1C1949 | sp-6 | an-64 |
| 1A1950 | sp-6 | an-65 | 1U1950 | sp-6 | an-65 | 1C1950 | sp-6 | an-65 |
| 1A1951 | sp-6 | an-66 | 1U1951 | sp-6 | an-66 | 1C1951 | sp-6 | an-66 |
| 1A1952 | sp-6 | an-67 | 1U1952 | sp-6 | an-67 | 1C1952 | sp-6 | an-67 |
| 1A1953 | sp-6 | an-68 | 1U1953 | sp-6 | an-68 | 1C1953 | sp-6 | an-68 |
| 1A1954 | sp-6 | an-69 | 1U1954 | sp-6 | an-69 | 1C1954 | sp-6 | an-69 |
| 1A1955 | sp-6 | an-70 | 1U1955 | sp-6 | an-70 | 1C1955 | sp-6 | an-70 |
| 1A1956 | sp-6 | an-71 | 1U1956 | sp-6 | an-71 | 1C1956 | sp-6 | an-71 |
| 1A1957 | sp-6 | an-72 | 1U1957 | sp-6 | an-72 | 1C1957 | sp-6 | an-72 |
| 1A1958 | sp-6 | an-73 | 1U1958 | sp-6 | an-73 | 1C1958 | sp-6 | an-73 |
| 1A1959 | sp-6 | an-74 | 1U1959 | sp-6 | an-74 | 1C1959 | sp-6 | an-74 |
| 1A1960 | sp-6 | an-75 | 1U1960 | sp-6 | an-75 | 1C1960 | sp-6 | an-75 |

Table 2-36

| Y = NHCS | | | Y = NHCSNH | | | Y = NHCSO | | |
|---|---|---|---|---|---|---|---|---|
| 1A1961 | sp-6 | an-76 | 1U1961 | sp-6 | an-76 | 1C1961 | sp-6 | an-76 |
| 1A1962 | sp-6 | an-77 | 1U1962 | sp-6 | an-77 | 1C1962 | sp-6 | an-77 |
| 1A1963 | sp-6 | an-78 | 1U1963 | sp-6 | an-78 | 1C1963 | sp-6 | an-78 |
| 1A1964 | sp-6 | an-79 | 1U1964 | sp-6 | an-79 | 1C1964 | sp-6 | an-79 |
| 1A1965 | sp-6 | an-80 | 1U1965 | sp-6 | an-80 | 1C1965 | sp-6 | an-80 |
| 1A1966 | sp-6 | an-81 | 1U1966 | sp-6 | an-81 | 1C1966 | sp-6 | an-81 |
| 1A1967 | sp-6 | an-82 | 1U1967 | sp-6 | an-82 | 1C1967 | sp-6 | an-82 |
| 1A1968 | sp-6 | an-83 | 1U1968 | sp-6 | an-83 | 1C1968 | sp-6 | an-83 |
| 1A1969 | sp-6 | an-84 | 1U1969 | sp-6 | an-84 | 1C1969 | sp-6 | an-84 |
| 1A1970 | sp-6 | an-85 | 1U1970 | sp-6 | an-85 | 1C1970 | sp-6 | an-85 |
| 1A1971 | sp-6 | an-86 | 1U1971 | sp-6 | an-86 | 1C1971 | sp-6 | an-86 |
| 1A1972 | sp-6 | an-87 | 1U1972 | sp-6 | an-87 | 1C1972 | sp-6 | an-87 |
| 1A1973 | sp-6 | an-88 | 1U1973 | sp-6 | an-88 | 1C1973 | sp-6 | an-88 |
| 1A1974 | sp-6 | an-89 | 1U1974 | sp-6 | an-89 | 1C1974 | sp-6 | an-89 |
| 1A1975 | sp-6 | an-90 | 1U1975 | sp-6 | an-90 | 1C1975 | sp-6 | an-90 |
| 1A1976 | sp-6 | an-91 | 1U1976 | sp-6 | an-91 | 1C1976 | sp-6 | an-91 |
| 1A1977 | sp-6 | an-92 | 1U1977 | sp-6 | an-92 | 1C1977 | sp-6 | an-92 |
| 1A1978 | sp-6 | an-93 | 1U1978 | sp-6 | an-93 | 1C1978 | sp-6 | an-93 |
| 1A1979 | sp-6 | an-94 | 1U1979 | sp-6 | an-94 | 1C1979 | sp-6 | an-94 |
| 1A1980 | sp-6 | an-95 | 1U1980 | sp-6 | an-95 | 1C1980 | sp-6 | an-95 |
| 1A1981 | sp-6 | an-96 | 1U1981 | sp-6 | an-96 | 1C1981 | sp-6 | an-96 |
| 1A1982 | sp-6 | an-97 | 1U1982 | sp-6 | an-97 | 1C1982 | sp-6 | an-97 |
| 1A1983 | sp-6 | an-98 | 1U1983 | sp-6 | an-98 | 1C1983 | sp-6 | an-98 |
| 1A1984 | sp-6 | an-99 | 1U1984 | sp-6 | an-99 | 1C1984 | sp-6 | an-99 |
| 1A1985 | sp-6 | an-100 | 1U1985 | sp-6 | an-100 | 1C1985 | sp-6 | an-100 |
| 1A1986 | sp-6 | an-101 | 1U1986 | sp-6 | an-101 | 1C1986 | sp-6 | an-101 |
| 1A1987 | sp-6 | an-102 | 1U1987 | sp-6 | an-102 | 1C1987 | sp-6 | an-102 |
| 1A1988 | sp-6 | an-103 | 1U1988 | sp-6 | an-103 | 1C1988 | sp-6 | an-103 |
| 1A1989 | sp-6 | an-104 | 1U1989 | sp-6 | an-104 | 1C1989 | sp-6 | an-104 |
| 1A1990 | sp-6 | an-105 | 1U1990 | sp-6 | an-105 | 1C1990 | sp-6 | an-105 |
| 1A1991 | sp-6 | an-106 | 1U1991 | sp-6 | an-106 | 1C1991 | sp-6 | an-106 |
| 1A1992 | sp-6 | an-107 | 1U1992 | sp-6 | an-107 | 1C1992 | sp-6 | an-107 |
| 1A1993 | sp-6 | an-108 | 1U1993 | sp-6 | an-108 | 1C1993 | sp-6 | an-108 |
| 1A1994 | sp-6 | an-109 | 1U1994 | sp-6 | an-109 | 1C1994 | sp-6 | an-109 |
| 1A1995 | sp-6 | an-110 | 1U1995 | sp-6 | an-110 | 1C1995 | sp-6 | an-110 |
| 1A1996 | sp-6 | an-111 | 1U1996 | sp-6 | an-111 | 1C1996 | sp-6 | an-111 |
| 1A1997 | sp-6 | an-112 | 1U1997 | sp-6 | an-112 | 1C1997 | sp-6 | an-112 |
| 1A1998 | sp-6 | an-113 | 1U1998 | sp-6 | an-113 | 1C1998 | sp-6 | an-113 |

-continued

| Ex. No. | Z | N⁺R⁵R⁶R⁷ | Ex. No. | Z | N⁺R⁵R⁶R⁷ | Ex. No. | Z | N⁺R⁵R⁶R⁷ |
|---|---|---|---|---|---|---|---|---|
| 1A1999 | sp-6 | an-114 | 1U1999 | sp-6 | an-114 | 1C1999 | sp-6 | an-114 |
| 1A2000 | sp-6 | an-115 | 1U2000 | sp-6 | an-115 | 1C2000 | sp-6 | an-115 |
| 1A2001 | sp-6 | an-116 | 1U2001 | sp-6 | an-116 | 1C2001 | sp-6 | an-116 |
| 1A2002 | sp-6 | an-117 | 1U2002 | sp-6 | an-117 | 1C2002 | sp-6 | an-117 |
| 1A2003 | sp-6 | an-118 | 1U2003 | sp-6 | an-118 | 1C2003 | sp-6 | an-118 |
| 1A2004 | sp-6 | an-119 | 1U2004 | sp-6 | an-119 | 1C2004 | sp-6 | an-119 |
| 1A2005 | sp-6 | an-120 | 1U2005 | sp-6 | an-120 | 1C2005 | sp-6 | an-120 |
| 1A2006 | sp-6 | an-121 | 1U2006 | sp-6 | an-121 | 1C2006 | sp-6 | an-121 |
| 1A2007 | sp-6 | an-122 | 1U2007 | sp-6 | an-122 | 1C2007 | sp-6 | an-122 |
| 1A2008 | sp-6 | an-123 | 1U2008 | sp-6 | an-123 | 1C2008 | sp-6 | an-123 |
| 1A2009 | sp-6 | an-124 | 1U2009 | sp-6 | an-124 | 1C2009 | sp-6 | an-124 |
| 1A2010 | sp-6 | an-125 | 1U2010 | sp-6 | an-125 | 1C2010 | sp-6 | an-125 |
| 1A2011 | sp-6 | an-126 | 1U2011 | sp-6 | an-126 | 1C2011 | sp-6 | an-126 |
| 1A2012 | sp-6 | an-127 | 1U2012 | sp-6 | an-127 | 1C2012 | sp-6 | an-127 |
| 1A2013 | sp-6 | an-128 | 1U2013 | sp-6 | an-128 | 1C2013 | sp-6 | an-128 |
| 1A2014 | sp-6 | an-129 | 1U2014 | sp-6 | an-129 | 1C2014 | sp-6 | an-129 |
| 1A2015 | sp-6 | an-130 | 1U2015 | sp-6 | an-130 | 1C2015 | sp-6 | an-130 |
| 1A2016 | sp-6 | an-131 | 1U2016 | sp-6 | an-131 | 1C2016 | sp-6 | an-131 |

Table 2-37

| Y = NHCS | | | Y = NHCSNH | | | Y = NHCSO | | |
|---|---|---|---|---|---|---|---|---|
| 1A2017 | sp-6 | an-132 | 1U2017 | sp-6 | an-132 | 1C2017 | sp-6 | an-132 |
| 1A2018 | sp-6 | an-133 | 1U2018 | sp-6 | an-133 | 1C2018 | sp-6 | an-133 |
| 1A2019 | sp-6 | an-134 | 1U2019 | sp-6 | an-134 | 1C2019 | sp-6 | an-134 |
| 1A2020 | sp-6 | an-135 | 1U2020 | sp-6 | an-135 | 1C2020 | sp-6 | an-135 |
| 1A2021 | sp-6 | an-136 | 1U2021 | sp-6 | an-136 | 1C2021 | sp-6 | an-136 |
| 1A2022 | sp-6 | an-137 | 1U2022 | sp-6 | an-137 | 1C2022 | sp-6 | an-137 |
| 1A2023 | sp-6 | an-138 | 1U2023 | sp-6 | an-138 | 1C2023 | sp-6 | an-138 |
| 1A2024 | sp-6 | an-139 | 1U2024 | sp-6 | an-139 | 1C2024 | sp-6 | an-139 |
| 1A2025 | sp-6 | an-140 | 1U2025 | sp-6 | an-140 | 1C2025 | sp-6 | an-140 |
| 1A2026 | sp-6 | an-141 | 1U2026 | sp-6 | an-141 | 1C2026 | sp-6 | an-141 |
| 1A2027 | sp-6 | an-142 | 1U2027 | sp-6 | an-142 | 1C2027 | sp-6 | an-142 |
| 1A2028 | sp-6 | an-143 | 1U2028 | sp-6 | an-143 | 1C2028 | sp-6 | an-143 |
| 1A2029 | sp-6 | an-144 | 1U2029 | sp-6 | an-144 | 1C2029 | sp-6 | an-144 |
| 1A2030 | sp-6 | an-145 | 1U2030 | sp-6 | an-145 | 1C2030 | sp-6 | an-145 |
| 1A2031 | sp-6 | an-146 | 1U2031 | sp-6 | an-146 | 1C2031 | sp-6 | an-146 |
| 1A2032 | sp-6 | an-147 | 1U2032 | sp-6 | an-147 | 1C2032 | sp-6 | an-147 |
| 1A2033 | sp-6 | an-148 | 1U2033 | sp-6 | an-148 | 1C2033 | sp-6 | an-148 |
| 1A2034 | sp-6 | an-149 | 1U2034 | sp-6 | an-149 | 1C2034 | sp-6 | an-149 |
| 1A2035 | sp-6 | an-150 | 1U2035 | sp-6 | an-150 | 1C2035 | sp-6 | an-150 |
| 1A2036 | sp-6 | an-151 | 1U2036 | sp-6 | an-151 | 1C2036 | sp-6 | an-151 |
| 1A2037 | sp-6 | an-152 | 1U2037 | sp-6 | an-152 | 1C2037 | sp-6 | an-152 |
| 1A2038 | sp-6 | an-153 | 1U2038 | sp-6 | an-153 | 1C2038 | sp-6 | an-153 |
| 1A2039 | sp-6 | an-154 | 1U2039 | sp-6 | an-154 | 1C2039 | sp-6 | an-154 |
| 1A2040 | sp-6 | an-155 | 1U2040 | sp-6 | an-155 | 1C2040 | sp-6 | an-155 |
| 1A2041 | sp-6 | an-156 | 1U2041 | sp-6 | an-156 | 1C2041 | sp-6 | an-156 |
| 1A2042 | sp-6 | an-157 | 1U2042 | sp-6 | an-157 | 1C2042 | sp-6 | an-157 |
| 1A2043 | sp-6 | an-158 | 1U2043 | sp-6 | an-158 | 1C2043 | sp-6 | an-158 |
| 1A2044 | sp-6 | an-159 | 1U2044 | sp-6 | an-159 | 1C2044 | sp-6 | an-159 |
| 1A2045 | sp-6 | an-160 | 1U2045 | sp-6 | an-160 | 1C2045 | sp-6 | an-160 |
| 1A2046 | sp-6 | an-161 | 1U2046 | sp-6 | an-161 | 1C2046 | sp-6 | an-161 |
| 1A2047 | sp-6 | an-162 | 1U2047 | sp-6 | an-162 | 1C2047 | sp-6 | an-162 |
| 1A2048 | sp-6 | an-163 | 1U2048 | sp-6 | an-163 | 1C2048 | sp-6 | an-163 |
| 1A2049 | sp-6 | an-164 | 1U2049 | sp-6 | an-164 | 1C2049 | sp-6 | an-164 |
| 1A2050 | sp-6 | an-165 | 1U2050 | sp-6 | an-165 | 1C2050 | sp-6 | an-165 |
| 1A2051 | sp-6 | an-166 | 1U2051 | sp-6 | an-166 | 1C2051 | sp-6 | an-166 |
| 1A2052 | sp-6 | an-167 | 1U2052 | sp-6 | an-167 | 1C2052 | sp-6 | an-167 |
| 1A2053 | sp-6 | an-168 | 1U2053 | sp-6 | an-168 | 1C2053 | sp-6 | an-168 |
| 1A2054 | sp-6 | an-169 | 1U2054 | sp-6 | an-169 | 1C2054 | sp-6 | an-169 |
| 1A2055 | sp-6 | an-170 | 1U2055 | sp-6 | an-170 | 1C2055 | sp-6 | an-170 |
| 1A2056 | sp-6 | an-171 | 1U2056 | sp-6 | an-171 | 1C2056 | sp-6 | an-171 |
| 1A2057 | sp-6 | an-172 | 1U2057 | sp-6 | an-172 | 1C2057 | sp-6 | an-172 |
| 1A2058 | sp-6 | an-173 | 1U2058 | sp-6 | an-173 | 1C2058 | sp-6 | an-173 |
| 1A2059 | sp-6 | an-174 | 1U2059 | sp-6 | an-174 | 1C2059 | sp-6 | an-174 |
| 1A2060 | sp-6 | an-175 | 1U2060 | sp-6 | an-175 | 1C2060 | sp-6 | an-175 |
| 1A2061 | sp-6 | an-176 | 1U2061 | sp-6 | an-176 | 1C2061 | sp-6 | an-176 |
| 1A2062 | sp-6 | an-177 | 1U2062 | sp-6 | an-177 | 1C2062 | sp-6 | an-177 |
| 1A2063 | sp-6 | an-178 | 1U2063 | sp-6 | an-178 | 1C2063 | sp-6 | an-178 |
| 1A2064 | sp-6 | an-179 | 1U2064 | sp-6 | an-179 | 1C2064 | sp-6 | an-179 |
| 1A2065 | sp-6 | an-180 | 1U2065 | sp-6 | an-180 | 1C2065 | sp-6 | an-180 |
| 1A2066 | sp-6 | an-181 | 1U2066 | sp-6 | an-181 | 1C2066 | sp-6 | an-181 |
| 1A2067 | sp-6 | an-182 | 1U2067 | sp-6 | an-182 | 1C2067 | sp-6 | an-182 |
| 1A2068 | sp-6 | an-183 | 1U2068 | sp-6 | an-183 | 1C2068 | sp-6 | an-183 |
| 1A2069 | sp-6 | an-184 | 1U2069 | sp-6 | an-184 | 1C2069 | sp-6 | an-184 |
| 1A2070 | sp-6 | an-185 | 1U2070 | sp-6 | an-185 | 1C2070 | sp-6 | an-185 |
| 1A2071 | sp-6 | an-186 | 1U2071 | sp-6 | an-186 | 1C2071 | sp-6 | an-186 |
| 1A2072 | sp-6 | an-187 | 1U2072 | sp-6 | an-187 | 1C2072 | sp-6 | an-187 |

-continued

| Ex. No. | Z | N+R5R6R7 | Ex. No. | Z | N+R5R6R7 | Ex. No. | Z | N+R5R6R7 |
|---|---|---|---|---|---|---|---|---|

Table 2-38

| Y = NHCS | | | Y = NHCSNH | | | Y = NHCSO | | |
|---|---|---|---|---|---|---|---|---|
| 1A2073 | sp-6 | an-188 | 1U2073 | sp-6 | an-188 | 1C2073 | sp-6 | an-188 |
| 1A2074 | sp-6 | an-189 | 1U2074 | sp-6 | an-189 | 1C2074 | sp-6 | an-189 |
| 1A2075 | sp-6 | an-190 | 1U2075 | sp-6 | an-190 | 1C2075 | sp-6 | an-190 |
| 1A2076 | sp-6 | an-191 | 1U2076 | sp-6 | an-191 | 1C2076 | sp-6 | an-191 |
| 1A2077 | sp-6 | an-192 | 1U2077 | sp-6 | an-192 | 1C2077 | sp-6 | an-192 |
| 1A2078 | sp-6 | an-193 | 1U2078 | sp-6 | an-193 | 1C2078 | sp-6 | an-193 |
| 1A2079 | sp-6 | an-194 | 1U2079 | sp-6 | an-194 | 1C2079 | sp-6 | an-194 |
| 1A2080 | sp-6 | an-195 | 1U2080 | sp-6 | an-195 | 1C2080 | sp-6 | an-195 |
| 1A2081 | sp-6 | an-196 | 1U2081 | sp-6 | an-196 | 1C2081 | sp-6 | an-196 |
| 1A2082 | sp-6 | an-197 | 1U2082 | sp-6 | an-197 | 1C2082 | sp-6 | an-197 |
| 1A2083 | sp-6 | an-198 | 1U2083 | sp-6 | an-198 | 1C2083 | sp-6 | an-198 |
| 1A2084 | sp-6 | an-199 | 1U2084 | sp-6 | an-199 | 1C2084 | sp-6 | an-199 |
| 1A2085 | sp-6 | an-200 | 1U2085 | sp-6 | an-200 | 1C2085 | sp-6 | an-200 |
| 1A2086 | sp-6 | an-201 | 1U2086 | sp-6 | an-201 | 1C2086 | sp-6 | an-201 |
| 1A2087 | sp-6 | an-202 | 1U2087 | sp-6 | an-202 | 1C2087 | sp-6 | an-202 |
| 1A2088 | sp-6 | an-203 | 1U2088 | sp-6 | an-203 | 1C2088 | sp-6 | an-203 |
| 1A2089 | sp-6 | an-204 | 1U2089 | sp-6 | an-204 | 1C2089 | sp-6 | an-204 |
| 1A2090 | sp-6 | an-205 | 1U2090 | sp-6 | an-205 | 1C2090 | sp-6 | an-205 |
| 1A2091 | sp-6 | an-206 | 1U2091 | sp-6 | an-206 | 1C2091 | sp-6 | an-206 |
| 1A2092 | sp-6 | an-207 | 1U2092 | sp-6 | an-207 | 1C2092 | sp-6 | an-207 |
| 1A2093 | sp-6 | an-208 | 1U2093 | sp-6 | an-208 | 1C2093 | sp-6 | an-208 |
| 1A2094 | sp-6 | an-209 | 1U2094 | sp-6 | an-209 | 1C2094 | sp-6 | an-209 |
| 1A2095 | sp-6 | an-210 | 1U2095 | sp-6 | an-210 | 1C2095 | sp-6 | an-210 |
| 1A2096 | sp-6 | an-211 | 1U2096 | sp-6 | an-211 | 1C2096 | sp-6 | an-211 |
| 1A2097 | sp-6 | an-212 | 1U2097 | sp-6 | an-212 | 1C2097 | sp-6 | an-212 |
| 1A2098 | sp-6 | an-213 | 1U2098 | sp-6 | an-213 | 1C2098 | sp-6 | an-213 |
| 1A2099 | sp-6 | an-214 | 1U2099 | sp-6 | an-214 | 1C2099 | sp-6 | an-214 |
| 1A2100 | sp-6 | an-215 | 1U2100 | sp-6 | an-215 | 1C2100 | sp-6 | an-215 |
| 1A2101 | sp-6 | an-216 | 1U2101 | sp-6 | an-216 | 1C2101 | sp-6 | an-216 |
| 1A2102 | sp-6 | an-217 | 1U2102 | sp-6 | an-217 | 1C2102 | sp-6 | an-217 |
| 1A2103 | sp-6 | an-218 | 1U2103 | sp-6 | an-218 | 1C2103 | sp-6 | an-218 |
| 1A2104 | sp-6 | an-219 | 1U2104 | sp-6 | an-219 | 1C2104 | sp-6 | an-219 |
| 1A2105 | sp-6 | an-220 | 1U2105 | sp-6 | an-220 | 1C2105 | sp-6 | an-220 |
| 1A2106 | sp-6 | an-221 | 1U2106 | sp-6 | an-221 | 1C2106 | sp-6 | an-221 |
| 1A2107 | sp-6 | an-222 | 1U2107 | sp-6 | an-222 | 1C2107 | sp-6 | an-222 |
| 1A2108 | sp-6 | an-223 | 1U2108 | sp-6 | an-223 | 1C2108 | sp-6 | an-223 |
| 1A2109 | sp-6 | an-224 | 1U2109 | sp-6 | an-224 | 1C2109 | sp-6 | an-224 |
| 1A2110 | sp-6 | an-225 | 1U2110 | sp-6 | an-225 | 1C2110 | sp-6 | an-225 |
| 1A2111 | sp-6 | an-226 | 1U2111 | sp-6 | an-226 | 1C2111 | sp-6 | an-226 |
| 1A2112 | sp-6 | an-227 | 1U2112 | sp-6 | an-227 | 1C2112 | sp-6 | an-227 |
| 1A2113 | sp-6 | an-228 | 1U2113 | sp-6 | an-228 | 1C2113 | sp-6 | an-228 |
| 1A2114 | sp-6 | an-229 | 1U2114 | sp-6 | an-229 | 1C2114 | sp-6 | an-229 |
| 1A2115 | sp-6 | an-230 | 1U2115 | sp-6 | an-230 | 1C2115 | sp-6 | an-230 |
| 1A2116 | sp-6 | an-231 | 1U2116 | sp-6 | an-231 | 1C2116 | sp-6 | an-231 |
| 1A2117 | sp-6 | an-232 | 1U2117 | sp-6 | an-232 | 1C2117 | sp-6 | an-232 |
| 1A2118 | sp-6 | an-233 | 1U2118 | sp-6 | an-233 | 1C2118 | sp-6 | an-233 |
| 1A2119 | sp-6 | an-234 | 1U2119 | sp-6 | an-234 | 1C2119 | sp-6 | an-234 |
| 1A2120 | sp-6 | an-235 | 1U2120 | sp-6 | an-235 | 1C2120 | sp-6 | an-235 |
| 1A2121 | sp-6 | an-236 | 1U2121 | sp-6 | an-236 | 1C2121 | sp-6 | an-236 |
| 1A2122 | sp-6 | an-237 | 1U2122 | sp-6 | an-237 | 1C2122 | sp-6 | an-237 |
| 1A2123 | sp-6 | an-238 | 1U2123 | sp-6 | an-238 | 1C2123 | sp-6 | an-238 |
| 1A2124 | sp-6 | an-239 | 1U2124 | sp-6 | an-239 | 1C2124 | sp-6 | an-239 |
| 1A2125 | sp-6 | an-240 | 1U2125 | sp-6 | an-240 | 1C2125 | sp-6 | an-240 |
| 1A2126 | sp-6 | an-241 | 1U2126 | sp-6 | an-241 | 1C2126 | sp-6 | an-241 |
| 1A2127 | sp-6 | an-242 | 1U2127 | sp-6 | an-242 | 1C2127 | sp-6 | an-242 |
| 1A2128 | sp-6 | an-243 | 1U2128 | sp-6 | an-243 | 1C2128 | sp-6 | an-243 |

Table 2-39

| Y = NHCS | | | Y = NHCSNH | | | Y = NHCSO | | |
|---|---|---|---|---|---|---|---|---|
| 1A2129 | sp-6 | an-244 | 1U2129 | sp-6 | an-244 | 1C2129 | sp-6 | an-244 |
| 1A2130 | sp-6 | an-245 | 1U2130 | sp-6 | an-245 | 1C2130 | sp-6 | an-245 |
| 1A2131 | sp-6 | an-246 | 1U2131 | sp-6 | an-246 | 1C2131 | sp-6 | an-246 |
| 1A2132 | sp-6 | an-247 | 1U2132 | sp-6 | an-247 | 1C2132 | sp-6 | an-247 |
| 1A2133 | sp-6 | an-248 | 1U2133 | sp-6 | an-248 | 1C2133 | sp-6 | an-248 |
| 1A2134 | sp-6 | an-249 | 1U2134 | sp-6 | an-249 | 1C2134 | sp-6 | an-249 |
| 1A2135 | sp-6 | an-250 | 1U2135 | sp-6 | an-250 | 1C2135 | sp-6 | an-250 |
| 1A2136 | sp-6 | an-251 | 1U2136 | sp-6 | an-251 | 1C2136 | sp-6 | an-251 |
| 1A2137 | sp-6 | an-252 | 1U2137 | sp-6 | an-252 | 1C2137 | sp-6 | an-252 |
| 1A2138 | sp-6 | an-253 | 1U2138 | sp-6 | an-253 | 1C2138 | sp-6 | an-253 |
| 1A2139 | sp-6 | an-254 | 1U2139 | sp-6 | an-254 | 1C2139 | sp-6 | an-254 |
| 1A2140 | sp-6 | an-255 | 1U2140 | sp-6 | an-255 | 1C2140 | sp-6 | an-255 |
| 1A2141 | sp-6 | an-256 | 1U2141 | sp-6 | an-256 | 1C2141 | sp-6 | an-256 |
| 1A2142 | sp-6 | an-257 | 1U2142 | sp-6 | an-257 | 1C2142 | sp-6 | an-257 |

-continued

| Ex. No. | Z | N⁺R⁵R⁶R⁷ | Ex. No. | Z | N⁺R⁵R⁶R⁷ | Ex. No. | Z | N⁺R⁵R⁶R⁷ |
|---|---|---|---|---|---|---|---|---|
| 1A2143 | sp-6 | an-258 | 1U2143 | sp-6 | an-258 | 1C2143 | sp-6 | an-258 |
| 1A2144 | sp-6 | an-259 | 1U2144 | sp-6 | an-259 | 1C2144 | sp-6 | an-259 |
| 1A2145 | sp-6 | an-260 | 1U2145 | sp-6 | an-260 | 1C2145 | sp-6 | an-260 |
| 1A2146 | sp-6 | an-261 | 1U2146 | sp-6 | an-261 | 1C2146 | sp-6 | an-261 |
| 1A2147 | sp-6 | an-262 | 1U2147 | sp-6 | an-262 | 1C2147 | sp-6 | an-262 |
| 1A2148 | sp-6 | an-263 | 1U2148 | sp-6 | an-263 | 1C2148 | sp-6 | an-263 |
| 1A2149 | sp-6 | an-264 | 1U2149 | sp-6 | an-264 | 1C2149 | sp-6 | an-264 |
| 1A2150 | sp-6 | an-265 | 1U2150 | sp-6 | an-265 | 1C2150 | sp-6 | an-265 |
| 1A2151 | sp-6 | an-266 | 1U2151 | sp-6 | an-266 | 1C2151 | sp-6 | an-266 |
| 1A2152 | sp-6 | an-267 | 1U2152 | sp-6 | an-267 | 1C2152 | sp-6 | an-267 |
| 1A2153 | sp-6 | an-268 | 1U2153 | sp-6 | an-268 | 1C2153 | sp-6 | an-268 |
| 1A2154 | sp-6 | an-269 | 1U2154 | sp-6 | an-269 | 1C2154 | sp-6 | an-269 |
| 1A2155 | sp-6 | an-270 | 1U2155 | sp-6 | an-270 | 1C2155 | sp-6 | an-270 |
| 1A2156 | sp-6 | an-271 | 1U2156 | sp-6 | an-271 | 1C2156 | sp-6 | an-271 |
| 1A2157 | sp-6 | an-272 | 1U2157 | sp-6 | an-272 | 1C2157 | sp-6 | an-272 |
| 1A2158 | sp-6 | an-273 | 1U2158 | sp-6 | an-273 | 1C2158 | sp-6 | an-273 |
| 1A2159 | sp-6 | an-274 | 1U2159 | sp-6 | an-274 | 1C2159 | sp-6 | an-274 |
| 1A2160 | sp-6 | an-275 | 1U2160 | sp-6 | an-275 | 1C2160 | sp-6 | an-275 |
| 1A2161 | sp-6 | an-276 | 1U2161 | sp-6 | an-276 | 1C2161 | sp-6 | an-276 |
| 1A2162 | sp-6 | an-277 | 1U2162 | sp-6 | an-277 | 1C2162 | sp-6 | an-277 |
| 1A2163 | sp-6 | an-278 | 1U2163 | sp-6 | an-278 | 1C2163 | sp-6 | an-278 |
| 1A2164 | sp-6 | an-279 | 1U2164 | sp-6 | an-279 | 1C2164 | sp-6 | an-279 |
| 1A2165 | sp-6 | an-280 | 1U2165 | sp-6 | an-280 | 1C2165 | sp-6 | an-280 |
| 1A2166 | sp-6 | an-281 | 1U2166 | sp-6 | an-281 | 1C2166 | sp-6 | an-281 |
| 1A2167 | sp-6 | an-282 | 1U2167 | sp-6 | an-282 | 1C2167 | sp-6 | an-282 |
| 1A2168 | sp-6 | an-283 | 1U2168 | sp-6 | an-283 | 1C2168 | sp-6 | an-283 |
| 1A2169 | sp-6 | an-284 | 1U2169 | sp-6 | an-284 | 1C2169 | sp-6 | an-284 |
| 1A2170 | sp-6 | an-285 | 1U2170 | sp-6 | an-285 | 1C2170 | sp-6 | an-285 |
| 1A2171 | sp-6 | an-286 | 1U2171 | sp-6 | an-286 | 1C2171 | sp-6 | an-286 |
| 1A2172 | sp-6 | an-287 | 1U2172 | sp-6 | an-287 | 1C2172 | sp-6 | an-287 |
| 1A2173 | sp-6 | an-288 | 1U2173 | sp-6 | an-288 | 1C2173 | sp-6 | an-288 |
| 1A2174 | sp-6 | an-289 | 1U2174 | sp-6 | an-289 | 1C2174 | sp-6 | an-289 |
| 1A2175 | sp-6 | an-290 | 1U2175 | sp-6 | an-290 | 1C2175 | sp-6 | an-290 |
| 1A2176 | sp-6 | an-291 | 1U2176 | sp-6 | an-291 | 1C2176 | sp-6 | an-291 |
| 1A2177 | sp-6 | an-292 | 1U2177 | sp-6 | an-292 | 1C2177 | sp-6 | an-292 |
| 1A2178 | sp-6 | an-293 | 1U2178 | sp-6 | an-293 | 1C2178 | sp-6 | an-293 |
| 1A2179 | sp-6 | an-294 | 1U2179 | sp-6 | an-294 | 1C2179 | sp-6 | an-294 |
| 1A2180 | sp-6 | an-295 | 1U2180 | sp-6 | an-295 | 1C2180 | sp-6 | an-295 |
| 1A2181 | sp-6 | an-296 | 1U2181 | sp-6 | an-296 | 1C2181 | sp-6 | an-296 |
| 1A2182 | sp-6 | an-297 | 1U2182 | sp-6 | an-297 | 1C2182 | sp-6 | an-297 |
| 1A2183 | sp-6 | an-298 | 1U2183 | sp-6 | an-298 | 1C2183 | sp-6 | an-298 |
| 1A2184 | sp-6 | an-299 | 1U2184 | sp-6 | an-299 | 1C2184 | sp-6 | an-299 |

Table 2-40

| Y = NHCS | | | Y = NHCSNH | | | Y = NHCSO | | |
|---|---|---|---|---|---|---|---|---|
| 1A2185 | sp-6 | an-300 | 1U2185 | sp-6 | an-300 | 1C2185 | sp-6 | an-300 |
| 1A2186 | sp-6 | an-301 | 1U2186 | sp-6 | an-301 | 1C2186 | sp-6 | an-301 |
| 1A2187 | sp-6 | an-302 | 1U2187 | sp-6 | an-302 | 1C2187 | sp-6 | an-302 |
| 1A2188 | sp-6 | an-303 | 1U2188 | sp-6 | an-303 | 1C2188 | sp-6 | an-303 |
| 1A2189 | sp-6 | an-304 | 1U2189 | sp-6 | an-304 | 1C2189 | sp-6 | an-304 |
| 1A2190 | sp-6 | an-305 | 1U2190 | sp-6 | an-305 | 1C2190 | sp-6 | an-305 |
| 1A2191 | sp-6 | an-306 | 1U2191 | sp-6 | an-306 | 1C2191 | sp-6 | an-306 |
| 1A2192 | sp-6 | an-307 | 1U2192 | sp-6 | an-307 | 1C2192 | sp-6 | an-307 |
| 1A2193 | sp-6 | an-308 | 1U2193 | sp-6 | an-308 | 1C2193 | sp-6 | an-308 |
| 1A2194 | sp-6 | an-309 | 1U2194 | sp-6 | an-309 | 1C2194 | sp-6 | an-309 |
| 1A2195 | sp-6 | an-310 | 1U2195 | sp-6 | an-310 | 1C2195 | sp-6 | an-310 |
| 1A2196 | sp-6 | an-311 | 1U2196 | sp-6 | an-311 | 1C2196 | sp-6 | an-311 |
| 1A2197 | sp-6 | an-312 | 1U2197 | sp-6 | an-312 | 1C2197 | sp-6 | an-312 |
| 1A2198 | sp-6 | an-313 | 1U2198 | sp-6 | an-313 | 1C2198 | sp-6 | an-313 |
| 1A2199 | sp-6 | an-314 | 1U2199 | sp-6 | an-314 | 1C2199 | sp-6 | an-314 |
| 1A2200 | sp-6 | an-315 | 1U2200 | sp-6 | an-315 | 1C2200 | sp-6 | an-315 |
| 1A2201 | sp-6 | an-316 | 1U2201 | sp-6 | an-316 | 1C2201 | sp-6 | an-316 |
| 1A2202 | sp-6 | an-317 | 1U2202 | sp-6 | an-317 | 1C2202 | sp-6 | an-317 |
| 1A2203 | sp-6 | an-318 | 1U2203 | sp-6 | an-318 | 1C2203 | sp-6 | an-318 |
| 1A2204 | sp-6 | an-319 | 1U2204 | sp-6 | an-319 | 1C2204 | sp-6 | an-319 |
| 1A2205 | sp-6 | an-320 | 1U2205 | sp-6 | an-320 | 1C2205 | sp-6 | an-320 |
| 1A2206 | sp-6 | an-321 | 1U2206 | sp-6 | an-321 | 1C2206 | sp-6 | an-321 |
| 1A2207 | sp-6 | an-322 | 1U2207 | sp-6 | an-322 | 1C2207 | sp-6 | an-322 |
| 1A2208 | sp-6 | an-323 | 1U2208 | sp-6 | an-323 | 1C2208 | sp-6 | an-323 |
| 1A2209 | sp-6 | an-324 | 1U2209 | sp-6 | an-324 | 1C2209 | sp-6 | an-324 |
| 1A2210 | sp-6 | an-325 | 1U2210 | sp-6 | an-325 | 1C2210 | sp-6 | an-325 |
| 1A2211 | sp-6 | an-326 | 1U2211 | sp-6 | an-326 | 1C2211 | sp-6 | an-326 |
| 1A2212 | sp-6 | an-327 | 1U2212 | sp-6 | an-327 | 1C2212 | sp-6 | an-327 |
| 1A2213 | sp-6 | an-328 | 1U2213 | sp-6 | an-328 | 1C2213 | sp-6 | an-328 |
| 1A2214 | sp-6 | an-329 | 1U2214 | sp-6 | an-329 | 1C2214 | sp-6 | an-329 |
| 1A2215 | sp-6 | an-330 | 1U2215 | sp-6 | an-330 | 1C2215 | sp-6 | an-330 |
| 1A2216 | sp-6 | an-331 | 1U2216 | sp-6 | an-331 | 1C2216 | sp-6 | an-331 |

-continued

| Ex. No. | Z | N⁺R⁵R⁶R⁷ | Ex. No. | Z | N⁺R⁵R⁶R⁷ | Ex. No. | Z | N⁺R⁵R⁶R⁷ |
|---|---|---|---|---|---|---|---|---|
| 1A2217 | sp-6 | an-332 | 1U2217 | sp-6 | an-332 | 1C2217 | sp-6 | an-332 |
| 1A2218 | sp-6 | an-333 | 1U2218 | sp-6 | an-333 | 1C2218 | sp-6 | an-333 |
| 1A2219 | sp-6 | an-334 | 1U2219 | sp-6 | an-334 | 1C2219 | sp-6 | an-334 |
| 1A2220 | sp-6 | an-335 | 1U2220 | sp-6 | an-335 | 1C2220 | sp-6 | an-335 |
| 1A2221 | sp-6 | an-336 | 1U2221 | sp-6 | an-336 | 1C2221 | sp-6 | an-336 |
| 1A2222 | sp-6 | an-337 | 1U2222 | sp-6 | an-337 | 1C2222 | sp-6 | an-337 |
| 1A2223 | sp-6 | an-338 | 1U2223 | sp-6 | an-338 | 1C2223 | sp-6 | an-338 |
| 1A2224 | sp-6 | an-339 | 1U2224 | sp-6 | an-339 | 1C2224 | sp-6 | an-339 |
| 1A2225 | sp-6 | an-340 | 1U2225 | sp-6 | an-340 | 1C2225 | sp-6 | an-340 |
| 1A2226 | sp-6 | an-341 | 1U2226 | sp-6 | an-341 | 1C2226 | sp-6 | an-341 |
| 1A2227 | sp-6 | an-342 | 1U2227 | sp-6 | an-342 | 1C2227 | sp-6 | an-342 |
| 1A2228 | sp-6 | an-343 | 1U2228 | sp-6 | an-343 | 1C2228 | sp-6 | an-343 |
| 1A2229 | sp-6 | an-344 | 1U2229 | sp-6 | an-344 | 1C2229 | sp-6 | an-344 |
| 1A2230 | sp-6 | an-345 | 1U2230 | sp-6 | an-345 | 1C2230 | sp-6 | an-345 |
| 1A2231 | sp-6 | an-346 | 1U2231 | sp-6 | an-346 | 1C2231 | sp-6 | an-346 |
| 1A2232 | sp-6 | an-347 | 1U2232 | sp-6 | an-347 | 1C2232 | sp-6 | an-347 |
| 1A2233 | sp-6 | an-348 | 1U2233 | sp-6 | an-348 | 1C2233 | sp-6 | an-348 |
| 1A2234 | sp-6 | an-349 | 1U2234 | sp-6 | an-349 | 1C2234 | sp-6 | an-349 |
| 1A2235 | sp-6 | an-350 | 1U2235 | sp-6 | an-350 | 1C2235 | sp-6 | an-350 |
| 1A2236 | sp-6 | an-351 | 1U2236 | sp-6 | an-351 | 1C2236 | sp-6 | an-351 |
| 1A2237 | sp-6 | an-352 | 1U2237 | sp-6 | an-352 | 1C2237 | sp-6 | an-352 |
| 1A2238 | sp-6 | an-353 | 1U2238 | sp-6 | an-353 | 1C2238 | sp-6 | an-353 |
| 1A2239 | sp-6 | an-354 | 1U2239 | sp-6 | an-354 | 1C2239 | sp-6 | an-354 |
| 1A2240 | sp-6 | an-355 | 1U2240 | sp-6 | an-355 | 1C2240 | sp-6 | an-355 |

Table 2-41

| Y = NHCS | | | Y = NHCSNH | | | Y = NHCSO | | |
|---|---|---|---|---|---|---|---|---|
| 1A2241 | sp-6 | an-356 | 1U2241 | sp-6 | an-356 | 1C2241 | sp-6 | an-356 |
| 1A2242 | sp-6 | an-357 | 1U2242 | sp-6 | an-357 | 1C2242 | sp-6 | an-357 |
| 1A2243 | sp-6 | an-358 | 1U2243 | sp-6 | an-358 | 1C2243 | sp-6 | an-358 |
| 1A2244 | sp-6 | an-359 | 1U2244 | sp-6 | an-359 | 1C2244 | sp-6 | an-359 |
| 1A2245 | sp-6 | an-360 | 1U2245 | sp-6 | an-360 | 1C2245 | sp-6 | an-360 |
| 1A2246 | sp-6 | an-361 | 1U2246 | sp-6 | an-361 | 1C2246 | sp-6 | an-361 |
| 1A2247 | sp-6 | an-362 | 1U2247 | sp-6 | an-362 | 1C2247 | sp-6 | an-362 |
| 1A2248 | sp-6 | an-363 | 1U2248 | sp-6 | an-363 | 1C2248 | sp-6 | an-363 |
| 1A2249 | sp-6 | an-364 | 1U2249 | sp-6 | an-364 | 1C2249 | sp-6 | an-364 |
| 1A2250 | sp-6 | an-365 | 1U2250 | sp-6 | an-365 | 1C2250 | sp-6 | an-365 |
| 1A2251 | sp-6 | an-366 | 1U2251 | sp-6 | an-366 | 1C2251 | sp-6 | an-366 |
| 1A2252 | sp-6 | an-367 | 1U2252 | sp-6 | an-367 | 1C2252 | sp-6 | an-367 |
| 1A2253 | sp-6 | an-368 | 1U2253 | sp-6 | an-368 | 1C2253 | sp-6 | an-368 |
| 1A2254 | sp-6 | an-369 | 1U2254 | sp-6 | an-369 | 1C2254 | sp-6 | an-369 |
| 1A2255 | sp-6 | an-370 | 1U2255 | sp-6 | an-370 | 1C2255 | sp-6 | an-370 |
| 1A2256 | sp-6 | an-371 | 1U2256 | sp-6 | an-371 | 1C2256 | sp-6 | an-371 |
| 1A2257 | sp-6 | an-372 | 1U2257 | sp-6 | an-372 | 1C2257 | sp-6 | an-372 |
| 1A2258 | sp-6 | an-373 | 1U2258 | sp-6 | an-373 | 1C2258 | sp-6 | an-373 |
| 1A2259 | sp-6 | an-374 | 1U2259 | sp-6 | an-374 | 1C2259 | sp-6 | an-374 |
| 1A2260 | sp-6 | an-375 | 1U2260 | sp-6 | an-375 | 1C2260 | sp-6 | an-375 |
| 1A2261 | sp-6 | an-376 | 1U2261 | sp-6 | an-376 | 1C2261 | sp-6 | an-376 |
| 1A2262 | sp-6 | an-377 | 1U2262 | sp-6 | an-377 | 1C2262 | sp-6 | an-377 |
| 1A2263 | sp-7 | an-1 | 1U2263 | sp-7 | an-1 | 1C2263 | sp-7 | an-1 |
| 1A2264 | sp-7 | an-2 | 1U2264 | sp-7 | an-2 | 1C2264 | sp-7 | an-2 |
| 1A2265 | sp-7 | an-3 | 1U2265 | sp-7 | an-3 | 1C2265 | sp-7 | an-3 |
| 1A2266 | sp-7 | an-4 | 1U2266 | sp-7 | an-4 | 1C2266 | sp-7 | an-4 |
| 1A2267 | sp-7 | an-5 | 1U2267 | sp-7 | an-5 | 1C2267 | sp-7 | an-5 |
| 1A2268 | sp-7 | an-6 | 1U2268 | sp-7 | an-6 | 1C2268 | sp-7 | an-6 |
| 1A2269 | sp-7 | an-7 | 1U2269 | sp-7 | an-7 | 1C2269 | sp-7 | an-7 |
| 1A2270 | sp-7 | an-8 | 1U2270 | sp-7 | an-8 | 1C2270 | sp-7 | an-8 |
| 1A2271 | sp-7 | an-9 | 1U2271 | sp-7 | an-9 | 1C2271 | sp-7 | an-9 |
| 1A2272 | sp-7 | an-10 | 1U2272 | sp-7 | an-10 | 1C2272 | sp-7 | an-10 |
| 1A2273 | sp-7 | an-11 | 1U2273 | sp-7 | an-11 | 1C2273 | sp-7 | an-11 |
| 1A2274 | sp-7 | an-12 | 1U2274 | sp-7 | an-12 | 1C2274 | sp-7 | an-12 |
| 1A2275 | sp-7 | an-13 | 1U2275 | sp-7 | an-13 | 1C2275 | sp-7 | an-13 |
| 1A2276 | sp-7 | an-14 | 1U2276 | sp-7 | an-14 | 1C2276 | sp-7 | an-14 |
| 1A2277 | sp-7 | an-15 | 1U2277 | sp-7 | an-15 | 1C2277 | sp-7 | an-15 |
| 1A2278 | sp-7 | an-16 | 1U2278 | sp-7 | an-16 | 1C2278 | sp-7 | an-16 |
| 1A2279 | sp-7 | an-17 | 1U2279 | sp-7 | an-17 | 1C2279 | sp-7 | an-17 |
| 1A2280 | sp-7 | an-18 | 1U2280 | sp-7 | an-18 | 1C2280 | sp-7 | an-18 |
| 1A2281 | sp-7 | an-19 | 1U2281 | sp-7 | an-19 | 1C2281 | sp-7 | an-19 |
| 1A2282 | sp-7 | an-20 | 1U2282 | sp-7 | an-20 | 1C2282 | sp-7 | an-20 |
| 1A2283 | sp-7 | an-21 | 1U2283 | sp-7 | an-21 | 1C2283 | sp-7 | an-21 |
| 1A2284 | sp-7 | an-22 | 1U2284 | sp-7 | an-22 | 1C2284 | sp-7 | an-22 |
| 1A2285 | sp-7 | an-23 | 1U2285 | sp-7 | an-23 | 1C2285 | sp-7 | an-23 |
| 1A2286 | sp-7 | an-24 | 1U2286 | sp-7 | an-24 | 1C2286 | sp-7 | an-24 |
| 1A2287 | sp-7 | an-25 | 1U2287 | sp-7 | an-25 | 1C2287 | sp-7 | an-25 |
| 1A2288 | sp-7 | an-26 | 1U2288 | sp-7 | an-26 | 1C2288 | sp-7 | an-26 |
| 1A2289 | sp-7 | an-27 | 1U2289 | sp-7 | an-27 | 1C2289 | sp-7 | an-27 |
| 1A2290 | sp-7 | an-28 | 1U2290 | sp-7 | an-28 | 1C2290 | sp-7 | an-28 |

| Ex. No. | Z | N⁺R⁵R⁶R⁷ | Ex. No. | Z | N⁺R⁵R⁶R⁷ | Ex. No. | Z | N⁺R⁵R⁶R⁷ |
|---|---|---|---|---|---|---|---|---|
| 1A2291 | sp-7 | an-29 | 1U2291 | sp-7 | an-29 | 1C2291 | sp-7 | an-29 |
| 1A2292 | sp-7 | an-30 | 1U2292 | sp-7 | an-30 | 1C2292 | sp-7 | an-30 |
| 1A2293 | sp-7 | an-31 | 1U2293 | sp-7 | an-31 | 1C2293 | sp-7 | an-31 |
| 1A2294 | sp-7 | an-32 | 1U2294 | sp-7 | an-32 | 1C2294 | sp-7 | an-32 |
| 1A2295 | sp-7 | an-33 | 1U2295 | sp-7 | an-33 | 1C2295 | sp-7 | an-33 |
| 1A2296 | sp-7 | an-34 | 1U2296 | sp-7 | an-34 | 1C2296 | sp-7 | an-34 |

Table 2-42

| Y = NHCS | | | Y = NHCSNH | | | Y = NHCSO | | |
|---|---|---|---|---|---|---|---|---|
| 1A2297 | sp-7 | an-35 | 1U2297 | sp-7 | an-35 | 1C2297 | sp-7 | an-35 |
| 1A2298 | sp-7 | an-36 | 1U2298 | sp-7 | an-36 | 1C2298 | sp-7 | an-36 |
| 1A2299 | sp-7 | an-37 | 1U2299 | sp-7 | an-37 | 1C2299 | sp-7 | an-37 |
| 1A2300 | sp-7 | an-38 | 1U2300 | sp-7 | an-38 | 1C2300 | sp-7 | an-38 |
| 1A2301 | sp-7 | an-39 | 1U2301 | sp-7 | an-39 | 1C2301 | sp-7 | an-39 |
| 1A2302 | sp-7 | an-40 | 1U2302 | sp-7 | an-40 | 1C2302 | sp-7 | an-40 |
| 1A2303 | sp-7 | an-41 | 1U2303 | sp-7 | an-41 | 1C2303 | sp-7 | an-41 |
| 1A2304 | sp-7 | an-42 | 1U2304 | sp-7 | an-42 | 1C2304 | sp-7 | an-42 |
| 1A2305 | sp-7 | an-43 | 1U2305 | sp-7 | an-43 | 1C2305 | sp-7 | an-43 |
| 1A2306 | sp-7 | an-44 | 1U2306 | sp-7 | an-44 | 1C2306 | sp-7 | an-44 |
| 1A2307 | sp-7 | an-45 | 1U2307 | sp-7 | an-45 | 1C2307 | sp-7 | an-45 |
| 1A2308 | sp-7 | an-46 | 1U2308 | sp-7 | an-46 | 1C2308 | sp-7 | an-46 |
| 1A2309 | sp-7 | an-47 | 1U2309 | sp-7 | an-47 | 1C2309 | sp-7 | an-47 |
| 1A2310 | sp-7 | an-48 | 1U2310 | sp-7 | an-48 | 1C2310 | sp-7 | an-48 |
| 1A2311 | sp-7 | an-49 | 1U2311 | sp-7 | an-49 | 1C2311 | sp-7 | an-49 |
| 1A2312 | sp-7 | an-50 | 1U2312 | sp-7 | an-50 | 1C2312 | sp-7 | an-50 |
| 1A2313 | sp-7 | an-51 | 1U2313 | sp-7 | an-51 | 1C2313 | sp-7 | an-51 |
| 1A2314 | sp-7 | an-52 | 1U2314 | sp-7 | an-52 | 1C2314 | sp-7 | an-52 |
| 1A2315 | sp-7 | an-53 | 1U2315 | sp-7 | an-53 | 1C2315 | sp-7 | an-53 |
| 1A2316 | sp-7 | an-54 | 1U2316 | sp-7 | an-54 | 1C2316 | sp-7 | an-54 |
| 1A2317 | sp-7 | an-55 | 1U2317 | sp-7 | an-55 | 1C2317 | sp-7 | an-55 |
| 1A2318 | sp-7 | an-56 | 1U2318 | sp-7 | an-56 | 1C2318 | sp-7 | an-56 |
| 1A2319 | sp-7 | an-57 | 1U2319 | sp-7 | an-57 | 1C2319 | sp-7 | an-57 |
| 1A2320 | sp-7 | an-58 | 1U2320 | sp-7 | an-58 | 1C2320 | sp-7 | an-58 |
| 1A2321 | sp-7 | an-59 | 1U2321 | sp-7 | an-59 | 1C2321 | sp-7 | an-59 |
| 1A2322 | sp-7 | an-60 | 1U2322 | sp-7 | an-60 | 1C2322 | sp-7 | an-60 |
| 1A2323 | sp-7 | an-61 | 1U2323 | sp-7 | an-61 | 1C2323 | sp-7 | an-61 |
| 1A2324 | sp-7 | an-62 | 1U2324 | sp-7 | an-62 | 1C2324 | sp-7 | an-62 |
| 1A2325 | sp-7 | an-63 | 1U2325 | sp-7 | an-63 | 1C2325 | sp-7 | an-63 |
| 1A2326 | sp-7 | an-64 | 1U2326 | sp-7 | an-64 | 1C2326 | sp-7 | an-64 |
| 1A2327 | sp-7 | an-65 | 1U2327 | sp-7 | an-65 | 1C2327 | sp-7 | an-65 |
| 1A2328 | sp-7 | an-66 | 1U2328 | sp-7 | an-66 | 1C2328 | sp-7 | an-66 |
| 1A2329 | sp-7 | an-67 | 1U2329 | sp-7 | an-67 | 1C2329 | sp-7 | an-67 |
| 1A2330 | sp-7 | an-68 | 1U2330 | sp-7 | an-68 | 1C2330 | sp-7 | an-68 |
| 1A2331 | sp-7 | an-69 | 1U2331 | sp-7 | an-69 | 1C2331 | sp-7 | an-69 |
| 1A2332 | sp-7 | an-70 | 1U2332 | sp-7 | an-70 | 1C2332 | sp-7 | an-70 |
| 1A2333 | sp-7 | an-71 | 1U2333 | sp-7 | an-71 | 1C2333 | sp-7 | an-71 |
| 1A2334 | sp-7 | an-72 | 1U2334 | sp-7 | an-72 | 1C2334 | sp-7 | an-72 |
| 1A2335 | sp-7 | an-73 | 1U2335 | sp-7 | an-73 | 1C2335 | sp-7 | an-73 |
| 1A2336 | sp-7 | an-74 | 1U2336 | sp-7 | an-74 | 1C2336 | sp-7 | an-74 |
| 1A2337 | sp-7 | an-75 | 1U2337 | sp-7 | an-75 | 1C2337 | sp-7 | an-75 |
| 1A2338 | sp-7 | an-76 | 1U2338 | sp-7 | an-76 | 1C2338 | sp-7 | an-76 |
| 1A2339 | sp-7 | an-77 | 1U2339 | sp-7 | an-77 | 1C2339 | sp-7 | an-77 |
| 1A2340 | sp-7 | an-78 | 1U2340 | sp-7 | an-78 | 1C2340 | sp-7 | an-78 |
| 1A2341 | sp-7 | an-79 | 1U2341 | sp-7 | an-79 | 1C2341 | sp-7 | an-79 |
| 1A2342 | sp-7 | an-80 | 1U2342 | sp-7 | an-80 | 1C2342 | sp-7 | an-80 |
| 1A2343 | sp-7 | an-81 | 1U2343 | sp-7 | an-81 | 1C2343 | sp-7 | an-81 |
| 1A2344 | sp-7 | an-82 | 1U2344 | sp-7 | an-82 | 1C2344 | sp-7 | an-82 |
| 1A2345 | sp-7 | an-83 | 1U2345 | sp-7 | an-83 | 1C2345 | sp-7 | an-83 |
| 1A2346 | sp-7 | an-84 | 1U2346 | sp-7 | an-84 | 1C2346 | sp-7 | an-84 |
| 1A2347 | sp-7 | an-85 | 1U2347 | sp-7 | an-85 | 1C2347 | sp-7 | an-85 |
| 1A2348 | sp-7 | an-86 | 1U2348 | sp-7 | an-86 | 1C2348 | sp-7 | an-86 |
| 1A2349 | sp-7 | an-87 | 1U2349 | sp-7 | an-87 | 1C2349 | sp-7 | an-87 |
| 1A2350 | sp-7 | an-88 | 1U2350 | sp-7 | an-88 | 1C2350 | sp-7 | an-88 |
| 1A2351 | sp-7 | an-89 | 1U2351 | sp-7 | an-89 | 1C2351 | sp-7 | an-89 |
| 1A2352 | sp-7 | an-90 | 1U2352 | sp-7 | an-90 | 1C2352 | sp-7 | an-90 |

Table 2-43

| Y = NHCS | | | Y = NHCSNH | | | Y = NHCSO | | |
|---|---|---|---|---|---|---|---|---|
| 1A2353 | sp-7 | an-91 | 1U2353 | sp-7 | an-91 | 1C2353 | sp-7 | an-91 |
| 1A2354 | sp-7 | an-92 | 1U2354 | sp-7 | an-92 | 1C2354 | sp-7 | an-92 |
| 1A2355 | sp-7 | an-93 | 1U2355 | sp-7 | an-93 | 1C2355 | sp-7 | an-93 |
| 1A2356 | sp-7 | an-94 | 1U2356 | sp-7 | an-94 | 1C2356 | sp-7 | an-94 |
| 1A2357 | sp-7 | an-95 | 1U2357 | sp-7 | an-95 | 1C2357 | sp-7 | an-95 |
| 1A2358 | sp-7 | an-96 | 1U2358 | sp-7 | an-96 | 1C2358 | sp-7 | an-96 |
| 1A2359 | sp-7 | an-97 | 1U2359 | sp-7 | an-97 | 1C2359 | sp-7 | an-97 |
| 1A2360 | sp-7 | an-98 | 1U2360 | sp-7 | an-98 | 1C2360 | sp-7 | an-98 |

-continued

| Ex. No. | Z | N⁺R⁵R⁶R⁷ | Ex. No. | Z | N⁺R⁵R⁶R⁷ | Ex. No. | Z | N⁺R⁵R⁶R⁷ |
|---|---|---|---|---|---|---|---|---|
| 1A2361 | sp-7 | an-99 | 1U2361 | sp-7 | an-99 | 1C2361 | sp-7 | an-99 |
| 1A2362 | sp-7 | an-100 | 1U2362 | sp-7 | an-100 | 1C2362 | sp-7 | an-100 |
| 1A2363 | sp-7 | an-101 | 1U2363 | sp-7 | an-101 | 1C2363 | sp-7 | an-101 |
| 1A2364 | sp-7 | an-102 | 1U2364 | sp-7 | an-102 | 1C2364 | sp-7 | an-102 |
| 1A2365 | sp-7 | an-103 | 1U2365 | sp-7 | an-103 | 1C2365 | sp-7 | an-103 |
| 1A2366 | sp-7 | an-104 | 1U2366 | sp-7 | an-104 | 1C2366 | sp-7 | an-104 |
| 1A2367 | sp-7 | an-105 | 1U2367 | sp-7 | an-105 | 1C2367 | sp-7 | an-105 |
| 1A2368 | sp-7 | an-106 | 1U2368 | sp-7 | an-106 | 1C2368 | sp-7 | an-106 |
| 1A2369 | sp-7 | an-107 | 1U2369 | sp-7 | an-107 | 1C2369 | sp-7 | an-107 |
| 1A2370 | sp-7 | an-108 | 1U2370 | sp-7 | an-108 | 1C2370 | sp-7 | an-108 |
| 1A2371 | sp-7 | an-109 | 1U2371 | sp-7 | an-109 | 1C2371 | sp-7 | an-109 |
| 1A2372 | sp-7 | an-110 | 1U2372 | sp-7 | an-110 | 1C2372 | sp-7 | an-110 |
| 1A2373 | sp-7 | an-111 | 1U2373 | sp-7 | an-111 | 1C2373 | sp-7 | an-111 |
| 1A2374 | sp-7 | an-112 | 1U2374 | sp-7 | an-112 | 1C2374 | sp-7 | an-112 |
| 1A2375 | sp-7 | an-113 | 1U2375 | sp-7 | an-113 | 1C2375 | sp-7 | an-113 |
| 1A2376 | sp-7 | an-114 | 1U2376 | sp-7 | an-114 | 1C2376 | sp-7 | an-114 |
| 1A2377 | sp-7 | an-115 | 1U2377 | sp-7 | an-115 | 1C2377 | sp-7 | an-115 |
| 1A2378 | sp-7 | an-116 | 1U2378 | sp-7 | an-116 | 1C2378 | sp-7 | an-116 |
| 1A2379 | sp-7 | an-117 | 1U2379 | sp-7 | an-117 | 1C2379 | sp-7 | an-117 |
| 1A2380 | sp-7 | an-118 | 1U2380 | sp-7 | an-118 | 1C2380 | sp-7 | an-118 |
| 1A2381 | sp-7 | an-119 | 1U2381 | sp-7 | an-119 | 1C2381 | sp-7 | an-119 |
| 1A2382 | sp-7 | an-120 | 1U2382 | sp-7 | an-120 | 1C2382 | sp-7 | an-120 |
| 1A2383 | sp-7 | an-121 | 1U2383 | sp-7 | an-121 | 1C2383 | sp-7 | an-121 |
| 1A2384 | sp-7 | an-122 | 1U2384 | sp-7 | an-122 | 1C2384 | sp-7 | an-122 |
| 1A2385 | sp-7 | an-123 | 1U2385 | sp-7 | an-123 | 1C2385 | sp-7 | an-123 |
| 1A2386 | sp-7 | an-124 | 1U2386 | sp-7 | an-124 | 1C2386 | sp-7 | an-124 |
| 1A2387 | sp-7 | an-125 | 1U2387 | sp-7 | an-125 | 1C2387 | sp-7 | an-125 |
| 1A2388 | sp-7 | an-126 | 1U2388 | sp-7 | an-126 | 1C2388 | sp-7 | an-126 |
| 1A2389 | sp-7 | an-127 | 1U2389 | sp-7 | an-127 | 1C2389 | sp-7 | an-127 |
| 1A2390 | sp-7 | an-128 | 1U2390 | sp-7 | an-128 | 1C2390 | sp-7 | an-128 |
| 1A2391 | sp-7 | an-129 | 1U2391 | sp-7 | an-129 | 1C2391 | sp-7 | an-129 |
| 1A2392 | sp-7 | an-130 | 1U2392 | sp-7 | an-130 | 1C2392 | sp-7 | an-130 |
| 1A2393 | sp-7 | an-131 | 1U2393 | sp-7 | an-131 | 1C2393 | sp-7 | an-131 |
| 1A2394 | sp-7 | an-132 | 1U2394 | sp-7 | an-132 | 1C2394 | sp-7 | an-132 |
| 1A2395 | sp-7 | an-133 | 1U2395 | sp-7 | an-133 | 1C2395 | sp-7 | an-133 |
| 1A2396 | sp-7 | an-134 | 1U2396 | sp-7 | an-134 | 1C2396 | sp-7 | an-134 |
| 1A2397 | sp-7 | an-135 | 1U2397 | sp-7 | an-135 | 1C2397 | sp-7 | an-135 |
| 1A2398 | sp-7 | an-136 | 1U2398 | sp-7 | an-136 | 1C2398 | sp-7 | an-136 |
| 1A2399 | sp-7 | an-137 | 1U2399 | sp-7 | an-137 | 1C2399 | sp-7 | an-137 |
| 1A2400 | sp-7 | an-138 | 1U2400 | sp-7 | an-138 | 1C2400 | sp-7 | an-138 |
| 1A2401 | sp-7 | an-139 | 1U2401 | sp-7 | an-139 | 1C2401 | sp-7 | an-139 |
| 1A2402 | sp-7 | an-140 | 1U2402 | sp-7 | an-140 | 1C2402 | sp-7 | an-140 |
| 1A2403 | sp-7 | an-141 | 1U2403 | sp-7 | an-141 | 1C2403 | sp-7 | an-141 |
| 1A2404 | sp-7 | an-142 | 1U2404 | sp-7 | an-142 | 1C2404 | sp-7 | an-142 |
| 1A2405 | sp-7 | an-143 | 1U2405 | sp-7 | an-143 | 1C2405 | sp-7 | an-143 |
| 1A2406 | sp-7 | an-144 | 1U2406 | sp-7 | an-144 | 1C2406 | sp-7 | an-144 |
| 1A2407 | sp-7 | an-145 | 1U2407 | sp-7 | an-145 | 1C2407 | sp-7 | an-145 |
| 1A2408 | sp-7 | an-146 | 1U2408 | sp-7 | an-146 | 1C2408 | sp-7 | an-146 |

Table 2-44

| Y = NHCS | | | Y = NHCSNH | | | Y = NHCSO | | |
|---|---|---|---|---|---|---|---|---|
| 1A2409 | sp-7 | an-147 | 1U2409 | sp-7 | an-147 | 1C2409 | sp-7 | an-147 |
| 1A2410 | sp-7 | an-148 | 1U2410 | sp-7 | an-148 | 1C2410 | sp-7 | an-148 |
| 1A2411 | sp-7 | an-149 | 1U2411 | sp-7 | an-149 | 1C2411 | sp-7 | an-149 |
| 1A2412 | sp-7 | an-150 | 1U2412 | sp-7 | an-150 | 1C2412 | sp-7 | an-150 |
| 1A2413 | sp-7 | an-151 | 1U2413 | sp-7 | an-151 | 1C2413 | sp-7 | an-151 |
| 1A2414 | sp-7 | an-152 | 1U2414 | sp-7 | an-152 | 1C2414 | sp-7 | an-152 |
| 1A2415 | sp-7 | an-153 | 1U2415 | sp-7 | an-153 | 1C2415 | sp-7 | an-153 |
| 1A2416 | sp-7 | an-154 | 1U2416 | sp-7 | an-154 | 1C2416 | sp-7 | an-154 |
| 1A2417 | sp-7 | an-155 | 1U2417 | sp-7 | an-155 | 1C2417 | sp-7 | an-155 |
| 1A2418 | sp-7 | an-156 | 1U2418 | sp-7 | an-156 | 1C2418 | sp-7 | an-156 |
| 1A2419 | sp-7 | an-157 | 1U2419 | sp-7 | an-157 | 1C2419 | sp-7 | an-157 |
| 1A2420 | sp-7 | an-158 | 1U2420 | sp-7 | an-158 | 1C2420 | sp-7 | an-158 |
| 1A2421 | sp-7 | an-159 | 1U2421 | sp-7 | an-159 | 1C2421 | sp-7 | an-159 |
| 1A2422 | sp-7 | an-160 | 1U2422 | sp-7 | an-160 | 1C2422 | sp-7 | an-160 |
| 1A2423 | sp-7 | an-161 | 1U2423 | sp-7 | an-161 | 1C2423 | sp-7 | an-161 |
| 1A2424 | sp-7 | an-162 | 1U2424 | sp-7 | an-162 | 1C2424 | sp-7 | an-162 |
| 1A2425 | sp-7 | an-163 | 1U2425 | sp-7 | an-163 | 1C2425 | sp-7 | an-163 |
| 1A2426 | sp-7 | an-164 | 1U2426 | sp-7 | an-164 | 1C2426 | sp-7 | an-164 |
| 1A2427 | sp-7 | an-165 | 1U2427 | sp-7 | an-165 | 1C2427 | sp-7 | an-165 |
| 1A2428 | sp-7 | an-166 | 1U2428 | sp-7 | an-166 | 1C2428 | sp-7 | an-166 |
| 1A2429 | sp-7 | an-167 | 1U2429 | sp-7 | an-167 | 1C2429 | sp-7 | an-167 |
| 1A2430 | sp-7 | an-168 | 1U2430 | sp-7 | an-168 | 1C2430 | sp-7 | an-168 |
| 1A2431 | sp-7 | an-169 | 1U2431 | sp-7 | an-169 | 1C2431 | sp-7 | an-169 |
| 1A2432 | sp-7 | an-170 | 1U2432 | sp-7 | an-170 | 1C2432 | sp-7 | an-170 |
| 1A2433 | sp-7 | an-171 | 1U2433 | sp-7 | an-171 | 1C2433 | sp-7 | an-171 |
| 1A2434 | sp-7 | an-172 | 1U2434 | sp-7 | an-172 | 1C2434 | sp-7 | an-172 |

-continued

| Ex. No. | Z | N⁺R⁵R⁶R⁷ | Ex. No. | Z | N⁺R⁵R⁶R⁷ | Ex. No. | Z | N⁺R⁵R⁶R⁷ |
|---|---|---|---|---|---|---|---|---|
| 1A2435 | sp-7 | an-173 | 1U2435 | sp-7 | an-173 | 1C2435 | sp-7 | an-173 |
| 1A2436 | sp-7 | an-174 | 1U2436 | sp-7 | an-174 | 1C2436 | sp-7 | an-174 |
| 1A2437 | sp-7 | an-175 | 1U2437 | sp-7 | an-175 | 1C2437 | sp-7 | an-175 |
| 1A2438 | sp-7 | an-176 | 1U2438 | sp-7 | an-176 | 1C2438 | sp-7 | an-176 |
| 1A2439 | sp-7 | an-177 | 1U2439 | sp-7 | an-177 | 1C2439 | sp-7 | an-177 |
| 1A2440 | sp-7 | an-178 | 1U2440 | sp-7 | an-178 | 1C2440 | sp-7 | an-178 |
| 1A2441 | sp-7 | an-179 | 1U2441 | sp-7 | an-179 | 1C2441 | sp-7 | an-179 |
| 1A2442 | sp-7 | an-180 | 1U2442 | sp-7 | an-180 | 1C2442 | sp-7 | an-180 |
| 1A2443 | sp-7 | an-181 | 1U2443 | sp-7 | an-181 | 1C2443 | sp-7 | an-181 |
| 1A2444 | sp-7 | an-182 | 1U2444 | sp-7 | an-182 | 1C2444 | sp-7 | an-182 |
| 1A2445 | sp-7 | an-183 | 1U2445 | sp-7 | an-183 | 1C2445 | sp-7 | an-183 |
| 1A2446 | sp-7 | an-184 | 1U2446 | sp-7 | an-184 | 1C2446 | sp-7 | an-184 |
| 1A2447 | sp-7 | an-185 | 1U2447 | sp-7 | an-185 | 1C2447 | sp-7 | an-185 |
| 1A2448 | sp-7 | an-186 | 1U2448 | sp-7 | an-186 | 1C2448 | sp-7 | an-186 |
| 1A2449 | sp-7 | an-187 | 1U2449 | sp-7 | an-187 | 1C2449 | sp-7 | an-187 |
| 1A2450 | sp-7 | an-188 | 1U2450 | sp-7 | an-188 | 1C2450 | sp-7 | an-188 |
| 1A2451 | sp-7 | an-189 | 1U2451 | sp-7 | an-189 | 1C2451 | sp-7 | an-189 |
| 1A2452 | sp-7 | an-190 | 1U2452 | sp-7 | an-190 | 1C2452 | sp-7 | an-190 |
| 1A2453 | sp-7 | an-191 | 1U2453 | sp-7 | an-191 | 1C2453 | sp-7 | an-191 |
| 1A2454 | sp-7 | an-192 | 1U2454 | sp-7 | an-192 | 1C2454 | sp-7 | an-192 |
| 1A2455 | sp-7 | an-193 | 1U2455 | sp-7 | an-193 | 1C2455 | sp-7 | an-193 |
| 1A2456 | sp-7 | an-194 | 1U2456 | sp-7 | an-194 | 1C2456 | sp-7 | an-194 |
| 1A2457 | sp-7 | an-195 | 1U2457 | sp-7 | an-195 | 1C2457 | sp-7 | an-195 |
| 1A2458 | sp-7 | an-196 | 1U2458 | sp-7 | an-196 | 1C2458 | sp-7 | an-196 |
| 1A2459 | sp-7 | an-197 | 1U2459 | sp-7 | an-197 | 1C2459 | sp-7 | an-197 |
| 1A2460 | sp-7 | an-198 | 1U2460 | sp-7 | an-198 | 1C2460 | sp-7 | an-198 |
| 1A2461 | sp-7 | an-199 | 1U2461 | sp-7 | an-199 | 1C2461 | sp-7 | an-199 |
| 1A2462 | sp-7 | an-200 | 1U2462 | sp-7 | an-200 | 1C2462 | sp-7 | an-200 |
| 1A2463 | sp-7 | an-201 | 1U2463 | sp-7 | an-201 | 1C2463 | sp-7 | an-201 |
| 1A2464 | sp-7 | an-202 | 1U2464 | sp-7 | an-202 | 1C2464 | sp-7 | an-202 |

Table 2-45

| Y = NHCS | | | Y = NHCSNH | | | Y = NHCSO | | |
|---|---|---|---|---|---|---|---|---|
| 1A2465 | sp-7 | an-203 | 1U2465 | sp-7 | an-203 | 1C2465 | sp-7 | an-203 |
| 1A2466 | sp-7 | an-204 | 1U2466 | sp-7 | an-204 | 1C2466 | sp-7 | an-204 |
| 1A2467 | sp-7 | an-205 | 1U2467 | sp-7 | an-205 | 1C2467 | sp-7 | an-205 |
| 1A2468 | sp-7 | an-206 | 1U2468 | sp-7 | an-206 | 1C2468 | sp-7 | an-206 |
| 1A2469 | sp-7 | an-207 | 1U2469 | sp-7 | an-207 | 1C2469 | sp-7 | an-207 |
| 1A2470 | sp-7 | an-208 | 1U2470 | sp-7 | an-208 | 1C2470 | sp-7 | an-208 |
| 1A2471 | sp-7 | an-209 | 1U2471 | sp-7 | an-209 | 1C2471 | sp-7 | an-209 |
| 1A2472 | sp-7 | an-210 | 1U2472 | sp-7 | an-210 | 1C2472 | sp-7 | an-210 |
| 1A2473 | sp-7 | an-211 | 1U2473 | sp-7 | an-211 | 1C2473 | sp-7 | an-211 |
| 1A2474 | sp-7 | an-212 | 1U2474 | sp-7 | an-212 | 1C2474 | sp-7 | an-212 |
| 1A2475 | sp-7 | an-213 | 1U2475 | sp-7 | an-213 | 1C2475 | sp-7 | an-213 |
| 1A2476 | sp-7 | an-214 | 1U2476 | sp-7 | an-214 | 1C2476 | sp-7 | an-214 |
| 1A2477 | sp-7 | an-215 | 1U2477 | sp-7 | an-215 | 1C2477 | sp-7 | an-215 |
| 1A2478 | sp-7 | an-216 | 1U2478 | sp-7 | an-216 | 1C2478 | sp-7 | an-216 |
| 1A2479 | sp-7 | an-217 | 1U2479 | sp-7 | an-217 | 1C2479 | sp-7 | an-217 |
| 1A2480 | sp-7 | an-218 | 1U2480 | sp-7 | an-218 | 1C2480 | sp-7 | an-218 |
| 1A2481 | sp-7 | an-219 | 1U2481 | sp-7 | an-219 | 1C2481 | sp-7 | an-219 |
| 1A2482 | sp-7 | an-220 | 1U2482 | sp-7 | an-220 | 1C2482 | sp-7 | an-220 |
| 1A2483 | sp-7 | an-221 | 1U2483 | sp-7 | an-221 | 1C2483 | sp-7 | an-221 |
| 1A2484 | sp-7 | an-222 | 1U2484 | sp-7 | an-222 | 1C2484 | sp-7 | an-222 |
| 1A2485 | sp-7 | an-223 | 1U2485 | sp-7 | an-223 | 1C2485 | sp-7 | an-223 |
| 1A2486 | sp-7 | an-224 | 1U2486 | sp-7 | an-224 | 1C2486 | sp-7 | an-224 |
| 1A2487 | sp-7 | an-225 | 1U2487 | sp-7 | an-225 | 1C2487 | sp-7 | an-225 |
| 1A2488 | sp-7 | an-226 | 1U2488 | sp-7 | an-226 | 1C2488 | sp-7 | an-226 |
| 1A2489 | sp-7 | an-227 | 1U2489 | sp-7 | an-227 | 1C2489 | sp-7 | an-227 |
| 1A2490 | sp-7 | an-228 | 1U2490 | sp-7 | an-228 | 1C2490 | sp-7 | an-228 |
| 1A2491 | sp-7 | an-229 | 1U2491 | sp-7 | an-229 | 1C2491 | sp-7 | an-229 |
| 1A2492 | sp-7 | an-230 | 1U2492 | sp-7 | an-230 | 1C2492 | sp-7 | an-230 |
| 1A2493 | sp-7 | an-231 | 1U2493 | sp-7 | an-231 | 1C2493 | sp-7 | an-231 |
| 1A2494 | sp-7 | an-232 | 1U2494 | sp-7 | an-232 | 1C2494 | sp-7 | an-232 |
| 1A2495 | sp-7 | an-233 | 1U2495 | sp-7 | an-233 | 1C2495 | sp-7 | an-233 |
| 1A2496 | sp-7 | an-234 | 1U2496 | sp-7 | an-234 | 1C2496 | sp-7 | an-234 |
| 1A2497 | sp-7 | an-235 | 1U2497 | sp-7 | an-235 | 1C2497 | sp-7 | an-235 |
| 1A2498 | sp-7 | an-236 | 1U2498 | sp-7 | an-236 | 1C2498 | sp-7 | an-236 |
| 1A2499 | sp-7 | an-237 | 1U2499 | sp-7 | an-237 | 1C2499 | sp-7 | an-237 |
| 1A2500 | sp-7 | an-238 | 1U2500 | sp-7 | an-238 | 1C2500 | sp-7 | an-238 |
| 1A2501 | sp-7 | an-239 | 1U2501 | sp-7 | an-239 | 1C2501 | sp-7 | an-239 |
| 1A2502 | sp-7 | an-240 | 1U2502 | sp-7 | an-240 | 1C2502 | sp-7 | an-240 |
| 1A2503 | sp-7 | an-241 | 1U2503 | sp-7 | an-241 | 1C2503 | sp-7 | an-241 |
| 1A2504 | sp-7 | an-242 | 1U2504 | sp-7 | an-242 | 1C2504 | sp-7 | an-242 |
| 1A2505 | sp-7 | an-243 | 1U2505 | sp-7 | an-243 | 1C2505 | sp-7 | an-243 |
| 1A2506 | sp-7 | an-244 | 1U2506 | sp-7 | an-244 | 1C2506 | sp-7 | an-244 |
| 1A2507 | sp-7 | an-245 | 1U2507 | sp-7 | an-245 | 1C2507 | sp-7 | an-245 |
| 1A2508 | sp-7 | an-246 | 1U2508 | sp-7 | an-246 | 1C2508 | sp-7 | an-246 |

| Ex. No. | Z | N⁺R⁵R⁶R⁷ | Ex. No. | Z | N⁺R⁵R⁶R⁷ | Ex. No. | Z | N⁺R⁵R⁶R⁷ |
|---|---|---|---|---|---|---|---|---|
| 1A2509 | sp-7 | an-247 | 1U2509 | sp-7 | an-247 | 1C2509 | sp-7 | an-247 |
| 1A2510 | sp-7 | an-248 | 1U2510 | sp-7 | an-248 | 1C2510 | sp-7 | an-248 |
| 1A2511 | sp-7 | an-249 | 1U2511 | sp-7 | an-249 | 1C2511 | sp-7 | an-249 |
| 1A2512 | sp-7 | an-250 | 1U2512 | sp-7 | an-250 | 1C2512 | sp-7 | an-250 |
| 1A2513 | sp-7 | an-251 | 1U2513 | sp-7 | an-251 | 1C2513 | sp-7 | an-251 |
| 1A2514 | sp-7 | an-252 | 1U2514 | sp-7 | an-252 | 1C2514 | sp-7 | an-252 |
| 1A2515 | sp-7 | an-253 | 1U2515 | sp-7 | an-253 | 1C2515 | sp-7 | an-253 |
| 1A2516 | sp-7 | an-254 | 1U2516 | sp-7 | an-254 | 1C2516 | sp-7 | an-254 |
| 1A2517 | sp-7 | an-255 | 1U2517 | sp-7 | an-255 | 1C2517 | sp-7 | an-255 |
| 1A2518 | sp-7 | an-256 | 1U2518 | sp-7 | an-256 | 1C2518 | sp-7 | an-256 |
| 1A2519 | sp-7 | an-257 | 1U2519 | sp-7 | an-257 | 1C2519 | sp-7 | an-257 |
| 1A2520 | sp-7 | an-258 | 1U2520 | sp-7 | an-258 | 1C2520 | sp-7 | an-258 |

Table 2-46

| Y = NHCS | | Y = NHCSNH | | Y = NHCSO | | | | |
|---|---|---|---|---|---|---|---|---|
| 1A2521 | sp-7 | an-259 | 1U2521 | sp-7 | an-259 | 1C2521 | sp-7 | an-259 |
| 1A2522 | sp-7 | an-260 | 1U2522 | sp-7 | an-260 | 1C2522 | sp-7 | an-260 |
| 1A2523 | sp-7 | an-261 | 1U2523 | sp-7 | an-261 | 1C2523 | sp-7 | an-261 |
| 1A2524 | sp-7 | an-262 | 1U2524 | sp-7 | an-262 | 1C2524 | sp-7 | an-262 |
| 1A2525 | sp-7 | an-263 | 1U2525 | sp-7 | an-263 | 1C2525 | sp-7 | an-263 |
| 1A2526 | sp-7 | an-264 | 1U2526 | sp-7 | an-264 | 1C2526 | sp-7 | an-264 |
| 1A2527 | sp-7 | an-265 | 1U2527 | sp-7 | an-265 | 1C2527 | sp-7 | an-265 |
| 1A2528 | sp-7 | an-266 | 1U2528 | sp-7 | an-266 | 1C2528 | sp-7 | an-266 |
| 1A2529 | sp-7 | an-267 | 1U2529 | sp-7 | an-267 | 1C2529 | sp-7 | an-267 |
| 1A2530 | sp-7 | an-268 | 1U2530 | sp-7 | an-268 | 1C2530 | sp-7 | an-268 |
| 1A2531 | sp-7 | an-269 | 1U2531 | sp-7 | an-269 | 1C2531 | sp-7 | an-269 |
| 1A2532 | sp-7 | an-270 | 1U2532 | sp-7 | an-270 | 1C2532 | sp-7 | an-270 |
| 1A2533 | sp-7 | an-271 | 1U2533 | sp-7 | an-271 | 1C2533 | sp-7 | an-271 |
| 1A2534 | sp-7 | an-272 | 1U2534 | sp-7 | an-272 | 1C2534 | sp-7 | an-272 |
| 1A2535 | sp-7 | an-273 | 1U2535 | sp-7 | an-273 | 1C2535 | sp-7 | an-273 |
| 1A2536 | sp-7 | an-274 | 1U2536 | sp-7 | an-274 | 1C2536 | sp-7 | an-274 |
| 1A2537 | sp-7 | an-275 | 1U2537 | sp-7 | an-275 | 1C2537 | sp-7 | an-275 |
| 1A2538 | sp-7 | an-276 | 1U2538 | sp-7 | an-276 | 1C2538 | sp-7 | an-276 |
| 1A2539 | sp-7 | an-277 | 1U2539 | sp-7 | an-277 | 1C2539 | sp-7 | an-277 |
| 1A2540 | sp-7 | an-278 | 1U2540 | sp-7 | an-278 | 1C2540 | sp-7 | an-278 |
| 1A2541 | sp-7 | an-279 | 1U2541 | sp-7 | an-279 | 1C2541 | sp-7 | an-279 |
| 1A2542 | sp-7 | an-280 | 1U2542 | sp-7 | an-280 | 1C2542 | sp-7 | an-280 |
| 1A2543 | sp-7 | an-281 | 1U2543 | sp-7 | an-281 | 1C2543 | sp-7 | an-281 |
| 1A2544 | sp-7 | an-282 | 1U2544 | sp-7 | an-282 | 1C2544 | sp-7 | an-282 |
| 1A2545 | sp-7 | an-283 | 1U2545 | sp-7 | an-283 | 1C2545 | sp-7 | an-283 |
| 1A2546 | sp-7 | an-284 | 1U2546 | sp-7 | an-284 | 1C2546 | sp-7 | an-284 |
| 1A2547 | sp-7 | an-285 | 1U2547 | sp-7 | an-285 | 1C2547 | sp-7 | an-285 |
| 1A2548 | sp-7 | an-286 | 1U2548 | sp-7 | an-286 | 1C2548 | sp-7 | an-286 |
| 1A2549 | sp-7 | an-287 | 1U2549 | sp-7 | an-287 | 1C2549 | sp-7 | an-287 |
| 1A2550 | sp-7 | an-288 | 1U2550 | sp-7 | an-288 | 1C2550 | sp-7 | an-288 |
| 1A2551 | sp-7 | an-289 | 1U2551 | sp-7 | an-289 | 1C2551 | sp-7 | an-289 |
| 1A2552 | sp-7 | an-290 | 1U2552 | sp-7 | an-290 | 1C2552 | sp-7 | an-290 |
| 1A2553 | sp-7 | an-291 | 1U2553 | sp-7 | an-291 | 1C2553 | sp-7 | an-291 |
| 1A2554 | sp-7 | an-292 | 1U2554 | sp-7 | an-292 | 1C2554 | sp-7 | an-292 |
| 1A2555 | sp-7 | an-293 | 1U2555 | sp-7 | an-293 | 1C2555 | sp-7 | an-293 |
| 1A2556 | sp-7 | an-294 | 1U2556 | sp-7 | an-294 | 1C2556 | sp-7 | an-294 |
| 1A2557 | sp-7 | an-295 | 1U2557 | sp-7 | an-295 | 1C2557 | sp-7 | an-295 |
| 1A2558 | sp-7 | an-296 | 1U2558 | sp-7 | an-296 | 1C2558 | sp-7 | an-296 |
| 1A2559 | sp-7 | an-297 | 1U2559 | sp-7 | an-297 | 1C2559 | sp-7 | an-297 |
| 1A2560 | sp-7 | an-298 | 1U2560 | sp-7 | an-298 | 1C2560 | sp-7 | an-298 |
| 1A2561 | sp-7 | an-299 | 1U2561 | sp-7 | an-299 | 1C2561 | sp-7 | an-299 |
| 1A2562 | sp-7 | an-300 | 1U2562 | sp-7 | an-300 | 1C2562 | sp-7 | an-300 |
| 1A2563 | sp-7 | an-301 | 1U2563 | sp-7 | an-301 | 1C2563 | sp-7 | an-301 |
| 1A2564 | sp-7 | an-302 | 1U2564 | sp-7 | an-302 | 1C2564 | sp-7 | an-302 |
| 1A2565 | sp-7 | an-303 | 1U2565 | sp-7 | an-303 | 1C2565 | sp-7 | an-303 |
| 1A2566 | sp-7 | an-304 | 1U2566 | sp-7 | an-304 | 1C2566 | sp-7 | an-304 |
| 1A2567 | sp-7 | an-305 | 1U2567 | sp-7 | an-305 | 1C2567 | sp-7 | an-305 |
| 1A2568 | sp-7 | an-306 | 1U2568 | sp-7 | an-306 | 1C2568 | sp-7 | an-306 |
| 1A2569 | sp-7 | an-307 | 1U2569 | sp-7 | an-307 | 1C2569 | sp-7 | an-307 |
| 1A2570 | sp-7 | an-308 | 1U2570 | sp-7 | an-308 | 1C2570 | sp-7 | an-308 |
| 1A2571 | sp-7 | an-309 | 1U2571 | sp-7 | an-309 | 1C2571 | sp-7 | an-309 |
| 1A2572 | sp-7 | an-310 | 1U2572 | sp-7 | an-310 | 1C2572 | sp-7 | an-310 |
| 1A2573 | sp-7 | an-311 | 1U2573 | sp-7 | an-311 | 1C2573 | sp-7 | an-311 |
| 1A2574 | sp-7 | an-312 | 1U2574 | sp-7 | an-312 | 1C2574 | sp-7 | an-312 |
| 1A2575 | sp-7 | an-313 | 1U2575 | sp-7 | an-313 | 1C2575 | sp-7 | an-313 |
| 1A2576 | sp-7 | an-314 | 1U2576 | sp-7 | an-314 | 1C2576 | sp-7 | an-314 |

Table 2-47

| Y = NHCS | | Y = NHCSNH | | Y = NHCSO | | | | |
|---|---|---|---|---|---|---|---|---|
| 1A2577 | sp-7 | an-315 | 1U2577 | sp-7 | an-315 | 1C2577 | sp-7 | an-315 |
| 1A2578 | sp-7 | an-316 | 1U2578 | sp-7 | an-316 | 1C2578 | sp-7 | an-316 |

| Ex. No. | Z | N⁺R⁵R⁶R⁷ | Ex. No. | Z | N⁺R⁵R⁶R⁷ | Ex. No. | Z | N⁺R⁵R⁶R⁷ |
|---|---|---|---|---|---|---|---|---|
| 1A2579 | sp-7 | an-317 | 1U2579 | sp-7 | an-317 | 1C2579 | sp-7 | an-317 |
| 1A2580 | sp-7 | an-318 | 1U2580 | sp-7 | an-318 | 1C2580 | sp-7 | an-318 |
| 1A2581 | sp-7 | an-319 | 1U2581 | sp-7 | an-319 | 1C2581 | sp-7 | an-319 |
| 1A2582 | sp-7 | an-320 | 1U2582 | sp-7 | an-320 | 1C2582 | sp-7 | an-320 |
| 1A2583 | sp-7 | an-321 | 1U2583 | sp-7 | an-321 | 1C2583 | sp-7 | an-321 |
| 1A2584 | sp-7 | an-322 | 1U2584 | sp-7 | an-322 | 1C2584 | sp-7 | an-322 |
| 1A2585 | sp-7 | an-323 | 1U2585 | sp-7 | an-323 | 1C2585 | sp-7 | an-323 |
| 1A2586 | sp-7 | an-324 | 1U2586 | sp-7 | an-324 | 1C2586 | sp-7 | an-324 |
| 1A2587 | sp-7 | an-325 | 1U2587 | sp-7 | an-325 | 1C2587 | sp-7 | an-325 |
| 1A2588 | sp-7 | an-326 | 1U2588 | sp-7 | an-326 | 1C2588 | sp-7 | an-326 |
| 1A2589 | sp-7 | an-327 | 1U2589 | sp-7 | an-327 | 1C2589 | sp-7 | an-327 |
| 1A2590 | sp-7 | an-328 | 1U2590 | sp-7 | an-328 | 1C2590 | sp-7 | an-328 |
| 1A2591 | sp-7 | an-329 | 1U2591 | sp-7 | an-329 | 1C2591 | sp-7 | an-329 |
| 1A2592 | sp-7 | an-330 | 1U2592 | sp-7 | an-330 | 1C2592 | sp-7 | an-330 |
| 1A2593 | sp-7 | an-331 | 1U2593 | sp-7 | an-331 | 1C2593 | sp-7 | an-331 |
| 1A2594 | sp-7 | an-332 | 1U2594 | sp-7 | an-332 | 1C2594 | sp-7 | an-332 |
| 1A2595 | sp-7 | an-333 | 1U2595 | sp-7 | an-333 | 1C2595 | sp-7 | an-333 |
| 1A2596 | sp-7 | an-334 | 1U2596 | sp-7 | an-334 | 1C2596 | sp-7 | an-334 |
| 1A2597 | sp-7 | an-335 | 1U2597 | sp-7 | an-335 | 1C2597 | sp-7 | an-335 |
| 1A2598 | sp-7 | an-336 | 1U2598 | sp-7 | an-336 | 1C2598 | sp-7 | an-336 |
| 1A2599 | sp-7 | an-337 | 1U2599 | sp-7 | an-337 | 1C2599 | sp-7 | an-337 |
| 1A2600 | sp-7 | an-338 | 1U2600 | sp-7 | an-338 | 1C2600 | sp-7 | an-338 |
| 1A2601 | sp-7 | an-339 | 1U2601 | sp-7 | an-339 | 1C2601 | sp-7 | an-339 |
| 1A2602 | sp-7 | an-340 | 1U2602 | sp-7 | an-340 | 1C2602 | sp-7 | an-340 |
| 1A2603 | sp-7 | an-341 | 1U2603 | sp-7 | an-341 | 1C2603 | sp-7 | an-341 |
| 1A2604 | sp-7 | an-342 | 1U2604 | sp-7 | an-342 | 1C2604 | sp-7 | an-342 |
| 1A2605 | sp-7 | an-343 | 1U2605 | sp-7 | an-343 | 1C2605 | sp-7 | an-343 |
| 1A2606 | sp-7 | an-344 | 1U2606 | sp-7 | an-344 | 1C2606 | sp-7 | an-344 |
| 1A2607 | sp-7 | an-345 | 1U2607 | sp-7 | an-345 | 1C2607 | sp-7 | an-345 |
| 1A2608 | sp-7 | an-346 | 1U2608 | sp-7 | an-346 | 1C2608 | sp-7 | an-346 |
| 1A2609 | sp-7 | an-347 | 1U2609 | sp-7 | an-347 | 1C2609 | sp-7 | an-347 |
| 1A2610 | sp-7 | an-348 | 1U2610 | sp-7 | an-348 | 1C2610 | sp-7 | an-348 |
| 1A2611 | sp-7 | an-349 | 1U2611 | sp-7 | an-349 | 1C2611 | sp-7 | an-349 |
| 1A2612 | sp-7 | an-350 | 1U2612 | sp-7 | an-350 | 1C2612 | sp-7 | an-350 |
| 1A2613 | sp-7 | an-351 | 1U2613 | sp-7 | an-351 | 1C2613 | sp-7 | an-351 |
| 1A2614 | sp-7 | an-352 | 1U2614 | sp-7 | an-352 | 1C2614 | sp-7 | an-352 |
| 1A2615 | sp-7 | an-353 | 1U2615 | sp-7 | an-353 | 1C2615 | sp-7 | an-353 |
| 1A2616 | sp-7 | an-354 | 1U2616 | sp-7 | an-354 | 1C2616 | sp-7 | an-354 |
| 1A2617 | sp-7 | an-355 | 1U2617 | sp-7 | an-355 | 1C2617 | sp-7 | an-355 |
| 1A2618 | sp-7 | an-356 | 1U2618 | sp-7 | an-356 | 1C2618 | sp-7 | an-356 |
| 1A2619 | sp-7 | an-357 | 1U2619 | sp-7 | an-357 | 1C2619 | sp-7 | an-357 |
| 1A2620 | sp-7 | an-358 | 1U2620 | sp-7 | an-358 | 1C2620 | sp-7 | an-358 |
| 1A2621 | sp-7 | an-359 | 1U2621 | sp-7 | an-359 | 1C2621 | sp-7 | an-359 |
| 1A2622 | sp-7 | an-360 | 1U2622 | sp-7 | an-360 | 1C2622 | sp-7 | an-360 |
| 1A2623 | sp-7 | an-361 | 1U2623 | sp-7 | an-361 | 1C2623 | sp-7 | an-361 |
| 1A2624 | sp-7 | an-362 | 1U2624 | sp-7 | an-362 | 1C2624 | sp-7 | an-362 |
| 1A2625 | sp-7 | an-363 | 1U2625 | sp-7 | an-363 | 1C2625 | sp-7 | an-363 |
| 1A2626 | sp-7 | an-364 | 1U2626 | sp-7 | an-364 | 1C2626 | sp-7 | an-364 |
| 1A2627 | sp-7 | an-365 | 1U2627 | sp-7 | an-365 | 1C2627 | sp-7 | an-365 |
| 1A2628 | sp-7 | an-366 | 1U2628 | sp-7 | an-366 | 1C2628 | sp-7 | an-366 |
| 1A2629 | sp-7 | an-367 | 1U2629 | sp-7 | an-367 | 1C2629 | sp-7 | an-367 |
| 1A2630 | sp-7 | an-368 | 1U2630 | sp-7 | an-368 | 1C2630 | sp-7 | an-368 |
| 1A2631 | sp-7 | an-369 | 1U2631 | sp-7 | an-369 | 1C2631 | sp-7 | an-369 |
| 1A2632 | sp-7 | an-370 | 1U2632 | sp-7 | an-370 | 1C2632 | sp-7 | an-370 |

Table 2-48

| Y = NHCS | | | Y = NHCSNH | | | Y = NHCSO | | |
|---|---|---|---|---|---|---|---|---|
| 1A2633 | sp-7 | an-371 | 1U2633 | sp-7 | an-371 | 1C2633 | sp-7 | an-371 |
| 1A2634 | sp-7 | an-372 | 1U2634 | sp-7 | an-372 | 1C2634 | sp-7 | an-372 |
| 1A2635 | sp-7 | an-373 | 1U2635 | sp-7 | an-373 | 1C2635 | sp-7 | an-373 |
| 1A2636 | sp-7 | an-374 | 1U2636 | sp-7 | an-374 | 1C2636 | sp-7 | an-374 |
| 1A2637 | sp-7 | an-375 | 1U2637 | sp-7 | an-375 | 1C2637 | sp-7 | an-375 |
| 1A2638 | sp-7 | an-376 | 1U2638 | sp-7 | an-376 | 1C2638 | sp-7 | an-376 |
| 1A2639 | sp-7 | an-377 | 1U2639 | sp-7 | an-377 | 1C2639 | sp-7 | an-377 |
| 1A2640 | sp-8 | an-1 | 1U2640 | sp-8 | an-1 | 1C2640 | sp-8 | an-1 |
| 1A2641 | sp-8 | an-2 | 1U2641 | sp-8 | an-2 | 1C2641 | sp-8 | an-2 |
| 1A2642 | sp-8 | an-3 | 1U2642 | sp-8 | an-3 | 1C2642 | sp-8 | an-3 |
| 1A2643 | sp-8 | an-4 | 1U2643 | sp-8 | an-4 | 1C2643 | sp-8 | an-4 |
| 1A2644 | sp-8 | an-5 | 1U2644 | sp-8 | an-5 | 1C2644 | sp-8 | an-5 |
| 1A2645 | sp-8 | an-6 | 1U2645 | sp-8 | an-6 | 1C2645 | sp-8 | an-6 |
| 1A2646 | sp-8 | an-7 | 1U2646 | sp-8 | an-7 | 1C2646 | sp-8 | an-7 |
| 1A2647 | sp-8 | an-8 | 1U2647 | sp-8 | an-8 | 1C2647 | sp-8 | an-8 |
| 1A2648 | sp-8 | an-9 | 1U2648 | sp-8 | an-9 | 1C2648 | sp-8 | an-9 |
| 1A2649 | sp-8 | an-10 | 1U2649 | sp-8 | an-10 | 1C2649 | sp-8 | an-10 |
| 1A2650 | sp-8 | an-11 | 1U2650 | sp-8 | an-11 | 1C2650 | sp-8 | an-11 |
| 1A2651 | sp-8 | an-12 | 1U2651 | sp-8 | an-12 | 1C2651 | sp-8 | an-12 |
| 1A2652 | sp-8 | an-13 | 1U2652 | sp-8 | an-13 | 1C2652 | sp-8 | an-13 |

| Ex. No. | Z | N+R5R6R7 | Ex. No. | Z | N+R5R6R7 | Ex. No. | Z | N+R5R6R7 |
|---|---|---|---|---|---|---|---|---|
| 1A2653 | sp-8 | an-14 | 1U2653 | sp-8 | an-14 | 1C2653 | sp-8 | an-14 |
| 1A2654 | sp-8 | an-15 | 1U2654 | sp-8 | an-15 | 1C2654 | sp-8 | an-15 |
| 1A2655 | sp-8 | an-16 | 1U2655 | sp-8 | an-16 | 1C2655 | sp-8 | an-16 |
| 1A2656 | sp-8 | an-17 | 1U2656 | sp-8 | an-17 | 1C2656 | sp-8 | an-17 |
| 1A2657 | sp-8 | an-18 | 1U2657 | sp-8 | an-18 | 1C2657 | sp-8 | an-18 |
| 1A2658 | sp-8 | an-19 | 1U2658 | sp-8 | an-19 | 1C2658 | sp-8 | an-19 |
| 1A2659 | sp-8 | an-20 | 1U2659 | sp-8 | an-20 | 1C2659 | sp-8 | an-20 |
| 1A2660 | sp-8 | an-21 | 1U2660 | sp-8 | an-21 | 1C2660 | sp-8 | an-21 |
| 1A2661 | sp-8 | an-22 | 1U2661 | sp-8 | an-22 | 1C2661 | sp-8 | an-22 |
| 1A2662 | sp-8 | an-23 | 1U2662 | sp-8 | an-23 | 1C2662 | sp-8 | an-23 |
| 1A2663 | sp-8 | an-24 | 1U2663 | sp-8 | an-24 | 1C2663 | sp-8 | an-24 |
| 1A2664 | sp-8 | an-25 | 1U2664 | sp-8 | an-25 | 1C2664 | sp-8 | an-25 |
| 1A2665 | sp-8 | an-26 | 1U2665 | sp-8 | an-26 | 1C2665 | sp-8 | an-26 |
| 1A2666 | sp-8 | an-27 | 1U2666 | sp-8 | an-27 | 1C2666 | sp-8 | an-27 |
| 1A2667 | sp-8 | an-28 | 1U2667 | sp-8 | an-28 | 1C2667 | sp-8 | an-28 |
| 1A2668 | sp-8 | an-29 | 1U2668 | sp-8 | an-29 | 1C2668 | sp-8 | an-29 |
| 1A2669 | sp-8 | an-30 | 1U2669 | sp-8 | an-30 | 1C2669 | sp-8 | an-30 |
| 1A2670 | sp-8 | an-31 | 1U2670 | sp-8 | an-31 | 1C2670 | sp-8 | an-31 |
| 1A2671 | sp-8 | an-32 | 1U2671 | sp-8 | an-32 | 1C2671 | sp-8 | an-32 |
| 1A2672 | sp-8 | an-33 | 1U2672 | sp-8 | an-33 | 1C2672 | sp-8 | an-33 |
| 1A2673 | sp-8 | an-34 | 1U2673 | sp-8 | an-34 | 1C2673 | sp-8 | an-34 |
| 1A2674 | sp-8 | an-35 | 1U2674 | sp-8 | an-35 | 1C2674 | sp-8 | an-35 |
| 1A2675 | sp-8 | an-36 | 1U2675 | sp-8 | an-36 | 1C2675 | sp-8 | an-36 |
| 1A2676 | sp-8 | an-37 | 1U2676 | sp-8 | an-37 | 1C2676 | sp-8 | an-37 |
| 1A2677 | sp-8 | an-38 | 1U2677 | sp-8 | an-38 | 1C2677 | sp-8 | an-38 |
| 1A2678 | sp-8 | an-39 | 1U2678 | sp-8 | an-39 | 1C2678 | sp-8 | an-39 |
| 1A2679 | sp-8 | an-40 | 1U2679 | sp-8 | an-40 | 1C2679 | sp-8 | an-40 |
| 1A2680 | sp-8 | an-41 | 1U2680 | sp-8 | an-41 | 1C2680 | sp-8 | an-41 |
| 1A2681 | sp-8 | an-42 | 1U2681 | sp-8 | an-42 | 1C2681 | sp-8 | an-42 |
| 1A2682 | sp-8 | an-43 | 1U2682 | sp-8 | an-43 | 1C2682 | sp-8 | an-43 |
| 1A2683 | sp-8 | an-44 | 1U2683 | sp-8 | an-44 | 1C2683 | sp-8 | an-44 |
| 1A2684 | sp-8 | an-45 | 1U2684 | sp-8 | an-45 | 1C2684 | sp-8 | an-45 |
| 1A2685 | sp-8 | an-46 | 1U2685 | sp-8 | an-46 | 1C2685 | sp-8 | an-46 |
| 1A2686 | sp-8 | an-47 | 1U2686 | sp-8 | an-47 | 1C2686 | sp-8 | an-47 |
| 1A2687 | sp-8 | an-48 | 1U2687 | sp-8 | an-48 | 1C2687 | sp-8 | an-48 |
| 1A2688 | sp-8 | an-49 | 1U2688 | sp-8 | an-49 | 1C2688 | sp-8 | an-49 |

Table 2-49

| | Y = NHCS | | | Y = NHCSNH | | | Y = NHCSO | |
|---|---|---|---|---|---|---|---|---|
| 1A2689 | sp-8 | an-50 | 1U2689 | sp-8 | an-50 | 1C2689 | sp-8 | an-50 |
| 1A2690 | sp-8 | an-51 | 1U2690 | sp-8 | an-51 | 1C2690 | sp-8 | an-51 |
| 1A2691 | sp-8 | an-52 | 1U2691 | sp-8 | an-52 | 1C2691 | sp-8 | an-52 |
| 1A2692 | sp-8 | an-53 | 1U2692 | sp-8 | an-53 | 1C2692 | sp-8 | an-53 |
| 1A2693 | sp-8 | an-54 | 1U2693 | sp-8 | an-54 | 1C2693 | sp-8 | an-54 |
| 1A2694 | sp-8 | an-55 | 1U2694 | sp-8 | an-55 | 1C2694 | sp-8 | an-55 |
| 1A2695 | sp-8 | an-56 | 1U2695 | sp-8 | an-56 | 1C2695 | sp-8 | an-56 |
| 1A2696 | sp-8 | an-57 | 1U2696 | sp-8 | an-57 | 1C2696 | sp-8 | an-57 |
| 1A2697 | sp-8 | an-58 | 1U2697 | sp-8 | an-58 | 1C2697 | sp-8 | an-58 |
| 1A2698 | sp-8 | an-59 | 1U2698 | sp-8 | an-59 | 1C2698 | sp-8 | an-59 |
| 1A2699 | sp-8 | an-60 | 1U2699 | sp-8 | an-60 | 1C2699 | sp-8 | an-60 |
| 1A2700 | sp-8 | an-61 | 1U2700 | sp-8 | an-61 | 1C2700 | sp-8 | an-61 |
| 1A2701 | sp-8 | an-62 | 1U2701 | sp-8 | an-62 | 1C2701 | sp-8 | an-62 |
| 1A2702 | sp-8 | an-63 | 1U2702 | sp-8 | an-63 | 1C2702 | sp-8 | an-63 |
| 1A2703 | sp-8 | an-64 | 1U2703 | sp-8 | an-64 | 1C2703 | sp-8 | an-64 |
| 1A2704 | sp-8 | an-65 | 1U2704 | sp-8 | an-65 | 1C2704 | sp-8 | an-65 |
| 1A2705 | sp-8 | an-66 | 1U2705 | sp-8 | an-66 | 1C2705 | sp-8 | an-66 |
| 1A2706 | sp-8 | an-67 | 1U2706 | sp-8 | an-67 | 1C2706 | sp-8 | an-67 |
| 1A2707 | sp-8 | an-68 | 1U2707 | sp-8 | an-68 | 1C2707 | sp-8 | an-68 |
| 1A2708 | sp-8 | an-69 | 1U2708 | sp-8 | an-69 | 1C2708 | sp-8 | an-69 |
| 1A2709 | sp-8 | an-70 | 1U2709 | sp-8 | an-70 | 1C2709 | sp-8 | an-70 |
| 1A2710 | sp-8 | an-71 | 1U2710 | sp-8 | an-71 | 1C2710 | sp-8 | an-71 |
| 1A2711 | sp-8 | an-72 | 1U2711 | sp-8 | an-72 | 1C2711 | sp-8 | an-72 |
| 1A2712 | sp-8 | an-73 | 1U2712 | sp-8 | an-73 | 1C2712 | sp-8 | an-73 |
| 1A2713 | sp-8 | an-74 | 1U2713 | sp-8 | an-74 | 1C2713 | sp-8 | an-74 |
| 1A2714 | sp-8 | an-75 | 1U2714 | sp-8 | an-75 | 1C2714 | sp-8 | an-75 |
| 1A2715 | sp-8 | an-76 | 1U2715 | sp-8 | an-76 | 1C2715 | sp-8 | an-76 |
| 1A2716 | sp-8 | an-77 | 1U2716 | sp-8 | an-77 | 1C2716 | sp-8 | an-77 |
| 1A2717 | sp-8 | an-78 | 1U2717 | sp-8 | an-78 | 1C2717 | sp-8 | an-78 |
| 1A2718 | sp-8 | an-79 | 1U2718 | sp-8 | an-79 | 1C2718 | sp-8 | an-79 |
| 1A2719 | sp-8 | an-80 | 1U2719 | sp-8 | an-80 | 1C2719 | sp-8 | an-80 |
| 1A2720 | sp-8 | an-81 | 1U2720 | sp-8 | an-81 | 1C2720 | sp-8 | an-81 |
| 1A2721 | sp-8 | an-82 | 1U2721 | sp-8 | an-82 | 1C2721 | sp-8 | an-82 |
| 1A2722 | sp-8 | an-83 | 1U2722 | sp-8 | an-83 | 1C2722 | sp-8 | an-83 |
| 1A2723 | sp-8 | an-84 | 1U2723 | sp-8 | an-84 | 1C2723 | sp-8 | an-84 |
| 1A2724 | sp-8 | an-85 | 1U2724 | sp-8 | an-85 | 1C2724 | sp-8 | an-85 |
| 1A2725 | sp-8 | an-86 | 1U2725 | sp-8 | an-86 | 1C2725 | sp-8 | an-86 |
| 1A2726 | sp-8 | an-87 | 1U2726 | sp-8 | an-87 | 1C2726 | sp-8 | an-87 |

| Ex. No. | Z | N⁺R⁵R⁶R⁷ | Ex. No. | Z | N⁺R⁵R⁶R⁷ | Ex. No. | Z | N⁺R⁵R⁶R⁷ |
|---|---|---|---|---|---|---|---|---|
| 1A2727 | sp-8 | an-88 | 1U2727 | sp-8 | an-88 | 1C2727 | sp-8 | an-88 |
| 1A2728 | sp-8 | an-89 | 1U2728 | sp-8 | an-89 | 1C2728 | sp-8 | an-89 |
| 1A2729 | sp-8 | an-90 | 1U2729 | sp-8 | an-90 | 1C2729 | sp-8 | an-90 |
| 1A2730 | sp-8 | an-91 | 1U2730 | sp-8 | an-91 | 1C2730 | sp-8 | an-91 |
| 1A2731 | sp-8 | an-92 | 1U2731 | sp-8 | an-92 | 1C2731 | sp-8 | an-92 |
| 1A2732 | sp-8 | an-93 | 1U2732 | sp-8 | an-93 | 1C2732 | sp-8 | an-93 |
| 1A2733 | sp-8 | an-94 | 1U2733 | sp-8 | an-94 | 1C2733 | sp-8 | an-94 |
| 1A2734 | sp-8 | an-95 | 1U2734 | sp-8 | an-95 | 1C2734 | sp-8 | an-95 |
| 1A2735 | sp-8 | an-96 | 1U2735 | sp-8 | an-96 | 1C2735 | sp-8 | an-96 |
| 1A2736 | sp-8 | an-97 | 1U2736 | sp-8 | an-97 | 1C2736 | sp-8 | an-97 |
| 1A2737 | sp-8 | an-98 | 1U2737 | sp-8 | an-98 | 1C2737 | sp-8 | an-98 |
| 1A2738 | sp-8 | an-99 | 1U2738 | sp-8 | an-99 | 1C2738 | sp-8 | an-99 |
| 1A2739 | sp-8 | an-100 | 1U2739 | sp-8 | an-100 | 1C2739 | sp-8 | an-100 |
| 1A2740 | sp-8 | an-101 | 1U2740 | sp-8 | an-101 | 1C2740 | sp-8 | an-101 |
| 1A2741 | sp-8 | an-102 | 1U2741 | sp-8 | an-102 | 1C2741 | sp-8 | an-102 |
| 1A2742 | sp-8 | an-103 | 1U2742 | sp-8 | an-103 | 1C2742 | sp-8 | an-103 |
| 1A2743 | sp-8 | an-104 | 1U2743 | sp-8 | an-104 | 1C2743 | sp-8 | an-104 |
| 1A2744 | sp-8 | an-105 | 1U2744 | sp-8 | an-105 | 1C2744 | sp-8 | an-105 |

Table 2-50

| Y = NHCS | | | Y = NHCSNH | | | Y = NHCSO | | |
|---|---|---|---|---|---|---|---|---|
| 1A2745 | sp-8 | an-106 | 1U2745 | sp-8 | an-106 | 1C2745 | sp-8 | an-106 |
| 1A2746 | sp-8 | an-107 | 1U2746 | sp-8 | an-107 | 1C2746 | sp-8 | an-107 |
| 1A2747 | sp-8 | an-108 | 1U2747 | sp-8 | an-108 | 1C2747 | sp-8 | an-108 |
| 1A2748 | sp-8 | an-109 | 1U2748 | sp-8 | an-109 | 1C2748 | sp-8 | an-109 |
| 1A2749 | sp-8 | an-110 | 1U2749 | sp-8 | an-110 | 1C2749 | sp-8 | an-110 |
| 1A2750 | sp-8 | an-111 | 1U2750 | sp-8 | an-111 | 1C2750 | sp-8 | an-111 |
| 1A2751 | sp-8 | an-112 | 1U2751 | sp-8 | an-112 | 1C2751 | sp-8 | an-112 |
| 1A2752 | sp-8 | an-113 | 1U2752 | sp-8 | an-113 | 1C2752 | sp-8 | an-113 |
| 1A2753 | sp-8 | an-114 | 1U2753 | sp-8 | an-114 | 1C2753 | sp-8 | an-114 |
| 1A2754 | sp-8 | an-115 | 1U2754 | sp-8 | an-115 | 1C2754 | sp-8 | an-115 |
| 1A2755 | sp-8 | an-116 | 1U2755 | sp-8 | an-116 | 1C2755 | sp-8 | an-116 |
| 1A2756 | sp-8 | an-117 | 1U2756 | sp-8 | an-117 | 1C2756 | sp-8 | an-117 |
| 1A2757 | sp-8 | an-118 | 1U2757 | sp-8 | an-118 | 1C2757 | sp-8 | an-118 |
| 1A2758 | sp-8 | an-119 | 1U2758 | sp-8 | an-119 | 1C2758 | sp-8 | an-119 |
| 1A2759 | sp-8 | an-120 | 1U2759 | sp-8 | an-120 | 1C2759 | sp-8 | an-120 |
| 1A2760 | sp-8 | an-121 | 1U2760 | sp-8 | an-121 | 1C2760 | sp-8 | an-121 |
| 1A2761 | sp-8 | an-122 | 1U2761 | sp-8 | an-122 | 1C2761 | sp-8 | an-122 |
| 1A2762 | sp-8 | an-123 | 1U2762 | sp-8 | an-123 | 1C2762 | sp-8 | an-123 |
| 1A2763 | sp-8 | an-124 | 1U2763 | sp-8 | an-124 | 1C2763 | sp-8 | an-124 |
| 1A2764 | sp-8 | an-125 | 1U2764 | sp-8 | an-125 | 1C2764 | sp-8 | an-125 |
| 1A2765 | sp-8 | an-126 | 1U2765 | sp-8 | an-126 | 1C2765 | sp-8 | an-126 |
| 1A2766 | sp-8 | an-127 | 1U2766 | sp-8 | an-127 | 1C2766 | sp-8 | an-127 |
| 1A2767 | sp-8 | an-128 | 1U2767 | sp-8 | an-128 | 1C2767 | sp-8 | an-128 |
| 1A2768 | sp-8 | an-129 | 1U2768 | sp-8 | an-129 | 1C2768 | sp-8 | an-129 |
| 1A2769 | sp-8 | an-130 | 1U2769 | sp-8 | an-130 | 1C2769 | sp-8 | an-130 |
| 1A2770 | sp-8 | an-131 | 1U2770 | sp-8 | an-131 | 1C2770 | sp-8 | an-131 |
| 1A2771 | sp-8 | an-132 | 1U2771 | sp-8 | an-132 | 1C2771 | sp-8 | an-132 |
| 1A2772 | sp-8 | an-133 | 1U2772 | sp-8 | an-133 | 1C2772 | sp-8 | an-133 |
| 1A2773 | sp-8 | an-134 | 1U2773 | sp-8 | an-134 | 1C2773 | sp-8 | an-134 |
| 1A2774 | sp-8 | an-135 | 1U2774 | sp-8 | an-135 | 1C2774 | sp-8 | an-135 |
| 1A2775 | sp-8 | an-136 | 1U2775 | sp-8 | an-136 | 1C2775 | sp-8 | an-136 |
| 1A2776 | sp-8 | an-137 | 1U2776 | sp-8 | an-137 | 1C2776 | sp-8 | an-137 |
| 1A2777 | sp-8 | an-138 | 1U2777 | sp-8 | an-138 | 1C2777 | sp-8 | an-138 |
| 1A2778 | sp-8 | an-139 | 1U2778 | sp-8 | an-139 | 1C2778 | sp-8 | an-139 |
| 1A2779 | sp-8 | an-140 | 1U2779 | sp-8 | an-140 | 1C2779 | sp-8 | an-140 |
| 1A2780 | sp-8 | an-141 | 1U2780 | sp-8 | an-141 | 1C2780 | sp-8 | an-141 |
| 1A2781 | sp-8 | an-142 | 1U2781 | sp-8 | an-142 | 1C2781 | sp-8 | an-142 |
| 1A2782 | sp-8 | an-143 | 1U2782 | sp-8 | an-143 | 1C2782 | sp-8 | an-143 |
| 1A2783 | sp-8 | an-144 | 1U2783 | sp-8 | an-144 | 1C2783 | sp-8 | an-144 |
| 1A2784 | sp-8 | an-145 | 1U2784 | sp-8 | an-145 | 1C2784 | sp-8 | an-145 |
| 1A2785 | sp-8 | an-146 | 1U2785 | sp-8 | an-146 | 1C2785 | sp-8 | an-146 |
| 1A2786 | sp-8 | an-147 | 1U2786 | sp-8 | an-147 | 1C2786 | sp-8 | an-147 |
| 1A2787 | sp-8 | an-148 | 1U2787 | sp-8 | an-148 | 1C2787 | sp-8 | an-148 |
| 1A2788 | sp-8 | an-149 | 1U2788 | sp-8 | an-149 | 1C2788 | sp-8 | an-149 |
| 1A2789 | sp-8 | an-150 | 1U2789 | sp-8 | an-150 | 1C2789 | sp-8 | an-150 |
| 1A2790 | sp-8 | an-151 | 1U2790 | sp-8 | an-151 | 1C2790 | sp-8 | an-151 |
| 1A2791 | sp-8 | an-152 | 1U2791 | sp-8 | an-152 | 1C2791 | sp-8 | an-152 |
| 1A2792 | sp-8 | an-153 | 1U2792 | sp-8 | an-153 | 1C2792 | sp-8 | an-153 |
| 1A2793 | sp-8 | an-154 | 1U2793 | sp-8 | an-154 | 1C2793 | sp-8 | an-154 |
| 1A2794 | sp-8 | an-155 | 1U2794 | sp-8 | an-155 | 1C2794 | sp-8 | an-155 |
| 1A2795 | sp-8 | an-156 | 1U2795 | sp-8 | an-156 | 1C2795 | sp-8 | an-156 |
| 1A2796 | sp-8 | an-157 | 1U2796 | sp-8 | an-157 | 1C2796 | sp-8 | an-157 |
| 1A2797 | sp-8 | an-158 | 1U2797 | sp-8 | an-158 | 1C2797 | sp-8 | an-158 |
| 1A2798 | sp-8 | an-159 | 1U2798 | sp-8 | an-159 | 1C2798 | sp-8 | an-159 |
| 1A2799 | sp-8 | an-160 | 1U2799 | sp-8 | an-160 | 1C2799 | sp-8 | an-160 |
| 1A2800 | sp-8 | an-161 | 1U2800 | sp-8 | an-161 | 1C2800 | sp-8 | an-161 |

| Ex. No. | Z | N⁺R⁵R⁶R⁷ | Ex. No. | Z | N⁺R⁵R⁶R⁷ | Ex. No. | Z | N⁺R⁵R⁶R⁷ |
|---|---|---|---|---|---|---|---|---|
| Table 2-51 | | | | | | | | |
| Y = NHCS | | | Y = NHCSNH | | | Y = NHCSO | | |
| 1A2801 | sp-8 | an-162 | 1U2801 | sp-8 | an-162 | 1C2801 | sp-8 | an-162 |
| 1A2802 | sp-8 | an-163 | 1U2802 | sp-8 | an-163 | 1C2802 | sp-8 | an-163 |
| 1A2803 | sp-8 | an-164 | 1U2803 | sp-8 | an-164 | 1C2803 | sp-8 | an-164 |
| 1A2804 | sp-8 | an-165 | 1U2804 | sp-8 | an-165 | 1C2804 | sp-8 | an-165 |
| 1A2805 | sp-8 | an-166 | 1U2805 | sp-8 | an-166 | 1C2805 | sp-8 | an-166 |
| 1A2806 | sp-8 | an-167 | 1U2806 | sp-8 | an-167 | 1C2806 | sp-8 | an-167 |
| 1A2807 | sp-8 | an-168 | 1U2807 | sp-8 | an-168 | 1C2807 | sp-8 | an-168 |
| 1A2808 | sp-8 | an-169 | 1U2808 | sp-8 | an-169 | 1C2808 | sp-8 | an-169 |
| 1A2809 | sp-8 | an-170 | 1U2809 | sp-8 | an-170 | 1C2809 | sp-8 | an-170 |
| 1A2810 | sp-8 | an-171 | 1U2810 | sp-8 | an-171 | 1C2810 | sp-8 | an-171 |
| 1A2811 | sp-8 | an-172 | 1U2811 | sp-8 | an-172 | 1C2811 | sp-8 | an-172 |
| 1A2812 | sp-8 | an-173 | 1U2812 | sp-8 | an-173 | 1C2812 | sp-8 | an-173 |
| 1A2813 | sp-8 | an-174 | 1U2813 | sp-8 | an-174 | 1C2813 | sp-8 | an-174 |
| 1A2814 | sp-8 | an-175 | 1U2814 | sp-8 | an-175 | 1C2814 | sp-8 | an-175 |
| 1A2815 | sp-8 | an-176 | 1U2815 | sp-8 | an-176 | 1C2815 | sp-8 | an-176 |
| 1A2816 | sp-8 | an-177 | 1U2816 | sp-8 | an-177 | 1C2816 | sp-8 | an-177 |
| 1A2817 | sp-8 | an-178 | 1U2817 | sp-8 | an-178 | 1C2817 | sp-8 | an-178 |
| 1A2818 | sp-8 | an-179 | 1U2818 | sp-8 | an-179 | 1C2818 | sp-8 | an-179 |
| 1A2819 | sp-8 | an-180 | 1U2819 | sp-8 | an-180 | 1C2819 | sp-8 | an-180 |
| 1A2820 | sp-8 | an-181 | 1U2820 | sp-8 | an-181 | 1C2820 | sp-8 | an-181 |
| 1A2821 | sp-8 | an-182 | 1U2821 | sp-8 | an-182 | 1C2821 | sp-8 | an-182 |
| 1A2822 | sp-8 | an-183 | 1U2822 | sp-8 | an-183 | 1C2822 | sp-8 | an-183 |
| 1A2823 | sp-8 | an-184 | 1U2823 | sp-8 | an-184 | 1C2823 | sp-8 | an-184 |
| 1A2824 | sp-8 | an-185 | 1U2824 | sp-8 | an-185 | 1C2824 | sp-8 | an-185 |
| 1A2825 | sp-8 | an-186 | 1U2825 | sp-8 | an-186 | 1C2825 | sp-8 | an-186 |
| 1A2826 | sp-8 | an-187 | 1U2826 | sp-8 | an-187 | 1C2826 | sp-8 | an-187 |
| 1A2827 | sp-8 | an-188 | 1U2827 | sp-8 | an-188 | 1C2827 | sp-8 | an-188 |
| 1A2828 | sp-8 | an-189 | 1U2828 | sp-8 | an-189 | 1C2828 | sp-8 | an-189 |
| 1A2829 | sp-8 | an-190 | 1U2829 | sp-8 | an-190 | 1C2829 | sp-8 | an-190 |
| 1A2830 | sp-8 | an-191 | 1U2830 | sp-8 | an-191 | 1C2830 | sp-8 | an-191 |
| 1A2831 | sp-8 | an-192 | 1U2831 | sp-8 | an-192 | 1C2831 | sp-8 | an-192 |
| 1A2832 | sp-8 | an-193 | 1U2832 | sp-8 | an-193 | 1C2832 | sp-8 | an-193 |
| 1A2833 | sp-8 | an-194 | 1U2833 | sp-8 | an-194 | 1C2833 | sp-8 | an-194 |
| 1A2834 | sp-8 | an-195 | 1U2834 | sp-8 | an-195 | 1C2834 | sp-8 | an-195 |
| 1A2835 | sp-8 | an-196 | 1U2835 | sp-8 | an-196 | 1C2835 | sp-8 | an-196 |
| 1A2836 | sp-8 | an-197 | 1U2836 | sp-8 | an-197 | 1C2836 | sp-8 | an-197 |
| 1A2837 | sp-8 | an-198 | 1U2837 | sp-8 | an-198 | 1C2837 | sp-8 | an-198 |
| 1A2838 | sp-8 | an-199 | 1U2838 | sp-8 | an-199 | 1C2838 | sp-8 | an-199 |
| 1A2839 | sp-8 | an-200 | 1U2839 | sp-8 | an-200 | 1C2839 | sp-8 | an-200 |
| 1A2840 | sp-8 | an-201 | 1U2840 | sp-8 | an-201 | 1C2840 | sp-8 | an-201 |
| 1A2841 | sp-8 | an-202 | 1U2841 | sp-8 | an-202 | 1C2841 | sp-8 | an-202 |
| 1A2842 | sp-8 | an-203 | 1U2842 | sp-8 | an-203 | 1C2842 | sp-8 | an-203 |
| 1A2843 | sp-8 | an-204 | 1U2843 | sp-8 | an-204 | 1C2843 | sp-8 | an-204 |
| 1A2844 | sp-8 | an-205 | 1U2844 | sp-8 | an-205 | 1C2844 | sp-8 | an-205 |
| 1A2845 | sp-8 | an-206 | 1U2845 | sp-8 | an-206 | 1C2845 | sp-8 | an-206 |
| 1A2846 | sp-8 | an-207 | 1U2846 | sp-8 | an-207 | 1C2846 | sp-8 | an-207 |
| 1A2847 | sp-8 | an-208 | 1U2847 | sp-8 | an-208 | 1C2847 | sp-8 | an-208 |
| 1A2848 | sp-8 | an-209 | 1U2848 | sp-8 | an-209 | 1C2848 | sp-8 | an-209 |
| 1A2849 | sp-8 | an-210 | 1U2849 | sp-8 | an-210 | 1C2849 | sp-8 | an-210 |
| 1A2850 | sp-8 | an-211 | 1U2850 | sp-8 | an-211 | 1C2850 | sp-8 | an-211 |
| 1A2851 | sp-8 | an-212 | 1U2851 | sp-8 | an-212 | 1C2851 | sp-8 | an-212 |
| 1A2852 | sp-8 | an-213 | 1U2852 | sp-8 | an-213 | 1C2852 | sp-8 | an-213 |
| 1A2853 | sp-8 | an-214 | 1U2853 | sp-8 | an-214 | 1C2853 | sp-8 | an-214 |
| 1A2854 | sp-8 | an-215 | 1U2854 | sp-8 | an-215 | 1C2854 | sp-8 | an-215 |
| 1A2855 | sp-8 | an-216 | 1U2855 | sp-8 | an-216 | 1C2855 | sp-8 | an-216 |
| 1A2856 | sp-8 | an-217 | 1U2856 | sp-8 | an-217 | 1C2856 | sp-8 | an-217 |
| Table 2-52 | | | | | | | | |
| Y = NHCS | | | Y = NHCSNH | | | Y = NHCSO | | |
| 1A2857 | sp-8 | an-218 | 1U2857 | sp-8 | an-218 | 1C2857 | sp-8 | an-218 |
| 1A2858 | sp-8 | an-219 | 1U2858 | sp-8 | an-219 | 1C2858 | sp-8 | an-219 |
| 1A2859 | sp-8 | an-220 | 1U2859 | sp-8 | an-220 | 1C2859 | sp-8 | an-220 |
| 1A2860 | sp-8 | an-221 | 1U2860 | sp-8 | an-221 | 1C2860 | sp-8 | an-221 |
| 1A2861 | sp-8 | an-222 | 1U2861 | sp-8 | an-222 | 1C2861 | sp-8 | an-222 |
| 1A2862 | sp-8 | an-223 | 1U2862 | sp-8 | an-223 | 1C2862 | sp-8 | an-223 |
| 1A2863 | sp-8 | an-224 | 1U2863 | sp-8 | an-224 | 1C2863 | sp-8 | an-224 |
| 1A2864 | sp-8 | an-225 | 1U2864 | sp-8 | an-225 | 1C2864 | sp-8 | an-225 |
| 1A2865 | sp-8 | an-226 | 1U2865 | sp-8 | an-226 | 1C2865 | sp-8 | an-226 |
| 1A2866 | sp-8 | an-227 | 1U2866 | sp-8 | an-227 | 1C2866 | sp-8 | an-227 |
| 1A2867 | sp-8 | an-228 | 1U2867 | sp-8 | an-228 | 1C2867 | sp-8 | an-228 |
| 1A2868 | sp-8 | an-229 | 1U2868 | sp-8 | an-229 | 1C2868 | sp-8 | an-229 |
| 1A2869 | sp-8 | an-230 | 1U2869 | sp-8 | an-230 | 1C2869 | sp-8 | an-230 |
| 1A2870 | sp-8 | an-231 | 1U2870 | sp-8 | an-231 | 1C2870 | sp-8 | an-231 |

| Ex. No. | Z | N⁺R⁵R⁶R⁷ | Ex. No. | Z | N⁺R⁵R⁶R⁷ | Ex. No. | Z | N⁺R⁵R⁶R⁷ |
|---|---|---|---|---|---|---|---|---|
| 1A2871 | sp-8 | an-232 | 1U2871 | sp-8 | an-232 | 1C2871 | sp-8 | an-232 |
| 1A2872 | sp-8 | an-233 | 1U2872 | sp-8 | an-233 | 1C2872 | sp-8 | an-233 |
| 1A2873 | sp-8 | an-234 | 1U2873 | sp-8 | an-234 | 1C2873 | sp-8 | an-234 |
| 1A2874 | sp-8 | an-235 | 1U2874 | sp-8 | an-235 | 1C2874 | sp-8 | an-235 |
| 1A2875 | sp-8 | an-236 | 1U2875 | sp-8 | an-236 | 1C2875 | sp-8 | an-236 |
| 1A2876 | sp-8 | an-237 | 1U2876 | sp-8 | an-237 | 1C2876 | sp-8 | an-237 |
| 1A2877 | sp-8 | an-238 | 1U2877 | sp-8 | an-238 | 1C2877 | sp-8 | an-238 |
| 1A2878 | sp-8 | an-239 | 1U2878 | sp-8 | an-239 | 1C2878 | sp-8 | an-239 |
| 1A2879 | sp-8 | an-240 | 1U2879 | sp-8 | an-240 | 1C2879 | sp-8 | an-240 |
| 1A2880 | sp-8 | an-241 | 1U2880 | sp-8 | an-241 | 1C2880 | sp-8 | an-241 |
| 1A2881 | sp-8 | an-242 | 1U2881 | sp-8 | an-242 | 1C2881 | sp-8 | an-242 |
| 1A2882 | sp-8 | an-243 | 1U2882 | sp-8 | an-243 | 1C2882 | sp-8 | an-243 |
| 1A2883 | sp-8 | an-244 | 1U2883 | sp-8 | an-244 | 1C2883 | sp-8 | an-244 |
| 1A2884 | sp-8 | an-245 | 1U2884 | sp-8 | an-245 | 1C2884 | sp-8 | an-245 |
| 1A2885 | sp-8 | an-246 | 1U2885 | sp-8 | an-246 | 1C2885 | sp-8 | an-246 |
| 1A2886 | sp-8 | an-247 | 1U2886 | sp-8 | an-247 | 1C2886 | sp-8 | an-247 |
| 1A2887 | sp-8 | an-248 | 1U2887 | sp-8 | an-248 | 1C2887 | sp-8 | an-248 |
| 1A2888 | sp-8 | an-249 | 1U2888 | sp-8 | an-249 | 1C2888 | sp-8 | an-249 |
| 1A2889 | sp-8 | an-250 | 1U2889 | sp-8 | an-250 | 1C2889 | sp-8 | an-250 |
| 1A2890 | sp-8 | an-251 | 1U2890 | sp-8 | an-251 | 1C2890 | sp-8 | an-251 |
| 1A2891 | sp-8 | an-252 | 1U2891 | sp-8 | an-252 | 1C2891 | sp-8 | an-252 |
| 1A2892 | sp-8 | an-253 | 1U2892 | sp-8 | an-253 | 1C2892 | sp-8 | an-253 |
| 1A2893 | sp-8 | an-254 | 1U2893 | sp-8 | an-254 | 1C2893 | sp-8 | an-254 |
| 1A2894 | sp-8 | an-255 | 1U2894 | sp-8 | an-255 | 1C2894 | sp-8 | an-255 |
| 1A2895 | sp-8 | an-256 | 1U2895 | sp-8 | an-256 | 1C2895 | sp-8 | an-256 |
| 1A2896 | sp-8 | an-257 | 1U2896 | sp-8 | an-257 | 1C2896 | sp-8 | an-257 |
| 1A2897 | sp-8 | an-258 | 1U2897 | sp-8 | an-258 | 1C2897 | sp-8 | an-258 |
| 1A2898 | sp-8 | an-259 | 1U2898 | sp-8 | an-259 | 1C2898 | sp-8 | an-259 |
| 1A2899 | sp-8 | an-260 | 1U2899 | sp-8 | an-260 | 1C2899 | sp-8 | an-260 |
| 1A2900 | sp-8 | an-261 | 1U2900 | sp-8 | an-261 | 1C2900 | sp-8 | an-261 |
| 1A2901 | sp-8 | an-262 | 1U2901 | sp-8 | an-262 | 1C2901 | sp-8 | an-262 |
| 1A2902 | sp-8 | an-263 | 1U2902 | sp-8 | an-263 | 1C2902 | sp-8 | an-263 |
| 1A2903 | sp-8 | an-264 | 1U2903 | sp-8 | an-264 | 1C2903 | sp-8 | an-264 |
| 1A2904 | sp-8 | an-265 | 1U2904 | sp-8 | an-265 | 1C2904 | sp-8 | an-265 |
| 1A2905 | sp-8 | an-266 | 1U2905 | sp-8 | an-266 | 1C2905 | sp-8 | an-266 |
| 1A2906 | sp-8 | an-267 | 1U2906 | sp-8 | an-267 | 1C2906 | sp-8 | an-267 |
| 1A2907 | sp-8 | an-268 | 1U2907 | sp-8 | an-268 | 1C2907 | sp-8 | an-268 |
| 1A2908 | sp-8 | an-269 | 1U2908 | sp-8 | an-269 | 1C2908 | sp-8 | an-269 |
| 1A2909 | sp-8 | an-270 | 1U2909 | sp-8 | an-270 | 1C2909 | sp-8 | an-270 |
| 1A2910 | sp-8 | an-271 | 1U2910 | sp-8 | an-271 | 1C2910 | sp-8 | an-271 |
| 1A2911 | sp-8 | an-272 | 1U2911 | sp-8 | an-272 | 1C2911 | sp-8 | an-272 |
| 1A2912 | sp-8 | an-273 | 1U2912 | sp-8 | an-273 | 1C2912 | sp-8 | an-273 |

Table 2-53

| Y = NHCS | | | Y = NHCSNH | | | Y = NHCSO | | |
|---|---|---|---|---|---|---|---|---|
| 1A2913 | sp-8 | an-274 | 1U2913 | sp-8 | an-274 | 1C2913 | sp-8 | an-274 |
| 1A2914 | sp-8 | an-275 | 1U2914 | sp-8 | an-275 | 1C2914 | sp-8 | an-275 |
| 1A2915 | sp-8 | an-276 | 1U2915 | sp-8 | an-276 | 1C2915 | sp-8 | an-276 |
| 1A2916 | sp-8 | an-277 | 1U2916 | sp-8 | an-277 | 1C2916 | sp-8 | an-277 |
| 1A2917 | sp-8 | an-278 | 1U2917 | sp-8 | an-278 | 1C2917 | sp-8 | an-278 |
| 1A2918 | sp-8 | an-279 | 1U2918 | sp-8 | an-279 | 1C2918 | sp-8 | an-279 |
| 1A2919 | sp-8 | an-280 | 1U2919 | sp-8 | an-280 | 1C2919 | sp-8 | an-280 |
| 1A2920 | sp-8 | an-281 | 1U2920 | sp-8 | an-281 | 1C2920 | sp-8 | an-281 |
| 1A2921 | sp-8 | an-282 | 1U2921 | sp-8 | an-282 | 1C2921 | sp-8 | an-282 |
| 1A2922 | sp-8 | an-283 | 1U2922 | sp-8 | an-283 | 1C2922 | sp-8 | an-283 |
| 1A2923 | sp-8 | an-284 | 1U2923 | sp-8 | an-284 | 1C2923 | sp-8 | an-284 |
| 1A2924 | sp-8 | an-285 | 1U2924 | sp-8 | an-285 | 1C2924 | sp-8 | an-285 |
| 1A2925 | sp-8 | an-286 | 1U2925 | sp-8 | an-286 | 1C2925 | sp-8 | an-286 |
| 1A2926 | sp-8 | an-287 | 1U2926 | sp-8 | an-287 | 1C2926 | sp-8 | an-287 |
| 1A2927 | sp-8 | an-288 | 1U2927 | sp-8 | an-288 | 1C2927 | sp-8 | an-288 |
| 1A2928 | sp-8 | an-289 | 1U2928 | sp-8 | an-289 | 1C2928 | sp-8 | an-289 |
| 1A2929 | sp-8 | an-290 | 1U2929 | sp-8 | an-290 | 1C2929 | sp-8 | an-290 |
| 1A2930 | sp-8 | an-291 | 1U2930 | sp-8 | an-291 | 1C2930 | sp-8 | an-291 |
| 1A2931 | sp-8 | an-292 | 1U2931 | sp-8 | an-292 | 1C2931 | sp-8 | an-292 |
| 1A2932 | sp-8 | an-293 | 1U2932 | sp-8 | an-293 | 1C2932 | sp-8 | an-293 |
| 1A2933 | sp-8 | an-294 | 1U2933 | sp-8 | an-294 | 1C2933 | sp-8 | an-294 |
| 1A2934 | sp-8 | an-295 | 1U2934 | sp-8 | an-295 | 1C2934 | sp-8 | an-295 |
| 1A2935 | sp-8 | an-296 | 1U2935 | sp-8 | an-296 | 1C2935 | sp-8 | an-296 |
| 1A2936 | sp-8 | an-297 | 1U2936 | sp-8 | an-297 | 1C2936 | sp-8 | an-297 |
| 1A2937 | sp-8 | an-298 | 1U2937 | sp-8 | an-298 | 1C2937 | sp-8 | an-298 |
| 1A2938 | sp-8 | an-299 | 1U2938 | sp-8 | an-299 | 1C2938 | sp-8 | an-299 |
| 1A2939 | sp-8 | an-300 | 1U2939 | sp-8 | an-300 | 1C2939 | sp-8 | an-300 |
| 1A2940 | sp-8 | an-301 | 1U2940 | sp-8 | an-301 | 1C2940 | sp-8 | an-301 |
| 1A2941 | sp-8 | an-302 | 1U2941 | sp-8 | an-302 | 1C2941 | sp-8 | an-302 |
| 1A2942 | sp-8 | an-303 | 1U2942 | sp-8 | an-303 | 1C2942 | sp-8 | an-303 |
| 1A2943 | sp-8 | an-304 | 1U2943 | sp-8 | an-304 | 1C2943 | sp-8 | an-304 |
| 1A2944 | sp-8 | an-305 | 1U2944 | sp-8 | an-305 | 1C2944 | sp-8 | an-305 |

-continued

| Ex. No. | Z | N+R5R6R7 | Ex. No. | Z | N+R5R6R7 | Ex. No. | Z | N+R5R6R7 |
|---|---|---|---|---|---|---|---|---|
| 1A2945 | sp-8 | an-306 | 1U2945 | sp-8 | an-306 | 1C2945 | sp-8 | an-306 |
| 1A2946 | sp-8 | an-307 | 1U2946 | sp-8 | an-307 | 1C2946 | sp-8 | an-307 |
| 1A2947 | sp-8 | an-308 | 1U2947 | sp-8 | an-308 | 1C2947 | sp-8 | an-308 |
| 1A2948 | sp-8 | an-309 | 1U2948 | sp-8 | an-309 | 1C2948 | sp-8 | an-309 |
| 1A2949 | sp-8 | an-310 | 1U2949 | sp-8 | an-310 | 1C2949 | sp-8 | an-310 |
| 1A2950 | sp-8 | an-311 | 1U2950 | sp-8 | an-311 | 1C2950 | sp-8 | an-311 |
| 1A2951 | sp-8 | an-312 | 1U2951 | sp-8 | an-312 | 1C2951 | sp-8 | an-312 |
| 1A2952 | sp-8 | an-313 | 1U2952 | sp-8 | an-313 | 1C2952 | sp-8 | an-313 |
| 1A2953 | sp-8 | an-314 | 1U2953 | sp-8 | an-314 | 1C2953 | sp-8 | an-314 |
| 1A2954 | sp-8 | an-315 | 1U2954 | sp-8 | an-315 | 1C2954 | sp-8 | an-315 |
| 1A2955 | sp-8 | an-316 | 1U2955 | sp-8 | an-316 | 1C2955 | sp-8 | an-316 |
| 1A2956 | sp-8 | an-317 | 1U2956 | sp-8 | an-317 | 1C2956 | sp-8 | an-317 |
| 1A2957 | sp-8 | an-318 | 1U2957 | sp-8 | an-318 | 1C2957 | sp-8 | an-318 |
| 1A2958 | sp-8 | an-319 | 1U2958 | sp-8 | an-319 | 1C2958 | sp-8 | an-319 |
| 1A2959 | sp-8 | an-320 | 1U2959 | sp-8 | an-320 | 1C2959 | sp-8 | an-320 |
| 1A2960 | sp-8 | an-321 | 1U2960 | sp-8 | an-321 | 1C2960 | sp-8 | an-321 |
| 1A2961 | sp-8 | an-322 | 1U2961 | sp-8 | an-322 | 1C2961 | sp-8 | an-322 |
| 1A2962 | sp-8 | an-323 | 1U2962 | sp-8 | an-323 | 1C2962 | sp-8 | an-323 |
| 1A2963 | sp-8 | an-324 | 1U2963 | sp-8 | an-324 | 1C2963 | sp-8 | an-324 |
| 1A2964 | sp-8 | an-325 | 1U2964 | sp-8 | an-325 | 1C2964 | sp-8 | an-325 |
| 1A2965 | sp-8 | an-326 | 1U2965 | sp-8 | an-326 | 1C2965 | sp-8 | an-326 |
| 1A2966 | sp-8 | an-327 | 1U2966 | sp-8 | an-327 | 1C2966 | sp-8 | an-327 |
| 1A2967 | sp-8 | an-328 | 1U2967 | sp-8 | an-328 | 1C2967 | sp-8 | an-328 |
| 1A2968 | sp-8 | an-329 | 1U2968 | sp-8 | an-329 | 1C2968 | sp-8 | an-329 |

Table 2-54

| Y = NHCS | | | Y = NHCSNH | | | Y = NHCSO | | |
|---|---|---|---|---|---|---|---|---|
| 1A2969 | sp-8 | an-330 | 1U2969 | sp-8 | an-330 | 1C2969 | sp-8 | an-330 |
| 1A2970 | sp-8 | an-331 | 1U2970 | sp-8 | an-331 | 1C2970 | sp-8 | an-331 |
| 1A2971 | sp-8 | an-332 | 1U2971 | sp-8 | an-332 | 1C2971 | sp-8 | an-332 |
| 1A2972 | sp-8 | an-333 | 1U2972 | sp-8 | an-333 | 1C2972 | sp-8 | an-333 |
| 1A2973 | sp-8 | an-334 | 1U2973 | sp-8 | an-334 | 1C2973 | sp-8 | an-334 |
| 1A2974 | sp-8 | an-335 | 1U2974 | sp-8 | an-335 | 1C2974 | sp-8 | an-335 |
| 1A2975 | sp-8 | an-336 | 1U2975 | sp-8 | an-336 | 1C2975 | sp-8 | an-336 |
| 1A2976 | sp-8 | an-337 | 1U2976 | sp-8 | an-337 | 1C2976 | sp-8 | an-337 |
| 1A2977 | sp-8 | an-338 | 1U2977 | sp-8 | an-338 | 1C2977 | sp-8 | an-338 |
| 1A2978 | sp-8 | an-339 | 1U2978 | sp-8 | an-339 | 1C2978 | sp-8 | an-339 |
| 1A2979 | sp-8 | an-340 | 1U2979 | sp-8 | an-340 | 1C2979 | sp-8 | an-340 |
| 1A2980 | sp-8 | an-341 | 1U2980 | sp-8 | an-341 | 1C2980 | sp-8 | an-341 |
| 1A2981 | sp-8 | an-342 | 1U2981 | sp-8 | an-342 | 1C2981 | sp-8 | an-342 |
| 1A2982 | sp-8 | an-343 | 1U2982 | sp-8 | an-343 | 1C2982 | sp-8 | an-343 |
| 1A2983 | sp-8 | an-344 | 1U2983 | sp-8 | an-344 | 1C2983 | sp-8 | an-344 |
| 1A2984 | sp-8 | an-345 | 1U2984 | sp-8 | an-345 | 1C2984 | sp-8 | an-345 |
| 1A2985 | sp-8 | an-346 | 1U2985 | sp-8 | an-346 | 1C2985 | sp-8 | an-346 |
| 1A2986 | sp-8 | an-347 | 1U2986 | sp-8 | an-347 | 1C2986 | sp-8 | an-347 |
| 1A2987 | sp-8 | an-348 | 1U2987 | sp-8 | an-348 | 1C2987 | sp-8 | an-348 |
| 1A2988 | sp-8 | an-349 | 1U2988 | sp-8 | an-349 | 1C2988 | sp-8 | an-349 |
| 1A2989 | sp-8 | an-350 | 1U2989 | sp-8 | an-350 | 1C2989 | sp-8 | an-350 |
| 1A2990 | sp-8 | an-351 | 1U2990 | sp-8 | an-351 | 1C2990 | sp-8 | an-351 |
| 1A2991 | sp-8 | an-352 | 1U2991 | sp-8 | an-352 | 1C2991 | sp-8 | an-352 |
| 1A2992 | sp-8 | an-353 | 1U2992 | sp-8 | an-353 | 1C2992 | sp-8 | an-353 |
| 1A2993 | sp-8 | an-354 | 1U2993 | sp-8 | an-354 | 1C2993 | sp-8 | an-354 |
| 1A2994 | sp-8 | an-355 | 1U2994 | sp-8 | an-355 | 1C2994 | sp-8 | an-355 |
| 1A2995 | sp-8 | an-356 | 1U2995 | sp-8 | an-356 | 1C2995 | sp-8 | an-356 |
| 1A2996 | sp-8 | an-357 | 1U2996 | sp-8 | an-357 | 1C2996 | sp-8 | an-357 |
| 1A2997 | sp-8 | an-358 | 1U2997 | sp-8 | an-358 | 1C2997 | sp-8 | an-358 |
| 1A2998 | sp-8 | an-359 | 1U2998 | sp-8 | an-359 | 1C2998 | sp-8 | an-359 |
| 1A2999 | sp-8 | an-360 | 1U2999 | sp-8 | an-360 | 1C2999 | sp-8 | an-360 |
| 1A3000 | sp-8 | an-361 | 1U3000 | sp-8 | an-361 | 1C3000 | sp-8 | an-361 |
| 1A3001 | sp-8 | an-362 | 1U3001 | sp-8 | an-362 | 1C3001 | sp-8 | an-362 |
| 1A3002 | sp-8 | an-363 | 1U3002 | sp-8 | an-363 | 1C3002 | sp-8 | an-363 |
| 1A3003 | sp-8 | an-364 | 1U3003 | sp-8 | an-364 | 1C3003 | sp-8 | an-364 |
| 1A3004 | sp-8 | an-365 | 1U3004 | sp-8 | an-365 | 1C3004 | sp-8 | an-365 |
| 1A3005 | sp-8 | an-366 | 1U3005 | sp-8 | an-366 | 1C3005 | sp-8 | an-366 |
| 1A3006 | sp-8 | an-367 | 1U3006 | sp-8 | an-367 | 1C3006 | sp-8 | an-367 |
| 1A3007 | sp-8 | an-368 | 1U3007 | sp-8 | an-368 | 1C3007 | sp-8 | an-368 |
| 1A3008 | sp-8 | an-369 | 1U3008 | sp-8 | an-369 | 1C3008 | sp-8 | an-369 |
| 1A3009 | sp-8 | an-370 | 1U3009 | sp-8 | an-370 | 1C3009 | sp-8 | an-370 |
| 1A3010 | sp-8 | an-371 | 1U3010 | sp-8 | an-371 | 1C3010 | sp-8 | an-371 |
| 1A3011 | sp-8 | an-372 | 1U3011 | sp-8 | an-372 | 1C3011 | sp-8 | an-372 |
| 1A3012 | sp-8 | an-373 | 1U3012 | sp-8 | an-373 | 1C3012 | sp-8 | an-373 |
| 1A3013 | sp-8 | an-374 | 1U3013 | sp-8 | an-374 | 1C3013 | sp-8 | an-374 |
| 1A3014 | sp-8 | an-375 | 1U3014 | sp-8 | an-375 | 1C3014 | sp-8 | an-375 |
| 1A3015 | sp-8 | an-376 | 1U3015 | sp-8 | an-376 | 1C3015 | sp-8 | an-376 |
| 1A3016 | sp-8 | an-377 | 1U3016 | sp-8 | an-377 | 1C3016 | sp-8 | an-377 |
| 1A3017 | sp-9 | an-1 | 1U3017 | sp-9 | an-1 | 1C3017 | sp-9 | an-1 |
| 1A3018 | sp-9 | an-2 | 1U3018 | sp-9 | an-2 | 1C3018 | sp-9 | an-2 |

-continued

| Ex. No. | Z | N⁺R⁵R⁶R⁷ | Ex. No. | Z | N⁺R⁵R⁶R⁷ | Ex. No. | Z | N⁺R⁵R⁶R⁷ |
|---|---|---|---|---|---|---|---|---|
| 1A3019 | sp-9 | an-3 | 1U3019 | sp-9 | an-3 | 1C3019 | sp-9 | an-3 |
| 1A3020 | sp-9 | an-4 | 1U3020 | sp-9 | an-4 | 1C3020 | sp-9 | an-4 |
| 1A3021 | sp-9 | an-5 | 1U3021 | sp-9 | an-5 | 1C3021 | sp-9 | an-5 |
| 1A3022 | sp-9 | an-6 | 1U3022 | sp-9 | an-6 | 1C3022 | sp-9 | an-6 |
| 1A3023 | sp-9 | an-7 | 1U3023 | sp-9 | an-7 | 1C3023 | sp-9 | an-7 |
| 1A3024 | sp-9 | an-8 | 1U3024 | sp-9 | an-8 | 1C3024 | sp-9 | an-8 |

Table 2-55

| Y = NHCS | | | Y = NHCSNH | | | Y = NHCSO | | |
|---|---|---|---|---|---|---|---|---|
| 1A3025 | sp-9 | an-9 | 1U3025 | sp-9 | an-9 | 1C3025 | sp-9 | an-9 |
| 1A3026 | sp-9 | an-10 | 1U3026 | sp-9 | an-10 | 1C3026 | sp-9 | an-10 |
| 1A3027 | sp-9 | an-11 | 1U3027 | sp-9 | an-11 | 1C3027 | sp-9 | an-11 |
| 1A3028 | sp-9 | an-12 | 1U3028 | sp-9 | an-12 | 1C3028 | sp-9 | an-12 |
| 1A3029 | sp-9 | an-13 | 1U3029 | sp-9 | an-13 | 1C3029 | sp-9 | an-13 |
| 1A3030 | sp-9 | an-14 | 1U3030 | sp-9 | an-14 | 1C3030 | sp-9 | an-14 |
| 1A3031 | sp-9 | an-15 | 1U3031 | sp-9 | an-15 | 1C3031 | sp-9 | an-15 |
| 1A3032 | sp-9 | an-16 | 1U3032 | sp-9 | an-16 | 1C3032 | sp-9 | an-16 |
| 1A3033 | sp-9 | an-17 | 1U3033 | sp-9 | an-17 | 1C3033 | sp-9 | an-17 |
| 1A3034 | sp-9 | an-18 | 1U3034 | sp-9 | an-18 | 1C3034 | sp-9 | an-18 |
| 1A3035 | sp-9 | an-19 | 1U3035 | sp-9 | an-19 | 1C3035 | sp-9 | an-19 |
| 1A3036 | sp-9 | an-20 | 1U3036 | sp-9 | an-20 | 1C3036 | sp-9 | an-20 |
| 1A3037 | sp-9 | an-21 | 1U3037 | sp-9 | an-21 | 1C3037 | sp-9 | an-21 |
| 1A3038 | sp-9 | an-22 | 1U3038 | sp-9 | an-22 | 1C3038 | sp-9 | an-22 |
| 1A3039 | sp-9 | an-23 | 1U3039 | sp-9 | an-23 | 1C3039 | sp-9 | an-23 |
| 1A3040 | sp-9 | an-24 | 1U3040 | sp-9 | an-24 | 1C3040 | sp-9 | an-24 |
| 1A3041 | sp-9 | an-25 | 1U3041 | sp-9 | an-25 | 1C3041 | sp-9 | an-25 |
| 1A3042 | sp-9 | an-26 | 1U3042 | sp-9 | an-26 | 1C3042 | sp-9 | an-26 |
| 1A3043 | sp-9 | an-27 | 1U3043 | sp-9 | an-27 | 1C3043 | sp-9 | an-27 |
| 1A3044 | sp-9 | an-28 | 1U3044 | sp-9 | an-28 | 1C3044 | sp-9 | an-28 |
| 1A3045 | sp-9 | an-29 | 1U3045 | sp-9 | an-29 | 1C3045 | sp-9 | an-29 |
| 1A3046 | sp-9 | an-30 | 1U3046 | sp-9 | an-30 | 1C3046 | sp-9 | an-30 |
| 1A3047 | sp-9 | an-31 | 1U3047 | sp-9 | an-31 | 1C3047 | sp-9 | an-31 |
| 1A3048 | sp-9 | an-32 | 1U3048 | sp-9 | an-32 | 1C3048 | sp-9 | an-32 |
| 1A3049 | sp-9 | an-33 | 1U3049 | sp-9 | an-33 | 1C3049 | sp-9 | an-33 |
| 1A3050 | sp-9 | an-34 | 1U3050 | sp-9 | an-34 | 1C3050 | sp-9 | an-34 |
| 1A3051 | sp-9 | an-35 | 1U3051 | sp-9 | an-35 | 1C3051 | sp-9 | an-35 |
| 1A3052 | sp-9 | an-36 | 1U3052 | sp-9 | an-36 | 1C3052 | sp-9 | an-36 |
| 1A3053 | sp-9 | an-37 | 1U3053 | sp-9 | an-37 | 1C3053 | sp-9 | an-37 |
| 1A3054 | sp-9 | an-38 | 1U3054 | sp-9 | an-38 | 1C3054 | sp-9 | an-38 |
| 1A3055 | sp-9 | an-39 | 1U3055 | sp-9 | an-39 | 1C3055 | sp-9 | an-39 |
| 1A3056 | sp-9 | an-40 | 1U3056 | sp-9 | an-40 | 1C3056 | sp-9 | an-40 |
| 1A3057 | sp-9 | an-41 | 1U3057 | sp-9 | an-41 | 1C3057 | sp-9 | an-41 |
| 1A3058 | sp-9 | an-42 | 1U3058 | sp-9 | an-42 | 1C3058 | sp-9 | an-42 |
| 1A3059 | sp-9 | an-43 | 1U3059 | sp-9 | an-43 | 1C3059 | sp-9 | an-43 |
| 1A3060 | sp-9 | an-44 | 1U3060 | sp-9 | an-44 | 1C3060 | sp-9 | an-44 |
| 1A3061 | sp-9 | an-45 | 1U3061 | sp-9 | an-45 | 1C3061 | sp-9 | an-45 |
| 1A3062 | sp-9 | an-46 | 1U3062 | sp-9 | an-46 | 1C3062 | sp-9 | an-46 |
| 1A3063 | sp-9 | an-47 | 1U3063 | sp-9 | an-47 | 1C3063 | sp-9 | an-47 |
| 1A3064 | sp-9 | an-48 | 1U3064 | sp-9 | an-48 | 1C3064 | sp-9 | an-48 |
| 1A3065 | sp-9 | an-49 | 1U3065 | sp-9 | an-49 | 1C3065 | sp-9 | an-49 |
| 1A3066 | sp-9 | an-50 | 1U3066 | sp-9 | an-50 | 1C3066 | sp-9 | an-50 |
| 1A3067 | sp-9 | an-51 | 1U3067 | sp-9 | an-51 | 1C3067 | sp-9 | an-51 |
| 1A3068 | sp-9 | an-52 | 1U3068 | sp-9 | an-52 | 1C3068 | sp-9 | an-52 |
| 1A3069 | sp-9 | an-53 | 1U3069 | sp-9 | an-53 | 1C3069 | sp-9 | an-53 |
| 1A3070 | sp-9 | an-54 | 1U3070 | sp-9 | an-54 | 1C3070 | sp-9 | an-54 |
| 1A3071 | sp-9 | an-55 | 1U3071 | sp-9 | an-55 | 1C3071 | sp-9 | an-55 |
| 1A3072 | sp-9 | an-56 | 1U3072 | sp-9 | an-56 | 1C3072 | sp-9 | an-56 |
| 1A3073 | sp-9 | an-57 | 1U3073 | sp-9 | an-57 | 1C3073 | sp-9 | an-57 |
| 1A3074 | sp-9 | an-58 | 1U3074 | sp-9 | an-58 | 1C3074 | sp-9 | an-58 |
| 1A3075 | sp-9 | an-59 | 1U3075 | sp-9 | an-59 | 1C3075 | sp-9 | an-59 |
| 1A3076 | sp-9 | an-60 | 1U3076 | sp-9 | an-60 | 1C3076 | sp-9 | an-60 |
| 1A3077 | sp-9 | an-61 | 1U3077 | sp-9 | an-61 | 1C3077 | sp-9 | an-61 |
| 1A3078 | sp-9 | an-62 | 1U3078 | sp-9 | an-62 | 1C3078 | sp-9 | an-62 |
| 1A3079 | sp-9 | an-63 | 1U3079 | sp-9 | an-63 | 1C3079 | sp-9 | an-63 |
| 1A3080 | sp-9 | an-64 | 1U3080 | sp-9 | an-64 | 1C3080 | sp-9 | an-64 |

Table 2-56

| Y = NHCS | | | Y = NHCSNH | | | Y = NHCSO | | |
|---|---|---|---|---|---|---|---|---|
| 1A3081 | sp-9 | an-65 | 1U3081 | sp-9 | an-65 | 1C3081 | sp-9 | an-65 |
| 1A3082 | sp-9 | an-66 | 1U3082 | sp-9 | an-66 | 1C3082 | sp-9 | an-66 |
| 1A3083 | sp-9 | an-67 | 1U3083 | sp-9 | an-67 | 1C3083 | sp-9 | an-67 |
| 1A3084 | sp-9 | an-68 | 1U3084 | sp-9 | an-68 | 1C3084 | sp-9 | an-68 |
| 1A3085 | sp-9 | an-69 | 1U3085 | sp-9 | an-69 | 1C3085 | sp-9 | an-69 |
| 1A3086 | sp-9 | an-70 | 1U3086 | sp-9 | an-70 | 1C3086 | sp-9 | an-70 |
| 1A3087 | sp-9 | an-71 | 1U3087 | sp-9 | an-71 | 1C3087 | sp-9 | an-71 |
| 1A3088 | sp-9 | an-72 | 1U3088 | sp-9 | an-72 | 1C3088 | sp-9 | an-72 |

-continued

| Ex. No. | Z | N+R5R6R7 | Ex. No. | Z | N+R5R6R7 | Ex. No. | Z | N+R5R6R7 |
|---|---|---|---|---|---|---|---|---|
| 1A3089 | sp-9 | an-73 | 1U3089 | sp-9 | an-73 | 1C3089 | sp-9 | an-73 |
| 1A3090 | sp-9 | an-74 | 1U3090 | sp-9 | an-74 | 1C3090 | sp-9 | an-74 |
| 1A3091 | sp-9 | an-75 | 1U3091 | sp-9 | an-75 | 1C3091 | sp-9 | an-75 |
| 1A3092 | sp-9 | an-76 | 1U3092 | sp-9 | an-76 | 1C3092 | sp-9 | an-76 |
| 1A3093 | sp-9 | an-77 | 1U3093 | sp-9 | an-77 | 1C3093 | sp-9 | an-77 |
| 1A3094 | sp-9 | an-78 | 1U3094 | sp-9 | an-78 | 1C3094 | sp-9 | an-78 |
| 1A3095 | sp-9 | an-79 | 1U3095 | sp-9 | an-79 | 1C3095 | sp-9 | an-79 |
| 1A3096 | sp-9 | an-80 | 1U3096 | sp-9 | an-80 | 1C3096 | sp-9 | an-80 |
| 1A3097 | sp-9 | an-81 | 1U3097 | sp-9 | an-81 | 1C3097 | sp-9 | an-81 |
| 1A3098 | sp-9 | an-82 | 1U3098 | sp-9 | an-82 | 1C3098 | sp-9 | an-82 |
| 1A3099 | sp-9 | an-83 | 1U3099 | sp-9 | an-83 | 1C3099 | sp-9 | an-83 |
| 1A3100 | sp-9 | an-84 | 1U3100 | sp-9 | an-84 | 1C3100 | sp-9 | an-84 |
| 1A3101 | sp-9 | an-85 | 1U3101 | sp-9 | an-85 | 1C3101 | sp-9 | an-85 |
| 1A3102 | sp-9 | an-86 | 1U3102 | sp-9 | an-86 | 1C3102 | sp-9 | an-86 |
| 1A3103 | sp-9 | an-87 | 1U3103 | sp-9 | an-87 | 1C3103 | sp-9 | an-87 |
| 1A3104 | sp-9 | an-88 | 1U3104 | sp-9 | an-88 | 1C3104 | sp-9 | an-88 |
| 1A3105 | sp-9 | an-89 | 1U3105 | sp-9 | an-89 | 1C3105 | sp-9 | an-89 |
| 1A3106 | sp-9 | an-90 | 1U3106 | sp-9 | an-90 | 1C3106 | sp-9 | an-90 |
| 1A3107 | sp-9 | an-91 | 1U3107 | sp-9 | an-91 | 1C3107 | sp-9 | an-91 |
| 1A3108 | sp-9 | an-92 | 1U3108 | sp-9 | an-92 | 1C3108 | sp-9 | an-92 |
| 1A3109 | sp-9 | an-93 | 1U3109 | sp-9 | an-93 | 1C3109 | sp-9 | an-93 |
| 1A3110 | sp-9 | an-94 | 1U3110 | sp-9 | an-94 | 1C3110 | sp-9 | an-94 |
| 1A3111 | sp-9 | an-95 | 1U3111 | sp-9 | an-95 | 1C3111 | sp-9 | an-95 |
| 1A3112 | sp-9 | an-96 | 1U3112 | sp-9 | an-96 | 1C3112 | sp-9 | an-96 |
| 1A3113 | sp-9 | an-97 | 1U3113 | sp-9 | an-97 | 1C3113 | sp-9 | an-97 |
| 1A3114 | sp-9 | an-98 | 1U3114 | sp-9 | an-98 | 1C3114 | sp-9 | an-98 |
| 1A3115 | sp-9 | an-99 | 1U3115 | sp-9 | an-99 | 1C3115 | sp-9 | an-99 |
| 1A3116 | sp-9 | an-100 | 1U3116 | sp-9 | an-100 | 1C3116 | sp-9 | an-100 |
| 1A3117 | sp-9 | an-101 | 1U3117 | sp-9 | an-101 | 1C3117 | sp-9 | an-101 |
| 1A3118 | sp-9 | an-102 | 1U3118 | sp-9 | an-102 | 1C3118 | sp-9 | an-102 |
| 1A3119 | sp-9 | an-103 | 1U3119 | sp-9 | an-103 | 1C3119 | sp-9 | an-103 |
| 1A3120 | sp-9 | an-104 | 1U3120 | sp-9 | an-104 | 1C3120 | sp-9 | an-104 |
| 1A3121 | sp-9 | an-105 | 1U3121 | sp-9 | an-105 | 1C3121 | sp-9 | an-105 |
| 1A3122 | sp-9 | an-106 | 1U3122 | sp-9 | an-106 | 1C3122 | sp-9 | an-106 |
| 1A3123 | sp-9 | an-107 | 1U3123 | sp-9 | an-107 | 1C3123 | sp-9 | an-107 |
| 1A3124 | sp-9 | an-108 | 1U3124 | sp-9 | an-108 | 1C3124 | sp-9 | an-108 |
| 1A3125 | sp-9 | an-109 | 1U3125 | sp-9 | an-109 | 1C3125 | sp-9 | an-109 |
| 1A3126 | sp-9 | an-110 | 1U3126 | sp-9 | an-110 | 1C3126 | sp-9 | an-110 |
| 1A3127 | sp-9 | an-111 | 1U3127 | sp-9 | an-111 | 1C3127 | sp-9 | an-111 |
| 1A3128 | sp-9 | an-112 | 1U3128 | sp-9 | an-112 | 1C3128 | sp-9 | an-112 |
| 1A3129 | sp-9 | an-113 | 1U3129 | sp-9 | an-113 | 1C3129 | sp-9 | an-113 |
| 1A3130 | sp-9 | an-114 | 1U3130 | sp-9 | an-114 | 1C3130 | sp-9 | an-114 |
| 1A3131 | sp-9 | an-115 | 1U3131 | sp-9 | an-115 | 1C3131 | sp-9 | an-115 |
| 1A3132 | sp-9 | an-116 | 1U3132 | sp-9 | an-116 | 1C3132 | sp-9 | an-116 |
| 1A3133 | sp-9 | an-117 | 1U3133 | sp-9 | an-117 | 1C3133 | sp-9 | an-117 |
| 1A3134 | sp-9 | an-118 | 1U3134 | sp-9 | an-118 | 1C3134 | sp-9 | an-118 |
| 1A3135 | sp-9 | an-119 | 1U3135 | sp-9 | an-119 | 1C3135 | sp-9 | an-119 |
| 1A3136 | sp-9 | an-120 | 1U3136 | sp-9 | an-120 | 1C3136 | sp-9 | an-120 |

Table 2-57

| Y = NHCS | | | Y = NHCSNH | | | Y = NHCSO | | |
|---|---|---|---|---|---|---|---|---|
| 1A3137 | sp-9 | an-121 | 1U3137 | sp-9 | an-121 | 1C3137 | sp-9 | an-121 |
| 1A3138 | sp-9 | an-122 | 1U3138 | sp-9 | an-122 | 1C3138 | sp-9 | an-122 |
| 1A3139 | sp-9 | an-123 | 1U3139 | sp-9 | an-123 | 1C3139 | sp-9 | an-123 |
| 1A3140 | sp-9 | an-124 | 1U3140 | sp-9 | an-124 | 1C3140 | sp-9 | an-124 |
| 1A3141 | sp-9 | an-125 | 1U3141 | sp-9 | an-125 | 1C3141 | sp-9 | an-125 |
| 1A3142 | sp-9 | an-126 | 1U3142 | sp-9 | an-126 | 1C3142 | sp-9 | an-126 |
| 1A3143 | sp-9 | an-127 | 1U3143 | sp-9 | an-127 | 1C3143 | sp-9 | an-127 |
| 1A3144 | sp-9 | an-128 | 1U3144 | sp-9 | an-128 | 1C3144 | sp-9 | an-128 |
| 1A3145 | sp-9 | an-129 | 1U3145 | sp-9 | an-129 | 1C3145 | sp-9 | an-129 |
| 1A3146 | sp-9 | an-130 | 1U3146 | sp-9 | an-130 | 1C3146 | sp-9 | an-130 |
| 1A3147 | sp-9 | an-131 | 1U3147 | sp-9 | an-131 | 1C3147 | sp-9 | an-131 |
| 1A3148 | sp-9 | an-132 | 1U3148 | sp-9 | an-132 | 1C3148 | sp-9 | an-132 |
| 1A3149 | sp-9 | an-133 | 1U3149 | sp-9 | an-133 | 1C3149 | sp-9 | an-133 |
| 1A3150 | sp-9 | an-134 | 1U3150 | sp-9 | an-134 | 1C3150 | sp-9 | an-134 |
| 1A3151 | sp-9 | an-135 | 1U3151 | sp-9 | an-135 | 1C3151 | sp-9 | an-135 |
| 1A3152 | sp-9 | an-136 | 1U3152 | sp-9 | an-136 | 1C3152 | sp-9 | an-136 |
| 1A3153 | sp-9 | an-137 | 1U3153 | sp-9 | an-137 | 1C3153 | sp-9 | an-137 |
| 1A3154 | sp-9 | an-138 | 1U3154 | sp-9 | an-138 | 1C3154 | sp-9 | an-138 |
| 1A3155 | sp-9 | an-139 | 1U3155 | sp-9 | an-139 | 1C3155 | sp-9 | an-139 |
| 1A3156 | sp-9 | an-140 | 1U3156 | sp-9 | an-140 | 1C3156 | sp-9 | an-140 |
| 1A3157 | sp-9 | an-141 | 1U3157 | sp-9 | an-141 | 1C3157 | sp-9 | an-141 |
| 1A3158 | sp-9 | an-142 | 1U3158 | sp-9 | an-142 | 1C3158 | sp-9 | an-142 |
| 1A3159 | sp-9 | an-143 | 1U3159 | sp-9 | an-143 | 1C3159 | sp-9 | an-143 |
| 1A3160 | sp-9 | an-144 | 1U3160 | sp-9 | an-144 | 1C3160 | sp-9 | an-144 |
| 1A3161 | sp-9 | an-145 | 1U3161 | sp-9 | an-145 | 1C3161 | sp-9 | an-145 |
| 1A3162 | sp-9 | an-146 | 1U3162 | sp-9 | an-146 | 1C3162 | sp-9 | an-146 |

-continued

| Ex. No. | Z | N⁺R⁵R⁶R⁷ | Ex. No. | Z | N⁺R⁵R⁶R⁷ | Ex. No. | Z | N⁺R⁵R⁶R⁷ |
|---|---|---|---|---|---|---|---|---|
| 1A3163 | sp-9 | an-147 | 1U3163 | sp-9 | an-147 | 1C3163 | sp-9 | an-147 |
| 1A3164 | sp-9 | an-148 | 1U3164 | sp-9 | an-148 | 1C3164 | sp-9 | an-148 |
| 1A3165 | sp-9 | an-149 | 1U3165 | sp-9 | an-149 | 1C3165 | sp-9 | an-149 |
| 1A3166 | sp-9 | an-150 | 1U3166 | sp-9 | an-150 | 1C3166 | sp-9 | an-150 |
| 1A3167 | sp-9 | an-151 | 1U3167 | sp-9 | an-151 | 1C3167 | sp-9 | an-151 |
| 1A3168 | sp-9 | an-152 | 1U3168 | sp-9 | an-152 | 1C3168 | sp-9 | an-152 |
| 1A3169 | sp-9 | an-153 | 1U3169 | sp-9 | an-153 | 1C3169 | sp-9 | an-153 |
| 1A3170 | sp-9 | an-154 | 1U3170 | sp-9 | an-154 | 1C3170 | sp-9 | an-154 |
| 1A3171 | sp-9 | an-155 | 1U3171 | sp-9 | an-155 | 1C3171 | sp-9 | an-155 |
| 1A3172 | sp-9 | an-156 | 1U3172 | sp-9 | an-156 | 1C3172 | sp-9 | an-156 |
| 1A3173 | sp-9 | an-157 | 1U3173 | sp-9 | an-157 | 1C3173 | sp-9 | an-157 |
| 1A3174 | sp-9 | an-158 | 1U3174 | sp-9 | an-158 | 1C3174 | sp-9 | an-158 |
| 1A3175 | sp-9 | an-159 | 1U3175 | sp-9 | an-159 | 1C3175 | sp-9 | an-159 |
| 1A3176 | sp-9 | an-160 | 1U3176 | sp-9 | an-160 | 1C3176 | sp-9 | an-160 |
| 1A3177 | sp-9 | an-161 | 1U3177 | sp-9 | an-161 | 1C3177 | sp-9 | an-161 |
| 1A3178 | sp-9 | an-162 | 1U3178 | sp-9 | an-162 | 1C3178 | sp-9 | an-162 |
| 1A3179 | sp-9 | an-163 | 1U3179 | sp-9 | an-163 | 1C3179 | sp-9 | an-163 |
| 1A3180 | sp-9 | an-164 | 1U3180 | sp-9 | an-164 | 1C3180 | sp-9 | an-164 |
| 1A3181 | sp-9 | an-165 | 1U3181 | sp-9 | an-165 | 1C3181 | sp-9 | an-165 |
| 1A3182 | sp-9 | an-166 | 1U3182 | sp-9 | an-166 | 1C3182 | sp-9 | an-166 |
| 1A3183 | sp-9 | an-167 | 1U3183 | sp-9 | an-167 | 1C3183 | sp-9 | an-167 |
| 1A3184 | sp-9 | an-168 | 1U3184 | sp-9 | an-168 | 1C3184 | sp-9 | an-168 |
| 1A3185 | sp-9 | an-169 | 1U3185 | sp-9 | an-169 | 1C3185 | sp-9 | an-169 |
| 1A3186 | sp-9 | an-170 | 1U3186 | sp-9 | an-170 | 1C3186 | sp-9 | an-170 |
| 1A3187 | sp-9 | an-171 | 1U3187 | sp-9 | an-171 | 1C3187 | sp-9 | an-171 |
| 1A3188 | sp-9 | an-172 | 1U3188 | sp-9 | an-172 | 1C3188 | sp-9 | an-172 |
| 1A3189 | sp-9 | an-173 | 1U3189 | sp-9 | an-173 | 1C3189 | sp-9 | an-173 |
| 1A3190 | sp-9 | an-174 | 1U3190 | sp-9 | an-174 | 1C3190 | sp-9 | an-174 |
| 1A3191 | sp-9 | an-175 | 1U3191 | sp-9 | an-175 | 1C3191 | sp-9 | an-175 |
| 1A3192 | sp-9 | an-176 | 1U3192 | sp-9 | an-176 | 1C3192 | sp-9 | an-176 |

Table 2-58

| Y = NHCS | | | Y = NHCSNH | | | Y = NHCSO | | |
|---|---|---|---|---|---|---|---|---|
| 1A3193 | sp-9 | an-177 | 1U3193 | sp-9 | an-177 | 1C3193 | sp-9 | an-177 |
| 1A3194 | sp-9 | an-178 | 1U3194 | sp-9 | an-178 | 1C3194 | sp-9 | an-178 |
| 1A3195 | sp-9 | an-179 | 1U3195 | sp-9 | an-179 | 1C3195 | sp-9 | an-179 |
| 1A3196 | sp-9 | an-180 | 1U3196 | sp-9 | an-180 | 1C3196 | sp-9 | an-180 |
| 1A3197 | sp-9 | an-181 | 1U3197 | sp-9 | an-181 | 1C3197 | sp-9 | an-181 |
| 1A3198 | sp-9 | an-182 | 1U3198 | sp-9 | an-182 | 1C3198 | sp-9 | an-182 |
| 1A3199 | sp-9 | an-183 | 1U3199 | sp-9 | an-183 | 1C3199 | sp-9 | an-183 |
| 1A3200 | sp-9 | an-184 | 1U3200 | sp-9 | an-184 | 1C3200 | sp-9 | an-184 |
| 1A3201 | sp-9 | an-185 | 1U3201 | sp-9 | an-185 | 1C3201 | sp-9 | an-185 |
| 1A3202 | sp-9 | an-186 | 1U3202 | sp-9 | an-186 | 1C3202 | sp-9 | an-186 |
| 1A3203 | sp-9 | an-187 | 1U3203 | sp-9 | an-187 | 1C3203 | sp-9 | an-187 |
| 1A3204 | sp-9 | an-188 | 1U3204 | sp-9 | an-188 | 1C3204 | sp-9 | an-188 |
| 1A3205 | sp-9 | an-189 | 1U3205 | sp-9 | an-189 | 1C3205 | sp-9 | an-189 |
| 1A3206 | sp-9 | an-190 | 1U3206 | sp-9 | an-190 | 1C3206 | sp-9 | an-190 |
| 1A3207 | sp-9 | an-191 | 1U3207 | sp-9 | an-191 | 1C3207 | sp-9 | an-191 |
| 1A3208 | sp-9 | an-192 | 1U3208 | sp-9 | an-192 | 1C3208 | sp-9 | an-192 |
| 1A3209 | sp-9 | an-193 | 1U3209 | sp-9 | an-193 | 1C3209 | sp-9 | an-193 |
| 1A3210 | sp-9 | an-194 | 1U3210 | sp-9 | an-194 | 1C3210 | sp-9 | an-194 |
| 1A3211 | sp-9 | an-195 | 1U3211 | sp-9 | an-195 | 1C3211 | sp-9 | an-195 |
| 1A3212 | sp-9 | an-196 | 1U3212 | sp-9 | an-196 | 1C3212 | sp-9 | an-196 |
| 1A3213 | sp-9 | an-197 | 1U3213 | sp-9 | an-197 | 1C3213 | sp-9 | an-197 |
| 1A3214 | sp-9 | an-198 | 1U3214 | sp-9 | an-198 | 1C3214 | sp-9 | an-198 |
| 1A3215 | sp-9 | an-199 | 1U3215 | sp-9 | an-199 | 1C3215 | sp-9 | an-199 |
| 1A3216 | sp-9 | an-200 | 1U3216 | sp-9 | an-200 | 1C3216 | sp-9 | an-200 |
| 1A3217 | sp-9 | an-201 | 1U3217 | sp-9 | an-201 | 1C3217 | sp-9 | an-201 |
| 1A3218 | sp-9 | an-202 | 1U3218 | sp-9 | an-202 | 1C3218 | sp-9 | an-202 |
| 1A3219 | sp-9 | an-203 | 1U3219 | sp-9 | an-203 | 1C3219 | sp-9 | an-203 |
| 1A3220 | sp-9 | an-204 | 1U3220 | sp-9 | an-204 | 1C3220 | sp-9 | an-204 |
| 1A3221 | sp-9 | an-205 | 1U3221 | sp-9 | an-205 | 1C3221 | sp-9 | an-205 |
| 1A3222 | sp-9 | an-206 | 1U3222 | sp-9 | an-206 | 1C3222 | sp-9 | an-206 |
| 1A3223 | sp-9 | an-207 | 1U3223 | sp-9 | an-207 | 1C3223 | sp-9 | an-207 |
| 1A3224 | sp-9 | an-208 | 1U3224 | sp-9 | an-208 | 1C3224 | sp-9 | an-208 |
| 1A3225 | sp-9 | an-209 | 1U3225 | sp-9 | an-209 | 1C3225 | sp-9 | an-209 |
| 1A3226 | sp-9 | an-210 | 1U3226 | sp-9 | an-210 | 1C3226 | sp-9 | an-210 |
| 1A3227 | sp-9 | an-211 | 1U3227 | sp-9 | an-211 | 1C3227 | sp-9 | an-211 |
| 1A3228 | sp-9 | an-212 | 1U3228 | sp-9 | an-212 | 1C3228 | sp-9 | an-212 |
| 1A3229 | sp-9 | an-213 | 1U3229 | sp-9 | an-213 | 1C3229 | sp-9 | an-213 |
| 1A3230 | sp-9 | an-214 | 1U3230 | sp-9 | an-214 | 1C3230 | sp-9 | an-214 |
| 1A3231 | sp-9 | an-215 | 1U3231 | sp-9 | an-215 | 1C3231 | sp-9 | an-215 |
| 1A3232 | sp-9 | an-216 | 1U3232 | sp-9 | an-216 | 1C3232 | sp-9 | an-216 |
| 1A3233 | sp-9 | an-217 | 1U3233 | sp-9 | an-217 | 1C3233 | sp-9 | an-217 |
| 1A3234 | sp-9 | an-218 | 1U3234 | sp-9 | an-218 | 1C3234 | sp-9 | an-218 |
| 1A3235 | sp-9 | an-219 | 1U3235 | sp-9 | an-219 | 1C3235 | sp-9 | an-219 |
| 1A3236 | sp-9 | an-220 | 1U3236 | sp-9 | an-220 | 1C3236 | sp-9 | an-220 |

-continued

| Ex. No. | Z | N+R5R6R7 | Ex. No. | Z | N+R5R6R7 | Ex. No. | Z | N+R5R6R7 |
|---|---|---|---|---|---|---|---|---|
| 1A3237 | sp-9 | an-221 | 1U3237 | sp-9 | an-221 | 1C3237 | sp-9 | an-221 |
| 1A3238 | sp-9 | an-222 | 1U3238 | sp-9 | an-222 | 1C3238 | sp-9 | an-222 |
| 1A3239 | sp-9 | an-223 | 1U3239 | sp-9 | an-223 | 1C3239 | sp-9 | an-223 |
| 1A3240 | sp-9 | an-224 | 1U3240 | sp-9 | an-224 | 1C3240 | sp-9 | an-224 |
| 1A3241 | sp-9 | an-225 | 1U3241 | sp-9 | an-225 | 1C3241 | sp-9 | an-225 |
| 1A3242 | sp-9 | an-226 | 1U3242 | sp-9 | an-226 | 1C3242 | sp-9 | an-226 |
| 1A3243 | sp-9 | an-227 | 1U3243 | sp-9 | an-227 | 1C3243 | sp-9 | an-227 |
| 1A3244 | sp-9 | an-228 | 1U3244 | sp-9 | an-228 | 1C3244 | sp-9 | an-228 |
| 1A3245 | sp-9 | an-229 | 1U3245 | sp-9 | an-229 | 1C3245 | sp-9 | an-229 |
| 1A3246 | sp-9 | an-230 | 1U3246 | sp-9 | an-230 | 1C3246 | sp-9 | an-230 |
| 1A3247 | sp-9 | an-231 | 1U3247 | sp-9 | an-231 | 1C3247 | sp-9 | an-231 |
| 1A3248 | sp-9 | an-232 | 1U3248 | sp-9 | an-232 | 1C3248 | sp-9 | an-232 |

Table 2-59

| Y = NHCS | | | Y = NHCSNH | | | Y = NHCSO | | |
|---|---|---|---|---|---|---|---|---|
| 1A3249 | sp-9 | an-233 | 1U3249 | sp-9 | an-233 | 1C3249 | sp-9 | an-233 |
| 1A3250 | sp-9 | an-234 | 1U3250 | sp-9 | an-234 | 1C3250 | sp-9 | an-234 |
| 1A3251 | sp-9 | an-235 | 1U3251 | sp-9 | an-235 | 1C3251 | sp-9 | an-235 |
| 1A3252 | sp-9 | an-236 | 1U3252 | sp-9 | an-236 | 1C3252 | sp-9 | an-236 |
| 1A3253 | sp-9 | an-237 | 1U3253 | sp-9 | an-237 | 1C3253 | sp-9 | an-237 |
| 1A3254 | sp-9 | an-238 | 1U3254 | sp-9 | an-238 | 1C3254 | sp-9 | an-238 |
| 1A3255 | sp-9 | an-239 | 1U3255 | sp-9 | an-239 | 1C3255 | sp-9 | an-239 |
| 1A3256 | sp-9 | an-240 | 1U3256 | sp-9 | an-240 | 1C3256 | sp-9 | an-240 |
| 1A3257 | sp-9 | an-241 | 1U3257 | sp-9 | an-241 | 1C3257 | sp-9 | an-241 |
| 1A3258 | sp-9 | an-242 | 1U3258 | sp-9 | an-242 | 1C3258 | sp-9 | an-242 |
| 1A3259 | sp-9 | an-243 | 1U3259 | sp-9 | an-243 | 1C3259 | sp-9 | an-243 |
| 1A3260 | sp-9 | an-244 | 1U3260 | sp-9 | an-244 | 1C3260 | sp-9 | an-244 |
| 1A3261 | sp-9 | an-245 | 1U3261 | sp-9 | an-245 | 1C3261 | sp-9 | an-245 |
| 1A3262 | sp-9 | an-246 | 1U3262 | sp-9 | an-246 | 1C3262 | sp-9 | an-246 |
| 1A3263 | sp-9 | an-247 | 1U3263 | sp-9 | an-247 | 1C3263 | sp-9 | an-247 |
| 1A3264 | sp-9 | an-248 | 1U3264 | sp-9 | an-248 | 1C3264 | sp-9 | an-248 |
| 1A3265 | sp-9 | an-249 | 1U3265 | sp-9 | an-249 | 1C3265 | sp-9 | an-249 |
| 1A3266 | sp-9 | an-250 | 1U3266 | sp-9 | an-250 | 1C3266 | sp-9 | an-250 |
| 1A3267 | sp-9 | an-251 | 1U3267 | sp-9 | an-251 | 1C3267 | sp-9 | an-251 |
| 1A3268 | sp-9 | an-252 | 1U3268 | sp-9 | an-252 | 1C3268 | sp-9 | an-252 |
| 1A3269 | sp-9 | an-253 | 1U3269 | sp-9 | an-253 | 1C3269 | sp-9 | an-253 |
| 1A3270 | sp-9 | an-254 | 1U3270 | sp-9 | an-254 | 1C3270 | sp-9 | an-254 |
| 1A3271 | sp-9 | an-255 | 1U3271 | sp-9 | an-255 | 1C3271 | sp-9 | an-255 |
| 1A3272 | sp-9 | an-256 | 1U3272 | sp-9 | an-256 | 1C3272 | sp-9 | an-256 |
| 1A3273 | sp-9 | an-257 | 1U3273 | sp-9 | an-257 | 1C3273 | sp-9 | an-257 |
| 1A3274 | sp-9 | an-258 | 1U3274 | sp-9 | an-258 | 1C3274 | sp-9 | an-258 |
| 1A3275 | sp-9 | an-259 | 1U3275 | sp-9 | an-259 | 1C3275 | sp-9 | an-259 |
| 1A3276 | sp-9 | an-260 | 1U3276 | sp-9 | an-260 | 1C3276 | sp-9 | an-260 |
| 1A3277 | sp-9 | an-261 | 1U3277 | sp-9 | an-261 | 1C3277 | sp-9 | an-261 |
| 1A3278 | sp-9 | an-262 | 1U3278 | sp-9 | an-262 | 1C3278 | sp-9 | an-262 |
| 1A3279 | sp-9 | an-263 | 1U3279 | sp-9 | an-263 | 1C3279 | sp-9 | an-263 |
| 1A3280 | sp-9 | an-264 | 1U3280 | sp-9 | an-264 | 1C3280 | sp-9 | an-264 |
| 1A3281 | sp-9 | an-265 | 1U3281 | sp-9 | an-265 | 1C3281 | sp-9 | an-265 |
| 1A3282 | sp-9 | an-266 | 1U3282 | sp-9 | an-266 | 1C3282 | sp-9 | an-266 |
| 1A3283 | sp-9 | an-267 | 1U3283 | sp-9 | an-267 | 1C3283 | sp-9 | an-267 |
| 1A3284 | sp-9 | an-268 | 1U3284 | sp-9 | an-268 | 1C3284 | sp-9 | an-268 |
| 1A3285 | sp-9 | an-269 | 1U3285 | sp-9 | an-269 | 1C3285 | sp-9 | an-269 |
| 1A3286 | sp-9 | an-270 | 1U3286 | sp-9 | an-270 | 1C3286 | sp-9 | an-270 |
| 1A3287 | sp-9 | an-271 | 1U3287 | sp-9 | an-271 | 1C3287 | sp-9 | an-271 |
| 1A3288 | sp-9 | an-272 | 1U3288 | sp-9 | an-272 | 1C3288 | sp-9 | an-272 |
| 1A3289 | sp-9 | an-273 | 1U3289 | sp-9 | an-273 | 1C3289 | sp-9 | an-273 |
| 1A3290 | sp-9 | an-274 | 1U3290 | sp-9 | an-274 | 1C3290 | sp-9 | an-274 |
| 1A3291 | sp-9 | an-275 | 1U3291 | sp-9 | an-275 | 1C3291 | sp-9 | an-275 |
| 1A3292 | sp-9 | an-276 | 1U3292 | sp-9 | an-276 | 1C3292 | sp-9 | an-276 |
| 1A3293 | sp-9 | an-277 | 1U3293 | sp-9 | an-277 | 1C3293 | sp-9 | an-277 |
| 1A3294 | sp-9 | an-278 | 1U3294 | sp-9 | an-278 | 1C3294 | sp-9 | an-278 |
| 1A3295 | sp-9 | an-279 | 1U3295 | sp-9 | an-279 | 1C3295 | sp-9 | an-279 |
| 1A3296 | sp-9 | an-280 | 1U3296 | sp-9 | an-280 | 1C3296 | sp-9 | an-280 |
| 1A3297 | sp-9 | an-281 | 1U3297 | sp-9 | an-281 | 1C3297 | sp-9 | an-281 |
| 1A3298 | sp-9 | an-282 | 1U3298 | sp-9 | an-282 | 1C3298 | sp-9 | an-282 |
| 1A3299 | sp-9 | an-283 | 1U3299 | sp-9 | an-283 | 1C3299 | sp-9 | an-283 |
| 1A3300 | sp-9 | an-284 | 1U3300 | sp-9 | an-284 | 1C3300 | sp-9 | an-284 |
| 1A3301 | sp-9 | an-285 | 1U3301 | sp-9 | an-285 | 1C3301 | sp-9 | an-285 |
| 1A3302 | sp-9 | an-286 | 1U3302 | sp-9 | an-286 | 1C3302 | sp-9 | an-286 |
| 1A3303 | sp-9 | an-287 | 1U3303 | sp-9 | an-287 | 1C3303 | sp-9 | an-287 |
| 1A3304 | sp-9 | an-288 | 1U3304 | sp-9 | an-288 | 1C3304 | sp-9 | an-288 |

Table 2-60

| Y = NHCS | | | Y = NHCSNH | | | Y = NHCSO | | |
|---|---|---|---|---|---|---|---|---|
| 1A3305 | sp-9 | an-289 | 1U3305 | sp-9 | an-289 | 1C3305 | sp-9 | an-289 |
| 1A3306 | sp-9 | an-290 | 1U3306 | sp-9 | an-290 | 1C3306 | sp-9 | an-290 |

-continued

| Ex. No. | Z | N⁺R⁵R⁶R⁷ | Ex. No. | Z | N⁺R⁵R⁶R⁷ | Ex. No. | Z | N⁺R⁵R⁶R⁷ |
|---|---|---|---|---|---|---|---|---|
| 1A3307 | sp-9 | an-291 | 1U3307 | sp-9 | an-291 | 1C3307 | sp-9 | an-291 |
| 1A3308 | sp-9 | an-292 | 1U3308 | sp-9 | an-292 | 1C3308 | sp-9 | an-292 |
| 1A3309 | sp-9 | an-293 | 1U3309 | sp-9 | an-293 | 1C3309 | sp-9 | an-293 |
| 1A3310 | sp-9 | an-294 | 1U3310 | sp-9 | an-294 | 1C3310 | sp-9 | an-294 |
| 1A3311 | sp-9 | an-295 | 1U3311 | sp-9 | an-295 | 1C3311 | sp-9 | an-295 |
| 1A3312 | sp-9 | an-296 | 1U3312 | sp-9 | an-296 | 1C3312 | sp-9 | an-296 |
| 1A3313 | sp-9 | an-297 | 1U3313 | sp-9 | an-297 | 1C3313 | sp-9 | an-297 |
| 1A3314 | sp-9 | an-298 | 1U3314 | sp-9 | an-298 | 1C3314 | sp-9 | an-298 |
| 1A3315 | sp-9 | an-299 | 1U3315 | sp-9 | an-299 | 1C3315 | sp-9 | an-299 |
| 1A3316 | sp-9 | an-300 | 1U3316 | sp-9 | an-300 | 1C3316 | sp-9 | an-300 |
| 1A3317 | sp-9 | an-301 | 1U3317 | sp-9 | an-301 | 1C3317 | sp-9 | an-301 |
| 1A3318 | sp-9 | an-302 | 1U3318 | sp-9 | an-302 | 1C3318 | sp-9 | an-302 |
| 1A3319 | sp-9 | an-303 | 1U3319 | sp-9 | an-303 | 1C3319 | sp-9 | an-303 |
| 1A3320 | sp-9 | an-304 | 1U3320 | sp-9 | an-304 | 1C3320 | sp-9 | an-304 |
| 1A3321 | sp-9 | an-305 | 1U3321 | sp-9 | an-305 | 1C3321 | sp-9 | an-305 |
| 1A3322 | sp-9 | an-306 | 1U3322 | sp-9 | an-306 | 1C3322 | sp-9 | an-306 |
| 1A3323 | sp-9 | an-307 | 1U3323 | sp-9 | an-307 | 1C3323 | sp-9 | an-307 |
| 1A3324 | sp-9 | an-308 | 1U3324 | sp-9 | an-308 | 1C3324 | sp-9 | an-308 |
| 1A3325 | sp-9 | an-309 | 1U3325 | sp-9 | an-309 | 1C3325 | sp-9 | an-309 |
| 1A3326 | sp-9 | an-310 | 1U3326 | sp-9 | an-310 | 1C3326 | sp-9 | an-310 |
| 1A3327 | sp-9 | an-311 | 1U3327 | sp-9 | an-311 | 1C3327 | sp-9 | an-311 |
| 1A3328 | sp-9 | an-312 | 1U3328 | sp-9 | an-312 | 1C3328 | sp-9 | an-312 |
| 1A3329 | sp-9 | an-313 | 1U3329 | sp-9 | an-313 | 1C3329 | sp-9 | an-313 |
| 1A3330 | sp-9 | an-314 | 1U3330 | sp-9 | an-314 | 1C3330 | sp-9 | an-314 |
| 1A3331 | sp-9 | an-315 | 1U3331 | sp-9 | an-315 | 1C3331 | sp-9 | an-315 |
| 1A3332 | sp-9 | an-316 | 1U3332 | sp-9 | an-316 | 1C3332 | sp-9 | an-316 |
| 1A3333 | sp-9 | an-317 | 1U3333 | sp-9 | an-317 | 1C3333 | sp-9 | an-317 |
| 1A3334 | sp-9 | an-318 | 1U3334 | sp-9 | an-318 | 1C3334 | sp-9 | an-318 |
| 1A3335 | sp-9 | an-319 | 1U3335 | sp-9 | an-319 | 1C3335 | sp-9 | an-319 |
| 1A3336 | sp-9 | an-320 | 1U3336 | sp-9 | an-320 | 1C3336 | sp-9 | an-320 |
| 1A3337 | sp-9 | an-321 | 1U3337 | sp-9 | an-321 | 1C3337 | sp-9 | an-321 |
| 1A3338 | sp-9 | an-322 | 1U3338 | sp-9 | an-322 | 1C3338 | sp-9 | an-322 |
| 1A3339 | sp-9 | an-323 | 1U3339 | sp-9 | an-323 | 1C3339 | sp-9 | an-323 |
| 1A3340 | sp-9 | an-324 | 1U3340 | sp-9 | an-324 | 1C3340 | sp-9 | an-324 |
| 1A3341 | sp-9 | an-325 | 1U3341 | sp-9 | an-325 | 1C3341 | sp-9 | an-325 |
| 1A3342 | sp-9 | an-326 | 1U3342 | sp-9 | an-326 | 1C3342 | sp-9 | an-326 |
| 1A3343 | sp-9 | an-327 | 1U3343 | sp-9 | an-327 | 1C3343 | sp-9 | an-327 |
| 1A3344 | sp-9 | an-328 | 1U3344 | sp-9 | an-328 | 1C3344 | sp-9 | an-328 |
| 1A3345 | sp-9 | an-329 | 1U3345 | sp-9 | an-329 | 1C3345 | sp-9 | an-329 |
| 1A3346 | sp-9 | an-330 | 1U3346 | sp-9 | an-330 | 1C3346 | sp-9 | an-330 |
| 1A3347 | sp-9 | an-331 | 1U3347 | sp-9 | an-331 | 1C3347 | sp-9 | an-331 |
| 1A3348 | sp-9 | an-332 | 1U3348 | sp-9 | an-332 | 1C3348 | sp-9 | an-332 |
| 1A3349 | sp-9 | an-333 | 1U3349 | sp-9 | an-333 | 1C3349 | sp-9 | an-333 |
| 1A3350 | sp-9 | an-334 | 1U3350 | sp-9 | an-334 | 1C3350 | sp-9 | an-334 |
| 1A3351 | sp-9 | an-335 | 1U3351 | sp-9 | an-335 | 1C3351 | sp-9 | an-335 |
| 1A3352 | sp-9 | an-336 | 1U3352 | sp-9 | an-336 | 1C3352 | sp-9 | an-336 |
| 1A3353 | sp-9 | an-337 | 1U3353 | sp-9 | an-337 | 1C3353 | sp-9 | an-337 |
| 1A3354 | sp-9 | an-338 | 1U3354 | sp-9 | an-338 | 1C3354 | sp-9 | an-338 |
| 1A3355 | sp-9 | an-339 | 1U3355 | sp-9 | an-339 | 1C3355 | sp-9 | an-339 |
| 1A3356 | sp-9 | an-340 | 1U3356 | sp-9 | an-340 | 1C3356 | sp-9 | an-340 |
| 1A3357 | sp-9 | an-341 | 1U3357 | sp-9 | an-341 | 1C3357 | sp-9 | an-341 |
| 1A3358 | sp-9 | an-342 | 1U3358 | sp-9 | an-342 | 1C3358 | sp-9 | an-342 |
| 1A3359 | sp-9 | an-343 | 1U3359 | sp-9 | an-343 | 1C3359 | sp-9 | an-343 |
| 1A3360 | sp-9 | an-344 | 1U3360 | sp-9 | an-344 | 1C3360 | sp-9 | an-344 |

Table 2-61

| Y = NHCS | | | Y = NHCSNH | | | Y = NHCSO | | |
|---|---|---|---|---|---|---|---|---|
| 1A3361 | sp-9 | an-345 | 1U3361 | sp-9 | an-345 | 1C3361 | sp-9 | an-345 |
| 1A3362 | sp-9 | an-346 | 1U3362 | sp-9 | an-346 | 1C3362 | sp-9 | an-346 |
| 1A3363 | sp-9 | an-347 | 1U3363 | sp-9 | an-347 | 1C3363 | sp-9 | an-347 |
| 1A3364 | sp-9 | an-348 | 1U3364 | sp-9 | an-348 | 1C3364 | sp-9 | an-348 |
| 1A3365 | sp-9 | an-349 | 1U3365 | sp-9 | an-349 | 1C3365 | sp-9 | an-349 |
| 1A3366 | sp-9 | an-350 | 1U3366 | sp-9 | an-350 | 1C3366 | sp-9 | an-350 |
| 1A3367 | sp-9 | an-351 | 1U3367 | sp-9 | an-351 | 1C3367 | sp-9 | an-351 |
| 1A3368 | sp-9 | an-352 | 1U3368 | sp-9 | an-352 | 1C3368 | sp-9 | an-352 |
| 1A3369 | sp-9 | an-353 | 1U3369 | sp-9 | an-353 | 1C3369 | sp-9 | an-353 |
| 1A3370 | sp-9 | an-354 | 1U3370 | sp-9 | an-354 | 1C3370 | sp-9 | an-354 |
| 1A3371 | sp-9 | an-355 | 1U3371 | sp-9 | an-355 | 1C3371 | sp-9 | an-355 |
| 1A3372 | sp-9 | an-356 | 1U3372 | sp-9 | an-356 | 1C3372 | sp-9 | an-356 |
| 1A3373 | sp-9 | an-357 | 1U3373 | sp-9 | an-357 | 1C3373 | sp-9 | an-357 |
| 1A3374 | sp-9 | an-358 | 1U3374 | sp-9 | an-358 | 1C3374 | sp-9 | an-358 |
| 1A3375 | sp-9 | an-359 | 1U3375 | sp-9 | an-359 | 1C3375 | sp-9 | an-359 |
| 1A3376 | sp-9 | an-360 | 1U3376 | sp-9 | an-360 | 1C3376 | sp-9 | an-360 |
| 1A3377 | sp-9 | an-361 | 1U3377 | sp-9 | an-361 | 1C3377 | sp-9 | an-361 |
| 1A3378 | sp-9 | an-362 | 1U3378 | sp-9 | an-362 | 1C3378 | sp-9 | an-362 |
| 1A3379 | sp-9 | an-363 | 1U3379 | sp-9 | an-363 | 1C3379 | sp-9 | an-363 |
| 1A3380 | sp-9 | an-364 | 1U3380 | sp-9 | an-364 | 1C3380 | sp-9 | an-364 |

| Ex. No. | Z | N⁺R⁵R⁶R⁷ | Ex. No. | Z | N⁺R⁵R⁶R⁷ | Ex. No. | Z | N⁺R⁵R⁶R⁷ |
|---|---|---|---|---|---|---|---|---|
| 1A3381 | sp-9 | an-365 | 1U3381 | sp-9 | an-365 | 1C3381 | sp-9 | an-365 |
| 1A3382 | sp-9 | an-366 | 1U3382 | sp-9 | an-366 | 1C3382 | sp-9 | an-366 |
| 1A3383 | sp-9 | an-367 | 1U3383 | sp-9 | an-367 | 1C3383 | sp-9 | an-367 |
| 1A3384 | sp-9 | an-368 | 1U3384 | sp-9 | an-368 | 1C3384 | sp-9 | an-368 |
| 1A3385 | sp-9 | an-369 | 1U3385 | sp-9 | an-369 | 1C3385 | sp-9 | an-369 |
| 1A3386 | sp-9 | an-370 | 1U3386 | sp-9 | an-370 | 1C3386 | sp-9 | an-370 |
| 1A3387 | sp-9 | an-371 | 1U3387 | sp-9 | an-371 | 1C3387 | sp-9 | an-371 |
| 1A3388 | sp-9 | an-372 | 1U3388 | sp-9 | an-372 | 1C3388 | sp-9 | an-372 |
| 1A3389 | sp-9 | an-373 | 1U3389 | sp-9 | an-373 | 1C3389 | sp-9 | an-373 |
| 1A3390 | sp-9 | an-374 | 1U3390 | sp-9 | an-374 | 1C3390 | sp-9 | an-374 |
| 1A3391 | sp-9 | an-375 | 1U3391 | sp-9 | an-375 | 1C3391 | sp-9 | an-375 |
| 1A3392 | sp-9 | an-376 | 1U3392 | sp-9 | an-376 | 1C3392 | sp-9 | an-376 |
| 1A3393 | sp-9 | an-377 | 1U3393 | sp-9 | an-377 | 1C3393 | sp-9 | an-377 |
| 1A3394 | sp-10 | an-1 | 1U3394 | sp-12 | an-1 | 1C3394 | sp-11 | an-1 |
| 1A3395 | sp-10 | an-2 | 1U3395 | sp-12 | an-2 | 1C3395 | sp-11 | an-2 |
| 1A3396 | sp-10 | an-3 | 1U3396 | sp-12 | an-3 | 1C3396 | sp-11 | an-3 |
| 1A3397 | sp-10 | an-4 | 1U3397 | sp-12 | an-4 | 1C3397 | sp-11 | an-4 |
| 1A3398 | sp-10 | an-5 | 1U3398 | sp-12 | an-5 | 1C3398 | sp-11 | an-5 |
| 1A3399 | sp-10 | an-6 | 1U3399 | sp-12 | an-6 | 1C3399 | sp-11 | an-6 |
| 1A3400 | sp-10 | an-7 | 1U3400 | sp-12 | an-7 | 1C3400 | sp-11 | an-7 |
| 1A3401 | sp-10 | an-8 | 1U3401 | sp-12 | an-8 | 1C3401 | sp-11 | an-8 |
| 1A3402 | sp-10 | an-9 | 1U3402 | sp-12 | an-9 | 1C3402 | sp-11 | an-9 |
| 1A3403 | sp-10 | an-10 | 1U3403 | sp-12 | an-10 | 1C3403 | sp-11 | an-10 |
| 1A3404 | sp-10 | an-11 | 1U3404 | sp-12 | an-11 | 1C3404 | sp-11 | an-11 |
| 1A3405 | sp-10 | an-12 | 1U3405 | sp-12 | an-12 | 1C3405 | sp-11 | an-12 |
| 1A3406 | sp-10 | an-13 | 1U3406 | sp-12 | an-13 | 1C3406 | sp-11 | an-13 |
| 1A3407 | sp-10 | an-14 | 1U3407 | sp-12 | an-14 | 1C3407 | sp-11 | an-14 |
| 1A3408 | sp-10 | an-15 | 1U3408 | sp-12 | an-15 | 1C3408 | sp-11 | an-15 |
| 1A3409 | sp-10 | an-16 | 1U3409 | sp-12 | an-16 | 1C3409 | sp-11 | an-16 |
| 1A3410 | sp-10 | an-17 | 1U3410 | sp-12 | an-17 | 1C3410 | sp-11 | an-17 |
| 1A3411 | sp-10 | an-18 | 1U3411 | sp-12 | an-18 | 1C3411 | sp-11 | an-18 |
| 1A3412 | sp-10 | an-19 | 1U3412 | sp-12 | an-19 | 1C3412 | sp-11 | an-19 |
| 1A3413 | sp-10 | an-20 | 1U3413 | sp-12 | an-20 | 1C3413 | sp-11 | an-20 |
| 1A3414 | sp-10 | an-21 | 1U3414 | sp-12 | an-21 | 1C3414 | sp-11 | an-21 |
| 1A3415 | sp-10 | an-22 | 1U3415 | sp-12 | an-22 | 1C3415 | sp-11 | an-22 |
| 1A3416 | sp-10 | an-23 | 1U3416 | sp-12 | an-23 | 1C3416 | sp-11 | an-23 |

Table 2-62

| Y = NHCS | | | Y = NHCSNH | | | Y = NHCSO | | |
|---|---|---|---|---|---|---|---|---|
| 1A3417 | sp-10 | an-24 | 1U3417 | sp-12 | an-24 | 1C3417 | sp-11 | an-24 |
| 1A3418 | sp-10 | an-25 | 1U3418 | sp-12 | an-25 | 1C3418 | sp-11 | an-25 |
| 1A3419 | sp-10 | an-26 | 1U3419 | sp-12 | an-26 | 1C3419 | sp-11 | an-26 |
| 1A3420 | sp-10 | an-27 | 1U3420 | sp-12 | an-27 | 1C3420 | sp-11 | an-27 |
| 1A3421 | sp-10 | an-28 | 1U3421 | sp-12 | an-28 | 1C3421 | sp-11 | an-28 |
| 1A3422 | sp-10 | an-29 | 1U3422 | sp-12 | an-29 | 1C3422 | sp-11 | an-29 |
| 1A3423 | sp-10 | an-30 | 1U3423 | sp-12 | an-30 | 1C3423 | sp-11 | an-30 |
| 1A3424 | sp-10 | an-31 | 1U3424 | sp-12 | an-31 | 1C3424 | sp-11 | an-31 |
| 1A3425 | sp-10 | an-32 | 1U3425 | sp-12 | an-32 | 1C3425 | sp-11 | an-32 |
| 1A3426 | sp-10 | an-33 | 1U3426 | sp-12 | an-33 | 1C3426 | sp-11 | an-33 |
| 1A3427 | sp-10 | an-34 | 1U3427 | sp-12 | an-34 | 1C3427 | sp-11 | an-34 |
| 1A3428 | sp-10 | an-35 | 1U3428 | sp-12 | an-35 | 1C3428 | sp-11 | an-35 |
| 1A3429 | sp-10 | an-36 | 1U3429 | sp-12 | an-36 | 1C3429 | sp-11 | an-36 |
| 1A3430 | sp-10 | an-37 | 1U3430 | sp-12 | an-37 | 1C3430 | sp-11 | an-37 |
| 1A3431 | sp-10 | an-38 | 1U3431 | sp-12 | an-38 | 1C3431 | sp-11 | an-38 |
| 1A3432 | sp-10 | an-39 | 1U3432 | sp-12 | an-39 | 1C3432 | sp-11 | an-39 |
| 1A3433 | sp-10 | an-40 | 1U3433 | sp-12 | an-40 | 1C3433 | sp-11 | an-40 |
| 1A3434 | sp-10 | an-41 | 1U3434 | sp-12 | an-41 | 1C3434 | sp-11 | an-41 |
| 1A3435 | sp-10 | an-42 | 1U3435 | sp-12 | an-42 | 1C3435 | sp-11 | an-42 |
| 1A3436 | sp-10 | an-43 | 1U3436 | sp-12 | an-43 | 1C3436 | sp-11 | an-43 |
| 1A3437 | sp-10 | an-44 | 1U3437 | sp-12 | an-44 | 1C3437 | sp-11 | an-44 |
| 1A3438 | sp-10 | an-45 | 1U3438 | sp-12 | an-45 | 1C3438 | sp-11 | an-45 |
| 1A3439 | sp-10 | an-46 | 1U3439 | sp-12 | an-46 | 1C3439 | sp-11 | an-46 |
| 1A3440 | sp-10 | an-47 | 1U3440 | sp-12 | an-47 | 1C3440 | sp-11 | an-47 |
| 1A3441 | sp-10 | an-48 | 1U3441 | sp-12 | an-48 | 1C3441 | sp-11 | an-48 |
| 1A3442 | sp-10 | an-49 | 1U3442 | sp-12 | an-49 | 1C3442 | sp-11 | an-49 |
| 1A3443 | sp-10 | an-50 | 1U3443 | sp-12 | an-50 | 1C3443 | sp-11 | an-50 |
| 1A3444 | sp-10 | an-51 | 1U3444 | sp-12 | an-51 | 1C3444 | sp-11 | an-51 |
| 1A3445 | sp-10 | an-52 | 1U3445 | sp-12 | an-52 | 1C3445 | sp-11 | an-52 |
| 1A3446 | sp-10 | an-53 | 1U3446 | sp-12 | an-53 | 1C3446 | sp-11 | an-53 |
| 1A3447 | sp-10 | an-54 | 1U3447 | sp-12 | an-54 | 1C3447 | sp-11 | an-54 |
| 1A3448 | sp-10 | an-55 | 1U3448 | sp-12 | an-55 | 1C3448 | sp-11 | an-55 |
| 1A3449 | sp-10 | an-56 | 1U3449 | sp-12 | an-56 | 1C3449 | sp-11 | an-56 |
| 1A3450 | sp-10 | an-57 | 1U3450 | sp-12 | an-57 | 1C3450 | sp-11 | an-57 |
| 1A3451 | sp-10 | an-58 | 1U3451 | sp-12 | an-58 | 1C3451 | sp-11 | an-58 |
| 1A3452 | sp-10 | an-59 | 1U3452 | sp-12 | an-59 | 1C3452 | sp-11 | an-59 |
| 1A3453 | sp-10 | an-60 | 1U3453 | sp-12 | an-60 | 1C3453 | sp-11 | an-60 |
| 1A3454 | sp-10 | an-61 | 1U3454 | sp-12 | an-61 | 1C3454 | sp-11 | an-61 |

-continued

| Ex. No. | Z | N⁺R⁵R⁶R⁷ | Ex. No. | Z | N⁺R⁵R⁶R⁷ | Ex. No. | Z | N⁺R⁵R⁶R⁷ |
|---|---|---|---|---|---|---|---|---|
| 1A3455 | sp-10 | an-62 | 1U3455 | sp-12 | an-62 | 1C3455 | sp-11 | an-62 |
| 1A3456 | sp-10 | an-63 | 1U3456 | sp-12 | an-63 | 1C3456 | sp-11 | an-63 |
| 1A3457 | sp-10 | an-64 | 1U3457 | sp-12 | an-64 | 1C3457 | sp-11 | an-64 |
| 1A3458 | sp-10 | an-65 | 1U3458 | sp-12 | an-65 | 1C3458 | sp-11 | an-65 |
| 1A3459 | sp-10 | an-66 | 1U3459 | sp-12 | an-66 | 1C3459 | sp-11 | an-66 |
| 1A3460 | sp-10 | an-67 | 1U3460 | sp-12 | an-67 | 1C3460 | sp-11 | an-67 |
| 1A3461 | sp-10 | an-68 | 1U3461 | sp-12 | an-68 | 1C3461 | sp-11 | an-68 |
| 1A3462 | sp-10 | an-69 | 1U3462 | sp-12 | an-69 | 1C3462 | sp-11 | an-69 |
| 1A3463 | sp-10 | an-70 | 1U3463 | sp-12 | an-70 | 1C3463 | sp-11 | an-70 |
| 1A3464 | sp-10 | an-71 | 1U3464 | sp-12 | an-71 | 1C3464 | sp-11 | an-71 |
| 1A3465 | sp-10 | an-72 | 1U3465 | sp-12 | an-72 | 1C3465 | sp-11 | an-72 |
| 1A3466 | sp-10 | an-73 | 1U3466 | sp-12 | an-73 | 1C3466 | sp-11 | an-73 |
| 1A3467 | sp-10 | an-74 | 1U3467 | sp-12 | an-74 | 1C3467 | sp-11 | an-74 |
| 1A3468 | sp-10 | an-75 | 1U3468 | sp-12 | an-75 | 1C3468 | sp-11 | an-75 |
| 1A3469 | sp-10 | an-76 | 1U3469 | sp-12 | an-76 | 1C3469 | sp-11 | an-76 |
| 1A3470 | sp-10 | an-77 | 1U3470 | sp-12 | an-77 | 1C3470 | sp-11 | an-77 |
| 1A3471 | sp-10 | an-78 | 1U3471 | sp-12 | an-78 | 1C3471 | sp-11 | an-78 |
| 1A3472 | sp-10 | an-79 | 1U3472 | sp-12 | an-79 | 1C3472 | sp-11 | an-79 |

Table 2-63

| Y = NHCS | | | Y = NHCSNH | | | Y = NHCSO | | |
|---|---|---|---|---|---|---|---|---|
| 1A3473 | sp-10 | an-80 | 1U3473 | sp-12 | an-80 | 1C3473 | sp-11 | an-80 |
| 1A3474 | sp-10 | an-81 | 1U3474 | sp-12 | an-81 | 1C3474 | sp-11 | an-81 |
| 1A3475 | sp-10 | an-82 | 1U3475 | sp-12 | an-82 | 1C3475 | sp-11 | an-82 |
| 1A3476 | sp-10 | an-83 | 1U3476 | sp-12 | an-83 | 1C3476 | sp-11 | an-83 |
| 1A3477 | sp-10 | an-84 | 1U3477 | sp-12 | an-84 | 1C3477 | sp-11 | an-84 |
| 1A3478 | sp-10 | an-85 | 1U3478 | sp-12 | an-85 | 1C3478 | sp-11 | an-85 |
| 1A3479 | sp-10 | an-86 | 1U3479 | sp-12 | an-86 | 1C3479 | sp-11 | an-86 |
| 1A3480 | sp-10 | an-87 | 1U3480 | sp-12 | an-87 | 1C3480 | sp-11 | an-87 |
| 1A3481 | sp-10 | an-88 | 1U3481 | sp-12 | an-88 | 1C3481 | sp-11 | an-88 |
| 1A3482 | sp-10 | an-89 | 1U3482 | sp-12 | an-89 | 1C3482 | sp-11 | an-89 |
| 1A3483 | sp-10 | an-90 | 1U3483 | sp-12 | an-90 | 1C3483 | sp-11 | an-90 |
| 1A3484 | sp-10 | an-91 | 1U3484 | sp-12 | an-91 | 1C3484 | sp-11 | an-91 |
| 1A3485 | sp-10 | an-92 | 1U3485 | sp-12 | an-92 | 1C3485 | sp-11 | an-92 |
| 1A3486 | sp-10 | an-93 | 1U3486 | sp-12 | an-93 | 1C3486 | sp-11 | an-93 |
| 1A3487 | sp-10 | an-94 | 1U3487 | sp-12 | an-94 | 1C3487 | sp-11 | an-94 |
| 1A3488 | sp-10 | an-95 | 1U3488 | sp-12 | an-95 | 1C3488 | sp-11 | an-95 |
| 1A3489 | sp-10 | an-96 | 1U3489 | sp-12 | an-96 | 1C3489 | sp-11 | an-96 |
| 1A3490 | sp-10 | an-97 | 1U3490 | sp-12 | an-97 | 1C3490 | sp-11 | an-97 |
| 1A3491 | sp-10 | an-98 | 1U3491 | sp-12 | an-98 | 1C3491 | sp-11 | an-98 |
| 1A3492 | sp-10 | an-99 | 1U3492 | sp-12 | an-99 | 1C3492 | sp-11 | an-99 |
| 1A3493 | sp-10 | an-100 | 1U3493 | sp-12 | an-100 | 1C3493 | sp-11 | an-100 |
| 1A3494 | sp-10 | an-101 | 1U3494 | sp-12 | an-101 | 1C3494 | sp-11 | an-101 |
| 1A3495 | sp-10 | an-102 | 1U3495 | sp-12 | an-102 | 1C3495 | sp-11 | an-102 |
| 1A3496 | sp-10 | an-103 | 1U3496 | sp-12 | an-103 | 1C3496 | sp-11 | an-103 |
| 1A3497 | sp-10 | an-104 | 1U3497 | sp-12 | an-104 | 1C3497 | sp-11 | an-104 |
| 1A3498 | sp-10 | an-105 | 1U3498 | sp-12 | an-105 | 1C3498 | sp-11 | an-105 |
| 1A3499 | sp-10 | an-106 | 1U3499 | sp-12 | an-106 | 1C3499 | sp-11 | an-106 |
| 1A3500 | sp-10 | an-107 | 1U3500 | sp-12 | an-107 | 1C3500 | sp-11 | an-107 |
| 1A3501 | sp-10 | an-108 | 1U3501 | sp-12 | an-108 | 1C3501 | sp-11 | an-108 |
| 1A3502 | sp-10 | an-109 | 1U3502 | sp-12 | an-109 | 1C3502 | sp-11 | an-109 |
| 1A3503 | sp-10 | an-110 | 1U3503 | sp-12 | an-110 | 1C3503 | sp-11 | an-110 |
| 1A3504 | sp-10 | an-111 | 1U3504 | sp-12 | an-111 | 1C3504 | sp-11 | an-111 |
| 1A3505 | sp-10 | an-112 | 1U3505 | sp-12 | an-112 | 1C3505 | sp-11 | an-112 |
| 1A3506 | sp-10 | an-113 | 1U3506 | sp-12 | an-113 | 1C3506 | sp-11 | an-113 |
| 1A3507 | sp-10 | an-114 | 1U3507 | sp-12 | an-114 | 1C3507 | sp-11 | an-114 |
| 1A3508 | sp-10 | an-115 | 1U3508 | sp-12 | an-115 | 1C3508 | sp-11 | an-115 |
| 1A3509 | sp-10 | an-116 | 1U3509 | sp-12 | an-116 | 1C3509 | sp-11 | an-116 |
| 1A3510 | sp-10 | an-117 | 1U3510 | sp-12 | an-117 | 1C3510 | sp-11 | an-117 |
| 1A3511 | sp-10 | an-118 | 1U3511 | sp-12 | an-118 | 1C3511 | sp-11 | an-118 |
| 1A3512 | sp-10 | an-119 | 1U3512 | sp-12 | an-119 | 1C3512 | sp-11 | an-119 |
| 1A3513 | sp-10 | an-120 | 1U3513 | sp-12 | an-120 | 1C3513 | sp-11 | an-120 |
| 1A3514 | sp-10 | an-121 | 1U3514 | sp-12 | an-121 | 1C3514 | sp-11 | an-121 |
| 1A3515 | sp-10 | an-122 | 1U3515 | sp-12 | an-122 | 1C3515 | sp-11 | an-122 |
| 1A3516 | sp-10 | an-123 | 1U3516 | sp-12 | an-123 | 1C3516 | sp-11 | an-123 |
| 1A3517 | sp-10 | an-124 | 1U3517 | sp-12 | an-124 | 1C3517 | sp-11 | an-124 |
| 1A3518 | sp-10 | an-125 | 1U3518 | sp-12 | an-125 | 1C3518 | sp-11 | an-125 |
| 1A3519 | sp-10 | an-126 | 1U3519 | sp-12 | an-126 | 1C3519 | sp-11 | an-126 |
| 1A3520 | sp-10 | an-127 | 1U3520 | sp-12 | an-127 | 1C3520 | sp-11 | an-127 |
| 1A3521 | sp-10 | an-128 | 1U3521 | sp-12 | an-128 | 1C3521 | sp-11 | an-128 |
| 1A3522 | sp-10 | an-129 | 1U3522 | sp-12 | an-129 | 1C3522 | sp-11 | an-129 |
| 1A3523 | sp-10 | an-130 | 1U3523 | sp-12 | an-130 | 1C3523 | sp-11 | an-130 |
| 1A3524 | sp-10 | an-131 | 1U3524 | sp-12 | an-131 | 1C3524 | sp-11 | an-131 |
| 1A3525 | sp-10 | an-132 | 1U3525 | sp-12 | an-132 | 1C3525 | sp-11 | an-132 |
| 1A3526 | sp-10 | an-133 | 1U3526 | sp-12 | an-133 | 1C3526 | sp-11 | an-133 |
| 1A3527 | sp-10 | an-134 | 1U3527 | sp-12 | an-134 | 1C3527 | sp-11 | an-134 |
| 1A3528 | sp-10 | an-135 | 1U3528 | sp-12 | an-135 | 1C3528 | sp-11 | an-135 |

-continued

| Ex. No. | Z | $N^+R^5R^6R^7$ | Ex. No. | Z | $N^+R^5R^6R^7$ | Ex. No. | Z | $N^+R^5R^6R^7$ |
|---|---|---|---|---|---|---|---|---|
| Table 2-64 ||||||||||
| Y = NHCS ||| Y = NHCSNH ||| Y = NHCSO |||
| 1A3529 | sp-10 | an-136 | 1U3529 | sp-12 | an-136 | 1C3529 | sp-11 | an-136 |
| 1A3530 | sp-10 | an-137 | 1U3530 | sp-12 | an-137 | 1C3530 | sp-11 | an-137 |
| 1A3531 | sp-10 | an-138 | 1U3531 | sp-12 | an-138 | 1C3531 | sp-11 | an-138 |
| 1A3532 | sp-10 | an-139 | 1U3532 | sp-12 | an-139 | 1C3532 | sp-11 | an-139 |
| 1A3533 | sp-10 | an-140 | 1U3533 | sp-12 | an-140 | 1C3533 | sp-11 | an-140 |
| 1A3534 | sp-10 | an-141 | 1U3534 | sp-12 | an-141 | 1C3534 | sp-11 | an-141 |
| 1A3535 | sp-10 | an-142 | 1U3535 | sp-12 | an-142 | 1C3535 | sp-11 | an-142 |
| 1A3536 | sp-10 | an-143 | 1U3536 | sp-12 | an-143 | 1C3536 | sp-11 | an-143 |
| 1A3537 | sp-10 | an-144 | 1U3537 | sp-12 | an-144 | 1C3537 | sp-11 | an-144 |
| 1A3538 | sp-10 | an-145 | 1U3538 | sp-12 | an-145 | 1C3538 | sp-11 | an-145 |
| 1A3539 | sp-10 | an-146 | 1U3539 | sp-12 | an-146 | 1C3539 | sp-11 | an-146 |
| 1A3540 | sp-10 | an-147 | 1U3540 | sp-12 | an-147 | 1C3540 | sp-11 | an-147 |
| 1A3541 | sp-10 | an-148 | 1U3541 | sp-12 | an-148 | 1C3541 | sp-11 | an-148 |
| 1A3542 | sp-10 | an-149 | 1U3542 | sp-12 | an-149 | 1C3542 | sp-11 | an-149 |
| 1A3543 | sp-10 | an-150 | 1U3543 | sp-12 | an-150 | 1C3543 | sp-11 | an-150 |
| 1A3544 | sp-10 | an-151 | 1U3544 | sp-12 | an-151 | 1C3544 | sp-11 | an-151 |
| 1A3545 | sp-10 | an-152 | 1U3545 | sp-12 | an-152 | 1C3545 | sp-11 | an-152 |
| 1A3546 | sp-10 | an-153 | 1U3546 | sp-12 | an-153 | 1C3546 | sp-11 | an-153 |
| 1A3547 | sp-10 | an-154 | 1U3547 | sp-12 | an-154 | 1C3547 | sp-11 | an-154 |
| 1A3548 | sp-10 | an-155 | 1U3548 | sp-12 | an-155 | 1C3548 | sp-11 | an-155 |
| 1A3549 | sp-10 | an-156 | 1U3549 | sp-12 | an-156 | 1C3549 | sp-11 | an-156 |
| 1A3550 | sp-10 | an-157 | 1U3550 | sp-12 | an-157 | 1C3550 | sp-11 | an-157 |
| 1A3551 | sp-10 | an-158 | 1U3551 | sp-12 | an-158 | 1C3551 | sp-11 | an-158 |
| 1A3552 | sp-10 | an-159 | 1U3552 | sp-12 | an-159 | 1C3552 | sp-11 | an-159 |
| 1A3553 | sp-10 | an-160 | 1U3553 | sp-12 | an-160 | 1C3553 | sp-11 | an-160 |
| 1A3554 | sp-10 | an-161 | 1U3554 | sp-12 | an-161 | 1C3554 | sp-11 | an-161 |
| 1A3555 | sp-10 | an-162 | 1U3555 | sp-12 | an-162 | 1C3555 | sp-11 | an-162 |
| 1A3556 | sp-10 | an-163 | 1U3556 | sp-12 | an-163 | 1C3556 | sp-11 | an-163 |
| 1A3557 | sp-10 | an-164 | 1U3557 | sp-12 | an-164 | 1C3557 | sp-11 | an-164 |
| 1A3558 | sp-10 | an-165 | 1U3558 | sp-12 | an-165 | 1C3558 | sp-11 | an-165 |
| 1A3559 | sp-10 | an-166 | 1U3559 | sp-12 | an-166 | 1C3559 | sp-11 | an-166 |
| 1A3560 | sp-10 | an-167 | 1U3560 | sp-12 | an-167 | 1C3560 | sp-11 | an-167 |
| 1A3561 | sp-10 | an-168 | 1U3561 | sp-12 | an-168 | 1C3561 | sp-11 | an-168 |
| 1A3562 | sp-10 | an-169 | 1U3562 | sp-12 | an-169 | 1C3562 | sp-11 | an-169 |
| 1A3563 | sp-10 | an-170 | 1U3563 | sp-12 | an-170 | 1C3563 | sp-11 | an-170 |
| 1A3564 | sp-10 | an-171 | 1U3564 | sp-12 | an-171 | 1C3564 | sp-11 | an-171 |
| 1A3565 | sp-10 | an-172 | 1U3565 | sp-12 | an-172 | 1C3565 | sp-11 | an-172 |
| 1A3566 | sp-10 | an-173 | 1U3566 | sp-12 | an-173 | 1C3566 | sp-11 | an-173 |
| 1A3567 | sp-10 | an-174 | 1U3567 | sp-12 | an-174 | 1C3567 | sp-11 | an-174 |
| 1A3568 | sp-10 | an-175 | 1U3568 | sp-12 | an-175 | 1C3568 | sp-11 | an-175 |
| 1A3569 | sp-10 | an-176 | 1U3569 | sp-12 | an-176 | 1C3569 | sp-11 | an-176 |
| 1A3570 | sp-10 | an-177 | 1U3570 | sp-12 | an-177 | 1C3570 | sp-11 | an-177 |
| 1A3571 | sp-10 | an-178 | 1U3571 | sp-12 | an-178 | 1C3571 | sp-11 | an-178 |
| 1A3572 | sp-10 | an-179 | 1U3572 | sp-12 | an-179 | 1C3572 | sp-11 | an-179 |
| 1A3573 | sp-10 | an-180 | 1U3573 | sp-12 | an-180 | 1C3573 | sp-11 | an-180 |
| 1A3574 | sp-10 | an-181 | 1U3574 | sp-12 | an-181 | 1C3574 | sp-11 | an-181 |
| 1A3575 | sp-10 | an-182 | 1U3575 | sp-12 | an-182 | 1C3575 | sp-11 | an-182 |
| 1A3576 | sp-10 | an-183 | 1U3576 | sp-12 | an-183 | 1C3576 | sp-11 | an-183 |
| 1A3577 | sp-10 | an-184 | 1U3577 | sp-12 | an-184 | 1C3577 | sp-11 | an-184 |
| 1A3578 | sp-10 | an-185 | 1U3578 | sp-12 | an-185 | 1C3578 | sp-11 | an-185 |
| 1A3579 | sp-10 | an-186 | 1U3579 | sp-12 | an-186 | 1C3579 | sp-11 | an-186 |
| 1A3580 | sp-10 | an-187 | 1U3580 | sp-12 | an-187 | 1C3580 | sp-11 | an-187 |
| 1A3581 | sp-10 | an-188 | 1U3581 | sp-12 | an-188 | 1C3581 | sp-11 | an-188 |
| 1A3582 | sp-10 | an-189 | 1U3582 | sp-12 | an-189 | 1C3582 | sp-11 | an-189 |
| 1A3583 | sp-10 | an-190 | 1U3583 | sp-12 | an-190 | 1C3583 | sp-11 | an-190 |
| 1A3584 | sp-10 | an-191 | 1U3584 | sp-12 | an-191 | 1C3584 | sp-11 | an-191 |
| Table 2-65 ||||||||||
| Y = NHCS ||| Y = NHCSNH ||| Y = NHCSO |||
| 1A3585 | sp-10 | an-192 | 1U3585 | sp-12 | an-192 | 1C3585 | sp-11 | an-192 |
| 1A3586 | sp-10 | an-193 | 1U3586 | sp-12 | an-193 | 1C3586 | sp-11 | an-193 |
| 1A3587 | sp-10 | an-194 | 1U3587 | sp-12 | an-194 | 1C3587 | sp-11 | an-194 |
| 1A3588 | sp-10 | an-195 | 1U3588 | sp-12 | an-195 | 1C3588 | sp-11 | an-195 |
| 1A3589 | sp-10 | an-196 | 1U3589 | sp-12 | an-196 | 1C3589 | sp-11 | an-196 |
| 1A3590 | sp-10 | an-197 | 1U3590 | sp-12 | an-197 | 1C3590 | sp-11 | an-197 |
| 1A3591 | sp-10 | an-198 | 1U3591 | sp-12 | an-198 | 1C3591 | sp-11 | an-198 |
| 1A3592 | sp-10 | an-199 | 1U3592 | sp-12 | an-199 | 1C3592 | sp-11 | an-199 |
| 1A3593 | sp-10 | an-200 | 1U3593 | sp-12 | an-200 | 1C3593 | sp-11 | an-200 |
| 1A3594 | sp-10 | an-201 | 1U3594 | sp-12 | an-201 | 1C3594 | sp-11 | an-201 |
| 1A3595 | sp-10 | an-202 | 1U3595 | sp-12 | an-202 | 1C3595 | sp-11 | an-202 |
| 1A3596 | sp-10 | an-203 | 1U3596 | sp-12 | an-203 | 1C3596 | sp-11 | an-203 |
| 1A3597 | sp-10 | an-204 | 1U3597 | sp-12 | an-204 | 1C3597 | sp-11 | an-204 |
| 1A3598 | sp-10 | an-205 | 1U3598 | sp-12 | an-205 | 1C3598 | sp-11 | an-205 |

-continued

| Ex. No. | Z | N⁺R⁵R⁶R⁷ | Ex. No. | Z | N⁺R⁵R⁶R⁷ | Ex. No. | Z | N⁺R⁵R⁶R⁷ |
|---|---|---|---|---|---|---|---|---|
| 1A3599 | sp-10 | an-206 | 1U3599 | sp-12 | an-206 | 1C3599 | sp-11 | an-206 |
| 1A3600 | sp-10 | an-207 | 1U3600 | sp-12 | an-207 | 1C3600 | sp-11 | an-207 |
| 1A3601 | sp-10 | an-208 | 1U3601 | sp-12 | an-208 | 1C3601 | sp-11 | an-208 |
| 1A3602 | sp-10 | an-209 | 1U3602 | sp-12 | an-209 | 1C3602 | sp-11 | an-209 |
| 1A3603 | sp-10 | an-210 | 1U3603 | sp-12 | an-210 | 1C3603 | sp-11 | an-210 |
| 1A3604 | sp-10 | an-211 | 1U3604 | sp-12 | an-211 | 1C3604 | sp-11 | an-211 |
| 1A3605 | sp-10 | an-212 | 1U3605 | sp-12 | an-212 | 1C3605 | sp-11 | an-212 |
| 1A3606 | sp-10 | an-213 | 1U3606 | sp-12 | an-213 | 1C3606 | sp-11 | an-213 |
| 1A3607 | sp-10 | an-214 | 1U3607 | sp-12 | an-214 | 1C3607 | sp-11 | an-214 |
| 1A3608 | sp-10 | an-215 | 1U3608 | sp-12 | an-215 | 1C3608 | sp-11 | an-215 |
| 1A3609 | sp-10 | an-216 | 1U3609 | sp-12 | an-216 | 1C3609 | sp-11 | an-216 |
| 1A3610 | sp-10 | an-217 | 1U3610 | sp-12 | an-217 | 1C3610 | sp-11 | an-217 |
| 1A3611 | sp-10 | an-218 | 1U3611 | sp-12 | an-218 | 1C3611 | sp-11 | an-218 |
| 1A3612 | sp-10 | an-219 | 1U3612 | sp-12 | an-219 | 1C3612 | sp-11 | an-219 |
| 1A3613 | sp-10 | an-220 | 1U3613 | sp-12 | an-220 | 1C3613 | sp-11 | an-220 |
| 1A3614 | sp-10 | an-221 | 1U3614 | sp-12 | an-221 | 1C3614 | sp-11 | an-221 |
| 1A3615 | sp-10 | an-222 | 1U3615 | sp-12 | an-222 | 1C3615 | sp-11 | an-222 |
| 1A3616 | sp-10 | an-223 | 1U3616 | sp-12 | an-223 | 1C3616 | sp-11 | an-223 |
| 1A3617 | sp-10 | an-224 | 1U3617 | sp-12 | an-224 | 1C3617 | sp-11 | an-224 |
| 1A3618 | sp-10 | an-225 | 1U3618 | sp-12 | an-225 | 1C3618 | sp-11 | an-225 |
| 1A3619 | sp-10 | an-226 | 1U3619 | sp-12 | an-226 | 1C3619 | sp-11 | an-226 |
| 1A3620 | sp-10 | an-227 | 1U3620 | sp-12 | an-227 | 1C3620 | sp-11 | an-227 |
| 1A3621 | sp-10 | an-228 | 1U3621 | sp-12 | an-228 | 1C3621 | sp-11 | an-228 |
| 1A3622 | sp-10 | an-229 | 1U3622 | sp-12 | an-229 | 1C3622 | sp-11 | an-229 |
| 1A3623 | sp-10 | an-230 | 1U3623 | sp-12 | an-230 | 1C3623 | sp-11 | an-230 |
| 1A3624 | sp-10 | an-231 | 1U3624 | sp-12 | an-231 | 1C3624 | sp-11 | an-231 |
| 1A3625 | sp-10 | an-232 | 1U3625 | sp-12 | an-232 | 1C3625 | sp-11 | an-232 |
| 1A3626 | sp-10 | an-233 | 1U3626 | sp-12 | an-233 | 1C3626 | sp-11 | an-233 |
| 1A3627 | sp-10 | an-234 | 1U3627 | sp-12 | an-234 | 1C3627 | sp-11 | an-234 |
| 1A3628 | sp-10 | an-235 | 1U3628 | sp-12 | an-235 | 1C3628 | sp-11 | an-235 |
| 1A3629 | sp-10 | an-236 | 1U3629 | sp-12 | an-236 | 1C3629 | sp-11 | an-236 |
| 1A3630 | sp-10 | an-237 | 1U3630 | sp-12 | an-237 | 1C3630 | sp-11 | an-237 |
| 1A3631 | sp-10 | an-238 | 1U3631 | sp-12 | an-238 | 1C3631 | sp-11 | an-238 |
| 1A3632 | sp-10 | an-239 | 1U3632 | sp-12 | an-239 | 1C3632 | sp-11 | an-239 |
| 1A3633 | sp-10 | an-240 | 1U3633 | sp-12 | an-240 | 1C3633 | sp-11 | an-240 |
| 1A3634 | sp-10 | an-241 | 1U3634 | sp-12 | an-241 | 1C3634 | sp-11 | an-241 |
| 1A3635 | sp-10 | an-242 | 1U3635 | sp-12 | an-242 | 1C3635 | sp-11 | an-242 |
| 1A3636 | sp-10 | an-243 | 1U3636 | sp-12 | an-243 | 1C3636 | sp-11 | an-243 |
| 1A3637 | sp-10 | an-244 | 1U3637 | sp-12 | an-244 | 1C3637 | sp-11 | an-244 |
| 1A3638 | sp-10 | an-245 | 1U3638 | sp-12 | an-245 | 1C3638 | sp-11 | an-245 |
| 1A3639 | sp-10 | an-246 | 1U3639 | sp-12 | an-246 | 1C3639 | sp-11 | an-246 |
| 1A3640 | sp-10 | an-247 | 1U3640 | sp-12 | an-247 | 1C3640 | sp-11 | an-247 |

Table 2-66

| Y = NHCS | | | Y = NHCSNH | | | Y = NHCSO | | |
|---|---|---|---|---|---|---|---|---|
| 1A3641 | sp-10 | an-248 | 1U3641 | sp-12 | an-248 | 1C3641 | sp-11 | an-248 |
| 1A3642 | sp-10 | an-249 | 1U3642 | sp-12 | an-249 | 1C3642 | sp-11 | an-249 |
| 1A3643 | sp-10 | an-250 | 1U3643 | sp-12 | an-250 | 1C3643 | sp-11 | an-250 |
| 1A3644 | sp-10 | an-251 | 1U3644 | sp-12 | an-251 | 1C3644 | sp-11 | an-251 |
| 1A3645 | sp-10 | an-252 | 1U3645 | sp-12 | an-252 | 1C3645 | sp-11 | an-252 |
| 1A3646 | sp-10 | an-253 | 1U3646 | sp-12 | an-253 | 1C3646 | sp-11 | an-253 |
| 1A3647 | sp-10 | an-254 | 1U3647 | sp-12 | an-254 | 1C3647 | sp-11 | an-254 |
| 1A3648 | sp-10 | an-255 | 1U3648 | sp-12 | an-255 | 1C3648 | sp-11 | an-255 |
| 1A3649 | sp-10 | an-256 | 1U3649 | sp-12 | an-256 | 1C3649 | sp-11 | an-256 |
| 1A3650 | sp-10 | an-257 | 1U3650 | sp-12 | an-257 | 1C3650 | sp-11 | an-257 |
| 1A3651 | sp-10 | an-258 | 1U3651 | sp-12 | an-258 | 1C3651 | sp-11 | an-258 |
| 1A3652 | sp-10 | an-259 | 1U3652 | sp-12 | an-259 | 1C3652 | sp-11 | an-259 |
| 1A3653 | sp-10 | an-260 | 1U3653 | sp-12 | an-260 | 1C3653 | sp-11 | an-260 |
| 1A3654 | sp-10 | an-261 | 1U3654 | sp-12 | an-261 | 1C3654 | sp-11 | an-261 |
| 1A3655 | sp-10 | an-262 | 1U3655 | sp-12 | an-262 | 1C3655 | sp-11 | an-262 |
| 1A3656 | sp-10 | an-263 | 1U3656 | sp-12 | an-263 | 1C3656 | sp-11 | an-263 |
| 1A3657 | sp-10 | an-264 | 1U3657 | sp-12 | an-264 | 1C3657 | sp-11 | an-264 |
| 1A3658 | sp-10 | an-265 | 1U3658 | sp-12 | an-265 | 1C3658 | sp-11 | an-265 |
| 1A3659 | sp-10 | an-266 | 1U3659 | sp-12 | an-266 | 1C3659 | sp-11 | an-266 |
| 1A3660 | sp-10 | an-267 | 1U3660 | sp-12 | an-267 | 1C3660 | sp-11 | an-267 |
| 1A3661 | sp-10 | an-268 | 1U3661 | sp-12 | an-268 | 1C3661 | sp-11 | an-268 |
| 1A3662 | sp-10 | an-269 | 1U3662 | sp-12 | an-269 | 1C3662 | sp-11 | an-269 |
| 1A3663 | sp-10 | an-270 | 1U3663 | sp-12 | an-270 | 1C3663 | sp-11 | an-270 |
| 1A3664 | sp-10 | an-271 | 1U3664 | sp-12 | an-271 | 1C3664 | sp-11 | an-271 |
| 1A3665 | sp-10 | an-272 | 1U3665 | sp-12 | an-272 | 1C3665 | sp-11 | an-272 |
| 1A3666 | sp-10 | an-273 | 1U3666 | sp-12 | an-273 | 1C3666 | sp-11 | an-273 |
| 1A3667 | sp-10 | an-274 | 1U3667 | sp-12 | an-274 | 1C3667 | sp-11 | an-274 |
| 1A3668 | sp-10 | an-275 | 1U3668 | sp-12 | an-275 | 1C3668 | sp-11 | an-275 |
| 1A3669 | sp-10 | an-276 | 1U3669 | sp-12 | an-276 | 1C3669 | sp-11 | an-276 |
| 1A3670 | sp-10 | an-277 | 1U3670 | sp-12 | an-277 | 1C3670 | sp-11 | an-277 |
| 1A3671 | sp-10 | an-278 | 1U3671 | sp-12 | an-278 | 1C3671 | sp-11 | an-278 |
| 1A3672 | sp-10 | an-279 | 1U3672 | sp-12 | an-279 | 1C3672 | sp-11 | an-279 |

| Ex. No. | Z | N⁺R⁵R⁶R⁷ | Ex. No. | Z | N⁺R⁵R⁶R⁷ | Ex. No. | Z | N⁺R⁵R⁶R⁷ |
|---|---|---|---|---|---|---|---|---|
| 1A3673 | sp-10 | an-280 | 1U3673 | sp-12 | an-280 | 1C3673 | sp-11 | an-280 |
| 1A3674 | sp-10 | an-281 | 1U3674 | sp-12 | an-281 | 1C3674 | sp-11 | an-281 |
| 1A3675 | sp-10 | an-282 | 1U3675 | sp-12 | an-282 | 1C3675 | sp-11 | an-282 |
| 1A3676 | sp-10 | an-283 | 1U3676 | sp-12 | an-283 | 1C3676 | sp-11 | an-283 |
| 1A3677 | sp-10 | an-284 | 1U3677 | sp-12 | an-284 | 1C3677 | sp-11 | an-284 |
| 1A3678 | sp-10 | an-285 | 1U3678 | sp-12 | an-285 | 1C3678 | sp-11 | an-285 |
| 1A3679 | sp-10 | an-286 | 1U3679 | sp-12 | an-286 | 1C3679 | sp-11 | an-286 |
| 1A3680 | sp-10 | an-287 | 1U3680 | sp-12 | an-287 | 1C3680 | sp-11 | an-287 |
| 1A3681 | sp-10 | an-288 | 1U3681 | sp-12 | an-288 | 1C3681 | sp-11 | an-288 |
| 1A3682 | sp-10 | an-289 | 1U3682 | sp-12 | an-289 | 1C3682 | sp-11 | an-289 |
| 1A3683 | sp-10 | an-290 | 1U3683 | sp-12 | an-290 | 1C3683 | sp-11 | an-290 |
| 1A3684 | sp-10 | an-291 | 1U3684 | sp-12 | an-291 | 1C3684 | sp-11 | an-291 |
| 1A3685 | sp-10 | an-292 | 1U3685 | sp-12 | an-292 | 1C3685 | sp-11 | an-292 |
| 1A3686 | sp-10 | an-293 | 1U3686 | sp-12 | an-293 | 1C3686 | sp-11 | an-293 |
| 1A3687 | sp-10 | an-294 | 1U3687 | sp-12 | an-294 | 1C3687 | sp-11 | an-294 |
| 1A3688 | sp-10 | an-295 | 1U3688 | sp-12 | an-295 | 1C3688 | sp-11 | an-295 |
| 1A3689 | sp-10 | an-296 | 1U3689 | sp-12 | an-296 | 1C3689 | sp-11 | an-296 |
| 1A3690 | sp-10 | an-297 | 1U3690 | sp-12 | an-297 | 1C3690 | sp-11 | an-297 |
| 1A3691 | sp-10 | an-298 | 1U3691 | sp-12 | an-298 | 1C3691 | sp-11 | an-298 |
| 1A3692 | sp-10 | an-299 | 1U3692 | sp-12 | an-299 | 1C3692 | sp-11 | an-299 |
| 1A3693 | sp-10 | an-300 | 1U3693 | sp-12 | an-300 | 1C3693 | sp-11 | an-300 |
| 1A3694 | sp-10 | an-301 | 1U3694 | sp-12 | an-301 | 1C3694 | sp-11 | an-301 |
| 1A3695 | sp-10 | an-302 | 1U3695 | sp-12 | an-302 | 1C3695 | sp-11 | an-302 |
| 1A3696 | sp-10 | an-303 | 1U3696 | sp-12 | an-303 | 1C3696 | sp-11 | an-303 |

Table 2-67

| Y = NHCS | | | Y = NHCSNH | | | Y = NHCSO | | |
|---|---|---|---|---|---|---|---|---|
| 1A3697 | sp-10 | an-304 | 1U3697 | sp-12 | an-304 | 1C3697 | sp-11 | an-304 |
| 1A3698 | sp-10 | an-305 | 1U3698 | sp-12 | an-305 | 1C3698 | sp-11 | an-305 |
| 1A3699 | sp-10 | an-306 | 1U3699 | sp-12 | an-306 | 1C3699 | sp-11 | an-306 |
| 1A3700 | sp-10 | an-307 | 1U3700 | sp-12 | an-307 | 1C3700 | sp-11 | an-307 |
| 1A3701 | sp-10 | an-308 | 1U3701 | sp-12 | an-308 | 1C3701 | sp-11 | an-308 |
| 1A3702 | sp-10 | an-309 | 1U3702 | sp-12 | an-309 | 1C3702 | sp-11 | an-309 |
| 1A3703 | sp-10 | an-310 | 1U3703 | sp-12 | an-310 | 1C3703 | sp-11 | an-310 |
| 1A3704 | sp-10 | an-311 | 1U3704 | sp-12 | an-311 | 1C3704 | sp-11 | an-311 |
| 1A3705 | sp-10 | an-312 | 1U3705 | sp-12 | an-312 | 1C3705 | sp-11 | an-312 |
| 1A3706 | sp-10 | an-313 | 1U3706 | sp-12 | an-313 | 1C3706 | sp-11 | an-313 |
| 1A3707 | sp-10 | an-314 | 1U3707 | sp-12 | an-314 | 1C3707 | sp-11 | an-314 |
| 1A3708 | sp-10 | an-315 | 1U3708 | sp-12 | an-315 | 1C3708 | sp-11 | an-315 |
| 1A3709 | sp-10 | an-316 | 1U3709 | sp-12 | an-316 | 1C3709 | sp-11 | an-316 |
| 1A3710 | sp-10 | an-317 | 1U3710 | sp-12 | an-317 | 1C3710 | sp-11 | an-317 |
| 1A3711 | sp-10 | an-318 | 1U3711 | sp-12 | an-318 | 1C3711 | sp-11 | an-318 |
| 1A3712 | sp-10 | an-319 | 1U3712 | sp-12 | an-319 | 1C3712 | sp-11 | an-319 |
| 1A3713 | sp-10 | an-320 | 1U3713 | sp-12 | an-320 | 1C3713 | sp-11 | an-320 |
| 1A3714 | sp-10 | an-321 | 1U3714 | sp-12 | an-321 | 1C3714 | sp-11 | an-321 |
| 1A3715 | sp-10 | an-322 | 1U3715 | sp-12 | an-322 | 1C3715 | sp-11 | an-322 |
| 1A3716 | sp-10 | an-323 | 1U3716 | sp-12 | an-323 | 1C3716 | sp-11 | an-323 |
| 1A3717 | sp-10 | an-324 | 1U3717 | sp-12 | an-324 | 1C3717 | sp-11 | an-324 |
| 1A3718 | sp-10 | an-325 | 1U3718 | sp-12 | an-325 | 1C3718 | sp-11 | an-325 |
| 1A3719 | sp-10 | an-326 | 1U3719 | sp-12 | an-326 | 1C3719 | sp-11 | an-326 |
| 1A3720 | sp-10 | an-327 | 1U3720 | sp-12 | an-327 | 1C3720 | sp-11 | an-327 |
| 1A3721 | sp-10 | an-328 | 1U3721 | sp-12 | an-328 | 1C3721 | sp-11 | an-328 |
| 1A3722 | sp-10 | an-329 | 1U3722 | sp-12 | an-329 | 1C3722 | sp-11 | an-329 |
| 1A3723 | sp-10 | an-330 | 1U3723 | sp-12 | an-330 | 1C3723 | sp-11 | an-330 |
| 1A3724 | sp-10 | an-331 | 1U3724 | sp-12 | an-331 | 1C3724 | sp-11 | an-331 |
| 1A3725 | sp-10 | an-332 | 1U3725 | sp-12 | an-332 | 1C3725 | sp-11 | an-332 |
| 1A3726 | sp-10 | an-333 | 1U3726 | sp-12 | an-333 | 1C3726 | sp-11 | an-333 |
| 1A3727 | sp-10 | an-334 | 1U3727 | sp-12 | an-334 | 1C3727 | sp-11 | an-334 |
| 1A3728 | sp-10 | an-335 | 1U3728 | sp-12 | an-335 | 1C3728 | sp-11 | an-335 |
| 1A3729 | sp-10 | an-336 | 1U3729 | sp-12 | an-336 | 1C3729 | sp-11 | an-336 |
| 1A3730 | sp-10 | an-337 | 1U3730 | sp-12 | an-337 | 1C3730 | sp-11 | an-337 |
| 1A3731 | sp-10 | an-338 | 1U3731 | sp-12 | an-338 | 1C3731 | sp-11 | an-338 |
| 1A3732 | sp-10 | an-339 | 1U3732 | sp-12 | an-339 | 1C3732 | sp-11 | an-339 |
| 1A3733 | sp-10 | an-340 | 1U3733 | sp-12 | an-340 | 1C3733 | sp-11 | an-340 |
| 1A3734 | sp-10 | an-341 | 1U3734 | sp-12 | an-341 | 1C3734 | sp-11 | an-341 |
| 1A3735 | sp-10 | an-342 | 1U3735 | sp-12 | an-342 | 1C3735 | sp-11 | an-342 |
| 1A3736 | sp-10 | an-343 | 1U3736 | sp-12 | an-343 | 1C3736 | sp-11 | an-343 |
| 1A3737 | sp-10 | an-344 | 1U3737 | sp-12 | an-344 | 1C3737 | sp-11 | an-344 |
| 1A3738 | sp-10 | an-345 | 1U3738 | sp-12 | an-345 | 1C3738 | sp-11 | an-345 |
| 1A3739 | sp-10 | an-346 | 1U3739 | sp-12 | an-346 | 1C3739 | sp-11 | an-346 |
| 1A3740 | sp-10 | an-347 | 1U3740 | sp-12 | an-347 | 1C3740 | sp-11 | an-347 |
| 1A3741 | sp-10 | an-348 | 1U3741 | sp-12 | an-348 | 1C3741 | sp-11 | an-348 |
| 1A3742 | sp-10 | an-349 | 1U3742 | sp-12 | an-349 | 1C3742 | sp-11 | an-349 |
| 1A3743 | sp-10 | an-350 | 1U3743 | sp-12 | an-350 | 1C3743 | sp-11 | an-350 |
| 1A3744 | sp-10 | an-351 | 1U3744 | sp-12 | an-351 | 1C3744 | sp-11 | an-351 |
| 1A3745 | sp-10 | an-352 | 1U3745 | sp-12 | an-352 | 1C3745 | sp-11 | an-352 |
| 1A3746 | sp-10 | an-353 | 1U3746 | sp-12 | an-353 | 1C3746 | sp-11 | an-353 |

-continued

| Ex. No. | Z | $N^+R^5R^6R^7$ | Ex. No. | Z | $N^+R^5R^6R^7$ | Ex. No. | Z | $N^+R^5R^6R^7$ |
|---|---|---|---|---|---|---|---|---|
| 1A3747 | sp-10 | an-354 | 1U3747 | sp-12 | an-354 | 1C3747 | sp-11 | an-354 |
| 1A3748 | sp-10 | an-355 | 1U3748 | sp-12 | an-355 | 1C3748 | sp-11 | an-355 |
| 1A3749 | sp-10 | an-356 | 1U3749 | sp-12 | an-356 | 1C3749 | sp-11 | an-356 |
| 1A3750 | sp-10 | an-357 | 1U3750 | sp-12 | an-357 | 1C3750 | sp-11 | an-357 |
| 1A3751 | sp-10 | an-358 | 1U3751 | sp-12 | an-358 | 1C3751 | sp-11 | an-358 |
| 1A3752 | sp-10 | an-359 | 1U3752 | sp-12 | an-359 | 1C3752 | sp-11 | an-359 |

Table 2-68

| Y = NHCS | | | Y = NHCSNH | | | Y = NHCSO | | |
|---|---|---|---|---|---|---|---|---|
| 1A3753 | sp-10 | an-360 | 1U3753 | sp-12 | an-360 | 1C3753 | sp-11 | an-360 |
| 1A3754 | sp-10 | an-361 | 1U3754 | sp-12 | an-361 | 1C3754 | sp-11 | an-361 |
| 1A3755 | sp-10 | an-362 | 1U3755 | sp-12 | an-362 | 1C3755 | sp-11 | an-362 |
| 1A3756 | sp-10 | an-363 | 1U3756 | sp-12 | an-363 | 1C3756 | sp-11 | an-363 |
| 1A3757 | sp-10 | an-364 | 1U3757 | sp-12 | an-364 | 1C3757 | sp-11 | an-364 |
| 1A3758 | sp-10 | an-365 | 1U3758 | sp-12 | an-365 | 1C3758 | sp-11 | an-365 |
| 1A3759 | sp-10 | an-366 | 1U3759 | sp-12 | an-366 | 1C3759 | sp-11 | an-366 |
| 1A3760 | sp-10 | an-367 | 1U3760 | sp-12 | an-367 | 1C3760 | sp-11 | an-367 |
| 1A3761 | sp-10 | an-368 | 1U3761 | sp-12 | an-368 | 1C3761 | sp-11 | an-368 |
| 1A3762 | sp-10 | an-369 | 1U3762 | sp-12 | an-369 | 1C3762 | sp-11 | an-369 |
| 1A3763 | sp-10 | an-370 | 1U3763 | sp-12 | an-370 | 1C3763 | sp-11 | an-370 |
| 1A3764 | sp-10 | an-371 | 1U3764 | sp-12 | an-371 | 1C3764 | sp-11 | an-371 |
| 1A3765 | sp-10 | an-372 | 1U3765 | sp-12 | an-372 | 1C3765 | sp-11 | an-372 |
| 1A3766 | sp-10 | an-373 | 1U3766 | sp-12 | an-373 | 1C3766 | sp-11 | an-373 |
| 1A3767 | sp-10 | an-374 | 1U3767 | sp-12 | an-374 | 1C3767 | sp-11 | an-374 |
| 1A3768 | sp-10 | an-375 | 1U3768 | sp-12 | an-375 | 1C3768 | sp-11 | an-375 |
| 1A3769 | sp-10 | an-376 | 1U3769 | sp-12 | an-376 | 1C3769 | sp-11 | an-376 |
| 1A3770 | sp-10 | an-377 | 1U3770 | sp-12 | an-377 | 1C3770 | sp-11 | an-377 |
| 1A3771 | sp-14 | an-1 | 1U3771 | sp-13 | an-1 | | | |
| 1A3772 | sp-14 | an-2 | 1U3772 | sp-13 | an-2 | | | |
| 1A3773 | sp-14 | an-3 | 1U3773 | sp-13 | an-3 | | | |
| 1A3774 | sp-14 | an-4 | 1U3774 | sp-13 | an-4 | | | |
| 1A3775 | sp-14 | an-5 | 1U3775 | sp-13 | an-5 | | | |
| 1A3776 | sp-14 | an-6 | 1U3776 | sp-13 | an-6 | | | |
| 1A3777 | sp-14 | an-7 | 1U3777 | sp-13 | an-7 | | | |
| 1A3778 | sp-14 | an-8 | 1U3778 | sp-13 | an-8 | | | |
| 1A3779 | sp-14 | an-9 | 1U3779 | sp-13 | an-9 | | | |
| 1A3780 | sp-14 | an-10 | 1U3780 | sp-13 | an-10 | | | |
| 1A3781 | sp-14 | an-11 | 1U3781 | sp-13 | an-11 | | | |
| 1A3782 | sp-14 | an-12 | 1U3782 | sp-13 | an-12 | | | |
| 1A3783 | sp-14 | an-13 | 1U3783 | sp-13 | an-13 | | | |
| 1A3784 | sp-14 | an-14 | 1U3784 | sp-13 | an-14 | | | |
| 1A3785 | sp-14 | an-15 | 1U3785 | sp-13 | an-15 | | | |
| 1A3786 | sp-14 | an-16 | 1U3786 | sp-13 | an-16 | | | |
| 1A3787 | sp-14 | an-17 | 1U3787 | sp-13 | an-17 | | | |
| 1A3788 | sp-14 | an-18 | 1U3788 | sp-13 | an-18 | | | |
| 1A3789 | sp-14 | an-19 | 1U3789 | sp-13 | an-19 | | | |
| 1A3790 | sp-14 | an-20 | 1U3790 | sp-13 | an-20 | | | |
| 1A3791 | sp-14 | an-21 | 1U3791 | sp-13 | an-21 | | | |
| 1A3792 | sp-14 | an-22 | 1U3792 | sp-13 | an-22 | | | |
| 1A3793 | sp-14 | an-23 | 1U3793 | sp-13 | an-23 | | | |
| 1A3794 | sp-14 | an-24 | 1U3794 | sp-13 | an-24 | | | |
| 1A3795 | sp-14 | an-25 | 1U3795 | sp-13 | an-25 | | | |
| 1A3796 | sp-14 | an-26 | 1U3796 | sp-13 | an-26 | | | |
| 1A3797 | sp-14 | an-27 | 1U3797 | sp-13 | an-27 | | | |
| 1A3798 | sp-14 | an-28 | 1U3798 | sp-13 | an-28 | | | |
| 1A3799 | sp-14 | an-29 | 1U3799 | sp-13 | an-29 | | | |
| 1A3800 | sp-14 | an-30 | 1U3800 | sp-13 | an-30 | | | |
| 1A3801 | sp-14 | an-31 | 1U3801 | sp-13 | an-31 | | | |
| 1A3802 | sp-14 | an-32 | 1U3802 | sp-13 | an-32 | | | |
| 1A3803 | sp-14 | an-33 | 1U3803 | sp-13 | an-33 | | | |
| 1A3804 | sp-14 | an-34 | 1U3804 | sp-13 | an-34 | | | |
| 1A3805 | sp-14 | an-35 | 1U3805 | sp-13 | an-35 | | | |
| 1A3806 | sp-14 | an-36 | 1U3806 | sp-13 | an-36 | | | |
| 1A3807 | sp-14 | an-37 | 1U3807 | sp-13 | an-37 | | | |

Table 2-69

| Y = NHCS | | | Y = NHCSNH | | | Y = NHCSO | | |
|---|---|---|---|---|---|---|---|---|
| 1A3808 | sp-14 | an-38 | 1U3808 | sp-13 | an-38 | | | |
| 1A3809 | sp-14 | an-39 | 1U3809 | sp-13 | an-39 | | | |
| 1A3810 | sp-14 | an-40 | 1U3810 | sp-13 | an-40 | | | |
| 1A3811 | sp-14 | an-41 | 1U3811 | sp-13 | an-41 | | | |
| 1A3812 | sp-14 | an-42 | 1U3812 | sp-13 | an-42 | | | |
| 1A3813 | sp-14 | an-43 | 1U3813 | sp-13 | an-43 | | | |
| 1A3814 | sp-14 | an-44 | 1U3814 | sp-13 | an-44 | | | |
| 1A3815 | sp-14 | an-45 | 1U3815 | sp-13 | an-45 | | | |
| 1A3816 | sp-14 | an-46 | 1U3816 | sp-13 | an-46 | | | |

-continued

| Ex. No. | Z | N⁺R⁵R⁶R⁷ | Ex. No. | Z | N⁺R⁵R⁶R⁷ | Ex. No. | Z | N⁺R⁵R⁶R⁷ |
|---|---|---|---|---|---|---|---|---|
| 1A3817 | sp-14 | an-47 | 1U3817 | sp-13 | an-47 | | | |
| 1A3818 | sp-14 | an-48 | 1U3818 | sp-13 | an-48 | | | |
| 1A3819 | sp-14 | an-49 | 1U3819 | sp-13 | an-49 | | | |
| 1A3820 | sp-14 | an-50 | 1U3820 | sp-13 | an-50 | | | |
| 1A3821 | sp-14 | an-51 | 1U3821 | sp-13 | an-51 | | | |
| 1A3822 | sp-14 | an-52 | 1U3822 | sp-13 | an-52 | | | |
| 1A3823 | sp-14 | an-53 | 1U3823 | sp-13 | an-53 | | | |
| 1A3824 | sp-14 | an-54 | 1U3824 | sp-13 | an-54 | | | |
| 1A3825 | sp-14 | an-55 | 1U3825 | sp-13 | an-55 | | | |
| 1A3826 | sp-14 | an-56 | 1U3826 | sp-13 | an-56 | | | |
| 1A3827 | sp-14 | an-57 | 1U3827 | sp-13 | an-57 | | | |
| 1A3828 | sp-14 | an-58 | 1U3828 | sp-13 | an-58 | | | |
| 1A3829 | sp-14 | an-59 | 1U3829 | sp-13 | an-59 | | | |
| 1A3830 | sp-14 | an-60 | 1U3830 | sp-13 | an-60 | | | |
| 1A3831 | sp-14 | an-61 | 1U3831 | sp-13 | an-61 | | | |
| 1A3832 | sp-14 | an-62 | 1U3832 | sp-13 | an-62 | | | |
| 1A3833 | sp-14 | an-63 | 1U3833 | sp-13 | an-63 | | | |
| 1A3834 | sp-14 | an-64 | 1U3834 | sp-13 | an-64 | | | |
| 1A3835 | sp-14 | an-65 | 1U3835 | sp-13 | an-65 | | | |
| 1A3836 | sp-14 | an-66 | 1U3836 | sp-13 | an-66 | | | |
| 1A3837 | sp-14 | an-67 | 1U3837 | sp-13 | an-67 | | | |
| 1A3838 | sp-14 | an-68 | 1U3838 | sp-13 | an-68 | | | |
| 1A3839 | sp-14 | an-69 | 1U3839 | sp-13 | an-69 | | | |
| 1A3840 | sp-14 | an-70 | 1U3840 | sp-13 | an-70 | | | |
| 1A3841 | sp-14 | an-71 | 1U3841 | sp-13 | an-71 | | | |
| 1A3842 | sp-14 | an-72 | 1U3842 | sp-13 | an-72 | | | |
| 1A3843 | sp-14 | an-73 | 1U3843 | sp-13 | an-73 | | | |
| 1A3844 | sp-14 | an-74 | 1U3844 | sp-13 | an-74 | | | |
| 1A3845 | sp-14 | an-75 | 1U3845 | sp-13 | an-75 | | | |
| 1A3846 | sp-14 | an-76 | 1U3846 | sp-13 | an-76 | | | |
| 1A3847 | sp-14 | an-77 | 1U3847 | sp-13 | an-77 | | | |
| 1A3848 | sp-14 | an-78 | 1U3848 | sp-13 | an-78 | | | |
| 1A3849 | sp-14 | an-79 | 1U3849 | sp-13 | an-79 | | | |
| 1A3850 | sp-14 | an-80 | 1U3850 | sp-13 | an-80 | | | |
| 1A3851 | sp-14 | an-81 | 1U3851 | sp-13 | an-81 | | | |
| 1A3852 | sp-14 | an-82 | 1U3852 | sp-13 | an-82 | | | |
| 1A3853 | sp-14 | an-83 | 1U3853 | sp-13 | an-83 | | | |
| 1A3854 | sp-14 | an-84 | 1U3854 | sp-13 | an-84 | | | |
| 1A3855 | sp-14 | an-85 | 1U3855 | sp-13 | an-85 | | | |
| 1A3856 | sp-14 | an-86 | 1U3856 | sp-13 | an-86 | | | |
| 1A3857 | sp-14 | an-87 | 1U3857 | sp-13 | an-87 | | | |
| 1A3858 | sp-14 | an-88 | 1U3858 | sp-13 | an-88 | | | |
| 1A3859 | sp-14 | an-89 | 1U3859 | sp-13 | an-89 | | | |
| 1A3860 | sp-14 | an-90 | 1U3860 | sp-13 | an-90 | | | |
| 1A3861 | sp-14 | an-91 | 1U3861 | sp-13 | an-91 | | | |
| 1A3862 | sp-14 | an-92 | 1U3862 | sp-13 | an-92 | | | |
| 1A3863 | sp-14 | an-93 | 1U3863 | sp-13 | an-93 | | | |

Table 2-70

| | Y = NHCS | | | Y = NHCSNH | | | Y = NHCSO | |
|---|---|---|---|---|---|---|---|---|
| 1A3864 | sp-14 | an-94 | 1U3864 | sp-13 | an-94 | | | |
| 1A3865 | sp-14 | an-95 | 1U3865 | sp-13 | an-95 | | | |
| 1A3866 | sp-14 | an-96 | 1U3866 | sp-13 | an-96 | | | |
| 1A3867 | sp-14 | an-97 | 1U3867 | sp-13 | an-97 | | | |
| 1A3868 | sp-14 | an-98 | 1U3868 | sp-13 | an-98 | | | |
| 1A3869 | sp-14 | an-99 | 1U3869 | sp-13 | an-99 | | | |
| 1A3870 | sp-14 | an-100 | 1U3870 | sp-13 | an-100 | | | |
| 1A3871 | sp-14 | an-101 | 1U3871 | sp-13 | an-101 | | | |
| 1A3872 | sp-14 | an-102 | 1U3872 | sp-13 | an-102 | | | |
| 1A3873 | sp-14 | an-103 | 1U3873 | sp-13 | an-103 | | | |
| 1A3874 | sp-14 | an-104 | 1U3874 | sp-13 | an-104 | | | |
| 1A3875 | sp-14 | an-105 | 1U3875 | sp-13 | an-105 | | | |
| 1A3876 | sp-14 | an-106 | 1U3876 | sp-13 | an-106 | | | |
| 1A3877 | sp-14 | an-107 | 1U3877 | sp-13 | an-107 | | | |
| 1A3878 | sp-14 | an-108 | 1U3878 | sp-13 | an-108 | | | |
| 1A3879 | sp-14 | an-109 | 1U3879 | sp-13 | an-109 | | | |
| 1A3880 | sp-14 | an-110 | 1U3880 | sp-13 | an-110 | | | |
| 1A3881 | sp-14 | an-111 | 1U3881 | sp-13 | an-111 | | | |
| 1A3882 | sp-14 | an-112 | 1U3882 | sp-13 | an-112 | | | |
| 1A3883 | sp-14 | an-113 | 1U3883 | sp-13 | an-113 | | | |
| 1A3884 | sp-14 | an-114 | 1U3884 | sp-13 | an-114 | | | |
| 1A3885 | sp-14 | an-115 | 1U3885 | sp-13 | an-115 | | | |
| 1A3886 | sp-14 | an-116 | 1U3886 | sp-13 | an-116 | | | |
| 1A3887 | sp-14 | an-117 | 1U3887 | sp-13 | an-117 | | | |
| 1A3888 | sp-14 | an-118 | 1U3888 | sp-13 | an-118 | | | |
| 1A3889 | sp-14 | an-119 | 1U3889 | sp-13 | an-119 | | | |
| 1A3890 | sp-14 | an-120 | 1U3890 | sp-13 | an-120 | | | |

-continued

| Ex. No. | Z | $N^+R^5R^6R^7$ | Ex. No. | Z | $N^+R^5R^6R^7$ | Ex. No. | Z | $N^+R^5R^6R^7$ |
|---|---|---|---|---|---|---|---|---|
| 1A3891 | sp-14 | an-121 | 1U3891 | sp-13 | an-121 | | | |
| 1A3892 | sp-14 | an-122 | 1U3892 | sp-13 | an-122 | | | |
| 1A3893 | sp-14 | an-123 | 1U3893 | sp-13 | an-123 | | | |
| 1A3894 | sp-14 | an-124 | 1U3894 | sp-13 | an-124 | | | |
| 1A3895 | sp-14 | an-125 | 1U3895 | sp-13 | an-125 | | | |
| 1A3896 | sp-14 | an-126 | 1U3896 | sp-13 | an-126 | | | |
| 1A3897 | sp-14 | an-127 | 1U3897 | sp-13 | an-127 | | | |
| 1A3898 | sp-14 | an-128 | 1U3898 | sp-13 | an-128 | | | |
| 1A3899 | sp-14 | an-129 | 1U3899 | sp-13 | an-129 | | | |
| 1A3900 | sp-14 | an-130 | 1U3900 | sp-13 | an-130 | | | |
| 1A3901 | sp-14 | an-131 | 1U3901 | sp-13 | an-131 | | | |
| 1A3902 | sp-14 | an-132 | 1U3902 | sp-13 | an-132 | | | |
| 1A3903 | sp-14 | an-133 | 1U3903 | sp-13 | an-133 | | | |
| 1A3904 | sp-14 | an-134 | 1U3904 | sp-13 | an-134 | | | |
| 1A3905 | sp-14 | an-135 | 1U3905 | sp-13 | an-135 | | | |
| 1A3906 | sp-14 | an-136 | 1U3906 | sp-13 | an-136 | | | |
| 1A3907 | sp-14 | an-137 | 1U3907 | sp-13 | an-137 | | | |
| 1A3908 | sp-14 | an-138 | 1U3908 | sp-13 | an-138 | | | |
| 1A3909 | sp-14 | an-139 | 1U3909 | sp-13 | an-139 | | | |
| 1A3910 | sp-14 | an-140 | 1U3910 | sp-13 | an-140 | | | |
| 1A3911 | sp-14 | an-141 | 1U3911 | sp-13 | an-141 | | | |
| 1A3912 | sp-14 | an-142 | 1U3912 | sp-13 | an-142 | | | |
| 1A3913 | sp-14 | an-143 | 1U3913 | sp-13 | an-143 | | | |
| 1A3914 | sp-14 | an-144 | 1U3914 | sp-13 | an-144 | | | |
| 1A3915 | sp-14 | an-145 | 1U3915 | sp-13 | an-145 | | | |
| 1A3916 | sp-14 | an-146 | 1U3916 | sp-13 | an-146 | | | |
| 1A3917 | sp-14 | an-147 | 1U3917 | sp-13 | an-147 | | | |
| 1A3918 | sp-14 | an-148 | 1U3918 | sp-13 | an-148 | | | |
| 1A3919 | sp-14 | an-149 | 1U3919 | sp-13 | an-149 | | | |

Table 2-71

| Y = NHCS | | | Y = NHCSNH | | | Y = NHCSO | | |
|---|---|---|---|---|---|---|---|---|
| 1A3920 | sp-14 | an-150 | 1U3920 | sp-13 | an-150 | | | |
| 1A3921 | sp-14 | an-151 | 1U3921 | sp-13 | an-151 | | | |
| 1A3922 | sp-14 | an-152 | 1U3922 | sp-13 | an-152 | | | |
| 1A3923 | sp-14 | an-153 | 1U3923 | sp-13 | an-153 | | | |
| 1A3924 | sp-14 | an-154 | 1U3924 | sp-13 | an-154 | | | |
| 1A3925 | sp-14 | an-155 | 1U3925 | sp-13 | an-155 | | | |
| 1A3926 | sp-14 | an-156 | 1U3926 | sp-13 | an-156 | | | |
| 1A3927 | sp-14 | an-157 | 1U3927 | sp-13 | an-157 | | | |
| 1A3928 | sp-14 | an-158 | 1U3928 | sp-13 | an-158 | | | |
| 1A3929 | sp-14 | an-159 | 1U3929 | sp-13 | an-159 | | | |
| 1A3930 | sp-14 | an-160 | 1U3930 | sp-13 | an-160 | | | |
| 1A3931 | sp-14 | an-161 | 1U3931 | sp-13 | an-161 | | | |
| 1A3932 | sp-14 | an-162 | 1U3932 | sp-13 | an-162 | | | |
| 1A3933 | sp-14 | an-163 | 1U3933 | sp-13 | an-163 | | | |
| 1A3934 | sp-14 | an-164 | 1U3934 | sp-13 | an-164 | | | |
| 1A3935 | sp-14 | an-165 | 1U3935 | sp-13 | an-165 | | | |
| 1A3936 | sp-14 | an-166 | 1U3936 | sp-13 | an-166 | | | |
| 1A3937 | sp-14 | an-167 | 1U3937 | sp-13 | an-167 | | | |
| 1A3938 | sp-14 | an-168 | 1U3938 | sp-13 | an-168 | | | |
| 1A3939 | sp-14 | an-169 | 1U3939 | sp-13 | an-169 | | | |
| 1A3940 | sp-14 | an-170 | 1U3940 | sp-13 | an-170 | | | |
| 1A3941 | sp-14 | an-171 | 1U3941 | sp-13 | an-171 | | | |
| 1A3942 | sp-14 | an-172 | 1U3942 | sp-13 | an-172 | | | |
| 1A3943 | sp-14 | an-173 | 1U3943 | sp-13 | an-173 | | | |
| 1A3944 | sp-14 | an-174 | 1U3944 | sp-13 | an-174 | | | |
| 1A3945 | sp-14 | an-175 | 1U3945 | sp-13 | an-175 | | | |
| 1A3946 | sp-14 | an-176 | 1U3946 | sp-13 | an-176 | | | |
| 1A3947 | sp-14 | an-177 | 1U3947 | sp-13 | an-177 | | | |
| 1A3948 | sp-14 | an-178 | 1U3948 | sp-13 | an-178 | | | |
| 1A3949 | sp-14 | an-179 | 1U3949 | sp-13 | an-179 | | | |
| 1A3950 | sp-14 | an-180 | 1U3950 | sp-13 | an-180 | | | |
| 1A3951 | sp-14 | an-181 | 1U3951 | sp-13 | an-181 | | | |
| 1A3952 | sp-14 | an-182 | 1U3952 | sp-13 | an-182 | | | |
| 1A3953 | sp-14 | an-183 | 1U3953 | sp-13 | an-183 | | | |
| 1A3954 | sp-14 | an-184 | 1U3954 | sp-13 | an-184 | | | |
| 1A3955 | sp-14 | an-185 | 1U3955 | sp-13 | an-185 | | | |
| 1A3956 | sp-14 | an-186 | 1U3956 | sp-13 | an-186 | | | |
| 1A3957 | sp-14 | an-187 | 1U3957 | sp-13 | an-187 | | | |
| 1A3958 | sp-14 | an-188 | 1U3958 | sp-13 | an-188 | | | |
| 1A3959 | sp-14 | an-189 | 1U3959 | sp-13 | an-189 | | | |
| 1A3960 | sp-14 | an-190 | 1U3960 | sp-13 | an-190 | | | |
| 1A3961 | sp-14 | an-191 | 1U3961 | sp-13 | an-191 | | | |
| 1A3962 | sp-14 | an-192 | 1U3962 | sp-13 | an-192 | | | |
| 1A3963 | sp-14 | an-193 | 1U3963 | sp-13 | an-193 | | | |
| 1A3964 | sp-14 | an-194 | 1U3964 | sp-13 | an-194 | | | |

-continued

| Ex. No. | Z | N⁺R⁵R⁶R⁷ | Ex. No. | Z | N⁺R⁵R⁶R⁷ | Ex. No. | Z | N⁺R⁵R⁶R⁷ |
|---|---|---|---|---|---|---|---|---|
| 1A3965 | sp-14 | an-195 | 1U3965 | sp-13 | an-195 | | | |
| 1A3966 | sp-14 | an-196 | 1U3966 | sp-13 | an-196 | | | |
| 1A3967 | sp-14 | an-197 | 1U3967 | sp-13 | an-197 | | | |
| 1A3968 | sp-14 | an-198 | 1U3968 | sp-13 | an-198 | | | |
| 1A3969 | sp-14 | an-199 | 1U3969 | sp-13 | an-199 | | | |
| 1A3970 | sp-14 | an-200 | 1U3970 | sp-13 | an-200 | | | |
| 1A3971 | sp-14 | an-201 | 1U3971 | sp-13 | an-201 | | | |
| 1A3972 | sp-14 | an-202 | 1U3972 | sp-13 | an-202 | | | |
| 1A3973 | sp-14 | an-203 | 1U3973 | sp-13 | an-203 | | | |
| 1A3974 | sp-14 | an-204 | 1U3974 | sp-13 | an-204 | | | |
| 1A3975 | sp-14 | an-205 | 1U3975 | sp-13 | an-205 | | | |

Table 2-72

| Y = NHCS | | | Y = NHCSNH | | | Y = NHCSO | | |
|---|---|---|---|---|---|---|---|---|
| 1A3976 | sp-14 | an-206 | 1U3976 | sp-13 | an-206 | | | |
| 1A3977 | sp-14 | an-207 | 1U3977 | sp-13 | an-207 | | | |
| 1A3978 | sp-14 | an-208 | 1U3978 | sp-13 | an-208 | | | |
| 1A3979 | sp-14 | an-209 | 1U3979 | sp-13 | an-209 | | | |
| 1A3980 | sp-14 | an-210 | 1U3980 | sp-13 | an-210 | | | |
| 1A3981 | sp-14 | an-211 | 1U3981 | sp-13 | an-211 | | | |
| 1A3982 | sp-14 | an-212 | 1U3982 | sp-13 | an-212 | | | |
| 1A3983 | sp-14 | an-213 | 1U3983 | sp-13 | an-213 | | | |
| 1A3984 | sp-14 | an-214 | 1U3984 | sp-13 | an-214 | | | |
| 1A3985 | sp-14 | an-215 | 1U3985 | sp-13 | an-215 | | | |
| 1A3986 | sp-14 | an-216 | 1U3986 | sp-13 | an-216 | | | |
| 1A3987 | sp-14 | an-217 | 1U3987 | sp-13 | an-217 | | | |
| 1A3988 | sp-14 | an-218 | 1U3988 | sp-13 | an-218 | | | |
| 1A3989 | sp-14 | an-219 | 1U3989 | sp-13 | an-219 | | | |
| 1A3990 | sp-14 | an-220 | 1U3990 | sp-13 | an-220 | | | |
| 1A3991 | sp-14 | an-221 | 1U3991 | sp-13 | an-221 | | | |
| 1A3992 | sp-14 | an-222 | 1U3992 | sp-13 | an-222 | | | |
| 1A3993 | sp-14 | an-223 | 1U3993 | sp-13 | an-223 | | | |
| 1A3994 | sp-14 | an-224 | 1U3994 | sp-13 | an-224 | | | |
| 1A3995 | sp-14 | an-225 | 1U3995 | sp-13 | an-225 | | | |
| 1A3996 | sp-14 | an-226 | 1U3996 | sp-13 | an-226 | | | |
| 1A3997 | sp-14 | an-227 | 1U3997 | sp-13 | an-227 | | | |
| 1A3998 | sp-14 | an-228 | 1U3998 | sp-13 | an-228 | | | |
| 1A3999 | sp-14 | an-229 | 1U3999 | sp-13 | an-229 | | | |
| 1A4000 | sp-14 | an-230 | 1U4000 | sp-13 | an-230 | | | |
| 1A4001 | sp-14 | an-231 | 1U4001 | sp-13 | an-231 | | | |
| 1A4002 | sp-14 | an-232 | 1U4002 | sp-13 | an-232 | | | |
| 1A4003 | sp-14 | an-233 | 1U4003 | sp-13 | an-233 | | | |
| 1A4004 | sp-14 | an-234 | 1U4004 | sp-13 | an-234 | | | |
| 1A4005 | sp-14 | an-235 | 1U4005 | sp-13 | an-235 | | | |
| 1A4006 | sp-14 | an-236 | 1U4006 | sp-13 | an-236 | | | |
| 1A4007 | sp-14 | an-237 | 1U4007 | sp-13 | an-237 | | | |
| 1A4008 | sp-14 | an-238 | 1U4008 | sp-13 | an-238 | | | |
| 1A4009 | sp-14 | an-239 | 1U4009 | sp-13 | an-239 | | | |
| 1A4010 | sp-14 | an-240 | 1U4010 | sp-13 | an-240 | | | |
| 1A4011 | sp-14 | an-241 | 1U4011 | sp-13 | an-241 | | | |
| 1A4012 | sp-14 | an-242 | 1U4012 | sp-13 | an-242 | | | |
| 1A4013 | sp-14 | an-243 | 1U4013 | sp-13 | an-243 | | | |
| 1A4014 | sp-14 | an-244 | 1U4014 | sp-13 | an-244 | | | |
| 1A4015 | sp-14 | an-245 | 1U4015 | sp-13 | an-245 | | | |
| 1A4016 | sp-14 | an-246 | 1U4016 | sp-13 | an-246 | | | |
| 1A4017 | sp-14 | an-247 | 1U4017 | sp-13 | an-247 | | | |
| 1A4018 | sp-14 | an-248 | 1U4018 | sp-13 | an-248 | | | |
| 1A4019 | sp-14 | an-249 | 1U4019 | sp-13 | an-249 | | | |
| 1A4020 | sp-14 | an-250 | 1U4020 | sp-13 | an-250 | | | |
| 1A4021 | sp-14 | an-251 | 1U4021 | sp-13 | an-251 | | | |
| 1A4022 | sp-14 | an-252 | 1U4022 | sp-13 | an-252 | | | |
| 1A4023 | sp-14 | an-253 | 1U4023 | sp-13 | an-253 | | | |
| 1A4024 | sp-14 | an-254 | 1U4024 | sp-13 | an-254 | | | |
| 1A4025 | sp-14 | an-255 | 1U4025 | sp-13 | an-255 | | | |
| 1A4026 | sp-14 | an-256 | 1U4026 | sp-13 | an-256 | | | |
| 1A4027 | sp-14 | an-257 | 1U4027 | sp-13 | an-257 | | | |
| 1A4028 | sp-14 | an-258 | 1U4028 | sp-13 | an-258 | | | |
| 1A4029 | sp-14 | an-259 | 1U4029 | sp-13 | an-259 | | | |
| 1A4030 | sp-14 | an-260 | 1U4030 | sp-13 | an-260 | | | |
| 1A4031 | sp-14 | an-261 | 1U4031 | sp-13 | an-261 | | | |

Table 2-73

| Y = NHCS | | | Y = NHCSNH | | | Y = NHCSO | | |
|---|---|---|---|---|---|---|---|---|
| 1A4032 | sp-14 | an-262 | 1U4032 | sp-13 | an-262 | | | |
| 1A4033 | sp-14 | an-263 | 1U4033 | sp-13 | an-263 | | | |
| 1A4034 | sp-14 | an-264 | 1U4034 | sp-13 | an-264 | | | |

-continued

| Ex. No. | Z | N⁺R⁵R⁶R⁷ | Ex. No. | Z | N⁺R⁵R⁶R⁷ | Ex. No. | Z | N⁺R⁵R⁶R⁷ |
|---|---|---|---|---|---|---|---|---|
| 1A4035 | sp-14 | an-265 | 1U4035 | sp-13 | an-265 | | | |
| 1A4036 | sp-14 | an-266 | 1U4036 | sp-13 | an-266 | | | |
| 1A4037 | sp-14 | an-267 | 1U4037 | sp-13 | an-267 | | | |
| 1A4038 | sp-14 | an-268 | 1U4038 | sp-13 | an-268 | | | |
| 1A4039 | sp-14 | an-269 | 1U4039 | sp-13 | an-269 | | | |
| 1A4040 | sp-14 | an-270 | 1U4040 | sp-13 | an-270 | | | |
| 1A4041 | sp-14 | an-271 | 1U4041 | sp-13 | an-271 | | | |
| 1A4042 | sp-14 | an-272 | 1U4042 | sp-13 | an-272 | | | |
| 1A4043 | sp-14 | an-273 | 1U4043 | sp-13 | an-273 | | | |
| 1A4044 | sp-14 | an-274 | 1U4044 | sp-13 | an-274 | | | |
| 1A4045 | sp-14 | an-275 | 1U4045 | sp-13 | an-275 | | | |
| 1A4046 | sp-14 | an-276 | 1U4046 | sp-13 | an-276 | | | |
| 1A4047 | sp-14 | an-277 | 1U4047 | sp-13 | an-277 | | | |
| 1A4048 | sp-14 | an-278 | 1U4048 | sp-13 | an-278 | | | |
| 1A4049 | sp-14 | an-279 | 1U4049 | sp-13 | an-279 | | | |
| 1A4050 | sp-14 | an-280 | 1U4050 | sp-13 | an-280 | | | |
| 1A4051 | sp-14 | an-281 | 1U4051 | sp-13 | an-281 | | | |
| 1A4052 | sp-14 | an-282 | 1U4052 | sp-13 | an-282 | | | |
| 1A4053 | sp-14 | an-283 | 1U4053 | sp-13 | an-283 | | | |
| 1A4054 | sp-14 | an-284 | 1U4054 | sp-13 | an-284 | | | |
| 1A4055 | sp-14 | an-285 | 1U4055 | sp-13 | an-285 | | | |
| 1A4056 | sp-14 | an-286 | 1U4056 | sp-13 | an-286 | | | |
| 1A4057 | sp-14 | an-287 | 1U4057 | sp-13 | an-287 | | | |
| 1A4058 | sp-14 | an-288 | 1U4058 | sp-13 | an-288 | | | |
| 1A4059 | sp-14 | an-289 | 1U4059 | sp-13 | an-289 | | | |
| 1A4060 | sp-14 | an-290 | 1U4060 | sp-13 | an-290 | | | |
| 1A4061 | sp-14 | an-291 | 1U4061 | sp-13 | an-291 | | | |
| 1A4062 | sp-14 | an-292 | 1U4062 | sp-13 | an-292 | | | |
| 1A4063 | sp-14 | an-293 | 1U4063 | sp-13 | an-293 | | | |
| 1A4064 | sp-14 | an-294 | 1U4064 | sp-13 | an-294 | | | |
| 1A4065 | sp-14 | an-295 | 1U4065 | sp-13 | an-295 | | | |
| 1A4066 | sp-14 | an-296 | 1U4066 | sp-13 | an-296 | | | |
| 1A4067 | sp-14 | an-297 | 1U4067 | sp-13 | an-297 | | | |
| 1A4068 | sp-14 | an-298 | 1U4068 | sp-13 | an-298 | | | |
| 1A4069 | sp-14 | an-299 | 1U4069 | sp-13 | an-299 | | | |
| 1A4070 | sp-14 | an-300 | 1U4070 | sp-13 | an-300 | | | |
| 1A4071 | sp-14 | an-301 | 1U4071 | sp-13 | an-301 | | | |
| 1A4072 | sp-14 | an-302 | 1U4072 | sp-13 | an-302 | | | |
| 1A4073 | sp-14 | an-303 | 1U4073 | sp-13 | an-303 | | | |
| 1A4074 | sp-14 | an-304 | 1U4074 | sp-13 | an-304 | | | |
| 1A4075 | sp-14 | an-305 | 1U4075 | sp-13 | an-305 | | | |
| 1A4076 | sp-14 | an-306 | 1U4076 | sp-13 | an-306 | | | |
| 1A4077 | sp-14 | an-307 | 1U4077 | sp-13 | an-307 | | | |
| 1A4078 | sp-14 | an-308 | 1U4078 | sp-13 | an-308 | | | |
| 1A4079 | sp-14 | an-309 | 1U4079 | sp-13 | an-309 | | | |
| 1A4080 | sp-14 | an-310 | 1U4080 | sp-13 | an-310 | | | |
| 1A4081 | sp-14 | an-311 | 1U4081 | sp-13 | an-311 | | | |
| 1A4082 | sp-14 | an-312 | 1U4082 | sp-13 | an-312 | | | |
| 1A4083 | sp-14 | an-313 | 1U4083 | sp-13 | an-313 | | | |
| 1A4084 | sp-14 | an-314 | 1U4084 | sp-13 | an-314 | | | |
| 1A4085 | sp-14 | an-315 | 1U4085 | sp-13 | an-315 | | | |
| 1A4086 | sp-14 | an-316 | 1U4086 | sp-13 | an-316 | | | |
| 1A4087 | sp-14 | an-317 | 1U4087 | sp-13 | an-317 | | | |

Table 2-74

| Y = NHCS | | | Y = NHCSNH | | | Y = NHCSO | | |
|---|---|---|---|---|---|---|---|---|
| 1A4088 | sp-14 | an-318 | 1U4088 | sp-13 | an-318 | | | |
| 1A4089 | sp-14 | an-319 | 1U4089 | sp-13 | an-319 | | | |
| 1A4090 | sp-14 | an-320 | 1U4090 | sp-13 | an-320 | | | |
| 1A4091 | sp-14 | an-321 | 1U4091 | sp-13 | an-321 | | | |
| 1A4092 | sp-14 | an-322 | 1U4092 | sp-13 | an-322 | | | |
| 1A4093 | sp-14 | an-323 | 1U4093 | sp-13 | an-323 | | | |
| 1A4094 | sp-14 | an-324 | 1U4094 | sp-13 | an-324 | | | |
| 1A4095 | sp-14 | an-325 | 1U4095 | sp-13 | an-325 | | | |
| 1A4096 | sp-14 | an-326 | 1U4096 | sp-13 | an-326 | | | |
| 1A4097 | sp-14 | an-327 | 1U4097 | sp-13 | an-327 | | | |
| 1A4098 | sp-14 | an-328 | 1U4098 | sp-13 | an-328 | | | |
| 1A4099 | sp-14 | an-329 | 1U4099 | sp-13 | an-329 | | | |
| 1A4100 | sp-14 | an-330 | 1U4100 | sp-13 | an-330 | | | |
| 1A4101 | sp-14 | an-331 | 1U4101 | sp-13 | an-331 | | | |
| 1A4102 | sp-14 | an-332 | 1U4102 | sp-13 | an-332 | | | |
| 1A4103 | sp-14 | an-333 | 1U4103 | sp-13 | an-333 | | | |
| 1A4104 | sp-14 | an-334 | 1U4104 | sp-13 | an-334 | | | |
| 1A4105 | sp-14 | an-335 | 1U4105 | sp-13 | an-335 | | | |
| 1A4106 | sp-14 | an-336 | 1U4106 | sp-13 | an-336 | | | |
| 1A4107 | sp-14 | an-337 | 1U4107 | sp-13 | an-337 | | | |
| 1A4108 | sp-14 | an-338 | 1U4108 | sp-13 | an-338 | | | |

-continued

| Ex. No. | Z | $N^+R^5R^6R^7$ | Ex. No. | Z | $N^+R^5R^6R^7$ | Ex. No. | Z | $N^+R^5R^6R^7$ |
|---|---|---|---|---|---|---|---|---|
| 1A4109 | sp-14 | an-339 | 1U4109 | sp-13 | an-339 | | | |
| 1A4110 | sp-14 | an-340 | 1U4110 | sp-13 | an-340 | | | |
| 1A4111 | sp-14 | an-341 | 1U4111 | sp-13 | an-341 | | | |
| 1A4112 | sp-14 | an-342 | 1U4112 | sp-13 | an-342 | | | |
| 1A4113 | sp-14 | an-343 | 1U4113 | sp-13 | an-343 | | | |
| 1A4114 | sp-14 | an-344 | 1U4114 | sp-13 | an-344 | | | |
| 1A4115 | sp-14 | an-345 | 1U4115 | sp-13 | an-345 | | | |
| 1A4116 | sp-14 | an-346 | 1U4116 | sp-13 | an-346 | | | |
| 1A4117 | sp-14 | an-347 | 1U4117 | sp-13 | an-347 | | | |
| 1A4118 | sp-14 | an-348 | 1U4118 | sp-13 | an-348 | | | |
| 1A4119 | sp-14 | an-349 | 1U4119 | sp-13 | an-349 | | | |
| 1A4120 | sp-14 | an-350 | 1U4120 | sp-13 | an-350 | | | |
| 1A4121 | sp-14 | an-351 | 1U4121 | sp-13 | an-351 | | | |
| 1A4122 | sp-14 | an-352 | 1U4122 | sp-13 | an-352 | | | |
| 1A4123 | sp-14 | an-353 | 1U4123 | sp-13 | an-353 | | | |
| 1A4124 | sp-14 | an-354 | 1U4124 | sp-13 | an-354 | | | |
| 1A4125 | sp-14 | an-355 | 1U4125 | sp-13 | an-355 | | | |
| 1A4126 | sp-14 | an-356 | 1U4126 | sp-13 | an-356 | | | |
| 1A4127 | sp-14 | an-357 | 1U4127 | sp-13 | an-357 | | | |
| 1A4128 | sp-14 | an-358 | 1U4128 | sp-13 | an-358 | | | |
| 1A4129 | sp-14 | an-359 | 1U4129 | sp-13 | an-359 | | | |
| 1A4130 | sp-14 | an-360 | 1U4130 | sp-13 | an-360 | | | |
| 1A4131 | sp-14 | an-361 | 1U4131 | sp-13 | an-361 | | | |
| 1A4132 | sp-14 | an-362 | 1U4132 | sp-13 | an-362 | | | |
| 1A4133 | sp-14 | an-363 | 1U4133 | sp-13 | an-363 | | | |
| 1A4134 | sp-14 | an-364 | 1U4134 | sp-13 | an-364 | | | |
| 1A4135 | sp-14 | an-365 | 1U4135 | sp-13 | an-365 | | | |
| 1A4136 | sp-14 | an-366 | 1U4136 | sp-13 | an-366 | | | |
| 1A4137 | sp-14 | an-367 | 1U4137 | sp-13 | an-367 | | | |
| 1A4138 | sp-14 | an-368 | 1U4138 | sp-13 | an-368 | | | |
| 1A4139 | sp-14 | an-369 | 1U4139 | sp-13 | an-369 | | | |
| 1A4140 | sp-14 | an-370 | 1U4140 | sp-13 | an-370 | | | |
| 1A4141 | sp-14 | an-371 | 1U4141 | sp-13 | an-371 | | | |
| 1A4142 | sp-14 | an-372 | 1U4142 | sp-13 | an-372 | | | |
| 1A4143 | sp-14 | an-373 | 1U4143 | sp-13 | an-373 | | | |

Table 2-75

| Y = NHCS | | | Y = NHCSNH | | | Y = NHCSO | | |
|---|---|---|---|---|---|---|---|---|
| 1A4144 | sp-14 | an-374 | 1U4144 | sp-13 | an-374 | | | |
| 1A4145 | sp-14 | an-375 | 1U4145 | sp-13 | an-375 | | | |
| 1A4146 | sp-14 | an-376 | 1U4146 | sp-13 | an-376 | | | |
| 1A4147 | sp-14 | an-377 | 1U4147 | sp-13 | an-377 | | | |
| | | | | | | Y = NHCS | | |
| 1A4148 | sp-15 | an-1 | 1U4148 | sp-14 | an-1 | 1A5279 | sp-19 | an-1 |
| 1A4149 | sp-15 | an-2 | 1U4149 | sp-14 | an-2 | 1A5280 | sp-19 | an-2 |
| 1A4150 | sp-15 | an-3 | 1U4150 | sp-14 | an-3 | 1A5281 | sp-19 | an-3 |
| 1A4151 | sp-15 | an-4 | 1U4151 | sp-14 | an-4 | 1A5282 | sp-19 | an-4 |
| 1A4152 | sp-15 | an-5 | 1U4152 | sp-14 | an-5 | 1A5283 | sp-19 | an-5 |
| 1A4153 | sp-15 | an-6 | 1U4153 | sp-14 | an-6 | 1A5284 | sp-19 | an-6 |
| 1A4154 | sp-15 | an-7 | 1U4154 | sp-14 | an-7 | 1A5285 | sp-19 | an-7 |
| 1A4155 | sp-15 | an-8 | 1U4155 | sp-14 | an-8 | 1A5286 | sp-19 | an-8 |
| 1A4156 | sp-15 | an-9 | 1U4156 | sp-14 | an-9 | 1A5287 | sp-19 | an-9 |
| 1A4157 | sp-15 | an-10 | 1U4157 | sp-14 | an-10 | 1A5288 | sp-19 | an-10 |
| 1A4158 | sp-15 | an-11 | 1U4158 | sp-14 | an-11 | 1A5289 | sp-19 | an-11 |
| 1A4159 | sp-15 | an-12 | 1U4159 | sp-14 | an-12 | 1A5290 | sp-19 | an-12 |
| 1A4160 | sp-15 | an-13 | 1U4160 | sp-14 | an-13 | 1A5291 | sp-19 | an-13 |
| 1A4161 | sp-15 | an-14 | 1U4161 | sp-14 | an-14 | 1A5292 | sp-19 | an-14 |
| 1A4162 | sp-15 | an-15 | 1U4162 | sp-14 | an-15 | 1A5293 | sp-19 | an-15 |
| 1A4163 | sp-15 | an-16 | 1U4163 | sp-14 | an-16 | 1A5294 | sp-19 | an-16 |
| 1A4164 | sp-15 | an-17 | 1U4164 | sp-14 | an-17 | 1A5295 | sp-19 | an-17 |
| 1A4165 | sp-15 | an-18 | 1U4165 | sp-14 | an-18 | 1A5296 | sp-19 | an-18 |
| 1A4166 | sp-15 | an-19 | 1U4166 | sp-14 | an-19 | 1A5297 | sp-19 | an-19 |
| 1A4167 | sp-15 | an-20 | 1U4167 | sp-14 | an-20 | 1A5298 | sp-19 | an-20 |
| 1A4168 | sp-15 | an-21 | 1U4168 | sp-14 | an-21 | 1A5299 | sp-19 | an-21 |
| 1A4169 | sp-15 | an-22 | 1U4169 | sp-14 | an-22 | 1A5300 | sp-19 | an-22 |
| 1A4170 | sp-15 | an-23 | 1U4170 | sp-14 | an-23 | 1A5301 | sp-19 | an-23 |
| 1A4171 | sp-15 | an-24 | 1U4171 | sp-14 | an-24 | 1A5302 | sp-19 | an-24 |
| 1A4172 | sp-15 | an-25 | 1U4172 | sp-14 | an-25 | 1A5303 | sp-19 | an-25 |
| 1A4173 | sp-15 | an-26 | 1U4173 | sp-14 | an-26 | 1A5304 | sp-19 | an-26 |
| 1A4174 | sp-15 | an-27 | 1U4174 | sp-14 | an-27 | 1A5305 | sp-19 | an-27 |
| 1A4175 | sp-15 | an-28 | 1U4175 | sp-14 | an-28 | 1A5306 | sp-19 | an-28 |
| 1A4176 | sp-15 | an-29 | 1U4176 | sp-14 | an-29 | 1A5307 | sp-19 | an-29 |
| 1A4177 | sp-15 | an-30 | 1U4177 | sp-14 | an-30 | 1A5308 | sp-19 | an-30 |
| 1A4178 | sp-15 | an-31 | 1U4178 | sp-14 | an-31 | 1A5309 | sp-19 | an-31 |
| 1A4179 | sp-15 | an-32 | 1U4179 | sp-14 | an-32 | 1A5310 | sp-19 | an-32 |
| 1A4180 | sp-15 | an-33 | 1U4180 | sp-14 | an-33 | 1A5311 | sp-19 | an-33 |
| 1A4181 | sp-15 | an-34 | 1U4181 | sp-14 | an-34 | 1A5312 | sp-19 | an-34 |

-continued

| Ex. No. | Z | N⁺R⁵R⁶R⁷ | Ex. No. | Z | N⁺R⁵R⁶R⁷ | Ex. No. | Z | N⁺R⁵R⁶R⁷ |
|---|---|---|---|---|---|---|---|---|
| 1A4182 | sp-15 | an-35 | 1U4182 | sp-14 | an-35 | 1A5313 | sp-19 | an-35 |
| 1A4183 | sp-15 | an-36 | 1U4183 | sp-14 | an-36 | 1A5314 | sp-19 | an-36 |
| 1A4184 | sp-15 | an-37 | 1U4184 | sp-14 | an-37 | 1A5315 | sp-19 | an-37 |
| 1A4185 | sp-15 | an-38 | 1U4185 | sp-14 | an-38 | 1A5316 | sp-19 | an-38 |
| 1A4186 | sp-15 | an-39 | 1U4186 | sp-14 | an-39 | 1A5317 | sp-19 | an-39 |
| 1A4187 | sp-15 | an-40 | 1U4187 | sp-14 | an-40 | 1A5318 | sp-19 | an-40 |
| 1A4188 | sp-15 | an-41 | 1U4188 | sp-14 | an-41 | 1A5319 | sp-19 | an-41 |
| 1A4189 | sp-15 | an-42 | 1U4189 | sp-14 | an-42 | 1A5320 | sp-19 | an-42 |
| 1A4190 | sp-15 | an-43 | 1U4190 | sp-14 | an-43 | 1A5321 | sp-19 | an-43 |
| 1A4191 | sp-15 | an-44 | 1U4191 | sp-14 | an-44 | 1A5322 | sp-19 | an-44 |
| 1A4192 | sp-15 | an-45 | 1U4192 | sp-14 | an-45 | 1A5323 | sp-19 | an-45 |
| 1A4193 | sp-15 | an-46 | 1U4193 | sp-14 | an-46 | 1A5324 | sp-19 | an-46 |
| 1A4194 | sp-15 | an-47 | 1U4194 | sp-14 | an-47 | 1A5325 | sp-19 | an-47 |
| 1A4195 | sp-15 | an-48 | 1U4195 | sp-14 | an-48 | 1A5326 | sp-19 | an-48 |
| 1A4196 | sp-15 | an-49 | 1U4196 | sp-14 | an-49 | 1A5327 | sp-19 | an-49 |
| 1A4197 | sp-15 | an-50 | 1U4197 | sp-14 | an-50 | 1A5328 | sp-19 | an-50 |
| 1A4198 | sp-15 | an-51 | 1U4198 | sp-14 | an-51 | 1A5329 | sp-19 | an-51 |

Table 2-76

| Y = NHCS | | | Y = NHCSNH | | | Y = NHCS | | |
|---|---|---|---|---|---|---|---|---|
| 1A4199 | sp-15 | an-52 | 1U4199 | sp-14 | an-52 | 1A5330 | sp-19 | an-52 |
| 1A4200 | sp-15 | an-53 | 1U4200 | sp-14 | an-53 | 1A5331 | sp-19 | an-53 |
| 1A4201 | sp-15 | an-54 | 1U4201 | sp-14 | an-54 | 1A5332 | sp-19 | an-54 |
| 1A4202 | sp-15 | an-55 | 1U4202 | sp-14 | an-55 | 1A5333 | sp-19 | an-55 |
| 1A4203 | sp-15 | an-56 | 1U4203 | sp-14 | an-56 | 1A5334 | sp-19 | an-56 |
| 1A4204 | sp-15 | an-57 | 1U4204 | sp-14 | an-57 | 1A5335 | sp-19 | an-57 |
| 1A4205 | sp-15 | an-58 | 1U4205 | sp-14 | an-58 | 1A5336 | sp-19 | an-58 |
| 1A4206 | sp-15 | an-59 | 1U4206 | sp-14 | an-59 | 1A5337 | sp-19 | an-59 |
| 1A4207 | sp-15 | an-60 | 1U4207 | sp-14 | an-60 | 1A5338 | sp-19 | an-60 |
| 1A4208 | sp-15 | an-61 | 1U4208 | sp-14 | an-61 | 1A5339 | sp-19 | an-61 |
| 1A4209 | sp-15 | an-62 | 1U4209 | sp-14 | an-62 | 1A5340 | sp-19 | an-62 |
| 1A4210 | sp-15 | an-63 | 1U4210 | sp-14 | an-63 | 1A5341 | sp-19 | an-63 |
| 1A4211 | sp-15 | an-64 | 1U4211 | sp-14 | an-64 | 1A5342 | sp-19 | an-64 |
| 1A4212 | sp-15 | an-65 | 1U4212 | sp-14 | an-65 | 1A5343 | sp-19 | an-65 |
| 1A4213 | sp-15 | an-66 | 1U4213 | sp-14 | an-66 | 1A5344 | sp-19 | an-66 |
| 1A4214 | sp-15 | an-67 | 1U4214 | sp-14 | an-67 | 1A5345 | sp-19 | an-67 |
| 1A4215 | sp-15 | an-68 | 1U4215 | sp-14 | an-68 | 1A5346 | sp-19 | an-68 |
| 1A4216 | sp-15 | an-69 | 1U4216 | sp-14 | an-69 | 1A5347 | sp-19 | an-69 |
| 1A4217 | sp-15 | an-70 | 1U4217 | sp-14 | an-70 | 1A5348 | sp-19 | an-70 |
| 1A4218 | sp-15 | an-71 | 1U4218 | sp-14 | an-71 | 1A5349 | sp-19 | an-71 |
| 1A4219 | sp-15 | an-72 | 1U4219 | sp-14 | an-72 | 1A5350 | sp-19 | an-72 |
| 1A4220 | sp-15 | an-73 | 1U4220 | sp-14 | an-73 | 1A5351 | sp-19 | an-73 |
| 1A4221 | sp-15 | an-74 | 1U4221 | sp-14 | an-74 | 1A5352 | sp-19 | an-74 |
| 1A4222 | sp-15 | an-75 | 1U4222 | sp-14 | an-75 | 1A5353 | sp-19 | an-75 |
| 1A4223 | sp-15 | an-76 | 1U4223 | sp-14 | an-76 | 1A5354 | sp-19 | an-76 |
| 1A4224 | sp-15 | an-77 | 1U4224 | sp-14 | an-77 | 1A5355 | sp-19 | an-77 |
| 1A4225 | sp-15 | an-78 | 1U4225 | sp-14 | an-78 | 1A5356 | sp-19 | an-78 |
| 1A4226 | sp-15 | an-79 | 1U4226 | sp-14 | an-79 | 1A5357 | sp-19 | an-79 |
| 1A4227 | sp-15 | an-80 | 1U4227 | sp-14 | an-80 | 1A5358 | sp-19 | an-80 |
| 1A4228 | sp-15 | an-81 | 1U4228 | sp-14 | an-81 | 1A5359 | sp-19 | an-81 |
| 1A4229 | sp-15 | an-82 | 1U4229 | sp-14 | an-82 | 1A5360 | sp-19 | an-82 |
| 1A4230 | sp-15 | an-83 | 1U4230 | sp-14 | an-83 | 1A5361 | sp-19 | an-83 |
| 1A4231 | sp-15 | an-84 | 1U4231 | sp-14 | an-84 | 1A5362 | sp-19 | an-84 |
| 1A4232 | sp-15 | an-85 | 1U4232 | sp-14 | an-85 | 1A5363 | sp-19 | an-85 |
| 1A4233 | sp-15 | an-86 | 1U4233 | sp-14 | an-86 | 1A5364 | sp-19 | an-86 |
| 1A4234 | sp-15 | an-87 | 1U4234 | sp-14 | an-87 | 1A5365 | sp-19 | an-87 |
| 1A4235 | sp-15 | an-88 | 1U4235 | sp-14 | an-88 | 1A5366 | sp-19 | an-88 |
| 1A4236 | sp-15 | an-89 | 1U4236 | sp-14 | an-89 | 1A5367 | sp-19 | an-89 |
| 1A4237 | sp-15 | an-90 | 1U4237 | sp-14 | an-90 | 1A5368 | sp-19 | an-90 |
| 1A4238 | sp-15 | an-91 | 1U4238 | sp-14 | an-91 | 1A5369 | sp-19 | an-91 |
| 1A4239 | sp-15 | an-92 | 1U4239 | sp-14 | an-92 | 1A5370 | sp-19 | an-92 |
| 1A4240 | sp-15 | an-93 | 1U4240 | sp-14 | an-93 | 1A5371 | sp-19 | an-93 |
| 1A4241 | sp-15 | an-94 | 1U4241 | sp-14 | an-94 | 1A5372 | sp-19 | an-94 |
| 1A4242 | sp-15 | an-95 | 1U4242 | sp-14 | an-95 | 1A5373 | sp-19 | an-95 |
| 1A4243 | sp-15 | an-96 | 1U4243 | sp-14 | an-96 | 1A5374 | sp-19 | an-96 |
| 1A4244 | sp-15 | an-97 | 1U4244 | sp-14 | an-97 | 1A5375 | sp-19 | an-97 |
| 1A4245 | sp-15 | an-98 | 1U4245 | sp-14 | an-98 | 1A5376 | sp-19 | an-98 |
| 1A4246 | sp-15 | an-99 | 1U4246 | sp-14 | an-99 | 1A5377 | sp-19 | an-99 |
| 1A4247 | sp-15 | an-100 | 1U4247 | sp-14 | an-100 | 1A5378 | sp-19 | an-100 |
| 1A4248 | sp-15 | an-101 | 1U4248 | sp-14 | an-101 | 1A5379 | sp-19 | an-101 |
| 1A4249 | sp-15 | an-102 | 1U4249 | sp-14 | an-102 | 1A5380 | sp-19 | an-102 |
| 1A4250 | sp-15 | an-103 | 1U4250 | sp-14 | an-103 | 1A5381 | sp-19 | an-103 |
| 1A4251 | sp-15 | an-104 | 1U4251 | sp-14 | an-104 | 1A5382 | sp-19 | an-104 |
| 1A4252 | sp-15 | an-105 | 1U4252 | sp-14 | an-105 | 1A5383 | sp-19 | an-105 |
| 1A4253 | sp-15 | an-106 | 1U4253 | sp-14 | an-106 | 1A5384 | sp-19 | an-106 |
| 1A4254 | sp-15 | an-107 | 1U4254 | sp-14 | an-107 | 1A5385 | sp-19 | an-107 |

-continued

| Ex. No. | Z | N⁺R⁵R⁶R⁷ | Ex. No. | Z | N⁺R⁵R⁶R⁷ | Ex. No. | Z | N⁺R⁵R⁶R⁷ |
|---|---|---|---|---|---|---|---|---|
| | | | | Table 2-77 | | | | |
| | Y = NHCS | | | Y = NHCSNH | | | Y = NHCS | |
| 1A4255 | sp-15 | an-108 | 1U4255 | sp-14 | an-108 | 1A5386 | sp-19 | an-108 |
| 1A4256 | sp-15 | an-109 | 1U4256 | sp-14 | an-109 | 1A5387 | sp-19 | an-109 |
| 1A4257 | sp-15 | an-110 | 1U4257 | sp-14 | an-110 | 1A5388 | sp-19 | an-110 |
| 1A4258 | sp-15 | an-111 | 1U4258 | sp-14 | an-111 | 1A5389 | sp-19 | an-111 |
| 1A4259 | sp-15 | an-112 | 1U4259 | sp-14 | an-112 | 1A5390 | sp-19 | an-112 |
| 1A4260 | sp-15 | an-113 | 1U4260 | sp-14 | an-113 | 1A5391 | sp-19 | an-113 |
| 1A4261 | sp-15 | an-114 | 1U4261 | sp-14 | an-114 | 1A5392 | sp-19 | an-114 |
| 1A4262 | sp-15 | an-115 | 1U4262 | sp-14 | an-115 | 1A5393 | sp-19 | an-115 |
| 1A4263 | sp-15 | an-116 | 1U4263 | sp-14 | an-116 | 1A5394 | sp-19 | an-116 |
| 1A4264 | sp-15 | an-117 | 1U4264 | sp-14 | an-117 | 1A5395 | sp-19 | an-117 |
| 1A4265 | sp-15 | an-118 | 1U4265 | sp-14 | an-118 | 1A5396 | sp-19 | an-118 |
| 1A4266 | sp-15 | an-119 | 1U4266 | sp-14 | an-119 | 1A5397 | sp-19 | an-119 |
| 1A4267 | sp-15 | an-120 | 1U4267 | sp-14 | an-120 | 1A5398 | sp-19 | an-120 |
| 1A4268 | sp-15 | an-121 | 1U4268 | sp-14 | an-121 | 1A5399 | sp-19 | an-121 |
| 1A4269 | sp-15 | an-122 | 1U4269 | sp-14 | an-122 | 1A5400 | sp-19 | an-122 |
| 1A4270 | sp-15 | an-123 | 1U4270 | sp-14 | an-123 | 1A5401 | sp-19 | an-123 |
| 1A4271 | sp-15 | an-124 | 1U4271 | sp-14 | an-124 | 1A5402 | sp-19 | an-124 |
| 1A4272 | sp-15 | an-125 | 1U4272 | sp-14 | an-125 | 1A5403 | sp-19 | an-125 |
| 1A4273 | sp-15 | an-126 | 1U4273 | sp-14 | an-126 | 1A5404 | sp-19 | an-126 |
| 1A4274 | sp-15 | an-127 | 1U4274 | sp-14 | an-127 | 1A5405 | sp-19 | an-127 |
| 1A4275 | sp-15 | an-128 | 1U4275 | sp-14 | an-128 | 1A5406 | sp-19 | an-128 |
| 1A4276 | sp-15 | an-129 | 1U4276 | sp-14 | an-129 | 1A5407 | sp-19 | an-129 |
| 1A4277 | sp-15 | an-130 | 1U4277 | sp-14 | an-130 | 1A5408 | sp-19 | an-130 |
| 1A4278 | sp-15 | an-131 | 1U4278 | sp-14 | an-131 | 1A5409 | sp-19 | an-131 |
| 1A4279 | sp-15 | an-132 | 1U4279 | sp-14 | an-132 | 1A5410 | sp-19 | an-132 |
| 1A4280 | sp-15 | an-133 | 1U4280 | sp-14 | an-133 | 1A5411 | sp-19 | an-133 |
| 1A4281 | sp-15 | an-134 | 1U4281 | sp-14 | an-134 | 1A5412 | sp-19 | an-134 |
| 1A4282 | sp-15 | an-135 | 1U4282 | sp-14 | an-135 | 1A5413 | sp-19 | an-135 |
| 1A4283 | sp-15 | an-136 | 1U4283 | sp-14 | an-136 | 1A5414 | sp-19 | an-136 |
| 1A4284 | sp-15 | an-137 | 1U4284 | sp-14 | an-137 | 1A5415 | sp-19 | an-137 |
| 1A4285 | sp-15 | an-138 | 1U4285 | sp-14 | an-138 | 1A5416 | sp-19 | an-138 |
| 1A4286 | sp-15 | an-139 | 1U4286 | sp-14 | an-139 | 1A5417 | sp-19 | an-139 |
| 1A4287 | sp-15 | an-140 | 1U4287 | sp-14 | an-140 | 1A5418 | sp-19 | an-140 |
| 1A4288 | sp-15 | an-141 | 1U4288 | sp-14 | an-141 | 1A5419 | sp-19 | an-141 |
| 1A4289 | sp-15 | an-142 | 1U4289 | sp-14 | an-142 | 1A5420 | sp-19 | an-142 |
| 1A4290 | sp-15 | an-143 | 1U4290 | sp-14 | an-143 | 1A5421 | sp-19 | an-143 |
| 1A4291 | sp-15 | an-144 | 1U4291 | sp-14 | an-144 | 1A5422 | sp-19 | an-144 |
| 1A4292 | sp-15 | an-145 | 1U4292 | sp-14 | an-145 | 1A5423 | sp-19 | an-145 |
| 1A4293 | sp-15 | an-146 | 1U4293 | sp-14 | an-146 | 1A5424 | sp-19 | an-146 |
| 1A4294 | sp-15 | an-147 | 1U4294 | sp-14 | an-147 | 1A5425 | sp-19 | an-147 |
| 1A4295 | sp-15 | an-148 | 1U4295 | sp-14 | an-148 | 1A5426 | sp-19 | an-148 |
| 1A4296 | sp-15 | an-149 | 1U4296 | sp-14 | an-149 | 1A5427 | sp-19 | an-149 |
| 1A4297 | sp-15 | an-150 | 1U4297 | sp-14 | an-150 | 1A5428 | sp-19 | an-150 |
| 1A4298 | sp-15 | an-151 | 1U4298 | sp-14 | an-151 | 1A5429 | sp-19 | an-151 |
| 1A4299 | sp-15 | an-152 | 1U4299 | sp-14 | an-152 | 1A5430 | sp-19 | an-152 |
| 1A4300 | sp-15 | an-153 | 1U4300 | sp-14 | an-153 | 1A5431 | sp-19 | an-153 |
| 1A4301 | sp-15 | an-154 | 1U4301 | sp-14 | an-154 | 1A5432 | sp-19 | an-154 |
| 1A4302 | sp-15 | an-155 | 1U4302 | sp-14 | an-155 | 1A5433 | sp-19 | an-155 |
| 1A4303 | sp-15 | an-156 | 1U4303 | sp-14 | an-156 | 1A5434 | sp-19 | an-156 |
| 1A4304 | sp-15 | an-157 | 1U4304 | sp-14 | an-157 | 1A5435 | sp-19 | an-157 |
| 1A4305 | sp-15 | an-158 | 1U4305 | sp-14 | an-158 | 1A5436 | sp-19 | an-158 |
| 1A4306 | sp-15 | an-159 | 1U4306 | sp-14 | an-159 | 1A5437 | sp-19 | an-159 |
| 1A4307 | sp-15 | an-160 | 1U4307 | sp-14 | an-160 | 1A5438 | sp-19 | an-160 |
| 1A4308 | sp-15 | an-161 | 1U4308 | sp-14 | an-161 | 1A5439 | sp-19 | an-161 |
| 1A4309 | sp-15 | an-162 | 1U4309 | sp-14 | an-162 | 1A5440 | sp-19 | an-162 |
| 1A4310 | sp-15 | an-163 | 1U4310 | sp-14 | an-163 | 1A5441 | sp-19 | an-163 |
| | | | | Table 2-78 | | | | |
| | Y = NHCS | | | Y = NHCSNH | | | Y = NHCS | |
| 1A4311 | sp-15 | an-164 | 1U4311 | sp-14 | an-164 | 1A5442 | sp-19 | an-164 |
| 1A4312 | sp-15 | an-165 | 1U4312 | sp-14 | an-165 | 1A5443 | sp-19 | an-165 |
| 1A4313 | sp-15 | an-166 | 1U4313 | sp-14 | an-166 | 1A5444 | sp-19 | an-166 |
| 1A4314 | sp-15 | an-167 | 1U4314 | sp-14 | an-167 | 1A5445 | sp-19 | an-167 |
| 1A4315 | sp-15 | an-168 | 1U4315 | sp-14 | an-168 | 1A5446 | sp-19 | an-168 |
| 1A4316 | sp-15 | an-169 | 1U4316 | sp-14 | an-169 | 1A5447 | sp-19 | an-169 |
| 1A4317 | sp-15 | an-170 | 1U4317 | sp-14 | an-170 | 1A5448 | sp-19 | an-170 |
| 1A4318 | sp-15 | an-171 | 1U4318 | sp-14 | an-171 | 1A5449 | sp-19 | an-171 |
| 1A4319 | sp-15 | an-172 | 1U4319 | sp-14 | an-172 | 1A5450 | sp-19 | an-172 |
| 1A4320 | sp-15 | an-173 | 1U4320 | sp-14 | an-173 | 1A5451 | sp-19 | an-173 |
| 1A4321 | sp-15 | an-174 | 1U4321 | sp-14 | an-174 | 1A5452 | sp-19 | an-174 |
| 1A4322 | sp-15 | an-175 | 1U4322 | sp-14 | an-175 | 1A5453 | sp-19 | an-175 |
| 1A4323 | sp-15 | an-176 | 1U4323 | sp-14 | an-176 | 1A5454 | sp-19 | an-176 |
| 1A4324 | sp-15 | an-177 | 1U4324 | sp-14 | an-177 | 1A5455 | sp-19 | an-177 |

-continued

| Ex. No. | Z | $N^+R^5R^6R^7$ | Ex. No. | Z | $N^+R^5R^6R^7$ | Ex. No. | Z | $N^+R^5R^6R^7$ |
|---|---|---|---|---|---|---|---|---|
| 1A4325 | sp-15 | an-178 | 1U4325 | sp-14 | an-178 | 1A5456 | sp-19 | an-178 |
| 1A4326 | sp-15 | an-179 | 1U4326 | sp-14 | an-179 | 1A5457 | sp-19 | an-179 |
| 1A4327 | sp-15 | an-180 | 1U4327 | sp-14 | an-180 | 1A5458 | sp-19 | an-180 |
| 1A4328 | sp-15 | an-181 | 1U4328 | sp-14 | an-181 | 1A5459 | sp-19 | an-181 |
| 1A4329 | sp-15 | an-182 | 1U4329 | sp-14 | an-182 | 1A5460 | sp-19 | an-182 |
| 1A4330 | sp-15 | an-183 | 1U4330 | sp-14 | an-183 | 1A5461 | sp-19 | an-183 |
| 1A4331 | sp-15 | an-184 | 1U4331 | sp-14 | an-184 | 1A5462 | sp-19 | an-184 |
| 1A4332 | sp-15 | an-185 | 1U4332 | sp-14 | an-185 | 1A5463 | sp-19 | an-185 |
| 1A4333 | sp-15 | an-186 | 1U4333 | sp-14 | an-186 | 1A5464 | sp-19 | an-186 |
| 1A4334 | sp-15 | an-187 | 1U4334 | sp-14 | an-187 | 1A5465 | sp-19 | an-187 |
| 1A4335 | sp-15 | an-188 | 1U4335 | sp-14 | an-188 | 1A5466 | sp-19 | an-188 |
| 1A4336 | sp-15 | an-189 | 1U4336 | sp-14 | an-189 | 1A5467 | sp-19 | an-189 |
| 1A4337 | sp-15 | an-190 | 1U4337 | sp-14 | an-190 | 1A5468 | sp-19 | an-190 |
| 1A4338 | sp-15 | an-191 | 1U4338 | sp-14 | an-191 | 1A5469 | sp-19 | an-191 |
| 1A4339 | sp-15 | an-192 | 1U4339 | sp-14 | an-192 | 1A5470 | sp-19 | an-192 |
| 1A4340 | sp-15 | an-193 | 1U4340 | sp-14 | an-193 | 1A5471 | sp-19 | an-193 |
| 1A4341 | sp-15 | an-194 | 1U4341 | sp-14 | an-194 | 1A5472 | sp-19 | an-194 |
| 1A4342 | sp-15 | an-195 | 1U4342 | sp-14 | an-195 | 1A5473 | sp-19 | an-195 |
| 1A4343 | sp-15 | an-196 | 1U4343 | sp-14 | an-196 | 1A5474 | sp-19 | an-196 |
| 1A4344 | sp-15 | an-197 | 1U4344 | sp-14 | an-197 | 1A5475 | sp-19 | an-197 |
| 1A4345 | sp-15 | an-198 | 1U4345 | sp-14 | an-198 | 1A5476 | sp-19 | an-198 |
| 1A4346 | sp-15 | an-199 | 1U4346 | sp-14 | an-199 | 1A5477 | sp-19 | an-199 |
| 1A4347 | sp-15 | an-200 | 1U4347 | sp-14 | an-200 | 1A5478 | sp-19 | an-200 |
| 1A4348 | sp-15 | an-201 | 1U4348 | sp-14 | an-201 | 1A5479 | sp-19 | an-201 |
| 1A4349 | sp-15 | an-202 | 1U4349 | sp-14 | an-202 | 1A5480 | sp-19 | an-202 |
| 1A4350 | sp-15 | an-203 | 1U4350 | sp-14 | an-203 | 1A5481 | sp-19 | an-203 |
| 1A4351 | sp-15 | an-204 | 1U4351 | sp-14 | an-204 | 1A5482 | sp-19 | an-204 |
| 1A4352 | sp-15 | an-205 | 1U4352 | sp-14 | an-205 | 1A5483 | sp-19 | an-205 |
| 1A4353 | sp-15 | an-206 | 1U4353 | sp-14 | an-206 | 1A5484 | sp-19 | an-206 |
| 1A4354 | sp-15 | an-207 | 1U4354 | sp-14 | an-207 | 1A5485 | sp-19 | an-207 |
| 1A4355 | sp-15 | an-208 | 1U4355 | sp-14 | an-208 | 1A5486 | sp-19 | an-208 |
| 1A4356 | sp-15 | an-209 | 1U4356 | sp-14 | an-209 | 1A5487 | sp-19 | an-209 |
| 1A4357 | sp-15 | an-210 | 1U4357 | sp-14 | an-210 | 1A5488 | sp-19 | an-210 |
| 1A4358 | sp-15 | an-211 | 1U4358 | sp-14 | an-211 | 1A5489 | sp-19 | an-211 |
| 1A4359 | sp-15 | an-212 | 1U4359 | sp-14 | an-212 | 1A5490 | sp-19 | an-212 |
| 1A4360 | sp-15 | an-213 | 1U4360 | sp-14 | an-213 | 1A5491 | sp-19 | an-213 |
| 1A4361 | sp-15 | an-214 | 1U4361 | sp-14 | an-214 | 1A5492 | sp-19 | an-214 |
| 1A4362 | sp-15 | an-215 | 1U4362 | sp-14 | an-215 | 1A5493 | sp-19 | an-215 |
| 1A4363 | sp-15 | an-216 | 1U4363 | sp-14 | an-216 | 1A5494 | sp-19 | an-216 |
| 1A4364 | sp-15 | an-217 | 1U4364 | sp-14 | an-217 | 1A5495 | sp-19 | an-217 |
| 1A4365 | sp-15 | an-218 | 1U4365 | sp-14 | an-218 | 1A5496 | sp-19 | an-218 |
| 1A4366 | sp-15 | an-219 | 1U4366 | sp-14 | an-219 | 1A5497 | sp-19 | an-219 |

Table 2-79

| Y = NHCS | | | Y = NHCSNH | | | Y = NHCS | | |
|---|---|---|---|---|---|---|---|---|
| 1A4367 | sp-15 | an-220 | 1U4367 | sp-14 | an-220 | 1A5498 | sp-19 | an-220 |
| 1A4368 | sp-15 | an-221 | 1U4368 | sp-14 | an-221 | 1A5499 | sp-19 | an-221 |
| 1A4369 | sp-15 | an-222 | 1U4369 | sp-14 | an-222 | 1A5500 | sp-19 | an-222 |
| 1A4370 | sp-15 | an-223 | 1U4370 | sp-14 | an-223 | 1A5501 | sp-19 | an-223 |
| 1A4371 | sp-15 | an-224 | 1U4371 | sp-14 | an-224 | 1A5502 | sp-19 | an-224 |
| 1A4372 | sp-15 | an-225 | 1U4372 | sp-14 | an-225 | 1A5503 | sp-19 | an-225 |
| 1A4373 | sp-15 | an-226 | 1U4373 | sp-14 | an-226 | 1A5504 | sp-19 | an-226 |
| 1A4374 | sp-15 | an-227 | 1U4374 | sp-14 | an-227 | 1A5505 | sp-19 | an-227 |
| 1A4375 | sp-15 | an-228 | 1U4375 | sp-14 | an-228 | 1A5506 | sp-19 | an-228 |
| 1A4376 | sp-15 | an-229 | 1U4376 | sp-14 | an-229 | 1A5507 | sp-19 | an-229 |
| 1A4377 | sp-15 | an-230 | 1U4377 | sp-14 | an-230 | 1A5508 | sp-19 | an-230 |
| 1A4378 | sp-15 | an-231 | 1U4378 | sp-14 | an-231 | 1A5509 | sp-19 | an-231 |
| 1A4379 | sp-15 | an-232 | 1U4379 | sp-14 | an-232 | 1A5510 | sp-19 | an-232 |
| 1A4380 | sp-15 | an-233 | 1U4380 | sp-14 | an-233 | 1A5511 | sp-19 | an-233 |
| 1A4381 | sp-15 | an-234 | 1U4381 | sp-14 | an-234 | 1A5512 | sp-19 | an-234 |
| 1A4382 | sp-15 | an-235 | 1U4382 | sp-14 | an-235 | 1A5513 | sp-19 | an-235 |
| 1A4383 | sp-15 | an-236 | 1U4383 | sp-14 | an-236 | 1A5514 | sp-19 | an-236 |
| 1A4384 | sp-15 | an-237 | 1U4384 | sp-14 | an-237 | 1A5515 | sp-19 | an-237 |
| 1A4385 | sp-15 | an-238 | 1U4385 | sp-14 | an-238 | 1A5516 | sp-19 | an-238 |
| 1A4386 | sp-15 | an-239 | 1U4386 | sp-14 | an-239 | 1A5517 | sp-19 | an-239 |
| 1A4387 | sp-15 | an-240 | 1U4387 | sp-14 | an-240 | 1A5518 | sp-19 | an-240 |
| 1A4388 | sp-15 | an-241 | 1U4388 | sp-14 | an-241 | 1A5519 | sp-19 | an-241 |
| 1A4389 | sp-15 | an-242 | 1U4389 | sp-14 | an-242 | 1A5520 | sp-19 | an-242 |
| 1A4390 | sp-15 | an-243 | 1U4390 | sp-14 | an-243 | 1A5521 | sp-19 | an-243 |
| 1A4391 | sp-15 | an-244 | 1U4391 | sp-14 | an-244 | 1A5522 | sp-19 | an-244 |
| 1A4392 | sp-15 | an-245 | 1U4392 | sp-14 | an-245 | 1A5523 | sp-19 | an-245 |
| 1A4393 | sp-15 | an-246 | 1U4393 | sp-14 | an-246 | 1A5524 | sp-19 | an-246 |
| 1A4394 | sp-15 | an-247 | 1U4394 | sp-14 | an-247 | 1A5525 | sp-19 | an-247 |
| 1A4395 | sp-15 | an-248 | 1U4395 | sp-14 | an-248 | 1A5526 | sp-19 | an-248 |
| 1A4396 | sp-15 | an-249 | 1U4396 | sp-14 | an-249 | 1A5527 | sp-19 | an-249 |
| 1A4397 | sp-15 | an-250 | 1U4397 | sp-14 | an-250 | 1A5528 | sp-19 | an-250 |
| 1A4398 | sp-15 | an-251 | 1U4398 | sp-14 | an-251 | 1A5529 | sp-19 | an-251 |

-continued

| Ex. No. | Z | N⁺R⁵R⁶R⁷ | Ex. No. | Z | N⁺R⁵R⁶R⁷ | Ex. No. | Z | N⁺R⁵R⁶R⁷ |
|---|---|---|---|---|---|---|---|---|
| 1A4399 | sp-15 | an-252 | 1U4399 | sp-14 | an-252 | 1A5530 | sp-19 | an-252 |
| 1A4400 | sp-15 | an-253 | 1U4400 | sp-14 | an-253 | 1A5531 | sp-19 | an-253 |
| 1A4401 | sp-15 | an-254 | 1U4401 | sp-14 | an-254 | 1A5532 | sp-19 | an-254 |
| 1A4402 | sp-15 | an-255 | 1U4402 | sp-14 | an-255 | 1A5533 | sp-19 | an-255 |
| 1A4403 | sp-15 | an-256 | 1U4403 | sp-14 | an-256 | 1A5534 | sp-19 | an-256 |
| 1A4404 | sp-15 | an-257 | 1U4404 | sp-14 | an-257 | 1A5535 | sp-19 | an-257 |
| 1A4405 | sp-15 | an-258 | 1U4405 | sp-14 | an-258 | 1A5536 | sp-19 | an-258 |
| 1A4406 | sp-15 | an-259 | 1U4406 | sp-14 | an-259 | 1A5537 | sp-19 | an-259 |
| 1A4407 | sp-15 | an-260 | 1U4407 | sp-14 | an-260 | 1A5538 | sp-19 | an-260 |
| 1A4408 | sp-15 | an-261 | 1U4408 | sp-14 | an-261 | 1A5539 | sp-19 | an-261 |
| 1A4409 | sp-15 | an-262 | 1U4409 | sp-14 | an-262 | 1A5540 | sp-19 | an-262 |
| 1A4410 | sp-15 | an-263 | 1U4410 | sp-14 | an-263 | 1A5541 | sp-19 | an-263 |
| 1A4411 | sp-15 | an-264 | 1U4411 | sp-14 | an-264 | 1A5542 | sp-19 | an-264 |
| 1A4412 | sp-15 | an-265 | 1U4412 | sp-14 | an-265 | 1A5543 | sp-19 | an-265 |
| 1A4413 | sp-15 | an-266 | 1U4413 | sp-14 | an-266 | 1A5544 | sp-19 | an-266 |
| 1A4414 | sp-15 | an-267 | 1U4414 | sp-14 | an-267 | 1A5545 | sp-19 | an-267 |
| 1A4415 | sp-15 | an-268 | 1U4415 | sp-14 | an-268 | 1A5546 | sp-19 | an-268 |
| 1A4416 | sp-15 | an-269 | 1U4416 | sp-14 | an-269 | 1A5547 | sp-19 | an-269 |
| 1A4417 | sp-15 | an-270 | 1U4417 | sp-14 | an-270 | 1A5548 | sp-19 | an-270 |
| 1A4418 | sp-15 | an-271 | 1U4418 | sp-14 | an-271 | 1A5549 | sp-19 | an-271 |
| 1A4419 | sp-15 | an-272 | 1U4419 | sp-14 | an-272 | 1A5550 | sp-19 | an-272 |
| 1A4420 | sp-15 | an-273 | 1U4420 | sp-14 | an-273 | 1A5551 | sp-19 | an-273 |
| 1A4421 | sp-15 | an-274 | 1U4421 | sp-14 | an-274 | 1A5552 | sp-19 | an-274 |
| 1A4422 | sp-15 | an-275 | 1U4422 | sp-14 | an-275 | 1A5553 | sp-19 | an-275 |

Table 2-80

| Y = NHCS | | | Y = NHCSNH | | | Y = NHCS | | |
|---|---|---|---|---|---|---|---|---|
| 1A4423 | sp-15 | an-276 | 1U4423 | sp-14 | an-276 | 1A5554 | sp-19 | an-276 |
| 1A4424 | sp-15 | an-277 | 1U4424 | sp-14 | an-277 | 1A5555 | sp-19 | an-277 |
| 1A4425 | sp-15 | an-278 | 1U4425 | sp-14 | an-278 | 1A5556 | sp-19 | an-278 |
| 1A4426 | sp-15 | an-279 | 1U4426 | sp-14 | an-279 | 1A5557 | sp-19 | an-279 |
| 1A4427 | sp-15 | an-280 | 1U4427 | sp-14 | an-280 | 1A5558 | sp-19 | an-280 |
| 1A4428 | sp-15 | an-281 | 1U4428 | sp-14 | an-281 | 1A5559 | sp-19 | an-281 |
| 1A4429 | sp-15 | an-282 | 1U4429 | sp-14 | an-282 | 1A5560 | sp-19 | an-282 |
| 1A4430 | sp-15 | an-283 | 1U4430 | sp-14 | an-283 | 1A5561 | sp-19 | an-283 |
| 1A4431 | sp-15 | an-284 | 1U4431 | sp-14 | an-284 | 1A5562 | sp-19 | an-284 |
| 1A4432 | sp-15 | an-285 | 1U4432 | sp-14 | an-285 | 1A5563 | sp-19 | an-285 |
| 1A4433 | sp-15 | an-286 | 1U4433 | sp-14 | an-286 | 1A5564 | sp-19 | an-286 |
| 1A4434 | sp-15 | an-287 | 1U4434 | sp-14 | an-287 | 1A5565 | sp-19 | an-287 |
| 1A4435 | sp-15 | an-288 | 1U4435 | sp-14 | an-288 | 1A5566 | sp-19 | an-288 |
| 1A4436 | sp-15 | an-289 | 1U4436 | sp-14 | an-289 | 1A5567 | sp-19 | an-289 |
| 1A4437 | sp-15 | an-290 | 1U4437 | sp-14 | an-290 | 1A5568 | sp-19 | an-290 |
| 1A4438 | sp-15 | an-291 | 1U4438 | sp-14 | an-291 | 1A5569 | sp-19 | an-291 |
| 1A4439 | sp-15 | an-292 | 1U4439 | sp-14 | an-292 | 1A5570 | sp-19 | an-292 |
| 1A4440 | sp-15 | an-293 | 1U4440 | sp-14 | an-293 | 1A5571 | sp-19 | an-293 |
| 1A4441 | sp-15 | an-294 | 1U4441 | sp-14 | an-294 | 1A5572 | sp-19 | an-294 |
| 1A4442 | sp-15 | an-295 | 1U4442 | sp-14 | an-295 | 1A5573 | sp-19 | an-295 |
| 1A4443 | sp-15 | an-296 | 1U4443 | sp-14 | an-296 | 1A5574 | sp-19 | an-296 |
| 1A4444 | sp-15 | an-297 | 1U4444 | sp-14 | an-297 | 1A5575 | sp-19 | an-297 |
| 1A4445 | sp-15 | an-298 | 1U4445 | sp-14 | an-298 | 1A5576 | sp-19 | an-298 |
| 1A4446 | sp-15 | an-299 | 1U4446 | sp-14 | an-299 | 1A5577 | sp-19 | an-299 |
| 1A4447 | sp-15 | an-300 | 1U4447 | sp-14 | an-300 | 1A5578 | sp-19 | an-300 |
| 1A4448 | sp-15 | an-301 | 1U4448 | sp-14 | an-301 | 1A5579 | sp-19 | an-301 |
| 1A4449 | sp-15 | an-302 | 1U4449 | sp-14 | an-302 | 1A5580 | sp-19 | an-302 |
| 1A4450 | sp-15 | an-303 | 1U4450 | sp-14 | an-303 | 1A5581 | sp-19 | an-303 |
| 1A4451 | sp-15 | an-304 | 1U4451 | sp-14 | an-304 | 1A5582 | sp-19 | an-304 |
| 1A4452 | sp-15 | an-305 | 1U4452 | sp-14 | an-305 | 1A5583 | sp-19 | an-305 |
| 1A4453 | sp-15 | an-306 | 1U4453 | sp-14 | an-306 | 1A5584 | sp-19 | an-306 |
| 1A4454 | sp-15 | an-307 | 1U4454 | sp-14 | an-307 | 1A5585 | sp-19 | an-307 |
| 1A4455 | sp-15 | an-308 | 1U4455 | sp-14 | an-308 | 1A5586 | sp-19 | an-308 |
| 1A4456 | sp-15 | an-309 | 1U4456 | sp-14 | an-309 | 1A5587 | sp-19 | an-309 |
| 1A4457 | sp-15 | an-310 | 1U4457 | sp-14 | an-310 | 1A5588 | sp-19 | an-310 |
| 1A4458 | sp-15 | an-311 | 1U4458 | sp-14 | an-311 | 1A5589 | sp-19 | an-311 |
| 1A4459 | sp-15 | an-312 | 1U4459 | sp-14 | an-312 | 1A5590 | sp-19 | an-312 |
| 1A4460 | sp-15 | an-313 | 1U4460 | sp-14 | an-313 | 1A5591 | sp-19 | an-313 |
| 1A4461 | sp-15 | an-314 | 1U4461 | sp-14 | an-314 | 1A5592 | sp-19 | an-314 |
| 1A4462 | sp-15 | an-315 | 1U4462 | sp-14 | an-315 | 1A5593 | sp-19 | an-315 |
| 1A4463 | sp-15 | an-316 | 1U4463 | sp-14 | an-316 | 1A5594 | sp-19 | an-316 |
| 1A4464 | sp-15 | an-317 | 1U4464 | sp-14 | an-317 | 1A5595 | sp-19 | an-317 |
| 1A4465 | sp-15 | an-318 | 1U4465 | sp-14 | an-318 | 1A5596 | sp-19 | an-318 |
| 1A4466 | sp-15 | an-319 | 1U4466 | sp-14 | an-319 | 1A5597 | sp-19 | an-319 |
| 1A4467 | sp-15 | an-320 | 1U4467 | sp-14 | an-320 | 1A5598 | sp-19 | an-320 |
| 1A4468 | sp-15 | an-321 | 1U4468 | sp-14 | an-321 | 1A5599 | sp-19 | an-321 |
| 1A4469 | sp-15 | an-322 | 1U4469 | sp-14 | an-322 | 1A5600 | sp-19 | an-322 |
| 1A4470 | sp-15 | an-323 | 1U4470 | sp-14 | an-323 | 1A5601 | sp-19 | an-323 |
| 1A4471 | sp-15 | an-324 | 1U4471 | sp-14 | an-324 | 1A5602 | sp-19 | an-324 |
| 1A4472 | sp-15 | an-325 | 1U4472 | sp-14 | an-325 | 1A5603 | sp-19 | an-325 |

-continued

| Ex. No. | Z | N⁺R⁵R⁶R⁷ | Ex. No. | Z | N⁺R⁵R⁶R⁷ | Ex. No. | Z | N⁺R⁵R⁶R⁷ |
|---|---|---|---|---|---|---|---|---|
| 1A4473 | sp-15 | an-326 | 1U4473 | sp-14 | an-326 | 1A5604 | sp-19 | an-326 |
| 1A4474 | sp-15 | an-327 | 1U4474 | sp-14 | an-327 | 1A5605 | sp-19 | an-327 |
| 1A4475 | sp-15 | an-328 | 1U4475 | sp-14 | an-328 | 1A5606 | sp-19 | an-328 |
| 1A4476 | sp-15 | an-329 | 1U4476 | sp-14 | an-329 | 1A5607 | sp-19 | an-329 |
| 1A4477 | sp-15 | an-330 | 1U4477 | sp-14 | an-330 | 1A5608 | sp-19 | an-330 |
| 1A4478 | sp-15 | an-331 | 1U4478 | sp-14 | an-331 | 1A5609 | sp-19 | an-331 |

Table 2-81

| Y = NHCS | | | Y = NHCSNH | | | Y = NHCS | | |
|---|---|---|---|---|---|---|---|---|
| 1A4479 | sp-15 | an-332 | 1U4479 | sp-14 | an-332 | 1A5610 | sp-19 | an-332 |
| 1A4480 | sp-15 | an-333 | 1U4480 | sp-14 | an-333 | 1A5611 | sp-19 | an-333 |
| 1A4481 | sp-15 | an-334 | 1U4481 | sp-14 | an-334 | 1A5612 | sp-19 | an-334 |
| 1A4482 | sp-15 | an-335 | 1U4482 | sp-14 | an-335 | 1A5613 | sp-19 | an-335 |
| 1A4483 | sp-15 | an-336 | 1U4483 | sp-14 | an-336 | 1A5614 | sp-19 | an-336 |
| 1A4484 | sp-15 | an-337 | 1U4484 | sp-14 | an-337 | 1A5615 | sp-19 | an-337 |
| 1A4485 | sp-15 | an-338 | 1U4485 | sp-14 | an-338 | 1A5616 | sp-19 | an-338 |
| 1A4486 | sp-15 | an-339 | 1U4486 | sp-14 | an-339 | 1A5617 | sp-19 | an-339 |
| 1A4487 | sp-15 | an-340 | 1U4487 | sp-14 | an-340 | 1A5618 | sp-19 | an-340 |
| 1A4488 | sp-15 | an-341 | 1U4488 | sp-14 | an-341 | 1A5619 | sp-19 | an-341 |
| 1A4489 | sp-15 | an-342 | 1U4489 | sp-14 | an-342 | 1A5620 | sp-19 | an-342 |
| 1A4490 | sp-15 | an-343 | 1U4490 | sp-14 | an-343 | 1A5621 | sp-19 | an-343 |
| 1A4491 | sp-15 | an-344 | 1U4491 | sp-14 | an-344 | 1A5622 | sp-19 | an-344 |
| 1A4492 | sp-15 | an-345 | 1U4492 | sp-14 | an-345 | 1A5623 | sp-19 | an-345 |
| 1A4493 | sp-15 | an-346 | 1U4493 | sp-14 | an-346 | 1A5624 | sp-19 | an-346 |
| 1A4494 | sp-15 | an-347 | 1U4494 | sp-14 | an-347 | 1A5625 | sp-19 | an-347 |
| 1A4495 | sp-15 | an-348 | 1U4495 | sp-14 | an-348 | 1A5626 | sp-19 | an-348 |
| 1A4496 | sp-15 | an-349 | 1U4496 | sp-14 | an-349 | 1A5627 | sp-19 | an-349 |
| 1A4497 | sp-15 | an-350 | 1U4497 | sp-14 | an-350 | 1A5628 | sp-19 | an-350 |
| 1A4498 | sp-15 | an-351 | 1U4498 | sp-14 | an-351 | 1A5629 | sp-19 | an-351 |
| 1A4499 | sp-15 | an-352 | 1U4499 | sp-14 | an-352 | 1A5630 | sp-19 | an-352 |
| 1A4500 | sp-15 | an-353 | 1U4500 | sp-14 | an-353 | 1A5631 | sp-19 | an-353 |
| 1A4501 | sp-15 | an-354 | 1U4501 | sp-14 | an-354 | 1A5632 | sp-19 | an-354 |
| 1A4502 | sp-15 | an-355 | 1U4502 | sp-14 | an-355 | 1A5633 | sp-19 | an-355 |
| 1A4503 | sp-15 | an-356 | 1U4503 | sp-14 | an-356 | 1A5634 | sp-19 | an-356 |
| 1A4504 | sp-15 | an-357 | 1U4504 | sp-14 | an-357 | 1A5635 | sp-19 | an-357 |
| 1A4505 | sp-15 | an-358 | 1U4505 | sp-14 | an-358 | 1A5636 | sp-19 | an-358 |
| 1A4506 | sp-15 | an-359 | 1U4506 | sp-14 | an-359 | 1A5637 | sp-19 | an-359 |
| 1A4507 | sp-15 | an-360 | 1U4507 | sp-14 | an-360 | 1A5638 | sp-19 | an-360 |
| 1A4508 | sp-15 | an-361 | 1U4508 | sp-14 | an-361 | 1A5639 | sp-19 | an-361 |
| 1A4509 | sp-15 | an-362 | 1U4509 | sp-14 | an-362 | 1A5640 | sp-19 | an-362 |
| 1A4510 | sp-15 | an-363 | 1U4510 | sp-14 | an-363 | 1A5641 | sp-19 | an-363 |
| 1A4511 | sp-15 | an-364 | 1U4511 | sp-14 | an-364 | 1A5642 | sp-19 | an-364 |
| 1A4512 | sp-15 | an-365 | 1U4512 | sp-14 | an-365 | 1A5643 | sp-19 | an-365 |
| 1A4513 | sp-15 | an-366 | 1U4513 | sp-14 | an-366 | 1A5644 | sp-19 | an-366 |
| 1A4514 | sp-15 | an-367 | 1U4514 | sp-14 | an-367 | 1A5645 | sp-19 | an-367 |
| 1A4515 | sp-15 | an-368 | 1U4515 | sp-14 | an-368 | 1A5646 | sp-19 | an-368 |
| 1A4516 | sp-15 | an-369 | 1U4516 | sp-14 | an-369 | 1A5647 | sp-19 | an-369 |
| 1A4517 | sp-15 | an-370 | 1U4517 | sp-14 | an-370 | 1A5648 | sp-19 | an-370 |
| 1A4518 | sp-15 | an-371 | 1U4518 | sp-14 | an-371 | 1A5649 | sp-19 | an-371 |
| 1A4519 | sp-15 | an-372 | 1U4519 | sp-14 | an-372 | 1A5650 | sp-19 | an-372 |
| 1A4520 | sp-15 | an-373 | 1U4520 | sp-14 | an-373 | 1A5651 | sp-19 | an-373 |
| 1A4521 | sp-15 | an-374 | 1U4521 | sp-14 | an-374 | 1A5652 | sp-19 | an-374 |
| 1A4522 | sp-15 | an-375 | 1U4522 | sp-14 | an-375 | 1A5653 | sp-19 | an-375 |
| 1A4523 | sp-15 | an-376 | 1U4523 | sp-14 | an-376 | 1A5654 | sp-19 | an-376 |
| 1A4524 | sp-15 | an-377 | 1U4524 | sp-14 | an-377 | 1A5655 | sp-19 | an-377 |
| 1A4525 | sp-16 | an-1 | 1U4525 | sp-17 | an-1 | 1A5656 | sp-21 | an-1 |
| 1A4526 | sp-16 | an-2 | 1U4526 | sp-17 | an-2 | 1A5657 | sp-21 | an-2 |
| 1A4527 | sp-16 | an-3 | 1U4527 | sp-17 | an-3 | 1A5658 | sp-21 | an-3 |
| 1A4528 | sp-16 | an-4 | 1U4528 | sp-17 | an-4 | 1A5659 | sp-21 | an-4 |
| 1A4529 | sp-16 | an-5 | 1U4529 | sp-17 | an-5 | 1A5660 | sp-21 | an-5 |
| 1A4530 | sp-16 | an-6 | 1U4530 | sp-17 | an-6 | 1A5661 | sp-21 | an-6 |
| 1A4531 | sp-16 | an-7 | 1U4531 | sp-17 | an-7 | 1A5662 | sp-21 | an-7 |
| 1A4532 | sp-16 | an-8 | 1U4532 | sp-17 | an-8 | 1A5663 | sp-21 | an-8 |
| 1A4533 | sp-16 | an-9 | 1U4533 | sp-17 | an-9 | 1A5664 | sp-21 | an-9 |
| 1A4534 | sp-16 | an-10 | 1U4534 | sp-17 | an-10 | 1A5665 | sp-21 | an-10 |

Table 2-82

| Y = NHCS | | | Y = NHCSNH | | | Y = NHCS | | |
|---|---|---|---|---|---|---|---|---|
| 1A4535 | sp-16 | an-11 | 1U4535 | sp-17 | an-11 | 1A5666 | sp-21 | an-11 |
| 1A4536 | sp-16 | an-12 | 1U4536 | sp-17 | an-12 | 1A5667 | sp-21 | an-12 |
| 1A4537 | sp-16 | an-13 | 1U4537 | sp-17 | an-13 | 1A5668 | sp-21 | an-13 |
| 1A4538 | sp-16 | an-14 | 1U4538 | sp-17 | an-14 | 1A5669 | sp-21 | an-14 |
| 1A4539 | sp-16 | an-15 | 1U4539 | sp-17 | an-15 | 1A5670 | sp-21 | an-15 |
| 1A4540 | sp-16 | an-16 | 1U4540 | sp-17 | an-16 | 1A5671 | sp-21 | an-16 |
| 1A4541 | sp-16 | an-17 | 1U4541 | sp-17 | an-17 | 1A5672 | sp-21 | an-17 |
| 1A4542 | sp-16 | an-18 | 1U4542 | sp-17 | an-18 | 1A5673 | sp-21 | an-18 |

-continued

| Ex. No. | Z | N⁺R⁵R⁶R⁷ | Ex. No. | Z | N⁺R⁵R⁶R⁷ | Ex. No. | Z | N⁺R⁵R⁶R⁷ |
|---|---|---|---|---|---|---|---|---|
| 1A4543 | sp-16 | an-19 | 1U4543 | sp-17 | an-19 | 1A5674 | sp-21 | an-19 |
| 1A4544 | sp-16 | an-20 | 1U4544 | sp-17 | an-20 | 1A5675 | sp-21 | an-20 |
| 1A4545 | sp-16 | an-21 | 1U4545 | sp-17 | an-21 | 1A5676 | sp-21 | an-21 |
| 1A4546 | sp-16 | an-22 | 1U4546 | sp-17 | an-22 | 1A5677 | sp-21 | an-22 |
| 1A4547 | sp-16 | an-23 | 1U4547 | sp-17 | an-23 | 1A5678 | sp-21 | an-23 |
| 1A4548 | sp-16 | an-24 | 1U4548 | sp-17 | an-24 | 1A5679 | sp-21 | an-24 |
| 1A4549 | sp-16 | an-25 | 1U4549 | sp-17 | an-25 | 1A5680 | sp-21 | an-25 |
| 1A4550 | sp-16 | an-26 | 1U4550 | sp-17 | an-26 | 1A5681 | sp-21 | an-26 |
| 1A4551 | sp-16 | an-27 | 1U4551 | sp-17 | an-27 | 1A5682 | sp-21 | an-27 |
| 1A4552 | sp-16 | an-28 | 1U4552 | sp-17 | an-28 | 1A5683 | sp-21 | an-28 |
| 1A4553 | sp-16 | an-29 | 1U4553 | sp-17 | an-29 | 1A5684 | sp-21 | an-29 |
| 1A4554 | sp-16 | an-30 | 1U4554 | sp-17 | an-30 | 1A5685 | sp-21 | an-30 |
| 1A4555 | sp-16 | an-31 | 1U4555 | sp-17 | an-31 | 1A5686 | sp-21 | an-31 |
| 1A4556 | sp-16 | an-32 | 1U4556 | sp-17 | an-32 | 1A5687 | sp-21 | an-32 |
| 1A4557 | sp-16 | an-33 | 1U4557 | sp-17 | an-33 | 1A5688 | sp-21 | an-33 |
| 1A4558 | sp-16 | an-34 | 1U4558 | sp-17 | an-34 | 1A5689 | sp-21 | an-34 |
| 1A4559 | sp-16 | an-35 | 1U4559 | sp-17 | an-35 | 1A5690 | sp-21 | an-35 |
| 1A4560 | sp-16 | an-36 | 1U4560 | sp-17 | an-36 | 1A5691 | sp-21 | an-36 |
| 1A4561 | sp-16 | an-37 | 1U4561 | sp-17 | an-37 | 1A5692 | sp-21 | an-37 |
| 1A4562 | sp-16 | an-38 | 1U4562 | sp-17 | an-38 | 1A5693 | sp-21 | an-38 |
| 1A4563 | sp-16 | an-39 | 1U4563 | sp-17 | an-39 | 1A5694 | sp-21 | an-39 |
| 1A4564 | sp-16 | an-40 | 1U4564 | sp-17 | an-40 | 1A5695 | sp-21 | an-40 |
| 1A4565 | sp-16 | an-41 | 1U4565 | sp-17 | an-41 | 1A5696 | sp-21 | an-41 |
| 1A4566 | sp-16 | an-42 | 1U4566 | sp-17 | an-42 | 1A5697 | sp-21 | an-42 |
| 1A4567 | sp-16 | an-43 | 1U4567 | sp-17 | an-43 | 1A5698 | sp-21 | an-43 |
| 1A4568 | sp-16 | an-44 | 1U4568 | sp-17 | an-44 | 1A5699 | sp-21 | an-44 |
| 1A4569 | sp-16 | an-45 | 1U4569 | sp-17 | an-45 | 1A5700 | sp-21 | an-45 |
| 1A4570 | sp-16 | an-46 | 1U4570 | sp-17 | an-46 | 1A5701 | sp-21 | an-46 |
| 1A4571 | sp-16 | an-47 | 1U4571 | sp-17 | an-47 | 1A5702 | sp-21 | an-47 |
| 1A4572 | sp-16 | an-48 | 1U4572 | sp-17 | an-48 | 1A5703 | sp-21 | an-48 |
| 1A4573 | sp-16 | an-49 | 1U4573 | sp-17 | an-49 | 1A5704 | sp-21 | an-49 |
| 1A4574 | sp-16 | an-50 | 1U4574 | sp-17 | an-50 | 1A5705 | sp-21 | an-50 |
| 1A4575 | sp-16 | an-51 | 1U4575 | sp-17 | an-51 | 1A5706 | sp-21 | an-51 |
| 1A4576 | sp-16 | an-52 | 1U4576 | sp-17 | an-52 | 1A5707 | sp-21 | an-52 |
| 1A4577 | sp-16 | an-53 | 1U4577 | sp-17 | an-53 | 1A5708 | sp-21 | an-53 |
| 1A4578 | sp-16 | an-54 | 1U4578 | sp-17 | an-54 | 1A5709 | sp-21 | an-54 |
| 1A4579 | sp-16 | an-55 | 1U4579 | sp-17 | an-55 | 1A5710 | sp-21 | an-55 |
| 1A4580 | sp-16 | an-56 | 1U4580 | sp-17 | an-56 | 1A5711 | sp-21 | an-56 |
| 1A4581 | sp-16 | an-57 | 1U4581 | sp-17 | an-57 | 1A5712 | sp-21 | an-57 |
| 1A4582 | sp-16 | an-58 | 1U4582 | sp-17 | an-58 | 1A5713 | sp-21 | an-58 |
| 1A4583 | sp-16 | an-59 | 1U4583 | sp-17 | an-59 | 1A5714 | sp-21 | an-59 |
| 1A4584 | sp-16 | an-60 | 1U4584 | sp-17 | an-60 | 1A5715 | sp-21 | an-60 |
| 1A4585 | sp-16 | an-61 | 1U4585 | sp-17 | an-61 | 1A5716 | sp-21 | an-61 |
| 1A4586 | sp-16 | an-62 | 1U4586 | sp-17 | an-62 | 1A5717 | sp-21 | an-62 |
| 1A4587 | sp-16 | an-63 | 1U4587 | sp-17 | an-63 | 1A5718 | sp-21 | an-63 |
| 1A4588 | sp-16 | an-64 | 1U4588 | sp-17 | an-64 | 1A5719 | sp-21 | an-64 |
| 1A4589 | sp-16 | an-65 | 1U4589 | sp-17 | an-65 | 1A5720 | sp-21 | an-65 |
| 1A4590 | sp-16 | an-66 | 1U4590 | sp-17 | an-66 | 1A5721 | sp-21 | an-66 |

Table 2-83

| Y = NHCS | | | Y = NHCSNH | | | Y = NHCS | | |
|---|---|---|---|---|---|---|---|---|
| 1A4591 | sp-16 | an-67 | 1U4591 | sp-17 | an-67 | 1A5722 | sp-21 | an-67 |
| 1A4592 | sp-16 | an-68 | 1U4592 | sp-17 | an-68 | 1A5723 | sp-21 | an-68 |
| 1A4593 | sp-16 | an-69 | 1U4593 | sp-17 | an-69 | 1A5724 | sp-21 | an-69 |
| 1A4594 | sp-16 | an-70 | 1U4594 | sp-17 | an-70 | 1A5725 | sp-21 | an-70 |
| 1A4595 | sp-16 | an-71 | 1U4595 | sp-17 | an-71 | 1A5726 | sp-21 | an-71 |
| 1A4596 | sp-16 | an-72 | 1U4596 | sp-17 | an-72 | 1A5727 | sp-21 | an-72 |
| 1A4597 | sp-16 | an-73 | 1U4597 | sp-17 | an-73 | 1A5728 | sp-21 | an-73 |
| 1A4598 | sp-16 | an-74 | 1U4598 | sp-17 | an-74 | 1A5729 | sp-21 | an-74 |
| 1A4599 | sp-16 | an-75 | 1U4599 | sp-17 | an-75 | 1A5730 | sp-21 | an-75 |
| 1A4600 | sp-16 | an-76 | 1U4600 | sp-17 | an-76 | 1A5731 | sp-21 | an-76 |
| 1A4601 | sp-16 | an-77 | 1U4601 | sp-17 | an-77 | 1A5732 | sp-21 | an-77 |
| 1A4602 | sp-16 | an-78 | 1U4602 | sp-17 | an-78 | 1A5733 | sp-21 | an-78 |
| 1A4603 | sp-16 | an-79 | 1U4603 | sp-17 | an-79 | 1A5734 | sp-21 | an-79 |
| 1A4604 | sp-16 | an-80 | 1U4604 | sp-17 | an-80 | 1A5735 | sp-21 | an-80 |
| 1A4605 | sp-16 | an-81 | 1U4605 | sp-17 | an-81 | 1A5736 | sp-21 | an-81 |
| 1A4606 | sp-16 | an-82 | 1U4606 | sp-17 | an-82 | 1A5737 | sp-21 | an-82 |
| 1A4607 | sp-16 | an-83 | 1U4607 | sp-17 | an-83 | 1A5738 | sp-21 | an-83 |
| 1A4608 | sp-16 | an-84 | 1U4608 | sp-17 | an-84 | 1A5739 | sp-21 | an-84 |
| 1A4609 | sp-16 | an-85 | 1U4609 | sp-17 | an-85 | 1A5740 | sp-21 | an-85 |
| 1A4610 | sp-16 | an-86 | 1U4610 | sp-17 | an-86 | 1A5741 | sp-21 | an-86 |
| 1A4611 | sp-16 | an-87 | 1U4611 | sp-17 | an-87 | 1A5742 | sp-21 | an-87 |
| 1A4612 | sp-16 | an-88 | 1U4612 | sp-17 | an-88 | 1A5743 | sp-21 | an-88 |
| 1A4613 | sp-16 | an-89 | 1U4613 | sp-17 | an-89 | 1A5744 | sp-21 | an-89 |
| 1A4614 | sp-16 | an-90 | 1U4614 | sp-17 | an-90 | 1A5745 | sp-21 | an-90 |
| 1A4615 | sp-16 | an-91 | 1U4615 | sp-17 | an-91 | 1A5746 | sp-21 | an-91 |
| 1A4616 | sp-16 | an-92 | 1U4616 | sp-17 | an-92 | 1A5747 | sp-21 | an-92 |

| Ex. No. | Z | N⁺R⁵R⁶R⁷ | Ex. No. | Z | N⁺R⁵R⁶R⁷ | Ex. No. | Z | N⁺R⁵R⁶R⁷ |
|---|---|---|---|---|---|---|---|---|
| 1A4617 | sp-16 | an-93 | 1U4617 | sp-17 | an-93 | 1A5748 | sp-21 | an-93 |
| 1A4618 | sp-16 | an-94 | 1U4618 | sp-17 | an-94 | 1A5749 | sp-21 | an-94 |
| 1A4619 | sp-16 | an-95 | 1U4619 | sp-17 | an-95 | 1A5750 | sp-21 | an-95 |
| 1A4620 | sp-16 | an-96 | 1U4620 | sp-17 | an-96 | 1A5751 | sp-21 | an-96 |
| 1A4621 | sp-16 | an-97 | 1U4621 | sp-17 | an-97 | 1A5752 | sp-21 | an-97 |
| 1A4622 | sp-16 | an-98 | 1U4622 | sp-17 | an-98 | 1A5753 | sp-21 | an-98 |
| 1A4623 | sp-16 | an-99 | 1U4623 | sp-17 | an-99 | 1A5754 | sp-21 | an-99 |
| 1A4624 | sp-16 | an-100 | 1U4624 | sp-17 | an-100 | 1A5755 | sp-21 | an-100 |
| 1A4625 | sp-16 | an-101 | 1U4625 | sp-17 | an-101 | 1A5756 | sp-21 | an-101 |
| 1A4626 | sp-16 | an-102 | 1U4626 | sp-17 | an-102 | 1A5757 | sp-21 | an-102 |
| 1A4627 | sp-16 | an-103 | 1U4627 | sp-17 | an-103 | 1A5758 | sp-21 | an-103 |
| 1A4628 | sp-16 | an-104 | 1U4628 | sp-17 | an-104 | 1A5759 | sp-21 | an-104 |
| 1A4629 | sp-16 | an-105 | 1U4629 | sp-17 | an-105 | 1A5760 | sp-21 | an-105 |
| 1A4630 | sp-16 | an-106 | 1U4630 | sp-17 | an-106 | 1A5761 | sp-21 | an-106 |
| 1A4631 | sp-16 | an-107 | 1U4631 | sp-17 | an-107 | 1A5762 | sp-21 | an-107 |
| 1A4632 | sp-16 | an-108 | 1U4632 | sp-17 | an-108 | 1A5763 | sp-21 | an-108 |
| 1A4633 | sp-16 | an-109 | 1U4633 | sp-17 | an-109 | 1A5764 | sp-21 | an-109 |
| 1A4634 | sp-16 | an-110 | 1U4634 | sp-17 | an-110 | 1A5765 | sp-21 | an-110 |
| 1A4635 | sp-16 | an-111 | 1U4635 | sp-17 | an-111 | 1A5766 | sp-21 | an-111 |
| 1A4636 | sp-16 | an-112 | 1U4636 | sp-17 | an-112 | 1A5767 | sp-21 | an-112 |
| 1A4637 | sp-16 | an-113 | 1U4637 | sp-17 | an-113 | 1A5768 | sp-21 | an-113 |
| 1A4638 | sp-16 | an-114 | 1U4638 | sp-17 | an-114 | 1A5769 | sp-21 | an-114 |
| 1A4639 | sp-16 | an-115 | 1U4639 | sp-17 | an-115 | 1A5770 | sp-21 | an-115 |
| 1A4640 | sp-16 | an-116 | 1U4640 | sp-17 | an-116 | 1A5771 | sp-21 | an-116 |
| 1A4641 | sp-16 | an-117 | 1U4641 | sp-17 | an-117 | 1A5772 | sp-21 | an-117 |
| 1A4642 | sp-16 | an-118 | 1U4642 | sp-17 | an-118 | 1A5773 | sp-21 | an-118 |
| 1A4643 | sp-16 | an-119 | 1U4643 | sp-17 | an-119 | 1A5774 | sp-21 | an-119 |
| 1A4644 | sp-16 | an-120 | 1U4644 | sp-17 | an-120 | 1A5775 | sp-21 | an-120 |
| 1A4645 | sp-16 | an-121 | 1U4645 | sp-17 | an-121 | 1A5776 | sp-21 | an-121 |
| 1A4646 | sp-16 | an-122 | 1U4646 | sp-17 | an-122 | 1A5777 | sp-21 | an-122 |

Table 2-84

| Y = NHCS | | | Y = NHCSNH | | | Y = NHCS | | |
|---|---|---|---|---|---|---|---|---|
| 1A4647 | sp-16 | an-123 | 1U4647 | sp-17 | an-123 | 1A5778 | sp-21 | an-123 |
| 1A4648 | sp-16 | an-124 | 1U4648 | sp-17 | an-124 | 1A5779 | sp-21 | an-124 |
| 1A4649 | sp-16 | an-125 | 1U4649 | sp-17 | an-125 | 1A5780 | sp-21 | an-125 |
| 1A4650 | sp-16 | an-126 | 1U4650 | sp-17 | an-126 | 1A5781 | sp-21 | an-126 |
| 1A4651 | sp-16 | an-127 | 1U4651 | sp-17 | an-127 | 1A5782 | sp-21 | an-127 |
| 1A4652 | sp-16 | an-128 | 1U4652 | sp-17 | an-128 | 1A5783 | sp-21 | an-128 |
| 1A4653 | sp-16 | an-129 | 1U4653 | sp-17 | an-129 | 1A5784 | sp-21 | an-129 |
| 1A4654 | sp-16 | an-130 | 1U4654 | sp-17 | an-130 | 1A5785 | sp-21 | an-130 |
| 1A4655 | sp-16 | an-131 | 1U4655 | sp-17 | an-131 | 1A5786 | sp-21 | an-131 |
| 1A4656 | sp-16 | an-132 | 1U4656 | sp-17 | an-132 | 1A5787 | sp-21 | an-132 |
| 1A4657 | sp-16 | an-133 | 1U4657 | sp-17 | an-133 | 1A5788 | sp-21 | an-133 |
| 1A4658 | sp-16 | an-134 | 1U4658 | sp-17 | an-134 | 1A5789 | sp-21 | an-134 |
| 1A4659 | sp-16 | an-135 | 1U4659 | sp-17 | an-135 | 1A5790 | sp-21 | an-135 |
| 1A4660 | sp-16 | an-136 | 1U4660 | sp-17 | an-136 | 1A5791 | sp-21 | an-136 |
| 1A4661 | sp-16 | an-137 | 1U4661 | sp-17 | an-137 | 1A5792 | sp-21 | an-137 |
| 1A4662 | sp-16 | an-138 | 1U4662 | sp-17 | an-138 | 1A5793 | sp-21 | an-138 |
| 1A4663 | sp-16 | an-139 | 1U4663 | sp-17 | an-139 | 1A5794 | sp-21 | an-139 |
| 1A4664 | sp-16 | an-140 | 1U4664 | sp-17 | an-140 | 1A5795 | sp-21 | an-140 |
| 1A4665 | sp-16 | an-141 | 1U4665 | sp-17 | an-141 | 1A5796 | sp-21 | an-141 |
| 1A4666 | sp-16 | an-142 | 1U4666 | sp-17 | an-142 | 1A5797 | sp-21 | an-142 |
| 1A4667 | sp-16 | an-143 | 1U4667 | sp-17 | an-143 | 1A5798 | sp-21 | an-143 |
| 1A4668 | sp-16 | an-144 | 1U4668 | sp-17 | an-144 | 1A5799 | sp-21 | an-144 |
| 1A4669 | sp-16 | an-145 | 1U4669 | sp-17 | an-145 | 1A5800 | sp-21 | an-145 |
| 1A4670 | sp-16 | an-146 | 1U4670 | sp-17 | an-146 | 1A5801 | sp-21 | an-146 |
| 1A4671 | sp-16 | an-147 | 1U4671 | sp-17 | an-147 | 1A5802 | sp-21 | an-147 |
| 1A4672 | sp-16 | an-148 | 1U4672 | sp-17 | an-148 | 1A5803 | sp-21 | an-148 |
| 1A4673 | sp-16 | an-149 | 1U4673 | sp-17 | an-149 | 1A5804 | sp-21 | an-149 |
| 1A4674 | sp-16 | an-150 | 1U4674 | sp-17 | an-150 | 1A5805 | sp-21 | an-150 |
| 1A4675 | sp-16 | an-151 | 1U4675 | sp-17 | an-151 | 1A5806 | sp-21 | an-151 |
| 1A4676 | sp-16 | an-152 | 1U4676 | sp-17 | an-152 | 1A5807 | sp-21 | an-152 |
| 1A4677 | sp-16 | an-153 | 1U4677 | sp-17 | an-153 | 1A5808 | sp-21 | an-153 |
| 1A4678 | sp-16 | an-154 | 1U4678 | sp-17 | an-154 | 1A5809 | sp-21 | an-154 |
| 1A4679 | sp-16 | an-155 | 1U4679 | sp-17 | an-155 | 1A5810 | sp-21 | an-155 |
| 1A4680 | sp-16 | an-156 | 1U4680 | sp-17 | an-156 | 1A5811 | sp-21 | an-156 |
| 1A4681 | sp-16 | an-157 | 1U4681 | sp-17 | an-157 | 1A5812 | sp-21 | an-157 |
| 1A4682 | sp-16 | an-158 | 1U4682 | sp-17 | an-158 | 1A5813 | sp-21 | an-158 |
| 1A4683 | sp-16 | an-159 | 1U4683 | sp-17 | an-159 | 1A5814 | sp-21 | an-159 |
| 1A4684 | sp-16 | an-160 | 1U4684 | sp-17 | an-160 | 1A5815 | sp-21 | an-160 |
| 1A4685 | sp-16 | an-161 | 1U4685 | sp-17 | an-161 | 1A5816 | sp-21 | an-161 |
| 1A4686 | sp-16 | an-162 | 1U4686 | sp-17 | an-162 | 1A5817 | sp-21 | an-162 |
| 1A4687 | sp-16 | an-163 | 1U4687 | sp-17 | an-163 | 1A5818 | sp-21 | an-163 |
| 1A4688 | sp-16 | an-164 | 1U4688 | sp-17 | an-164 | 1A5819 | sp-21 | an-164 |
| 1A4689 | sp-16 | an-165 | 1U4689 | sp-17 | an-165 | 1A5820 | sp-21 | an-165 |
| 1A4690 | sp-16 | an-166 | 1U4690 | sp-17 | an-166 | 1A5821 | sp-21 | an-166 |

| Ex. No. | Z | N⁺R⁵R⁶R⁷ | Ex. No. | Z | N⁺R⁵R⁶R⁷ | Ex. No. | Z | N⁺R⁵R⁶R⁷ |
|---|---|---|---|---|---|---|---|---|
| 1A4691 | sp-16 | an-167 | 1U4691 | sp-17 | an-167 | 1A5822 | sp-21 | an-167 |
| 1A4692 | sp-16 | an-168 | 1U4692 | sp-17 | an-168 | 1A5823 | sp-21 | an-168 |
| 1A4693 | sp-16 | an-169 | 1U4693 | sp-17 | an-169 | 1A5824 | sp-21 | an-169 |
| 1A4694 | sp-16 | an-170 | 1U4694 | sp-17 | an-170 | 1A5825 | sp-21 | an-170 |
| 1A4695 | sp-16 | an-171 | 1U4695 | sp-17 | an-171 | 1A5826 | sp-21 | an-171 |
| 1A4696 | sp-16 | an-172 | 1U4696 | sp-17 | an-172 | 1A5827 | sp-21 | an-172 |
| 1A4697 | sp-16 | an-173 | 1U4697 | sp-17 | an-173 | 1A5828 | sp-21 | an-173 |
| 1A4698 | sp-16 | an-174 | 1U4698 | sp-17 | an-174 | 1A5829 | sp-21 | an-174 |
| 1A4699 | sp-16 | an-175 | 1U4699 | sp-17 | an-175 | 1A5830 | sp-21 | an-175 |
| 1A4700 | sp-16 | an-176 | 1U4700 | sp-17 | an-176 | 1A5831 | sp-21 | an-176 |
| 1A4701 | sp-16 | an-177 | 1U4701 | sp-17 | an-177 | 1A5832 | sp-21 | an-177 |
| 1A4702 | sp-16 | an-178 | 1U4702 | sp-17 | an-178 | 1A5833 | sp-21 | an-178 |

Table 2-85

| Y = NHCS | | | Y = NHCSNH | | | Y = NHCS | | |
|---|---|---|---|---|---|---|---|---|
| 1A4703 | sp-16 | an-179 | 1U4703 | sp-17 | an-179 | 1A5834 | sp-21 | an-179 |
| 1A4704 | sp-16 | an-180 | 1U4704 | sp-17 | an-180 | 1A5835 | sp-21 | an-180 |
| 1A4705 | sp-16 | an-181 | 1U4705 | sp-17 | an-181 | 1A5836 | sp-21 | an-181 |
| 1A4706 | sp-16 | an-182 | 1U4706 | sp-17 | an-182 | 1A5837 | sp-21 | an-182 |
| 1A4707 | sp-16 | an-183 | 1U4707 | sp-17 | an-183 | 1A5838 | sp-21 | an-183 |
| 1A4708 | sp-16 | an-184 | 1U4708 | sp-17 | an-184 | 1A5839 | sp-21 | an-184 |
| 1A4709 | sp-16 | an-185 | 1U4709 | sp-17 | an-185 | 1A5840 | sp-21 | an-185 |
| 1A4710 | sp-16 | an-186 | 1U4710 | sp-17 | an-186 | 1A5841 | sp-21 | an-186 |
| 1A4711 | sp-16 | an-187 | 1U4711 | sp-17 | an-187 | 1A5842 | sp-21 | an-187 |
| 1A4712 | sp-16 | an-188 | 1U4712 | sp-17 | an-188 | 1A5843 | sp-21 | an-188 |
| 1A4713 | sp-16 | an-189 | 1U4713 | sp-17 | an-189 | 1A5844 | sp-21 | an-189 |
| 1A4714 | sp-16 | an-190 | 1U4714 | sp-17 | an-190 | 1A5845 | sp-21 | an-190 |
| 1A4715 | sp-16 | an-191 | 1U4715 | sp-17 | an-191 | 1A5846 | sp-21 | an-191 |
| 1A4716 | sp-16 | an-192 | 1U4716 | sp-17 | an-192 | 1A5847 | sp-21 | an-192 |
| 1A4717 | sp-16 | an-193 | 1U4717 | sp-17 | an-193 | 1A5848 | sp-21 | an-193 |
| 1A4718 | sp-16 | an-194 | 1U4718 | sp-17 | an-194 | 1A5849 | sp-21 | an-194 |
| 1A4719 | sp-16 | an-195 | 1U4719 | sp-17 | an-195 | 1A5850 | sp-21 | an-195 |
| 1A4720 | sp-16 | an-196 | 1U4720 | sp-17 | an-196 | 1A5851 | sp-21 | an-196 |
| 1A4721 | sp-16 | an-197 | 1U4721 | sp-17 | an-197 | 1A5852 | sp-21 | an-197 |
| 1A4722 | sp-16 | an-198 | 1U4722 | sp-17 | an-198 | 1A5853 | sp-21 | an-198 |
| 1A4723 | sp-16 | an-199 | 1U4723 | sp-17 | an-199 | 1A5854 | sp-21 | an-199 |
| 1A4724 | sp-16 | an-200 | 1U4724 | sp-17 | an-200 | 1A5855 | sp-21 | an-200 |
| 1A4725 | sp-16 | an-201 | 1U4725 | sp-17 | an-201 | 1A5856 | sp-21 | an-201 |
| 1A4726 | sp-16 | an-202 | 1U4726 | sp-17 | an-202 | 1A5857 | sp-21 | an-202 |
| 1A4727 | sp-16 | an-203 | 1U4727 | sp-17 | an-203 | 1A5858 | sp-21 | an-203 |
| 1A4728 | sp-16 | an-204 | 1U4728 | sp-17 | an-204 | 1A5859 | sp-21 | an-204 |
| 1A4729 | sp-16 | an-205 | 1U4729 | sp-17 | an-205 | 1A5860 | sp-21 | an-205 |
| 1A4730 | sp-16 | an-206 | 1U4730 | sp-17 | an-206 | 1A5861 | sp-21 | an-206 |
| 1A4731 | sp-16 | an-207 | 1U4731 | sp-17 | an-207 | 1A5862 | sp-21 | an-207 |
| 1A4732 | sp-16 | an-208 | 1U4732 | sp-17 | an-208 | 1A5863 | sp-21 | an-208 |
| 1A4733 | sp-16 | an-209 | 1U4733 | sp-17 | an-209 | 1A5864 | sp-21 | an-209 |
| 1A4734 | sp-16 | an-210 | 1U4734 | sp-17 | an-210 | 1A5865 | sp-21 | an-210 |
| 1A4735 | sp-16 | an-211 | 1U4735 | sp-17 | an-211 | 1A5866 | sp-21 | an-211 |
| 1A4736 | sp-16 | an-212 | 1U4736 | sp-17 | an-212 | 1A5867 | sp-21 | an-212 |
| 1A4737 | sp-16 | an-213 | 1U4737 | sp-17 | an-213 | 1A5868 | sp-21 | an-213 |
| 1A4738 | sp-16 | an-214 | 1U4738 | sp-17 | an-214 | 1A5869 | sp-21 | an-214 |
| 1A4739 | sp-16 | an-215 | 1U4739 | sp-17 | an-215 | 1A5870 | sp-21 | an-215 |
| 1A4740 | sp-16 | an-216 | 1U4740 | sp-17 | an-216 | 1A5871 | sp-21 | an-216 |
| 1A4741 | sp-16 | an-217 | 1U4741 | sp-17 | an-217 | 1A5872 | sp-21 | an-217 |
| 1A4742 | sp-16 | an-218 | 1U4742 | sp-17 | an-218 | 1A5873 | sp-21 | an-218 |
| 1A4743 | sp-16 | an-219 | 1U4743 | sp-17 | an-219 | 1A5874 | sp-21 | an-219 |
| 1A4744 | sp-16 | an-220 | 1U4744 | sp-17 | an-220 | 1A5875 | sp-21 | an-220 |
| 1A4745 | sp-16 | an-221 | 1U4745 | sp-17 | an-221 | 1A5876 | sp-21 | an-221 |
| 1A4746 | sp-16 | an-222 | 1U4746 | sp-17 | an-222 | 1A5877 | sp-21 | an-222 |
| 1A4747 | sp-16 | an-223 | 1U4747 | sp-17 | an-223 | 1A5878 | sp-21 | an-223 |
| 1A4748 | sp-16 | an-224 | 1U4748 | sp-17 | an-224 | 1A5879 | sp-21 | an-224 |
| 1A4749 | sp-16 | an-225 | 1U4749 | sp-17 | an-225 | 1A5880 | sp-21 | an-225 |
| 1A4750 | sp-16 | an-226 | 1U4750 | sp-17 | an-226 | 1A5881 | sp-21 | an-226 |
| 1A4751 | sp-16 | an-227 | 1U4751 | sp-17 | an-227 | 1A5882 | sp-21 | an-227 |
| 1A4752 | sp-16 | an-228 | 1U4752 | sp-17 | an-228 | 1A5883 | sp-21 | an-228 |
| 1A4753 | sp-16 | an-229 | 1U4753 | sp-17 | an-229 | 1A5884 | sp-21 | an-229 |
| 1A4754 | sp-16 | an-230 | 1U4754 | sp-17 | an-230 | 1A5885 | sp-21 | an-230 |
| 1A4755 | sp-16 | an-231 | 1U4755 | sp-17 | an-231 | 1A5886 | sp-21 | an-231 |
| 1A4756 | sp-16 | an-232 | 1U4756 | sp-17 | an-232 | 1A5887 | sp-21 | an-232 |
| 1A4757 | sp-16 | an-233 | 1U4757 | sp-17 | an-233 | 1A5888 | sp-21 | an-233 |
| 1A4758 | sp-16 | an-234 | 1U4758 | sp-17 | an-234 | 1A5889 | sp-21 | an-234 |

Table 2-86

| Y = NHCS | | | Y = NHCSNH | | | Y = NHCS | | |
|---|---|---|---|---|---|---|---|---|
| 1A4759 | sp-16 | an-235 | 1U4759 | sp-17 | an-235 | 1A5890 | sp-21 | an-235 |
| 1A4760 | sp-16 | an-236 | 1U4760 | sp-17 | an-236 | 1A5891 | sp-21 | an-236 |

-continued

| Ex. No. | Z | $N^+R^5R^6R^7$ | Ex. No. | Z | $N^+R^5R^6R^7$ | Ex. No. | Z | $N^+R^5R^6R^7$ |
|---|---|---|---|---|---|---|---|---|
| 1A4761 | sp-16 | an-237 | 1U4761 | sp-17 | an-237 | 1A5892 | sp-21 | an-237 |
| 1A4762 | sp-16 | an-238 | 1U4762 | sp-17 | an-238 | 1A5893 | sp-21 | an-238 |
| 1A4763 | sp-16 | an-239 | 1U4763 | sp-17 | an-239 | 1A5894 | sp-21 | an-239 |
| 1A4764 | sp-16 | an-240 | 1U4764 | sp-17 | an-240 | 1A5895 | sp-21 | an-240 |
| 1A4765 | sp-16 | an-241 | 1U4765 | sp-17 | an-241 | 1A5896 | sp-21 | an-241 |
| 1A4766 | sp-16 | an-242 | 1U4766 | sp-17 | an-242 | 1A5897 | sp-21 | an-242 |
| 1A4767 | sp-16 | an-243 | 1U4767 | sp-17 | an-243 | 1A5898 | sp-21 | an-243 |
| 1A4768 | sp-16 | an-244 | 1U4768 | sp-17 | an-244 | 1A5899 | sp-21 | an-244 |
| 1A4769 | sp-16 | an-245 | 1U4769 | sp-17 | an-245 | 1A5900 | sp-21 | an-245 |
| 1A4770 | sp-16 | an-246 | 1U4770 | sp-17 | an-246 | 1A5901 | sp-21 | an-246 |
| 1A4771 | sp-16 | an-247 | 1U4771 | sp-17 | an-247 | 1A5902 | sp-21 | an-247 |
| 1A4772 | sp-16 | an-248 | 1U4772 | sp-17 | an-248 | 1A5903 | sp-21 | an-248 |
| 1A4773 | sp-16 | an-249 | 1U4773 | sp-17 | an-249 | 1A5904 | sp-21 | an-249 |
| 1A4774 | sp-16 | an-250 | 1U4774 | sp-17 | an-250 | 1A5905 | sp-21 | an-250 |
| 1A4775 | sp-16 | an-251 | 1U4775 | sp-17 | an-251 | 1A5906 | sp-21 | an-251 |
| 1A4776 | sp-16 | an-252 | 1U4776 | sp-17 | an-252 | 1A5907 | sp-21 | an-252 |
| 1A4777 | sp-16 | an-253 | 1U4777 | sp-17 | an-253 | 1A5908 | sp-21 | an-253 |
| 1A4778 | sp-16 | an-254 | 1U4778 | sp-17 | an-254 | 1A5909 | sp-21 | an-254 |
| 1A4779 | sp-16 | an-255 | 1U4779 | sp-17 | an-255 | 1A5910 | sp-21 | an-255 |
| 1A4780 | sp-16 | an-256 | 1U4780 | sp-17 | an-256 | 1A5911 | sp-21 | an-256 |
| 1A4781 | sp-16 | an-257 | 1U4781 | sp-17 | an-257 | 1A5912 | sp-21 | an-257 |
| 1A4782 | sp-16 | an-258 | 1U4782 | sp-17 | an-258 | 1A5913 | sp-21 | an-258 |
| 1A4783 | sp-16 | an-259 | 1U4783 | sp-17 | an-259 | 1A5914 | sp-21 | an-259 |
| 1A4784 | sp-16 | an-260 | 1U4784 | sp-17 | an-260 | 1A5915 | sp-21 | an-260 |
| 1A4785 | sp-16 | an-261 | 1U4785 | sp-17 | an-261 | 1A5916 | sp-21 | an-261 |
| 1A4786 | sp-16 | an-262 | 1U4786 | sp-17 | an-262 | 1A5917 | sp-21 | an-262 |
| 1A4787 | sp-16 | an-263 | 1U4787 | sp-17 | an-263 | 1A5918 | sp-21 | an-263 |
| 1A4788 | sp-16 | an-264 | 1U4788 | sp-17 | an-264 | 1A5919 | sp-21 | an-264 |
| 1A4789 | sp-16 | an-265 | 1U4789 | sp-17 | an-265 | 1A5920 | sp-21 | an-265 |
| 1A4790 | sp-16 | an-266 | 1U4790 | sp-17 | an-266 | 1A5921 | sp-21 | an-266 |
| 1A4791 | sp-16 | an-267 | 1U4791 | sp-17 | an-267 | 1A5922 | sp-21 | an-267 |
| 1A4792 | sp-16 | an-268 | 1U4792 | sp-17 | an-268 | 1A5923 | sp-21 | an-268 |
| 1A4793 | sp-16 | an-269 | 1U4793 | sp-17 | an-269 | 1A5924 | sp-21 | an-269 |
| 1A4794 | sp-16 | an-270 | 1U4794 | sp-17 | an-270 | 1A5925 | sp-21 | an-270 |
| 1A4795 | sp-16 | an-271 | 1U4795 | sp-17 | an-271 | 1A5926 | sp-21 | an-271 |
| 1A4796 | sp-16 | an-272 | 1U4796 | sp-17 | an-272 | 1A5927 | sp-21 | an-272 |
| 1A4797 | sp-16 | an-273 | 1U4797 | sp-17 | an-273 | 1A5928 | sp-21 | an-273 |
| 1A4798 | sp-16 | an-274 | 1U4798 | sp-17 | an-274 | 1A5929 | sp-21 | an-274 |
| 1A4799 | sp-16 | an-275 | 1U4799 | sp-17 | an-275 | 1A5930 | sp-21 | an-275 |
| 1A4800 | sp-16 | an-276 | 1U4800 | sp-17 | an-276 | 1A5931 | sp-21 | an-276 |
| 1A4801 | sp-16 | an-277 | 1U4801 | sp-17 | an-277 | 1A5932 | sp-21 | an-277 |
| 1A4802 | sp-16 | an-278 | 1U4802 | sp-17 | an-278 | 1A5933 | sp-21 | an-278 |
| 1A4803 | sp-16 | an-279 | 1U4803 | sp-17 | an-279 | 1A5934 | sp-21 | an-279 |
| 1A4804 | sp-16 | an-280 | 1U4804 | sp-17 | an-280 | 1A5935 | sp-21 | an-280 |
| 1A4805 | sp-16 | an-281 | 1U4805 | sp-17 | an-281 | 1A5936 | sp-21 | an-281 |
| 1A4806 | sp-16 | an-282 | 1U4806 | sp-17 | an-282 | 1A5937 | sp-21 | an-282 |
| 1A4807 | sp-16 | an-283 | 1U4807 | sp-17 | an-283 | 1A5938 | sp-21 | an-283 |
| 1A4808 | sp-16 | an-284 | 1U4808 | sp-17 | an-284 | 1A5939 | sp-21 | an-284 |
| 1A4809 | sp-16 | an-285 | 1U4809 | sp-17 | an-285 | 1A5940 | sp-21 | an-285 |
| 1A4810 | sp-16 | an-286 | 1U4810 | sp-17 | an-286 | 1A5941 | sp-21 | an-286 |
| 1A4811 | sp-16 | an-287 | 1U4811 | sp-17 | an-287 | 1A5942 | sp-21 | an-287 |
| 1A4812 | sp-16 | an-288 | 1U4812 | sp-17 | an-288 | 1A5943 | sp-21 | an-288 |
| 1A4813 | sp-16 | an-289 | 1U4813 | sp-17 | an-289 | 1A5944 | sp-21 | an-289 |
| 1A4814 | sp-16 | an-290 | 1U4814 | sp-17 | an-290 | 1A5945 | sp-21 | an-290 |

Table 2-87

| Y = NHCS | | | Y = NHCSNH | | | Y = NHCS | | |
|---|---|---|---|---|---|---|---|---|
| 1A4815 | sp-16 | an-291 | 1U4815 | sp-17 | an-291 | 1A5946 | sp-21 | an-291 |
| 1A4816 | sp-16 | an-292 | 1U4816 | sp-17 | an-292 | 1A5947 | sp-21 | an-292 |
| 1A4817 | sp-16 | an-293 | 1U4817 | sp-17 | an-293 | 1A5948 | sp-21 | an-293 |
| 1A4818 | sp-16 | an-294 | 1U4818 | sp-17 | an-294 | 1A5949 | sp-21 | an-294 |
| 1A4819 | sp-16 | an-295 | 1U4819 | sp-17 | an-295 | 1A5950 | sp-21 | an-295 |
| 1A4820 | sp-16 | an-296 | 1U4820 | sp-17 | an-296 | 1A5951 | sp-21 | an-296 |
| 1A4821 | sp-16 | an-297 | 1U4821 | sp-17 | an-297 | 1A5952 | sp-21 | an-297 |
| 1A4822 | sp-16 | an-298 | 1U4822 | sp-17 | an-298 | 1A5953 | sp-21 | an-298 |
| 1A4823 | sp-16 | an-299 | 1U4823 | sp-17 | an-299 | 1A5954 | sp-21 | an-299 |
| 1A4824 | sp-16 | an-300 | 1U4824 | sp-17 | an-300 | 1A5955 | sp-21 | an-300 |
| 1A4825 | sp-16 | an-301 | 1U4825 | sp-17 | an-301 | 1A5956 | sp-21 | an-301 |
| 1A4826 | sp-16 | an-302 | 1U4826 | sp-17 | an-302 | 1A5957 | sp-21 | an-302 |
| 1A4827 | sp-16 | an-303 | 1U4827 | sp-17 | an-303 | 1A5958 | sp-21 | an-303 |
| 1A4828 | sp-16 | an-304 | 1U4828 | sp-17 | an-304 | 1A5959 | sp-21 | an-304 |
| 1A4829 | sp-16 | an-305 | 1U4829 | sp-17 | an-305 | 1A5960 | sp-21 | an-305 |
| 1A4830 | sp-16 | an-306 | 1U4830 | sp-17 | an-306 | 1A5961 | sp-21 | an-306 |
| 1A4831 | sp-16 | an-307 | 1U4831 | sp-17 | an-307 | 1A5962 | sp-21 | an-307 |
| 1A4832 | sp-16 | an-308 | 1U4832 | sp-17 | an-308 | 1A5963 | sp-21 | an-308 |
| 1A4833 | sp-16 | an-309 | 1U4833 | sp-17 | an-309 | 1A5964 | sp-21 | an-309 |
| 1A4834 | sp-16 | an-310 | 1U4834 | sp-17 | an-310 | 1A5965 | sp-21 | an-310 |

| Ex. No. | Z | N⁺R⁵R⁶R⁷ | Ex. No. | Z | N⁺R⁵R⁶R⁷ | Ex. No. | Z | N⁺R⁵R⁶R⁷ |
|---|---|---|---|---|---|---|---|---|
| 1A4835 | sp-16 | an-311 | 1U4835 | sp-17 | an-311 | 1A5966 | sp-21 | an-311 |
| 1A4836 | sp-16 | an-312 | 1U4836 | sp-17 | an-312 | 1A5967 | sp-21 | an-312 |
| 1A4837 | sp-16 | an-313 | 1U4837 | sp-17 | an-313 | 1A5968 | sp-21 | an-313 |
| 1A4838 | sp-16 | an-314 | 1U4838 | sp-17 | an-314 | 1A5969 | sp-21 | an-314 |
| 1A4839 | sp-16 | an-315 | 1U4839 | sp-17 | an-315 | 1A5970 | sp-21 | an-315 |
| 1A4840 | sp-16 | an-316 | 1U4840 | sp-17 | an-316 | 1A5971 | sp-21 | an-316 |
| 1A4841 | sp-16 | an-317 | 1U4841 | sp-17 | an-317 | 1A5972 | sp-21 | an-317 |
| 1A4842 | sp-16 | an-318 | 1U4842 | sp-17 | an-318 | 1A5973 | sp-21 | an-318 |
| 1A4843 | sp-16 | an-319 | 1U4843 | sp-17 | an-319 | 1A5974 | sp-21 | an-319 |
| 1A4844 | sp-16 | an-320 | 1U4844 | sp-17 | an-320 | 1A5975 | sp-21 | an-320 |
| 1A4845 | sp-16 | an-321 | 1U4845 | sp-17 | an-321 | 1A5976 | sp-21 | an-321 |
| 1A4846 | sp-16 | an-322 | 1U4846 | sp-17 | an-322 | 1A5977 | sp-21 | an-322 |
| 1A4847 | sp-16 | an-323 | 1U4847 | sp-17 | an-323 | 1A5978 | sp-21 | an-323 |
| 1A4848 | sp-16 | an-324 | 1U4848 | sp-17 | an-324 | 1A5979 | sp-21 | an-324 |
| 1A4849 | sp-16 | an-325 | 1U4849 | sp-17 | an-325 | 1A5980 | sp-21 | an-325 |
| 1A4850 | sp-16 | an-326 | 1U4850 | sp-17 | an-326 | 1A5981 | sp-21 | an-326 |
| 1A4851 | sp-16 | an-327 | 1U4851 | sp-17 | an-327 | 1A5982 | sp-21 | an-327 |
| 1A4852 | sp-16 | an-328 | 1U4852 | sp-17 | an-328 | 1A5983 | sp-21 | an-328 |
| 1A4853 | sp-16 | an-329 | 1U4853 | sp-17 | an-329 | 1A5984 | sp-21 | an-329 |
| 1A4854 | sp-16 | an-330 | 1U4854 | sp-17 | an-330 | 1A5985 | sp-21 | an-330 |
| 1A4855 | sp-16 | an-331 | 1U4855 | sp-17 | an-331 | 1A5986 | sp-21 | an-331 |
| 1A4856 | sp-16 | an-332 | 1U4856 | sp-17 | an-332 | 1A5987 | sp-21 | an-332 |
| 1A4857 | sp-16 | an-333 | 1U4857 | sp-17 | an-333 | 1A5988 | sp-21 | an-333 |
| 1A4858 | sp-16 | an-334 | 1U4858 | sp-17 | an-334 | 1A5989 | sp-21 | an-334 |
| 1A4859 | sp-16 | an-335 | 1U4859 | sp-17 | an-335 | 1A5990 | sp-21 | an-335 |
| 1A4860 | sp-16 | an-336 | 1U4860 | sp-17 | an-336 | 1A5991 | sp-21 | an-336 |
| 1A4861 | sp-16 | an-337 | 1U4861 | sp-17 | an-337 | 1A5992 | sp-21 | an-337 |
| 1A4862 | sp-16 | an-338 | 1U4862 | sp-17 | an-338 | 1A5993 | sp-21 | an-338 |
| 1A4863 | sp-16 | an-339 | 1U4863 | sp-17 | an-339 | 1A5994 | sp-21 | an-339 |
| 1A4864 | sp-16 | an-340 | 1U4864 | sp-17 | an-340 | 1A5995 | sp-21 | an-340 |
| 1A4865 | sp-16 | an-341 | 1U4865 | sp-17 | an-341 | 1A5996 | sp-21 | an-341 |
| 1A4866 | sp-16 | an-342 | 1U4866 | sp-17 | an-342 | 1A5997 | sp-21 | an-342 |
| 1A4867 | sp-16 | an-343 | 1U4867 | sp-17 | an-343 | 1A5998 | sp-21 | an-343 |
| 1A4868 | sp-16 | an-344 | 1U4868 | sp-17 | an-344 | 1A5999 | sp-21 | an-344 |
| 1A4869 | sp-16 | an-345 | 1U4869 | sp-17 | an-345 | 1A6000 | sp-21 | an-345 |
| 1A4870 | sp-16 | an-346 | 1U4870 | sp-17 | an-346 | 1A6001 | sp-21 | an-346 |

Table 2-88

| Y = NHCS | | | Y = NHCSNH | | | Y = NHCS | | |
|---|---|---|---|---|---|---|---|---|
| 1A4871 | sp-16 | an-347 | 1U4871 | sp-17 | an-347 | 1A6002 | sp-21 | an-347 |
| 1A4872 | sp-16 | an-348 | 1U4872 | sp-17 | an-348 | 1A6003 | sp-21 | an-348 |
| 1A4873 | sp-16 | an-349 | 1U4873 | sp-17 | an-349 | 1A6004 | sp-21 | an-349 |
| 1A4874 | sp-16 | an-350 | 1U4874 | sp-17 | an-350 | 1A6005 | sp-21 | an-350 |
| 1A4875 | sp-16 | an-351 | 1U4875 | sp-17 | an-351 | 1A6006 | sp-21 | an-351 |
| 1A4876 | sp-16 | an-352 | 1U4876 | sp-17 | an-352 | 1A6007 | sp-21 | an-352 |
| 1A4877 | sp-16 | an-353 | 1U4877 | sp-17 | an-353 | 1A6008 | sp-21 | an-353 |
| 1A4878 | sp-16 | an-354 | 1U4878 | sp-17 | an-354 | 1A6009 | sp-21 | an-354 |
| 1A4879 | sp-16 | an-355 | 1U4879 | sp-17 | an-355 | 1A6010 | sp-21 | an-355 |
| 1A4880 | sp-16 | an-356 | 1U4880 | sp-17 | an-356 | 1A6011 | sp-21 | an-356 |
| 1A4881 | sp-16 | an-357 | 1U4881 | sp-17 | an-357 | 1A6012 | sp-21 | an-357 |
| 1A4882 | sp-16 | an-358 | 1U4882 | sp-17 | an-358 | 1A6013 | sp-21 | an-358 |
| 1A4883 | sp-16 | an-359 | 1U4883 | sp-17 | an-359 | 1A6014 | sp-21 | an-359 |
| 1A4884 | sp-16 | an-360 | 1U4884 | sp-17 | an-360 | 1A6015 | sp-21 | an-360 |
| 1A4885 | sp-16 | an-361 | 1U4885 | sp-17 | an-361 | 1A6016 | sp-21 | an-361 |
| 1A4886 | sp-16 | an-362 | 1U4886 | sp-17 | an-362 | 1A6017 | sp-21 | an-362 |
| 1A4887 | sp-16 | an-363 | 1U4887 | sp-17 | an-363 | 1A6018 | sp-21 | an-363 |
| 1A4888 | sp-16 | an-364 | 1U4888 | sp-17 | an-364 | 1A6019 | sp-21 | an-364 |
| 1A4889 | sp-16 | an-365 | 1U4889 | sp-17 | an-365 | 1A6020 | sp-21 | an-365 |
| 1A4890 | sp-16 | an-366 | 1U4890 | sp-17 | an-366 | 1A6021 | sp-21 | an-366 |
| 1A4891 | sp-16 | an-367 | 1U4891 | sp-17 | an-367 | 1A6022 | sp-21 | an-367 |
| 1A4892 | sp-16 | an-368 | 1U4892 | sp-17 | an-368 | 1A6023 | sp-21 | an-368 |
| 1A4893 | sp-16 | an-369 | 1U4893 | sp-17 | an-369 | 1A6024 | sp-21 | an-369 |
| 1A4894 | sp-16 | an-370 | 1U4894 | sp-17 | an-370 | 1A6025 | sp-21 | an-370 |
| 1A4895 | sp-16 | an-371 | 1U4895 | sp-17 | an-371 | 1A6026 | sp-21 | an-371 |
| 1A4896 | sp-16 | an-372 | 1U4896 | sp-17 | an-372 | 1A6027 | sp-21 | an-372 |
| 1A4897 | sp-16 | an-373 | 1U4897 | sp-17 | an-373 | 1A6028 | sp-21 | an-373 |
| 1A4898 | sp-16 | an-374 | 1U4898 | sp-17 | an-374 | 1A6029 | sp-21 | an-374 |
| 1A4899 | sp-16 | an-375 | 1U4899 | sp-17 | an-375 | 1A6030 | sp-21 | an-375 |
| 1A4900 | sp-16 | an-376 | 1U4900 | sp-17 | an-376 | 1A6031 | sp-21 | an-376 |
| 1A4901 | sp-16 | an-377 | 1U4901 | sp-17 | an-377 | 1A6032 | sp-21 | an-377 |
| 1A4902 | sp-18 | an-1 | 1U4902 | sp-20 | an-1 | 1A6033 | sp-22 | an-1 |
| 1A4903 | sp-18 | an-2 | 1U4903 | sp-20 | an-2 | 1A6034 | sp-22 | an-2 |
| 1A4904 | sp-18 | an-3 | 1U4904 | sp-20 | an-3 | 1A6035 | sp-22 | an-3 |
| 1A4905 | sp-18 | an-4 | 1U4905 | sp-20 | an-4 | 1A6036 | sp-22 | an-4 |
| 1A4906 | sp-18 | an-5 | 1U4906 | sp-20 | an-5 | 1A6037 | sp-22 | an-5 |
| 1A4907 | sp-18 | an-6 | 1U4907 | sp-20 | an-6 | 1A6038 | sp-22 | an-6 |
| 1A4908 | sp-18 | an-7 | 1U4908 | sp-20 | an-7 | 1A6039 | sp-22 | an-7 |

| Ex. No. | Z | N+R5R6R7 | Ex. No. | Z | N+R5R6R7 | Ex. No. | Z | N+R5R6R7 |
|---|---|---|---|---|---|---|---|---|
| 1A4909 | sp-18 | an-8 | 1U4909 | sp-20 | an-8 | 1A6040 | sp-22 | an-8 |
| 1A4910 | sp-18 | an-9 | 1U4910 | sp-20 | an-9 | 1A6041 | sp-22 | an-9 |
| 1A4911 | sp-18 | an-10 | 1U4911 | sp-20 | an-10 | 1A6042 | sp-22 | an-10 |
| 1A4912 | sp-18 | an-11 | 1U4912 | sp-20 | an-11 | 1A6043 | sp-22 | an-11 |
| 1A4913 | sp-18 | an-12 | 1U4913 | sp-20 | an-12 | 1A6044 | sp-22 | an-12 |
| 1A4914 | sp-18 | an-13 | 1U4914 | sp-20 | an-13 | 1A6045 | sp-22 | an-13 |
| 1A4915 | sp-18 | an-14 | 1U4915 | sp-20 | an-14 | 1A6046 | sp-22 | an-14 |
| 1A4916 | sp-18 | an-15 | 1U4916 | sp-20 | an-15 | 1A6047 | sp-22 | an-15 |
| 1A4917 | sp-18 | an-16 | 1U4917 | sp-20 | an-16 | 1A6048 | sp-22 | an-16 |
| 1A4918 | sp-18 | an-17 | 1U4918 | sp-20 | an-17 | 1A6049 | sp-22 | an-17 |
| 1A4919 | sp-18 | an-18 | 1U4919 | sp-20 | an-18 | 1A6050 | sp-22 | an-18 |
| 1A4920 | sp-18 | an-19 | 1U4920 | sp-20 | an-19 | 1A6051 | sp-22 | an-19 |
| 1A4921 | sp-18 | an-20 | 1U4921 | sp-20 | an-20 | 1A6052 | sp-22 | an-20 |
| 1A4922 | sp-18 | an-21 | 1U4922 | sp-20 | an-21 | 1A6053 | sp-22 | an-21 |
| 1A4923 | sp-18 | an-22 | 1U4923 | sp-20 | an-22 | 1A6054 | sp-22 | an-22 |
| 1A4924 | sp-18 | an-23 | 1U4924 | sp-20 | an-23 | 1A6055 | sp-22 | an-23 |
| 1A4925 | sp-18 | an-24 | 1U4925 | sp-20 | an-24 | 1A6056 | sp-22 | an-24 |
| 1A4926 | sp-18 | an-25 | 1U4926 | sp-20 | an-25 | 1A6057 | sp-22 | an-25 |

Table 2-89

| Y = NHCS | | | Y = NHCSNH | | | Y = NHCS | | |
|---|---|---|---|---|---|---|---|---|
| 1A4927 | sp-18 | an-26 | 1U4927 | sp-20 | an-26 | 1A6058 | sp-22 | an-26 |
| 1A4928 | sp-18 | an-27 | 1U4928 | sp-20 | an-27 | 1A6059 | sp-22 | an-27 |
| 1A4929 | sp-18 | an-28 | 1U4929 | sp-20 | an-28 | 1A6060 | sp-22 | an-28 |
| 1A4930 | sp-18 | an-29 | 1U4930 | sp-20 | an-29 | 1A6061 | sp-22 | an-29 |
| 1A4931 | sp-18 | an-30 | 1U4931 | sp-20 | an-30 | 1A6062 | sp-22 | an-30 |
| 1A4932 | sp-18 | an-31 | 1U4932 | sp-20 | an-31 | 1A6063 | sp-22 | an-31 |
| 1A4933 | sp-18 | an-32 | 1U4933 | sp-20 | an-32 | 1A6064 | sp-22 | an-32 |
| 1A4934 | sp-18 | an-33 | 1U4934 | sp-20 | an-33 | 1A6065 | sp-22 | an-33 |
| 1A4935 | sp-18 | an-34 | 1U4935 | sp-20 | an-34 | 1A6066 | sp-22 | an-34 |
| 1A4936 | sp-18 | an-35 | 1U4936 | sp-20 | an-35 | 1A6067 | sp-22 | an-35 |
| 1A4937 | sp-18 | an-36 | 1U4937 | sp-20 | an-36 | 1A6068 | sp-22 | an-36 |
| 1A4938 | sp-18 | an-37 | 1U4938 | sp-20 | an-37 | 1A6069 | sp-22 | an-37 |
| 1A4939 | sp-18 | an-38 | 1U4939 | sp-20 | an-38 | 1A6070 | sp-22 | an-38 |
| 1A4940 | sp-18 | an-39 | 1U4940 | sp-20 | an-39 | 1A6071 | sp-22 | an-39 |
| 1A4941 | sp-18 | an-40 | 1U4941 | sp-20 | an-40 | 1A6072 | sp-22 | an-40 |
| 1A4942 | sp-18 | an-41 | 1U4942 | sp-20 | an-41 | 1A6073 | sp-22 | an-41 |
| 1A4943 | sp-18 | an-42 | 1U4943 | sp-20 | an-42 | 1A6074 | sp-22 | an-42 |
| 1A4944 | sp-18 | an-43 | 1U4944 | sp-20 | an-43 | 1A6075 | sp-22 | an-43 |
| 1A4945 | sp-18 | an-44 | 1U4945 | sp-20 | an-44 | 1A6076 | sp-22 | an-44 |
| 1A4946 | sp-18 | an-45 | 1U4946 | sp-20 | an-45 | 1A6077 | sp-22 | an-45 |
| 1A4947 | sp-18 | an-46 | 1U4947 | sp-20 | an-46 | 1A6078 | sp-22 | an-46 |
| 1A4948 | sp-18 | an-47 | 1U4948 | sp-20 | an-47 | 1A6079 | sp-22 | an-47 |
| 1A4949 | sp-18 | an-48 | 1U4949 | sp-20 | an-48 | 1A6080 | sp-22 | an-48 |
| 1A4950 | sp-18 | an-49 | 1U4950 | sp-20 | an-49 | 1A6081 | sp-22 | an-49 |
| 1A4951 | sp-18 | an-50 | 1U4951 | sp-20 | an-50 | 1A6082 | sp-22 | an-50 |
| 1A4952 | sp-18 | an-51 | 1U4952 | sp-20 | an-51 | 1A6083 | sp-22 | an-51 |
| 1A4953 | sp-18 | an-52 | 1U4953 | sp-20 | an-52 | 1A6084 | sp-22 | an-52 |
| 1A4954 | sp-18 | an-53 | 1U4954 | sp-20 | an-53 | 1A6085 | sp-22 | an-53 |
| 1A4955 | sp-18 | an-54 | 1U4955 | sp-20 | an-54 | 1A6086 | sp-22 | an-54 |
| 1A4956 | sp-18 | an-55 | 1U4956 | sp-20 | an-55 | 1A6087 | sp-22 | an-55 |
| 1A4957 | sp-18 | an-56 | 1U4957 | sp-20 | an-56 | 1A6088 | sp-22 | an-56 |
| 1A4958 | sp-18 | an-57 | 1U4958 | sp-20 | an-57 | 1A6089 | sp-22 | an-57 |
| 1A4959 | sp-18 | an-58 | 1U4959 | sp-20 | an-58 | 1A6090 | sp-22 | an-58 |
| 1A4960 | sp-18 | an-59 | 1U4960 | sp-20 | an-59 | 1A6091 | sp-22 | an-59 |
| 1A4961 | sp-18 | an-60 | 1U4961 | sp-20 | an-60 | 1A6092 | sp-22 | an-60 |
| 1A4962 | sp-18 | an-61 | 1U4962 | sp-20 | an-61 | 1A6093 | sp-22 | an-61 |
| 1A4963 | sp-18 | an-62 | 1U4963 | sp-20 | an-62 | 1A6094 | sp-22 | an-62 |
| 1A4964 | sp-18 | an-63 | 1U4964 | sp-20 | an-63 | 1A6095 | sp-22 | an-63 |
| 1A4965 | sp-18 | an-64 | 1U4965 | sp-20 | an-64 | 1A6096 | sp-22 | an-64 |
| 1A4966 | sp-18 | an-65 | 1U4966 | sp-20 | an-65 | 1A6097 | sp-22 | an-65 |
| 1A4967 | sp-18 | an-66 | 1U4967 | sp-20 | an-66 | 1A6098 | sp-22 | an-66 |
| 1A4968 | sp-18 | an-67 | 1U4968 | sp-20 | an-67 | 1A6099 | sp-22 | an-67 |
| 1A4969 | sp-18 | an-68 | 1U4969 | sp-20 | an-68 | 1A6100 | sp-22 | an-68 |
| 1A4970 | sp-18 | an-69 | 1U4970 | sp-20 | an-69 | 1A6101 | sp-22 | an-69 |
| 1A4971 | sp-18 | an-70 | 1U4971 | sp-20 | an-70 | 1A6102 | sp-22 | an-70 |
| 1A4972 | sp-18 | an-71 | 1U4972 | sp-20 | an-71 | 1A6103 | sp-22 | an-71 |
| 1A4973 | sp-18 | an-72 | 1U4973 | sp-20 | an-72 | 1A6104 | sp-22 | an-72 |
| 1A4974 | sp-18 | an-73 | 1U4974 | sp-20 | an-73 | 1A6105 | sp-22 | an-73 |
| 1A4975 | sp-18 | an-74 | 1U4975 | sp-20 | an-74 | 1A6106 | sp-22 | an-74 |
| 1A4976 | sp-18 | an-75 | 1U4976 | sp-20 | an-75 | 1A6107 | sp-22 | an-75 |
| 1A4977 | sp-18 | an-76 | 1U4977 | sp-20 | an-76 | 1A6108 | sp-22 | an-76 |
| 1A4978 | sp-18 | an-77 | 1U4978 | sp-20 | an-77 | 1A6109 | sp-22 | an-77 |
| 1A4979 | sp-18 | an-78 | 1U4979 | sp-20 | an-78 | 1A6110 | sp-22 | an-78 |
| 1A4980 | sp-18 | an-79 | 1U4980 | sp-20 | an-79 | 1A6111 | sp-22 | an-79 |
| 1A4981 | sp-18 | an-80 | 1U4981 | sp-20 | an-80 | 1A6112 | sp-22 | an-80 |
| 1A4982 | sp-18 | an-81 | 1U4982 | sp-20 | an-81 | 1A6113 | sp-22 | an-81 |

-continued

| Ex. No. | Z | N⁺R⁵R⁶R⁷ | Ex. No. | Z | N⁺R⁵R⁶R⁷ | Ex. No. | Z | N⁺R⁵R⁶R⁷ |
|---|---|---|---|---|---|---|---|---|
| Table 2-90 ||||||||||
| Y = NHCS ||| Y = NHCSNH ||| Y = NHCS |||
| 1A4983 | sp-18 | an-82 | 1U4983 | sp-20 | an-82 | 1A6114 | sp-22 | an-82 |
| 1A4984 | sp-18 | an-83 | 1U4984 | sp-20 | an-83 | 1A6115 | sp-22 | an-83 |
| 1A4985 | sp-18 | an-84 | 1U4985 | sp-20 | an-84 | 1A6116 | sp-22 | an-84 |
| 1A4986 | sp-18 | an-85 | 1U4986 | sp-20 | an-85 | 1A6117 | sp-22 | an-85 |
| 1A4987 | sp-18 | an-86 | 1U4987 | sp-20 | an-86 | 1A6118 | sp-22 | an-86 |
| 1A4988 | sp-18 | an-87 | 1U4988 | sp-20 | an-87 | 1A6119 | sp-22 | an-87 |
| 1A4989 | sp-18 | an-88 | 1U4989 | sp-20 | an-88 | 1A6120 | sp-22 | an-88 |
| 1A4990 | sp-18 | an-89 | 1U4990 | sp-20 | an-89 | 1A6121 | sp-22 | an-89 |
| 1A4991 | sp-18 | an-90 | 1U4991 | sp-20 | an-90 | 1A6122 | sp-22 | an-90 |
| 1A4992 | sp-18 | an-91 | 1U4992 | sp-20 | an-91 | 1A6123 | sp-22 | an-91 |
| 1A4993 | sp-18 | an-92 | 1U4993 | sp-20 | an-92 | 1A6124 | sp-22 | an-92 |
| 1A4994 | sp-18 | an-93 | 1U4994 | sp-20 | an-93 | 1A6125 | sp-22 | an-93 |
| 1A4995 | sp-18 | an-94 | 1U4995 | sp-20 | an-94 | 1A6126 | sp-22 | an-94 |
| 1A4996 | sp-18 | an-95 | 1U4996 | sp-20 | an-95 | 1A6127 | sp-22 | an-95 |
| 1A4997 | sp-18 | an-96 | 1U4997 | sp-20 | an-96 | 1A6128 | sp-22 | an-96 |
| 1A4998 | sp-18 | an-97 | 1U4998 | sp-20 | an-97 | 1A6129 | sp-22 | an-97 |
| 1A4999 | sp-18 | an-98 | 1U4999 | sp-20 | an-98 | 1A6130 | sp-22 | an-98 |
| 1A5000 | sp-18 | an-99 | 1U5000 | sp-20 | an-99 | 1A6131 | sp-22 | an-99 |
| 1A5001 | sp-18 | an-100 | 1U5001 | sp-20 | an-100 | 1A6132 | sp-22 | an-100 |
| 1A5002 | sp-18 | an-101 | 1U5002 | sp-20 | an-101 | 1A6133 | sp-22 | an-101 |
| 1A5003 | sp-18 | an-102 | 1U5003 | sp-20 | an-102 | 1A6134 | sp-22 | an-102 |
| 1A5004 | sp-18 | an-103 | 1U5004 | sp-20 | an-103 | 1A6135 | sp-22 | an-103 |
| 1A5005 | sp-18 | an-104 | 1U5005 | sp-20 | an-104 | 1A6136 | sp-22 | an-104 |
| 1A5006 | sp-18 | an-105 | 1U5006 | sp-20 | an-105 | 1A6137 | sp-22 | an-105 |
| 1A5007 | sp-18 | an-106 | 1U5007 | sp-20 | an-106 | 1A6138 | sp-22 | an-106 |
| 1A5008 | sp-18 | an-107 | 1U5008 | sp-20 | an-107 | 1A6139 | sp-22 | an-107 |
| 1A5009 | sp-18 | an-108 | 1U5009 | sp-20 | an-108 | 1A6140 | sp-22 | an-108 |
| 1A5010 | sp-18 | an-109 | 1U5010 | sp-20 | an-109 | 1A6141 | sp-22 | an-109 |
| 1A5011 | sp-18 | an-110 | 1U5011 | sp-20 | an-110 | 1A6142 | sp-22 | an-110 |
| 1A5012 | sp-18 | an-111 | 1U5012 | sp-20 | an-111 | 1A6143 | sp-22 | an-111 |
| 1A5013 | sp-18 | an-112 | 1U5013 | sp-20 | an-112 | 1A6144 | sp-22 | an-112 |
| 1A5014 | sp-18 | an-113 | 1U5014 | sp-20 | an-113 | 1A6145 | sp-22 | an-113 |
| 1A5015 | sp-18 | an-114 | 1U5015 | sp-20 | an-114 | 1A6146 | sp-22 | an-114 |
| 1A5016 | sp-18 | an-115 | 1U5016 | sp-20 | an-115 | 1A6147 | sp-22 | an-115 |
| 1A5017 | sp-18 | an-116 | 1U5017 | sp-20 | an-116 | 1A6148 | sp-22 | an-116 |
| 1A5018 | sp-18 | an-117 | 1U5018 | sp-20 | an-117 | 1A6149 | sp-22 | an-117 |
| 1A5019 | sp-18 | an-118 | 1U5019 | sp-20 | an-118 | 1A6150 | sp-22 | an-118 |
| 1A5020 | sp-18 | an-119 | 1U5020 | sp-20 | an-119 | 1A6151 | sp-22 | an-119 |
| 1A5021 | sp-18 | an-120 | 1U5021 | sp-20 | an-120 | 1A6152 | sp-22 | an-120 |
| 1A5022 | sp-18 | an-121 | 1U5022 | sp-20 | an-121 | 1A6153 | sp-22 | an-121 |
| 1A5023 | sp-18 | an-122 | 1U5023 | sp-20 | an-122 | 1A6154 | sp-22 | an-122 |
| 1A5024 | sp-18 | an-123 | 1U5024 | sp-20 | an-123 | 1A6155 | sp-22 | an-123 |
| 1A5025 | sp-18 | an-124 | 1U5025 | sp-20 | an-124 | 1A6156 | sp-22 | an-124 |
| 1A5026 | sp-18 | an-125 | 1U5026 | sp-20 | an-125 | 1A6157 | sp-22 | an-125 |
| 1A5027 | sp-18 | an-126 | 1U5027 | sp-20 | an-126 | 1A6158 | sp-22 | an-126 |
| 1A5028 | sp-18 | an-127 | 1U5028 | sp-20 | an-127 | 1A6159 | sp-22 | an-127 |
| 1A5029 | sp-18 | an-128 | 1U5029 | sp-20 | an-128 | 1A6160 | sp-22 | an-128 |
| 1A5030 | sp-18 | an-129 | 1U5030 | sp-20 | an-129 | 1A6161 | sp-22 | an-129 |
| 1A5031 | sp-18 | an-130 | 1U5031 | sp-20 | an-130 | 1A6162 | sp-22 | an-130 |
| 1A5032 | sp-18 | an-131 | 1U5032 | sp-20 | an-131 | 1A6163 | sp-22 | an-131 |
| 1A5033 | sp-18 | an-132 | 1U5033 | sp-20 | an-132 | 1A6164 | sp-22 | an-132 |
| 1A5034 | sp-18 | an-133 | 1U5034 | sp-20 | an-133 | 1A6165 | sp-22 | an-133 |
| 1A5035 | sp-18 | an-134 | 1U5035 | sp-20 | an-134 | 1A6166 | sp-22 | an-134 |
| 1A5036 | sp-18 | an-135 | 1U5036 | sp-20 | an-135 | 1A6167 | sp-22 | an-135 |
| 1A5037 | sp-18 | an-136 | 1U5037 | sp-20 | an-136 | 1A6168 | sp-22 | an-136 |
| 1A5038 | sp-18 | an-137 | 1U5038 | sp-20 | an-137 | 1A6169 | sp-22 | an-137 |
| Table 2-91 ||||||||||
| Y = NHCS ||| Y = NHCSNH ||| Y = NHCS |||
| 1A5039 | sp-18 | an-138 | 1U5039 | sp-20 | an-138 | 1A6170 | sp-22 | an-138 |
| 1A5040 | sp-18 | an-139 | 1U5040 | sp-20 | an-139 | 1A6171 | sp-22 | an-139 |
| 1A5041 | sp-18 | an-140 | 1U5041 | sp-20 | an-140 | 1A6172 | sp-22 | an-140 |
| 1A5042 | sp-18 | an-141 | 1U5042 | sp-20 | an-141 | 1A6173 | sp-22 | an-141 |
| 1A5043 | sp-18 | an-142 | 1U5043 | sp-20 | an-142 | 1A6174 | sp-22 | an-142 |
| 1A5044 | sp-18 | an-143 | 1U5044 | sp-20 | an-143 | 1A6175 | sp-22 | an-143 |
| 1A5045 | sp-18 | an-144 | 1U5045 | sp-20 | an-144 | 1A6176 | sp-22 | an-144 |
| 1A5046 | sp-18 | an-145 | 1U5046 | sp-20 | an-145 | 1A6177 | sp-22 | an-145 |
| 1A5047 | sp-18 | an-146 | 1U5047 | sp-20 | an-146 | 1A6178 | sp-22 | an-146 |
| 1A5048 | sp-18 | an-147 | 1U5048 | sp-20 | an-147 | 1A6179 | sp-22 | an-147 |
| 1A5049 | sp-18 | an-148 | 1U5049 | sp-20 | an-148 | 1A6180 | sp-22 | an-148 |
| 1A5050 | sp-18 | an-149 | 1U5050 | sp-20 | an-149 | 1A6181 | sp-22 | an-149 |
| 1A5051 | sp-18 | an-150 | 1U5051 | sp-20 | an-150 | 1A6182 | sp-22 | an-150 |
| 1A5052 | sp-18 | an-151 | 1U5052 | sp-20 | an-151 | 1A6183 | sp-22 | an-151 |

-continued

| Ex. No. | Z | N⁺R⁵R⁶R⁷ | Ex. No. | Z | N⁺R⁵R⁶R⁷ | Ex. No. | Z | N⁺R⁵R⁶R⁷ |
|---|---|---|---|---|---|---|---|---|
| 1A5053 | sp-18 | an-152 | 1U5053 | sp-20 | an-152 | 1A6184 | sp-22 | an-152 |
| 1A5054 | sp-18 | an-153 | 1U5054 | sp-20 | an-153 | 1A6185 | sp-22 | an-153 |
| 1A5055 | sp-18 | an-154 | 1U5055 | sp-20 | an-154 | 1A6186 | sp-22 | an-154 |
| 1A5056 | sp-18 | an-155 | 1U5056 | sp-20 | an-155 | 1A6187 | sp-22 | an-155 |
| 1A5057 | sp-18 | an-156 | 1U5057 | sp-20 | an-156 | 1A6188 | sp-22 | an-156 |
| 1A5058 | sp-18 | an-157 | 1U5058 | sp-20 | an-157 | 1A6189 | sp-22 | an-157 |
| 1A5059 | sp-18 | an-158 | 1U5059 | sp-20 | an-158 | 1A6190 | sp-22 | an-158 |
| 1A5060 | sp-18 | an-159 | 1U5060 | sp-20 | an-159 | 1A6191 | sp-22 | an-159 |
| 1A5061 | sp-18 | an-160 | 1U5061 | sp-20 | an-160 | 1A6192 | sp-22 | an-160 |
| 1A5062 | sp-18 | an-161 | 1U5062 | sp-20 | an-161 | 1A6193 | sp-22 | an-161 |
| 1A5063 | sp-18 | an-162 | 1U5063 | sp-20 | an-162 | 1A6194 | sp-22 | an-162 |
| 1A5064 | sp-18 | an-163 | 1U5064 | sp-20 | an-163 | 1A6195 | sp-22 | an-163 |
| 1A5065 | sp-18 | an-164 | 1U5065 | sp-20 | an-164 | 1A6196 | sp-22 | an-164 |
| 1A5066 | sp-18 | an-165 | 1U5066 | sp-20 | an-165 | 1A6197 | sp-22 | an-165 |
| 1A5067 | sp-18 | an-166 | 1U5067 | sp-20 | an-166 | 1A6198 | sp-22 | an-166 |
| 1A5068 | sp-18 | an-167 | 1U5068 | sp-20 | an-167 | 1A6199 | sp-22 | an-167 |
| 1A5069 | sp-18 | an-168 | 1U5069 | sp-20 | an-168 | 1A6200 | sp-22 | an-168 |
| 1A5070 | sp-18 | an-169 | 1U5070 | sp-20 | an-169 | 1A6201 | sp-22 | an-169 |
| 1A5071 | sp-18 | an-170 | 1U5071 | sp-20 | an-170 | 1A6202 | sp-22 | an-170 |
| 1A5072 | sp-18 | an-171 | 1U5072 | sp-20 | an-171 | 1A6203 | sp-22 | an-171 |
| 1A5073 | sp-18 | an-172 | 1U5073 | sp-20 | an-172 | 1A6204 | sp-22 | an-172 |
| 1A5074 | sp-18 | an-173 | 1U5074 | sp-20 | an-173 | 1A6205 | sp-22 | an-173 |
| 1A5075 | sp-18 | an-174 | 1U5075 | sp-20 | an-174 | 1A6206 | sp-22 | an-174 |
| 1A5076 | sp-18 | an-175 | 1U5076 | sp-20 | an-175 | 1A6207 | sp-22 | an-175 |
| 1A5077 | sp-18 | an-176 | 1U5077 | sp-20 | an-176 | 1A6208 | sp-22 | an-176 |
| 1A5078 | sp-18 | an-177 | 1U5078 | sp-20 | an-177 | 1A6209 | sp-22 | an-177 |
| 1A5079 | sp-18 | an-178 | 1U5079 | sp-20 | an-178 | 1A6210 | sp-22 | an-178 |
| 1A5080 | sp-18 | an-179 | 1U5080 | sp-20 | an-179 | 1A6211 | sp-22 | an-179 |
| 1A5081 | sp-18 | an-180 | 1U5081 | sp-20 | an-180 | 1A6212 | sp-22 | an-180 |
| 1A5082 | sp-18 | an-181 | 1U5082 | sp-20 | an-181 | 1A6213 | sp-22 | an-181 |
| 1A5083 | sp-18 | an-182 | 1U5083 | sp-20 | an-182 | 1A6214 | sp-22 | an-182 |
| 1A5084 | sp-18 | an-183 | 1U5084 | sp-20 | an-183 | 1A6215 | sp-22 | an-183 |
| 1A5085 | sp-18 | an-184 | 1U5085 | sp-20 | an-184 | 1A6216 | sp-22 | an-184 |
| 1A5086 | sp-18 | an-185 | 1U5086 | sp-20 | an-185 | 1A6217 | sp-22 | an-185 |
| 1A5087 | sp-18 | an-186 | 1U5087 | sp-20 | an-186 | 1A6218 | sp-22 | an-186 |
| 1A5088 | sp-18 | an-187 | 1U5088 | sp-20 | an-187 | 1A6219 | sp-22 | an-187 |
| 1A5089 | sp-18 | an-188 | 1U5089 | sp-20 | an-188 | 1A6220 | sp-22 | an-188 |
| 1A5090 | sp-18 | an-189 | 1U5090 | sp-20 | an-189 | 1A6221 | sp-22 | an-189 |
| 1A5091 | sp-18 | an-190 | 1U5091 | sp-20 | an-190 | 1A6222 | sp-22 | an-190 |
| 1A5092 | sp-18 | an-191 | 1U5092 | sp-20 | an-191 | 1A6223 | sp-22 | an-191 |
| 1A5093 | sp-18 | an-192 | 1U5093 | sp-20 | an-192 | 1A6224 | sp-22 | an-192 |
| 1A5094 | sp-18 | an-193 | 1U5094 | sp-20 | an-193 | 1A6225 | sp-22 | an-193 |

Table 2-92

| | Y = NHCS | | | Y = NHCSNH | | | Y = NHCS | |
|---|---|---|---|---|---|---|---|---|
| 1A5095 | sp-18 | an-194 | 1U5095 | sp-20 | an-194 | 1A6226 | sp-22 | an-194 |
| 1A5096 | sp-18 | an-195 | 1U5096 | sp-20 | an-195 | 1A6227 | sp-22 | an-195 |
| 1A5097 | sp-18 | an-196 | 1U5097 | sp-20 | an-196 | 1A6228 | sp-22 | an-196 |
| 1A5098 | sp-18 | an-197 | 1U5098 | sp-20 | an-197 | 1A6229 | sp-22 | an-197 |
| 1A5099 | sp-18 | an-198 | 1U5099 | sp-20 | an-198 | 1A6230 | sp-22 | an-198 |
| 1A5100 | sp-18 | an-199 | 1U5100 | sp-20 | an-199 | 1A6231 | sp-22 | an-199 |
| 1A5101 | sp-18 | an-200 | 1U5101 | sp-20 | an-200 | 1A6232 | sp-22 | an-200 |
| 1A5102 | sp-18 | an-201 | 1U5102 | sp-20 | an-201 | 1A6233 | sp-22 | an-201 |
| 1A5103 | sp-18 | an-202 | 1U5103 | sp-20 | an-202 | 1A6234 | sp-22 | an-202 |
| 1A5104 | sp-18 | an-203 | 1U5104 | sp-20 | an-203 | 1A6235 | sp-22 | an-203 |
| 1A5105 | sp-18 | an-204 | 1U5105 | sp-20 | an-204 | 1A6236 | sp-22 | an-204 |
| 1A5106 | sp-18 | an-205 | 1U5106 | sp-20 | an-205 | 1A6237 | sp-22 | an-205 |
| 1A5107 | sp-18 | an-206 | 1U5107 | sp-20 | an-206 | 1A6238 | sp-22 | an-206 |
| 1A5108 | sp-18 | an-207 | 1U5108 | sp-20 | an-207 | 1A6239 | sp-22 | an-207 |
| 1A5109 | sp-18 | an-208 | 1U5109 | sp-20 | an-208 | 1A6240 | sp-22 | an-208 |
| 1A5110 | sp-18 | an-209 | 1U5110 | sp-20 | an-209 | 1A6241 | sp-22 | an-209 |
| 1A5111 | sp-18 | an-210 | 1U5111 | sp-20 | an-210 | 1A6242 | sp-22 | an-210 |
| 1A5112 | sp-18 | an-211 | 1U5112 | sp-20 | an-211 | 1A6243 | sp-22 | an-211 |
| 1A5113 | sp-18 | an-212 | 1U5113 | sp-20 | an-212 | 1A6244 | sp-22 | an-212 |
| 1A5114 | sp-18 | an-213 | 1U5114 | sp-20 | an-213 | 1A6245 | sp-22 | an-213 |
| 1A5115 | sp-18 | an-214 | 1U5115 | sp-20 | an-214 | 1A6246 | sp-22 | an-214 |
| 1A5116 | sp-18 | an-215 | 1U5116 | sp-20 | an-215 | 1A6247 | sp-22 | an-215 |
| 1A5117 | sp-18 | an-216 | 1U5117 | sp-20 | an-216 | 1A6248 | sp-22 | an-216 |
| 1A5118 | sp-18 | an-217 | 1U5118 | sp-20 | an-217 | 1A6249 | sp-22 | an-217 |
| 1A5119 | sp-18 | an-218 | 1U5119 | sp-20 | an-218 | 1A6250 | sp-22 | an-218 |
| 1A5120 | sp-18 | an-219 | 1U5120 | sp-20 | an-219 | 1A6251 | sp-22 | an-219 |
| 1A5121 | sp-18 | an-220 | 1U5121 | sp-20 | an-220 | 1A6252 | sp-22 | an-220 |
| 1A5122 | sp-18 | an-221 | 1U5122 | sp-20 | an-221 | 1A6253 | sp-22 | an-221 |
| 1A5123 | sp-18 | an-222 | 1U5123 | sp-20 | an-222 | 1A6254 | sp-22 | an-222 |
| 1A5124 | sp-18 | an-223 | 1U5124 | sp-20 | an-223 | 1A6255 | sp-22 | an-223 |
| 1A5125 | sp-18 | an-224 | 1U5125 | sp-20 | an-224 | 1A6256 | sp-22 | an-224 |
| 1A5126 | sp-18 | an-225 | 1U5126 | sp-20 | an-225 | 1A6257 | sp-22 | an-225 |

-continued

| Ex. No. | Z | N⁺R⁵R⁶R⁷ | Ex. No. | Z | N⁺R⁵R⁶R⁷ | Ex. No. | Z | N⁺R⁵R⁶R⁷ |
|---|---|---|---|---|---|---|---|---|
| 1A5127 | sp-18 | an-226 | 1U5127 | sp-20 | an-226 | 1A6258 | sp-22 | an-226 |
| 1A5128 | sp-18 | an-227 | 1U5128 | sp-20 | an-227 | 1A6259 | sp-22 | an-227 |
| 1A5129 | sp-18 | an-228 | 1U5129 | sp-20 | an-228 | 1A6260 | sp-22 | an-228 |
| 1A5130 | sp-18 | an-229 | 1U5130 | sp-20 | an-229 | 1A6261 | sp-22 | an-229 |
| 1A5131 | sp-18 | an-230 | 1U5131 | sp-20 | an-230 | 1A6262 | sp-22 | an-230 |
| 1A5132 | sp-18 | an-231 | 1U5132 | sp-20 | an-231 | 1A6263 | sp-22 | an-231 |
| 1A5133 | sp-18 | an-232 | 1U5133 | sp-20 | an-232 | 1A6264 | sp-22 | an-232 |
| 1A5134 | sp-18 | an-233 | 1U5134 | sp-20 | an-233 | 1A6265 | sp-22 | an-233 |
| 1A5135 | sp-18 | an-234 | 1U5135 | sp-20 | an-234 | 1A6266 | sp-22 | an-234 |
| 1A5136 | sp-18 | an-235 | 1U5136 | sp-20 | an-235 | 1A6267 | sp-22 | an-235 |
| 1A5137 | sp-18 | an-236 | 1U5137 | sp-20 | an-236 | 1A6268 | sp-22 | an-236 |
| 1A5138 | sp-18 | an-237 | 1U5138 | sp-20 | an-237 | 1A6269 | sp-22 | an-237 |
| 1A5139 | sp-18 | an-238 | 1U5139 | sp-20 | an-238 | 1A6270 | sp-22 | an-238 |
| 1A5140 | sp-18 | an-239 | 1U5140 | sp-20 | an-239 | 1A6271 | sp-22 | an-239 |
| 1A5141 | sp-18 | an-240 | 1U5141 | sp-20 | an-240 | 1A6272 | sp-22 | an-240 |
| 1A5142 | sp-18 | an-241 | 1U5142 | sp-20 | an-241 | 1A6273 | sp-22 | an-241 |
| 1A5143 | sp-18 | an-242 | 1U5143 | sp-20 | an-242 | 1A6274 | sp-22 | an-242 |
| 1A5144 | sp-18 | an-243 | 1U5144 | sp-20 | an-243 | 1A6275 | sp-22 | an-243 |
| 1A5145 | sp-18 | an-244 | 1U5145 | sp-20 | an-244 | 1A6276 | sp-22 | an-244 |
| 1A5146 | sp-18 | an-245 | 1U5146 | sp-20 | an-245 | 1A6277 | sp-22 | an-245 |
| 1A5147 | sp-18 | an-246 | 1U5147 | sp-20 | an-246 | 1A6278 | sp-22 | an-246 |
| 1A5148 | sp-18 | an-247 | 1U5148 | sp-20 | an-247 | 1A6279 | sp-22 | an-247 |
| 1A5149 | sp-18 | an-248 | 1U5149 | sp-20 | an-248 | 1A6280 | sp-22 | an-248 |
| 1A5150 | sp-18 | an-249 | 1U5150 | sp-20 | an-249 | 1A6281 | sp-22 | an-249 |

Table 2-93

| Y = NHCS | | | Y = NHCSNH | | | Y = NHCS | | |
|---|---|---|---|---|---|---|---|---|
| 1A5151 | sp-18 | an-250 | 1U5151 | sp-20 | an-250 | 1A6282 | sp-22 | an-250 |
| 1A5152 | sp-18 | an-251 | 1U5152 | sp-20 | an-251 | 1A6283 | sp-22 | an-251 |
| 1A5153 | sp-18 | an-252 | 1U5153 | sp-20 | an-252 | 1A6284 | sp-22 | an-252 |
| 1A5154 | sp-18 | an-253 | 1U5154 | sp-20 | an-253 | 1A6285 | sp-22 | an-253 |
| 1A5155 | sp-18 | an-254 | 1U5155 | sp-20 | an-254 | 1A6286 | sp-22 | an-254 |
| 1A5156 | sp-18 | an-255 | 1U5156 | sp-20 | an-255 | 1A6287 | sp-22 | an-255 |
| 1A5157 | sp-18 | an-256 | 1U5157 | sp-20 | an-256 | 1A6288 | sp-22 | an-256 |
| 1A5158 | sp-18 | an-257 | 1U5158 | sp-20 | an-257 | 1A6289 | sp-22 | an-257 |
| 1A5159 | sp-18 | an-258 | 1U5159 | sp-20 | an-258 | 1A6290 | sp-22 | an-258 |
| 1A5160 | sp-18 | an-259 | 1U5160 | sp-20 | an-259 | 1A6291 | sp-22 | an-259 |
| 1A5161 | sp-18 | an-260 | 1U5161 | sp-20 | an-260 | 1A6292 | sp-22 | an-260 |
| 1A5162 | sp-18 | an-261 | 1U5162 | sp-20 | an-261 | 1A6293 | sp-22 | an-261 |
| 1A5163 | sp-18 | an-262 | 1U5163 | sp-20 | an-262 | 1A6294 | sp-22 | an-262 |
| 1A5164 | sp-18 | an-263 | 1U5164 | sp-20 | an-263 | 1A6295 | sp-22 | an-263 |
| 1A5165 | sp-18 | an-264 | 1U5165 | sp-20 | an-264 | 1A6296 | sp-22 | an-264 |
| 1A5166 | sp-18 | an-265 | 1U5166 | sp-20 | an-265 | 1A6297 | sp-22 | an-265 |
| 1A5167 | sp-18 | an-266 | 1U5167 | sp-20 | an-266 | 1A6298 | sp-22 | an-266 |
| 1A5168 | sp-18 | an-267 | 1U5168 | sp-20 | an-267 | 1A6299 | sp-22 | an-267 |
| 1A5169 | sp-18 | an-268 | 1U5169 | sp-20 | an-268 | 1A6300 | sp-22 | an-268 |
| 1A5170 | sp-18 | an-269 | 1U5170 | sp-20 | an-269 | 1A6301 | sp-22 | an-269 |
| 1A5171 | sp-18 | an-270 | 1U5171 | sp-20 | an-270 | 1A6302 | sp-22 | an-270 |
| 1A5172 | sp-18 | an-271 | 1U5172 | sp-20 | an-271 | 1A6303 | sp-22 | an-271 |
| 1A5173 | sp-18 | an-272 | 1U5173 | sp-20 | an-272 | 1A6304 | sp-22 | an-272 |
| 1A5174 | sp-18 | an-273 | 1U5174 | sp-20 | an-273 | 1A6305 | sp-22 | an-273 |
| 1A5175 | sp-18 | an-274 | 1U5175 | sp-20 | an-274 | 1A6306 | sp-22 | an-274 |
| 1A5176 | sp-18 | an-275 | 1U5176 | sp-20 | an-275 | 1A6307 | sp-22 | an-275 |
| 1A5177 | sp-18 | an-276 | 1U5177 | sp-20 | an-276 | 1A6308 | sp-22 | an-276 |
| 1A5178 | sp-18 | an-277 | 1U5178 | sp-20 | an-277 | 1A6309 | sp-22 | an-277 |
| 1A5179 | sp-18 | an-278 | 1U5179 | sp-20 | an-278 | 1A6310 | sp-22 | an-278 |
| 1A5180 | sp-18 | an-279 | 1U5180 | sp-20 | an-279 | 1A6311 | sp-22 | an-279 |
| 1A5181 | sp-18 | an-280 | 1U5181 | sp-20 | an-280 | 1A6312 | sp-22 | an-280 |
| 1A5182 | sp-18 | an-281 | 1U5182 | sp-20 | an-281 | 1A6313 | sp-22 | an-281 |
| 1A5183 | sp-18 | an-282 | 1U5183 | sp-20 | an-282 | 1A6314 | sp-22 | an-282 |
| 1A5184 | sp-18 | an-283 | 1U5184 | sp-20 | an-283 | 1A6315 | sp-22 | an-283 |
| 1A5185 | sp-18 | an-284 | 1U5185 | sp-20 | an-284 | 1A6316 | sp-22 | an-284 |
| 1A5186 | sp-18 | an-285 | 1U5186 | sp-20 | an-285 | 1A6317 | sp-22 | an-285 |
| 1A5187 | sp-18 | an-286 | 1U5187 | sp-20 | an-286 | 1A6318 | sp-22 | an-286 |
| 1A5188 | sp-18 | an-287 | 1U5188 | sp-20 | an-287 | 1A6319 | sp-22 | an-287 |
| 1A5189 | sp-18 | an-288 | 1U5189 | sp-20 | an-288 | 1A6320 | sp-22 | an-288 |
| 1A5190 | sp-18 | an-289 | 1U5190 | sp-20 | an-289 | 1A6321 | sp-22 | an-289 |
| 1A5191 | sp-18 | an-290 | 1U5191 | sp-20 | an-290 | 1A6322 | sp-22 | an-290 |
| 1A5192 | sp-18 | an-291 | 1U5192 | sp-20 | an-291 | 1A6323 | sp-22 | an-291 |
| 1A5193 | sp-18 | an-292 | 1U5193 | sp-20 | an-292 | 1A6324 | sp-22 | an-292 |
| 1A5194 | sp-18 | an-293 | 1U5194 | sp-20 | an-293 | 1A6325 | sp-22 | an-293 |
| 1A5195 | sp-18 | an-294 | 1U5195 | sp-20 | an-294 | 1A6326 | sp-22 | an-294 |
| 1A5196 | sp-18 | an-295 | 1U5196 | sp-20 | an-295 | 1A6327 | sp-22 | an-295 |
| 1A5197 | sp-18 | an-296 | 1U5197 | sp-20 | an-296 | 1A6328 | sp-22 | an-296 |
| 1A5198 | sp-18 | an-297 | 1U5198 | sp-20 | an-297 | 1A6329 | sp-22 | an-297 |
| 1A5199 | sp-18 | an-298 | 1U5199 | sp-20 | an-298 | 1A6330 | sp-22 | an-298 |
| 1A5200 | sp-18 | an-299 | 1U5200 | sp-20 | an-299 | 1A6331 | sp-22 | an-299 |

-continued

| Ex. No. | Z | N⁺R⁵R⁶R⁷ | Ex. No. | Z | N⁺R⁵R⁶R⁷ | Ex. No. | Z | N⁺R⁵R⁶R⁷ |
|---|---|---|---|---|---|---|---|---|
| 1A5201 | sp-18 | an-300 | 1U5201 | sp-20 | an-300 | 1A6332 | sp-22 | an-300 |
| 1A5202 | sp-18 | an-301 | 1U5202 | sp-20 | an-301 | 1A6333 | sp-22 | an-301 |
| 1A5203 | sp-18 | an-302 | 1U5203 | sp-20 | an-302 | 1A6334 | sp-22 | an-302 |
| 1A5204 | sp-18 | an-303 | 1U5204 | sp-20 | an-303 | 1A6335 | sp-22 | an-303 |
| 1A5205 | sp-18 | an-304 | 1U5205 | sp-20 | an-304 | 1A6336 | sp-22 | an-304 |
| 1A5206 | sp-18 | an-305 | 1U5206 | sp-20 | an-305 | 1A6337 | sp-22 | an-305 |

Table 2-94

| Y = NHCS | | | Y = NHCSNH | | | Y = NHCS | | |
|---|---|---|---|---|---|---|---|---|
| 1A5207 | sp-18 | an-306 | 1U5207 | sp-20 | an-306 | 1A6338 | sp-22 | an-306 |
| 1A5208 | sp-18 | an-307 | 1U5208 | sp-20 | an-307 | 1A6339 | sp-22 | an-307 |
| 1A5209 | sp-18 | an-308 | 1U5209 | sp-20 | an-308 | 1A6340 | sp-22 | an-308 |
| 1A5210 | sp-18 | an-309 | 1U5210 | sp-20 | an-309 | 1A6341 | sp-22 | an-309 |
| 1A5211 | sp-18 | an-310 | 1U5211 | sp-20 | an-310 | 1A6342 | sp-22 | an-310 |
| 1A5212 | sp-18 | an-311 | 1U5212 | sp-20 | an-311 | 1A6343 | sp-22 | an-311 |
| 1A5213 | sp-18 | an-312 | 1U5213 | sp-20 | an-312 | 1A6344 | sp-22 | an-312 |
| 1A5214 | sp-18 | an-313 | 1U5214 | sp-20 | an-313 | 1A6345 | sp-22 | an-313 |
| 1A5215 | sp-18 | an-314 | 1U5215 | sp-20 | an-314 | 1A6346 | sp-22 | an-314 |
| 1A5216 | sp-18 | an-315 | 1U5216 | sp-20 | an-315 | 1A6347 | sp-22 | an-315 |
| 1A5217 | sp-18 | an-316 | 1U5217 | sp-20 | an-316 | 1A6348 | sp-22 | an-316 |
| 1A5218 | sp-18 | an-317 | 1U5218 | sp-20 | an-317 | 1A6349 | sp-22 | an-317 |
| 1A5219 | sp-18 | an-318 | 1U5219 | sp-20 | an-318 | 1A6350 | sp-22 | an-318 |
| 1A5220 | sp-18 | an-319 | 1U5220 | sp-20 | an-319 | 1A6351 | sp-22 | an-319 |
| 1A5221 | sp-18 | an-320 | 1U5221 | sp-20 | an-320 | 1A6352 | sp-22 | an-320 |
| 1A5222 | sp-18 | an-321 | 1U5222 | sp-20 | an-321 | 1A6353 | sp-22 | an-321 |
| 1A5223 | sp-18 | an-322 | 1U5223 | sp-20 | an-322 | 1A6354 | sp-22 | an-322 |
| 1A5224 | sp-18 | an-323 | 1U5224 | sp-20 | an-323 | 1A6355 | sp-22 | an-323 |
| 1A5225 | sp-18 | an-324 | 1U5225 | sp-20 | an-324 | 1A6356 | sp-22 | an-324 |
| 1A5226 | sp-18 | an-325 | 1U5226 | sp-20 | an-325 | 1A6357 | sp-22 | an-325 |
| 1A5227 | sp-18 | an-326 | 1U5227 | sp-20 | an-326 | 1A6358 | sp-22 | an-326 |
| 1A5228 | sp-18 | an-327 | 1U5228 | sp-20 | an-327 | 1A6359 | sp-22 | an-327 |
| 1A5229 | sp-18 | an-328 | 1U5229 | sp-20 | an-328 | 1A6360 | sp-22 | an-328 |
| 1A5230 | sp-18 | an-329 | 1U5230 | sp-20 | an-329 | 1A6361 | sp-22 | an-329 |
| 1A5231 | sp-18 | an-330 | 1U5231 | sp-20 | an-330 | 1A6362 | sp-22 | an-330 |
| 1A5232 | sp-18 | an-331 | 1U5232 | sp-20 | an-331 | 1A6363 | sp-22 | an-331 |
| 1A5233 | sp-18 | an-332 | 1U5233 | sp-20 | an-332 | 1A6364 | sp-22 | an-332 |
| 1A5234 | sp-18 | an-333 | 1U5234 | sp-20 | an-333 | 1A6365 | sp-22 | an-333 |
| 1A5235 | sp-18 | an-334 | 1U5235 | sp-20 | an-334 | 1A6366 | sp-22 | an-334 |
| 1A5236 | sp-18 | an-335 | 1U5236 | sp-20 | an-335 | 1A6367 | sp-22 | an-335 |
| 1A5237 | sp-18 | an-336 | 1U5237 | sp-20 | an-336 | 1A6368 | sp-22 | an-336 |
| 1A5238 | sp-18 | an-337 | 1U5238 | sp-20 | an-337 | 1A6369 | sp-22 | an-337 |
| 1A5239 | sp-18 | an-338 | 1U5239 | sp-20 | an-338 | 1A6370 | sp-22 | an-338 |
| 1A5240 | sp-18 | an-339 | 1U5240 | sp-20 | an-339 | 1A6371 | sp-22 | an-339 |
| 1A5241 | sp-18 | an-340 | 1U5241 | sp-20 | an-340 | 1A6372 | sp-22 | an-340 |
| 1A5242 | sp-18 | an-341 | 1U5242 | sp-20 | an-341 | 1A6373 | sp-22 | an-341 |
| 1A5243 | sp-18 | an-342 | 1U5243 | sp-20 | an-342 | 1A6374 | sp-22 | an-342 |
| 1A5244 | sp-18 | an-343 | 1U5244 | sp-20 | an-343 | 1A6375 | sp-22 | an-343 |
| 1A5245 | sp-18 | an-344 | 1U5245 | sp-20 | an-344 | 1A6376 | sp-22 | an-344 |
| 1A5246 | sp-18 | an-345 | 1U5246 | sp-20 | an-345 | 1A6377 | sp-22 | an-345 |
| 1A5247 | sp-18 | an-346 | 1U5247 | sp-20 | an-346 | 1A6378 | sp-22 | an-346 |
| 1A5248 | sp-18 | an-347 | 1U5248 | sp-20 | an-347 | 1A6379 | sp-22 | an-347 |
| 1A5249 | sp-18 | an-348 | 1U5249 | sp-20 | an-348 | 1A6380 | sp-22 | an-348 |
| 1A5250 | sp-18 | an-349 | 1U5250 | sp-20 | an-349 | 1A6381 | sp-22 | an-349 |
| 1A5251 | sp-18 | an-350 | 1U5251 | sp-20 | an-350 | 1A6382 | sp-22 | an-350 |
| 1A5252 | sp-18 | an-351 | 1U5252 | sp-20 | an-351 | 1A6383 | sp-22 | an-351 |
| 1A5253 | sp-18 | an-352 | 1U5253 | sp-20 | an-352 | 1A6384 | sp-22 | an-352 |
| 1A5254 | sp-18 | an-353 | 1U5254 | sp-20 | an-353 | 1A6385 | sp-22 | an-353 |
| 1A5255 | sp-18 | an-354 | 1U5255 | sp-20 | an-354 | 1A6386 | sp-22 | an-354 |
| 1A5256 | sp-18 | an-355 | 1U5256 | sp-20 | an-355 | 1A6387 | sp-22 | an-355 |
| 1A5257 | sp-18 | an-356 | 1U5257 | sp-20 | an-356 | 1A6388 | sp-22 | an-356 |
| 1A5258 | sp-18 | an-357 | 1U5258 | sp-20 | an-357 | 1A6389 | sp-22 | an-357 |
| 1A5259 | sp-18 | an-358 | 1U5259 | sp-20 | an-358 | 1A6390 | sp-22 | an-358 |
| 1A5260 | sp-18 | an-359 | 1U5260 | sp-20 | an-359 | 1A6391 | sp-22 | an-359 |
| 1A5261 | sp-18 | an-360 | 1U5261 | sp-20 | an-360 | 1A6392 | sp-22 | an-360 |
| 1A5262 | sp-18 | an-361 | 1U5262 | sp-20 | an-361 | 1A6393 | sp-22 | an-361 |

Table 2-95

| Y = NHCS | | | Y = NHCSNH | | | Y = NHCS | | |
|---|---|---|---|---|---|---|---|---|
| 1A5263 | sp-18 | an-362 | 1U5263 | sp-20 | an-362 | 1A6394 | sp-22 | an-362 |
| 1A5264 | sp-18 | an-363 | 1U5264 | sp-20 | an-363 | 1A6395 | sp-22 | an-363 |
| 1A5265 | sp-18 | an-364 | 1U5265 | sp-20 | an-364 | 1A6396 | sp-22 | an-364 |
| 1A5266 | sp-18 | an-365 | 1U5266 | sp-20 | an-365 | 1A6397 | sp-22 | an-365 |
| 1A5267 | sp-18 | an-366 | 1U5267 | sp-20 | an-366 | 1A6398 | sp-22 | an-366 |
| 1A5268 | sp-18 | an-367 | 1U5268 | sp-20 | an-367 | 1A6399 | sp-22 | an-367 |
| 1A5269 | sp-18 | an-368 | 1U5269 | sp-20 | an-368 | 1A6400 | sp-22 | an-368 |
| 1A5270 | sp-18 | an-369 | 1U5270 | sp-20 | an-369 | 1A6401 | sp-22 | an-369 |

| Ex. No. | Z | $N^+R^5R^6R^7$ | Ex. No. | Z | $N^+R^5R^6R^7$ | Ex. No. | Z | $N^+R^5R^6R^7$ |
|---|---|---|---|---|---|---|---|---|
| 1A5271 | sp-18 | an-370 | 1U5271 | sp-20 | an-370 | 1A6402 | sp-22 | an-370 |
| 1A5272 | sp-18 | an-371 | 1U5272 | sp-20 | an-371 | 1A6403 | sp-22 | an-371 |
| 1A5273 | sp-18 | an-372 | 1U5273 | sp-20 | an-372 | 1A6404 | sp-22 | an-372 |
| 1A5274 | sp-18 | an-373 | 1U5274 | sp-20 | an-373 | 1A6405 | sp-22 | an-373 |
| 1A5275 | sp-18 | an-374 | 1U5275 | sp-20 | an-374 | 1A6406 | sp-22 | an-374 |
| 1A5276 | sp-18 | an-375 | 1U5276 | sp-20 | an-375 | 1A6407 | sp-22 | an-375 |
| 1A5277 | sp-18 | an-376 | 1U5277 | sp-20 | an-376 | 1A6408 | sp-22 | an-376 |
| 1A5278 | sp-18 | an-377 | 1U5278 | sp-20 | an-377 | 1A6409 | sp-22 | an-377 |
| Y = NHCS | | | Y = NHCSNH | | | Y = NHCSO | | |
| 1A6410 | sp-1 | an-378 | 1U5279 | sp-1 | an-378 | 1C3771 | sp-1 | an-378 |
| 1A6411 | sp-1 | an-379 | 1U5280 | sp-1 | an-379 | 1C3772 | sp-1 | an-379 |
| 1A6412 | sp-1 | an-380 | 1U5281 | sp-1 | an-380 | 1C3773 | sp-1 | an-380 |
| 1A6413 | sp-1 | an-381 | 1U5282 | sp-1 | an-381 | 1C3774 | sp-1 | an-381 |
| 1A6414 | sp-1 | an-382 | 1U5283 | sp-1 | an-382 | 1C3775 | sp-1 | an-382 |
| 1A6415 | sp-1 | an-383 | 1U5284 | sp-1 | an-383 | 1C3776 | sp-1 | an-383 |
| 1A6416 | sp-1 | an-384 | 1U5285 | sp-1 | an-384 | 1C3777 | sp-1 | an-384 |
| 1A6417 | sp-1 | an-385 | 1U5286 | sp-1 | an-385 | 1C3778 | sp-1 | an-385 |
| 1A6418 | sp-1 | an-386 | 1U5287 | sp-1 | an-386 | 1C3779 | sp-1 | an-386 |
| 1A6419 | sp-1 | an-387 | 1U5288 | sp-1 | an-387 | 1C3780 | sp-1 | an-387 |
| 1A6420 | sp-1 | an-388 | 1U5289 | sp-1 | an-388 | 1C3781 | sp-1 | an-388 |
| 1A6421 | sp-1 | an-389 | 1U5290 | sp-1 | an-389 | 1C3782 | sp-1 | an-389 |
| 1A6422 | sp-1 | an-390 | 1U5291 | sp-1 | an-390 | 1C3783 | sp-1 | an-390 |
| 1A6423 | sp-1 | an-391 | 1U5292 | sp-1 | an-391 | 1C3784 | sp-1 | an-391 |
| 1A6424 | sp-1 | an-392 | 1U5293 | sp-1 | an-392 | 1C3785 | sp-1 | an-392 |
| 1A6425 | sp-1 | an-393 | 1U5294 | sp-1 | an-393 | 1C3786 | sp-1 | an-393 |
| 1A6426 | sp-2 | an-378 | 1U5295 | sp-2 | an-378 | 1C3787 | sp-2 | an-378 |
| 1A6427 | sp-2 | an-379 | 1U5296 | sp-2 | an-379 | 1C3788 | sp-2 | an-379 |
| 1A6428 | sp-2 | an-380 | 1U5297 | sp-2 | an-380 | 1C3789 | sp-2 | an-380 |
| 1A6429 | sp-2 | an-381 | 1U5298 | sp-2 | an-381 | 1C3790 | sp-2 | an-381 |
| 1A6430 | sp-2 | an-382 | 1U5299 | sp-2 | an-382 | 1C3791 | sp-2 | an-382 |
| 1A6431 | sp-2 | an-383 | 1U5300 | sp-2 | an-383 | 1C3792 | sp-2 | an-383 |
| 1A6432 | sp-2 | an-384 | 1U5301 | sp-2 | an-384 | 1C3793 | sp-2 | an-384 |
| 1A6433 | sp-2 | an-385 | 1U5302 | sp-2 | an-385 | 1C3794 | sp-2 | an-385 |
| 1A6434 | sp-2 | an-386 | 1U5303 | sp-2 | an-386 | 1C3795 | sp-2 | an-386 |
| 1A6435 | sp-2 | an-387 | 1U5304 | sp-2 | an-387 | 1C3796 | sp-2 | an-387 |
| 1A6436 | sp-2 | an-388 | 1U5305 | sp-2 | an-388 | 1C3797 | sp-2 | an-388 |
| 1A6437 | sp-2 | an-389 | 1U5306 | sp-2 | an-389 | 1C3798 | sp-2 | an-389 |
| 1A6438 | sp-2 | an-390 | 1U5307 | sp-2 | an-390 | 1C3799 | sp-2 | an-390 |
| 1A6439 | sp-2 | an-391 | 1U5308 | sp-2 | an-391 | 1C3800 | sp-2 | an-391 |
| 1A6440 | sp-2 | an-392 | 1U5309 | sp-2 | an-392 | 1C3801 | sp-2 | an-392 |
| 1A6441 | sp-2 | an-393 | 1U5310 | sp-2 | an-393 | 1C3802 | sp-2 | an-393 |
| 1A6442 | sp-3 | an-378 | 1U5311 | sp-3 | an-378 | 1C3803 | sp-3 | an-378 |
| 1A6443 | sp-3 | an-379 | 1U5312 | sp-3 | an-379 | 1C3804 | sp-3 | an-379 |
| 1A6444 | sp-3 | an-380 | 1U5313 | sp-3 | an-380 | 1C3805 | sp-3 | an-380 |
| 1A6445 | sp-3 | an-381 | 1U5314 | sp-3 | an-381 | 1C3806 | sp-3 | an-381 |
| 1A6446 | sp-3 | an-382 | 1U5315 | sp-3 | an-382 | 1C3807 | sp-3 | an-382 |

Table 2-96

| Ex. No. | Z | $N^+R^5R^6R^7$ | Ex. No. | Z | $N^+R^5R^6R^7$ | Ex. No. | Z | $N^+R^5R^6R^7$ |
|---|---|---|---|---|---|---|---|---|
| Y = NHCS | | | Y = NHCSNH | | | Y = NHCSO | | |
| 1A6447 | sp-3 | an-383 | 1U5316 | sp-3 | an-383 | 1C3808 | sp-3 | an-383 |
| 1A6448 | sp-3 | an-384 | 1U5317 | sp-3 | an-384 | 1C3809 | sp-3 | an-384 |
| 1A6449 | sp-3 | an-385 | 1U5318 | sp-3 | an-385 | 1C3810 | sp-3 | an-385 |
| 1A6450 | sp-3 | an-386 | 1U5319 | sp-3 | an-386 | 1C3811 | sp-3 | an-386 |
| 1A6451 | sp-3 | an-387 | 1U5320 | sp-3 | an-387 | 1C3812 | sp-3 | an-387 |
| 1A6452 | sp-3 | an-388 | 1U5321 | sp-3 | an-388 | 1C3813 | sp-3 | an-388 |
| 1A6453 | sp-3 | an-389 | 1U5322 | sp-3 | an-389 | 1C3814 | sp-3 | an-389 |
| 1A6454 | sp-3 | an-390 | 1U5323 | sp-3 | an-390 | 1C3815 | sp-3 | an-390 |
| 1A6455 | sp-3 | an-391 | 1U5324 | sp-3 | an-391 | 1C3816 | sp-3 | an-391 |
| 1A6456 | sp-3 | an-392 | 1U5325 | sp-3 | an-392 | 1C3817 | sp-3 | an-392 |
| 1A6457 | sp-3 | an-393 | 1U5326 | sp-3 | an-393 | 1C3818 | sp-3 | an-393 |
| 1A6458 | sp-4 | an-378 | 1U5327 | sp-4 | an-378 | 1C3819 | sp-4 | an-378 |
| 1A6459 | sp-4 | an-379 | 1U5328 | sp-4 | an-379 | 1C3820 | sp-4 | an-379 |
| 1A6460 | sp-4 | an-380 | 1U5329 | sp-4 | an-380 | 1C3821 | sp-4 | an-380 |
| 1A6461 | sp-4 | an-381 | 1U5330 | sp-4 | an-381 | 1C3822 | sp-4 | an-381 |
| 1A6462 | sp-4 | an-382 | 1U5331 | sp-4 | an-382 | 1C3823 | sp-4 | an-382 |
| 1A6463 | sp-4 | an-383 | 1U5332 | sp-4 | an-383 | 1C3824 | sp-4 | an-383 |
| 1A6464 | sp-4 | an-384 | 1U5333 | sp-4 | an-384 | 1C3825 | sp-4 | an-384 |
| 1A6465 | sp-4 | an-385 | 1U5334 | sp-4 | an-385 | 1C3826 | sp-4 | an-385 |
| 1A6466 | sp-4 | an-386 | 1U5335 | sp-4 | an-386 | 1C3827 | sp-4 | an-386 |
| 1A6467 | sp-4 | an-387 | 1U5336 | sp-4 | an-387 | 1C3828 | sp-4 | an-387 |
| 1A6468 | sp-4 | an-388 | 1U5337 | sp-4 | an-388 | 1C3829 | sp-4 | an-388 |
| 1A6469 | sp-4 | an-389 | 1U5338 | sp-4 | an-389 | 1C3830 | sp-4 | an-389 |
| 1A6470 | sp-4 | an-390 | 1U5339 | sp-4 | an-390 | 1C3831 | sp-4 | an-390 |
| 1A6471 | sp-4 | an-391 | 1U5340 | sp-4 | an-391 | 1C3832 | sp-4 | an-391 |
| 1A6472 | sp-4 | an-392 | 1U5341 | sp-4 | an-392 | 1C3833 | sp-4 | an-392 |
| 1A6473 | sp-4 | an-393 | 1U5342 | sp-4 | an-393 | 1C3834 | sp-4 | an-393 |

-continued

| Ex. No. | Z | N⁺R⁵R⁶R⁷ | Ex. No. | Z | N⁺R⁵R⁶R⁷ | Ex. No. | Z | N⁺R⁵R⁶R⁷ |
|---|---|---|---|---|---|---|---|---|
| 1A6474 | sp-5 | an-378 | 1U5343 | sp-5 | an-378 | 1C3835 | sp-5 | an-378 |
| 1A6475 | sp-5 | an-379 | 1U5344 | sp-5 | an-379 | 1C3836 | sp-5 | an-379 |
| 1A6476 | sp-5 | an-380 | 1U5345 | sp-5 | an-380 | 1C3837 | sp-5 | an-380 |
| 1A6477 | sp-5 | an-381 | 1U5346 | sp-5 | an-381 | 1C3838 | sp-5 | an-381 |
| 1A6478 | sp-5 | an-382 | 1U5347 | sp-5 | an-382 | 1C3839 | sp-5 | an-382 |
| 1A6479 | sp-5 | an-383 | 1U5348 | sp-5 | an-383 | 1C3840 | sp-5 | an-383 |
| 1A6480 | sp-5 | an-384 | 1U5349 | sp-5 | an-384 | 1C3841 | sp-5 | an-384 |
| 1A6481 | sp-5 | an-385 | 1U5350 | sp-5 | an-385 | 1C3842 | sp-5 | an-385 |
| 1A6482 | sp-5 | an-386 | 1U5351 | sp-5 | an-386 | 1C3843 | sp-5 | an-386 |
| 1A6483 | sp-5 | an-387 | 1U5352 | sp-5 | an-387 | 1C3844 | sp-5 | an-387 |
| 1A6484 | sp-5 | an-388 | 1U5353 | sp-5 | an-388 | 1C3845 | sp-5 | an-388 |
| 1A6485 | sp-5 | an-389 | 1U5354 | sp-5 | an-389 | 1C3846 | sp-5 | an-389 |
| 1A6486 | sp-5 | an-390 | 1U5355 | sp-5 | an-390 | 1C3847 | sp-5 | an-390 |
| 1A6487 | sp-5 | an-391 | 1U5356 | sp-5 | an-391 | 1C3848 | sp-5 | an-391 |
| 1A6488 | sp-5 | an-392 | 1U5357 | sp-5 | an-392 | 1C3849 | sp-5 | an-392 |
| 1A6489 | sp-5 | an-393 | 1U5358 | sp-5 | an-393 | 1C3850 | sp-5 | an-393 |
| 1A6490 | sp-6 | an-378 | 1U5359 | sp-6 | an-378 | 1C3851 | sp-6 | an-378 |
| 1A6491 | sp-6 | an-379 | 1U5360 | sp-6 | an-379 | 1C3852 | sp-6 | an-379 |
| 1A6492 | sp-6 | an-380 | 1U5361 | sp-6 | an-380 | 1C3853 | sp-6 | an-380 |
| 1A6493 | sp-6 | an-381 | 1U5362 | sp-6 | an-381 | 1C3854 | sp-6 | an-381 |
| 1A6494 | sp-6 | an-382 | 1U5363 | sp-6 | an-382 | 1C3855 | sp-6 | an-382 |
| 1A6495 | sp-6 | an-383 | 1U5364 | sp-6 | an-383 | 1C3856 | sp-6 | an-383 |
| 1A6496 | sp-6 | an-384 | 1U5365 | sp-6 | an-384 | 1C3857 | sp-6 | an-384 |
| 1A6497 | sp-6 | an-385 | 1U5366 | sp-6 | an-385 | 1C3858 | sp-6 | an-385 |
| 1A6498 | sp-6 | an-386 | 1U5367 | sp-6 | an-386 | 1C3859 | sp-6 | an-386 |
| 1A6499 | sp-6 | an-387 | 1U5368 | sp-6 | an-387 | 1C3860 | sp-6 | an-387 |
| 1A6500 | sp-6 | an-388 | 1U5369 | sp-6 | an-388 | 1C3861 | sp-6 | an-388 |
| 1A6501 | sp-6 | an-389 | 1U5370 | sp-6 | an-389 | 1C3862 | sp-6 | an-389 |
| 1A6502 | sp-6 | an-390 | 1U5371 | sp-6 | an-390 | 1C3863 | sp-6 | an-390 |

Table 2-97

| Y = NHCS | | | Y = NHCSNH | | | Y = NHCSO | | |
|---|---|---|---|---|---|---|---|---|
| 1A6503 | sp-6 | an-391 | 1U5372 | sp-6 | an-391 | 1C3864 | sp-6 | an-391 |
| 1A6504 | sp-6 | an-392 | 1U5373 | sp-6 | an-392 | 1C3865 | sp-6 | an-392 |
| 1A6505 | sp-6 | an-393 | 1U5374 | sp-6 | an-393 | 1C3866 | sp-6 | an-393 |
| 1A6506 | sp-7 | an-378 | 1U5375 | sp-7 | an-378 | 1C3867 | sp-7 | an-378 |
| 1A6507 | sp-7 | an-379 | 1U5376 | sp-7 | an-379 | 1C3868 | sp-7 | an-379 |
| 1A6508 | sp-7 | an-380 | 1U5377 | sp-7 | an-380 | 1C3869 | sp-7 | an-380 |
| 1A6509 | sp-7 | an-381 | 1U5378 | sp-7 | an-381 | 1C3870 | sp-7 | an-381 |
| 1A6510 | sp-7 | an-382 | 1U5379 | sp-7 | an-382 | 1C3871 | sp-7 | an-382 |
| 1A6511 | sp-7 | an-383 | 1U5380 | sp-7 | an-383 | 1C3872 | sp-7 | an-383 |
| 1A6512 | sp-7 | an-384 | 1U5381 | sp-7 | an-384 | 1C3873 | sp-7 | an-384 |
| 1A6513 | sp-7 | an-385 | 1U5382 | sp-7 | an-385 | 1C3874 | sp-7 | an-385 |
| 1A6514 | sp-7 | an-386 | 1U5383 | sp-7 | an-386 | 1C3875 | sp-7 | an-386 |
| 1A6515 | sp-7 | an-387 | 1U5384 | sp-7 | an-387 | 1C3876 | sp-7 | an-387 |
| 1A6516 | sp-7 | an-388 | 1U5385 | sp-7 | an-388 | 1C3877 | sp-7 | an-388 |
| 1A6517 | sp-7 | an-389 | 1U5386 | sp-7 | an-389 | 1C3878 | sp-7 | an-389 |
| 1A6518 | sp-7 | an-390 | 1U5387 | sp-7 | an-390 | 1C3879 | sp-7 | an-390 |
| 1A6519 | sp-7 | an-391 | 1U5388 | sp-7 | an-391 | 1C3880 | sp-7 | an-391 |
| 1A6520 | sp-7 | an-392 | 1U5389 | sp-7 | an-392 | 1C3881 | sp-7 | an-392 |
| 1A6521 | sp-7 | an-393 | 1U5390 | sp-7 | an-393 | 1C3882 | sp-7 | an-393 |
| 1A6522 | sp-8 | an-378 | 1U5391 | sp-8 | an-378 | 1C3883 | sp-8 | an-378 |
| 1A6523 | sp-8 | an-379 | 1U5392 | sp-8 | an-379 | 1C3884 | sp-8 | an-379 |
| 1A6524 | sp-8 | an-380 | 1U5393 | sp-8 | an-380 | 1C3885 | sp-8 | an-380 |
| 1A6525 | sp-8 | an-381 | 1U5394 | sp-8 | an-381 | 1C3886 | sp-8 | an-381 |
| 1A6526 | sp-8 | an-382 | 1U5395 | sp-8 | an-382 | 1C3887 | sp-8 | an-382 |
| 1A6527 | sp-8 | an-383 | 1U5396 | sp-8 | an-383 | 1C3888 | sp-8 | an-383 |
| 1A6528 | sp-8 | an-384 | 1U5397 | sp-8 | an-384 | 1C3889 | sp-8 | an-384 |
| 1A6529 | sp-8 | an-385 | 1U5398 | sp-8 | an-385 | 1C3890 | sp-8 | an-385 |
| 1A6530 | sp-8 | an-386 | 1U5399 | sp-8 | an-386 | 1C3891 | sp-8 | an-386 |
| 1A6531 | sp-8 | an-387 | 1U5400 | sp-8 | an-387 | 1C3892 | sp-8 | an-387 |
| 1A6532 | sp-8 | an-388 | 1U5401 | sp-8 | an-388 | 1C3893 | sp-8 | an-388 |
| 1A6533 | sp-8 | an-389 | 1U5402 | sp-8 | an-389 | 1C3894 | sp-8 | an-389 |
| 1A6534 | sp-8 | an-390 | 1U5403 | sp-8 | an-390 | 1C3895 | sp-8 | an-390 |
| 1A6535 | sp-8 | an-391 | 1U5404 | sp-8 | an-391 | 1C3896 | sp-8 | an-391 |
| 1A6536 | sp-8 | an-392 | 1U5405 | sp-8 | an-392 | 1C3897 | sp-8 | an-392 |
| 1A6537 | sp-8 | an-393 | 1U5406 | sp-8 | an-393 | 1C3898 | sp-8 | an-393 |
| 1A6538 | sp-9 | an-378 | 1U5407 | sp-9 | an-378 | 1C3899 | sp-9 | an-378 |
| 1A6539 | sp-9 | an-379 | 1U5408 | sp-9 | an-379 | 1C3900 | sp-9 | an-379 |
| 1A6540 | sp-9 | an-380 | 1U5409 | sp-9 | an-380 | 1C3901 | sp-9 | an-380 |
| 1A6541 | sp-9 | an-381 | 1U5410 | sp-9 | an-381 | 1C3902 | sp-9 | an-381 |
| 1A6542 | sp-9 | an-382 | 1U5411 | sp-9 | an-382 | 1C3903 | sp-9 | an-382 |
| 1A6543 | sp-9 | an-383 | 1U5412 | sp-9 | an-383 | 1C3904 | sp-9 | an-383 |
| 1A6544 | sp-9 | an-384 | 1U5413 | sp-9 | an-384 | 1C3905 | sp-9 | an-384 |
| 1A6545 | sp-9 | an-385 | 1U5414 | sp-9 | an-385 | 1C3906 | sp-9 | an-385 |
| 1A6546 | sp-9 | an-386 | 1U5415 | sp-9 | an-386 | 1C3907 | sp-9 | an-386 |
| 1A6547 | sp-9 | an-387 | 1U5416 | sp-9 | an-387 | 1C3908 | sp-9 | an-387 |

-continued

| Ex. No. | Z | N⁺R⁵R⁶R⁷ | Ex. No. | Z | N⁺R⁵R⁶R⁷ | Ex. No. | Z | N⁺R⁵R⁶R⁷ |
|---|---|---|---|---|---|---|---|---|
| 1A6548 | sp-9 | an-388 | 1U5417 | sp-9 | an-388 | 1C3909 | sp-9 | an-388 |
| 1A6549 | sp-9 | an-389 | 1U5418 | sp-9 | an-389 | 1C3910 | sp-9 | an-389 |
| 1A6550 | sp-9 | an-390 | 1U5419 | sp-9 | an-390 | 1C3911 | sp-9 | an-390 |
| 1A6551 | sp-9 | an-391 | 1U5420 | sp-9 | an-391 | 1C3912 | sp-9 | an-391 |
| 1A6552 | sp-9 | an-392 | 1U5421 | sp-9 | an-392 | 1C3913 | sp-9 | an-392 |
| 1A6553 | sp-9 | an-393 | 1U5422 | sp-9 | an-393 | 1C3914 | sp-9 | an-393 |
| 1A6554 | sp-10 | an-378 | 1U5423 | sp-12 | an-378 | 1C3915 | sp-11 | an-378 |
| 1A6555 | sp-10 | an-379 | 1U5424 | sp-12 | an-379 | 1C3916 | sp-11 | an-379 |
| 1A6556 | sp-10 | an-380 | 1U5425 | sp-12 | an-380 | 1C3917 | sp-11 | an-380 |
| 1A6557 | sp-10 | an-381 | 1U5426 | sp-12 | an-381 | 1C3918 | sp-11 | an-381 |
| 1A6558 | sp-10 | an-382 | 1U5427 | sp-12 | an-382 | 1C3919 | sp-11 | an-382 |

Table 2-98

| Y = NHCS | | | Y = NHCSNH | | | Y = NHCSO | | |
|---|---|---|---|---|---|---|---|---|
| 1A6559 | sp-10 | an-383 | 1U5428 | sp-12 | an-383 | 1C3920 | sp-11 | an-383 |
| 1A6560 | sp-10 | an-384 | 1U5429 | sp-12 | an-384 | 1C3921 | sp-11 | an-384 |
| 1A6561 | sp-10 | an-385 | 1U5430 | sp-12 | an-385 | 1C3922 | sp-11 | an-385 |
| 1A6562 | sp-10 | an-386 | 1U5431 | sp-12 | an-386 | 1C3923 | sp-11 | an-386 |
| 1A6563 | sp-10 | an-387 | 1U5432 | sp-12 | an-387 | 1C3924 | sp-11 | an-387 |
| 1A6564 | sp-10 | an-388 | 1U5433 | sp-12 | an-388 | 1C3925 | sp-11 | an-388 |
| 1A6565 | sp-10 | an-389 | 1U5434 | sp-12 | an-389 | 1C3926 | sp-11 | an-389 |
| 1A6566 | sp-10 | an-390 | 1U5435 | sp-12 | an-390 | 1C3927 | sp-11 | an-390 |
| 1A6567 | sp-10 | an-391 | 1U5436 | sp-12 | an-391 | 1C3928 | sp-11 | an-391 |
| 1A6568 | sp-10 | an-392 | 1U5437 | sp-12 | an-392 | 1C3929 | sp-11 | an-392 |
| 1A6569 | sp-10 | an-393 | 1U5438 | sp-12 | an-393 | 1C3930 | sp-11 | an-393 |
| 1A6570 | sp-14 | an-378 | 1U5439 | sp-13 | an-378 | | | |
| 1A6571 | sp-14 | an-379 | 1U5440 | sp-13 | an-379 | | | |
| 1A6572 | sp-14 | an-380 | 1U5441 | sp-13 | an-380 | | | |
| 1A6573 | sp-14 | an-381 | 1U5442 | sp-13 | an-381 | | | |
| 1A6574 | sp-14 | an-382 | 1U5443 | sp-13 | an-382 | | | |
| 1A6575 | sp-14 | an-383 | 1U5444 | sp-13 | an-383 | | | |
| 1A6576 | sp-14 | an-384 | 1U5445 | sp-13 | an-384 | | | |
| 1A6577 | sp-14 | an-385 | 1U5446 | sp-13 | an-385 | | | |
| 1A6578 | sp-14 | an-386 | 1U5447 | sp-13 | an-386 | | | |
| 1A6579 | sp-14 | an-387 | 1U5448 | sp-13 | an-387 | | | |
| 1A6580 | sp-14 | an-388 | 1U5449 | sp-13 | an-388 | | | |
| 1A6581 | sp-14 | an-389 | 1U5450 | sp-13 | an-389 | | | |
| 1A6582 | sp-14 | an-390 | 1U5451 | sp-13 | an-390 | | | |
| 1A6583 | sp-14 | an-391 | 1U5452 | sp-13 | an-391 | | | |
| 1A6584 | sp-14 | an-392 | 1U5453 | sp-13 | an-392 | | | |
| 1A6585 | sp-14 | an-393 | 1U5454 | sp-13 | an-393 | | | |
| | | | | | | Y = NHCS | | |
| 1A6586 | sp-15 | an-378 | 1U5455 | sp-14 | an-378 | 1A6634 | sp-19 | an-378 |
| 1A6587 | sp-15 | an-379 | 1U5456 | sp-14 | an-379 | 1A6635 | sp-19 | an-379 |
| 1A6588 | sp-15 | an-380 | 1U5457 | sp-14 | an-380 | 1A6636 | sp-19 | an-380 |
| 1A6589 | sp-15 | an-381 | 1U5458 | sp-14 | an-381 | 1A6637 | sp-19 | an-381 |
| 1A6590 | sp-15 | an-382 | 1U5459 | sp-14 | an-382 | 1A6638 | sp-19 | an-382 |
| 1A6591 | sp-15 | an-383 | 1U5460 | sp-14 | an-383 | 1A6639 | sp-19 | an-383 |
| 1A6592 | sp-15 | an-384 | 1U5461 | sp-14 | an-384 | 1A6640 | sp-19 | an-384 |
| 1A6593 | sp-15 | an-385 | 1U5462 | sp-14 | an-385 | 1A6641 | sp-19 | an-385 |
| 1A6594 | sp-15 | an-386 | 1U5463 | sp-14 | an-386 | 1A6642 | sp-19 | an-386 |
| 1A6595 | sp-15 | an-387 | 1U5464 | sp-14 | an-387 | 1A6643 | sp-19 | an-387 |
| 1A6596 | sp-15 | an-388 | 1U5465 | sp-14 | an-388 | 1A6644 | sp-19 | an-388 |
| 1A6597 | sp-15 | an-389 | 1U5466 | sp-14 | an-389 | 1A6645 | sp-19 | an-389 |
| 1A6598 | sp-15 | an-390 | 1U5467 | sp-14 | an-390 | 1A6646 | sp-19 | an-390 |
| 1A6599 | sp-15 | an-391 | 1U5468 | sp-14 | an-391 | 1A6647 | sp-19 | an-391 |
| 1A6600 | sp-15 | an-392 | 1U5469 | sp-14 | an-392 | 1A6648 | sp-19 | an-392 |
| 1A6601 | sp-15 | an-393 | 1U5470 | sp-14 | an-393 | 1A6649 | sp-19 | an-393 |
| 1A6602 | sp-16 | an-378 | 1U5471 | sp-17 | an-378 | 1A6650 | sp-21 | an-378 |
| 1A6603 | sp-16 | an-379 | 1U5472 | sp-17 | an-379 | 1A6651 | sp-21 | an-379 |
| 1A6604 | sp-16 | an-380 | 1U5473 | sp-17 | an-380 | 1A6652 | sp-21 | an-380 |
| 1A6605 | sp-16 | an-381 | 1U5474 | sp-17 | an-381 | 1A6653 | sp-21 | an-381 |
| 1A6606 | sp-16 | an-382 | 1U5475 | sp-17 | an-382 | 1A6654 | sp-21 | an-382 |
| 1A6607 | sp-16 | an-383 | 1U5476 | sp-17 | an-383 | 1A6655 | sp-21 | an-383 |
| 1A6608 | sp-16 | an-384 | 1U5477 | sp-17 | an-384 | 1A6656 | sp-21 | an-384 |
| 1A6609 | sp-16 | an-385 | 1U5478 | sp-17 | an-385 | 1A6657 | sp-21 | an-385 |
| 1A6610 | sp-16 | an-386 | 1U5479 | sp-17 | an-386 | 1A6658 | sp-21 | an-386 |
| 1A6611 | sp-16 | an-387 | 1U5480 | sp-17 | an-387 | 1A6659 | sp-21 | an-387 |
| 1A6612 | sp-16 | an-388 | 1U5481 | sp-17 | an-388 | 1A6660 | sp-21 | an-388 |
| 1A6613 | sp-16 | an-389 | 1U5482 | sp-17 | an-389 | 1A6661 | sp-21 | an-389 |

Table 2-99

| Y = NHCS | | | Y = NHCSNH | | | Y = NHCS | | |
|---|---|---|---|---|---|---|---|---|
| 1A6614 | sp-16 | an-390 | 1U5483 | sp-17 | an-390 | 1A6662 | sp-21 | an-390 |
| 1A6615 | sp-16 | an-391 | 1U5484 | sp-17 | an-391 | 1A6663 | sp-21 | an-391 |
| 1A6616 | sp-16 | an-392 | 1U5485 | sp-17 | an-392 | 1A6664 | sp-21 | an-392 |

-continued

| Ex. No. | Z | N⁺R⁵R⁶R⁷ | Ex. No. | Z | N⁺R⁵R⁶R⁷ | Ex. No. | Z | N⁺R⁵R⁶R⁷ |
|---|---|---|---|---|---|---|---|---|
| 1A6617 | sp-16 | an-393 | 1U5486 | sp-17 | an-393 | 1A6665 | sp-21 | an-393 |
| 1A6618 | sp-18 | an-378 | 1U5487 | sp-20 | an-378 | 1A6666 | sp-22 | an-378 |
| 1A6619 | sp-18 | an-379 | 1U5488 | sp-20 | an-379 | 1A6667 | sp-22 | an-379 |
| 1A6620 | sp-18 | an-380 | 1U5489 | sp-20 | an-380 | 1A6668 | sp-22 | an-380 |
| 1A6621 | sp-18 | an-381 | 1U5490 | sp-20 | an-381 | 1A6669 | sp-22 | an-381 |
| 1A6622 | sp-18 | an-382 | 1U5491 | sp-20 | an-382 | 1A6670 | sp-22 | an-382 |
| 1A6623 | sp-18 | an-383 | 1U5492 | sp-20 | an-383 | 1A6671 | sp-22 | an-383 |
| 1A6624 | sp-18 | an-384 | 1U5493 | sp-20 | an-384 | 1A6672 | sp-22 | an-384 |
| 1A6625 | sp-18 | an-385 | 1U5494 | sp-20 | an-385 | 1A6673 | sp-22 | an-385 |
| 1A6626 | sp-18 | an-386 | 1U5495 | sp-20 | an-386 | 1A6674 | sp-22 | an-386 |
| 1A6627 | sp-18 | an-387 | 1U5496 | sp-20 | an-387 | 1A6675 | sp-22 | an-387 |
| 1A6628 | sp-18 | an-388 | 1U5497 | sp-20 | an-388 | 1A6676 | sp-22 | an-388 |
| 1A6629 | sp-18 | an-389 | 1U5498 | sp-20 | an-389 | 1A6677 | sp-22 | an-389 |
| 1A6630 | sp-18 | an-390 | 1U5499 | sp-20 | an-390 | 1A6678 | sp-22 | an-390 |
| 1A6631 | sp-18 | an-391 | 1U5500 | sp-20 | an-391 | 1A6679 | sp-22 | an-391 |
| 1A6632 | sp-18 | an-392 | 1U5501 | sp-20 | an-392 | 1A6680 | sp-22 | an-392 |
| 1A6633 | sp-18 | an-393 | 1U5502 | sp-20 | an-393 | 1A6681 | sp-22 | an-393 |
| Y = NHCSNH | | | Y = NHCSNH | | | Y = NHCSNH | | |
| 1U5503 | sp-23 | an-1 | 1U5896 | sp-24 | an-1 | 1U6289 | sp-25 | an-1 |
| 1U5504 | sp-23 | an-2 | 1U5897 | sp-24 | an-2 | 1U6290 | sp-25 | an-2 |
| 1U5505 | sp-23 | an-3 | 1U5898 | sp-24 | an-3 | 1U6291 | sp-25 | an-3 |
| 1U5506 | sp-23 | an-4 | 1U5899 | sp-24 | an-4 | 1U6292 | sp-25 | an-4 |
| 1U5507 | sp-23 | an-5 | 1U5900 | sp-24 | an-5 | 1U6293 | sp-25 | an-5 |
| 1U5508 | sp-23 | an-6 | 1U5901 | sp-24 | an-6 | 1U6294 | sp-25 | an-6 |
| 1U5509 | sp-23 | an-7 | 1U5902 | sp-24 | an-7 | 1U6295 | sp-25 | an-7 |
| 1U5510 | sp-23 | an-8 | 1U5903 | sp-24 | an-8 | 1U6296 | sp-25 | an-8 |
| 1U5511 | sp-23 | an-9 | 1U5904 | sp-24 | an-9 | 1U6297 | sp-25 | an-9 |
| 1U5512 | sp-23 | an-10 | 1U5905 | sp-24 | an-10 | 1U6298 | sp-25 | an-10 |
| 1U5513 | sp-23 | an-11 | 1U5906 | sp-24 | an-11 | 1U6299 | sp-25 | an-11 |
| 1U5514 | sp-23 | an-12 | 1U5907 | sp-24 | an-12 | 1U6300 | sp-25 | an-12 |
| 1U5515 | sp-23 | an-13 | 1U5908 | sp-24 | an-13 | 1U6301 | sp-25 | an-13 |
| 1U5516 | sp-23 | an-14 | 1U5909 | sp-24 | an-14 | 1U6302 | sp-25 | an-14 |
| 1U5517 | sp-23 | an-15 | 1U5910 | sp-24 | an-15 | 1U6303 | sp-25 | an-15 |
| 1U5518 | sp-23 | an-16 | 1U5911 | sp-24 | an-16 | 1U6304 | sp-25 | an-16 |
| 1U5519 | sp-23 | an-17 | 1U5912 | sp-24 | an-17 | 1U6305 | sp-25 | an-17 |
| 1U5520 | sp-23 | an-18 | 1U5913 | sp-24 | an-18 | 1U6306 | sp-25 | an-18 |
| 1U5521 | sp-23 | an-19 | 1U5914 | sp-24 | an-19 | 1U6307 | sp-25 | an-19 |
| 1U5522 | sp-23 | an-20 | 1U5915 | sp-24 | an-20 | 1U6308 | sp-25 | an-20 |
| 1U5523 | sp-23 | an-21 | 1U5916 | sp-24 | an-21 | 1U6309 | sp-25 | an-21 |
| 1U5524 | sp-23 | an-22 | 1U5917 | sp-24 | an-22 | 1U6310 | sp-25 | an-22 |
| 1U5525 | sp-23 | an-23 | 1U5918 | sp-24 | an-23 | 1U6311 | sp-25 | an-23 |
| 1U5526 | sp-23 | an-24 | 1U5919 | sp-24 | an-24 | 1U6312 | sp-25 | an-24 |
| 1U5527 | sp-23 | an-25 | 1U5920 | sp-24 | an-25 | 1U6313 | sp-25 | an-25 |
| 1U5528 | sp-23 | an-26 | 1U5921 | sp-24 | an-26 | 1U6314 | sp-25 | an-26 |
| 1U5529 | sp-23 | an-27 | 1U5922 | sp-24 | an-27 | 1U6315 | sp-25 | an-27 |
| 1U5530 | sp-23 | an-28 | 1U5923 | sp-24 | an-28 | 1U6316 | sp-25 | an-28 |
| 1U5531 | sp-23 | an-29 | 1U5924 | sp-24 | an-29 | 1U6317 | sp-25 | an-29 |
| 1U5532 | sp-23 | an-30 | 1U5925 | sp-24 | an-30 | 1U6318 | sp-25 | an-30 |
| 1U5533 | sp-23 | an-31 | 1U5926 | sp-24 | an-31 | 1U6319 | sp-25 | an-31 |
| 1U5534 | sp-23 | an-32 | 1U5927 | sp-24 | an-32 | 1U6320 | sp-25 | an-32 |
| 1U5535 | sp-23 | an-33 | 1U5928 | sp-24 | an-33 | 1U6321 | sp-25 | an-33 |

Table 2-100

| Y = NHCSNH | | | Y = NHCSNH | | | Y = NHCSNH | | |
|---|---|---|---|---|---|---|---|---|
| 1U5536 | sp-23 | an-34 | 1U5929 | sp-24 | an-34 | 1U6322 | sp-25 | an-34 |
| 1U5537 | sp-23 | an-35 | 1U5930 | sp-24 | an-35 | 1U6323 | sp-25 | an-35 |
| 1U5538 | sp-23 | an-36 | 1U5931 | sp-24 | an-36 | 1U6324 | sp-25 | an-36 |
| 1U5539 | sp-23 | an-37 | 1U5932 | sp-24 | an-37 | 1U6325 | sp-25 | an-37 |
| 1U5540 | sp-23 | an-38 | 1U5933 | sp-24 | an-38 | 1U6326 | sp-25 | an-38 |
| 1U5541 | sp-23 | an-39 | 1U5934 | sp-24 | an-39 | 1U6327 | sp-25 | an-39 |
| 1U5542 | sp-23 | an-40 | 1U5935 | sp-24 | an-40 | 1U6328 | sp-25 | an-40 |
| 1U5543 | sp-23 | an-41 | 1U5936 | sp-24 | an-41 | 1U6329 | sp-25 | an-41 |
| 1U5544 | sp-23 | an-42 | 1U5937 | sp-24 | an-42 | 1U6330 | sp-25 | an-42 |
| 1U5545 | sp-23 | an-43 | 1U5938 | sp-24 | an-43 | 1U6331 | sp-25 | an-43 |
| 1U5546 | sp-23 | an-44 | 1U5939 | sp-24 | an-44 | 1U6332 | sp-25 | an-44 |
| 1U5547 | sp-23 | an-45 | 1U5940 | sp-24 | an-45 | 1U6333 | sp-25 | an-45 |
| 1U5548 | sp-23 | an-46 | 1U5941 | sp-24 | an-46 | 1U6334 | sp-25 | an-46 |
| 1U5549 | sp-23 | an-47 | 1U5942 | sp-24 | an-47 | 1U6335 | sp-25 | an-47 |
| 1U5550 | sp-23 | an-48 | 1U5943 | sp-24 | an-48 | 1U6336 | sp-25 | an-48 |
| 1U5551 | sp-23 | an-49 | 1U5944 | sp-24 | an-49 | 1U6337 | sp-25 | an-49 |
| 1U5552 | sp-23 | an-50 | 1U5945 | sp-24 | an-50 | 1U6338 | sp-25 | an-50 |
| 1U5553 | sp-23 | an-51 | 1U5946 | sp-24 | an-51 | 1U6339 | sp-25 | an-51 |
| 1U5554 | sp-23 | an-52 | 1U5947 | sp-24 | an-52 | 1U6340 | sp-25 | an-52 |
| 1U5555 | sp-23 | an-53 | 1U5948 | sp-24 | an-53 | 1U6341 | sp-25 | an-53 |
| 1U5556 | sp-23 | an-54 | 1U5949 | sp-24 | an-54 | 1U6342 | sp-25 | an-54 |
| 1U5557 | sp-23 | an-55 | 1U5950 | sp-24 | an-55 | 1U6343 | sp-25 | an-55 |

-continued

| Ex. No. | Z | N⁺R⁵R⁶R⁷ | Ex. No. | Z | N⁺R⁵R⁶R⁷ | Ex. No. | Z | N⁺R⁵R⁶R⁷ |
|---|---|---|---|---|---|---|---|---|
| 1U5558 | sp-23 | an-56 | 1U5951 | sp-24 | an-56 | 1U6344 | sp-25 | an-56 |
| 1U5559 | sp-23 | an-57 | 1U5952 | sp-24 | an-57 | 1U6345 | sp-25 | an-57 |
| 1U5560 | sp-23 | an-58 | 1U5953 | sp-24 | an-58 | 1U6346 | sp-25 | an-58 |
| 1U5561 | sp-23 | an-59 | 1U5954 | sp-24 | an-59 | 1U6347 | sp-25 | an-59 |
| 1U5562 | sp-23 | an-60 | 1U5955 | sp-24 | an-60 | 1U6348 | sp-25 | an-60 |
| 1U5563 | sp-23 | an-61 | 1U5956 | sp-24 | an-61 | 1U6349 | sp-25 | an-61 |
| 1U5564 | sp-23 | an-62 | 1U5957 | sp-24 | an-62 | 1U6350 | sp-25 | an-62 |
| 1U5565 | sp-23 | an-63 | 1U5958 | sp-24 | an-63 | 1U6351 | sp-25 | an-63 |
| 1U5566 | sp-23 | an-64 | 1U5959 | sp-24 | an-64 | 1U6352 | sp-25 | an-64 |
| 1U5567 | sp-23 | an-65 | 1U5960 | sp-24 | an-65 | 1U6353 | sp-25 | an-65 |
| 1U5568 | sp-23 | an-66 | 1U5961 | sp-24 | an-66 | 1U6354 | sp-25 | an-66 |
| 1U5569 | sp-23 | an-67 | 1U5962 | sp-24 | an-67 | 1U6355 | sp-25 | an-67 |
| 1U5570 | sp-23 | an-68 | 1U5963 | sp-24 | an-68 | 1U6356 | sp-25 | an-68 |
| 1U5571 | sp-23 | an-69 | 1U5964 | sp-24 | an-69 | 1U6357 | sp-25 | an-69 |
| 1U5572 | sp-23 | an-70 | 1U5965 | sp-24 | an-70 | 1U6358 | sp-25 | an-70 |
| 1U5573 | sp-23 | an-71 | 1U5966 | sp-24 | an-71 | 1U6359 | sp-25 | an-71 |
| 1U5574 | sp-23 | an-72 | 1U5967 | sp-24 | an-72 | 1U6360 | sp-25 | an-72 |
| 1U5575 | sp-23 | an-73 | 1U5968 | sp-24 | an-73 | 1U6361 | sp-25 | an-73 |
| 1U5576 | sp-23 | an-74 | 1U5969 | sp-24 | an-74 | 1U6362 | sp-25 | an-74 |
| 1U5577 | sp-23 | an-75 | 1U5970 | sp-24 | an-75 | 1U6363 | sp-25 | an-75 |
| 1U5578 | sp-23 | an-76 | 1U5971 | sp-24 | an-76 | 1U6364 | sp-25 | an-76 |
| 1U5579 | sp-23 | an-77 | 1U5972 | sp-24 | an-77 | 1U6365 | sp-25 | an-77 |
| 1U5580 | sp-23 | an-78 | 1U5973 | sp-24 | an-78 | 1U6366 | sp-25 | an-78 |
| 1U5581 | sp-23 | an-79 | 1U5974 | sp-24 | an-79 | 1U6367 | sp-25 | an-79 |
| 1U5582 | sp-23 | an-80 | 1U5975 | sp-24 | an-80 | 1U6368 | sp-25 | an-80 |
| 1U5583 | sp-23 | an-81 | 1U5976 | sp-24 | an-81 | 1U6369 | sp-25 | an-81 |
| 1U5584 | sp-23 | an-82 | 1U5977 | sp-24 | an-82 | 1U6370 | sp-25 | an-82 |
| 1U5585 | sp-23 | an-83 | 1U5978 | sp-24 | an-83 | 1U6371 | sp-25 | an-83 |
| 1U5586 | sp-23 | an-84 | 1U5979 | sp-24 | an-84 | 1U6372 | sp-25 | an-84 |
| 1U5587 | sp-23 | an-85 | 1U5980 | sp-24 | an-85 | 1U6373 | sp-25 | an-85 |
| 1U5588 | sp-23 | an-86 | 1U5981 | sp-24 | an-86 | 1U6374 | sp-25 | an-86 |
| 1U5589 | sp-23 | an-87 | 1U5982 | sp-24 | an-87 | 1U6375 | sp-25 | an-87 |
| 1U5590 | sp-23 | an-88 | 1U5983 | sp-24 | an-88 | 1U6376 | sp-25 | an-88 |
| 1U5591 | sp-23 | an-89 | 1U5984 | sp-24 | an-89 | 1U6377 | sp-25 | an-89 |

Table 2-101

| Y = NHCSNH | | | Y = NHCSNH | | | Y = NHCSNH | | |
|---|---|---|---|---|---|---|---|---|
| 1U5592 | sp-23 | an-90 | 1U5985 | sp-24 | an-90 | 1U6378 | sp-25 | an-90 |
| 1U5593 | sp-23 | an-91 | 1U5986 | sp-24 | an-91 | 1U6379 | sp-25 | an-91 |
| 1U5594 | sp-23 | an-92 | 1U5987 | sp-24 | an-92 | 1U6380 | sp-25 | an-92 |
| 1U5595 | sp-23 | an-93 | 1U5988 | sp-24 | an-93 | 1U6381 | sp-25 | an-93 |
| 1U5596 | sp-23 | an-94 | 1U5989 | sp-24 | an-94 | 1U6382 | sp-25 | an-94 |
| 1U5597 | sp-23 | an-95 | 1U5990 | sp-24 | an-95 | 1U6383 | sp-25 | an-95 |
| 1U5598 | sp-23 | an-96 | 1U5991 | sp-24 | an-96 | 1U6384 | sp-25 | an-96 |
| 1U5599 | sp-23 | an-97 | 1U5992 | sp-24 | an-97 | 1U6385 | sp-25 | an-97 |
| 1U5600 | sp-23 | an-98 | 1U5993 | sp-24 | an-98 | 1U6386 | sp-25 | an-98 |
| 1U5601 | sp-23 | an-99 | 1U5994 | sp-24 | an-99 | 1U6387 | sp-25 | an-99 |
| 1U5602 | sp-23 | an-100 | 1U5995 | sp-24 | an-100 | 1U6388 | sp-25 | an-100 |
| 1U5603 | sp-23 | an-101 | 1U5996 | sp-24 | an-101 | 1U6389 | sp-25 | an-101 |
| 1U5604 | sp-23 | an-102 | 1U5997 | sp-24 | an-102 | 1U6390 | sp-25 | an-102 |
| 1U5605 | sp-23 | an-103 | 1U5998 | sp-24 | an-103 | 1U6391 | sp-25 | an-103 |
| 1U5606 | sp-23 | an-104 | 1U5999 | sp-24 | an-104 | 1U6392 | sp-25 | an-104 |
| 1U5607 | sp-23 | an-105 | 1U6000 | sp-24 | an-105 | 1U6393 | sp-25 | an-105 |
| 1U5608 | sp-23 | an-106 | 1U6001 | sp-24 | an-106 | 1U6394 | sp-25 | an-106 |
| 1U5609 | sp-23 | an-107 | 1U6002 | sp-24 | an-107 | 1U6395 | sp-25 | an-107 |
| 1U5610 | sp-23 | an-108 | 1U6003 | sp-24 | an-108 | 1U6396 | sp-25 | an-108 |
| 1U5611 | sp-23 | an-109 | 1U6004 | sp-24 | an-109 | 1U6397 | sp-25 | an-109 |
| 1U5612 | sp-23 | an-110 | 1U6005 | sp-24 | an-110 | 1U6398 | sp-25 | an-110 |
| 1U5613 | sp-23 | an-111 | 1U6006 | sp-24 | an-111 | 1U6399 | sp-25 | an-111 |
| 1U5614 | sp-23 | an-112 | 1U6007 | sp-24 | an-112 | 1U6400 | sp-25 | an-112 |
| 1U5615 | sp-23 | an-113 | 1U6008 | sp-24 | an-113 | 1U6401 | sp-25 | an-113 |
| 1U5616 | sp-23 | an-114 | 1U6009 | sp-24 | an-114 | 1U6402 | sp-25 | an-114 |
| 1U5617 | sp-23 | an-115 | 1U6010 | sp-24 | an-115 | 1U6403 | sp-25 | an-115 |
| 1U5618 | sp-23 | an-116 | 1U6011 | sp-24 | an-116 | 1U6404 | sp-25 | an-116 |
| 1U5619 | sp-23 | an-117 | 1U6012 | sp-24 | an-117 | 1U6405 | sp-25 | an-117 |
| 1U5620 | sp-23 | an-118 | 1U6013 | sp-24 | an-118 | 1U6406 | sp-25 | an-118 |
| 1U5621 | sp-23 | an-119 | 1U6014 | sp-24 | an-119 | 1U6407 | sp-25 | an-119 |
| 1U5622 | sp-23 | an-120 | 1U6015 | sp-24 | an-120 | 1U6408 | sp-25 | an-120 |
| 1U5623 | sp-23 | an-121 | 1U6016 | sp-24 | an-121 | 1U6409 | sp-25 | an-121 |
| 1U5624 | sp-23 | an-122 | 1U6017 | sp-24 | an-122 | 1U6410 | sp-25 | an-122 |
| 1U5625 | sp-23 | an-123 | 1U6018 | sp-24 | an-123 | 1U6411 | sp-25 | an-123 |
| 1U5626 | sp-23 | an-124 | 1U6019 | sp-24 | an-124 | 1U6412 | sp-25 | an-124 |
| 1U5627 | sp-23 | an-125 | 1U6020 | sp-24 | an-125 | 1U6413 | sp-25 | an-125 |
| 1U5628 | sp-23 | an-126 | 1U6021 | sp-24 | an-126 | 1U6414 | sp-25 | an-126 |
| 1U5629 | sp-23 | an-127 | 1U6022 | sp-24 | an-127 | 1U6415 | sp-25 | an-127 |
| 1U5630 | sp-23 | an-128 | 1U6023 | sp-24 | an-128 | 1U6416 | sp-25 | an-128 |
| 1U5631 | sp-23 | an-129 | 1U6024 | sp-24 | an-129 | 1U6417 | sp-25 | an-129 |

| Ex. No. | Z | N⁺R⁵R⁶R⁷ | Ex. No. | Z | N⁺R⁵R⁶R⁷ | Ex. No. | Z | N⁺R⁵R⁶R⁷ |
|---|---|---|---|---|---|---|---|---|
| 1U5632 | sp-23 | an-130 | 1U6025 | sp-24 | an-130 | 1U6418 | sp-25 | an-130 |
| 1U5633 | sp-23 | an-131 | 1U6026 | sp-24 | an-131 | 1U6419 | sp-25 | an-131 |
| 1U5634 | sp-23 | an-132 | 1U6027 | sp-24 | an-132 | 1U6420 | sp-25 | an-132 |
| 1U5635 | sp-23 | an-133 | 1U6028 | sp-24 | an-133 | 1U6421 | sp-25 | an-133 |
| 1U5636 | sp-23 | an-134 | 1U6029 | sp-24 | an-134 | 1U6422 | sp-25 | an-134 |
| 1U5637 | sp-23 | an-135 | 1U6030 | sp-24 | an-135 | 1U6423 | sp-25 | an-135 |
| 1U5638 | sp-23 | an-136 | 1U6031 | sp-24 | an-136 | 1U6424 | sp-25 | an-136 |
| 1U5639 | sp-23 | an-137 | 1U6032 | sp-24 | an-137 | 1U6425 | sp-25 | an-137 |
| 1U5640 | sp-23 | an-138 | 1U6033 | sp-24 | an-138 | 1U6426 | sp-25 | an-138 |
| 1U5641 | sp-23 | an-139 | 1U6034 | sp-24 | an-139 | 1U6427 | sp-25 | an-139 |
| 1U5642 | sp-23 | an-140 | 1U6035 | sp-24 | an-140 | 1U6428 | sp-25 | an-140 |
| 1U5643 | sp-23 | an-141 | 1U6036 | sp-24 | an-141 | 1U6429 | sp-25 | an-141 |
| 1U5644 | sp-23 | an-142 | 1U6037 | sp-24 | an-142 | 1U6430 | sp-25 | an-142 |
| 1U5645 | sp-23 | an-143 | 1U6038 | sp-24 | an-143 | 1U6431 | sp-25 | an-143 |
| 1U5646 | sp-23 | an-144 | 1U6039 | sp-24 | an-144 | 1U6432 | sp-25 | an-144 |
| 1U5647 | sp-23 | an-145 | 1U6040 | sp-24 | an-145 | 1U6433 | sp-25 | an-145 |

Table 2-102

| Y = NHCSNH | | | Y = NHCSNH | | | Y = NHCSNH | | |
|---|---|---|---|---|---|---|---|---|
| 1U5648 | sp-23 | an-146 | 1U6041 | sp-24 | an-146 | 1U6434 | sp-25 | an-146 |
| 1U5649 | sp-23 | an-147 | 1U6042 | sp-24 | an-147 | 1U6435 | sp-25 | an-147 |
| 1U5650 | sp-23 | an-148 | 1U6043 | sp-24 | an-148 | 1U6436 | sp-25 | an-148 |
| 1U5651 | sp-23 | an-149 | 1U6044 | sp-24 | an-149 | 1U6437 | sp-25 | an-149 |
| 1U5652 | sp-23 | an-150 | 1U6045 | sp-24 | an-150 | 1U6438 | sp-25 | an-150 |
| 1U5653 | sp-23 | an-151 | 1U6046 | sp-24 | an-151 | 1U6439 | sp-25 | an-151 |
| 1U5654 | sp-23 | an-152 | 1U6047 | sp-24 | an-152 | 1U6440 | sp-25 | an-152 |
| 1U5655 | sp-23 | an-153 | 1U6048 | sp-24 | an-153 | 1U6441 | sp-25 | an-153 |
| 1U5656 | sp-23 | an-154 | 1U6049 | sp-24 | an-154 | 1U6442 | sp-25 | an-154 |
| 1U5657 | sp-23 | an-155 | 1U6050 | sp-24 | an-155 | 1U6443 | sp-25 | an-155 |
| 1U5658 | sp-23 | an-156 | 1U6051 | sp-24 | an-156 | 1U6444 | sp-25 | an-156 |
| 1U5659 | sp-23 | an-157 | 1U6052 | sp-24 | an-157 | 1U6445 | sp-25 | an-157 |
| 1U5660 | sp-23 | an-158 | 1U6053 | sp-24 | an-158 | 1U6446 | sp-25 | an-158 |
| 1U5661 | sp-23 | an-159 | 1U6054 | sp-24 | an-159 | 1U6447 | sp-25 | an-159 |
| 1U5662 | sp-23 | an-160 | 1U6055 | sp-24 | an-160 | 1U6448 | sp-25 | an-160 |
| 1U5663 | sp-23 | an-161 | 1U6056 | sp-24 | an-161 | 1U6449 | sp-25 | an-161 |
| 1U5664 | sp-23 | an-162 | 1U6057 | sp-24 | an-162 | 1U6450 | sp-25 | an-162 |
| 1U5665 | sp-23 | an-163 | 1U6058 | sp-24 | an-163 | 1U6451 | sp-25 | an-163 |
| 1U5666 | sp-23 | an-164 | 1U6059 | sp-24 | an-164 | 1U6452 | sp-25 | an-164 |
| 1U5667 | sp-23 | an-165 | 1U6060 | sp-24 | an-165 | 1U6453 | sp-25 | an-165 |
| 1U5668 | sp-23 | an-166 | 1U6061 | sp-24 | an-166 | 1U6454 | sp-25 | an-166 |
| 1U5669 | sp-23 | an-167 | 1U6062 | sp-24 | an-167 | 1U6455 | sp-25 | an-167 |
| 1U5670 | sp-23 | an-168 | 1U6063 | sp-24 | an-168 | 1U6456 | sp-25 | an-168 |
| 1U5671 | sp-23 | an-169 | 1U6064 | sp-24 | an-169 | 1U6457 | sp-25 | an-169 |
| 1U5672 | sp-23 | an-170 | 1U6065 | sp-24 | an-170 | 1U6458 | sp-25 | an-170 |
| 1U5673 | sp-23 | an-171 | 1U6066 | sp-24 | an-171 | 1U6459 | sp-25 | an-171 |
| 1U5674 | sp-23 | an-172 | 1U6067 | sp-24 | an-172 | 1U6460 | sp-25 | an-172 |
| 1U5675 | sp-23 | an-173 | 1U6068 | sp-24 | an-173 | 1U6461 | sp-25 | an-173 |
| 1U5676 | sp-23 | an-174 | 1U6069 | sp-24 | an-174 | 1U6462 | sp-25 | an-174 |
| 1U5677 | sp-23 | an-175 | 1U6070 | sp-24 | an-175 | 1U6463 | sp-25 | an-175 |
| 1U5678 | sp-23 | an-176 | 1U6071 | sp-24 | an-176 | 1U6464 | sp-25 | an-176 |
| 1U5679 | sp-23 | an-177 | 1U6072 | sp-24 | an-177 | 1U6465 | sp-25 | an-177 |
| 1U5680 | sp-23 | an-178 | 1U6073 | sp-24 | an-178 | 1U6466 | sp-25 | an-178 |
| 1U5681 | sp-23 | an-179 | 1U6074 | sp-24 | an-179 | 1U6467 | sp-25 | an-179 |
| 1U5682 | sp-23 | an-180 | 1U6075 | sp-24 | an-180 | 1U6468 | sp-25 | an-180 |
| 1U5683 | sp-23 | an-181 | 1U6076 | sp-24 | an-181 | 1U6469 | sp-25 | an-181 |
| 1U5684 | sp-23 | an-182 | 1U6077 | sp-24 | an-182 | 1U6470 | sp-25 | an-182 |
| 1U5685 | sp-23 | an-183 | 1U6078 | sp-24 | an-183 | 1U6471 | sp-25 | an-183 |
| 1U5686 | sp-23 | an-184 | 1U6079 | sp-24 | an-184 | 1U6472 | sp-25 | an-184 |
| 1U5687 | sp-23 | an-185 | 1U6080 | sp-24 | an-185 | 1U6473 | sp-25 | an-185 |
| 1U5688 | sp-23 | an-186 | 1U6081 | sp-24 | an-186 | 1U6474 | sp-25 | an-186 |
| 1U5689 | sp-23 | an-187 | 1U6082 | sp-24 | an-187 | 1U6475 | sp-25 | an-187 |
| 1U5690 | sp-23 | an-188 | 1U6083 | sp-24 | an-188 | 1U6476 | sp-25 | an-188 |
| 1U5691 | sp-23 | an-189 | 1U6084 | sp-24 | an-189 | 1U6477 | sp-25 | an-189 |
| 1U5692 | sp-23 | an-190 | 1U6085 | sp-24 | an-190 | 1U6478 | sp-25 | an-190 |
| 1U5693 | sp-23 | an-191 | 1U6086 | sp-24 | an-191 | 1U6479 | sp-25 | an-191 |
| 1U5694 | sp-23 | an-192 | 1U6087 | sp-24 | an-192 | 1U6480 | sp-25 | an-192 |
| 1U5695 | sp-23 | an-193 | 1U6088 | sp-24 | an-193 | 1U6481 | sp-25 | an-193 |
| 1U5696 | sp-23 | an-194 | 1U6089 | sp-24 | an-194 | 1U6482 | sp-25 | an-194 |
| 1U5697 | sp-23 | an-195 | 1U6090 | sp-24 | an-195 | 1U6483 | sp-25 | an-195 |
| 1U5698 | sp-23 | an-196 | 1U6091 | sp-24 | an-196 | 1U6484 | sp-25 | an-196 |
| 1U5699 | sp-23 | an-197 | 1U6092 | sp-24 | an-197 | 1U6485 | sp-25 | an-197 |
| 1U5700 | sp-23 | an-198 | 1U6093 | sp-24 | an-198 | 1U6486 | sp-25 | an-198 |
| 1U5701 | sp-23 | an-199 | 1U6094 | sp-24 | an-199 | 1U6487 | sp-25 | an-199 |
| 1U5702 | sp-23 | an-200 | 1U6095 | sp-24 | an-200 | 1U6488 | sp-25 | an-200 |
| 1U5703 | sp-23 | an-201 | 1U6096 | sp-24 | an-201 | 1U6489 | sp-25 | an-201 |

-continued

| Ex. No. | Z | N⁺R⁵R⁶R⁷ | Ex. No. | Z | N⁺R⁵R⁶R⁷ | Ex. No. | Z | N⁺R⁵R⁶R⁷ |
|---|---|---|---|---|---|---|---|---|
| | | | | Table 2-103 | | | | |
| | Y = NHCSNH | | | Y = NHCSNH | | | Y = NHCSNH | |
| 1U5704 | sp-23 | an-202 | 1U6097 | sp-24 | an-202 | 1U6490 | sp-25 | an-202 |
| 1U5705 | sp-23 | an-203 | 1U6098 | sp-24 | an-203 | 1U6491 | sp-25 | an-203 |
| 1U5706 | sp-23 | an-204 | 1U6099 | sp-24 | an-204 | 1U6492 | sp-25 | an-204 |
| 1U5707 | sp-23 | an-205 | 1U6100 | sp-24 | an-205 | 1U6493 | sp-25 | an-205 |
| 1U5708 | sp-23 | an-206 | 1U6101 | sp-24 | an-206 | 1U6494 | sp-25 | an-206 |
| 1U5709 | sp-23 | an-207 | 1U6102 | sp-24 | an-207 | 1U6495 | sp-25 | an-207 |
| 1U5710 | sp-23 | an-208 | 1U6103 | sp-24 | an-208 | 1U6496 | sp-25 | an-208 |
| 1U5711 | sp-23 | an-209 | 1U6104 | sp-24 | an-209 | 1U6497 | sp-25 | an-209 |
| 1U5712 | sp-23 | an-210 | 1U6105 | sp-24 | an-210 | 1U6498 | sp-25 | an-210 |
| 1U5713 | sp-23 | an-211 | 1U6106 | sp-24 | an-211 | 1U6499 | sp-25 | an-211 |
| 1U5714 | sp-23 | an-212 | 1U6107 | sp-24 | an-212 | 1U6500 | sp-25 | an-212 |
| 1U5715 | sp-23 | an-213 | 1U6108 | sp-24 | an-213 | 1U6501 | sp-25 | an-213 |
| 1U5716 | sp-23 | an-214 | 1U6109 | sp-24 | an-214 | 1U6502 | sp-25 | an-214 |
| 1U5717 | sp-23 | an-215 | 1U6110 | sp-24 | an-215 | 1U6503 | sp-25 | an-215 |
| 1U5718 | sp-23 | an-216 | 1U6111 | sp-24 | an-216 | 1U6504 | sp-25 | an-216 |
| 1U5719 | sp-23 | an-217 | 1U6112 | sp-24 | an-217 | 1U6505 | sp-25 | an-217 |
| 1U5720 | sp-23 | an-218 | 1U6113 | sp-24 | an-218 | 1U6506 | sp-25 | an-218 |
| 1U5721 | sp-23 | an-219 | 1U6114 | sp-24 | an-219 | 1U6507 | sp-25 | an-219 |
| 1U5722 | sp-23 | an-220 | 1U6115 | sp-24 | an-220 | 1U6508 | sp-25 | an-220 |
| 1U5723 | sp-23 | an-221 | 1U6116 | sp-24 | an-221 | 1U6509 | sp-25 | an-221 |
| 1U5724 | sp-23 | an-222 | 1U6117 | sp-24 | an-222 | 1U6510 | sp-25 | an-222 |
| 1U5725 | sp-23 | an-223 | 1U6118 | sp-24 | an-223 | 1U6511 | sp-25 | an-223 |
| 1U5726 | sp-23 | an-224 | 1U6119 | sp-24 | an-224 | 1U6512 | sp-25 | an-224 |
| 1U5727 | sp-23 | an-225 | 1U6120 | sp-24 | an-225 | 1U6513 | sp-25 | an-225 |
| 1U5728 | sp-23 | an-226 | 1U6121 | sp-24 | an-226 | 1U6514 | sp-25 | an-226 |
| 1U5729 | sp-23 | an-227 | 1U6122 | sp-24 | an-227 | 1U6515 | sp-25 | an-227 |
| 1U5730 | sp-23 | an-228 | 1U6123 | sp-24 | an-228 | 1U6516 | sp-25 | an-228 |
| 1U5731 | sp-23 | an-229 | 1U6124 | sp-24 | an-229 | 1U6517 | sp-25 | an-229 |
| 1U5732 | sp-23 | an-230 | 1U6125 | sp-24 | an-230 | 1U6518 | sp-25 | an-230 |
| 1U5733 | sp-23 | an-231 | 1U6126 | sp-24 | an-231 | 1U6519 | sp-25 | an-231 |
| 1U5734 | sp-23 | an-232 | 1U6127 | sp-24 | an-232 | 1U6520 | sp-25 | an-232 |
| 1U5735 | sp-23 | an-233 | 1U6128 | sp-24 | an-233 | 1U6521 | sp-25 | an-233 |
| 1U5736 | sp-23 | an-234 | 1U6129 | sp-24 | an-234 | 1U6522 | sp-25 | an-234 |
| 1U5737 | sp-23 | an-235 | 1U6130 | sp-24 | an-235 | 1U6523 | sp-25 | an-235 |
| 1U5738 | sp-23 | an-236 | 1U6131 | sp-24 | an-236 | 1U6524 | sp-25 | an-236 |
| 1U5739 | sp-23 | an-237 | 1U6132 | sp-24 | an-237 | 1U6525 | sp-25 | an-237 |
| 1U5740 | sp-23 | an-238 | 1U6133 | sp-24 | an-238 | 1U6526 | sp-25 | an-238 |
| 1U5741 | sp-23 | an-239 | 1U6134 | sp-24 | an-239 | 1U6527 | sp-25 | an-239 |
| 1U5742 | sp-23 | an-240 | 1U6135 | sp-24 | an-240 | 1U6528 | sp-25 | an-240 |
| 1U5743 | sp-23 | an-241 | 1U6136 | sp-24 | an-241 | 1U6529 | sp-25 | an-241 |
| 1U5744 | sp-23 | an-242 | 1U6137 | sp-24 | an-242 | 1U6530 | sp-25 | an-242 |
| 1U5745 | sp-23 | an-243 | 1U6138 | sp-24 | an-243 | 1U6531 | sp-25 | an-243 |
| 1U5746 | sp-23 | an-244 | 1U6139 | sp-24 | an-244 | 1U6532 | sp-25 | an-244 |
| 1U5747 | sp-23 | an-245 | 1U6140 | sp-24 | an-245 | 1U6533 | sp-25 | an-245 |
| 1U5748 | sp-23 | an-246 | 1U6141 | sp-24 | an-246 | 1U6534 | sp-25 | an-246 |
| 1U5749 | sp-23 | an-247 | 1U6142 | sp-24 | an-247 | 1U6535 | sp-25 | an-247 |
| 1U5750 | sp-23 | an-248 | 1U6143 | sp-24 | an-248 | 1U6536 | sp-25 | an-248 |
| 1U5751 | sp-23 | an-249 | 1U6144 | sp-24 | an-249 | 1U6537 | sp-25 | an-249 |
| 1U5752 | sp-23 | an-250 | 1U6145 | sp-24 | an-250 | 1U6538 | sp-25 | an-250 |
| 1U5753 | sp-23 | an-251 | 1U6146 | sp-24 | an-251 | 1U6539 | sp-25 | an-251 |
| 1U5754 | sp-23 | an-252 | 1U6147 | sp-24 | an-252 | 1U6540 | sp-25 | an-252 |
| 1U5755 | sp-23 | an-253 | 1U6148 | sp-24 | an-253 | 1U6541 | sp-25 | an-253 |
| 1U5756 | sp-23 | an-254 | 1U6149 | sp-24 | an-254 | 1U6542 | sp-25 | an-254 |
| 1U5757 | sp-23 | an-255 | 1U6150 | sp-24 | an-255 | 1U6543 | sp-25 | an-255 |
| 1U5758 | sp-23 | an-256 | 1U6151 | sp-24 | an-256 | 1U6544 | sp-25 | an-256 |
| 1U5759 | sp-23 | an-257 | 1U6152 | sp-24 | an-257 | 1U6545 | sp-25 | an-257 |
| | | | | Table 2-104 | | | | |
| | Y = NHCSNH | | | Y = NHCSNH | | | Y = NHCSNH | |
| 1U5760 | sp-23 | an-258 | 1U6153 | sp-24 | an-258 | 1U6546 | sp-25 | an-258 |
| 1U5761 | sp-23 | an-259 | 1U6154 | sp-24 | an-259 | 1U6547 | sp-25 | an-259 |
| 1U5762 | sp-23 | an-260 | 1U6155 | sp-24 | an-260 | 1U6548 | sp-25 | an-260 |
| 1U5763 | sp-23 | an-261 | 1U6156 | sp-24 | an-261 | 1U6549 | sp-25 | an-261 |
| 1U5764 | sp-23 | an-262 | 1U6157 | sp-24 | an-262 | 1U6550 | sp-25 | an-262 |
| 1U5765 | sp-23 | an-263 | 1U6158 | sp-24 | an-263 | 1U6551 | sp-25 | an-263 |
| 1U5766 | sp-23 | an-264 | 1U6159 | sp-24 | an-264 | 1U6552 | sp-25 | an-264 |
| 1U5767 | sp-23 | an-265 | 1U6160 | sp-24 | an-265 | 1U6553 | sp-25 | an-265 |
| 1U5768 | sp-23 | an-266 | 1U6161 | sp-24 | an-266 | 1U6554 | sp-25 | an-266 |
| 1U5769 | sp-23 | an-267 | 1U6162 | sp-24 | an-267 | 1U6555 | sp-25 | an-267 |
| 1U5770 | sp-23 | an-268 | 1U6163 | sp-24 | an-268 | 1U6556 | sp-25 | an-268 |
| 1U5771 | sp-23 | an-269 | 1U6164 | sp-24 | an-269 | 1U6557 | sp-25 | an-269 |
| 1U5772 | sp-23 | an-270 | 1U6165 | sp-24 | an-270 | 1U6558 | sp-25 | an-270 |
| 1U5773 | sp-23 | an-271 | 1U6166 | sp-24 | an-271 | 1U6559 | sp-25 | an-271 |

-continued

| Ex. No. | Z | $N^+R^5R^6R^7$ | Ex. No. | Z | $N^+R^5R^6R^7$ | Ex. No. | Z | $N^+R^5R^6R^7$ |
|---|---|---|---|---|---|---|---|---|
| 1U5774 | sp-23 | an-272 | 1U6167 | sp-24 | an-272 | 1U6560 | sp-25 | an-272 |
| 1U5775 | sp-23 | an-273 | 1U6168 | sp-24 | an-273 | 1U6561 | sp-25 | an-273 |
| 1U5776 | sp-23 | an-274 | 1U6169 | sp-24 | an-274 | 1U6562 | sp-25 | an-274 |
| 1U5777 | sp-23 | an-275 | 1U6170 | sp-24 | an-275 | 1U6563 | sp-25 | an-275 |
| 1U5778 | sp-23 | an-276 | 1U6171 | sp-24 | an-276 | 1U6564 | sp-25 | an-276 |
| 1U5779 | sp-23 | an-277 | 1U6172 | sp-24 | an-277 | 1U6565 | sp-25 | an-277 |
| 1U5780 | sp-23 | an-278 | 1U6173 | sp-24 | an-278 | 1U6566 | sp-25 | an-278 |
| 1U5781 | sp-23 | an-279 | 1U6174 | sp-24 | an-279 | 1U6567 | sp-25 | an-279 |
| 1U5782 | sp-23 | an-280 | 1U6175 | sp-24 | an-280 | 1U6568 | sp-25 | an-280 |
| 1U5783 | sp-23 | an-281 | 1U6176 | sp-24 | an-281 | 1U6569 | sp-25 | an-281 |
| 1U5784 | sp-23 | an-282 | 1U6177 | sp-24 | an-282 | 1U6570 | sp-25 | an-282 |
| 1U5785 | sp-23 | an-283 | 1U6178 | sp-24 | an-283 | 1U6571 | sp-25 | an-283 |
| 1U5786 | sp-23 | an-284 | 1U6179 | sp-24 | an-284 | 1U6572 | sp-25 | an-284 |
| 1U5787 | sp-23 | an-285 | 1U6180 | sp-24 | an-285 | 1U6573 | sp-25 | an-285 |
| 1U5788 | sp-23 | an-286 | 1U6181 | sp-24 | an-286 | 1U6574 | sp-25 | an-286 |
| 1U5789 | sp-23 | an-287 | 1U6182 | sp-24 | an-287 | 1U6575 | sp-25 | an-287 |
| 1U5790 | sp-23 | an-288 | 1U6183 | sp-24 | an-288 | 1U6576 | sp-25 | an-288 |
| 1U5791 | sp-23 | an-289 | 1U6184 | sp-24 | an-289 | 1U6577 | sp-25 | an-289 |
| 1U5792 | sp-23 | an-290 | 1U6185 | sp-24 | an-290 | 1U6578 | sp-25 | an-290 |
| 1U5793 | sp-23 | an-291 | 1U6186 | sp-24 | an-291 | 1U6579 | sp-25 | an-291 |
| 1U5794 | sp-23 | an-292 | 1U6187 | sp-24 | an-292 | 1U6580 | sp-25 | an-292 |
| 1U5795 | sp-23 | an-293 | 1U6188 | sp-24 | an-293 | 1U6581 | sp-25 | an-293 |
| 1U5796 | sp-23 | an-294 | 1U6189 | sp-24 | an-294 | 1U6582 | sp-25 | an-294 |
| 1U5797 | sp-23 | an-295 | 1U6190 | sp-24 | an-295 | 1U6583 | sp-25 | an-295 |
| 1U5798 | sp-23 | an-296 | 1U6191 | sp-24 | an-296 | 1U6584 | sp-25 | an-296 |
| 1U5799 | sp-23 | an-297 | 1U6192 | sp-24 | an-297 | 1U6585 | sp-25 | an-297 |
| 1U5800 | sp-23 | an-298 | 1U6193 | sp-24 | an-298 | 1U6586 | sp-25 | an-298 |
| 1U5801 | sp-23 | an-299 | 1U6194 | sp-24 | an-299 | 1U6587 | sp-25 | an-299 |
| 1U5802 | sp-23 | an-300 | 1U6195 | sp-24 | an-300 | 1U6588 | sp-25 | an-300 |
| 1U5803 | sp-23 | an-301 | 1U6196 | sp-24 | an-301 | 1U6589 | sp-25 | an-301 |
| 1U5804 | sp-23 | an-302 | 1U6197 | sp-24 | an-302 | 1U6590 | sp-25 | an-302 |
| 1U5805 | sp-23 | an-303 | 1U6198 | sp-24 | an-303 | 1U6591 | sp-25 | an-303 |
| 1U5806 | sp-23 | an-304 | 1U6199 | sp-24 | an-304 | 1U6592 | sp-25 | an-304 |
| 1U5807 | sp-23 | an-305 | 1U6200 | sp-24 | an-305 | 1U6593 | sp-25 | an-305 |
| 1U5808 | sp-23 | an-306 | 1U6201 | sp-24 | an-306 | 1U6594 | sp-25 | an-306 |
| 1U5809 | sp-23 | an-307 | 1U6202 | sp-24 | an-307 | 1U6595 | sp-25 | an-307 |
| 1U5810 | sp-23 | an-308 | 1U6203 | sp-24 | an-308 | 1U6596 | sp-25 | an-308 |
| 1U5811 | sp-23 | an-309 | 1U6204 | sp-24 | an-309 | 1U6597 | sp-25 | an-309 |
| 1U5812 | sp-23 | an-310 | 1U6205 | sp-24 | an-310 | 1U6598 | sp-25 | an-310 |
| 1U5813 | sp-23 | an-311 | 1U6206 | sp-24 | an-311 | 1U6599 | sp-25 | an-311 |
| 1U5814 | sp-23 | an-312 | 1U6207 | sp-24 | an-312 | 1U6600 | sp-25 | an-312 |
| 1U5815 | sp-23 | an-313 | 1U6208 | sp-24 | an-313 | 1U6601 | sp-25 | an-313 |

Table 2-105

| Y = NHCSNH | | | Y = NHCSNH | | | Y = NHCSNH | | |
|---|---|---|---|---|---|---|---|---|
| 1U5816 | sp-23 | an-314 | 1U6209 | sp-24 | an-314 | 1U6602 | sp-25 | an-314 |
| 1U5817 | sp-23 | an-315 | 1U6210 | sp-24 | an-315 | 1U6603 | sp-25 | an-315 |
| 1U5818 | sp-23 | an-316 | 1U6211 | sp-24 | an-316 | 1U6604 | sp-25 | an-316 |
| 1U5819 | sp-23 | an-317 | 1U6212 | sp-24 | an-317 | 1U6605 | sp-25 | an-317 |
| 1U5820 | sp-23 | an-318 | 1U6213 | sp-24 | an-318 | 1U6606 | sp-25 | an-318 |
| 1U5821 | sp-23 | an-319 | 1U6214 | sp-24 | an-319 | 1U6607 | sp-25 | an-319 |
| 1U5822 | sp-23 | an-320 | 1U6215 | sp-24 | an-320 | 1U6608 | sp-25 | an-320 |
| 1U5823 | sp-23 | an-321 | 1U6216 | sp-24 | an-321 | 1U6609 | sp-25 | an-321 |
| 1U5824 | sp-23 | an-322 | 1U6217 | sp-24 | an-322 | 1U6610 | sp-25 | an-322 |
| 1U5825 | sp-23 | an-323 | 1U6218 | sp-24 | an-323 | 1U6611 | sp-25 | an-323 |
| 1U5826 | sp-23 | an-324 | 1U6219 | sp-24 | an-324 | 1U6612 | sp-25 | an-324 |
| 1U5827 | sp-23 | an-325 | 1U6220 | sp-24 | an-325 | 1U6613 | sp-25 | an-325 |
| 1U5828 | sp-23 | an-326 | 1U6221 | sp-24 | an-326 | 1U6614 | sp-25 | an-326 |
| 1U5829 | sp-23 | an-327 | 1U6222 | sp-24 | an-327 | 1U6615 | sp-25 | an-327 |
| 1U5830 | sp-23 | an-328 | 1U6223 | sp-24 | an-328 | 1U6616 | sp-25 | an-328 |
| 1U5831 | sp-23 | an-329 | 1U6224 | sp-24 | an-329 | 1U6617 | sp-25 | an-329 |
| 1U5832 | sp-23 | an-330 | 1U6225 | sp-24 | an-330 | 1U6618 | sp-25 | an-330 |
| 1U5833 | sp-23 | an-331 | 1U6226 | sp-24 | an-331 | 1U6619 | sp-25 | an-331 |
| 1U5834 | sp-23 | an-332 | 1U6227 | sp-24 | an-332 | 1U6620 | sp-25 | an-332 |
| 1U5835 | sp-23 | an-333 | 1U6228 | sp-24 | an-333 | 1U6621 | sp-25 | an-333 |
| 1U5836 | sp-23 | an-334 | 1U6229 | sp-24 | an-334 | 1U6622 | sp-25 | an-334 |
| 1U5837 | sp-23 | an-335 | 1U6230 | sp-24 | an-335 | 1U6623 | sp-25 | an-335 |
| 1U5838 | sp-23 | an-336 | 1U6231 | sp-24 | an-336 | 1U6624 | sp-25 | an-336 |
| 1U5839 | sp-23 | an-337 | 1U6232 | sp-24 | an-337 | 1U6625 | sp-25 | an-337 |
| 1U5840 | sp-23 | an-338 | 1U6233 | sp-24 | an-338 | 1U6626 | sp-25 | an-338 |
| 1U5841 | sp-23 | an-339 | 1U6234 | sp-24 | an-339 | 1U6627 | sp-25 | an-339 |
| 1U5842 | sp-23 | an-340 | 1U6235 | sp-24 | an-340 | 1U6628 | sp-25 | an-340 |
| 1U5843 | sp-23 | an-341 | 1U6236 | sp-24 | an-341 | 1U6629 | sp-25 | an-341 |
| 1U5844 | sp-23 | an-342 | 1U6237 | sp-24 | an-342 | 1U6630 | sp-25 | an-342 |
| 1U5845 | sp-23 | an-343 | 1U6238 | sp-24 | an-343 | 1U6631 | sp-25 | an-343 |
| 1U5846 | sp-23 | an-344 | 1U6239 | sp-24 | an-344 | 1U6632 | sp-25 | an-344 |
| 1U5847 | sp-23 | an-345 | 1U6240 | sp-24 | an-345 | 1U6633 | sp-25 | an-345 |

-continued

| Ex. No. | Z | N⁺R⁵R⁶R⁷ | Ex. No. | Z | N⁺R⁵R⁶R⁷ | Ex. No. | Z | N⁺R⁵R⁶R⁷ |
|---|---|---|---|---|---|---|---|---|
| 1U5848 | sp-23 | an-346 | 1U6241 | sp-24 | an-346 | 1U6634 | sp-25 | an-346 |
| 1U5849 | sp-23 | an-347 | 1U6242 | sp-24 | an-347 | 1U6635 | sp-25 | an-347 |
| 1U5850 | sp-23 | an-348 | 1U6243 | sp-24 | an-348 | 1U6636 | sp-25 | an-348 |
| 1U5851 | sp-23 | an-349 | 1U6244 | sp-24 | an-349 | 1U6637 | sp-25 | an-349 |
| 1U5852 | sp-23 | an-350 | 1U6245 | sp-24 | an-350 | 1U6638 | sp-25 | an-350 |
| 1U5853 | sp-23 | an-351 | 1U6246 | sp-24 | an-351 | 1U6639 | sp-25 | an-351 |
| 1U5854 | sp-23 | an-352 | 1U6247 | sp-24 | an-352 | 1U6640 | sp-25 | an-352 |
| 1U5855 | sp-23 | an-353 | 1U6248 | sp-24 | an-353 | 1U6641 | sp-25 | an-353 |
| 1U5856 | sp-23 | an-354 | 1U6249 | sp-24 | an-354 | 1U6642 | sp-25 | an-354 |
| 1U5857 | sp-23 | an-355 | 1U6250 | sp-24 | an-355 | 1U6643 | sp-25 | an-355 |
| 1U5858 | sp-23 | an-356 | 1U6251 | sp-24 | an-356 | 1U6644 | sp-25 | an-356 |
| 1U5859 | sp-23 | an-357 | 1U6252 | sp-24 | an-357 | 1U6645 | sp-25 | an-357 |
| 1U5860 | sp-23 | an-358 | 1U6253 | sp-24 | an-358 | 1U6646 | sp-25 | an-358 |
| 1U5861 | sp-23 | an-359 | 1U6254 | sp-24 | an-359 | 1U6647 | sp-25 | an-359 |
| 1U5862 | sp-23 | an-360 | 1U6255 | sp-24 | an-360 | 1U6648 | sp-25 | an-360 |
| 1U5863 | sp-23 | an-361 | 1U6256 | sp-24 | an-361 | 1U6649 | sp-25 | an-361 |
| 1U5864 | sp-23 | an-362 | 1U6257 | sp-24 | an-362 | 1U6650 | sp-25 | an-362 |
| 1U5865 | sp-23 | an-363 | 1U6258 | sp-24 | an-363 | 1U6651 | sp-25 | an-363 |
| 1U5866 | sp-23 | an-364 | 1U6259 | sp-24 | an-364 | 1U6652 | sp-25 | an-364 |
| 1U5867 | sp-23 | an-365 | 1U6260 | sp-24 | an-365 | 1U6653 | sp-25 | an-365 |
| 1U5868 | sp-23 | an-366 | 1U6261 | sp-24 | an-366 | 1U6654 | sp-25 | an-366 |
| 1U5869 | sp-23 | an-367 | 1U6262 | sp-24 | an-367 | 1U6655 | sp-25 | an-367 |
| 1U5870 | sp-23 | an-368 | 1U6263 | sp-24 | an-368 | 1U6656 | sp-25 | an-368 |
| 1U5871 | sp-23 | an-369 | 1U6264 | sp-24 | an-369 | 1U6657 | sp-25 | an-369 |

Table 2-106

| Y = NHCSNH | | | Y = NHCSNH | | | Y = NHCSNH | | |
|---|---|---|---|---|---|---|---|---|
| 1U5872 | sp-23 | an-370 | 1U6265 | sp-24 | an-370 | 1U6658 | sp-25 | an-370 |
| 1U5873 | sp-23 | an-371 | 1U6266 | sp-24 | an-371 | 1U6659 | sp-25 | an-371 |
| 1U5874 | sp-23 | an-372 | 1U6267 | sp-24 | an-372 | 1U6660 | sp-25 | an-372 |
| 1U5875 | sp-23 | an-373 | 1U6268 | sp-24 | an-373 | 1U6661 | sp-25 | an-373 |
| 1U5876 | sp-23 | an-374 | 1U6269 | sp-24 | an-374 | 1U6662 | sp-25 | an-374 |
| 1U5877 | sp-23 | an-375 | 1U6270 | sp-24 | an-375 | 1U6663 | sp-25 | an-375 |
| 1U5878 | sp-23 | an-376 | 1U6271 | sp-24 | an-376 | 1U6664 | sp-25 | an-376 |
| 1U5879 | sp-23 | an-377 | 1U6272 | sp-24 | an-377 | 1U6665 | sp-25 | an-377 |
| 1U5880 | sp-23 | an-378 | 1U6273 | sp-24 | an-378 | 1U6666 | sp-25 | an-378 |
| 1U5881 | sp-23 | an-379 | 1U6274 | sp-24 | an-379 | 1U6667 | sp-25 | an-379 |
| 1U5882 | sp-23 | an-380 | 1U6275 | sp-24 | an-380 | 1U6668 | sp-25 | an-380 |
| 1U5883 | sp-23 | an-381 | 1U6276 | sp-24 | an-381 | 1U6669 | sp-25 | an-381 |
| 1U5884 | sp-23 | an-382 | 1U6277 | sp-24 | an-382 | 1U6670 | sp-25 | an-382 |
| 1U5885 | sp-23 | an-383 | 1U6278 | sp-24 | an-383 | 1U6671 | sp-25 | an-383 |
| 1U5886 | sp-23 | an-384 | 1U6279 | sp-24 | an-384 | 1U6672 | sp-25 | an-384 |
| 1U5887 | sp-23 | an-385 | 1U6280 | sp-24 | an-385 | 1U6673 | sp-25 | an-385 |
| 1U5888 | sp-23 | an-386 | 1U6281 | sp-24 | an-386 | 1U6674 | sp-25 | an-386 |
| 1U5889 | sp-23 | an-387 | 1U6282 | sp-24 | an-387 | 1U6675 | sp-25 | an-387 |
| 1U5890 | sp-23 | an-388 | 1U6283 | sp-24 | an-388 | 1U6676 | sp-25 | an-388 |
| 1U5891 | sp-23 | an-389 | 1U6284 | sp-24 | an-389 | 1U6677 | sp-25 | an-389 |
| 1U5892 | sp-23 | an-390 | 1U6285 | sp-24 | an-390 | 1U6678 | sp-25 | an-390 |
| 1U5893 | sp-23 | an-391 | 1U6286 | sp-24 | an-391 | 1U6679 | sp-25 | an-391 |
| 1U5894 | sp-23 | an-392 | 1U6287 | sp-24 | an-392 | 1U6680 | sp-25 | an-392 |
| 1U5895 | sp-23 | an-393 | 1U6288 | sp-24 | an-393 | 1U6681 | sp-25 | an-393 |

Further examples are the compounds (2A0001 to 2A6681, 2U0001 to 2U16681, 2C0001 to 2C3930) in which the binding position of Y has been changed to the para position in the compounds (1A0001 to 1A6681, 1U0001 to E1U6681, 1C0001 to E1C3930) described in Table 2 (Table 2-1 to Table 2-106). For example, it is meant herein that the compound 1A0001 has been changed to the compound 2A0001, and the same meaning is also applied to the subsequent compounds.

Further examples are the compounds (3A0001 to 3A6681, 3U0001 to 3U6681, 3C0001 to 3C3930) in which $(R^3R^4N)_m$ has been changed to 7-diethylamino group in the compounds (1A0001 to 1A6681, 1U0001 to 1U6681, 1C0001 to 1C3930) described in Table 2.

Further examples are the compounds (4A0001 to 4A6681, 4U0001 to 4U6681, 4C0001 to 4C3930) in which $(R^3R^4N)_m$ has been changed to 7-ethylmethylamino group in the compounds (1A0001 to 1A6681, 1U0001 to 1U6681, 1C0001 to 1C3930) described in Table 2.

Further examples are the compounds (5A0001 to 5A6681, 5U0001 to 5U6681, 5C0001 to 5C3930) in which $(R^3R^4N)_m$ has been changed to 9-dimethylamino group in the compounds (1A0001 to 1A6681, 1U0001 to 1U6681, 1C0001 to 1C3930) described in Table 2.

Further examples are the compounds (6A0001 to 6A6681, 6U0001 to 6U6681, 6C0001 to 6C3930) in which $(R^3R^4N)_m$ has been changed to 7,9-bis(dimethylamino) group in the compounds (1A0001 to 1A6681, 1U0001 to 1U6681, 1C0001 to 1C3930) described in Table 2.

Further examples are the compounds (7A0001 to 7A6681, 7U0001 to 7U6681, 7C0001 to 7C3930) in which both $R^1$ and $R^2$ have been changed to propyl groups in the compounds (1A0001 to 1A6681, 1U0001 to 1U6681, 1C0001 to 1C3930) described in Table 2.

Further examples are the compounds (8A0001 to 8A6681, 8U0001 to 8U6681, 8C0001 to 8C3930) in which both $R^1$ and $R^2$ have been changed to pentyl groups in the compounds (1A0001 to 1A6681, 1U0001 to 1U6681, 1C0001 to 1C3930) described in Table 2.

Further examples are the compounds (9A0001 to 9A6681, 9U0001 to 9U6681, 9C0001 to 9C3930) in which both $R^1$ and R² have been changed to hexyl groups in the compounds (1A0001 to 1A6681, 1U0001 to 1U6681, 1C0001 to 1C3930) described in Table 2.

Further examples are the compounds (10A0001 to 10A6681, 10U0001 to 10U6681, 10C0001 to 10C3930) in which R¹ has been changed to ethyl groups in the compounds (1A0001 to 1A6681, 1U0001 to 1U6681, 1C0001 to 1C3930) described in Table 2.

The compounds represented by the formulae (1A) and (1B) of the present invention may be produced by the following production methods. The compound represented by the formula (1) may also be produced by the same methods.
(Production Methods)

Among the compounds represented by the formula (1A), the compound in which Y is —NHCS— may be obtained by reacting a compound represented by the following formula (2A):

(2A)

(wherein R⁵ᵃ, R⁶ᵃ and R⁷ᵃ are the same as the above; replacement of the above quaternary ammonium structure with a tertiary amine structure will result in this compound) with a compound represented by the following formula (3A):

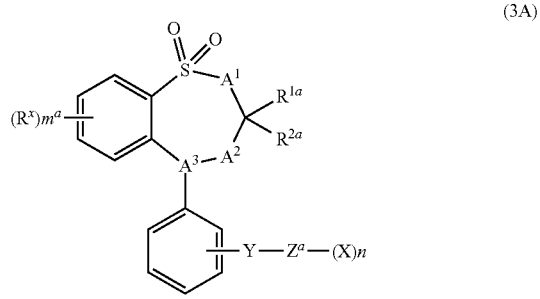

(3A)

(wherein A¹, A², A³, RˣR¹ᵃ, R²ᵃ, mᵃ, n and Zᵃ are the same as the above; Y represents —NHCS— and X represents a group capable of forming an anion).

The reaction may be performed by reacting the compound represented by the formula (3A) with an equivalent or more amount of, preferably with 1 to 5 fold molar excess of the compound represented by the formula (2A) in, if necessary, a solvent such as acetonitrile or N,N-dimethylformamide (abbreviated hereinbelow as DMF) at room temperature or at 40 to 100° C. for 1 to 48 hours.

X in the formula (3A) is a group which undergoes nucleophilic substitution by the compound represented by the formula (2A) to become an anion and leave, preferably to become a pharmaceutically acceptable anion and leave. Preferable examples of X may include F, Cl, Br, I, mesylate and tosylate, and more preferable are Cl, Br and I.

Examples of the compounds represented by the formula (2A) may include the compounds represented by the formulae (ta-1) to (ta-407). Abbreviation following each formula number means manufacturers thereof in accordance with the following. "AC" means Acros, "AL" means Aldrich, "BO" means Bio Net, "FL" means Fluka, "IC" means ICN-RF, "LN" means Lancaster, "MY" means Maybridge, "NC" means Nacalai, "PF" means Pfalzbauer, "SG" means Sigma, "SL" means Seiler, "TK" means Tokyo Chemical Industry, "WK" means Wako Pure Chemical Industries and "WT" means Watanabe Chemical Industries. The compound ta-37 may be prepared by reacting benzyl bromide supplied from Tokyo Chemical Industry with dipropylamine supplied from Tokyo Chemical Industry in the presence of potassium carbonate. The compound ta-56 may be prepared by reacting 3-bromopropanol supplied from Tokyo Chemical Industry with dibutylamine supplied from Tokyo Chemical Industry in the presence of potassium carbonate. The compound ta-57 may be prepared by reacting 4-bromobutanol supplied from Tokyo Chemical Industry with dibutylamine in the presence of potassium carbonate. The compound ta-117 may be prepared by neutralizing hydrochloride salt supplied from Seiler. The compound ta-137 may be prepared by reacting benzyl bromide with N-ethyl ethanolamine supplied from Tokyo Chemical Industry in the presence of potassium carbonate. The compound ta-138 may be prepared by reacting benzyl bromide with N-propyl ethanolamine supplied from Aldrich in the presence of potassium carbonate. The compound ta-139 may be prepared by reacting benzyl bromide with N-butyl ethanolamine supplied from Tokyo Chemical Industry in the presence of potassium carbonate. The compound ta-145 may be prepared by neutralizing hydrochloride salt supplied from Aldrich. The compound ta-148 may be prepared by neutralizing hydrochloride salt supplied from Tokyo Chemical Industry. The compound ta-152 may be prepared by reacting benzyl bromide with the compound ta-99. The compound ta-153 may be prepared by reacting benzyl bromide with the compound ta-100. The compound ta-154 may be prepared by reacting benzyl bromide with the compound ta-101. The compound ta-155 may be prepared by reacting benzyl bromide with the compound ta-105. The compound ta-156 may be prepared by reacting benzyl bromide with the compound ta-106. The compound ta-157 may be prepared by reacting benzyl bromide with the compound ta-108. The compound ta-158 may be prepared by reacting benzyl bromide with the compound ta-112. The compound ta-162 may be prepared by reacting pentyl iodide supplied from Tokyo Chemical Industry with pyrrolidine supplied from Tokyo Chemical Industry in the presence of potassium carbonate. The compound ta-172 may be prepared by neutralizing hydrochloride salt supplied from Maybridge. The compound ta-178 may be prepared by neutralizing hydrochloride salt supplied from Nacalai. The compound ta-181 may be prepared by reacting butyl iodide supplied from Tokyo Chemical Industry with piperidine supplied from Tokyo Chemical Industry in the presence of potassium carbonate. The compound ta-182 may be prepared by reacting pentyl iodide with piperidine in the presence of potassium carbonate. The compound ta-185 may be prepared by reacting benzyl bromide with piperidine in the presence of potassium carbonate. The compound ta-193 may be prepared by reacting sodium borohydride with the compound ta-207. The compound ta-212 may be prepared by neutralizing hydrochloride salt supplied from Tokyo Chemical Industry. The compound ta-234 may be prepared by reacting pentyl iodide with morpholine supplied from Tokyo Chemical Industry in the presence of potassium carbonate. The compound ta-237 may be prepared by reacting benzyl bromide with morpholine in the presence of potassium carbonate. The compound ta-255 may be prepared by reacting ethyl iodide supplied from Tokyo Chemical Industry with piperazine supplied from Tokyo Chemical Industry in the presence of potassium carbonate. The compound ta-256 may be prepared by reacting butyl iodide with piperazine in the presence of potassium carbonate. The compound ta-257 may be prepared by reacting pentyl iodide with piperazine in the presence of potassium carbonate. The compound ta-259 may be prepared by reacting benzyl bromide with piperazine in the presence of potassium carbonate. The compound ta-264 may be prepared by reacting benzyl bromide with the compound ta-254. The compound ta-265 may be prepared by reacting benzyl bromide with the compound ta-256. The compound ta-266 may be prepared by reacting benzyl bromide with the compound ta-260. The compound ta-279 may be prepared by reacting butyl iodide with azepan supplied from Tokyo Chemical Industry in the presence of potassium carbonate. The compound ta-280 may be prepared by reacting pentyl iodide with azepan in the presence of potassium carbonate. The compound ta-281 may be prepared by reacting benzyl bromide with azepan in the presence of potassium carbonate. The compound ta-290 may be prepared by neutralizing hydrochloride salt supplied from Tokyo Chemical Industry. The compound ta-294 may be prepared by reacting phenylacetyl chloride supplied from Aldrich with 3-aminoquinuclidine hydrochloride salt supplied from Tokyo Chemical Industry in the presence of potassium carbonate. The compound ta-295 may be prepared by reacting butyl chloride supplied from Aldrich with 3-aminoquinuclidine hydrochloride salt in the presence of potassium carbonate. The compound ta-296 may be prepared by reacting valeryl chloride supplied from Aldrich with 3-aminoquinuclidine hydrochloride salt in the presence of potassium carbonate. The compound ta-298 may be prepared by reacting butyl bromide supplied from Tokyo Chemical Industry with the compound ta-297. The compound ta-299 may be prepared by reacting benzyl bromide with the compound ta-297.

The compounds (ta-1) to (ta-407) correspond to the above (an-1) to (an-407), respectively.

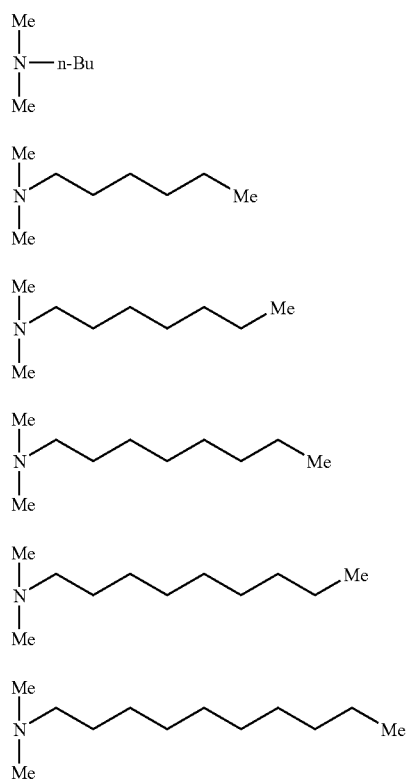
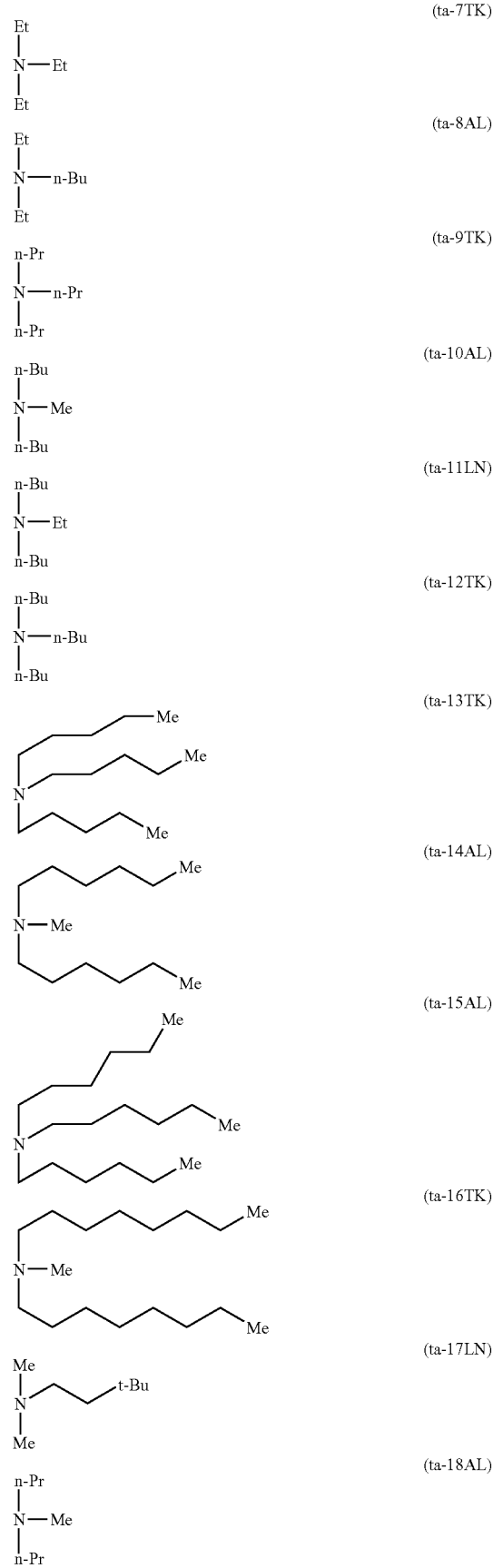

| | |
|---|---|
| (ta-19TK) 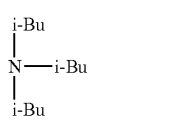 | (ta-31TK) 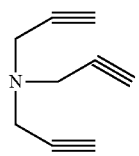 |
| (ta-20TK) 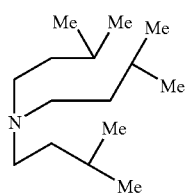 | (ta-32TK) 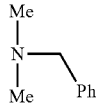 |
| (ta-21TK) 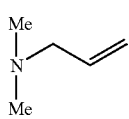 | (ta-33TK) 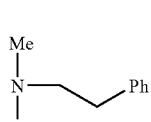 |
| (ta-22TK) 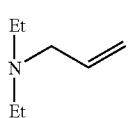 | (ta-34AL) 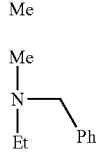 |
| (ta-23TK) 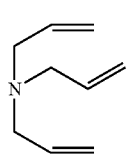 | (ta-35LN) 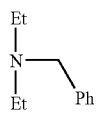 |
| (ta-24AL) 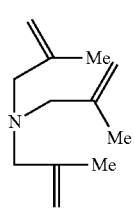 | (ta-36TK) 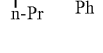 |
| (ta-25AL) 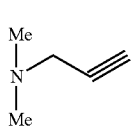 | (ta37*)  |
| (ta-26LN) 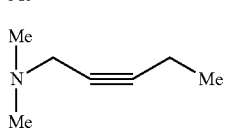 | (ta-38AL) 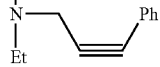 |
| (ta-27LN) 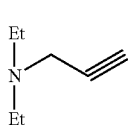 | (ta-39PF) 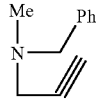 |
| (ta-28LN) 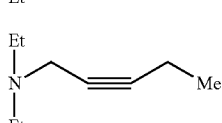 | (ta-40AL) 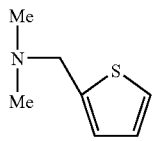 |
| (ta-29LN) 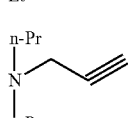 | (ta-41AL) |
| (ta-30LN) 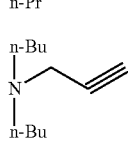 | (ta-42AL) 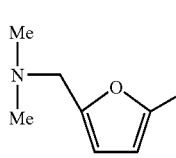 |

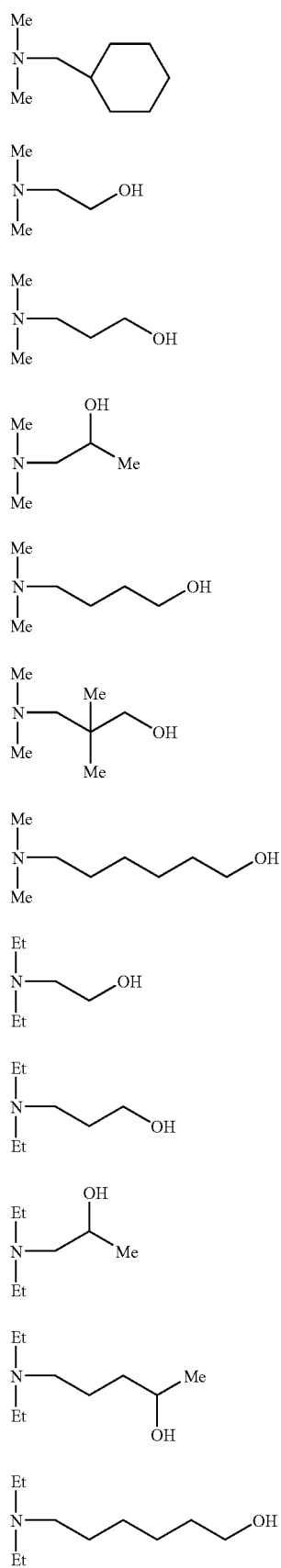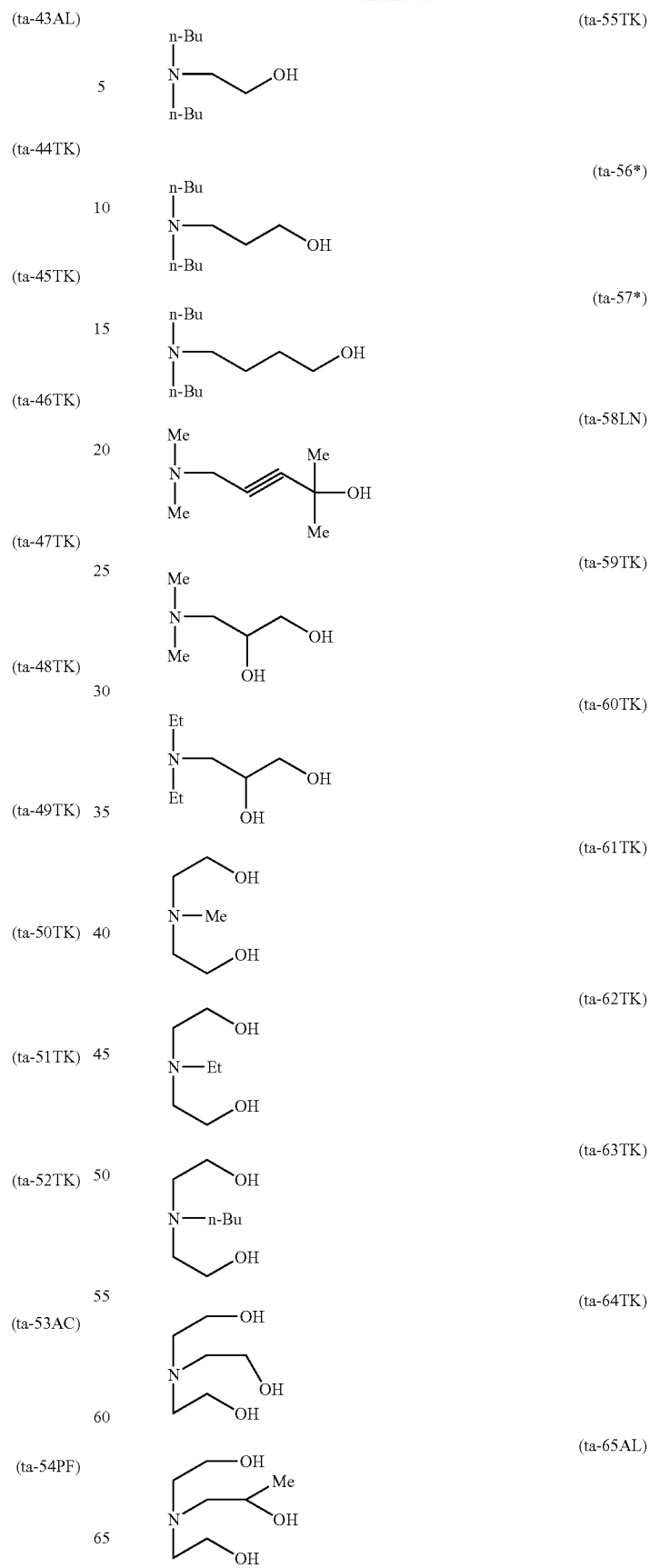

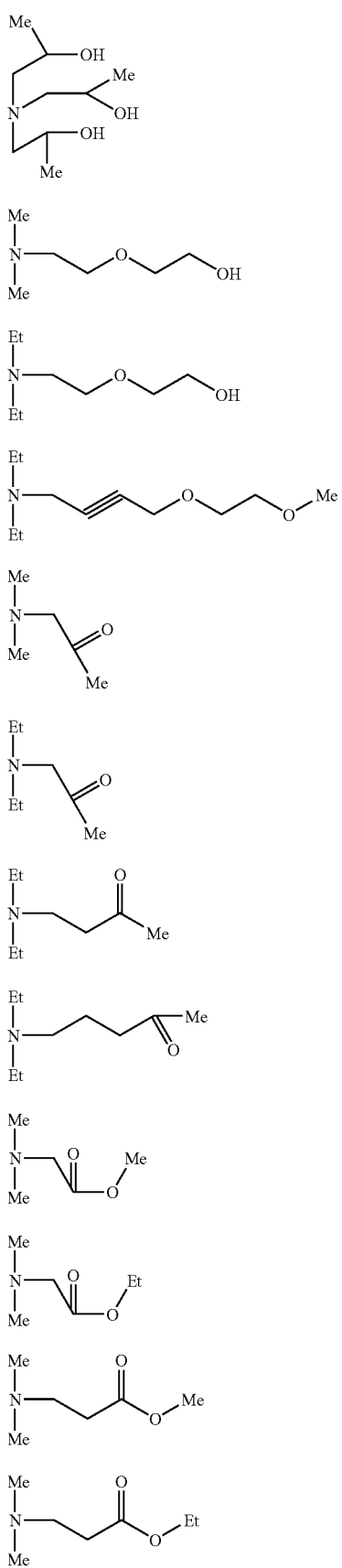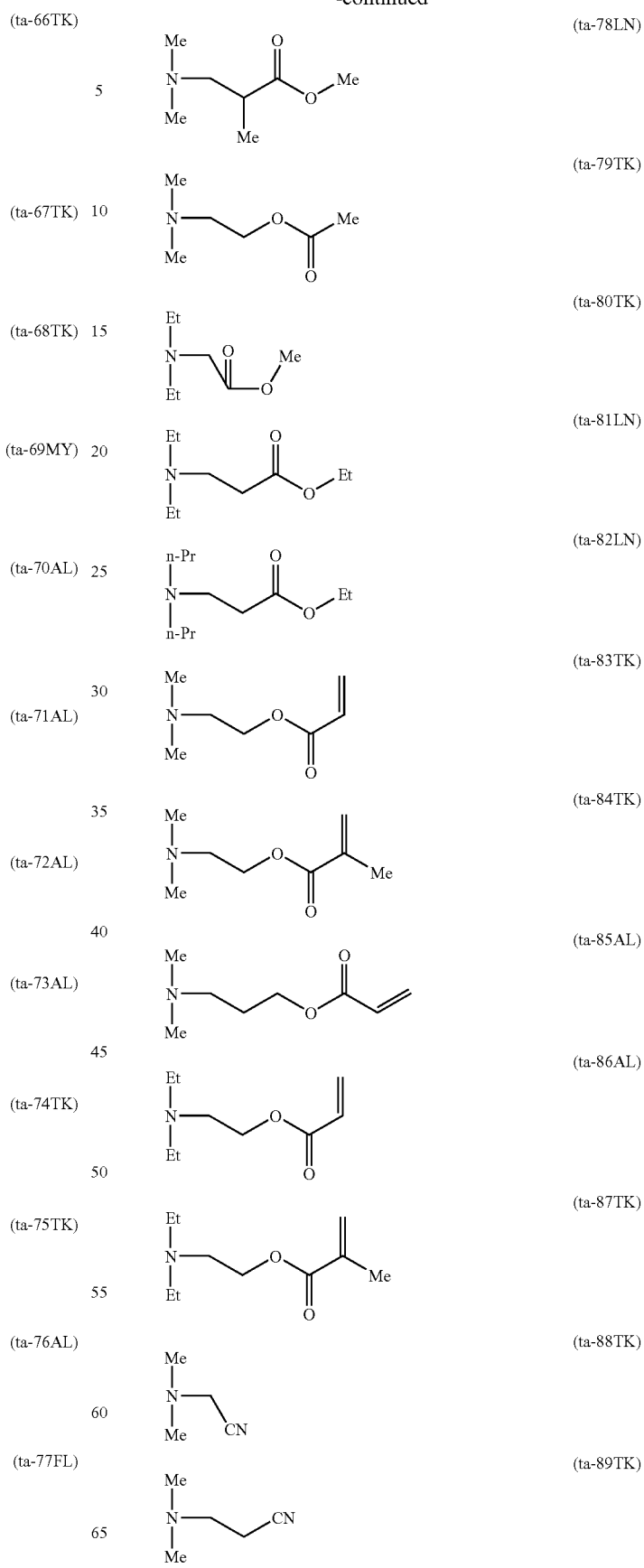

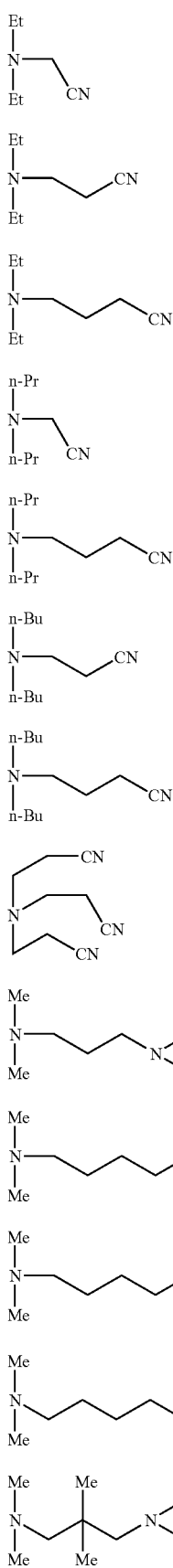
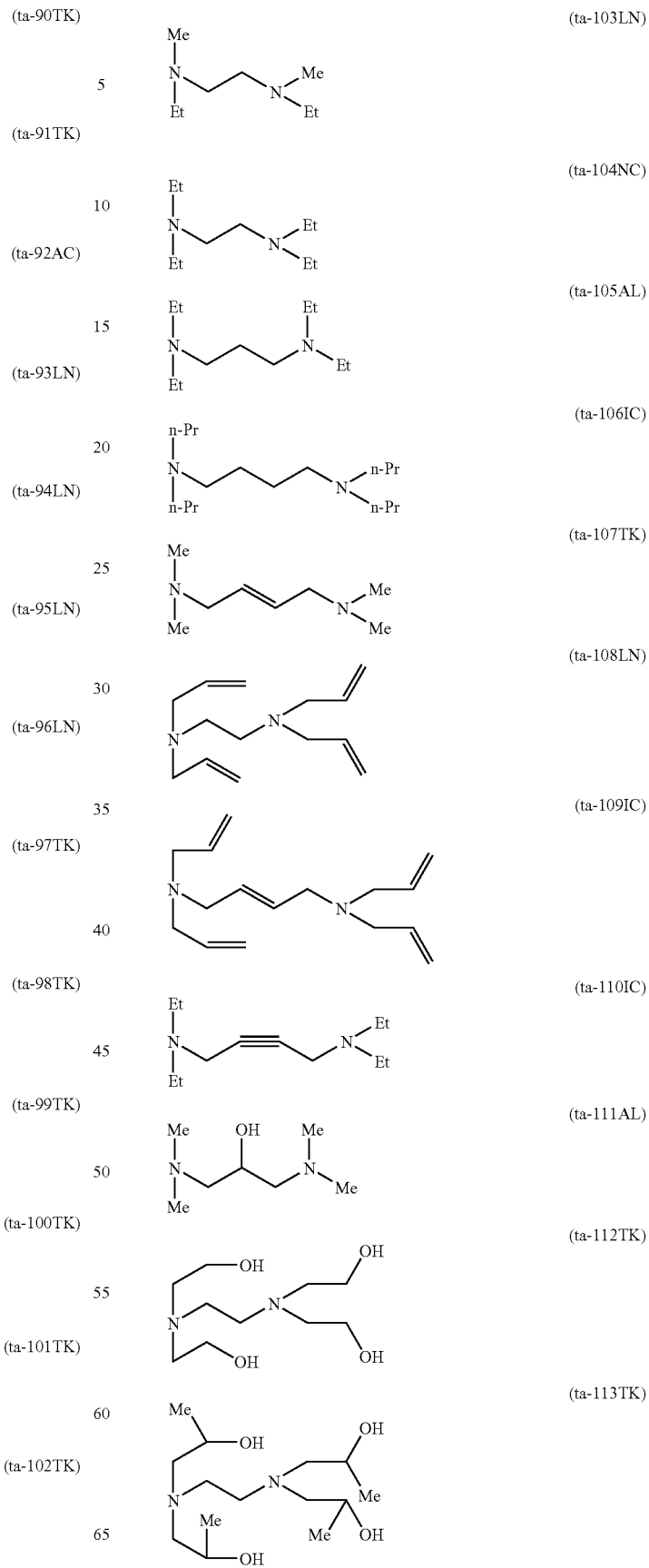

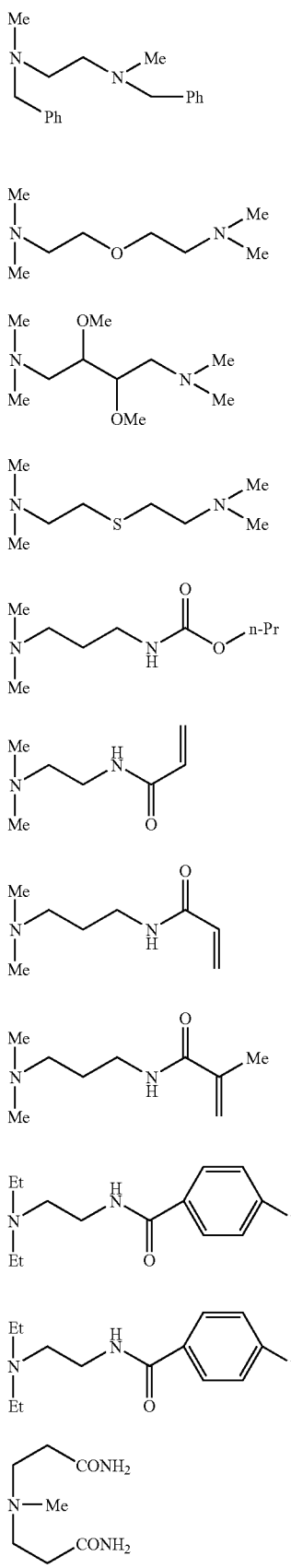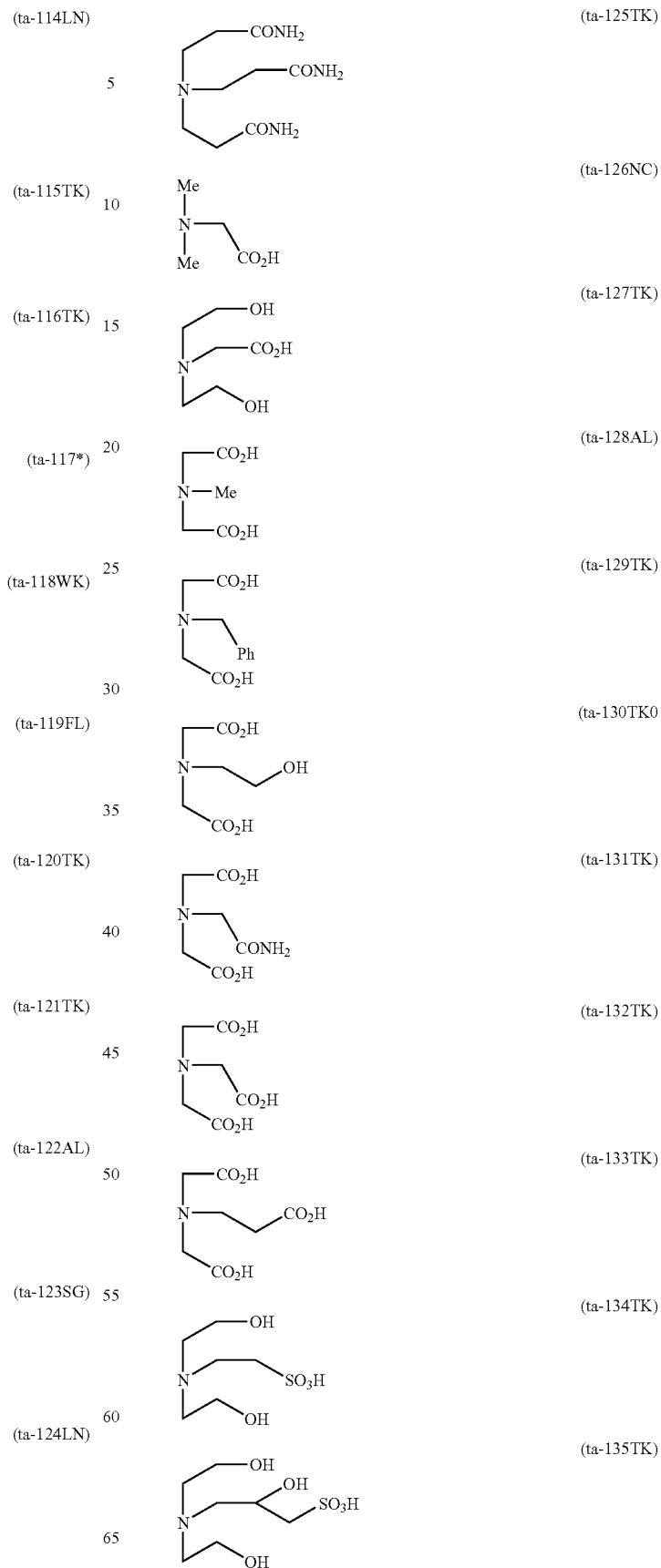

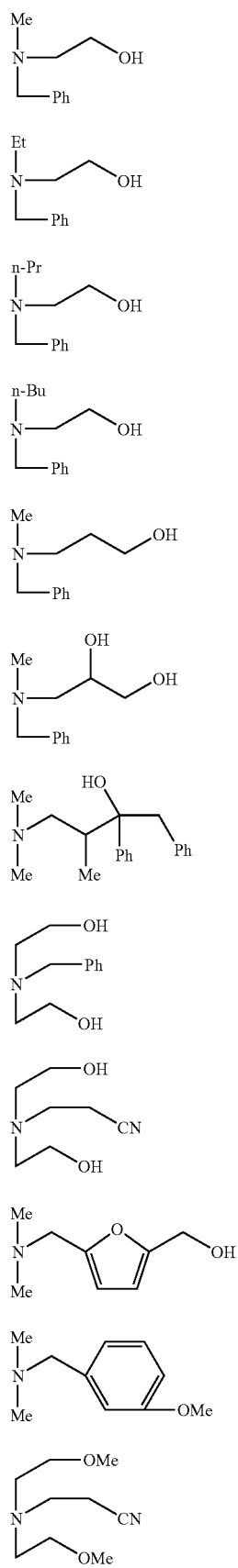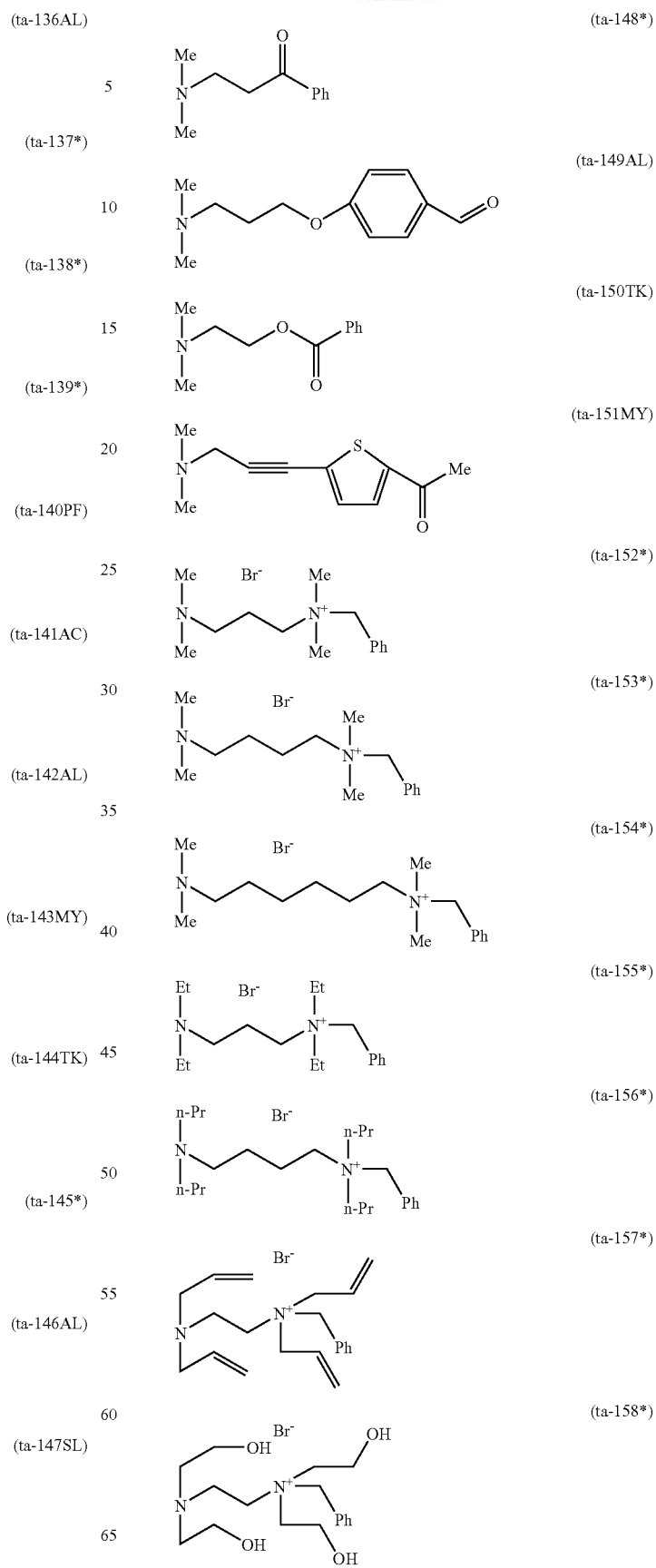

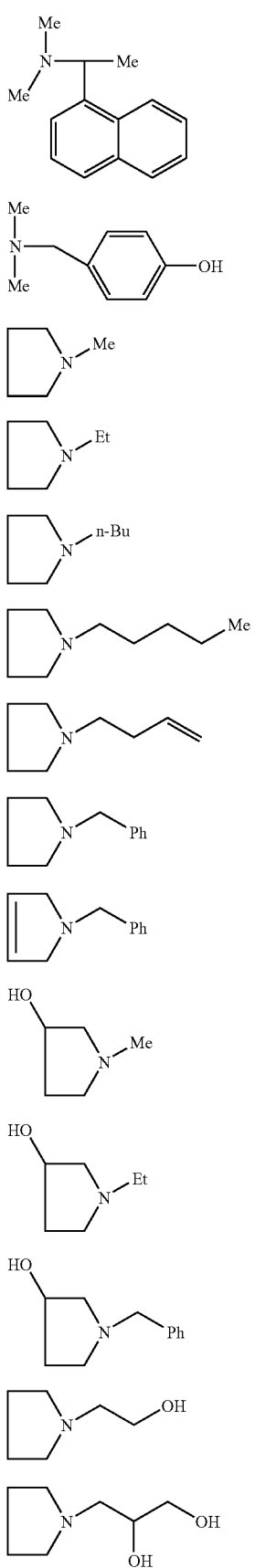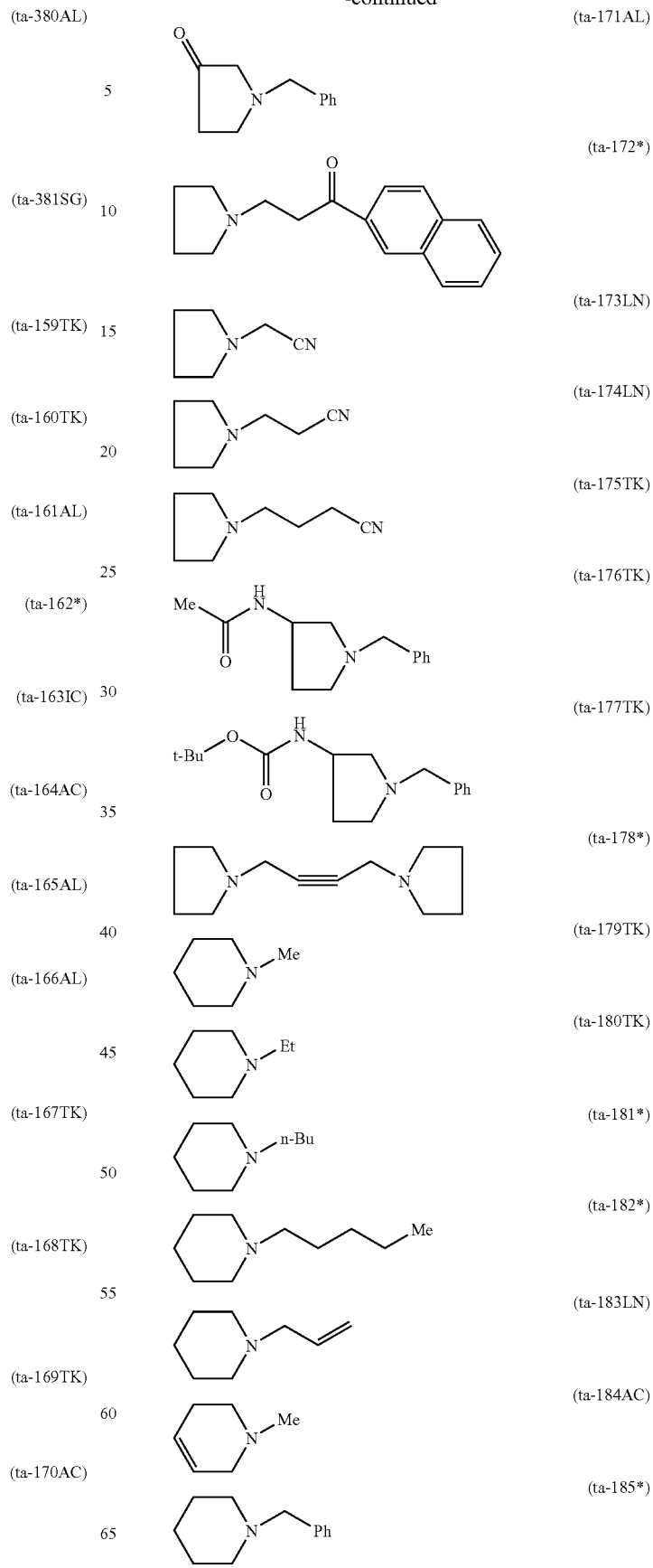

501
-continued
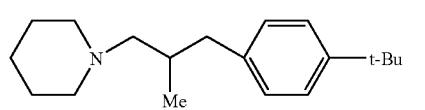 (ta-186FL)
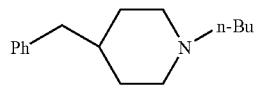 (ta-187SL)
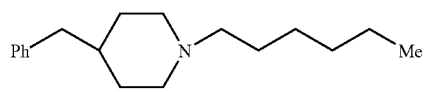 (ta-188SL)
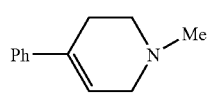 (ta-189SG)
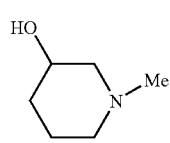 (ta-190TK)
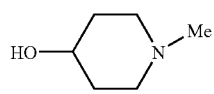 (ta-191TK)
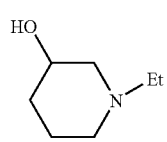 (ta-192TK)
 (ta-193*)
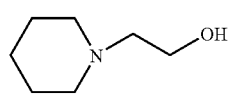 (ta-194TK)
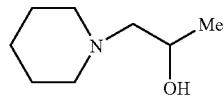 (ta-195AC)
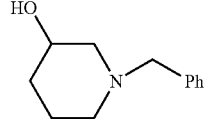 (ta-196LN)
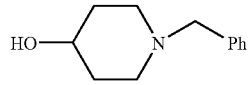 (ta-197AL)
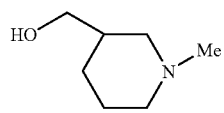 (ta-198TK)
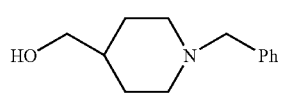 (ta-199MY)
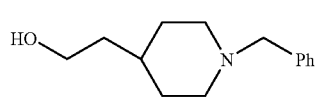 (ta-200AC)
502
-continued
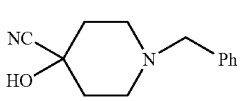 (ta-201LN)
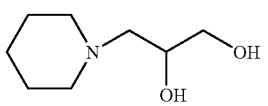 (ta-202AL)
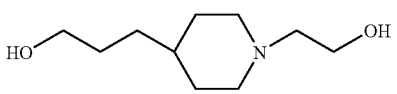 (ta-203TK)
 (ta-204MY)
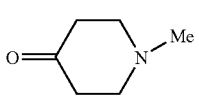 (ta-205TK)
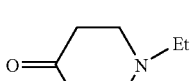 (ta-206TK)
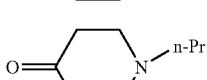 (ta-207AL)
 (ta-208LN)
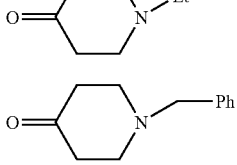 (ta-209TK)
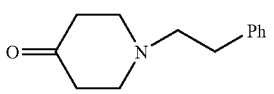 (ta-210TK)
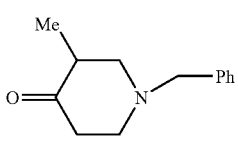 (ta-211AC)
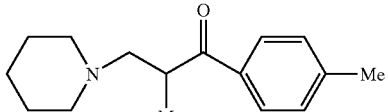 (ta-212*)
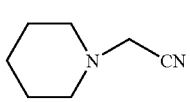 (ta-213TK)
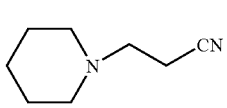 (ta-214TK)
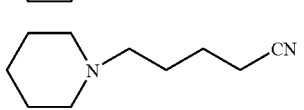 (ta-215AC)

503
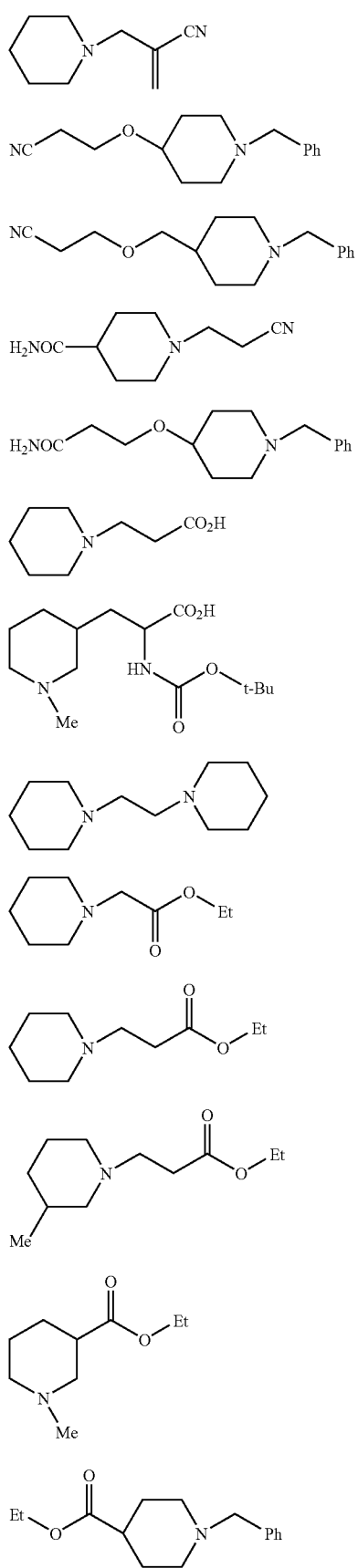
504
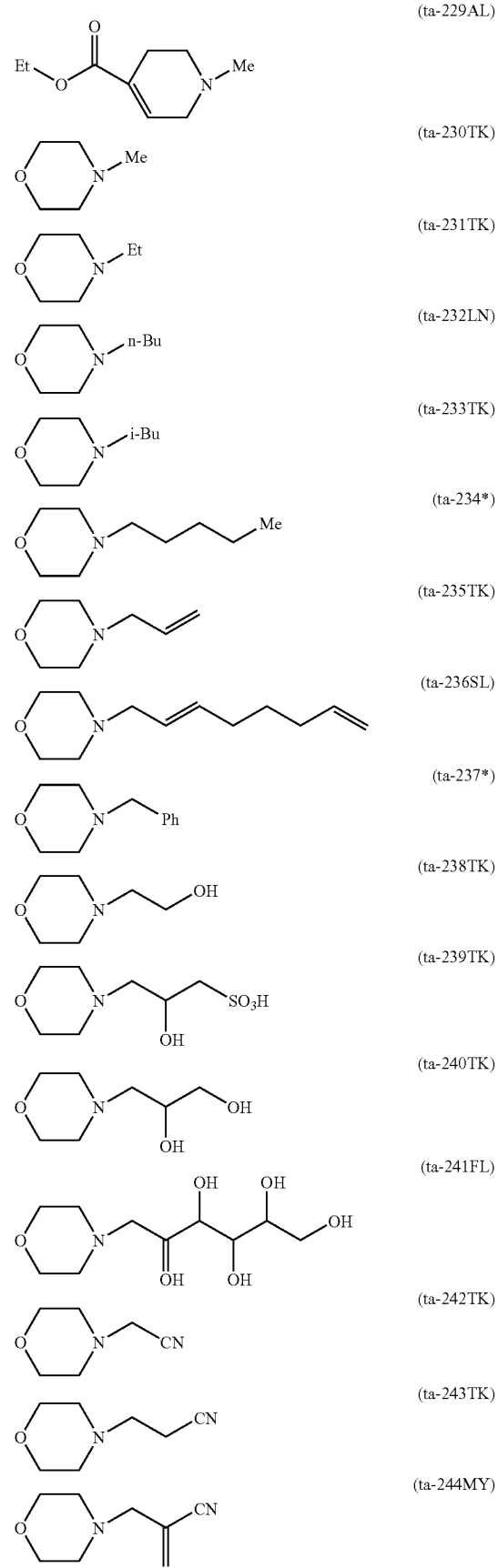

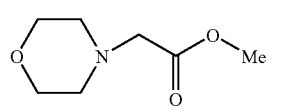 (ta-245AC)
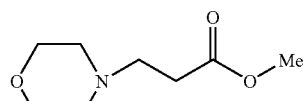 (ta-246AL)
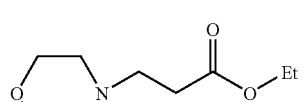 (ta-247LN)
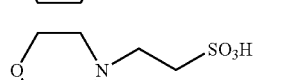 (ta-248TK)
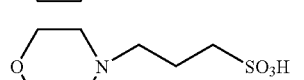 (ta-249TK)
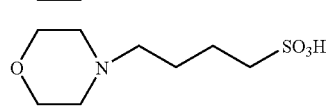 (ta-250SG)
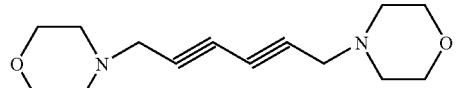 (ta-251LN)
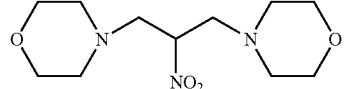 (ta-252AL)
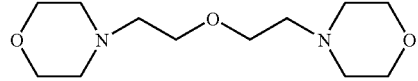 (ta-253TK)
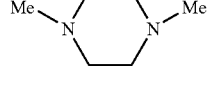 (ta-254TK)
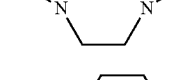 (ta-255*)
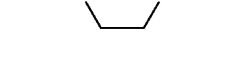 (ta-256*)
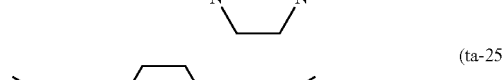 (ta-257*)
 (ta-258IC)
 (ta-259*)
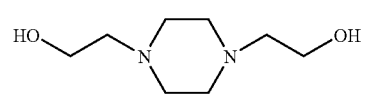 (ta-260NC)
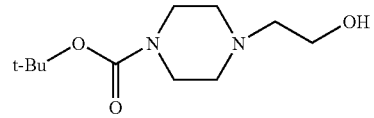 (ta-261MY)
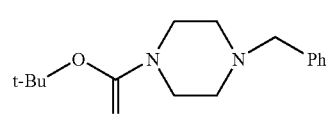 (ta-262AL)
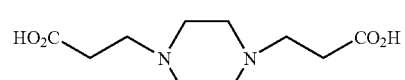 (ta-263TK)
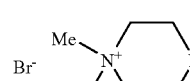 (ta-264*)
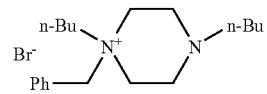 (ta-265*)
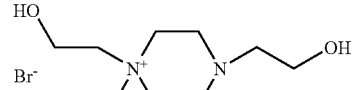 (ta-266*)
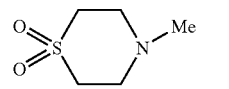 (ta-267LN)
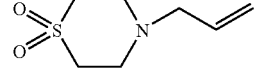 (ta-268MY)
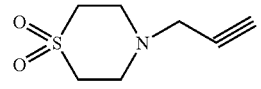 (ta-269MY)
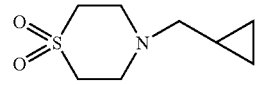 (ta-270BO)
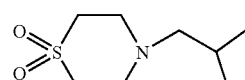 (ta-271BO)
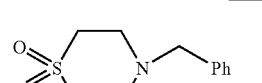 (ta-272MY)
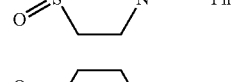 (ta-273BO)
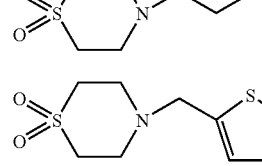 (ta-274MY)

507
-continued
(ta-275MY)
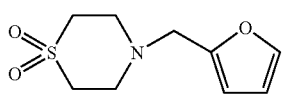
(ta-276MY)
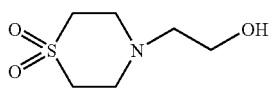
(ta-277MY)
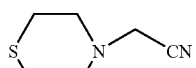
(ta-278LN)
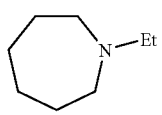
(ta-279*)
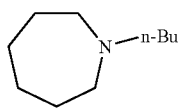
(ta-280*)
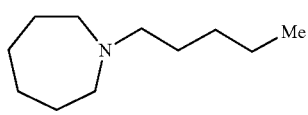
(ta-281*)
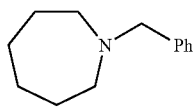
(ta-282LN)
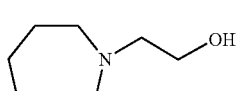
(ta-283LN)
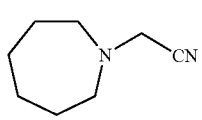
(ta-284LN)
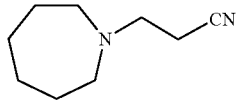
(ta-285LN)
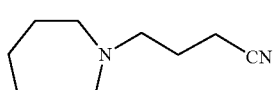
(ta-286LN)
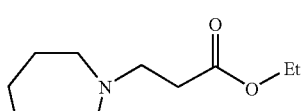
(ta-287NC)
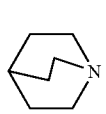
(ta-288LN)
508
-continued
(ta-289TK)
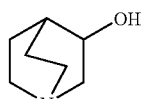
(ta-290*)
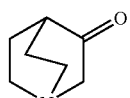
(ta-291MY)
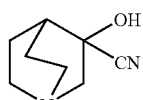
(ta-292MY)
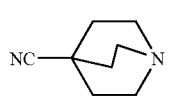
(ta-293SG)
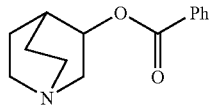
(ta-294*)
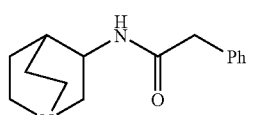
(ta-295*)
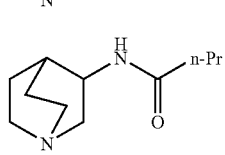
(ta-296*)
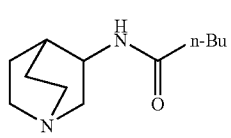
(ta-297TK)
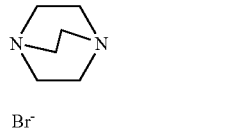
(ta-298*)
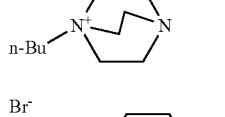
(ta-299*)
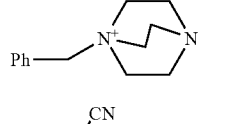
(ta-382TK)
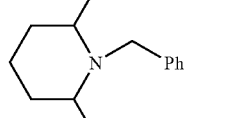
(ta-300TK)
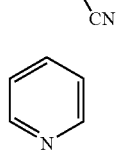

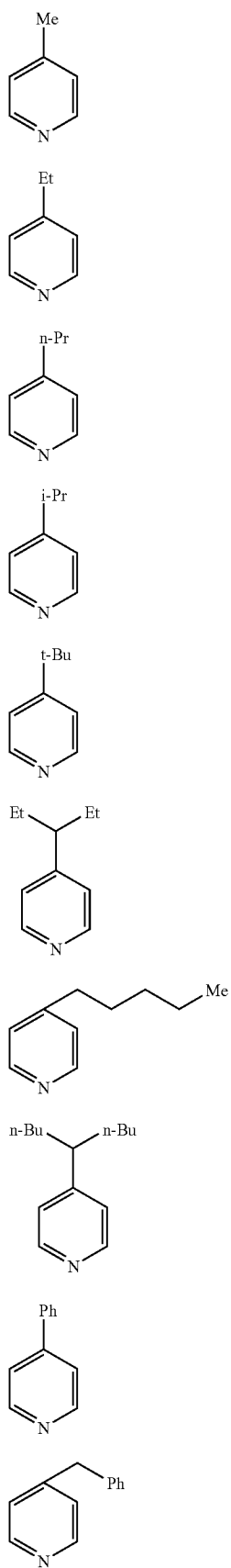
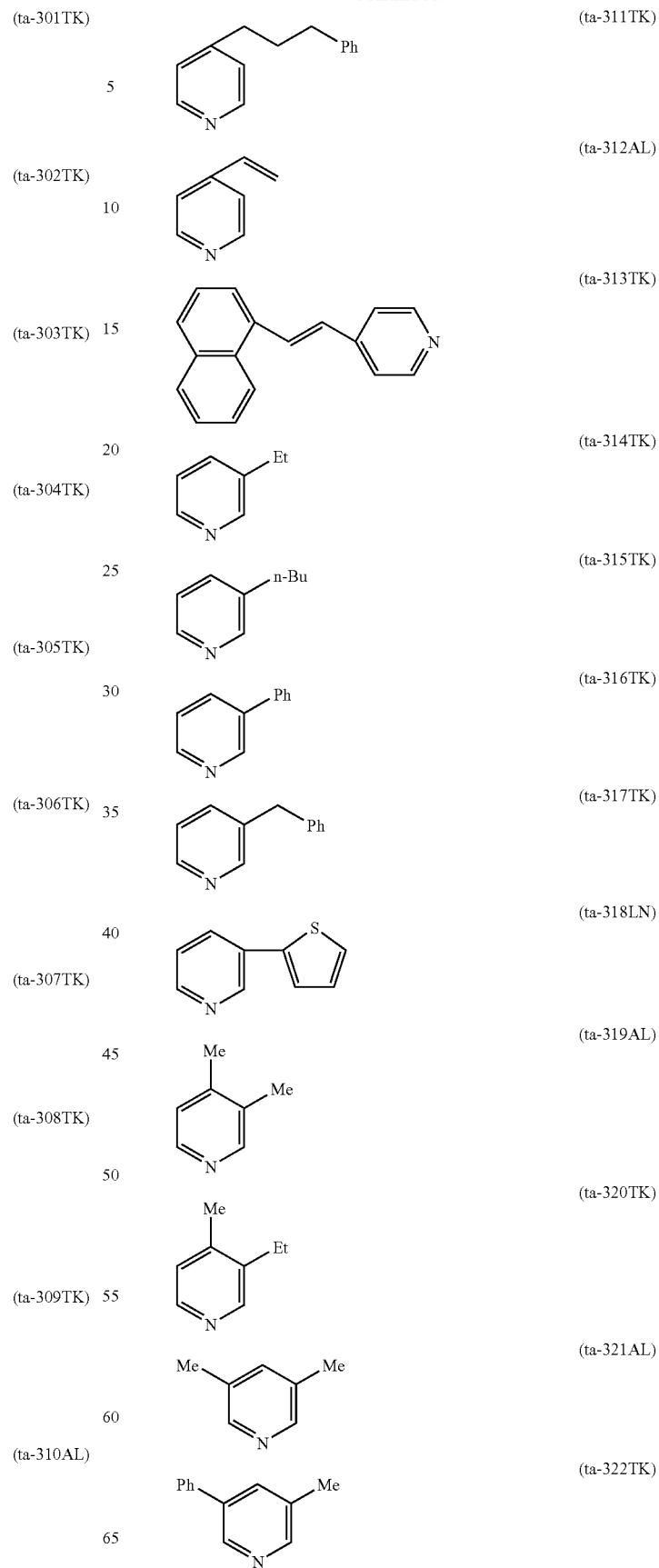

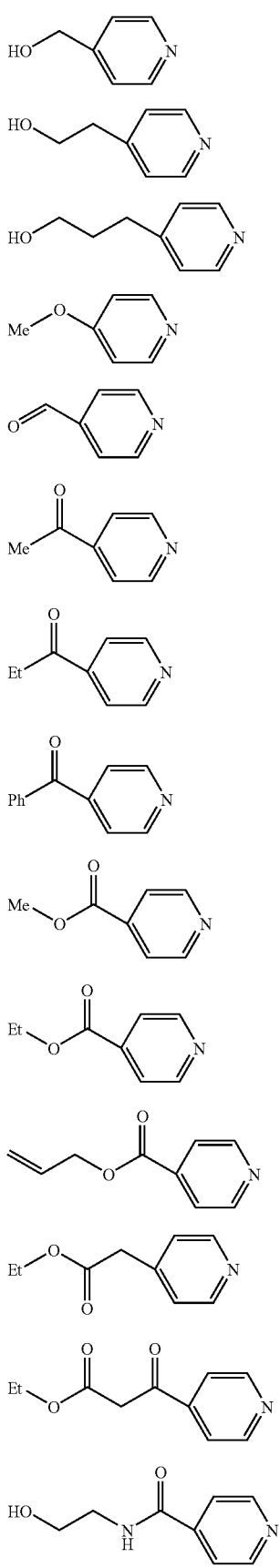
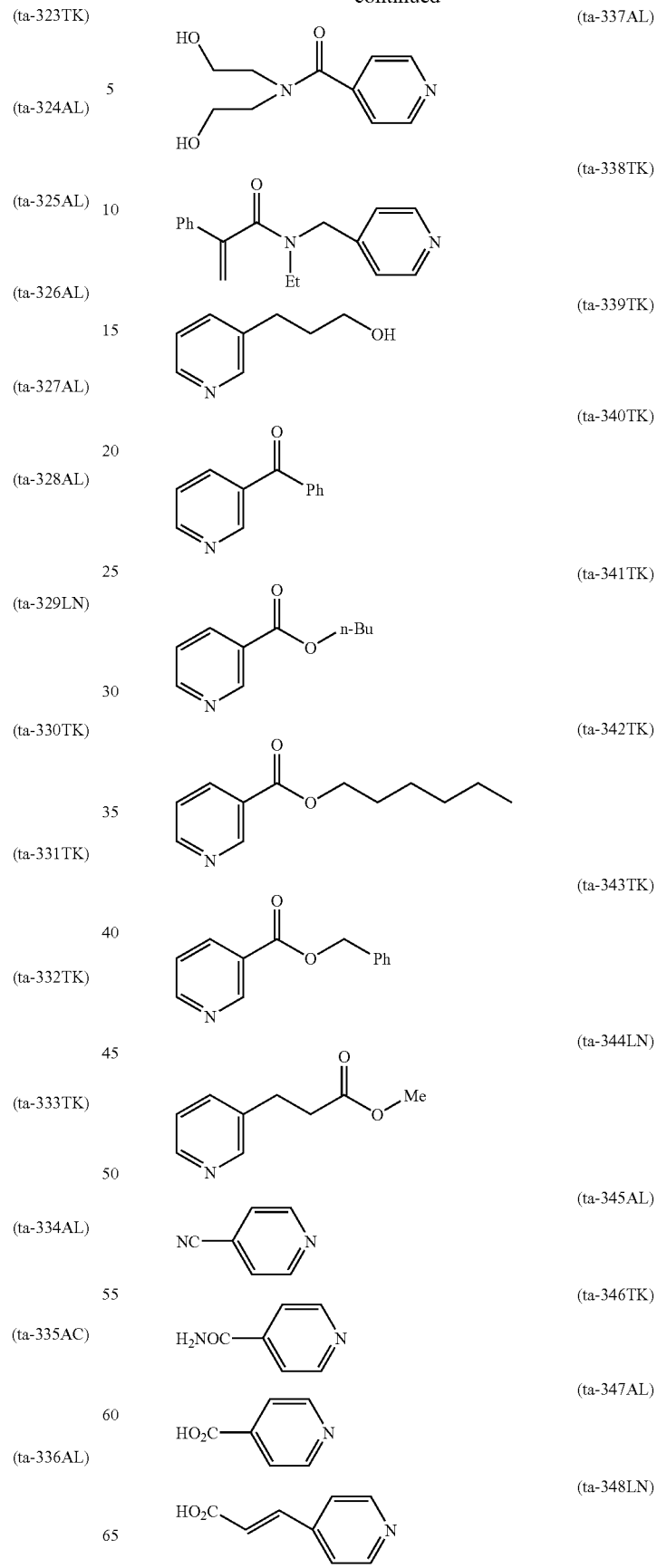

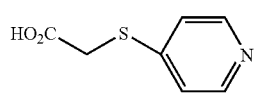 (ta-349TK)
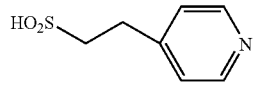 (ta-350TK)
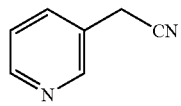 (ta-351TK)
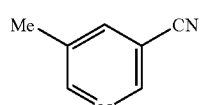 (ta-352LN)
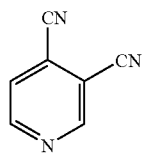 (ta-353AL)
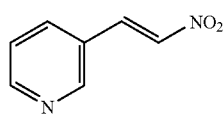 (ta-354TK)
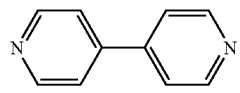 (ta-355AL)
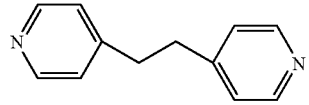 (ta-356AL)
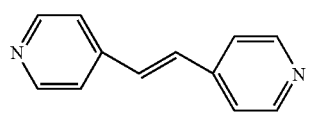 (ta-357TK)
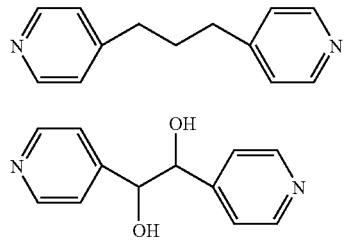 (ta-358TK)
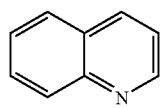 (ta-359TK)
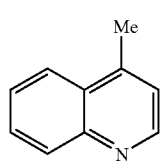 (ta-360TK)
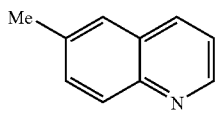 (ta-361TK)
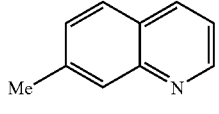 (ta-362TK)
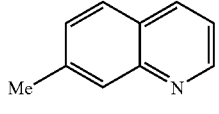 (ta-363TK)
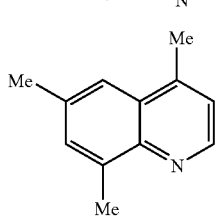 (ta-364TK)
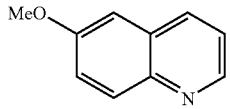 (ta-365TK)
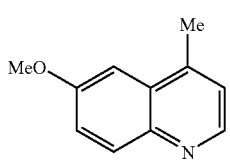 (ta-366TK)
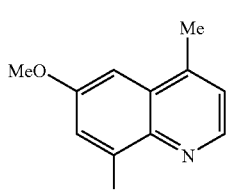 (ta-367TK)
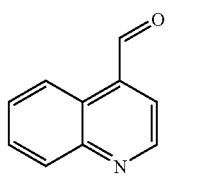 (ta-368TK)
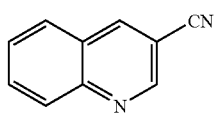 (ta-369TK)
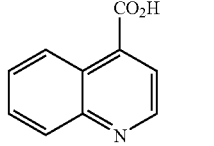 (ta-370AL)
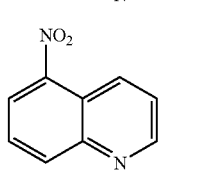 (ta-371AL)
(ta-372TK)

515
-continued
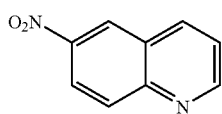 (ta-373TK)
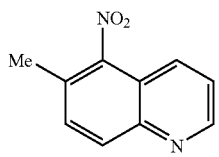 (ta-374LN)
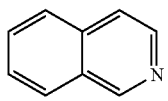 (ta-375TK)
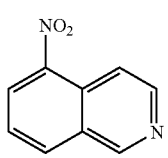 (ta-376TK)
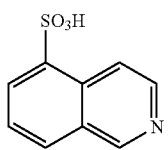 (ta-377TK)
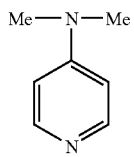 (ta-378TK)
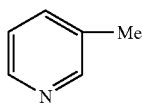 (ta-379TK)
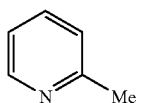 (ta-394TK)
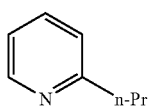 (ta-395TK)
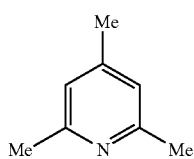 (ta-396TK)
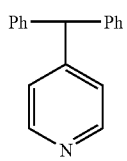 (ta-397TK)
516
-continued
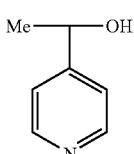 (ta-398AL)
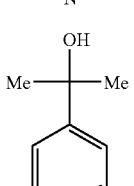 (ta-399SL)
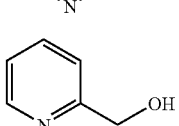 (ta-400TK)
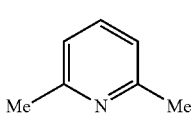 (ta-401TK)
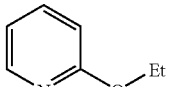 (ta-402LN)
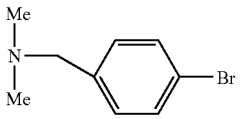 (ta-383SL)
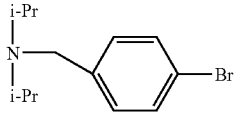 (ta-384AL)
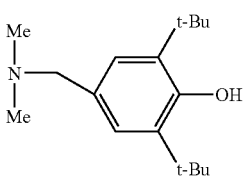 (ta-385TK)
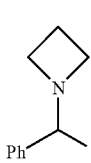 (ta-386AL)
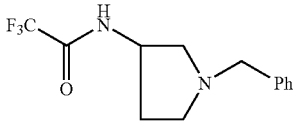 (ta-397TK)
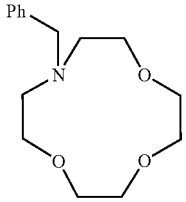 (ta-388FL)

-continued (ta-389TK)
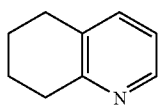

(ta-390TK)
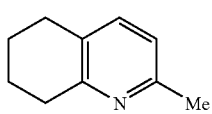

(ta-391TK)
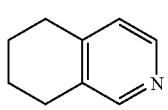

(ta-392TK)
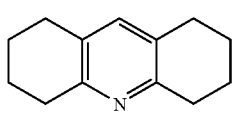

(ta-393TK)
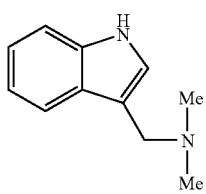

(ta-403TK)
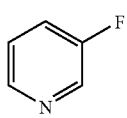

(ta-404TK)
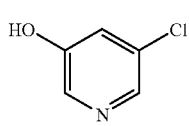

(ta-405TK)
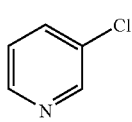

(ta-406SL)
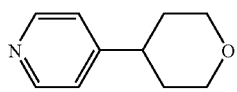

(ta-407AL)
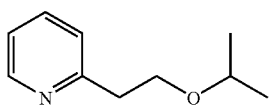

Likewise, among the compounds represented by the formula (1B), the compound in which Y is —NHCS— may be synthesized from a compound represented by the following formula (3B):

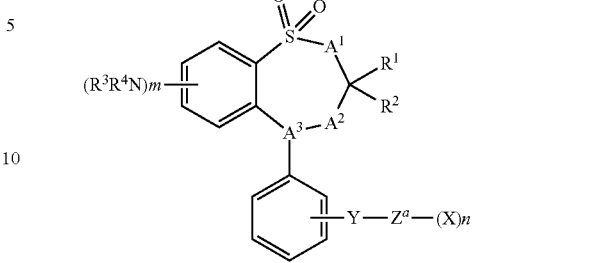
(3B)

(wherein $A^1$, $A^2$, $A^3$, $R^1$, $R^2$, $R^3$, $R^4$, m, n and $Z^a$ are the same as the above; Y represents —NHCS—; and X represents a group capable of forming an anion).

Likewise, among the compounds represented by the formula (1), the compound in which Y is —NHCS— may be obtained by reacting a compound represented by the following formula (2):

$$R^5-N-R^7 \atop R^6 \qquad (2)$$

(wherein $R^5$, $R^6$ and $R^7$ are the same as the above; replacement of the above quaternary ammonium structure with a tertiary amine structure will result in this compound) with a compound represented by the following formula (3):

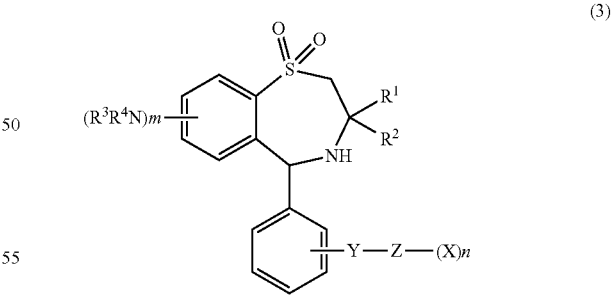
(3)

(wherein $R^1$, $R^2$, $R^3$, $R^4$, m, n and Z are the same as the above; Y represents —NHCS—; and X represents a group capable of forming an anion).

The compound represented by the formula (3A) may be obtained by reacting various sulfurizing agents with a compound represented by the following formula (4A-1):

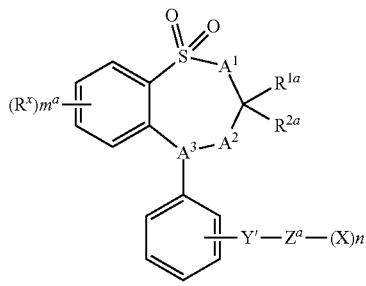

(4A-1)

(wherein $A^1$, $A^2$, $A^3$, $R^x$, $R^{1a}$, $R^{2a}$, $m^a$, n, $Z^a$ and X are the same as the above; Y' represents —NHCO—, with a proviso that —NH and CO— in —NHCO— represent a bond which binds to the adjacent benzene ring and a bond which binds to the adjacent $Z^a$, respectively).

The reaction may be performed by reacting the compound represented by the formula (4A-1) with an equivalent amount of, preferably with 1 to 10 fold molar excess of the sulfurizing agent in a solvent such as tetrahydrofuran (THF), 1,4-dioxane or toluene at room temperature or at 50 to 100° C. for 1 to 48 hours. Preferable examples of the sulfurizing agent may include Lawesson reagent (supplied from Tokyo Chemical Industry) and diphosphorus pentasulfide (supplied from Wako Pure Chemical Industries).

The position for the substitution of Y' in the formula (4A-1) may be any of ortho, meta or para position. The position is preferably the meta or para position, and most preferably the meta position.

Likewise, the compound represented by the formula (3B) may be synthesized from a compound represented by the following formula (4B-1):

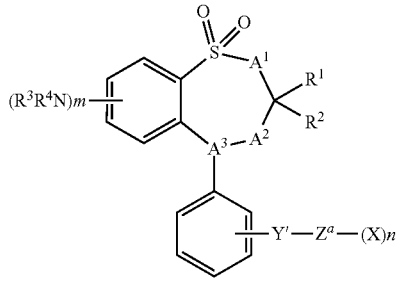

(4B-1)

(wherein $A^1$, $A^2$, $A^3$, $R^1$, $R^2$, $R^3$, $R^4$, m, n, $Z^a$ and X are the same as the above; Y' represents —NHCO—, with a proviso that —NH and CO— in —NHCO— represent a bond which binds to the adjacent benzene ring and a bond which binds to the adjacent $Z^a$, respectively).

Likewise, the compound represented by the formula (3) may be synthesized from a compound represented by the following formula (4-1):

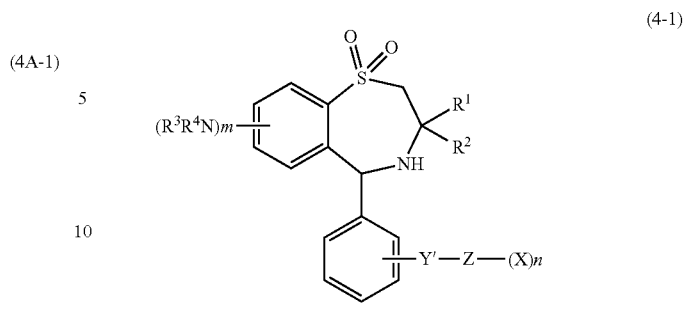

(4-1)

(wherein $R^1$, $R^2$, $R^3$, $R^4$, m, n, Z and X are the same as the above; Y' represents —NHCO—, with a proviso that —NH and CO— in —NHCO— represent a bond which binds to the adjacent benzene ring and a bond which binds to the adjacent Z, respectively).

The compound represented by the formula (4A-1) may be obtained by reacting a compound represented by the formula (5A-1):

(5A-1)

(wherein n, $Z^a$ and X are the same as the above, and $L^1$ represents a leaving group) with a compound represented by the following formula (6A-1):

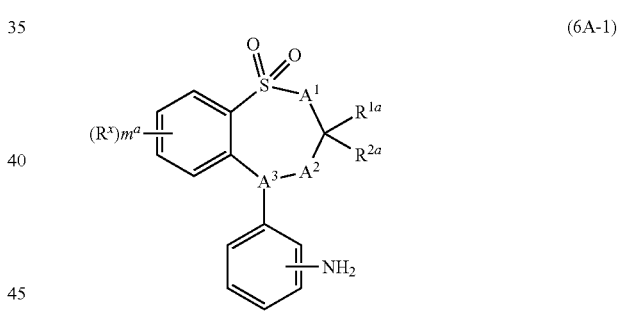

(6A-1)

(wherein $A^1$, $A^3$, $A^3$, $R^x$, $R^{1a}$, $R^{2a}$, and $m^a$ are the same as the above).

The reaction may be performed by reacting the compound represented by the formula (6A-1) with an equivalent or more amount of, preferably with 1 to 1.2 fold molar excess of the compound represented by the above formula (5A-1) in the presence of an excess amount of, preferably 1.5 to 3 fold molar excess of a base, preferably an organic base such as triethylamine or an inorganic base such as potassium carbonate, in a solvent such as dichloroethane or THF at room temperature to 60° C. for 1 to 24 hours.

$L^1$ in the formula (5A-1) is a group which undergoes nucleophilic substitution by the compound represented by the formula (6A-1) to leave. Preferable examples thereof may include F, Cl, Br, I, mesylate or tosylate, and more preferable are Cl and Br. $L^1$ may be different from X, but it is preferable that $L^1$ and X are the same. Examples of the preferable compounds represented by the formula (5A-1) may include 3-bromopropionyl chloride (ac-1), 4-bromobutyryl chloride (ac-2), 5-bromovaleryl chloride (ac-3), 6-bromo-n-caproyl chloride (ac-4) (ac-1 to ac-4 are supplied from Tokyo Chemical Industry), 7-bromo-n-heptanoyl chloride (ac-5) (prepared by oxidizing 7-bromo-1-heptanol supplied from Tokyo Chemical Industry with chromium oxide VI in the presence of concentrated sulfuric acid and subsequently reacting thionyl chloride), 8-bromo-n-octanoyl chloride (ac-6) (prepared by reacting thionyl chloride with 8-bromooctanoic acid supplied from Tokyo Chemical Industry), 9-bromo-n-nonanoyl chloride (ac-7) (prepared by oxidizing 9-bromo-1-nonanol supplied from Tokyo Chemical Industry with chromium oxide VI in the presence of concentrated sulfuric acid and subsequently reacting thionyl chloride), 10-bromo-n-decanoyl chloride (ac-8) (prepared by reacting thionyl chloride with 10-bromodecanoic acid supplied from Pfalzbauer), 11-bromo-n-undecanoyl chloride (ac-9) (prepared by reacting thionyl chloride with 11-bromoundecanoic acid supplied from Tokyo Chemical Industry), 3-bromo-2-methylpropionyl chloride (ac-10) (prepared by reacting thionyl chloride with 3-bromo-2-methylpropionic acid supplied from Fluka), 4-(chloromethyl)benzoyl chloride (ac-11) (supplied from Aldrich), 4-(bromomethyl)phenylacetyl chloride (ac-12) (prepared by reacting thionyl chloride with 4-(bromomethyl)phenylacetic acid supplied from Tokyo Chemical Industry), 2-[4-(bromomethyl)phenyl]propionyl chloride (ac-13) (prepared by reacting thionyl chloride with 2-[4-(bromomethyl)phenyl] propionic acid supplied from Tokyo Chemical Industry), 3-(bromomethyl)phenoxyacetyl chloride (ac-14) (prepared by reacting thionyl chloride with 3-(bromomethyl) phenoxyacetic acid supplied from Lancaster), 3-bromo-2-(bromomethyl)propionyl chloride (ac-15) (prepared by reacting thionyl chloride with 3-bromo-2-(bromomethyl) propionic acid supplied from Aldrich), 3-bromoacryloyl chloride (ac-16) (prepared by reacting thionyl chloride with 3-bromoacrylic acid supplied from Maybridge) or 3-(bromomethyl) crotonyl chloride (ac-17) (prepared by reacting thionyl chloride with 3-(bromomethyl) crotonic acid supplied from Seiler).

The position for the substitution of the primary amino group in the formula (6A-1) may be any of ortho, meta or para position. The position is preferably meta or para position, and most preferably meta position.

Likewise, the compound represented by the formula (4B-1) may be synthesized from a compound represented by the following formula (6B-1):

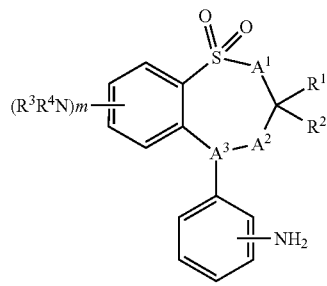
(6B-1)

wherein $A^1$, $A^2$, $A^3$, $R^1$, $R^2$, $R^3$, $R^4$ and m are the same as the above.

Likewise, the compound represented by the formula (4-1) may be obtained by reacting a compound represented by the following formula (5-1):

(5-1)

(wherein n, Z and X are the same as the above and $L^1$ represents a leaving group) with a compound represented by the following formula (6-1):

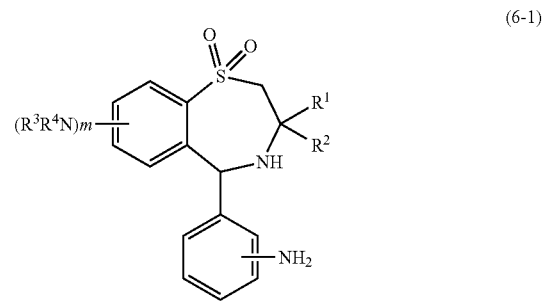
(6-1)

(wherein $R^1$, $R^2$, $R^3$, $R^4$ and m are the same as the above).

Among the compounds represented by the formula (1A), the compound in which Y is —NHCS— may also be obtained by reacting various sulfurizing agents with a compound represented by the following formula (4A-2):

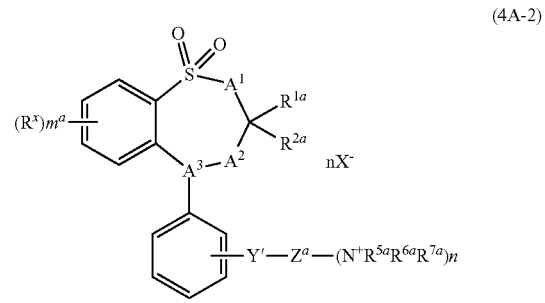
(4A-2)

wherein $A^1$, $A^2$, $A^3$, $R^x$, $R^{1a}$, $R^{2a}$, $m^a$, n, $R^{5a}$, $R^{6a}$, $R^{7a}$, Y', $Z^a$ and $X^-$ are the same as the above.

The reaction may be performed by reacting the compound represented by the formula (4A-2) with an equivalent or more amount of, preferably with 1 to 10 fold molar excess of the sulfurizing agent in a solvent such as ethanol, 1,4-dioxane, chloroform or 1,2-dichloroethane at room temperature or at 50 to 100° C. for 1 to 48 hours. Preferable examples of the sulfurizing agent may include Lawesson reagent and diphosphorus pentasulfide.

Likewise, among the compounds represented by the formula (1B), the compound in which Y is —NHCS— may be synthesized from a compound represented by the following formula (4B-2):

(4B-2)

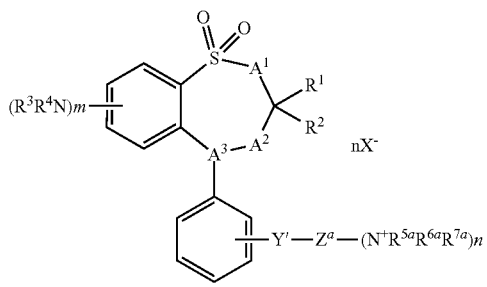

wherein $A^1$, $A^2$, $A^3$, $R^1$, $R^2$, $R^3$, $R^4$, m, n, $R^{5a}$, $R^{6a}$, $R^{7a}$, Y', $Z^a$ and $X^-$ are the same as the above.

Likewise, among the compounds represented by the formula (1), the compound in which Y is —NHCS— may be synthesized from a compound represented by the following formula (4-2):

(4-2)

wherein $R^1$, $R^2$, $R^3$, $R^4$, m, n, $R^5$, $R^6$, $R^7$, Y', Z and $X^-$ are the same as the above.

The compound represented by the formula (4A-2) may be obtained by reacting the compound represented by the formula (2A) with the compound represented by the formula (4A-1).

The reaction may be performed by reacting the compound represented by the formula (4A-1) with an equivalent or more of, preferably with 1 to 5 fold molar excess of the compound represented by the formula (2A) in, if necessary, a solvent such as acetonitrile or DMF at room temperature or at 40 to 100° C. for 1 to 48 hours.

Likewise, the compound represented by the formula (4B-2) may be synthesized from the compound represented by the formula (4B-1).

Likewise, the compound represented by the formula (4-2) may be obtained by reacting the compound represented by the formula (2) with the compound represented by the formula (4-1).

Among the compounds represented by the formula (1A), the compound in which Y is —NHCSNH— may be obtained by reacting a compound represented by the following formula (5A-2a):

(5A-2a)

$S=\!\!=\!\!N-Z^a-(N^+R^{5a}R^{6a}R^{7a})n$
$nX^-$ (wherein n, $R^{5a}$, $R^{6a}$, $R^{7a}$, $Z^a$ and $X^-$ are the same as the above) with the compound represented by the formula (6A-1).

The reaction may be performed by reacting the compound represented by the formula (6A-1) with an equivalent amount of the compound represented by the formula (5A-2a) in a solvent such as chloroform, acetonitrile or DMF at room temperature or at 40 to 100° C. for 1 to 48 hours.

The compound represented by the formula (5A-2a) may be obtained by reacting the compound represented by the formula (2A) with the compound represented by the following formula (5A-2b):

(5A-2b)

$S=\!\!=\!\!N-Z^a-(X)n$ wherein n, $Z^a$ and X are the same as the above.

The reaction may be performed by reacting the compound represented by the formula (5A-2b) with an equivalent or more amount of, preferably with 1 to 5 fold molar excess of the compound represented by the formula (2A) in, if necessary, a solvent such as acetonitrile or DMF at room temperature or at 40 to 100° C. for 1 to 48 hours.

Examples of the compounds represented by the formula (5A-2b) may include 2-bromoethyl isothiocyanate (is-1), 3-bromopropyl isothiocyanate (is-2) (is-1 and is-2 are supplied from Trans World Chemicals), 4-bromobutyl isothiocyanate (is-3) (prepared by brominating 4-aminobutanol supplied from Tokyo Chemical Industry with hydrobromic acid and subsequently reacting thiophosgen according to the method described in Canadian Journal of Chemistry, Vol. 49, 971-974, 1971), 5-bromopentyl isothiocyanate (is-4) (similarly prepared from 5-aminopentanol supplied from Tokyo Chemical Industry), 6-bromohexyl isothiocyanate (is-5) (similarly prepared from 6-aminohexanol supplied from Tokyo Chemical Industry), 7-bromoheptyl isothiocyanate (is-6) (similarly prepared from 7-aminoheptanol supplied from Tokyo Chemical Industry), 8-bromooctyl isothiocyanate (is-7) (similarly prepared from 8-aminooctanol supplied from Watanabe Chemical Industries), 9-bromononyl isothiocyanate (is-8) (similarly prepared from 9-aminononanol supplied from Watanabe Chemical Industries), 10-bromodecyl isothiocyanate (is-9) (similarly prepared from 10-aminodecanol supplied from Watanabe Chemical Industries), 3-bromo-2,2-dimethylpropyl isothiocyanate (is-10) (similarly prepared from 3-amino-2,2-dimethyl propanol supplied from Tokyo Chemical Industry), 5-bromo-4,4-dimethylpentyl isothiocyanate (is-11) (similarly prepared from 5-amino-2,2-dimethyl pentanol supplied from ICN-RF), 2-(2-bromoethoxy)ethyl isothiocyanate (is-12) (similarly prepared from 2-(2-aminoethoxy)ethanol supplied from Tokyo Chemical Industry), 2,2-bis(bromomethyl)butyl isothiocyanate (is-13) (similarly prepared from 2-(aminoethyl)-2-ethyl-1,3-propanediol supplied from Seiler), 4-(bromomethyl)phenyl isothiocyanate (is-14) (prepared from p-tolyl isothiocyanate supplied from Aldrich according to the method described in Journal of Heterocyclic Chemistry, Vol. 31, 457-480, 1994), 3-(bromomethyl)phenyl isothiocyanate (is-15) (prepared from m-tolyl isothiocyanate supplied from Aldrich according to the method described in the same reference), 2-(bromomethyl)phenyl isothiocyanate (is-16) (prepared from o-tolyl isothiocyanate supplied from Aldrich according to the method described in the same reference), 4-(2-bromoethyl) phenyl isothiocyanate (is-17) (prepared by brominating 2-(4-aminophenyl)ethanol supplied from Tokyo Chemical Industry with hydrobromic acid and subsequently reacting thiophosgen according to the method described in Canadian Journal of Chemistry, Vol. 49, 971-974, 1971), 4-(bromomethyl)-2-methylphenyl isothiocyanate (is-18) (prepared by reacting thiophosgen with 2,4-dimethylaniline supplied from Aldrich and subsequently preparing according to the method described in Journal of Heterocyclic Chemistry, Vol. 31, 457-480, 1994), 4-(bromomethyl)-3-methylphenyl isothiocyanate (is-19) (prepared from 3,4-dimethylaniline supplied from Aldrich by the same way as in is-18), 4-(bromomethyl)-2-fluorophenyl isothiocyanate (is-20) (prepared from 2-fluoro-4-methylaniline supplied from Aldrich by the same way as in is-18), 4-(bromomethyl)-3-fluorophenyl isothiocyanate (is-21) (prepared from 3-fluoro-4-methylaniline supplied from Aldrich by the same way as in is-18), 4-(bromomethyl)-2-chlorophenyl isothiocyanate (is-22) (prepared from 2-chloro-4-methylaniline supplied from Aldrich by the same way as in is-18), 4-(bromomethyl)-3-chlorophenyl isothiocyanate (is-23) (prepared from 3-chloro-4-methylaniline supplied from Aldrich by the same way as in is-18), 4-(bromomethyl)-2-bromophenyl isothiocyanate (is-24) (prepared from 2-bromo-4-methylaniline supplied from Aldrich by the same way as in is-18), 4-(bromomethyl)-3-boromophenyl isothiocyanate (is-25) (prepared from 3-bromo-4-methylaniline supplied from Aldrich by the same way as in is-18), 4-(bromomethyl)-2-trifluoromethylphenyl isothiocyanate (is-26) (prepared from 2-trifluoromethyl-4-methylaniline supplied from JRD-Fluorochemical by the same way as in is-18), 4-(bromomethyl)-3-trifluoromethylphenyl isothiocyanate (is-27) (prepared from 3-trifluoromethyl-4-methylaniline supplied from Lancaster by the same way as in is-18), 4-(bromomethyl)-2-nitrophenyl isothiocyanate (is-28) (prepared from 2-nitro-4-methylaniline supplied from Aldrich by the same way as in is-18), 4-(bromomethyl)-3-nitrophenyl isothiocyanate (is-29) (prepared from 3-nitro-4-methylaniline supplied from Aldrich by the same way as in is-18), 4-(bromomethyl)-3-methoxyphenyl isothiocyanate (is-30) (prepared from 3-methoxy-4-methylaniline supplied from Kanto Chemical by the same way as in is-18), 4-(bromomethyl)-2,6-dibromophenyl isothiocyanate (is-31) (prepared from 2,6-dibromo-4-methylaniline supplied from Aldrich by the same way as in is-18), 4-(bromomethyl)-2-methyl-6-nitrophenyl isothiocyanate (is-32) (prepared from 2-nitro-4,6-dimethylaniline supplied from Aldrich by the same way as in is-18), 4-(bromomethyl)-5-methyl-2-nitrophenyl isothiocyanate (is-33) (prepared from 2-nitro-4,5-dimethylaniline supplied from Aldrich by the same way as in is-18), 4-(bromomethyl)-2,6-dimethylphenyl isothiocyanate (is-34) (prepared from 2,4,6-trimethylaniline supplied from Aldrich by the same way as in is-18), 3,4-bis(bromomethyl)phenyl isothiocyanate (is-35) (simultaneously prepared when is-19 is prepared) and 2,4-bis(bromomethyl)phenyl isothiocyanate (is-36) (simultaneously prepared when is-18 is prepared).

Likewise, among the compounds represented by the formula (1B), the compound in which Y is —NHCSNH— may be synthesized from the compound represented by the formula (6B-1).

Likewise, among the compounds represented by the formula (1), the compound in which Y is —NHCSNH— is obtained by reacting a compound represented by the following formula (5-2a):

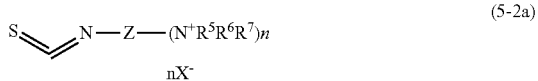

(5-2a)

(wherein n, $R^5$, $R^6$, $R^7$, Z and $X^-$ are the same as the above) with the compound represented by the formula (6-1).

The compound represented by the formula (5-2a) may be obtained by reacting the compound represented by the formula (2) with the compound represented by the following formula (5-2b):

(5-2b)

wherein n, Z and X are the same as the above.

Among the compounds represented by the formula (1A), the compound in which Y is —NHCSO— may be obtained by reacting a compound represented by the following formula (5A-3a):

(5A-3a)

(wherein n, $R^{5a}$, $R^{6a}$, $R^{7a}$, $Z^a$ and $X^-$ are the same as the above) with a compound represented by the following formula (6A-2):

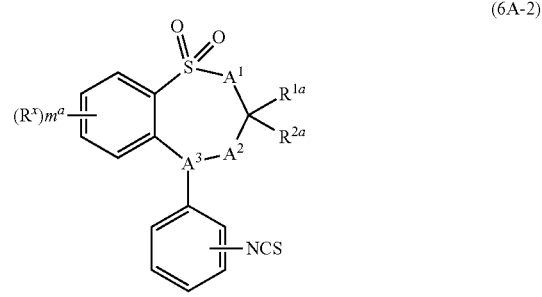

(6A-2)

(wherein $A^1$, $A^2$, $A^3$, $R^x$, $R^{1a}$, $R^{2a}$ and $m^a$ are the same as the above).

The reaction may be performed by reacting the compound represented by the formula (6A-2) with an equivalent amount of the compound represented by the formula (5A-3a) in the presence of an equivalent or more amount of, preferably 1 to 5 fold molar excess of a base, preferably an inorganic base such as hydrogenated sodium or metal sodium in a solvent such as THF, 1,4-dioxane or 2-ethoxyethyl ether at 50 to 150° C. for 1 to 48 hours.

The position for the substitution of —NCS in the formula (6A-2) may be any of ortho, meta or para position. The position is preferably the meta or para position, and most preferably the meta position.

The compound represented by the formula (5A-3a) may be obtained by reacting the compound represented by the formula (2A) with a compound represented by the following formula (5A-3b):

(5A-3b)

wherein n, $Z^a$ and X are the same as the above.

The reaction may be performed by reacting the compound represented by the formula (5A-3b) with an equivalent or more amount of, preferably 1 to 5 fold molar excess of the compound represented by the formula (2A) in, if necessary, a solvent such as acetonitrile or DMF at room temperature or at 40 to 100° C. for 1 to 48 hours.

Examples of the compounds represented by the formula (5A-3b) may include 2-bromoethanol (al-1), 3-bromopropanol (al-2), 4-bromobutanol (al-3), 5-bromopentanol (al-4), 6-bromohexanol (al-5), 7-bromoheptanol (al-6), 8-bromooctanol (al-7), 9-bromononanol (al-8), 10-bromodecanol (al-9) (all, of (al-1) to (al-9) are supplied from Tokyo Chemical Industry), 3-bromo-2-methylpropanol (al-10) and 3-bromo-2,2-dimethylpropanol (al-11) (al-10 and al-11 are supplied from Aldrich).

Likewise, among the compounds represented by the formula (1B), the compound in which Y is —NHCSO— may be synthesized from the compound represented by the following formula (6B-2):

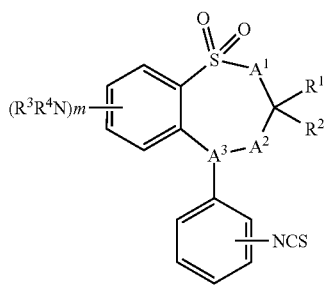
(6B-2)

wherein $A^1$, $A^2$, $A^3$, $R^1$, $R^2$, $R^3$, $R^4$ and m are the same as the above.

Likewise, among the compounds represented by the formula (1), the compound in which Y is —NHCSO— may be obtained by reacting a compound represented by the following formula (5-3a):

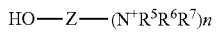
(5-3a)

(wherein n, $R^5$, $R^6$, $R^7$, Z and $X^-$ are the same as the above) with a compound represented by the following formula (6-2):

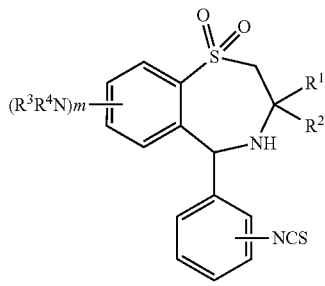
(6-2)

(wherein $R^1$, $R^2$, $R^3$, $R^4$ and m are the same as the above)

The compounds represented by the formula (5-3a) may be obtained by reacting the compounds represented by the formula (2) with a compound represented by the following formula (5-3b):

(5-3b)

wherein n, Z and X are the same as the above.

The compounds represented by the formula (6A-2) may be obtained by reacting thiophosgen with the compounds represented by the formula (6A-1).

The reaction may be performed by reacting the compound represented by the formula (6A-1) with an equivalent amount of thiophosgen (supplied from Aldrich) in the presence of an equivalent amount of, preferably 1 to 5 fold molar excess of a base, preferably an organic base such as triethylamine in, if necessary, a solvent such as THF or dichloromethane at room temperature or at 0 to 10° C. for 1 to 24 hours.

Likewise, the compound represented by the formula (6B-2) may be synthesized from the compound represented by the formula (6B-1).

Likewise, the compound represented by the formula (6-2) may be synthesized from the compound represented by the formula (6-1).

Among the compounds represented by the formula (6B-1), the compound in which the combination of ($A^1$, $A^2$, $A^3$) is ($CH_2$, NH, CH) may be synthesized according to the methods described in the references (WO02/08211, WO93/16055).

Among the compounds represented by the formula (6B-1), the compound in which the combination of ($A^1$, $A^2$, $A^3$) is ($CH_2$, CH(OH), CH) may be synthesized according to the methods described in the reference (WO97/33882).

Among the compounds represented by the formula (6B-1), the compound in which the combination of ($A^1$, $A^2$, $A^3$) is (NH, CH(OH), CH) may be synthesized according to the methods described in the reference (WO00/47568).

Among the compounds represented by the formula (6B-1), the compound in which the combination of ($A^1$, $A^2$, $A^3$) is ($CH_2$, $CH_2$, N) may be prepared by synthesizing a compound represented by the following formula (7B):

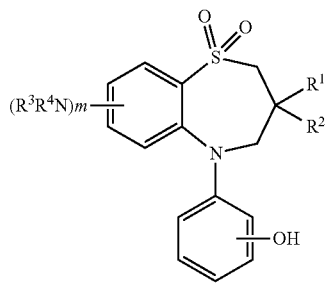
(7B)

(wherein $R^1$, $R^2$, $R^3$, $R^4$ and m are the same as the above), and subsequently applying Buchwald reaction according to the method described in the reference (WO02/08211).

In the compounds represented by the formulae (1A), (1B) and (1), a plurality of stereoisomers can be present depending on the number of asymmetrical centers. Isomers in diastereomer relationship can be separated by silica gel column chromatography or fractional crystallization at any synthetic stage of the compounds represented by the formulae (1A), (1B), (1), (3A), (3B), (3), (4A-1), (4B-1), (4-1), (4A-2), (4B-2), (4-2), (6A-1), (6B-1), (6-1), (6A-2), (6B-2) and (6-2) or any preceding synthetic stage of their material compounds. Isomers in enantiomer relationship can be separated by column chromatography using an optically active carrier, or by silica gel column chromatography or fractional crystallization after derivatizing the isomers into the diastereomer relation, at any synthetic stage of the compounds represented by the formulae (1A), (1B), (1), (3A), (3B), (3), (4A-1), (4B-1), (4-1), (4A-2), (4B-2), (4-2), (6A-1), (6B-1), (6-1), (6A-2), (6B-2) and (6-2) or any preceding synthetic stage of their material compounds. Meanwhile, geometrical isomers can be separated by silica gel column chromatography or fractional crystallization at any synthetic stage of the compounds represented by the formulae (1A), (1B), (1), (3A), (3B), (3), (4A-1), (4B-1), (4-1), (4A-2), (4B-2) and (4-2).

The compounds represented by the formulae (1A), (1B) and (1) of the present invention include acid addition salts. The acid addition salts are preferably the pharmaceutically acceptable salts, and examples thereof may include various publicly known salts, such as hydrochloride salts, hydrobromide salts, sulfate salts, hydrogen sulfate salts, dihydrogen phosphate salts, citrate salts, maleate salts, tartrate salts, fumarate salts, gluconate salts and methanesulfonate salts. For preparing the acid addition salt, the compound represented by the formula (1A), (1B) or (1) may be admixed with an equivalent amount or a several times amount of an acid component, to thereby obtain the acid addition salt thereof. Examples of the acid component for use may include pharmaceutically acceptable mineral acids or organic acids such as hydrochloric acid, hydrobromic acid, sulfuric acid, hydrogen sulfuric acid, dihydrogen phosphoric acid, citric acid, maleic acid, tartaric acid, fumaric acid, gluconic acid and methanesulfonic acid.

The compound of the present invention exhibited the inhibitory activity against ileal bile acid transportation, the blood cholesterol lowering effect and the improvement effect on the hepatic disorders associated with cholestasis. Therefore, it has been confirmed that the compound of the present invention can be utilized as the cholesterol lowering agent or the improver of the hepatic disorders associated with cholestasis. When 3 mg per kg body weight per day of the compound of the present invention was orally administered to rats twice a day for 3.5 days, no death case was observed, and further no mutagenicity in microorganisms was observed. Thus, it has been confirmed that the compound of the present invention can be safely used.

The cholesterol lowering agent may specifically include pharmaceutical compositions for treatment and prevention of hyperlipemia, arteriosclerosis or syndrome X. These diseases will be described more specifically hereinbelow.

That is, hyperlipemia may include hyperchylomicronemia, hyper low density lipoproteinemia, familial hypercholesterolemia, very low density lipoproteinemia and hypertriglyceridemia, as well as complication diseases thereof. A preferred example of the arteriosclerosis to be treated or prevented by the present invention may include atherosclerosis. As described above, hyperlipemia is one of the factors for syndrome X, and syndrome X may cause arteriosclerosis.

The compound and the pharmaceutical composition of the present invention are also useful as the pharmaceuticals for the purpose of the treatment and the prevention of the hepatic disorders associated with cholestasis, and are particularly useful as the therapeutic agent and the preventive agent for primary biliary cirrhosis and primary sclerosing cholangitis.

Cholestasis refers to a state where the bile is not excreted from liver to duodenum as a result of some reason. Cholestasis may cause a disorder in liver, which is referred to as the hepatic disorder associated with cholestasis. Specific diseases of the hepatic disorder associated with cholestasis may include primary biliary cirrhosis, primary sclerosing cholangitis and cholestasis hepatitis (cholangiolitic hepatitis) (*Igaku Daijiten* (Nanzando's Medical Dictionary), Nanzando, 1333-1334). Direct causes of cholestasis may also include gallstones appearing in bile duct and gall bladder. The primary biliary cirrhosis and the primary sclerosing cholangitis are not directly caused by the gallstone.

The compound or the pharmaceutical composition of the present invention is also useful as the pharmaceutical for the purpose of the treatment and the prevention of obesity or fatty liver. The obesity is a state where fat is excessively accumulated in the body, and specifically refers to the state in which BMI (body mass index) exceeds 26 (Yoshio Ikeda et al., *Nippon Rinsho* (Japanese Journal of Clinical Medicine) 53:229-236, 1995). The fatty liver usually refers to a state where neutral fat is abundantly accumulated in the liver. In general, the liver in which lipid droplets are accumulated in 30% or more of hepatic lobule is diagnosed as the fatty liver (Kyoichiro Toshima et al., *Nippon Rinsho* (Japanese Journal of Clinical Medicine) 53:354-358, 1995).

The compound or the pharmaceutical composition of the present invention is also useful as the pharmaceutical for the purpose of the treatment and the prevention of steatohepatitis. Steatohepatitis is the disease in which fat deposition, and inflammation and fibrosis of hepatic parenchyma are observed. Steatohepatitis is quite different from the fatty liver in being associated with inflammatory feature (Toshifumi Azuma et al., *Kan Tan Sui* (Liver, gall bladder and pancreas) 44:429-433, 2002). Among the steatohepatitis, those in which causal relationship with alcohol ingestion is not observed are referred to as non-alcoholic steatohepatitis (NASH).

Upon producing the pharmaceutical of the present invention, it is preferable to, if necessary, add the pharmaceutically acceptable carrier to the effective amount of the compound represented by the formula (1A), (1B) or (1) or the salt thereof, to formulate the pharmaceutical composition. As the pharmaceutically acceptable carrier, excipients, binders such as carboxymethylcellulose, disintegrants, lubricants and additives are exemplified. For administering the compound of the present invention to human, it is possible to orally administer the compound in a variety of forms such as tablets, powers, granules, capsules, sugar-coated tablets, liquids and syrups. A dosage may vary depending on age, body weight and condition of patients. In general, 0.1 to 500 mg per adult person per day is administered as a single dose or several divided doses. The administration time period may be generally consecutive several weeks to several months. Both the dosage per day and the administration time period may be increased and decreased depending on the condition of the patient.

EXAMPLES

The present invention will be further described by the following Examples, but the present invention is not limited thereto. Precoated silicagel 60 F254 (supplied from Merck) was used for thin layer chromatography (TLC), and spots were detected by irradiating UV (254 nm). Nuclear magnetic resonance (NMR) spectra were measured using AL-300 (FT-NMR, supplied from JEOL). Chemical shifts were represented in terms of δ (ppm) using tetramethylsilane (TMS) as an internal standard. Mass spectra were measured by fast atom bombardment mass spectrometry (FAB-MS) using JMS-SX102 (supplied from JEOL).

Silica gel 60 (230 to 400 meshes) (supplied from Merck) was used as a filler of a silica gel column. In the manipulation in Examples, "filtration" means the filtration using Kiriyama funnel and filter paper for the funnel (both are supplied from Tokyo Rikakikai), and "concentration" means distilling off the solvent or the excessive reagent under reduced pressure using an evaporator (supplied from Tokyo Rikakikai)

Example P1

1-(4-{3-[3-(3,3-dibutyl-7-dimethylamono-1,1-dioxo-4-hydroxy-2,3,4,5-tetrahydro-1-benzothiepine-5-yl)phenyl]thioureido}benzyl)-1-azoniabicyclo[2.2.2]octane bromide

(Step a) Synthesis of 2-butyl-2-(hydroxymethyl)hexanal

An aqueous solution of 1 N sodium hydroxide (150 mL) was added dropwise to a solution of 209 g of dibutylacetaldehyde (supplied from Aldrich) and 127 g of an aqueous solution of 35% formalin (supplied from Wako Pure Chemical Industries) in 1500 mL of methanol under ice cooling, and stirred at room temperature overnight. Then 2 L of ether and 2 L of water were added to the reaction solution, and the mixture was separated into two liquid phases. The organic layer was dried on sodium sulfate anhydrate and concentrated, to yield 248 g of the title compound.

(Step b) Synthesis of 2-butyl-2-formylhexyl methanesulfonate

Trimethylamine (146 mL) (supplied from Wako Pure Chemical Industries) was added dropwise to a solution of 140 g of the compound obtained at the step a in 600 mL of chloroform under ice cooling. Subsequently, keeping the mixture under ice cooling, 70 mL of mesyl chloride (supplied from Tokyo Chemical Industry) was added dropwise thereto, and the mixture was stirred at room temperature for 2.5 hours. Then 300 mL of chloroform and 500 mL of 1 N hydrochloric acid were added to the reaction solution, and the mixture was separated into two liquid phases. The organic layer was washed with 300 mL of water, dried on sodium sulfate anhydrate and subsequently concentrated, to yield 212 g of the crudely purified title compound.

(Step c) Synthesis of 2-(2-butyl-2-formylhexylthio)-5-fluoro-benzaldehyde

Lithium sulfide (11.5 g) (supplied from Aldrich) was added to a solution of 32 g of 2,5-difluorobenzaldehyde (supplied from Aldrich) in 1200 mL of dimethylsulfoxide, and stirred at 75° C. for 2 hours. Then 106 g of the compound obtained at the step b was added thereto at the same temperature and stirred for 4 hours. After air cooling at room temperature, 2 L of ethyl acetate and 5 L of saturated brine were added thereto, and the mixture was separated into two liquid phases. The organic layer was washed with 2 L of water, dried on sodium sulfate anhydrate and subsequently concentrated. The residue was applied onto a silica gel column and eluted with hexane-ethyl acetate (30:1), to yield 28.8 g of the title compound.

(Step d) Synthesis of 2-(2-butyl-2-formylhexylthio)-5-fluoro-benzylalcohol 1200 mL of solution of hydrogenated diisobutyl aluminium (1 mol/L) in THF was added dropwise to a solution of 41.5 g of the compound obtained at the step c in 1200 mL of THF at −60° C., and stirred at the same temperature for 3 hours. A small amount of water was added dropwise to the reaction solution at the same temperature until bubbling stopped. Then 1 L of ethyl acetate and 1 L of 1 N hydrochloric acid were added thereto at room temperature, and the mixture was separated into two liquid phases. The organic layer was washed with 1 L of water, dried on sodium sulfate anhydrate and subsequently concentrated. The residue was applied onto the silica gel column and eluted with hexane-ethyl acetate (5:1), to yield 18.2 g of the title compound.

(Step e) Synthesis of 2-(2-butyl-2-formylhexylthio)-5-fluoro-benzyl bromide

Triphenylphonsphine dibromide (46.8 g) (supplied from Aldrich) was added to a solution of 18.1 g of the compound obtained at the step d in 250 mL of DMF at −40° C., and stirred at the same temperature for one hour. Then 400 mL of an aqueous solution of 10% sodium sulfite and 300 mL of ethyl acetate were added to the reaction solution at room temperature, and the mixture was separated into two liquid phases. The organic layer was washed with 300 mL of water, dried on sodium sulfate anhydrate and subsequently concentrated. The residue was applied onto the silica gel column and eluted with hexane-ethyl acetate (5:1), to yield 21.6 g of the title compound.

(Step f) 2-(2-butyl-2-formylhexylsulfonyl)-5-fluoro-benzyl bromide

Metachloroperbenzoic acid (35.2 g) (supplied from Aldrich) was added to a solution of 21.5 g of the compound obtained at the step e in 450 mL of dichloromethane under ice cooling, stirred at the same temperature for 30 minutes, and further stirred at room temperature for one hour. Then 500 mL of an aqueous solution of 10% sodium sulfite and 300 mL of ethyl acetate were added to the reaction solution, and the mixture was separated into two liquid phases. The organic layer was washed with 100 mL of the aqueous solution of 10% sodium sulfite, and further washed with 100 mL of saturated sodium bicarbonate water, dried on sodium sulfate anhydrate and subsequently concentrated, to yield 22.8 g of the title compound.

(Step g) Synthesis of 2-butyl-2-[4-fluoro-2-(3-nitrobenzyl)benzenesulfonylmethyl]hexanal Ethanol (200 mL), 18.0 g of 3-nitrophenylboronic acid (supplied from Aldrich), 3.1 g of tetraxis (triphenylphosphine)palladium (supplied from Aldrich) and 175 mL of an aqueous solution of 2 mol/L sodium carbonate were sequentially added to a solution of 22.7 g of the compound obtained at the step f in 270 mL of toluene, and stirred with heating reflux for 3.5 hours. Then, 1000 mL of ethyl acetate and 600 mL of saturated brine were added to the reaction suspension at room temperature, and the mixture was separated into two liquid phases. The organic layer was dried on sodium sulfate anhydrate and subsequently concentrated. The residue was applied onto the silica gel column and eluted with hexane-ethyl acetate (5:1), to yield 21.4 g of the title compound.

(Step h) Synthesis of 3,3-dibutyl-7-fluoro-4-hydroxy-5-(3-nitrophenyl)-2,3,4,5-tetrahydro-1-benzothiepine-1,1-dioxide A solution of 1 mol/L potassium t-butoxide in THF (92 mL) (supplied from Aldrich) was added dropwise to a solution of 21.3 g of the compound obtained at the step g in 2000 mL of THF under ice cooling, and stirred at the same temperature for one hour. Under ice cooling, 400 mL of an aqueous solution of saturated ammonium chloride was added dropwise to the reaction solution, and stirred at room temperature for one hour. Then, 800 mL of ethyl acetate and 800 mL of water were added thereto, and the mixture was separated into two liquid phases. The organic layer was washed with 800 mL of saturated brine, dried on sodium sulfate anhydrate and subsequently concentrated. The residue was applied onto the silica gel column and eluted with chloroform, to yield 17.2 g of the title compound having cis configuration.

(Step i) Synthesis of 3,3-dibutyl-7-dimethylamino-4-hydroxy-5-(3-nitrophenyl)-2,3,4,5-tetrahydro-1-benzothiepine-1,1-dioxide A solution of dimethylamine (2 mol/L) in THF (370 mL) (supplied from Aldrich) was added to a solution of 17.1 g of the compound obtained at the step h in 50 mL of THF. Then, the test tube was sealed, and heated at 110° C. for 24 hours. The reaction solution was concentrated, and the residue was applied onto the silica gel column and eluted with hexane-ethyl acetate (2:1), to yield 13.3 of the title compound.

(Step j) Synthesis of 5-(3-aminophenyl)-3,3-dibutyl-7-dimethylamino-4-hydroxy-2,3,4,5-tetrahydro-1-benzothiepine-1,1-dioxide 10% Palladium-carbon (3.0 g) (supplied from Merck) was added to a solution of 13.2 g of the compound obtained at the step i in 600 mL of ethanol, and stirred at 45° C. under a hydrogen atmosphere at 7 kg·f/cm² for 20 hours. The reaction suspension was filtrated and the filtrate was concentrated. The residue was applied onto an alumina column and eluted with chloroform-methanol (10:1), to yield 11.9 g of the title compound.

(Step k) Synthesis of 4-(bromomethyl)phenyl isothiocyanate (is-14)

N-bromosuccinimide (6.26 g) (supplied from Tokyo Chemical Industry) and 1.13 g of 70% benzoyl peroxide (supplied from Aldrich) were added to a solution of 5.02 g of p-tolyl isothiocyanate (supplied from Tokyo Chemical Industry) in 100 mL of carbon tetrachloride, and stirred with heating reflux for 19 hours. The reaction suspension was filtrated and the filtrate was concentrated. The residue was applied onto the silica gel column and eluted with hexane, to yield 4.85 g of the title compound.

(Step l) Synthesis of 1-(4-isothiocyanatobenzyl)-1-azoniabicyclo[2.2.2]octane bromide Quinuclidine (316 mg) (supplied from Aldrich) was added to a solution of 600 mg of the compound obtained at the step k in 19 mL of acetone, and stirred at 40° C. for 2 hours. The precipitate therein was collected by filtration, and washed with 10 mL of acetone, to yield 594 mg of the title compound.

(Step m) Synthesis of 1-(4-{3-[3-(3,3-dibutyl-7-dimethylamono-1,1-dioxo-4-hydroxy-2,3,4,5-tetrahydro-1-benzothiepine-5-yl)phenyl]thioureido}benzyl)-1-azoniabicyclo[2.2.2]octane bromide The compound (95 mg) obtained at the step l was added to a solution of 116 mg of the compound obtained at the step j in 3 mL of chloroform, and stirred at 50° C. for 2 hours. The reaction solution was concentrated. The residue was then dissolved in 0.5 mL of chloroform, and 4 mL of ether was added thereto. The precipitate therein was collected by filtration, and washed with 2 mL of ether, to yield 190 mg of the title compound. MS (m/z): 717 (M⁺).

Example P2

1-(4-{3-[3-(3,3-dibutyl-7-dimethylamono-1,1-dioxo-4-hydroxy-2,3,4,5-tetrahydro-1-benzothiepine-5-yl)phenyl]thioureido}-3-fluorobenzyl)-1-azoniabicyclo [2.2.2]octane bromide (Step a) Synthesis of 2-fluoro-4-methylphenyl isothiocyanate Thiophosgen (4.0 mL) (supplied from Aldrich) was added dropwise to a solution of 2-fluoro-4-methylaniline (6.31 g) (supplied from Aldrich) in 70 mL of chloroform under ice cooling, and subsequently 15 mL of triethylamine was added dropwise thereto at the same temperature. The reaction solution was stirred at room temperature overnight. Then 70 mL of 1 N hydrochloric acid was added thereto, and the mixture was separated into two liquid phases. The organic layer was washed with 70 mL of water, dried on sodium sulfate anhydrate and subsequently concentrated The residue was applied onto the silica gel column and eluted with hexane, to yield 7.72 g of the title compound.

(Step b) Synthesis of 2-fluoro-4-(bromomethyl)phenyl isothiocyanate (is-20)

The title compound was obtained using the compound obtained at the step a in the present Example according to the procedure in the step k in Example P1.

(Step c) Synthesis of 1-(3-fluoro-4-isothiocyanatobenzyl)-1-azoniabicyclo[2.2.2]octane bromide The title compound was obtained using the compound obtained at the step b in the present Example according to the procedure in the step l in Example P1.

(Step d) Synthesis of 1-(4-{3-[3-(3,3-dibutyl-7-dimethylamono-1,1-dioxo-4-hydroxy-2,3,4,5-tetrahydro-1-benzothiepine-5-yl)phenyl]thioureido}-3-fluorobenzyl)-1-azoniabicyclo[2.2.2]octane bromide The title compound was obtained using the compound obtained at the step c in the present Example according to the procedure in the step m in Example P1.

Examples P3 to P315

According to the procedures in the steps l to m in Example P1, as shown in the following figure:

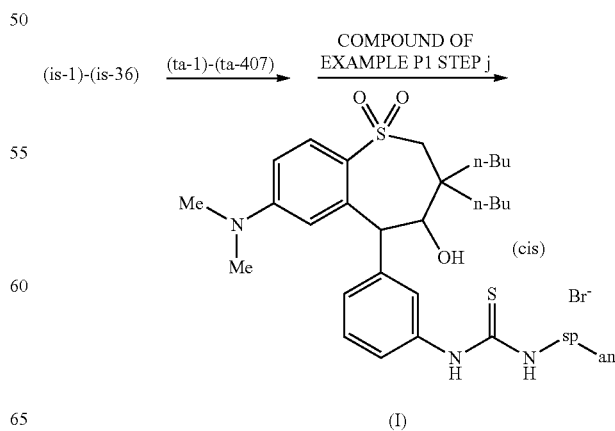

the compounds of Examples P3 to P315 described in Table 3 (Tables 3-1 to 3-3) represented by the formula (I) were obtained using any one of various isothiocyanate (is-1) to (is-36) represented by the above formula (5A-2b), and any one of various tertiary amine (ta-1) to (ta-407) represented by the above formula (2A) and the compound obtained at the step j in Example P1. In the formula (I), -sp- represents any of the above (sp-1) to (sp-44) and -an represents any of the above (an-1) to (an-407).

| EXAMPLE No. | REAGENT is | REAGENT ta | PRODUCT sp | PRODUCT an | EXAMPLE No. | REAGENT is | REAGENT ta | PRODUCT sp | PRODUCT an |
|---|---|---|---|---|---|---|---|---|---|
| | | | | Table 3-1 | | | | | |
| P3  | is-14 | ta-1   | sp-14 | an-1   | P157 | is-1  | ta-287 | sp-1  | an-287 |
| P4  | is-14 | ta-2   | sp-14 | an-2   | P158 | is-2  | ta-287 | sp-2  | an-287 |
| P5  | is-14 | ta-4   | sp-14 | an-4   | P159 | is-3  | ta-287 | sp-3  | an-287 |
| P6  | is-14 | ta-5   | sp-14 | an-5   | P160 | is-4  | ta-287 | sp-4  | an-287 |
| P7  | is-14 | ta-6   | sp-14 | an-6   | P161 | is-5  | ta-287 | sp-5  | an-287 |
| P8  | is-14 | ta-7   | sp-14 | an-7   | P162 | is-15 | ta-287 | sp-23 | an-287 |
| P9  | is-14 | ta-8   | sp-14 | an-8   | P163 | is-16 | ta-287 | sp-24 | an-287 |
| P10 | is-14 | ta-9   | sp-14 | an-9   | P164 | is-17 | ta-287 | sp-25 | an-287 |
| P11 | is-14 | ta-10  | sp-14 | an-10  | P165 | is-18 | ta-287 | sp-26 | an-287 |
| P12 | is-14 | ta-11  | sp-14 | an-11  | P166 | is-19 | ta-287 | sp-27 | an-287 |
| P13 | is-14 | ta-12  | sp-14 | an-12  | P2   | is-20 | ta-287 | sp-28 | an-287 |
| P14 | is-14 | ta-13  | sp-14 | an-13  | P167 | is-21 | ta-287 | sp-29 | an-287 |
| P15 | is-14 | ta-14  | sp-14 | an-14  | P168 | is-22 | ta-287 | sp-30 | an-287 |
| P16 | is-14 | ta-16  | sp-14 | an-16  | P169 | is-23 | ta-287 | sp-31 | an-287 |
| P17 | is-14 | ta-18  | sp-14 | an-18  | P170 | is-24 | ta-287 | sp-32 | an-287 |
| P18 | is-14 | ta-19  | sp-14 | an-19  | P171 | is-25 | ta-287 | sp-33 | an-287 |
| P19 | is-14 | ta-20  | sp-14 | an-20  | P172 | is-27 | ta-287 | sp-35 | an-287 |
| P20 | is-14 | ta-21  | sp-14 | an-21  | P173 | is-29 | ta-287 | sp-37 | an-287 |
| P21 | is-14 | ta-22  | sp-14 | an-22  | P174 | is-34 | ta-287 | sp-42 | an-287 |
| P22 | is-14 | ta-23  | sp-14 | an-23  | P175 | is-35 | ta-287 | sp-43 | an-287 |
| P23 | is-14 | ta-25  | sp-14 | an-25  | P176 | is-1  | ta-32  | sp-1  | an-32  |
| P24 | is-14 | ta-26  | sp-14 | an-26  | P177 | is-2  | ta-32  | sp-2  | an-32  |
| P25 | is-14 | ta-32  | sp-14 | an-32  | P178 | is-3  | ta-32  | sp-3  | an-32  |
| P26 | is-14 | ta-33  | sp-14 | an-33  | P179 | is-4  | ta-32  | sp-4  | an-32  |
| P27 | is-14 | ta-34  | sp-14 | an-34  | P180 | is-5  | ta-32  | sp-5  | an-32  |
| P28 | is-14 | ta-35  | sp-14 | an-35  | P181 | is-15 | ta-32  | sp-23 | an-32  |
| P29 | is-14 | ta-36  | sp-14 | an-36  | P182 | is-16 | ta-32  | sp-24 | an-32  |
| P30 | is-14 | ta-38  | sp-14 | an-38  | P183 | is-17 | ta-32  | sp-25 | an-32  |
| P31 | is-14 | ta-40  | sp-14 | an-40  | P184 | is-18 | ta-32  | sp-26 | an-32  |
| P32 | is-14 | ta-41  | sp-14 | an-41  | P185 | is-19 | ta-32  | sp-27 | an-32  |
| P33 | is-14 | ta-42  | sp-14 | an-42  | P186 | is-20 | ta-32  | sp-28 | an-32  |
| P34 | is-14 | ta-43  | sp-14 | an-43  | P187 | is-21 | ta-32  | sp-29 | an-32  |
| P35 | is-14 | ta-46  | sp-14 | an-46  | P188 | is-22 | ta-32  | sp-30 | an-32  |
| P36 | is-14 | ta-67  | sp-14 | an-67  | P189 | is-23 | ta-32  | sp-31 | an-32  |
| P37 | is-14 | ta-98  | sp-14 | an-98  | P190 | is-24 | ta-32  | sp-32 | an-32  |
| P38 | is-14 | ta-99  | sp-14 | an-99  | P191 | is-25 | ta-32  | sp-33 | an-32  |
| P39 | is-14 | ta-101 | sp-14 | an-101 | P192 | is-27 | ta-32  | sp-35 | an-32  |
| P40 | is-14 | ta-102 | sp-14 | an-102 | P193 | is-29 | ta-32  | sp-37 | an-32  |
| P41 | is-14 | ta-103 | sp-14 | an-103 | P194 | is-34 | ta-32  | sp-42 | an-32  |
| P42 | is-14 | ta-105 | sp-14 | an-105 | P195 | is-35 | ta-32  | sp-43 | an-32  |
| P43 | is-14 | ta-107 | sp-14 | an-107 | P196 | is-1  | ta-288 | sp-1  | an-288 |
| P44 | is-14 | ta-108 | sp-14 | an-108 | P197 | is-2  | ta-288 | sp-2  | an-288 |
| P45 | is-14 | ta-114 | sp-14 | an-114 | P198 | is-3  | ta-288 | sp-3  | an-288 |
| P46 | is-14 | ta-115 | sp-14 | an-115 | P199 | is-4  | ta-288 | sp-4  | an-288 |
| P47 | is-14 | ta-136 | sp-14 | an-136 | P200 | is-5  | ta-288 | sp-5  | an-288 |
| P48 | is-14 | ta-146 | sp-14 | an-146 | P201 | is-15 | ta-288 | sp-23 | an-288 |
| P49 | is-14 | ta-150 | sp-14 | an-150 | P202 | is-16 | ta-288 | sp-24 | an-288 |
| P50 | is-14 | ta-159 | sp-14 | an-159 | P203 | is-17 | ta-288 | sp-25 | an-288 |
| P51 | is-14 | ta-160 | sp-14 | an-160 | P204 | is-18 | ta-288 | sp-26 | an-288 |
| P52 | is-14 | ta-164 | sp-14 | an-164 | P205 | is-19 | ta-288 | sp-27 | an-288 |
| P53 | is-14 | ta-165 | sp-14 | an-165 | P206 | is-20 | ta-288 | sp-28 | an-288 |
| P54 | is-14 | ta-166 | sp-14 | an-166 | P207 | is-21 | ta-288 | sp-29 | an-288 |
| P55 | is-14 | ta-168 | sp-14 | an-168 | P208 | is-22 | ta-288 | sp-30 | an-288 |
| P56 | is-14 | ta-169 | sp-14 | an-169 | P209 | is-23 | ta-288 | sp-31 | an-288 |
| | | | | Table 3-2 | | | | | |
| P57 | is-14 | ta-176 | sp-14 | an-176 | P210 | is-24 | ta-288 | sp-32 | an-288 |
| P58 | is-14 | ta-177 | sp-14 | an-177 | P211 | is-25 | ta-288 | sp-33 | an-288 |
| P59 | is-14 | ta-179 | sp-14 | an-179 | P212 | is-27 | ta-288 | sp-35 | an-288 |
| P60 | is-14 | ta-180 | sp-14 | an-180 | P213 | is-29 | ta-288 | sp-37 | an-288 |
| P61 | is-14 | ta-183 | sp-14 | an-183 | P214 | is-34 | te-288 | sp-42 | an-288 |
| P62 | is-14 | ta-185 | sp-14 | an-185 | P215 | is-35 | ta-288 | sp-43 | an-288 |
| P63 | is-14 | ta-187 | sp-14 | an-187 | P216 | is-1  | ta-297 | sp-1  | an-297 |
| P64 | is-14 | ta-188 | sp-14 | an-188 | P217 | is-2  | ta-297 | sp-2  | an-297 |
| P65 | is-14 | ta-191 | sp-14 | an-191 | P218 | is-3  | ta-297 | sp-3  | an-297 |
| P66 | is-14 | ta-196 | sp-14 | an-196 | P219 | is-4  | ta-297 | sp-4  | an-297 |
| P67 | is-14 | ta-197 | sp-14 | an-197 | P220 | is-5  | ta-297 | sp-5  | an-297 |

-continued

| EXAMPLE | REAGENT | | PRODUCT | | EXAMPLE | REAGENT | | PRODUCT | |
|---|---|---|---|---|---|---|---|---|---|
| No. | is | ta | sp | an | No. | is | ta | sp | an |
| P68 | is-14 | ta-199 | sp-14 | an-199 | P221 | is-15 | ta-297 | sp-23 | an-297 |
| P69 | is-14 | ta-200 | sp-14 | an-200 | P222 | is-16 | ta-297 | sp-24 | an-297 |
| P70 | is-14 | ta-203 | sp-14 | an-203 | P223 | is-17 | ta-297 | sp-25 | an-297 |
| P71 | is-14 | ta-221 | sp-14 | an-221 | P224 | is-18 | ta-297 | sp-26 | an-297 |
| P72 | is-14 | ta-223 | sp-14 | an-223 | P225 | is-19 | ta-297 | sp-27 | an-297 |
| P73 | is-14 | ta-230 | sp-14 | an-230 | P226 | is-20 | ta-297 | sp-28 | an-297 |
| P74 | is-14 | ta-231 | sp-14 | an-231 | P227 | is-21 | ta-297 | sp-29 | an-297 |
| P75 | is-14 | ta-233 | sp-14 | an-233 | P228 | is-22 | ta-297 | sp-30 | an-297 |
| P76 | is-14 | ta-235 | sp-14 | an-235 | P229 | is-23 | ta-297 | sp-31 | an-297 |
| P77 | is-14 | ta-253 | sp-14 | an-253 | P230 | is-24 | ta-297 | sp-32 | an-297 |
| P78 | is-14 | ta-254 | sp-14 | an-254 | P231 | is-25 | ta-297 | sp-33 | an-297 |
| P79 | is-14 | ta-267 | sp-14 | an-267 | P232 | is-27 | ta-297 | sp-35 | an-297 |
| P80 | is-14 | ta-270 | sp-14 | an-270 | P233 | is-29 | ta-297 | sp-37 | an-297 |
| P81 | is-14 | ta-272 | sp-14 | an-272 | P234 | is-34 | ta-297 | sp-42 | an-297 |
| P82 | is-14 | ta-274 | sp-14 | an-274 | P235 | is-35 | ta-297 | sp-43 | an-297 |
| P83 | is-14 | ta-275 | sp-14 | an-275 | P236 | is-1 | ta-305 | sp-1 | an-305 |
| P1 | is-14 | ta-287 | sp-14 | an-287 | P237 | is-2 | ta-305 | sp-2 | an-305 |
| P84 | is-14 | ta-288 | sp-14 | an-288 | P238 | is-3 | ta-305 | sp-3 | an-305 |
| P85 | is-14 | ta-289 | sp-14 | an-289 | P239 | is-4 | ta-305 | sp-4 | an-305 |
| P86 | is-14 | ta-290 | sp-14 | an-290 | P240 | is-5 | ta-305 | sp-5 | an-305 |
| P87 | is-14 | ta-297 | sp-14 | an-297 | P241 | is-15 | ta-305 | sp-23 | an-305 |
| P88 | is-14 | ta-299 | sp-14 | an-299 | P242 | is-16 | ta-305 | sp-24 | an-305 |
| P89 | is-14 | ta-300 | sp-14 | an-300 | P243 | is-17 | ta-305 | sp-25 | an-305 |
| P90 | is-14 | ta-301 | sp-14 | an-301 | P244 | is-18 | ta-305 | sp-26 | an-305 |
| P91 | is-14 | ta-302 | sp-14 | an-302 | P245 | is-19 | ta-305 | sp-27 | an-305 |
| P92 | is-14 | ta-303 | sp-14 | an-303 | P246 | is-20 | ta-305 | sp-28 | an-305 |
| P93 | is-14 | ta-305 | sp-14 | an-305 | P247 | is-21 | ta-305 | sp-29 | an-305 |
| P94 | is-14 | ta-306 | sp-14 | an-306 | P248 | is-22 | ta-305 | sp-30 | an-305 |
| P95 | is-14 | ta-307 | sp-14 | an-307 | P249 | is-23 | ta-305 | sp-31 | an-305 |
| P96 | is-14 | ta-308 | sp-14 | an-308 | P250 | is-24 | ta-305 | sp-32 | an-305 |
| P97 | is-14 | ta-309 | sp-14 | an-309 | P251 | is-25 | ta-305 | sp-33 | an-305 |
| P98 | is-14 | ta-310 | sp-14 | an-310 | P252 | is-27 | ta-305 | sp-35 | an-305 |
| P99 | is-14 | ta-311 | sp-14 | an-311 | P253 | is-29 | ta-305 | sp-37 | an-305 |
| P100 | is-14 | ta-313 | sp-14 | an-313 | P254 | is-34 | ta-305 | sp-42 | an-305 |
| P101 | is-14 | ta-314 | sp-14 | an-314 | P255 | is-35 | ta-305 | sp-43 | an-305 |
| P102 | is-14 | ta-315 | sp-14 | an-315 | P256 | is-1 | ta-339 | sp-1 | an-339 |
| P103 | is-14 | ta-316 | sp-14 | an-316 | P257 | is-2 | ta-339 | sp-2 | an-339 |
| P104 | is-14 | ta-317 | sp-14 | an-317 | P258 | is-3 | ta-339 | sp-3 | an-339 |
| P105 | is-14 | ta-318 | sp-14 | an-318 | P259 | is-4 | ta-339 | sp-4 | an-339 |
| P106 | is-14 | ta-319 | sp-14 | an-319 | P260 | is-5 | ta-339 | sp-5 | an-339 |
| P107 | is-14 | ta-321 | sp-14 | an-321 | P261 | is-15 | ta-339 | sp-23 | an-339 |
| P108 | is-14 | ta-322 | sp-14 | an-322 | P262 | is-16 | ta-339 | sp-24 | an-339 |
| P109 | is-14 | ta-325 | sp-14 | an-325 | P263 | is-17 | ta-339 | sp-25 | an-339 |

Table 3-3

| P110 | is-14 | ta-326 | sp-14 | an-326 | P264 | is-18 | ta-339 | sp-26 | an-339 |
|---|---|---|---|---|---|---|---|---|---|
| P111 | is-14 | ta-328 | sp-14 | an-328 | P265 | is-19 | ta-339 | sp-27 | an-339 |
| P112 | is-14 | ta-330 | sp-14 | an-330 | P266 | is-20 | ta-339 | sp-28 | an-339 |
| P113 | is-14 | ta-331 | sp-14 | an-331 | P267 | is-21 | ta-339 | sp-29 | an-339 |
| P114 | is-14 | ta-332 | sp-14 | an-332 | P268 | is-22 | ta-339 | sp-30 | an-339 |
| P115 | is-14 | ta-333 | sp-14 | an-333 | P269 | is-23 | ta-339 | sp-31 | an-339 |
| P116 | is-14 | ta-334 | sp-14 | an-334 | P270 | is-24 | ta-339 | sp-32 | an-339 |
| P117 | is-14 | ta-335 | sp-14 | an-335 | P271 | is-25 | ta-339 | sp-33 | an-339 |
| P118 | is-14 | ta-339 | sp-14 | an-339 | P272 | is-27 | ta-339 | sp-35 | an-339 |
| P119 | is-14 | ta-340 | sp-14 | an-340 | P273 | is-29 | ta-339 | sp-37 | an-339 |
| P120 | is-14 | ta-341 | sp-14 | an-341 | P274 | is-34 | ta-339 | sp-42 | an-339 |
| P121 | is-14 | ta-342 | sp-14 | an-342 | P275 | is-35 | ta-339 | sp-43 | an-339 |
| P122 | is-14 | ta-344 | sp-14 | an-344 | P276 | is-1 | ta-344 | sp-1 | an-344 |
| P123 | is-14 | ta-345 | sp-14 | an-345 | P277 | is-2 | ta-344 | sp-2 | an-344 |
| P124 | is-14 | ta-346 | sp-14 | an-346 | P278 | is-3 | ta-344 | sp-3 | an-344 |
| P125 | is-14 | ta-351 | sp-14 | an-351 | P279 | is-4 | ta-344 | sp-4 | an-344 |
| P126 | is-14 | ta-355 | sp-14 | an-355 | P280 | is-5 | ta-344 | sp-5 | an-344 |
| P127 | is-14 | ta-356 | sp-14 | an-356 | P281 | is-15 | ta-344 | sp-23 | an-344 |
| P128 | is-14 | ta-357 | sp-14 | an-357 | P282 | is-16 | ta-344 | sp-24 | an-344 |
| P129 | is-14 | ta-358 | sp-14 | an-358 | P283 | is-17 | ta-344 | sp-25 | an-344 |
| P130 | is-14 | ta-360 | sp-14 | an-360 | P284 | is-18 | ta-344 | sp-26 | an-344 |
| P131 | is-14 | ta-361 | sp-14 | an-361 | P285 | is-19 | ta-344 | sp-27 | an-344 |
| P132 | is-14 | ta-362 | sp-14 | an-362 | P286 | is-20 | ta-344 | sp-28 | an-344 |
| P133 | is-14 | ta-363 | sp-14 | an-363 | P287 | is-21 | ta-344 | sp-29 | an-344 |
| P134 | is-14 | ta-364 | sp-14 | an-364 | P288 | is-22 | ta-344 | sp-30 | an-344 |
| P135 | is-14 | ta-366 | sp-14 | an-366 | P289 | is-23 | ta-344 | sp-31 | an-344 |
| P136 | is-14 | ta-367 | sp-14 | an-367 | P290 | is-24 | ta-344 | sp-32 | an-344 |
| P137 | is-14 | ta-375 | sp-14 | an-375 | P291 | is-25 | ta-344 | sp-33 | an-344 |
| P138 | is-14 | ta-378 | sp-14 | an-378 | P292 | is-27 | ta-344 | sp-35 | an-344 |
| P139 | is-14 | ta-380 | sp-14 | an-380 | P293 | is-29 | ta-344 | sp-37 | an-344 |
| P140 | is-14 | ta-388 | sp-14 | an-388 | P294 | is-34 | ta-344 | sp-42 | an-344 |

-continued

| EXAMPLE No. | REAGENT is | REAGENT ta | PRODUCT sp | PRODUCT an | EXAMPLE No. | REAGENT is | REAGENT ta | PRODUCT sp | PRODUCT an |
|---|---|---|---|---|---|---|---|---|---|
| P141 | is-14 | ta-389 | sp-14 | an-389 | P295 | is-35 | ta-344 | sp-43 | an-344 |
| P142 | is-14 | ta-391 | sp-14 | an-391 | P296 | is-1 | ta-395 | sp-1 | an-395 |
| P143 | is-14 | ta-394 | sp-14 | an-394 | P297 | is-2 | ta-395 | sp-2 | an-395 |
| P144 | is-14 | ta-395 | sp-14 | an-395 | P298 | is-3 | ta-395 | sp-3 | an-395 |
| P145 | is-14 | ta-396 | sp-14 | an-396 | P299 | is-4 | ta-395 | sp-4 | an-395 |
| P146 | is-14 | ta-397 | sp-14 | an-397 | P300 | is-5 | ta-395 | sp-5 | an-395 |
| P147 | is-14 | ta-398 | sp-14 | an-398 | P301 | is-15 | ta-395 | sp-23 | an-395 |
| P148 | is-14 | ta-399 | sp-14 | an-399 | P302 | is-16 | ta-395 | sp-24 | an-395 |
| P149 | is-14 | ta-400 | sp-14 | an-400 | P303 | is-17 | ta-395 | sp-25 | an-395 |
| P150 | is-14 | ta-401 | sp-14 | an-401 | P304 | is-18 | ta-395 | sp-26 | an-395 |
| P151 | is-14 | ta-402 | sp-14 | an-402 | P305 | is-19 | ta-395 | sp-27 | an-395 |
| P152 | is-14 | ta-403 | sp-14 | an-403 | P306 | is-20 | ta-395 | sp-28 | an-395 |
| P153 | is-14 | ta-404 | sp-14 | an-404 | P307 | is-21 | ta-395 | sp-29 | an-395 |
| P154 | is-14 | ta-405 | sp-14 | an-405 | P308 | is-22 | ta-395 | sp-30 | an-395 |
| P155 | is-14 | ta-406 | sp-14 | an-406 | P309 | is-23 | ta-395 | sp-31 | an-395 |
| P156 | is-14 | ta-407 | sp-14 | an-407 | P310 | is-24 | ta-395 | sp-32 | an-395 |
|  |  |  |  |  | P311 | is-25 | ta-395 | sp-33 | an-395 |
|  |  |  |  |  | P312 | is-27 | ta-395 | sp-35 | an-395 |
|  |  |  |  |  | P313 | is-29 | ta-395 | sp-37 | an-395 |
|  |  |  |  |  | P314 | is-34 | ta-395 | sp-42 | an-395 |
|  |  |  |  |  | P315 | is-35 | ta-395 | sp-43 | an-395 |

Example P316

1-(4-{3-[3-(3,3-dibutyl-7-dimethylamono-1,1-dioxo-2,3,4,5-tetrahydro-1,4-benzothiazepine-5-yl)phenyl]thioureido}-3-fluorobenzyl)-4-phenyl-1-azoniabicyclo[2.2.2]octane bromide (Step a) Synthesis of methyl 2-benzylideneaminohexanoate Triethylamine (8.67 g) (supplied from Wako Pure Chemical Industries), 7.74 g of magnesium sulfate anhydrate and 4.55 g of benzaldehyde (supplied from Wako Pure Chemical Industries) were added to a suspension of 7.79 g of methyl 2-aminohexanoate hydrochloride (supplied from BACHEM) in 70 mL of dichloromethane, and stirred at room temperature overnight. The reaction suspension was filtrated and the filtrate was concentrated. Then 280 mL of ether was added to the residue. The resulting suspension was filtrated and the filtrate was concentrated. Again 280 mL of ether was added to the residue, and the filtration and the concentration were repeated in the same manner, to yield 10.0 g of the title compound.

(Step b) Synthesis of methyl 2-benzylideneamino-2-butylhexanoate

Hydrogenated sodium (1.66 g) (60% dispersion in oil) (supplied from Wako Pure Chemical Industries) was added to a solution of 8.06 g of the compound obtained at the step a in 25 mL of DMF in an argon atmosphere under ice cooling, and stirred at room temperature for 2 hours. Then, a solution of 8.90 g of 1-iodobutane (supplied from Tokyo Chemical Industry) in 15 mL of DMF was added dropwise to the reaction suspension in the argon atmosphere under ice cooling, and stirred at room temperature for 3 hours. Under ice cooling, a solution of 5.5 g of ammonium chloride in 50 mL of water was added dropwise to the reaction suspension. 80 mL of ether and 30 mL of water were then added thereto, and the mixture was separated into two liquid phases. The organic layer was dried on sodium sulfate anhydrate and subsequently concentrated, to yield 10.0 g of the title compound.

(Step c) Synthesis of methyl 2-amino-2-butylhexanoate

Hydrochloric acid (1 N, 30 mL) was added to a solution of 15.46 g of the compound obtained at the step b in 70 mL of petroleum ether, and stirred at room temperature for one hour. Then 60 mL of water was added to the reaction solution, and the mixture was separated into two liquid phases. The aqueous layer was washed twice with 80 mL of ether, and an aqueous solution of 5 N sodium hydroxide was added thereto, to adjust to pH 9 to 10. Subsequently, 160 mL of ethyl acetate was added to the aqueous layer, and the mixture was separated into two liquid phases. The organic layer was washed with 160 mL of saturated brine. The organic layer was dried on sodium sulfate anhydrate and subsequently concentrated, to yield 10.0 g of the title compound.

(Step d) Synthesis of 2-amino-2-butylhexanol

A solution of the compound (17.34 g) obtained at the step c in 120 mL of THF was added dropwise to a suspension of 7.52 g of hydrogenated lithium aluminium (supplied from Wako Pure Chemical Industries) in 50 mL of THF under ice cooling, and stirred at 60° C. for one hour. Under ice cooling, 25 mL of water was added dropwise to the reaction suspension, and 600 mL of ethyl acetate was added thereto at room temperature. The mixture was filtrated with celite, and washed with 900 mL of ethyl acetate. The filtrate was concentrated, to yield 10.0 g of the title compound.

(Step e) Synthesis of 2-amino-2-butylhexyl hydrogen sulfate

Chlorosulfonic acid (8.04 g) was added dropwise to a solution of 7.97 g of the compound obtained at the step d in 90 mL of dichloromethane under ice cooling, and stirred at room temperature overnight. The reaction solution was concentrated, and 90 mL of acetone-ether (1:1) was added to the residue, which was then left stand at −20° C. for 3 hours. The produced precipitate was collected by filtration, and washed with 300 mL of acetone-ether (1:1), to yield 10.0 g of the title compound.

(Step f) Synthesis of 4-fluoro-2-benzoylthiophenol

Lithium sulfide (3.5 g) (supplied from Aldrich) was added to a solution of 10.1 g of 2,5-difluorobenzophenone in 200 mL of DMSO, and stirred at 120° C. under a nitrogen atmosphere for 3 hours. Under ice cooling, 200 mL of 1 N hydrochloric acid was added to the reaction solution. Further 400 mL of ethyl acetate and 200 mL of water were added thereto, and the mixture was separated into two liquid phases. The organic layer was washed with 400 mL of water, and then washed with 200 mL of saturated brine. The organic layer was dried on sodium sulfate anhydrate and subsequently concentrated, to yield 10.54 g of the title compound.

(Step g) Synthesis of 2-(2-amino-2-butylhexylthio)-5-fluoro-benzophenone

A solution of 11.50 g of the compound obtained at the step e and 7.25 g of sodium hydroxide in 100 mL of water were added to a solution of 10.54 g of the compound obtained at the step f in 100 mL of butyl acetate, and stirred at 90° C. for one hour. Then 300 mL of ethyl acetate and 300 mL of water were added to the reaction solution, and the mixture was separated into two liquid phases. The organic layer was dried on sodium sulfate anhydrate and subsequently concentrated. The residue was applied onto the silica gel column and eluted with chloroform-methanol-28% ammonia water (50:1:0.1), to yield 10.09 g of the title compound.

(Step h) Synthesis of 3,3-dibutyl-2,3-dihydro-7-fluoro-5-phenyl-1,4-benzothiazepine p-Toluene sulfonic acid monohydrate (0.60 g) (supplied from Wako Pure Chemical Industries) was added to a solution of 10.08 g of the compound obtained at the step g in 40 mL of 2,6-lutidine (supplied from Wako Pure Chemical Industries), and stirred at 130° C. for 34 hours. Then 400 mL of ethyl acetate and 400 mL of water were added to the reaction solution, and the mixture was separated into two liquid phases. The organic layer was dried on sodium sulfate anhydrate and subsequently concentrated. The residue was applied onto the silica gel column and eluted with hexane-ethyl acetate (30:1), to yield 7.87 g of the title compound.

(Step i) Synthesis of 3,3-dibutyl-2,3-dihydro-7-fluoro-5-phenyl-1,4-benzothiazepine-1,1-dioxide Acetonitrile (150 mL), a solution of 13.3 g of sodium periodate (supplied from Wako Pure Chemical Industries) in 70 mL of water and 0.42 g of ruthenium trichloride (supplied from Wako Pure Chemical Industries) were added to a solution of 7.86 g of the compound obtained at the step h in 50 mL dichloromethane, and stirred at room temperature for 24 hours. Then 300 mL of dichloromethane and 300 mL of water were added to the reaction suspension, and the mixture was separated into two liquid phases. The organic layer was dried on sodium sulfate anhydrate and subsequently concentrated. The residue was applied onto the silica gel column and eluted with hexane-ethyl acetate (6:1), to yield 5.72 g of the title compound.

(Step j) Synthesis of 3,3-dibutyl-2,3-dihydro-7-fluoro-5-(3-nitrophenyl)-1,4-benzothiazepine-1,1-dioxide A mixed solution of 20 mL of smoking nitric acid and 15 mL of concentrated sulfuric acid was added to 5.32 g of the compound obtained at the step i under ice cooling, and stirred at room temperature for one hour. The reaction solution was added dropwise to 5N sodium hydroxide solution under ice cooling. Further 150 mL of dichloromethane and 50 mL of water were added thereto at room temperature, and the mixture was separated into two liquid phases. The organic layer was washed with 150 mL of saturated brine, dried on sodium sulfate anhydrate and subsequently concentrated. The residue was applied onto the silica gel column and eluted with hexane-ethyl acetate (5:1), to yield 5.48 g of the title compound.

(Step k) Synthesis of 3,3-dibutyl-2,3-dihydro-7-dimethylamino-5-(3-nitrophenyl)-1,4-benzothiazepine-1,1-dioxide 200 mL of a solution of dimethylamine (2 mol/L) in THF (supplied from Aldrich) was added to 5.48 g of the compound obtained at the step j, and heated at 55° C. for 14 hours. The reaction solution was concentrated. The residue was applied onto the silica gel column and eluted with hexane-ethyl acetate (2:1). The eluate was washed with 50 mL of ether, to yield 5.69 g of the title compound.

(Step l) Synthesis of 3,3-dibutyl-2,3-dihydro-7-dimethylamino-5-(3-aminophenyl)-1,4-benzothiazepine-1,1-dioxide Methanol (100 mL) and 1.2 g of 10% palladium-carbon (supplied from Merck) were added to a solution of 5.9 g of the compound obtained at the step k in 100 mL of chloroform, and stirred at room temperature under a hydrogen atmosphere for 4 hours. The catalyst in the reaction suspension was filtrated off, and the filtrate was concentrated. The residue was applied onto the silica gel column and eluted with chloroform-methanol (30:1), to yield 4.38 g of the title compound.

(Step m) Synthesis of 3,3-dibutyl-2,3,4,5-tetrahydro-7-dimethylamino-5-(3-aminophenyl)-1,4-benzothiazepine-1,1-dioxide 150 mL of a solution of borane THF complex (1 mol/L) in THF (supplied from Kanto Chemical) was added to 4.38 g of the compound obtained at the step l, and stirred at room temperature for one hour. Then 10 mL of water was added dropwise to the reaction solution until bubbling stopped, and stirred at room temperature for 1.5 hours. Further, 150 mL of ethyl acetate, 50 mL of water and 100 mL of an aqueous solution of 1 N sodium hydroxide were added thereto at room temperature, and the mixture was separated into two liquid phases. The organic layer was washed with 150 mL of water, and left stand at room temperature for 1.5 hours. The organic layer was dried on sodium sulfate anhydrate and subsequently concentrated. The residue was applied onto the silica gel column and eluted with hexane-ethyl acetate (1:1), to yield 3.83 g of the title compound.

(Step n) Synthesis of 1-(4-{3-[3-(3,3-dibutyl-7-dimethylamono-1,1-dioxo-2,3,4,5-tetrahydro-1,4-benzothiazepine-5-yl)phenyl]thioureido}-3-fluorobenzyl)-4-phenyl-1-azoniabicyclo[2.2.2]octane bromide The title compound was obtained using the compound obtained at the step m in the present Example and the compound obtained at the step c in the Example P2 according to the procedure in the step m in Example P1.

Examples P317 to P423

As shown in the following figure:

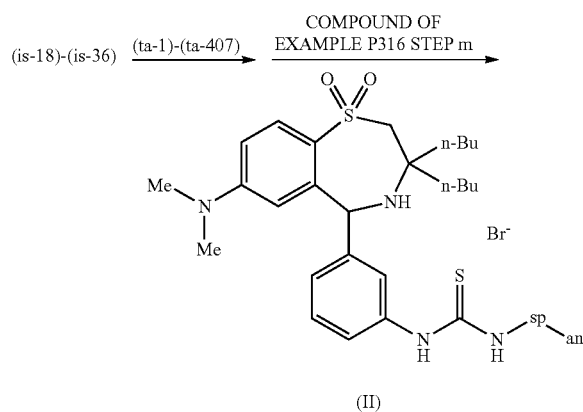

the compounds of Examples P317 to P423 described in Table 4 (Tables 4-1 to 4-2) represented by the formula (II) are obtained using any one of various isothiocyanate (is-18) to (is-36) represented by the above formula (5A-2b), and any one of various tertiary amine (ta-1) to (ta-407) represented by the above formula (2A) and the compound obtained at the step m in Example P316. In the formula (II), -sp- represents any of the above (sp-26) to (sp-44) and -an represents any of the above (an-1) to (an-407).

| EXAMPLE | REAGENT | | PRODUCT | |
|---|---|---|---|---|
| No. | is | ta | sp | an |
| Table 4-1 | | | | |
| P317 | is-18 | ta-287 | sp-26 | an-287 |
| P318 | is-19 | ta-287 | sp-27 | an-287 |
| P316 | is-20 | ta-287 | sp-28 | an-287 |
| P319 | is-21 | ta-287 | sp-29 | an-287 |
| P320 | is-22 | ta-287 | sp-30 | an-287 |
| P321 | is-23 | ta-287 | sp-31 | an-287 |
| P322 | is-24 | ta-287 | sp-32 | an-287 |
| P323 | is-25 | ta-287 | sp-33 | an-287 |
| P324 | is-27 | ta-287 | sp-35 | an-287 |
| P325 | is-29 | ta-287 | sp-37 | an-287 |
| P326 | is-34 | ta-287 | sp-42 | an-287 |
| P327 | is-35 | ta-287 | sp-43 | an-287 |
| P328 | is-18 | ta-32 | sp-26 | an-32 |
| P329 | is-19 | ta-32 | sp-27 | an-32 |
| P330 | is-20 | ta-32 | sp-28 | an-32 |
| P331 | is-21 | ta-32 | sp-29 | an-32 |
| P332 | is-22 | ta-32 | sp-30 | an-32 |
| P333 | is-23 | ta-32 | sp-31 | an-32 |
| P334 | is-24 | ta-32 | sp-32 | an-32 |
| P335 | is-25 | ta-32 | sp-33 | an-32 |
| P336 | is-27 | ta-32 | sp-35 | an-32 |
| P337 | is-29 | ta-32 | sp-37 | an-32 |
| P338 | is-34 | ta-32 | sp-42 | an-32 |
| P339 | is-35 | ta-32 | sp-43 | an-32 |
| P340 | is-18 | ta-288 | sp-26 | an-288 |
| P341 | is-19 | ta-288 | sp-27 | an-288 |
| P342 | is-20 | ta-288 | sp-28 | an-288 |
| P343 | is-21 | ta-288 | sp-29 | an-288 |
| P344 | is-22 | ta-288 | sp-30 | an-288 |
| P345 | is-23 | ta-288 | sp-31 | an-288 |
| P346 | is-24 | ta-288 | sp-32 | an-288 |
| P347 | is-25 | ta-288 | sp-33 | an-288 |
| P348 | is-27 | ta-288 | sp-35 | an-288 |
| P349 | is-29 | ta-288 | sp-37 | an-288 |
| P350 | is-34 | ta-288 | sp-42 | an-288 |
| P351 | is-35 | ta-288 | sp-43 | an-288 |
| P352 | is-18 | ta-297 | sp-26 | an-297 |
| P353 | is-19 | ta-297 | sp-27 | an-297 |
| P354 | is-20 | ta-297 | sp-28 | an-297 |
| P355 | is-21 | ta-297 | sp-29 | an-297 |
| P356 | is-22 | ta-297 | sp-30 | an-297 |
| P357 | is-23 | ta-297 | sp-31 | an-297 |
| P358 | is-24 | ta-297 | sp-32 | an-297 |
| P359 | is-25 | ta-297 | sp-33 | an-297 |
| P360 | is-27 | ta-297 | sp-35 | an-297 |
| P361 | is-29 | ta-297 | sp-37 | an-297 |
| P362 | is-34 | ta-297 | sp-42 | an-297 |
| P363 | is-35 | ta-297 | sp-43 | an-297 |
| P364 | is-18 | ta-305 | sp-26 | an-305 |
| P365 | is-19 | ta-305 | sp-27 | an-305 |
| P366 | is-20 | ta-305 | sp-28 | an-305 |
| P367 | is-21 | ta-305 | sp-29 | an-305 |
| P368 | is-22 | ta-305 | sp-30 | an-305 |
| P369 | is-23 | ta-305 | sp-31 | an-305 |
| Table 4-2 | | | | |
| P370 | is-24 | ta-305 | sp-32 | an-305 |
| P371 | is-25 | ta-305 | sp-33 | an-305 |
| P372 | is-27 | ta-305 | sp-35 | an-305 |
| P373 | is-29 | ta-305 | sp-37 | an-305 |
| P374 | is-34 | ta-305 | sp-42 | an-305 |
| P375 | is-35 | ta-305 | sp-43 | an-305 |
| P376 | is-18 | ta-309 | sp-26 | an-309 |
| P377 | is-19 | ta-309 | sp-27 | an-309 |
| P378 | is-20 | ta-309 | sp-28 | an-309 |
| P379 | is-21 | ta-309 | sp-29 | an-309 |
| P380 | is-22 | ta-309 | sp-30 | an-309 |
| P381 | is-23 | ta-309 | sp-31 | an-309 |
| P382 | is-24 | ta-309 | sp-32 | an-309 |
| P383 | is-25 | ta-309 | sp-33 | an-309 |
| P384 | is-27 | ta-309 | sp-35 | an-309 |
| P385 | is-29 | ta-309 | sp-37 | an-309 |
| P386 | is-34 | ta-309 | sp-42 | an-309 |
| P387 | is-35 | ta-309 | sp-43 | an-309 |
| P388 | is-18 | ta-339 | sp-26 | an-339 |
| P389 | is-19 | ta-339 | sp-27 | an-339 |
| P390 | is-20 | ta-339 | sp-28 | an-339 |
| P391 | is-21 | ta-339 | sp-29 | an-339 |
| P392 | is-22 | ta-339 | sp-30 | an-339 |
| P393 | is-23 | ta-339 | sp-31 | an-339 |
| P394 | is-24 | ta-339 | sp-32 | an-339 |
| P395 | is-25 | ta-339 | sp-33 | an-339 |
| P396 | is-27 | ta-339 | sp-35 | an-339 |
| P397 | is-29 | ta-339 | sp-37 | an-339 |
| P398 | is-34 | ta-339 | sp-42 | an-339 |
| P399 | is-35 | ta-339 | sp-43 | an-339 |
| P400 | is-18 | ta-344 | sp-26 | an-344 |
| P401 | is-19 | ta-344 | sp-27 | an-344 |
| P402 | is-20 | ta-344 | sp-28 | an-344 |
| P403 | is-21 | ta-344 | sp-29 | an-344 |
| P404 | is-22 | ta-344 | sp-30 | an-344 |
| P405 | is-23 | ta-344 | sp-31 | an-344 |
| P406 | is-24 | ta-344 | sp-32 | an-344 |
| P407 | is-25 | ta-344 | sp-33 | an-344 |
| P408 | is-27 | ta-344 | sp-35 | an-344 |
| P409 | is-29 | ta-344 | sp-37 | an-344 |
| P410 | is-34 | ta-344 | sp-42 | an-344 |
| P411 | is-35 | ta-344 | sp-43 | an-344 |
| P412 | is-18 | ta-395 | sp-26 | an-395 |
| P413 | is-19 | ta-395 | sp-27 | an-395 |
| P414 | is-20 | ta-395 | sp-28 | an-395 |
| P415 | is-21 | ta-395 | sp-29 | an-395 |
| P416 | is-22 | ta-395 | sp-30 | an-395 |
| P417 | is-23 | ta-395 | sp-31 | an-395 |
| P418 | is-24 | ta-395 | sp-32 | an-395 |
| P419 | is-25 | ta-395 | sp-33 | an-395 |
| P420 | is-27 | ta-395 | sp-35 | an-395 |
| P421 | is-29 | ta-395 | sp-37 | an-395 |
| P422 | is-34 | ta-395 | sp-42 | an-395 |
| P423 | is-35 | ta-395 | sp-43 | an-395 |

Example P424

1-(4-{3-[4-(3,3-dibutyl-7-dimethylamono-1,1-dioxo-2,3,4,5-tetrahydro-1,4-benzothiazepine-5-yl)phenyl]thioureido}-3-fluorobenzyl)-4-phenyl-1-azoniabicyclo[2.2.2]octane bromide

(Step a) Synthesis of 4-fluorophenyl 4-methoxybenzoate

Triethylamine (6 mL) and a solution of 4.0 g of 4-methoxybenzoyl chloride (supplied from Tokyo Chemical Industry) in 40 mL of chloroform were added to a solution of 6.0 g of 4-fluorophenol (supplied from Tokyo Chemical Industry) in 60 mL of chloroform, and stirred at 55° C. for one hour. Then 100 mL of dichloromethane, 200 mL of water and 25 mL of an aqueous solution of 1 N sodium hydroxide were added to the reaction solution, and the mixture was separated into two liquid phases. The organic layer was dried on sodium sulfate anhydrate and subsequently concentrated, to yield 8.1 g of the title compound.

(Step b) Synthesis of 4-fluoro-2-(4-methoxybenzoyl)phenol

Titanium tetrachloride (10 mL) (supplied from Wako Pure Chemical Industries) was added to 6.55 g of the compound obtained at the step a, and heated at 160° C. for 4 hours. Under ice cooling, 10 mL of water was added dropwise to the reaction mixture. Further 400 mL of ether and 400 mL of water were added thereto at room temperature, and the mixture was separated into two liquid phases. The organic layer was dried on sodium sulfate anhydrate and subsequently concentrated. The residue was applied onto the silica gel and eluted with hexane-ethyl acetate (8:1), to yield 3.44 g of the title compound.

(Step c) Synthesis of O-[4-fluoro-2-(4-methoxybenzoyl)phenyl] N,N-dimethylthiocarbamate Triethylamine (4.24 g), 0.34 g of dimethylaminopyridine (supplied from Wako Pure Chemical Industries) and 2.10 g of N,N-dimethylthiocarbamoyl chloride (supplied from Tokyo Chemical Industry) were added to a solution of 3.44 g of the compound obtained at the step b in 70 mL of dioxane, and stirred at 100° C. for 24 hours. Then, 200 mL of ethyl acetate and 200 mL of water were added to the reaction suspension, and the mixture was separated into two liquid phases. The organic layer was dried on sodium sulfate anhydrate and subsequently concentrated. The residue was applied onto the silica gel and eluted with hexane-ethyl acetate (3:1), to yield 4.65 g of the title compound.

(Step d) Synthesis of S-[4-fluoro-2-(4-methoxybenzoyl)phenyl] N,N-dimethylthiocarbamate A suspension of the compound (4.65 g) obtained at the step c in 30 mL of tetradecane (supplied from Wako Pure Chemical Industries) was heated at 250° C. for 5 hours. Then 12 mL of chloroform was added to the reaction suspension at room temperature to dissolve the reaction product. This solution was applied onto the silica gel column and eluted with hexane-ethyl acetate (2:1), to yield 2.10 g of the title compound.

(Step e) Synthesis of 4-fluoro-2-(4-methoxybenzoyl)thiophenol

Methanol (20 mL) and 1.88 g of potassium hydroxide were added to a solution of 2.10 g of the compound obtained at the step d in 20 mL of THF, and stirred at 60° C. for 2 hours. Then, 30 mL of 1 N hydrochloric acid was added to the reaction suspension under ice cooling. Further 100 mL of ethyl acetate and 100 mL of water were added thereto at room temperature, and the mixture was separated into two liquid phases. The organic layer was washed with 150 mL of saturated brine, dried on sodium sulfate anhydrate and subsequently concentrated, to yield 1.63 g of the title compound.

(Step f) Synthesis of 3,3-dibutyl-2,3-dihydro-7-fluoro-5-(4-methoxyphenyl)-1,4-benzothiazepine-1,1-dioxide The title compound was obtained using the compound obtained at the step e in the present Example according to the procedures in the steps g to i in Example 1.

(Step g) Synthesis of 3,3-dibutyl-2,3-dihydro-7-dimethylamino-5-(4-methoxyphenyl)-1,4-benzothiazepine-1,1-dioxide The title compound was obtained using the compound obtained at the step f in the present Example according to the procedures in the step k in Example 1.

(Step h) Synthesis of 3,3-dibutyl-7-dimethylamino-2,3,4,5-tetrahydro-5-(4-methoxyphenyl)-1,4-benzothiazepine-1,1-dioxide The title compound was obtained using the compound obtained at the step g in the present Example according to the procedures in the step m in Example 1.

(Step i) Synthesis of 3,3-dibutyl-7-dimethylamino-2,3,4,5-tetrahydro-5-(4-hydroxyphenyl)-1,4-benzothiazepine-1,1-dioxide 9 mL of a solution of boron tribromide (1 mol/L) in dichloromethane (supplied from Aldrich) was added dropwise to a solution of 1.15 g of the compound obtained at the step h in 10 mL of dichloromethane at −20° C., and stirred under ice cooling for one hour. The reaction solution was added dropwise to 200 mL of 5% sodium bicarbonate water under ice cooling. Further 100 mL of dichloromethane was added thereto at room temperature, and the mixture was separated into two liquid phases. The organic layer was dried on sodium sulfate anhydrate and subsequently concentrated. The residue was applied onto the silica gel column and eluted with hexane-ethyl acetate (2:1), to yield 1.00 g of the title compound.

(Step j) 4-(3,3-dibutyl-7-dimethylamino-1,1-dioxo-2,3,4,5-tetrahydro-1,4-benzothiazepine-5-yl)phenyl trifluoromethanesulfonate Trifluoromethanesulfonic acid anhydride (388 μL) (supplied from Aldrich) was added dropwise to a solution of 735 mg of the compound obtained at the step i in 3.3 mL of pyridine at 0° C., and stirred at room temperature for one hour. Then 10 mL of ethyl acetate and 10 mL of water were added to the reaction solution, and the mixture was separated into two liquid phases. The organic layer was washed with 10 mL of an aqueous solution of saturated copper sulfate, further washed with 10 mL of saturated sodium bicarbonate water and further washed with 10 mL of saturated brine. The organic layer was dried on sodium sulfate anhydrate and subsequently concentrated, to yield 916 mg of the title compound.

(Step k) Synthesis of 3,3-dibutyl-7-dimethylamino-2, 3,4,5-tetrahydro-5-(4-aminophenyl)-1,4-benzothiazepine-1,1-dioxide Palladium acetate II (303 mg) (supplied from Aldrich), 986 mg of 2,2'-bis(diphenylphosphenyl)-1,1'-binaphthyl (supplied from Aldrich) and 4.42 g of cesium carbonate (supplied from Wako Pure chemical Industries) were added to a solution of 3.77 g of the compound obtained at the step j in 38 mL of THF, and 2.2 mL of benzophenone imine (supplied from Aldrich) was further added thereto. The mixture was refluxed under heating with stirring for 2 hours. Insoluble matters in the reaction suspension were filtrated off, and the filtrate was concentrated. The residue was dissolved in 65 mL of methanol, and 2.15 g of sodium acetate (supplied from Wako Pure chemical Industries) and 1.38 g of hydroxylamine hydrochloride (supplied from Tokyo Chemical Industry) were added and stirred at room temperature for one hour. Then, 70 mL of dichloromethane and 70 mL of saturated sodium bicarbonate water were added to the reaction suspension, and the mixture was separated into two liquid phases. The organic layer was washed with 70 mL of saturated brine, dried on sodium sulfate anhydrate and subsequently concentrated. The residue was applied onto the silica gel column and eluted with hexane-ethyl acetate (2:1), to yield 2.48 g of the title compound.

(Step l) Synthesis of 1-(4-{3-[4-(3,3-dibutyl-7-dimethylamono-1,1-dioxo-2,3,4,5-tetrahydro-1,4-benzothiazepine-5-yl)phenyl]thioureido}-3-fluorobenzyl)-4-phenyl-1-azoniabicyclo[2.2.2]octane bromide The title compound was obtained using the compound obtained at the step k in the present Example and the compound obtained at the step c in Example P2 according to the procedure in the step m in Example P1.

Example 1

1-{5-[3-(3,3-dibutyl-7-dimethylamono-1,1-dioxo-2,3,4,5-tetrahydro-1,4-benzothiazepine-5-yl)phenylthiocarbamoyl]pentyl}-1-azoniabicyclo[2.2.2]octane bromide (Step a) Synthesis of methyl 2-benzylideneaminohexanoate Triethylamine (8.67 g) (supplied from Wako Pure chemical Industries), 7.74 g of magnesium sulfate anhydrate and 4.55 g of benzaldehyde were added to a suspension of 7.79 g of methyl 2-aminohexanoate hydrochloride in 70 mL of dichloromethane, and stirred at room temperature overnight. The reaction suspension was filtrated, and the filtrate was concentrated. Then 280 mL of ether was added to the residue. The resulting suspension was filtrated and the filtrate was concentrated. Again 280 mL of ether was added to the residue, and the filtration and the concentration were repeated in the same manner, to yield 10.0 g of the title compound.

(Step b) Synthesis of methyl 2-benzylideneamino-2-butylhexanoate

Hydrogenated sodium (60% dispersion in oil) (1.66 g) (supplied from Wako Pure chemical Industries) was added to a solution of 8.06 g of the compound obtained at the step a in 25 mL DMF under ice cooling in the argon atmosphere, and stirred at room temperature for 2 hours. Under ice cooling in the argon atmosphere, a solution of 8.90 g of 1-iodobutane in 15 mL of DMF was added dropwise to the reaction suspension, and stirred at room temperature for 3 hours. Under ice cooling, a solution of 5.5 g of ammonium chloride in 50 mL of water was added dropwise to the reaction suspension. Further 80 mL of ether and 30 mL of water were added thereto, and the mixture was separated into two liquid phases. The organic layer was dried on sodium sulfate anhydrate and subsequently concentrated, to yield 10.0 g of the title compound.

(Step c) Synthesis of methyl 2-amino-2-butylhexanoate

1 N hydrochloric acid (30 mL) was added to a solution of 15.46 g of the compound obtained at the step b in 70 mL of petroleum ether, and stirred at room temperature for one hour. Then, 60 mL of water was added to the reaction solution, and the mixture was separated into two liquid phases. The aqueous layer was washed twice with 80 mL of ether, and an aqueous solution of 5 N sodium hydroxide was added thereto for adjusting pH to 9 to 10. Subsequently, 160 mL of ethyl acetate was added to the aqueous layer, and the mixture was separated into two liquid phases. The organic layer was washed with 160 mL of saturated brine. The organic layer was dried on sodium sulfate anhydrate and subsequently concentrated, to yield 10.0 g of the title compound.

(Step d) Synthesis of 2-amino-2-butylhexanol

A solution of the compound (17.34 g) obtained at the step c in 120 mL of THF was added dropwise to a suspension of 7.52 g of hydrogenated lithium aluminium (supplied from Wako Pure Chemical Industries) in 50 mL of THF under ice cooling, and stirred at 60° C. for one hour. Under ice cooling, 25 mL of water was added dropwise to the reaction suspension, and 600 mL of ethyl acetate was added thereto at room temperature. The mixture was filtrated with celite, and washed with 900 mL of ethyl acetate. The filtrate was concentrated, to yield 10.0 g of the title compound.

(Step e) Synthesis of 2-amino-2-butylhexyl hydrogen sulfate

Chlorosulfonic acid (8.04 g) was added dropwise to a solution of 7.97 g of the compound obtained at the step d in 90 mL of dichloromethane under ice cooling, and stirred at room temperature overnight. The reaction solution was concentrated, and 90 mL of acetone-ether (1:1) was added to the residue, which was then left stand at −20° C. for 3 hours. The produced precipitate was collected by filtration, and washed with 300 mL of acetone-ether (1:1), to yield 10.0 g of the title compound.

(Step f) Synthesis of 4-fluoro-2-benzoylthiophenol

Lithium sulfide (3.5 g) (supplied from Aldrich) was added to a solution of 10.1 g of 2,5-difluorobenzophenone in 200 mL of DMSO, and stirred at 120° C. under a nitrogen atmosphere for 3 hours. Under ice cooling, 200 mL of 1 N hydrochloric acid was added to the reaction solution. Further 400 mL of ethyl acetate and 200 mL of water were added thereto, and the mixture was separated into two liquid phases. The organic layer was washed with 400 mL of water, and then washed with 200 mL of saturated brine. The organic layer was dried on sodium sulfate anhydrate and subsequently concentrated, to yield 10.54 g of the title compound.

(Step g) Synthesis of 2-(2-amino-2-butylhexylthio)-5-fluoro-benzophenone

The compound (11.50 g) obtained at the step e and a solution of 7.25 g of sodium hydroxide in 100 mL of water were added to a solution of 10.54 g of the compound obtained at the step f in 100 mL of butyl acetate, and stirred at 90° C. for one hour. Then 300 mL of ethyl acetate and 300 mL of water were added to the reaction solution, and the mixture was separated into two liquid phases. The organic layer was dried on sodium sulfate anhydrate and subsequently concentrated. The residue was applied onto the silica gel column and eluted with chloroform-methanol-28% ammonia water (50:1:0.1), to yield 10.09 g of the title compound.

(Step h) Synthesis of 3,3-dibutyl-2,3-dihydro-7-fluoro-5-phenyl-1,4-benzothiazepine p-Toluene sulfonic acid monohydrate (0.60 g) (supplied from Wako Pure Chemical Industries) was added to a solution of 10.08 g of the compound obtained at the step g in 40 mL of 2,6-lutidine (supplied from Wako Pure Chemical Industries), and stirred at 130° C. for 34 hours. Then 400 mL of ethyl acetate and 400 mL of water were added to the reaction solution, and the mixture was separated into two liquid phases. The organic layer was dried on sodium sulfate anhydrate and subsequently concentrated. The residue was applied onto the silica gel column and eluted with hexane-ethyl acetate (30:1), to yield 7.87 g of the title compound.

(Step i) Synthesis of 3,3-dibutyl-2,3-dihydro-7-fluoro-5-phenyl-1,4-benzothiazepine-1,1-dioxide Acetonitrile (150 mL), a solution of 13.3 g of sodium periodate (supplied from Wako Pure Chemical Industries) in 70 mL of water and 0.42 g of ruthenium trichloride (supplied from Wako Pure Chemical Industries) were added to a solution of 7.86 g of the compound obtained at the step h in 50 mL dichloromethane, and stirred at room temperature for 24 hours. Then 300 mL of dichloromethane and 300 mL of water were added to the reaction suspension, and the mixture was separated into two liquid phases. The organic layer was dried on sodium sulfate anhydrate and subsequently concentrated. The residue was applied onto the silica gel column and eluted with hexane-ethyl acetate (6:1), to yield 5.72 g of the title compound.

(Step j) Synthesis of 3,3-dibutyl-2,3-dihydro-7-fluoro-5-(3-nitrophenyl)-1,4-benzothiazepine-1,1-dioxide A mixed solution of 20 mL of smoking nitric acid and 15 mL of concentrated sulfuric acid was added to 5.32 g of the compound obtained at the step i under ice cooling, and stirred at room temperature for one hour. The reaction solution was added dropwise to 5N sodium hydroxide solution under ice cooling. Further 150 mL of dichloromethane and 50 mL of water were added thereto at room temperature, and the mixture was separated into two liquid phases. The organic layer was washed with 150 mL of saturated brine, dried on sodium sulfate anhydrate and subsequently concentrated. The residue was applied onto the silica gel column and eluted with hexane-ethyl acetate (5:1), to yield 5.48 g of the title compound.

(Step k) Synthesis of 3,3-dibutyl-2,3-dihydro-7-dimethylamino-5-(3-nitrophenyl)-1,4-benzothiazepine-1,1-dioxide 200 mL of a solution of dimethylamine (2 mol/L) in THF (supplied from Aldrich) was added to 5.48 g of the compound obtained at the step j, and heated at 55° C. for 14 hours. The reaction solution was concentrated. The residue was applied onto the silica gel column and eluted with hexane-ethyl acetate (2:1). The eluate was washed with 50 mL of ether, to yield 5.69 g of the title compound.

(Step l) Synthesis of 3,3-dibutyl-2,3-dihydro-7-dimethylamino-5-(3-aminophenyl)-1,4-benzothiazepine-1,1-dioxide Methanol (100 mL) and 1.2 g of 10% palladium-carbon (supplied from Merck) were added to a solution of 5.9 g of the compound obtained at the step k in 100 mL of chloroform, and stirred at room temperature under a hydrogen atmosphere for 4 hours. The catalyst in the reaction suspension was filtrated off, and the filtrate was concentrated. The residue was applied onto the silica gel column and eluted with chloroform-methanol (30:1), to yield 4.38 g of the title compound.

(Step m) Synthesis of 3,3-dibutyl-2,3,4,5-tetrahydro-7-dimethylamino-5-(3-aminophenyl)-1,4-benzothiazepine-1,1-dioxide 150 mL of a solution of borane THF complex (1 mol/L) in THF (supplied from Kanto Chemical) was added to 4.38 g of the compound obtained at the step l, and stirred at room temperature for one hour. Then 10 mL of water was added dropwise to the reaction solution until bubbling stopped, and stirred at room temperature for 1.5 hours. Further, 150 mL of ethyl acetate, 50 mL of water and 100 mL of an aqueous solution of 1 N sodium hydroxide were added thereto at room temperature, and the mixture was separated into two liquid phases. The organic layer was washed with 150 mL of water, and left stand at room temperature for 1.5 hours. The organic layer was dried on sodium sulfate anhydrate and subsequently concentrated. The residue was applied onto the silica gel column and eluted with hexane-ethyl acetate (1:1), to yield 3.83 g of the title compound.

(Step n) Synthesis of 3,3-dibutyl-2,3,4,5-tetrahydro-7-dimethylamino-5-[3-(6-bromohexanoyl)aminophenyl]-1,4-benzothiazepine-1,1-dioxide Potassium carbonate (0.27 g) was added to a solution of 0.73 g of the compound obtained at the step m in 15 mL of dichloromethane. Subsequently 0.37 g of 6-bromo-n-caproyl chloride was added thereto, and stirred at room temperature for 20 minutes. Then 35 mL of dichloromethane and 50 mL of water were added to the reaction solution, and the mixture was separated into two liquid phases. The organic layer was dried on sodium sulfate anhydrate and subsequently concentrated. The residue was applied onto the silica gel column and eluted with hexane-ethyl acetate (1:1), to yield 1.00 g of the title compound.

(Step o) Synthesis of 3,3-dibutyl-2,3,4,5-tetrahydro-7-dimethylamino-5-[3-(6-bromothiohexanoyl)aminophenyl]-1,4-benzothiazepine-1,1-dioxide Lawesson reagent (90 mg) was added to a solution of 50 mg of the compound obtained at the step n in 1.5 mL of THF, and stirred at room temperature for 40 hours. Then 6 mL of ethyl acetate and 8 mL of water were added to the reaction solution, and the mixture was separated into two liquid phases. The organic layer was dried on sodium sulfate anhydrate and subsequently concentrated. The residue was applied onto the silica gel column and eluted with hexane-ethyl acetate (2:1), to yield 37 mg of the title compound. Rf value 0.41 (developed in hexane:ethyl acetate=3:1)

(Step p) Synthesis of 1-{5-[3-(3,3-dibutyl-7-dimethylamono-1,1-dioxo-2,3,4,5-tetrahydro-1,4-benzothiazepine-5-yl)phenylthiocarbamoyl]pentyl}-1-azoniabicyclo[2.2.2]octane bromide Quinuclidine (7 mg, aforementioned ta-287) was added to a solution of 36 mg of the compound obtained at the step o in 1 mL of acetonitrile, and heated at 50° C. for 22 hours. The reaction solution was concentrated. The residue was dissolved in 0.2 mL of dichloromethane, and 2 mL of ether was added thereto. The produced precipitate was washed with 2 mL of ether, to yield 32 mg of the title compound. $^1$H-NMR (CDCl$_3$) δ: 0.84 (3H, t); 0.90 (3H, t); 1.18-1.51 (8H, m); 1.60-2.23 (17H, m); 2.84 (6H, s); 2.95-3.12 (3H, m); 3.26-3.43 (3H, m); 3.58 (6H, t); 6.03-6.07 (2H, m); 6.47 (1H, dd); 7.34-7.39 (2H, m); 7.72-7.76 (1H, m); 7.84 (1H, d); 7.98 (1H, s); 11.56 (1H, s). MS (m/z): 667 (M+).

Example 2

1-{5-[3-(3-butyl-3-ethyl-7-dimethylamino-1,1-dioxo-2,3,4,5-tetrahydro-1,4-benzothiazepine-5-yl)phenylthiocarbamoyl]pentyl}-1-azoniabicyclo[2.2.2]octane bromide (Step a) Synthesis of 3-butyl-3-ethyl-2,3,4,5-tetrahydro-7-dimethylamino-5-(3-aminophenyl)-1,4-benzothiazepine-1,1-dioxide The title compound was obtained according to the procedures in the steps a to m in Example 1, except for using methyl 2-aminobutylate hydrochloride in place of methyl 2-aminohexanoate hydrochloride used in the step a in Example 1.

(Step b) Synthesis of 1-{5-[3-(3-butyl-3-ethyl-7-dimethylamino-1,1-dioxo-2,3,4,5-tetrahydro-1,4-benzothiazepine-5-yl)phenylthiocarbamoyl]pentyl}-1-azoniabicyclo[2.2.2]octane bromide The title compound was obtained using the compound obtained at the step a in the present Example according to the procedures in the steps n to p in Example 1.

Example 3

1-{5-[3-(3,3-dipropyl-7-dimethylamino-1,1-dioxo-2,3,4,5-tetrahydro-1,4-benzothiazepine-5-yl)phenylthiocarbamoyl]pentyl}-1-azoniabicyclo[2.2.2]octane bromide (Step a) Synthesis of 3,3-dipropyl-2,3,4,5-tetrahydro-7-dimethylamino-5-(3-aminophenyl)-1,4-benzothiazepine-1,1-dioxide The title compound was obtained according to the procedures in the steps d to m in Example 1, except for using 2-amino-2-propyl pentanoic acid (supplied from Advanced ChemTech) in place of the compound obtained at the step c in Example 1.

(Step b) Synthesis of 1-{5-[3-(3,3-dipropyl-7-dimethylamino-1,1-dioxo-2,3,4,5-tetrahydro-1,4-benzothiazepine-5-yl)phenylthiocarbamoyl]pentyl}-1-azoniabicyclo[2.2.2]octane bromide The title compound was obtained using the compound obtained at the step a in the present Example according to the procedures in the steps n to p in Example 1.

Example 4

1-{5-[3-(3,3-dipentyl-7-dimethylamino-1,1-dioxo-2,3,4,5-tetrahydro-1,4-benzothiazepine-5-yl)phenylthiocarbamoyl]pentyl}-1-azoniabicyclo[2.2.2]octane bromide (Step a) Synthesis of methyl 2-aminoheptanoate hydrochloride Thionyl chloride (2.19 g) (supplied from Wako Pure Chemical Industries) was added dropwise to a suspension of 2.18 g of 2-aminoheptanoic acid in 50 mL of methanol, and stirred at 60° C. overnight. Methanol and thionyl chloride were distilled off, and the residue was washed with 20 mL of ether, to yield 2.84 g of the title compound.

(Step b) Synthesis of 3,3-dipentyl-2,3,4,5-tetrahydro-7-dimethylamino-5-(3-aminophenyl)-1,4-benzothiazepine-1,1-dioxide The title compound was obtained using the compound obtained at the step a in the present Example according to the procedures in the steps a to m in Example 1 although 1-iodopentane was reacted in place of 1-iodobutane at the step b.

(Step c) Synthesis of 1-{5-[3-(3,3-dipentyl-7-dimethylamino-1,1-dioxo-2,3,4,5-tetrahydro-1,4-benzothiazepine-5-yl)phenylthiocarbamoyl]pentyl}-1-azoniabicyclo[2.2.2]octane bromide The title compound was obtained using the compound obtained at the step b in the present Example according to the procedures in the steps n to p in Example 1.

Example 5

1-{5-[3-(3,3-dihexyl-7-dimethylamino-1,1-dioxo-2,3,4,5-tetrahydro-1,4-benzothiazepine-5-yl)phenylthiocarbamoyl]pentyl}-1-azoniabicyclo[2.2.2]octane bromide (Step a) Synthesis of methyl 2-aminooctanoate hydrochloride The title compound was obtained except for using 2-aminocaprylic acid in place of 2-aminoheptanoic acid used in the step a in Example 4.

(Step b) Synthesis of 3,3-dihexyl-2,3,4,5-tetrahydro-7-dimethylamino-5-(3-aminophenyl)-1,4-benzothiazepine-1,1-dioxide The title compound was obtained using the compound obtained at the step a in the present Example according to the procedures in the steps a to m in Example 1 although 1-iodohexane was reacted in place of 1-iodobutane at the step b.

(Step c) Synthesis of 1-{5-[3-(3,3-dihexyl-7-dimethylamino-1,1-dioxo-2,3,4,5-tetrahydro-1,4-benzothiazepine-5-yl)phenylthiocarbamoyl]pentyl}-1-azoniabicyclo[2.2.2]octane bromide The title compound was obtained using the compound obtained at the step b in the present Example according to the procedures in the steps n to p in Example 1.

Example 6

1-{5-[3-(3,3-dibutyl-7-diethylamino-1,1-dioxo-2,3,4,5-tetrahydro-1,4-benzothiazepine-5-yl)phenylthiocarbamoyl]pentyl}-1-azoniabicyclo[2.2.2]octane bromide (Step a) Synthesis of 3,3-dibutyl-2,3,4,5-tetrahydro-7-diethylamino-5-(3-aminophenyl)-1,4-benzothiazepine-1,1-dioxide The title compound was obtained according to the procedures in the steps a to m in Example 1 except for reacting diethylamine in place of dimethylamine in the step k.

(Step b) Synthesis of 1-{5-[3-(3,3-dibutyl-7-diethylamino-1,1-dioxo-2,3,4,5-tetrahydro-1,4-benzothiazepine-5-yl)phenylthiocarbamoyl]pentyl}-1-azoniabicyclo[2.2.2]octane bromide The title compound was obtained using the compound obtained at the step a in the present Example according to the procedures in the steps n to p in Example 1.

Example 7

1-{5-[3-(3,3-dibutyl-7-ethylmethylamino-1,1-dioxo-2,3,4,5-tetrahydro-1,4-benzothiazepine-5-yl)phenylthiocarbamoyl]pentyl}-1-azoniabicyclo[2.2.2]octane bromide (Step a) Synthesis of 3,3-dibutyl-2,3,4,5-tetrahydro-7-ethylmethylamino-5-(3-aminophenyl)-1,4-benzothiazepine-1,1-dioxide The title compound was obtained according to the procedures in the steps a to m in Example 1 except for reacting ethylmethylamine in place of dimethylamine in the step k.

(Step b) Synthesis of 1-{5-[3-(3,3-dibutyl-7-ethylmethylamino-1,1-dioxo-2,3,4,5-tetrahydro-1,4-benzothiazepine-5-yl)phenylthiocarbamoyl]pentyl}-1-azoniabicyclo[2.2.2]octane bromide The title compound was obtained using the compound obtained at the step a in the present Example according to the procedures in the steps n to p in Example 1.

Example 8

1-{5-[3-(3,3-dibutyl-7-dimethylamino-1,1-dioxo-2,3,4,5-tetrahydro-1,4-benzothiazepine-5-yl)phenylthiocarbamoyl]pentyl}-1-azoniabicyclo[2.2.2]octane bromide (optically active isomers)

(Step a) Synthesis of 3,3-dibutyl-2,3,4,5-tetrahydro-7-dimethylamino-5-(3-aminophenyl)-1,4-benzothiazepine-1,1-dioxide (optically active isomer)

The compound obtained at the step m in Example 1 was applied onto a column for optical isolation CHIRALCEL-OJ (particle diameter: 10 μm, diameter: 2 cm, length: 25 cm, supplied from Daicel Chemical Industries), and eluted with methanol at a flow rate of 18.9 mL/min, and an S-type isomer and an R-type isomer are separated. Retention times of the resulting isomers in an analytical optical column were 7 and 14 minutes, respectively. Column: CHIRALPAK-OJ (particle diameter: 10 μm, diameter: 0.46 cm, length: 25 cm, supplied from Daicel Chemical Industries), mobile phase: methanol, flow rate: 0.5 mL/min and detection UV wavelength: 288 nm.

(Step b) Synthesis of 1-{5-[3-(3,3-dibutyl-7-dimethylamino-1,1-dioxo-2,3,4,5-tetrahydro-1,4-benzothiazepine-5-yl)phenylthiocarbamoyl]pentyl}-1-azoniabicyclo[2.2.2]octane bromide (optically active isomers)

The title compound was obtained using the optically active synthetic intermediates obtained at the step a in the present Example according to the procedures in the steps n to p in Example 1.

Example 9

1-(3-{3-[3-(3,3-dibutyl-7-dimethylamino-1,1-dioxo-2,3,4,5-tetrahydro-1,4-benzothiazepine-5-yl)phenyl]thioureido}propyl)-1-azoniabicyclo[2.2.2]octane bromide (Step a) Synthesis of 1-(3-isothiocyanatopropyl)-1-azoniabicyclo[2.2.2]octane bromide Quinuclidine (33 mg) was added to a solution of 55 mg of 3-bromopropyl isothiocyanate in 1 mL of acetonitrile, and heated at 50° C. for 19 hours. The reaction solution was concentrated and then a residue was washed three times with 1 mL of ether, to yield the title compound.

(Step b) Synthesis of 1-(3-{3-[3-(3,3-dibutyl-7-dimethylamino-1,1-dioxo-2,3,4,5-tetrahydro-1,4-benzothiazepine-5-yl)phenyl]thioureido}propyl)-1-azoniabicyclo[2.2.2]octane bromide A solution of 43 mg of the compound obtained at the step a in the present Example in 0.5 mL of acetonitrile was added to a solution of 60 mg of the compound obtained at the step m in Example 1 in 1.5 mL of chloroform, and heated at 55° C. overnight. The reaction solution was concentrated. The residue was dissolved in 0.3 mL of dichloromethane, and 1.5 mL of ether was added thereto. The resulting precipitate was washed with 2 mL of ether, to yield 77 mg of the title compound. $^1$H-NMR (CDCl$_3$) δ: 0.84 (3H, t); 0.90 (3H, t); 1.13-1.49 (8H, m); 1.68-2.23 (13H, m); 2.84 (6H, s); 2.99 (1H, d); 3.40 (1H, d); 3.52 (6H, t); 3.59-3.75 (4H, m); 6.00 (1H, s); 6.02 (1H, d); 6.48 (1H, dd); 7.24-7.34 (2H, m); 7.46 (1H, d); 7.62 (1H, s); 7.85 (1H, d); 8.58 (1H, s); 9.40 (1H, s). MS (m/z):654 (M+).

Example 10

1-(3-{3-[3-(3-butyl-3-ethyl-7-dimethylamino-1,1-dioxo-2,3,4,5-tetrahydro-1,4-benzothiazepine-5-yl)phenyl]thioureido}propyl)-1-azoniabicyclo[2.2.2]octane bromide The title compound was obtained according to the procedure in the step b in Example 9 except for using the compound obtained at the step a in Example 2 in place of the compound obtained at the step m in Example 1.

Example 11

1-(3-{3-[3-(3,3-dipropyl-7-dimethylamino-1,1-dioxo-2,3,4,5-tetrahydro-1,4-benzothiazepine-5-yl)phenyl]thioureido}propyl)-1-azoniabicyclo[2.2.2]octane bromide The title compound was obtained according to the procedure in the step b in Example 9 except for using the compound obtained at the step a in Example 3 in place of the compound obtained at the step m in Example 1.

Example 12

1-(3-{3-[3-(3,3-dipentyl-7-dimethylamino-1,1-dioxo-2,3,4,5-tetrahydro-1,4-benzothiazepine-5-yl)phenyl]thioureido}propyl)-1-azoniabicyclo[2.2.2]octane bromide The title compound was obtained according to the procedure in the step b in Example 9 except for using the compound obtained at the step b in Example 4 in place of the compound obtained at the step m in Example 1.

Example 13

1-(3-{3-[3-(3,3-dihexyl-7-dimethylamino-1,1-dioxo-2,3,4,5-tetrahydro-1,4-benzothiazepine-5-yl)phenyl]thioureido}propyl)-1-azoniabicyclo[2.2.2]octane bromide The title compound was obtained according to the procedure in the step b in Example 9 except for using the compound obtained at the step b in Example 5 in place of the compound obtained at the step m in Example 1.

Example 14

1-(3-{3-[3-(3,3-dibutyl-7-diethylamino-1,1-dioxo-2,3,4,5-tetrahydro-1,4-benzothiazepine-5-yl)phenyl]thioureido}propyl)-1-azoniabicyclo[2.2.2]octane bromide The title compound was obtained according to the procedure in the step b in Example 9 except for using the compound obtained at the step a in Example 6 in place of the compound obtained at the step m in Example 1.

Example 15

1-(3-{3-[3-(3,3-dibutyl-7-ethylmethylamino-1,1-dioxo-2,3,4,5-tetrahydro-1,4-benzothiazepine-5-yl)phenyl]thioureido}propyl)-1-azoniabicyclo[2.2.2]octane bromide The title compound was obtained according to the procedure in the step b in Example 9 except for using the compound obtained at the step a in Example 7 in place of the compound obtained at the step m in Example 1.

Example 16

1-(3-{3-[3-(3,3-dibutyl-7-dimethylamino-1,1-dioxo-2,3,4,5-tetrahydro-1,4-benzothiazepine-5-yl)phenyl]thioureido}propyl)-1-azoniabicyclo[2.2.2]octane bromide (optically active isomers)

The title compound was obtained according to the procedure in the step b in Example 9 except for using the compound obtained at the step a in Example 8 in place of the compound obtained at the step m in Example 1.

Examples 17 to 3785, 4067 to 5404, 5407 to 5448

According to the procedures in the steps a to b in Example 9, as shown in the following formula:

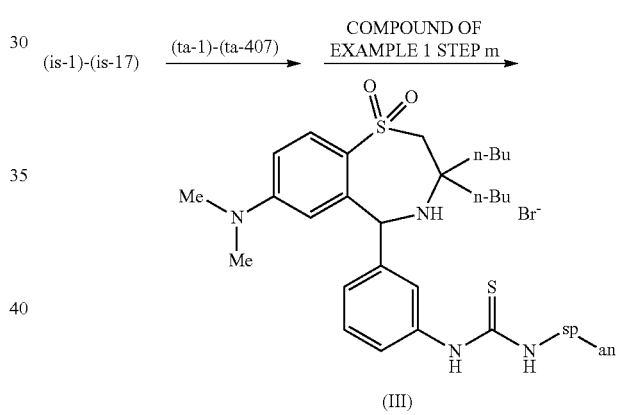

the compounds of Examples 17 to 3785, 4067 to 5404, and 5407 to 5448 described in Table 5 (Tables 5-1 to 5-52) represented by the formula (III) are obtained using any of isothiocyanate (is-1) to (is-17) represented by the aforementioned formula (5-2b), any of tertiary amine (ta-1) to (ta-407) represented by the aforementioned formula (2) and the compound obtained in the step m in Example 1. In the formula (III), -sp- represents any of (sp-1) to (sp-25) and -an represents any of (an-1) to (an-407).

| EXAMPLE No. | REAGENT is | ta | PRODUCT sp | an | EXAMPLE No. | REAGENT is | ta | PRODUCT sp | an |
|---|---|---|---|---|---|---|---|---|---|
| Table 5-1 | | | | | | | | | |
| 17 | is-1 | ta-1 | sp-1 | an-1 | 1901 | is-6 | ta-1 | sp-6 | an-1 |
| 18 | is-1 | ta-2 | sp-1 | an-2 | 1902 | is-6 | ta-2 | sp-6 | an-2 |
| 19 | is-1 | ta-3 | sp-1 | an-3 | 1903 | is-6 | ta-3 | sp-6 | an-3 |
| 20 | is-1 | ta-4 | sp-1 | an-4 | 1904 | is-6 | ta-4 | sp-6 | an-4 |
| 21 | is-1 | ta-5 | sp-1 | an-5 | 1905 | is-6 | ta-5 | sp-6 | an-5 |
| 22 | is-1 | ta-6 | sp-1 | an-6 | 1906 | is-6 | ta-6 | sp-6 | an-6 |

-continued

| EXAMPLE | REAGENT | | PRODUCT | EXAMPLE | REAGENT | | PRODUCT |
|---|---|---|---|---|---|---|---|
| No. | is | ta | sp | an | No. | is | ta | sp | an |
| 23 | is-1 | ta-7 | sp-1 | an-7 | 1907 | is-6 | ta-7 | sp-6 | an-7 |
| 24 | is-1 | ta-8 | sp-1 | an-8 | 1908 | is-6 | ta-8 | sp-6 | an-8 |
| 25 | is-1 | ta-9 | sp-1 | an-9 | 1909 | is-6 | ta-9 | sp-6 | an-9 |
| 26 | is-1 | ta-10 | sp-1 | an-10 | 1910 | is-6 | ta-10 | sp-6 | an-10 |
| 27 | is-1 | ta-11 | sp-1 | an-11 | 1911 | is-6 | ta-11 | sp-6 | an-11 |
| 28 | is-1 | ta-12 | sp-1 | an-12 | 1912 | is-6 | ta-12 | sp-6 | an-12 |
| 29 | is-1 | ta-13 | sp-1 | an-13 | 1913 | is-6 | ta-13 | sp-6 | an-13 |
| 30 | is-1 | ta-14 | sp-1 | an-14 | 1914 | is-6 | ta-14 | sp-6 | an-14 |
| 31 | is-1 | ta-15 | sp-1 | an-15 | 1915 | is-6 | ta-15 | sp-6 | an-15 |
| 32 | is-1 | ta-16 | sp-1 | an-16 | 1916 | is-6 | ta-16 | sp-6 | an-16 |
| 33 | is-1 | ta-17 | sp-1 | an-17 | 1917 | is-6 | ta-17 | sp-6 | an-17 |
| 34 | is-1 | ta-18 | sp-1 | an-18 | 1918 | is-6 | ta-18 | sp-6 | an-18 |
| 35 | is-1 | ta-19 | sp-1 | an-19 | 1919 | is-6 | ta-19 | sp-6 | an-19 |
| 36 | is-1 | ta-20 | sp-1 | an-20 | 1920 | is-6 | ta-20 | sp-6 | an-20 |
| 37 | is-1 | ta-21 | sp-1 | an-21 | 1921 | is-6 | ta-21 | sp-6 | an-21 |
| 38 | is-1 | ta-22 | sp-1 | an-22 | 1922 | is-6 | ta-22 | sp-6 | an-22 |
| 39 | is-1 | ta-23 | sp-1 | an-23 | 1923 | is-6 | ta-23 | sp-6 | an-23 |
| 40 | is-1 | ta-24 | sp-1 | an-24 | 1924 | is-6 | ta-24 | sp-6 | an-24 |
| 41 | is-1 | ta-25 | sp-1 | an-25 | 1925 | is-6 | ta-25 | sp-6 | an-25 |
| 42 | is-1 | ta-26 | sp-1 | an-26 | 1926 | is-6 | ta-26 | sp-6 | an-26 |
| 43 | is-1 | ta-27 | sp-1 | an-27 | 1927 | is-6 | ta-27 | sp-6 | an-27 |
| 44 | is-1 | ta-28 | sp-1 | an-28 | 1928 | is-6 | ta-28 | sp-6 | an-28 |
| 45 | is-1 | ta-29 | sp-1 | an-29 | 1929 | is-6 | ta-29 | sp-6 | an-29 |
| 46 | is-1 | ta-30 | sp-1 | an-30 | 1930 | is-6 | ta-30 | sp-6 | an-30 |
| 47 | is-1 | ta-31 | sp-1 | an-31 | 1931 | is-6 | ta-31 | sp-6 | an-31 |
| 48 | is-1 | ta-32 | sp-1 | an-32 | 1932 | is-6 | ta-32 | sp-6 | an-32 |
| 49 | is-1 | ta-33 | sp-1 | an-33 | 1933 | is-6 | ta-33 | sp-6 | an-33 |
| 50 | is-1 | ta-34 | sp-1 | an-34 | 1934 | is-6 | ta-34 | sp-6 | an-34 |
| 51 | is-1 | ta-35 | sp-1 | an-35 | 1935 | is-6 | ta-35 | sp-6 | an-35 |
| 52 | is-1 | ta-36 | sp-1 | an-36 | 1936 | is-6 | ta-36 | sp-6 | an-36 |
| 53 | is-1 | ta-37 | sp-1 | an-37 | 1937 | is-6 | ta-37 | sp-6 | an-37 |
| 54 | is-1 | ta-38 | sp-1 | an-38 | 1938 | is-6 | ta-38 | sp-6 | an-38 |
| 55 | is-1 | ta-39 | sp-1 | an-39 | 1939 | is-6 | ta-39 | sp-6 | an-39 |
| 56 | is-1 | ta-40 | sp-1 | an-40 | 1940 | is-6 | ta-40 | sp-6 | an-40 |
| 57 | is-1 | ta-41 | sp-1 | an-41 | 1941 | is-6 | ta-41 | sp-6 | an-41 |
| 58 | is-1 | ta-42 | sp-1 | an-42 | 1942 | is-6 | ta-42 | sp-6 | an-42 |
| 59 | is-1 | ta-43 | sp-1 | an-43 | 1943 | is-6 | ta-43 | sp-6 | an-43 |
| 60 | is-1 | ta-44 | sp-1 | an-44 | 1944 | is-6 | ta-44 | sp-6 | an-44 |
| 61 | is-1 | ta-45 | sp-1 | an-45 | 1945 | is-6 | ta-45 | sp-6 | an-45 |
| 62 | is-1 | ta-46 | sp-1 | an-46 | 1946 | is-6 | ta-46 | sp-6 | an-46 |
| 63 | is-1 | ta-47 | sp-1 | an-47 | 1947 | is-6 | ta-47 | sp-6 | an-47 |
| 64 | is-1 | ta-48 | sp-1 | an-48 | 1948 | is-6 | ta-48 | sp-6 | an-48 |
| 65 | is-1 | ta-49 | sp-1 | an-49 | 1949 | is-6 | ta-49 | sp-6 | an-49 |
| 66 | is-1 | ta-50 | sp-1 | an-50 | 1950 | is-6 | ta-50 | sp-6 | an-50 |
| 67 | is-1 | ta-51 | sp-1 | an-51 | 1951 | is-6 | ta-51 | sp-6 | an-51 |
| 68 | is-1 | ta-52 | sp-1 | an-52 | 1952 | is-6 | ta-52 | sp-6 | an-52 |
| 69 | is-1 | ta-53 | sp-1 | an-53 | 1953 | is-6 | ta-53 | sp-6 | an-53 |

Table 5-2

| 70 | is-1 | ta-54 | sp-1 | an-54 | 1954 | is-6 | ta-54 | sp-6 | an-54 |
|---|---|---|---|---|---|---|---|---|---|
| 71 | is-1 | ta-55 | sp-1 | an-55 | 1955 | is-6 | ta-55 | sp-6 | an-55 |
| 72 | is-1 | ta-56 | sp-1 | an-56 | 1956 | is-6 | ta-56 | sp-6 | an-56 |
| 73 | is-1 | ta-57 | sp-1 | an-57 | 1957 | is-6 | ta-57 | sp-6 | an-57 |
| 74 | is-1 | ta-58 | sp-1 | an-58 | 1958 | is-6 | ta-58 | sp-6 | an-58 |
| 75 | is-1 | ta-59 | sp-1 | an-59 | 1959 | is-6 | ta-59 | sp-6 | an-59 |
| 76 | is-1 | ta-60 | sp-1 | an-60 | 1960 | is-6 | ta-60 | sp-6 | an-60 |
| 77 | is-1 | ta-61 | sp-1 | an-61 | 1961 | is-6 | ta-61 | sp-6 | an-61 |
| 78 | is-1 | ta-62 | sp-1 | an-62 | 1962 | is-6 | ta-62 | sp-6 | an-62 |
| 79 | is-1 | ta-63 | sp-1 | an-63 | 1963 | is-6 | ta-63 | sp-6 | an-63 |
| 80 | is-1 | ta-64 | sp-1 | an-64 | 1964 | is-6 | ta-64 | sp-6 | an-64 |
| 81 | is-1 | ta-65 | sp-1 | an-65 | 1965 | is-6 | ta-65 | sp-6 | an-65 |
| 82 | is-1 | ta-66 | sp-1 | an-66 | 1966 | is-6 | ta-66 | sp-6 | an-66 |
| 83 | is-1 | ta-67 | sp-1 | an-67 | 1967 | is-6 | ta-67 | sp-6 | an-67 |
| 84 | is-1 | ta-68 | sp-1 | an-68 | 1968 | is-6 | ta-68 | sp-6 | an-68 |
| 85 | is-1 | ta-69 | sp-1 | an-69 | 1969 | is-6 | ta-69 | sp-6 | an-69 |
| 86 | is-1 | ta-70 | sp-1 | an-70 | 1970 | is-6 | ta-70 | sp-6 | an-70 |
| 87 | is-1 | ta-71 | sp-1 | an-71 | 1971 | is-6 | ta-71 | sp-6 | an-71 |
| 88 | is-1 | ta-72 | sp-1 | an-72 | 1972 | is-6 | ta-72 | sp-6 | an-72 |
| 89 | is-1 | ta-73 | sp-1 | an-73 | 1973 | is-6 | ta-73 | sp-6 | an-73 |
| 90 | is-1 | ta-74 | sp-1 | an-74 | 1974 | is-6 | ta-74 | sp-6 | an-74 |
| 91 | is-1 | ta-75 | sp-1 | an-75 | 1975 | is-6 | ta-75 | sp-6 | an-75 |
| 92 | is-1 | ta-76 | sp-1 | an-76 | 1976 | is-6 | ta-76 | sp-6 | an-76 |
| 93 | is-1 | ta-77 | sp-1 | an-77 | 1977 | is-6 | ta-77 | sp-6 | an-77 |
| 94 | is-1 | ta-78 | sp-1 | an-78 | 1978 | is-6 | ta-78 | sp-6 | an-78 |
| 95 | is-1 | ta-79 | sp-1 | an-79 | 1979 | is-6 | ta-79 | sp-6 | an-79 |
| 96 | is-1 | ta-80 | sp-1 | an-80 | 1980 | is-6 | ta-80 | sp-6 | an-80 |

-continued

| EXAMPLE | REAGENT | | PRODUCT | EXAMPLE | REAGENT | | PRODUCT |
|---|---|---|---|---|---|---|---|
| No. | is | ta | sp | an | No. | is | ta | sp | an |
| 97 | is-1 | ta-81 | sp-1 | an-81 | 1981 | is-6 | ta-81 | sp-6 | an-81 |
| 98 | is-1 | ta-82 | sp-1 | an-82 | 1982 | is-6 | ta-82 | sp-6 | an-82 |
| 99 | is-1 | ta-83 | sp-1 | an-83 | 1983 | is-6 | ta-83 | sp-6 | an-83 |
| 100 | is-1 | ta-84 | sp-1 | an-84 | 1984 | is-6 | ta-84 | sp-6 | an-84 |
| 101 | is-1 | ta-85 | sp-1 | an-85 | 1985 | is-6 | ta-85 | sp-6 | an-85 |
| 102 | is-1 | ta-86 | sp-1 | an-86 | 1986 | is-6 | ta-86 | sp-6 | an-86 |
| 103 | is-1 | ta-87 | sp-1 | an-87 | 1987 | is-6 | ta-87 | sp-6 | an-87 |
| 104 | is-1 | ta-88 | sp-1 | an-88 | 1988 | is-6 | ta-88 | sp-6 | an-88 |
| 105 | is-1 | ta-89 | sp-1 | an-89 | 1989 | is-6 | ta-89 | sp-6 | an-89 |
| 106 | is-1 | ta-90 | sp-1 | an-90 | 1990 | is-6 | ta-90 | sp-6 | an-90 |
| 107 | is-1 | ta-91 | sp-1 | an-91 | 1991 | is-6 | ta-91 | sp-6 | an-91 |
| 108 | is-1 | ta-92 | sp-1 | an-92 | 1992 | is-6 | ta-92 | sp-6 | an-92 |
| 109 | is-1 | ta-93 | sp-1 | an-93 | 1993 | is-6 | ta-93 | sp-6 | an-93 |
| 110 | is-1 | ta-94 | sp-1 | an-94 | 1994 | is-6 | ta-94 | sp-6 | an-94 |
| 111 | is-1 | ta-95 | sp-1 | an-95 | 1995 | is-6 | ta-95 | sp-6 | an-95 |
| 112 | is-1 | ta-96 | sp-1 | an-96 | 1996 | is-6 | ta-96 | sp-6 | an-96 |
| 113 | is-1 | ta-97 | sp-1 | an-97 | 1997 | is-6 | ta-97 | sp-6 | an-97 |
| 114 | is-1 | ta-98 | sp-1 | an-98 | 1998 | is-6 | ta-98 | sp-6 | an-98 |
| 115 | is-1 | ta-99 | sp-1 | an-99 | 1999 | is-6 | ta-99 | sp-6 | an-99 |
| 116 | is-1 | ta-100 | sp-1 | an-100 | 2000 | is-6 | ta-100 | sp-6 | an-100 |
| 117 | is-1 | ta-101 | sp-1 | an-101 | 2001 | is-6 | ta-101 | sp-6 | an-101 |
| 118 | is-1 | ta-102 | sp-1 | an-102 | 2002 | is-6 | ta-102 | sp-6 | an-102 |
| 119 | is-1 | ta-103 | sp-1 | an-103 | 2003 | is-6 | ta-103 | sp-6 | an-103 |
| 120 | is-1 | ta-104 | sp-1 | an-104 | 2004 | is-6 | ta-104 | sp-6 | an-104 |
| 121 | is-1 | ta-105 | sp-1 | an-105 | 2005 | is-6 | ta-105 | sp-6 | an-105 |
| 122 | is-1 | ta-106 | sp-1 | an-106 | 2006 | is-6 | ta-106 | sp-6 | an-106 |

Table 5-3

| 123 | is-1 | ta-107 | sp-1 | an-107 | 2007 | is-6 | ta-107 | sp-6 | an-107 |
|---|---|---|---|---|---|---|---|---|---|
| 124 | is-1 | ta-108 | sp-1 | an-108 | 2008 | is-6 | ta-108 | sp-6 | an-108 |
| 125 | is-1 | ta-109 | sp-1 | an-109 | 2009 | is-6 | ta-109 | sp-6 | an-109 |
| 126 | is-1 | ta-110 | sp-1 | an-110 | 2010 | is-6 | ta-110 | sp-6 | an-110 |
| 127 | is-1 | ta-111 | sp-1 | an-111 | 2011 | is-6 | ta-111 | sp-6 | an-111 |
| 128 | is-1 | ta-112 | sp-1 | an-112 | 2012 | is-6 | ta-112 | sp-6 | an-112 |
| 129 | is-1 | ta-113 | sp-1 | an-113 | 2013 | is-6 | ta-113 | sp-6 | an-113 |
| 130 | is-1 | ta-114 | sp-1 | an-114 | 2014 | is-6 | ta-114 | sp-6 | an-114 |
| 131 | is-1 | ta-115 | sp-1 | an-115 | 2015 | is-6 | ta-115 | sp-6 | an-115 |
| 132 | is-1 | ta-116 | sp-1 | an-116 | 2016 | is-6 | ta-116 | sp-6 | an-116 |
| 133 | is-1 | ta-117 | sp-1 | an-117 | 2017 | is-6 | ta-117 | sp-6 | an-117 |
| 134 | is-1 | ta-118 | sp-1 | an-118 | 2018 | is-6 | ta-118 | sp-6 | an-118 |
| 135 | is-1 | ta-119 | sp-1 | an-119 | 2019 | is-6 | ta-119 | sp-6 | an-119 |
| 136 | is-1 | ta-120 | sp-1 | an-120 | 2020 | is-6 | ta-120 | sp-6 | an-120 |
| 137 | is-1 | ta-121 | sp-1 | an-121 | 2021 | is-6 | ta-121 | sp-6 | an-121 |
| 138 | is-1 | ta-122 | sp-1 | an-122 | 2022 | is-6 | ta-122 | sp-6 | an-122 |
| 139 | is-1 | ta-123 | sp-1 | an-123 | 2023 | is-6 | ta-123 | sp-6 | an-123 |
| 140 | is-1 | ta-124 | sp-1 | an-124 | 2024 | is-6 | ta-124 | sp-6 | an-124 |
| 141 | is-1 | ta-125 | sp-1 | an-125 | 2025 | is-6 | ta-125 | sp-6 | an-125 |
| 142 | is-1 | ta-126 | sp-1 | an-126 | 2026 | is-6 | ta-126 | sp-6 | an-126 |
| 143 | is-1 | ta-127 | sp-1 | an-127 | 2027 | is-6 | ta-127 | sp-6 | an-127 |
| 144 | is-1 | ta-128 | sp-1 | an-128 | 2028 | is-6 | ta-128 | sp-6 | an-128 |
| 145 | is-1 | ta-129 | sp-1 | an-129 | 2029 | is-6 | ta-129 | sp-6 | an-129 |
| 146 | is-1 | ta-130 | sp-1 | an-130 | 2030 | is-6 | ta-130 | sp-6 | an-130 |
| 147 | is-1 | ta-131 | sp-1 | an-131 | 2031 | is-6 | ta-131 | sp-6 | an-131 |
| 148 | is-1 | ta-132 | sp-1 | an-132 | 2032 | is-6 | ta-132 | sp-6 | an-132 |
| 149 | is-1 | ta-133 | sp-1 | an-133 | 2033 | is-6 | ta-133 | sp-6 | an-133 |
| 150 | is-1 | ta-134 | sp-1 | an-134 | 2034 | is-6 | ta-134 | sp-6 | an-134 |
| 151 | is-1 | ta-135 | sp-1 | an-135 | 2035 | is-6 | ta-135 | sp-6 | an-135 |
| 152 | is-1 | ta-136 | sp-1 | an-136 | 2036 | is-6 | ta-136 | sp-6 | an-136 |
| 153 | is-1 | ta-137 | sp-1 | an-137 | 2037 | is-6 | ta-137 | sp-6 | an-137 |
| 154 | is-1 | ta-138 | sp-1 | an-138 | 2038 | is-6 | ta-138 | sp-6 | an-138 |
| 155 | is-1 | ta-139 | sp-1 | an-139 | 2039 | is-6 | ta-139 | sp-6 | an-139 |
| 156 | is-1 | ta-140 | sp-1 | an-140 | 2040 | is-6 | ta-140 | sp-6 | an-140 |
| 157 | is-1 | ta-141 | sp-1 | an-141 | 2041 | is-6 | ta-141 | sp-6 | an-141 |
| 158 | is-1 | ta-142 | sp-1 | an-142 | 2042 | is-6 | ta-142 | sp-6 | an-142 |
| 159 | is-1 | ta-143 | sp-1 | an-143 | 2043 | is-6 | ta-143 | sp-6 | an-143 |
| 160 | is-1 | ta-144 | sp-1 | an-144 | 2044 | is-6 | ta-144 | sp-6 | an-144 |
| 161 | is-1 | ta-145 | sp-1 | an-145 | 2045 | is-6 | ta-145 | sp-6 | an-145 |
| 162 | is-1 | ta-146 | sp-1 | an-146 | 2046 | is-6 | ta-146 | sp-6 | an-146 |
| 163 | is-1 | ta-147 | sp-1 | an-147 | 2047 | is-6 | ta-147 | sp-6 | an-147 |
| 164 | is-1 | ta-148 | sp-1 | an-148 | 2048 | is-6 | ta-148 | sp-6 | an-148 |
| 165 | is-1 | ta-149 | sp-1 | an-149 | 2049 | is-6 | ta-149 | sp-6 | an-149 |
| 166 | is-1 | ta-150 | sp-1 | an-150 | 2050 | is-6 | ta-150 | sp-6 | an-150 |
| 167 | is-1 | ta-151 | sp-1 | an-151 | 2051 | is-6 | ta-151 | sp-6 | an-151 |
| 168 | is-1 | ta-152 | sp-1 | an-152 | 2052 | is-6 | ta-152 | sp-6 | an-152 |
| 169 | is-1 | ta-153 | sp-1 | an-153 | 2053 | is-6 | ta-153 | sp-6 | an-153 |
| 170 | is-1 | ta-154 | sp-1 | an-154 | 2054 | is-6 | ta-154 | sp-6 | an-154 |

-continued

| EXAMPLE | REAGENT | | PRODUCT | EXAMPLE | REAGENT | | PRODUCT |
|---|---|---|---|---|---|---|---|
| No. | is | ta | sp | an | No. | is | ta | sp | an |
| 171 | is-1 | ta-155 | sp-1 | an-155 | 2055 | is-6 | ta-155 | sp-6 | an-155 |
| 172 | is-1 | ta-156 | sp-1 | an-156 | 2056 | is-6 | ta-156 | sp-6 | an-156 |
| 173 | is-1 | ta-157 | sp-1 | an-157 | 2057 | is-6 | ta-157 | sp-6 | an-157 |
| 174 | is-1 | ta-158 | sp-1 | an-158 | 2058 | is-6 | ta-158 | sp-6 | an-158 |
| 175 | is-1 | ta-159 | sp-1 | an-159 | 2059 | is-6 | ta-159 | sp-6 | an-159 |

Table 5-4

| 176 | is-1 | ta-160 | sp-1 | an-160 | 2060 | is-6 | ta-160 | sp-6 | an-160 |
|---|---|---|---|---|---|---|---|---|---|
| 177 | is-1 | ta-161 | sp-1 | an-161 | 2061 | is-6 | ta-161 | sp-6 | an-161 |
| 178 | is-1 | ta-162 | sp-1 | an-162 | 2062 | is-6 | ta-162 | sp-6 | an-162 |
| 179 | is-1 | ta-163 | sp-1 | an-163 | 2063 | is-6 | ta-163 | sp-6 | an-163 |
| 180 | is-1 | ta-164 | sp-1 | an-164 | 2064 | is-6 | ta-164 | sp-6 | an-164 |
| 181 | is-1 | ta-165 | sp-1 | an-165 | 2065 | is-6 | ta-165 | sp-6 | an-165 |
| 182 | is-1 | ta-166 | sp-1 | an-166 | 2066 | is-6 | ta-166 | sp-6 | an-166 |
| 183 | is-1 | ta-167 | sp-1 | an-167 | 2067 | is-6 | ta-167 | sp-6 | an-167 |
| 184 | is-1 | ta-168 | sp-1 | an-168 | 2068 | is-6 | ta-168 | sp-6 | an-168 |
| 185 | is-1 | ta-169 | sp-1 | an-169 | 2069 | is-6 | ta-169 | sp-6 | an-169 |
| 186 | is-1 | ta-170 | sp-1 | an-170 | 2070 | is-6 | ta-170 | sp-6 | an-170 |
| 187 | is-1 | ta-171 | sp-1 | an-171 | 2071 | is-6 | ta-171 | sp-6 | an-171 |
| 188 | is-1 | ta-172 | sp-1 | an-172 | 2072 | is-6 | ta-172 | sp-6 | an-172 |
| 189 | is-1 | ta-173 | sp-1 | an-173 | 2073 | is-6 | ta-173 | sp-6 | an-173 |
| 190 | is-1 | ta-174 | sp-1 | an-174 | 2074 | is-6 | ta-174 | sp-6 | an-174 |
| 191 | is-1 | ta-175 | sp-1 | an-175 | 2075 | is-6 | ta-175 | sp-6 | an-175 |
| 192 | is-1 | ta-176 | sp-1 | an-176 | 2076 | is-6 | ta-176 | sp-6 | an-176 |
| 193 | is-1 | ta-177 | sp-1 | an-177 | 2077 | is-6 | ta-177 | sp-6 | an-177 |
| 194 | is-1 | ta-178 | sp-1 | an-178 | 2078 | is-6 | ta-178 | sp-6 | an-178 |
| 195 | is-1 | ta-179 | sp-1 | an-179 | 2079 | is-6 | ta-179 | sp-6 | an-179 |
| 196 | is-1 | ta-180 | sp-1 | an-180 | 2080 | is-6 | ta-180 | sp-6 | an-180 |
| 197 | is-1 | ta-181 | sp-1 | an-181 | 2081 | is-6 | ta-181 | sp-6 | an-181 |
| 198 | is-1 | ta-182 | sp-1 | an-182 | 2082 | is-6 | ta-182 | sp-6 | an-182 |
| 199 | is-1 | ta-183 | sp-1 | an-183 | 2083 | is-6 | ta-183 | sp-6 | an-183 |
| 200 | is-1 | ta-184 | sp-1 | an-184 | 2084 | is-6 | ta-184 | sp-6 | an-184 |
| 201 | is-1 | ta-185 | sp-1 | an-185 | 2085 | is-6 | ta-185 | sp-6 | an-185 |
| 202 | is-1 | ta-186 | sp-1 | an-186 | 2086 | is-6 | ta-186 | sp-6 | an-186 |
| 203 | is-1 | ta-187 | sp-1 | an-187 | 2087 | is-6 | ta-187 | sp-6 | an-187 |
| 204 | is-1 | ta-188 | sp-1 | an-188 | 2088 | is-6 | ta-188 | sp-6 | an-188 |
| 205 | is-1 | ta-189 | sp-1 | an-189 | 2089 | is-6 | ta-189 | sp-6 | an-189 |
| 206 | is-1 | ta-190 | sp-1 | an-190 | 2090 | is-6 | ta-190 | sp-6 | an-190 |
| 207 | is-1 | ta-191 | sp-1 | an-191 | 2091 | is-6 | ta-191 | sp-6 | an-191 |
| 208 | is-1 | ta-192 | sp-1 | an-192 | 2092 | is-6 | ta-192 | sp-6 | an-192 |
| 209 | is-1 | ta-193 | sp-1 | an-193 | 2093 | is-6 | ta-193 | sp-6 | an-193 |
| 210 | is-1 | ta-194 | sp-1 | an-194 | 2094 | is-6 | ta-194 | sp-6 | an-194 |
| 211 | is-1 | ta-195 | sp-1 | an-195 | 2095 | is-6 | ta-195 | sp-6 | an-195 |
| 212 | is-1 | ta-196 | sp-1 | an-196 | 2096 | is-6 | ta-196 | sp-6 | an-196 |
| 213 | is-1 | ta-197 | sp-1 | an-197 | 2097 | is-6 | ta-197 | sp-6 | an-197 |
| 214 | is-1 | ta-198 | sp-1 | an-198 | 2098 | is-6 | ta-198 | sp-6 | an-198 |
| 215 | is-1 | ta-199 | sp-1 | an-199 | 2099 | is-6 | ta-199 | sp-6 | an-199 |
| 216 | is-1 | ta-200 | sp-1 | an-200 | 2100 | is-6 | ta-200 | sp-6 | an-200 |
| 217 | is-1 | ta-201 | sp-1 | an-201 | 2101 | is-6 | ta-201 | sp-6 | an-201 |
| 218 | is-1 | ta-202 | sp-1 | an-202 | 2102 | is-6 | ta-202 | sp-6 | an-202 |
| 219 | is-1 | ta-203 | sp-1 | an-203 | 2103 | is-6 | ta-203 | sp-6 | an-203 |
| 220 | is-1 | ta-204 | sp-1 | an-204 | 2104 | is-6 | ta-204 | sp-6 | an-204 |
| 221 | is-1 | ta-205 | sp-1 | an-205 | 2105 | is-6 | ta-205 | sp-6 | an-205 |
| 222 | is-1 | ta-206 | sp-1 | an-206 | 2106 | is-6 | ta-206 | sp-6 | an-206 |
| 223 | is-1 | ta-207 | sp-1 | an-207 | 2107 | is-6 | ta-207 | sp-6 | an-207 |
| 224 | is-1 | ta-208 | sp-1 | an-208 | 2108 | is-6 | ta-208 | sp-6 | an-208 |
| 225 | is-1 | ta-209 | sp-1 | an-209 | 2109 | is-6 | ta-209 | sp-6 | an-209 |
| 226 | is-1 | ta-210 | sp-1 | an-210 | 2110 | is-6 | ta-210 | sp-6 | an-210 |
| 227 | is-1 | ta-211 | sp-1 | an-211 | 2111 | is-6 | ta-211 | sp-6 | an-211 |
| 228 | is-1 | ta-212 | sp-1 | an-212 | 2112 | is-6 | ta-212 | sp-6 | an-212 |

Table 5-5

| 229 | is-1 | ta-213 | sp-1 | an-213 | 2113 | is-6 | ta-213 | sp-6 | an-213 |
|---|---|---|---|---|---|---|---|---|---|
| 230 | is-1 | ta-214 | sp-1 | an-214 | 2114 | is-6 | ta-214 | sp-6 | an-214 |
| 231 | is-1 | ta-215 | sp-1 | an-215 | 2115 | is-6 | ta-215 | sp-6 | an-215 |
| 232 | is-1 | ta-216 | sp-1 | an-216 | 2116 | is-6 | ta-216 | sp-6 | an-216 |
| 233 | is-1 | ta-217 | sp-1 | an-217 | 2117 | is-6 | ta-217 | sp-6 | an-217 |
| 234 | is-1 | ta-218 | sp-1 | an-218 | 2118 | is-6 | ta-218 | sp-6 | an-218 |
| 235 | is-1 | ta-219 | sp-1 | an-219 | 2119 | is-6 | ta-219 | sp-6 | an-219 |
| 236 | is-1 | ta-220 | sp-1 | an-220 | 2120 | is-6 | ta-220 | sp-6 | an-220 |
| 237 | is-1 | ta-221 | sp-1 | an-221 | 2121 | is-6 | ta-221 | sp-6 | an-221 |
| 238 | is-1 | ta-222 | sp-1 | an-222 | 2122 | is-6 | ta-222 | sp-6 | an-222 |
| 239 | is-1 | ta-223 | sp-1 | an-223 | 2123 | is-6 | ta-223 | sp-6 | an-223 |
| 240 | is-1 | ta-224 | sp-1 | an-224 | 2124 | is-6 | ta-224 | sp-6 | an-224 |
| 241 | is-1 | ta-225 | sp-1 | an-225 | 2125 | is-6 | ta-225 | sp-6 | an-225 |
| 242 | is-1 | ta-226 | sp-1 | an-226 | 2126 | is-6 | ta-226 | sp-6 | an-226 |

-continued

| EXAMPLE | REAGENT | | PRODUCT | EXAMPLE | REAGENT | | PRODUCT |
|---|---|---|---|---|---|---|---|
| No. | is | ta | sp an | No. | is | ta | sp an |
| 243 | is-1 | ta-227 | sp-1 an-227 | 2127 | is-6 | ta-227 | sp-6 an-227 |
| 244 | is-1 | ta-228 | sp-1 an-228 | 2128 | is-6 | ta-228 | sp-6 an-228 |
| 245 | is-1 | ta-229 | sp-1 an-229 | 2129 | is-6 | ta-229 | sp-6 an-229 |
| 246 | is-1 | ta-230 | sp-1 an-230 | 2130 | is-6 | ta-230 | sp-6 an-230 |
| 247 | is-1 | ta-231 | sp-1 an-231 | 2131 | is-6 | ta-231 | sp-6 an-231 |
| 248 | is-1 | ta-232 | sp-1 an-232 | 2132 | is-6 | ta-232 | sp-6 an-232 |
| 249 | is-1 | ta-233 | sp-1 an-233 | 2133 | is-6 | ta-233 | sp-6 an-233 |
| 250 | is-1 | ta-234 | sp-1 an-234 | 2134 | is-6 | ta-234 | sp-6 an-234 |
| 251 | is-1 | ta-235 | sp-1 an-235 | 2135 | is-6 | ta-235 | sp-6 an-235 |
| 252 | is-1 | ta-236 | sp-1 an-236 | 2136 | is-6 | ta-236 | sp-6 an-236 |
| 253 | is-1 | ta-237 | sp-1 an-237 | 2137 | is-6 | ta-237 | sp-6 an-237 |
| 254 | is-1 | ta-238 | sp-1 an-238 | 2138 | is-6 | ta-238 | sp-6 an-238 |
| 255 | is-1 | ta-239 | sp-1 an-239 | 2139 | is-6 | ta-239 | sp-6 an-239 |
| 256 | is-1 | ta-240 | sp-1 an-240 | 2140 | is-6 | ta-240 | sp-6 an-240 |
| 257 | is-1 | ta-241 | sp-1 an-241 | 2141 | is-6 | ta-241 | sp-6 an-241 |
| 258 | is-1 | ta-242 | sp-1 an-242 | 2142 | is-6 | ta-242 | sp-6 an-242 |
| 259 | is-1 | ta-243 | sp-1 an-243 | 2143 | is-6 | ta-243 | sp-6 an-243 |
| 260 | is-1 | ta-244 | sp-1 an-244 | 2144 | is-6 | ta-244 | sp-6 an-244 |
| 261 | is-1 | ta-245 | sp-1 an-245 | 2145 | is-6 | ta-245 | sp-6 an-245 |
| 262 | is-1 | ta-246 | sp-1 an-246 | 2146 | is-6 | ta-246 | sp-6 an-246 |
| 263 | is-1 | ta-247 | sp-1 an-247 | 2147 | is-6 | ta-247 | sp-6 an-247 |
| 264 | is-1 | ta-248 | sp-1 an-248 | 2148 | is-6 | ta-248 | sp-6 an-248 |
| 265 | is-1 | ta-249 | sp-1 an-249 | 2149 | is-6 | ta-249 | sp-6 an-249 |
| 266 | is-1 | ta-250 | sp-1 an-250 | 2150 | is-6 | ta-250 | sp-6 an-250 |
| 267 | is-1 | ta-251 | sp-1 an-251 | 2151 | is-6 | ta-251 | sp-6 an-251 |
| 268 | is-1 | ta-252 | sp-1 an-252 | 2152 | is-6 | ta-252 | sp-6 an-252 |
| 269 | is-1 | ta-253 | sp-1 an-253 | 2153 | is-6 | ta-253 | sp-6 an-253 |
| 270 | is-1 | ta-254 | sp-1 an-254 | 2154 | is-6 | ta-254 | sp-6 an-254 |
| 271 | is-1 | ta-255 | sp-1 an-255 | 2155 | is-6 | ta-255 | sp-6 an-255 |
| 272 | is-1 | ta-256 | sp-1 an-256 | 2156 | is-6 | ta-256 | sp-6 an-256 |
| 273 | is-1 | ta-257 | sp-1 an-257 | 2157 | is-6 | ta-257 | sp-6 an-257 |
| 274 | is-1 | ta-258 | sp-1 an-258 | 2158 | is-6 | ta-258 | sp-6 an-258 |
| 275 | is-1 | ta-259 | sp-1 an-259 | 2159 | is-6 | ta-259 | sp-6 an-259 |
| 276 | is-1 | ta-260 | sp-1 an-260 | 2160 | is-6 | ta-260 | sp-6 an-260 |
| 277 | is-1 | ta-261 | sp-1 an-261 | 2161 | is-6 | ta-261 | sp-6 an-261 |
| 278 | is-1 | ta-262 | sp-1 an-262 | 2162 | is-6 | ta-262 | sp-6 an-262 |
| 279 | is-1 | ta-263 | sp-1 an-263 | 2163 | is-6 | ta-263 | sp-6 an-263 |
| 280 | is-1 | ta-264 | sp-1 an-264 | 2164 | is-6 | ta-264 | sp-6 an-264 |
| 281 | is-1 | ta-265 | sp-1 an-265 | 2165 | is-6 | ta-265 | sp-6 an-265 |

Table 5-6

| 282 | is-1 | ta-266 | sp-1 an-266 | 2166 | is-6 | ta-266 | sp-6 an-266 |
|---|---|---|---|---|---|---|---|
| 283 | is-1 | ta-267 | sp-1 an-267 | 2167 | is-6 | ta-267 | sp-6 an-267 |
| 284 | is-1 | ta-268 | sp-1 an-268 | 2168 | is-6 | ta-268 | sp-6 an-268 |
| 285 | is-1 | ta-269 | sp-1 an-269 | 2169 | is-6 | ta-269 | sp-6 an-269 |
| 286 | is-1 | ta-270 | sp-1 an-270 | 2170 | is-6 | ta-270 | sp-6 an-270 |
| 287 | is-1 | ta-271 | sp-1 an-271 | 2171 | is-6 | ta-271 | sp-6 an-271 |
| 288 | is-1 | ta-272 | sp-1 an-272 | 2172 | is-6 | ta-272 | sp-6 an-272 |
| 289 | is-1 | ta-273 | sp-1 an-273 | 2173 | is-6 | ta-273 | sp-6 an-273 |
| 290 | is-1 | ta-274 | sp-1 an-274 | 2174 | is-6 | ta-274 | sp-6 an-274 |
| 291 | is-1 | ta-275 | sp-1 an-275 | 2175 | is-6 | ta-275 | sp-6 an-275 |
| 292 | is-1 | ta-276 | sp-1 an-276 | 2176 | is-6 | ta-276 | sp-6 an-276 |
| 293 | is-1 | ta-277 | sp-1 an-277 | 2177 | is-6 | ta-277 | sp-6 an-277 |
| 294 | is-1 | ta-278 | sp-1 an-278 | 2178 | is-6 | ta-278 | sp-6 an-278 |
| 295 | is-1 | ta-279 | sp-1 an-279 | 2179 | is-6 | ta-279 | sp-6 an-279 |
| 296 | is-1 | ta-280 | sp-1 an-280 | 2180 | is-6 | ta-280 | sp-6 an-280 |
| 297 | is-1 | ta-281 | sp-1 an-281 | 2181 | is-6 | ta-281 | sp-6 an-281 |
| 298 | is-1 | ta-282 | sp-1 an-282 | 2182 | is-6 | ta-282 | sp-6 an-282 |
| 299 | is-1 | ta-283 | sp-1 an-283 | 2183 | is-6 | ta-283 | sp-6 an-283 |
| 300 | is-1 | ta-284 | sp-1 an-284 | 2184 | is-6 | ta-284 | sp-6 an-284 |
| 301 | is-1 | ta-285 | sp-1 an-285 | 2185 | is-6 | ta-285 | sp-6 an-285 |
| 302 | is-1 | ta-286 | sp-1 an-286 | 2186 | is-6 | ta-286 | sp-6 an-286 |
| 303 | is-1 | ta-287 | sp-1 an-287 | 2187 | is-6 | ta-287 | sp-6 an-287 |
| 304 | is-1 | ta-288 | sp-1 an-288 | 2188 | is-6 | ta-288 | sp-6 an-288 |
| 305 | is-1 | ta-289 | sp-1 an-289 | 2189 | is-6 | ta-289 | sp-6 an-289 |
| 306 | is-1 | ta-290 | sp-1 an-290 | 2190 | is-6 | ta-290 | sp-6 an-290 |
| 307 | is-1 | ta-291 | sp-1 an-291 | 2191 | is-6 | ta-291 | sp-6 an-291 |
| 308 | is-1 | ta-292 | sp-1 an-292 | 2192 | is-6 | ta-292 | sp-6 an-292 |
| 309 | is-1 | ta-293 | sp-1 an-293 | 2193 | is-6 | ta-293 | sp-6 an-293 |
| 310 | is-1 | ta-294 | sp-1 an-294 | 2194 | is-6 | ta-294 | sp-6 an-294 |
| 311 | is-1 | ta-295 | sp-1 an-295 | 2195 | is-6 | ta-295 | sp-6 an-295 |
| 312 | is-1 | ta-296 | sp-1 an-296 | 2196 | is-6 | ta-296 | sp-6 an-296 |
| 313 | is-1 | ta-297 | sp-1 an-297 | 2197 | is-6 | ta-297 | sp-6 an-297 |
| 314 | is-1 | ta-298 | sp-1 an-298 | 2198 | is-6 | ta-298 | sp-6 an-298 |
| 315 | is-1 | ta-299 | sp-1 an-299 | 2199 | is-6 | ta-299 | sp-6 an-299 |
| 316 | is-1 | ta-300 | sp-1 an-300 | 2200 | is-6 | ta-300 | sp-6 an-300 |

-continued

| EXAMPLE | REAGENT | | PRODUCT | EXAMPLE | REAGENT | | PRODUCT |
|---|---|---|---|---|---|---|---|
| No. | is | ta | sp | an | No. | is | ta | sp | an |
| 317 | is-1 | ta-301 | sp-1 | an-301 | 2201 | is-6 | ta-301 | sp-6 | an-301 |
| 318 | is-1 | ta-302 | sp-1 | an-302 | 2202 | is-6 | ta-302 | sp-6 | an-302 |
| 319 | is-1 | ta-303 | sp-1 | an-303 | 2203 | is-6 | ta-303 | sp-6 | an-303 |
| 320 | is-1 | ta-304 | sp-1 | an-304 | 2204 | is-6 | ta-304 | sp-6 | an-304 |
| 321 | is-1 | ta-305 | sp-1 | an-305 | 2205 | is-6 | ta-305 | sp-6 | an-305 |
| 322 | is-1 | ta-306 | sp-1 | an-306 | 2206 | is-6 | ta-306 | sp-6 | an-306 |
| 323 | is-1 | ta-307 | sp-1 | an-307 | 2207 | is-6 | ta-307 | sp-6 | an-307 |
| 324 | is-1 | ta-308 | sp-1 | an-308 | 2208 | is-6 | ta-308 | sp-6 | an-308 |
| 325 | is-1 | ta-309 | sp-1 | an-309 | 2209 | is-6 | ta-309 | sp-6 | an-309 |
| 326 | is-1 | ta-310 | sp-1 | an-310 | 2210 | is-6 | ta-310 | sp-6 | an-310 |
| 327 | is-1 | ta-311 | sp-1 | an-311 | 2211 | is-6 | ta-311 | sp-6 | an-311 |
| 328 | is-1 | ta-312 | sp-1 | an-312 | 2212 | is-6 | ta-312 | sp-6 | an-312 |
| 329 | is-1 | ta-313 | sp-1 | an-313 | 2213 | is-6 | ta-313 | sp-6 | an-313 |
| 330 | is-1 | ta-314 | sp-1 | an-314 | 2214 | is-6 | ta-314 | sp-6 | an-314 |
| 331 | is-1 | ta-315 | sp-1 | an-315 | 2215 | is-6 | ta-315 | sp-6 | an-315 |
| 332 | is-1 | ta-316 | sp-1 | an-316 | 2216 | is-6 | ta-316 | sp-6 | an-316 |
| 333 | is-1 | ta-317 | sp-1 | an-317 | 2217 | is-6 | ta-317 | sp-6 | an-317 |
| 334 | is-1 | ta-318 | sp-1 | an-318 | 2218 | is-6 | ta-318 | sp-6 | an-318 |

Table 5-7

| EXAMPLE | REAGENT | | PRODUCT | EXAMPLE | REAGENT | | PRODUCT |
|---|---|---|---|---|---|---|---|
| 335 | is-1 | ta-319 | sp-1 | an-319 | 2219 | is-6 | ta-319 | sp-6 | an-319 |
| 336 | is-1 | ta-320 | sp-1 | an-320 | 2220 | is-6 | ta-320 | sp-6 | an-320 |
| 337 | is-1 | ta-321 | sp-1 | an-321 | 2221 | is-6 | ta-321 | sp-6 | an-321 |
| 338 | is-1 | ta-322 | sp-1 | an-322 | 2222 | is-6 | ta-322 | sp-6 | an-322 |
| 339 | is-1 | ta-323 | sp-1 | an-323 | 2223 | is-6 | ta-323 | sp-6 | an-323 |
| 340 | is-1 | ta-324 | sp-1 | an-324 | 2224 | is-6 | ta-324 | sp-6 | an-324 |
| 341 | is-1 | ta-325 | sp-1 | an-325 | 2225 | is-6 | ta-325 | sp-6 | an-325 |
| 342 | is-1 | ta-326 | sp-1 | an-326 | 2226 | is-6 | ta-326 | sp-6 | an-326 |
| 343 | is-1 | ta-327 | sp-1 | an-327 | 2227 | is-6 | ta-327 | sp-6 | an-327 |
| 344 | is-1 | ta-328 | sp-1 | an-328 | 2228 | is-6 | ta-328 | sp-6 | an-328 |
| 345 | is-1 | ta-329 | sp-1 | an-329 | 2229 | is-6 | ta-329 | sp-6 | an-329 |
| 346 | is-1 | ta-330 | sp-1 | an-330 | 2230 | is-6 | ta-330 | sp-6 | an-330 |
| 347 | is-1 | ta-331 | sp-1 | an-331 | 2231 | is-6 | ta-331 | sp-6 | an-331 |
| 348 | is-1 | ta-332 | sp-1 | an-332 | 2232 | is-6 | ta-332 | sp-6 | an-332 |
| 349 | is-1 | ta-333 | sp-1 | an-333 | 2233 | is-6 | ta-333 | sp-6 | an-333 |
| 350 | is-1 | ta-334 | sp-1 | an-334 | 2234 | is-6 | ta-334 | sp-6 | an-334 |
| 351 | is-1 | ta-335 | sp-1 | an-335 | 2235 | is-6 | ta-335 | sp-6 | an-335 |
| 352 | is-1 | ta-336 | sp-1 | an-336 | 2236 | is-6 | ta-336 | sp-6 | an-336 |
| 353 | is-1 | ta-337 | sp-1 | an-337 | 2237 | is-6 | ta-337 | sp-6 | an-337 |
| 354 | is-1 | ta-338 | sp-1 | an-338 | 2238 | is-6 | ta-338 | sp-6 | an-338 |
| 355 | is-1 | ta-339 | sp-1 | an-339 | 2239 | is-6 | ta-339 | sp-6 | an-339 |
| 356 | is-1 | ta-340 | sp-1 | an-340 | 2240 | is-6 | ta-340 | sp-6 | an-340 |
| 357 | is-1 | ta-341 | sp-1 | an-341 | 2241 | is-6 | ta-341 | sp-6 | an-341 |
| 358 | is-1 | ta-342 | sp-1 | an-342 | 2242 | is-6 | ta-342 | sp-6 | an-342 |
| 359 | is-1 | ta-343 | sp-1 | an-343 | 2243 | is-6 | ta-343 | sp-6 | an-343 |
| 360 | is-1 | ta-344 | sp-1 | an-344 | 2244 | is-6 | ta-344 | sp-6 | an-344 |
| 361 | is-1 | ta-345 | sp-1 | an-345 | 2245 | is-6 | ta-345 | sp-6 | an-345 |
| 362 | is-1 | ta-346 | sp-1 | an-346 | 2246 | is-6 | ta-346 | sp-6 | an-346 |
| 363 | is-1 | ta-347 | sp-1 | an-347 | 2247 | is-6 | ta-347 | sp-6 | an-347 |
| 364 | is-1 | ta-348 | sp-1 | an-348 | 2248 | is-6 | ta-348 | sp-6 | an-348 |
| 365 | is-1 | ta-349 | sp-1 | an-349 | 2249 | is-6 | ta-349 | sp-6 | an-349 |
| 366 | is-1 | ta-350 | sp-1 | an-350 | 2250 | is-6 | ta-350 | sp-6 | an-350 |
| 367 | is-1 | ta-351 | sp-1 | an-351 | 2251 | is-6 | ta-351 | sp-6 | an-351 |
| 368 | is-1 | ta-352 | sp-1 | an-352 | 2252 | is-6 | ta-352 | sp-6 | an-352 |
| 369 | is-1 | ta-353 | sp-1 | an-353 | 2253 | is-6 | ta-353 | sp-6 | an-353 |
| 370 | is-1 | ta-354 | sp-1 | an-354 | 2254 | is-6 | ta-354 | sp-6 | an-354 |
| 371 | is-1 | ta-355 | sp-1 | an-355 | 2255 | is-6 | ta-355 | sp-6 | an-355 |
| 372 | is-1 | ta-356 | sp-1 | an-356 | 2256 | is-6 | ta-356 | sp-6 | an-356 |
| 373 | is-1 | ta-357 | sp-1 | an-357 | 2257 | is-6 | ta-357 | sp-6 | an-357 |
| 374 | is-1 | ta-358 | sp-1 | an-358 | 2258 | is-6 | ta-358 | sp-6 | an-358 |
| 375 | is-1 | ta-359 | sp-1 | an-359 | 2259 | is-6 | ta-359 | sp-6 | an-359 |
| 376 | is-1 | ta-360 | sp-1 | an-360 | 2260 | is-6 | ta-360 | sp-6 | an-360 |
| 377 | is-1 | ta-361 | sp-1 | an-361 | 2261 | is-6 | ta-361 | sp-6 | an-361 |
| 378 | is-1 | ta-362 | sp-1 | an-362 | 2262 | is-6 | ta-362 | sp-6 | an-362 |
| 379 | is-1 | ta-363 | sp-1 | an-363 | 2263 | is-6 | ta-363 | sp-6 | an-363 |
| 380 | is-1 | ta-364 | sp-1 | an-364 | 2264 | is-6 | ta-364 | sp-6 | an-364 |
| 381 | is-1 | ta-365 | sp-1 | an-365 | 2265 | is-6 | ta-365 | sp-6 | an-365 |
| 382 | is-1 | ta-366 | sp-1 | an-366 | 2266 | is-6 | ta-366 | sp-6 | an-366 |
| 383 | is-1 | ta-367 | sp-1 | an-367 | 2267 | is-6 | ta-367 | sp-6 | an-367 |
| 384 | is-1 | ta-368 | sp-1 | an-368 | 2268 | is-6 | ta-388 | sp-6 | an-368 |
| 385 | is-1 | ta-369 | sp-1 | an-369 | 2269 | is-6 | ta-369 | sp-6 | an-369 |
| 386 | is-1 | ta-370 | sp-1 | an-370 | 2270 | is-6 | ta-370 | sp-6 | an-370 |
| 387 | is-1 | ta-371 | sp-1 | an-371 | 2271 | is-6 | ta-371 | sp-6 | an-371 |

-continued

| EXAMPLE | REAGENT | | PRODUCT | EXAMPLE | REAGENT | | PRODUCT |
|---|---|---|---|---|---|---|---|
| No. | is | ta | sp | an | No. | is | ta | sp | an |

Table 5-8

| EXAMPLE No. | is | ta | sp | an | EXAMPLE No. | is | ta | sp | an |
|---|---|---|---|---|---|---|---|---|---|
| 388 | is-1 | ta-372 | sp-1 | an-372 | 2272 | is-6 | ta-372 | sp-6 | an-372 |
| 389 | is-1 | ta-373 | sp-1 | an-373 | 2273 | is-6 | ta-373 | sp-6 | an-373 |
| 390 | is-1 | ta-374 | sp-1 | an-374 | 2274 | is-6 | ta-374 | sp-6 | an-374 |
| 391 | is-1 | ta-375 | sp-1 | an-375 | 2275 | is-6 | ta-375 | sp-6 | an-375 |
| 392 | is-1 | ta-376 | sp-1 | an-376 | 2276 | is-6 | ta-376 | sp-6 | an-376 |
| 393 | is-1 | ta-377 | sp-1 | an-377 | 2277 | is-6 | ta-377 | sp-6 | an-377 |
| 394 | is-2 | ta-1 | sp-2 | an-1 | 2278 | is-7 | ta-1 | sp-7 | an-1 |
| 395 | is-2 | ta-2 | sp-2 | an-2 | 2279 | is-7 | ta-2 | sp-7 | an-2 |
| 396 | is-2 | ta-3 | sp-2 | an-3 | 2280 | is-7 | ta-3 | sp-7 | an-3 |
| 397 | is-2 | ta-4 | sp-2 | an-4 | 2281 | is-7 | ta-4 | sp-7 | an-4 |
| 398 | is-2 | ta-5 | sp-2 | an-5 | 2282 | is-7 | ta-5 | sp-7 | an-5 |
| 399 | is-2 | ta-6 | sp-2 | an-6 | 2283 | is-7 | ta-6 | sp-7 | an-6 |
| 400 | is-2 | ta-7 | sp-2 | an-7 | 2284 | is-7 | ta-7 | sp-7 | an-7 |
| 401 | is-2 | ta-8 | sp-2 | an-8 | 2285 | is-7 | ta-8 | sp-7 | an-8 |
| 402 | is-2 | ta-9 | sp-2 | an-9 | 2286 | is-7 | ta-9 | sp-7 | an-9 |
| 403 | is-2 | ta-10 | sp-2 | an-10 | 2287 | is-7 | ta-10 | sp-7 | an-10 |
| 404 | is-2 | ta-11 | sp-2 | an-11 | 2288 | is-7 | ta-11 | sp-7 | an-11 |
| 405 | is-2 | ta-12 | sp-2 | an-12 | 2289 | is-7 | ta-12 | sp-7 | an-12 |
| 406 | is-2 | ta-13 | sp-2 | an-13 | 2290 | is-7 | ta-13 | sp-7 | an-13 |
| 407 | is-2 | ta-14 | sp-2 | an-14 | 2291 | is-7 | ta-14 | sp-7 | an-14 |
| 408 | is-2 | ta-15 | sp-2 | an-15 | 2292 | is-7 | ta-15 | sp-7 | an-15 |
| 409 | is-2 | ta-16 | sp-2 | an-16 | 2293 | is-7 | ta-16 | sp-7 | an-16 |
| 410 | is-2 | ta-17 | sp-2 | an-17 | 2294 | is-7 | ta-17 | sp-7 | an-17 |
| 411 | is-2 | ta-18 | sp-2 | an-18 | 2295 | is-7 | ta-18 | sp-7 | an-18 |
| 412 | is-2 | ta-19 | sp-2 | an-19 | 2296 | is-7 | ta-19 | sp-7 | an-19 |
| 413 | is-2 | ta-20 | sp-2 | an-20 | 2297 | is-7 | ta-20 | sp-7 | an-20 |
| 414 | is-2 | ta-21 | sp-2 | an-21 | 2298 | is-7 | ta-21 | sp-7 | an-21 |
| 415 | is-2 | ta-22 | sp-2 | an-22 | 2299 | is-7 | ta-22 | sp-7 | an-22 |
| 416 | is-2 | ta-23 | sp-2 | an-23 | 2300 | is-7 | ta-23 | sp-7 | an-23 |
| 417 | is-2 | ta-24 | sp-2 | an-24 | 2301 | is-7 | ta-24 | sp-7 | an-24 |
| 418 | is-2 | ta-25 | sp-2 | an-25 | 2302 | is-7 | ta-25 | sp-7 | an-25 |
| 419 | is-2 | ta-26 | sp-2 | an-26 | 2303 | is-7 | ta-26 | sp-7 | an-26 |
| 420 | is-2 | ta-27 | sp-2 | an-27 | 2304 | is-7 | ta-27 | sp-7 | an-27 |
| 421 | is-2 | ta-28 | sp-2 | an-28 | 2305 | is-7 | ta-28 | sp-7 | an-28 |
| 422 | is-2 | ta-29 | sp-2 | an-29 | 2306 | is-7 | ta-29 | sp-7 | an-29 |
| 423 | is-2 | ta-30 | sp-2 | an-30 | 2307 | is-7 | ta-30 | sp-7 | an-30 |
| 424 | is-2 | ta-31 | sp-2 | an-31 | 2308 | is-7 | ta-31 | sp-7 | an-31 |
| 425 | is-2 | ta-32 | sp-2 | an-32 | 2309 | is-7 | ta-32 | sp-7 | an-32 |
| 426 | is-2 | ta-33 | sp-2 | an-33 | 2310 | is-7 | ta-33 | sp-7 | an-33 |
| 427 | is-2 | ta-34 | sp-2 | an-34 | 2311 | is-7 | ta-34 | sp-7 | an-34 |
| 428 | is-2 | ta-35 | sp-2 | an-35 | 2312 | is-7 | ta-35 | sp-7 | an-35 |
| 429 | is-2 | ta-36 | sp-2 | an-36 | 2313 | is-7 | ta-36 | sp-7 | an-36 |
| 430 | is-2 | ta-37 | sp-2 | an-37 | 2314 | is-7 | ta-37 | sp-7 | an-37 |
| 431 | is-2 | ta-38 | sp-2 | an-38 | 2315 | is-7 | ta-38 | sp-7 | an-38 |
| 432 | is-2 | ta-39 | sp-2 | an-39 | 2316 | is-7 | ta-39 | sp-7 | an-39 |
| 433 | is-2 | ta-40 | sp-2 | an-40 | 2317 | is-7 | ta-40 | sp-7 | an-40 |
| 434 | is-2 | ta-41 | sp-2 | an-41 | 2318 | is-7 | ta-41 | sp-7 | an-41 |
| 435 | is-2 | ta-42 | sp-2 | an-42 | 2319 | is-7 | ta-42 | sp-7 | an-42 |
| 436 | is-2 | ta-43 | sp-2 | an-43 | 2320 | is-7 | ta-43 | sp-7 | an-43 |
| 437 | is-2 | ta-44 | sp-2 | an-44 | 2321 | is-7 | ta-44 | sp-7 | an-44 |
| 438 | is-2 | ta-45 | sp-2 | an-45 | 2322 | is-7 | ta-45 | sp-7 | an-45 |
| 439 | is-2 | ta-46 | sp-2 | an-46 | 2323 | is-7 | ta-46 | sp-7 | an-46 |
| 440 | is-2 | ta-47 | sp-2 | an-47 | 2324 | is-7 | ta-47 | sp-7 | an-47 |

Table 5-9

| EXAMPLE No. | is | ta | sp | an | EXAMPLE No. | is | ta | sp | an |
|---|---|---|---|---|---|---|---|---|---|
| 441 | is-2 | ta-48 | sp-2 | an-48 | 2325 | is-7 | ta-48 | sp-7 | an-48 |
| 442 | is-2 | ta-49 | sp-2 | an-49 | 2326 | is-7 | ta-49 | sp-7 | an-49 |
| 443 | is-2 | ta-50 | sp-2 | an-50 | 2327 | is-7 | ta-50 | sp-7 | an-50 |
| 444 | is-2 | ta-51 | sp-2 | an-51 | 2328 | is-7 | ta-51 | sp-7 | an-51 |
| 445 | is-2 | ta-52 | sp-2 | an-52 | 2329 | is-7 | ta-52 | sp-7 | an-52 |
| 446 | is-2 | ta-53 | sp-2 | an-53 | 2330 | is-7 | ta-53 | sp-7 | an-53 |
| 447 | is-2 | ta-54 | sp-2 | an-54 | 2331 | is-7 | ta-54 | sp-7 | an-54 |
| 448 | is-2 | ta-55 | sp-2 | an-55 | 2332 | is-7 | ta-55 | sp-7 | an-55 |
| 449 | is-2 | ta-56 | sp-2 | an-56 | 2333 | is-7 | ta-56 | sp-7 | an-56 |
| 450 | is-2 | ta-57 | sp-2 | an-57 | 2334 | is-7 | ta-57 | sp-7 | an-57 |
| 451 | is-2 | ta-58 | sp-2 | an-58 | 2335 | is-7 | ta-58 | sp-7 | an-58 |
| 452 | is-2 | ta-59 | sp-2 | an-59 | 2336 | is-7 | ta-59 | sp-7 | an-59 |
| 453 | is-2 | ta-60 | sp-2 | an-60 | 2337 | is-7 | ta-60 | sp-7 | an-60 |
| 454 | is-2 | ta-61 | sp-2 | an-61 | 2338 | is-7 | ta-61 | sp-7 | an-61 |
| 455 | is-2 | ta-62 | sp-2 | an-62 | 2339 | is-7 | ta-62 | sp-7 | an-62 |
| 456 | is-2 | ta-63 | sp-2 | an-63 | 2340 | is-7 | ta-63 | sp-7 | an-63 |
| 457 | is-2 | ta-64 | sp-2 | an-64 | 2341 | is-7 | ta-64 | sp-7 | an-64 |
| 458 | is-2 | ta-65 | sp-2 | an-65 | 2342 | is-7 | ta-65 | sp-7 | an-65 |
| 459 | is-2 | ta-66 | sp-2 | an-66 | 2343 | is-7 | ta-66 | sp-7 | an-66 |

-continued

| EXAMPLE | REAGENT | | PRODUCT | EXAMPLE | REAGENT | | PRODUCT |
|---|---|---|---|---|---|---|---|
| No. | is | ta | sp | an | No. | is | ta | sp | an |
| 460 | is-2 | ta-67 | sp-2 | an-67 | 2344 | is-7 | ta-67 | sp-7 | an-67 |
| 461 | is-2 | ta-68 | sp-2 | an-68 | 2345 | is-7 | ta-68 | sp-7 | an-68 |
| 462 | is-2 | ta-69 | sp-2 | an-69 | 2346 | is-7 | ta-69 | sp-7 | an-69 |
| 463 | is-2 | ta-70 | sp-2 | an-70 | 2347 | is-7 | ta-70 | sp-7 | an-70 |
| 464 | is-2 | ta-71 | sp-2 | an-71 | 2348 | is-7 | ta-71 | sp-7 | an-71 |
| 465 | is-2 | ta-72 | sp-2 | an-72 | 2349 | is-7 | ta-72 | sp-7 | an-72 |
| 466 | is-2 | ta-73 | sp-2 | an-73 | 2350 | is-7 | ta-73 | sp-7 | an-73 |
| 467 | is-2 | ta-74 | sp-2 | an-74 | 2351 | is-7 | ta-74 | sp-7 | an-74 |
| 468 | is-2 | ta-75 | sp-2 | an-75 | 2352 | is-7 | ta-75 | sp-7 | an-75 |
| 469 | is-2 | ta-76 | sp-2 | an-76 | 2353 | is-7 | ta-76 | sp-7 | an-76 |
| 470 | is-2 | ta-77 | sp-2 | an-77 | 2354 | is-7 | ta-77 | sp-7 | an-77 |
| 471 | is-2 | ta-78 | sp-2 | an-78 | 2355 | is-7 | ta-78 | sp-7 | an-78 |
| 472 | is-2 | ta-79 | sp-2 | an-79 | 2356 | is-7 | ta-79 | sp-7 | an-79 |
| 473 | is-2 | ta-80 | sp-2 | an-80 | 2357 | is-7 | ta-80 | sp-7 | an-80 |
| 474 | is-2 | ta-81 | sp-2 | an-81 | 2358 | is-7 | ta-81 | sp-7 | an-81 |
| 475 | is-2 | ta-82 | sp-2 | an-82 | 2359 | is-7 | ta-82 | sp-7 | an-82 |
| 476 | is-2 | ta-83 | sp-2 | an-83 | 2360 | is-7 | ta-83 | sp-7 | an-83 |
| 477 | is-2 | ta-84 | sp-2 | an-84 | 2361 | is-7 | ta-84 | sp-7 | an-84 |
| 478 | is-2 | ta-85 | sp-2 | an-85 | 2362 | is-7 | ta-85 | sp-7 | an-85 |
| 479 | is-2 | ta-86 | sp-2 | an-86 | 2363 | is-7 | ta-86 | sp-7 | an-86 |
| 480 | is-2 | ta-87 | sp-2 | an-87 | 2364 | is-7 | ta-87 | sp-7 | an-87 |
| 481 | is-2 | ta-88 | sp-2 | an-88 | 2365 | is-7 | ta-88 | sp-7 | an-88 |
| 482 | is-2 | ta-89 | sp-2 | an-89 | 2366 | is-7 | ta-89 | sp-7 | an-89 |
| 483 | is-2 | ta-90 | sp-2 | an-90 | 2367 | is-7 | ta-90 | sp-7 | an-90 |
| 484 | is-2 | ta-91 | sp-2 | an-91 | 2368 | is-7 | ta-91 | sp-7 | an-91 |
| 485 | is-2 | ta-92 | sp-2 | an-92 | 2369 | is-7 | ta-92 | sp-7 | an-92 |
| 486 | is-2 | ta-93 | sp-2 | an-93 | 2370 | is-7 | ta-93 | sp-7 | an-93 |
| 487 | is-2 | ta-94 | sp-2 | an-94 | 2371 | is-7 | ta-94 | sp-7 | an-94 |
| 488 | is-2 | ta-95 | sp-2 | an-95 | 2372 | is-7 | ta-95 | sp-7 | an-95 |
| 489 | is-2 | ta-96 | sp-2 | an-96 | 2373 | is-7 | ta-96 | sp-7 | an-96 |
| 490 | is-2 | ta-97 | sp-2 | an-97 | 2374 | is-7 | ta-97 | sp-7 | an-97 |
| 491 | is-2 | ta-98 | sp-2 | an-98 | 2375 | is-7 | ta-98 | sp-7 | an-98 |
| 492 | is-2 | ta-99 | sp-2 | an-99 | 2376 | is-7 | ta-99 | sp-7 | an-99 |
| 493 | is-2 | ta-100 | sp-2 | an-100 | 2377 | is-7 | ta-100 | sp-7 | an-100 |

Table 5-10

| EXAMPLE | REAGENT | | PRODUCT | EXAMPLE | REAGENT | | PRODUCT |
|---|---|---|---|---|---|---|---|
| No. | is | ta | sp | an | No. | is | ta | sp | an |
| 494 | is-2 | ta-101 | sp-2 | an-101 | 2378 | is-7 | ta-101 | sp-7 | an-101 |
| 495 | is-2 | ta-102 | sp-2 | an-102 | 2379 | is-7 | ta-102 | sp-7 | an-102 |
| 496 | is-2 | ta-103 | sp-2 | an-103 | 2380 | is-7 | ta-103 | sp-7 | an-103 |
| 497 | is-2 | ta-104 | sp-2 | an-104 | 2381 | is-7 | ta-104 | sp-7 | an-104 |
| 498 | is-2 | ta-105 | sp-2 | an-105 | 2382 | is-7 | ta-105 | sp-7 | an-105 |
| 499 | is-2 | ta-106 | sp-2 | an-106 | 2383 | is-7 | ta-106 | sp-7 | an-106 |
| 500 | is-2 | ta-107 | sp-2 | an-107 | 2384 | is-7 | ta-107 | sp-7 | an-107 |
| 501 | is-2 | ta-108 | sp-2 | an-108 | 2385 | is-7 | ta-108 | sp-7 | an-108 |
| 502 | is-2 | ta-109 | sp-2 | an-109 | 2386 | is-7 | ta-109 | sp-7 | an-109 |
| 503 | is-2 | ta-110 | sp-2 | an-110 | 2387 | is-7 | ta-110 | sp-7 | an-110 |
| 504 | is-2 | ta-111 | sp-2 | an-111 | 2388 | is-7 | ta-111 | sp-7 | an-111 |
| 505 | is-2 | ta-112 | sp-2 | an-112 | 2389 | is-7 | ta-112 | sp-7 | an-112 |
| 506 | is-2 | ta-113 | sp-2 | an-113 | 2390 | is-7 | ta-113 | sp-7 | an-113 |
| 507 | is-2 | ta-114 | sp-2 | an-114 | 2391 | is-7 | ta-114 | sp-7 | an-114 |
| 508 | is-2 | ta-115 | sp-2 | an-115 | 2392 | is-7 | ta-115 | sp-7 | an-115 |
| 509 | is-2 | ta-116 | sp-2 | an-116 | 2393 | is-7 | ta-116 | sp-7 | an-116 |
| 510 | is-2 | ta-117 | sp-2 | an-117 | 2394 | is-7 | ta-117 | sp-7 | an-117 |
| 511 | is-2 | ta-118 | sp-2 | an-118 | 2395 | is-7 | ta-118 | sp-7 | an-118 |
| 512 | is-2 | ta-119 | sp-2 | an-119 | 2396 | is-7 | ta-119 | sp-7 | an-119 |
| 513 | is-2 | ta-120 | sp-2 | an-120 | 2397 | is-7 | ta-120 | sp-7 | an-120 |
| 514 | is-2 | ta-121 | sp-2 | an-121 | 2398 | is-7 | ta-121 | sp-7 | an-121 |
| 515 | is-2 | ta-122 | sp-2 | an-122 | 2399 | is-7 | ta-122 | sp-7 | an-122 |
| 516 | is-2 | ta-123 | sp-2 | an-123 | 2400 | is-7 | ta-123 | sp-7 | an-123 |
| 517 | is-2 | ta-124 | sp-2 | an-124 | 2401 | is-7 | ta-124 | sp-7 | an-124 |
| 518 | is-2 | ta-125 | sp-2 | an-125 | 2402 | is-7 | ta-125 | sp-7 | an-125 |
| 519 | is-2 | ta-126 | sp-2 | an-126 | 2403 | is-7 | ta-126 | sp-7 | an-126 |
| 520 | is-2 | ta-127 | sp-2 | an-127 | 2404 | is-7 | ta-127 | sp-7 | an-127 |
| 521 | is-2 | ta-128 | sp-2 | an-128 | 2405 | is-7 | ta-128 | sp-7 | an-128 |
| 522 | is-2 | ta-129 | sp-2 | an-129 | 2406 | is-7 | ta-129 | sp-7 | an-129 |
| 523 | is-2 | ta-130 | sp-2 | an-130 | 2407 | is-7 | ta-130 | sp-7 | an-130 |
| 524 | is-2 | ta-131 | sp-2 | an-131 | 2408 | is-7 | ta-131 | sp-7 | an-131 |
| 525 | is-2 | ta-132 | sp-2 | an-132 | 2409 | is-7 | ta-132 | sp-7 | an-132 |
| 526 | is-2 | ta-133 | sp-2 | an-133 | 2410 | is-7 | ta-133 | sp-7 | an-133 |
| 527 | is-2 | ta-134 | sp-2 | an-134 | 2411 | is-7 | ta-134 | sp-7 | an-134 |
| 528 | is-2 | ta-135 | sp-2 | an-135 | 2412 | is-7 | ta-135 | sp-7 | an-135 |
| 529 | is-2 | ta-136 | sp-2 | an-136 | 2413 | is-7 | ta-136 | sp-7 | an-136 |
| 530 | is-2 | ta-137 | sp-2 | an-137 | 2414 | is-7 | ta-137 | sp-7 | an-137 |
| 531 | is-2 | ta-138 | sp-2 | an-138 | 2415 | is-7 | ta-138 | sp-7 | an-138 |
| 532 | is-2 | ta-139 | sp-2 | an-139 | 2416 | is-7 | ta-139 | sp-7 | an-139 |
| 533 | is-2 | ta-140 | sp-2 | an-140 | 2417 | is-7 | ta-140 | sp-7 | an-140 |

-continued

| EXAMPLE | REAGENT | | PRODUCT | EXAMPLE | REAGENT | | PRODUCT |
|---|---|---|---|---|---|---|---|
| No. | is | ta | sp | an | No. | is | ta | sp | an |
| 534 | is-2 | ta-141 | sp-2 | an-141 | 2418 | is-7 | ta-141 | sp-7 | an-141 |
| 535 | is-2 | ta-142 | sp-2 | an-142 | 2419 | is-7 | ta-142 | sp-7 | an-142 |
| 536 | is-2 | ta-143 | sp-2 | an-143 | 2420 | is-7 | ta-143 | sp-7 | an-143 |
| 537 | is-2 | ta-144 | sp-2 | an-144 | 2421 | is-7 | ta-144 | sp-7 | an-144 |
| 538 | is-2 | ta-145 | sp-2 | an-145 | 2422 | is-7 | ta-145 | sp-7 | an-145 |
| 539 | is-2 | ta-146 | sp-2 | an-146 | 2423 | is-7 | ta-146 | sp-7 | an-146 |
| 540 | is-2 | ta-147 | sp-2 | an-147 | 2424 | is-7 | ta-147 | sp-7 | an-147 |
| 541 | is-2 | ta-148 | sp-2 | an-148 | 2425 | is-7 | ta-148 | sp-7 | an-148 |
| 542 | is-2 | ta-149 | sp-2 | an-149 | 2426 | is-7 | ta-149 | sp-7 | an-149 |
| 543 | is-2 | ta-150 | sp-2 | an-150 | 2427 | is-7 | ta-150 | sp-7 | an-150 |
| 544 | is-2 | ta-151 | sp-2 | an-151 | 2428 | is-7 | ta-151 | sp-7 | an-151 |
| 545 | is-2 | ta-152 | sp-2 | an-152 | 2429 | is-7 | ta-152 | sp-7 | an-152 |
| 546 | is-2 | ta-153 | sp-2 | an-153 | 2430 | is-7 | ta-153 | sp-7 | an-153 |

Table 5-11

| 547 | is-2 | ta-154 | sp-2 | an-154 | 2431 | is-7 | ta-154 | sp-7 | an-154 |
|---|---|---|---|---|---|---|---|---|---|
| 548 | is-2 | ta-155 | sp-2 | an-155 | 2432 | is-7 | ta-155 | sp-7 | an-155 |
| 549 | is-2 | ta-156 | sp-2 | an-156 | 2433 | is-7 | ta-156 | sp-7 | an-156 |
| 550 | is-2 | ta-157 | sp-2 | an-157 | 2434 | is-7 | ta-157 | sp-7 | an-157 |
| 551 | is-2 | ta-158 | sp-2 | an-158 | 2435 | is-7 | ta-158 | sp-7 | an-158 |
| 552 | is-2 | ta-159 | sp-2 | an-159 | 2436 | is-7 | ta-159 | sp-7 | an-159 |
| 553 | is-2 | ta-160 | sp-2 | an-160 | 2437 | is-7 | ta-160 | sp-7 | an-160 |
| 554 | is-2 | ta-161 | sp-2 | an-161 | 2438 | is-7 | ta-161 | sp-7 | an-161 |
| 555 | is-2 | ta-162 | sp-2 | an-162 | 2439 | is-7 | ta-162 | sp-7 | an-162 |
| 556 | is-2 | ta-163 | sp-2 | an-163 | 2440 | is-7 | ta-163 | sp-7 | an-163 |
| 557 | is-2 | ta-164 | sp-2 | an-164 | 2441 | is-7 | ta-164 | sp-7 | an-164 |
| 558 | is-2 | ta-165 | sp-2 | an-165 | 2442 | is-7 | ta-165 | sp-7 | an-165 |
| 559 | is-2 | ta-166 | sp-2 | an-166 | 2443 | is-7 | ta-166 | sp-7 | an-166 |
| 560 | is-2 | ta-167 | sp-2 | an-167 | 2444 | is-7 | ta-167 | sp-7 | an-167 |
| 561 | is-2 | ta-168 | sp-2 | an-168 | 2445 | is-7 | ta-168 | sp-7 | an-168 |
| 562 | is-2 | ta-169 | sp-2 | an-169 | 2446 | is-7 | ta-169 | sp-7 | an-169 |
| 563 | is-2 | ta-170 | sp-2 | an-170 | 2447 | is-7 | ta-170 | sp-7 | an-170 |
| 564 | is-2 | ta-171 | sp-2 | an-171 | 2448 | is-7 | ta-171 | sp-7 | an-171 |
| 565 | is-2 | ta-172 | sp-2 | an-172 | 2449 | is-7 | ta-172 | sp-7 | an-172 |
| 566 | is-2 | ta-173 | sp-2 | an-173 | 2450 | is-7 | ta-173 | sp-7 | an-173 |
| 567 | is-2 | ta-174 | sp-2 | an-174 | 2451 | is-7 | ta-174 | sp-7 | an-174 |
| 568 | is-2 | ta-175 | sp-2 | an-175 | 2452 | is-7 | ta-175 | sp-7 | an-175 |
| 569 | is-2 | ta-176 | sp-2 | an-176 | 2453 | is-7 | ta-176 | sp-7 | an-176 |
| 570 | is-2 | ta-177 | sp-2 | an-177 | 2454 | is-7 | ta-177 | sp-7 | an-177 |
| 571 | is-2 | ta-178 | sp-2 | an-178 | 2455 | is-7 | ta-178 | sp-7 | an-178 |
| 572 | is-2 | ta-179 | sp-2 | an-179 | 2456 | is-7 | ta-179 | sp-7 | an-179 |
| 573 | is-2 | ta-180 | sp-2 | an-180 | 2457 | is-7 | ta-180 | sp-7 | an-180 |
| 574 | is-2 | ta-181 | sp-2 | an-181 | 2458 | is-7 | ta-181 | sp-7 | an-181 |
| 575 | is-2 | ta-182 | sp-2 | an-182 | 2459 | is-7 | ta-182 | sp-7 | an-182 |
| 576 | is-2 | ta-183 | sp-2 | an-183 | 2460 | is-7 | ta-183 | sp-7 | an-183 |
| 577 | is-2 | ta-184 | sp-2 | an-184 | 2461 | is-7 | ta-184 | sp-7 | an-184 |
| 578 | is-2 | ta-185 | sp-2 | an-185 | 2462 | is-7 | ta-185 | sp-7 | an-185 |
| 579 | is-2 | ta-186 | sp-2 | an-186 | 2463 | is-7 | ta-186 | sp-7 | an-186 |
| 580 | is-2 | ta-187 | sp-2 | an-187 | 2464 | is-7 | ta-187 | sp-7 | an-187 |
| 581 | is-2 | ta-188 | sp-2 | an-188 | 2465 | is-7 | ta-188 | sp-7 | an-188 |
| 582 | is-2 | ta-189 | sp-2 | an-189 | 2466 | is-7 | ta-189 | sp-7 | an-189 |
| 583 | is-2 | ta-190 | sp-2 | an-190 | 2467 | is-7 | ta-190 | sp-7 | an-190 |
| 584 | is-2 | ta-191 | sp-2 | an-191 | 2468 | is-7 | ta-191 | sp-7 | an-191 |
| 585 | is-2 | ta-192 | sp-2 | an-192 | 2469 | is-7 | ta-192 | sp-7 | an-192 |
| 586 | is-2 | ta-193 | sp-2 | an-193 | 2470 | is-7 | ta-193 | sp-7 | an-193 |
| 587 | is-2 | ta-194 | sp-2 | an-194 | 2471 | is-7 | ta-194 | sp-7 | an-194 |
| 588 | is-2 | ta-195 | sp-2 | an-195 | 2472 | is-7 | ta-195 | sp-7 | an-195 |
| 589 | is-2 | ta-196 | sp-2 | an-196 | 2473 | is-7 | ta-196 | sp-7 | an-196 |
| 590 | is-2 | ta-197 | sp-2 | an-197 | 2474 | is-7 | ta-197 | sp-7 | an-197 |
| 591 | is-2 | ta-198 | sp-2 | an-198 | 2475 | is-7 | ta-198 | sp-7 | an-198 |
| 592 | is-2 | ta-199 | sp-2 | an-199 | 2476 | is-7 | ta-199 | sp-7 | an-199 |
| 593 | is-2 | ta-200 | sp-2 | an-200 | 2477 | is-7 | ta-200 | sp-7 | an-200 |
| 594 | is-2 | ta-201 | sp-2 | an-201 | 2478 | is-7 | ta-201 | sp-7 | an-201 |
| 595 | is-2 | ta-202 | sp-2 | an-202 | 2479 | is-7 | ta-202 | sp-7 | an-202 |
| 596 | is-2 | ta-203 | sp-2 | an-203 | 2480 | is-7 | ta-203 | sp-7 | an-203 |
| 597 | is-2 | ta-204 | sp-2 | an-204 | 2481 | is-7 | ta-204 | sp-7 | an-204 |
| 598 | is-2 | ta-205 | sp-2 | an-205 | 2482 | is-7 | ta-205 | sp-7 | an-205 |
| 599 | is-2 | ta-206 | sp-2 | an-206 | 2483 | is-7 | ta-206 | sp-7 | an-206 |

Table 5-12

| 600 | is-2 | ta-207 | sp-2 | an-207 | 2484 | is-7 | ta-207 | sp-7 | an-207 |
|---|---|---|---|---|---|---|---|---|---|
| 601 | is-2 | ta-208 | sp-2 | an-208 | 2485 | is-7 | ta-208 | sp-7 | an-208 |
| 602 | is-2 | ta-209 | sp-2 | an-209 | 2486 | is-7 | ta-209 | sp-7 | an-209 |
| 603 | is-2 | ta-210 | sp-2 | an-210 | 2487 | is-7 | ta-210 | sp-7 | an-210 |
| 604 | is-2 | ta-211 | sp-2 | an-211 | 2488 | is-7 | ta-211 | sp-7 | an-211 |
| 605 | is-2 | ta-212 | sp-2 | an-212 | 2489 | is-7 | ta-212 | sp-7 | an-212 |

-continued

| EXAMPLE | REAGENT | | PRODUCT | EXAMPLE | REAGENT | | PRODUCT |
|---|---|---|---|---|---|---|---|
| No. | is | ta | sp | an | No. | is | ta | sp | an |
| 606 | is-2 | ta-213 | sp-2 | an-213 | 2490 | is-7 | ta-213 | sp-7 | an-213 |
| 607 | is-2 | ta-214 | sp-2 | an-214 | 2491 | is-7 | ta-214 | sp-7 | an-214 |
| 608 | is-2 | ta-215 | sp-2 | an-215 | 2492 | is-7 | ta-215 | sp-7 | an-215 |
| 609 | is-2 | ta-216 | sp-2 | an-216 | 2493 | is-7 | ta-216 | sp-7 | an-216 |
| 610 | is-2 | ta-217 | sp-2 | an-217 | 2494 | is-7 | ta-217 | sp-7 | an-217 |
| 611 | is-2 | ta-218 | sp-2 | an-218 | 2495 | is-7 | ta-218 | sp-7 | an-218 |
| 612 | is-2 | ta-219 | sp-2 | an-219 | 2496 | is-7 | ta-219 | sp-7 | an-219 |
| 613 | is-2 | ta-220 | sp-2 | an-220 | 2497 | is-7 | ta-220 | sp-7 | an-220 |
| 614 | is-2 | ta-221 | sp-2 | an-221 | 2498 | is-7 | ta-221 | sp-7 | an-221 |
| 615 | is-2 | ta-222 | sp-2 | an-222 | 2499 | is-7 | ta-222 | sp-7 | an-222 |
| 616 | is-2 | ta-223 | sp-2 | an-223 | 2500 | is-7 | ta-223 | sp-7 | an-223 |
| 617 | is-2 | ta-224 | sp-2 | an-224 | 2501 | is-7 | ta-224 | sp-7 | an-224 |
| 618 | is-2 | ta-225 | sp-2 | an-225 | 2502 | is-7 | ta-225 | sp-7 | an-225 |
| 619 | is-2 | ta-226 | sp-2 | an-226 | 2503 | is-7 | ta-226 | sp-7 | an-226 |
| 620 | is-2 | ta-227 | sp-2 | an-227 | 2504 | is-7 | ta-227 | sp-7 | an-227 |
| 621 | is-2 | ta-228 | sp-2 | an-228 | 2505 | is-7 | ta-228 | sp-7 | an-228 |
| 622 | is-2 | ta-229 | sp-2 | an-229 | 2506 | is-7 | ta-229 | sp-7 | an-229 |
| 623 | is-2 | ta-230 | sp-2 | an-230 | 2507 | is-7 | ta-230 | sp-7 | an-230 |
| 624 | is-2 | ta-231 | sp-2 | an-231 | 2508 | is-7 | ta-231 | sp-7 | an-231 |
| 625 | is-2 | ta-232 | sp-2 | an-232 | 2509 | is-7 | ta-232 | sp-7 | an-232 |
| 626 | is-2 | ta-233 | sp-2 | an-233 | 2510 | is-7 | ta-233 | sp-7 | an-233 |
| 627 | is-2 | ta-234 | sp-2 | an-234 | 2511 | is-7 | ta-234 | sp-7 | an-234 |
| 628 | is-2 | ta-235 | sp-2 | an-235 | 2512 | is-7 | ta-235 | sp-7 | an-235 |
| 629 | is-2 | ta-236 | sp-2 | an-236 | 2513 | is-7 | ta-236 | sp-7 | an-236 |
| 630 | is-2 | ta-237 | sp-2 | an-237 | 2514 | is-7 | ta-237 | sp-7 | an-237 |
| 631 | is-2 | ta-238 | sp-2 | an-238 | 2515 | is-7 | ta-238 | sp-7 | an-238 |
| 632 | is-2 | ta-239 | sp-2 | an-239 | 2516 | is-7 | ta-239 | sp-7 | an-239 |
| 633 | is-2 | ta-240 | sp-2 | an-240 | 2517 | is-7 | ta-240 | sp-7 | an-240 |
| 634 | is-2 | ta-241 | sp-2 | an-241 | 2518 | is-7 | ta-241 | sp-7 | an-241 |
| 635 | is-2 | ta-242 | sp-2 | an-242 | 2519 | is-7 | ta-242 | sp-7 | an-242 |
| 636 | is-2 | ta-243 | sp-2 | an-243 | 2520 | is-7 | ta-243 | sp-7 | an-243 |
| 637 | is-2 | ta-244 | sp-2 | an-244 | 2521 | is-7 | ta-244 | sp-7 | an-244 |
| 638 | is-2 | ta-245 | sp-2 | an-245 | 2522 | is-7 | ta-245 | sp-7 | an-245 |
| 639 | is-2 | ta-246 | sp-2 | an-246 | 2523 | is-7 | ta-246 | sp-7 | an-246 |
| 640 | is-2 | ta-247 | sp-2 | an-247 | 2524 | is-7 | ta-247 | sp-7 | an-247 |
| 641 | is-2 | ta-248 | sp-2 | an-248 | 2525 | is-7 | ta-248 | sp-7 | an-248 |
| 642 | is-2 | ta-249 | sp-2 | an-249 | 2526 | is-7 | ta-249 | sp-7 | an-249 |
| 643 | is-2 | ta-250 | sp-2 | an-250 | 2527 | is-7 | ta-250 | sp-7 | an-250 |
| 644 | is-2 | ta-251 | sp-2 | an-251 | 2528 | is-7 | ta-251 | sp-7 | an-251 |
| 645 | is-2 | ta-252 | sp-2 | an-252 | 2529 | is-7 | ta-252 | sp-7 | an-252 |
| 646 | is-2 | ta-253 | sp-2 | an-253 | 2530 | is-7 | ta-253 | sp-7 | an-253 |
| 647 | is-2 | ta-254 | sp-2 | an-254 | 2531 | is-7 | ta-254 | sp-7 | an-254 |
| 648 | is-2 | ta-255 | sp-2 | an-255 | 2532 | is-7 | ta-255 | sp-7 | an-255 |
| 649 | is-2 | ta-256 | sp-2 | an-256 | 2533 | is-7 | ta-256 | sp-7 | an-256 |
| 650 | is-2 | ta-257 | sp-2 | an-257 | 2534 | is-7 | ta-257 | sp-7 | an-257 |
| 651 | is-2 | ta-258 | sp-2 | an-258 | 2535 | is-7 | ta-258 | sp-7 | an-258 |
| 652 | is-2 | ta-259 | sp-2 | an-259 | 2536 | is-7 | ta-259 | sp-7 | an-259 |

Table 5-13

| 653 | is-2 | ta-260 | sp-2 | an-260 | 2537 | is-7 | ta-260 | sp-7 | an-260 |
|---|---|---|---|---|---|---|---|---|---|
| 654 | is-2 | ta-261 | sp-2 | an-261 | 2538 | is-7 | ta-261 | sp-7 | an-261 |
| 655 | is-2 | ta-262 | sp-2 | an-262 | 2539 | is-7 | ta-262 | sp-7 | an-262 |
| 656 | is-2 | ta-263 | sp-2 | an-263 | 2540 | is-7 | ta-263 | sp-7 | an-263 |
| 657 | is-2 | ta-264 | sp-2 | an-264 | 2541 | is-7 | ta-264 | sp-7 | an-264 |
| 658 | is-2 | ta-265 | sp-2 | an-265 | 2542 | is-7 | ta-265 | sp-7 | an-265 |
| 659 | is-2 | ta-266 | sp-2 | an-266 | 2543 | is-7 | ta-266 | sp-7 | an-266 |
| 660 | is-2 | ta-267 | sp-2 | an-267 | 2544 | is-7 | ta-267 | sp-7 | an-267 |
| 661 | is-2 | ta-268 | sp-2 | an-268 | 2545 | is-7 | ta-268 | sp-7 | an-268 |
| 662 | is-2 | ta-269 | sp-2 | an-269 | 2546 | is-7 | ta-269 | sp-7 | an-269 |
| 663 | is-2 | ta-270 | sp-2 | an-270 | 2547 | is-7 | ta-270 | sp-7 | an-270 |
| 664 | is-2 | ta-271 | sp-2 | an-271 | 2548 | is-7 | ta-271 | sp-7 | an-271 |
| 665 | is-2 | ta-272 | sp-2 | an-272 | 2549 | is-7 | ta-272 | sp-7 | an-272 |
| 666 | is-2 | ta-273 | sp-2 | an-273 | 2550 | is-7 | ta-273 | sp-7 | an-273 |
| 667 | is-2 | ta-274 | sp-2 | an-274 | 2551 | is-7 | ta-274 | sp-7 | an-274 |
| 668 | is-2 | ta-275 | sp-2 | an-275 | 2552 | is-7 | ta-275 | sp-7 | an-275 |
| 669 | is-2 | ta-276 | sp-2 | an-276 | 2553 | is-7 | ta-276 | sp-7 | an-276 |
| 670 | is-2 | ta-277 | sp-2 | an-277 | 2554 | is-7 | ta-277 | sp-7 | an-277 |
| 671 | is-2 | ta-278 | sp-2 | an-278 | 2555 | is-7 | ta-278 | sp-7 | an-278 |
| 672 | is-2 | ta-279 | sp-2 | an-279 | 2556 | is-7 | ta-279 | sp-7 | an-279 |
| 673 | is-2 | ta-280 | sp-2 | an-280 | 2557 | is-7 | ta-280 | sp-7 | an-280 |
| 674 | is-2 | ta-281 | sp-2 | an-281 | 2558 | is-7 | ta-281 | sp-7 | an-281 |
| 675 | is-2 | ta-282 | sp-2 | an-282 | 2559 | is-7 | ta-282 | sp-7 | an-282 |
| 676 | is-2 | ta-283 | sp-2 | an-283 | 2560 | is-7 | ta-283 | sp-7 | an-283 |
| 677 | is-2 | ta-284 | sp-2 | an-284 | 2561 | is-7 | ta-284 | sp-7 | an-284 |
| 678 | is-2 | ta-285 | sp-2 | an-285 | 2562 | is-7 | ta-285 | sp-7 | an-285 |
| 679 | is-2 | ta-286 | sp-2 | an-286 | 2563 | is-7 | ta-286 | sp-7 | an-286 |

| EXAMPLE | REAGENT | | PRODUCT | EXAMPLE | REAGENT | | PRODUCT |
|---|---|---|---|---|---|---|---|
| No. | is | ta | sp | an | No. | is | ta | sp | an |
| 9 | is-2 | ta-287 | sp-2 | an-287 | 2564 | is-7 | ta-287 | sp-7 | an-287 |
| 680 | is-2 | ta-288 | sp-2 | an-288 | 2565 | is-7 | ta-288 | sp-7 | an-288 |
| 681 | is-2 | ta-289 | sp-2 | an-289 | 2566 | is-7 | ta-289 | sp-7 | an-289 |
| 682 | is-2 | ta-290 | sp-2 | an-290 | 2567 | is-7 | ta-290 | sp-7 | an-290 |
| 683 | is-2 | ta-291 | sp-2 | an-291 | 2568 | is-7 | ta-291 | sp-7 | an-291 |
| 684 | is-2 | ta-292 | sp-2 | an-292 | 2569 | is-7 | ta-292 | sp-7 | an-292 |
| 685 | is-2 | ta-293 | sp-2 | an-293 | 2570 | is-7 | ta-293 | sp-7 | an-293 |
| 686 | is-2 | ta-294 | sp-2 | an-294 | 2571 | is-7 | ta-294 | sp-7 | an-294 |
| 687 | is-2 | ta-295 | sp-2 | an-295 | 2572 | is-7 | ta-295 | sp-7 | an-295 |
| 688 | is-2 | ta-296 | sp-2 | an-296 | 2573 | is-7 | ta-296 | sp-7 | an-296 |
| 689 | is-2 | ta-297 | sp-2 | an-297 | 2574 | is-7 | ta-297 | sp-7 | an-297 |
| 690 | is-2 | ta-298 | sp-2 | an-298 | 2575 | is-7 | ta-298 | sp-7 | an-298 |
| 691 | is-2 | ta-299 | sp-2 | an-299 | 2576 | is-7 | ta-299 | sp-7 | an-299 |
| 692 | is-2 | ta-300 | sp-2 | an-300 | 2577 | is-7 | ta-300 | sp-7 | an-300 |
| 693 | is-2 | ta-301 | sp-2 | an-301 | 2578 | is-7 | ta-301 | sp-7 | an-301 |
| 694 | is-2 | ta-302 | sp-2 | an-302 | 2579 | is-7 | ta-302 | sp-7 | an-302 |
| 695 | is-2 | ta-303 | sp-2 | an-303 | 2580 | is-7 | ta-303 | sp-7 | an-303 |
| 696 | is-2 | ta-304 | sp-2 | an-304 | 2581 | is-7 | ta-304 | sp-7 | an-304 |
| 697 | is-2 | ta-305 | sp-2 | an-305 | 2582 | is-7 | ta-305 | sp-7 | an-305 |
| 698 | is-2 | ta-306 | sp-2 | an-306 | 2583 | is-7 | ta-306 | sp-7 | an-306 |
| 699 | is-2 | ta-307 | sp-2 | an-307 | 2584 | is-7 | ta-307 | sp-7 | an-307 |
| 700 | is-2 | ta-308 | sp-2 | an-308 | 2585 | is-7 | ta-308 | sp-7 | an-308 |
| 701 | is-2 | ta-309 | sp-2 | an-309 | 2586 | is-7 | ta-309 | sp-7 | an-309 |
| 702 | is-2 | ta-310 | sp-2 | an-310 | 2587 | is-7 | ta-310 | sp-7 | an-310 |
| 703 | is-2 | ta-311 | sp-2 | an-311 | 2588 | is-7 | ta-311 | sp-7 | an-311 |
| 704 | is-2 | ta-312 | sp-2 | an-312 | 2589 | is-7 | ta-312 | sp-7 | an-312 |

Table 5-14

| 705 | is-2 | ta-313 | sp-2 | an-313 | 2590 | is-7 | ta-313 | sp-7 | an-313 |
|---|---|---|---|---|---|---|---|---|---|
| 706 | is-2 | ta-314 | sp-2 | an-314 | 2591 | is-7 | ta-314 | sp-7 | an-314 |
| 707 | is-2 | ta-315 | sp-2 | an-315 | 2592 | is-7 | ta-315 | sp-7 | an-315 |
| 708 | is-2 | ta-316 | sp-2 | an-316 | 2593 | is-7 | ta-316 | sp-7 | an-316 |
| 709 | is-2 | ta-317 | sp-2 | an-317 | 2594 | is-7 | ta-317 | sp-7 | an-317 |
| 710 | is-2 | ta-318 | sp-2 | an-318 | 2595 | is-7 | ta-318 | sp-7 | an-318 |
| 711 | is-2 | ta-319 | sp-2 | an-319 | 2596 | is-7 | ta-319 | sp-7 | an-319 |
| 712 | is-2 | ta-320 | sp-2 | an-320 | 2597 | is-7 | ta-320 | sp-7 | an-320 |
| 713 | is-2 | ta-321 | sp-2 | an-321 | 2598 | is-7 | ta-321 | sp-7 | an-321 |
| 714 | is-2 | ta-322 | sp-2 | an-322 | 2599 | is-7 | ta-322 | sp-7 | an-322 |
| 715 | is-2 | ta-323 | sp-2 | an-323 | 2600 | is-7 | ta-323 | sp-7 | an-323 |
| 716 | is-2 | ta-324 | sp-2 | an-324 | 2601 | is-7 | ta-324 | sp-7 | an-324 |
| 717 | is-2 | ta-325 | sp-2 | an-325 | 2602 | is-7 | ta-325 | sp-7 | an-325 |
| 718 | is-2 | ta-326 | sp-2 | an-326 | 2603 | is-7 | ta-326 | sp-7 | an-326 |
| 719 | is-2 | ta-327 | sp-2 | an-327 | 2604 | is-7 | ta-327 | sp-7 | an-327 |
| 720 | is-2 | ta-328 | sp-2 | an-328 | 2605 | is-7 | ta-328 | sp-7 | an-328 |
| 721 | is-2 | ta-329 | sp-2 | an-329 | 2606 | is-7 | ta-329 | sp-7 | an-329 |
| 722 | is-2 | ta-330 | sp-2 | an-330 | 2607 | is-7 | ta-330 | sp-7 | an-330 |
| 723 | is-2 | ta-331 | sp-2 | an-331 | 2608 | is-7 | ta-331 | sp-7 | an-331 |
| 724 | is-2 | ta-332 | sp-2 | an-332 | 2609 | is-7 | ta-332 | sp-7 | an-332 |
| 725 | is-2 | ta-333 | sp-2 | an-333 | 2610 | is-7 | ta-333 | sp-7 | an-333 |
| 726 | is-2 | ta-334 | sp-2 | an-334 | 2611 | is-7 | ta-334 | sp-7 | an-334 |
| 727 | is-2 | ta-335 | sp-2 | an-335 | 2612 | is-7 | ta-335 | sp-7 | an-335 |
| 728 | is-2 | ta-336 | sp-2 | an-336 | 2613 | is-7 | ta-336 | sp-7 | an-336 |
| 729 | is-2 | ta-337 | sp-2 | an-337 | 2614 | is-7 | ta-337 | sp-7 | an-337 |
| 730 | is-2 | ta-338 | sp-2 | an-338 | 2615 | is-7 | ta-338 | sp-7 | an-338 |
| 731 | is-2 | ta-339 | sp-2 | an-339 | 2616 | is-7 | ta-339 | sp-7 | an-339 |
| 732 | is-2 | ta-340 | sp-2 | an-340 | 2617 | is-7 | ta-340 | sp-7 | an-340 |
| 733 | is-2 | ta-341 | sp-2 | an-341 | 2618 | is-7 | ta-341 | sp-7 | an-341 |
| 734 | is-2 | ta-342 | sp-2 | an-342 | 2619 | is-7 | ta-342 | sp-7 | an-342 |
| 735 | is-2 | ta-343 | sp-2 | an-343 | 2620 | is-7 | ta-343 | sp-7 | an-343 |
| 736 | is-2 | ta-344 | sp-2 | an-344 | 2621 | is-7 | ta-344 | sp-7 | an-344 |
| 737 | is-2 | ta-345 | sp-2 | an-345 | 2622 | is-7 | ta-345 | sp-7 | an-345 |
| 738 | is-2 | ta-346 | sp-2 | an-346 | 2623 | is-7 | ta-346 | sp-7 | an-346 |
| 739 | is-2 | ta-347 | sp-2 | an-347 | 2624 | is-7 | ta-347 | sp-7 | an-347 |
| 740 | is-2 | ta-348 | sp-2 | an-348 | 2625 | is-7 | ta-348 | sp-7 | an-348 |
| 741 | is-2 | ta-349 | sp-2 | an-349 | 2626 | is-7 | ta-349 | sp-7 | an-349 |
| 742 | is-2 | ta-350 | sp-2 | an-350 | 2627 | is-7 | ta-350 | sp-7 | an-350 |
| 743 | is-2 | ta-351 | sp-2 | an-351 | 2628 | is-7 | ta-351 | sp-7 | an-351 |
| 744 | is-2 | ta-352 | sp-2 | an-352 | 2629 | is-7 | ta-352 | sp-7 | an-352 |
| 745 | is-2 | ta-353 | sp-2 | an-353 | 2630 | is-7 | ta-353 | sp-7 | an-353 |
| 746 | is-2 | ta-354 | sp-2 | an-354 | 2631 | is-7 | ta-354 | sp-7 | an-354 |
| 747 | is-2 | ta-355 | sp-2 | an-355 | 2632 | is-7 | ta-355 | sp-7 | an-355 |
| 748 | is-2 | ta-356 | sp-2 | an-356 | 2633 | is-7 | ta-356 | sp-7 | an-356 |
| 749 | is-2 | ta-357 | sp-2 | an-357 | 2634 | is-7 | ta-357 | sp-7 | an-357 |
| 750 | is-2 | ta-358 | sp-2 | an-358 | 2635 | is-7 | ta-358 | sp-7 | an-358 |
| 751 | is-2 | ta-359 | sp-2 | an-359 | 2636 | is-7 | ta-359 | sp-7 | an-359 |
| 752 | is-2 | ta-360 | sp-2 | an-360 | 2637 | is-7 | ta-360 | sp-7 | an-360 |

-continued

| EXAMPLE | REAGENT | | PRODUCT | EXAMPLE | REAGENT | | PRODUCT |
|---|---|---|---|---|---|---|---|
| No. | is | ta | sp | an | No. | is | ta | sp | an |
| 753 | is-2 | ta-361 | sp-2 | an-361 | 2638 | is-7 | ta-361 | sp-7 | an-361 |
| 754 | is-2 | ta-362 | sp-2 | an-362 | 2639 | is-7 | ta-362 | sp-7 | an-362 |
| 755 | is-2 | ta-363 | sp-2 | an-363 | 2640 | is-7 | ta-363 | sp-7 | an-363 |
| 756 | is-2 | ta-364 | sp-2 | an-364 | 2641 | is-7 | ta-364 | sp-7 | an-364 |
| 757 | is-2 | ta-365 | sp-2 | an-365 | 2642 | is-7 | ta-365 | sp-7 | an-365 |

Table 5-15

| 758 | is-2 | ta-366 | sp-2 | an-366 | 2643 | is-7 | ta-366 | sp-7 | an-366 |
|---|---|---|---|---|---|---|---|---|---|
| 759 | is-2 | ta-367 | sp-2 | an-367 | 2644 | is-7 | ta-367 | sp-7 | an-367 |
| 760 | is-2 | ta-368 | sp-2 | an-368 | 2645 | is-7 | ta-368 | sp-7 | an-368 |
| 761 | is-2 | ta-369 | sp-2 | an-369 | 2646 | is-7 | ta-369 | sp-7 | an-369 |
| 762 | is-2 | ta-370 | sp-2 | an-370 | 2647 | is-7 | ta-370 | sp-7 | an-370 |
| 763 | is-2 | ta-371 | sp-2 | an-371 | 2648 | is-7 | ta-371 | sp-7 | an-371 |
| 764 | is-2 | ta-372 | sp-2 | an-372 | 2649 | is-7 | ta-372 | sp-7 | an-372 |
| 765 | is-2 | ta-373 | sp-2 | an-373 | 2650 | is-7 | ta-373 | sp-7 | an-373 |
| 766 | is-2 | ta-374 | sp-2 | an-374 | 2651 | is-7 | ta-374 | sp-7 | an-374 |
| 767 | is-2 | ta-375 | sp-2 | an-375 | 2652 | is-7 | ta-375 | sp-7 | an-375 |
| 768 | is-2 | ta-376 | sp-2 | an-376 | 2653 | is-7 | ta-376 | sp-7 | an-376 |
| 769 | is-2 | ta-377 | sp-2 | an-377 | 2654 | is-7 | ta-377 | sp-7 | an-377 |
| 770 | is-3 | ta-1 | sp-3 | an-1 | 2655 | is-8 | ta-1 | sp-8 | an-1 |
| 771 | is-3 | ta-2 | sp-3 | an-2 | 2656 | is-8 | ta-2 | sp-8 | an-2 |
| 772 | is-3 | ta-3 | sp-3 | an-3 | 2657 | is-8 | ta-3 | sp-8 | an-3 |
| 773 | is-3 | ta-4 | sp-3 | an-4 | 2658 | is-8 | ta-4 | sp-8 | an-4 |
| 774 | is-3 | ta-5 | sp-3 | an-5 | 2659 | is-8 | ta-5 | sp-8 | an-5 |
| 775 | is-3 | ta-6 | sp-3 | an-6 | 2660 | is-8 | ta-6 | sp-8 | an-6 |
| 776 | is-3 | ta-7 | sp-3 | an-7 | 2661 | is-8 | ta-7 | sp-8 | an-7 |
| 777 | is-3 | ta-8 | sp-3 | an-8 | 2662 | is-8 | ta-8 | sp-8 | an-8 |
| 778 | is-3 | ta-9 | sp-3 | an-9 | 2663 | is-8 | ta-9 | sp-8 | an-9 |
| 779 | is-3 | ta-10 | sp-3 | an-10 | 2664 | is-8 | ta-10 | sp-8 | an-10 |
| 780 | is-3 | ta-11 | sp-3 | an-11 | 2665 | is-8 | ta-11 | sp-8 | an-11 |
| 781 | is-3 | ta-12 | sp-3 | an-12 | 2666 | is-8 | ta-12 | sp-8 | an-12 |
| 782 | is-3 | ta-13 | sp-3 | an-13 | 2667 | is-8 | ta-13 | sp-8 | an-13 |
| 783 | is-3 | ta-14 | sp-3 | an-14 | 2668 | is-8 | ta-14 | sp-8 | an-14 |
| 784 | is-3 | ta-15 | sp-3 | an-15 | 2669 | is-8 | ta-15 | sp-8 | an-15 |
| 785 | is-3 | ta-16 | sp-3 | an-16 | 2670 | is-8 | ta-16 | sp-8 | an-16 |
| 786 | is-3 | ta-17 | sp-3 | an-17 | 2671 | is-8 | ta-17 | sp-8 | an-17 |
| 787 | is-3 | ta-18 | sp-3 | an-18 | 2672 | is-8 | ta-18 | sp-8 | an-18 |
| 788 | is-3 | ta-19 | sp-3 | an-19 | 2673 | is-8 | ta-19 | sp-8 | an-19 |
| 789 | is-3 | ta-20 | sp-3 | an-20 | 2674 | is-8 | ta-20 | sp-8 | an-20 |
| 790 | is-3 | ta-21 | sp-3 | an-21 | 2675 | is-8 | ta-21 | sp-8 | an-21 |
| 791 | is-3 | ta-22 | sp-3 | an-22 | 2676 | is-8 | ta-22 | sp-8 | an-22 |
| 792 | is-3 | ta-23 | sp-3 | an-23 | 2677 | is-8 | ta-23 | sp-8 | an-23 |
| 793 | is-3 | ta-24 | sp-3 | an-24 | 2678 | is-8 | ta-24 | sp-8 | an-24 |
| 794 | is-3 | ta-25 | sp-3 | an-25 | 2679 | is-8 | ta-25 | sp-8 | an-25 |
| 795 | is-3 | ta-26 | sp-3 | an-26 | 2680 | is-8 | ta-26 | sp-8 | an-26 |
| 796 | is-3 | ta-27 | sp-3 | an-27 | 2681 | is-8 | ta-27 | sp-8 | an-27 |
| 797 | is-3 | ta-28 | sp-3 | an-28 | 2682 | is-8 | ta-28 | sp-8 | an-28 |
| 798 | is-3 | ta-29 | sp-3 | an-29 | 2683 | is-8 | ta-29 | sp-8 | an-29 |
| 799 | is-3 | ta-30 | sp-3 | an-30 | 2684 | is-8 | ta-30 | sp-8 | an-30 |
| 800 | is-3 | ta-31 | sp-3 | an-31 | 2685 | is-8 | ta-31 | sp-8 | an-31 |
| 801 | is-3 | ta-32 | sp-3 | an-32 | 2686 | is-8 | ta-32 | sp-8 | an-32 |
| 802 | is-3 | ta-33 | sp-3 | an-33 | 2687 | is-8 | ta-33 | sp-8 | an-33 |
| 803 | is-3 | ta-34 | sp-3 | an-34 | 2688 | is-8 | ta-34 | sp-8 | an-34 |
| 804 | is-3 | ta-35 | sp-3 | an-35 | 2689 | is-8 | ta-35 | sp-8 | an-35 |
| 805 | is-3 | ta-36 | sp-3 | an-36 | 2690 | is-8 | ta-36 | sp-8 | an-36 |
| 806 | is-3 | ta-37 | sp-3 | an-37 | 2691 | is-8 | ta-37 | sp-8 | an-37 |
| 807 | is-3 | ta-38 | sp-3 | an-38 | 2692 | is-8 | ta-38 | sp-8 | an-38 |
| 808 | is-3 | ta-39 | sp-3 | an-39 | 2693 | is-8 | ta-39 | sp-8 | an-39 |
| 809 | is-3 | ta-40 | sp-3 | an-40 | 2694 | is-8 | ta-40 | sp-8 | an-40 |
| 810 | is-3 | ta-41 | sp-3 | an-41 | 2695 | is-8 | ta-41 | sp-8 | an-41 |

Table 5-16

| 811 | is-3 | ta-42 | sp-3 | an-42 | 2696 | is-8 | ta-42 | sp-8 | an-42 |
|---|---|---|---|---|---|---|---|---|---|
| 812 | is-3 | ta-43 | sp-3 | an-43 | 2697 | is-8 | ta-43 | sp-8 | an-43 |
| 813 | is-3 | ta-44 | sp-3 | an-44 | 2698 | is-8 | ta-44 | sp-8 | an-44 |
| 814 | is-3 | ta-45 | sp-3 | an-45 | 2699 | is-8 | ta-45 | sp-8 | an-45 |
| 815 | is-3 | ta-46 | sp-3 | an-46 | 2700 | is-8 | ta-46 | sp-8 | an-46 |
| 816 | is-3 | ta-47 | sp-3 | an-47 | 2701 | is-8 | ta-47 | sp-8 | an-47 |
| 817 | is-3 | ta-48 | sp-3 | an-48 | 2702 | is-8 | ta-48 | sp-8 | an-48 |
| 818 | is-3 | ta-49 | sp-3 | an-49 | 2703 | is-8 | ta-49 | sp-8 | an-49 |
| 819 | is-3 | ta-50 | sp-3 | an-50 | 2704 | is-8 | ta-50 | sp-8 | an-50 |
| 820 | is-3 | ta-51 | sp-3 | an-51 | 2705 | is-8 | ta-51 | sp-8 | an-51 |
| 821 | is-3 | ta-52 | sp-3 | an-52 | 2706 | is-8 | ta-52 | sp-8 | an-52 |
| 822 | is-3 | ta-53 | sp-3 | an-53 | 2707 | is-8 | ta-53 | sp-8 | an-53 |
| 823 | is-3 | ta-54 | sp-3 | an-54 | 2708 | is-8 | ta-54 | sp-8 | an-54 |
| 824 | is-3 | ta-55 | sp-3 | an-55 | 2709 | is-8 | ta-55 | sp-8 | an-55 |

| EXAMPLE | REAGENT | | PRODUCT | EXAMPLE | REAGENT | | PRODUCT |
| --- | --- | --- | --- | --- | --- | --- | --- |
| No. | is | ta | sp | an | No. | is | ta | sp | an |
| 825 | is-3 | ta-56 | sp-3 | an-56 | 2710 | is-8 | ta-56 | sp-8 | an-56 |
| 826 | is-3 | ta-57 | sp-3 | an-57 | 2711 | is-8 | ta-57 | sp-8 | an-57 |
| 827 | is-3 | ta-58 | sp-3 | an-58 | 2712 | is-8 | ta-58 | sp-8 | an-58 |
| 828 | is-3 | ta-59 | sp-3 | an-59 | 2713 | is-8 | ta-59 | sp-8 | an-59 |
| 829 | is-3 | ta-60 | sp-3 | an-60 | 2714 | is-8 | ta-60 | sp-8 | an-60 |
| 830 | is-3 | ta-61 | sp-3 | an-61 | 2715 | is-8 | ta-61 | sp-8 | an-61 |
| 831 | is-3 | ta-62 | sp-3 | an-62 | 2716 | is-8 | ta-62 | sp-8 | an-62 |
| 832 | is-3 | ta-63 | sp-3 | an-63 | 2717 | is-8 | ta-63 | sp-8 | an-63 |
| 833 | is-3 | ta-64 | sp-3 | an-64 | 2718 | is-8 | ta-64 | sp-8 | an-64 |
| 834 | is-3 | ta-65 | sp-3 | an-65 | 2719 | is-8 | ta-65 | sp-8 | an-65 |
| 835 | is-3 | ta-66 | sp-3 | an-66 | 2720 | is-8 | ta-66 | sp-8 | an-66 |
| 836 | is-3 | ta-67 | sp-3 | an-67 | 2721 | is-8 | ta-67 | sp-8 | an-67 |
| 837 | is-3 | ta-68 | sp-3 | an-68 | 2722 | is-8 | ta-68 | sp-8 | an-68 |
| 838 | is-3 | ta-69 | sp-3 | an-69 | 2723 | is-8 | ta-69 | sp-8 | an-69 |
| 839 | is-3 | ta-70 | sp-3 | an-70 | 2724 | is-8 | ta-70 | sp-8 | an-70 |
| 840 | is-3 | ta-71 | sp-3 | an-71 | 2725 | is-8 | ta-71 | sp-8 | an-71 |
| 841 | is-3 | ta-72 | sp-3 | an-72 | 2726 | is-8 | ta-72 | sp-8 | an-72 |
| 842 | is-3 | ta-73 | sp-3 | an-73 | 2727 | is-8 | ta-73 | sp-8 | an-73 |
| 843 | is-3 | ta-74 | sp-3 | an-74 | 2728 | is-8 | ta-74 | sp-8 | an-74 |
| 844 | is-3 | ta-75 | sp-3 | an-75 | 2729 | is-8 | ta-75 | sp-8 | an-75 |
| 845 | is-3 | ta-76 | sp-3 | an-76 | 2730 | is-8 | ta-76 | sp-8 | an-76 |
| 846 | is-3 | ta-77 | sp-3 | an-77 | 2731 | is-8 | ta-77 | sp-8 | an-77 |
| 847 | is-3 | ta-78 | sp-3 | an-78 | 2732 | is-8 | ta-78 | sp-8 | an-78 |
| 848 | is-3 | ta-79 | sp-3 | an-79 | 2733 | is-8 | ta-79 | sp-8 | an-79 |
| 849 | is-3 | ta-80 | sp-3 | an-80 | 2734 | is-8 | ta-80 | sp-8 | an-80 |
| 850 | is-3 | ta-81 | sp-3 | an-81 | 2735 | is-8 | ta-81 | sp-8 | an-81 |
| 851 | is-3 | ta-82 | sp-3 | an-82 | 2736 | is-8 | ta-82 | sp-8 | an-82 |
| 852 | is-3 | ta-83 | sp-3 | an-83 | 2737 | is-8 | ta-83 | sp-8 | an-83 |
| 853 | is-3 | ta-84 | sp-3 | an-84 | 2738 | is-8 | ta-84 | sp-8 | an-84 |
| 854 | is-3 | ta-85 | sp-3 | an-85 | 2739 | is-8 | ta-85 | sp-8 | an-85 |
| 855 | is-3 | ta-86 | sp-3 | an-86 | 2740 | is-8 | ta-86 | sp-8 | an-86 |
| 856 | is-3 | ta-87 | sp-3 | an-87 | 2741 | is-8 | ta-87 | sp-8 | an-87 |
| 857 | is-3 | ta-88 | sp-3 | an-88 | 2742 | is-8 | ta-88 | sp-8 | an-88 |
| 858 | is-3 | ta-89 | sp-3 | an-89 | 2743 | is-8 | ta-89 | sp-8 | an-89 |
| 859 | is-3 | ta-90 | sp-3 | an-90 | 2744 | is-8 | ta-90 | sp-8 | an-90 |
| 860 | is-3 | ta-91 | sp-3 | an-91 | 2745 | is-8 | ta-91 | sp-8 | an-91 |
| 861 | is-3 | ta-92 | sp-3 | an-92 | 2746 | is-8 | ta-92 | sp-8 | an-92 |
| 862 | is-3 | ta-93 | sp-3 | an-93 | 2747 | is-8 | ta-93 | sp-8 | an-93 |
| 863 | is-3 | ta-94 | sp-3 | an-94 | 2748 | is-8 | ta-94 | sp-8 | an-94 |

Table 5-17

| EXAMPLE | REAGENT | | PRODUCT | EXAMPLE | REAGENT | | PRODUCT |
| --- | --- | --- | --- | --- | --- | --- | --- |
| No. | is | ta | sp | an | No. | is | ta | sp | an |
| 864 | is-3 | ta-95 | sp-3 | an-95 | 2749 | is-8 | ta-95 | sp-8 | an-95 |
| 865 | is-3 | ta-96 | sp-3 | an-96 | 2750 | is-8 | ta-96 | sp-8 | an-96 |
| 866 | is-3 | ta-97 | sp-3 | an-97 | 2751 | is-8 | ta-97 | sp-8 | an-97 |
| 867 | is-3 | ta-98 | sp-3 | an-98 | 2752 | is-8 | ta-98 | sp-8 | an-98 |
| 868 | is-3 | ta-99 | sp-3 | an-99 | 2753 | is-8 | ta-99 | sp-8 | an-99 |
| 869 | is-3 | ta-100 | sp-3 | an-100 | 2754 | is-8 | ta-100 | sp-8 | an-100 |
| 870 | is-3 | ta-101 | sp-3 | an-101 | 2755 | is-8 | ta-101 | sp-8 | an-101 |
| 871 | is-3 | ta-102 | sp-3 | an-102 | 2756 | is-8 | ta-102 | sp-8 | an-102 |
| 872 | is-3 | ta-103 | sp-3 | an-103 | 2757 | is-8 | ta-103 | sp-8 | an-103 |
| 873 | is-3 | ta-104 | sp-3 | an-104 | 2758 | is-8 | ta-104 | sp-8 | an-104 |
| 874 | is-3 | ta-105 | sp-3 | an-105 | 2759 | is-8 | ta-105 | sp-8 | an-105 |
| 875 | is-3 | ta-106 | sp-3 | an-106 | 2760 | is-8 | ta-106 | sp-8 | an-106 |
| 876 | is-3 | ta-107 | sp-3 | an-107 | 2761 | is-8 | ta-107 | sp-8 | an-107 |
| 877 | is-3 | ta-108 | sp-3 | an-108 | 2762 | is-8 | ta-108 | sp-8 | an-108 |
| 878 | is-3 | ta-109 | sp-3 | an-109 | 2763 | is-8 | ta-109 | sp-8 | an-109 |
| 879 | is-3 | ta-110 | sp-3 | an-110 | 2764 | is-8 | ta-110 | sp-8 | an-110 |
| 880 | is-3 | ta-111 | sp-3 | an-111 | 2765 | is-8 | ta-111 | sp-8 | an-111 |
| 881 | is-3 | ta-112 | sp-3 | an-112 | 2766 | is-8 | ta-112 | sp-8 | an-112 |
| 882 | is-3 | ta-113 | sp-3 | an-113 | 2767 | is-8 | ta-113 | sp-8 | an-113 |
| 883 | is-3 | ta-114 | sp-3 | an-114 | 2768 | is-8 | ta-114 | sp-8 | an-114 |
| 884 | is-3 | ta-115 | sp-3 | an-115 | 2769 | is-8 | ta-115 | sp-8 | an-115 |
| 885 | is-3 | ta-116 | sp-3 | an-116 | 2770 | is-8 | ta-116 | sp-8 | an-116 |
| 886 | is-3 | ta-117 | sp-3 | an-117 | 2771 | is-8 | ta-117 | sp-8 | an-117 |
| 887 | is-3 | ta-118 | sp-3 | an-118 | 2772 | is-8 | ta-118 | sp-8 | an-118 |
| 888 | is-3 | ta-119 | sp-3 | an-119 | 2773 | is-8 | ta-119 | sp-8 | an-119 |
| 889 | is-3 | ta-120 | sp-3 | an-120 | 2774 | is-8 | ta-120 | sp-8 | an-120 |
| 890 | is-3 | ta-121 | sp-3 | an-121 | 2775 | is-8 | ta-121 | sp-8 | an-121 |
| 891 | is-3 | ta-122 | sp-3 | an-122 | 2776 | is-8 | ta-122 | sp-8 | an-122 |
| 892 | is-3 | ta-123 | sp-3 | an-123 | 2777 | is-8 | ta-123 | sp-8 | an-123 |
| 893 | is-3 | ta-124 | sp-3 | an-124 | 2778 | is-8 | ta-124 | sp-8 | an-124 |
| 894 | is-3 | ta-125 | sp-3 | an-125 | 2779 | is-8 | ta-125 | sp-8 | an-125 |
| 895 | is-3 | ta-126 | sp-3 | an-126 | 2780 | is-8 | ta-126 | sp-8 | an-126 |
| 896 | is-3 | ta-127 | sp-3 | an-127 | 2781 | is-8 | ta-127 | sp-8 | an-127 |
| 897 | is-3 | ta-128 | sp-3 | an-128 | 2782 | is-8 | ta-128 | sp-8 | an-128 |
| 898 | is-3 | ta-129 | sp-3 | an-129 | 2783 | is-8 | ta-129 | sp-8 | an-129 |

-continued

| EXAMPLE | REAGENT | | PRODUCT | EXAMPLE | REAGENT | | PRODUCT |
|---|---|---|---|---|---|---|---|
| No. | is | ta | sp  an | No. | is | ta | sp  an |
| 899 | is-3 | ta-130 | sp-3  an-130 | 2784 | is-8 | ta-130 | sp-8  an-130 |
| 900 | is-3 | ta-131 | sp-3  an-131 | 2785 | is-8 | ta-131 | sp-8  an-131 |
| 901 | is-3 | ta-132 | sp-3  an-132 | 2786 | is-8 | ta-132 | sp-8  an-132 |
| 902 | is-3 | ta-133 | sp-3  an-133 | 2787 | is-8 | ta-133 | sp-8  an-133 |
| 903 | is-3 | ta-134 | sp-3  an-134 | 2788 | is-8 | ta-134 | sp-8  an-134 |
| 904 | is-3 | ta-135 | sp-3  an-135 | 2789 | is-8 | ta-135 | sp-8  an-135 |
| 905 | is-3 | ta-136 | sp-3  an-136 | 2790 | is-8 | ta-136 | sp-8  an-136 |
| 906 | is-3 | ta-137 | sp-3  an-137 | 2791 | is-8 | ta-137 | sp-8  an-137 |
| 907 | is-3 | ta-138 | sp-3  an-138 | 2792 | is-8 | ta-138 | sp-8  an-138 |
| 908 | is-3 | ta-139 | sp-3  an-139 | 2793 | is-8 | ta-139 | sp-8  an-139 |
| 909 | is-3 | ta-140 | sp-3  an-140 | 2794 | is-8 | ta-140 | sp-8  an-140 |
| 910 | is-3 | ta-141 | sp-3  an-141 | 2795 | is-8 | ta-141 | sp-8  an-141 |
| 911 | is-3 | ta-142 | sp-3  an-142 | 2796 | is-8 | ta-142 | sp-8  an-142 |
| 912 | is-3 | ta-143 | sp-3  an-143 | 2797 | is-8 | ta-143 | sp-8  an-143 |
| 913 | is-3 | ta-144 | sp-3  an-144 | 2798 | is-8 | ta-144 | sp-8  an-144 |
| 914 | is-3 | ta-145 | sp-3  an-145 | 2799 | is-8 | ta-145 | sp-8  an-145 |
| 915 | is-3 | ta-146 | sp-3  an-146 | 2800 | is-8 | ta-146 | sp-8  an-146 |
| 916 | is-3 | ta-147 | sp-3  an-147 | 2801 | is-8 | ta-147 | sp-8  an-147 |

Table 5-18

| 917 | is-3 | ta-148 | sp-3  an-148 | 2802 | is-8 | ta-148 | sp-8  an-148 |
|---|---|---|---|---|---|---|---|
| 918 | is-3 | ta-149 | sp-3  an-149 | 2803 | is-8 | ta-149 | sp-8  an-149 |
| 919 | is-3 | ta-150 | sp-3  an-150 | 2804 | is-8 | ta-150 | sp-8  an-150 |
| 920 | is-3 | ta-151 | sp-3  an-151 | 2805 | is-8 | ta-151 | sp-8  an-151 |
| 921 | is-3 | ta-152 | sp-3  an-152 | 2806 | is-8 | ta-152 | sp-8  an-152 |
| 922 | is-3 | ta-153 | sp-3  an-153 | 2807 | is-8 | ta-153 | sp-8  an-153 |
| 923 | is-3 | ta-154 | sp-3  an-154 | 2808 | is-8 | ta-154 | sp-8  an-154 |
| 924 | is-3 | ta-155 | sp-3  an-155 | 2809 | is-8 | ta-155 | sp-8  an-155 |
| 925 | is-3 | ta-156 | sp-3  an-156 | 2810 | is-8 | ta-156 | sp-8  an-156 |
| 926 | is-3 | ta-157 | sp-3  an-157 | 2811 | is-8 | ta-157 | sp-8  an-157 |
| 927 | is-3 | ta-158 | sp-3  an-158 | 2812 | is-8 | ta-158 | sp-8  an-158 |
| 928 | is-3 | ta-159 | sp-3  an-159 | 2813 | is-8 | ta-159 | sp-8  an-159 |
| 929 | is-3 | ta-160 | sp-3  an-160 | 2814 | is-8 | ta-160 | sp-8  an-160 |
| 930 | is-3 | ta-161 | sp-3  an-161 | 2815 | is-8 | ta-161 | sp-8  an-161 |
| 931 | is-3 | ta-162 | sp-3  an-162 | 2816 | is-8 | ta-162 | sp-8  an-162 |
| 932 | is-3 | ta-163 | sp-3  an-163 | 2817 | is-8 | ta-163 | sp-8  an-163 |
| 933 | is-3 | ta-164 | sp-3  an-164 | 2818 | is-8 | ta-164 | sp-8  an-164 |
| 934 | is-3 | ta-165 | sp-3  an-165 | 2819 | is-8 | ta-165 | sp-8  an-165 |
| 935 | is-3 | ta-166 | sp-3  an-166 | 2820 | is-8 | ta-166 | sp-8  an-166 |
| 936 | is-3 | ta-167 | sp-3  an-167 | 2821 | is-8 | ta-167 | sp-8  an-167 |
| 937 | is-3 | ta-168 | sp-3  an-168 | 2822 | is-8 | ta-168 | sp-8  an-168 |
| 938 | is-3 | ta-169 | sp-3  an-169 | 2823 | is-8 | ta-169 | sp-8  an-169 |
| 939 | is-3 | ta-170 | sp-3  an-170 | 2824 | is-8 | ta-170 | sp-8  an-170 |
| 940 | is-3 | ta-171 | sp-3  an-171 | 2825 | is-8 | ta-171 | sp-8  an-171 |
| 941 | is-3 | ta-172 | sp-3  an-172 | 2826 | is-8 | ta-172 | sp-8  an-172 |
| 942 | is-3 | ta-173 | sp-3  an-173 | 2827 | is-8 | ta-173 | sp-8  an-173 |
| 943 | is-3 | ta-174 | sp-3  an-174 | 2828 | is-8 | ta-174 | sp-8  an-174 |
| 944 | is-3 | ta-175 | sp-3  an-175 | 2829 | is-8 | ta-175 | sp-8  an-175 |
| 945 | is-3 | ta-176 | sp-3  an-176 | 2830 | is-8 | ta-176 | sp-8  an-176 |
| 946 | is-3 | ta-177 | sp-3  an-177 | 2831 | is-8 | ta-177 | sp-8  an-177 |
| 947 | is-3 | ta-178 | sp-3  an-178 | 2832 | is-8 | ta-178 | sp-8  an-178 |
| 948 | is-3 | ta-179 | sp-3  an-179 | 2833 | is-8 | ta-179 | sp-8  an-179 |
| 949 | is-3 | ta-180 | sp-3  an-180 | 2834 | is-8 | ta-180 | sp-8  an-180 |
| 950 | is-3 | ta-181 | sp-3  an-181 | 2835 | is-8 | ta-181 | sp-8  an-181 |
| 951 | is-3 | ta-182 | sp-3  an-182 | 2836 | is-8 | ta-182 | sp-8  an-182 |
| 952 | is-3 | ta-183 | sp-3  an-183 | 2837 | is-8 | ta-183 | sp-8  an-183 |
| 953 | is-3 | ta-184 | sp-3  an-184 | 2838 | is-8 | ta-184 | sp-8  an-184 |
| 954 | is-3 | ta-185 | sp-3  an-185 | 2839 | is-8 | ta-185 | sp-8  an-185 |
| 955 | is-3 | ta-186 | sp-3  an-186 | 2840 | is-8 | ta-186 | sp-8  an-186 |
| 956 | is-3 | ta-187 | sp-3  an-187 | 2841 | is-8 | ta-187 | sp-8  an-187 |
| 957 | is-3 | ta-188 | sp-3  an-188 | 2842 | is-8 | ta-188 | sp-8  an-188 |
| 958 | is-3 | ta-189 | sp-3  an-189 | 2843 | is-8 | ta-189 | sp-8  an-189 |
| 959 | is-3 | ta-190 | sp-3  an-190 | 2844 | is-8 | ta-190 | sp-8  an-190 |
| 960 | is-3 | ta-191 | sp-3  an-191 | 2845 | is-8 | ta-191 | sp-8  an-191 |
| 961 | is-3 | ta-192 | sp-3  an-192 | 2846 | is-8 | ta-192 | sp-8  an-192 |
| 962 | is-3 | ta-193 | sp-3  an-193 | 2847 | is-8 | ta-193 | sp-8  an-193 |
| 963 | is-3 | ta-194 | sp-3  an-194 | 2848 | is-8 | ta-194 | sp-8  an-194 |
| 964 | is-3 | ta-195 | sp-3  an-195 | 2849 | is-8 | ta-195 | sp-8  an-195 |
| 965 | is-3 | ta-196 | sp-3  an-196 | 2850 | is-8 | ta-196 | sp-8  an-196 |
| 966 | is-3 | ta-197 | sp-3  an-197 | 2851 | is-8 | ta-197 | sp-8  an-197 |
| 967 | is-3 | ta-198 | sp-3  an-198 | 2852 | is-8 | ta-198 | sp-8  an-198 |
| 968 | is-3 | ta-199 | sp-3  an-199 | 2853 | is-8 | ta-199 | sp-8  an-199 |
| 969 | is-3 | ta-200 | sp-3  an-200 | 2854 | is-8 | ta-200 | sp-8  an-200 |

-continued

| EXAMPLE No. | REAGENT is | REAGENT ta | PRODUCT sp | PRODUCT an | EXAMPLE No. | REAGENT is | REAGENT ta | PRODUCT sp | PRODUCT an |
|---|---|---|---|---|---|---|---|---|---|
| \multicolumn{10}{c}{Table 5-19} |
| 970 | is-3 | ta-201 | sp-3 | an-201 | 2855 | is-8 | ta-201 | sp-8 | an-201 |
| 971 | is-3 | ta-202 | sp-3 | an-202 | 2856 | is-8 | ta-202 | sp-8 | an-202 |
| 972 | is-3 | ta-203 | sp-3 | an-203 | 2857 | is-8 | ta-203 | sp-8 | an-203 |
| 973 | is-3 | ta-204 | sp-3 | an-204 | 2858 | is-8 | ta-204 | sp-8 | an-204 |
| 974 | is-3 | ta-205 | sp-3 | an-205 | 2859 | is-8 | ta-205 | sp-8 | an-205 |
| 975 | is-3 | ta-206 | sp-3 | an-206 | 2860 | is-8 | ta-206 | sp-8 | an-206 |
| 976 | is-3 | ta-207 | sp-3 | an-207 | 2861 | is-8 | ta-207 | sp-8 | an-207 |
| 977 | is-3 | ta-208 | sp-3 | an-208 | 2862 | is-8 | ta-208 | sp-8 | an-208 |
| 978 | is-3 | ta-209 | sp-3 | an-209 | 2863 | is-8 | ta-209 | sp-8 | an-209 |
| 979 | is-3 | ta-210 | sp-3 | an-210 | 2864 | is-8 | ta-210 | sp-8 | an-210 |
| 980 | is-3 | ta-211 | sp-3 | an-211 | 2865 | is-8 | ta-211 | sp-8 | an-211 |
| 981 | is-3 | ta-212 | sp-3 | an-212 | 2866 | is-8 | ta-212 | sp-8 | an-212 |
| 982 | is-3 | ta-213 | sp-3 | an-213 | 2867 | is-8 | ta-213 | sp-8 | an-213 |
| 983 | is-3 | ta-214 | sp-3 | an-214 | 2868 | is-8 | ta-214 | sp-8 | an-214 |
| 984 | is-3 | ta-215 | sp-3 | an-215 | 2869 | is-8 | ta-215 | sp-8 | an-215 |
| 985 | is-3 | ta-216 | sp-3 | an-216 | 2870 | is-8 | ta-216 | sp-8 | an-216 |
| 986 | is-3 | ta-217 | sp-3 | an-217 | 2871 | is-8 | ta-217 | sp-8 | an-217 |
| 987 | is-3 | ta-218 | sp-3 | an-218 | 2872 | is-8 | ta-218 | sp-8 | an-218 |
| 988 | is-3 | ta-219 | sp-3 | an-219 | 2873 | is-8 | ta-219 | sp-8 | an-219 |
| 989 | is-3 | ta-220 | sp-3 | an-220 | 2874 | is-8 | ta-220 | sp-8 | an-220 |
| 990 | is-3 | ta-221 | sp-3 | an-221 | 2875 | is-8 | ta-221 | sp-8 | an-221 |
| 991 | is-3 | ta-222 | sp-3 | an-222 | 2876 | is-8 | ta-222 | sp-8 | an-222 |
| 992 | is-3 | ta-223 | sp-3 | an-223 | 2877 | is-8 | ta-223 | sp-8 | an-223 |
| 993 | is-3 | ta-224 | sp-3 | an-224 | 2878 | is-8 | ta-224 | sp-8 | an-224 |
| 994 | is-3 | ta-225 | sp-3 | an-225 | 2879 | is-8 | ta-225 | sp-8 | an-225 |
| 995 | is-3 | ta-228 | sp-3 | an-226 | 2880 | is-8 | ta-226 | sp-8 | an-226 |
| 996 | is-3 | ta-227 | sp-3 | an-227 | 2881 | is-8 | ta-227 | sp-8 | an-227 |
| 997 | is-3 | ta-228 | sp-3 | an-228 | 2882 | is-8 | ta-228 | sp-8 | an-228 |
| 998 | is-3 | ta-229 | sp-3 | an-229 | 2883 | is-8 | ta-229 | sp-8 | an-229 |
| 999 | is-3 | ta-230 | sp-3 | an-230 | 2884 | is-8 | ta-230 | sp-8 | an-230 |
| 1000 | is-3 | ta-231 | sp-3 | an-231 | 2885 | is-8 | ta-231 | sp-8 | an-231 |
| 1001 | is-3 | ta-232 | sp-3 | an-232 | 2886 | is-8 | ta-232 | sp-8 | an-232 |
| 1002 | is-3 | ta-233 | sp-3 | an-233 | 2887 | is-8 | ta-233 | sp-8 | an-233 |
| 1003 | is-3 | ta-234 | sp-3 | an-234 | 2888 | is-8 | ta-234 | sp-8 | an-234 |
| 1004 | is-3 | ta-235 | sp-3 | an-235 | 2889 | is-8 | ta-235 | sp-8 | an-235 |
| 1005 | is-3 | ta-236 | sp-3 | an-236 | 2890 | is-8 | ta-236 | sp-8 | an-236 |
| 1006 | is-3 | ta-237 | sp-3 | an-237 | 2891 | is-8 | ta-237 | sp-8 | an-237 |
| 1007 | is-3 | ta-238 | sp-3 | an-238 | 2892 | is-8 | ta-238 | sp-8 | an-238 |
| 1008 | is-3 | ta-239 | sp-3 | an-239 | 2893 | is-8 | ta-239 | sp-8 | an-239 |
| 1009 | is-3 | ta-240 | sp-3 | an-240 | 2894 | is-8 | ta-240 | sp-8 | an-240 |
| 1010 | is-3 | ta-241 | sp-3 | an-241 | 2895 | is-8 | ta-241 | sp-8 | an-241 |
| 1011 | is-3 | ta-242 | sp-3 | an-242 | 2896 | is-8 | ta-242 | sp-8 | an-242 |
| 1012 | is-3 | ta-243 | sp-3 | an-243 | 2897 | is-8 | ta-243 | sp-8 | an-243 |
| 1013 | is-3 | ta-244 | sp-3 | an-244 | 2898 | is-8 | ta-244 | sp-8 | an-244 |
| 1014 | is-3 | ta-245 | sp-3 | an-245 | 2899 | is-8 | ta-245 | sp-8 | an-245 |
| 1015 | is-3 | ta-246 | sp-3 | an-246 | 2900 | is-8 | ta-246 | sp-8 | an-246 |
| 1016 | is-3 | ta-247 | sp-3 | an-247 | 2901 | is-8 | ta-247 | sp-8 | an-247 |
| 1017 | is-3 | ta-248 | sp-3 | an-248 | 2902 | is-8 | ta-248 | sp-8 | an-248 |
| 1018 | is-3 | ta-249 | sp-3 | an-249 | 2903 | is-8 | ta-249 | sp-8 | an-249 |
| 1019 | is-3 | ta-250 | sp-3 | an-250 | 2904 | is-8 | ta-250 | sp-8 | an-250 |
| 1020 | is-3 | ta-251 | sp-3 | an-251 | 2905 | is-8 | ta-251 | sp-8 | an-251 |
| 1021 | is-3 | ta-252 | sp-3 | an-252 | 2906 | is-8 | ta-252 | sp-8 | an-252 |
| 1022 | is-3 | ta-253 | sp-3 | an-253 | 2907 | is-8 | ta-253 | sp-8 | an-253 |
| \multicolumn{10}{c}{Table 5-20} |
| 1023 | is-3 | ta-254 | sp-3 | an-254 | 2908 | is-8 | ta-254 | sp-8 | an-254 |
| 1024 | is-3 | ta-255 | sp-3 | an-255 | 2909 | is-8 | ta-255 | sp-8 | an-255 |
| 1025 | is-3 | ta-256 | sp-3 | an-256 | 2910 | is-8 | ta-256 | sp-8 | an-256 |
| 1026 | is-3 | ta-257 | sp-3 | an-257 | 2911 | is-8 | ta-257 | sp-8 | an-257 |
| 1027 | is-3 | ta-258 | sp-3 | an-258 | 2912 | is-8 | ta-258 | sp-8 | an-258 |
| 1028 | is-3 | ta-259 | sp-3 | an-259 | 2913 | is-8 | ta-259 | sp-8 | an-259 |
| 1029 | is-3 | ta-260 | sp-3 | an-260 | 2914 | is-8 | ta-260 | sp-8 | an-260 |
| 1030 | is-3 | ta-261 | sp-3 | an-261 | 2915 | is-8 | ta-261 | sp-8 | an-261 |
| 1031 | is-3 | ta-262 | sp-3 | an-262 | 2916 | is-8 | ta-262 | sp-8 | an-262 |
| 1032 | is-3 | ta-263 | sp-3 | an-263 | 2917 | is-8 | ta-263 | sp-8 | an-263 |
| 1033 | is-3 | ta-264 | sp-3 | an-264 | 2918 | is-8 | ta-264 | sp-8 | an-264 |
| 1034 | is-3 | ta-265 | sp-3 | an-265 | 2919 | is-8 | ta-265 | sp-8 | an-265 |
| 1035 | is-3 | ta-266 | sp-3 | an-266 | 2920 | is-8 | ta-266 | sp-8 | an-266 |
| 1036 | is-3 | ta-267 | sp-3 | an-267 | 2921 | is-8 | ta-267 | sp-8 | an-267 |
| 1037 | is-3 | ta-268 | sp-3 | an-268 | 2922 | is-8 | ta-268 | sp-8 | an-268 |
| 1038 | is-3 | ta-269 | sp-3 | an-269 | 2923 | is-8 | ta-269 | sp-8 | an-269 |
| 1039 | is-3 | ta-270 | sp-3 | an-270 | 2924 | is-8 | ta-270 | sp-8 | an-270 |
| 1040 | is-3 | ta-271 | sp-3 | an-271 | 2925 | is-8 | ta-271 | sp-8 | an-271 |
| 1041 | is-3 | ta-272 | sp-3 | an-272 | 2926 | is-8 | ta-272 | sp-8 | an-272 |

-continued

| EXAMPLE | REAGENT | | PRODUCT | EXAMPLE | REAGENT | | PRODUCT |
|---|---|---|---|---|---|---|---|
| No. | is | ta | sp  an | No. | is | ta | sp  an |
| 1042 | is-3 | ta-273 | sp-3  an-273 | 2927 | is-8 | ta-273 | sp-8  an-273 |
| 1043 | is-3 | ta-274 | sp-3  an-274 | 2928 | is-8 | ta-274 | sp-8  an-274 |
| 1044 | is-3 | ta-275 | sp-3  an-275 | 2929 | is-8 | ta-275 | sp-8  an-275 |
| 1045 | is-3 | ta-276 | sp-3  an-276 | 2930 | is-8 | ta-276 | sp-8  an-276 |
| 1046 | is-3 | ta-277 | sp-3  an-277 | 2931 | is-8 | ta-277 | sp-8  an-277 |
| 1047 | is-3 | ta-278 | sp-3  an-278 | 2932 | is-8 | ta-278 | sp-8  an-278 |
| 1048 | is-3 | ta-279 | sp-3  an-279 | 2933 | is-8 | ta-279 | sp-8  an-279 |
| 1049 | is-3 | ta-280 | sp-3  an-280 | 2934 | is-8 | ta-280 | sp-8  an-280 |
| 1050 | is-3 | ta-281 | sp-3  an-281 | 2935 | is-8 | ta-281 | sp-8  an-281 |
| 1051 | is-3 | ta-282 | sp-3  an-282 | 2936 | is-8 | ta-282 | sp-8  an-282 |
| 1052 | is-3 | ta-283 | sp-3  an-283 | 2937 | is-8 | ta-283 | sp-8  an-283 |
| 1053 | is-3 | ta-284 | sp-3  an-284 | 2938 | is-8 | ta-284 | sp-8  an-284 |
| 1054 | is-3 | ta-285 | sp-3  an-285 | 2939 | is-8 | ta-285 | sp-8  an-285 |
| 1055 | is-3 | ta-286 | sp-3  an-286 | 2940 | is-8 | ta-286 | sp-8  an-286 |
| 1056 | is-3 | ta-287 | sp-3  an-287 | 2941 | is-8 | ta-287 | sp-8  an-287 |
| 1057 | is-3 | ta-288 | sp-3  an-288 | 2942 | is-8 | ta-288 | sp-8  an-288 |
| 1058 | is-3 | ta-289 | sp-3  an-289 | 2943 | is-8 | ta-289 | sp-8  an-289 |
| 1059 | is-3 | ta-290 | sp-3  an-290 | 2944 | is-8 | ta-290 | sp-8  an-290 |
| 1060 | is-3 | ta-291 | sp-3  an-291 | 2945 | is-8 | ta-291 | sp-8  an-291 |
| 1061 | is-3 | ta-292 | sp-3  an-292 | 2946 | is-8 | ta-292 | sp-8  an-292 |
| 1062 | is-3 | ta-293 | sp-3  an-293 | 2947 | is-8 | ta-293 | sp-8  an-293 |
| 1063 | is-3 | ta-294 | sp-3  an-294 | 2948 | is-8 | ta-294 | sp-8  an-294 |
| 1064 | is-3 | ta-295 | sp-3  an-295 | 2949 | is-8 | ta-295 | sp-8  an-295 |
| 1065 | is-3 | ta-296 | sp-3  an-296 | 2950 | is-8 | ta-296 | sp-8  an-296 |
| 1066 | is-3 | ta-297 | sp-3  an-297 | 2951 | is-8 | ta-297 | sp-8  an-297 |
| 1067 | is-3 | ta-298 | sp-3  an-298 | 2952 | is-8 | ta-298 | sp-8  an-298 |
| 1068 | is-3 | ta-299 | sp-3  an-299 | 2953 | is-8 | ta-299 | sp-8  an-299 |
| 1069 | is-3 | ta-300 | sp-3  an-300 | 2954 | is-8 | ta-300 | sp-8  an-300 |
| 1070 | is-3 | ta-301 | sp-3  an-301 | 2955 | is-8 | ta-301 | sp-8  an-301 |
| 1071 | is-3 | ta-302 | sp-3  an-302 | 2956 | is-8 | ta-302 | sp-8  an-302 |
| 1072 | is-3 | ta-303 | sp-3  an-303 | 2957 | is-8 | ta-303 | sp-8  an-303 |
| 1073 | is-3 | ta-304 | sp-3  an-304 | 2958 | is-8 | ta-304 | sp-8  an-304 |
| 1074 | is-3 | ta-305 | sp-3  an-305 | 2959 | is-8 | ta-305 | sp-8  an-305 |
| 1075 | is-3 | ta-306 | sp-3  an-306 | 2960 | is-8 | ta-306 | sp-8  an-306 |

Table 5-21

| 1076 | is-3 | ta-307 | sp-3  an-307 | 2961 | is-8 | ta-307 | sp-8  an-307 |
|---|---|---|---|---|---|---|---|
| 1077 | is-3 | ta-308 | sp-3  an-308 | 2962 | is-8 | ta-308 | sp-8  an-308 |
| 1078 | is-3 | ta-309 | sp-3  an-309 | 2963 | is-8 | ta-309 | sp-8  an-309 |
| 1079 | is-3 | ta-310 | sp-3  an-310 | 2964 | is-8 | ta-310 | sp-8  an-310 |
| 1080 | is-3 | ta-311 | sp-3  an-311 | 2965 | is-8 | ta-311 | sp-8  an-311 |
| 1081 | is-3 | ta-312 | sp-3  an-312 | 2966 | is-8 | ta-312 | sp-8  an-312 |
| 1082 | is-3 | ta-313 | sp-3  an-313 | 2967 | is-8 | ta-313 | sp-8  an-313 |
| 1083 | is-3 | ta-314 | sp-3  an-314 | 2968 | is-8 | ta-314 | sp-8  an-314 |
| 1084 | is-3 | ta-315 | sp-3  an-315 | 2969 | is-8 | ta-315 | sp-8  an-315 |
| 1085 | is-3 | ta-316 | sp-3  an-316 | 2970 | is-8 | ta-316 | sp-8  an-316 |
| 1086 | is-3 | ta-317 | sp-3  an-317 | 2971 | is-8 | ta-317 | sp-8  an-317 |
| 1087 | is-3 | ta-318 | sp-3  an-318 | 2972 | is-8 | ta-318 | sp-8  an-318 |
| 1088 | is-3 | ta-319 | sp-3  an-319 | 2973 | is-8 | ta-319 | sp-8  an-319 |
| 1089 | is-3 | ta-320 | sp-3  an-320 | 2974 | is-8 | ta-320 | sp-8  an-320 |
| 1090 | is-3 | ta-321 | sp-3  an-321 | 2975 | is-8 | ta-321 | sp-8  an-321 |
| 1091 | is-3 | ta-322 | sp-3  an-322 | 2976 | is-8 | ta-322 | sp-8  an-322 |
| 1092 | is-3 | ta-323 | sp-3  an-323 | 2977 | is-8 | ta-323 | sp-8  an-323 |
| 1093 | is-3 | ta-324 | sp-3  an-324 | 2978 | is-8 | ta-324 | sp-8  an-324 |
| 1094 | is-3 | ta-325 | sp-3  an-325 | 2979 | is-8 | ta-325 | sp-8  an-325 |
| 1095 | is-3 | ta-326 | sp-3  an-326 | 2980 | is-8 | ta-326 | sp-8  an-326 |
| 1096 | is-3 | ta-327 | sp-3  an-327 | 2981 | is-8 | ta-327 | sp-8  an-327 |
| 1097 | is-3 | ta-328 | sp-3  an-328 | 2982 | is-8 | ta-328 | sp-8  an-328 |
| 1098 | is-3 | ta-329 | sp-3  an-329 | 2983 | is-8 | ta-329 | sp-8  an-329 |
| 1099 | is-3 | ta-330 | sp-3  an-330 | 2984 | is-8 | ta-330 | sp-8  an-330 |
| 1100 | is-3 | ta-331 | sp-3  an-331 | 2985 | is-8 | ta-331 | sp-8  an-331 |
| 1101 | is-3 | ta-332 | sp-3  an-332 | 2986 | is-8 | ta-332 | sp-8  an-332 |
| 1102 | is-3 | ta-333 | sp-3  an-333 | 2987 | is-8 | ta-333 | sp-8  an-333 |
| 1103 | is-3 | ta-334 | sp-3  an-334 | 2988 | is-8 | ta-334 | sp-8  an-334 |
| 1104 | is-3 | ta-335 | sp-3  an-335 | 2989 | is-8 | ta-335 | sp-8  an-335 |
| 1105 | is-3 | ta-336 | sp-3  an-336 | 2990 | is-8 | ta-336 | sp-8  an-336 |
| 1106 | is-3 | ta-337 | sp-3  an-337 | 2991 | is-8 | ta-337 | sp-8  an-337 |
| 1107 | is-3 | ta-338 | sp-3  an-338 | 2992 | is-8 | ta-338 | sp-8  an-338 |
| 1108 | is-3 | ta-339 | sp-3  an-339 | 2993 | is-8 | ta-339 | sp-8  an-339 |
| 1109 | is-3 | ta-340 | sp-3  an-340 | 2994 | is-8 | ta-340 | sp-8  an-340 |
| 1110 | is-3 | ta-341 | sp-3  an-341 | 2995 | is-8 | ta-341 | sp-8  an-341 |
| 1111 | is-3 | ta-342 | sp-3  an-342 | 2996 | is-8 | ta-342 | sp-8  an-342 |
| 1112 | is-3 | ta-343 | sp-3  an-343 | 2997 | is-8 | ta-343 | sp-8  an-343 |
| 1113 | is-3 | ta-344 | sp-3  an-344 | 2998 | is-8 | ta-344 | sp-8  an-344 |
| 1114 | is-3 | ta-345 | sp-3  an-345 | 2999 | is-8 | ta-345 | sp-8  an-345 |
| 1115 | is-3 | ta-346 | sp-3  an-346 | 3000 | is-8 | ta-346 | sp-8  an-346 |

-continued

| EXAMPLE | REAGENT | | PRODUCT | EXAMPLE | REAGENT | | PRODUCT |
|---|---|---|---|---|---|---|---|
| No. | is | ta | sp  an | No. | is | ta | sp  an |
| 1116 | is-3 | ta-347 | sp-3  an-347 | 3001 | is-8 | ta-347 | sp-8  an-347 |
| 1117 | is-3 | ta-348 | sp-3  an-348 | 3002 | is-8 | ta-348 | sp-8  an-348 |
| 1118 | is-3 | ta-349 | sp-3  an-349 | 3003 | is-8 | ta-349 | sp-8  an-349 |
| 1119 | is-3 | ta-350 | sp-3  an-350 | 3004 | is-8 | ta-350 | sp-8  an-350 |
| 1120 | is-3 | ta-351 | sp-3  an-351 | 3005 | is-8 | ta-351 | sp-8  an-351 |
| 1121 | is-3 | ta-352 | sp-3  an-352 | 3006 | is-8 | ta-352 | sp-8  an-352 |
| 1122 | is-3 | ta-353 | sp-3  an-353 | 3007 | is-8 | ta-353 | sp-8  an-353 |
| 1123 | is-3 | ta-354 | sp-3  an-354 | 3008 | is-8 | ta-354 | sp-8  an-354 |
| 1124 | is-3 | ta-355 | sp-3  an-355 | 3009 | is-8 | ta-355 | sp-8  an-355 |
| 1125 | is-3 | ta-356 | sp-3  an-356 | 3010 | is-8 | ta-356 | sp-8  an-356 |
| 1126 | is-3 | ta-357 | sp-3  an-357 | 3011 | is-8 | ta-357 | sp-8  an-357 |
| 1127 | is-3 | ta-358 | sp-3  an-358 | 3012 | is-8 | ta-358 | sp-8  an-358 |
| 1128 | is-3 | ta-359 | sp-3  an-359 | 3013 | is-8 | ta-359 | sp-8  an-359 |

Table 5-22

| 1129 | is-3 | ta-360 | sp-3  an-360 | 3014 | is-8 | ta-360 | sp-8  an-360 |
|---|---|---|---|---|---|---|---|
| 1130 | is-3 | ta-361 | sp-3  an-361 | 3015 | is-8 | ta-361 | sp-8  an-361 |
| 1131 | is-3 | ta-362 | sp-3  an-362 | 3016 | is-8 | ta-362 | sp-8  an-362 |
| 1132 | is-3 | ta-363 | sp-3  an-363 | 3017 | is-8 | ta-363 | sp-8  an-363 |
| 1133 | is-3 | ta-364 | sp-3  an-364 | 3018 | is-8 | ta-364 | sp-8  an-364 |
| 1134 | is-3 | ta-365 | sp-3  an-365 | 3019 | is-8 | ta-365 | sp-8  an-365 |
| 1135 | is-3 | ta-366 | sp-3  an-366 | 3020 | is-8 | ta-366 | sp-8  an-366 |
| 1136 | is-3 | ta-367 | sp-3  an-367 | 3021 | is-8 | ta-367 | sp-8  an-367 |
| 1137 | is-3 | ta-368 | sp-3  an-368 | 3022 | is-8 | ta-368 | sp-8  an-368 |
| 1138 | is-3 | ta-369 | sp-3  an-369 | 3023 | is-8 | ta-369 | sp-8  an-369 |
| 1139 | is-3 | ta-370 | sp-3  an-370 | 3024 | is-8 | ta-370 | sp-8  an-370 |
| 1140 | is-3 | ta-371 | sp-3  an-371 | 3025 | is-8 | ta-371 | sp-8  an-371 |
| 1141 | is-3 | ta-372 | sp-3  an-372 | 3026 | is-8 | ta-372 | sp-8  an-372 |
| 1142 | is-3 | ta-373 | sp-3  an-373 | 3027 | is-8 | ta-373 | sp-8  an-373 |
| 1143 | is-3 | ta-374 | sp-3  an-374 | 3028 | is-8 | ta-374 | sp-8  an-374 |
| 1144 | is-3 | ta-375 | sp-3  an-375 | 3029 | is-8 | ta-375 | sp-8  an-375 |
| 1145 | is-3 | ta-376 | sp-3  an-376 | 3030 | is-8 | ta-376 | sp-8  an-376 |
| 1146 | is-3 | ta-377 | sp-3  an-377 | 3031 | is-8 | ta-377 | sp-8  an-377 |
| 1147 | is-4 | ta-1 | sp-4  an-1 | 3032 | is-9 | ta-1 | sp-9  an-1 |
| 1148 | is-4 | ta-2 | sp-4  an-2 | 3033 | is-9 | ta-2 | sp-9  an-2 |
| 1149 | is-4 | ta-3 | sp-4  an-3 | 3034 | is-9 | ta-3 | sp-9  an-3 |
| 1150 | is-4 | ta-4 | sp-4  an-4 | 3035 | is-9 | ta-4 | sp-9  an-4 |
| 1151 | is-4 | ta-5 | sp-4  an-5 | 3036 | is-9 | ta-5 | sp-9  an-5 |
| 1152 | is-4 | ta-6 | sp-4  an-6 | 3037 | is-9 | ta-6 | sp-9  an-6 |
| 1153 | is-4 | ta-7 | sp-4  an-7 | 3038 | is-9 | ta-7 | sp-9  an-7 |
| 1154 | is-4 | ta-8 | sp-4  an-8 | 3039 | is-9 | ta-8 | sp-9  an-8 |
| 1155 | is-4 | ta-9 | sp-4  an-9 | 3040 | is-9 | ta-9 | sp-9  an-9 |
| 1156 | is-4 | ta-10 | sp-4  an-10 | 3041 | is-9 | ta-10 | sp-9  an-10 |
| 1157 | is-4 | ta-11 | sp-4  an-11 | 3042 | is-9 | ta-11 | sp-9  an-11 |
| 1158 | is-4 | ta-12 | sp-4  an-12 | 3043 | is-9 | ta-12 | sp-9  an-12 |
| 1159 | is-4 | ta-13 | sp-4  an-13 | 3044 | is-9 | ta-13 | sp-9  an-13 |
| 1160 | is-4 | ta-14 | sp-4  an-14 | 3045 | is-9 | ta-14 | sp-9  an-14 |
| 1161 | is-4 | ta-15 | sp-4  an-15 | 3046 | is-9 | ta-15 | sp-9  an-15 |
| 1162 | is-4 | ta-16 | sp-4  an-16 | 3047 | is-9 | ta-16 | sp-9  an-16 |
| 1163 | is-4 | ta-17 | sp-4  an-17 | 3048 | is-9 | ta-17 | sp-9  an-17 |
| 1164 | is-4 | ta-18 | sp-4  an-18 | 3049 | is-9 | ta-18 | sp-9  an-18 |
| 1165 | is-4 | ta-19 | sp-4  an-19 | 3050 | is-9 | ta-19 | sp-9  an-19 |
| 1166 | is-4 | ta-20 | sp-4  an-20 | 3051 | is-9 | ta-20 | sp-9  an-20 |
| 1167 | is-4 | ta-21 | sp-4  an-21 | 3052 | is-9 | ta-21 | sp-9  an-21 |
| 1168 | is-4 | ta-22 | sp-4  an-22 | 3053 | is-9 | ta-22 | sp-9  an-22 |
| 1169 | is-4 | ta-23 | sp-4  an-23 | 3054 | is-9 | ta-23 | sp-9  an-23 |
| 1170 | is-4 | ta-24 | sp-4  an-24 | 3055 | is-9 | ta-24 | sp-9  an-24 |
| 1171 | is-4 | ta-25 | sp-4  an-25 | 3056 | is-9 | ta-25 | sp-9  an-25 |
| 1172 | is-4 | ta-26 | sp-4  an-26 | 3057 | is-9 | ta-26 | sp-9  an-26 |
| 1173 | is-4 | ta-27 | sp-4  an-27 | 3058 | is-9 | ta-27 | sp-9  an-27 |
| 1174 | is-4 | ta-28 | sp-4  an-28 | 3059 | is-9 | ta-28 | sp-9  an-28 |
| 1175 | is-4 | ta-29 | sp-4  an-29 | 3060 | is-9 | ta-29 | sp-9  an-29 |
| 1176 | is-4 | ta-30 | sp-4  an-30 | 3061 | is-9 | ta-30 | sp-9  an-30 |
| 1177 | is-4 | ta-31 | sp-4  an-31 | 3062 | is-9 | ta-31 | sp-9  an-31 |
| 1178 | is-4 | ta-32 | sp-4  an-32 | 3063 | is-9 | ta-32 | sp-9  an-32 |
| 1179 | is-4 | ta-33 | sp-4  an-33 | 3064 | is-9 | ta-33 | sp-9  an-33 |
| 1180 | is-4 | ta-34 | sp-4  an-34 | 3065 | is-9 | ta-34 | sp-9  an-34 |
| 1181 | is-4 | ta-35 | sp-4  an-35 | 3066 | is-9 | ta-35 | sp-9  an-35 |

Table 5-23

| 1182 | is-4 | ta-36 | sp-4  an-36 | 3067 | is-9 | ta-36 | sp-9  an-36 |
|---|---|---|---|---|---|---|---|
| 1183 | is-4 | ta-37 | sp-4  an-37 | 3068 | is-9 | ta-37 | sp-9  an-37 |
| 1184 | is-4 | ta-38 | sp-4  an-38 | 3069 | is-9 | ta-38 | sp-9  an-38 |
| 1185 | is-4 | ta-39 | sp-4  an-39 | 3070 | is-9 | ta-39 | sp-9  an-39 |
| 1186 | is-4 | ta-40 | sp-4  an-40 | 3071 | is-9 | ta-40 | sp-9  an-40 |
| 1187 | is-4 | ta-41 | sp-4  an-41 | 3072 | is-9 | ta-41 | sp-9  an-41 |

-continued

| EXAMPLE | REAGENT | | PRODUCT | EXAMPLE | REAGENT | | PRODUCT |
|---|---|---|---|---|---|---|---|
| No. | is | ta | sp | an | No. | is | ta | sp | an |
| 1188 | is-4 | ta-42 | sp-4 | an-42 | 3073 | is-9 | ta-42 | sp-9 | an-42 |
| 1189 | is-4 | ta-43 | sp-4 | an-43 | 3074 | is-9 | ta-43 | sp-9 | an-43 |
| 1190 | is-4 | ta-44 | sp-4 | an-44 | 3075 | is-9 | ta-44 | sp-9 | an-44 |
| 1191 | is-4 | ta-45 | sp-4 | an-45 | 3076 | is-9 | ta-45 | sp-9 | an-45 |
| 1192 | is-4 | ta-46 | sp-4 | an-46 | 3077 | is-9 | ta-46 | sp-9 | an-46 |
| 1193 | is-4 | ta-47 | sp-4 | an-47 | 3078 | is-9 | ta-47 | sp-9 | an-47 |
| 1194 | is-4 | ta-48 | sp-4 | an-48 | 3079 | is-9 | ta-48 | sp-9 | an-48 |
| 1195 | is-4 | ta-49 | sp-4 | an-49 | 3080 | is-9 | ta-49 | sp-9 | an-49 |
| 1196 | is-4 | ta-50 | sp-4 | an-50 | 3081 | is-9 | ta-50 | sp-9 | an-50 |
| 1197 | is-4 | ta-51 | sp-4 | an-51 | 3082 | is-9 | ta-51 | sp-9 | an-51 |
| 1198 | is-4 | ta-52 | sp-4 | an-52 | 3083 | is-9 | ta-52 | sp-9 | an-52 |
| 1199 | is-4 | ta-53 | sp-4 | an-53 | 3084 | is-9 | ta-53 | sp-9 | an-53 |
| 1200 | is-4 | ta-54 | sp-4 | an-54 | 3085 | is-9 | ta-54 | sp-9 | an-54 |
| 1201 | is-4 | ta-55 | sp-4 | an-55 | 3086 | is-9 | ta-55 | sp-9 | an-55 |
| 1202 | is-4 | ta-56 | sp-4 | an-56 | 3087 | is-9 | ta-56 | sp-9 | an-56 |
| 1203 | is-4 | ta-57 | sp-4 | an-57 | 3088 | is-9 | ta-57 | sp-9 | an-57 |
| 1204 | is-4 | ta-58 | sp-4 | an-58 | 3089 | is-9 | ta-58 | sp-9 | an-58 |
| 1205 | is-4 | ta-59 | sp-4 | an-59 | 3090 | is-9 | ta-59 | sp-9 | an-59 |
| 1206 | is-4 | ta-60 | sp-4 | an-60 | 3091 | is-9 | ta-60 | sp-9 | an-60 |
| 1207 | is-4 | ta-61 | sp-4 | an-61 | 3092 | is-9 | ta-61 | sp-9 | an-61 |
| 1208 | is-4 | ta-62 | sp-4 | an-62 | 3093 | is-9 | ta-62 | sp-9 | an-62 |
| 1209 | is-4 | ta-63 | sp-4 | an-63 | 3094 | is-9 | ta-63 | sp-9 | an-63 |
| 1210 | is-4 | ta-64 | sp-4 | an-64 | 3095 | is-9 | ta-64 | sp-9 | an-64 |
| 1211 | is-4 | ta-65 | sp-4 | an-65 | 3096 | is-9 | ta-65 | sp-9 | an-65 |
| 1212 | is-4 | ta-66 | sp-4 | an-66 | 3097 | is-9 | ta-66 | sp-9 | an-66 |
| 1213 | is-4 | ta-67 | sp-4 | an-67 | 3098 | is-9 | ta-67 | sp-9 | an-67 |
| 1214 | is-4 | ta-68 | sp-4 | an-68 | 3099 | is-9 | ta-68 | sp-9 | an-68 |
| 1215 | is-4 | ta-69 | sp-4 | an-69 | 3100 | is-9 | ta-69 | sp-9 | an-69 |
| 1216 | is-4 | ta-70 | sp-4 | an-70 | 3101 | is-9 | ta-70 | sp-9 | an-70 |
| 1217 | is-4 | ta-71 | sp-4 | an-71 | 3102 | is-9 | ta-71 | sp-9 | an-71 |
| 1218 | is-4 | ta-72 | sp-4 | an-72 | 3103 | is-9 | ta-72 | sp-9 | an-72 |
| 1219 | is-4 | ta-73 | sp-4 | an-73 | 3104 | is-9 | ta-73 | sp-9 | an-73 |
| 1220 | is-4 | ta-74 | sp-4 | an-74 | 3105 | is-9 | ta-74 | sp-9 | an-74 |
| 1221 | is-4 | ta-75 | sp-4 | an-75 | 3106 | is-9 | ta-75 | sp-9 | an-75 |
| 1222 | is-4 | ta-76 | sp-4 | an-76 | 3107 | is-9 | ta-76 | sp-9 | an-76 |
| 1223 | is-4 | ta-77 | sp-4 | an-77 | 3108 | is-9 | ta-77 | sp-9 | an-77 |
| 1224 | is-4 | ta-78 | sp-4 | an-78 | 3109 | is-9 | ta-78 | sp-9 | an-78 |
| 1225 | is-4 | ta-79 | sp-4 | an-79 | 3110 | is-9 | ta-79 | sp-9 | an-79 |
| 1226 | is-4 | ta-80 | sp-4 | an-80 | 3111 | is-9 | ta-80 | sp-9 | an-80 |
| 1227 | is-4 | ta-81 | sp-4 | an-81 | 3112 | is-9 | ta-81 | sp-9 | an-81 |
| 1228 | is-4 | ta-82 | sp-4 | an-82 | 3113 | is-9 | ta-82 | sp-9 | an-82 |
| 1229 | is-4 | ta-83 | sp-4 | an-83 | 3114 | is-9 | ta-83 | sp-9 | an-83 |
| 1230 | is-4 | ta-84 | sp-4 | an-84 | 3115 | is-9 | ta-84 | sp-9 | an-84 |
| 1231 | is-4 | ta-85 | sp-4 | an-85 | 3116 | is-9 | ta-85 | sp-9 | an-85 |
| 1232 | is-4 | ta-86 | sp-4 | an-86 | 3117 | is-9 | ta-86 | sp-9 | an-86 |
| 1233 | is-4 | ta-87 | sp-4 | an-87 | 3118 | is-9 | ta-87 | sp-9 | an-87 |
| 1234 | is-4 | ta-88 | sp-4 | an-88 | 3119 | is-9 | ta-88 | sp-9 | an-88 |

Table 5-24

| 1235 | is-4 | ta-89 | sp-4 | an-89 | 3120 | is-9 | ta-89 | sp-9 | an-89 |
|---|---|---|---|---|---|---|---|---|---|
| 1236 | is-4 | ta-90 | sp-4 | an-90 | 3121 | is-9 | ta-90 | sp-9 | an-90 |
| 1237 | is-4 | ta-91 | sp-4 | an-91 | 3122 | is-9 | ta-91 | sp-9 | an-91 |
| 1238 | is-4 | ta-92 | sp-4 | an-92 | 3123 | is-9 | ta-92 | sp-9 | an-92 |
| 1239 | is-4 | ta-93 | sp-4 | an-93 | 3124 | is-9 | ta-93 | sp-9 | an-93 |
| 1240 | is-4 | ta-94 | sp-4 | an-94 | 3125 | is-9 | ta-94 | sp-9 | an-94 |
| 1241 | is-4 | ta-95 | sp-4 | an-95 | 3126 | is-9 | ta-95 | sp-9 | an-95 |
| 1242 | is-4 | ta-96 | sp-4 | an-96 | 3127 | is-9 | ta-96 | sp-9 | an-96 |
| 1243 | is-4 | ta-97 | sp-4 | an-97 | 3128 | is-9 | ta-97 | sp-9 | an-97 |
| 1244 | is-4 | ta-98 | sp-4 | an-98 | 3129 | is-9 | ta-98 | sp-9 | an-98 |
| 1245 | is-4 | ta-99 | sp-4 | an-99 | 3130 | is-9 | ta-99 | sp-9 | an-99 |
| 1246 | is-4 | ta-100 | sp-4 | an-100 | 3131 | is-9 | ta-100 | sp-9 | an-100 |
| 1247 | is-4 | ta-101 | sp-4 | an-101 | 3132 | is-9 | ta-101 | sp-9 | an-101 |
| 1248 | is-4 | ta-102 | sp-4 | an-102 | 3133 | is-9 | ta-102 | sp-9 | an-102 |
| 1249 | is-4 | ta-103 | sp-4 | an-103 | 3134 | is-9 | ta-103 | sp-9 | an-103 |
| 1250 | is-4 | ta-104 | sp-4 | an-104 | 3135 | is-9 | ta-104 | sp-9 | an-104 |
| 1251 | is-4 | ta-105 | sp-4 | an-105 | 3136 | is-9 | ta-105 | sp-9 | an-105 |
| 1252 | is-4 | ta-106 | sp-4 | an-106 | 3137 | is-9 | ta-106 | sp-9 | an-106 |
| 1253 | is-4 | ta-107 | sp-4 | an-107 | 3138 | is-9 | ta-107 | sp-9 | an-107 |
| 1254 | is-4 | ta-108 | sp-4 | an-108 | 3139 | is-9 | ta-108 | sp-9 | an-108 |
| 1255 | is-4 | ta-109 | sp-4 | an-109 | 3140 | is-9 | ta-109 | sp-9 | an-109 |
| 1256 | is-4 | ta-110 | sp-4 | an-110 | 3141 | is-9 | ta-110 | sp-9 | an-110 |
| 1257 | is-4 | ta-111 | sp-4 | an-111 | 3142 | is-9 | ta-111 | sp-9 | an-111 |
| 1258 | is-4 | ta-112 | sp-4 | an-112 | 3143 | is-9 | ta-112 | sp-9 | an-112 |
| 1259 | is-4 | ta-113 | sp-4 | an-113 | 3144 | is-9 | ta-113 | sp-9 | an-113 |
| 1260 | is-4 | ta-114 | sp-4 | an-114 | 3145 | is-9 | ta-114 | sp-9 | an-114 |
| 1261 | is-4 | ta-115 | sp-4 | an-115 | 3146 | is-9 | ta-115 | sp-9 | an-115 |

-continued

| EXAMPLE | REAGENT | | PRODUCT | EXAMPLE | REAGENT | | PRODUCT |
|---|---|---|---|---|---|---|---|
| No. | is | ta | sp | an | No. | is | ta | sp | an |
| 1262 | is-4 | ta-116 | sp-4 | an-116 | 3147 | is-9 | ta-116 | sp-9 | an-116 |
| 1263 | is-4 | ta-117 | sp-4 | an-117 | 3148 | is-9 | ta-117 | sp-9 | an-117 |
| 1264 | is-4 | ta-118 | sp-4 | an-118 | 3149 | is-9 | ta-118 | sp-9 | an-118 |
| 1265 | is-4 | ta-119 | sp-4 | an-119 | 3150 | is-9 | ta-119 | sp-9 | an-119 |
| 1266 | is-4 | ta-120 | sp-4 | an-120 | 3151 | is-9 | ta-120 | sp-9 | an-120 |
| 1267 | is-4 | ta-121 | sp-4 | an-121 | 3152 | is-9 | ta-121 | sp-9 | an-121 |
| 1268 | is-4 | ta-122 | sp-4 | an-122 | 3153 | is-9 | ta-122 | sp-9 | an-122 |
| 1269 | is-4 | ta-123 | sp-4 | an-123 | 3154 | is-9 | ta-123 | sp-9 | an-123 |
| 1270 | is-4 | ta-124 | sp-4 | an-124 | 3155 | is-9 | ta-124 | sp-9 | an-124 |
| 1271 | is-4 | ta-125 | sp-4 | an-125 | 3156 | is-9 | ta-125 | sp-9 | an-125 |
| 1272 | is-4 | ta-126 | sp-4 | an-126 | 3157 | is-9 | ta-126 | sp-9 | an-126 |
| 1273 | is-4 | ta-127 | sp-4 | an-127 | 3158 | is-9 | ta-127 | sp-9 | an-127 |
| 1274 | is-4 | ta-128 | sp-4 | an-128 | 3159 | is-9 | ta-128 | sp-9 | an-128 |
| 1275 | is-4 | ta-129 | sp-4 | an-129 | 3160 | is-9 | ta-129 | sp-9 | an-129 |
| 1276 | is-4 | ta-130 | sp-4 | an-130 | 3161 | is-9 | ta-130 | sp-9 | an-130 |
| 1277 | is-4 | ta-131 | sp-4 | an-131 | 3162 | is-9 | ta-131 | sp-9 | an-131 |
| 1278 | is-4 | ta-132 | sp-4 | an-132 | 3163 | is-9 | ta-132 | sp-9 | an-132 |
| 1279 | is-4 | ta-133 | sp-4 | an-133 | 3164 | is-9 | ta-133 | sp-9 | an-133 |
| 1280 | is-4 | ta-134 | sp-4 | an-134 | 3165 | is-9 | ta-134 | sp-9 | an-134 |
| 1281 | is-4 | ta-135 | sp-4 | an-135 | 3166 | is-9 | ta-135 | sp-9 | an-135 |
| 1282 | is-4 | ta-136 | sp-4 | an-136 | 3167 | is-9 | ta-136 | sp-9 | an-136 |
| 1283 | is-4 | ta-137 | sp-4 | an-137 | 3168 | is-9 | ta-137 | sp-9 | an-137 |
| 1284 | is-4 | ta-138 | sp-4 | an-138 | 3169 | is-9 | ta-138 | sp-9 | an-138 |
| 1285 | is-4 | ta-139 | sp-4 | an-139 | 3170 | is-9 | ta-139 | sp-9 | an-139 |
| 1286 | is-4 | ta-140 | sp-4 | an-140 | 3171 | is-9 | ta-140 | sp-9 | an-140 |
| 1287 | is-4 | ta-141 | sp-4 | an-141 | 3172 | is-9 | ta-141 | sp-9 | an-141 |

Table 5-25

| EXAMPLE | REAGENT | | PRODUCT | EXAMPLE | REAGENT | | PRODUCT |
|---|---|---|---|---|---|---|---|
| No. | is | ta | sp | an | No. | is | ta | sp | an |
| 1288 | is-4 | ta-142 | sp-4 | an-142 | 3173 | is-9 | ta-142 | sp-9 | an-142 |
| 1289 | is-4 | ta-143 | sp-4 | an-143 | 3174 | is-9 | ta-143 | sp-9 | an-143 |
| 1290 | is-4 | ta-144 | sp-4 | an-144 | 3175 | is-9 | ta-144 | sp-9 | an-144 |
| 1291 | is-4 | ta-145 | sp-4 | an-145 | 3176 | is-9 | ta-145 | sp-9 | an-145 |
| 1292 | is-4 | ta-146 | sp-4 | an-146 | 3177 | is-9 | ta-146 | sp-9 | an-146 |
| 1293 | is-4 | ta-147 | sp-4 | an-147 | 3178 | is-9 | ta-147 | sp-9 | an-147 |
| 1294 | is-4 | ta-148 | sp-4 | an-148 | 3179 | is-9 | ta-148 | sp-9 | an-148 |
| 1295 | is-4 | ta-149 | sp-4 | an-149 | 3180 | is-9 | ta-149 | sp-9 | an-149 |
| 1296 | is-4 | ta-150 | sp-4 | an-150 | 3181 | is-9 | ta-150 | sp-9 | an-150 |
| 1297 | is-4 | ta-151 | sp-4 | an-151 | 3182 | is-9 | ta-151 | sp-9 | an-151 |
| 1298 | is-4 | ta-152 | sp-4 | an-152 | 3183 | is-9 | ta-152 | sp-9 | an-152 |
| 1299 | is-4 | ta-153 | sp-4 | an-153 | 3184 | is-9 | ta-153 | sp-9 | an-153 |
| 1300 | is-4 | ta-154 | sp-4 | an-154 | 3185 | is-9 | ta-154 | sp-9 | an-154 |
| 1301 | is-4 | ta-155 | sp-4 | an-155 | 3186 | is-9 | ta-155 | sp-9 | an-155 |
| 1302 | is-4 | ta-156 | sp-4 | an-156 | 3187 | is-9 | ta-156 | sp-9 | an-156 |
| 1303 | is-4 | ta-157 | sp-4 | an-157 | 3188 | is-9 | ta-157 | sp-9 | an-157 |
| 1304 | is-4 | ta-158 | sp-4 | an-158 | 3189 | is-9 | ta-158 | sp-9 | an-158 |
| 1305 | is-4 | ta-159 | sp-4 | an-159 | 3190 | is-9 | ta-159 | sp-9 | an-159 |
| 1306 | is-4 | ta-160 | sp-4 | an-160 | 3191 | is-9 | ta-160 | sp-9 | an-160 |
| 1307 | is-4 | ta-161 | sp-4 | an-161 | 3192 | is-9 | ta-161 | sp-9 | an-161 |
| 1308 | is-4 | ta-162 | sp-4 | an-162 | 3193 | is-9 | ta-162 | sp-9 | an-162 |
| 1309 | is-4 | ta-163 | sp-4 | an-163 | 3194 | is-9 | ta-163 | sp-9 | an-163 |
| 1310 | is-4 | ta-164 | sp-4 | an-164 | 3195 | is-9 | ta-164 | sp-9 | an-164 |
| 1311 | is-4 | ta-165 | sp-4 | an-165 | 3196 | is-9 | ta-165 | sp-9 | an-165 |
| 1312 | is-4 | ta-166 | sp-4 | an-166 | 3197 | is-9 | ta-166 | sp-9 | an-166 |
| 1313 | is-4 | ta-167 | sp-4 | an-167 | 3198 | is-9 | ta-167 | sp-9 | an-167 |
| 1314 | is-4 | ta-168 | sp-4 | an-168 | 3199 | is-9 | ta-168 | sp-9 | an-168 |
| 1315 | is-4 | ta-169 | sp-4 | an-169 | 3200 | is-9 | ta-169 | sp-9 | an-169 |
| 1316 | is-4 | ta-170 | sp-4 | an-170 | 3201 | is-9 | ta-170 | sp-9 | an-170 |
| 1317 | is-4 | ta-171 | sp-4 | an-171 | 3202 | is-9 | ta-171 | sp-9 | an-171 |
| 1318 | is-4 | ta-172 | sp-4 | an-172 | 3203 | is-9 | ta-172 | sp-9 | an-172 |
| 1319 | is-4 | ta-173 | sp-4 | an-173 | 3204 | is-9 | ta-173 | sp-9 | an-173 |
| 1320 | is-4 | ta-174 | sp-4 | an-174 | 3205 | is-9 | ta-174 | sp-9 | an-174 |
| 1321 | is-4 | ta-175 | sp-4 | an-175 | 3206 | is-9 | ta-175 | sp-9 | an-175 |
| 1322 | is-4 | ta-176 | sp-4 | an-176 | 3207 | is-9 | ta-176 | sp-9 | an-176 |
| 1323 | is-4 | ta-177 | sp-4 | an-177 | 3208 | is-9 | ta-177 | sp-9 | an-177 |
| 1324 | is-4 | ta-178 | sp-4 | an-178 | 3209 | is-9 | ta-178 | sp-9 | an-178 |
| 1325 | is-4 | ta-179 | sp-4 | an-179 | 3210 | is-9 | ta-179 | sp-9 | an-179 |
| 1326 | is-4 | ta-180 | sp-4 | an-180 | 3211 | is-9 | ta-180 | sp-9 | an-180 |
| 1327 | is-4 | ta-181 | sp-4 | an-181 | 3212 | is-9 | ta-181 | sp-9 | an-181 |
| 1328 | is-4 | ta-182 | sp-4 | an-182 | 3213 | is-9 | ta-182 | sp-9 | an-182 |
| 1329 | is-4 | ta-183 | sp-4 | an-183 | 3214 | is-9 | ta-183 | sp-9 | an-183 |
| 1330 | is-4 | ta-184 | sp-4 | an-184 | 3215 | is-9 | ta-184 | sp-9 | an-184 |
| 1331 | is-4 | ta-185 | sp-4 | an-185 | 3216 | is-9 | ta-185 | sp-9 | an-185 |
| 1332 | is-4 | ta-186 | sp-4 | an-186 | 3217 | is-9 | ta-186 | sp-9 | an-186 |
| 1333 | is-4 | ta-187 | sp-4 | an-187 | 3218 | is-9 | ta-187 | sp-9 | an-187 |
| 1334 | is-4 | ta-188 | sp-4 | an-188 | 3219 | is-9 | ta-188 | sp-9 | an-188 |
| 1335 | is-4 | ta-189 | sp-4 | an-189 | 3220 | is-9 | ta-189 | sp-9 | an-189 |

-continued

| EXAMPLE | REAGENT | | PRODUCT | EXAMPLE | REAGENT | | PRODUCT |
|---|---|---|---|---|---|---|---|
| No. | is | ta | sp | an | No. | is | ta | sp | an |
| 1336 | is-4 | ta-190 | sp-4 | an-190 | 3221 | is-9 | ta-190 | sp-9 | an-190 |
| 1337 | is-4 | ta-191 | sp-4 | an-191 | 3222 | is-9 | ta-191 | sp-9 | an-191 |
| 1338 | is-4 | ta-192 | sp-4 | an-192 | 3223 | is-9 | ta-192 | sp-9 | an-192 |
| 1339 | is-4 | ta-193 | sp-4 | an-193 | 3224 | is-9 | ta-193 | sp-9 | an-193 |
| 1340 | is-4 | ta-194 | sp-4 | an-194 | 3225 | is-9 | ta-194 | sp-9 | an-194 |

Table 5-26

| 1341 | is-4 | ta-195 | sp-4 | an-195 | 3226 | is-9 | ta-195 | sp-9 | an-195 |
|---|---|---|---|---|---|---|---|---|---|
| 1342 | is-4 | ta-196 | sp-4 | an-196 | 3227 | is-9 | ta-196 | sp-9 | an-196 |
| 1343 | is-4 | ta-197 | sp-4 | an-197 | 3228 | is-9 | ta-197 | sp-9 | an-197 |
| 1344 | is-4 | ta-198 | sp-4 | an-198 | 3229 | is-9 | ta-198 | sp-9 | an-198 |
| 1345 | is-4 | ta-199 | sp-4 | an-199 | 3230 | is-9 | ta-199 | sp-9 | an-199 |
| 1346 | is-4 | ta-200 | sp-4 | an-200 | 3231 | is-9 | ta-200 | sp-9 | an-200 |
| 1347 | is-4 | ta-201 | sp-4 | an-201 | 3232 | is-9 | ta-201 | sp-9 | an-201 |
| 1348 | is-4 | ta-202 | sp-4 | an-202 | 3233 | is-9 | ta-202 | sp-9 | an-202 |
| 1349 | is-4 | ta-203 | sp-4 | an-203 | 3234 | is-9 | ta-203 | sp-9 | an-203 |
| 1350 | is-4 | ta-204 | sp-4 | an-204 | 3235 | is-9 | ta-204 | sp-9 | an-204 |
| 1351 | is-4 | ta-205 | sp-4 | an-205 | 3236 | is-9 | ta-205 | sp-9 | an-205 |
| 1352 | is-4 | ta-206 | sp-4 | an-206 | 3237 | is-9 | ta-206 | sp-9 | an-206 |
| 1353 | is-4 | ta-207 | sp-4 | an-207 | 3238 | is-9 | ta-207 | sp-9 | an-207 |
| 1354 | is-4 | ta-208 | sp-4 | an-208 | 3239 | is-9 | ta-208 | sp-9 | an-208 |
| 1355 | is-4 | ta-209 | sp-4 | an-209 | 3240 | is-9 | ta-209 | sp-9 | an-209 |
| 1356 | is-4 | ta-210 | sp-4 | an-210 | 3241 | is-9 | ta-210 | sp-9 | an-210 |
| 1357 | is-4 | ta-211 | sp-4 | an-211 | 3242 | is-9 | ta-211 | sp-9 | an-211 |
| 1358 | is-4 | ta-212 | sp-4 | an-212 | 3243 | is-9 | ta-212 | sp-9 | an-212 |
| 1359 | is-4 | ta-213 | sp-4 | an-213 | 3244 | is-9 | ta-213 | sp-9 | an-213 |
| 1360 | is-4 | ta-214 | sp-4 | an-214 | 3245 | is-9 | ta-214 | sp-9 | an-214 |
| 1361 | is-4 | ta-215 | sp-4 | an-215 | 3246 | is-9 | ta-215 | sp-9 | an-215 |
| 1362 | is-4 | ta-216 | sp-4 | an-216 | 3247 | is-9 | ta-216 | sp-9 | an-216 |
| 1363 | is-4 | ta-217 | sp-4 | an-217 | 3248 | is-9 | ta-217 | sp-9 | an-217 |
| 1364 | is-4 | ta-218 | sp-4 | an-218 | 3249 | is-9 | ta-218 | sp-9 | an-218 |
| 1365 | is-4 | ta-219 | sp-4 | an-219 | 3250 | is-9 | ta-219 | sp-9 | an-219 |
| 1366 | is-4 | ta-220 | sp-4 | an-220 | 3251 | is-9 | ta-220 | sp-9 | an-220 |
| 1367 | is-4 | ta-221 | sp-4 | an-221 | 3252 | is-9 | ta-221 | sp-9 | an-221 |
| 1368 | is-4 | ta-222 | sp-4 | an-222 | 3253 | is-9 | ta-222 | sp-9 | an-222 |
| 1369 | is-4 | ta-223 | sp-4 | an-223 | 3254 | is-9 | ta-223 | sp-9 | an-223 |
| 1370 | is-4 | ta-224 | sp-4 | an-224 | 3255 | is-9 | ta-224 | sp-9 | an-224 |
| 1371 | is-4 | ta-225 | sp-4 | an-225 | 3256 | is-9 | ta-225 | sp-9 | an-225 |
| 1372 | is-4 | ta-226 | sp-4 | an-226 | 3257 | is-9 | ta-226 | sp-9 | an-226 |
| 1373 | is-4 | ta-227 | sp-4 | an-227 | 3258 | is-9 | ta-227 | sp-9 | an-227 |
| 1374 | is-4 | ta-228 | sp-4 | an-228 | 3259 | is-9 | ta-228 | sp-9 | an-228 |
| 1375 | is-4 | ta-229 | sp-4 | an-229 | 3260 | is-9 | ta-229 | sp-9 | an-229 |
| 1376 | is-4 | ta-230 | sp-4 | an-230 | 3261 | is-9 | ta-230 | sp-9 | an-230 |
| 1377 | is-4 | ta-231 | sp-4 | an-231 | 3262 | is-9 | ta-231 | sp-9 | an-231 |
| 1378 | is-4 | ta-232 | sp-4 | an-232 | 3263 | is-9 | ta-232 | sp-9 | an-232 |
| 1379 | is-4 | ta-233 | sp-4 | an-233 | 3264 | is-9 | ta-233 | sp-9 | an-233 |
| 1380 | is-4 | ta-234 | sp-4 | an-234 | 3265 | is-9 | ta-234 | sp-9 | an-234 |
| 1381 | is-4 | ta-235 | sp-4 | an-235 | 3266 | is-9 | ta-235 | sp-9 | an-235 |
| 1382 | is-4 | ta-236 | sp-4 | an-236 | 3267 | is-9 | ta-236 | sp-9 | an-236 |
| 1383 | is-4 | ta-237 | sp-4 | an-237 | 3268 | is-9 | ta-237 | sp-9 | an-237 |
| 1384 | is-4 | ta-238 | sp-4 | an-238 | 3269 | is-9 | ta-238 | sp-9 | an-238 |
| 1385 | is-4 | ta-239 | sp-4 | an-239 | 3270 | is-9 | ta-239 | sp-9 | an-239 |
| 1386 | is-4 | ta-240 | sp-4 | an-240 | 3271 | is-9 | ta-240 | sp-9 | an-240 |
| 1387 | is-4 | ta-241 | sp-4 | an-241 | 3272 | is-9 | ta-241 | sp-9 | an-241 |
| 1388 | is-4 | ta-242 | sp-4 | an-242 | 3273 | is-9 | ta-242 | sp-9 | an-242 |
| 1389 | is-4 | ta-243 | sp-4 | an-243 | 3274 | is-9 | ta-243 | sp-9 | an-243 |
| 1390 | is-4 | ta-244 | sp-4 | an-244 | 3275 | is-9 | ta-244 | sp-9 | an-244 |
| 1391 | is-4 | ta-245 | sp-4 | an-245 | 3276 | is-9 | ta-245 | sp-9 | an-245 |
| 1392 | is-4 | ta-246 | sp-4 | an-246 | 3277 | is-9 | ta-246 | sp-9 | an-246 |
| 1393 | is-4 | ta-247 | sp-4 | an-247 | 3278 | is-9 | ta-247 | sp-9 | an-247 |

Table 5-27

| 1394 | is-4 | ta-248 | sp-4 | an-248 | 3279 | is-9 | ta-248 | sp-9 | an-248 |
|---|---|---|---|---|---|---|---|---|---|
| 1395 | is-4 | ta-249 | sp-4 | an-249 | 3280 | is-9 | ta-249 | sp-9 | an-249 |
| 1396 | is-4 | ta-250 | sp-4 | an-250 | 3281 | is-9 | ta-250 | sp-9 | an-250 |
| 1397 | is-4 | ta-251 | sp-4 | an-251 | 3282 | is-9 | ta-251 | sp-9 | an-251 |
| 1398 | is-4 | ta-252 | sp-4 | an-252 | 3283 | is-9 | ta-252 | sp-9 | an-252 |
| 1399 | is-4 | ta-253 | sp-4 | an-253 | 3284 | is-9 | ta-253 | sp-9 | an-253 |
| 1400 | is-4 | ta-254 | sp-4 | an-254 | 3285 | is-9 | ta-254 | sp-9 | an-254 |
| 1401 | is-4 | ta-255 | sp-4 | an-255 | 3286 | is-9 | ta-255 | sp-9 | an-255 |
| 1402 | is-4 | ta-256 | sp-4 | an-256 | 3287 | is-9 | ta-256 | sp-9 | an-256 |
| 1403 | is-4 | ta-257 | sp-4 | an-257 | 3288 | is-9 | ta-257 | sp-9 | an-257 |
| 1404 | is-4 | ta-258 | sp-4 | an-258 | 3289 | is-9 | ta-258 | sp-9 | an-258 |
| 1405 | is-4 | ta-259 | sp-4 | an-259 | 3290 | is-9 | ta-259 | sp-9 | an-259 |
| 1406 | is-4 | ta-260 | sp-4 | an-260 | 3291 | is-9 | ta-260 | sp-9 | an-260 |
| 1407 | is-4 | ta-261 | sp-4 | an-261 | 3292 | is-9 | ta-261 | sp-9 | an-261 |

-continued

| EXAMPLE | REAGENT | | PRODUCT | EXAMPLE | REAGENT | | PRODUCT |
|---|---|---|---|---|---|---|---|
| No. | is | ta | sp an | No. | is | ta | sp an |
| 1408 | is-4 | ta-262 | sp-4 an-262 | 3293 | is-9 | ta-262 | sp-9 an-262 |
| 1409 | is-4 | ta-263 | sp-4 an-263 | 3294 | is-9 | ta-263 | sp-9 an-263 |
| 1410 | is-4 | ta-264 | sp-4 an-264 | 3295 | is-9 | ta-264 | sp-9 an-264 |
| 1411 | is-4 | ta-265 | sp-4 an-265 | 3296 | is-9 | ta-265 | sp-9 an-265 |
| 1412 | is-4 | ta-266 | sp-4 an-266 | 3297 | is-9 | ta-266 | sp-9 an-266 |
| 1413 | is-4 | ta-267 | sp-4 an-267 | 3298 | is-9 | ta-267 | sp-9 an-267 |
| 1414 | is-4 | ta-268 | sp-4 an-268 | 3299 | is-9 | ta-268 | sp-9 an-268 |
| 1415 | is-4 | ta-269 | sp-4 an-269 | 3300 | is-9 | ta-269 | sp-9 an-269 |
| 1416 | is-4 | ta-270 | sp-4 an-270 | 3301 | is-9 | ta-270 | sp-9 an-270 |
| 1417 | is-4 | ta-271 | sp-4 an-271 | 3302 | is-9 | ta-271 | sp-9 an-271 |
| 1418 | is-4 | ta-272 | sp-4 an-272 | 3303 | is-9 | ta-272 | sp-9 an-272 |
| 1419 | is-4 | ta-273 | sp-4 an-273 | 3304 | is-9 | ta-273 | sp-9 an-273 |
| 1420 | is-4 | ta-274 | sp-4 an-274 | 3305 | is-9 | ta-274 | sp-9 an-274 |
| 1421 | is-4 | ta-275 | sp-4 an-275 | 3306 | is-9 | ta-275 | sp-9 an-275 |
| 1422 | is-4 | ta-276 | sp-4 an-276 | 3307 | is-9 | ta-276 | sp-9 an-276 |
| 1423 | is-4 | ta-277 | sp-4 an-277 | 3308 | is-9 | ta-277 | sp-9 an-277 |
| 1424 | is-4 | ta-278 | sp-4 an-278 | 3309 | is-9 | ta-278 | sp-9 an-278 |
| 1425 | is-4 | ta-279 | sp-4 an-279 | 3310 | is-9 | ta-279 | sp-9 an-279 |
| 1426 | is-4 | ta-280 | sp-4 an-280 | 3311 | is-9 | ta-280 | sp-9 an-280 |
| 1427 | is-4 | ta-281 | sp-4 an-281 | 3312 | is-9 | ta-281 | sp-9 an-281 |
| 1428 | is-4 | ta-282 | sp-4 an-282 | 3313 | is-9 | ta-282 | sp-9 an-282 |
| 1429 | is-4 | ta-283 | sp-4 an-283 | 3314 | is-9 | ta-283 | sp-9 an-283 |
| 1430 | is-4 | ta-284 | sp-4 an-284 | 3315 | is-9 | ta-284 | sp-9 an-284 |
| 1431 | is-4 | ta-285 | sp-4 an-285 | 3316 | is-9 | ta-285 | sp-9 an-285 |
| 1432 | is-4 | ta-286 | sp-4 an-286 | 3317 | is-9 | ta-286 | sp-9 an-286 |
| 1433 | is-4 | ta-287 | sp-4 an-287 | 3318 | is-9 | ta-287 | sp-9 an-287 |
| 1434 | is-4 | ta-288 | sp-4 an-288 | 3319 | is-9 | ta-288 | sp-9 an-288 |
| 1435 | is-4 | ta-289 | sp-4 an-289 | 3320 | is-9 | ta-289 | sp-9 an-289 |
| 1436 | is-4 | ta-290 | sp-4 an-290 | 3321 | is-9 | ta-290 | sp-9 an-290 |
| 1437 | is-4 | ta-291 | sp-4 an-291 | 3322 | is-9 | ta-291 | sp-9 an-291 |
| 1438 | is-4 | ta-292 | sp-4 an-292 | 3323 | is-9 | ta-292 | sp-9 an-292 |
| 1439 | is-4 | ta-293 | sp-4 an-293 | 3324 | is-9 | ta-293 | sp-9 an-293 |
| 1440 | is-4 | ta-294 | sp-4 an-294 | 3325 | is-9 | ta-294 | sp-9 an-294 |
| 1441 | is-4 | ta-295 | sp-4 an-295 | 3326 | is-9 | ta-295 | sp-9 an-295 |
| 1442 | is-4 | ta-296 | sp-4 an-296 | 3327 | is-9 | ta-296 | sp-9 an-296 |
| 1443 | is-4 | ta-297 | sp-4 an-297 | 3328 | is-9 | ta-297 | sp-9 an-297 |
| 1444 | is-4 | ta-298 | sp-4 an-298 | 3329 | is-9 | ta-298 | sp-9 an-298 |
| 1445 | is-4 | ta-299 | sp-4 an-299 | 3330 | is-9 | ta-299 | sp-9 an-299 |
| 1446 | is-4 | ta-300 | sp-4 an-300 | 3331 | is-9 | ta-300 | sp-9 an-300 |

Table 5-28

| EXAMPLE | REAGENT | | PRODUCT | EXAMPLE | REAGENT | | PRODUCT |
|---|---|---|---|---|---|---|---|
| 1447 | is-4 | ta-301 | sp-4 an-301 | 3332 | is-9 | ta-301 | sp-9 an-301 |
| 1448 | is-4 | ta-302 | sp-4 an-302 | 3333 | is-9 | ta-302 | sp-9 an-302 |
| 1449 | is-4 | ta-303 | sp-4 an-303 | 3334 | is-9 | ta-303 | sp-9 an-303 |
| 1450 | is-4 | ta-304 | sp-4 an-304 | 3335 | is-9 | ta-304 | sp-9 an-304 |
| 1451 | is-4 | ta-305 | sp-4 an-305 | 3336 | is-9 | ta-305 | sp-9 an-305 |
| 1452 | is-4 | ta-306 | sp-4 an-306 | 3337 | is-9 | ta-306 | sp-9 an-306 |
| 1453 | is-4 | ta-307 | sp-4 an-307 | 3338 | is-9 | ta-307 | sp-9 an-307 |
| 1454 | is-4 | ta-308 | sp-4 an-308 | 3339 | is-9 | ta-308 | sp-9 an-308 |
| 1455 | is-4 | ta-309 | sp-4 an-309 | 3340 | is-9 | ta-309 | sp-9 an-309 |
| 1456 | is-4 | ta-310 | sp-4 an-310 | 3341 | is-9 | ta-310 | sp-9 an-310 |
| 1457 | is-4 | ta-311 | sp-4 an-311 | 3342 | is-9 | ta-311 | sp-9 an-311 |
| 1458 | is-4 | ta-312 | sp-4 an-312 | 3343 | is-9 | ta-312 | sp-9 an-312 |
| 1459 | is-4 | ta-313 | sp-4 an-313 | 3344 | is-9 | ta-313 | sp-9 an-313 |
| 1460 | is-4 | ta-314 | sp-4 an-314 | 3345 | is-9 | ta-314 | sp-9 an-314 |
| 1461 | is-4 | ta-315 | sp-4 an-315 | 3346 | is-9 | ta-315 | sp-9 an-315 |
| 1462 | is-4 | ta-316 | sp-4 an-316 | 3347 | is-9 | ta-316 | sp-9 an-316 |
| 1463 | is-4 | ta-317 | sp-4 an-317 | 3348 | is-9 | ta-317 | sp-9 an-317 |
| 1464 | is-4 | ta-318 | sp-4 an-318 | 3349 | is-9 | ta-318 | sp-9 an-318 |
| 1465 | is-4 | ta-319 | sp-4 an-319 | 3350 | is-9 | ta-319 | sp-9 an-319 |
| 1466 | is-4 | ta-320 | sp-4 an-320 | 3351 | is-9 | ta-320 | sp-9 an-320 |
| 1467 | is-4 | ta-321 | sp-4 an-321 | 3352 | is-9 | ta-321 | sp-9 an-321 |
| 1468 | is-4 | ta-322 | sp-4 an-322 | 3353 | is-9 | ta-322 | sp-9 an-322 |
| 1469 | is-4 | ta-323 | sp-4 an-323 | 3354 | is-9 | ta-323 | sp-9 an-323 |
| 1470 | is-4 | ta-324 | sp-4 an-324 | 3355 | is-9 | ta-324 | sp-9 an-324 |
| 1471 | is-4 | ta-325 | sp-4 an-325 | 3356 | is-9 | ta-325 | sp-9 an-325 |
| 1472 | is-4 | ta-326 | sp-4 an-326 | 3357 | is-9 | ta-326 | sp-9 an-326 |
| 1473 | is-4 | ta-327 | sp-4 an-327 | 3358 | is-9 | ta-327 | sp-9 an-327 |
| 1474 | is-4 | ta-328 | sp-4 an-328 | 3359 | is-9 | ta-328 | sp-9 an-328 |
| 1475 | is-4 | ta-329 | sp-4 an-329 | 3360 | is-9 | ta-329 | sp-9 an-329 |
| 1476 | is-4 | ta-330 | sp-4 an-330 | 3361 | is-9 | ta-330 | sp-9 an-330 |
| 1477 | is-4 | ta-331 | sp-4 an-331 | 3362 | is-9 | ta-331 | sp-9 an-331 |
| 1478 | is-4 | ta-332 | sp-4 an-332 | 3363 | is-9 | ta-332 | sp-9 an-332 |
| 1479 | is-4 | ta-333 | sp-4 an-333 | 3364 | is-9 | ta-333 | sp-9 an-333 |
| 1480 | is-4 | ta-334 | sp-4 an-334 | 3365 | is-9 | ta-334 | sp-9 an-334 |
| 1481 | is-4 | ta-335 | sp-4 an-335 | 3366 | is-9 | ta-335 | sp-9 an-335 |

-continued

| EXAMPLE | REAGENT | | PRODUCT | EXAMPLE | REAGENT | | PRODUCT |
|---|---|---|---|---|---|---|---|
| No. | is | ta | sp | an | No. | is | ta | sp | an |
| 1482 | is-4 | ta-336 | sp-4 | an-336 | 3367 | is-9 | ta-336 | sp-9 | an-336 |
| 1483 | is-4 | ta-337 | sp-4 | an-337 | 3368 | is-9 | ta-337 | sp-9 | an-337 |
| 1484 | is-4 | ta-338 | sp-4 | an-338 | 3369 | is-9 | ta-338 | sp-9 | an-338 |
| 1485 | is-4 | ta-339 | sp-4 | an-339 | 3370 | is-9 | ta-339 | sp-9 | an-339 |
| 1486 | is-4 | ta-340 | sp-4 | an-340 | 3371 | is-9 | ta-340 | sp-9 | an-340 |
| 1487 | is-4 | ta-341 | sp-4 | an-341 | 3372 | is-9 | ta-341 | sp-9 | an-341 |
| 1488 | is-4 | ta-342 | sp-4 | an-342 | 3373 | is-9 | ta-342 | sp-9 | an-342 |
| 1489 | is-4 | ta-343 | sp-4 | an-343 | 3374 | is-9 | ta-343 | sp-9 | an-343 |
| 1490 | is-4 | ta-344 | sp-4 | an-344 | 3375 | is-9 | ta-344 | sp-9 | an-344 |
| 1491 | is-4 | ta-345 | sp-4 | an-345 | 3376 | is-9 | ta-345 | sp-9 | an-345 |
| 1492 | is-4 | ta-346 | sp-4 | an-346 | 3377 | is-9 | ta-346 | sp-9 | an-346 |
| 1493 | is-4 | ta-347 | sp-4 | an-347 | 3378 | is-9 | ta-347 | sp-9 | an-347 |
| 1494 | is-4 | ta-348 | sp-4 | an-348 | 3379 | is-9 | ta-348 | sp-9 | an-348 |
| 1495 | is-4 | ta-349 | sp-4 | an-349 | 3380 | is-9 | ta-349 | sp-9 | an-349 |
| 1496 | is-4 | ta-350 | sp-4 | an-350 | 3381 | is-9 | ta-350 | sp-9 | an-350 |
| 1497 | is-4 | ta-351 | sp-4 | an-351 | 3382 | is-9 | ta-351 | sp-9 | an-351 |
| 1498 | is-4 | ta-352 | sp-4 | an-352 | 3383 | is-9 | ta-352 | sp-9 | an-352 |
| 1499 | is-4 | ta-353 | sp-4 | an-353 | 3384 | is-9 | ta-353 | sp-9 | an-353 |

Table 5-29

| EXAMPLE | REAGENT | | PRODUCT | EXAMPLE | REAGENT | | PRODUCT |
|---|---|---|---|---|---|---|---|
| 1500 | is-4 | ta-354 | sp-4 | an-354 | 3385 | is-9 | ta-354 | sp-9 | an-354 |
| 1501 | is-4 | ta-355 | sp-4 | an-355 | 3386 | is-9 | ta-355 | sp-9 | an-355 |
| 1502 | is-4 | ta-356 | sp-4 | an-356 | 3387 | is-9 | ta-356 | sp-9 | an-356 |
| 1503 | is-4 | ta-357 | sp-4 | an-357 | 3388 | is-9 | ta-357 | sp-9 | an-357 |
| 1504 | is-4 | ta-358 | sp-4 | an-358 | 3389 | is-9 | ta-358 | sp-9 | an-358 |
| 1505 | is-4 | ta-359 | sp-4 | an-359 | 3390 | is-9 | ta-359 | sp-9 | an-359 |
| 1506 | is-4 | ta-360 | sp-4 | an-360 | 3391 | is-9 | ta-360 | sp-9 | an-360 |
| 1507 | is-4 | ta-361 | sp-4 | an-361 | 3392 | is-9 | ta-361 | sp-9 | an-361 |
| 1508 | is-4 | ta-362 | sp-4 | an-362 | 3393 | is-9 | ta-362 | sp-9 | an-362 |
| 1509 | is-4 | ta-363 | sp-4 | an-363 | 3394 | is-9 | ta-363 | sp-9 | an-363 |
| 1510 | is-4 | ta-364 | sp-4 | an-364 | 3395 | is-9 | ta-364 | sp-9 | an-364 |
| 1511 | is-4 | ta-365 | sp-4 | an-365 | 3396 | is-9 | ta-365 | sp-9 | an-365 |
| 1512 | is-4 | ta-366 | sp-4 | an-366 | 3397 | is-9 | ta-366 | sp-9 | an-366 |
| 1513 | is-4 | ta-367 | sp-4 | an-367 | 3398 | is-9 | ta-367 | sp-9 | an-367 |
| 1514 | is-4 | ta-368 | sp-4 | an-368 | 3399 | is-9 | ta-368 | sp-9 | an-368 |
| 1515 | is-4 | ta-369 | sp-4 | an-369 | 3400 | is-9 | ta-369 | sp-9 | an-369 |
| 1516 | is-4 | ta-370 | sp-4 | an-370 | 3401 | is-9 | ta-370 | sp-9 | an-370 |
| 1517 | is-4 | ta-371 | sp-4 | an-371 | 3402 | is-9 | ta-371 | sp-9 | an-371 |
| 1518 | is-4 | ta-372 | sp-4 | an-372 | 3403 | is-9 | ta-372 | sp-9 | an-372 |
| 1519 | is-4 | ta-373 | sp-4 | an-373 | 3404 | is-9 | ta-373 | sp-9 | an-373 |
| 1520 | is-4 | ta-374 | sp-4 | an-374 | 3405 | is-9 | ta-374 | sp-9 | an-374 |
| 1521 | is-4 | ta-375 | sp-4 | an-375 | 3406 | is-9 | ta-375 | sp-9 | an-375 |
| 1522 | is-4 | ta-376 | sp-4 | an-376 | 3407 | is-9 | ta-376 | sp-9 | an-376 |
| 1523 | is-4 | ta-377 | sp-4 | an-377 | 3408 | is-9 | ta-377 | sp-9 | an-377 |
| 1524 | is-5 | ta-1 | sp-5 | an-1 | 3409 | is-14 | ta-1 | sp-14 | an-1 |
| 1525 | is-5 | ta-2 | sp-5 | an-2 | 3410 | is-14 | ta-2 | sp-14 | an-2 |
| 1526 | is-5 | ta-3 | sp-5 | an-3 | 3411 | is-14 | ta-3 | sp-14 | an-3 |
| 1527 | is-5 | ta-4 | sp-5 | an-4 | 3412 | is-14 | ta-4 | sp-14 | an-4 |
| 1528 | is-5 | ta-5 | sp-5 | an-5 | 3413 | is-14 | ta-5 | sp-14 | an-5 |
| 1529 | is-5 | ta-6 | sp-5 | an-6 | 3414 | is-14 | ta-6 | sp-14 | an-6 |
| 1530 | is-5 | ta-7 | sp-5 | an-7 | 3415 | is-14 | ta-7 | sp-14 | an-7 |
| 1531 | is-5 | ta-8 | sp-5 | an-8 | 3416 | is-14 | ta-8 | sp-14 | an-8 |
| 1532 | is-5 | ta-9 | sp-5 | an-9 | 3417 | is-14 | ta-9 | sp-14 | an-9 |
| 1533 | is-5 | ta-10 | sp-5 | an-10 | 3418 | is-14 | ta-10 | sp-14 | an-10 |
| 1534 | is-5 | ta-11 | sp-5 | an-11 | 3419 | is-14 | ta-11 | sp-14 | an-11 |
| 1535 | is-5 | ta-12 | sp-5 | an-12 | 3420 | is-14 | ta-12 | sp-14 | an-12 |
| 1536 | is-5 | ta-13 | sp-5 | an-13 | 3421 | is-14 | ta-13 | sp-14 | an-13 |
| 1537 | is-5 | ta-14 | sp-5 | an-14 | 3422 | is-14 | ta-14 | sp-14 | an-14 |
| 1538 | is-5 | ta-15 | sp-5 | an-15 | 3423 | is-14 | ta-15 | sp-14 | an-15 |
| 1539 | is-5 | ta-16 | sp-5 | an-16 | 3424 | is-14 | ta-16 | sp-14 | an-16 |
| 1540 | is-5 | ta-17 | sp-5 | an-17 | 3425 | is-14 | ta-17 | sp-14 | an-17 |
| 1541 | is-5 | ta-18 | sp-5 | an-18 | 3426 | is-14 | ta-18 | sp-14 | an-18 |
| 1542 | is-5 | ta-19 | sp-5 | an-19 | 3427 | is-14 | ta-19 | sp-14 | an-19 |
| 1543 | is-5 | ta-20 | sp-5 | an-20 | 3428 | is-14 | ta-20 | sp-14 | an-20 |
| 1544 | is-5 | ta-21 | sp-5 | an-21 | 3429 | is-14 | ta-21 | sp-14 | an-21 |
| 1545 | is-5 | ta-22 | sp-5 | an-22 | 3430 | is-14 | ta-22 | sp-14 | an-22 |
| 1546 | is-5 | ta-23 | sp-5 | an-23 | 3431 | is-14 | ta-23 | sp-14 | an-23 |
| 1547 | is-5 | ta-24 | sp-5 | an-24 | 3432 | is-14 | ta-24 | sp-14 | an-24 |
| 1548 | is-5 | ta-25 | sp-5 | an-25 | 3433 | is-14 | ta-25 | sp-14 | an-25 |
| 1549 | is-5 | ta-26 | sp-5 | an-26 | 3434 | is-14 | ta-26 | sp-14 | an-26 |
| 1550 | is-5 | ta-27 | sp-5 | an-27 | 3435 | is-14 | ta-27 | sp-14 | an-27 |
| 1551 | is-5 | ta-28 | sp-5 | an-28 | 3436 | is-14 | ta-28 | sp-14 | an-28 |
| 1552 | is-5 | ta-29 | sp-5 | an-29 | 3437 | is-14 | ta-29 | sp-14 | an-29 |

| EXAMPLE | REAGENT | | PRODUCT | | EXAMPLE | REAGENT | | PRODUCT | |
|---|---|---|---|---|---|---|---|---|---|
| No. | is | ta | sp | an | No. | is | ta | sp | an |
| | | | | Table 5-30 | | | | | |
| 1553 | is-5 | ta-30 | sp-5 | an-30 | 3438 | is-14 | ta-30 | sp-14 | an-30 |
| 1554 | is-5 | ta-31 | sp-5 | an-31 | 3439 | is-14 | ta-31 | sp-14 | an-31 |
| 1555 | is-5 | ta-32 | sp-5 | an-32 | 3440 | is-14 | ta-32 | sp-14 | an-32 |
| 1556 | is-5 | ta-33 | sp-5 | an-33 | 3441 | is-14 | ta-33 | sp-14 | an-33 |
| 1557 | is-5 | ta-34 | sp-5 | an-34 | 3442 | is-14 | ta-34 | sp-14 | an-34 |
| 1558 | is-5 | ta-35 | sp-5 | an-35 | 3443 | is-14 | ta-35 | sp-14 | an-35 |
| 1559 | is-5 | ta-36 | sp-5 | an-36 | 3444 | is-14 | ta-36 | sp-14 | an-36 |
| 1560 | is-5 | ta-37 | sp-5 | an-37 | 3445 | is-14 | ta-37 | sp-14 | an-37 |
| 1561 | is-5 | ta-38 | sp-5 | an-38 | 3446 | is-14 | ta-38 | sp-14 | an-38 |
| 1562 | is-5 | ta-39 | sp-5 | an-39 | 3447 | is-14 | ta-39 | sp-14 | an-39 |
| 1563 | is-5 | ta-40 | sp-5 | an-40 | 3448 | is-14 | ta-40 | sp-14 | an-40 |
| 1564 | is-5 | ta-41 | sp-5 | an-41 | 3449 | is-14 | ta-41 | sp-14 | an-41 |
| 1565 | is-5 | ta-42 | sp-5 | an-42 | 3450 | is-14 | ta-42 | sp-14 | an-42 |
| 1566 | is-5 | ta-43 | sp-5 | an-43 | 3451 | is-14 | ta-43 | sp-14 | an-43 |
| 1567 | is-5 | ta-44 | sp-5 | an-44 | 3452 | is-14 | ta-44 | sp-14 | an-44 |
| 1568 | is-5 | ta-45 | sp-5 | an-45 | 3453 | is-14 | ta-45 | sp-14 | an-45 |
| 1569 | is-5 | ta-46 | sp-5 | an-46 | 3454 | is-14 | ta-46 | sp-14 | an-46 |
| 1570 | is-5 | ta-47 | sp-5 | an-47 | 3455 | is-14 | ta-47 | sp-14 | an-47 |
| 1571 | is-5 | ta-48 | sp-5 | an-48 | 3456 | is-14 | ta-48 | sp-14 | an-48 |
| 1572 | is-5 | ta-49 | sp-5 | an-49 | 3457 | is-14 | ta-49 | sp-14 | an-49 |
| 1573 | is-5 | ta-50 | sp-5 | an-50 | 3458 | is-14 | ta-50 | sp-14 | an-50 |
| 1574 | is-5 | ta-51 | sp-5 | an-51 | 3459 | is-14 | ta-51 | sp-14 | an-51 |
| 1575 | is-5 | ta-52 | sp-5 | an-52 | 3460 | is-14 | ta-52 | sp-14 | an-52 |
| 1576 | is-5 | ta-53 | sp-5 | an-53 | 3461 | is-14 | ta-53 | sp-14 | an-53 |
| 1577 | is-5 | ta-54 | sp-5 | an-54 | 3462 | is-14 | ta-54 | sp-14 | an-54 |
| 1578 | is-5 | ta-55 | sp-5 | an-55 | 3463 | is-14 | ta-55 | sp-14 | an-55 |
| 1579 | is-5 | ta-56 | sp-5 | an-56 | 3464 | is-14 | ta-56 | sp-14 | an-56 |
| 1580 | is-5 | ta-57 | sp-5 | an-57 | 3465 | is-14 | ta-57 | sp-14 | an-57 |
| 1581 | is-5 | ta-58 | sp-5 | an-58 | 3466 | is-14 | ta-58 | sp-14 | an-58 |
| 1582 | is-5 | ta-59 | sp-5 | an-59 | 3467 | is-14 | ta-59 | sp-14 | an-59 |
| 1583 | is-5 | ta-60 | sp-5 | an-60 | 3468 | is-14 | ta-60 | sp-14 | an-60 |
| 1584 | is-5 | ta-61 | sp-5 | an-61 | 3469 | is-14 | ta-61 | sp-14 | an-61 |
| 1585 | is-5 | ta-62 | sp-5 | an-62 | 3470 | is-14 | ta-62 | sp-14 | an-62 |
| 1586 | is-5 | ta-63 | sp-5 | an-63 | 3471 | is-14 | ta-63 | sp-14 | an-63 |
| 1587 | is-5 | ta-64 | sp-5 | an-64 | 3472 | is-14 | ta-64 | sp-14 | an-64 |
| 1588 | is-5 | ta-65 | sp-5 | an-65 | 3473 | is-14 | ta-65 | sp-14 | an-65 |
| 1589 | is-5 | ta-66 | sp-5 | an-66 | 3474 | is-14 | ta-66 | sp-14 | an-66 |
| 1590 | is-5 | ta-67 | sp-5 | an-67 | 3475 | is-14 | ta-67 | sp-14 | an-67 |
| 1591 | is-5 | ta-68 | sp-5 | an-68 | 3476 | is-14 | ta-68 | sp-14 | an-68 |
| 1592 | is-5 | ta-69 | sp-5 | an-69 | 3477 | is-14 | ta-69 | sp-14 | an-69 |
| 1593 | is-5 | ta-70 | sp-5 | an-70 | 3478 | is-14 | ta-70 | sp-14 | an-70 |
| 1594 | is-5 | ta-71 | sp-5 | an-71 | 3479 | is-14 | ta-71 | sp-14 | an-71 |
| 1595 | is-5 | ta-72 | sp-5 | an-72 | 3480 | is-14 | ta-72 | sp-14 | an-72 |
| 1596 | is-5 | ta-73 | sp-5 | an-73 | 3481 | is-14 | ta-73 | sp-14 | an-73 |
| 1597 | is-5 | ta-74 | sp-5 | an-74 | 3482 | is-14 | ta-74 | sp-14 | an-74 |
| 1598 | is-5 | ta-75 | sp-5 | an-75 | 3483 | is-14 | ta-75 | sp-14 | an-75 |
| 1599 | is-5 | ta-76 | sp-5 | an-76 | 3484 | is-14 | ta-76 | sp-14 | an-76 |
| 1600 | is-5 | ta-77 | sp-5 | an-77 | 3485 | is-14 | ta-77 | sp-14 | an-77 |
| 1601 | is-5 | ta-78 | sp-5 | an-78 | 3486 | is-14 | ta-78 | sp-14 | an-78 |
| 1602 | is-5 | ta-79 | sp-5 | an-79 | 3487 | is-14 | ta-79 | sp-14 | an-79 |
| 1603 | is-5 | ta-80 | sp-5 | an-80 | 3488 | is-14 | ta-80 | sp-14 | an-80 |
| 1604 | is-5 | ta-81 | sp-5 | an-81 | 3489 | is-14 | ta-81 | sp-14 | an-81 |
| 1605 | is-5 | ta-82 | sp-5 | an-82 | 3490 | is-14 | ta-82 | sp-14 | an-82 |
| | | | | Table 5-31 | | | | | |
| 1606 | is-5 | ta-83 | sp-5 | an-83 | 3491 | is-14 | ta-83 | sp-14 | an-83 |
| 1607 | is-5 | ta-84 | sp-5 | an-84 | 3492 | is-14 | ta-84 | sp-14 | an-84 |
| 1608 | is-5 | ta-85 | sp-5 | an-85 | 3493 | is-14 | ta-85 | sp-14 | an-85 |
| 1609 | is-5 | ta-86 | sp-5 | an-86 | 3494 | is-14 | ta-86 | sp-14 | an-86 |
| 1610 | is-5 | ta-87 | sp-5 | an-87 | 3495 | is-14 | ta-87 | sp-14 | an-87 |
| 1611 | is-5 | ta-88 | sp-5 | an-88 | 3496 | is-14 | ta-88 | sp-14 | an-88 |
| 1612 | is-5 | ta-89 | sp-5 | an-89 | 3497 | is-14 | ta-89 | sp-14 | an-89 |
| 1613 | is-5 | ta-90 | sp-5 | an-90 | 3498 | is-14 | ta-90 | sp-14 | an-90 |
| 1614 | is-5 | ta-91 | sp-5 | an-91 | 3499 | is-14 | ta-91 | sp-14 | an-91 |
| 1615 | is-5 | ta-92 | sp-5 | an-92 | 3500 | is-14 | ta-92 | sp-14 | an-92 |
| 1616 | is-5 | ta-93 | sp-5 | an-93 | 3501 | is-14 | ta-93 | sp-14 | an-93 |
| 1617 | is-5 | ta-94 | sp-5 | an-94 | 3502 | is-14 | ta-94 | sp-14 | an-94 |
| 1618 | is-5 | ta-95 | sp-5 | an-95 | 3503 | is-14 | ta-95 | sp-14 | an-95 |
| 1619 | is-5 | ta-96 | sp-5 | an-96 | 3504 | is-14 | ta-96 | sp-14 | an-96 |
| 1620 | is-5 | ta-97 | sp-5 | an-97 | 3505 | is-14 | ta-97 | sp-14 | an-97 |
| 1621 | is-5 | ta-98 | sp-5 | an-98 | 3506 | is-14 | ta-98 | sp-14 | an-98 |
| 1622 | is-5 | ta-99 | sp-5 | an-99 | 3507 | is-14 | ta-99 | sp-14 | an-99 |
| 1623 | is-5 | ta-100 | sp-5 | an-100 | 3508 | is-14 | ta-100 | sp-14 | an-100 |
| 1624 | is-5 | ta-101 | sp-5 | an-101 | 3509 | is-14 | ta-101 | sp-14 | an-101 |

-continued

| EXAMPLE | REAGENT | | PRODUCT | EXAMPLE | REAGENT | | PRODUCT |
|---|---|---|---|---|---|---|---|
| No. | is | ta | sp | an | No. | is | ta | sp | an |
| 1625 | is-5 | ta-102 | sp-5 | an-102 | 3510 | is-14 | ta-102 | sp-14 | an-102 |
| 1626 | is-5 | ta-103 | sp-5 | an-103 | 3511 | is-14 | ta-103 | sp-14 | an-103 |
| 1627 | is-5 | ta-104 | sp-5 | an-104 | 3512 | is-14 | ta-104 | sp-14 | an-104 |
| 1628 | is-5 | ta-105 | sp-5 | an-105 | 3513 | is-14 | ta-105 | sp-14 | an-105 |
| 1629 | is-5 | ta-106 | sp-5 | an-106 | 3514 | is-14 | ta-106 | sp-14 | an-106 |
| 1630 | is-5 | ta-107 | sp-5 | an-107 | 3515 | is-14 | ta-107 | sp-14 | an-107 |
| 1631 | is-5 | ta-108 | sp-5 | an-108 | 3516 | is-14 | ta-108 | sp-14 | an-108 |
| 1632 | is-5 | ta-109 | sp-5 | an-109 | 3517 | is-14 | ta-109 | sp-14 | an-109 |
| 1633 | is-5 | ta-110 | sp-5 | an-110 | 3518 | is-14 | ta-110 | sp-14 | an-110 |
| 1634 | is-5 | ta-111 | sp-5 | an-111 | 3519 | is-14 | ta-111 | sp-14 | an-111 |
| 1635 | is-5 | ta-112 | sp-5 | an-112 | 3520 | is-14 | ta-112 | sp-14 | an-112 |
| 1636 | is-5 | ta-113 | sp-5 | an-113 | 3521 | is-14 | ta-113 | sp-14 | an-113 |
| 1637 | is-5 | ta-114 | sp-5 | an-114 | 3522 | is-14 | ta-114 | sp-14 | an-114 |
| 1638 | is-5 | ta-115 | sp-5 | an-115 | 3523 | is-14 | ta-115 | sp-14 | an-115 |
| 1639 | is-5 | ta-116 | sp-5 | an-116 | 3524 | is-14 | ta-116 | sp-14 | an-116 |
| 1640 | is-5 | ta-117 | sp-5 | an-117 | 3525 | is-14 | ta-117 | sp-14 | an-117 |
| 1641 | is-5 | ta-118 | sp-5 | an-118 | 3526 | is-14 | ta-118 | sp-14 | an-118 |
| 1642 | is-5 | ta-119 | sp-5 | an-119 | 3527 | is-14 | ta-119 | sp-14 | an-119 |
| 1643 | is-5 | ta-120 | sp-5 | an-120 | 3528 | is-14 | ta-120 | sp-14 | an-120 |
| 1644 | is-5 | ta-121 | sp-5 | an-121 | 3529 | is-14 | ta-121 | sp-14 | an-121 |
| 1645 | is-5 | ta-122 | sp-5 | an-122 | 3530 | is-14 | ta-122 | sp-14 | an-122 |
| 1646 | is-5 | ta-123 | sp-5 | an-123 | 3531 | is-14 | ta-123 | sp-14 | an-123 |
| 1647 | is-5 | ta-124 | sp-5 | an-124 | 3532 | is-14 | ta-124 | sp-14 | an-124 |
| 1648 | is-5 | ta-125 | sp-5 | an-125 | 3533 | is-14 | ta-125 | sp-14 | an-125 |
| 1649 | is-5 | ta-126 | sp-5 | an-126 | 3534 | is-14 | ta-126 | sp-14 | an-126 |
| 1650 | is-5 | ta-127 | sp-5 | an-127 | 3535 | is-14 | ta-127 | sp-14 | an-127 |
| 1651 | is-5 | ta-128 | sp-5 | an-128 | 3536 | is-14 | ta-128 | sp-14 | an-128 |
| 1652 | is-5 | ta-129 | sp-5 | an-129 | 3537 | is-14 | ta-129 | sp-14 | an-129 |
| 1653 | is-5 | ta-130 | sp-5 | an-130 | 3538 | is-14 | ta-130 | sp-14 | an-130 |
| 1654 | is-5 | ta-131 | sp-5 | an-131 | 3539 | is-14 | ta-131 | sp-14 | an-131 |
| 1655 | is-5 | ta-132 | sp-5 | an-132 | 3540 | is-14 | ta-132 | sp-14 | an-132 |
| 1656 | is-5 | ta-133 | sp-5 | an-133 | 3541 | is-14 | ta-133 | sp-14 | an-133 |
| 1657 | is-5 | ta-134 | sp-5 | an-134 | 3542 | is-14 | ta-134 | sp-14 | an-134 |
| 1658 | is-5 | ta-135 | sp-5 | an-135 | 3543 | is-14 | ta-135 | sp-14 | an-135 |

Table 5-32

| 1659 | is-5 | ta-136 | sp-5 | an-136 | 3544 | is-14 | ta-136 | sp-14 | an-136 |
|---|---|---|---|---|---|---|---|---|---|
| 1660 | is-5 | ta-137 | sp-5 | an-137 | 3545 | is-14 | ta-137 | sp-14 | an-137 |
| 1661 | is-5 | ta-138 | sp-5 | an-138 | 3546 | is-14 | ta-138 | sp-14 | an-138 |
| 1662 | is-5 | ta-139 | sp-5 | an-139 | 3547 | is-14 | ta-139 | sp-14 | an-139 |
| 1663 | is-5 | ta-140 | sp-5 | an-140 | 3548 | is-14 | ta-140 | sp-14 | an-140 |
| 1664 | is-5 | ta-141 | sp-5 | an-141 | 3549 | is-14 | ta-141 | sp-14 | an-141 |
| 1665 | is-5 | ta-142 | sp-5 | an-142 | 3550 | is-14 | ta-142 | sp-14 | an-142 |
| 1666 | is-5 | ta-143 | sp-5 | an-143 | 3551 | is-14 | ta-143 | sp-14 | an-143 |
| 1667 | is-5 | ta-144 | sp-5 | an-144 | 3552 | is-14 | ta-144 | sp-14 | an-144 |
| 1668 | is-5 | ta-145 | sp-5 | an-145 | 3553 | is-14 | ta-145 | sp-14 | an-145 |
| 1669 | is-5 | ta-146 | sp-5 | an-146 | 3554 | is-14 | ta-146 | sp-14 | an-146 |
| 1670 | is-5 | ta-147 | sp-5 | an-147 | 3555 | is-14 | ta-147 | sp-14 | an-147 |
| 1671 | is-5 | ta-148 | sp-5 | an-148 | 3556 | is-14 | ta-148 | sp-14 | an-148 |
| 1672 | is-5 | ta-149 | sp-5 | an-149 | 3557 | is-14 | ta-149 | sp-14 | an-149 |
| 1673 | is-5 | ta-150 | sp-5 | an-150 | 3558 | is-14 | ta-150 | sp-14 | an-150 |
| 1674 | is-5 | ta-151 | sp-5 | an-151 | 3559 | is-14 | ta-151 | sp-14 | an-151 |
| 1675 | is-5 | ta-152 | sp-5 | an-152 | 3560 | is-14 | ta-152 | sp-14 | an-152 |
| 1676 | is-5 | ta-153 | sp-5 | an-153 | 3561 | is-14 | ta-153 | sp-14 | an-153 |
| 1677 | is-5 | ta-154 | sp-5 | an-154 | 3562 | is-14 | ta-154 | sp-14 | an-154 |
| 1678 | is-5 | ta-155 | sp-5 | an-155 | 3563 | is-14 | ta-155 | sp-14 | an-155 |
| 1679 | is-5 | ta-156 | sp-5 | an-156 | 3564 | is-14 | ta-156 | sp-14 | an-156 |
| 1680 | is-5 | ta-157 | sp-5 | an-157 | 3565 | is-14 | ta-157 | sp-14 | an-157 |
| 1681 | is-5 | ta-158 | sp-5 | an-158 | 3566 | is-14 | ta-158 | sp-14 | an-158 |
| 1682 | is-5 | ta-159 | sp-5 | an-159 | 3567 | is-14 | ta-159 | sp-14 | an-159 |
| 1683 | is-5 | ta-160 | sp-5 | an-160 | 3568 | is-14 | ta-160 | sp-14 | an-160 |
| 1684 | is-5 | ta-161 | sp-5 | an-161 | 3569 | is-14 | ta-161 | sp-14 | an-161 |
| 1685 | is-5 | ta-162 | sp-5 | an-162 | 3570 | is-14 | ta-162 | sp-14 | an-162 |
| 1686 | is-5 | ta-163 | sp-5 | an-163 | 3571 | is-14 | ta-163 | sp-14 | an-163 |
| 1687 | is-5 | ta-164 | sp-5 | an-164 | 3572 | is-14 | ta-164 | sp-14 | an-164 |
| 1688 | is-5 | ta-165 | sp-5 | an-165 | 3573 | is-14 | ta-165 | sp-14 | an-165 |
| 1689 | is-5 | ta-166 | sp-5 | an-166 | 3574 | is-14 | ta-166 | sp-14 | an-166 |
| 1690 | is-5 | ta-167 | sp-5 | an-167 | 3575 | is-14 | ta-167 | sp-14 | an-167 |
| 1691 | is-5 | ta-168 | sp-5 | an-168 | 3576 | is-14 | ta-168 | sp-14 | an-168 |
| 1692 | is-5 | ta-169 | sp-5 | an-169 | 3577 | is-14 | ta-169 | sp-14 | an-169 |
| 1693 | is-5 | ta-170 | sp-5 | an-170 | 3578 | is-14 | ta-170 | sp-14 | an-170 |
| 1694 | is-5 | ta-171 | sp-5 | an-171 | 3579 | is-14 | ta-171 | sp-14 | an-171 |
| 1695 | is-5 | ta-172 | sp-5 | an-172 | 3580 | is-14 | ta-172 | sp-14 | an-172 |
| 1696 | is-5 | ta-173 | sp-5 | an-173 | 3581 | is-14 | ta-173 | sp-14 | an-173 |
| 1697 | is-5 | ta-174 | sp-5 | an-174 | 3582 | is-14 | ta-174 | sp-14 | an-174 |
| 1698 | is-5 | ta-175 | sp-5 | an-175 | 3583 | is-14 | ta-175 | sp-14 | an-175 |

-continued

| EXAMPLE | REAGENT | | PRODUCT | EXAMPLE | REAGENT | | PRODUCT |
| --- | --- | --- | --- | --- | --- | --- | --- |
| No. | is | ta | sp | an | No. | is | ta | sp | an |
| 1699 | is-5 | ta-176 | sp-5 | an-176 | 3584 | is-14 | ta-176 | sp-14 | an-176 |
| 1700 | is-5 | ta-177 | sp-5 | an-177 | 3585 | is-14 | ta-177 | sp-14 | an-177 |
| 1701 | is-5 | ta-178 | sp-5 | an-178 | 3586 | is-14 | ta-178 | sp-14 | an-178 |
| 1702 | is-5 | ta-179 | sp-5 | an-179 | 3587 | is-14 | ta-179 | sp-14 | an-179 |
| 1703 | is-5 | ta-180 | sp-5 | an-180 | 3588 | is-14 | ta-180 | sp-14 | an-180 |
| 1704 | is-5 | ta-181 | sp-5 | an-181 | 3589 | is-14 | ta-181 | sp-14 | an-181 |
| 1705 | is-5 | ta-182 | sp-5 | an-182 | 3590 | is-14 | ta-182 | sp-14 | an-182 |
| 1706 | is-5 | ta-183 | sp-5 | an-183 | 3591 | is-14 | ta-183 | sp-14 | an-183 |
| 1707 | is-5 | ta-184 | sp-5 | an-184 | 3592 | is-14 | ta-184 | sp-14 | an-184 |
| 1708 | is-5 | ta-185 | sp-5 | an-185 | 3593 | is-14 | ta-185 | sp-14 | an-185 |
| 1709 | is-5 | ta-186 | sp-5 | an-186 | 3594 | is-14 | ta-186 | sp-14 | an-186 |
| 1710 | is-5 | ta-187 | sp-5 | an-187 | 3595 | is-14 | ta-187 | sp-14 | an-187 |
| 1711 | is-5 | ta-188 | sp-5 | an-188 | 3596 | is-14 | ta-188 | sp-14 | an-188 |

Table 5-33

| 1712 | is-5 | ta-189 | sp-5 | an-189 | 3597 | is-14 | ta-189 | sp-14 | an-189 |
| --- | --- | --- | --- | --- | --- | --- | --- | --- | --- |
| 1713 | is-5 | ta-190 | sp-5 | an-190 | 3598 | is-14 | ta-190 | sp-14 | an-190 |
| 1714 | is-5 | ta-191 | sp-5 | an-191 | 3599 | is-14 | ta-191 | sp-14 | an-191 |
| 1715 | is-5 | ta-192 | sp-5 | an-192 | 3600 | is-14 | ta-192 | sp-14 | an-192 |
| 1716 | is-5 | ta-193 | sp-5 | an-193 | 3601 | is-14 | ta-193 | sp-14 | an-193 |
| 1717 | is-5 | ta-194 | sp-5 | an-194 | 3602 | is-14 | ta-194 | sp-14 | an-194 |
| 1718 | is-5 | ta-195 | sp-5 | an-195 | 3603 | is-14 | ta-195 | sp-14 | an-195 |
| 1719 | is-5 | ta-196 | sp-5 | an-196 | 3604 | is-14 | ta-196 | sp-14 | an-196 |
| 1720 | is-5 | ta-197 | sp-5 | an-197 | 3605 | is-14 | ta-197 | sp-14 | an-197 |
| 1721 | is-5 | ta-198 | sp-5 | an-198 | 3606 | is-14 | ta-198 | sp-14 | an-198 |
| 1722 | is-5 | ta-199 | sp-5 | an-199 | 3607 | is-14 | ta-199 | sp-14 | an-199 |
| 1723 | is-5 | ta-200 | sp-5 | an-200 | 3608 | is-14 | ta-200 | sp-14 | an-200 |
| 1724 | is-5 | ta-201 | sp-5 | an-201 | 3609 | is-14 | ta-201 | sp-14 | an-201 |
| 1725 | is-5 | ta-202 | sp-5 | an-202 | 3610 | is-14 | ta-202 | sp-14 | an-202 |
| 1726 | is-5 | ta-203 | sp-5 | an-203 | 3611 | is-14 | ta-203 | sp-14 | an-203 |
| 1727 | is-5 | ta-204 | sp-5 | an-204 | 3612 | is-14 | ta-204 | sp-14 | an-204 |
| 1728 | is-5 | ta-205 | sp-5 | an-205 | 3613 | is-14 | ta-205 | sp-14 | an-205 |
| 1729 | is-5 | ta-206 | sp-5 | an-206 | 3614 | is-14 | ta-206 | sp-14 | an-206 |
| 1730 | is-5 | ta-207 | sp-5 | an-207 | 3615 | is-14 | ta-207 | sp-14 | an-207 |
| 1731 | is-5 | ta-208 | sp-5 | an-208 | 3616 | is-14 | ta-208 | sp-14 | an-208 |
| 1732 | is-5 | ta-209 | sp-5 | an-209 | 3617 | is-14 | ta-209 | sp-14 | an-209 |
| 1733 | is-5 | ta-210 | sp-5 | an-210 | 3618 | is-14 | ta-210 | sp-14 | an-210 |
| 1734 | is-5 | ta-211 | sp-5 | an-211 | 3619 | is-14 | ta-211 | sp-14 | an-211 |
| 1735 | is-5 | ta-212 | sp-5 | an-212 | 3620 | is-14 | ta-212 | sp-14 | an-212 |
| 1736 | is-5 | ta-213 | sp-5 | an-213 | 3621 | is-14 | ta-213 | sp-14 | an-213 |
| 1737 | is-5 | ta-214 | sp-5 | an-214 | 3622 | is-14 | ta-214 | sp-14 | an-214 |
| 1738 | is-5 | ta-215 | sp-5 | an-215 | 3623 | is-14 | ta-215 | sp-14 | an-215 |
| 1739 | is-5 | ta-216 | sp-5 | an-216 | 3624 | is-14 | ta-216 | sp-14 | an-216 |
| 1740 | is-5 | ta-217 | sp-5 | an-217 | 3625 | is-14 | ta-217 | sp-14 | an-217 |
| 1741 | is-5 | ta-218 | sp-5 | an-218 | 3626 | is-14 | ta-218 | sp-14 | an-218 |
| 1742 | is-5 | ta-219 | sp-5 | an-219 | 3627 | is-14 | ta-219 | sp-14 | an-219 |
| 1743 | is-5 | ta-220 | sp-5 | an-220 | 3628 | is-14 | ta-220 | sp-14 | an-220 |
| 1744 | is-5 | ta-221 | sp-5 | an-221 | 3629 | is-14 | ta-221 | sp-14 | an-221 |
| 1745 | is-5 | ta-222 | sp-5 | an-222 | 3630 | is-14 | ta-222 | sp-14 | an-222 |
| 1746 | is-5 | ta-223 | sp-5 | an-223 | 3631 | is-14 | ta-223 | sp-14 | an-223 |
| 1747 | is-5 | ta-224 | sp-5 | an-224 | 3632 | is-14 | ta-224 | sp-14 | an-224 |
| 1748 | is-5 | ta-225 | sp-5 | an-225 | 3633 | is-14 | ta-225 | sp-14 | an-225 |
| 1749 | is-5 | ta-226 | sp-5 | an-226 | 3634 | is-14 | ta-226 | sp-14 | an-226 |
| 1750 | is-5 | ta-227 | sp-5 | an-227 | 3635 | is-14 | ta-227 | sp-14 | an-227 |
| 1751 | is-5 | ta-228 | sp-5 | an-228 | 3636 | is-14 | ta-228 | sp-14 | an-228 |
| 1752 | is-5 | ta-229 | sp-5 | an-229 | 3637 | is-14 | ta-229 | sp-14 | an-229 |
| 1753 | is-5 | ta-230 | sp-5 | an-230 | 3638 | is-14 | ta-230 | sp-14 | an-230 |
| 1754 | is-5 | ta-231 | sp-5 | an-231 | 3639 | is-14 | ta-231 | sp-14 | an-231 |
| 1755 | is-5 | ta-232 | sp-5 | an-232 | 3640 | is-14 | ta-232 | sp-14 | an-232 |
| 1756 | is-5 | ta-233 | sp-5 | an-233 | 3641 | is-14 | ta-233 | sp-14 | an-233 |
| 1757 | is-5 | ta-234 | sp-5 | an-234 | 3642 | is-14 | ta-234 | sp-14 | an-234 |
| 1758 | is-5 | ta-235 | sp-5 | an-235 | 3643 | is-14 | ta-235 | sp-14 | an-235 |
| 1759 | is-5 | ta-236 | sp-5 | an-236 | 3644 | is-14 | ta-236 | sp-14 | an-236 |
| 1760 | is-5 | ta-237 | sp-5 | an-237 | 3645 | is-14 | ta-237 | sp-14 | an-237 |
| 1761 | is-5 | ta-238 | sp-5 | an-238 | 3646 | is-14 | ta-238 | sp-14 | an-238 |
| 1762 | is-5 | ta-239 | sp-5 | an-239 | 3647 | is-14 | ta-239 | sp-14 | an-239 |
| 1763 | is-5 | ta-240 | sp-5 | an-240 | 3648 | is-14 | ta-240 | sp-14 | an-240 |
| 1764 | is-5 | ta-241 | sp-5 | an-241 | 3649 | is-14 | ta-241 | sp-14 | an-241 |

Table 5-34

| 1765 | is-5 | ta-242 | sp-5 | an-242 | 3650 | is-14 | ta-242 | sp-14 | an-242 |
| --- | --- | --- | --- | --- | --- | --- | --- | --- | --- |
| 1766 | is-5 | ta-243 | sp-5 | an-243 | 3651 | is-14 | ta-243 | sp-14 | an-243 |
| 1767 | is-5 | ta-244 | sp-5 | an-244 | 3652 | is-14 | ta-244 | sp-14 | an-244 |
| 1768 | is-5 | ta-245 | sp-5 | an-245 | 3653 | is-14 | ta-245 | sp-14 | an-245 |
| 1769 | is-5 | ta-246 | sp-5 | an-246 | 3654 | is-14 | ta-246 | sp-14 | an-246 |
| 1770 | is-5 | ta-247 | sp-5 | an-247 | 3655 | is-14 | ta-247 | sp-14 | an-247 |

-continued

| EXAMPLE | REAGENT | | PRODUCT | EXAMPLE | REAGENT | | PRODUCT |
|---|---|---|---|---|---|---|---|
| No. | is | ta | sp | an | No. | is | ta | sp | an |
| 1771 | is-5 | ta-248 | sp-5 | an-248 | 3656 | is-14 | ta-248 | sp-14 | an-248 |
| 1772 | is-5 | ta-249 | sp-5 | an-249 | 3657 | is-14 | ta-249 | sp-14 | an-249 |
| 1773 | is-5 | ta-250 | sp-5 | an-250 | 3658 | is-14 | ta-250 | sp-14 | an-250 |
| 1774 | is-5 | ta-251 | sp-5 | an-251 | 3659 | is-14 | ta-251 | sp-14 | an-251 |
| 1775 | is-5 | ta-252 | sp-5 | an-252 | 3660 | is-14 | ta-252 | sp-14 | an-252 |
| 1776 | is-5 | ta-253 | sp-5 | an-253 | 3661 | is-14 | ta-253 | sp-14 | an-253 |
| 1777 | is-5 | ta-254 | sp-5 | an-254 | 3662 | is-14 | ta-254 | sp-14 | an-254 |
| 1778 | is-5 | ta-255 | sp-5 | an-255 | 3663 | is-14 | ta-255 | sp-14 | an-255 |
| 1779 | is-5 | ta-256 | sp-5 | an-256 | 3664 | is-14 | ta-256 | sp-14 | an-256 |
| 1780 | is-5 | ta-257 | sp-5 | an-257 | 3665 | is-14 | ta-257 | sp-14 | an-257 |
| 1781 | is-5 | ta-258 | sp-5 | an-258 | 3666 | is-14 | ta-258 | sp-14 | an-258 |
| 1782 | is-5 | ta-259 | sp-5 | an-259 | 3667 | is-14 | ta-259 | sp-14 | an-259 |
| 1783 | is-5 | ta-260 | sp-5 | an-260 | 3668 | is-14 | ta-260 | sp-14 | an-260 |
| 1784 | is-5 | ta-261 | sp-5 | an-261 | 3669 | is-14 | ta-261 | sp-14 | an-261 |
| 1785 | is-5 | ta-262 | sp-5 | an-262 | 3670 | is-14 | ta-262 | sp-14 | an-262 |
| 1786 | is-5 | ta-263 | sp-5 | an-263 | 3671 | is-14 | ta-263 | sp-14 | an-263 |
| 1787 | is-5 | ta-264 | sp-5 | an-264 | 3672 | is-14 | ta-264 | sp-14 | an-264 |
| 1788 | is-5 | ta-265 | sp-5 | an-265 | 3673 | is-14 | ta-265 | sp-14 | an-265 |
| 1789 | is-5 | ta-266 | sp-5 | an-266 | 3674 | is-14 | ta-266 | sp-14 | an-266 |
| 1790 | is-5 | ta-267 | sp-5 | an-267 | 3675 | is-14 | ta-267 | sp-14 | an-267 |
| 1791 | is-5 | ta-268 | sp-5 | an-268 | 3676 | is-14 | ta-268 | sp-14 | an-268 |
| 1792 | is-5 | ta-269 | sp-5 | an-269 | 3677 | is-14 | ta-269 | sp-14 | an-269 |
| 1793 | is-5 | ta-270 | sp-5 | an-270 | 3678 | is-14 | ta-270 | sp-14 | an-270 |
| 1794 | is-5 | ta-271 | sp-5 | an-271 | 3679 | is-14 | ta-271 | sp-14 | an-271 |
| 1795 | is-5 | ta-272 | sp-5 | an-272 | 3680 | is-14 | ta-272 | sp-14 | an-272 |
| 1796 | is-5 | ta-273 | sp-5 | an-273 | 3681 | is-14 | ta-273 | sp-14 | an-273 |
| 1797 | is-5 | ta-274 | sp-5 | an-274 | 3682 | is-14 | ta-274 | sp-14 | an-274 |
| 1798 | is-5 | ta-275 | sp-5 | an-275 | 3683 | is-14 | ta-275 | sp-14 | an-275 |
| 1799 | is-5 | ta-276 | sp-5 | an-276 | 3684 | is-14 | ta-276 | sp-14 | an-276 |
| 1800 | is-5 | ta-277 | sp-5 | an-277 | 3685 | is-14 | ta-277 | sp-14 | an-277 |
| 1801 | is-5 | ta-278 | sp-5 | an-278 | 3686 | is-14 | ta-278 | sp-14 | an-278 |
| 1802 | is-5 | ta-279 | sp-5 | an-279 | 3687 | is-14 | ta-279 | sp-14 | an-279 |
| 1803 | is-5 | ta-280 | sp-5 | an-280 | 3688 | is-14 | ta-280 | sp-14 | an-280 |
| 1804 | is-5 | ta-281 | sp-5 | an-281 | 3689 | is-14 | ta-281 | sp-14 | an-281 |
| 1805 | is-5 | ta-282 | sp-5 | an-282 | 3690 | is-14 | ta-282 | sp-14 | an-282 |
| 1806 | is-5 | ta-283 | sp-5 | an-283 | 3691 | is-14 | ta-283 | sp-14 | an-283 |
| 1807 | is-5 | ta-284 | sp-5 | an-284 | 3692 | is-14 | ta-284 | sp-14 | an-284 |
| 1808 | is-5 | ta-285 | sp-5 | an-285 | 3693 | is-14 | ta-285 | sp-14 | an-285 |
| 1809 | is-5 | ta-286 | sp-5 | an-286 | 3694 | is-14 | ta-286 | sp-14 | an-286 |
| 1810 | is-5 | ta-287 | sp-5 | an-287 | 3695 | is-14 | ta-287 | sp-14 | an-287 |
| 1811 | is-5 | ta-288 | sp-5 | an-288 | 3696 | is-14 | ta-288 | sp-14 | an-288 |
| 1812 | is-5 | ta-289 | sp-5 | an-289 | 3697 | is-14 | ta-289 | sp-14 | an-289 |
| 1813 | is-5 | ta-290 | sp-5 | an-290 | 3698 | is-14 | ta-290 | sp-14 | an-290 |
| 1814 | is-5 | ta-291 | sp-5 | an-291 | 3699 | is-14 | ta-291 | sp-14 | an-291 |
| 1815 | is-5 | ta-292 | sp-5 | an-292 | 3700 | is-14 | ta-292 | sp-14 | an-292 |
| 1816 | is-5 | ta-293 | sp-5 | an-293 | 3701 | is-14 | ta-293 | sp-14 | an-293 |
| 1817 | is-5 | ta-294 | sp-5 | an-294 | 3702 | is-14 | ta-294 | sp-14 | an-294 |

Table 5-35

| 1818 | is-5 | ta-295 | sp-5 | an-295 | 3703 | is-14 | ta-295 | sp-14 | an-295 |
|---|---|---|---|---|---|---|---|---|---|
| 1819 | is-5 | ta-296 | sp-5 | an-296 | 3704 | is-14 | ta-296 | sp-14 | an-296 |
| 1820 | is-5 | ta-297 | sp-5 | an-297 | 3705 | is-14 | ta-297 | sp-14 | an-297 |
| 1821 | is-5 | ta-298 | sp-5 | an-298 | 3706 | is-14 | ta-298 | sp-14 | an-298 |
| 1822 | is-5 | ta-299 | sp-5 | an-299 | 3707 | is-14 | ta-299 | sp-14 | an-299 |
| 1823 | is-5 | ta-300 | sp-5 | an-300 | 3708 | is-14 | ta-300 | sp-14 | an-300 |
| 1824 | is-5 | ta-301 | sp-5 | an-301 | 3709 | is-14 | ta-301 | sp-14 | an-301 |
| 1825 | is-5 | ta-302 | sp-5 | an-302 | 3710 | is-14 | ta-302 | sp-14 | an-302 |
| 1826 | is-5 | ta-303 | sp-5 | an-303 | 3711 | is-14 | ta-303 | sp-14 | an-303 |
| 1827 | is-5 | ta-304 | sp-5 | an-304 | 3712 | is-14 | ta-304 | sp-14 | an-304 |
| 1828 | is-5 | ta-305 | sp-5 | an-305 | 3713 | is-14 | ta-305 | sp-14 | an-305 |
| 1829 | is-5 | ta-306 | sp-5 | an-306 | 3714 | is-14 | ta-306 | sp-14 | an-306 |
| 1830 | is-5 | ta-307 | sp-5 | an-307 | 3715 | is-14 | ta-307 | sp-14 | an-307 |
| 1831 | is-5 | ta-308 | sp-5 | an-308 | 3716 | is-14 | ta-308 | sp-14 | an-308 |
| 1832 | is-5 | ta-309 | sp-5 | an-309 | 3717 | is-14 | ta-309 | sp-14 | an-309 |
| 1833 | is-5 | ta-310 | sp-5 | an-310 | 3718 | is-14 | ta-310 | sp-14 | an-310 |
| 1834 | is-5 | ta-311 | sp-5 | an-311 | 3719 | is-14 | ta-311 | sp-14 | an-311 |
| 1835 | is-5 | ta-312 | sp-5 | an-312 | 3720 | is-14 | ta-312 | sp-14 | an-312 |
| 1836 | is-5 | ta-313 | sp-5 | an-313 | 3721 | is-14 | ta-313 | sp-14 | an-313 |
| 1837 | is-5 | ta-314 | sp-5 | an-314 | 3722 | is-14 | ta-314 | sp-14 | an-314 |
| 1838 | is-5 | ta-315 | sp-5 | an-315 | 3723 | is-14 | ta-315 | sp-14 | an-315 |
| 1839 | is-5 | ta-316 | sp-5 | an-316 | 3724 | is-14 | ta-316 | sp-14 | an-316 |
| 1840 | is-5 | ta-317 | sp-5 | an-317 | 3725 | is-14 | ta-317 | sp-14 | an-317 |
| 1841 | is-5 | ta-318 | sp-5 | an-318 | 3726 | is-14 | ta-318 | sp-14 | an-318 |
| 1842 | is-5 | ta-319 | sp-5 | an-319 | 3727 | is-14 | ta-319 | sp-14 | an-319 |
| 1843 | is-5 | ta-320 | sp-5 | an-320 | 3728 | is-14 | ta-320 | sp-14 | an-320 |
| 1844 | is-5 | ta-321 | sp-5 | an-321 | 3729 | is-14 | ta-321 | sp-14 | an-321 |

-continued

| EXAMPLE | REAGENT | | PRODUCT | EXAMPLE | REAGENT | | PRODUCT |
|---|---|---|---|---|---|---|---|
| No. | is | ta | sp | an | No. | is | ta | sp | an |
| 1845 | is-5 | ta-322 | sp-5 | an-322 | 3730 | is-14 | ta-322 | sp-14 | an-322 |
| 1846 | is-5 | ta-323 | sp-5 | an-323 | 3731 | is-14 | ta-323 | sp-14 | an-323 |
| 1847 | is-5 | ta-324 | sp-5 | an-324 | 3732 | is-14 | ta-324 | sp-14 | an-324 |
| 1848 | is-5 | ta-325 | sp-5 | an-325 | 3733 | is-14 | ta-325 | sp-14 | an-325 |
| 1849 | is-5 | ta-326 | sp-5 | an-326 | 3734 | is-14 | ta-326 | sp-14 | an-326 |
| 1850 | is-5 | ta-327 | sp-5 | an-327 | 3735 | is-14 | ta-327 | sp-14 | an-327 |
| 1851 | is-5 | ta-328 | sp-5 | an-328 | 3736 | is-14 | ta-328 | sp-14 | an-328 |
| 1852 | is-5 | ta-329 | sp-5 | an-329 | 3737 | is-14 | ta-329 | sp-14 | an-329 |
| 1853 | is-5 | ta-330 | sp-5 | an-330 | 3738 | is-14 | ta-330 | sp-14 | an-330 |
| 1854 | is-5 | ta-331 | sp-5 | an-331 | 3739 | is-14 | ta-331 | sp-14 | an-331 |
| 1855 | is-5 | ta-332 | sp-5 | an-332 | 3740 | is-14 | ta-332 | sp-14 | an-332 |
| 1856 | is-5 | ta-333 | sp-5 | an-333 | 3741 | is-14 | ta-333 | sp-14 | an-333 |
| 1857 | is-5 | ta-334 | sp-5 | an-334 | 3742 | is-14 | ta-334 | sp-14 | an-334 |
| 1858 | is-5 | ta-335 | sp-5 | an-335 | 3743 | is-14 | ta-335 | sp-14 | an-335 |
| 1859 | is-5 | ta-336 | sp-5 | an-336 | 3744 | is-14 | ta-336 | sp-14 | an-336 |
| 1860 | is-5 | ta-337 | sp-5 | an-337 | 3745 | is-14 | ta-337 | sp-14 | an-337 |
| 1861 | is-5 | ta-338 | sp-5 | an-338 | 3746 | is-14 | ta-338 | sp-14 | an-338 |
| 1862 | is-5 | ta-339 | sp-5 | an-339 | 3747 | is-14 | ta-339 | sp-14 | an-339 |
| 1863 | is-5 | ta-340 | sp-5 | an-340 | 3748 | is-14 | ta-340 | sp-14 | an-340 |
| 1864 | is-5 | ta-341 | sp-5 | an-341 | 3749 | is-14 | ta-341 | sp-14 | an-341 |
| 1865 | is-5 | ta-342 | sp-5 | an-342 | 3750 | is-14 | ta-342 | sp-14 | an-342 |
| 1866 | is-5 | ta-343 | sp-5 | an-343 | 3751 | is-14 | ta-343 | sp-14 | an-343 |
| 1867 | is-5 | ta-344 | sp-5 | an-344 | 3752 | is-14 | ta-344 | sp-14 | an-344 |
| 1868 | is-5 | ta-345 | sp-5 | an-345 | 3753 | is-14 | ta-345 | sp-14 | an-345 |
| 1869 | is-5 | ta-346 | sp-5 | an-346 | 3754 | is-14 | ta-346 | sp-14 | an-346 |
| 1870 | is-5 | ta-347 | sp-5 | an-347 | 3755 | is-14 | ta-347 | sp-14 | an-347 |

Table 5-36

| EXAMPLE | REAGENT | | PRODUCT | EXAMPLE | REAGENT | | PRODUCT |
|---|---|---|---|---|---|---|---|
| 1871 | is-5 | ta-348 | sp-5 | an-348 | 3756 | is-14 | ta-348 | sp-14 | an-348 |
| 1872 | is-5 | ta-349 | sp-5 | an-349 | 3757 | is-14 | ta-349 | sp-14 | an-349 |
| 1873 | is-5 | ta-350 | sp-5 | an-350 | 3758 | is-14 | ta-350 | sp-14 | an-350 |
| 1874 | is-5 | ta-351 | sp-5 | an-351 | 3759 | is-14 | ta-351 | sp-14 | an-351 |
| 1875 | is-5 | ta-352 | sp-5 | an-352 | 3760 | is-14 | ta-352 | sp-14 | an-352 |
| 1876 | is-5 | ta-353 | sp-5 | an-353 | 3761 | is-14 | ta-353 | sp-14 | an-353 |
| 1877 | is-5 | ta-354 | sp-5 | an-354 | 3762 | is-14 | ta-354 | sp-14 | an-354 |
| 1878 | is-5 | ta-355 | sp-5 | an-355 | 3763 | is-14 | ta-355 | sp-14 | an-355 |
| 1879 | is-5 | ta-356 | sp-5 | an-356 | 3764 | is-14 | ta-356 | sp-14 | an-356 |
| 1880 | is-5 | ta-357 | sp-5 | an-357 | 3765 | is-14 | ta-357 | sp-14 | an-357 |
| 1881 | is-5 | ta-358 | sp-5 | an-358 | 3766 | is-14 | ta-358 | sp-14 | an-358 |
| 1882 | is-5 | ta-359 | sp-5 | an-359 | 3767 | is-14 | ta-359 | sp-14 | an-359 |
| 1883 | is-5 | ta-360 | sp-5 | an-360 | 3768 | is-14 | ta-360 | sp-14 | an-360 |
| 1884 | is-5 | ta-361 | sp-5 | an-361 | 3769 | is-14 | ta-361 | sp-14 | an-361 |
| 1885 | is-5 | ta-362 | sp-5 | an-362 | 3770 | is-14 | ta-362 | sp-14 | an-362 |
| 1886 | is-5 | ta-363 | sp-5 | an-363 | 3771 | is-14 | ta-363 | sp-14 | an-363 |
| 1887 | is-5 | ta-364 | sp-5 | an-364 | 3772 | is-14 | ta-364 | sp-14 | an-364 |
| 1888 | is-5 | ta-365 | sp-5 | an-365 | 3773 | is-14 | ta-365 | sp-14 | an-365 |
| 1889 | is-5 | ta-366 | sp-5 | an-366 | 3774 | is-14 | ta-366 | sp-14 | an-366 |
| 1890 | is-5 | ta-367 | sp-5 | an-367 | 3775 | is-14 | ta-367 | sp-14 | an-367 |
| 1891 | is-5 | ta-368 | sp-5 | an-368 | 3776 | is-14 | ta-368 | sp-14 | an-368 |
| 1892 | is-5 | ta-369 | sp-5 | an-369 | 3777 | is-14 | ta-369 | sp-14 | an-369 |
| 1893 | is-5 | ta-370 | sp-5 | an-370 | 3778 | is-14 | ta-370 | sp-14 | an-370 |
| 1894 | is-5 | ta-371 | sp-5 | an-371 | 3779 | is-14 | ta-371 | sp-14 | an-371 |
| 1895 | is-5 | ta-372 | sp-5 | an-372 | 3780 | is-14 | ta-372 | sp-14 | an-372 |
| 1896 | is-5 | ta-373 | sp-5 | an-373 | 3781 | is-14 | ta-373 | sp-14 | an-373 |
| 1897 | is-5 | ta-374 | sp-5 | an-374 | 3782 | is-14 | ta-374 | sp-14 | an-374 |
| 1898 | is-5 | ta-375 | sp-5 | an-375 | 3783 | is-14 | ta-375 | sp-14 | an-375 |
| 1899 | is-5 | ta-376 | sp-5 | an-376 | 3784 | is-14 | ta-376 | sp-14 | an-376 |
| 1900 | is-5 | ta-377 | sp-5 | an-377 | 3785 | is-14 | ta-377 | sp-14 | an-377 |
| 4067 | is-1 | ta-378 | sp-1 | an-378 | 4146 | is-6 | ta-378 | sp-6 | an-378 |
| 4068 | is-1 | ta-379 | sp-1 | an-379 | 4147 | is-6 | ta-379 | sp-6 | an-379 |
| 4069 | is-1 | ta-380 | sp-1 | an-380 | 4148 | is-6 | ta-380 | sp-6 | an-380 |
| 4070 | is-1 | ta-381 | sp-1 | an-381 | 4149 | is-6 | ta-381 | sp-6 | an-381 |
| 4071 | is-1 | ta-382 | sp-1 | an-382 | 4150 | is-6 | ta-382 | sp-6 | an-382 |
| 4072 | is-1 | ta-383 | sp-1 | an-383 | 4151 | is-6 | ta-383 | sp-6 | an-383 |
| 4073 | is-1 | ta-384 | sp-1 | an-384 | 4152 | is-6 | ta-384 | sp-6 | an-384 |
| 4074 | is-1 | ta-385 | sp-1 | an-385 | 4153 | is-6 | ta-385 | sp-6 | an-385 |
| 4075 | is-1 | ta-386 | sp-1 | an-386 | 4154 | is-6 | ta-386 | sp-6 | an-386 |
| 4076 | is-1 | ta-387 | sp-1 | an-387 | 4155 | is-6 | ta-387 | sp-6 | an-387 |
| 4077 | is-1 | ta-388 | sp-1 | an-388 | 4156 | is-6 | ta-388 | sp-6 | an-388 |
| 4078 | is-1 | ta-389 | sp-1 | an-389 | 4157 | is-6 | ta-389 | sp-6 | an-389 |
| 4079 | is-1 | ta-390 | sp-1 | an-390 | 4158 | is-6 | ta-390 | sp-6 | an-390 |
| 4080 | is-1 | ta-391 | sp-1 | an-391 | 4159 | is-6 | ta-391 | sp-6 | an-391 |
| 4081 | is-1 | ta-392 | sp-1 | an-392 | 4160 | is-6 | ta-392 | sp-6 | an-392 |
| 4082 | is-1 | ta-393 | sp-1 | an-393 | 4161 | is-6 | ta-393 | sp-6 | an-393 |
| 4083 | is-2 | ta-378 | sp-2 | an-378 | 4162 | is-7 | ta-378 | sp-7 | an-378 |
| 4084 | is-2 | ta-379 | sp-2 | an-379 | 4163 | is-7 | ta-379 | sp-7 | an-379 |

-continued

| EXAMPLE | REAGENT | | PRODUCT | EXAMPLE | REAGENT | | PRODUCT |
|---|---|---|---|---|---|---|---|
| No. | is | ta | sp | an | No. | is | ta | sp | an |
| 4085 | is-2 | ta-380 | sp-2 | an-380 | 4164 | is-7 | ta-380 | sp-7 | an-380 |
| 4086 | is-2 | ta-381 | sp-2 | an-381 | 4165 | is-7 | ta-381 | sp-7 | an-381 |
| 4087 | is-2 | ta-382 | sp-2 | an-382 | 4166 | is-7 | ta-382 | sp-7 | an-382 |
| 4088 | is-2 | ta-383 | sp-2 | an-383 | 4167 | is-7 | ta-383 | sp-7 | an-383 |
| 4089 | is-2 | ta-384 | sp-2 | an-384 | 4168 | is-7 | ta-384 | sp-7 | an-384 |

Table 5-37

| 4090 | is-2 | ta-385 | sp-2 | an-385 | 4169 | is-7 | ta-385 | sp-7 | an-385 |
|---|---|---|---|---|---|---|---|---|---|
| 4091 | is-2 | ta-386 | sp-2 | an-386 | 4170 | is-7 | ta-386 | sp-7 | an-386 |
| 4092 | is-2 | ta-387 | sp-2 | an-387 | 4171 | is-7 | ta-387 | sp-7 | an-387 |
| 4093 | is-2 | ta-388 | sp-2 | an-388 | 4172 | is-7 | ta-388 | sp-7 | an-388 |
| 4094 | is-2 | ta-389 | sp-2 | an-389 | 4173 | is-7 | ta-389 | sp-7 | an-389 |
| 4095 | is-2 | ta-390 | sp-2 | an-390 | 4174 | is-7 | ta-390 | sp-7 | an-390 |
| 4096 | is-2 | ta-391 | sp-2 | an-391 | 4175 | is-7 | ta-391 | sp-7 | an-391 |
| 4097 | is-2 | ta-392 | sp-2 | an-392 | 4176 | is-7 | ta-392 | sp-7 | an-392 |
| 4098 | is-2 | ta-393 | sp-2 | an-393 | 4177 | is-7 | ta-393 | sp-7 | an-393 |
| 4099 | is-3 | ta-378 | sp-3 | an-378 | 4178 | is-8 | ta-378 | sp-8 | an-378 |
| 4100 | is-3 | ta-379 | sp-3 | an-379 | 4179 | is-8 | ta-379 | sp-8 | an-379 |
| 4101 | is-3 | ta-380 | sp-3 | an-380 | 4180 | is-8 | ta-380 | sp-8 | an-380 |
| 4102 | is-3 | ta-381 | sp-3 | an-381 | 4181 | is-8 | ta-381 | sp-8 | an-381 |
| 4103 | is-3 | ta-382 | sp-3 | an-382 | 4182 | is-8 | ta-382 | sp-8 | an-382 |
| 4104 | is-3 | ta-383 | sp-3 | an-383 | 4183 | is-8 | ta-383 | sp-8 | an-383 |
| 4105 | is-3 | ta-384 | sp-3 | an-384 | 4184 | is-8 | ta-384 | sp-8 | an-384 |
| 4106 | is-3 | ta-385 | sp-3 | an-385 | 4185 | is-8 | ta-385 | sp-8 | an-385 |
| 4107 | is-3 | ta-386 | sp-3 | an-386 | 4186 | is-8 | ta-386 | sp-8 | an-386 |
| 4108 | is-3 | ta-387 | sp-3 | an-387 | 4187 | is-8 | ta-387 | sp-8 | an-387 |
| 4109 | is-3 | ta-388 | sp-3 | an-388 | 4188 | is-8 | ta-388 | sp-8 | an-388 |
| 4110 | is-3 | ta-389 | sp-3 | an-389 | 4189 | is-8 | ta-389 | sp-8 | an-389 |
| 4111 | is-3 | ta-390 | sp-3 | an-390 | 4190 | is-8 | ta-390 | sp-8 | an-390 |
| 4112 | is-3 | ta-391 | sp-3 | an-391 | 4191 | is-8 | ta-391 | sp-8 | an-391 |
| 4113 | is-3 | ta-392 | sp-3 | an-392 | 4192 | is-8 | ta-392 | sp-8 | an-392 |
| 4114 | is-3 | ta-393 | sp-3 | an-393 | 4193 | is-8 | ta-393 | sp-8 | an-393 |
| 4115 | is-4 | ta-378 | sp-4 | an-378 | 4194 | is-9 | ta-378 | sp-9 | an-378 |
| 4116 | is-4 | ta-379 | sp-4 | an-379 | 4195 | is-9 | ta-379 | sp-9 | an-379 |
| 4117 | is-4 | ta-380 | sp-4 | an-380 | 4196 | is-9 | ta-380 | sp-9 | an-380 |
| 4118 | is-4 | ta-381 | sp-4 | an-381 | 4197 | is-9 | ta-381 | sp-9 | an-381 |
| 4119 | is-4 | ta-382 | sp-4 | an-382 | 4198 | is-9 | ta-382 | sp-9 | an-382 |
| 4120 | is-4 | ta-383 | sp-4 | an-383 | 4199 | is-9 | ta-383 | sp-9 | an-383 |
| 4121 | is-4 | ta-384 | sp-4 | an-384 | 4200 | is-9 | ta-384 | sp-9 | an-384 |
| 4122 | is-4 | ta-385 | sp-4 | an-385 | 4201 | is-9 | ta-385 | sp-9 | an-385 |
| 4123 | is-4 | ta-386 | sp-4 | an-386 | 4202 | is-9 | ta-386 | sp-9 | an-386 |
| 4124 | is-4 | ta-387 | sp-4 | an-387 | 4203 | is-9 | ta-387 | sp-9 | an-387 |
| 4125 | is-4 | ta-388 | sp-4 | an-388 | 4204 | is-9 | ta-388 | sp-9 | an-388 |
| 4126 | is-4 | ta-389 | sp-4 | an-389 | 4205 | is-9 | ta-389 | sp-9 | an-389 |
| 4127 | is-4 | ta-390 | sp-4 | an-390 | 4206 | is-9 | ta-390 | sp-9 | an-390 |
| 4128 | is-4 | ta-391 | sp-4 | an-391 | 4207 | is-9 | ta-391 | sp-9 | an-391 |
| 4129 | is-4 | ta-392 | sp-4 | an-392 | 4208 | is-9 | ta-392 | sp-9 | an-392 |
| 4130 | is-4 | ta-393 | sp-4 | an-393 | 4209 | is-9 | ta-393 | sp-9 | an-393 |
| 4131 | is-5 | ta-378 | sp-5 | an-378 | 4210 | is-14 | ta-378 | sp-14 | an-378 |
| 4132 | is-5 | ta-379 | sp-5 | an-379 | 4211 | is-14 | ta-379 | sp-14 | an-379 |
| 4133 | is-5 | ta-380 | sp-5 | an-380 | 4212 | is-14 | ta-380 | sp-14 | an-380 |
| 4134 | is-5 | ta-381 | sp-5 | an-381 | 4213 | is-14 | ta-381 | sp-14 | an-381 |
| 4135 | is-5 | ta-382 | sp-5 | an-382 | 4214 | is-14 | ta-382 | sp-14 | an-382 |
| 4136 | is-5 | ta-383 | sp-5 | an-383 | 4215 | is-14 | ta-383 | sp-14 | an-383 |
| 4137 | is-5 | ta-384 | sp-5 | an-384 | 4216 | is-14 | ta-384 | sp-14 | an-384 |
| 4138 | is-5 | ta-385 | sp-5 | an-385 | 4217 | is-14 | ta-385 | sp-14 | an-385 |
| 4139 | is-5 | ta-386 | sp-5 | an-386 | 4218 | is-14 | ta-386 | sp-14 | an-386 |
| 4140 | is-5 | ta-387 | sp-5 | an-387 | 4219 | is-14 | ta-387 | sp-14 | an-387 |
| 4141 | is-5 | ta-388 | sp-5 | an-388 | 4220 | is-14 | ta-388 | sp-14 | an-388 |
| 4142 | is-5 | ta-389 | sp-5 | an-389 | 4221 | is-14 | ta-389 | sp-14 | an-389 |

Table 5-38

| 4143 | is-5 | ta-390 | sp-5 | an-390 | 4222 | is-14 | ta-390 | sp-14 | an-390 |
|---|---|---|---|---|---|---|---|---|---|
| 4144 | is-5 | ta-391 | sp-5 | an-391 | 4223 | is-14 | ta-391 | sp-14 | an-391 |
| 4145 | is-5 | ta-392 | sp-5 | an-392 | 4224 | is-14 | ta-392 | sp-14 | an-392 |
| 4146 | is-5 | ta-393 | sp-5 | an-393 | 4225 | is-14 | ta-393 | sp-14 | an-393 |
| 4226 | is-15 | ta-1 | sp-23 | an-1 | 4619 | is-16 | ta-1 | sp-24 | an-1 |
| 4227 | is-15 | ta-2 | sp-23 | an-2 | 4620 | is-16 | ta-2 | sp-24 | an-2 |
| 4228 | is-15 | ta-3 | sp-23 | an-3 | 4621 | is-16 | ta-3 | sp-24 | an-3 |
| 4229 | is-15 | ta-4 | sp-23 | an-4 | 4622 | is-16 | ta-4 | sp-24 | an-4 |
| 4230 | is-15 | ta-5 | sp-23 | an-5 | 4623 | is-16 | ta-5 | sp-24 | an-5 |
| 4231 | is-15 | ta-6 | sp-23 | an-6 | 4624 | is-16 | ta-6 | sp-24 | an-6 |
| 4232 | is-15 | ta-7 | sp-23 | an-7 | 4625 | is-16 | ta-7 | sp-24 | an-7 |
| 4233 | is-15 | ta-8 | sp-23 | an-8 | 4626 | is-16 | ta-8 | sp-24 | an-8 |
| 4234 | is-15 | ta-9 | sp-23 | an-9 | 4627 | is-16 | ta-9 | sp-24 | an-9 |
| 4235 | is-15 | ta-10 | sp-23 | an-10 | 4628 | is-16 | ta-10 | sp-24 | an-10 |

-continued

| EXAMPLE | REAGENT | | PRODUCT | EXAMPLE | REAGENT | | PRODUCT |
|---|---|---|---|---|---|---|---|
| No. | is | ta | sp an | No. | is | ta | sp an |
| 4236 | is-15 | ta-11 | sp-23 an-11 | 4629 | is-16 | ta-11 | sp-24 an-11 |
| 4237 | is-15 | ta-12 | sp-23 an-12 | 4630 | is-16 | ta-12 | sp-24 an-12 |
| 4238 | is-15 | ta-13 | sp-23 an-13 | 4631 | is-16 | ta-13 | sp-24 an-13 |
| 4239 | is-15 | ta-14 | sp-23 an-14 | 4632 | is-16 | ta-14 | sp-24 an-14 |
| 4240 | is-15 | ta-15 | sp-23 an-15 | 4633 | is-16 | ta-15 | sp-24 an-15 |
| 4241 | is-15 | ta-16 | sp-23 an-16 | 4634 | is-16 | ta-16 | sp-24 an-16 |
| 4242 | is-15 | ta-17 | sp-23 an-17 | 4635 | is-16 | ta-17 | sp-24 an-17 |
| 4243 | is-15 | ta-18 | sp-23 an-18 | 4636 | is-16 | ta-18 | sp-24 an-18 |
| 4244 | is-15 | ta-19 | sp-23 an-19 | 4637 | is-16 | ta-19 | sp-24 an-19 |
| 4245 | is-15 | ta-20 | sp-23 an-20 | 4638 | is-16 | ta-20 | sp-24 an-20 |
| 4246 | is-15 | ta-21 | sp-23 an-21 | 4639 | is-16 | ta-21 | sp-24 an-21 |
| 4247 | is-15 | ta-22 | sp-23 an-22 | 4640 | is-16 | ta-22 | sp-24 an-22 |
| 4248 | is-15 | ta-23 | sp-23 an-23 | 4641 | is-16 | ta-23 | sp-24 an-23 |
| 4249 | is-15 | ta-24 | sp-23 an-24 | 4642 | is-16 | ta-24 | sp-24 an-24 |
| 4250 | is-15 | ta-25 | sp-23 an-25 | 4643 | is-16 | ta-25 | sp-24 an-25 |
| 4251 | is-15 | ta-26 | sp-23 an-26 | 4644 | is-16 | ta-26 | sp-24 an-26 |
| 4252 | is-15 | ta-27 | sp-23 an-27 | 4645 | is-16 | ta-27 | sp-24 an-27 |
| 4253 | is-15 | ta-28 | sp-23 an-28 | 4646 | is-16 | ta-28 | sp-24 an-28 |
| 4254 | is-15 | ta-29 | sp-23 an-29 | 4647 | is-16 | ta-29 | sp-24 an-29 |
| 4255 | is-15 | ta-30 | sp-23 an-30 | 4648 | is-16 | ta-30 | sp-24 an-30 |
| 4256 | is-15 | ta-31 | sp-23 an-31 | 4649 | is-16 | ta-31 | sp-24 an-31 |
| 4257 | is-15 | ta-32 | sp-23 an-32 | 4650 | is-16 | ta-32 | sp-24 an-32 |
| 4258 | is-15 | ta-33 | sp-23 an-33 | 4651 | is-16 | ta-33 | sp-24 an-33 |
| 4259 | is-15 | ta-34 | sp-23 an-34 | 4652 | is-16 | ta-34 | sp-24 an-34 |
| 4260 | is-15 | ta-35 | sp-23 an-35 | 4653 | is-16 | ta-35 | sp-24 an-35 |
| 4261 | is-15 | ta-36 | sp-23 an-36 | 4654 | is-16 | ta-36 | sp-24 an-36 |
| 4262 | is-15 | ta-37 | sp-23 an-37 | 4655 | is-16 | ta-37 | sp-24 an-37 |
| 4263 | is-15 | ta-38 | sp-23 an-38 | 4656 | is-16 | ta-38 | sp-24 an-38 |
| 4264 | is-15 | ta-39 | sp-23 an-39 | 4657 | is-16 | ta-39 | sp-24 an-39 |
| 4265 | is-15 | ta-40 | sp-23 an-40 | 4658 | is-16 | ta-40 | sp-24 an-40 |
| 4266 | is-15 | ta-41 | sp-23 an-41 | 4659 | is-16 | ta-41 | sp-24 an-41 |
| 4267 | is-15 | ta-42 | sp-23 an-42 | 4660 | is-16 | ta-42 | sp-24 an-42 |
| 4268 | is-15 | ta-43 | sp-23 an-43 | 4661 | is-16 | ta-43 | sp-24 an-43 |
| 4269 | is-15 | ta-44 | sp-23 an-44 | 4662 | is-16 | ta-44 | sp-24 an-44 |
| 4270 | is-15 | ta-45 | sp-23 an-45 | 4663 | is-16 | ta-45 | sp-24 an-45 |
| 4271 | is-15 | ta-46 | sp-23 an-46 | 4664 | is-16 | ta-46 | sp-24 an-46 |
| 4272 | is-15 | ta-47 | sp-23 an-47 | 4665 | is-16 | ta-47 | sp-24 an-47 |
| 4273 | is-15 | ta-48 | sp-23 an-48 | 4666 | is-16 | ta-48 | sp-24 an-48 |
| 4274 | is-15 | ta-49 | sp-23 an-49 | 4667 | is-16 | ta-49 | sp-24 an-49 |

Table 5-39

| 4275 | is-15 | ta-50 | sp-23 an-50 | 4668 | is-16 | ta-50 | sp-24 an-50 |
|---|---|---|---|---|---|---|---|
| 4276 | is-15 | ta-51 | sp-23 an-51 | 4669 | is-16 | ta-51 | sp-24 an-51 |
| 4277 | is-15 | ta-52 | sp-23 an-52 | 4670 | is-16 | ta-52 | sp-24 an-52 |
| 4278 | is-15 | ta-53 | sp-23 an-53 | 4671 | is-16 | ta-53 | sp-24 an-53 |
| 4279 | is-15 | ta-54 | sp-23 an-54 | 4672 | is-16 | ta-54 | sp-24 an-54 |
| 4280 | is-15 | ta-55 | sp-23 an-55 | 4673 | is-16 | ta-55 | sp-24 an-55 |
| 4281 | is-15 | ta-56 | sp-23 an-56 | 4674 | is-16 | ta-56 | sp-24 an-56 |
| 4282 | is-15 | ta-57 | sp-23 an-57 | 4675 | is-16 | ta-57 | sp-24 an-57 |
| 4283 | is-15 | ta-58 | sp-23 an-58 | 4676 | is-16 | ta-58 | sp-24 an-58 |
| 4284 | is-15 | ta-59 | sp-23 an-59 | 4677 | is-16 | ta-59 | sp-24 an-59 |
| 4285 | is-15 | ta-60 | sp-23 an-60 | 4678 | is-16 | ta-60 | sp-24 an-60 |
| 4286 | is-15 | ta-61 | sp-23 an-61 | 4679 | is-16 | ta-61 | sp-24 an-61 |
| 4287 | is-15 | ta-62 | sp-23 an-62 | 4680 | is-16 | ta-62 | sp-24 an-62 |
| 4288 | is-15 | ta-63 | sp-23 an-63 | 4681 | is-16 | ta-63 | sp-24 an-63 |
| 4289 | is-15 | ta-64 | sp-23 an-64 | 4682 | is-16 | ta-64 | sp-24 an-64 |
| 4290 | is-15 | ta-65 | sp-23 an-65 | 4683 | is-16 | ta-65 | sp-24 an-65 |
| 4291 | is-15 | ta-66 | sp-23 an-66 | 4684 | is-16 | ta-66 | sp-24 an-66 |
| 4292 | is-15 | ta-67 | sp-23 an-67 | 4685 | is-16 | ta-67 | sp-24 an-67 |
| 4293 | is-15 | ta-68 | sp-23 an-68 | 4686 | is-16 | ta-68 | sp-24 an-68 |
| 4294 | is-15 | ta-69 | sp-23 an-69 | 4687 | is-16 | ta-69 | sp-24 an-69 |
| 4295 | is-15 | ta-70 | sp-23 an-70 | 4688 | is-16 | ta-70 | sp-24 an-70 |
| 4296 | is-15 | ta-71 | sp-23 an-71 | 4689 | is-16 | ta-71 | sp-24 an-71 |
| 4297 | is-15 | ta-72 | sp-23 an-72 | 4690 | is-16 | ta-72 | sp-24 an-72 |
| 4298 | is-15 | ta-73 | sp-23 an-73 | 4691 | is-16 | ta-73 | sp-24 an-73 |
| 4299 | is-15 | ta-74 | sp-23 an-74 | 4692 | is-16 | ta-74 | sp-24 an-74 |
| 4300 | is-15 | ta-75 | sp-23 an-75 | 4693 | is-16 | ta-75 | sp-24 an-75 |
| 4301 | is-15 | ta-76 | sp-23 an-76 | 4694 | is-16 | ta-76 | sp-24 an-76 |
| 4302 | is-15 | ta-77 | sp-23 an-77 | 4695 | is-16 | ta-77 | sp-24 an-77 |
| 4303 | is-15 | ta-78 | sp-23 an-78 | 4696 | is-16 | ta-78 | sp-24 an-78 |
| 4304 | is-15 | ta-79 | sp-23 an-79 | 4697 | is-16 | ta-79 | sp-24 an-79 |
| 4305 | is-15 | ta-80 | sp-23 an-80 | 4698 | is-16 | ta-80 | sp-24 an-80 |
| 4306 | is-15 | ta-81 | sp-23 an-81 | 4699 | is-16 | ta-81 | sp-24 an-81 |
| 4307 | is-15 | ta-82 | sp-23 an-82 | 4700 | is-16 | ta-82 | sp-24 an-82 |
| 4308 | is-15 | ta-83 | sp-23 an-83 | 4701 | is-16 | ta-83 | sp-24 an-83 |
| 4309 | is-15 | ta-84 | sp-23 an-84 | 4702 | is-16 | ta-84 | sp-24 an-84 |

-continued

| EXAMPLE | REAGENT | | PRODUCT | | EXAMPLE | REAGENT | | PRODUCT | |
|---|---|---|---|---|---|---|---|---|---|
| No. | is | ta | sp | an | No. | is | ta | sp | an |
| 4310 | is-15 | ta-85 | sp-23 | an-85 | 4703 | is-16 | ta-85 | sp-24 | an-85 |
| 4311 | is-15 | ta-86 | sp-23 | an-86 | 4704 | is-16 | ta-86 | sp-24 | an-86 |
| 4312 | is-15 | ta-87 | sp-23 | an-87 | 4705 | is-16 | ta-87 | sp-24 | an-87 |
| 4313 | is-15 | ta-88 | sp-23 | an-88 | 4706 | is-16 | ta-88 | sp-24 | an-88 |
| 4314 | is-15 | ta-89 | sp-23 | an-89 | 4707 | is-16 | ta-89 | sp-24 | an-89 |
| 4315 | is-15 | ta-90 | sp-23 | an-90 | 4708 | is-16 | ta-90 | sp-24 | an-90 |
| 4316 | is-15 | ta-91 | sp-23 | an-91 | 4709 | is-16 | ta-91 | sp-24 | an-91 |
| 4317 | is-15 | ta-92 | sp-23 | an-92 | 4710 | is-16 | ta-92 | sp-24 | an-92 |
| 4318 | is-15 | ta-93 | sp-23 | an-93 | 4711 | is-16 | ta-93 | sp-24 | an-93 |
| 4319 | is-15 | ta-94 | sp-23 | an-94 | 4712 | is-16 | ta-94 | sp-24 | an-94 |
| 4320 | is-15 | ta-95 | sp-23 | an-95 | 4713 | is-16 | ta-95 | sp-24 | an-95 |
| 4321 | is-15 | ta-96 | sp-23 | an-96 | 4714 | is-16 | ta-96 | sp-24 | an-96 |
| 4322 | is-15 | ta-97 | sp-23 | an-97 | 4715 | is-16 | ta-97 | sp-24 | an-97 |
| 4323 | is-15 | ta-98 | sp-23 | an-98 | 4716 | is-16 | ta-98 | sp-24 | an-98 |
| 4324 | is-15 | ta-99 | sp-23 | an-99 | 4717 | is-16 | ta-99 | sp-24 | an-99 |
| 4325 | is-15 | ta-100 | sp-23 | an-100 | 4718 | is-16 | ta-100 | sp-24 | an-100 |
| 4326 | is-15 | ta-101 | sp-23 | an-101 | 4719 | is-16 | ta-101 | sp-24 | an-101 |
| 4327 | is-15 | ta-102 | sp-23 | an-102 | 4720 | is-16 | ta-102 | sp-24 | an-102 |

Table 5-40

| EXAMPLE | REAGENT | | PRODUCT | | EXAMPLE | REAGENT | | PRODUCT | |
|---|---|---|---|---|---|---|---|---|---|
| 4328 | is-15 | ta-103 | sp-23 | an-103 | 4721 | is-16 | ta-103 | sp-24 | an-103 |
| 4329 | is-15 | ta-104 | sp-23 | an-104 | 4722 | is-16 | ta-104 | sp-24 | an-104 |
| 4330 | is-15 | ta-105 | sp-23 | an-105 | 4723 | is-16 | ta-105 | sp-24 | an-105 |
| 4331 | is-15 | ta-106 | sp-23 | an-106 | 4724 | is-16 | ta-106 | sp-24 | an-106 |
| 4332 | is-15 | ta-107 | sp-23 | an-107 | 4725 | is-16 | ta-107 | sp-24 | an-107 |
| 4333 | is-15 | ta-108 | sp-23 | an-108 | 4726 | is-16 | ta-108 | sp-24 | an-108 |
| 4334 | is-15 | ta-109 | sp-23 | an-109 | 4727 | is-16 | ta-109 | sp-24 | an-109 |
| 4335 | is-15 | ta-110 | sp-23 | an-110 | 4728 | is-16 | ta-110 | sp-24 | an-110 |
| 4336 | is-15 | ta-111 | sp-23 | an-111 | 4729 | is-16 | ta-111 | sp-24 | an-111 |
| 4337 | is-15 | ta-112 | sp-23 | an-112 | 4730 | is-16 | ta-112 | sp-24 | an-112 |
| 4338 | is-15 | ta-113 | sp-23 | an-113 | 4731 | is-16 | ta-113 | sp-24 | an-113 |
| 4339 | is-15 | ta-114 | sp-23 | an-114 | 4732 | is-16 | ta-114 | sp-24 | an-114 |
| 4340 | is-15 | ta-115 | sp-23 | an-115 | 4733 | is-16 | ta-115 | sp-24 | an-115 |
| 4341 | is-15 | ta-116 | sp-23 | an-116 | 4734 | is-16 | ta-116 | sp-24 | an-116 |
| 4342 | is-15 | ta-117 | sp-23 | an-117 | 4735 | is-16 | ta-117 | sp-24 | an-117 |
| 4343 | is-15 | ta-118 | sp-23 | an-118 | 4736 | is-16 | ta-118 | sp-24 | an-118 |
| 4344 | is-15 | ta-119 | sp-23 | an-119 | 4737 | is-16 | ta-119 | sp-24 | an-119 |
| 4345 | is-15 | ta-120 | sp-23 | an-120 | 4738 | is-16 | ta-120 | sp-24 | an-120 |
| 4346 | is-15 | ta-121 | sp-23 | an-121 | 4739 | is-16 | ta-121 | sp-24 | an-121 |
| 4347 | is-15 | ta-122 | sp-23 | an-122 | 4740 | is-16 | ta-122 | sp-24 | an-122 |
| 4348 | is-15 | ta-123 | sp-23 | an-123 | 4741 | is-16 | ta-123 | sp-24 | an-123 |
| 4349 | is-15 | ta-124 | sp-23 | an-124 | 4742 | is-16 | ta-124 | sp-24 | an-124 |
| 4350 | is-15 | ta-125 | sp-23 | an-125 | 4743 | is-16 | ta-125 | sp-24 | an-125 |
| 4351 | is-15 | ta-126 | sp-23 | an-126 | 4744 | is-16 | ta-126 | sp-24 | an-126 |
| 4352 | is-15 | ta-127 | sp-23 | an-127 | 4745 | is-16 | ta-127 | sp-24 | an-127 |
| 4353 | is-15 | ta-128 | sp-23 | an-128 | 4746 | is-16 | ta-128 | sp-24 | an-128 |
| 4354 | is-15 | ta-129 | sp-23 | an-129 | 4747 | is-16 | ta-129 | sp-24 | an-129 |
| 4355 | is-15 | ta-130 | sp-23 | an-130 | 4748 | is-16 | ta-130 | sp-24 | an-130 |
| 4356 | is-15 | ta-131 | sp-23 | an-131 | 4749 | is-16 | ta-131 | sp-24 | an-131 |
| 4357 | is-15 | ta-132 | sp-23 | an-132 | 4750 | is-16 | ta-132 | sp-24 | an-132 |
| 4358 | is-15 | ta-133 | sp-23 | an-133 | 4751 | is-16 | ta-133 | sp-24 | an-133 |
| 4359 | is-15 | ta-134 | sp-23 | an-134 | 4752 | is-16 | ta-134 | sp-24 | an-134 |
| 4360 | is-15 | ta-135 | sp-23 | an-135 | 4753 | is-16 | ta-135 | sp-24 | an-135 |
| 4361 | is-15 | ta-136 | sp-23 | an-136 | 4754 | is-16 | ta-136 | sp-24 | an-136 |
| 4362 | is-15 | ta-137 | sp-23 | an-137 | 4755 | is-16 | ta-137 | sp-24 | an-137 |
| 4363 | is-15 | ta-138 | sp-23 | an-138 | 4756 | is-16 | ta-138 | sp-24 | an-138 |
| 4364 | is-15 | ta-139 | sp-23 | an-139 | 4757 | is-16 | ta-139 | sp-24 | an-139 |
| 4365 | is-15 | ta-140 | sp-23 | an-140 | 4758 | is-16 | ta-140 | sp-24 | an-140 |
| 4366 | is-15 | ta-141 | sp-23 | an-141 | 4759 | is-16 | ta-141 | sp-24 | an-141 |
| 4367 | is-15 | ta-142 | sp-23 | an-142 | 4760 | is-16 | ta-142 | sp-24 | an-142 |
| 4368 | is-15 | ta-143 | sp-23 | an-143 | 4761 | is-16 | ta-143 | sp-24 | an-143 |
| 4369 | is-15 | ta-144 | sp-23 | an-144 | 4762 | is-16 | ta-144 | sp-24 | an-144 |
| 4370 | is-15 | ta-145 | sp-23 | an-145 | 4763 | is-16 | ta-145 | sp-24 | an-145 |
| 4371 | is-15 | ta-146 | sp-23 | an-146 | 4764 | is-16 | ta-146 | sp-24 | an-146 |
| 4372 | is-15 | ta-147 | sp-23 | an-147 | 4765 | is-16 | ta-147 | sp-24 | an-147 |
| 4373 | is-15 | ta-148 | sp-23 | an-148 | 4766 | is-16 | ta-148 | sp-24 | an-148 |
| 4374 | is-15 | ta-149 | sp-23 | an-149 | 4767 | is-16 | ta-149 | sp-24 | an-149 |
| 4375 | is-15 | ta-150 | sp-23 | an-150 | 4768 | is-16 | ta-150 | sp-24 | an-150 |
| 4376 | is-15 | ta-151 | sp-23 | an-151 | 4769 | is-16 | ta-151 | sp-24 | an-151 |
| 4377 | is-15 | ta-152 | sp-23 | an-152 | 4770 | is-16 | ta-152 | sp-24 | an-152 |
| 4378 | is-15 | ta-153 | sp-23 | an-153 | 4771 | is-16 | ta-153 | sp-24 | an-153 |
| 4379 | is-15 | ta-154 | sp-23 | an-154 | 4772 | is-16 | ta-154 | sp-24 | an-154 |
| 4380 | is-15 | ta-155 | sp-23 | an-155 | 4773 | is-16 | ta-155 | sp-24 | an-155 |

-continued

| EXAMPLE | REAGENT | | PRODUCT | | EXAMPLE | REAGENT | | PRODUCT | |
|---|---|---|---|---|---|---|---|---|---|
| No. | is | ta | sp | an | No. | is | ta | sp | an |
| Table 5-41 | | | | | | | | | |
| 4381 | is-15 | ta-156 | sp-23 | an-156 | 4774 | is-16 | ta-156 | sp-24 | an-156 |
| 4382 | is-15 | ta-157 | sp-23 | an-157 | 4775 | is-16 | ta-157 | sp-24 | an-157 |
| 4383 | is-15 | ta-158 | sp-23 | an-158 | 4776 | is-16 | ta-158 | sp-24 | an-158 |
| 4384 | is-15 | ta-159 | sp-23 | an-159 | 4777 | is-16 | ta-159 | sp-24 | an-159 |
| 4385 | is-15 | ta-160 | sp-23 | an-160 | 4778 | is-16 | ta-160 | sp-24 | an-160 |
| 4386 | is-15 | ta-161 | sp-23 | an-161 | 4779 | is-16 | ta-161 | sp-24 | an-161 |
| 4387 | is-15 | ta-162 | sp-23 | an-162 | 4780 | is-16 | ta-162 | sp-24 | an-162 |
| 4388 | is-15 | ta-163 | sp-23 | an-163 | 4781 | is-16 | ta-163 | sp-24 | an-163 |
| 4389 | is-15 | ta-164 | sp-23 | an-164 | 4782 | is-16 | ta-164 | sp-24 | an-164 |
| 4390 | is-15 | ta-165 | sp-23 | an-165 | 4783 | is-16 | ta-165 | sp-24 | an-165 |
| 4391 | is-15 | ta-166 | sp-23 | an-166 | 4784 | is-16 | ta-166 | sp-24 | an-166 |
| 4392 | is-15 | ta-167 | sp-23 | an-167 | 4785 | is-16 | ta-167 | sp-24 | an-167 |
| 4393 | is-15 | ta-168 | sp-23 | an-168 | 4786 | is-16 | ta-168 | sp-24 | an-168 |
| 4394 | is-15 | ta-169 | sp-23 | an-169 | 4787 | is-16 | ta-169 | sp-24 | an-169 |
| 4395 | is-15 | ta-170 | sp-23 | an-170 | 4788 | is-16 | ta-170 | sp-24 | an-170 |
| 4396 | is-15 | ta-171 | sp-23 | an-171 | 4789 | is-16 | ta-171 | sp-24 | an-171 |
| 4397 | is-15 | ta-172 | sp-23 | an-172 | 4790 | is-16 | ta-172 | sp-24 | an-172 |
| 4398 | is-15 | ta-173 | sp-23 | an-173 | 4791 | is-16 | ta-173 | sp-24 | an-173 |
| 4399 | is-15 | ta-174 | sp-23 | an-174 | 4792 | is-16 | ta-174 | sp-24 | an-174 |
| 4400 | is-15 | ta-175 | sp-23 | an-175 | 4793 | is-16 | ta-175 | sp-24 | an-175 |
| 4401 | is-15 | ta-176 | sp-23 | an-176 | 4794 | is-16 | ta-176 | sp-24 | an-176 |
| 4402 | is-15 | ta-177 | sp-23 | an-177 | 4795 | is-16 | ta-177 | sp-24 | an-177 |
| 4403 | is-15 | ta-178 | sp-23 | an-178 | 4796 | is-16 | ta-178 | sp-24 | an-178 |
| 4404 | is-15 | ta-179 | sp-23 | an-179 | 4797 | is-16 | ta-179 | sp-24 | an-179 |
| 4405 | is-15 | ta-180 | sp-23 | an-180 | 4798 | is-16 | ta-180 | sp-24 | an-180 |
| 4406 | is-15 | ta-181 | sp-23 | an-181 | 4799 | is-16 | ta-181 | sp-24 | an-181 |
| 4407 | is-15 | ta-182 | sp-23 | an-182 | 4800 | is-16 | ta-182 | sp-24 | an-182 |
| 4408 | is-15 | ta-183 | sp-23 | an-183 | 4801 | is-16 | ta-183 | sp-24 | an-183 |
| 4409 | is-15 | ta-184 | sp-23 | an-184 | 4802 | is-16 | ta-184 | sp-24 | an-184 |
| 4410 | is-15 | ta-185 | sp-23 | an-185 | 4803 | is-16 | ta-185 | sp-24 | an-185 |
| 4411 | is-15 | ta-186 | sp-23 | an-186 | 4804 | is-16 | ta-186 | sp-24 | an-186 |
| 4412 | is-15 | ta-187 | sp-23 | an-187 | 4805 | is-16 | ta-187 | sp-24 | an-187 |
| 4413 | is-15 | ta-188 | sp-23 | an-188 | 4806 | is-16 | ta-188 | sp-24 | an-188 |
| 4414 | is-15 | ta-189 | sp-23 | an-189 | 4807 | is-16 | ta-189 | sp-24 | an-189 |
| 4415 | is-15 | ta-190 | sp-23 | an-190 | 4808 | is-16 | ta-190 | sp-24 | an-190 |
| 4416 | is-15 | ta-191 | sp-23 | an-191 | 4809 | is-16 | ta-191 | sp-24 | an-191 |
| 4417 | is-15 | ta-192 | sp-23 | an-192 | 4810 | is-16 | ta-192 | sp-24 | an-192 |
| 4418 | is-15 | ta-193 | sp-23 | an-193 | 4811 | is-16 | ta-193 | sp-24 | an-193 |
| 4419 | is-15 | ta-194 | sp-23 | an-194 | 4812 | is-16 | ta-194 | sp-24 | an-194 |
| 4420 | is-15 | ta-195 | sp-23 | an-195 | 4813 | is-16 | ta-195 | sp-24 | an-195 |
| 4421 | is-15 | ta-196 | sp-23 | an-196 | 4814 | is-16 | ta-196 | sp-24 | an-196 |
| 4422 | is-15 | ta-197 | sp-23 | an-197 | 4815 | is-16 | ta-197 | sp-24 | an-197 |
| 4423 | is-15 | ta-198 | sp-23 | an-198 | 4816 | is-16 | ta-198 | sp-24 | an-198 |
| 4424 | is-15 | ta-199 | sp-23 | an-199 | 4817 | is-16 | ta-199 | sp-24 | an-199 |
| 4425 | is-15 | ta-200 | sp-23 | an-200 | 4818 | is-16 | ta-200 | sp-24 | an-200 |
| 4426 | is-15 | ta-201 | sp-23 | an-201 | 4819 | is-16 | ta-201 | sp-24 | an-201 |
| 4427 | is-15 | ta-202 | sp-23 | an-202 | 4820 | is-16 | ta-202 | sp-24 | an-202 |
| 4428 | is-15 | ta-203 | sp-23 | an-203 | 4821 | is-16 | ta-203 | sp-24 | an-203 |
| 4429 | is-15 | ta-204 | sp-23 | an-204 | 4822 | is-16 | ta-204 | sp-24 | an-204 |
| 4430 | is-15 | ta-205 | sp-23 | an-205 | 4823 | is-16 | ta-205 | sp-24 | an-205 |
| 4431 | is-15 | ta-206 | sp-23 | an-206 | 4824 | is-16 | ta-206 | sp-24 | an-206 |
| 4432 | is-15 | ta-207 | sp-23 | an-207 | 4825 | is-16 | ta-207 | sp-24 | an-207 |
| 4433 | is-15 | ta-208 | sp-23 | an-208 | 4826 | is-16 | ta-208 | sp-24 | an-208 |
| Table 5-42 | | | | | | | | | |
| 4434 | is-15 | ta-209 | sp-23 | an-209 | 4827 | is-16 | ta-209 | sp-24 | an-209 |
| 4435 | is-15 | ta-210 | sp-23 | an-210 | 4828 | is-16 | ta-210 | sp-24 | an-210 |
| 4436 | is-15 | ta-211 | sp-23 | an-211 | 4829 | is-16 | ta-211 | sp-24 | an-211 |
| 4437 | is-15 | ta-212 | sp-23 | an-212 | 4830 | is-16 | ta-212 | sp-24 | an-212 |
| 4438 | is-15 | ta-213 | sp-23 | an-213 | 4831 | is-16 | ta-213 | sp-24 | an-213 |
| 4439 | is-15 | ta-214 | sp-23 | an-214 | 4832 | is-16 | ta-214 | sp-24 | an-214 |
| 4440 | is-15 | ta-215 | sp-23 | an-215 | 4833 | is-16 | ta-215 | sp-24 | an-215 |
| 4441 | is-15 | ta-216 | sp-23 | an-216 | 4834 | is-16 | ta-216 | sp-24 | an-216 |
| 4442 | is-15 | ta-217 | sp-23 | an-217 | 4835 | is-16 | ta-217 | sp-24 | an-217 |
| 4443 | is-15 | ta-218 | sp-23 | an-218 | 4836 | is-16 | ta-218 | sp-24 | an-218 |
| 4444 | is-15 | ta-219 | sp-23 | an-219 | 4837 | is-16 | ta-219 | sp-24 | an-219 |
| 4445 | is-15 | ta-220 | sp-23 | an-220 | 4838 | is-16 | ta-220 | sp-24 | an-220 |
| 4446 | is-15 | ta-221 | sp-23 | an-221 | 4839 | is-16 | ta-221 | sp-24 | an-221 |
| 4447 | is-15 | ta-222 | sp-23 | an-222 | 4840 | is-16 | ta-222 | sp-24 | an-222 |
| 4448 | is-15 | ta-223 | sp-23 | an-223 | 4841 | is-16 | ta-223 | sp-24 | an-223 |
| 4449 | is-15 | ta-224 | sp-23 | an-224 | 4842 | is-16 | ta-224 | sp-24 | an-224 |
| 4450 | is-15 | ta-225 | sp-23 | an-225 | 4843 | is-16 | ta-225 | sp-24 | an-225 |
| 4451 | is-15 | ta-226 | sp-23 | an-226 | 4844 | is-16 | ta-226 | sp-24 | an-226 |
| 4452 | is-15 | ta-227 | sp-23 | an-227 | 4845 | is-16 | ta-227 | sp-24 | an-227 |

-continued

| EXAMPLE | REAGENT | | PRODUCT | | EXAMPLE | REAGENT | | PRODUCT | |
|---|---|---|---|---|---|---|---|---|---|
| No. | is | ta | sp | an | No. | is | ta | sp | an |
| 4453 | is-15 | ta-228 | sp-23 | an-228 | 4846 | is-16 | ta-228 | sp-24 | an-228 |
| 4454 | is-15 | ta-229 | sp-23 | an-229 | 4847 | is-16 | ta-229 | sp-24 | an-229 |
| 4455 | is-15 | ta-230 | sp-23 | an-230 | 4848 | is-16 | ta-230 | sp-24 | an-230 |
| 4456 | is-15 | ta-231 | sp-23 | an-231 | 4849 | is-16 | ta-231 | sp-24 | an-231 |
| 4457 | is-15 | ta-232 | sp-23 | an-232 | 4850 | is-16 | ta-232 | sp-24 | an-232 |
| 4458 | is-15 | ta-233 | sp-23 | an-233 | 4851 | is-16 | ta-233 | sp-24 | an-233 |
| 4459 | is-15 | ta-234 | sp-23 | an-234 | 4852 | is-16 | ta-234 | sp-24 | an-234 |
| 4460 | is-15 | ta-235 | sp-23 | an-235 | 4853 | is-16 | ta-235 | sp-24 | an-235 |
| 4461 | is-15 | ta-236 | sp-23 | an-236 | 4854 | is-16 | ta-236 | sp-24 | an-236 |
| 4462 | is-15 | ta-237 | sp-23 | an-237 | 4855 | is-16 | ta-237 | sp-24 | an-237 |
| 4463 | is-15 | ta-238 | sp-23 | an-238 | 4856 | is-16 | ta-238 | sp-24 | an-238 |
| 4464 | is-15 | ta-239 | sp-23 | an-239 | 4857 | is-16 | ta-239 | sp-24 | an-239 |
| 4465 | is-15 | ta-240 | sp-23 | an-240 | 4858 | is-16 | ta-240 | sp-24 | an-240 |
| 4466 | is-15 | ta-241 | sp-23 | an-241 | 4859 | is-16 | ta-241 | sp-24 | an-241 |
| 4467 | is-15 | ta-242 | sp-23 | an-242 | 4860 | is-16 | ta-242 | sp-24 | an-242 |
| 4468 | is-15 | ta-243 | sp-23 | an-243 | 4861 | is-16 | ta-243 | sp-24 | an-243 |
| 4469 | is-15 | ta-244 | sp-23 | an-244 | 4862 | is-16 | ta-244 | sp-24 | an-244 |
| 4470 | is-15 | ta-245 | sp-23 | an-245 | 4863 | is-16 | ta-245 | sp-24 | an-245 |
| 4471 | is-15 | ta-246 | sp-23 | an-246 | 4864 | is-16 | ta-246 | sp-24 | an-246 |
| 4472 | is-15 | ta-247 | sp-23 | an-247 | 4865 | is-16 | ta-247 | sp-24 | an-247 |
| 4473 | is-15 | ta-248 | sp-23 | an-248 | 4866 | is-16 | ta-248 | sp-24 | an-248 |
| 4474 | is-15 | ta-249 | sp-23 | an-249 | 4867 | is-16 | ta-249 | sp-24 | an-249 |
| 4475 | is-15 | ta-250 | sp-23 | an-250 | 4868 | is-16 | ta-250 | sp-24 | an-250 |
| 4476 | is-15 | ta-251 | sp-23 | an-251 | 4869 | is-16 | ta-251 | sp-24 | an-251 |
| 4477 | is-15 | ta-252 | sp-23 | an-252 | 4870 | is-16 | ta-252 | sp-24 | an-252 |
| 4478 | is-15 | ta-253 | sp-23 | an-253 | 4871 | is-16 | ta-253 | sp-24 | an-253 |
| 4479 | is-15 | ta-254 | sp-23 | an-254 | 4872 | is-16 | ta-254 | sp-24 | an-254 |
| 4480 | is-15 | ta-255 | sp-23 | an-255 | 4873 | is-16 | ta-255 | sp-24 | an-255 |
| 4481 | is-15 | ta-256 | sp-23 | an-256 | 4874 | is-16 | ta-256 | sp-24 | an-256 |
| 4482 | is-15 | ta-257 | sp-23 | an-257 | 4875 | is-16 | ta-257 | sp-24 | an-257 |
| 4483 | is-15 | ta-258 | sp-23 | an-258 | 4876 | is-16 | ta-258 | sp-24 | an-258 |
| 4484 | is-15 | ta-259 | sp-23 | an-259 | 4877 | is-16 | ta-259 | sp-24 | an-259 |
| 4485 | is-15 | ta-260 | sp-23 | an-260 | 4878 | is-16 | ta-260 | sp-24 | an-260 |
| 4486 | is-15 | ta-261 | sp-23 | an-261 | 4879 | is-16 | ta-261 | sp-24 | an-261 |

Table 5-43

| EXAMPLE | REAGENT | | PRODUCT | | EXAMPLE | REAGENT | | PRODUCT | |
|---|---|---|---|---|---|---|---|---|---|
| No. | is | ta | sp | an | No. | is | ta | sp | an |
| 4487 | is-15 | ta-262 | sp-23 | an-262 | 4880 | is-16 | ta-262 | sp-24 | an-262 |
| 4488 | is-15 | ta-263 | sp-23 | an-263 | 4881 | is-16 | ta-263 | sp-24 | an-263 |
| 4489 | is-15 | ta-264 | sp-23 | an-264 | 4882 | is-16 | ta-264 | sp-24 | an-264 |
| 4490 | is-15 | ta-265 | sp-23 | an-265 | 4883 | is-16 | ta-265 | sp-24 | an-265 |
| 4491 | is-15 | ta-266 | sp-23 | an-266 | 4884 | is-16 | ta-266 | sp-24 | an-266 |
| 4492 | is-15 | ta-267 | sp-23 | an-267 | 4885 | is-16 | ta-267 | sp-24 | an-267 |
| 4493 | is-15 | ta-268 | sp-23 | an-268 | 4886 | is-16 | ta-268 | sp-24 | an-268 |
| 4494 | is-15 | ta-269 | sp-23 | an-269 | 4887 | is-16 | ta-269 | sp-24 | an-269 |
| 4495 | is-15 | ta-270 | sp-23 | an-270 | 4888 | is-16 | ta-270 | sp-24 | an-270 |
| 4496 | is-15 | ta-271 | sp-23 | an-271 | 4889 | is-16 | ta-271 | sp-24 | an-271 |
| 4497 | is-15 | ta-272 | sp-23 | an-272 | 4890 | is-16 | ta-272 | sp-24 | an-272 |
| 4498 | is-15 | ta-273 | sp-23 | an-273 | 4891 | is-16 | ta-273 | sp-24 | an-273 |
| 4499 | is-15 | ta-274 | sp-23 | an-274 | 4892 | is-16 | ta-274 | sp-24 | an-274 |
| 4500 | is-15 | ta-275 | sp-23 | an-275 | 4893 | is-16 | ta-275 | sp-24 | an-275 |
| 4501 | is-15 | ta-276 | sp-23 | an-276 | 4894 | is-16 | ta-276 | sp-24 | an-276 |
| 4502 | is-15 | ta-277 | sp-23 | an-277 | 4895 | is-16 | ta-277 | sp-24 | an-277 |
| 4503 | is-15 | ta-278 | sp-23 | an-278 | 4896 | is-16 | ta-278 | sp-24 | an-278 |
| 4504 | is-15 | ta-279 | sp-23 | an-279 | 4897 | is-16 | ta-279 | sp-24 | an-279 |
| 4505 | is-15 | ta-280 | sp-23 | an-280 | 4898 | is-16 | ta-280 | sp-24 | an-280 |
| 4506 | is-15 | ta-281 | sp-23 | an-281 | 4899 | is-16 | ta-281 | sp-24 | an-281 |
| 4507 | is-15 | ta-282 | sp-23 | an-282 | 4900 | is-16 | ta-282 | sp-24 | an-282 |
| 4508 | is-15 | ta-283 | sp-23 | an-283 | 4901 | is-16 | ta-283 | sp-24 | an-283 |
| 4509 | is-15 | ta-284 | sp-23 | an-284 | 4902 | is-16 | ta-284 | sp-24 | an-284 |
| 4510 | is-15 | ta-285 | sp-23 | an-285 | 4903 | is-16 | ta-285 | sp-24 | an-285 |
| 4511 | is-15 | ta-286 | sp-23 | an-286 | 4904 | is-16 | ta-286 | sp-24 | an-286 |
| 4512 | is-15 | ta-287 | sp-23 | an-287 | 4905 | is-16 | ta-287 | sp-24 | an-287 |
| 4513 | is-15 | ta-288 | sp-23 | an-288 | 4906 | is-16 | ta-288 | sp-24 | an-288 |
| 4514 | is-15 | ta-289 | sp-23 | an-289 | 4907 | is-16 | ta-289 | sp-24 | an-289 |
| 4515 | is-15 | ta-290 | sp-23 | an-290 | 4908 | is-16 | ta-290 | sp-24 | an-290 |
| 4516 | is-15 | ta-291 | sp-23 | an-291 | 4909 | is-16 | ta-291 | sp-24 | an-291 |
| 4517 | is-15 | ta-292 | sp-23 | an-292 | 4910 | is-16 | ta-292 | sp-24 | an-292 |
| 4518 | is-15 | ta-293 | sp-23 | an-293 | 4911 | is-16 | ta-293 | sp-24 | an-293 |
| 4519 | is-15 | ta-294 | sp-23 | an-294 | 4912 | is-16 | ta-294 | sp-24 | an-294 |
| 4520 | is-15 | ta-295 | sp-23 | an-295 | 4913 | is-16 | ta-295 | sp-24 | an-295 |
| 4521 | is-15 | ta-296 | sp-23 | an-296 | 4914 | is-16 | ta-296 | sp-24 | an-296 |
| 4522 | is-15 | ta-297 | sp-23 | an-297 | 4915 | is-16 | ta-297 | sp-24 | an-297 |
| 4523 | is-15 | ta-298 | sp-23 | an-298 | 4916 | is-16 | ta-298 | sp-24 | an-298 |
| 4524 | is-15 | ta-299 | sp-23 | an-299 | 4917 | is-16 | ta-299 | sp-24 | an-299 |
| 4525 | is-15 | ta-300 | sp-23 | an-300 | 4918 | is-16 | ta-300 | sp-24 | an-300 |
| 4526 | is-15 | ta-301 | sp-23 | an-301 | 4919 | is-16 | ta-301 | sp-24 | an-301 |

-continued

| EXAMPLE | REAGENT | | PRODUCT | EXAMPLE | REAGENT | | PRODUCT | |
|---|---|---|---|---|---|---|---|---|
| No. | is | ta | sp | an | No. | is | ta | sp | an |
| 4527 | is-15 | ta-302 | sp-23 | an-302 | 4920 | is-16 | ta-302 | sp-24 | an-302 |
| 4528 | is-15 | ta-303 | sp-23 | an-303 | 4921 | is-16 | ta-303 | sp-24 | an-303 |
| 4529 | is-15 | ta-304 | sp-23 | an-304 | 4922 | is-16 | ta-304 | sp-24 | an-304 |
| 4530 | is-15 | ta-305 | sp-23 | an-305 | 4923 | is-16 | ta-305 | sp-24 | an-305 |
| 4531 | is-15 | ta-306 | sp-23 | an-306 | 4924 | is-16 | ta-306 | sp-24 | an-306 |
| 4532 | is-15 | ta-307 | sp-23 | an-307 | 4925 | is-16 | ta-307 | sp-24 | an-307 |
| 4533 | is-15 | ta-308 | sp-23 | an-308 | 4926 | is-16 | ta-308 | sp-24 | an-308 |
| 4534 | is-15 | ta-309 | sp-23 | an-309 | 4927 | is-16 | ta-309 | sp-24 | an-309 |
| 4535 | is-15 | ta-310 | sp-23 | an-310 | 4928 | is-16 | ta-310 | sp-24 | an-310 |
| 4536 | is-15 | ta-311 | sp-23 | an-311 | 4929 | is-16 | ta-311 | sp-24 | an-311 |
| 4537 | is-15 | ta-312 | sp-23 | an-312 | 4930 | is-16 | ta-312 | sp-24 | an-312 |
| 4538 | is-15 | ta-313 | sp-23 | an-313 | 4931 | is-16 | ta-313 | sp-24 | an-313 |
| 4539 | is-15 | ta-314 | sp-23 | an-314 | 4932 | is-16 | ta-314 | sp-24 | an-314 |
| | | | | Table 5-44 | | | | | |
| 4540 | is-15 | ta-315 | sp-23 | an-315 | 4933 | is-16 | ta-315 | sp-24 | an-315 |
| 4541 | is-15 | ta-316 | sp-23 | an-316 | 4934 | is-16 | ta-316 | sp-24 | an-316 |
| 4542 | is-15 | ta-317 | sp-23 | an-317 | 4935 | is-16 | ta-317 | sp-24 | an-317 |
| 4543 | is-15 | ta-318 | sp-23 | an-318 | 4936 | is-16 | ta-318 | sp-24 | an-318 |
| 4544 | is-15 | ta-319 | sp-23 | an-319 | 4937 | is-16 | ta-319 | sp-24 | an-319 |
| 4545 | is-15 | ta-320 | sp-23 | an-320 | 4938 | is-16 | ta-320 | sp-24 | an-320 |
| 4546 | is-15 | ta-321 | sp-23 | an-321 | 4939 | is-16 | ta-321 | sp-24 | an-321 |
| 4547 | is-15 | ta-322 | sp-23 | an-322 | 4940 | is-16 | ta-322 | sp-24 | an-322 |
| 4548 | is-15 | ta-323 | sp-23 | an-323 | 4941 | is-16 | ta-323 | sp-24 | an-323 |
| 4549 | is-15 | ta-324 | sp-23 | an-324 | 4942 | is-16 | ta-324 | sp-24 | an-324 |
| 4550 | is-15 | ta-325 | sp-23 | an-325 | 4943 | is-16 | ta-325 | sp-24 | an-325 |
| 4551 | is-15 | ta-326 | sp-23 | an-326 | 4944 | is-16 | ta-326 | sp-24 | an-326 |
| 4552 | is-15 | ta-327 | sp-23 | an-327 | 4945 | is-16 | ta-327 | sp-24 | an-327 |
| 4553 | is-15 | ta-328 | sp-23 | an-328 | 4946 | is-16 | ta-328 | sp-24 | an-328 |
| 4554 | is-15 | ta-329 | sp-23 | an-329 | 4947 | is-16 | ta-329 | sp-24 | an-329 |
| 4555 | is-15 | ta-330 | sp-23 | an-330 | 4948 | is-16 | ta-330 | sp-24 | an-330 |
| 4556 | is-15 | ta-331 | sp-23 | an-331 | 4949 | is-16 | ta-331 | sp-24 | an-331 |
| 4557 | is-15 | ta-332 | sp-23 | an-332 | 4950 | is-16 | ta-332 | sp-24 | an-332 |
| 4558 | is-15 | ta-333 | sp-23 | an-333 | 4951 | is-16 | ta-333 | sp-24 | an-333 |
| 4559 | is-15 | ta-334 | sp-23 | an-334 | 4952 | is-16 | ta-334 | sp-24 | an-334 |
| 4560 | is-15 | ta-335 | sp-23 | an-335 | 4953 | is-16 | ta-335 | sp-24 | an-335 |
| 4561 | is-15 | ta-336 | sp-23 | an-336 | 4954 | is-16 | ta-336 | sp-24 | an-336 |
| 4562 | is-15 | ta-337 | sp-23 | an-337 | 4955 | is-16 | ta-337 | sp-24 | an-337 |
| 4563 | is-15 | ta-338 | sp-23 | an-338 | 4956 | is-16 | ta-338 | sp-24 | an-338 |
| 4564 | is-15 | ta-339 | sp-23 | an-339 | 4957 | is-16 | ta-339 | sp-24 | an-339 |
| 4565 | is-15 | ta-340 | sp-23 | an-340 | 4958 | is-16 | ta-340 | sp-24 | an-340 |
| 4566 | is-15 | ta-341 | sp-23 | an-341 | 4959 | is-16 | ta-341 | sp-24 | an-341 |
| 4567 | is-15 | ta-342 | sp-23 | an-342 | 4960 | is-16 | ta-342 | sp-24 | an-342 |
| 4568 | is-15 | ta-343 | sp-23 | an-343 | 4961 | is-16 | ta-343 | sp-24 | an-343 |
| 4569 | is-15 | ta-344 | sp-23 | an-344 | 4962 | is-16 | ta-344 | sp-24 | an-344 |
| 4570 | is-15 | ta-345 | sp-23 | an-345 | 4963 | is-16 | ta-345 | sp-24 | an-345 |
| 4571 | is-15 | ta-346 | sp-23 | an-346 | 4964 | is-16 | ta-346 | sp-24 | an-346 |
| 4572 | is-15 | ta-347 | sp-23 | an-347 | 4965 | is-16 | ta-347 | sp-24 | an-347 |
| 4573 | is-15 | ta-348 | sp-23 | an-348 | 4966 | is-16 | ta-348 | sp-24 | an-348 |
| 4574 | is-15 | ta-349 | sp-23 | an-349 | 4967 | is-16 | ta-349 | sp-24 | an-349 |
| 4575 | is-15 | ta-350 | sp-23 | an-350 | 4968 | is-16 | ta-350 | sp-24 | an-350 |
| 4576 | is-15 | ta-351 | sp-23 | an-351 | 4969 | is-16 | ta-351 | sp-24 | an-351 |
| 4577 | is-15 | ta-352 | sp-23 | an-352 | 4970 | is-16 | ta-352 | sp-24 | an-352 |
| 4578 | is-15 | ta-353 | sp-23 | an-353 | 4971 | is-16 | ta-353 | sp-24 | an-353 |
| 4579 | is-15 | ta-354 | sp-23 | an-354 | 4972 | is-16 | ta-354 | sp-24 | an-354 |
| 4580 | is-15 | ta-355 | sp-23 | an-355 | 4973 | is-16 | ta-355 | sp-24 | an-355 |
| 4581 | is-15 | ta-356 | sp-23 | an-356 | 4974 | is-16 | ta-356 | sp-24 | an-356 |
| 4582 | is-15 | ta-357 | sp-23 | an-357 | 4975 | is-16 | ta-357 | sp-24 | an-357 |
| 4583 | is-15 | ta-358 | sp-23 | an-358 | 4976 | is-16 | ta-358 | sp-24 | an-358 |
| 4584 | is-15 | ta-359 | sp-23 | an-359 | 4977 | is-16 | ta-359 | sp-24 | an-359 |
| 4585 | is-15 | ta-360 | sp-23 | an-360 | 4978 | is-16 | ta-360 | sp-24 | an-360 |
| 4586 | is-15 | ta-361 | sp-23 | an-361 | 4979 | is-16 | ta-361 | sp-24 | an-361 |
| 4587 | is-15 | ta-362 | sp-23 | an-362 | 4980 | is-16 | ta-362 | sp-24 | an-362 |
| 4588 | is-15 | ta-363 | sp-23 | an-363 | 4981 | is-16 | ta-363 | sp-24 | an-363 |
| 4589 | is-15 | ta-364 | sp-23 | an-364 | 4982 | is-16 | ta-364 | sp-24 | an-364 |
| 4590 | is-15 | ta-365 | sp-23 | an-365 | 4983 | is-16 | ta-365 | sp-24 | an-365 |
| 4591 | is-15 | ta-366 | sp-23 | an-366 | 4984 | is-16 | ta-366 | sp-24 | an-366 |
| 4592 | is-15 | ta-367 | sp-23 | an-367 | 4985 | is-16 | ta-367 | sp-24 | an-367 |
| | | | | Table 5-45 | | | | | |
| 4593 | is-15 | ta-368 | sp-23 | an-368 | 4986 | is-16 | ta-368 | sp-24 | an-368 |
| 4594 | is-15 | ta-369 | sp-23 | an-369 | 4987 | is-16 | ta-369 | sp-24 | an-369 |
| 4595 | is-15 | ta-370 | sp-23 | an-370 | 4988 | is-16 | ta-370 | sp-24 | an-370 |
| 4596 | is-15 | ta-371 | sp-23 | an-371 | 4989 | is-16 | ta-371 | sp-24 | an-371 |
| 4597 | is-15 | ta-372 | sp-23 | an-372 | 4990 | is-16 | ta-372 | sp-24 | an-372 |
| 4598 | is-15 | ta-373 | sp-23 | an-373 | 4991 | is-16 | ta-373 | sp-24 | an-373 |

-continued

| EXAMPLE | REAGENT | | PRODUCT | | EXAMPLE | REAGENT | | PRODUCT | |
|---|---|---|---|---|---|---|---|---|---|
| No. | is | ta | sp | an | No. | is | ta | sp | an |
| 4599 | is-15 | ta-374 | sp-23 | an-374 | 4992 | is-16 | ta-374 | sp-24 | an-374 |
| 4600 | is-15 | ta-375 | sp-23 | an-375 | 4993 | is-16 | ta-375 | sp-24 | an-375 |
| 4601 | is-15 | ta-376 | sp-23 | an-376 | 4994 | is-16 | ta-376 | sp-24 | an-376 |
| 4602 | is-15 | ta-377 | sp-23 | an-377 | 4995 | is-16 | ta-377 | sp-24 | an-377 |
| 4603 | is-15 | ta-378 | sp-23 | an-378 | 4996 | is-16 | ta-378 | sp-24 | an-378 |
| 4604 | is-15 | ta-379 | sp-23 | an-379 | 4997 | is-16 | ta-379 | sp-24 | an-379 |
| 4605 | is-15 | ta-380 | sp-23 | an-380 | 4998 | is-16 | ta-380 | sp-24 | an-380 |
| 4606 | is-15 | ta-381 | sp-23 | an-381 | 4999 | is-16 | ta-381 | sp-24 | an-381 |
| 4607 | is-15 | ta-382 | sp-23 | an-382 | 5000 | is-16 | ta-382 | sp-24 | an-382 |
| 4608 | is-15 | ta-383 | sp-23 | an-383 | 5001 | is-16 | ta-383 | sp-24 | an-383 |
| 4609 | is-15 | ta-384 | sp-23 | an-384 | 5002 | is-16 | ta-384 | sp-24 | an-384 |
| 4610 | is-15 | ta-385 | sp-23 | an-385 | 5003 | is-16 | ta-385 | sp-24 | an-385 |
| 4611 | is-15 | ta-386 | sp-23 | an-386 | 5004 | is-16 | ta-386 | sp-24 | an-386 |
| 4612 | is-15 | ta-387 | sp-23 | an-387 | 5005 | is-16 | ta-387 | sp-24 | an-387 |
| 4613 | is-15 | ta-388 | sp-23 | an-388 | 5006 | is-16 | ta-388 | sp-24 | an-388 |
| 4614 | is-15 | ta-389 | sp-23 | an-389 | 5007 | is-16 | ta-389 | sp-24 | an-389 |
| 4615 | is-15 | ta-390 | sp-23 | an-390 | 5008 | is-16 | ta-390 | sp-24 | an-390 |
| 4616 | is-15 | ta-391 | sp-23 | an-391 | 5009 | is-16 | ta-391 | sp-24 | an-391 |
| 4617 | is-15 | ta-392 | sp-23 | an-392 | 5010 | is-16 | ta-392 | sp-24 | an-392 |
| 4618 | is-15 | ta-393 | sp-23 | an-393 | 5011 | is-16 | ta-393 | sp-24 | an-393 |
| 5012 | is-17 | ta-1 | sp-25 | an-1 | 5407 | is-14 | ta-394 | sp-14 | an-394 |
| 5013 | is-17 | ta-2 | sp-25 | an-2 | 5408 | is-14 | ta-395 | sp-14 | an-395 |
| 5014 | is-17 | ta-3 | sp-25 | an-3 | 5409 | is-14 | ta-396 | sp-14 | an-396 |
| 5015 | is-17 | ta-4 | sp-25 | an-4 | 5410 | is-14 | ta-397 | sp-14 | an-397 |
| 5016 | is-17 | ta-5 | sp-25 | an-5 | 5411 | is-14 | ta-398 | sp-14 | an-398 |
| 5017 | is-17 | ta-6 | sp-25 | an-6 | 5412 | is-14 | ta-399 | sp-14 | an-399 |
| 5018 | is-17 | ta-7 | sp-25 | an-7 | 5413 | is-14 | ta-400 | sp-14 | an-400 |
| 5019 | is-17 | ta-8 | sp-25 | an-8 | 5414 | is-14 | ta-401 | sp-14 | an-401 |
| 5020 | is-17 | ta-9 | sp-25 | an-9 | 5415 | is-14 | ta-402 | sp-14 | an-402 |
| 5021 | is-17 | ta-10 | sp-25 | an-10 | 5416 | is-14 | ta-403 | sp-14 | an-403 |
| 5022 | is-17 | ta-11 | sp-25 | an-11 | 5417 | is-14 | ta-404 | sp-14 | an-404 |
| 5023 | is-17 | ta-12 | sp-25 | an-12 | 5418 | is-14 | ta-405 | sp-14 | an-405 |
| 5024 | is-17 | ta-13 | sp-25 | an-13 | 5419 | is-14 | ta-406 | sp-14 | an-406 |
| 5025 | is-17 | ta-14 | sp-25 | an-14 | 5420 | is-14 | ta-407 | sp-14 | an-407 |
| 5026 | is-17 | ta-15 | sp-25 | an-15 | 5421 | is-15 | ta-394 | sp-23 | an-394 |
| 5027 | is-17 | ta-16 | sp-25 | an-16 | 5422 | is-15 | ta-395 | sp-23 | an-395 |
| 5028 | is-17 | ta-17 | sp-25 | an-17 | 5423 | is-15 | ta-396 | sp-23 | an-396 |
| 5029 | is-17 | ta-18 | sp-25 | an-18 | 5424 | is-15 | ta-397 | sp-23 | an-397 |
| 5030 | is-17 | ta-19 | sp-25 | an-19 | 5425 | is-15 | ta-398 | sp-23 | an-398 |
| 5031 | is-17 | ta-20 | sp-25 | an-20 | 5426 | is-15 | ta-399 | sp-23 | an-399 |
| 5032 | is-17 | ta-21 | sp-25 | an-21 | 5427 | is-15 | ta-400 | sp-23 | an-400 |
| 5033 | is-17 | ta-22 | sp-25 | an-22 | 5428 | is-15 | ta-401 | sp-23 | an-401 |
| 5034 | is-17 | ta-23 | sp-25 | an-23 | 5429 | is-15 | ta-402 | sp-23 | an-402 |
| 5035 | is-17 | ta-24 | sp-25 | an-24 | 5430 | is-15 | ta-403 | sp-23 | an-403 |
| 5036 | is-17 | ta-25 | sp-25 | an-25 | 5431 | is-15 | ta-404 | sp-23 | an-404 |
| 5037 | is-17 | ta-26 | sp-25 | an-26 | 5432 | is-15 | ta-405 | sp-23 | an-405 |
| 5038 | is-17 | ta-27 | sp-25 | an-27 | 5433 | is-15 | ta-406 | sp-23 | an-406 |

Table 5-46

| 5039 | is-17 | ta-28 | sp-25 | an-28 | 5434 | is-15 | ta-407 | sp-23 | an-407 |
|---|---|---|---|---|---|---|---|---|---|
| 5040 | is-17 | ta-29 | sp-25 | an-29 | 5435 | is-17 | ta-394 | sp-25 | an-394 |
| 5041 | is-17 | ta-30 | sp-25 | an-30 | 5436 | is-17 | ta-395 | sp-25 | an-395 |
| 5042 | is-17 | ta-31 | sp-25 | an-31 | 5437 | is-17 | ta-396 | sp-25 | an-396 |
| 5043 | is-17 | ta-32 | sp-25 | an-32 | 5438 | is-17 | ta-397 | sp-25 | an-397 |
| 5044 | is-17 | ta-33 | sp-25 | an-33 | 5439 | is-17 | ta-398 | sp-25 | an-398 |
| 5045 | is-17 | ta-34 | sp-25 | an-34 | 5440 | is-17 | ta-399 | sp-25 | an-399 |
| 5046 | is-17 | ta-35 | sp-25 | an-35 | 5441 | is-17 | ta-400 | sp-25 | an-400 |
| 5047 | is-17 | ta-36 | sp-25 | an-36 | 5442 | is-17 | ta-401 | sp-25 | an-401 |
| 5048 | is-17 | ta-37 | sp-25 | an-37 | 5443 | is-17 | ta-402 | sp-25 | an-402 |
| 5049 | is-17 | ta-38 | sp-25 | an-38 | 5444 | is-17 | ta-403 | sp-25 | an-403 |
| 5050 | is-17 | ta-39 | sp-25 | an-39 | 5445 | is-17 | ta-404 | sp-25 | an-404 |
| 5051 | is-17 | ta-40 | sp-25 | an-40 | 5446 | is-17 | ta-405 | sp-25 | an-405 |
| 5052 | is-17 | ta-41 | sp-25 | an-41 | 5447 | is-17 | ta-406 | sp-25 | an-406 |
| 5053 | is-17 | ta-42 | sp-25 | an-42 | 5448 | is-17 | ta-407 | sp-25 | an-407 |
| 5054 | is-17 | ta-43 | sp-25 | an-43 | | | | | |
| 5055 | is-17 | ta-44 | sp-25 | an-44 | | | | | |
| 5056 | is-17 | ta-45 | sp-25 | an-45 | | | | | |
| 5057 | is-17 | ta-46 | sp-25 | an-46 | | | | | |
| 5058 | is-17 | ta-47 | sp-25 | an-47 | | | | | |
| 5059 | is-17 | ta-48 | sp-25 | an-48 | | | | | |
| 5060 | is-17 | ta-49 | sp-25 | an-49 | | | | | |
| 5061 | is-17 | ta-50 | sp-25 | an-50 | | | | | |
| 5062 | is-17 | ta-51 | sp-25 | an-51 | | | | | |
| 5063 | is-17 | ta-52 | sp-25 | an-52 | | | | | |
| 5064 | is-17 | ta-53 | sp-25 | an-53 | | | | | |
| 5065 | is-17 | ta-54 | sp-25 | an-54 | | | | | |

-continued

| EXAMPLE | REAGENT | | PRODUCT | EXAMPLE | REAGENT | | PRODUCT |
|---|---|---|---|---|---|---|---|
| No. | is | ta | sp an | No. | is | ta | sp an |
| 5066 | is-17 | ta-55 | sp-25 an-55 | | | | |
| 5067 | is-17 | ta-56 | sp-25 an-56 | | | | |
| 5068 | is-17 | ta-57 | sp-25 an-57 | | | | |
| 5069 | is-17 | ta-58 | sp-25 an-58 | | | | |
| 5070 | is-17 | ta-59 | sp-25 an-59 | | | | |
| 5071 | is-17 | ta-60 | sp-25 an-60 | | | | |
| 5072 | is-17 | ta-61 | sp-25 an-61 | | | | |
| 5073 | is-17 | ta-62 | sp-25 an-62 | | | | |
| 5074 | is-17 | ta-63 | sp-25 an-63 | | | | |
| 5075 | is-17 | ta-64 | sp-25 an-64 | | | | |
| 5076 | is-17 | ta-65 | sp-25 an-65 | | | | |
| 5077 | is-17 | ta-66 | sp-25 an-66 | | | | |
| 5078 | is-17 | ta-67 | sp-25 an-67 | | | | |
| 5079 | is-17 | ta-68 | sp-25 an-68 | | | | |
| 5080 | is-17 | ta-69 | sp-25 an-69 | | | | |
| 5081 | is-17 | ta-70 | sp-25 an-70 | | | | |
| 5082 | is-17 | ta-71 | sp-25 an-71 | | | | |
| 5083 | is-17 | ta-72 | sp-25 an-72 | | | | |
| 5084 | is-17 | ta-73 | sp-25 an-73 | | | | |
| 5085 | is-17 | ta-74 | sp-25 an-74 | | | | |
| 5086 | is-17 | ta-75 | sp-25 an-75 | | | | |
| 5087 | is-17 | ta-76 | sp-25 an-76 | | | | |
| 5088 | is-17 | ta-77 | sp-25 an-77 | | | | |
| 5089 | is-17 | ta-78 | sp-25 an-78 | | | | |
| 5090 | is-17 | ta-79 | sp-25 an-79 | | | | |
| 5091 | is-17 | ta-80 | sp-25 an-80 | | | | |

Table 5-47

| EXAMPLE | REAGENT | | PRODUCT |
|---|---|---|---|
| No. | is | ta | sp an |
| 5092 | is-17 | ta-81 | sp-25 an-81 |
| 5093 | is-17 | ta-82 | sp-25 an-82 |
| 5094 | is-17 | ta-83 | sp-25 an-83 |
| 5095 | is-17 | ta-84 | sp-25 an-84 |
| 5096 | is-17 | ta-85 | sp-25 an-85 |
| 5097 | is-17 | ta-86 | sp-25 an-86 |
| 5098 | is-17 | ta-87 | sp-25 an-87 |
| 5099 | is-17 | ta-88 | sp-25 an-88 |
| 5100 | is-17 | ta-89 | sp-25 an-89 |
| 5101 | is-17 | ta-90 | sp-25 an-90 |
| 5102 | is-17 | ta-91 | sp-25 an-91 |
| 5103 | is-17 | ta-92 | sp-25 an-92 |
| 5104 | is-17 | ta-93 | sp-25 an-93 |
| 5105 | is-17 | ta-94 | sp-25 an-94 |
| 5106 | is-17 | ta-95 | sp-25 an-95 |
| 5107 | is-17 | ta-96 | sp-25 an-96 |
| 5108 | is-17 | ta-97 | sp-25 an-97 |
| 5109 | is-17 | ta-98 | sp-25 an-98 |
| 5110 | is-17 | ta-99 | sp-25 an-99 |
| 5111 | is-17 | ta-100 | sp-25 an-100 |
| 5112 | is-17 | ta-101 | sp-25 an-101 |
| 5113 | is-17 | ta-102 | sp-25 an-102 |
| 5114 | is-17 | ta-103 | sp-25 an-103 |
| 5115 | is-17 | ta-104 | sp-25 an-104 |
| 5116 | is-17 | ta-105 | sp-25 an-105 |
| 5117 | is-17 | ta-106 | sp-25 an-106 |
| 5118 | is-17 | ta-107 | sp-25 an-107 |
| 5119 | is-17 | ta-108 | sp-25 an-108 |
| 5120 | is-17 | ta-109 | sp-25 an-109 |
| 5121 | is-17 | ta-110 | sp-25 an-110 |
| 5122 | is-17 | ta-111 | sp-25 an-111 |
| 5123 | is-17 | ta-112 | sp-25 an-112 |
| 5124 | is-17 | ta-113 | sp-25 an-113 |
| 5125 | is-17 | ta-114 | sp-25 an-114 |
| 5126 | is-17 | ta-115 | sp-25 an-115 |
| 5127 | is-17 | ta-116 | sp-25 an-116 |
| 5128 | is-17 | ta-117 | sp-25 an-117 |
| 5129 | is-17 | ta-118 | sp-25 an-118 |
| 5130 | is-17 | ta-119 | sp-25 an-119 |
| 5131 | is-17 | ta-120 | sp-25 an-120 |
| 5132 | is-17 | ta-121 | sp-25 an-121 |
| 5133 | is-17 | ta-122 | sp-25 an-122 |
| 5134 | is-17 | ta-123 | sp-25 an-123 |
| 5135 | is-17 | ta-124 | sp-25 an-124 |
| 5136 | is-17 | ta-125 | sp-25 an-125 |
| 5137 | is-17 | ta-126 | sp-25 an-126 |
| 5138 | is-17 | ta-127 | sp-25 an-127 |
| 5139 | is-17 | ta-128 | sp-25 an-128 |

-continued

| EXAMPLE | REAGENT | | PRODUCT | EXAMPLE | REAGENT | | PRODUCT |
|---|---|---|---|---|---|---|---|
| No. | is | ta | sp  an | No. | is | ta | sp  an |
| 5140 | is-17 | ta-129 | sp-25  an-129 | | | | |
| 5141 | is-17 | ta-130 | sp-25  an-130 | | | | |
| 5142 | is-17 | ta-131 | sp-25  an-131 | | | | |
| 5143 | is-17 | ta-132 | sp-25  an-132 | | | | |
| 5144 | is-17 | ta-133 | sp-25  an-133 | | | | |

Table 5-48

| 5145 | is-17 | ta-134 | sp-25  an-134 |
| 5146 | is-17 | ta-135 | sp-25  an-135 |
| 5147 | is-17 | ta-136 | sp-25  an-136 |
| 5148 | is-17 | ta-137 | sp-25  an-137 |
| 5149 | is-17 | ta-138 | sp-25  an-138 |
| 5150 | is-17 | ta-139 | sp-25  an-139 |
| 5151 | is-17 | ta-140 | sp-25  an-140 |
| 5152 | is-17 | ta-141 | sp-25  an-141 |
| 5153 | is-17 | ta-142 | sp-25  an-142 |
| 5154 | is-17 | ta-143 | sp-25  an-143 |
| 5155 | is-17 | ta-144 | sp-25  an-144 |
| 5156 | is-17 | ta-145 | sp-25  an-145 |
| 5157 | is-17 | ta-146 | sp-25  an-146 |
| 5158 | is-17 | ta-147 | sp-25  an-147 |
| 5159 | is-17 | ta-148 | sp-25  an-148 |
| 5160 | is-17 | ta-149 | sp-25  an-149 |
| 5161 | is-17 | ta-150 | sp-25  an-150 |
| 5162 | is-17 | ta-151 | sp-25  an-151 |
| 5163 | is-17 | ta-152 | sp-25  an-152 |
| 5164 | is-17 | ta-153 | sp-25  an-153 |
| 5165 | is-17 | ta-154 | sp-25  an-154 |
| 5166 | is-17 | ta-155 | sp-25  an-155 |
| 5167 | is-17 | ta-156 | sp-25  an-156 |
| 5168 | is-17 | ta-157 | sp-25  an-157 |
| 5169 | is-17 | ta-158 | sp-25  an-158 |
| 5170 | is-17 | ta-159 | sp-25  an-159 |
| 5171 | is-17 | ta-160 | sp-25  an-160 |
| 5172 | is-17 | ta-161 | sp-25  an-161 |
| 5173 | is-17 | ta-162 | sp-25  an-162 |
| 5174 | is-17 | ta-163 | sp-25  an-163 |
| 5175 | is-17 | ta-164 | sp-25  an-164 |
| 5176 | is-17 | ta-165 | sp-25  an-165 |
| 5177 | is-17 | ta-166 | sp-25  an-166 |
| 5178 | is-17 | ta-167 | sp-25  an-167 |
| 5179 | is-17 | ta-168 | sp-25  an-168 |
| 5180 | is-17 | ta-169 | sp-25  an-169 |
| 5181 | is-17 | ta-170 | sp-25  an-170 |
| 5182 | is-17 | ta-171 | sp-25  an-171 |
| 5183 | is-17 | ta-172 | sp-25  an-172 |
| 5184 | is-17 | ta-173 | sp-25  an-173 |
| 5185 | is-17 | ta-174 | sp-25  an-174 |
| 5186 | is-17 | ta-175 | sp-25  an-175 |
| 5187 | is-17 | ta-176 | sp-25  an-176 |
| 5188 | is-17 | ta-177 | sp-25  an-177 |
| 5189 | is-17 | ta-178 | sp-25  an-178 |
| 5190 | is-17 | ta-179 | sp-25  an-179 |
| 5191 | is-17 | ta-180 | sp-25  an-180 |
| 5192 | is-17 | ta-181 | sp-25  an-181 |
| 5193 | is-17 | ta-182 | sp-25  an-182 |
| 5194 | is-17 | ta-183 | sp-25  an-183 |
| 5195 | is-17 | ta-184 | sp-25  an-184 |
| 5196 | is-17 | ta-185 | sp-25  an-185 |
| 5197 | is-17 | ta-186 | sp-25  an-186 |

Table 5-49

| 5198 | is-17 | ta-187 | sp-25  an-187 |
| 5199 | is-17 | ta-188 | sp-25  an-188 |
| 5200 | is-17 | ta-189 | sp-25  an-189 |
| 5201 | is-17 | ta-190 | sp-25  an-190 |
| 5202 | is-17 | ta-191 | sp-25  an-191 |
| 5203 | is-17 | ta-192 | sp-25  an-192 |
| 5204 | is-17 | ta-193 | sp-25  an-193 |
| 5205 | is-17 | ta-194 | sp-25  an-194 |
| 5206 | is-17 | ta-195 | sp-25  an-195 |
| 5207 | is-17 | ta-196 | sp-25  an-196 |
| 5208 | is-17 | ta-197 | sp-25  an-197 |
| 5209 | is-17 | ta-198 | sp-25  an-198 |
| 5210 | is-17 | ta-199 | sp-25  an-199 |
| 5211 | is-17 | ta-200 | sp-25  an-200 |

-continued

| EXAMPLE No. | REAGENT is | ta | PRODUCT sp | an |
|---|---|---|---|---|
| 5212 | is-17 | ta-201 | sp-25 | an-201 |
| 5213 | is-17 | ta-202 | sp-25 | an-202 |
| 5214 | is-17 | ta-203 | sp-25 | an-203 |
| 5215 | is-17 | ta-204 | sp-25 | an-204 |
| 5216 | is-17 | ta-205 | sp-25 | an-205 |
| 5217 | is-17 | ta-206 | sp-25 | an-206 |
| 5218 | is-17 | ta-207 | sp-25 | an-207 |
| 5219 | is-17 | ta-208 | sp-25 | an-208 |
| 5220 | is-17 | ta-209 | sp-25 | an-209 |
| 5221 | is-17 | ta-210 | sp-25 | an-210 |
| 5222 | is-17 | ta-211 | sp-25 | an-211 |
| 5223 | is-17 | ta-212 | sp-25 | an-212 |
| 5224 | is-17 | ta-213 | sp-25 | an-213 |
| 5225 | is-17 | ta-214 | sp-25 | an-214 |
| 5226 | is-17 | ta-215 | sp-25 | an-215 |
| 5227 | is-17 | ta-216 | sp-25 | an-216 |
| 5228 | is-17 | ta-217 | sp-25 | an-217 |
| 5229 | is-17 | ta-218 | sp-25 | an-218 |
| 5230 | is-17 | ta-219 | sp-25 | an-219 |
| 5231 | is-17 | ta-220 | sp-25 | an-220 |
| 5232 | is-17 | ta-221 | sp-25 | an-221 |
| 5233 | is-17 | ta-222 | sp-25 | an-222 |
| 5234 | is-17 | ta-223 | sp-25 | an-223 |
| 5235 | is-17 | ta-224 | sp-25 | an-224 |
| 5236 | is-17 | ta-225 | sp-25 | an-225 |
| 5237 | is-17 | ta-226 | sp-25 | an-226 |
| 5238 | is-17 | ta-227 | sp-25 | an-227 |
| 5239 | is-17 | ta-228 | sp-25 | an-228 |
| 5240 | is-17 | ta-229 | sp-25 | an-229 |
| 5241 | is-17 | ta-230 | sp-25 | an-230 |
| 5242 | is-17 | ta-231 | sp-25 | an-231 |
| 5243 | is-17 | ta-232 | sp-25 | an-232 |
| 5244 | is-17 | ta-233 | sp-25 | an-233 |
| 5245 | is-17 | ta-234 | sp-25 | an-234 |
| 5246 | is-17 | ta-235 | sp-25 | an-235 |
| 5247 | is-17 | ta-236 | sp-25 | an-236 |
| 5248 | is-17 | ta-237 | sp-25 | an-237 |
| 5249 | is-17 | ta-238 | sp-25 | an-238 |
| 5250 | is-17 | ta-239 | sp-25 | an-239 |

Table 5-50

| EXAMPLE No. | REAGENT is | ta | PRODUCT sp | an |
|---|---|---|---|---|
| 5251 | is-17 | ta-240 | sp-25 | an-240 |
| 5252 | is-17 | ta-241 | sp-25 | an-241 |
| 5253 | is-17 | ta-242 | sp-25 | an-242 |
| 5254 | is-17 | ta-243 | sp-25 | an-243 |
| 5255 | is-17 | ta-244 | sp-25 | an-244 |
| 5256 | is-17 | ta-245 | sp-25 | an-245 |
| 5257 | is-17 | ta-246 | sp-25 | an-246 |
| 5258 | is-17 | ta-247 | sp-25 | an-247 |
| 5259 | is-17 | ta-248 | sp-25 | an-248 |
| 5260 | is-17 | ta-249 | sp-25 | an-249 |
| 5261 | is-17 | ta-250 | sp-25 | an-250 |
| 5262 | is-17 | ta-251 | sp-25 | an-251 |
| 5263 | is-17 | ta-252 | sp-25 | an-252 |
| 5264 | is-17 | ta-253 | sp-25 | an-253 |
| 5265 | is-17 | ta-254 | sp-25 | an-254 |
| 5266 | is-17 | ta-255 | sp-25 | an-255 |
| 5267 | is-17 | ta-256 | sp-25 | an-256 |
| 5268 | is-17 | ta-257 | sp-25 | an-257 |
| 5269 | is-17 | ta-258 | sp-25 | an-258 |
| 5270 | is-17 | ta-259 | sp-25 | an-259 |
| 5271 | is-17 | ta-260 | sp-25 | an-260 |
| 5272 | is-17 | ta-261 | sp-25 | an-261 |
| 5273 | is-17 | ta-262 | sp-25 | an-262 |
| 5274 | is-17 | ta-263 | sp-25 | an-263 |
| 5275 | is-17 | ta-264 | sp-25 | an-264 |
| 5276 | is-17 | ta-265 | sp-25 | an-265 |
| 5277 | is-17 | ta-266 | sp-25 | an-266 |
| 5278 | is-17 | ta-267 | sp-25 | an-267 |
| 5279 | is-17 | ta-268 | sp-25 | an-268 |
| 5280 | is-17 | ta-269 | sp-25 | an-269 |
| 5281 | is-17 | ta-270 | sp-25 | an-270 |
| 5282 | is-17 | ta-271 | sp-25 | an-271 |
| 5283 | is-17 | ta-272 | sp-25 | an-272 |
| 5284 | is-17 | ta-273 | sp-25 | an-273 |
| 5285 | is-17 | ta-274 | sp-25 | an-274 |

|  EXAMPLE | REAGENT | | PRODUCT | EXAMPLE | REAGENT | | PRODUCT |
|---|---|---|---|---|---|---|---|
| No. | is | ta | sp     an | No. | is | ta | sp     an |
| 5286 | is-17 | ta-275 | sp-25  an-275 | | | | |
| 5287 | is-17 | ta-276 | sp-25  an-276 | | | | |
| 5288 | is-17 | ta-277 | sp-25  an-277 | | | | |
| 5289 | is-17 | ta-278 | sp-25  an-278 | | | | |
| 5290 | is-17 | ta-279 | sp-25  an-279 | | | | |
| 5291 | is-17 | ta-280 | sp-25  an-280 | | | | |
| 5292 | is-17 | ta-281 | sp-25  an-281 | | | | |
| 5293 | is-17 | ta-282 | sp-25  an-282 | | | | |
| 5294 | is-17 | ta-283 | sp-25  an-283 | | | | |
| 5295 | is-17 | ta-284 | sp-25  an-284 | | | | |
| 5296 | is-17 | ta-285 | sp-25  an-285 | | | | |
| 5297 | is-17 | ta-286 | sp-25  an-286 | | | | |
| 5298 | is-17 | ta-287 | sp-25  an-287 | | | | |
| 5299 | is-17 | ta-288 | sp-25  an-288 | | | | |
| 5300 | is-17 | ta-289 | sp-25  an-289 | | | | |
| 5301 | is-17 | ta-290 | sp-25  an-290 | | | | |
| 5302 | is-17 | ta-291 | sp-25  an-291 | | | | |
| 5303 | is-17 | ta-292 | sp-25  an-292 | | | | |

Table 5-51

| 5304 | is-17 | ta-293 | sp-25  an-293 | | | | |
|---|---|---|---|---|---|---|---|
| 5305 | is-17 | ta-294 | sp-25  an-294 | | | | |
| 5306 | is-17 | ta-295 | sp-25  an-295 | | | | |
| 5307 | is-17 | ta-296 | sp-25  an-296 | | | | |
| 5308 | is-17 | ta-297 | sp-25  an-297 | | | | |
| 5309 | is-17 | ta-298 | sp-25  an-298 | | | | |
| 5310 | is-17 | ta-299 | sp-25  an-299 | | | | |
| 5311 | is-17 | ta-300 | sp-25  an-300 | | | | |
| 5312 | is-17 | ta-301 | sp-25  an-301 | | | | |
| 5313 | is-17 | ta-302 | sp-25  an-302 | | | | |
| 5314 | is-17 | ta-303 | sp-25  an-303 | | | | |
| 5315 | is-17 | ta-304 | sp-25  an-304 | | | | |
| 5316 | is-17 | ta-305 | sp-25  an-305 | | | | |
| 5317 | is-17 | ta-306 | sp-25  an-306 | | | | |
| 5318 | is-17 | ta-307 | sp-25  an-307 | | | | |
| 5319 | is-17 | ta-308 | sp-25  an-308 | | | | |
| 5320 | is-17 | ta-309 | sp-25  an-309 | | | | |
| 5321 | is-17 | ta-310 | sp-25  an-310 | | | | |
| 5322 | is-17 | ta-311 | sp-25  an-311 | | | | |
| 5323 | is-17 | ta-312 | sp-25  an-312 | | | | |
| 5324 | is-17 | ta-313 | sp-25  an-313 | | | | |
| 5325 | is-17 | ta-314 | sp-25  an-314 | | | | |
| 5326 | is-17 | ta-315 | sp-25  an-315 | | | | |
| 5327 | is-17 | ta-316 | sp-25  an-316 | | | | |
| 5328 | is-17 | ta-317 | sp-25  an-317 | | | | |
| 5329 | is-17 | ta-318 | sp-25  an-318 | | | | |
| 5330 | is-17 | ta-319 | sp-25  an-319 | | | | |
| 5331 | is-17 | ta-320 | sp-25  an-320 | | | | |
| 5332 | is-17 | ta-321 | sp-25  an-321 | | | | |
| 5333 | is-17 | ta-322 | sp-25  an-322 | | | | |
| 5334 | is-17 | ta-323 | sp-25  an-323 | | | | |
| 5335 | is-17 | ta-324 | sp-25  an-324 | | | | |
| 5336 | is-17 | ta-325 | sp-25  an-325 | | | | |
| 5337 | is-17 | ta-326 | sp-25  an-326 | | | | |
| 5338 | is-17 | ta-327 | sp-25  an-327 | | | | |
| 5339 | is-17 | ta-328 | sp-25  an-328 | | | | |
| 5340 | is-17 | ta-329 | sp-25  an-329 | | | | |
| 5341 | is-17 | ta-330 | sp-25  an-330 | | | | |
| 5342 | is-17 | ta-331 | sp-25  an-331 | | | | |
| 5343 | is-17 | ta-332 | sp-25  an-332 | | | | |
| 5344 | is-17 | ta-333 | sp-25  an-333 | | | | |
| 5345 | is-17 | ta-334 | sp-25  an-334 | | | | |
| 5346 | is-17 | ta-335 | sp-25  an-335 | | | | |
| 5347 | is-17 | ta-336 | sp-25  an-336 | | | | |
| 5348 | is-17 | ta-337 | sp-25  an-337 | | | | |
| 5349 | is-17 | ta-338 | sp-25  an-338 | | | | |
| 5350 | is-17 | ta-339 | sp-25  an-339 | | | | |
| 5351 | is-17 | ta-340 | sp-25  an-340 | | | | |
| 5352 | is-17 | ta-341 | sp-25  an-341 | | | | |
| 5353 | is-17 | ta-342 | sp-25  an-342 | | | | |
| 5354 | is-17 | ta-343 | sp-25  an-343 | | | | |
| 5355 | is-17 | ta-344 | sp-25  an-344 | | | | |
| 5356 | is-17 | ta-345 | sp-25  an-345 | | | | |

Table 5-52

| EXAMPLE No. | REAGENT is | REAGENT ta | PRODUCT sp | PRODUCT an | EXAMPLE No. | REAGENT is | REAGENT ta | PRODUCT sp | PRODUCT an |
|---|---|---|---|---|---|---|---|---|---|
| 5357 | is-17 | ta-346 | sp-25 | an-346 | | | | | |
| 5358 | is-17 | ta-347 | sp-25 | an-347 | | | | | |
| 5359 | is-17 | ta-348 | sp-25 | an-348 | | | | | |
| 5360 | is-17 | ta-349 | sp-25 | an-349 | | | | | |
| 5361 | is-17 | ta-350 | sp-25 | an-350 | | | | | |
| 5362 | is-17 | ta-351 | sp-25 | an-351 | | | | | |
| 5363 | is-17 | ta-352 | sp-25 | an-352 | | | | | |
| 5364 | is-17 | ta-353 | sp-25 | an-353 | | | | | |
| 5365 | is-17 | ta-354 | sp-25 | an-354 | | | | | |
| 5366 | is-17 | ta-355 | sp-25 | an-355 | | | | | |
| 5367 | is-17 | ta-356 | sp-25 | an-356 | | | | | |
| 5368 | is-17 | ta-357 | sp-25 | an-357 | | | | | |
| 5369 | is-17 | ta-358 | sp-25 | an-358 | | | | | |
| 5370 | is-17 | ta-359 | sp-25 | an-359 | | | | | |
| 5371 | is-17 | ta-360 | sp-25 | an-360 | | | | | |
| 5372 | is-17 | ta-361 | sp-25 | an-361 | | | | | |
| 5373 | is-17 | ta-362 | sp-25 | an-362 | | | | | |
| 5374 | is-17 | ta-363 | sp-25 | an-363 | | | | | |
| 5375 | is-17 | ta-364 | sp-25 | an-364 | | | | | |
| 5376 | is-17 | ta-365 | sp-25 | an-365 | | | | | |
| 5377 | is-17 | ta-366 | sp-25 | an-366 | | | | | |
| 5378 | is-17 | ta-367 | sp-25 | an-367 | | | | | |
| 5379 | is-17 | ta-368 | sp-25 | an-368 | | | | | |
| 5380 | is-17 | ta-369 | sp-25 | an-369 | | | | | |
| 5381 | is-17 | ta-370 | sp-25 | an-370 | | | | | |
| 5382 | is-17 | ta-371 | sp-25 | an-371 | | | | | |
| 5383 | is-17 | ta-372 | sp-25 | an-372 | | | | | |
| 5384 | is-17 | ta-373 | sp-25 | an-373 | | | | | |
| 5385 | is-17 | ta-374 | sp-25 | an-374 | | | | | |
| 5386 | is-17 | ta-375 | sp-25 | an-375 | | | | | |
| 5387 | is-17 | ta-376 | sp-25 | an-376 | | | | | |
| 5388 | is-17 | ta-377 | sp-25 | an-377 | | | | | |
| 5389 | is-17 | ta-378 | sp-25 | an-378 | | | | | |
| 5390 | is-17 | ta-379 | sp-25 | an-379 | | | | | |
| 5391 | is-17 | ta-380 | sp-25 | an-380 | | | | | |
| 5392 | is-17 | ta-381 | sp-25 | an-381 | | | | | |
| 5393 | is-17 | ta-382 | sp-25 | an-382 | | | | | |
| 5394 | is-17 | ta-383 | sp-25 | an-383 | | | | | |
| 5395 | is-17 | ta-384 | sp-25 | an-384 | | | | | |
| 5396 | is-17 | ta-385 | sp-25 | an-385 | | | | | |
| 5397 | is-17 | ta-386 | sp-25 | an-386 | | | | | |
| 5398 | is-17 | ta-387 | sp-25 | an-387 | | | | | |
| 5399 | is-17 | ta-388 | sp-25 | an-388 | | | | | |
| 5400 | is-17 | ta-389 | sp-25 | an-389 | | | | | |
| 5401 | is-17 | ta-390 | sp-25 | an-390 | | | | | |
| 5402 | is-17 | ta-391 | sp-25 | an-391 | | | | | |
| 5403 | is-17 | ta-392 | sp-25 | an-392 | | | | | |
| 5404 | is-17 | ta-393 | sp-25 | an-393 | | | | | |

Examples 3786 to 4064

According to the procedures in the steps n to p in Example 1, as shown in the following formula:

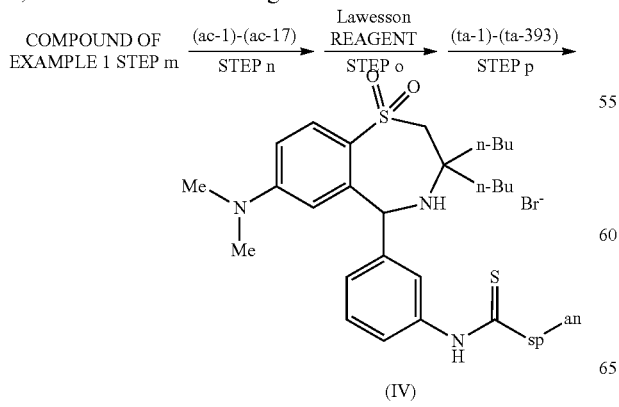

(IV)

the compounds of Examples 3786 to 4064 described in Table 6 (Tables 6-1 to 6-3) represented by the formula (IV) are obtained using the compound obtained in the step m in Example 1, any of acyl halide (ac-1) to (ac-17) represented by the aforementioned formula (5-1) and any of tertiary amine (ta-1) to (ta-393) represented by the aforementioned formula (2). In the formula (IV), -sp- represents any of (sp-1) to (sp-25) and -an represents any of (an-1) to (an-393).

| EXAMPLE | REAGENT | | PRODUCT | | EXAMPLE | REAGENT | | PRODUCT | |
|---|---|---|---|---|---|---|---|---|---|
| No. | ac | ta | sp | an | No. | ac | ta | sp | an |
| Table 6-1 | | | | | | | | | |
| 3786 | ac-3 | ta-1 | sp-3 | an-1 | 3945 | ac-7 | ta-1 | sp-7 | an-1 |
| 3787 | ac-3 | ta-2 | sp-3 | an-2 | 3946 | ac-7 | ta-2 | sp-7 | an-2 |
| 3788 | ac-3 | ta-3 | sp-3 | an-3 | 3947 | ac-7 | ta-3 | sp-7 | an-3 |
| 3789 | ac-3 | ta-4 | sp-3 | an-4 | 3948 | ac-7 | ta-4 | sp-7 | an-4 |
| 3790 | ac-3 | ta-5 | sp-3 | an-5 | 3949 | ac-7 | ta-5 | sp-7 | an-5 |
| 3791 | ac-3 | ta-6 | sp-3 | an-6 | 3950 | ac-7 | ta-6 | sp-7 | an-6 |
| 3792 | ac-3 | ta-21 | sp-3 | an-21 | 3951 | ac-7 | ta-21 | sp-7 | an-21 |
| 3793 | ac-3 | ta-25 | sp-3 | an-25 | 3952 | ac-7 | ta-25 | sp-7 | an-25 |
| 3794 | ac-3 | ta-26 | sp-3 | an-26 | 3953 | ac-7 | ta-26 | sp-7 | an-26 |
| 3795 | ac-3 | ta-32 | sp-3 | an-32 | 3954 | ac-7 | ta-32 | sp-7 | an-32 |
| 3796 | ac-3 | ta-34 | sp-3 | an-34 | 3955 | ac-7 | ta-34 | sp-7 | an-34 |
| 3797 | ac-3 | ta-38 | sp-3 | an-38 | 3956 | ac-7 | ta-38 | sp-7 | an-38 |
| 3798 | ac-3 | ta-41 | sp-3 | an-41 | 3957 | ac-7 | ta-41 | sp-7 | an-41 |
| 3799 | ac-3 | ta-42 | sp-3 | an-42 | 3958 | ac-7 | ta-42 | sp-7 | an-42 |
| 3800 | ac-3 | ta-44 | sp-3 | an-44 | 3959 | ac-7 | ta-44 | sp-7 | an-44 |
| 3801 | ac-3 | ta-45 | sp-3 | an-45 | 3960 | ac-7 | ta-45 | sp-7 | an-45 |
| 3802 | ac-3 | ta-47 | sp-3 | an-47 | 3961 | ac-7 | ta-47 | sp-7 | an-47 |
| 3803 | ac-3 | ta-49 | sp-3 | an-49 | 3962 | ac-7 | ta-49 | sp-7 | an-49 |
| 3804 | ac-3 | ta-67 | sp-3 | an-67 | 3963 | ac-7 | ta-67 | sp-7 | an-67 |
| 3805 | ac-3 | ta-88 | sp-3 | an-88 | 3964 | ac-7 | ta-88 | sp-7 | an-88 |
| 3806 | ac-3 | ta-89 | sp-3 | an-89 | 3965 | ac-7 | ta-89 | sp-7 | an-89 |
| 3807 | ac-3 | ta-98 | sp-3 | an-98 | 3966 | ac-7 | ta-98 | sp-7 | an-98 |
| 3808 | ac-3 | ta-99 | sp-3 | an-99 | 3967 | ac-7 | ta-99 | sp-7 | an-99 |
| 3809 | ac-3 | ta-100 | sp-3 | an-100 | 3968 | ac-7 | ta-100 | sp-7 | an-100 |
| 3810 | ac-3 | ta-101 | sp-3 | an-101 | 3969 | ac-7 | ta-101 | sp-7 | an-101 |
| 3811 | ac-3 | ta-107 | sp-3 | an-107 | 3970 | ac-7 | ta-107 | sp-7 | an-107 |
| 3812 | ac-3 | ta-115 | sp-3 | an-115 | 3971 | ac-7 | ta-115 | sp-7 | an-115 |
| 3813 | ac-3 | ta-287 | sp-3 | an-287 | 3972 | ac-7 | ta-287 | sp-7 | an-287 |
| 3814 | ac-3 | ta-288 | sp-3 | an-288 | 3973 | ac-7 | ta-288 | sp-7 | an-288 |
| 3815 | ac-3 | ta-289 | sp-3 | an-289 | 3974 | ac-7 | ta-289 | sp-7 | an-289 |
| 3816 | ac-3 | ta-290 | sp-3 | an-290 | 3975 | ac-7 | ta-290 | sp-7 | an-290 |
| 3817 | ac-3 | ta-291 | sp-3 | an-291 | 3976 | ac-7 | ta-291 | sp-7 | an-291 |
| 3818 | ac-3 | ta-292 | sp-3 | an-292 | 3977 | ac-7 | ta-292 | sp-7 | an-292 |
| 3819 | ac-3 | ta-293 | sp-3 | an-293 | 3978 | ac-7 | ta-293 | sp-7 | an-293 |
| 3820 | ac-3 | ta-294 | sp-3 | an-294 | 3979 | ac-7 | ta-294 | sp-7 | an-294 |
| 3821 | ac-3 | ta-295 | sp-3 | an-295 | 3980 | ac-7 | ta-295 | sp-7 | an-295 |
| 3822 | ac-3 | ta-296 | sp-3 | an-296 | 3981 | ac-7 | ta-296 | sp-7 | an-296 |
| 3823 | ac-3 | ta-297 | sp-3 | an-297 | 3982 | ac-7 | ta-297 | sp-7 | an-297 |
| 3824 | ac-3 | ta-298 | sp-3 | an-298 | 3983 | ac-7 | ta-298 | sp-7 | an-298 |
| 3825 | ac-3 | ta-299 | sp-3 | an-299 | 3984 | ac-7 | ta-299 | sp-7 | an-299 |
| 3826 | ac-4 | ta-1 | sp-4 | an-1 | 3985 | ac-8 | ta-1 | sp-8 | an-1 |
| 3827 | ac-4 | ta-2 | sp-4 | an-2 | 3986 | ac-8 | ta-2 | sp-8 | an-2 |
| 3828 | ac-4 | ta-3 | sp-4 | an-3 | 3987 | ac-8 | ta-3 | sp-8 | an-3 |
| 3829 | ac-4 | ta-4 | sp-4 | an-4 | 3988 | ac-8 | ta-4 | sp-8 | an-4 |
| 3830 | ac-4 | ta-5 | sp-4 | an-5 | 3989 | ac-8 | ta-5 | sp-8 | an-5 |
| 3831 | ac-4 | ta-6 | sp-4 | an-6 | 3990 | ac-8 | ta-6 | sp-8 | an-6 |
| 3832 | ac-4 | ta-21 | sp-4 | an-21 | 3991 | ac-8 | ta-21 | sp-8 | an-21 |
| 3833 | ac-4 | ta-25 | sp-4 | an-25 | 3992 | ac-8 | ta-25 | sp-8 | an-25 |
| 3834 | ac-4 | ta-26 | sp-4 | an-26 | 3993 | ac-8 | ta-26 | sp-8 | an-26 |
| 3835 | ac-4 | ta-32 | sp-4 | an-32 | 3994 | ac-8 | ta-32 | sp-8 | an-32 |
| 3836 | ac-4 | ta-34 | sp-4 | an-34 | 3995 | ac-8 | ta-34 | sp-8 | an-34 |
| 3837 | ac-4 | ta-38 | sp-4 | an-38 | 3996 | ac-8 | ta-38 | sp-8 | an-38 |
| 3838 | ac-4 | ta-41 | sp-4 | an-41 | 3997 | ac-8 | ta-41 | sp-8 | an-41 |
| 3839 | ac-4 | ta-42 | sp-4 | an-42 | 3998 | ac-8 | ta-42 | sp-8 | an-42 |
| Table 6-2 | | | | | | | | | |
| 3840 | ac-4 | ta-44 | sp-4 | an-44 | 3999 | ac-8 | ta-44 | sp-8 | an-44 |
| 3841 | ac-4 | ta-45 | sp-4 | an-45 | 4000 | ac-8 | ta-45 | sp-8 | an-45 |
| 3842 | ac-4 | ta-47 | sp-4 | an-47 | 4001 | ac-8 | ta-47 | sp-8 | an-47 |
| 3843 | ac-4 | ta-49 | sp-4 | an-49 | 4002 | ac-8 | ta-49 | sp-8 | an-49 |
| 3844 | ac-4 | ta-67 | sp-4 | an-67 | 4003 | ac-8 | ta-67 | sp-8 | an-67 |
| 3845 | ac-4 | ta-88 | sp-4 | an-88 | 4004 | ac-8 | ta-88 | sp-8 | an-88 |
| 3846 | ac-4 | ta-89 | sp-4 | an-89 | 4005 | ac-8 | ta-89 | sp-8 | an-89 |
| 3847 | ac-4 | ta-98 | sp-4 | an-98 | 4006 | ac-8 | ta-98 | sp-8 | an-98 |
| 3848 | ac-4 | ta-99 | sp-4 | an-99 | 4007 | ac-8 | ta-99 | sp-8 | an-99 |
| 3849 | ac-4 | ta-100 | sp-4 | an-100 | 4008 | ac-8 | ta-100 | sp-8 | an-100 |
| 3850 | ac-4 | ta-101 | sp-4 | an-101 | 4009 | ac-8 | ta-101 | sp-8 | an-101 |
| 3851 | ac-4 | ta-107 | sp-4 | an-107 | 4010 | ac-8 | ta-107 | sp-8 | an-107 |
| 3852 | ac-4 | ta-115 | sp-4 | an-115 | 4011 | ac-8 | ta-115 | sp-8 | an-115 |
| 1 | ac-4 | ta-287 | sp-4 | an-287 | 4012 | ac-8 | ta-287 | sp-8 | an-287 |
| 3853 | ac-4 | ta-288 | sp-4 | an-288 | 4013 | ac-8 | ta-288 | sp-8 | an-288 |
| 3854 | ac-4 | ta-289 | sp-4 | an-289 | 4014 | ac-8 | ta-289 | sp-8 | an-289 |
| 3855 | ac-4 | ta-290 | sp-4 | an-290 | 4015 | ac-8 | ta-290 | sp-8 | an-290 |
| 3856 | ac-4 | ta-291 | sp-4 | an-291 | 4016 | ac-8 | ta-291 | sp-8 | an-291 |

-continued

| EXAMPLE | REAGENT | | PRODUCT | EXAMPLE | REAGENT | | PRODUCT |
|---|---|---|---|---|---|---|---|
| No. | ac | ta | sp | an | No. | ac | ta | sp | an |
| 3857 | ac-4 | ta-292 | sp-4 | an-292 | 4017 | ac-8 | ta-292 | sp-8 | an-292 |
| 3858 | ac-4 | ta-293 | sp-4 | an-293 | 4018 | ac-8 | ta-293 | sp-8 | an-293 |
| 3859 | ac-4 | ta-294 | sp-4 | an-294 | 4019 | ac-8 | ta-294 | sp-8 | an-294 |
| 3860 | ac-4 | ta-295 | sp-4 | an-295 | 4020 | ac-8 | ta-295 | sp-8 | an-295 |
| 3861 | ac-4 | ta-296 | sp-4 | an-296 | 4021 | ac-8 | ta-296 | sp-8 | an-296 |
| 3862 | ac-4 | ta-297 | sp-4 | an-297 | 4022 | ac-8 | ta-297 | sp-8 | an-297 |
| 3863 | ac-4 | ta-298 | sp-4 | an-298 | 4023 | ac-8 | ta-298 | sp-8 | an-298 |
| 3864 | ac-4 | ta-299 | sp-4 | an-299 | 4024 | ac-8 | ta-299 | sp-8 | an-299 |
| 3865 | ac-5 | ta-1 | sp-5 | an-1 | 4025 | ac-9 | ta-1 | sp-9 | an-1 |
| 3866 | ac-5 | ta-2 | sp-5 | an-2 | 4026 | ac-9 | ta-2 | sp-9 | an-2 |
| 3867 | ac-5 | ta-3 | sp-5 | an-3 | 4027 | ac-9 | ta-3 | sp-9 | an-3 |
| 3868 | ac-5 | ta-4 | sp-5 | an-4 | 4028 | ac-9 | ta-4 | sp-9 | an-4 |
| 3869 | ac-5 | ta-5 | sp-5 | an-5 | 4029 | ac-9 | ta-5 | sp-9 | an-5 |
| 3870 | ac-5 | ta-6 | sp-5 | an-6 | 4030 | ac-9 | ta-6 | sp-9 | an-6 |
| 3871 | ac-5 | ta-21 | sp-5 | an-21 | 4031 | ac-9 | ta-21 | sp-9 | an-21 |
| 3872 | ac-5 | ta-25 | sp-5 | an-25 | 4032 | ac-9 | ta-25 | sp-9 | an-25 |
| 3873 | ac-5 | ta-26 | sp-5 | an-26 | 4033 | ac-9 | ta-26 | sp-9 | an-26 |
| 3874 | ac-5 | ta-32 | sp-5 | an-32 | 4034 | ac-9 | ta-32 | sp-9 | an-32 |
| 3875 | ac-5 | ta-34 | sp-5 | an-34 | 4035 | ac-9 | ta-34 | sp-9 | an-34 |
| 3876 | ac-5 | ta-38 | sp-5 | an-38 | 4036 | ac-9 | ta-38 | sp-9 | an-38 |
| 3877 | ac-5 | ta-41 | sp-5 | an-41 | 4037 | ac-9 | ta-41 | sp-9 | an-41 |
| 3878 | ac-5 | ta-42 | sp-5 | an-42 | 4038 | ac-9 | ta-42 | sp-9 | an-42 |
| 3879 | ac-5 | ta-44 | sp-5 | an-44 | 4039 | ac-9 | ta-44 | sp-9 | an-44 |
| 3880 | ac-5 | ta-45 | sp-5 | an-45 | 4040 | ac-9 | ta-45 | sp-9 | an-45 |
| 3881 | ac-5 | ta-47 | sp-5 | an-47 | 4041 | ac-9 | ta-47 | sp-9 | an-47 |
| 3882 | ac-5 | ta-49 | sp-5 | an-49 | 4042 | ac-9 | ta-49 | sp-9 | an-49 |
| 3883 | ac-5 | ta-67 | sp-5 | an-67 | 4043 | ac-9 | ta-67 | sp-9 | an-67 |
| 3884 | ac-5 | ta-88 | sp-5 | an-88 | 4044 | ac-9 | ta-88 | sp-9 | an-88 |
| 3885 | ac-5 | ta-89 | sp-5 | an-89 | 4045 | ac-9 | ta-89 | sp-9 | an-89 |
| 3886 | ac-5 | ta-98 | sp-5 | an-98 | 4046 | ac-9 | ta-98 | sp-9 | an-98 |
| 3887 | ac-5 | ta-99 | sp-5 | an-99 | 4047 | ac-9 | ta-99 | sp-9 | an-99 |
| 3888 | ac-5 | ta-100 | sp-5 | an-100 | 4048 | ac-9 | ta-100 | sp-9 | an-100 |
| 3889 | ac-5 | ta-101 | sp-5 | an-101 | 4049 | ac-9 | ta-101 | sp-9 | an-101 |
| 3890 | ac-5 | ta-107 | sp-5 | an-107 | 4050 | ac-9 | ta-107 | sp-9 | an-107 |
| 3891 | ac-5 | ta-115 | sp-5 | an-115 | 4051 | ac-9 | ta-115 | sp-9 | an-115 |
| 3892 | ac-5 | ta-287 | sp-5 | an-287 | 4052 | ac-9 | ta-287 | sp-9 | an-287 |

Table 6-3

| 3893 | ac-5 | ta-288 | sp-5 | an-288 | 4053 | ac-9 | ta-288 | sp-9 | an-288 |
|---|---|---|---|---|---|---|---|---|---|
| 3894 | ac-5 | ta-289 | sp-5 | an-289 | 4054 | ac-9 | ta-289 | sp-9 | an-289 |
| 3895 | ac-5 | ta-290 | sp-5 | an-290 | 4055 | ac-9 | ta-290 | sp-9 | an-290 |
| 3896 | ac-5 | ta-291 | sp-5 | an-291 | 4056 | ac-9 | ta-291 | sp-9 | an-291 |
| 3897 | ac-5 | ta-292 | sp-5 | an-292 | 4057 | ac-9 | ta-292 | sp-9 | an-292 |
| 3898 | ac-5 | ta-293 | sp-5 | an-293 | 4058 | ac-9 | ta-293 | sp-9 | an-293 |
| 3899 | ac-5 | ta-294 | sp-5 | an-294 | 4059 | ac-9 | ta-294 | sp-9 | an-294 |
| 3900 | ac-5 | ta-295 | sp-5 | an-295 | 4060 | ac-9 | ta-295 | sp-9 | an-295 |
| 3901 | ac-5 | ta-296 | sp-5 | an-296 | 4061 | ac-9 | ta-296 | sp-9 | an-296 |
| 3902 | ac-5 | ta-297 | sp-5 | an-297 | 4062 | ac-9 | ta-297 | sp-9 | an-297 |
| 3903 | ac-5 | ta-298 | sp-5 | an-298 | 4063 | ac-9 | ta-298 | sp-9 | an-298 |
| 3904 | ac-5 | ta-299 | sp-5 | an-299 | 4064 | ac-9 | ta-299 | sp-9 | an-299 |
| 3905 | ac-6 | ta-1 | sp-6 | an-1 | | | | | |
| 3906 | ac-6 | ta-2 | sp-6 | an-2 | | | | | |
| 3907 | ac-6 | ta-3 | sp-6 | an-3 | | | | | |
| 3908 | ac-6 | ta-4 | sp-6 | an-4 | | | | | |
| 3909 | ac-6 | ta-5 | sp-6 | an-5 | | | | | |
| 3910 | ac-6 | ta-6 | sp-6 | an-6 | | | | | |
| 3911 | ac-6 | ta-21 | sp-6 | an-21 | | | | | |
| 3912 | ac-6 | ta-25 | sp-6 | an-25 | | | | | |
| 3913 | ac-6 | ta-26 | sp-6 | an-26 | | | | | |
| 3914 | ac-6 | ta-32 | sp-6 | an-32 | | | | | |
| 3915 | ac-6 | ta-34 | sp-6 | an-34 | | | | | |
| 3916 | ac-6 | ta-38 | sp-6 | an-38 | | | | | |
| 3917 | ac-6 | ta-41 | sp-6 | an-41 | | | | | |
| 3918 | ac-6 | ta-42 | sp-6 | an-42 | | | | | |
| 3919 | ac-6 | ta-44 | sp-6 | an-44 | | | | | |
| 3920 | ac-6 | ta-45 | sp-6 | an-45 | | | | | |
| 3921 | ac-6 | ta-47 | sp-6 | an-47 | | | | | |
| 3922 | ac-6 | ta-49 | sp-6 | an-49 | | | | | |
| 3923 | ac-6 | ta-67 | sp-6 | an-67 | | | | | |
| 3924 | ac-6 | ta-88 | sp-6 | an-88 | | | | | |
| 3925 | ac-6 | ta-89 | sp-6 | an-89 | | | | | |
| 3926 | ac-6 | ta-98 | sp-6 | an-98 | | | | | |
| 3927 | ac-6 | ta-99 | sp-6 | an-99 | | | | | |
| 3928 | ac-6 | ta-100 | sp-6 | an-100 | | | | | |
| 3929 | ac-6 | ta-101 | sp-6 | an-101 | | | | | |
| 3930 | ac-6 | ta-107 | sp-6 | an-107 | | | | | |

| EXAMPLE | REAGENT | | PRODUCT | | EXAMPLE | REAGENT | | PRODUCT | |
|---|---|---|---|---|---|---|---|---|---|
| No. | ac | ta | sp | an | No. | ac | ta | sp | an |
| 3931 | ac-6 | ta-115 | sp-6 | an-115 | | | | | |
| 3932 | ac-6 | ta-287 | sp-6 | an-287 | | | | | |
| 3933 | ac-6 | ta-288 | sp-6 | an-288 | | | | | |
| 3934 | ac-6 | ta-289 | sp-6 | an-289 | | | | | |
| 3935 | ac-6 | ta-290 | sp-6 | an-290 | | | | | |
| 3936 | ac-6 | ta-291 | sp-6 | an-291 | | | | | |
| 3937 | ac-6 | ta-292 | sp-6 | an-292 | | | | | |
| 3938 | ac-6 | ta-293 | sp-6 | an-293 | | | | | |
| 3939 | ac-6 | ta-294 | sp-6 | an-294 | | | | | |
| 3940 | ac-6 | ta-295 | sp-6 | an-295 | | | | | |
| 3941 | ac-6 | ta-296 | sp-6 | an-296 | | | | | |
| 3942 | ac-6 | ta-297 | sp-6 | an-297 | | | | | |
| 3943 | ac-6 | ta-298 | sp-6 | an-298 | | | | | |
| 3944 | ac-6 | ta-299 | sp-6 | an-299 | | | | | |

Example 4065

1-{5-[4-(3,3-dibutyl-7-dimethylamino-1,1-dioxo-2,3,4,5-tetrahydro-1,4-benzothiazepine-5-yl)phenylthiocarbamoyl]pentyl}-1-azoniabicyclo[2.2.2]octane bromide (Step a) Synthesis of 4-chlorophenyl 4-methoxybenzoate Triethylamine (6 mL) and a solution of 4.0 g of 4-methoxybenzoyl chloride (supplied from Tokyo Chemical industry) in 40 mL of chloroform were added to a solution of 6.0 g of 4-chlorophenol (supplied from Tokyo Chemical industry) in 60 mL of chloroform, and stirred at 55° C. for one hour. Then, 100 mL of dichloromethane, 200 mL of water and 25 mL of an aqueous solution of 1 N sodium hydroxide were added to the reaction solution, and the mixture was separated into two liquid phases. The organic layer was dried on sodium sulfate anhydrate and subsequently concentrated, to yield 8.1 g of the title compound.

(Step b) Synthesis of 4-fluoro-2-(4-methoxybenzoyl)phenol

Titanium tetrachloride (10 mL) (supplied from Wako Pure chemical Industries) was added to 6.55 g of the compound obtained at the step a, and heated at 160° C. for 4 hours. Under ice cooling, 10 mL of water was added dropwise to the reaction mixture. Further 400 mL of ether and 400 mL of water were added thereto at room temperature, and the mixture was separated into two liquid phases. The organic layer was dried on sodium sulfate anhydrate and subsequently concentrated. The residue was applied onto the silica gel column and eluted with hexane-ethyl acetate (8:1), to yield 3.44 g of the title compound.

(Step c) Synthesis of O-[4-fluoro-2-(4-methoxybenzoyl)phenyl] N,N-dimethylthiocarbamate Triethylamine (4.24 g), 0.34 g of dimethylaminopyridine (supplied from Wako Pure chemical Industries) and 2.10 g of N,N-dimethylthiocarbamoyl chloride (supplied from Tokyo Chemical industry) were added to a solution of 3.44 g of the compound obtained at the step b in 70 mL of dioxane, and stirred at 100° C. for 24 hours. Then, 200 mL of ethyl acetate and 200 mL of water were added to the reaction suspension, and the mixture was separated into two liquid phases. The organic layer was dried on sodium sulfate anhydrate and subsequently concentrated. The residue was applied onto the silica gel column and eluted with hexane-ethyl acetate (3:1), to yield 4.65 g of the title compound.

(Step d) Synthesis of S-[4-fluoro-2-(4-methoxybenzoyl)phenyl] N,N-dimethylthiocarbamate A suspension of 4.65 g of the compound obtained at the step c in 30 mL of tetradecane (supplied from Wako Pure chemical Industries) was heated at 250° C. for 5 hours. At room temperature, 12 mL of chloroform was added to the reaction suspension to dissolve a reaction product. This solution was applied onto the silica gel column and eluted with hexane-ethyl acetate (2:1), to yield 2.10 g of the title compound.

(Step e) Synthesis of 4-fluoro-2-(4-methoxybenzoyl)thiophenol

Methanol (20 mL) and 1.88 g of potassium hydroxide were added to a solution of 2.10 g of the compound obtained at the step d in 20 mL of THF, and stirred at 60° C. for 2 hours. Under ice cooling, 30 mL of 1 N hydrochloric acid was added to the reaction suspension. Further 100 mL of ethyl acetate and 100 mL of water were added thereto at room temperature, and the mixture was separated into two liquid phases. The organic layer was washed with 150 mL of saturated brine, dried on sodium sulfate anhydrate and subsequently concentrated, to yield 1.63 g of the title compound.

(Step f) Synthesis of 3,3-dibutyl-2,3-dihydro-7-fluoro-5-(4-methoxyphenyl)-1,4-benzothiazepine-1,1-dioxide The title compound was obtained using the compound obtained in the step e in the present Example according to the procedures in the steps g to i in Example 1.

(Step g) Synthesis of 3,3-dibutyl-2,3-dihydro-7-dimethylamino-5-(4-methoxyphenyl)-1,4-benzothiazepine-1,1-dioxide The title compound was obtained using the compound obtained in the step f in the present Example according to the procedure in the step k in Example 1.

(Step h) Synthesis of 3,3-dibutyl-7-dimethylamino-2,3,4,5-tetrahydro-5-(4-methoxyphenyl)-1,4-benzothiazepine-1,1-dioxide The title compound was obtained using the compound obtained in the step g in the present Example according to the procedure in the step m in Example 1.

(Step i) Synthesis of 3,3-dibutyl-7-dimethylamino-2,3,4,5-tetrahydro-5-(4-hydroxyphenyl)-1,4-benzothiazepine-1,1-dioxide 9 mL of a solution of boron tribromide (1 mol/L) in dichloromethane (supplied from Aldrich) was added dropwise to a solution of 1.15 g of the compound obtained at the step h in 10 mL of dichloromethane at −20° C., and stirred under ice cooling for one hour. The reaction solution was added dropwise to 200 mL of 5% sodium bicarbonate water under ice cooling. Further 100 mL of dichloromethane was added thereto at room temperature, and the mixture was separated into two liquid phases. The organic layer was dried on sodium sulfate anhydrate and subsequently concentrated. The residue was applied onto the silica gel column and eluted with hexane-ethyl acetate (2:1), to yield 1.00 g of the title compound.

(Step j) 4-(3,3-dibutyl-7-dimethylamino-1,1-dioxo-2,3,4,5-tetrahydro-1,4-benzothiazepine-5-yl)phenyl trifluoromethanesulfonate Trifluoromethanesulfonic acid anhydride (388 μL) (supplied from Aldrich) was added dropwise to a solution of 735 mg of the compound obtained at the step i in 3.3 mL of pyridine at 0° C., and stirred at room temperature for one hour. Then 10 mL of ethyl acetate and 10 mL of water were added to the reaction solution, and the mixture was separated into two liquid phases. The organic layer was washed with 10 mL of an aqueous solution of saturated copper sulfate, then washed with 10 mL of saturated sodium bicarbonate water, and further washed with 10 mL of saturated brine. The organic layer was dried on sodium sulfate anhydrate and subsequently concentrated, to yield 916 mg of the title compound.

(Step k) Synthesis of 3,3-dibutyl-7-dimethylamino-2,3,4,5-tetrahydro-5-(4-aminiophenyl)-1,4-benzothiazepine-1,1-dioxide Palladium II acetate (303 mg) (supplied from Aldrich), 986 mg of 2,2'-bis(diphenylphosphenyl)-1,1'-binaphthyl (supplied from Aldrich) and 4.42 g of cesium carbonate (supplied from Wako Pure Chemical Industries) were added to a solution of 3.77 g of the compound obtained at the step j in 38 mL of THF. Further 2.2 mL of benzophenone imine (supplied from Aldrich) was added thereto, and refluxed under heating for 2 hours with stirring. Insoluble matters in the reaction suspension were filtrated off, and the filtrate was concentrated. The residue was dissolved in 65 mL of methanol. Subsequently 2.15 g of sodium acetate (supplied from Wako Pure Chemical Industries) and 1.38 g of hydroxylamine hydrochloride (supplied from Tokyo Chemical industry) were added thereto, and stirred at room temperature for one hour. Then, 70 mL of dichloromethane and 70 ml of saturated sodium bicarbonate water were added to the reaction suspension, and the mixture was separated into two liquid phases. The organic layer was washed with 70 mL of saturated brine, dried on sodium sulfate anhydrate and subsequently concentrated. The residue was applied onto the silica gel column and eluted with hexane-ethyl acetate (2:1), to yield 2.48 g of the title compound.

(Step l) Synthesis of 1-{5-[4-(3,3-dibutyl-7-dimethylamino-1,1-dioxo-2,3,4,5-tetrahydro-1,4-benzothiazepine-5-yl)phenylthiocarbamoyl]pentyl}-1-azoniabicyclo[2.2.2]octane bromide The title compound was obtained using the compound obtained at the step k in the present Example according to the procedures in the steps n to p in Example 1. $^1$H-NMR (CDCl$_3$) δ: 0.85 (3H, t); 0.90 (3H, t); 1.12-1.48 (8H, m); 1.53-2.25 (17H, m); 2.82 (6H, s); 2.99 (1H, d); 3.10-3.51 (5H, m); 3.61 (6H, t); 5.94 (1H, d); 6.01 (1H, s); 6.47 (1H, dd); 7.41 (2H, d); 7.87 (1H, d); 8.22 (2H, d); 11.62 (1H, s). MS (m/z): 667 (M$^+$).

Example 4066

1-(3-{3-[4-(3,3-dibutyl-7-dimethylamino-1,1-dioxo-2,3,4,5-tetrahydro-1,4-benzothiazepine-5-yl)phenyl]thioureido}propyl)-1-azoniabicyclo[2.2.2]octane bromide The title compound was obtained according to the procedure in the step b in Example 9 except for using the compound obtained at the step k in Example 4065 in place of the compound obtained at the step m in Example 1. MS (m/z):654 (M$^+$).

Example 5405

Benzyl-(4-{3-[4-(3,3-dibutyl-7-dimethylamino-1,1-dioxo-2,3,4,5-tetrahydro-1,4-benzothiazepine-5-yl)phenyl]thioureido}benzyl)dimethylammonium bromide (Step a) Synthesis of benzyl-(4-isothiocyanatobenzyl)dimethylammonium bromide The title compound was obtained according to the procedure in the step a in Example 9 except for using 4-(bromomethyl)phenyl isothiocyanate (aforementioned is-14) in place of 3-bromopropyl isothiocyanate, and using N,N-dimethylbenzylamine (aforementioned ta-32) in place of quinuclidine.

(Step b) Synthesis of benzyl-(4-{3-[4-(3,3-dibutyl-7-dimethylamino-1,1-dioxo-2,3,4,5-tetrahydro-1,4-benzothiazepine-5-yl)phenyl]thioureido}benzyl)dimethylammonium bromide The title compound was obtained according to the procedure in the step b in Example 9 using the compound obtained at the step a in the present Example and the compound obtained at the step k in Example 4065.

Example 5406

1-(3-{3-[4-(3,3-dibutyl-7-dimethylamino-1,1-dioxo-2,3,4,5-tetrahydro-1,4-benzothiazepine-5-yl)phenyl]thioureido}benzyl)-1-azoniabicyclo[2.2.2]octane bromide (Step a) Synthesis of 1-(3-isothiocyanatobenzyl)-1-azoniabicyclo[2.2.2]octane bromide The title compound was obtained according to the procedure in the step a in Example 9 except for using 3-(bromomethyl)phenyl isothiocyanate (aforementioned is-15) in place of 3-bromopropyl isothiocyanate.

(Step b) Synthesis of 1-(3-{3-[4-(3,3-dibutyl-7-dimethylamino-1,1-dioxo-2,3,4,5-tetrahydro-1,4-benzothiazepine-5-yl)phenyl]thioureido}benzyl)-1-azoniabicyclo[2.2.2]octane bromide The title compound was obtained according to the procedure in the step b in Example 9 using the compound obtained at the step a in the present Example and the compound obtained at the step k in Example 4065.

Examples 5449 to 5858

According to the procedures in the steps a to b in Example 9, as shown in the following figure:

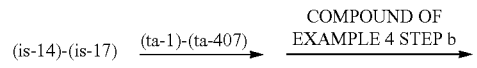

the compounds of Examples 5449 to 5858 described in Table 7 (Tables 7-1 to 7-4) represented by the formula (V) are obtained using any of isothiocyanate (is-14) to (is-17) represented by the aforementioned formula (5-2b), any of tertiary amine (ta-1) to (ta-407) represented by the aforementioned formula (2) and the compound obtained at the step b in Example 4. In the formula (V), -sp- represents any of (sp-14) and (sp-25) and -an represents any of (an-1) to (an-407).

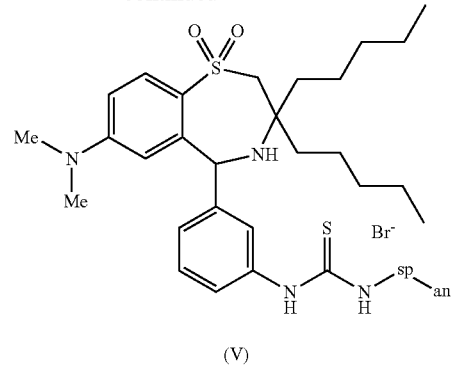

(V)

| EXAMPLE No. | REAGENT is | REAGENT ta | PRODUCT sp | PRODUCT an | EXAMPLE No. | REAGENT is | REAGENT ta | PRODUCT sp | PRODUCT an |
|---|---|---|---|---|---|---|---|---|---|
| \multicolumn{10}{c}{Table 7-1} |
| 5449 | is-14 | ta-1 | sp-14 | an-1 | 5654 | is-14 | ta-206 | sp-14 | an-206 |
| 5450 | is-14 | ta-2 | sp-14 | an-2 | 5655 | is-14 | ta-207 | sp-14 | an-207 |
| 5451 | is-14 | ta-3 | sp-14 | an-3 | 5656 | is-14 | ta-208 | sp-14 | an-208 |
| 5452 | is-14 | ta-4 | sp-14 | an-4 | 5657 | is-14 | ta-209 | sp-14 | an-209 |
| 5453 | is-14 | ta-5 | sp-14 | an-5 | 5658 | is-14 | ta-210 | sp-14 | an-210 |
| 5454 | is-14 | ta-6 | sp-14 | an-6 | 5659 | is-14 | ta-211 | sp-14 | an-211 |
| 5455 | is-14 | ta-7 | sp-14 | an-7 | 5660 | is-14 | ta-212 | sp-14 | an-212 |
| 5456 | is-14 | ta-8 | sp-14 | an-8 | 5661 | is-14 | ta-213 | sp-14 | an-213 |
| 5457 | is-14 | ta-9 | sp-14 | an-9 | 5662 | is-14 | ta-214 | sp-14 | an-214 |
| 5458 | is-14 | ta-10 | sp-14 | an-10 | 5663 | is-14 | ta-215 | sp-14 | an-215 |
| 5459 | is-14 | ta-11 | sp-14 | an-11 | 5664 | is-14 | ta-216 | sp-14 | an-216 |
| 5460 | is-14 | ta-12 | sp-14 | an-12 | 5665 | is-14 | ta-217 | sp-14 | an-217 |
| 5461 | is-14 | ta-13 | sp-14 | an-13 | 5666 | is-14 | ta-218 | sp-14 | an-218 |
| 5462 | is-14 | ta-14 | sp-14 | an-14 | 5667 | is-14 | ta-219 | sp-14 | an-219 |
| 5463 | is-14 | ta-15 | sp-14 | an-15 | 5668 | is-14 | ta-220 | sp-14 | an-220 |
| 5464 | is-14 | ta-16 | sp-14 | an-16 | 5669 | is-14 | ta-221 | sp-14 | an-221 |
| 5465 | is-14 | ta-17 | sp-14 | an-17 | 5670 | is-14 | ta-222 | sp-14 | an-222 |
| 5466 | is-14 | ta-18 | sp-14 | an-18 | 5671 | is-14 | ta-223 | sp-14 | an-223 |
| 5467 | is-14 | ta-19 | sp-14 | an-19 | 5672 | is-14 | ta-224 | sp-14 | an-224 |
| 5468 | is-14 | ta-20 | sp-14 | an-20 | 5673 | is-14 | ta-225 | sp-14 | an-225 |
| 5469 | is-14 | ta-21 | sp-14 | an-21 | 5674 | is-14 | ta-226 | sp-14 | an-226 |
| 5470 | is-14 | ta-22 | sp-14 | an-22 | 5675 | is-14 | ta-227 | sp-14 | an-227 |
| 5471 | is-14 | ta-23 | sp-14 | an-23 | 5676 | is-14 | ta-228 | sp-14 | an-228 |
| 5472 | is-14 | ta-24 | sp-14 | an-24 | 5677 | is-14 | ta-229 | sp-14 | an-229 |
| 5473 | is-14 | ta-25 | sp-14 | an-25 | 5678 | is-14 | ta-230 | sp-14 | an-230 |
| 5474 | is-14 | ta-26 | sp-14 | an-26 | 5679 | is-14 | ta-231 | sp-14 | an-231 |
| 5475 | is-14 | ta-27 | sp-14 | an-27 | 5680 | is-14 | ta-232 | sp-14 | an-232 |
| 5476 | is-14 | ta-28 | sp-14 | an-28 | 5681 | is-14 | ta-233 | sp-14 | an-233 |
| 5477 | is-14 | ta-29 | sp-14 | an-29 | 5682 | is-14 | ta-234 | sp-14 | an-234 |
| 5478 | is-14 | ta-30 | sp-14 | an-30 | 5683 | is-14 | ta-235 | sp-14 | an-235 |
| 5479 | is-14 | ta-31 | sp-14 | an-31 | 5684 | is-14 | ta-236 | sp-14 | an-236 |
| 5480 | is-14 | ta-32 | sp-14 | an-32 | 5685 | is-14 | ta-237 | sp-14 | an-237 |
| 5481 | is-14 | ta-33 | sp-14 | an-33 | 5686 | is-14 | ta-238 | sp-14 | an-238 |
| 5482 | is-14 | ta-34 | sp-14 | an-34 | 5687 | is-14 | ta-239 | sp-14 | an-239 |
| 5483 | is-14 | ta-35 | sp-14 | an-35 | 5688 | is-14 | ta-240 | sp-14 | an-240 |
| 5484 | is-14 | ta-36 | sp-14 | an-36 | 5689 | is-14 | ta-241 | sp-14 | an-241 |
| 5485 | is-14 | ta-37 | sp-14 | an-37 | 5690 | is-14 | ta-242 | sp-14 | an-242 |
| 5486 | is-14 | ta-38 | sp-14 | an-38 | 5691 | is-14 | ta-243 | sp-14 | an-243 |
| 5487 | is-14 | ta-39 | sp-14 | an-39 | 5692 | is-14 | ta-244 | sp-14 | an-244 |
| 5488 | is-14 | ta-40 | sp-14 | an-40 | 5693 | is-14 | ta-245 | sp-14 | an-245 |
| 5489 | is-14 | ta-41 | sp-14 | an-41 | 5694 | is-14 | ta-246 | sp-14 | an-246 |
| 5490 | is-14 | ta-42 | sp-14 | an-42 | 5695 | is-14 | ta-247 | sp-14 | an-247 |
| 5491 | is-14 | ta-43 | sp-14 | an-43 | 5696 | is-14 | ta-248 | sp-14 | an-248 |

-continued

| EXAMPLE | REAGENT | | PRODUCT | EXAMPLE | REAGENT | | PRODUCT |
|---|---|---|---|---|---|---|---|
| No. | is | ta | sp | an | No. | is | ta | sp | an |
| 5492 | is-14 | ta-44 | sp-14 | an-44 | 5697 | is-14 | ta-249 | sp-14 | an-249 |
| 5493 | is-14 | ta-45 | sp-14 | an-45 | 5698 | is-14 | ta-250 | sp-14 | an-250 |
| 5494 | is-14 | ta-46 | sp-14 | an-46 | 5699 | is-14 | ta-251 | sp-14 | an-251 |
| 5495 | is-14 | ta-47 | sp-14 | an-47 | 5700 | is-14 | ta-252 | sp-14 | an-252 |
| 5496 | is-14 | ta-48 | sp-14 | an-48 | 5701 | is-14 | ta-253 | sp-14 | an-253 |
| 5497 | is-14 | ta-49 | sp-14 | an-49 | 5702 | is-14 | ta-254 | sp-14 | an-254 |
| 5498 | is-14 | ta-50 | sp-14 | an-50 | 5703 | is-14 | ta-255 | sp-14 | an-255 |
| 5499 | is-14 | ta-51 | sp-14 | an-51 | 5704 | is-14 | ta-256 | sp-14 | an-256 |
| 5500 | is-14 | ta-52 | sp-14 | an-52 | 5705 | is-14 | ta-257 | sp-14 | an-257 |
| 5501 | is-14 | ta-53 | sp-14 | an-53 | 5706 | is-14 | ta-258 | sp-14 | an-258 |

Table 7-2

| EXAMPLE | REAGENT | | PRODUCT | EXAMPLE | REAGENT | | PRODUCT |
|---|---|---|---|---|---|---|---|
| No. | is | ta | sp | an | No. | is | ta | sp | an |
| 5502 | is-14 | ta-54 | sp-14 | an-54 | 5707 | is-14 | ta-259 | sp-14 | an-259 |
| 5503 | is-14 | ta-55 | sp-14 | an-55 | 5708 | is-14 | ta-260 | sp-14 | an-260 |
| 5504 | is-14 | ta-56 | sp-14 | an-56 | 5709 | is-14 | ta-261 | sp-14 | an-261 |
| 5505 | is-14 | ta-57 | sp-14 | an-57 | 5710 | is-14 | ta-262 | sp-14 | an-262 |
| 5506 | is-14 | ta-58 | sp-14 | an-58 | 5711 | is-14 | ta-263 | sp-14 | an-263 |
| 5507 | is-14 | ta-59 | sp-14 | an-59 | 5712 | is-14 | ta-264 | sp-14 | an-264 |
| 5508 | is-14 | ta-60 | sp-14 | an-60 | 5713 | is-14 | ta-265 | sp-14 | an-265 |
| 5509 | is-14 | ta-61 | sp-14 | an-61 | 5714 | is-14 | ta-266 | sp-14 | an-266 |
| 5510 | is-14 | ta-62 | sp-14 | an-62 | 5715 | is-14 | ta-267 | sp-14 | an-267 |
| 5511 | is-14 | ta-63 | sp-14 | an-63 | 5716 | is-14 | ta-268 | sp-14 | an-268 |
| 5512 | is-14 | ta-64 | sp-14 | an-64 | 5717 | is-14 | ta-269 | sp-14 | an-269 |
| 5513 | is-14 | ta-65 | sp-14 | an-65 | 5718 | is-14 | ta-270 | sp-14 | an-270 |
| 5514 | is-14 | ta-66 | sp-14 | an-66 | 5719 | is-14 | ta-271 | sp-14 | an-271 |
| 5515 | is-14 | ta-67 | sp-14 | an-67 | 5720 | is-14 | ta-272 | sp-14 | an-272 |
| 5516 | is-14 | ta-68 | sp-14 | an-68 | 5721 | is-14 | ta-273 | sp-14 | an-273 |
| 5517 | is-14 | ta-69 | sp-14 | an-69 | 5722 | is-14 | ta-274 | sp-14 | an-274 |
| 5518 | is-14 | ta-70 | sp-14 | an-70 | 5723 | is-14 | ta-275 | sp-14 | an-275 |
| 5519 | is-14 | ta-71 | sp-14 | an-71 | 5724 | is-14 | ta-276 | sp-14 | an-276 |
| 5520 | is-14 | ta-72 | sp-14 | an-72 | 5725 | is-14 | ta-277 | sp-14 | an-277 |
| 5521 | is-14 | ta-73 | sp-14 | an-73 | 5726 | is-14 | ta-278 | sp-14 | an-278 |
| 5522 | is-14 | ta-74 | sp-14 | an-74 | 5727 | is-14 | ta-279 | sp-14 | an-279 |
| 5523 | is-14 | ta-75 | sp-14 | an-75 | 5728 | is-14 | ta-280 | sp-14 | an-280 |
| 5524 | is-14 | ta-76 | sp-14 | an-76 | 5729 | is-14 | ta-281 | sp-14 | an-281 |
| 5525 | is-14 | ta-77 | sp-14 | an-77 | 5730 | is-14 | ta-282 | sp-14 | an-282 |
| 5526 | is-14 | ta-78 | sp-14 | an-78 | 5731 | is-14 | ta-283 | sp-14 | an-283 |
| 5527 | is-14 | ta-79 | sp-14 | an-79 | 5732 | is-14 | ta-284 | sp-14 | an-284 |
| 5528 | is-14 | ta-80 | sp-14 | an-80 | 5733 | is-14 | ta-285 | sp-14 | an-285 |
| 5529 | is-14 | ta-81 | sp-14 | an-81 | 5734 | is-14 | ta-286 | sp-14 | an-286 |
| 5530 | is-14 | ta-82 | sp-14 | an-82 | 5735 | is-14 | ta-287 | sp-14 | an-287 |
| 5531 | is-14 | ta-83 | sp-14 | an-83 | 5736 | is-14 | ta-288 | sp-14 | an-288 |
| 5532 | is-14 | ta-84 | sp-14 | an-84 | 5737 | is-14 | ta-289 | sp-14 | an-289 |
| 5533 | is-14 | ta-85 | sp-14 | an-85 | 5738 | is-14 | ta-290 | sp-14 | an-290 |
| 5534 | is-14 | ta-86 | sp-14 | an-86 | 5739 | is-14 | ta-291 | sp-14 | an-291 |
| 5535 | is-14 | ta-87 | sp-14 | an-87 | 5740 | is-14 | ta-292 | sp-14 | an-292 |
| 5536 | is-14 | ta-88 | sp-14 | an-88 | 5741 | is-14 | ta-293 | sp-14 | an-293 |
| 5537 | is-14 | ta-89 | sp-14 | an-89 | 5742 | is-14 | ta-294 | sp-14 | an-294 |
| 5538 | is-14 | ta-90 | sp-14 | an-90 | 5743 | is-14 | ta-295 | sp-14 | an-295 |
| 5539 | is-14 | ta-91 | sp-14 | an-91 | 5744 | is-14 | ta-296 | sp-14 | an-296 |
| 5540 | is-14 | ta-92 | sp-14 | an-92 | 5745 | is-14 | ta-297 | sp-14 | an-297 |
| 5541 | is-14 | ta-93 | sp-14 | an-93 | 5746 | is-14 | ta-298 | sp-14 | an-298 |
| 5542 | is-14 | ta-94 | sp-14 | an-94 | 5747 | is-14 | ta-299 | sp-14 | an-299 |
| 5543 | is-14 | ta-95 | sp-14 | an-95 | 5748 | is-14 | ta-300 | sp-14 | an-300 |
| 5544 | is-14 | ta-96 | sp-14 | an-96 | 5749 | is-14 | ta-301 | sp-14 | an-301 |
| 5545 | is-14 | ta-97 | sp-14 | an-97 | 5750 | is-14 | ta-302 | sp-14 | an-302 |
| 5546 | is-14 | ta-98 | sp-14 | an-98 | 5751 | is-14 | ta-303 | sp-14 | an-303 |
| 5547 | is-14 | ta-99 | sp-14 | an-99 | 5752 | is-14 | ta-304 | sp-14 | an-304 |
| 5548 | is-14 | ta-100 | sp-14 | an-100 | 5753 | is-14 | ta-305 | sp-14 | an-305 |
| 5549 | is-14 | ta-101 | sp-14 | an-101 | 5754 | is-14 | ta-306 | sp-14 | an-306 |
| 5550 | is-14 | ta-102 | sp-14 | an-102 | 5755 | is-14 | ta-307 | sp-14 | an-307 |
| 5551 | is-14 | ta-103 | sp-14 | an-103 | 5756 | is-14 | ta-308 | sp-14 | an-308 |
| 5552 | is-14 | ta-104 | sp-14 | an-104 | 5757 | is-14 | ta-309 | sp-14 | an-309 |
| 5553 | is-14 | ta-105 | sp-14 | an-105 | 5758 | is-14 | ta-310 | sp-14 | an-310 |
| 5554 | is-14 | ta-106 | sp-14 | an-106 | 5759 | is-14 | ta-311 | sp-14 | an-311 |

Table 7-3

| EXAMPLE | REAGENT | | PRODUCT | EXAMPLE | REAGENT | | PRODUCT |
|---|---|---|---|---|---|---|---|
| No. | is | ta | sp | an | No. | is | ta | sp | an |
| 5555 | is-14 | ta-107 | sp-14 | an-107 | 5760 | is-14 | ta-312 | sp-14 | an-312 |
| 5556 | is-14 | ta-108 | sp-14 | an-108 | 5761 | is-14 | ta-313 | sp-14 | an-313 |
| 5557 | is-14 | ta-109 | sp-14 | an-109 | 5762 | is-14 | ta-314 | sp-14 | an-314 |
| 5558 | is-14 | ta-110 | sp-14 | an-110 | 5763 | is-14 | ta-315 | sp-14 | an-315 |
| 5559 | is-14 | ta-111 | sp-14 | an-111 | 5764 | is-14 | ta-316 | sp-14 | an-316 |
| 5560 | is-14 | ta-112 | sp-14 | an-112 | 5765 | is-14 | ta-317 | sp-14 | an-317 |
| 5561 | is-14 | ta-113 | sp-14 | an-113 | 5766 | is-14 | ta-318 | sp-14 | an-318 |
| 5562 | is-14 | ta-114 | sp-14 | an-114 | 5767 | is-14 | ta-319 | sp-14 | an-319 |
| 5563 | is-14 | ta-115 | sp-14 | an-115 | 5768 | is-14 | ta-320 | sp-14 | an-320 |

-continued

| EXAMPLE | REAGENT | | PRODUCT | EXAMPLE | REAGENT | | PRODUCT |
|---|---|---|---|---|---|---|---|
| No. | is | ta | sp an | No. | is | ta | sp an |
| 5564 | is-14 | ta-116 | sp-14 an-116 | 5769 | is-14 | ta-321 | sp-14 an-321 |
| 5565 | is-14 | ta-117 | sp-14 an-117 | 5770 | is-14 | ta-322 | sp-14 an-322 |
| 5566 | is-14 | ta-118 | sp-14 an-118 | 5771 | is-14 | ta-323 | sp-14 an-323 |
| 5567 | is-14 | ta-119 | sp-14 an-119 | 5772 | is-14 | ta-324 | sp-14 an-324 |
| 5568 | is-14 | ta-120 | sp-14 an-120 | 5773 | is-14 | ta-325 | sp-14 an-325 |
| 5569 | is-14 | ta-121 | sp-14 an-121 | 5774 | is-14 | ta-326 | sp-14 an-326 |
| 5570 | is-14 | ta-122 | sp-14 an-122 | 5775 | is-14 | ta-327 | sp-14 an-327 |
| 5571 | is-14 | ta-123 | sp-14 an-123 | 5776 | is-14 | ta-328 | sp-14 an-328 |
| 5572 | is-14 | ta-124 | sp-14 an-124 | 5777 | is-14 | ta-329 | sp-14 an-329 |
| 5573 | is-14 | ta-125 | sp-14 an-125 | 5778 | is-14 | ta-330 | sp-14 an-330 |
| 5574 | is-14 | ta-126 | sp-14 an-126 | 5779 | is-14 | ta-331 | sp-14 an-331 |
| 5575 | is-14 | ta-127 | sp-14 an-127 | 5780 | is-14 | ta-332 | sp-14 an-332 |
| 5576 | is-14 | ta-128 | sp-14 an-128 | 5781 | is-14 | ta-333 | sp-14 an-333 |
| 5577 | is-14 | ta-129 | sp-14 an-129 | 5782 | is-14 | ta-334 | sp-14 an-334 |
| 5578 | is-14 | ta-130 | sp-14 an-130 | 5783 | is-14 | ta-335 | sp-14 an-335 |
| 5579 | is-14 | ta-131 | sp-14 an-131 | 5784 | is-14 | ta-336 | sp-14 an-336 |
| 5580 | is-14 | ta-132 | sp-14 an-132 | 5785 | is-14 | ta-337 | sp-14 an-337 |
| 5581 | is-14 | ta-133 | sp-14 an-133 | 5786 | is-14 | ta-338 | sp-14 an-338 |
| 5582 | is-14 | ta-134 | sp-14 an-134 | 5787 | is-14 | ta-339 | sp-14 an-339 |
| 5583 | is-14 | ta-135 | sp-14 an-135 | 5788 | is-14 | ta-340 | sp-14 an-340 |
| 5584 | is-14 | ta-136 | sp-14 an-136 | 5789 | is-14 | ta-341 | sp-14 an-341 |
| 5585 | is-14 | ta-137 | sp-14 an-137 | 5790 | is-14 | ta-342 | sp-14 an-342 |
| 5586 | is-14 | ta-138 | sp-14 an-138 | 5791 | is-14 | ta-343 | sp-14 an-343 |
| 5587 | is-14 | ta-139 | sp-14 an-139 | 5792 | is-14 | ta-344 | sp-14 an-344 |
| 5588 | is-14 | ta-140 | sp-14 an-140 | 5793 | is-14 | ta-345 | sp-14 an-345 |
| 5589 | is-14 | ta-141 | sp-14 an-141 | 5794 | is-14 | ta-346 | sp-14 an-346 |
| 5590 | is-14 | ta-142 | sp-14 an-142 | 5795 | is-14 | ta-347 | sp-14 an-347 |
| 5591 | is-14 | ta-143 | sp-14 an-143 | 5796 | is-14 | ta-348 | sp-14 an-348 |
| 5592 | is-14 | ta-144 | sp-14 an-144 | 5797 | is-14 | ta-349 | sp-14 an-349 |
| 5593 | is-14 | ta-145 | sp-14 an-145 | 5798 | is-14 | ta-350 | sp-14 an-350 |
| 5594 | is-14 | ta-146 | sp-14 an-146 | 5799 | is-14 | ta-351 | sp-14 an-351 |
| 5595 | is-14 | ta-147 | sp-14 an-147 | 5800 | is-14 | ta-352 | sp-14 an-352 |
| 5596 | is-14 | ta-148 | sp-14 an-148 | 5801 | is-14 | ta-353 | sp-14 an-353 |
| 5597 | is-14 | ta-149 | sp-14 an-149 | 5802 | is-14 | ta-354 | sp-14 an-354 |
| 5598 | is-14 | ta-150 | sp-14 an-150 | 5803 | is-14 | ta-355 | sp-14 an-355 |
| 5599 | is-14 | ta-151 | sp-14 an-151 | 5804 | is-14 | ta-356 | sp-14 an-356 |
| 5600 | is-14 | ta-152 | sp-14 an-152 | 5805 | is-14 | ta-357 | sp-14 an-357 |
| 5601 | is-14 | ta-153 | sp-14 an-153 | 5806 | is-14 | ta-358 | sp-14 an-358 |
| 5602 | is-14 | ta-154 | sp-14 an-154 | 5807 | is-14 | ta-359 | sp-14 an-359 |
| 5603 | is-14 | ta-155 | sp-14 an-155 | 5808 | is-14 | ta-360 | sp-14 an-360 |
| 5604 | is-14 | ta-156 | sp-14 an-156 | 5809 | is-14 | ta-361 | sp-14 an-361 |
| 5605 | is-14 | ta-157 | sp-14 an-157 | 5810 | is-14 | ta-362 | sp-14 an-362 |
| 5606 | is-14 | ta-158 | sp-14 an-158 | 5811 | is-14 | ta-363 | sp-14 an-363 |
| 5607 | is-14 | ta-159 | sp-14 an-159 | 5812 | is-14 | ta-364 | sp-14 an-364 |

Table 7-4

| 5608 | is-14 | ta-160 | sp-14 an-160 | 5813 | is-14 | ta-365 | sp-14 an-365 |
|---|---|---|---|---|---|---|---|
| 5609 | is-14 | ta-161 | sp-14 an-161 | 5814 | is-14 | ta-366 | sp-14 an-366 |
| 5610 | is-14 | ta-162 | sp-14 an-162 | 5815 | is-14 | ta-367 | sp-14 an-367 |
| 5611 | is-14 | ta-163 | sp-14 an-163 | 5816 | is-14 | ta-368 | sp-14 an-368 |
| 5612 | is-14 | ta-164 | sp-14 an-164 | 5817 | is-14 | ta-369 | sp-14 an-369 |
| 5613 | is-14 | ta-165 | sp-14 an-165 | 5818 | is-14 | ta-370 | sp-14 an-370 |
| 5614 | is-14 | ta-166 | sp-14 an-166 | 5819 | is-14 | ta-371 | sp-14 an-371 |
| 5615 | is-14 | ta-167 | sp-14 an-167 | 5820 | is-14 | ta-372 | sp-14 an-372 |
| 5616 | is-14 | ta-168 | sp-14 an-168 | 5821 | is-14 | ta-373 | sp-14 an-373 |
| 5617 | is-14 | ta-169 | sp-14 an-169 | 5822 | is-14 | ta-374 | sp-14 an-374 |
| 5618 | is-14 | ta-170 | sp-14 an-170 | 5823 | is-14 | ta-375 | sp-14 an-375 |
| 5619 | is-14 | ta-171 | sp-14 an-171 | 5824 | is-14 | ta-376 | sp-14 an-376 |
| 5620 | is-14 | ta-172 | sp-14 an-172 | 5825 | is-14 | ta-377 | sp-14 an-377 |
| 5621 | is-14 | ta-173 | sp-14 an-173 | 5826 | is-14 | ta-378 | sp-14 an-378 |
| 5622 | is-14 | ta-174 | sp-14 an-174 | 5827 | is-14 | ta-379 | sp-14 an-379 |
| 5623 | is-14 | ta-175 | sp-14 an-175 | 5828 | is-14 | ta-380 | sp-14 an-380 |
| 5624 | is-14 | ta-176 | sp-14 an-176 | 5829 | is-14 | ta-381 | sp-14 an-381 |
| 5625 | is-14 | ta-177 | sp-14 an-177 | 5830 | is-14 | ta-382 | sp-14 an-382 |
| 5626 | is-14 | ta-178 | sp-14 an-178 | 5831 | is-14 | ta-383 | sp-14 an-383 |
| 5627 | is-14 | ta-179 | sp-14 an-179 | 5832 | is-14 | ta-384 | sp-14 an-384 |
| 5628 | is-14 | ta-180 | sp-14 an-180 | 5833 | is-14 | ta-385 | sp-14 an-385 |
| 5629 | is-14 | ta-181 | sp-14 an-181 | 5834 | is-14 | ta-386 | sp-14 an-386 |
| 5630 | is-14 | ta-182 | sp-14 an-182 | 5835 | is-14 | ta-387 | sp-14 an-387 |
| 5631 | is-14 | ta-183 | sp-14 an-183 | 5836 | is-14 | ta-388 | sp-14 an-388 |
| 5632 | is-14 | ta-184 | sp-14 an-184 | 5837 | is-14 | ta-389 | sp-14 an-389 |
| 5633 | is-14 | ta-185 | sp-14 an-185 | 5838 | is-14 | ta-390 | sp-14 an-390 |
| 5634 | is-14 | ta-186 | sp-14 an-186 | 5839 | is-14 | ta-391 | sp-14 an-391 |
| 5635 | is-14 | ta-187 | sp-14 an-187 | 5840 | is-14 | ta-392 | sp-14 an-392 |
| 5636 | is-14 | ta-188 | sp-14 an-188 | 5841 | is-14 | ta-393 | sp-14 an-393 |
| 5637 | is-14 | ta-189 | sp-14 an-189 | 5842 | is-14 | ta-394 | sp-14 an-394 |

-continued

| EXAMPLE | REAGENT | | PRODUCT | | EXAMPLE | REAGENT | | PRODUCT | |
|---|---|---|---|---|---|---|---|---|---|
| No. | is | ta | sp | an | No. | is | ta | sp | an |
| 5638 | is-14 | ta-190 | sp-14 | an-190 | 5843 | is-14 | ta-395 | sp-14 | an-395 |
| 5639 | is-14 | ta-191 | sp-14 | an-191 | 5844 | is-14 | ta-396 | sp-14 | an-396 |
| 5640 | is-14 | ta-192 | sp-14 | an-192 | 5845 | is-14 | ta-397 | sp-14 | an-397 |
| 5641 | is-14 | ta-193 | sp-14 | an-193 | 5846 | is-14 | ta-398 | sp-14 | an-398 |
| 5642 | is-14 | ta-194 | sp-14 | an-194 | 5847 | is-14 | ta-399 | sp-14 | an-399 |
| 5643 | is-14 | ta-195 | sp-14 | an-195 | 5848 | is-14 | ta-400 | sp-14 | an-400 |
| 5644 | is-14 | ta-196 | sp-14 | an-196 | 5849 | is-14 | ta-401 | sp-14 | an-401 |
| 5645 | is-14 | ta-197 | sp-14 | an-197 | 5850 | is-14 | ta-402 | sp-14 | an-402 |
| 5646 | is-14 | ta-198 | sp-14 | an-198 | 5851 | is-14 | ta-403 | sp-14 | an-403 |
| 5647 | is-14 | ta-199 | sp-14 | an-199 | 5852 | is-14 | ta-404 | sp-14 | an-404 |
| 5648 | is-14 | ta-200 | sp-14 | an-200 | 5853 | is-14 | ta-405 | sp-14 | an-405 |
| 5649 | is-14 | ta-201 | sp-14 | an-201 | 5854 | is-14 | ta-406 | sp-14 | an-406 |
| 5650 | is-14 | ta-202 | sp-14 | an-202 | 5855 | is-14 | ta-407 | sp-14 | an-407 |
| 5651 | is-14 | ta-203 | sp-14 | an-203 | 5856 | is-14 | ta-32 | sp-25 | an-32 |
| 5652 | is-14 | ta-204 | sp-14 | an-204 | 5857 | is-14 | ta-287 | sp-25 | an-287 |
| 5653 | is-14 | ta-205 | sp-14 | an-205 | 5858 | is-14 | ta-305 | sp-25 | an-305 |

With each of the compounds of the Examples used in the following Test Examples, the M+ peak was confirmed as the main peak in mass spectrum.

Test Example 1

Blood Cholesterol Lowering Effect in Rats Fed Cholesterol Food

In the present Test Example, a blood cholesterol lowering effect on rats fed cholesterol food was evaluated according to the method described in J. Lipid Res., 1995, 36, 1098-1105.

That is, the food containing 0.4% cholesterol and 0.5% bile acid was given to SD (IGS) strain male rats at 7 to 9 weeks of age for 5 days in advance of the test date, to increase blood cholesterol levels. The rats in which the blood cholesterol level had been obviously elevated from the level before loading the cholesterol food were selected as the subjects in the test. Colestimide (brand name: Cholebine 70% granules, supplied from Mitsubishi Tokyo Pharmaceutical Inc.) which is an anion exchange resin drug was suspended in distilled water, and the test compound was dissolved or suspended in distilled water. They were orally administered forcibly twice per day everyday from the starting date (each n=8). The blood was collected from jugular vein 3 hours after the drug administration on the final day of the experiment, and the cholesterol level in serum was measured to examine the effect of the test compound. As a control, another group (n=8) was merely fed cholesterol food, to which distilled water (1 mL/kg) was administered and the same procedure was applied. The total cholesterol value and the HDL cholesterol value were measured using commercially available kits. The value obtained by subtracting the HDL cholesterol value from the total cholesterol value was regarded as an LDL+VLDL cholesterol value. Defining the LDL+VLDL cholesterol value in the control group to which no test compound had been administered as being 100%, a reduction rate (%) of the LDL+VLDL cholesterol value when a certain amount of the test compound had been administered was calculated.

The results are shown in Table 8. The compounds of the present invention reduced the LDL+VLDL cholesterol value. It was thus confirmed that the present compound has an excellent blood cholesterol lowering effect, and is therefore useful as the therapeutic agent and the preventive agent for hyperlipemia. It was also confirmed that the present compound has the inhibitory effect on blood cholesterol elevation when the present compound was orally administered forcibly together with giving the food containing 0.4% cholesterol and 0.5% bile acid, whereby the present compound was also proven to be useful as the preventive agent for hyperlipemia. It was also confirmed that the compounds of the Examples of the present invention other than those shown in Table 8 have an excellent blood cholesterol lowering effect, whereby they were proven to be particularly useful as the therapeutic agent and the preventive agent for hyperlipemia.

TABLE 8

| COMPOUND | LDL + VLDL REDUCTION RATE (%) IN CHOLESTEROL FED RAT MODEL (THERAPEUTIC MODEL) AMOUNT PER ADMINISTRATION IS SHOWN IN PARENTHESES |
|---|---|
| COMPARATIVE EXAMPLE* | 29.0 (25 mg/kg) |
| EXAMPLE 1 | 68.4 (1 mg/kg) |
| EXAMPLE 1 | 49 (0.3 mg/kg) |
| EXAMPLE 3713 | 41 (0.3 mg/kg) |
| EXAMPLE 3747 | 48 (0.3 mg/kg) |
| EXAMPLE 3752 | 50 (0.3 mg/kg) |
| EXAMPLE 5408 | 43 (0.3 mg/kg) |
| EXAMPLE 3696 | 25 (0.3 mg/kg) |
| EXAMPLE 3440 | 36 (0.3 mg/kg) |
| EXAMPLE 3448 | 20 (0.3 mg/kg) |
| EXAMPLE 3605 | 28 (0.3 mg/kg) |
| EXAMPLE P341 | 33 (0.3 mg/kg) |
| EXAMPLE P365 | 44 (0.3 mg/kg) |
| EXAMPLE P342 | 46 (0.3 mg/kg) |
| EXAMPLE P366 | 31 (0.3 mg/kg) |
| EXAMPLE P84 | 35 (0.1 mg/kg) |
| EXAMPLE P93 | 40 (0.1 mg/kg) |
| EXAMPLE P122 | 42 (0.1 mg/kg) |
| EXAMPLE P144 | 47 (0.1 mg/kg) |

*In Comparative Example, colestimide (brand name: Cholebine 70% granules, supplied from Mitsubishi Tokyo Pharmaceutical Inc.) was used.

Test Example 2

Lowering Effect on Bile Acid Concentrations in Portal Vein Blood in Rats Dosed Cholic Acid In the present Test Example, a lowering effect on bile acid concentrations in portal vein blood in rats dosed cholic acid was evaluated according to the method described in Jpn. Pharmacol. Ther., Vol. 24 Supplement, 1996, 103(S-577)-110 (S-584).

That is, SD (IGS) strain male rats at 7 to 9 weeks of age were fasted one day before the administration date. Cholic acid (200 mg/kg) and the test compound were dissolved or suspended in distilled water containing a surfactant (Tween 20, Bio-Rad, or HCO-60, Nippon Chemicals) at a final concentration of 0.05% or 1%, and orally administered forcibly to the rats. The blood was collected from the portal vein 2 hours after the forced oral administration, and a total bile acid value in serum was measured to examine the effect of the test compound (n=6). As a control, another group (n=6) merely received cholic acid (200 mg/kg), to which the same procedure was applied. The cholic acid value was measured using the commercially available kit (brand name: Total Bile Acid-Test Wako, supplied form Wako Pure Chemical Industries). Defining the value in the control group to which no test compound had been administered as being 100%, a reduction rate (%) of the bile acid value when a certain amount of the test compound had been administered was calculated.

The results are shown in Table 9 (Tables 9-1 to 9-2). The compounds of the present invention reduced the bile acid value. It was thus confirmed that the present compound has an excellent inhibitory effect on bile acid reabsorption, and is therefore useful as the therapeutic agent and the preventive agent for hyperlipemia, as well as the therapeutic agent for hepatic disorders associated with cholestasis. It was also confirmed that the compounds of the Examples of the present invention other than those shown in Table 9 have an excellent inhibitory effect on bile acid reabsorption, whereby they were proven to be useful as the therapeutic agent and the preventive agent for hyperlipemia, as well as the therapeutic agent for hepatic disorders associated with cholestasis.

| COMPOUND | BILE ACID REDUCTION RATE (%) IN RAT MODEL WITH CHOLIC ACID LOADING AMOUNT PER ADMINISTRATION IS SHOWN IN PARENTHESES |
|---|---|
| Table 9-1 | |
| COMPARATIVE EXAMPLE 1* | 16 (25 mg/kg) # |
| COMPARATIVE EXAMPLE 2** | 3 (0.1 mg/kg) # |
| EXAMPLE 3835 | 23 (0.1 mg/kg) # |
| EXAMPLE 1 | 51 (0.1 mg/kg) # |
| EXAMPLE 3932 | 30 (0.1 mg/kg) # |
| EXAMPLE 9 | 13 (0.1 mg/kg) # |
| EXAMPLE 425 | 21 (0.1 mg/kg) # |
| EXAMPLE 801 | 33 (0.1 mg/kg) ## |
| EXAMPLE 1178 | 18 (0.1 mg/kg) ## |
| EXAMPLE 3440 | 26 (0.1 mg/kg) ## |
| EXAMPLE 3695 | 23 (0.1 mg/kg) ## |
| EXAMPLE 3853 | 36 (0.1 mg/kg) ## |
| EXAMPLE 3607 | 36 (0.1 mg/kg) ## |
| EXAMPLE 3608 | 43 (0.1 mg/kg) ## |
| EXAMPLE 5405 | 16 (0.1 mg/kg) ## |
| EXAMPLE 4512 | 37 (0.1 mg/kg) ## |
| EXAMPLE 4257 | 30 (0.1 mg/kg) ## |
| EXAMPLE 4424 | 17 (0.1 mg/kg) ## |
| EXAMPLE 4425 | 22 (0.1 mg/kg) ## |
| Table 9-2 | |
| EXAMPLE 4905 | 28 (0.1 mg/kg) ## |
| EXAMPLE 3696 | 13 (0.1 mg/kg) ## |
| EXAMPLE 3605 | 24 (0.1 mg/kg) ## |
| EXAMPLE 3475 | 19 (0.1 mg/kg) ## |
| EXAMPLE 3448 | 25 (0.1 mg/kg) ## |
| EXAMPLE 5406 | 15 (0.1 mg/kg) ## |
| EXAMPLE 3409 | 28 (0.1 mg/kg) ## |
| EXAMPLE 3783 | 16 (0.1 mg/kg) ## |
| EXAMPLE 3710 | 20 (0.1 mg/kg) ## |
| EXAMPLE 3713 | 32 (0.1 mg/kg) ## |
| EXAMPLE 3753 | 8.5 (0.3 mg/kg) ## |
| EXAMPLE 3759 | 36 (0.3 mg/kg) ## |
| EXAMPLE 5043 | 39 (0.3 mg/kg) ## |
| EXAMPLE 5298 | 40 (0.3 mg/kg) ## |
| EXAMPLE 3747 | 40 (0.1 mg/kg) ## |
| EXAMPLE 3752 | 42 (0.1 mg/kg) ## |
| EXAMPLE 5408 | 35 (0.1 mg/kg) ## |
| EXAMPLE P341 | 32 (0.1 mg/kg) ## |
| EXAMPLE P365 | 40 (0.1 mg/kg) ## |
| EXAMPLE P342 | 39 (0.1 mg/kg) ## |
| EXAMPLE P366 | 45 (0.1 mg/kg) ## |
| EXAMPLE P84 | 52 (0.03 mg/kg) ## |
| EXAMPLE P93 | 60 (0.03 mg/kg) ## |
| EXAMPLE P122 | 63 (0.03 mg/kg) ## |
| EXAMPLE P144 | 58 (0.03 mg/kg) ## |

*In Comparative Example 1, colestimide (brand name: Cholebine 70% granules, supplied from Mitsubishi Tokyo Pharmaceutical Inc.) was used.
**In Comparative Example 2, the compound 5 (Synthetic Example 19): 1-{4-[4-(3,3-dibutyl-7-dimethylamino-1,1-dioxo-2,3,4,5-tetrahydro-1,4-benzothiazepine-5-yl)phenoxymethyl]benzyl}-4-aza-1-azoniabicyclo[2.2.2]octane chloride which is reported to have the strongest activity among compounds specifically described in WO02/08211. was used.
As the surfactant, Tween 20 at a final concentration of 0.05% was used.
As the surfactant, HCO-60 at a final concentration of 0.1% was used.

Test Example 3

Effect on Rat Hepatic Cholesterol 7-α-hydroxylase (7α-OHase) Activity

In the present Test Example, an effect on rat hepatic cholesterol 7-α-hydroxylase (7α-OHase) activity was evaluated according to the method described in Analytical Biochemistry, 1986, 158, 228-232.

That is, the test compound and vehicle (Water for Injection, brand name: Otsuka Pharmaceutical Factory Inc.) were administered to SD (IGS) strain rats at 6 weeks of age using an oral sonde for 14 days (n=5). Solid feedstuff (brand name: CRF-1, Oriental Yeast Co., Ltd.) as the food was given ad libitum and tap water sterilized by adding chlorine was given ad libitum as drinking water using a water supply bottle. After autopsy, the liver was removed and pre-stored at −80° C. The frozen and then melt hepatic sample was homogenized in 1.15% KCl, and then centrifuged to prepare hepatic microsome. The final pelletized sample was resuspended in sodium phosphate/potassium phosphate buffer, and an aliquot was incubated in the presence of NADPH at 37° C. for 20 minutes. Produced 7α-hydroxycholesterol was converted into 7α-hydroxy-4-cholesten-3-one by cholesterol oxidase. After being extracted with petroleum ether, the organic solvent was evaporated, and the residue was dissolved in isopropanol. The aliquot of the extract was applied onto a reverse phase HPLC column (brand name: Finepak SIL-5, JASCO) to separate the enzymatic product, and the eluted substance was quantified using an UV detector at 240 nm.

The compound of the present invention exhibited the augmentation effect on hepatic cholesterol 7-α-hydroxylase activity (7α-OHase) involved in blood cholesterol lowering mechanism by IBAT, i.e., the ileal bile acid transporter (Arterioscler Thromb. Vasc. Biol., 1998, 18, 1304-1311). It was therefore confirmed that the present compound has a possibility to be the therapeutic agent and the preventive agent for hyperlipemia.

Test example 4

Model for Hepatic Disorder Associated with Cholestasis (Hepatic Cell Apoptosis)

In the present Test Example, a model for the hepatic disorder associated with cholestasis was employed with reference to apoptosis induction in hepatic cells in a hypercholesterolemia model described in Am. J. Physiol., 1995, 268, G613-G621.

That is, the food containing 0.4% cholesterol and 0.5% bile acid was given to SD (IGS) strain male rats at 7 to 9 weeks of age for 4 days, and the test compound was orally administered forcibly twice per day everyday from the starting date of cholesterol food feeding (each n=8). As a control, another group (n=8) were merely fed cholesterol food. The blood was exsanguinated from abdominal aorta 3 hours after the drug administration on the final day of the experiment. Then the liver was immediately removed and fixed in 10% neutral buffered formalin solution (brand name: FA-F96, supplied from Kokusan Chemical Co. Ltd.). After fixing, the sample was dehydrated and embedded using a closed type automatic embedding apparatus (brand name: ETP-180B, supplied from Sakura Finetek Japan). Sliced sections with thickness of 2 to 5 μm were prepared with a microtome (brand name: IVS-410, supplied from Sakura Finetek Japan), and hematoxylin and eosin staining was given thereto using an automatic staining apparatus (brand name: DRS-60, supplied from Sakura Finetek japan). A total number of mitotic cells in different 10 sites in the range of 200 μm×200 μm on each section was counted.

The results are shown in the following Table 10. The compound of the present invention reduced the number of mitotic cells in the liver. It was thus confirmed that the present compound has an improvement effect on the hepatic disorder associated with cholestasis, whereby the present compound was proven to be useful as the therapeutic agent and the preventive agent for the hepatic disorder associated with cholestasis.

TABLE 10

| COMPOUND | MITOTIC CELLS IN LIVER (AVERAGE ± STANDARD ERROR, n = 8) AMOUNT PER ADMINISTRATION IS SHOWN IN PARENTHESES |
|---|---|
| EXAMPLE 1 | 50 ± 13 (CONTROL GROUP) |
|  | 28 ± 7 (1 mg/kg) |
|  | 36 ± 13 (0.1 mg/kg) |

Test Example 5

Model for Hepatic Disorder Associated with Cholestasis (Partial Bile Duct Ligation Model)

In the present Test Example, a model for the hepatic disorder caused by partial ligation of the bile duct was employed with reference to Kanno's method (Liver, 43, Suppl (1):A126, 2002).

That is, to the SD (IGS) strain male rats at 7 to 10 weeks of age, the partial ligation of the bile duct was given with opening the abdominal cavity under anesthesia with pentobarbital. Before the operation, the blood was collected from femoral vein, in order to obtain the value before the administration. From the day after the operation, 200 mg/kg of bile acid and the test compound were orally administered forcibly twice per day for 3.5 days (Protocol A). Without giving the partial ligation of the bile duct, 200 mg/kg of bile acid and the test compound were also orally administered forcibly twice per day for 3.5 days (Protocol B). In both cases, the test compound was dissolved or suspended in distilled water or an aqueous solution of 1% HCO 60 (Nippon Chemicals). To the control group, saline was administered. As comparative examples, 25 mg/kg of cholestyramine (supplied from Sigma) or 50 mg/kg of ursodeoxycholic acid (supplied from Mitsubishi Pharma) was administered. For considering the effect of the operation, sham operation (sham group) was performed in some cases. The blood was collected from the abdominal aorta 6 hours after the drug administration on the final day of the experiment. AST (GOT), ALT (GPT) and ALP in the blood were measured using measurement kits (GOT II-HA Test Wako, GPT II-HA Test Wako and Alkaline Phosphor HA Test Wako, all were supplied from Wako Pure Chemical Industries) and using an automatic analyzer (Ni-tech ANALAYZER SUPER Z818).

The results are shown in the following Tables 11 to 13. The compounds of the present invention inhibited the elevation of AST, ALT and ALP caused by the partial ligation of the bile duct and the bile acid administration. It was thus confirmed that the present compound has an improvement effect on the hepatic disorder associated with cholestasis, whereby the present compound was proven to be useful as the therapeutic agent and the preventive agent for the hepatic disorder associated with cholestasis, and particularly as the therapeutic agent and the preventive agent for primary biliary cirrhosis and primary sclerosing cholangitis. It was also confirmed that the compounds of the Examples of the present invention other than those shown in Tables 11 to 13 have an excellent improvement effect on the hepatic disorder associated with cholestasis.

(Protocol A)

TABLE 11

| COMPOUND | AST (IU/L) | ALT (IU/L) | ALP (IU/L) |
|---|---|---|---|
| (BEFORE ADMINISTRATION) | 108 ± 6 | 38 ± 2 | 591 ± 116 |
| CONTROL GROUP | 400 ± 160 | 200 ± 81 | 1120 ± 410 |
| COMPARATIVE EXAMPLE 1 | 385 ± 214 | 208 ± 123 | 1280 ± 660 |
| COMPARATIVE EXAMPLE 2 | 256 ± 64 | 98 ± 25 | 785 ± 120 |
| EXAMPLE 1 (0.1 mg/kg) | 182 ± 42 | 61 ± 4 | 603 ± 78 |

(All of the results are N=8 and shown as mean±standard error) As Comparative Example 1, 25 mg/kg of cholestyramine was administered. As Comparative Example 2, 50 mg/kg of ursodeoxycholic acid was administered. As the solvent, distilled water was used.

| (PROTOCOL A) | | | |
|---|---|---|---|
| COMPOUND | AST(IU/L) | ALT(IU/L) | ALP(IU/L) |
| Table 12-1 | | | |
| Sham GROUP | 141 ± 26 | 43 ± 1 | 665 ± 94 |
| CONTROL GROUP | 589 ± 221 | 417 ± 185 | 2318 ± 583 |
| COMPARATIVE EXAMPLE | 916 ± 146 | 527 ± 118 | 2042 ± 235 |

-continued (PROTOCOL A)

| COMPOUND | AST(IU/L) | ALT(IU/L) | ALP(IU/L) |
|---|---|---|---|
| EXAMPLE 3440 (1 mg/kg) | 309 ± 37 | 155 ± 38 | 1614 ± 189 |
| EXAMPLE 3605 (1 mg/kg) | 487 ± 382 | 258 ± 219 | 1489 ± 533 |
| EXAMPLE 3448 (1 mg/kg) | 352 ± 210 | 181 ± 79 | 1148 ± 332 |

Table 12-2

| | | | |
|---|---|---|---|
| Sham GROUP | 128 ± 18 | 48 ± 5 | 630 ± 87 |
| CONTROL GROUP | 643 ± 125 | 384 ± 156 | 2204 ± 327 |
| EXAMPLE 3696 (1 mg/kg) | 325 ± 87 | 191 ± 21 | 1209 ± 125 |
| EXAMPLE 3713 (1 mg/kg) | 280 ± 61 | 163 ± 96 | 1008 ± 289 |
| EXAMPLE 3747 (1 mg/kg) | 245 ± 81 | 146 ± 70 | 960 ± 259 |
| EXAMPLE 3752 (1 mg/kg) | 358 ± 87 | 165 ± 47 | 1112 ± 184 |
| EXAMPLE 5408 (1 mg/kg) | 198 ± 65 | 197 ± 45 | 1005 ± 102 |

Table 12-3

| | | | |
|---|---|---|---|
| Sham GROUP | 106 ± 32 | 53 ± 8 | 654 ± 102 |
| CONTROL GROUP | 711 ± 131 | 402 ± 130 | 1904 ± 210 |
| EXAMPLE P84 (0.3 mg/kg) | 411 ± 102 | 205 ± 68 | 1200 ± 321 |
| EXAMPLE P93 (0.3 mg/kg) | 178 ± 49 | 156 ± 56 | 1103 ± 199 |
| EXAMPLE P122 (0.3 mg/kg) | 256 ± 113 | 148 ± 89 | 1026 ± 321 |
| EXAMPLE P144 (0.3 mg/kg) | 231 ± 87 | 102 ± 34 | 988 ± 287 |

(All of the results are N = 3 and shown as mean ± standard error) As Comparative Example 1, 25 mg/kg of cholestyramine was administered. With the compound of the present invention, the aqueous solution of 1% HCO 60 was used as the solvent.

TABLE 13

(PROTOCOL B)

| COMPOUND | AST (IU/L) | ALT (IU/L) | ALP (IU/L) |
|---|---|---|---|
| (BEFORE ADMINISTRATION) | 102 ± 5 | 38 ± 5 | 608 ± 54 |
| CONTROL GROUP | 157 ± 35 | 82 ± 17 | 593 ± 77 |
| COMPARATIVE EXAMPLE 1 | 149 ± 10 | 70 ± 6 | 602 ± 78 |
| COMPARATIVE EXAMPLE 2 | 109 ± 11 | 62 ± 9 | 453 ± 58 |
| EXAMPLE 1 (0.1 mg/kg) | 100 ± 2 | 53 ± 6 | 453 ± 50 |

(All off the results are N = 8 and shown as mean ± standard error) As Comparative Example 1, 25 mg/kg of cholestyramine was administered. As Comparative Example 2, 50 mg/kg of ursodeoxycholic acid was administered. As the solvent, the distilled water was used.

Test Example 6

Obesity and Fatty Liver Model

In the present Test Example, an obesity and fatty liver model was employed with reference to the method described in WO02/09757.

That is, KKA$^y$/Ta Jcl male mice at 10 weeks of age were used as obese mice (N=4 to 7). The test compound was dissolved or suspended in the aqueous solution of 1% HCO 60 (supplied from Nippon Chemicals). The aqueous solution of 1% HCO 60 (supplied from Nippon Chemicals) was used as the control. The consecutive administration was performed once a day for 2 weeks, and body weight was measured daily and compared with the body weight on the day before the administration. On the day after the final administration, the liver was removed, and a triglyceride concentration in liver tissue was measured using a measurement kit (Triglyceride Test Wako, supplied from Wako Pure Chemical Industries). The results are shown in the following Table 14 (Tables 14-1 to 14-3).

The compounds of the present invention exhibited the inhibitory effect on weight gain and the triglyceride lowering effect in the obese mice, whereby they were proven to be useful as the therapeutic agent and the preventive agent for obesity and fatty liver. It was also confirmed that the compounds of the Examples of the present invention other than those shown in Table 14 have excellent effect of inhibiting weight gain and the hepatic triglyceride lowering.

| | BODY WEIGHT (g) | | | LIVER TRI- |
|---|---|---|---|---|
| COMPOUND | BEFORE ADMINIS- TRATION | TWO WEEKS | DIFFER- ENCE | GLYC- ERIDE (mg/g) |

Table 14-1

| | | | | |
|---|---|---|---|---|
| CONTROL GROUP (N = 7) | 42.8 ± 0.4 | 42.0 ± 0.7 | −0.8 ± 0.5 | 94 ± 18 |
| EXAMPLE 1 (N = 7) (1 mg/kg) | 43.0 ± 0.5 | 41.0 ± 0.6 | −1.9 ± 0.3 | 71 ± 13 |
| EXAMPLE 3605 (N = 4) (1 mg/kg) | 42.9 ± 1.1 | 41.4 ± 1.0 | −1.5 ± 0.4 | 65 ± 7 |

Table 14-2

| | | | | |
|---|---|---|---|---|
| CONTROL GROUP (N = 7) | 44.1 ± 0.6 | 44.8 ± 0.9 | 0.7 ± 0.4 | 103 ± 19 |
| EXAMPLE 3713 (N = 4) (1 mg/kg) | 44.0 ± 1.1 | 41.5 ± 2.4 | −2.5 ± 0.6 | 59 ± 33 |
| EXAMPLE 3747 (N = 4) (1 mg/kg) | 44.3 ± 0.8 | 42.2 ± 1.8 | −2.1 ± 1.0 | 47 ± 23 |
| EXAMPLE 3752 (N = 4) (1 mg/kg) | 43.8 ± 1.2 | 41.5 ± 1.0 | −2.3 ± 0.9 | 56 ± 23 |
| EXAMPLE 5408 (N = 4) (1 mg/kg) | 44.0 ± 0.9 | 42.2 ± 1.6 | −1.8 ± 0.5 | 70 ± 11 |
| EXAMPLE 3696 (N = 4) (1 mg/kg) | 43.5 ± 1.3 | 42.2 ± 2.2 | −1.3 ± 0.3 | 76 ± 12 |
| EXAMPLE 3440 (N = 4) (1 mg/kg) | 44.6 ± 0.8 | 43.9 ± 1.8 | −0.7 ± 1.0 | 88 ± 6 |
| EXAMPLE 3448 (N = 4) (1 mg/kg) | 44.1 ± 0.7 | 42.1 ± 3.2 | −2.0 ± 0.7 | 74 ± 8 |

Table 14-3

| | | | | |
|---|---|---|---|---|
| CONTROL GROUP (N = 4) | 49.8 ± 1.2 | 51.6 ± 1.3 | 1.8 ± 0.6 | 112 ± 17 |
| EXAMPLE P84 (N = 4) (0.3 mg/kg) | 48.9 ± 1.0 | 47.6 ± 1.3 | −1.3 ± 0.5 | 79 ± 9 |
| EXAMPLE P93 (N = 4) (0.3 mg/kg) | 49.5 ± 1.1 | 46.4 ± 0.8 | −3.1 ± 1.4 | 85 ± 12 |
| EXAMPLE P122 (N = 4) (0.3 mg/kg) | 49.9 ± 1.2 | 48.2 ± 1.6 | −1.7 ± 0.4 | 81 ± 11 |
| EXAMPLE P144 (N = 4) (0.3 mg/kg) | 49.6 ± 1.1 | 47.1 ± 0.8 | −2.5 ± 1.2 | 77 ± 9 |

(AVERAGE ± STANDARD ERROR)

Test Example 7

In Vitro Assay of Compounds Using Caco-2 Cells as to Inhibitory Activity on Ileal Bile Acid Transporter (IBAT)

In the present Test Example, an in vitro assay of compounds using Caco-2 cells as to inhibitory activity on IBAT was performed according to Test Example 1 described in WO00/35889.

That is, Caco-2 cells were seeded at $1\times10^{-5}$ cells/well in a 24-well plate. The cells cultured for 14 days or more were used for the assay. The cells were washed once with the assay buffer, i.e., Hanks buffer containing 25 mM glucose and 10 mM HEPES (pH 7.4), which was then replaced with the assay buffer containing the test compound. [$^3$H]-Taurocholate (brand name: NET-322, Daiich Pure Chemical) at a final concentration of 8 μM was added thereto, and the cells were incubated at 37° C. for 30 minutes so that [$^3$H]-Taurocholate was taken into Caco-2 cells by the action of IBAT. The cells were washed twice with the assay buffer containing 1 mM taurocholate (brand name: T-4009, Sigma), and subsequently lysed with 0.2 M NaOH to stop the reaction. The cell lysate was added to 4 mL of liquid scintillation cocktail (brand name: Clear Sol 1, supplied from Nacalai Tesque), which was then thoroughly vortexed. Then the radioactivity was measured using a liquid scintillation counter (supplied from Packard). The inhibitory rate (%) was calculated from the radioactivity in the control in which no test compound had been used and the radioactivity when the test compound at the certain concentration had been used, and the concentration of the compound which inhibited 50% of the IBAT activity was calculated. By this method, it was confirmed that the compound of the present invention exhibited the potent inhibitory activity against IBAT and therefore the present compound has a possibility to be the therapeutic agent and the preventive agent for hyperlipemia.

Test Example 8

In Vitro Assay of Compounds Using Cos 7 Cells as to Inhibitory Activity on Transiently Expressed Human IBAT or Rat IBAT Transporter In the present Test Example, an in vitro assay of compounds using Cos 7 cells as to inhibitory activity on transiently expressed human IBAT or rat IBAT transporter was performed according to the method described in Am. J. Physiol., 274, G157-169.

That is, $2.5\times10^{-5}$ cells/well of Cos 7 cells were seeded in a 24-well plate, and after one day, the cells were transfected with 0.3 μg/well of cDNA of human IBAT or rat IBAT using FuGENE6 (supplied from Roche). After culturing for one day after the transfection, the cells were washed once with the assay buffer, i.e., Hanks buffer containing 25 mM glucose and 10 mM HEPES (pH 7.4). The assay buffer was then replaced with the assay buffer containing the test compound. [$^3$H]-Taurocholate at a final concentration of 8 μM was added thereto and incubated at 37° C. for 60 minutes so that [$^3$H]-taurocholate was taken into Cos 7 cells by the action of human IBAT or rat IBAT. The cells were washed twice with the assay buffer containing 1 mM taurocholate, and subsequently lysed with 0.2 M NaOH to stop the reaction. The cell lysate was added to 4 mL of liquid scintillation cocktail, which was then thoroughly vortexed. Then the radioactivity was measured using the liquid scintillation counter. The inhibitory rate (%) was calculated from the radioactivity in the control in which no test compound had been used and the radioactivity when the test compound at the certain concentration had been used, and the concentration of the compound which inhibited 50% of the human IBAT or rat IBAT activity was calculated.

The results are shown in the following Table 15 (Tables 15-1 to 15-12). It was confirmed that the compound of the present invention exhibited the potent inhibitory activity against human IBAT and rat IBAT and therefore the present compound has a possibility to be the therapeutic agent and the preventive agent for hyperlipemia. It was also confirmed that the compounds of the Examples of the present invention other than those shown in Table 15 exhibit the potent inhibitory activity against human IBAT and rat IBAT.

| COMPOUND | Cos 7/human IBAT IC50(μM) | Cos 7/rat IBAT IC50(μM) |
|---|---|---|
| Table 15-1 | | |
| COMPARATIVE EXAMPLE* | 10 | 0.2 |
| EXAMPLE 3835 | 0.043 | NO EXPERIMENT |
| EXAMPLE 1 | 0.025 | 0.007 |
| EXAMPLE 3932 | 0.036 | 0.009 |
| EXAMPLE 9 | 0.076 | 0.036 |
| EXAMPLE 425 | 0.17 | NO EXPERIMENT |
| EXAMPLE 801 | 0.1 | NO EXPERIMENT |
| EXAMPLE 1056 | 0.1 | NO EXPERIMENT |
| EXAMPLE 1178 | 0.093 | NO EXPERIMENT |
| EXAMPLE 1433 | 0.103 | NO EXPERIMENT |
| EXAMPLE 1555 | 0.153 | NO EXPERIMENT |
| EXAMPLE 1810 | 0.167 | NO EXPERIMENT |
| EXAMPLE 3440 | 0.037 | 0.010 |
| EXAMPLE 3695 | 0.037 | 0.005 |
| EXAMPLE 969 | 0.1 | NO EXPERIMENT |
| EXAMPLE 968 | 0.083 | NO EXPERIMENT |
| EXAMPLE 593 | 0.092 | NO EXPERIMENT |
| EXAMPLE 592 | 0.1 | NO EXPERIMENT |
| EXAMPLE 3853 | 0.028 | 0.009 |
| EXAMPLE 3607 | 0.041 | NO EXPERIMENT |
| Table 15-2 | | |
| EXAMPLE 3608 | 0.059 | NO EXPERIMENT |
| EXAMPLE 4512 | 0.063 | NO EXPERIMENT |
| EXAMPLE 4424 | 0.091 | NO EXPERIMENT |
| EXAMPLE 4425 | 0.089 | NO EXPERIMENT |
| EXAMPLE 4905 | 0.1 | NO EXPERIMENT |
| EXAMPLE 1069 | 0.1 | NO EXPERIMENT |
| EXAMPLE 867 | 0.1 | NO EXPERIMENT |
| EXAMPLE 3708 | 0.07 | NO EXPERIMENT |
| EXAMPLE 3506 | 0.127 | NO EXPERIMENT |
| EXAMPLE 3696 | 0.039 | NO EXPERIMENT |
| EXAMPLE 3605 | 0.039 | NO EXPERIMENT |
| EXAMPLE 3475 | 0.1 | NO EXPERIMENT |
| EXAMPLE 3558 | 0.07 | NO EXPERIMENT |
| EXAMPLE 3448 | 0.037 | NO EXPERIMENT |
| EXAMPLE 3572 | 0.1 | NO EXPERIMENT |
| EXAMPLE 3593 | 0.07 | NO EXPERIMENT |
| EXAMPLE 3554 | 0.065 | NO EXPERIMENT |
| EXAMPLE 3698 | 0.072 | NO EXPERIMENT |
| EXAMPLE 4210 | 0.1 | NO EXPERIMENT |
| EXAMPLE 3409 | 0.045 | NO EXPERIMENT |
| Table 15-3 | | |
| EXAMPLE 3433 | 0.055 | NO EXPERIMENT |
| EXAMPLE 3449 | 0.055 | NO EXPERIMENT |
| EXAMPLE 3441 | 0.085 | NO EXPERIMENT |
| EXAMPLE 3444 | 0.1 | NO EXPERIMENT |
| EXAMPLE 3567 | 0.1 | NO EXPERIMENT |
| EXAMPLE 3662 | 0.1 | NO EXPERIMENT |
| EXAMPLE 3709 | 0.049 | NO EXPERIMENT |
| EXAMPLE 3717 | 0.03 | NO EXPERIMENT |
| EXAMPLE 3722 | 0.039 | NO EXPERIMENT |
| EXAMPLE 3725 | 0.052 | NO EXPERIMENT |
| EXAMPLE 3783 | 0.048 | NO EXPERIMENT |
| EXAMPLE 3429 | 0.055 | NO EXPERIMENT |
| EXAMPLE 3568 | 0.094 | NO EXPERIMENT |
| EXAMPLE 3587 | 0.07 | NO EXPERIMENT |
| EXAMPLE 3705 | 0.054 | NO EXPERIMENT |
| EXAMPLE 3724 | 0.069 | NO EXPERIMENT |
| EXAMPLE 3764 | 0.08 | NO EXPERIMENT |
| EXAMPLE 3723 | 0.025 | NO EXPERIMENT |
| EXAMPLE 3768 | 0.072 | NO EXPERIMENT |
| EXAMPLE 3770 | 0.057 | NO EXPERIMENT |
| Table 15-4 | | |
| EXAMPLE 3774 | 0.1 | NO EXPERIMENT |
| EXAMPLE 3454 | 0.068 | NO EXPERIMENT |
| EXAMPLE 3544 | 0.1 | NO EXPERIMENT |

| COMPOUND | Cos 7/human IBAT IC50(μM) | Cos 7/rat IBAT IC50(μM) |
|---|---|---|
| EXAMPLE 3599 | 0.054 | NO EXPERIMENT |
| EXAMPLE 3604 | 0.045 | NO EXPERIMENT |
| EXAMPLE 3697 | 0.069 | NO EXPERIMENT |
| EXAMPLE 4226 | 0.099 | NO EXPERIMENT |
| EXAMPLE 4250 | 0.1 | NO EXPERIMENT |
| EXAMPLE 4266 | 0.1 | NO EXPERIMENT |
| EXAMPLE 4258 | 0.1 | NO EXPERIMENT |
| EXAMPLE 4261 | 0.1 | NO EXPERIMENT |
| EXAMPLE 4232 | 0.099 | NO EXPERIMENT |
| EXAMPLE 4248 | 0.1 | NO EXPERIMENT |
| EXAMPLE 4384 | 0.1 | NO EXPERIMENT |
| EXAMPLE 4405 | 0.062 | NO EXPERIMENT |
| EXAMPLE 4456 | 0.1 | NO EXPERIMENT |
| EXAMPLE 4458 | 0.1 | NO EXPERIMENT |
| EXAMPLE 4479 | 0.078 | NO EXPERIMENT |
| EXAMPLE 4526 | 0.1 | NO EXPERIMENT |
| EXAMPLE 4534 | 0.076 | NO EXPERIMENT |
| Table 15-5 | | |
| EXAMPLE 4539 | 0.064 | NO EXPERIMENT |
| EXAMPLE 4600 | 0.078 | NO EXPERIMENT |
| EXAMPLE 3414 | 0.088 | NO EXPERIMENT |
| EXAMPLE 3410 | 0.068 | NO EXPERIMENT |
| EXAMPLE 3710 | 0.052 | NO EXPERIMENT |
| EXAMPLE 3714 | 0.058 | NO EXPERIMENT |
| EXAMPLE 3719 | 0.1 | NO EXPERIMENT |
| EXAMPLE 3412 | 0.075 | NO EXPERIMENT |
| EXAMPLE 3434 | 0.071 | NO EXPERIMENT |
| EXAMPLE 3426 | 0.058 | NO EXPERIMENT |
| EXAMPLE 3713 | 0.037 | NO EXPERIMENT |
| EXAMPLE 3729 | 0.088 | NO EXPERIMENT |
| EXAMPLE 3413 | 0.073 | NO EXPERIMENT |
| EXAMPLE 3416 | 0.1 | NO EXPERIMENT |
| EXAMPLE 3711 | 0.063 | NO EXPERIMENT |
| EXAMPLE 3716 | 0.089 | NO EXPERIMENT |
| EXAMPLE 3727 | 0.066 | NO EXPERIMENT |
| EXAMPLE 3726 | 0.073 | NO EXPERIMENT |
| EXAMPLE 3730 | 0.084 | NO EXPERIMENT |
| EXAMPLE 3765 | 0.1 | NO EXPERIMENT |
| Table 15-6 | | |
| EXAMPLE 3772 | 0.089 | NO EXPERIMENT |
| EXAMPLE 3854 | 0.028 | NO EXPERIMENT |
| EXAMPLE 4233 | 0.046 | NO EXPERIMENT |
| EXAMPLE 4259 | 0.067 | NO EXPERIMENT |
| EXAMPLE 4408 | 0.073 | NO EXPERIMENT |
| EXAMPLE 4412 | 0.1 | NO EXPERIMENT |
| EXAMPLE 4528 | 0.091 | NO EXPERIMENT |
| EXAMPLE 4543 | 0.082 | NO EXPERIMENT |
| EXAMPLE 4547 | 0.072 | NO EXPERIMENT |
| EXAMPLE 4589 | 0.046 | NO EXPERIMENT |
| EXAMPLE 4402 | 0.043 | NO EXPERIMENT |
| EXAMPLE 4613 | 0.1 | NO EXPERIMENT |
| EXAMPLE 4246 | 0.072 | NO EXPERIMENT |
| EXAMPLE 4263 | 0.072 | NO EXPERIMENT |
| EXAMPLE 4258 | 0.074 | NO EXPERIMENT |
| EXAMPLE 4268 | 0.1 | NO EXPERIMENT |
| EXAMPLE 4247 | 0.091 | NO EXPERIMENT |
| EXAMPLE 4234 | 0.1 | NO EXPERIMENT |
| EXAMPLE 4385 | 0.1 | NO EXPERIMENT |
| EXAMPLE 4460 | 0.1 | NO EXPERIMENT |
| Table 15-7 | | |
| EXAMPLE 4522 | 0.097 | NO EXPERIMENT |
| EXAMPLE 4527 | 0.073 | NO EXPERIMENT |
| EXAMPLE 4531 | 0.1 | NO EXPERIMENT |
| EXAMPLE 4581 | 0.1 | NO EXPERIMENT |
| EXAMPLE 4540 | 0.1 | NO EXPERIMENT |
| EXAMPLE 4585 | 0.078 | NO EXPERIMENT |
| EXAMPLE 4587 | 0.060 | NO EXPERIMENT |
| EXAMPLE 4251 | 0.1 | NO EXPERIMENT |
| EXAMPLE 4371 | 0.074 | NO EXPERIMENT |
| EXAMPLE 4260 | 0.074 | NO EXPERIMENT |
| EXAMPLE 4243 | 0.078 | NO EXPERIMENT |
| EXAMPLE 4236 | 0.10 | NO EXPERIMENT |
| EXAMPLE 4513 | 0.092 | NO EXPERIMENT |
| EXAMPLE 4546 | 0.087 | NO EXPERIMENT |
| EXAMPLE 4401 | 0.061 | NO EXPERIMENT |
| EXAMPLE 4605 | 0.079 | NO EXPERIMENT |
| EXAMPLE 4448 | 0.10 | NO EXPERIMENT |
| EXAMPLE 3733 | 0.057 | NO EXPERIMENT |
| EXAMPLE 3736 | 0.05 | NO EXPERIMENT |
| EXAMPLE 3747 | 0.045 | NO EXPERIMENT |
| Table 15-8 | | |
| EXAMPLE 3748 | 0.081 | NO EXPERIMENT |
| EXAMPLE 3750 | 0.075 | NO EXPERIMENT |
| EXAMPLE 3752 | 0.041 | NO EXPERIMENT |
| EXAMPLE 3754 | 0.092 | NO EXPERIMENT |
| EXAMPLE 5043 | 0.062 | NO EXPERIMENT |
| EXAMPLE 5298 | 0.076 | NO EXPERIMENT |
| EXAMPLE 4551 | 0.076 | NO EXPERIMENT |
| EXAMPLE 5416 | 0.077 | NO EXPERIMENT |
| EXAMPLE 5417 | 0.026 | NO EXPERIMENT |
| EXAMPLE 5407 | 0.052 | NO EXPERIMENT |
| EXAMPLE 5408 | 0.032 | NO EXPERIMENT |
| EXAMPLE 5409 | 0.042 | NO EXPERIMENT |
| EXAMPLE 4221 | 0.043 | NO EXPERIMENT |
| EXAMPLE 4223 | 0.025 | NO EXPERIMENT |
| EXAMPLE 5410 | 0.1 | NO EXPERIMENT |
| EXAMPLE 5411 | 0.097 | NO EXPERIMENT |
| EXAMPLE 5412 | 0.037 | NO EXPERIMENT |
| EXAMPLE 5418 | 0.069 | NO EXPERIMENT |
| EXAMPLE 5419 | 0.039 | NO EXPERIMENT |
| EXAMPLE 5420 | 0.068 | NO EXPERIMENT |
| Table 15-9 | | |
| EXAMPLE 5413 | 0.065 | NO EXPERIMENT |
| EXAMPLE 5414 | 0.1 | NO EXPERIMENT |
| EXAMPLE 5415 | 0.044 | NO EXPERIMENT |
| EXAMPLE P341 | 0.022 | 0.0043 |
| EXAMPLE P365 | 0.047 | NO EXPERIMENT |
| Table 15-10 | | |
| EXAMPLE P317 | 0.049 | NO EXPERIMENT |
| EXAMPLE P340 | 0.028 | NO EXPERIMENT |
| EXAMPLE P364 | 0.048 | NO EXPERIMENT |
| EXAMPLE P376 | 0.037 | NO EXPERIMENT |
| EXAMPLE P328 | 0.038 | NO EXPERIMENT |
| EXAMPLE P321 | 0.045 | NO EXPERIMENT |
| EXAMPLE P345 | 0.023 | NO EXPERIMENT |
| EXAMPLE P369 | 0.034 | NO EXPERIMENT |
| EXAMPLE P381 | 0.028 | NO EXPERIMENT |
| EXAMPLE P333 | 0.044 | NO EXPERIMENT |
| EXAMPLE P320 | 0.041 | NO EXPERIMENT |
| EXAMPLE P344 | 0.019 | NO EXPERIMENT |
| EXAMPLE P368 | 0.029 | NO EXPERIMENT |
| EXAMPLE P380 | 0.018 | NO EXPERIMENT |
| EXAMPLE P332 | 0.046 | NO EXPERIMENT |
| EXAMPLE P373 | 0.097 | NO EXPERIMENT |
| EXAMPLE P385 | 0.056 | NO EXPERIMENT |
| EXAMPLE P319 | 0.042 | NO EXPERIMENT |
| Table 15-11 | | |
| EXAMPLE P343 | 0.016 | 0.0055 |
| EXAMPLE P367 | 0.023 | NO EXPERIMENT |
| EXAMPLE P379 | 0.026 | NO EXPERIMENT |
| EXAMPLE P331 | 0.035 | NO EXPERIMENT |
| EXAMPLE P326 | 0.1 | NO EXPERIMENT |
| EXAMPLE P350 | 0.040 | NO EXPERIMENT |
| EXAMPLE P374 | 0.033 | NO EXPERIMENT |
| EXAMPLE P386 | 0.060 | NO EXPERIMENT |
| EXAMPLE P338 | 0.047 | NO EXPERIMENT |
| EXAMPLE P323 | 0.032 | NO EXPERIMENT |
| EXAMPLE P347 | 0.024 | NO EXPERIMENT |
| EXAMPLE P371 | 0.028 | NO EXPERIMENT |
| EXAMPLE P383 | 0.026 | NO EXPERIMENT |
| EXAMPLE P335 | 0.068 | NO EXPERIMENT |
| EXAMPLE P324 | 0.037 | NO EXPERIMENT |
| EXAMPLE P348 | 0.022 | NO EXPERIMENT |
| EXAMPLE P372 | 0.035 | NO EXPERIMENT |
| EXAMPLE P384 | 0.032 | NO EXPERIMENT |
| EXAMPLE P349 | 0.041 | NO EXPERIMENT |
| EXAMPLE P316 | 0.028 | NO EXPERIMENT |

-continued

| COMPOUND | Cos 7/human IBAT IC50(μM) | Cos 7/rat IBAT IC50(μM) |
|---|---|---|
| Table 15-12 | | |
| EXAMPLE P342 | 0.015 | 0.0048 |
| EXAMPLE P366 | 0.025 | NO EXPERIMENT |
| EXAMPLE P378 | 0.034 | NO EXPERIMENT |
| EXAMPLE P330 | 0.032 | NO EXPERIMENT |
| EXAMPLE P322 | 0.062 | NO EXPERIMENT |
| EXAMPLE P346 | 0.019 | 0.006 |
| EXAMPLE P370 | 0.030 | NO EXPERIMENT |
| EXAMPLE P382 | 0.028 | NO EXPERIMENT |
| EXAMPLE P334 | 0.037 | NO EXPERIMENT |
| EXAMPLE P84 | 0.00066 | 0.00034 |
| EXAMPLE P93 | 0.00048 | 0.00021 |
| EXAMPLE P122 | 0.00043 | 0.00015 |
| EXAMPLE P144 | 0.00052 | 0.00019 |

*In Comparative Example, the compound of Synthetic Example 1: (−)-trans-3-butyl-3-ethyl-2,3,4,5-tetrahydro-5-phenyl-1,4-benzothiazepine-1,1-dioxide which is specifically described in WO93/16055 was used.

Test Example 9

In Vitro Assay of Compounds Using Cos 7 Cells as to Inhibitory Activity on Transiently Expressed Human IBAT Transporter in which Alanine at Position 171 has been Substituted with Serine In the present Test Example, an in vitro assay of compounds using Cos 7 cells as to inhibitory activity on transiently expressed human IBAT transporter in which alanine at position 171 had been substituted with serine was performed by the same way as in the present test Example 8, except for using cDNA in which alanine at position 171 had been substituted with serine in an amino acid sequence of human IBAT.

It has been estimated that the rate of humans having the IBAT in which alanine at position 171 has been substituted with serine is 28% (J. Clin. Invest., 1997, 99, 1880-1887).

The results are shown in the following Table 16. The value is the inhibitory rate (%) with respect to the radioactivity of the control in which no test compound has been used. It was confirmed that the compound of the present invention exhibits the potent inhibitory activity against human IBAT in which alanine at position 171 had been substituted with serine, which is equivalent to that for unsubstituted human IBAT, and the present compound thus has a possibility to be the therapeutic agent and the preventive agent for hyperlipemia. It was also confirmed that the compounds of the Examples of the present invention other than those shown in Table 16 exhibit the potent inhibitory activity against human IBAT in which alanine at position 171 had been substituted with serine.

TABLE 16

| COMPOUND | Cos 7 WITH HUMAN IBAT IN WHICH 171ST ALANINE IS SUBSTITUTED WITH SERINE INHIBITION (%) AT TEST COMPOUND CONCENTRATION OF 10 nM |
|---|---|
| EXAMPLE 1 | 53 |

Test Example 10

In Vitro Assay of Compounds Using Cos 7 Cells for $Na^+$ Dependent Amino Acid Transporter and $Na^+$ Dependent Water Soluble Vitamin Transporter In the present Test Example, in vitro assays of the compounds using Cos 7 cells for various transporters were performed according to the description in JP-H10-505830 A.

That is, $2.5 \times 10^5$ cells/well of Cos 7 cells were seeded in a 24-well plate, and after two days, the cells were washed once with the assay buffer, i.e., Hanks buffer containing 25 mM glucose and 10 mM HEPES (pH 7.4). The assay buffer was then replaced with the assay buffer containing the test compound. [$^3$H]-alanine (brand name: NET-348, Daiich Pure chemical) or [$^3$H]-leucine (brand name: NET-460, Daiich Pure chemical) or [$^3$H]-phenylalanine (brand name: MT903, MORAVEK) or [$^3$H]-methionine (brand name: MT862, MORAVEK) or [$^3$H]-lysine (brand name: MT909, MORAVEK) or [$^3$H]-choline (brand name: TRK593, Amersham Biosciences) at a final concentration of 8 μM was added thereto and incubated at 37° C. for 60 minutes so that they were taken into Cos 7 cells. The cells were washed twice with the assay buffer, and subsequently lysed with 0.2 M NaOH to stop the reaction. The cell lysate was added to 4 mL of liquid scintillation cocktail, which was then thoroughly vortexed. Then the radioactivity was measured using the liquid scintillation counter. The inhibitory rate (%) was calculated from the radioactivity in the control in which no test compound had been used and the radioactivity when the test compound at the certain concentration had been used, and the concentration of the compound which inhibited 50% of the transporter activity was calculated.

Various $Na^+$ dependent transporters in addition to IBAT are present in small intestine epithelial cells where IBAT is present, including the amino acid transporter and the water soluble vitamin transporter. Essential amino acids are essential for normal growth and healthy life maintenance (*Seikagaku Jiten* (Dictionary of Biochemistry) 2nd Edition p 1052, Tokyo Kagaku Dojin). Choline is one of water soluble vitamins, and deficiency diseases thereof include fatty liver and cirrhosis (*Seikagaku Jiten* 2nd Edition p 1050, Tokyo Kagaku Dojin).

The results are shown in the following Table 17. It was confirmed that the compound of the present invention exhibits a significant inhibitory specificity for human IBAT and rat IBAT, and the present compound thus has a possibility to be the therapeutic agent and the preventive agent for hyperlipemia. The similar effects were confirmed on leucine, phenylalanine, methionine and lysine which are other amino acids, and choline which is the water soluble vitamin. It was also confirmed that the compounds of the Examples of the present invention other than those shown in Table 17 exhibit the significant inhibitory specificity for human IBAT and rat IBAT.

TABLE 17

| COMPOUND | $IC_{50}$ (μM) AGAINST ALANINE TRANSPORTER |
|---|---|
| EXAMPLE 1 | 33 |

Test Example 11

Microorganism Mutagenicity Test (Ames Test)

In the present Test Example, a microorganism mutagenicity test was performed according to Ames *Salmonella* Mutation Assay.

As bacterial strains, *Salmonella typhimurium* TA98 and *Salmonella typhimurium* TA100 were used. One platinum loopful of *Salmonella typhimurium* TA98 or *Salmonella typhimurium* TA100 cells were added to an L-shaped tube in which sterilized medium for preculture (brand name: Nutrient Broth No. 2, supplied from Kanto Chemical) had been placed, and cultured in a shaking incubator at 37° C. with shaking at 100 times per minute for 8 hours. The aforementioned bacterial suspension (0.1 mL) was added to 2 ml of sterilized soft agar warmed at 45° C. containing 0.05 mM L-histidine and 0.5 mM (+)-biotin. This was then stirred and subsequently spread out on a minimum glucose agar plate medium (brand name: Tesmedia AN, supplied from Oriental Yeast Co., Ltd.) on dish and solidified. Filter paper (brand name: Quantitative Ashless No. 7, supplied from Advantech) was cut out using a punch to prepare circular filter paper, which was then sterilized and placed on the solidified agar, and 1 μL of 10 mM test compound was applied onto the circular filter paper, and cultivation was performed at 37° C. for 48 hours. The microorganism mutagenicity was determined as follows: the case in which mutant colonies occurred in a diffusion zone around the paper filter of the test compound was determined to be positive, and the case in which nothing occurred was determined to be negative.

In the results, all of the compounds of Examples of the present invention were negative for both TA98 and TA100, indicating that there was no mutagenicity. Thus the compounds of the present invention were confirmed to be safe. Therefore, it was confirmed that the compound of the present invention can be used as a pharmaceutical for the purpose of the treatment and the prevention of hyperlipemia.

Test Example 12

Gastrointestinal Toxicity

In order to evaluate the toxicity of the compound of the present invention for the gastrointestinal tract, cytotoxicity against Caco-2 cell which is human-derived small intestine epithelial cell line was examined with reference to the method of Bestwick C S et al. (Biochimica et Biophysica Acta 1474: 47-55, 1999).

That is, 10,000 cells/well of Caco-2 cells (purchased from ATCC) were seeded in a 96-well plate [MEM-E medium, 10% FBS (Fetal Bovine Serum), 1% NEAA (Non Essential Amino Acid) solution, supplied from Gibco]. After culturing for 48 hours, the test compound diluted with the medium was added to each well. After 2 hours, 50 μL of the medium was collected, and an LDH activity in the medium was measured using an LDH activity measurement kit (CytoTox96 Non-Radioactive Cytotoxicity Assay, supplied from Promega). Defining the LDH activity of the Caco-2 cells treated with a cell lysis agent as being 100%, the relative activity was calculated as a index of the cytotoxicity.

The results are shown in the following Table 18 (Tables 18-1 to 18-2). As a result, it was revealed that the compound of the present invention has slight or no cytotoxicity to the Caco-2 cell, and it was thus revealed that the compound of the present invention has slight or no gastrointestinal toxicity. The IBAT inhibitor having the quaternary ammonium structure used as the comparative example to the present invention (the compound 5 (Synthetic example 19): 1-{4-[4-(3,3-dibutyl-7-dimethylamino-1,1-dioxo-2,3,4,5-tetrahydro-1,4-benzothiazepine-5-yl)phenoxymethyl]benzyl}-4-aza-1-azoniabicyclo[2.2.2]octane chloride which exhibits the strongest activity among the compounds specifically described in WO02/08211) exhibited the cytotoxicity to the small intestine epithelial cell line at low concentrations, i.e., had the gastrointestinal toxicity. On the contrary, it was revealed that the compound of the present invention has slight or no gastrointestinal toxicity or is less toxic, and is thus more preferable as the pharmaceutical products.

| | CELL TOXICITY AGAINST Caco2 | | |
|---|---|---|---|
| COMPOUND | 30 μM | 10 μM | 3 μM |
| Table 18-1 | | | |
| COMPARATIVE EXAMPLE* | 79 | 22 | 1.5 |
| EXAMPLE 3853 | <1 | <1 | <1 |
| EXAMPLE 3605 | <1 | <1 | <1 |
| EXAMPLE 3835 | <1 | <1 | <1 |
| EXAMPLE 3440 | <1 | <1 | <1 |
| EXAMPLE 3695 | <1 | <1 | <1 |
| EXAMPLE 3607 | <1 | <1 | <1 |
| EXAMPLE 3608 | <1 | <1 | <1 |
| Table 18-2 | | | |
| EXAMPLE 3696 | <1 | <1 | <1 |
| EXAMPLE 3448 | <1 | <1 | <1 |
| EXAMPLE 3409 | <1 | <1 | <1 |
| EXAMPLE 3709 | <1 | <1 | <1 |
| EXAMPLE 3783 | <1 | <1 | <1 |
| EXAMPLE 3723 | <1 | <1 | <1 |
| EXAMPLE 3710 | <1 | <1 | <1 |
| EXAMPLE 3713 | <1 | <1 | <1 |
| EXAMPLE 3759 | <1 | <1 | <1 |
| EXAMPLE 5043 | <1 | <1 | <1 |
| EXAMPLE 5298 | <1 | <1 | <1 |
| EXAMPLE 5480 | <1 | <1 | <1 |
| EXAMPLE 5735 | <1 | <1 | <1 |
| EXAMPLE 5856 | <1 | <1 | <1 |
| EXAMPLE 5857 | <1 | <1 | <1 |
| EXAMPLE 3705 | <1 | <1 | <1 |
| EXAMPLE 3747 | <1 | <1 | <1 |
| EXAMPLE 3752 | <1 | <1 | <1 |
| EXAMPLE 5408 | <1 | <1 | <1 |
| EXAMPLE P341 | <1 | <1 | NO EXPERIMENT |
| EXAMPLE P340 | <1 | <1 | NO EXPERIMENT |
| EXAMPLE P345 | <1 | <1 | NO EXPERIMENT |
| EXAMPLE P344 | <1 | <1 | NO EXPERIMENT |
| EXAMPLE P343 | <1 | <1 | NO EXPERIMENT |
| EXAMPLE P347 | <1 | <1 | NO EXPERIMENT |
| EXAMPLE P348 | <1 | <1 | NO EXPERIMENT |
| EXAMPLE P342 | <1 | <1 | NO EXPERIMENT |
| EXAMPLE P346 | <1 | <1 | NO EXPERIMENT |
| EXAMPLE P84 | <1 | <1 | NO EXPERIMENT |
| EXAMPLE P93 | <1 | <1 | NO EXPERIMENT |
| EXAMPLE P122 | <1 | <1 | NO EXPERIMENT |
| EXAMPLE P144 | <1 | <1 | NO EXPERIMENT |

*In Comparative Example, the compound 5 (Synthetic example 19): 1-{4-[4-(3,3-dibutyl-7-dimethylamino-1,1-dioxo-2,3,4,5-tetrahydro-1,4-benzothiazepine-5-yl)phenoxymethyl]benzyl}-4-aza-1-azoniabicyclo[2.2.2]octane chloride which exhibits the strongest activity among compounds specifically described in WO02/08211 was used.

Test Example 13

Steatohepatitis Model

In the present Test Example, a steatohepatitis model was employed with reference to the method of Okan A et al. (Dig. Dis. Sci., 47:2389-2397, 2002).

That is, choline-deficient food (supplied from Oriental Yeast Co., Ltd.) was given to Wistar rats at 7 weeks of age for two weeks to prepare a steatohepatitis model. The test compound was suspended in an aqueous solution of 0.5% methylcellulose (supplied from Wako Pure Chemical Industries), and the aqueous solution of 0.5% methylcellulose (supplied from Wako Pure Chemical Industries) was used as the control. They were orally administered once a day for consecutive 2 weeks. The blood was collected from the abdominal aorta on the day after the final drug administration. AST (GOT) and ALT (GPT) in the blood were measured using the measurement kits (GOT II-HA Test Wako and GPT II Test Wako, supplied from Wako Pure Chemical Industries) with an automatic analyzer (Nitech ANALAYZER SUPER Z818). The results are shown in the following Table 19.

The compound of the present invention exhibited the lowering effect on AST and ALT levels in the blood in the steatohepatitis model rats, and was proven to be useful as the therapeutic agent and the preventive agent for steatohepatitis. It was also confirmed that the compounds in Examples of the present invention other than those shown in Table 19 have an excellent lowering effect on AST and ALT levels.

TABLE 19

| COMPOUND | AST(IU/L) | ALT(IU/L) |
|---|---|---|
| CONTROL GROUP (n = 6) | 180 ± 46 | 245 ± 57 |
| EXAMPLE 3713 (3 mg/kg, n = 4) | 77 ± 37 | 118 ± 36 |
| EXAMPLE 3747 (3 mg/kg, n = 4) | 63 ± 86 | 102 ± 50 |
| EXAMPLE 3752 (3 mg/kg, n = 4) | 69 ± 98 | 88 ± 45 |
| EXAMPLE 5408 (3 mg/kg, n = 4) | 103 ± 45 | 149 ± 38 |
| EXAMPLE 3696 (3 mg/kg, n = 4) | 98 ± 23 | 145 ± 34 |
| EXAMPLE 3440 (3 mg/kg, n = 4) | 125 ± 34 | 167 ± 93 |
| EXAMPLE 3448 (3 mg/kg, n = 4) | 134 ± 23 | 143 ± 79 |
| EXAMPLE 3605 (3 mg/kg, n = 4) | 80 ± 34 | 121 ± 36 |
| CONTROL GROUP (n = 4) | 213 ± 56 | 375 ± 89 |
| EXAMPLE P84 (1 mg/kg, n = 4) | 98 ± 32 | 126 ± 30 |
| EXAMPLE P93 (1 mg/kg, n = 4) | 100 ± 11 | 98 ± 18 |
| EXAMPLE P122 (1 mg/kg, n = 4) | 104 ± 36 | 97 ± 25 |
| EXAMPLE P144 (1 mg/kg, n = 4) | 87 ± 25 | 93 ± 11 |

(AVERAGE ± STANDARD ERROR)

Test Example 14

Effect of Combination with Pravastatin on Plasma Total Cholesterol Levels in Dogs The effect of the combination of the compounds described in Example with pravastatin (HMG-CoA reductase inhibitor) on plasma cholesterol levels in dogs was examined.

To male beagle dogs (supplied from Kitayama Labes, body weight 9 to 13 kg), usual solid feedstuff (DS-A: Oriental Yeast Co., Ltd.) was given once daily at 13:00 to 14:00. The light was turned on from 7:00 to 19:00 as a light period, and the remaining was defined as a dark period. Water was given ad libitum. In the morning in the week prior to the administration, the blood was collected with heparin from forearm cephalic vein, and plasma was collected by centrifugation. The total cholesterol level of this plasma was measured using the commercially available cholesterol level measurement kit by the enzymatic method (Cholesterol-E Test Wako). The dogs were grouped so that the total cholesterol levels were almost equal. Sodium pravastatin (1 mg/kg, Sankyo) alone or 3 mg/kg of the compound described in each of Examples alone or the combination thereof was orally administered once daily just before feeding for 7 days. Pravastatin was dissolved in distilled water, and the compound described in Example was suspended in 0.5% methylcellulose solution for administration. On the day after the final administration, the blood was collected from the forearm cephalic vein under starving, to which plasma was obtained. The total cholesterol level therein was measured by the same way. As a result, the total cholesterol level in the plasma was reduced by 7 mg/dL (6%) by orally administering 1 mg/kg/day of pravastatin for 7 days. The total cholesterol level in the plasma was reduced by 1 to 10 mg/dL (3 to 8%) by orally administering 3 mg/kg/day of the compound described in each of Examples for 7 days. When pravastatin and the compound described in each of Examples were co-administered at this dosages, the total cholesterol in the plasma was reduced by 14 to 24 mg/dL (12 to 20%). The reduction rate of the total cholesterol level was larger in the co-administration with the compound described in Example than in the administration of pravastatin alone, and the augmented effect by the co-administration was observed. The results are shown in Table 20. The similar results are obtained when simvastatin, atorvastatin, pitavastatin or lovastatin is used in place of pravastatin.

TABLE 20

| TREATMENT | BEFORE TREATMENT (mg/dL) | AFTER TREATMENT (mg/dL) | BEFORE TREATMENT – AFTER TREATMENT (mg/dL) |
|---|---|---|---|
| Vehicle | 119 ± 8 | 118 ± 9 | 1 (1) |
| PRAVASTATIN (1 mg/kg) | 114 ± 6 | 106 ± 5 | 7 (6) |
| EXAMPLE 3696 (3 mg/kg) | 119 ± 2 | 115 ± 3 | 3 (3) |
| EXAMPLE 3696 + PRAVASTATIN | 112 ± 5 | 94 ± 3 | 18 (16) |
| EXAMPLE 3713 (3 mg/kg) | 117 ± 4 | 113 ± 3 | 4 (3) |
| EXAMPLE 3713 + PRAVASTATIN | 112 ± 6 | 94 ± 6 | 18 (16) |
| EXAMPLE 5408 (3 mg/kg) | 128 ± 4 | 122 ± 4 | 6 (5) |
| EXAMPLE 5408 + PRAVASTATIN | 129 ± 7 | 108 ± 8 | 21 (17) |
| EXAMPLE P84 (1 mg/kg) | 119 ± 2 | 109 ± 5 | 10 (8) |
| EXAMPLE P84 + PRAVASTATIN | 122 ± 3 | 97 ± 2 | 24 (20) |
| EXAMPLE P93 (1 mg/kg) | 123 ± 3 | 119 ± 6 | 4 (4) |
| EXAMPLE P93 + PRAVASTATIN | 125 ± 5 | 108 ± 7 | 17 (13) |
| EXAMPLE P144 (1 mg/kg) | 125 ± 4 | 124 ± 4 | 1 (1) |
| EXAMPLE P144 + PRAVASTATIN | 118 ± 3 | 104 ± 6 | 14 (12) |

Data are represented by mean ± standard error. N = 4. The number in parenthesis in a column "before treatment – after treatment" represents the reduction rate with respect to the data before administration.

Test Example 15

Measurement of Permeability Through Caco-2 Cell

Permeability of the compound described in Examples through Caco-2 cells was studied with reference to Artursson Per et al.'s method (Journal of Pharmaceutical Sciences, 79(6): 476-482: 1990).

Transwell cell culture chamber (Costar) having a membrane filter coated with collagen (3 µm pores, 0.33 cm$^2$ growth area) was placed on a 24-well plate. Caco-2 cells (purchased from ATCC) were seeded at the amount of 6.6× 10$^4$ cells/filter (2×10$^5$ cells/cm$^2$) (D-MEM medium, 10% FBS (Fetal Bovine Serum), 0.1 mM NEAA (Non Essential Amino Acid), 100 U/mL penicillin, 100 µg/mL streptomycin, supplied from Gibco, and 25 mM glucose). Each Transwell cell culture chamber was placed in each well in a 24-well plate. 0.75 mL of the medium was filled in an external chamber and 0.15 mL of the medium was filled in an internal chamber. The medium was changed every 2 to 3 days, and 18 to 25 days after seeding when a single layer of Caco-2 cells was formed, the cells were used for the test.

In the test for examining the permeability of the compound, the Caco-2 cells cultured in the chamber were used. The internal and external chamber solutions were replaced twice with Hanks balanced salt solution (HBSS) containing 25 mM glucose, 10 mM Hepes and 0.05% Tween 80. Electric resistance between the external solution and the internal solution in the culture of Caco-2 cells was examined using Endohm chamber and EVOM epithelial voltohmmeter (World Precision Instruments), and those which had exhibited the resistance of 200 $\Omega \cdot cm^2$ or more were used for the test. The Caco-2 cells usable for the test were preincubated in the above HBSS buffer at 37° C. for 10 minutes. The compound described in each Example was prepared at a concentration of 100 µM (HBSS containing 1% DMSO, pH 7.4), and the test was started by replacing the internal chamber solution with the compound-containing HBSS. After incubating at 37° C. for 2 hours, the external chamber solution was taken, and the concentration of the compound which had permeated into the external solution was analyzed using a liquid chromatography tandem mass spectrometer (LC/MS/MS, LC:NANOSPACE SI-1 [Shiseido], MS:VG QUATTRO2 (Micromass)). A permeability coefficient (Papp) was calculated from the formula Papp=dQ/dt/(Co×A). In this formula, dQ/dt represents a permeated amount per unit time (µg/s), Co represents the drug concentration (µg/mL) when the test was started, and A represents an area ($cm^2$) of the membrane filter.

The results are shown in Table 21. As a result, the permeability coefficient of the compound described in Example through Caco-2 cells was as small as 0.2 or less, and it was predicted that the absorbability of the compound from human intestine would be low. Propranolol used as the control drug which was easily permeated and atenolol used as the control drug which was permeated at an appropriate level exhibited the high permeability coefficients. From these results, the compound of the present invention is considered to be poorly absorbed from the gastrointestinal tract and thus have low risk to cause drug interaction. Therefore, it has been found out that the compound has preferable nature as the pharmaceutical products which is highly safe when co-administered with other drugs.

TABLE 21

| COMPOUND | PERMEATION RATIO (PERMEATION × $10^{-6}$ cm/s) |
|---|---|
| EXAMPLE 3696 | 0.15 |
| EXAMPLE 3605 | 0.19 |
| EXAMPLE 3448 | 0.15 |
| EXAMPLE 3713 | 0.19 |
| EXAMPLE 3752 | 0.08 |
| EXAMPLE 5408 | 0.11 |
| EXAMPLE P343 | <0.01 |
| EXAMPLE P342 | 0.03 |
| EXAMPLE P346 | 0.003 |
| EXAMPLE P84 | 0.03 |
| EXAMPLE P93 | 0.02 |
| EXAMPLE P122 | 0.02 |
| EXAMPLE P144 | 0.03 |
| Propranolol | 29.4 |
| Atenolol | 1.80 |

Test Example 16

Measurement of Facilitation Effect on Permeability of Combined Compound Through Caco-2 Cells The permeability through Caco-2 cells was measured by the same way as in Test Example 15.

However, in the present Test Example, the compound described in Example or the control compound was prepared at a final concentration of 30 µM or 100 µM (Hanks Balanced Salt Solution (HBSS) containing 0.1-1% DMSO and 0.05% Tween80, pH7.4) with which the internal chamber solution was replaced, and, after performing incubation at 37° C. for 2 hours, potassium atorvastatin (Yamanouchi Pharmaceutical) or sodium pravastatin (Sankyo) was added at a final concentration of 25 µM to the internal chamber solution to perform the test. After incubating at 37° C. for additional 2 hours, the external chamber solution was taken, and the concentration of the compound which had permeated into the external solution was analyzed using the liquid chromatography tandem mass spectrometer (LC/MS/MS, LC:NANOSPACE SI-1 (Shiseido), MS:VG QUATTRO II (Micromass)). It was examined whether the permeability coefficient of the combined compound was changed in the presence of the compound described in Examples or the compound in Comparative Examples.

The results are shown in the following Table 22. The permeability coefficients of pravastatin and atorvastatin through Caco-2 cells were increased by 461% and 154%, respectively, in the presence of the compound in Comparative Example. However, the compounds described in Examples of the present invention did not affect the permeability coefficients of pravastatin and atorvastatin through Caco-2 cells (<120%). Therefore, it has been found out that the compound of the present invention does not affect the absorbability of the co-administered drug, i.e., has no risk to cause the side effect by increasing the blood concentration of the co-administered drug and is more preferable as the pharmaceutical products. It has been also found out that the compound of the present invention provides more preferable combination of the pharmaceutical products for co-administration with a drug which exhibits its effect by being absorbed from the gastrointestinal tract.

TABLE 22

| COMPOUND | PERMEATION RATIO (PERMEATION × $10^{-6}$ cm/s) | RATE OF INCREASE (%) |
|---|---|---|
| PRAVASTATIN | 0.33 | 100 |
| ATORVASTATIN | 2.28 | 100 |
| COMPARATIVE EXAMPLE (100 µM) + PRAVASTATIN | 1.52 | 461 |
| COMPARATIVE EXAMPLE (30 µM) + ATORVASTATIN | 3.52 | 154 |
| EXAMPLE 3696 (100 µM) + PRAVASTATIN | 0.39 | 118 |
| EXAMPLE 3696 (30 µM) + ATORVASTATI | 2.58 | 113 |
| EXAMPLE 3713 (100 µM) + PRAVASTATIN | 0.35 | 106 |
| EXAMPLE 3713 (30 µM) + ATORVASTATIN | 2.43 | 107 |
| EXAMPLE 5408 (100 µM) + PRAVASTATIN | 0.31 | 94 |
| EXAMPLE 5408 (30 µM) + ATORVASTATIN | 2.30 | 101 |
| EXAMPLE P84 (100 µM) + PRAVASTATIN | 0.32 | 97 |

TABLE 22-continued

| COMPOUND | PERMEATION RATIO (PERMEATION × $10^{-6}$ cm/s) | RATE OF INCREASE (%) |
|---|---|---|
| EXAMPLE P84 (30 μM) + ATORVASTATIN | 2.21 | 97 |
| EXAMPLE P93 (100 μM) + PRAVASTATIN | 0.35 | 106 |
| EXAMPLE P93 (30 μM) + ATORVASTATIN | 2.25 | 99 |
| EXAMPLE P144 (100 μM) + PRAVASTATIN | 0.30 | 91 |
| EXAMPLE P144 (30 μM) + ATORVASTATIN | 2.40 | 105 |

*In Comparative Example, the compound 5 (Synthetic Example 19): 1-{4-[4-(3,3-dibutyl-7-dimethylamino-1,1-dioxo-2,3,4,5-tetrahydro-1,4-benzothiazepine-5-yl)phenoxymethyl]benzyl}-4-aza-1-azoniabicyclo[2.2.2]octane chloride which exhibits the strongest activity among compounds specifically described in WO02/08211 was used.

INDUSTRIAL APPLICABILITY

The present invention exhibits the blood cholesterol lowering effect and high safety, and thus suitable as a pharmaceutical.

The present invention has been described with reference to the specific examples in order to completely and clearly disclose the present invention. However, attached claims are not limited to the aforementioned examples. The present invention is to be constituted so as to embody all modification examples and possible substitutable constitutions which those skilled in the art can create within the scope of basic features shown in the present specification.

The invention claimed is:
1. A compound represented by the following formula (IA):

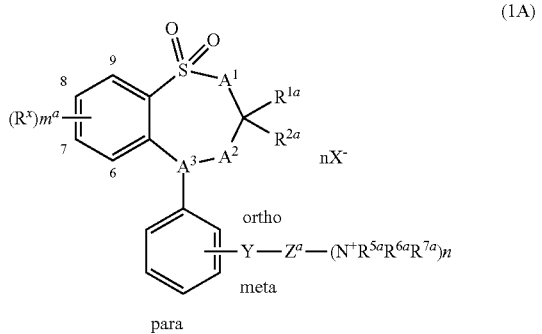

(IA)

wherein,
$R^{1a}$ and $R^{2a}$ may be the same as or different from each other and each represents alkyl group having 1 to 10 carbon atoms, alkenyl group having 2 to 10 carbon atoms or alkynyl group having 2 to 10 carbon atoms;
$m^a$ is an integer of 0 to 4;
$R^x$ represents halogen atom, nitro group, amino group, cyano group, hydroxy group, carboxy group, -$NR^3R^4$ where $R^3$ and $R^4$ may be the same as or different from each other and each represents alkyl group having 1 to 5 carbon atoms, —$CONH_2$, —$SO_3H$, alkyl group having 1 to 10 carbon atoms, alkenyl group having 2 to 10 carbon atoms or alkynyl group having 2 to 10 carbon atoms; wherein the alkyl group, the alkenyl group and the alkynyl group may be substituted with one or more groups of phenyl, naphthyl, pyridyl, quinolyl, thienyl, furyl, piperidyl, pyrrolidyl, morpholyl, cycloalkyl having 3 to 7 carbon atoms, cyano, nitro, hydroxy, oxo, thioxo, carboxy, —$CONH_2$ and —$SO_3H$; one or more methylenes which constitute the alkyl group, the alkenyl group and the alkynyl group may be replaced with any of phenylene, thienylene, furylene, cyclohexylene, cyclopentylene, —O—, —S—, —$CO_2$—, —NHCO—, —$NR^{8a}$—, and —$N^+W^{a-}R^{9a}R^{10a}$—,
$R^{8a}$ represents alkyl group having 1 to 5 carbon atoms or alkenyl group having 2 to 5 carbon atoms; the alkyl group and the alkenyl group in $R^{8a}$ may be substituted with one or more groups of phenyl, cycloalkyl having 3 to 7 carbon atoms and hydroxyl,
$R^{9a}$ and $R^{10a}$ may be the same as or different from each other and each represents alkyl group having 1 to 5 carbon atoms or alkenyl group having 2 to 5 carbon atoms, and may be substituted with one or more groups of phenyl, cycloalkyl having 3 to 7 carbon atoms and hydroxyl, and
$W^{a-}$ represents a counteranion;
the combination of $(A^1, A^2, A^3)$ represents $(CH_2, CH(OH), CH)$; Y represents any of —NHCS—, —NHCSNH— or —NHCSO—, wherein —NH of —NHCS— represents a bond which binds to the adjacent benzene ring and CS— represents a bond which binds to the adjacent $Z^a$, and —NH of —NHCSO— represents a bond which binds to the adjacent benzene ring and CSO— represents a bond which binds to the adjacent $Z^a$;
$Z^a$—$(N^+R^{5a}R^{6a}R^{7a})_n$ represents an alkyl group or alkenyl group having 2 to 10 carbon atoms which is substituted with —$N^+R^{5a}R^{6a}R^{7a}$, the number of the substituents being n; wherein one or more methylenes which constitute $Z^a$ may be replaced with any of phenylene which may have a substitutent or —O—; wherein the substitutent(s) in the phenylene which may have the substitutent are 1 to 4 substitutents selected from the group consisting of alkyl groups having 1 to 5 carbon atoms, alkoxy groups having 1 to 5 carbon atoms, nitro group, halogen atoms, trifluoromethyl group and —$CH_2N^+R^{5a}R^{6a}R^{7a}$; wherein the substitutents may be the same as or different from each other; and wherein n is an integer of 1 or 2; and
each of $N^+R^{5a}R^{6a}R^{7a}$ is independently any of the following I), II) or III):
I) $R^{5a}$, $R^{6a}$ and $R^{7a}$ may be the same as or different from one another, and each represents alkyl group having 1 to 10 carbon atoms, alkenyl group having 2 to 10 carbon atoms or alkynyl group having 2 to 10 carbon atoms; wherein the alkyl group, the alkenyl group and the alkynyl group may be substituted with one or more groups of phenyl, naphthyl, pyridyl, quinolyl, thienyl, furyl, piperidyl, pyrrolidyl, morpholyl, cycloalkyl having 3 to 7 carbon atoms, cyano, nitro, hydroxy, oxo, thioxo, carboxy, —$CONH_2$ and —$SO_3H$; and wherein one or more methylenes which constitute the alkyl group, the alkenyl group and the alkynyl group may be replaced with any of phenylene, thienylene, furylene, cyclohexylene, cyclopentylene, —O—, —S—, —$CO_2$—, —NHCO—, —$NR^8$—, and —$N^+W^-R^9R^{10}$—,
$R^8$ represents alkyl group having 1 to 5 carbon atoms or alkenyl group having 2 to 5 carbon atoms, the alkyl group and the alkenyl group in $R^8$ may be substituted with one or more groups of phenyl, cycloalkyl having 3 to 7 carbon atoms and hydroxyl,
$R^9$ and $R^{10}$ may be the same as or different from each other and each represents alkyl group having 1 to 5 carbon atoms or alkenyl group having 2 to 5 carbon atoms, and may be substituted with one or more groups of phenyl, cycloalkyl having 3 to 7 carbon atoms and hydroxyl, and
$W^-$ represents a counteranion;
II) $N^+R^{5a}R^{6a}R^{7a}$ represents a monocyclo or bicyclo ring formed of 4 to 9 carbon atoms in addition to the ammonium nitrogen atom, with a proviso that a position of binding to $Z^a$ is the ammonium nitrogen atom; wherein, in the monocyclo and bicyclo rings, one of the carbon atoms which constitutes the ring may be replaced with any of oxygen, nitrogen or sulfur atom; and the monocyclo and bicyclo rings may be substituted with one or more groups of hydroxy, oxo, thioxo, cyano, phenyl, naphthyl, thienyl, pyridyl, cycloalkyl having 3 to 7 carbon atoms, carboxy, —CONH$_2$, —SO$_3$H and —R$^{11}$, R$^{11}$ represents alkyl group having 1 to 8 carbon atoms or alkenyl group having 2 to 8 carbon atoms, the alkyl group and the alkenyl group in R$^{11}$ may be substituted with one or more groups of phenyl, naphthyl, pyridyl, quinolyl, thienyl, furyl, piperidyl, pyrrolidyl, morpholyl, cycloalkyl having 3 to 7 carbon atoms, cyano, nitro, hydroxy, oxo, thioxo, carboxy, —CONH$_2$ and —SO$_3$H; and one or more methylenes which constitute the alkyl group and the alkenyl group may be replaced with any of phenylene, thienylene, furylene, cyclohexylene, cyclopentylene, —O—, —S—, —CO$_2$—, —NHCO—, —NR$^8$—, and —N$^+$W$^-$R$^9$R$^{10}$; R$^8$, R$^9$, R$^{10}$ and W$^-$ are the same as the above; and the group which is not involved in the formation of the monocyclo ring and the bicyclo ring in R$^{5a}$, R$^{6a}$ and R$^{7a}$ is the same as the above I); and III) N$^+$R$^{5a}$R$^{6a}$R$^{7a}$ represents a pyridinium ring, a quinolinium ring or an isoquinolinium ring with a proviso that a position of binding to $Z^a$ is the ammonium nitrogen atom; wherein the pyridinium ring, the quinolinium ring and the isoquinolinium ring may be substituted with one or more groups of cyano, nitro, phenyl, naphthyl, thienyl, pyridyl, cycloalkyl having 3 to 7 carbon atoms, alkoxy having 1 to 5 carbon atoms, carboxy, —CONH$_2$, —SO$_3$H, halogen, hydroxy, tetrahydropyranyl and —R$^{12a}$, R$^{12a}$ represents alkyl group having 1 to 9 carbon atoms or alkenyl group having 2 to 9 carbon atoms, the alkyl group and the alkenyl group in R$^{12a}$ may be substituted with one or more groups of phenyl, naphthyl, pyridyl, quinolyl, thienyl, furyl, cycloalkyl having 3 to 7 carbon atoms, cyano, nitro, hydroxy, oxo, thioxo, carboxy, —CONH$_2$ and —SO$_3$H; and one or more methylenes which constitute the alkyl group and the alkenyl group may be replaced with any of phenylene, thienylene, furylene, cyclohexylene, cyclopentylene, —S—, —O—, —CO$_2$—, —NHCO—, —NR$^8$—, and —N$^+$W$^-$R$^9$R$^{10}$—;

R$^8$, R$^9$, R$^{10}$ and W$^-$ are the same as the above; and X$^-$ represents a counteranion.

2. A compound represented by the following formula (IB):

(IB)

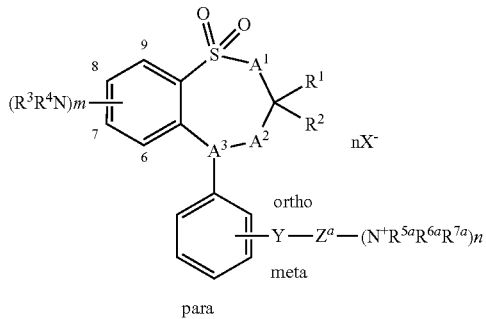

wherein,

R$^1$ and R$^2$ may be the same as or different from each other and each represents alkyl group having 1 to 10 carbon atoms;

m is an integer of 1 or 2;

R$^3$ and R$^4$ may be the same as or different from each other and each represents alkyl group having 1 to 5 carbon atoms; the combination of (A$^1$, A$^2$, A$^3$) represents (CH$_2$, CH(OH), CH);

Y represents any of —NHCS—, —NHCSNH— or —NHCSO—, wherein —NH of —NHCS— represents a bond which binds to the adjacent benzene ring and CS— represents a bond which binds to the adjacent $Z^a$, and —NH of —NHCSO— represents a bond which binds to the adjacent benzene ring and CSO— represents a bond which binds to the adjacent $Z^a$;

$Z^a$—(N$^+$R$^{5a}$R$^{6a}$R$^{7a}$)$_n$ represents an alkyl group or alkenyl group having 2 to 10 carbon atoms which is substituted with —N$^+$R$^{5a}$R$^{6a}$R$^{7a}$, the number of the substituents being n; wherein one or more methylenes which constitute $Z^a$ may be replaced with any of phenylene which may have a substitutent or —O—; wherein the substitutent(s) in the phenylene which may have the substitutent are 1 to 4 substitutents selected from the group consisting of alkyl groups having 1 to 5 carbon atoms, alkoxy groups having 1 to 5 carbon atoms, nitro group, halogen atoms, trifluoromethyl group and —CH$_2$N$^+$R$^{5a}$R$^{6a}$R$^{7a}$; wherein the substitutents may be the same as or different from each other; and wherein n is an integer of 1 or 2; and each of N$^+$R$^{5a}$R$^{6a}$R$^{7a}$ is independently any of the following I), II) or III):

I) R$^{5a}$, R$^{6a}$ and R$^{7a}$ may be the same as or different from one another, and each represents alkyl group having 1 to 10 carbon atoms, alkenyl group having 2 to 10 carbon atoms or alkynyl group having 2 to 10 carbon atoms; wherein the alkyl group, the alkenyl group and the alkynyl group may be substituted with one or more groups of phenyl, naphthyl, pyridyl, quinolyl, thienyl, furyl, piperidyl, pyrrolidyl, morpholyl, cycloalkyl having 3 to 7 carbon atoms, cyano, nitro, hydroxy, oxo, thioxo, carboxy, —CONH$_2$ and —SO$_3$H; and wherein one or more methylenes which constitute the alkyl group, the alkenyl group and the alkynyl group may be replaced with any of phenylene, thienylene, furylene, cyclohexylene, cyclopentylene, —O—, —S—, —CO$_2$—, —NHCO—, —NR$^8$—, and —N$^+$W$^-$R$^9$R$^{10}$—, R$^8$ represents alkyl group having 1 to 5 carbon atoms or alkenyl group having 2 to 5 carbon atoms, the alkyl group and the alkenyl group in R$^8$ may be substituted with one or more groups of phenyl, cycloalkyl having 3 to 7 carbon atoms and hydroxyl, R$^9$ and R$^{10}$ may be the same as or different from each other and each represents alkyl group having 1 to 5 carbon atoms or alkenyl group having 2 to 5 carbon atoms, and may be substituted with one or more groups of phenyl, cycloalkyl having 3 to 7 carbon atoms and hydroxyl, and W$^-$ represents a counteranion;

II) N$^+$R$^{5a}$R$^{6a}$R$^{7a}$ represents a monocyclo or bicyclo ring formed of 4 to 9 carbon atoms in addition to the ammonium nitrogen atom, with a proviso that a position of binding to $Z^a$ is the ammonium nitrogen atom; wherein, in the monocyclo and bicyclo rings, one of the carbon atoms which constitutes the ring may be replaced with any of oxygen, nitrogen or sulfur atom; and the monocyclo and bicyclo rings may be substituted with one or more groups of hydroxy, oxo, thioxo, cyano, phenyl, naphthyl, thienyl, pyridyl, cycloalkyl having 3 to 7 carbon atoms, carboxy, —CONH$_2$, —SO$_3$H and —R$^{11}$, R$^{11}$ represents alkyl group having 1 to 8 carbon atoms or alkenyl group having 2 to 8 carbon atoms, the alkyl group and the alkenyl group in R$^{11}$ may be substituted with one or more groups of phenyl, naphthyl, pyridyl, quinolyl, thienyl, furyl, piperidyl, pyrrolidyl, morpholyl, cycloalkyl having 3 to 7 carbon atoms, cyano, nitro, hydroxy, oxo, thioxo, carboxy, —CONH$_2$ and —SO$_3$H; and one or more methylenes which constitute the alkyl group and the alkenyl group may be replaced with any of phenylene, thienylene, furylene, cyclohexylene, cyclopentylene, —O—, —S—, —CO$_2$—, —NHCO—, —NR$^8$—, and —N$^+$W$^-$R$^9$R$^{10}$; R$^8$, R$^9$, R$^{10}$ and W$^-$ are the same as the above; and the group which is not involved in the formation of the monocyclo ring and the bicyclo ring in R$^{5a}$, R$^{6a}$ and R$^{7a}$ is the same as the above I); and III) N$^+$R$^{5a}$R$^{6a}$R$^{7a}$ represents a pyridinium ring, a quinolinium ring or an isoquinolinium ring with a proviso that a position of binding to Z$^a$ is the ammonium nitrogen atom; wherein the pyridinium ring, the quinolinium ring and the isoquinolinium ring may be substituted with one or more groups of cyano, nitro, phenyl, naphthyl, thienyl, pyridyl, cycloalkyl having 3 to 7 carbon atoms, alkoxy having 1 to 5 carbon atoms, carboxy, —CONH$_2$, —SO$_3$H, halogen, hydroxy, tetrahydropyranyl and —R$^{12a}$, R$^{12a}$ represents alkyl group having 1 to 9 carbon atoms or alkenyl group having 2 to 9 carbon atoms, the alkyl group and the alkenyl group in R$^{12a}$ may be substituted with one or more groups of phenyl, naphthyl, pyridyl, quinolyl, thienyl, furyl, cycloalkyl having 3 to 7 carbon atoms, cyano, nitro, hydroxy, oxo, thioxo, carboxy, —CONH$_2$ and —SO$_3$H; and one or more methylenes which constitute the alkyl group and the alkenyl group may be replaced with any of phenylene, thienylene, furylene, cyclohexylene, cyclopentylene, —S—, —O—, —CO$_2$—, —NHCO—, —NR$^8$—, and —N$^+$W$^-$R$^9$R$^{10}$;

R$^8$, R$^9$, R$^{10}$ and W$^-$ are the same as the above; and X$^-$ represents a counteranion.

3. A pharmaceutical composition containing the compound according to claim 1 as an active component.

4. A pharmaceutical composition containing the compound according to claim 2 as an active component.

5. The compound according to claim 2 wherein Y represents —NHCSNH— at meta position, and Z$^a$ represents the following formula (sp-14):

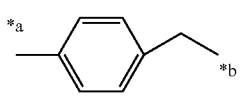

(sp-14)

wherein *a binds to Y and *b binds to N$^+$R$^{5a}$R$^{6a}$R$^{7a}$ in the formula (1B).

6. The compound according to claim 5 wherein R$^2$ and R$^2$ may be the same as or different from each other and each represents straight alkyl groups having 2 to 6 carbon atoms, and wherein (R$^3$R$^4$N)$_m$ represents any of dimethylamino group substituted at position 7, diethylamino group substituted at position 7, ethylmethylamino group substituted at position 7, dimethylamino group substituted at position 9 and dimethylamino groups substituted at two positions 7 and 9.

7. The compound according to claim 6 wherein (R$^3$R$^4$N)$_m$ represents any of dimethylamino group substituted at position 7, diethylamino group substituted at position 7 or ethylmethylamino group substituted at position 7, and wherein N$^+$R$^{5a}$R$^{6a}$R$^{7a}$ represents a group selected from the group consisting of:

4-t-butylpyridinium;

3-(3-hydroxypropyl)-pyridinium;

3-[2-(methoxycarbonyl)ethyl]-pyridinium;

2-(n-propyl)-pyridinium;

4-phenylquinuclidinium; and 1,4-diazabicyclo[2.2.2]octanium.

8. A compound represented by the following formula (I):

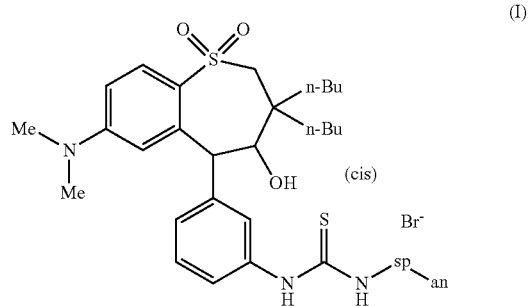

(I)

wherein (sp) is the following formula (sp-14)

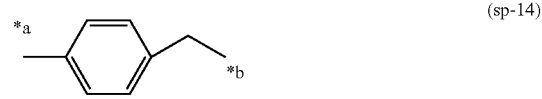

(sp-14)

wherein *a binds to —NHCSNH— and *b binds to (an); and (an) is selected from the group consisting of:

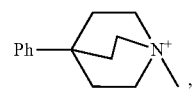

(an-288)

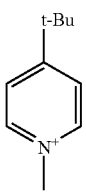

(an-305)

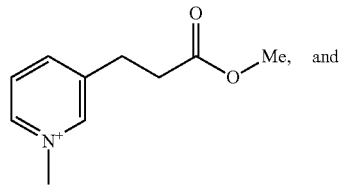

(an-344)

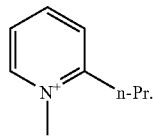
(an-395)

9. The compound according to claim 8 wherein (sp) is the formula (sp-14), and (an) is the formula (an-288).

10. A pharmaceutical composition containing the compound according to claim 5 as an active component.

11. A pharmaceutical composition containing the compound according to claim 6 as an active component.

12. A pharmaceutical composition containing the compound according to claim 7 as an active component.

13. A pharmaceutical composition containing the compound according to claim 8 as an active component.

14. A pharmaceutical composition containing the compound according to claim 9 as an active component.

15. A method of lowering cholesterol, comprising administering to a patient in need thereof an effective amount of a pharmaceutical composition containing the compound according to claim 1 as an active component.

16. A method for treating any of hyperlipemia, arteriosclerosis or syndrome X, comprising administering to a patient in need thereof an effective amount of a pharmaceutical composition containing the compound according to claim 1 as an active component.

17. A method of lowering cholesterol, comprising administering to a patient in need thereof an effective amount of a pharmaceutical composition containing the compound according to claim 2 as an active component.

18. A method for treating any of hyperlipemia, arteriosclerosis or syndrome X, comprising administering to a patient in need thereof an effective amount of a pharmaceutical composition containing the compound according to claim 2 as an active component.

19. A method of lowering cholesterol, comprising administering to a patient in need thereof an effective amount of a pharmaceutical composition containing the compound according to claim 5 as an active component.

20. A method for treating any of hyperlipemia, arteriosclerosis or syndrome X, comprising administering to a patient in need thereof an effective amount of a pharmaceutical composition containing the compound according to claim 5 as an active component.

21. A method of lowering cholesterol, comprising administering to a patient in need thereof an effective amount of a pharmaceutical composition containing the compound according to claim 6 as an active component.

22. A method for treating any of hyperlipemia, arteriosclerosis or syndrome X, comprising administering to a patient in need thereof an effective amount of a pharmaceutical composition containing the compound according to claim 6 as an active component.

23. A method of lowering cholesterol, comprising administering to a patient in need thereof an effective amount of a pharmaceutical composition containing the compound according to claim 7 as an active component.

24. A method for treating any of hyperlipemia, arteriosclerosis or syndrome X, comprising administering to a patient in need thereof an effective amount of a pharmaceutical composition containing the compound according to claim 7 as an active component.

25. A method of lowering cholesterol, comprising administering to a patient in need thereof an effective amount of a pharmaceutical composition containing the compound according to claim 8 as an active component.

26. A method for treating any of hyperlipemia, arteriosclerosis or syndrome X, comprising administering to a patient in need thereof an effective amount of a pharmaceutical composition containing the compound according to claim 8 as an active component.

27. A method of lowering cholesterol, comprising administering to a patient in need thereof an effective amount of a pharmaceutical composition containing the compound according to claim 9 as an active component.

28. A method for treating any of hiperlipemia, arteriosclerosis or syndrome X, comprising administering to a patient in need thereof an effective amount of a pharmaceutical composition containing the compound according to claim 9 as an active component.

* * * * *